(12) United States Patent
Bondy et al.

(10) Patent No.: US 10,370,358 B2
(45) Date of Patent: *Aug. 6, 2019

(54) COMPOUNDS FOR THE TREATMENT OF HIV

(71) Applicant: Gilead Sciences, Inc., Foster City, CA (US)

(72) Inventors: Steven S. Bondy, Haiku, HI (US); Carina E. Cannizzaro, Foster City, CA (US); Chien-Hung Chou, Dublin, CA (US); Randall L. Halcomb, Foster City, CA (US); Yunfeng Eric Hu, San Mateo, CA (US); John O. Link, San Francisco, CA (US); Qi Liu, Union City, CA (US); Scott D. Schroeder, Union City, CA (US); Winston C. Tse, Redwood City, CA (US); Jennifer R. Zhang, Union City, CA (US)

(73) Assignee: Gilead Sciences, Inc., Foster City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/902,883

(22) Filed: Feb. 22, 2018

(65) Prior Publication Data
US 2018/0194746 A1    Jul. 12, 2018

Related U.S. Application Data

(60) Division of application No. 15/357,290, filed on Feb. 3, 2017, now Pat. No. 9,944,619, which is a
(Continued)

(51) Int. Cl.
| | |
|---|---|
| *A61K 31/50* | (2006.01) |
| *A61K 45/06* | (2006.01) |
| *A61K 31/444* | (2006.01) |
| *A61K 31/506* | (2006.01) |
| *C07D 213/40* | (2006.01) |
| *C07D 401/12* | (2006.01) |
| *C07D 401/14* | (2006.01) |
| *C07D 403/12* | (2006.01) |
| *C07D 403/14* | (2006.01) |
| *C07D 405/12* | (2006.01) |
| *C07D 409/14* | (2006.01) |
| *C07D 413/14* | (2006.01) |
| *C07D 471/04* | (2006.01) |
| *C07D 471/06* | (2006.01) |
| *C07D 487/04* | (2006.01) |
| *C07D 491/04* | (2006.01) |

(Continued)

(52) U.S. Cl.
CPC .......... *C07D 401/12* (2013.01); *A61K 31/444* (2013.01); *A61K 31/4439* (2013.01); *A61K 31/4545* (2013.01); *A61K 31/4709* (2013.01); *A61K 31/4985* (2013.01); *A61K 31/50* (2013.01); *A61K 31/506* (2013.01); *A61K 31/5377* (2013.01); *A61K 45/06* (2013.01); *C07D 213/40* (2013.01); *C07D 401/14* (2013.01); *C07D 403/12* (2013.01); *C07D 403/14* (2013.01); *C07D 405/12* (2013.01); *C07D 409/14* (2013.01); *C07D 413/14* (2013.01); *C07D 471/04* (2013.01); *C07D 471/06* (2013.01); *C07D 487/04* (2013.01); *C07D 491/04* (2013.01); *C07D 491/052* (2013.01); *C07D 495/04* (2013.01)

(58) Field of Classification Search
CPC .............. C07D 401/12; A61K 31/4439; A61K 31/4545
See application file for complete search history.

(56) References Cited

U.S. PATENT DOCUMENTS

| | | |
|---|---|---|
| 4,816,570 A | 3/1989 | Farquhar |
| 4,968,788 A | 11/1990 | Farquhar |

(Continued)

FOREIGN PATENT DOCUMENTS

| | | |
|---|---|---|
| JP | 2009-519967 | 5/2009 |
| JP | 2011-514910 | 5/2011 |

(Continued)

OTHER PUBLICATIONS

AU Office Action in Australian Appln. No. 2017213517, dated Jul. 17, 2018, 3 pages.
(Continued)

*Primary Examiner* — Jean P Cornet
(74) *Attorney, Agent, or Firm* — Fish & Richardson P.C.

(57) ABSTRACT

The invention provides compounds of formula (I): or a salt thereof as described herein. The invention also provides pharmaceutical compositions comprising a compound of formula (I), processes for preparing compounds of formula (I), intermediates useful for preparing compounds of formula I and therapeutic methods for treating a Retroviridae viral infection including an infection caused by the HIV virus.

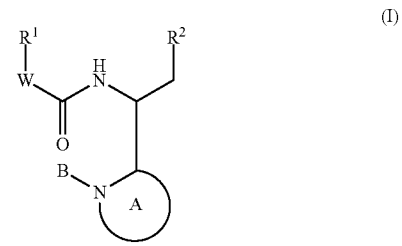

12 Claims, No Drawings

Related U.S. Application Data continuation of application No. 14/130,882, filed as application No. PCT/US2012/045630 on Jul. 5, 2012, now Pat. No. 9,540,343.

(60) Provisional application No. 61/505,032, filed on Jul. 6, 2011.

(51) Int. Cl.

| | |
|---|---|
| *C07D 495/04* | (2006.01) |
| *A61K 31/4439* | (2006.01) |
| *A61K 31/4545* | (2006.01) |
| *A61K 31/4709* | (2006.01) |
| *A61K 31/4985* | (2006.01) |
| *A61K 31/5377* | (2006.01) |
| *C07D 491/052* | (2006.01) |

(56) References Cited

U.S. PATENT DOCUMENTS

| | | |
|---|---|---|
| 5,663,159 A | 9/1997 | Starrett, Jr. et al. |
| 5,792,756 A | 8/1998 | Starrett, Jr. et al. |
| 8,263,627 B2 | 9/2012 | Barrow et al. |
| 8,748,412 B2 | 6/2014 | Liao et al. |
| 8,835,488 B2 | 9/2014 | Yamashita et al. |
| 9,012,441 B2 | 4/2015 | Bondy et al. |
| 9,050,344 B2 | 6/2015 | Brizgys et al. |
| 9,220,710 B2 | 12/2015 | Bondy et al. |
| 9,540,343 B2 | 1/2017 | Bondy et al. |
| 9,789,089 B2 | 10/2017 | Bondy et al. |
| 9,944,619 B2 | 4/2018 | Bondy et al. |
| 9,951,043 B2 | 4/2018 | Brizgys et al. |
| 10,171,985 B1 | 1/2019 | Czajka, II et al. |
| 2005/0282805 A1 | 12/2005 | Hangeland et al. |
| 2007/0032469 A1 | 2/2007 | Isaac et al. |
| 2007/0032649 A1 | 2/2007 | Isaac et al. |
| 2007/0083045 A1 | 4/2007 | Di Francesco et al. |
| 2010/0249176 A1 | 9/2010 | Barrow et al. |
| 2012/0045761 A1 | 2/2012 | Jagannath et al. |
| 2013/0165489 A1 | 6/2013 | Cocklin et al. |
| 2014/0142085 A1 | 5/2014 | Bondy et al. |
| 2014/0221346 A1 | 8/2014 | Halcomb et al. |
| 2014/0221347 A1 | 8/2014 | Brizgys et al. |
| 2014/0221417 A1 | 8/2014 | Halcomb et al. |
| 2014/0221421 A1 | 8/2014 | Bondy et al. |
| 2014/0296266 A1 | 10/2014 | Hu et al. |
| 2014/0303164 A1 | 10/2014 | Brizgys et al. |
| 2016/0067224 A1 | 3/2016 | Bondy et al. |
| 2016/0083368 A1 | 3/2016 | Brizgys et al. |
| 2016/0108030 A1 | 4/2016 | Brizgys et al. |
| 2016/0368881 A1 | 12/2016 | Bondy et al. |
| 2017/0137405 A1 | 5/2017 | Bondy et al. |
| 2018/0051005 A1 | 2/2018 | Graupe et al. |
| 2018/0273508 A1 | 9/2018 | Brizgys et al. |

FOREIGN PATENT DOCUMENTS

| | | |
|---|---|---|
| WO | WO 91/19721 | 12/1991 |
| WO | WO 03/002530 | 1/2003 |
| WO | WO 03/002553 | 1/2003 |
| WO | WO 2004/050643 | 6/2004 |
| WO | WO 2004/071448 | 8/2004 |
| WO | WO 05/087725 | 9/2005 |
| WO | WO 2005/087725 | 9/2005 |
| WO | WO 2005/123680 | 12/2005 |
| WO | WO 2008/013622 | 1/2008 |
| WO | WO-2009/005677 | 1/2009 |
| WO | WO 2009/010804 | 1/2009 |
| WO | WO 2009/062285 | 5/2009 |
| WO | WO 2010/130034 | 11/2010 |
| WO | WO 2011/059887 | 5/2011 |
| WO | WO 2011/143772 | 11/2011 |
| WO | WO 2012/003497 | 1/2012 |
| WO | WO 2012/003498 | 1/2012 |
| WO | WO 2012/065062 | 5/2012 |
| WO | WO 2012/145728 | 10/2012 |
| WO | WO 2013/006738 | 1/2013 |
| WO | WO 2013/006792 | 1/2013 |
| WO | WO 2013/159064 | 10/2013 |
| WO | WO 2014/016358 | 1/2014 |
| WO | WO 2014/028931 | 2/2014 |
| WO | WO 2014/110297 | 7/2014 |
| WO | WO 2014/110298 | 7/2014 |
| WO | WO 2014/134566 | 9/2014 |
| WO | WO 2015/008097 | 1/2015 |
| WO | WO 2015/061518 | 4/2015 |
| WO | WO 2015/130966 | 9/2015 |
| WO | WO 2016/040084 | 3/2016 |
| WO | WO 2016/172424 | 10/2016 |
| WO | WO 2016/172425 | 10/2016 |
| WO | WO2017/007689 | 1/2017 |

OTHER PUBLICATIONS

BO Technical Report in Bolivian Appln. No. SNP/2018-04184, dated Jun 6, 2018, 17 pages (with English tmnslation).
CA Office Action in Canadian Appln. No. 2,840,095, dated May 3, 2018, 4 pages.
CL Office Action dated Mar. 30, 2017 for Chile Application No. 2445-2015 (with English translation).
CL Office Action issued in Chilean Patent Application No. 2015-002445, dated Dec. 20, 2017, 16 pages (with English translation).
CL Pre-grant opposition dated Jun. 15, 2016 for Chilean Application No. 2445-2015.
CN Office Action dated Jan. 16, 2017 for Chinese Application No. 201480020587.0.
CN Search Report dated Jan. 16, 2017 for Chinese Application No. 201480020587.0.
CO Office Action dated Dec. 7, 2015 for Colombian Patent Application No. 15-199.357 1 with English translaton.
EA Office Action dated Aug. 17, 2016 for Eurasian Patent Application No. 201591457. (with English translation).
EA Office Action issued in Eurasian Patent Application No. 201591457/28, dated Nov. 14, 2017, 12 pages (English Translation).
EP Communication in European Appln. No. 17758388, dated May 15, 2018, 5 pages.
EP Extended European Search Report in European Appln. No. 18181536.6, dated Aug. 21, 2018, 8 pages.
GC Examination Report in Gulf Cooperation Council Appln. No. GC2014-26552, dated Mar. 25, 2018.
GC Second Examination Report issued in GCC Patent Application No. 2014/26552, dated Oct. 17, 2017.
ID Substantive Examination Report Stage 1 in Indonesian Appln. No. P-00201505361, dated Apr. 12, 2018, 8 pages.
IL Office Action issued in Israeli Patent Application No. 240519, dated Dec. 20, 2017, 9 pages.
IN Office Action in Indian Application No. 7440/DELNP/2015, dated Apr. 27, 2018, 7 pages.
JP Office Action issued in Japanese Application No. 2015-560381, dated Jan. 18, 2018, 12 pages (with English translation).
PA Office Action dated Mar. 28, 2017 for Panama Application No. 90820-01. (with English translation).
PCT International Search Report and Written Opinion in International Appln. No. PCT/US2017/047416, dated Oct. 27, 2017, 10 pages.
PH Substantive Examination Report in Philippines Appln. No. 1/2015/501881, dated May 8, 2018, 3 pages.
Pornillos et al., (2009) "X-ray Structures of the Hexameric Building Block of the HIV Capsid," Cell 137(7):1282-92.
STN Registry No. 137349-29-2, Nov. 15, 1991.
SUBLOCADE Product Label, issued: Nov. 2017, 43 pages.
SV Office Action issued in Patent Application No. 2015005048, dated Sep. 26, 2017, 10 pages (with English translation).
TW Office Action in Taiwanese Application No. 103106785, dated Apr. 24, 2018, 7 pages (with English translation).
UA Office Action in Ukrainian Appln. No. 2015 08564, dated Jul. 17, 2018, 6 pages (with English translation).

(56) References Cited

OTHER PUBLICATIONS

VN Notification No. 34475 dated Oct. 13, 2015 for Vietnam Patent Application No. 1-2015-03220.
Yant et al., (2014) "PF74 Inhibits Multiple HIV Capsid Functions Independently of Host Cyclophilin A and CPSF6," Abstract for Poster Presented at the Conference on Retroviruses and Opportunistic Infections (CROI), Boston, Massachusetts, 534.
U.S. Appl. No. 14/130,882, filed Jan. 3, 2014.
U.S. Appl. No. 15/357,290, filed Feb. 3, 2017.
Benzaria, S. et al. (Dec. 6, 1996). "Synthesis, In Vitro Antiviral Evaluation, and Stability Studies of Bis(S-Acyl-2-Thioethyl) Ester Derivatives of 9-[2-(Phosphonomethoxy) Ethyl] adenine (PMEA) as Potential PMEA Prodrugs with Improved Oral Bioavailability," J. Med. Chem. 39(25):4958-4965.
Bundgaard, H. (1991). "Design and Application of Prodrugs," Chapter 5 in "A Textbook of Drug Design and Development," Krogsgaard-Larsen, P. et al. eds., Harwood Academic Publishers, Chur, Switzerland, pp. 113-191.
Cossy, J. et al. (Oct. 23, 1995). "Ring Opening of Cyclopropylketones Induced by Photochemical Electron Transfer," Tetrahedron 51 (43):11751-11764.
De Lombaert, S. et al. (Feb. 18, 1994). "N-Phosphonomethyl Dipeptides and Their Phosphonate Prodrugs, A New Generation of Neutral Endopeptidase (NEP, EC 3.4.24.11) Inhibitors," J. Med. Chem. 37(4):498-511.
Examination Report dated May 3, 2016 for Australian Patent Application No. 2012278976.
Farquhar, D. et al. (Mar. 1983). "Biologically Reversible Phosphate-Protective Groups," J. Pharm. Sci. 72(3):324-325.
Hammer, S. et al. (Aug. 6, 2008). "Antiretroviral Treatment of Adult HIV Infection. 2008 Recommendations of the International AIDS Society: USA Panel," JAMA 300(5):555-570.
Hodgson, D.M. et al. (Jul. 21, 2004, e-pub. Jun. 24, 2004). "Intramolecular Cyclopropanation of Unsaturated Terminal Epoxides," J. Am. Chem. Soc. 126(28):8664-8665.
Khamnei S. et al. (Sep. 27, 1996). "Neighboring Group Catalysis in the Design of Nucleotide Prodrugs," J. Med. Chem. 39(20):4109-4115.
Kocienski, P.J. (May 1994). "Carbonyl Protecting Groups," Chapter 5 in "Protecting Groups," Thieme Publishing Group: New York, NY, pp. 155-184.
Kocienski, P.J. (May 1994). "Carboxyl Protecting Groups," Chapter 4 in "Protecting Groups," Thieme Publishing Group: New York, NY, pp. 118-154.
Kocienski, P.J. (May 1994). "Diol Protecting Groups," Chapter 3 in "Protecting Groups," Thieme Publishing Group: New York, NY, pp. 95-117.
Kocienski, P.J. (May 1994). "Hydroxyl Protecting Groups," Chapter 2 in "Protecting Groups," Thieme Publishing Group: New York, NY, pp. 21-94.
Kocienski, P.J. (May 1994). "Protecting Groups: An Overview," Chapter 1 in "Protecting Groups," Thieme Publishing Group: New York, NY, pp. 1-20.
Lemke, C.T. et al. (Jun. 2012). "Distinct Effects of Two HIV-1 Capsid Assembly Inhibitor Families That Bind the Same Site Within the N-Terminal Domain of the Viral CA Protein," J. Viral. 86(12):6643-6655.
Mitchell, A.G. et al. (1992). "Bioreversible Protection for the Phospho Group: Bioactivation of the Di(4-Acyloxybenzyl) and Mono(4-acyloxybenzyl) Phosphoesters of Methylphosphonate and Phosphonoacetate," J. Chem. Soc. Perkin Trans. 1, pp. 2345-2353.
Office Action dated Feb. 9, 2016 for Japanese Patent Appl. No. 2014-519308.
Office Action for Japanese Application No. 2014-519308 dated Mar. 10, 2017.
Office Action for Japanese Application No. 2014-519308 dated Mar. 10, 2017—English Translation.
Puech, F. et al. (Oct. 1993). "Intracellular Delivery of Nucleoside Monophosphates Through a Reductase-Mediated Activation Process," Antiviral Res. 22(2-3):155-174.

Smith, R.J. et al. (Feb. 5, 201 O; e-pub. Jan. 14, 2010). "Evolutionary Dynamics of Complex Networks of HIV Drug Resistant Strains: The Case of San Francisco," Science 327(5966):697-701.
Taiwo, B. (Sep. 2009; e-pub. Jan. 10, 2009). "Understanding Transmitted HIV Resistance Through the Experience in the USA," Int J. of Infectious Diseases 13(5):552-559.
Berge, S.M. et al. (Jan. 1977). "Pharmaceutical Salts," J. Pharma. Sci. 66(1):1-19.
Bhattacharya et al. (2014) Structural Basis of HIV-1 Capsid Recognition by PF74 and CPSF6, PNAS; 111 (52):18625-18630.
Blair et al., (2010) "HIV Capsid is a Tractable Target for Small Molecule Therapeutic Intervention," PLoS Pathog. 6(12): e1001220.
Brown, M.K. et al. ( 2005) "Highly Enantioselective Cu-Catalyzed Conjugate Additions of Dialkylzinc Reagents to Unsaturated Furanones and Pyranones: Preparation of Air-Stable and Catalytically Active Cu-Peptide," Angew Chem. Int. Ed. Engl. 44(33):5306-5310.
Briggs et al., (2003) "Structural Organization of Authentic, Mature HIV-1 Virions and Cores," The EMBO Journal; vol. 22 No. 7 pp. 1707-1715.
Campbell et al., (2015) "HIV-1 Capsid: The Multifaceted Key Player in HIV-1 Infection," Nat Rev Microbial.; 13(8): 471-483.
Chin et al. (2015) "Direct Visualization of HIV-1 Replication Intermediates Shows That Capsid and CPSF6 Modulate HIV-1 Intra-Nuclear Invasion and Integration", Cell Reports 13:1717-1731.
Cos, P. et al. (1998) "Structure-Activity Relationship and Classification of Flavonoids as Inhibitors of Xanthine Oxidase and Su peroxide Scavengers," J. Natl. Prod. 61 :71-76.
Curreli et al., (2011) "Virtual Screening Based Identification of Novel Small-molecule Inhibitors Targeted to the HIV-1 Capsid," Bioorganic & Medicinal Chemistry 19:77-90.
English language translation of Office Action dated Jan. 18, 2017 for Eurasian Patent Application No. 201591457, 9 pages.
English language translation of Office Action dated Jan. 18, 2017 for Panama Application No. 90820-01, 4 pages.
English language translation of Office Action dated Mar. 30, 2017 for Chile Application No. 2445-2015, 11 pages.
English language translation of Pre-grant opposition dated Jun. 15, 2016 for Chilean Application No. 2445-2015.
English language translation of Search Report dated Jan. 6, 2017 for Chinese Application No. 201480020587.0.
English language translation of Office Action dated Jan. 16, 2017 for Chinese Application No. 201480020587.0, 5 pages.
First Examination Report dated Nov. 2, 2015 for New Zealand Patent Application No. 631754, 2 pages.
Fader et al., (2013) Optimization of a 1,5-dihydrobenzo[b][1,4]diazepine-2,4-dione Series of HIV Capsid Assembly Inhibitors 2: Structure-Activity Relationships (SAR) of the C3-Phenyl Moiety, Bioorganic & Medicinal Chemistry Letters, doi: <httQ://dx.doi.org/10.1016/j.bmc1.2013.03.074>.
Forshey et al., (2002) "Formation of a Human Immunodeficiency Virus Type 1 Core of Optimal Stability Is Crucial for Viral Replication," J. Virology, 76(11) p. 5667-5677.
Ganser et al., (1999) "Assembly and Analysis of Conical Models for the HIV-1 Core," Science 283. 80-82.
Ganser-Pornillos et al., (2007) "Structure of Full-Length HIV-1 CA: A Model for the Mature Capsid Lattice," Cell.; 131(1):70-9, 29 pages.
Hodgson, D.M. et al. (2007) "lntramolecular Cyclopropanation of Unsaturated Terminal Epoxides and Chlorohydrins," JACS 129(14):4456-4462.
Hung et al. (2013) "Large-Scale Functional Purification of Recombinant HIV-1 Capsid," PLOS One, vol. 8, Issue 3, e58035, 11 pages.
International Search Report and Written Opinion dated Oct. 12, 2015 for PCT/US2015/047040, 8 pages.
International Preliminary Report on Patentability issued Feb. 28, 2017 for PCT/US2015/047040, 6 pages.
International Search Report and Written Opinion dated Mar. 11, 2014 for PCT/US2014/010938, 8 pages.
International Search Report and Written Opinion dated Apr. 11, 2014 for PCT/US2014/010937, 9 pages.
International Search Report and Written Opinion dated Oct. 15, 2014 for PCT/US2014/019663.

(56) References Cited

OTHER PUBLICATIONS

International Search Report and Written Opinion dated Sep. 19, 2012 for PCT/US2012/045630, 15 pages.
International Search Report and Written Opinion dated Mar. 21, 2014 for PCT/US2014/010939.
IPRP for International Application No. PCT/US2015/017820 dated Sep. 6, 2016, 7 pages.
Jeong, .J.U. (2010) "Synthesis of Tetrasubstituted Pyrazones and Pyrazone N-Oxides," Tetrahedron Letters 51 (6):974-976.
Jin et al., (2010) "SAR and Molecular Mechanism Study of Novel Acylhydrazone Compounds Targeting HIV-1 CA," Bioorganic & Medicinal Chemistry; 18: 2135-2140.
Jouvenet et al., (2006) "Plasma Membrane Is the Site of Productive HIV-1 Particle Assembly," PLoS Biol.;4(12):e435, 15 pages.
Kashima, C. et al. (Aug.-Sep. 1991). "New Peptide Synthesis Using the Ozonolysate of 2-(1-Phthalimido)alkyl-5-Phenyloxazoles," J. Heterocyclic Chem. 28: 1241-1244 (abstract only).
Kelly, et al., (2007) "Structure of the Antiviral Assembly Inhibitor CAP-1 Bound to the HIV-1 CA Protein," Journal of Molecular Biology, doi: 10.1016/j.jmb.2007.07.070, 40 pages.
"Kim et al., (2013) ""Discovery of a New HIV-1 Inhibitor Scaffold and Synthesis of Potential Prodrugs of lndazoles,""" Bioorganic & Medicinal Chemistry Letters, doi: <http://dx.doi.org/10.1016/j.bmcl.2013.03.075> 8 pages".
Lad et al., (2015) "Functional Label-Free Assays for Characterizing the in Vitro Mechanism of Action of Small Molecule Modulators of Capsid Assembly," Biochemistry, 54, 2240-2248.
Lamorte et al. (2015) "Discovery of Novel Small-Molecule HIV-1 Replication Inhibitors That Stabilize Capsid Complexes," Antimicrobial Agents and Chemotherapy, 57(10): 4622-4631.
Lazerwith et al., (2017) "New Antiretrovirals for HIV and Antivirals for HBV," in Comprehensive Medicinal Chemistry, 3rd Edition, 1-36.
Lee et al., (2010) "Flexible Use of Nuclear Import Pathways by HIV-1," Cell Host & Microbe; 7, 221-233.
Matreyek et al., (2013) "Nucleoporin NUP153 Phenylalanine-Glycine Motifs Engage a Common Binding Pocket within the HIV-1 Capsid Protein to Mediate Lentiviral Infectivity" PLOS Pathogens vol. 9, Issue 10, e1003693.
Restriction Requirement dated Jul. 28, 2014, for U.S. Appl. No. 14/151,752, filed Jan. 9, 2014, six pages.
Rihn et al., (2013) "Extreme Genetic Fragility of the HIV-1 Capsid," PLOS One, vol. 9 Issue 6 e1003461, 25 pages.
Pornillos et al., (2009) Supplemental Data for "X-ray Structures of the Hexameric Building Block of the HIV Capsid," Cell. Jun. 26, 2009;137(7):1282-92.
Powers, J.J. et al. (2009) "Synthesis of Methyl-, Fluoro-, and Chloro-Substituted 6-Hydroxyisoindolin-1-Ones," Tetrahedron Letters 50(12): 1267-1269.
Price et al. (2012) "CPSF6 Defines a Conserved Capsid Interface That Modulates HIV-1 Replication," PLOS Pathogens, 8(8):e1002896, 14 pages.
Wong et al., (2014) "SPR Assay Development to Characterize Capsid Inhibitors Binding & MOA," Poster Presented at the Developments in Protein Interaction (DiPIA), La Jolla, CA, 1 page.
Tang et al., (2003) "Antiviral Inhibition of the HIV-1 Capsid Protein," J. Mo/. Biol., 327, 1013-1020.
Tanaka, R. et al. (2005) "One-Pot Synthesis of Metalated Pyridines from Two Acetylenes, a Nitrile, and a Titanium (II) Alkoxide," J. Am. Chem. Soc. 127(21):7774-7780.
Tsiang et al., (2012) "A Trimer of Dimers Is the Basic Building Block for Human Immunodeficiency Virus-1 Capsid Assembly" Biochemistry, 51, 4416-4428.
Tse et al., (2017) "Discovery of Novel Potent HIV Capsid Inhibitors with Long-Acting Potential," Abstract for Oral Presentation at the Conference on Retroviruses and Opportunistic Infections (CROI), Seattle, WA, 18 pages.
Siddiqui, A. et al. (1999) "The Presence of Substituents on the Aryl Moiety of the Aryl Phosphoramidate Derivative of d4T Enhances Anti-HIV Efficacy in Cell Culture: A Structure-Activity Relationship," J. Med. Chem. 42:393-399.
Shi et al. (2011) "Small-Molecule Inhibition of Human Immunodeficiency Virus Type 1 Capsid Destabilization," Journal of Virology 85(1) 542-549.
Smith, R.J. et al. (2010) "Evolutionary Dynamics of Complex Networks of HIV Drug-Resistant Strains: The Case of San Francisco," Science 327(5966):697-701.
Search Report and Written Opinion for International Application No. PCT/US2015/017820 dated May 13, 2015, 10 pages.
Sticht et al., (2005) "A peptide inhibitor of HIV-1 assembly in vitro," Nature Structural & Molecular Biology, vol. 12 No. 8 671-677.
Owen et al., "Strengths, weaknesses, opportunities and challenges for long acting injectable therapies: Insights for applications in HIV therapy," Advances Drug Delivery Reviews 103 (2016) 144-156.
Office Action dated Nov. 8, 2015 for Australian Application No. 2014205317, 3 pages.
Office Action dated May 6, 2016 for Canadian Application No. 2,896,244, 4 pages.
Office Action dated Jan. 7, 2016 for Japanese Application No. 2015-551874—English translation.
Yant et al., (2014) "An Improved PF74 Analog Inhibits Multiple HIV Capsid Functions Independently of Host Cyclophilin A and CPSF6," Poster Presented at the Conference on Retroviruses and Opportunistic Infections (CROI), Boston, Massachusetts, 1 page.
Office Action dated Oct. 18, 2017 for Australian Application No. 2016262671, 3 pages.
Office Action dated Sep. 8, 2016 English Translation for Colombia Application No. 15199357, 7 pages.
Office Action dated Jun. 4, 2015 for U.S. Appl. No. 14/194,611, 11 pages.
Office Action dated Jun. 19, 2015 for U.S. Appl. No. 14/194,623, 13 pages.
Office Action dated Dec. 1, 2015 for Australian Patent Application No. 2014223973, 3 pages.
Office Action dated Dec. 4, 2015 for EP 14712844.1-1462, 2 pages.
Office Action dated Apr. 12, 2017 for Gulf Cooperation Council Application No. 2014/26552, 6 pages.
Office Action dated Feb. 22, 2017 for New Zealand Application No. 728537, 2 pages.
Office Action dated Jun. 28, 2016 for Eurasian Patent Application No. 201591457/28, 9 pages.
Office Action dated Oct. 17, 2017 for Taiwan Patent Application No. 103106785 (English translation), 1 page.
Office Action dated Jul. 19, 2017 for Chinese Application No. 2014800205870 (English translation), 9 pages.
Office Action dated Mar. 29, 2017 for European Patent Application No. 14712844.1.
Zhou et al. (2015) "HIV-1 Resistance to the Capsid-Targeting Inhibitor PF74 Results in Altered Dependence on Host Factors Required for Virus Nuclear Entry" Journal of Virology, doi 10.1128/JVI.00340-15. Published online Jun. 24, 2015, 37 pages.
U.S. Appl. No. 15/988,717, filed Aug. 16, 2018, Houston et al.
Fields, "Methods for Removing the Fmoc Group," Methods in Molecular Biology, 1994, 35:17-27.
MacMillan et al., "Evaluation of alternative solvent in common amide coupling reactions: replacement of dichloromethane and N,N-dimethylformamide," Green Chem, 2013, 15: 596-600.
Miyaura and Suzuki, "Palladium-Catalyzed Cross-Coupling Reactions of Organoboron Compounds," Chem Rev, 1995, 95: 2457-2483.
Montalbetti and Falque, "Amide bond formation and peptide coupling," Tetrahedron, 2005, 61:10827-10852.
Nicolaou et al., "Palladium-Catalyzed Cross-Coupling Reactions in Total Synthesis," Angew Chem Int, 2005, 44:4442-4489.

COMPOUNDS FOR THE TREATMENT OF HIV

CROSS REFERENCE TO RELATED APPLICATIONS

This patent application is a divisional of U.S. patent application Ser. No. 15/357,290, filed Feb. 3, 2017, which is a continuation of U.S. patent application Ser. No. 14/130,882, filed Jan. 3, 2014, now U.S. Pat. No. 9,540,343, which is a national stage filing under 35 U.S.C. § 371 of International Patent Application No. PCT/US2012/045630, filed on Jul. 5, 2012, which claims the benefit of priority of U.S. Provisional Patent Application Ser. No. 61/505,032, filed Jul. 6, 2011. The contents of each application are incorporated by reference.

BACKGROUND OF THE INVENTION

Positive-single stranded RNA viruses comprising the Retroviridae family include those of the subfamily Orthoretrovirinae and genera Alpharetrovirus, Betaretrovirus, Gamaretrovirus, Deltaretrovirus, Epsilonretrovirus, Lentivirus, and Spumavirus which cause many human and animal diseases. Among the Lentivirus, HIV-1 infection in humans leads to depletion of T helper cells and immune dysfunction, producing immunodeficiency and vulnerability to opportunistic infections. Treating HIV-1 infections with highly active antiretroviral therapies (HAART) has proven to be effective at reducing viral load and significantly delaying disease progression (Hammer, S. M., et al.; *JAMA* 2008, 300: 555-570). However, these treatments do lead to the emergence of HIV strains that are resistant to current therapies (Taiwo, B., *International Journal of Infectious Diseases* 2009, 13:552-559; Smith, R. J., et al., *Science* 2010, 327: 697-701). Therefore, there is a pressing need to discover new antiretroviral agents that are active against emerging drug-resistant HIV variants.

SUMMARY OF THE INVENTION

The present invention provides compounds and methods for the treatment of an HIV infection. In one embodiment, the invention provides a compound of the invention which is a compound of formula I:

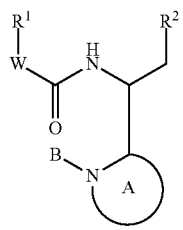

(I)

wherein:

A is a 6-membered heteroaryl comprising one or two nitrogens, wherein the 6-membered heteroaryl is substituted with one $Z^1$ group and optionally substituted with one or more (e.g. 1, 2, or 3) $Z^2$ groups;

B is absent; or B is $-O^-$ and the nitrogen to which the $-O^-$ group is attached is $N^+$;

W is $-CR^{3a}R^{3b}-$, $-O-$, $-NR^4-$, $-OCR^{3a}R^{3b}-$ or absent;

$R^1$ is aryl, heteroaryl or heterocycle, wherein any aryl, heteroaryl or heterocycle of $R^1$ is optionally substituted with one or more (e.g. 1, 2, 3, 4 or 5) $Z^3$ groups;

$R^2$ is a 6-membered aryl, 5-membered heteroaryl or 6-membered heteroaryl, wherein any 6-membered aryl, 5-membered heteroaryl or 6-membered heteroaryl of $R^2$ is optionally substituted with one or more (e.g. 1, 2 or 3) $Z^4$ groups;

each $R^{3a}$ and $R^{3b}$ is independently selected from H, halogen, $(C_1-C_6)$alkyl, $(C_3-C_7)$carbocycle, $(C_1-C_3)$haloalkyl, $(C_1-C_6)$heteroalkyl, heteroaryl$(C_1-C_6)$alkyl-, heterocyclyl$(C_1-C_6)$alkyl-, $-NR_aR_b$, and $-NR_cCOR_d$, wherein any $(C_1-C_6)$alkyl of $R^{3a}$ and $R^{3b}$ is optionally substituted with one or more OH groups; or $R^{3a}$ and $R^{3b}$ together with the carbon to which they are attached form a $(C_3-C_6)$carbocycle;

$R^4$ is selected from H, $(C_1-C_6)$alkyl, $(C_3-C_6)$carbocycle, aryl$(C_1-C_6)$alkyl- and heteroaryl$(C_1-C_6)$alkyl-;

$R_a$ and $R_b$ are each independently selected from H, $(C_1-C_8)$alkyl, $(C_2-C_8)$alkenyl, $(C_2-C_8)$alkynyl, $(C_3-C_7)$carbocycle, heterocycle, heteroaryl, aryl, haloaryl, haloheteroaryl, haloheterocycle, $(C_1-C_8)$haloalkyl and $(C_1-C_8)$heteroalkyl, or $R_a$ and $R_b$ together with the nitrogen to which they are attached form a 5, 6 or 7-membered heterocycle;

each $R_c$ is independently selected from H, $(C_1-C_8)$alkyl, $(C_2-C_8)$alkenyl, $(C_2-C_8)$alkynyl, $(C_3-C_7)$carbocycle, heterocycle, heteroaryl, aryl, haloaryl, haloheteroaryl, haloheterocycle, $(C_1-C_8)$haloalkyl and $(C_1-C_8)$heteroalkyl;

each $R_d$ is independently selected from $(C_1-C_8)$alkyl, $(C_2-C_8)$alkenyl, $(C_2-C_8)$alkynyl, $(C_3-C_7)$carbocycle, heterocycle, heteroaryl, aryl, haloaryl, haloheteroaryl, haloheterocycle, $(C_1-C_8)$haloalkyl and $(C_1-C_8)$heteroalkyl;

each $Z^1$ is independently selected from $(C_2-C_8)$alkyl, $(C_2-C_8)$alkenyl, $(C_2-C_8)$alkynyl, $(C_3-C_7)$carbocycle, aryl, heteroaryl, heterocycle and $-OR_{n1}$, wherein any $(C_3-C_7)$ carbocycle, aryl, heteroaryl and heterocycle of $Z^1$ is optionally substituted with one or more (e.g. 1, 2, 3, 4 or 5) $Z^{1a}$ or $Z^{1b}$ groups and wherein any $(C_1-C_8)$alkyl, $(C_2-C_8)$alkenyl and $(C_2-C_8)$alkynyl of $Z^1$ is optionally substituted with one or more (e.g. 1, 2, 3, 4 or 5) $Z^{1a}$ groups;

each $Z^{1a}$ is independently selected from $(C_3-C_7)$carbocycle, aryl, heteroaryl, heterocycle, halogen, $-CN$, $-OR_{n2}$, $-OC(O)R_{p2}$, $-OC(O)NR_{q2}R_{r2}$, $-SR_{n2}$, $-S(O)R_{p2}$, $-S(O)_2OH$, $-S(O)_2R_{p2}$, $-S(O)_2NR_{q2}R_{r2}$, $-NR_{q2}R_{r2}$, $-NR_{n2}COR_{p2}$, $-NR_{n2}CO_2R_{p2}$, $-NR_{n2}CONR_{q2}R_{r2}$, $-NR_{n2}S(O)_2R_{p2}$, $-NR_{n2}S(O)_2OR_{p2}$, $-NR_{n2}S(O)_2NR_{q2}R_{r2}$, $NO_2$, $-C(O)R_{n2}$, $-C(O)OR_{n2}$, $-C(O)NR_{q2}R_{r2}$ and $-S(O)_2NR_{n2}COR_{p2}$, wherein any $(C_3-C_7)$carbocycle, aryl, heteroaryl and heterocycle of $Z^{1a}$ is optionally substituted with one or more (e.g. 1, 2, 3, 4 or 5) $Z^{1c}$ or $Z^{1d}$ groups;

each $Z^{1b}$ is independently selected from $(C_1-C_8)$alkyl, $(C_2-C_8)$alkenyl and $(C_2-C_8)$alkynyl, wherein any $(C_1-C_8)$ alkyl, $(C_2-C_8)$alkenyl and $(C_2-C_8)$alkynyl of $Z^{1b}$ is optionally substituted with one or more (e.g. 1, 2, 3, 4 or 5) $Z^{1c}$ groups;

each $Z^{1c}$ is independently selected from $(C_3-C_7)$carbocycle, aryl, heteroaryl, heterocycle, halogen, $-CN$, $-OR_{n3}$, $-OC(O)R_{p3}$, $-OC(O)NR_{q3}R_{r3}$, $-SR_{n3}$, $-S(O)R_{p3}$, $-S(O)_2OH$, $-S(O)_2R_{p3}$, $-S(O)_2NR_{q3}R_{r3}$, $-NR_{q3}R_{r3}$, $-NR_{n3}COR_{p3}$, $-NR_{n3}CO_2R_{p3}$, $-NR_{n3}CONR_{q3}R_{r3}$, $-NR_{n3}S(O)_2R_{p3}$, $-NR_{n3}S(O)_2OR_{p3}$, $-NR_{n3}S(O)_2NR_{q3}R_{r3}$, $NO_2$, $-C(O)R_{n3}$, $-C(O)OR_{n3}$, $-C(O)NR_{q3}R_{r3}$, haloaryl, haloheteroaryl, haloheterocycle and $(C_1-C_8)$heteroalkyl;

each $Z^{1d}$ is independently selected from $(C_1-C_8)$alkyl, $(C_2-C_8)$alkenyl, $(C_2-C_8)$alkynyl and $(C_1-C_8)$haloalkyl;

each $R_{n1}$ is independently selected from $(C_1\text{-}C_8)$alkyl, $(C_2\text{-}C_8)$alkenyl, $(C_2\text{-}C_8)$alkynyl, $(C_3\text{-}C_7)$carbocycle, heterocycle, heteroaryl and aryl, wherein any $(C_3\text{-}C_7)$carbocycle, aryl, heteroaryl and heterocycle of $R_{n1}$ is optionally substituted with one or more (e.g. 1, 2, 3, 4 or 5) $Z^{1a}$ or $Z^{1b}$ groups, and wherein any $(C_1\text{-}C_8)$alkyl, $(C_2\text{-}C_8)$alkenyl and $(C_2\text{-}C_8)$alkynyl of $R_{n1}$ is optionally substituted with one or more (e.g. 1, 2, 3, 4 or 5) $Z^{1a}$ groups;

each $R_{n2}$ is independently selected from H, $(C_1\text{-}C_8)$alkyl, $(C_2\text{-}C_8)$alkenyl, $(C_2\text{-}C_8)$alkynyl, $(C_3\text{-}C_7)$carbocycle, heterocycle, heteroaryl and aryl, wherein any $(C_3\text{-}C_7)$carbocycle, aryl, heteroaryl and heterocycle of $R_{n2}$ is optionally substituted with one or more (e.g. 1, 2, 3, 4 or 5) $Z^{1c}$ or $Z^{1d}$ groups, and wherein any $(C_1\text{-}C_8)$alkyl, $(C_2\text{-}C_8)$alkenyl and $(C_2\text{-}C_8)$alkynyl of $R_{n2}$ is optionally substituted with one or more (e.g. 1, 2, 3, 4 or 5) $Z^{1c}$ groups;

each $R_{p2}$ is independently selected from $(C_1\text{-}C_8)$alkyl, $(C_2\text{-}C_8)$alkenyl, $(C_2\text{-}C_8)$alkynyl, $(C_3\text{-}C_7)$carbocycle, heterocycle, heteroaryl and aryl, wherein any $(C_3\text{-}C_7)$carbocycle, aryl, heteroaryl and heterocycle of $R_{p2}$ is optionally substituted with one or more (e.g. 1, 2, 3, 4 or 5) $Z^{1c}$ or $Z^{1a}$ groups, and wherein any $(C_1\text{-}C_8)$alkyl, $(C_2\text{-}C_8)$alkenyl and $(C_2\text{-}C_8)$alkynyl of $R_{p2}$ is optionally substituted with one or more (e.g. 1, 2, 3, 4 or 5) $Z^{1c}$ groups;

$R_{q2}$ and $R_{r2}$ are each independently selected from H, $(C_1\text{-}C_8)$alkyl, $(C_2\text{-}C_8)$alkenyl, $(C_2\text{-}C_8)$alkynyl, $(C_3\text{-}C_7)$carbocycle, heterocycle, heteroaryl and aryl, wherein any $(C_3\text{-}C_7)$carbocycle, aryl, heteroaryl and heterocycle of $R_{q2}$ or $R_{r2}$ is optionally substituted with one or more (e.g. 1, 2, 3, 4 or 5) $Z^{1c}$ or $Z^{1d}$ d groups, and wherein any $(C_1\text{-}C_8)$alkyl, $(C_2\text{-}C_8)$alkenyl and $(C_2\text{-}C_8)$alkynyl of $R_{q2}$ or $R_{r2}$ is optionally substituted with one or more (e.g. 1, 2, 3, 4 or 5) $Z^{1c}$ groups, or $R_{q2}$ and $R_{r2}$ together with the nitrogen to which they are attached form a 5, 6 or 7-membered heterocycle, wherein the 5, 6 or 7-membered heterocycle is optionally substituted with one or more (e.g. 1, 2, 3, 4 or 5) $Z^{1c}$ or $Z^{1d}$ groups;

each $R_{n3}$ is independently selected from H, $(C_1\text{-}C_8)$alkyl, $(C_2\text{-}C_8)$alkenyl, $(C_2\text{-}C_8)$alkynyl, $(C_3\text{-}C_7)$carbocycle, heterocycle, heteroaryl, aryl, haloaryl, haloheteroaryl, haloheterocycle, $(C_1\text{-}C_8)$haloalkyl and $(C_1\text{-}C_8)$heteroalkyl;

each $R_{p3}$ is independently selected from $(C_1\text{-}C_8)$alkyl, $(C_2\text{-}C_8)$alkenyl, $(C_2\text{-}C_8)$alkynyl, $(C_3\text{-}C_7)$carbocycle, heterocycle, heteroaryl, aryl, haloaryl, haloheteroaryl, haloheterocycle, $(C_1\text{-}C_8)$haloalkyl and $(C_1\text{-}C_8)$heteroalkyl;

$R_{q3}$ and $R_{r3}$ are each independently selected from H, $(C_1\text{-}C_8)$alkyl, $(C_2\text{-}C_8)$alkenyl, $(C_2\text{-}C_8)$alkynyl, $(C_3\text{-}C_7)$carbocycle, heterocycle, heteroaryl, aryl, haloaryl, haloheteroaryl, haloheterocycle, $(C_1\text{-}C_8)$haloalkyl and $(C_1\text{-}C_8)$heteroalkyl, or $R_{q3}$ and $R_{r3}$ together with the nitrogen to which they are attached form a 5, 6 or 7-membered heterocycle;

each $Z^2$ is independently selected from $(C_1\text{-}C_6)$alkyl, $(C_1\text{-}C_6)$haloalkyl, $(C_3\text{-}C_7)$carbocycle, halogen, CN, OH and $-O(C_1\text{-}C_6)$alkyl;

each $Z^3$ is independently selected from $(C_1\text{-}C_8)$alkyl, $(C_2\text{-}C_8)$alkenyl, $(C_2\text{-}C_8)$alkynyl, $(C_3\text{-}C_7)$carbocycle, aryl, heteroaryl, heterocycle, halogen, $-CN$, $-OR_{n4}$, $-OC(O)R_{p4}$, $-OC(O)NR_{q4}R_{r4}$, $-SR_{n4}$, $-S(O)R_{p4}$, $-S(O)_2OH$, $-S(O)_2R_{p4}$, $-S(O)_2NR_{q4}R_{r4}$, $-NR_{q4}R_{r4}$, $-NR_{n4}COR_{p4}$, $-NR_{n4}CO_2R_{p4}$, $-NR_{n4}CONR_{q4}R_{r4}$, $-NR_{n4}S(O)_2R_{p4}$, $-NR_{n4}S(O)_2OR_{p4}$, $-NR_{n4}S(O)_2NR_{q4}R_{r4}$, $NO_2$, $-C(O)R_{n4}$, $-C(O)OR_{n4}$, $-C(O)NR_{q4}R_{r4}$ and $-B(OR_{q4})(OR_{r4})$ wherein any $(C_3\text{-}C_7)$carbocycle, aryl, heteroaryl and heterocycle of $Z^3$ is optionally substituted with one or more (e.g. 1, 2, 3, 4 or 5) $Z^{3a}$ or $Z^{3b}$ groups, and wherein any $(C_1\text{-}C_8)$alkyl, $(C_2\text{-}C_8)$alkenyl and $(C_2\text{-}C_8)$alkynyl of $Z^3$ is optionally substituted with one or more (e.g. 1, 2, 3, 4 or 5) $Z^{3a}$ groups;

each $Z^{3a}$ is independently selected from $(C_3\text{-}C_7)$carbocycle, aryl, heteroaryl, heterocycle, halogen, $-CN$, $-OR_{n5}$, $-OC(O)R_{p5}$, $-OC(O)NR_{q5}R_{r5}$, $-SR_{n5}$, $-S(O)R_{p5}$, $-S(O)_2OH$, $-S(O)_2R_{p5}$, $-S(O)_2NR_{q5}R_{r5}$, $-NR_{q5}R_{r5}$, $-NR_{n5}COR_{p5}$, $-NR_{n5}CO_2R_{p5}$, $-NR_{n5}CONR_{q5}R_{r5}$, $-NR_{n5}S(O)_2R_{p5}$, $-NR_{n5}S(O)_2OR_{p5}$, $-NR_{n5}S(O)_2NR_{q5}R_{r5}$, $NO_2$, $-C(O)R_{n5}$, $-C(O)OR_{n5}$, and $-C(O)NR_{q5}R_{r5}$, wherein any $(C_3\text{-}C_7)$carbocycle, aryl, heteroaryl and heterocycle of $Z^{3a}$ is optionally substituted with one or more (e.g. 1, 2, 3, 4 or 5) $Z^{3c}$ or $Z^{3d}$ groups;

each $Z^{3b}$ is independently selected from $(C_1\text{-}C_8)$alkyl, $(C_2\text{-}C_8)$alkenyl and $(C_2\text{-}C_8)$alkynyl, wherein any $(C_1\text{-}C_8)$alkyl, $(C_2\text{-}C_8)$alkenyl and $(C_2\text{-}C_8)$alkynyl of $Z^{3b}$ is optionally substituted with one or more (e.g. 1, 2, 3, 4 or 5) $Z^{3c}$ groups;

each $Z^{3c}$ is independently selected from $(C_3\text{-}C_7)$carbocycle, aryl, heteroaryl, heterocycle, halogen, $-CN$, $-OR_{n6}$, $-OC(O)R_{p6}$, $-OC(O)NR_{q6}R_{r6}$, $-SR_{n6}$, $-S(O)R_{p6}$, $-S(O)_2OH$, $-S(O)_2R_{p6}$, $-S(O)_2NR_{q6}R_{r6}$, $-NR_{q6}R_{r6}$, $-NR_{n6}COR_{p6}$, $-NR_{n6}CO_2R_{p6}$, $-NR_{n6}CONR_{q6}R_{r6}$, $-NR_{n6}S(O)_2R_{p6}$, $-NR_{n6}S(O)_2OR_{p6}$, $-NR_{n6}S(O)_2NR_{q6}R_{r6}$, $NO_2$, $-C(O)R_{n6}$, $-C(O)OR_{n6}$, $-C(O)NR_{q6}R_{r6}$, haloaryl, haloheteroaryl, haloheterocycle and $(C_1\text{-}C_8)$heteroalkyl;

each $Z^{3d}$ is independently selected from $(C_1\text{-}C_8)$alkyl, $(C_2\text{-}C_8)$alkenyl, $(C_2\text{-}C_8)$alkynyl, and $(C_1\text{-}C_8)$haloalkyl;

each $R_{n4}$ is independently selected from H, $(C_1\text{-}C_8)$alkyl, $(C_2\text{-}C_8)$alkenyl, $(C_2\text{-}C_8)$alkynyl, $(C_3\text{-}C_7)$carbocycle, heterocycle, heteroaryl and aryl, wherein any $(C_3\text{-}C_7)$carbocycle, aryl, heteroaryl and heterocycle of $R_{n4}$ is optionally substituted with one or more (e.g. 1, 2, 3, 4 or 5) $Z^{3a}$ or $Z^{3b}$ groups, and wherein any $(C_1\text{-}C_8)$alkyl, $(C_2\text{-}C_8)$alkenyl and $(C_2\text{-}C_8)$alkynyl of $R_{n4}$ is optionally substituted with one or more (e.g. 1, 2, 3, 4 or 5) $Z^{3a}$ groups;

each $R_{p4}$ is independently selected from $(C_1\text{-}C_8)$alkyl, $(C_2\text{-}C_8)$alkenyl, $(C_2\text{-}C_8)$alkynyl, $(C_3\text{-}C_7)$carbocycle, heterocycle, heteroaryl and aryl, wherein any $(C_3\text{-}C_7)$carbocycle, aryl, heteroaryl, or heterocycle of $R_{p4}$ is optionally substituted with one or more (e.g. 1, 2, 3, 4 or 5) $Z^{3a}$ or $Z^{3b}$ groups, and wherein any $(C_1\text{-}C_8)$alkyl, $(C_2\text{-}C_8)$alkenyl or $(C_2\text{-}C_8)$alkynyl of $R_{p4}$ is optionally substituted with one or more (e.g. 1, 2, 3, 4 or 5) $Z^{3a}$ groups;

$R_{q4}$ and $R_{r4}$ are each independently selected from H, $(C_1\text{-}C_8)$alkyl, $(C_2\text{-}C_8)$alkenyl, $(C_2\text{-}C_8)$alkynyl, $(C_3\text{-}C_7)$carbocycle, heterocycle, heteroaryl and aryl, wherein any $(C_3\text{-}C_7)$carbocycle, aryl, heteroaryl and heterocycle of $R_{q4}$ or $R_{r4}$ is optionally substituted with one or more (e.g. 1, 2, 3, 4 or 5) $Z^{3a}$ or $Z^{3b}$ groups, and wherein any $(C_1\text{-}C_8)$alkyl, $(C_2\text{-}C_8)$alkenyl and $(C_2\text{-}C_8)$alkynyl of $R_{q4}$ or $R_{r4}$ is optionally substituted with one or more (e.g. 1, 2, 3, 4 or 5) $Z^{3a}$ groups, or $R_{q4}$ and $R_{r4}$ together with the nitrogen to which they are attached form a 5, 6 or 7-membered heterocycle, wherein the 5, 6 or 7-membered heterocycle is optionally substituted with one or more (e.g. 1, 2, 3, 4 or 5) $Z^{3a}$ or $Z^{3b}$ groups;

each $R_{n5}$ is independently selected from H, $(C_1\text{-}C_8)$alkyl, $(C_2\text{-}C_8)$alkenyl, $(C_2\text{-}C_8)$alkynyl, $(C_3\text{-}C_7)$carbocycle, heterocycle, heteroaryl and aryl, wherein any $(C_3\text{-}C_7)$carbocycle, aryl, heteroaryl and heterocycle of $R_{n5}$ is optionally substituted with one or more (e.g. 1, 2, 3, 4 or 5) $Z^{3c}$ or $Z^{3d}$ groups, and wherein any $(C_1\text{-}C_8)$alkyl, $(C_2\text{-}C_8)$alkenyl and $(C_2\text{-}C_8)$alkynyl of $R_{n5}$ is optionally substituted with one or more (e.g. 1, 2, 3, 4 or 5) $Z^{3c}$ groups;

each $R_{p5}$ is independently selected from $(C_1\text{-}C_8)$alkyl, $(C_2\text{-}C_8)$alkenyl, $(C_2\text{-}C_8)$alkynyl, $(C_3\text{-}C_7)$carbocycle, heterocycle, heteroaryl and aryl, wherein any $(C_3-C_7)$carbocycle, aryl, heteroaryl and heterocycle of $R_{p5}$ is optionally substituted with one or more (e.g. 1, 2, 3, 4 or 5) $Z^{3c}$ or $Z^{3d}$ groups, and wherein any $(C_1-C_8)$alkyl, $(C_2-C_8)$alkenyl and $(C_2-C_8)$alkynyl of $R_{p5}$ is optionally substituted with one or more (e.g. 1, 2, 3, 4 or 5) $Z^{3c}$ groups;

$R_{q5}$ and $R_{r5}$ are each independently selected from H, $(C_1-C_8)$alkyl, $(C_2-C_8)$alkenyl, $(C_2-C_8)$alkynyl, $(C_3-C_7)$carbocycle, heterocycle, heteroaryl and aryl, wherein any $(C_3-C_7)$carbocycle, aryl, heteroaryl and heterocycle of $R_{q5}$ or $R_{r5}$ is optionally substituted with one or more (e.g. 1, 2, 3, 4 or 5) $Z^{3c}$ or $Z^{3d}$ groups, and wherein any $(C_1-C_8)$alkyl, $(C_2-C_8)$alkenyl and $(C_2-C_8)$alkynyl of $R_{q5}$ or $R_{r5}$ is optionally substituted with one or more (e.g. 1, 2, 3, 4 or 5) $Z^{3c}$ groups, or $R_{q5}$ and $R_{r5}$ together with the nitrogen to which they are attached form a 5, 6 or 7-membered heterocycle, wherein the 5, 6 or 7-membered heterocycle is optionally substituted with one or more (e.g. 1, 2, 3, 4 or 5) $Z^{3c}$ or $Z^{3d}$ groups;

each $R_{n6}$ is independently selected from H, $(C_1-C_8)$alkyl, $(C_2-C_8)$alkenyl, $(C_2-C_8)$alkynyl, $(C_3-C_7)$carbocycle, heterocycle, heteroaryl, aryl, haloaryl, haloheteroaryl, haloheterocycle, $(C_1-C_8)$haloalkyl and $(C_1-C_8)$heteroalkyl;

each $R_{p6}$ is independently selected from $(C_1-C_8)$alkyl, $(C_2-C_8)$alkenyl, $(C_2-C_8)$alkynyl, $(C_3-C_7)$carbocycle, heterocycle, heteroaryl, aryl, haloaryl, haloheteroaryl, haloheterocycle, $(C_1-C_8)$haloalkyl and $(C_1-C_8)$heteroalkyl;

$R_{q6}$ and $R_{r6}$ are each independently selected from H, $(C_1-C_8)$alkyl, $(C_2-C_8)$alkenyl, $(C_2-C_8)$alkynyl, $(C_3-C_7)$carbocycle, heterocycle, heteroaryl, aryl, haloaryl, haloheteroaryl, haloheterocycle, $(C_1-C_8)$haloalkyl and $(C_1-C_8)$heteroalkyl, or $R_{q6}$ and $R_{r6}$ together with the nitrogen to which they are attached form a 5, 6 or 7-membered heterocycle;

each $Z^4$ is independently selected from $(C_1-C_8)$alkyl, $(C_2-C_8)$alkenyl, $(C_2-C_8)$alkynyl, $(C_3-C_7)$carbocycle, aryl, heteroaryl, heterocycle, halogen, —CN, —$OR_{n8}$, —OC(O)$R_{p8}$, —OC(O)$NR_{q8}R_{r8}$, —$SR_{n8}$, —S(O)$R_{p8}$, —S(O)$_2$OH, —S(O)$_2R_{p8}$, —S(O)$_2NR_{q8}R_{r8}$, —$NR_{q8}R_{r8}$, —$NR_{n8}COR_{p8}$, —$NR_{n8}CO_2R_{p8}$, —$NR_{n8}CONR_{q8}R_{r8}$, —$NR_{n8}S(O)_2R_{p8}$, —$NR_{n8}S(O)_2OR_{p8}$, —$NR_{n8}S(O)_2$ $NR_{q8}R_{r8}$, $NO_2$, —C(O)$R_{n8}$, —C(O)$OR_{n8}$, and —C(O)$NR_{q8}R_{r8}$, wherein any $(C_3-C_7)$carbocycle, aryl, heteroaryl and heterocycle of $Z^4$ is optionally substituted with one or more (e.g. 1, 2, 3, 4 or 5) $Z^{4c}$ or $Z^{4d}$ groups and wherein any $(C_1-C_8)$alkyl, $(C_2-C_8)$alkenyl and $(C_2-C_8)$alkynyl of $Z^4$ is optionally substituted with one or more (e.g. 1, 2, 3, 4 or 5) $Z^{4c}$ groups;

each $Z^{4c}$ is independently selected from of $(C_3-C_7)$carbocycle, aryl, heteroaryl, heterocycle, halogen, —CN, —$OR_{n9}$, —OC(O)$R_{p9}$, —OC(O)$NR_{q9}R_{r9}$, —$SR_{n9}$, —S(O)$R_{p9}$, —S(O)$_2$OH, —S(O)$_2R_{p9}$, —S(O)$_2NR_{q9}R_{r9}$, —$NR_{q9}R_{r9}$, —$NR_{n9}COR_{p9}$, —$NR_{n9}CO_2R_{p9}$, —$NR_{n9}CONR_{q9}R_{r9}$, —$NR_{n9}S(O)_2R_{p9}$, —$NR_{n9}S(O)_2OR_{p9}$, —$NR_{n9}S(O)_2$ $NR_{q9}R_{r9}$, $NO_2$, —C(O)$R_{n9}$, —C(O)$OR_{n9}$, —C(O)$NR_{q9}R_{r9}$, haloaryl, haloheteroaryl, haloheterocycle and $(C_1-C_8)$heteroalkyl;

each $Z^{4d}$ is independently selected from of $(C_1-C_8)$alkyl, $(C_2-C_8)$alkenyl, $(C_2-C_8)$alkynyl and $(C_1-C_8)$haloalkyl;

each $R_{n8}$ is independently selected from H, $(C_1-C_8)$alkyl, $(C_2-C_8)$alkenyl, $(C_2-C_8)$alkynyl, $(C_3-C_7)$carbocycle, heterocycle, heteroaryl and aryl, wherein any $(C_3-C_7)$carbocycle, aryl, heteroaryl and heterocycle of $R_{n8}$ is optionally substituted with one or more (e.g. 1, 2, 3, 4 or 5) $Z^{4c}$ or $Z^{4d}$ groups, and wherein any $(C_1-C_8)$alkyl, $(C_2-C_8)$alkenyl or $(C_2-C_8)$alkynyl of $R_{n8}$ is optionally substituted with one or more (e.g. 1, 2, 3, 4 or 5) $Z^{4c}$ groups;

each $R_{p8}$ is independently selected from $(C_1-C_8)$alkyl, $(C_1-C_6)$haloalkyl, $(C_2-C_8)$alkenyl, $(C_2-C_8)$alkynyl, $(C_3-C_7)$carbocycle, heterocycle, heteroaryl and aryl, wherein any $(C_3-C_7)$carbocycle, aryl, heteroaryl and heterocycle of $R_{p8}$ is optionally substituted with one or more (e.g. 1, 2, 3, 4 or 5) $Z^{4c}$ or $Z^{4d}$ groups, and wherein any $(C_1-C_8)$alkyl, $(C_2-C_8)$alkenyl and $(C_2-C_8)$alkynyl of $R_{p8}$ is optionally substituted with one or more (e.g. 1, 2, 3, 4 or 5) $Z^{4c}$ groups;

$R_{q8}$ and $R_{r8}$ are each independently selected from H, $(C_1-C_8)$alkyl, $(C_2-C_8)$alkenyl, $(C_2-C_8)$alkynyl, $(C_3-C_7)$carbocycle, heterocycle, heteroaryl and aryl, wherein any $(C_3-C_7)$carbocycle, aryl, heteroaryl and heterocycle of $R_{q8}$ or $R_{r8}$ is optionally substituted with one or more (e.g. 1, 2, 3, 4 or 5) $Z^{4c}$ or $Z^{4d}$ groups, and wherein any $(C_1-C_8)$alkyl, $(C_2-C_8)$alkenyl and $(C_2-C_8)$alkynyl of $R_{q8}$ or $R_{r8}$ is optionally substituted with one or more (e.g. 1, 2, 3, 4 or 5) $Z^{4c}$ groups, or $R_{q8}$ and $R_{r8}$ together with the nitrogen to which they are attached form a 5, 6 or 7-membered heterocycle, wherein the 5, 6 or 7-membered heterocycle is optionally substituted with one or more (e.g. 1, 2, 3, 4 or 5) $Z^{4c}$ or $Z^{4d}$ groups;

each $R_{n9}$ is independently selected from H, $(C_1-C_8)$alkyl, $(C_2-C_8)$alkenyl, $(C_2-C_8)$alkynyl, $(C_3-C_7)$carbocycle, heterocycle, heteroaryl, aryl, haloaryl, haloheteroaryl, haloheterocycle, $(C_1-C_8)$haloalkyl and $(C_1-C_8)$heteroalkyl;

each $R_{p9}$ is independently selected from $(C_1-C_8)$alkyl, $(C_2-C_8)$alkenyl, $(C_2-C_8)$alkynyl, $(C_3-C_7)$carbocycle, heterocycle, heteroaryl, aryl, haloaryl, haloheteroaryl, haloheterocycle, $(C_1-C_8)$haloalkyl and $(C_1-C_8)$heteroalkyl; and $R_{q9}$ and $R_{r9}$ are each independently selected from H, $(C_1-C_8)$alkyl, $(C_2-C_8)$alkenyl, $(C_2-C_8)$alkynyl, $(C_3-C_7)$carbocycle, heterocycle, heteroaryl, aryl, haloaryl, haloheteroaryl, haloheterocycle, $(C_1-C_8)$haloalkyl and $(C_1-C_8)$heteroalkyl; or $R_{q9}$ and $R_{r9}$ together with the nitrogen to which they are attached form a 5, 6 or 7-membered heterocycle;

or a salt thereof.

The invention also provides a pharmaceutical composition comprising a compound of formula I or a pharmaceutically acceptable salt thereof, in combination with a pharmaceutically acceptable carrier.

The invention also provides a method for treating (e.g. preventing, mediating or inhibiting) a Retroviridae viral infection (e.g. an HIV viral infection) in a mammal (e.g. a human), comprising administering a compound of formula I, or a pharmaceutically acceptable salt thereof, to the mammal.

The invention also provides a method for treating (e.g. preventing, mediating or inhibiting) the proliferation of the HIV virus, treating AIDS or delaying the onset of AIDS or ARC symptoms in a mammal (e.g. a human), comprising administering a compound of formula I, or a pharmaceutically acceptable salt thereof, to the mammal.

The invention also provides a method for treating (e.g. preventing, mediating or inhibiting) an HIV infection in a mammal (e.g. a human), comprising administering a compound of formula I, or a pharmaceutically acceptable salt thereof, to the mammal.

The invention also provides a method for treating an HIV infection in a mammal (e.g. a human), comprising administering to the mammal in need thereof a therapeutically effective amount of a compound of formula I, or a pharmaceutically acceptable salt thereof, in combination with a therapeutically effective amount of one or more additional therapeutic agents selected from the group consisting HIV protease inhibiting compounds, HIV non-nucleoside inhibitors of reverse transcriptase, HIV nucleoside inhibitors of reverse transcriptase, HIV nucleotide inhibitors of reverse transcriptase, HIV integrase inhibitors, gp41 inhibitors, CXCR4 inhibitors, gp120 inhibitors, CCR5 inhibitors, capsid polymerization inhibitors, and other drugs for treating HIV, and combinations thereof.

The invention also provides a compound of formula I, or a pharmaceutically acceptable salt thereof for use in medical therapy (e.g. for use in treating (e.g. preventing, mediating or inhibiting) a Retroviridae viral infection (e.g. an HIV viral infection) or the proliferation of the HIV virus or AIDS or delaying the onset of AIDS or ARC symptoms in a mammal (e.g. a human)).

The invention also provides a compound of formula I, or a pharmaceutically acceptable salt thereof for use in the manufacture of a medicament for treating (e.g. preventing, mediating or inhibiting) a Retroviridae viral infection (e.g. an HIV viral infection) or the proliferation of the HIV virus or AIDS or delaying the onset of AIDS or ARC symptoms in a mammal (e.g. a human).

The invention also provides a compound of formula I, or a pharmaceutically acceptable salt thereof, for use in the prophylactic or therapeutic treatment (e.g. prevention, mediation or inhibition) of the proliferation of a Retroviridae virus, an HIV virus or AIDS or for use in the therapeutic treatment of delaying the onset of AIDS or ARC symptoms.

The invention also provides a compound of formula I, or a pharmaceutically acceptable salt thereof, for use in the prophylactic or therapeutic treatment (e.g. prevention, mediation or inhibition) of a Retroviridae virus infection or an HIV virus infection.

The invention also provides the use of a compound of formula I, or a pharmaceutically acceptable salt thereof, for the manufacture of a medicament for treating (e.g. preventing, mediating or inhibiting) a Retroviridae virus infection or an HIV virus infection.

The invention also provides processes and intermediates disclosed herein that are useful for preparing compounds of formula I or salts thereof.

DETAILED DESCRIPTION OF THE INVENTION

Definitions

Unless stated otherwise, the following terms and phrases as used herein are intended to have the following meanings:

When trade names are used herein, applicants intend to independently include the tradename product and the active pharmaceutical ingredient(s) of the tradename product.

"Alkyl" is hydrocarbon containing primary, secondary or tertiary atoms. For example, an alkyl group can have 1 to 20 carbon atoms (i.e, ($C_1$-$C_{20}$)alkyl), 1 to 10 carbon atoms (i.e., ($C_1$-$C_{10}$)alkyl), 1 to 8 carbon atoms (i.e., ($C_1$-$C_8$)alkyl) or 1 to 6 carbon atoms (i.e., ($C_1$-$C_6$) alkyl). Examples of suitable alkyl groups include, but are not limited to, methyl (Me, —$CH_3$), ethyl (Et, —$CH_2CH_3$), 1-propyl (n-Pr, n-propyl, —$CH_2CH_2CH_3$), 2-propyl (i-Pr, i-propyl, —$CH(CH_3)_2$), 1-butyl (n-Bu, n-butyl, —$CH_2CH_2CH_2CH_3$), 2-methyl-1-propyl (i-Bu, i-butyl, —$CH_2CH(CH_3)_2$), 2-butyl (s-Bu, s-butyl, —$CH(CH_3)CH_2CH_3$), 2-methyl-2-propyl (t-Bu, t-butyl, —$C(CH_3)_3$), 1-pentyl (n-pentyl, —$CH_2CH_2CH_2CH_2CH_3$), 2-pentyl (—$CH(CH_3)CH_2CH_2CH_3$), 3-pentyl (—$CH(CH_2CH_3)_2$), 2-methyl-2-butyl (—$C(CH_3)_2CH_2CH_3$), 3-methyl-2-butyl (—$CH(CH_3)CH(CH_3)_2$), 3-methyl-1-butyl (—$CH_2CH_2CH(CH_3)_2$), 2-methyl-1-butyl (—$CH_2CH(CH_3)CH_2CH_3$), 1-hexyl (—$CH_2CH_2CH_2CH_2CH_2CH_3$), 2-hexyl (—$CH(CH_3)CH_2CH_2CH_2CH_3$), 3-hexyl (—$CH(CH_2CH_3)(CH_2CH_2CH_3)$), 2-methyl-2-pentyl (—$C(CH_3)_2CH_2CH_2CH_3$), 3-methyl-2-pentyl (—$CH(CH_3)CH(CH_3)CH_2CH_3$), 4-methyl-2-pentyl (—$CH(CH_3)CH_2CH(CH_3)_2$), 3-methyl-3-pentyl (—$C(CH_3)(CH_2CH_3)_2$), 2-methyl-3-pentyl (—$CH(CH_2CH_3)CH(CH_3)_2$), 2,3-dimethyl-2-butyl (—$C(CH_3)_2CH(CH_3)_2$), 3,3-dimethyl-2-butyl (—$CH(CH_3)C(CH_3)_3$), and octyl (—$(CH_2)_7CH_3$). "Alkyl" also refers to a saturated, branched or straight chain hydrocarbon radical having two monovalent radical centers derived by the removal of two hydrogen atoms from the same or two different carbon atoms of a parent alkane. For example, an alkyl group can have 1 to 10 carbon atoms (i.e., ($C_1$-$C_{10}$) alkyl), or 1 to 6 carbon atoms (i.e., ($C_1$-$C_6$)alkyl) or 1-3 carbon atoms (i.e., ($C_1$-$C_3$)alkyl). Typical alkyl radicals include, but are not limited to, methylene (—$CH_2$—), 1,1-ethyl (—$CH(CH_3)$—), 1,2-ethyl (—$CH_2CH_2$—), 1,1-propyl (—$CH(CH_2CH_3)$—), 1,2-propyl (—$CH_2CH(CH_3)$—), 1,3-propyl (—$CH_2CH_2CH_2$—), 1,4-butyl (—$CH_2CH_2CH_2CH_2$—), and the like.

"Alkenyl" is a straight or branched hydrocarbon containing primary, secondary or tertiary carbon atoms with at least one site of unsaturation, i.e. a carbon-carbon, $sp^2$ double bond. For example, an alkenyl group can have 2 to 20 carbon atoms (i.e., $C_2$-$C_{20}$ alkenyl), 2 to 8 carbon atoms (i.e., $C_2$-$C_8$ alkenyl), or 2 to 6 carbon atoms (i.e., $C_2$-$C_6$ alkenyl). Examples of suitable alkenyl groups include, but are not limited to, ethylene or vinyl (—CH═$CH_2$), allyl (—$CH_2$CH═$CH_2$) and 5-hexenyl (—$CH_2CH_2CH_2CH_2$CH═$CH_2$).

"Alkynyl" is a straight or branched hydrocarbon containing primary, secondary or tertiary carbon atoms with at least one site of unsaturation, i.e. a carbon-carbon, sp triple bond. For example, an alkynyl group can have 2 to 20 carbon atoms (i.e., $C_2$-$C_{20}$ alkynyl), 2 to 8 carbon atoms (i.e., $C_2$-$C_8$ alkynyl), or 2 to 6 carbon atoms (i.e., $C_2$-$C_6$ alkynyl). Examples of suitable alkynyl groups include, but are not limited to, acetylenic (—C≡CH), propargyl (—$CH_2$C≡CH), and the like.

The term "halo" or "halogen" as used herein refers to fluoro, chloro, bromo and iodo.

The term "haloalkyl" as used herein refers to an alkyl as defined herein, wherein one or more hydrogen atoms are each replaced by a halo substituent. For example, a ($C_1$-$C_6$) haloalkyl is a ($C_1$-$C_6$)alkyl wherein one or more of the hydrogen atoms have been replaced by a halo substituent. Such a range includes one halo substituent on the alkyl group to complete halogenation of the alkyl group.

The term "heteroalkyl" as used herein refers to an alkyl as defined herein, wherein one or more of the carbon atoms of the alkyl are replaced by an O, S, or $NR_q$, (or if the carbon atom being replaced is a terminal carbon with an OH, SH or $NR_{q2}$) wherein each $R_q$ is independently H or ($C_1$-$C_6$)alkyl.

The term "aryl" as used herein refers to a single aromatic ring or a multiple condensed ring system. For example, an aryl group can have 6 to 20 carbon atoms, 6 to 14 carbon atoms, or 6 to 12 carbon atoms. Aryl includes a phenyl radical. Aryl also includes multiple condensed ring systems (e.g. ring systems comprising 2, 3 or 4 rings) having about 9 to 20 carbon atoms in which at least one ring is aromatic. Such multiple condensed ring systems may be optionally substituted with one or more (e.g. 1, 2 or 3) oxo groups on any carbocycle portion of the multiple condensed ring system. It is to be understood that the point of attachment of a multiple condensed ring system, as defined above, can be at any position of the ring system including an aryl or a carbocycle portion of the ring. Typical aryl groups include, but are not limited to, phenyl, indenyl, naphthyl, 1,2,3,4-tetrahydronaphthyl, anthracenyl, and the like.

"Arylalkyl" refers to an alkyl radical as defined herein in which one of the hydrogen atoms bonded to a carbon atom is replaced with an aryl radical as described herein (i.e., an aryl-alkyl-moiety). The alkyl group of the "arylalkyl" is typically 1 to 6 carbon atoms (i.e. aryl($C_1$-$C_6$)alkyl). Arylalkyl groups include, but are not limited to, benzyl, 2-phenylethan-1-yl, 1-phenylpropan-1-yl, naphthylmethyl, 2-naphthylethan-1-yl and the like.

The term "heteroaryl" as used herein refers to a single aromatic ring or a multiple condensed ring system. The term includes single aromatic rings of from about 1 to 6 carbon atoms and about 1-4 heteroatoms selected from the group consisting of oxygen, nitrogen and sulfur in the rings. The sulfur and nitrogen atoms may also be present in an oxidized form provided the ring is aromatic. Such rings include but are not limited to pyridyl, pyrimidinyl, oxazolyl or furyl. The term also includes multiple condensed ring systems (e.g. ring systems comprising 2, 3 or 4 rings) wherein a heteroaryl group, as defined above, can be condensed with one or more heteroaryls (e.g. naphthyridinyl), heterocycles, (e.g. 1,2,3,4-tetrahydronaphthyridinyl), carbocycles (e.g. 5,6,7,8-tetrahydroquinolyl) or aryls (e.g. indazolyl) to form a multiple condensed ring system. Such multiple condensed ring systems may be optionally substituted with one or more (e.g. 1, 2, 3 or 4) oxo groups on the carbocycle or heterocycle portions of the condensed ring. It is to be understood that the point of attachment of a multiple condensed ring system (as defined above for a heteroaryl) can be at any position of the multiple condensed ring system including a heteroaryl, heterocycle, aryl or carbocycle portion of the multiple condensed ring system and at any suitable atom of the multiple condensed ring system including a carbon atom and heteroatom (e.g. a nitrogen). Exemplary heteroaryls include but are not limited to pyridyl, pyrrolyl, pyrazinyl, pyrimidinyl, pyridazinyl, pyrazolyl, thienyl, indolyl, imidazolyl, oxazolyl, thiazolyl, furyl, oxadiazolyl, thiadiazolyl, quinolyl, isoquinolyl, benzothiazolyl, benzoxazolyl, indazolyl, quinoxalyl, quinazolyl, 5,6,7,8-tetrahydroisoquinolinyl benzofuranyl, benzimidazolyl and thianaphthenyl.

The term "heterocyclyl" or "heterocycle" as used herein refers to a single saturated or partially unsaturated ring or a multiple condensed ring system. The term includes single saturated or partially unsaturated rings (e.g. 3, 4, 5, 6 or 7-membered rings) from about 1 to 6 carbon atoms and from about 1 to 3 heteroatoms selected from the group consisting of oxygen, nitrogen and sulfur in the ring. The ring may be substituted with one or more (e.g. 1, 2 or 3) oxo groups and the sulfur and nitrogen atoms may also be present in their oxidized forms. Such rings include but are not limited to azetidinyl, tetrahydrofuranyl or piperidinyl. The term "heterocycle" also includes multiple condensed ring systems (e.g. ring systems comprising 2, 3 or 4 rings) wherein a single heterocycle ring (as defined above) can be condensed with one or more heterocycles (e.g. decahydronapthyridinyl), carbocycles (e.g. decahydroquinolyl) or aryls. The rings of a multiple condensed ring system can be connected to each other via fused, spiro and bridged bonds when allowed by valency requirements. It is to be understood that the point of attachment of a multiple condensed ring system (as defined above for a heterocycle) can be at any position of the multiple condensed ring system including a heterocycle, aryl and carbocycle portion of the ring. It is also to be understood that the point of attachment for a heterocycle or heterocycle multiple condensed ring system can be at any suitable atom of the heterocycle or heterocycle multiple condensed ring system including a carbon atom and a heteroatom (e.g. a nitrogen). Exemplary heterocycles include, but are not limited to aziridinyl, azetidinyl, pyrrolidinyl, piperidinyl, homopiperidinyl, morpholinyl, thiomorpholinyl, piperazinyl, tetrahydrofuranyl, dihydrooxazolyl, tetrahydropyranyl, tetrahydrothiopyranyl, 1,2,3,4-tetrahydroquinolyl, benzoxazinyl, dihydrooxazolyl, chromanyl, 1,2-dihydropyridinyl, 2,3-dihydrobenzofuranyl, 1,3-benzodioxolyl and 1,4-benzodioxanyl.

"Heteroarylalkyl" refers to an alkyl radical as defined herein in which one of the hydrogen atoms bonded to a carbon atom is replaced with a heteroaryl radical as described herein (i.e., a heteroaryl-alkyl-moiety). The alkyl group of the "heteroarylalkyl" is typically 1 to 6 carbon atoms (i.e. heteroaryl($C_1$-$C_6$)alkyl). Heteroarylalkyl groups include, but are not limited to heteroaryl-$CH_2$—, heteroaryl-$CH(CH_3)$—, heteroaryl-$CH_2CH_2$—, 2-(heteroaryl)ethan-1-yl, and the like, wherein the "heteroaryl" portion includes any of the heteroaryl groups described above. One skilled in the art will also understand that the heteroaryl group can be attached to the alkyl portion of the heteroarylalkyl by means of a carbon-carbon bond or a carbon-heteroatom bond, with the proviso that the resulting group is chemically stable. Examples of heteroarylalkyls include by way of example and not limitation 5-membered sulfur, oxygen, and/or nitrogen containing heteroaryls such as thiazolylmethyl, 2-thiazolylethan-1-yl, imidazolylmethyl, oxazolylmethyl, thiadiazolylmethyl, etc., 6-membered sulfur, oxygen, and/or nitrogen containing heteroaryls such pyridinylmethyl, pyridizylmethyl, pyrimidylmethyl, pyrazinylmethyl, etc.

"Heterocyclylalkyl" refers to an alkyl radical as defined herein in which one of the hydrogen atoms bonded to a carbon atom is replaced with a heterocyclyl radical as described herein (i.e., a heterocyclyl-alkyl-moiety). The alkyl group of the "heterocyclylalkyl" is typically 1 to 6 carbon atoms (i.e. heterocyclyl($C_1$-$C_6$)alkyl). Typical heterocyclylalkyl groups include, but are not limited to heterocyclyl-$CH_2$—, heterocyclyl-$CH(CH_3)$—, heterocyclyl-$CH_2CH_2$—, 2-(heterocyclyl)ethan-1-yl, and the like, wherein the "heterocyclyl" portion includes any of the heterocyclyl groups described above. One skilled in the art will also understand that the heterocyclyl group can be attached to the alkyl portion of the heterocyclyl alkyl by means of a carbon-carbon bond or a carbon-heteroatom bond, with the proviso that the resulting group is chemically stable. Examples of heterocyclylalkyls include by way of example and not limitation 5-membered sulfur, oxygen, and/or nitrogen containing heterocycles such as tetrahydrofuranylmethyl and pyrroldinylmethyl, etc., and 6-membered sulfur, oxygen, and/or nitrogen containing heterocycles such as piperidinylmethyl, piperazinylmethyl, morpholinylmethyl, etc.

The term "carbocycle" or "carbocyclyl" refers to a single saturated (i.e., cycloalkyl) or a single partially unsaturated (e.g., cycloalkenyl, cycloalkadienyl, etc.) ring having 3 to 7 carbon atoms (i.e. ($C_3$-$C_7$)carbocycle). The term "carbocycle" or "carbocyclyl" also includes multiple condensed ring systems (e.g. ring systems comprising 2, 3 or 4 carbocyclic rings). Accordingly, carbocycle includes multicyclic carbocyles having 6 to 12 carbon atoms as a bicycle (e.g. bicyclo[3.1.0]hexane, bicyclo[2.1.1]hexane), and up to about 20 carbon atoms as a polycycle.

Multicyclic carbocyles can be connected to each other via a single carbon atom to form a spiro connection (e.g. spiropentane, spiro[4,5]decane, spiro[4.5]decane, etc), via two adjacent carbon atoms to form a fused connection such as a bicyclo [4,5], [5,5], [5,6] or [6,6] system, or 9 or 10 ring atoms arranged as a bicyclo [5,6] or [6,6] system (e.g. decahydronaphthalene, norsabinane, norcarane) or via two non-adjacent carbon atoms to form a bridged connection (e.g. norbornane, bicyclo[2.2.2]octane, etc). The "carbocycle" or "carbocyclyl" can also be optionally substituted with one or more (e.g. 1, 2 or 3) oxo groups. Non-limiting examples of monocyclic carbocycles include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl and 1-cyclohex-3-enyl.

"Carbocyclylalkyl" refers to an alkyl radical as defined herein in which one of the hydrogen atoms bonded to a carbon atom is replaced with a carbocyclyl radical as described herein (i.e., a carbocyclyl-alkyl-moiety). The alkyl group of the "carbocyclylalkyl" is typically 1 to 6 carbon atoms (i.e. carbocyclyl($C_1$-$C_6$)alkyl). Typical carbocyclyl alkyl groups include, but are not limited to carbocyclyl-$CH_2$—, carbocyclyl-$CH(CH_3)$—, carbocyclyl-$CH_2CH_2$—, 2-(carbocyclyl)ethan-1-yl, and the like, wherein the "carbocyclyl" portion includes any of the carbocyclyl groups described above.

The term "haloaryl" as used herein refers to an aryl as defined herein, wherein one or more hydrogen atoms of the aryl are each replaced independently by a halo substituent. Such a range includes one halo substituent on the aryl group to complete halogenation of the aryl group.

The term "haloheteroaryl" as used herein refers to a heteroaryl as defined herein, wherein one or more hydrogen atoms of the heteroaryl are each replaced independently by a halo substituent. Such a range includes one halo substituent on the heteroaryl group to complete halogenation of the heteroaryl group.

The term "haloheterocycle" as used herein refers to a heterocycle as defined herein, wherein one or more hydrogen atoms of the heterocycle are each replaced independently by a halo substituent. Such a range includes one halo substituent on the heterocycle group to complete halogenation of the heterocycle group.

One skilled in the art will recognize that substituents and other moieties of the compounds of formula I should be selected in order to provide a compound which is sufficiently stable to provide a pharmaceutically useful compound which can be formulated into an acceptably stable pharmaceutical composition. Compounds of formula I which have such stability are contemplated as falling within the scope of the present invention.

The modifier "about" used in connection with a quantity is inclusive of the stated value and has the meaning dictated by the context (e.g., includes the degree of error associated with measurement of the particular quantity).

The term "chiral" refers to molecules which have the property of non-superimposability of the mirror image partner, while the term "achiral" refers to molecules which are superimposable on their mirror image partner.

The term "stereoisomers" refers to compounds which have identical chemical constitution, but differ with regard to the arrangement of the atoms or groups in space.

"Diastereomer" refers to a stereoisomer with two or more centers or axes of chirality and whose molecules are not mirror images of one another. Diastereomers typically have different physical properties, e.g., melting points, boiling points, spectral properties, and reactivities. Mixtures of diastereomers may separate under high resolution analytical procedures such as electrophoresis and chromatography.

"Enantiomers" refer to two stereoisomers of a compound which are non-superimposable mirror images of one another.

It is to be understood that certain variables of formula I may have alternative orientations. For example, the —$OCR^{3a}R^{3b}$— variable for W may be oriented in a manner in which the $CR^{3a}R^{3b}$ group is connected to the carbonyl of formula I and the O is connected to the $R^1$ group of formula I and also in a manner in which the $CR^{3a}R^{3b}$ group is connected to the $R^1$ group of formula I and the O is connected to the carbonyl of formula I. In one embodiment of the invention the $CR^{3a}R^{3b}$ group is connected to the carbonyl of formula I and the O is connected to the $R^1$ group of formula I. In another embodiment of the invention the $CR^{3a}R^{3b}$ group is connected to the $R^1$ group of formula I and the O is connected to the carbonyl of formula I.

The term "treatment" or "treating," to the extent it relates to a disease or condition includes preventing the disease or condition from occurring, inhibiting the disease or condition, eliminating the disease or condition, and/or relieving one or more symptoms of the disease or condition.

Stereochemical definitions and conventions used herein generally follow S. P. Parker, Ed., *McGraw-Hill Dictionary of Chemical Terms* (1984) McGraw-Hill Book Company, New York; and Eliel, E. and Wilen, S., *Stereochemistry of Organic Compounds* (1994) John Wiley & Sons, Inc., New York. Many organic compounds exist in optically active forms, i.e., they have the ability to rotate the plane of plane-polarized light. In describing an optically active compound, the prefixes (D and L) or (R and S) are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

Protecting Groups

In the context of the present invention, protecting groups include prodrug moieties and chemical protecting groups.

"Protecting group" refers to a moiety of a compound that masks or alters the properties of a functional group or the properties of the compound as a whole. Chemical protecting groups and strategies for protection/deprotection are well known in the art. See e.g., *Protective Groups in Organic Chemistry*, Theodora W. Greene, John Wiley & Sons, Inc., New York, 1991. Protecting groups are often utilized to mask the reactivity of certain functional groups, to assist in the efficiency of desired chemical reactions, e.g., making and breaking chemical bonds in an ordered and planned fashion. Protection of functional groups of a compound alters other physical properties besides the reactivity of the protected functional group, such as the polarity, lipophilicity (hydrophobicity), and other properties which can be measured by common analytical tools. Chemically protected intermediates may themselves be biologically active or inactive.

Protected compounds may also exhibit altered, and in some cases, optimized properties in vitro and in vivo, such as passage through cellular membranes and resistance to enzymatic degradation or sequestration. In this role, protected compounds with intended therapeutic effects may be referred to as prodrugs. Another function of a protecting group is to convert the parental drug into a prodrug, whereby the parental drug is released upon conversion of the prodrug in vivo. Because active prodrugs may be absorbed more effectively than the parental drug, prodrugs may possess greater potency in vivo than the parental drug. Protecting groups are removed either in vitro, in the instance of chemical intermediates, or in vivo, in the case of prodrugs. With chemical intermediates, it is not particularly important that the resulting products after deprotection, e.g., alcohols, be physiologically acceptable, although in general it is more desirable if the products are pharmacologically innocuous.

Protecting groups are available, commonly known and used, and are optionally used to prevent side reactions with the protected group during synthetic procedures, i.e. routes or methods to prepare the compounds of the invention. For the most part the decision as to which groups to protect, when to do so, and the nature of the chemical protecting group "PG" will be dependent upon the chemistry of the reaction to be protected against (e.g., acidic, basic, oxidative, reductive or other conditions) and the intended direction of the synthesis. PGs do not need to be, and generally are not, the same if the compound is substituted with multiple PG. In general, PG will be used to protect functional groups such as carboxyl, hydroxyl, thio, or amino groups and to thus prevent side reactions or to otherwise facilitate the synthetic efficiency. The order of deprotection to yield free deprotected groups is dependent upon the intended direction of the synthesis and the reaction conditions to be encountered, and may occur in any order as determined by the artisan.

Various functional groups of the compounds of the invention may be protected. For example, protecting groups for —OH groups (whether hydroxyl, carboxylic acid, phosphonic acid, or other functions) include "ether- or ester-forming groups". Ether- or ester-forming groups are capable of functioning as chemical protecting groups in the synthetic schemes set forth herein. However, some hydroxyl and thio protecting groups are neither ether-nor ester-forming groups, as will be understood by those skilled in the art, and are included with amides, discussed below.

A very large number of hydroxyl protecting groups and amide-forming groups and corresponding chemical cleavage reactions are described in *Protective Groups in Organic Synthesis*, Theodora W. Greene (John Wiley & Sons, Inc., New York, 1991, ISBN 0-471-62301-6) ("Greene"). See also Kocienski, Philip J.; *Protecting Groups* (Georg Thieme Verlag Stuttgart, New York, 1994), which is incorporated by reference in its entirety herein. In particular Chapter 1, Protecting Groups: An Overview, pages 1-20, Chapter 2, Hydroxyl Protecting Groups, pages 21-94, Chapter 3, Diol Protecting Groups, pages 95-117, Chapter 4, Carboxyl Protecting Groups, pages 118-154, Chapter 5, Carbonyl Protecting Groups, pages 155-184. For protecting groups for carboxylic acid, phosphonic acid, phosphonate, sulfonic acid and other protecting groups for acids see Greene as set forth below.

Stereoisomers

The compounds of the invention may have chiral centers, e.g., chiral carbon or phosphorus atoms. The compounds of the invention thus include racemic mixtures of all stereoisomers, including enantiomers, diastereomers, and atropisomers. In addition, the compounds of the invention include enriched or resolved optical isomers at any or all asymmetric, chiral atoms. In other words, the chiral centers apparent from the depictions are provided as the chiral isomers or racemic mixtures. Both racemic and diastereomeric mixtures, as well as the individual optical isomers isolated or synthesized, substantially free of their enantiomeric or diastereomeric partners, are all within the scope of the invention. The racemic mixtures can be separated into their individual, substantially optically pure isomers through well-known techniques such as, for example, the separation of diastereomeric salts formed with optically active adjuncts, e.g., acids or bases followed by conversion back to the optically active substances. In most instances, the desired optical isomer is synthesized by means of stereospecific reactions, beginning with the appropriate stereoisomer of the desired starting material.

It is to be understood that for compounds of the invention when a bond is drawn in a non-stereochemical manner (e.g. flat) the atom to which the bond is attached includes all stereochemical possibilities. It is also to be understood that when a bond is drawn in a stereochemical manner (e.g. bold, bold-wedge, dashed or dashed-wedge) the atom to which the stereochemical bond is attached has the stereochemistry as shown unless otherwise noted.

Accordingly, in one embodiment, a compound of the invention may be greater than 50% a single enantiomer. In another embodiment, a compound of the invention may be at least 51% a single enantiomer. In another embodiment, a compound of the invention may be at least 60% a single enantiomer. In another embodiment, a compound of the invention may be at least 70% a single enantiomer. In another embodiment, a compound of the invention may be at least 80% a single enantiomer. In another embodiment, a compound of the invention may be at least 90% a single enantiomer. In another embodiment, a compound of the invention may be at least 95% a single enantiomer. In another embodiment, a compound of the invention may be at least 98% a single enantiomer. In another embodiment, a compound of the invention may be at least 99% a single enantiomer. In another embodiment, a compound of the invention may be greater than 50% a single diasteromer. In another embodiment, a compound of the invention may be at least 51% a single diastereomer. In another embodiment, a compound of the invention may be at least 60% a single diastereomer. In another embodiment, a compound of the invention may be at least 70% a single diastereomer. In another embodiment, a compound of the invention may be at least 80% a single diastereomer. In another embodiment, a compound of the invention may be at least 90% a single diastereomer. In another embodiment, the compounds of the invention are at least 95% a single diastereomer. In another embodiment, a compound of the invention may be at least 98% a single diastereomer. In another embodiment, a compound of the invention may be at least 99% a single diastereomer.

The compounds of the invention can also exist as tautomeric isomers in certain cases. Although only one delocalized resonance structure may be depicted, all such forms are contemplated within the scope of the invention. For example, ene-amine tautomers can exist for purine, pyrimidine, imidazole, guanidine, amidine, and tetrazole systems and all their possible tautomeric forms are within the scope of the invention. Other examples include keto-enol tautomers of hydroxy heterocycles such as hydroxy quinolines (e.g. 2-hydroxy quinoline and quinolin-2-ones).

Salts and Hydrates

Examples of pharmaceutically acceptable salts of the compounds of the invention include salts derived from an appropriate base, such as an alkali metal (for example, sodium), an alkaline earth metal (for example, magnesium), ammonium and $NX_4^+$ (wherein X is $C_1$-$C_4$ alkyl). Pharmaceutically acceptable salts of a hydrogen atom or an amino group include for example salts of organic carboxylic acids such as acetic, benzoic, lactic, fumaric, tartaric, maleic, malonic, malic, isethionic, lactobionic and succinic acids;

organic sulfonic acids, such as methanesulfonic, ethanesulfonic, benzenesulfonic and p-toluenesulfonic acids; and inorganic acids, such as hydrochloric, hydrobromic, sulfuric, phosphoric and sulfamic acids. Pharmaceutically acceptable salts of a compound of a hydroxy group include the anion of said compound in combination with a suitable cation such as Na+ and NX$_4^+$ (wherein X is independently selected from H or a C$_1$-C$_4$ alkyl group).

For therapeutic use, salts of active ingredients of the compounds of the invention will typically be pharmaceutically acceptable, i.e. they will be salts derived from a physiologically acceptable acid or base. However, salts of acids or bases which are not pharmaceutically acceptable may also find use, for example, in the preparation or purification of a compound of formula I or another compound of the invention. All salts, whether or not derived from a physiologically acceptable acid or base, are within the scope of the present invention.

Metal salts typically are prepared by reacting the metal hydroxide with a compound of this invention. Examples of metal salts which are prepared in this way are salts containing Li+, Na+, and K+. A less soluble metal salt can be precipitated from the solution of a more soluble salt by addition of the suitable metal compound.

In addition, salts may be formed from acid addition of certain organic and inorganic acids, e.g., HCl, HBr, H$_2$SO$_4$, H$_3$PO$_4$ or organic sulfonic acids, to basic centers, typically amines, or to acidic groups. Finally, it is to be understood that the compositions herein comprise compounds of the invention in their un-ionized, as well as zwitterionic form, and combinations with stoichiometric amounts of water as in hydrates.

Also included within the scope of this invention are the salts of the parental compounds with one or more amino acids. Any of the natural or unnatural amino acids are suitable, especially the naturally-occurring amino acids found as protein components, although the amino acid typically is one bearing a side chain with a basic or acidic group, e.g., lysine, arginine or glutamic acid, or a neutral group such as glycine, serine, threonine, alanine, isoleucine, or leucine.

Specific values listed below for radicals, substituents, and ranges in the embodiments of the invention are for illustration only; they do not exclude other defined values or other values within defined ranges for the radicals and substituents.

Isotopes

It is understood by one skilled in the art that this invention also includes any compound claimed that may be enriched at any or all atoms above naturally occurring isotopic ratios with one or more isotopes such as, but not limited to, deuterium ($^2$H or D). As a non-limiting example, a —CH$_3$ group may be substituted with —CD$_3$.

Compounds of Formula I.

A specific group of compounds of formula I are compounds of formula I':

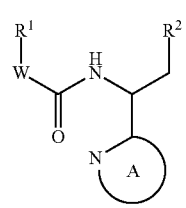

or a salt thereof.

A specific group of compounds of formula I are compounds of formula Ia:

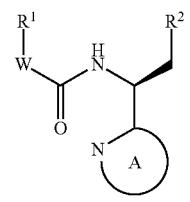

or a salt thereof.

Another specific group of compounds of formula I are compounds of formula Ia':

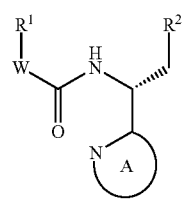

or a salt thereof.

Another specific group of compounds of formula I are compounds of formula Ib:

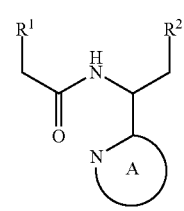

or a salt thereof.

Another specific group of compounds of formula I are compounds of formula Ic:

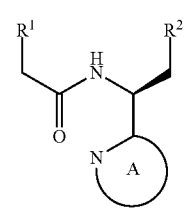

or a salt thereof.

Another specific group of compounds of formula I are compounds of formula Ic':

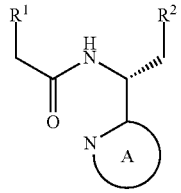

or a salt thereof.

Another specific group of compounds of formula I are compounds of formula Id:

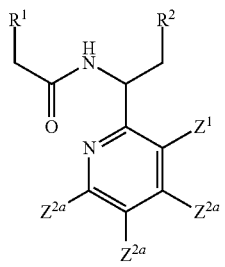

wherein each $Z^{2a}$ is independently H or $Z^2$, or a salt thereof.

Another specific group of compounds of formula I are compounds of formula Ie:

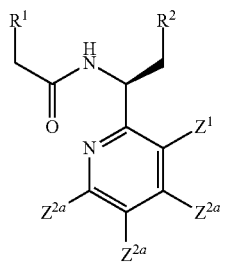

wherein each $Z^{2a}$ is independently H or $Z^2$, or a salt thereof.

Another specific group of compounds of formula I are compounds of formula Ie':

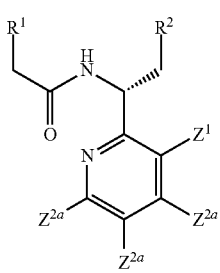

wherein each $Z^{2a}$ is independently H or $Z^2$, or a salt thereof.

Another specific group of compounds of formula I are compounds of formula Ibb:

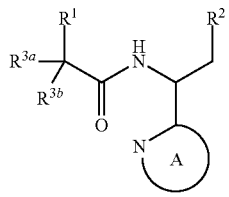

or a salt thereof.

Another specific group of compounds of formula I are compounds of formula Icc:

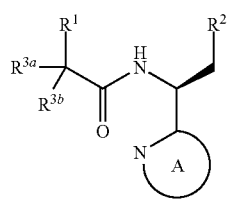

or a salt thereof.

Another specific group of compounds of formula I are compounds of formula Icc':

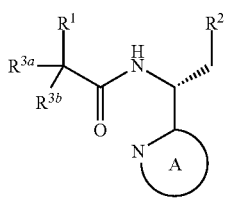

or a salt thereof.

Another specific group of compounds of formula I are compounds of formula Idd:

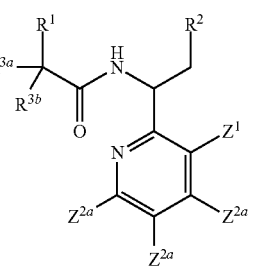

wherein each $Z^{2a}$ is independently H or $Z^2$, or a salt thereof.

Another specific group of compounds of formula I are compounds of formula Iee:

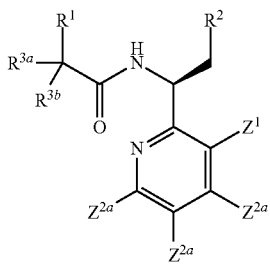

wherein each $Z^{2a}$ is independently H or $Z^2$, or a salt thereof.

Another specific group of compounds of formula I are compounds of formula Iee':

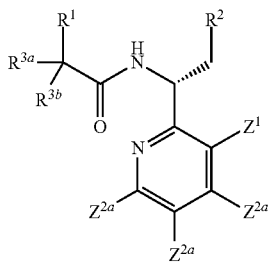

wherein each $Z^{2a}$ is independently H or $Z^2$, or a salt thereof.

Another specific group of compounds of formula I are compounds of formula If:

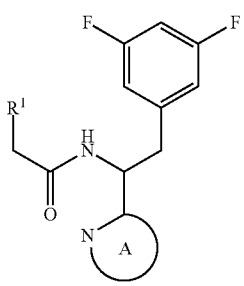

or a salt thereof.

Another specific group of compounds of formula I are compounds of formula If':

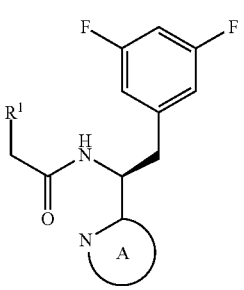

or a salt thereof.

Another specific group of compounds of formula I are compounds of formula Ig:

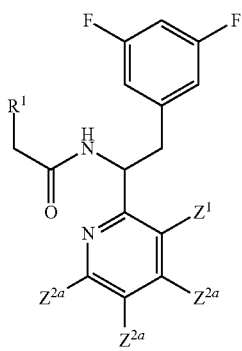

wherein each $Z^{2a}$ is independently H or $Z^2$, or a salt thereof.

Another specific group of compounds of formula I are compounds of formula Ih.

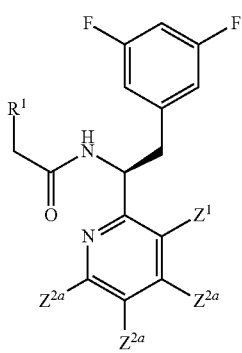

wherein each $Z^{2a}$ is independently H or $Z^2$, or a salt thereof.

Another specific group of compounds of formula I are compounds of formula Ii:

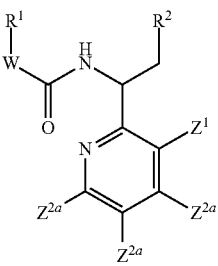

wherein each $Z^{2a}$ is independently H or $Z^2$, or a salt thereof.

Another specific group of compounds of formula I are compounds of formula Ij:

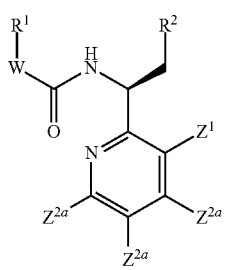

Ij wherein each $Z^{2a}$ is independently H or $Z^2$, or a salt thereof.

Another specific group of compounds of formula I are compounds of formula Ij':

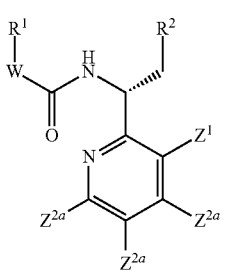

Ij' wherein each $Z^{2a}$ is independently H or $Z^2$, or a salt thereof.

Another specific group of compounds of formula I are compounds of formula Ik:

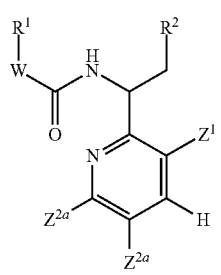

Ik wherein each $Z^{2a}$ is independently H or $Z^2$, or a salt thereof.

Another specific group of compounds of formula I are compounds of formula Im:

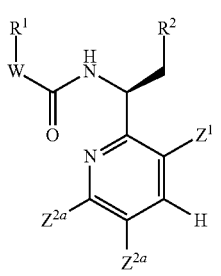

Im wherein each $Z^{2a}$ is independently H or $Z^2$, or a salt thereof.

Another specific group of compounds of formula I are compounds of formula Im':

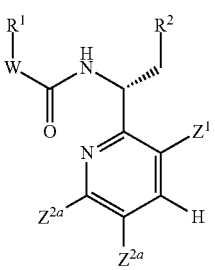

Im' wherein each $Z^{2a}$ is independently H or $Z^2$, or a salt thereof.

Another specific group of compounds of formula I are compounds of formula In, Io, Io', Ip, Iq, Iq', Ir, Is or Is':

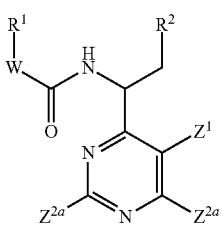

In

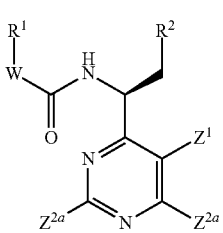

Io

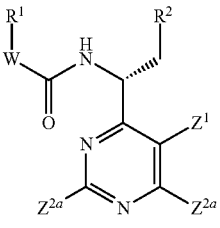

Io'

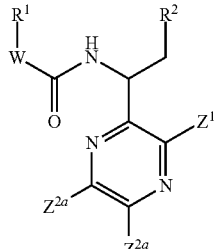

Ip

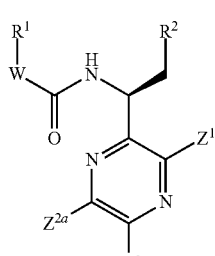

Iq

Iq'

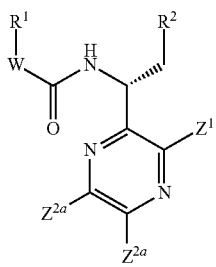

Ir

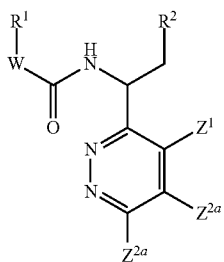

Is

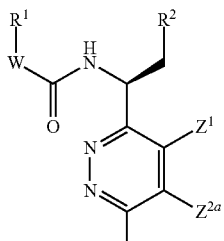

Is'

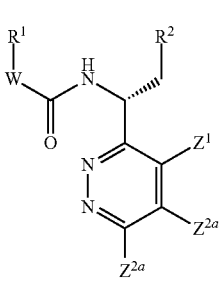

In wherein each $Z^{2a}$ is independently H or $Z^2$, or a salt thereof.

Another specific group of compounds of formula I are compounds of formula It:

It

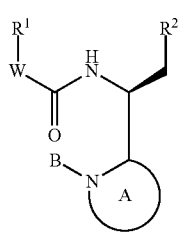

or a salt thereof.

Another specific group of compounds of formula I are compounds of formula It':

It'

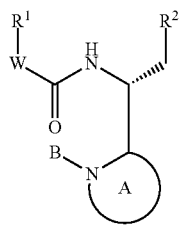

or a salt thereof.

Specific values listed herein below are values for compounds of formula I as well as compounds of sub-formulas of formula I (e.g. formulas I' Ia, Ia', Ib, Ic, Ic', Id, Ie, Ie', Ibb, Icc, Icc', Idd, Iee, Iee, If, If', Ig, Ih Ii, Ij, Ij', Ik, Im, Im', In, Io, Io', Ip, Iq, Iq', Ir, Is, Is', It and It') A specific value for W is $CR^{3a}R^{3b}$ or $NR^4$.

Another specific value for W is —$CR^{3a}R^{3b}$—, —O—, —$NR^4$— or —$OCR^{3a}R^{3b}$—.

Another specific value for W is —$CR^{3a}R^{3b}$—, —$OCR^{3a}R^{3b}$— or absent.

Another specific value for W is —$CR^{3a}R^{3b}$—.

A specific group of compounds of formula I are compounds wherein $R^4$ is H and, wherein each $R^{3a}$ and $R^{3b}$ is independently selected from H, $(C_1-C_3)$alkyl, $(C_1-C_3)$haloalkyl, $NR_aR_b$, and —$NR_cCOR_d$, or $R^{3a}$ and $R^{3b}$ together with the carbon to which they are attached form a $(C_3-C_6)$ carbocycle.

Another specific value for W is —$CH_2$—, —$CH(CH_3)$—, —$CH(CH_2CH_3)$—, —$CH(CF_3)$—, —$CH(CH_2CF_3)$—, —$CH(CH_2CHF_2)$—, —$CH(NH_2)$—, —$CH(NHC(=O)CH_3)$—, 1,1-cyclopropyldiyl or —NH—.

Another specific value for W is —$CH_2$—, —$CH(CH_3)$—, —$CH(NH_3)$—, —$CH(NHC(=O)CH_3)$—, 1,1-cyclopropyldiyl or —NH—.

Another specific value for W is —$CH_2$—.

A specific group of compounds of formula I are compounds wherein B is absent.

A specific value for $R^2$ is a 6-membered aryl wherein the 6-membered aryl is optionally substituted with one or more (e.g. 1, 2 or 3) $Z^4$ groups.

A specific value for $Z^4$ is $(C_3-C_7)$carbocycle, halogen or —CN.

Another specific value for $Z^4$ is cyclopropyl, fluoro or —CN.

Another specific value for $Z^4$ is fluoro.

Another specific value for $Z^4$ is fluoro or chloro.

Another specific value for $Z^4$ is $(C_1-C_8)$alkyl, $(C_3-C_7)$ carbocycle, halogen or $OR_{n6}$, wherein any $(C_1-C_8)$alkyl of $Z^4$ is optionally substituted with one or more halogens.

Another specific value for $Z^4$ is $(C_3-C_7)$carbocycle, halogen, methyl or —CN.

Another specific value for $Z^4$ is halogen.

Another specific value for $R^2$ is:

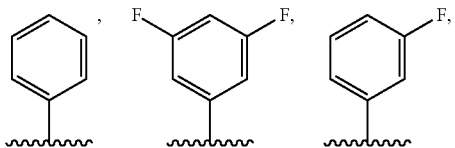

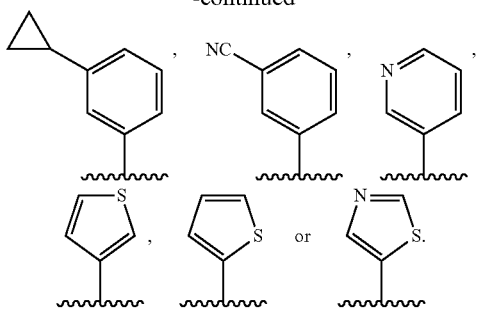

Another specific value for $R^2$ is:

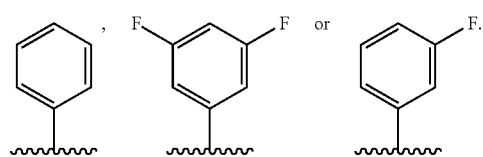

Another specific value for $R^2$ is:

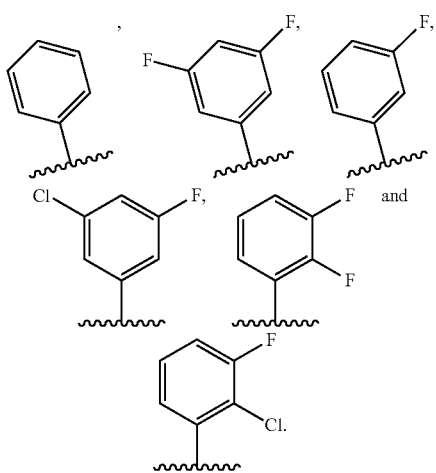

Another specific value for $R^2$ is:

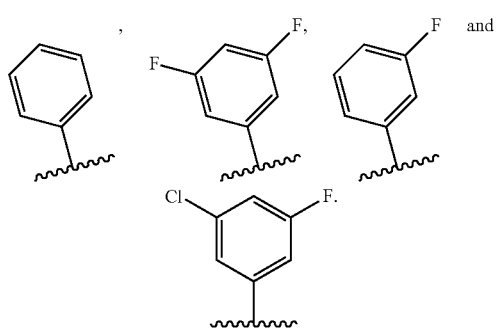

A specific value for $R^1$ is heteroaryl or heterocycle, wherein any heteroaryl or heterocycle of $R^1$ is optionally substituted with one or more $Z^3$ groups.

Another specific value for $R^1$ is bicyclic-heteroaryl, tricyclic-heteroaryl, bicyclic-heterocycle or tricyclic-heterocycle, wherein any bicyclic-heteroaryl, tricyclic-heteroaryl, bicyclic-heterocycle or tricyclic-heterocycle, of $R^1$ is optionally substituted with one or more $Z^3$ groups.

Another specific value for $R^1$ is 4,5,6,7-tetrahydroindazolyl, 5-oxo-4,5-dihydro-1H-pyrrolo[3,2-b]pyridinyl, 1,4,5,7-tetrahydropyranopyrazolyl, 3-oxo-2,3,4,5,6,7-hexahydro-indazolyl, pyrrolo[2,3-c]pyridinyl, pyrrolo[2,3-b]pyridinyl, 1H-pyrrolo[3,2-c]pyridinyl, 1H-pyrrolo[3,2-b]pyridinyl, benzoimidazolyl, 5-phenyl-pyrazolyl, pyrrolo[3,2-d]pyrimidinyl, 5-oxo-5,6-dihydro-1H-pyrrolo[2,3-c]pyridinyl, 6-oxo-6,7-dihydro-1H-pyrrolo[2,3-b]pyridinyl, 1,7-dihydropyrrolo[3,2-f]indazolyl, 1,6-dihydropyrrolo[2,3-e]indazolyl, 2-oxo-2H-thiazolo[5,4-f]indoly, 2-oxoindolin-3-yl or indolyl, wherein any 4,5,6,7-tetrahydroindazolyl, 5-oxo-4,5-dihydro-1H-pyrrolo[3,2-b]pyridinyl, 1,4,5,7-tetrahydropyranopyrazolyl, 3-oxo-2,3,4,5,6,7-hexahydro-indazolyl, pyrrolo[2,3-c]pyridinyl, pyrrolo[2,3-b]pyridinyl, 1H-pyrrolo[3,2-c]pyridinyl, 1H-pyrrolo[3,2-b]pyridinyl, benzoimidazolyl, 5-phenyl-pyrazolyl, pyrrolo[3,2-d]pyrimidinyl, 5-oxo-5,6-dihydro-1H-pyrrolo[2,3-c]pyridinyl, 6-oxo-6,7-dihydro-1H-pyrrolo[2,3-b]pyridinyl, 1,7-dihydropyrrolo[3,2-f]indazolyl, 1,6-dihydropyrrolo[2,3-e]indazolyl, 2-oxo-2H-thiazolo[5,4-f]indolyl, 2-oxoindolin-3-yl or indolyl of $R^1$ is optionally substituted with one or more $Z^3$ groups.

Another specific value for $R^1$ is 4,5,6,7-tetrahydroindazolyl or indolyl, wherein any 4,5,6,7-tetrahydroindazolyl or indolyl of $R^1$ is optionally substituted with one or more $Z^3$ groups.

Another specific value for $R^1$ is 4,5,6,7-tetrahydroindazolyl, 5-oxo-4,5-dihydro-1H-pyrrolo[3,2-b]pyridinyl or indolyl, wherein any 4,5,6,7-tetrahydroindazolyl, 5-oxo-4,5-dihydro-1H-pyrrolo[3,2-b]pyridinyl or indolyl of $R^1$ is optionally substituted with one or more $Z^3$ groups.

Another specific value for $R^1$ is tricyclic-heteroaryl or tricyclic-heterocycle, wherein any tricyclic-heteroaryl or tricyclic-heterocycle of $R^1$ is optionally substituted with one or more $Z^3$ groups.

Another specific value for $R^1$ is bicyclic-heteroaryl, tricyclic-heteroaryl, bicyclic-heterocycle or tricyclic-heterocycle, wherein any bicyclic-heteroaryl, tricyclic-heteroaryl, bicyclic-heterocycle or tricyclic-heterocycle of $R^1$ contains at least one partially unsaturated ring, and wherein any bicyclic-heteroaryl, tricyclic-heteroaryl, bicyclic-heterocycle or tricyclic-heterocycle of $R^1$ is optionally substituted with one or more $Z^3$ groups.

Another specific value for $R^1$ is tricyclic-heteroaryl or tricyclic-heterocycle, wherein any tricyclic-heteroaryl or tricyclic-heterocycle of $R^1$ contains one aromatic ring, one partially unsaturated ring, and one fully saturated ring, and wherein any tricyclic-heteroaryl or tricyclic-heterocycle of $R^1$ is optionally substituted with one or more $Z^3$ groups.

Another specific value for $R^1$ is bicyclic-heteroaryl, tricyclic-heteroaryl, bicyclic-heterocycle or tricyclic-heterocycle, wherein any bicyclic-heteroaryl, tricyclic-heteroaryl, bicyclic-heterocycle or tricyclic-heterocycle of $R^1$ contains 5 or more halogen atoms, and wherein any bicyclic-heteroaryl, tricyclic-heteroaryl, bicyclic-heterocycle or tricyclic-heterocycle of $R^1$ is optionally additionally substituted with one or more $Z^3$ groups.

Another specific value for $R^1$ is tricyclic-heteroaryl or tricyclic-heterocycle, wherein any tricyclic-heteroaryl or tricyclic-heterocycle of $R^1$ contains a bridged bicyclic carbocycle or a bridged bicyclic heterocycle, and wherein any tricyclic-heteroaryl or tricyclic-heterocycle of $R^1$ is optionally substituted with one or more $Z^3$ groups.

Another specific value for $R^1$ is tricyclic-heteroaryl or tricyclic-heterocycle, wherein any tricyclic-heteroaryl or tricyclic-heterocycle of R contains a spiro-connected bicyclic carbocycle or a spiro-connected bicyclic heterocycle, and wherein any tricyclic-heteroaryl or tricyclic-heterocycle of $R^1$ is optionally substituted with one or more $Z^3$ groups.

Another specific value for $R^1$ is:

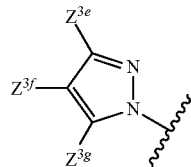

wherein $Z^{3e}$, $Z^{3f}$, and $Z^{3g}$ are each independently selected from H and $Z^3$; or $Z^{3e}$ is H or $Z^3$, and $Z^{3f}$ and $Z^{3g}$ together with the carbons to which they are attached form a 5, 6, or 7-membered heterocycle or a 5, 6, or 7-membered carbocycle, which 5, 6, or 7-membered heterocycle or a 5, 6, or 7-membered carbocycle is optionally substituted with one or more $Z^3$ groups.

Another specific value for $R^1$ is:

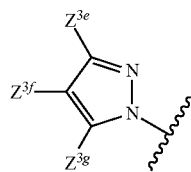

wherein $Z^{3e}$ is H or $Z^3$, and $Z^{3f}$ and $Z^{3g}$ together with the carbons to which they are attached form a 5, 6, or 7-membered heterocycle or a 5, 6, or 7-membered carbocycle, which 5, 6, or 7-membered heterocycle or a 5, 6, or 7-membered carbocycle is optionally substituted with one or more $Z^3$ groups.

Another specific value for $R^1$ is heteroaryl or heterocycle, wherein any heteroaryl or heterocycle of $R^1$ is optionally substituted with one or more $Z^3$ groups, provided $R^1$ does not include indolyl.

Another specific value for $R^1$ is bicyclic-heteroaryl, tricyclic-heteroaryl, bicyclic-heterocycle or tricyclic-heterocycle, wherein any bicyclic-heteroaryl, tricyclic-heteroaryl, bicyclic-heterocycle or tricyclic-heterocycle, of $R^1$ is optionally substituted with one or more $Z^3$ groups, provided $R^1$ does not include indolyl.

Another specific value for $R^1$ is bicyclic-heteroaryl, tricyclic-heteroaryl, bicyclic-heterocycle or tricyclic-heterocycle, wherein any bicyclic-heteroaryl, tricyclic-heteroaryl, bicyclic-heterocycle or tricyclic-heterocycle of $R^1$ contains 5 or more halogen atoms, and wherein any bicyclic-heteroaryl, tricyclic-heteroaryl, bicyclic-heterocycle or tricyclic-heterocycle of $R^1$ is optionally additionally substituted with one or more $Z^3$ groups, provided $R^1$ does not include indolyl.

Another specific value for $R^1$ is aryl, heteroaryl or heterocycle, wherein any aryl, heteroaryl or heterocycle of $R^1$ is optionally substituted with one or more (e.g. 1, 2, 3, 4 or 5) $Z^3$ groups, provided $R^1$ does not include indolyl.

A specific value for $Z^3$ is $(C_1-C_8)$alkyl, halogen, $-OR_{n4}$, $-NR_{q4}R_{r4}$ or $-NR_{n4}S(O)_2R_{p4}$, wherein any $(C_1-C_8)$alkyl of $Z^3$ is optionally substituted with one or more $Z^{3a}$ groups.

Another specific value for $Z^3$ is $(C_1-C_8)$alkyl, $(C_2-C_8)$alkenyl, $(C_2-C_8)$alkynyl, $(C_3-C_7)$carbocycle, aryl, halogen, $-CN$, $-OR_{n4}$, $-S(O)_2R_{p4}$, $-NR_{n4}CO_2R_{p4}$, $-NR_{n4}S(O)_2R_{p4}$, $-C(O)R_{n4}$, $-C(O)OR_{n4}$, $-C(O)NR_{q4}R_{r4}$ or $-B(OR_{q4})(OR_{r4})$, wherein any $(C_3-C_7)$carbocycle and aryl of $Z^3$ is optionally substituted with one or more (e.g. 1, 2, 3, 4 or 5) $Z^{3a}$ or $Z^{3b}$ groups, and wherein any $(C_1-C_8)$alkyl, $(C_2-C_8)$alkenyl and $(C_2-C_8)$alkynyl of $Z^3$ is optionally substituted with one or more (e.g. 1, 2, 3, 4 or 5) $Z^{3a}$ groups.

Another specific value for $Z^3$ is $(C_1-C_8)$alkyl, $(C_2-C_8)$alkenyl, $(C_2-C_8)$alkynyl, $(C_3-C_7)$carbocycle, aryl, halogen, $-CN$, $-OR_{n4}$, $-S(O)_2R_{p4}$, $-NR_{n4}S(O)_2R_{p4}$, $-S(O)_2NR_{q4}R_{r4}$, $-NR_{q4}R_{r4}$, $-C(O)R_{n4}$, $-C(O)NR_{q4}R_{r4}$ or $-NR_{n4}COR_{q4}$ wherein any $(C_3-C_7)$carbocycle and aryl of $Z^3$ is optionally substituted with one or more (e.g. 1, 2, 3, 4 or 5) $Z^{3a}$ or $Z^{3b}$ groups, and wherein any $(C_1-C_8)$alkyl, $(C_2-C_8)$alkenyl and $(C_2-C_8)$alkynyl of $Z^3$ is optionally substituted with one or more (e.g. 1, 2, 3, 4 or 5) $Z^{3a}$ groups Another specific value for $Z^3$ is methyl, trifluoromethyl, hydroxy, methoxy, benzyloxy, fluoro, $-NHSO_2CH_3$, 2-hydroxyprop-2yl, difluoromethyl or amino.

A specific value for $Z^{3a}$ is halogen.

Another specific value for $Z^{3a}$ is halogen and $-OR_{n5}$.

Another specific value for $Z^{3a}$ is, aryl, heterocycle, halogen, $-OR_{n5}$, $-NR_{q5}R_{r5}$ or $-NR_{5n}CO_2R_{p5}$, wherein any aryl, heteroaryl and heterocycle of $Z^{3a}$ is optionally substituted with one or more (e.g. 1, 2, 3, 4 or 5) $Z^{3c}$ or $Z^{3d}$ groups.

Another specific value for $Z^3$ is methyl, trifluoromethyl, hydroxy, methoxy, benzyloxy, fluoro, $-NHSO_2CH_3$, 2-hydroxyprop-2yl, difluoromethyl or amino.

Another specific value for $Z^3$ is methyl, trifluoromethyl, hydroxy, methoxy, benzyloxy, fluoro or $-NHSO_2CH_3$.

A specific value for $R^1$ is:

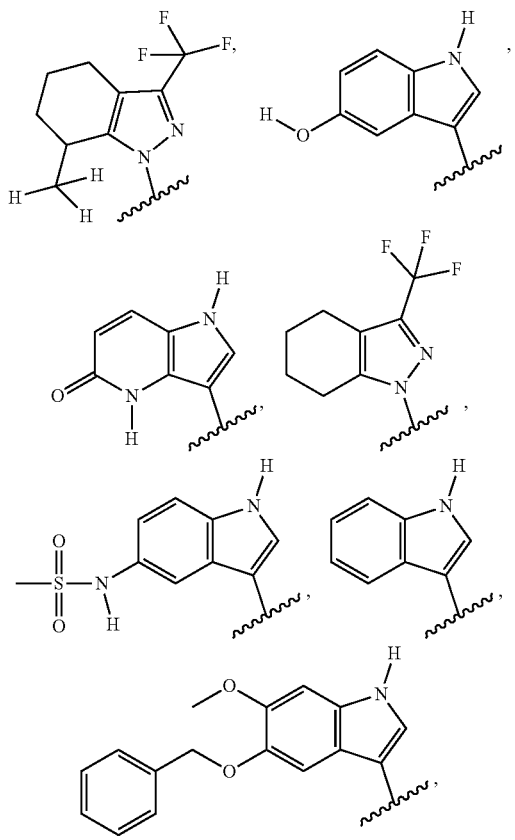

-continued
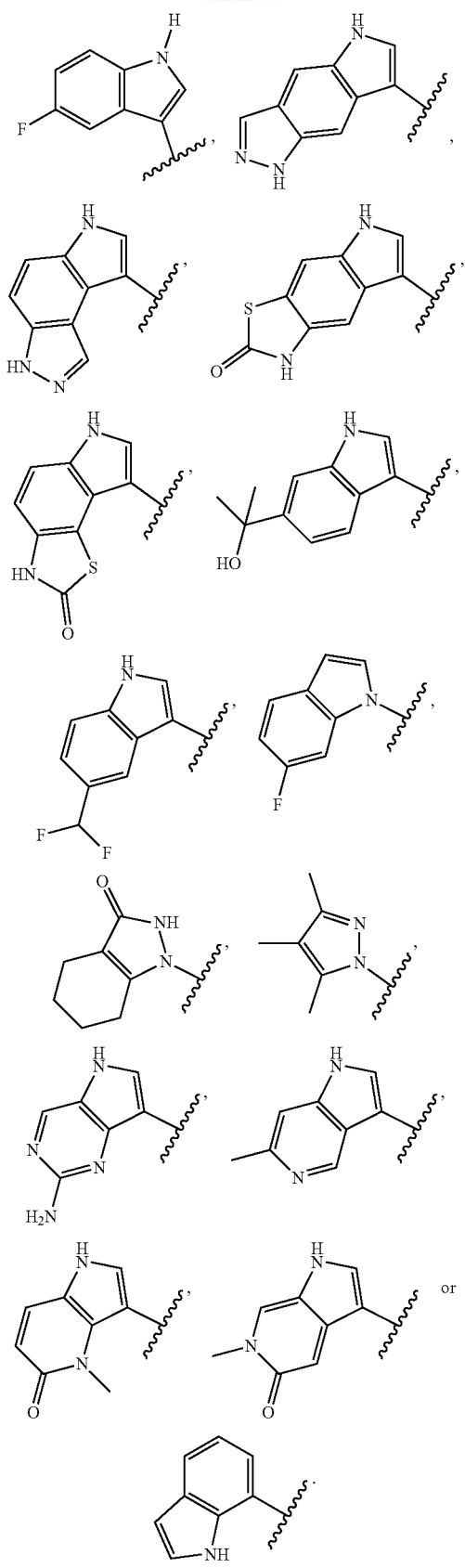
Another specific value for R¹ is:
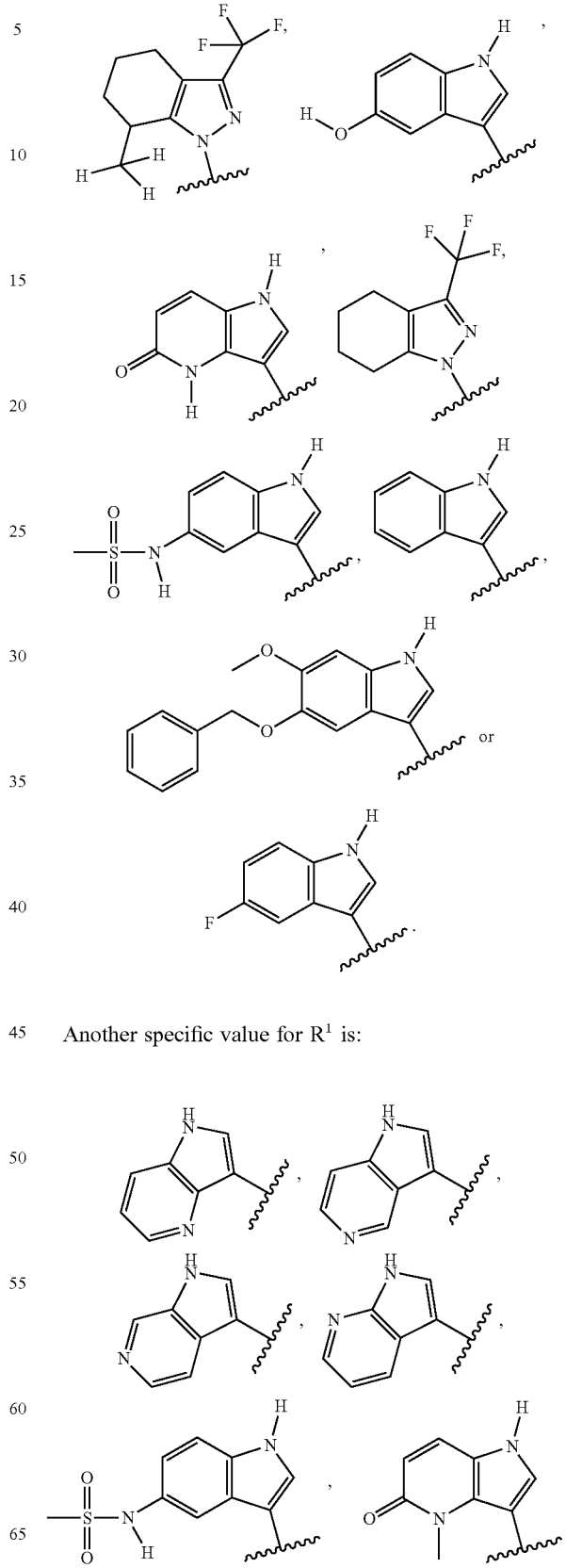
Another specific value for R¹ is:

-continued
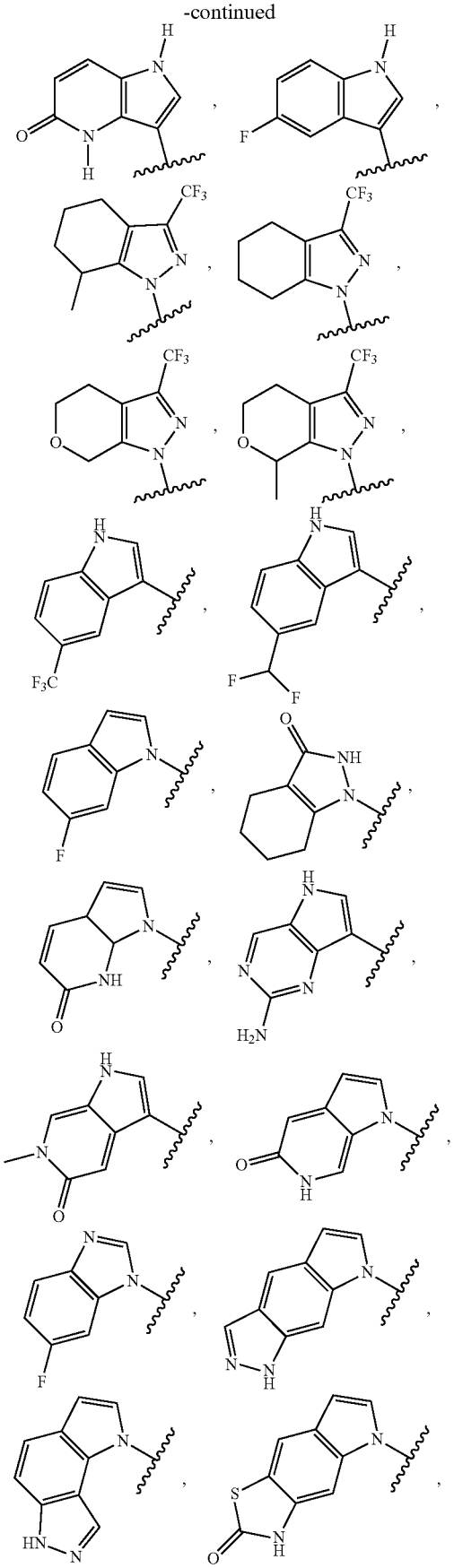
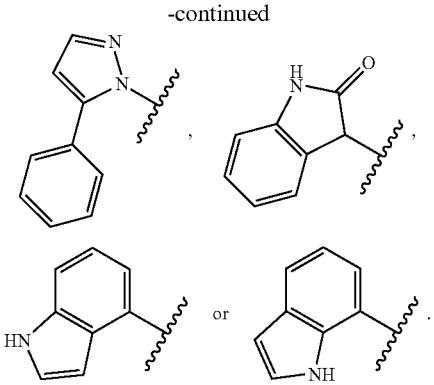
Another specific value for R[1] is:
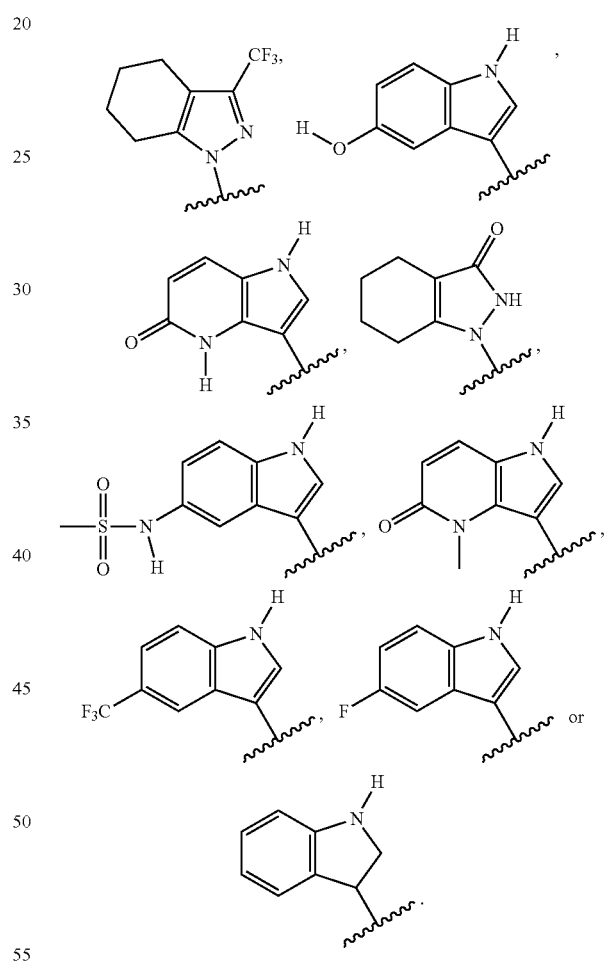
Another specific value for R[1] is:
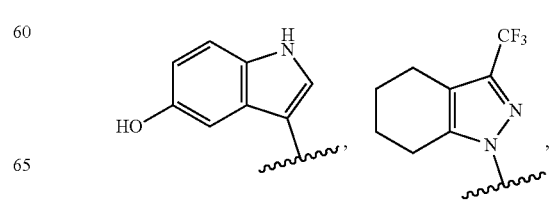

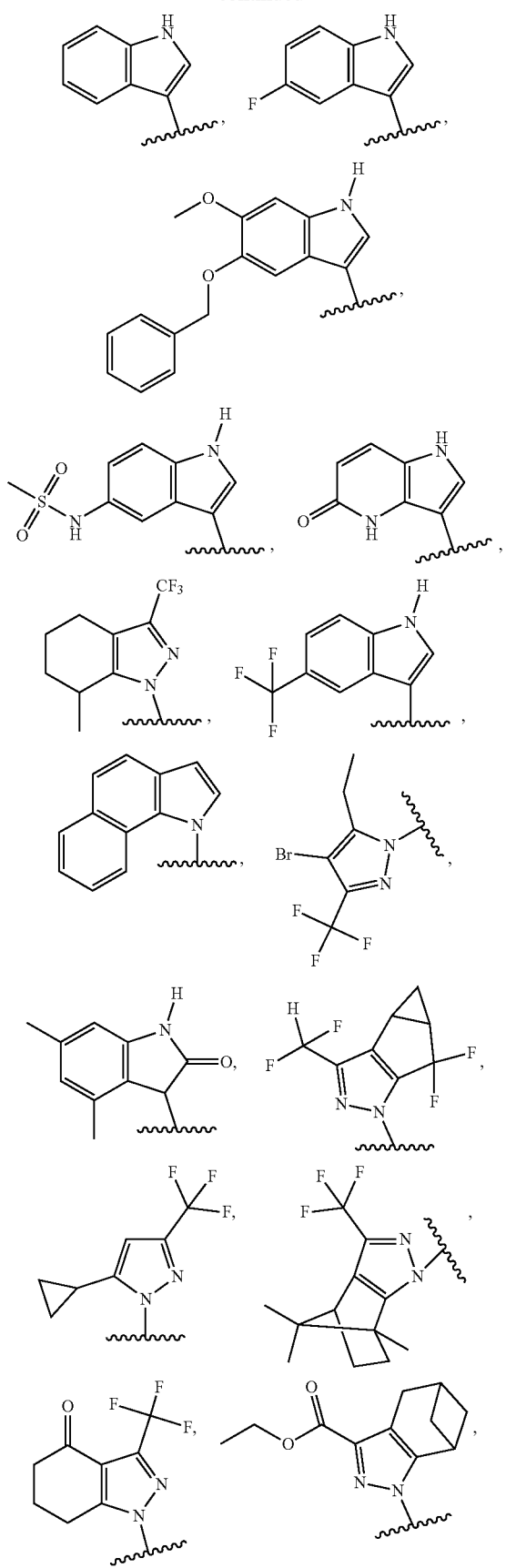
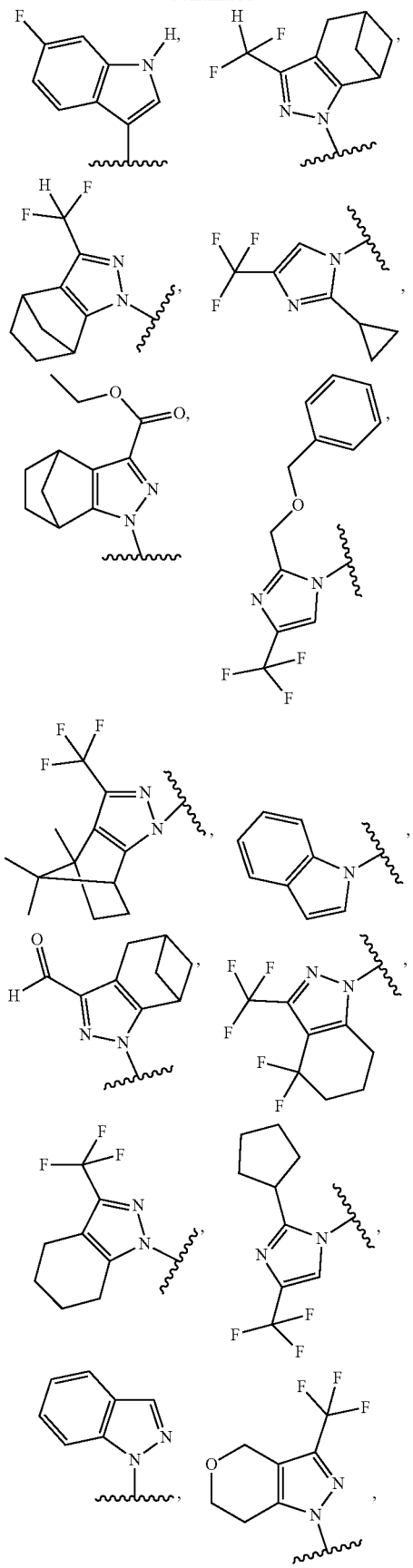

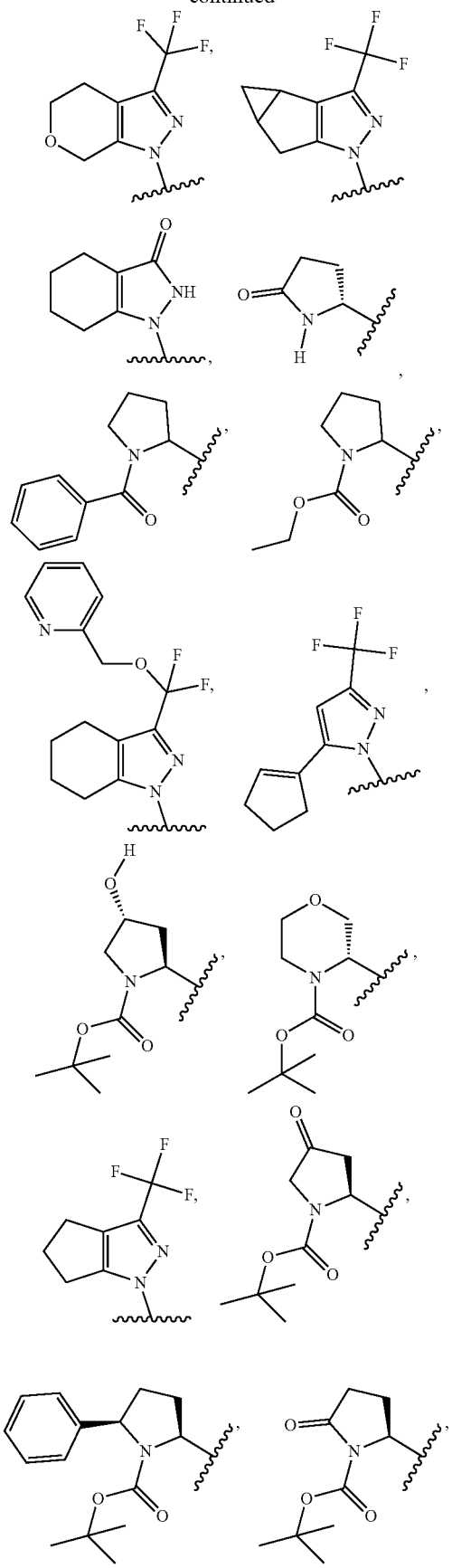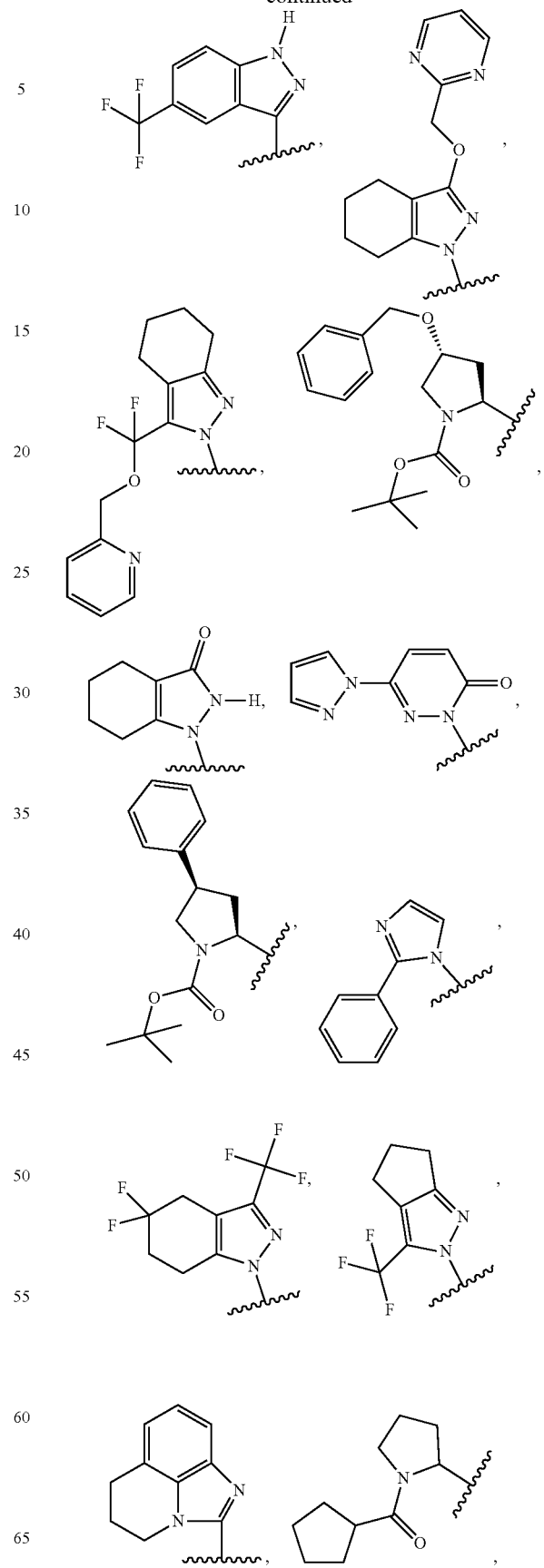

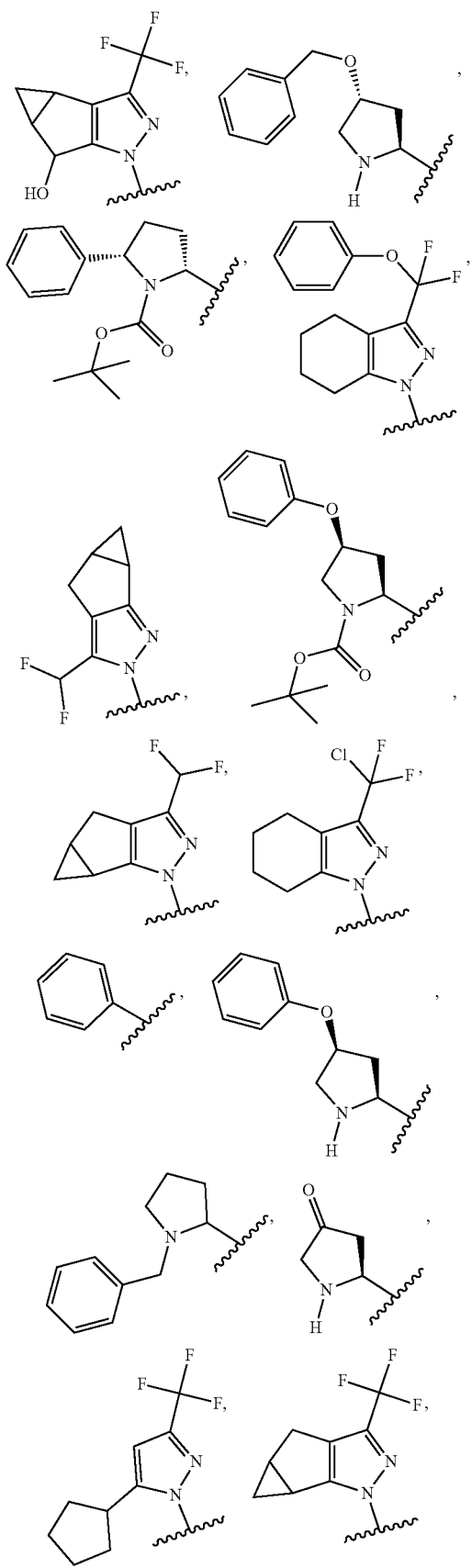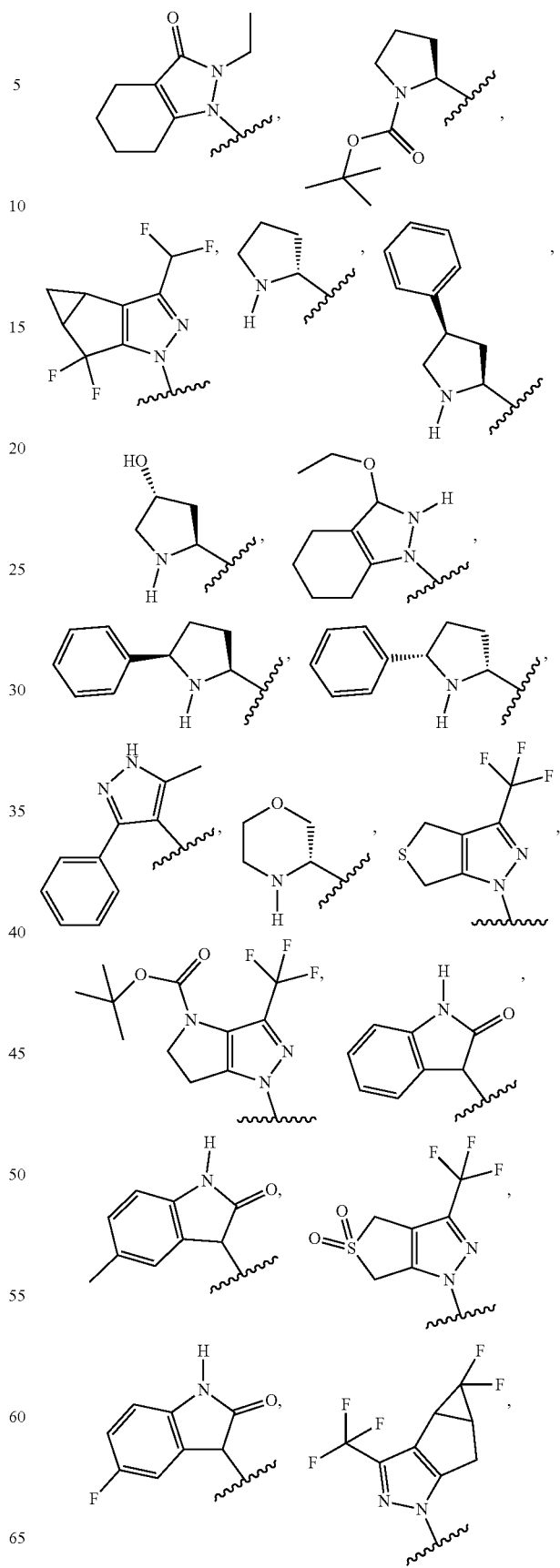

-continued
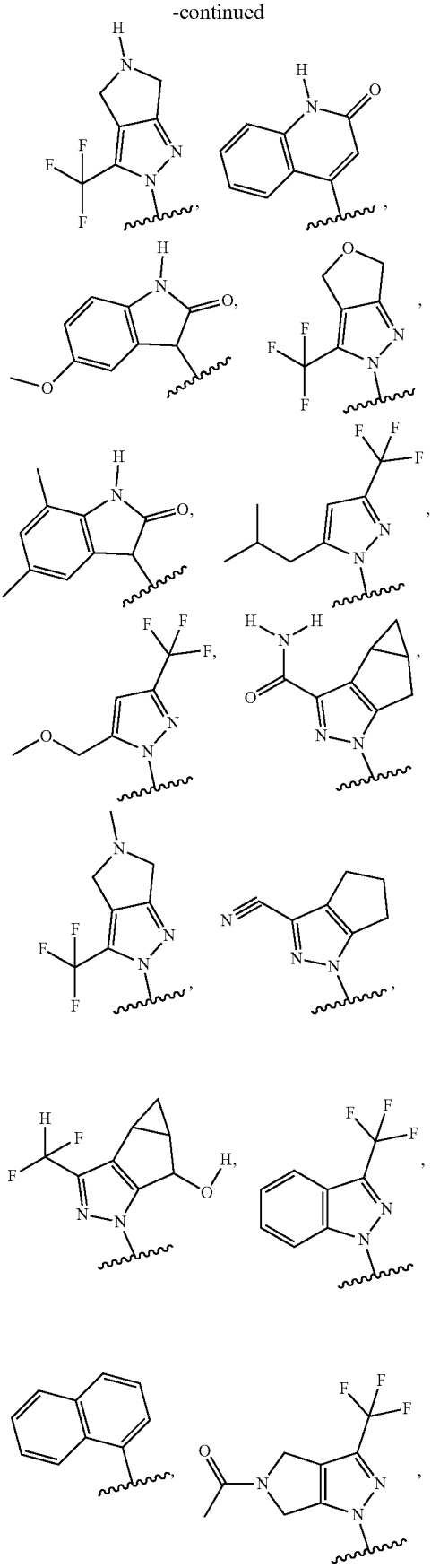
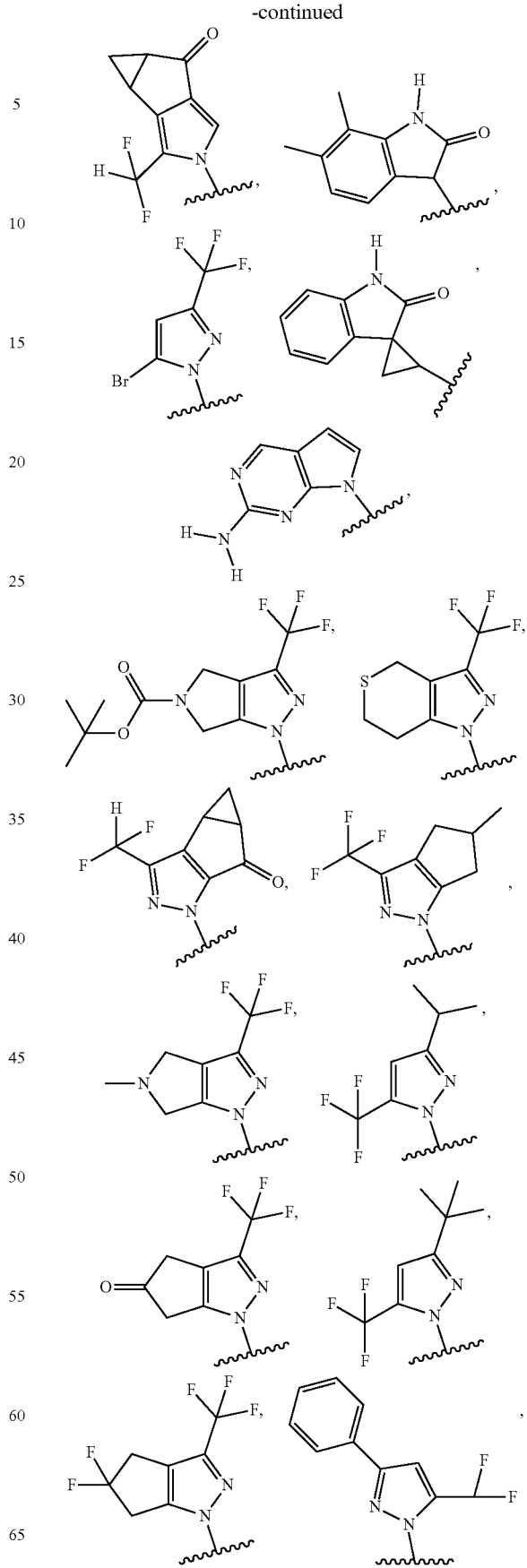

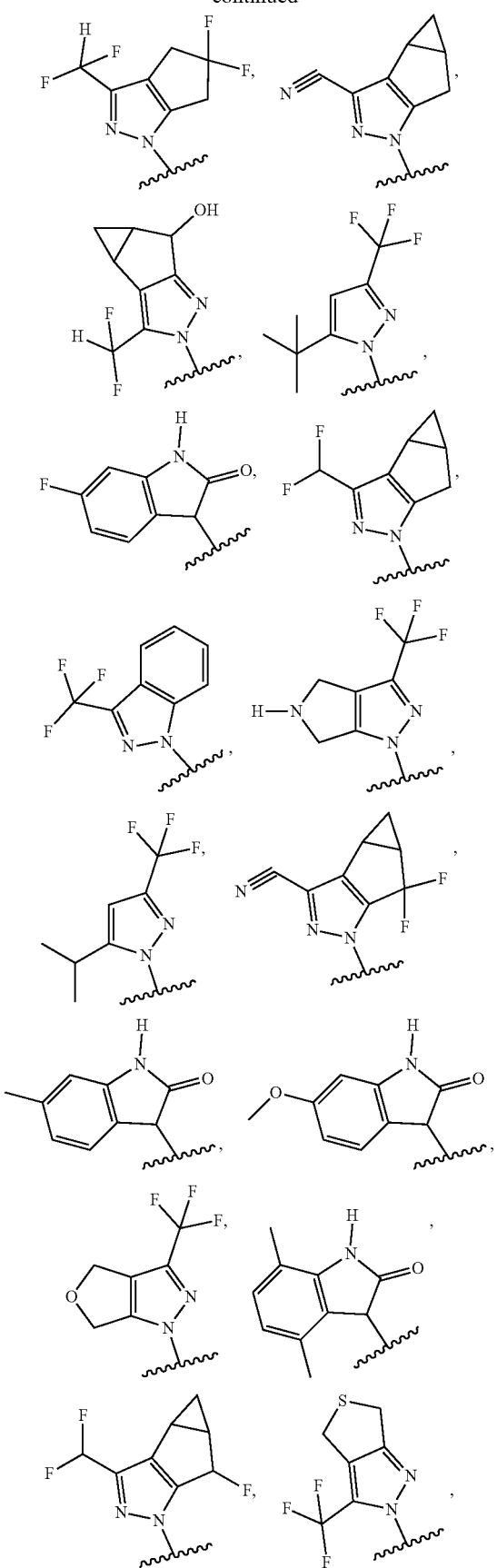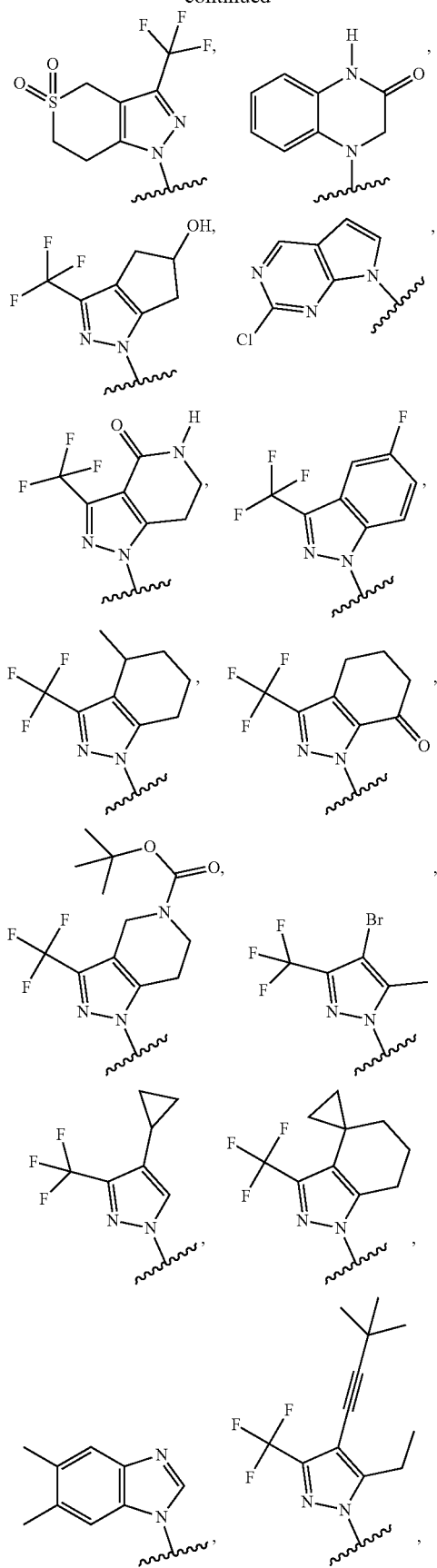

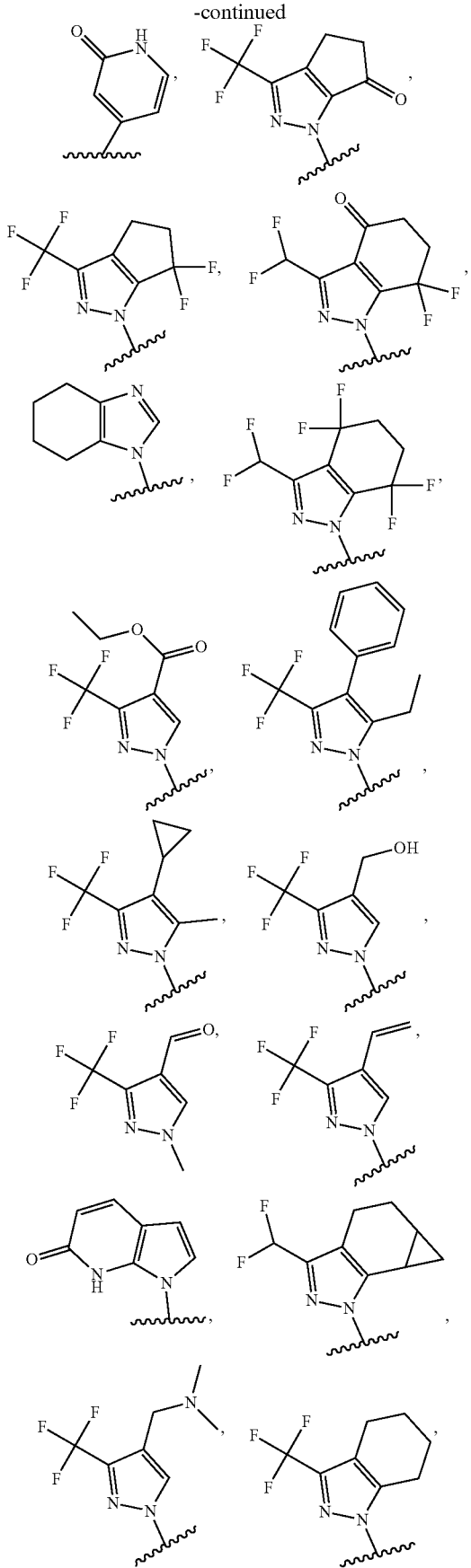
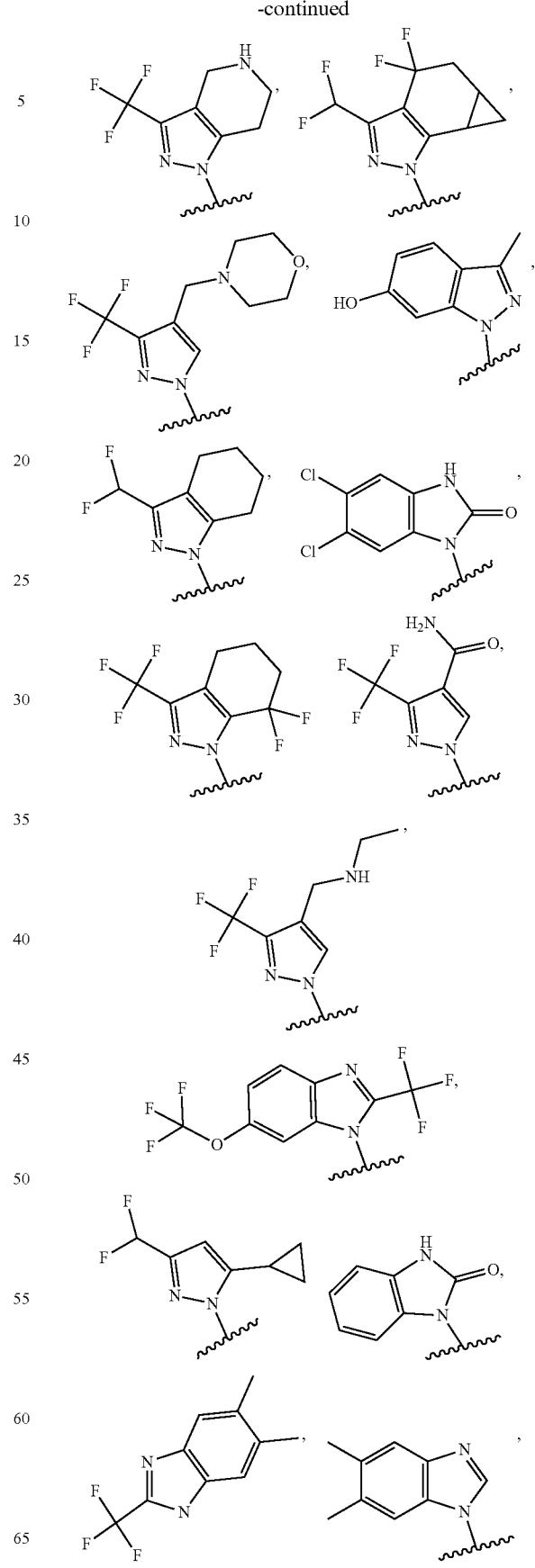

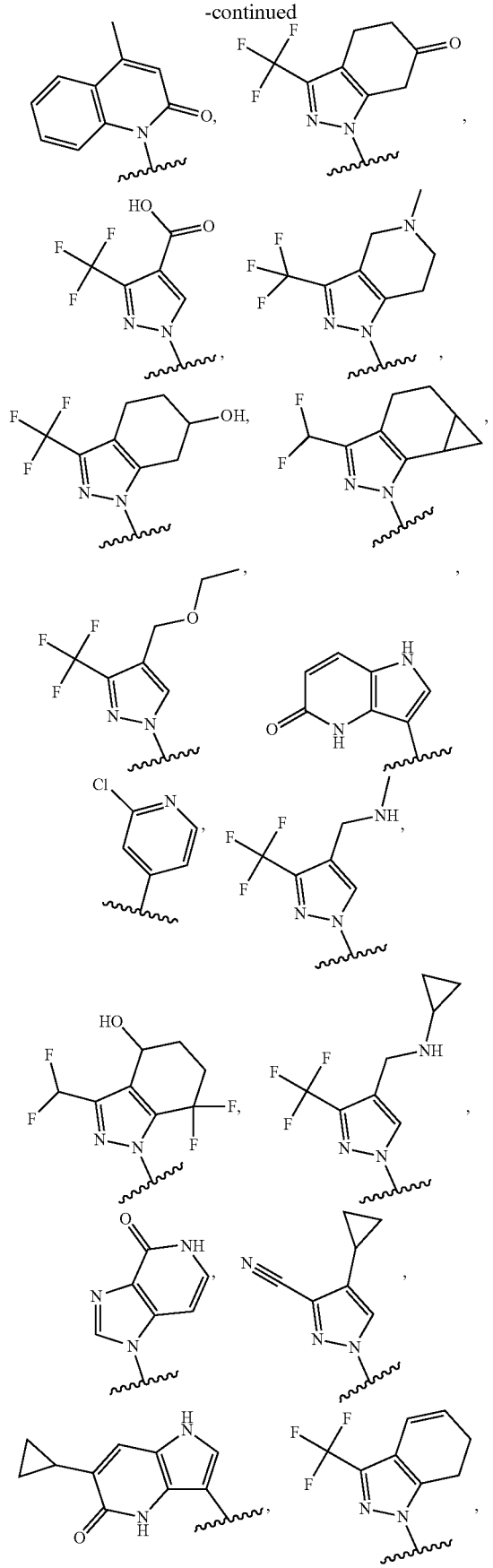
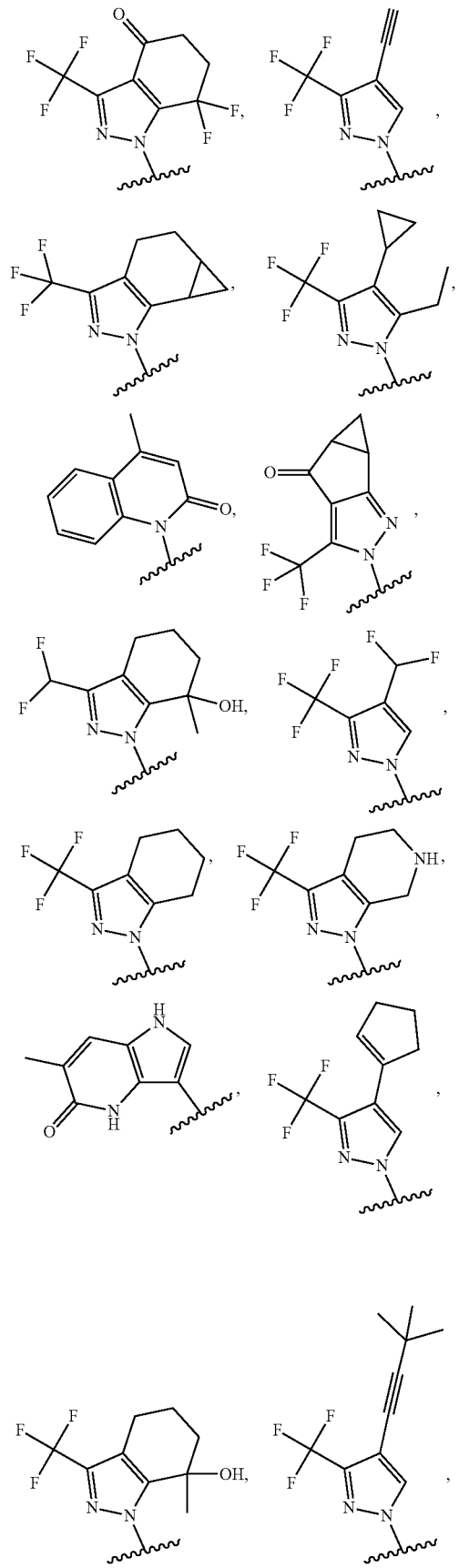

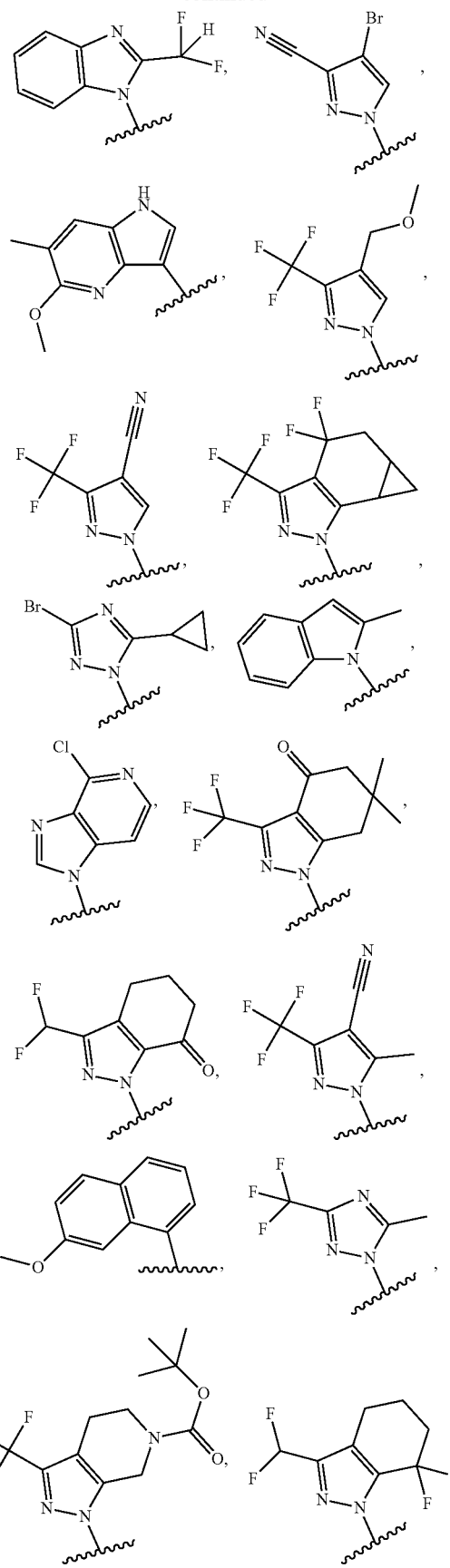
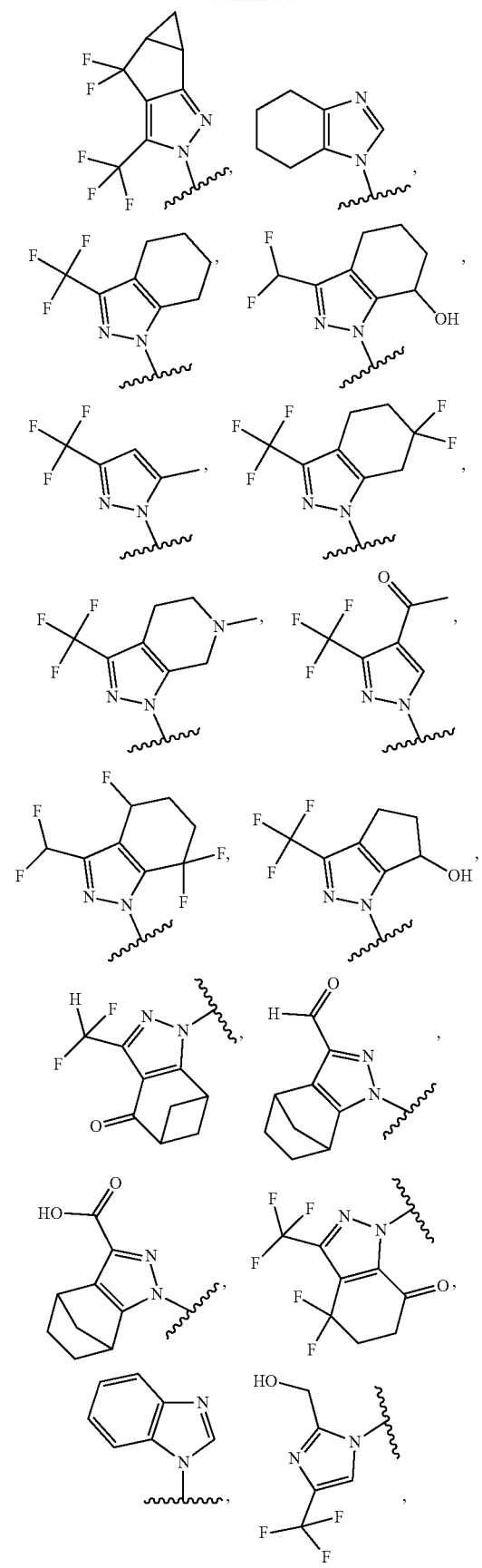

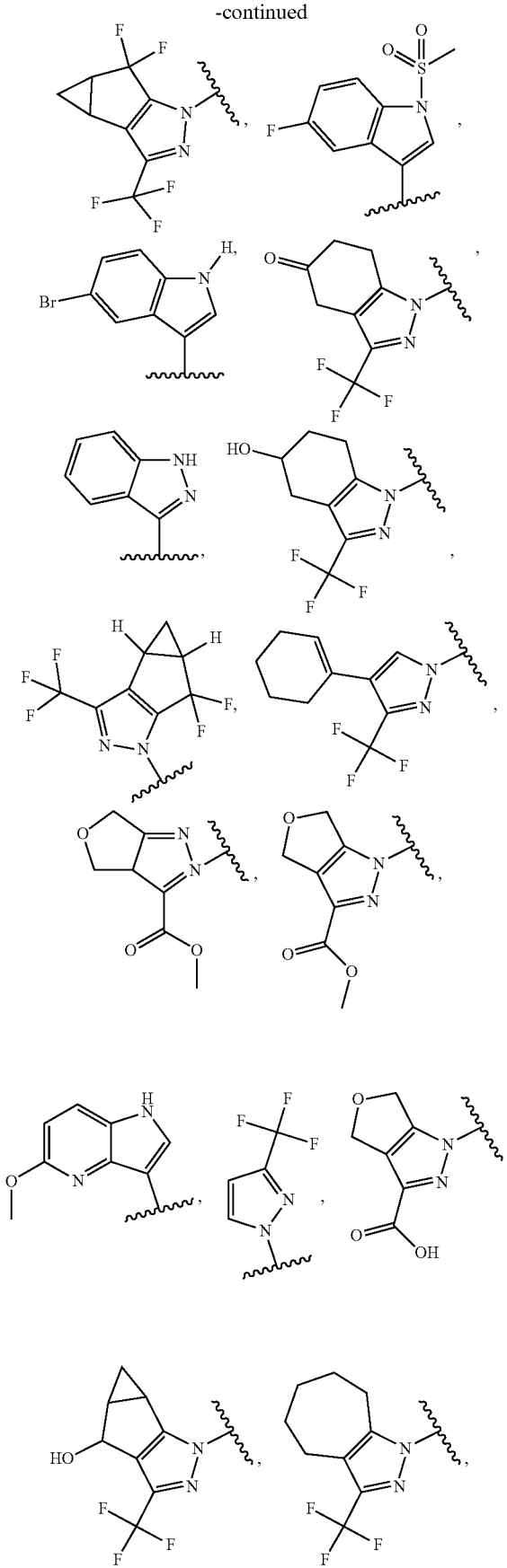
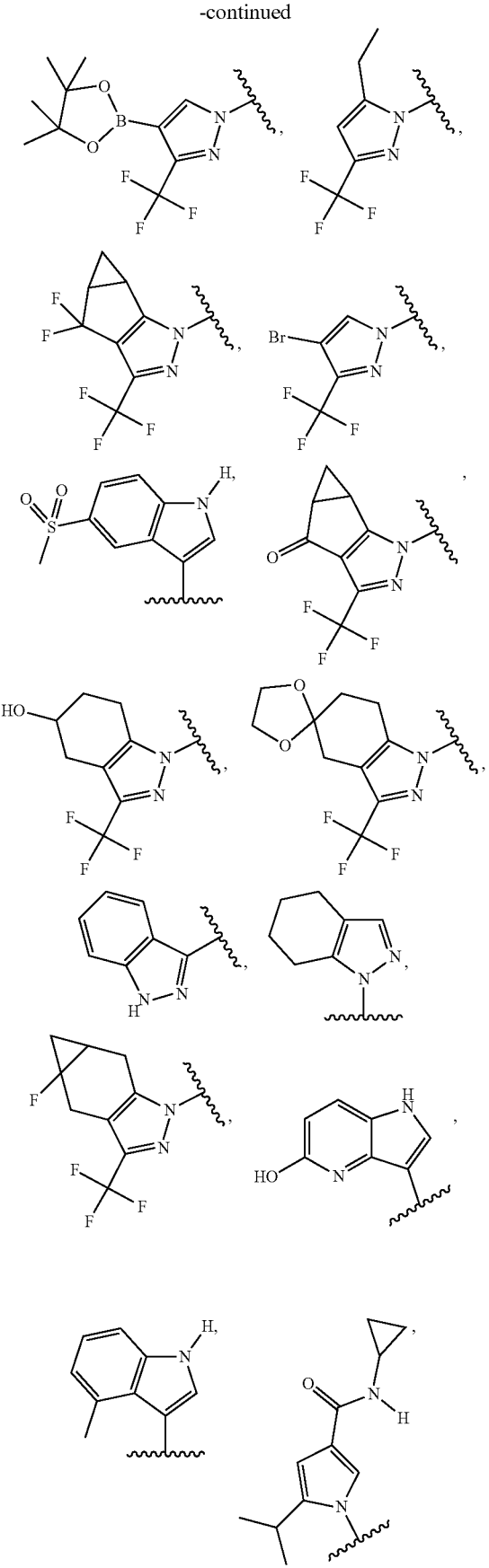

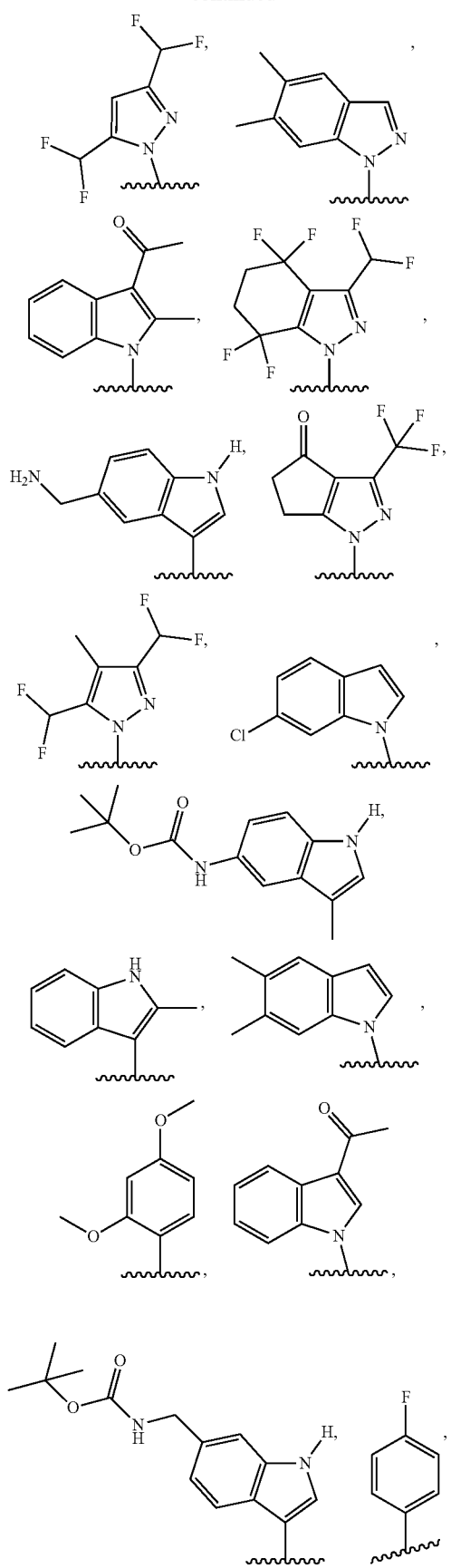
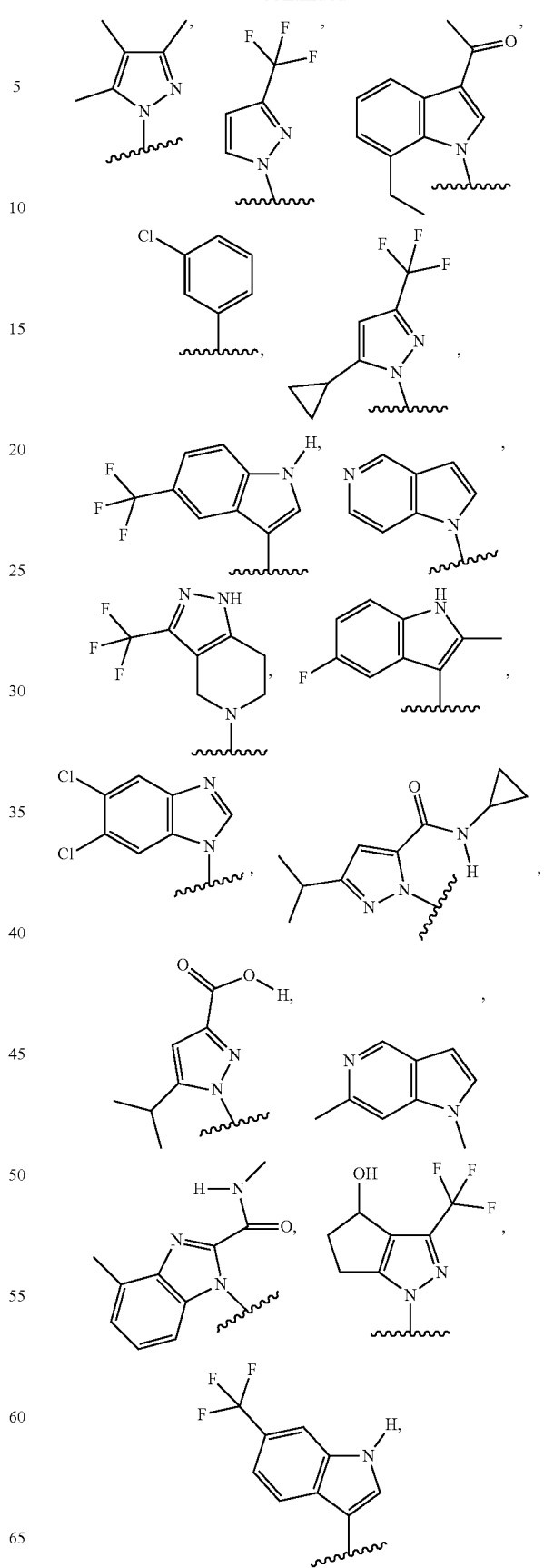

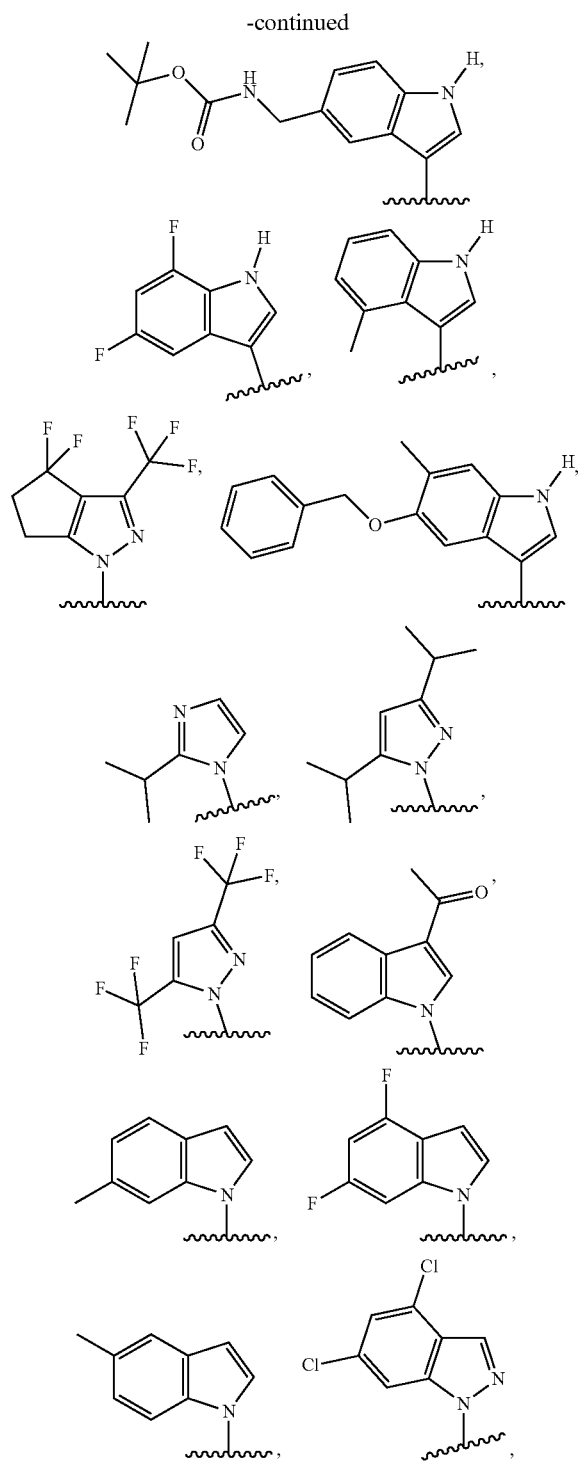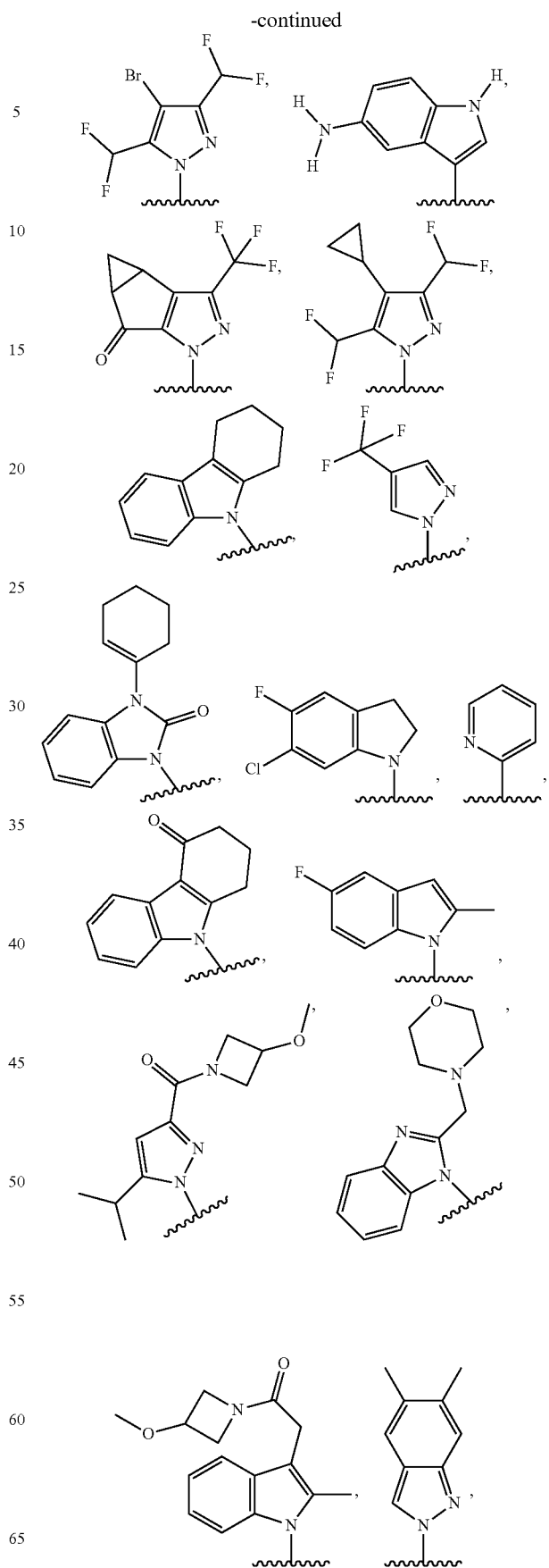

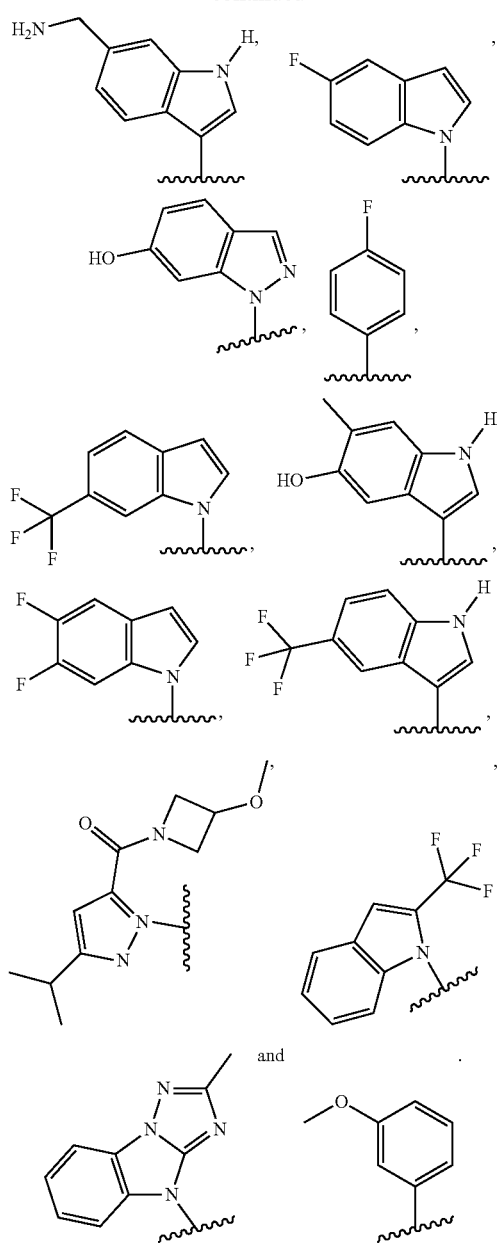
Another specific value for $R^1$ is:
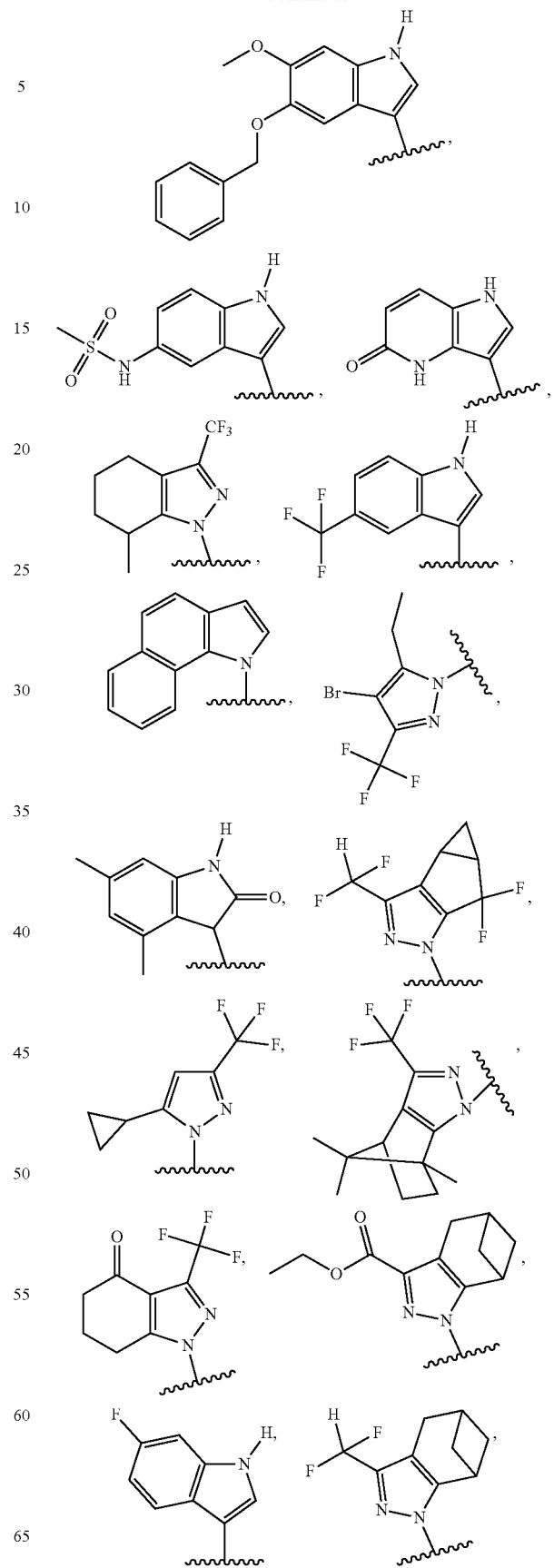

-continued
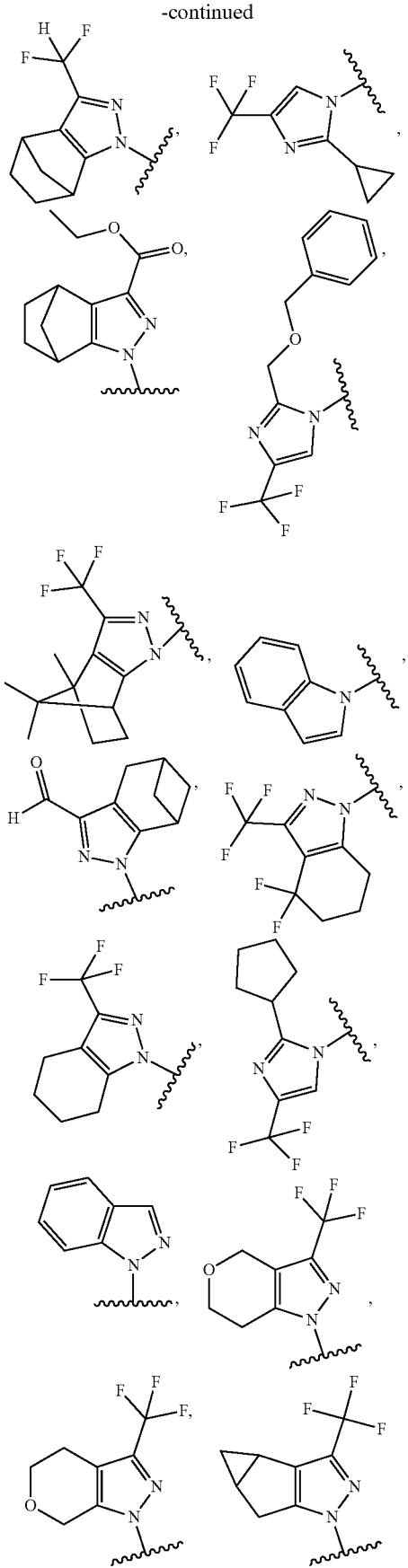
-continued
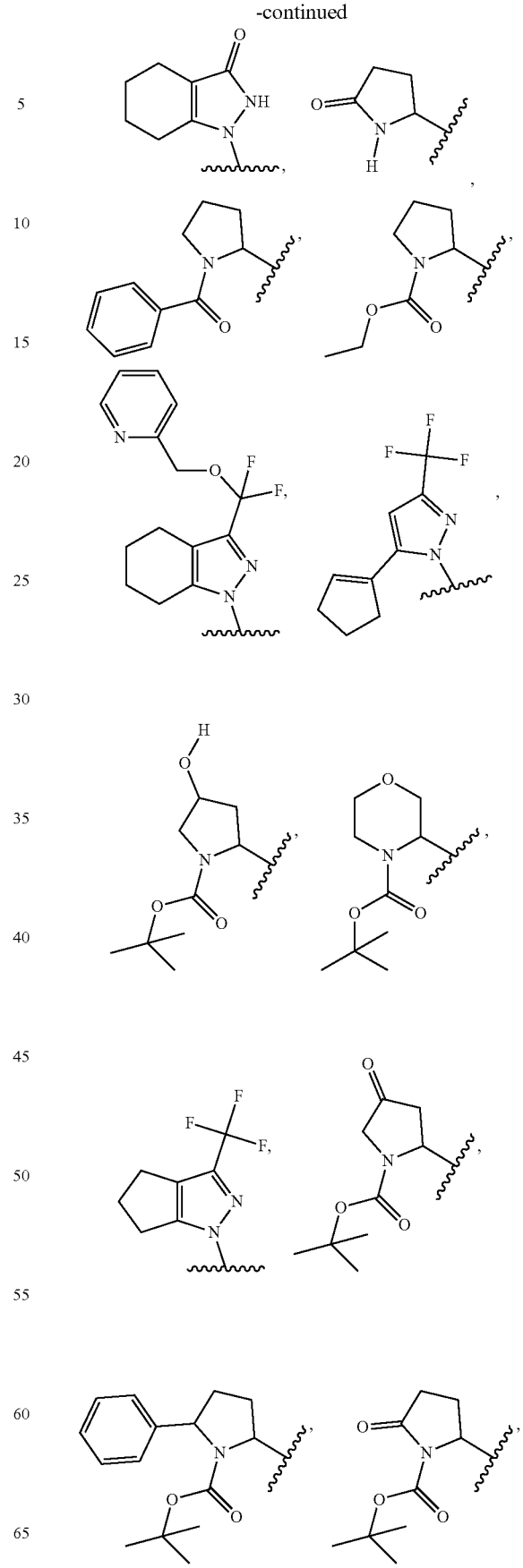

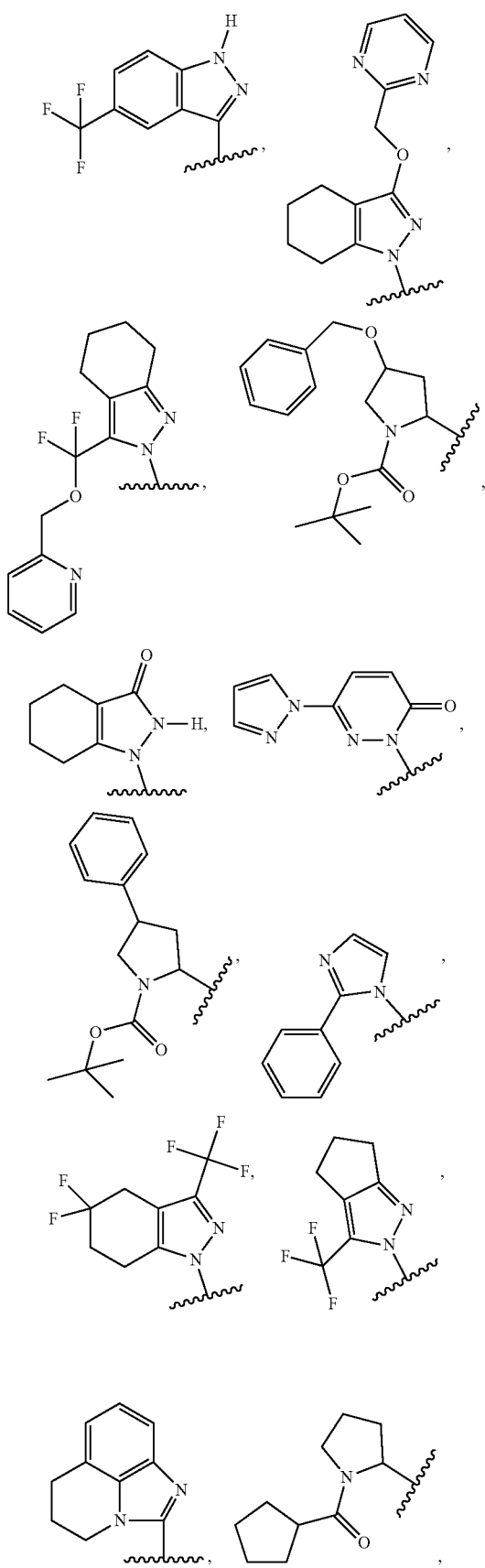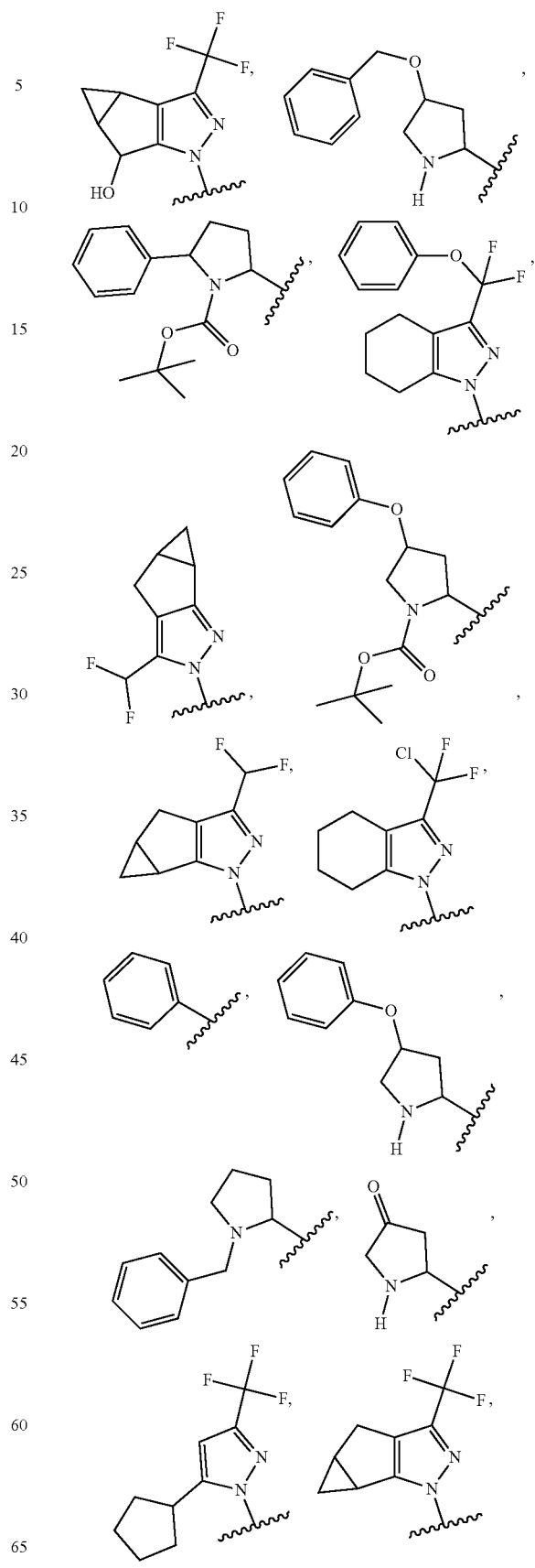

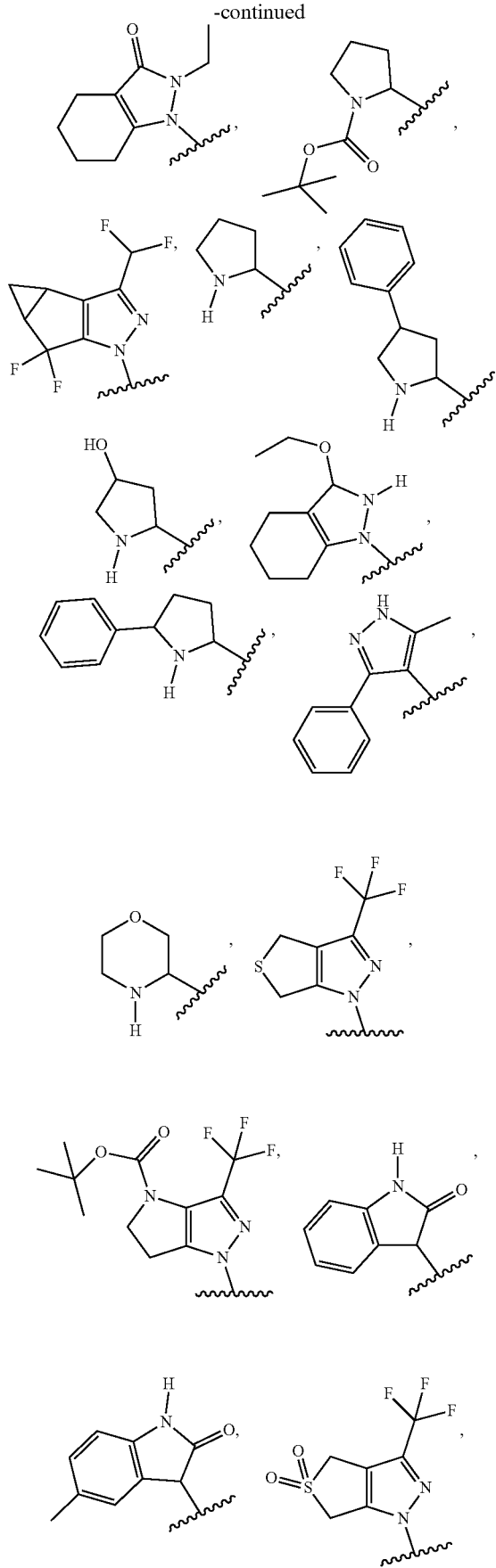
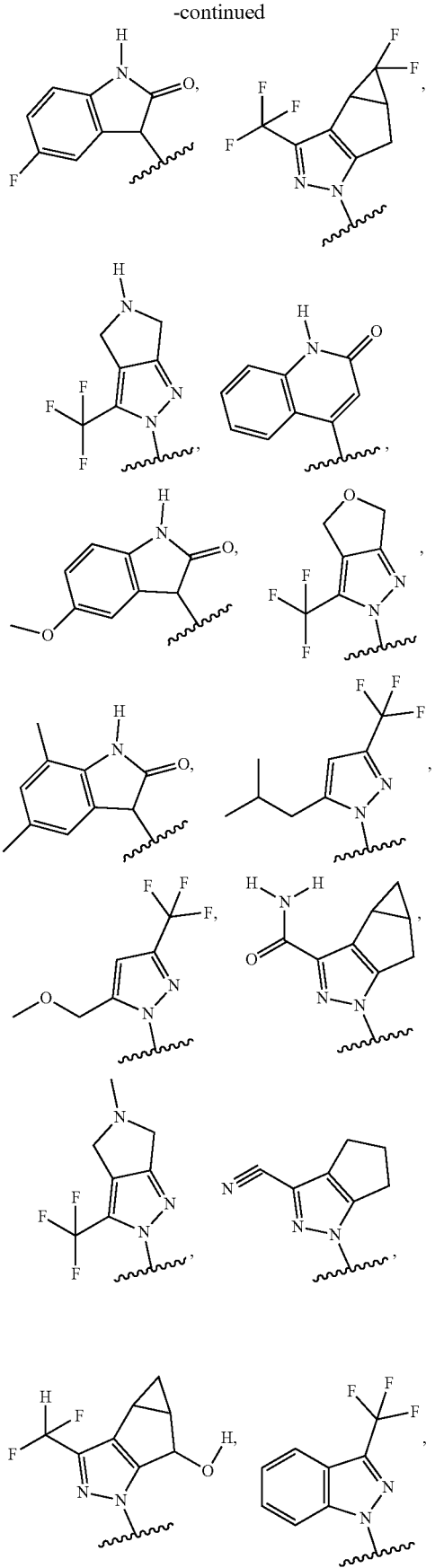

-continued
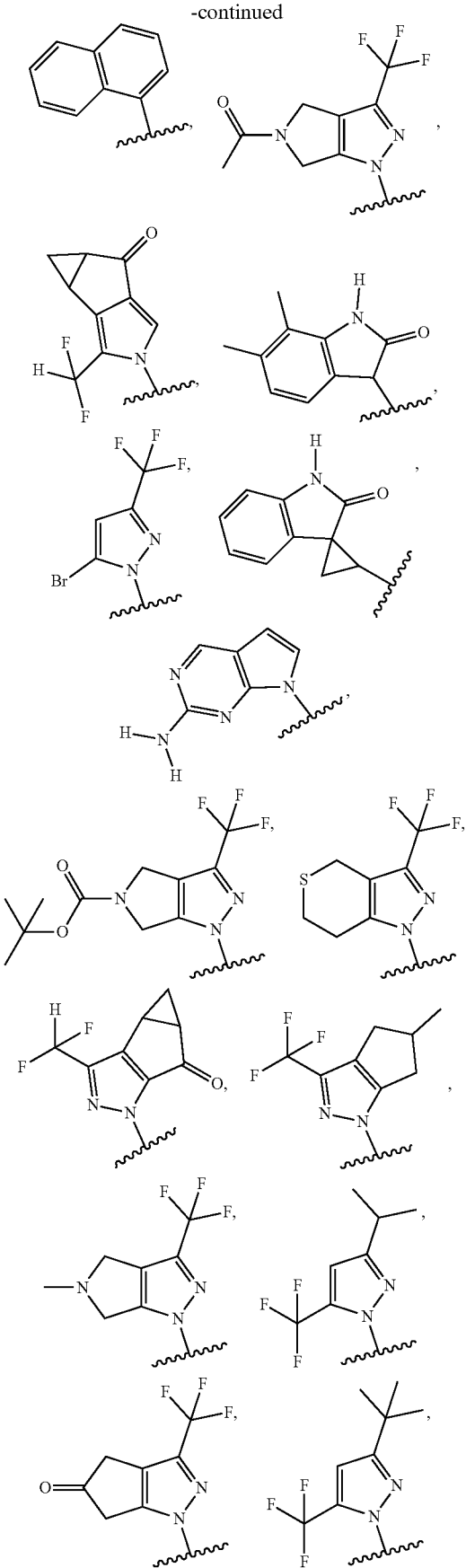
-continued
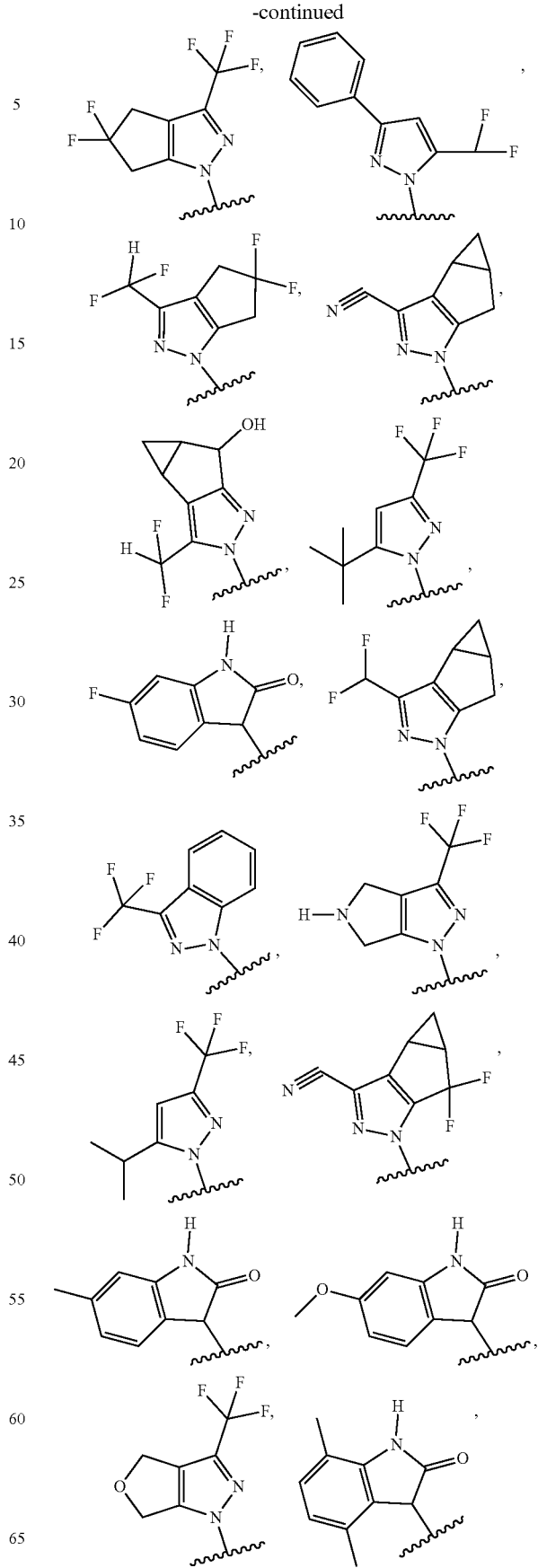

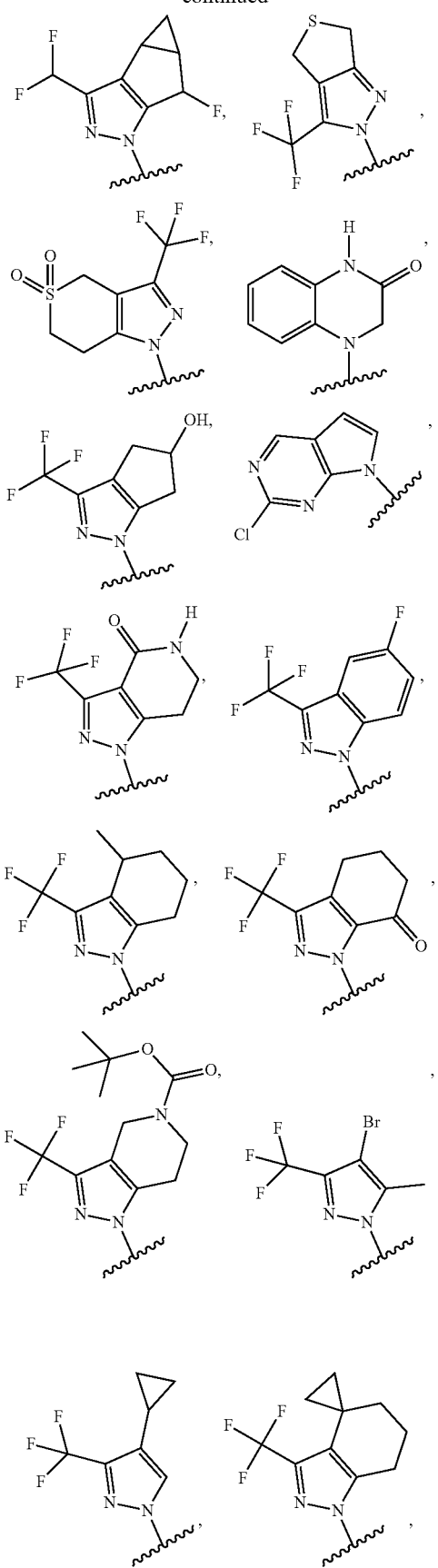
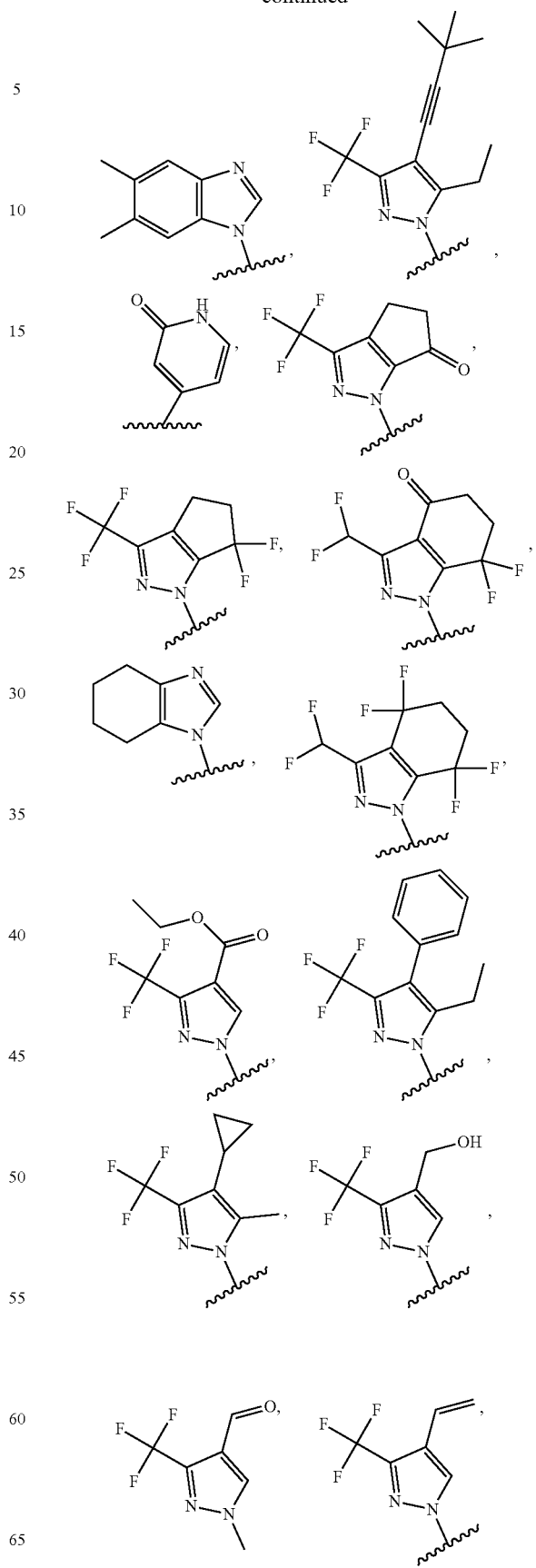

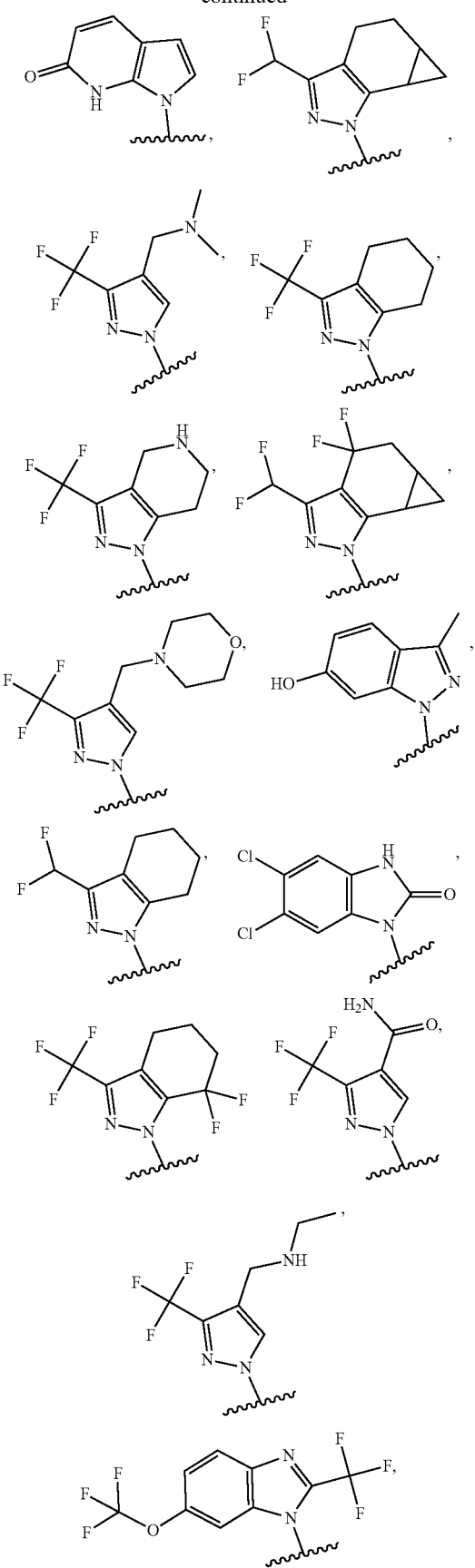
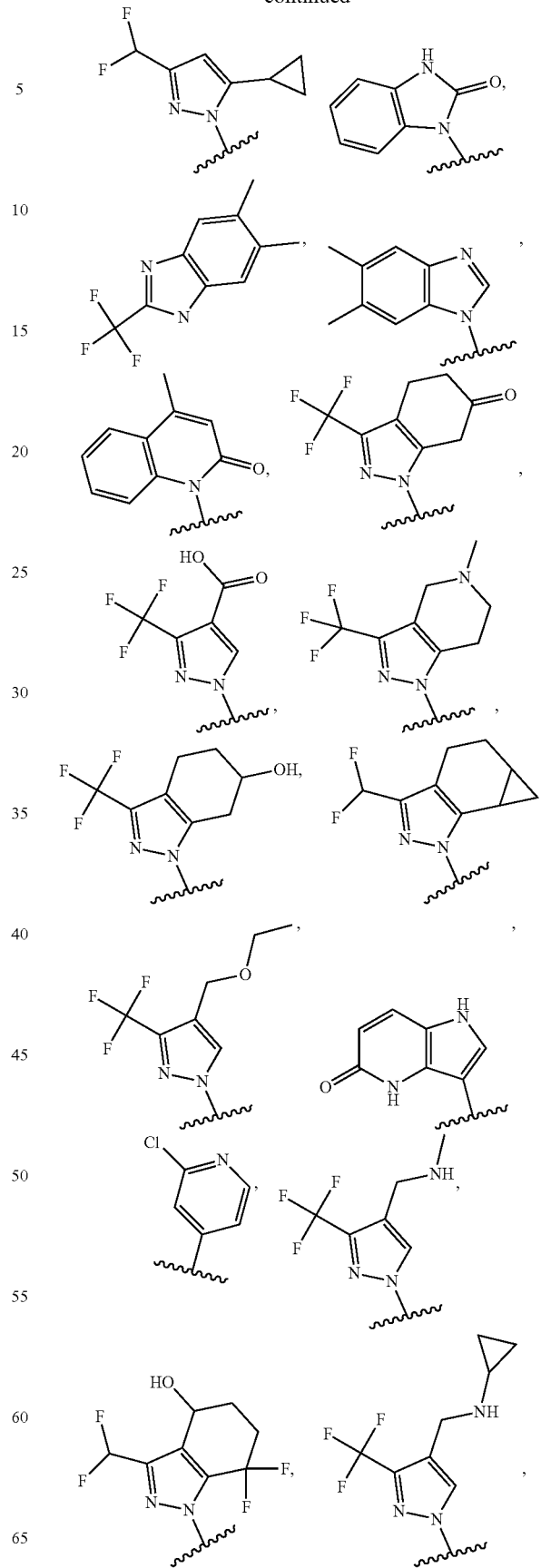

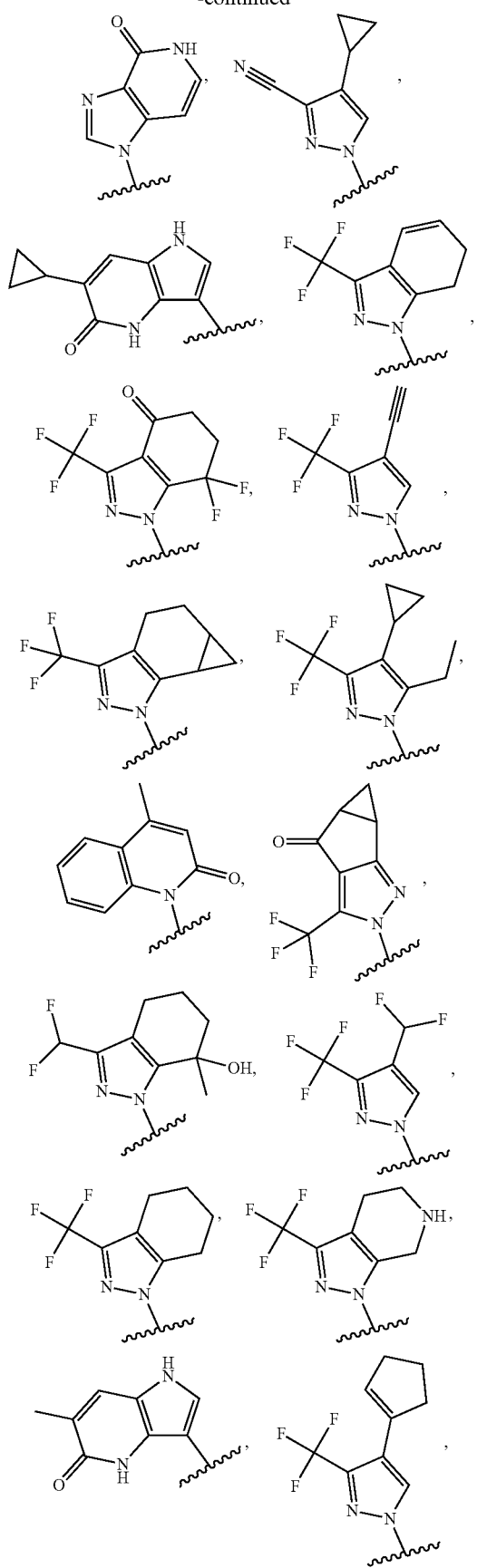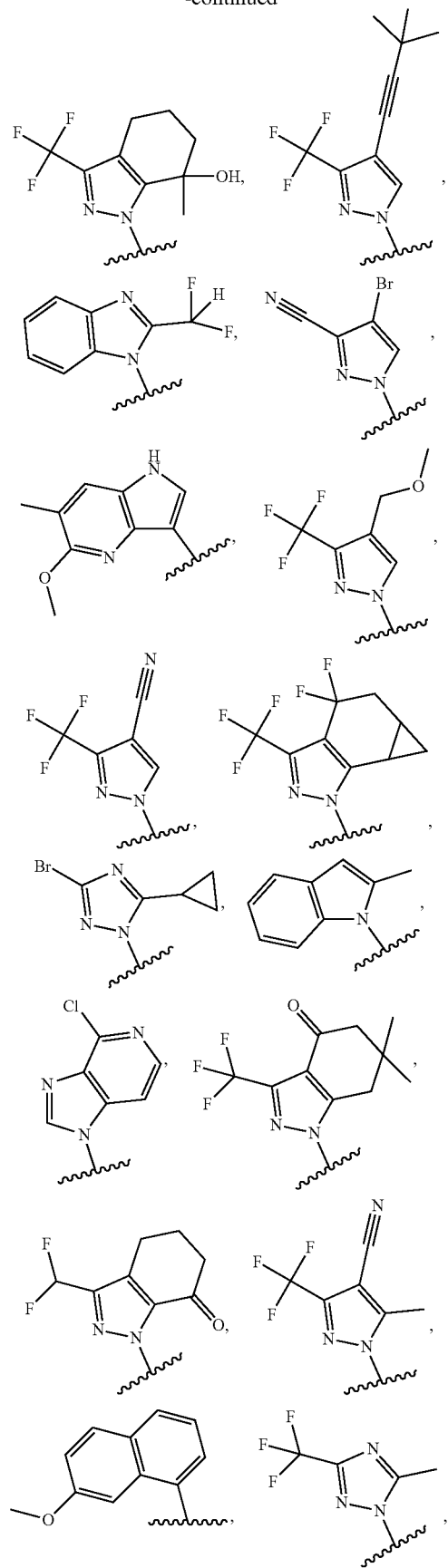

-continued
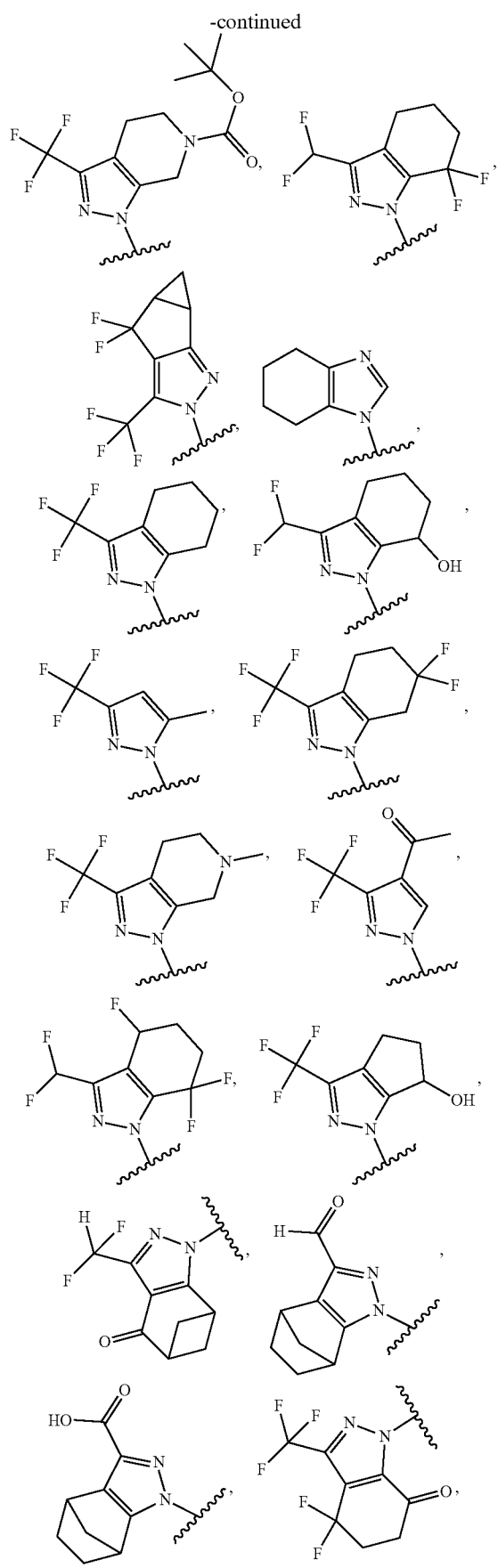 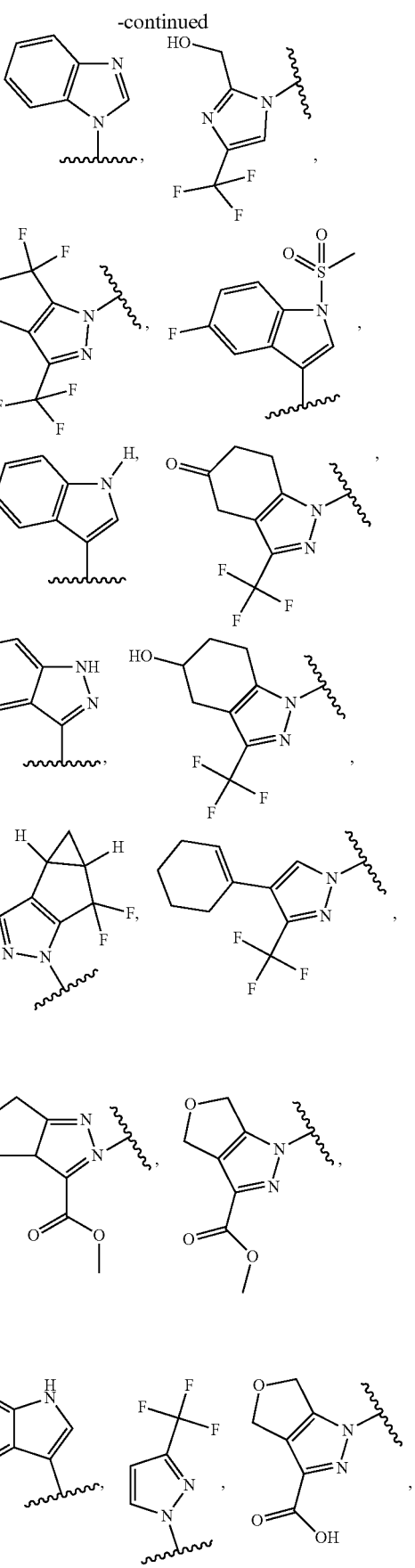

-continued
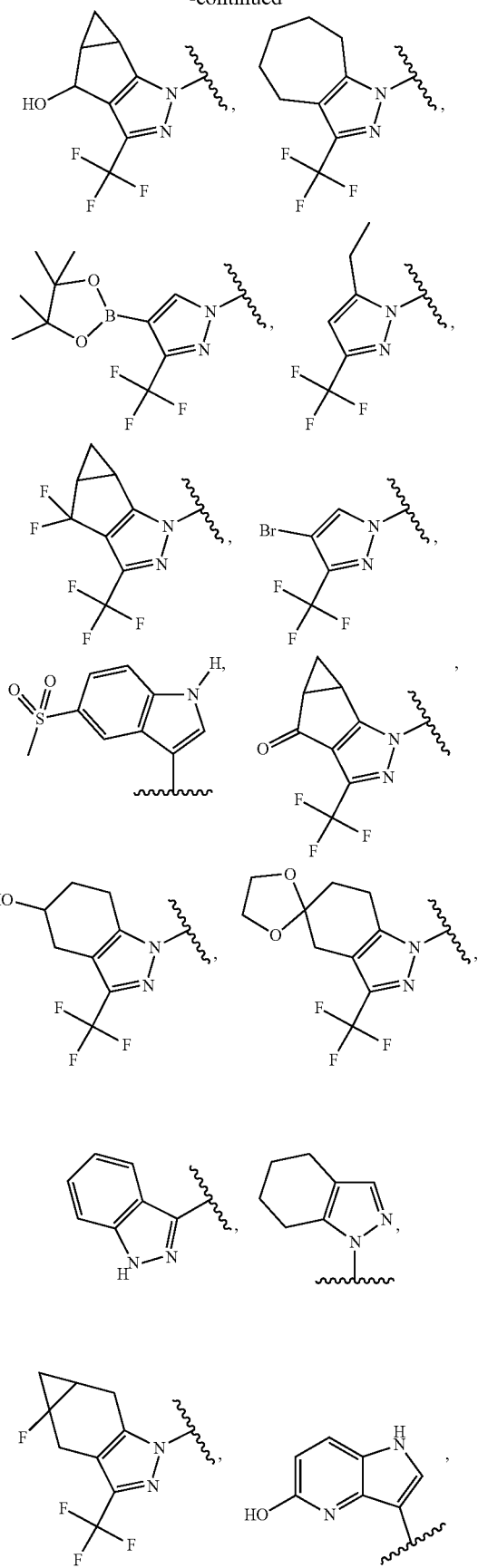
-continued
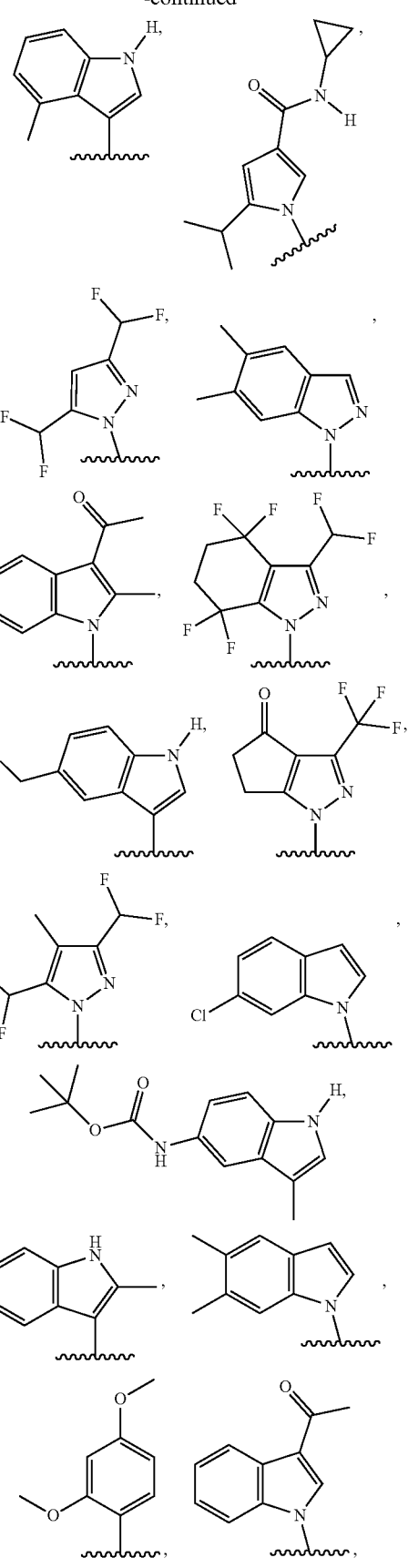

75
-continued
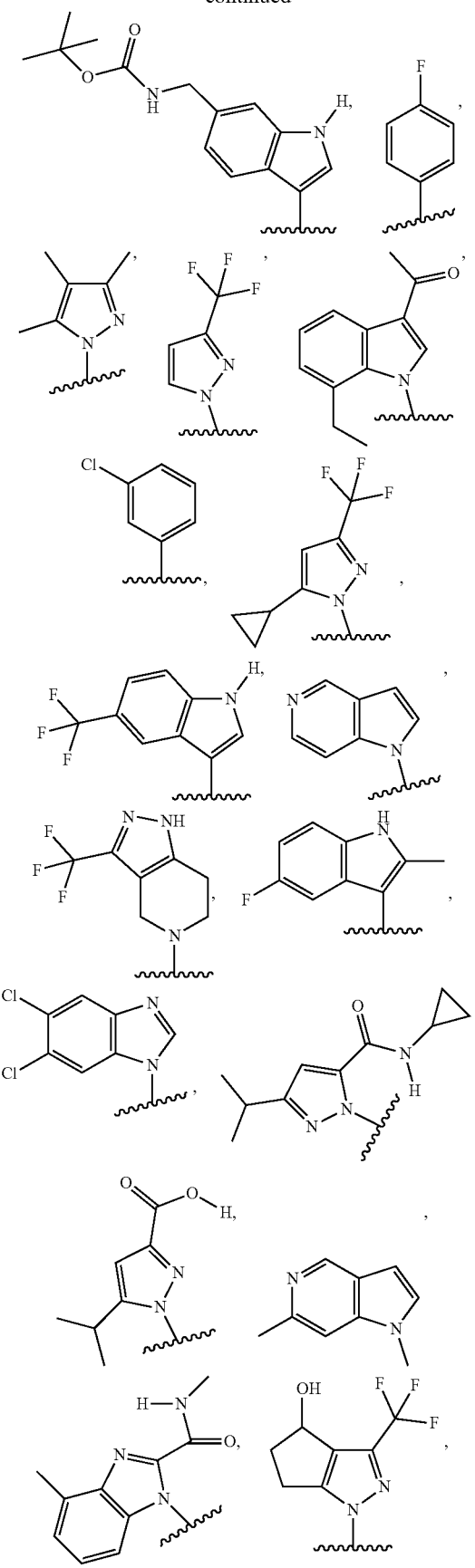
76
-continued
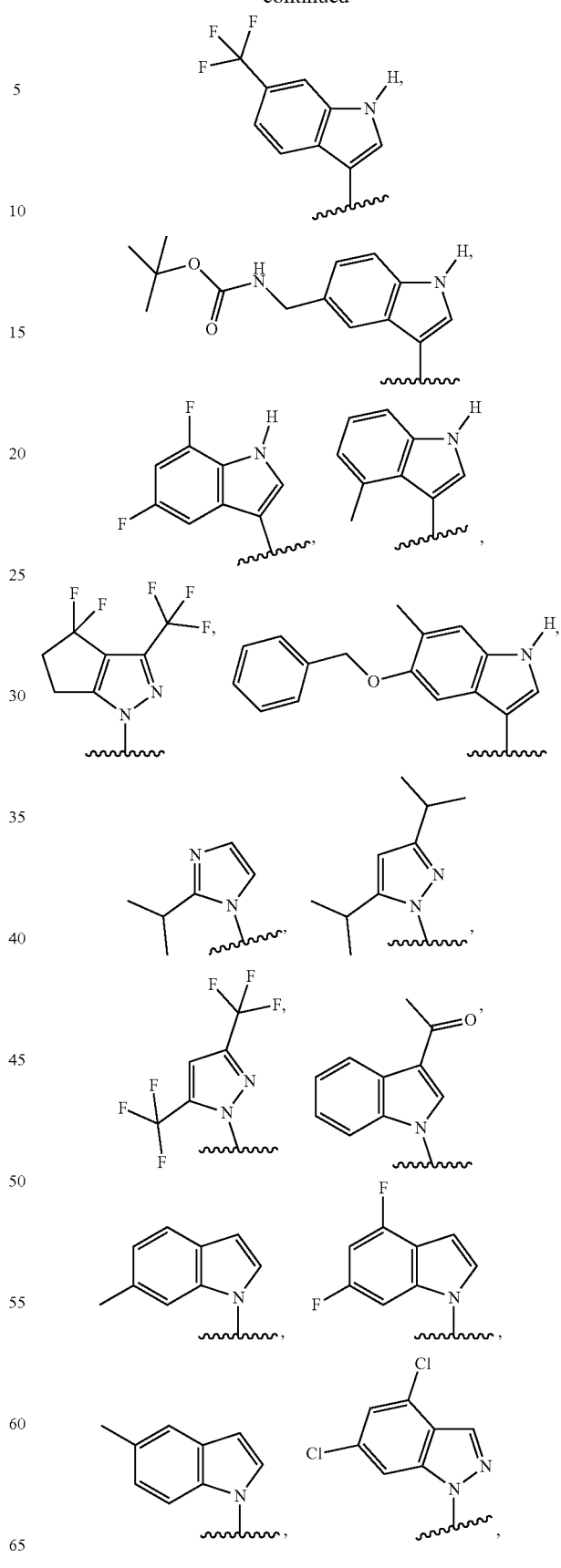

-continued
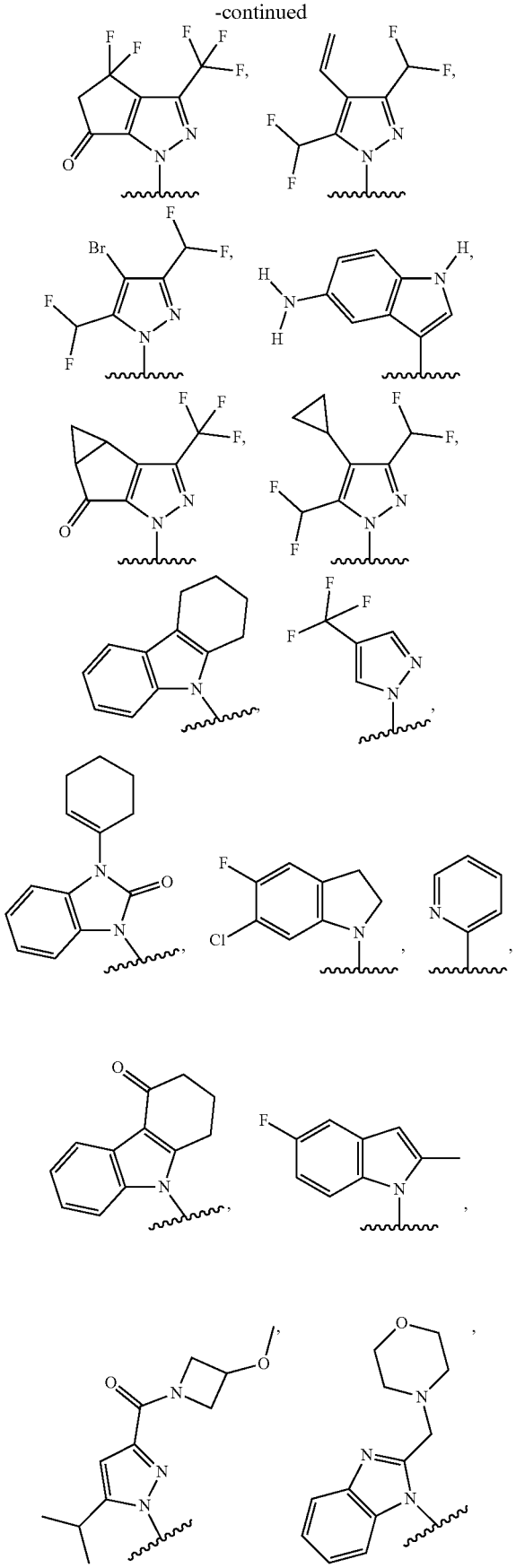
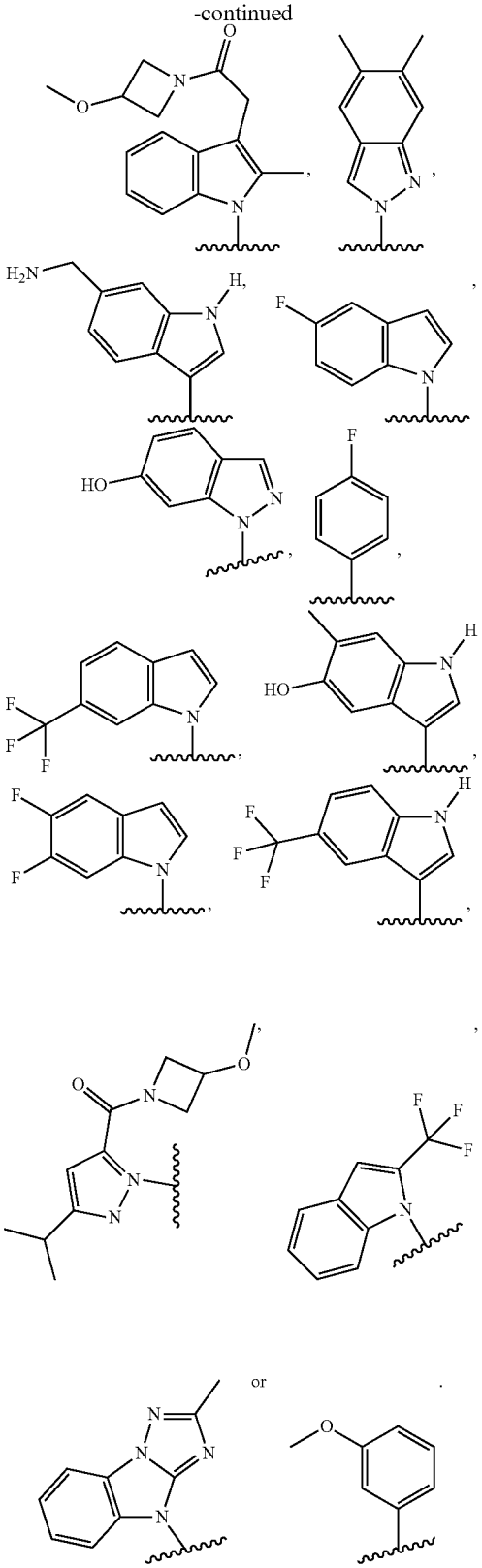
A specific value for A is pyridinyl, pyrimidinyl, pyrazinyl or pyridazinyl, wherein any pyridinyl, pyrimidinyl, pyrazinyl, or pyridazinyl of A is substituted with one $Z^1$ group and optionally substituted with one or more $Z^2$ groups.

Another specific value for A is:

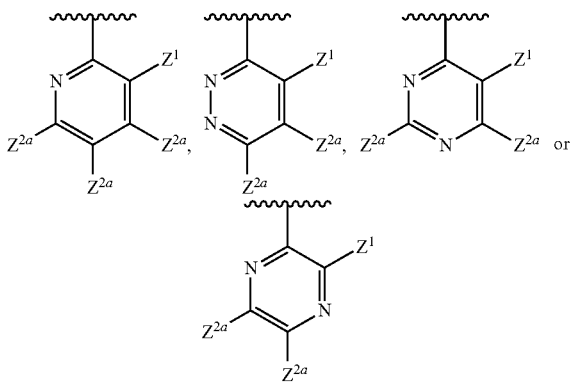

wherein each $Z^{2a}$ is independently selected from H and $Z^2$.

Another specific value for A is:

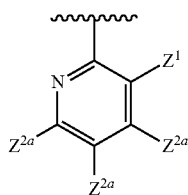

wherein each $Z^{2a}$ is independently selected from H and $Z^2$.

Another specific value for A is:

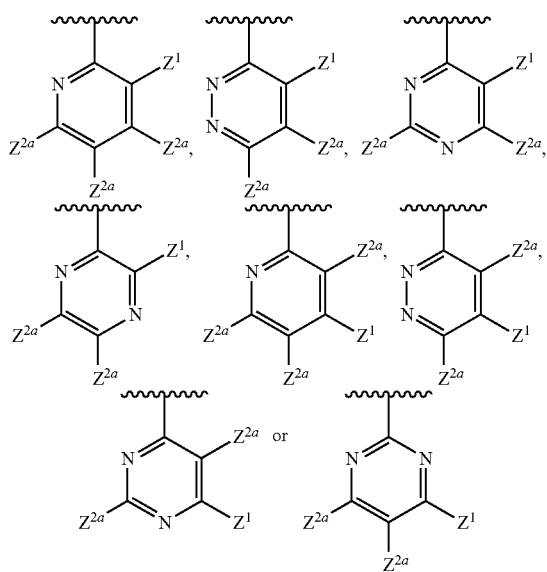

wherein each $Z^{2a}$ is independently selected from H and $Z^2$.

A specific value for $Z^{2a}$ is H.

A specific value for $Z^1$ is $(C_2-C_8)$alkynyl, $(C_3-C_7)$carbocycle, aryl, heteroaryl or heterocycle, wherein any $(C_3-C_7)$carbocycle, aryl, heteroaryl or heterocycle of $Z^1$ is optionally substituted with one or more $Z^{1a}$ or $Z^{1b}$ groups and wherein any $(C_2-C_8)$alkynyl of $Z^1$ is optionally substituted with one or more $Z^{1a}$ groups.

Another specific value for $Z^1$ is ethynyl, cyclohexyl, phenyl, pyridyl, thiophenyl, isoquinolinyl, 1,2,3,4-tetrahydroisoquinolinyl, indazolyl or isoindolin-1-one, wherein any cyclohexyl, phenyl, pyridyl, thiophenyl, isoquinolinyl, 1,2,3,4-tetrahydroisoquinolinyl, indazolyl or isoindolin-1-one of $Z^1$ is optionally substituted with one or more $Z^{1a}$ or $Z^{1b}$ groups, and wherein any ethynyl of $Z^1$ is optionally substituted with one or more $Z^{1a}$ groups.

Another specific value for $Z^1$ is $(C_2-C_8)$alkynyl or aryl, wherein any aryl of $Z^1$ is optionally substituted with one or more $Z^{1a}$ or $Z^{1b}$ groups and wherein any $(C_2-C_8)$alkynyl of $Z^1$ is optionally substituted with one or more $Z^{1a}$ groups.

Another specific value for $Z^1$ is ethynyl or phenyl, wherein any phenyl of $Z^1$ is optionally substituted with one or more $Z^{1a}$ or $Z^{1b}$ groups, and wherein any ethynyl of $Z^1$ is optionally substituted with one or more $Z^{1a}$ groups.

Another specific value for $Z^1$ is $(C_2-C_8)$alkynyl, $(C_3-C_7)$carbocycle, aryl, heteroaryl or heterocycle, wherein any $(C_3-C_7)$carbocycle, aryl, heteroaryl, or heterocycle of $Z^1$ is optionally substituted with one or more $Z^{1a}$ or $Z^{1b}$ groups and wherein any $(C_2-C_8)$alkynyl of $Z^1$ is optionally substituted with one or more $Z^{1a}$ groups.

Another specific value for $Z^1$ is $(C_2-C_8)$alkynyl, aryl, heteroaryl or heterocycle, wherein any aryl, heteroaryl, or heterocycle of $Z^1$ is optionally substituted with one or more $Z^{1a}$ or $Z^{1b}$ groups and wherein any $(C_2-C_8)$alkynyl of $Z^1$ is optionally substituted with one or more Z a groups.

Another specific value for $Z^1$ is aryl, heteroaryl or heterocycle, wherein any aryl, heteroaryl, or heterocycle of $Z^1$ is optionally substituted with one or more $Z^{1a}$ or $Z^{1b}$ groups.

A specific value for $Z^{1a}$ is $(C_3-C_7)$carbocycle, heteroaryl, heterocycle, halogen, —CN, —$OR_{n2}$, —$S(O)_2NR_{q2}R_{r2}$, —$NR_{q2}R_{r2}$, —$C(O)R_{n2}$, —$C(O)NR_{p2}R_{q2}$ or —$C(=NOR_{n2})$CN, wherein any $(C_3-C_7)$carbocycle, heteroaryl or heterocycle of $Z^{1a}$ is optionally substituted with one or more $Z^{1c}$ or $Z^{1d}$ groups, and each $Z^{1b}$ is independently selected from $(C_1-C_8)$alkyl, wherein any $(C_1-C_8)$alkyl of $Z^{1b}$ is optionally substituted with one or more $Z^{1c}$ groups.

Another specific value for $Z^{1a}$ is cyclopropyl, N-ethyl-3-amine-oxetan-3-yl, N-ethyl-1amine-2,2,2-trifluoroethanyl, triazol-1-yl, tetrazol-5-yl, 3-trifluoromethylisoxazol-5-yl, 2-carboxy-ethyl, 2-morpholinoethoxy, fluoro, chloro, —CN, methoxy, —$S(O)_2NH_2$, —$C(=NOCH_3)CN$, —$C(O)NH_2$, —$C(O)N(CH_3)_2$ or —$C(O)NH(CH_3)$, and wherein each $Z^{1b}$ is methyl.

Another specific value for $Z^{1a}$ is aryl, heteroaryl, heterocycle, $(C_3-C_7)$carbocycle, halogen, CN, —$OR_{n2}$, —$S(O)_2R_{p2}$, —$S(O)_2NR_{q2}R_{r2}$, —$NR_{q2}R_{r2}$, —$NR_{n2}COR_{p2}$, —$NR_{n2}CO_2R_{p2}$, —$NR_{n2}CONR_{q2}R_{r2}$, —$NR_{n2}S(O)_2R_{p2}$, —$C(O)R_{n2}$ and —$C(O)NR_{q2}R_{r2}$, wherein any aryl, heteroaryl, heterocycle and $(C_3-C_7)$carbocycle of $Z^{1a}$ is optionally substituted with one or more (e.g. 1, 2, 3, 4 or 5) $Z^{1c}$ or $Z^{1d}$ groups; and each $Z^{1b}$ is independently selected from $(C_1-C_8)$alkyl and $(C_2-C_8)$alkynyl, wherein any $(C_1-C_8)$alkyl and $(C_2-C_8)$alkynyl of $Z^{1b}$ is optionally substituted with one or more (e.g. 1, 2, 3, 4 or 5) $Z^{1c}$ groups.

Another specific value for $Z^{1a}$ is aryl, heteroaryl, heterocycle, halogen, CN, —$OR_{n2}$, —$S(O)_2R_{p2}$, —$S(O)_2NR_{q2}R_{r2}$, —$NR_{q2}R_{r2}$, —$NR_{n2}COR_{p2}$, —$NR_{n2}CO_2R_{p2}$, —$NR_{n2}CONR_{q2}R_{r2}$, —$NR_{n2}S(O)_2R_{p2}$, —$C(O)R_{n2}$ and —$C(O)NR_{q2}R_{r2}$, wherein any aryl, heteroaryl, heterocycle and $(C_3-C_7)$carbocycle of $Z^{1a}$ is optionally substituted with one or more (e.g. 1, 2, 3, 4 or 5) $Z^{1c}$ or $Z^{1d}$ groups; and each $Z^{1b}$ is independently selected from $(C_1-C_8)$alkyl and $(C_2-C_8)$alkynyl, wherein any $(C_1-C_8)$alkyl and $(C_2-C_8)$alkynyl of $Z^{1b}$ is optionally substituted with one or more (e.g. 1, 2, 3, 4 or 5) $Z^{1c}$ groups.

A specific value for $Z^1$ is:
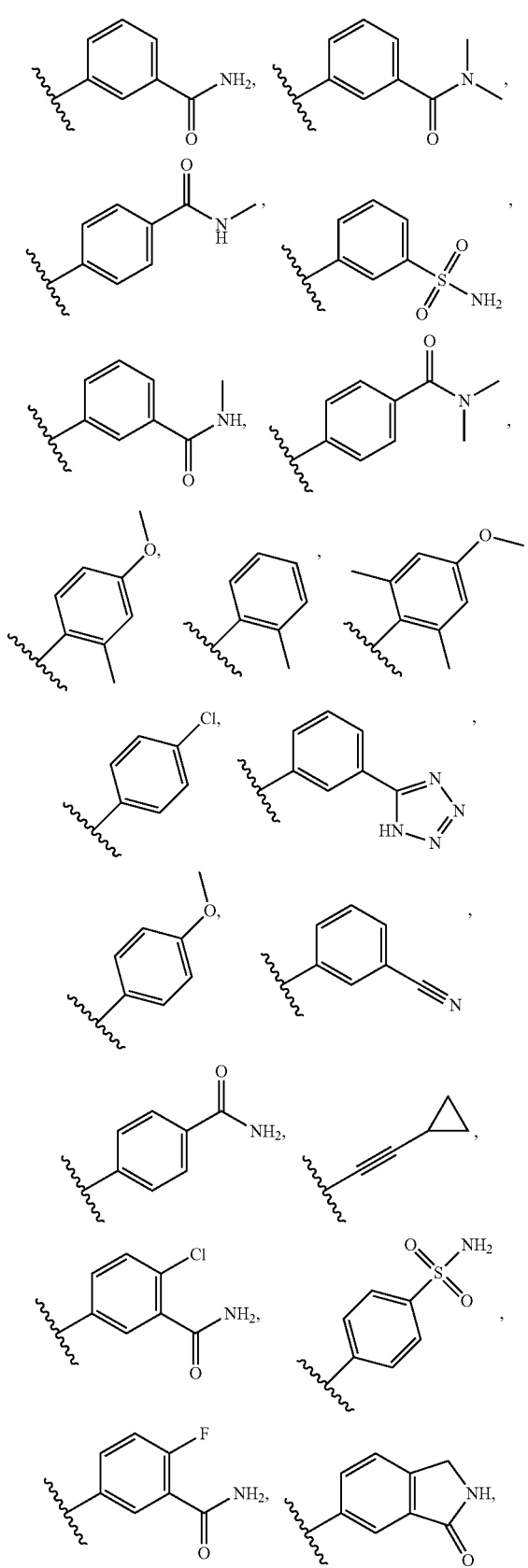
-continued
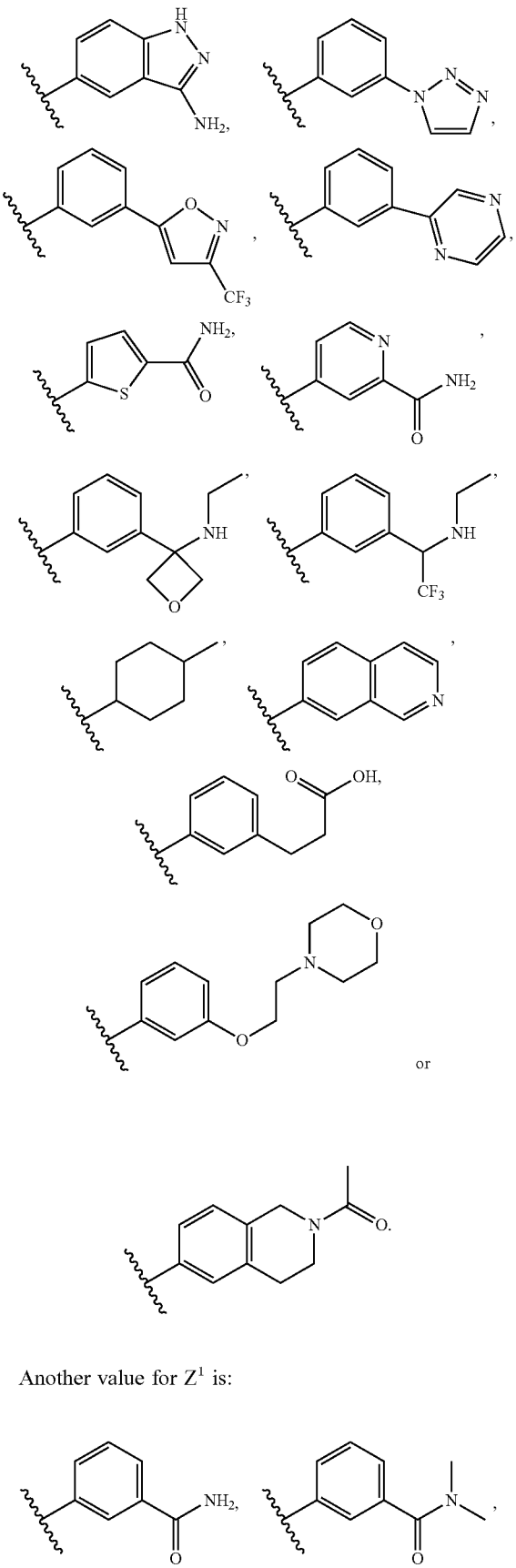
Another value for $Z^1$ is:

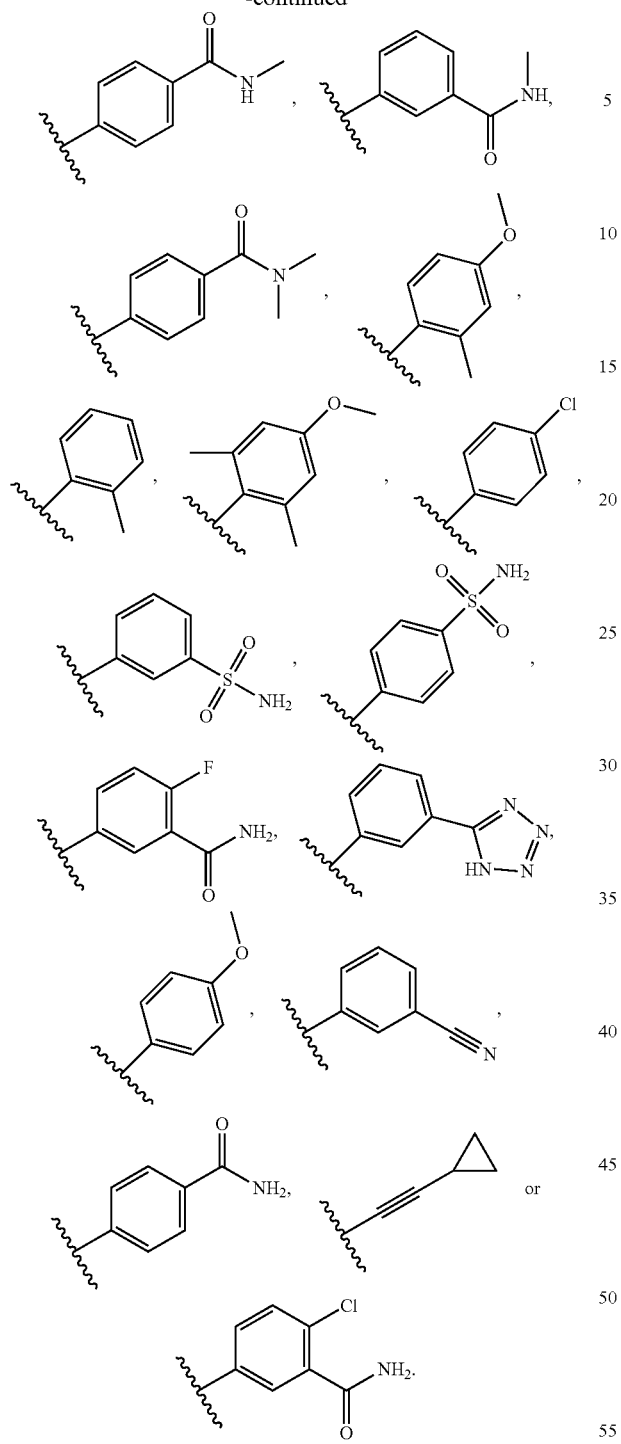
A specific value for A is:
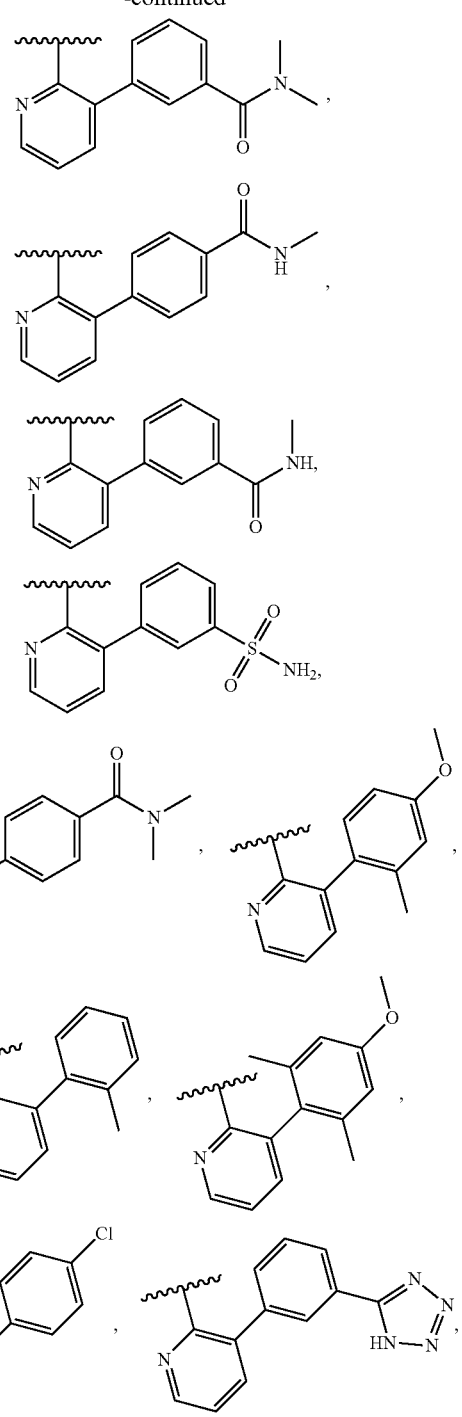
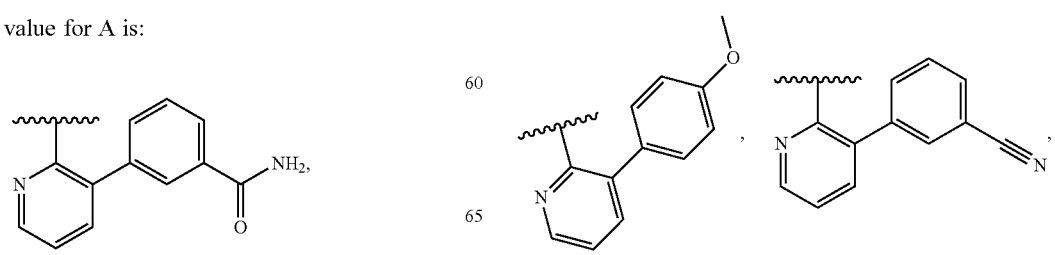

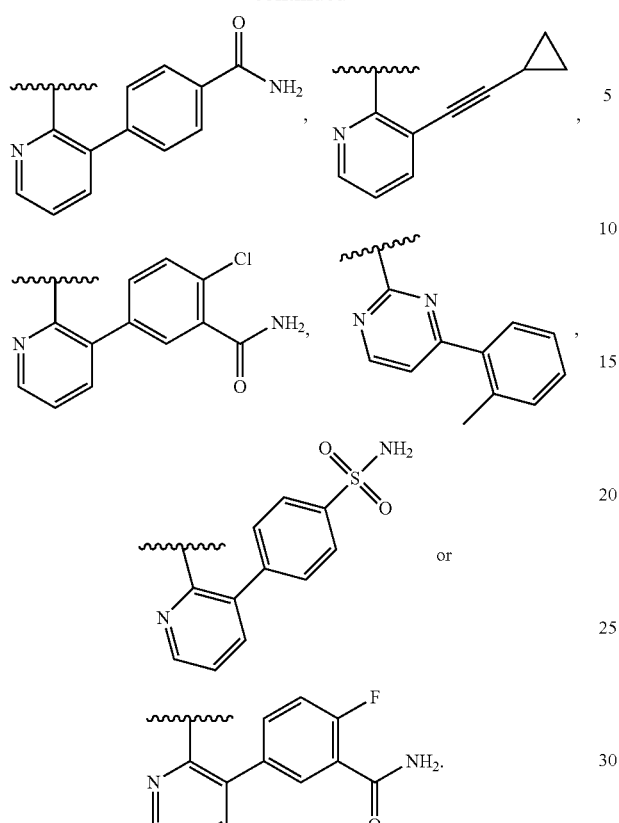
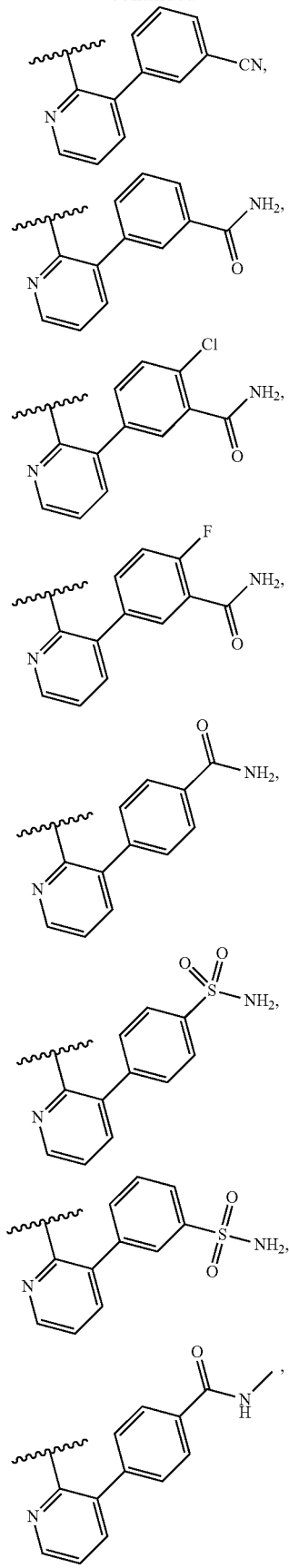
Another specific value for A is:
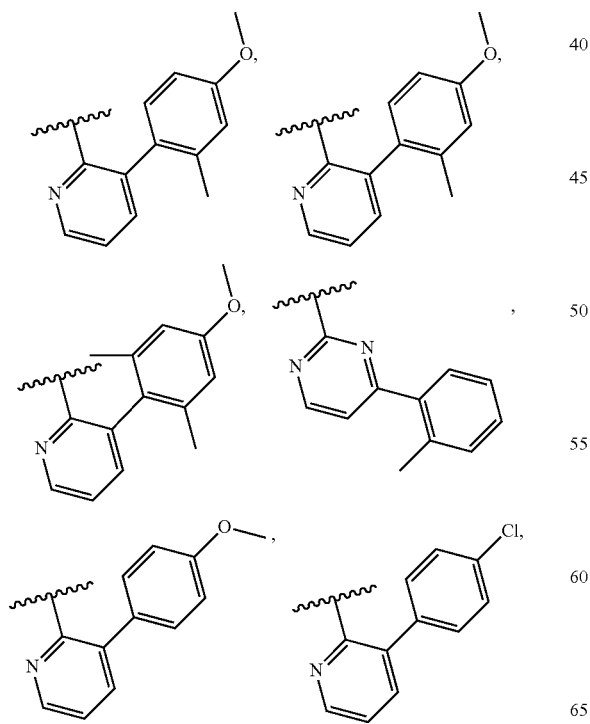

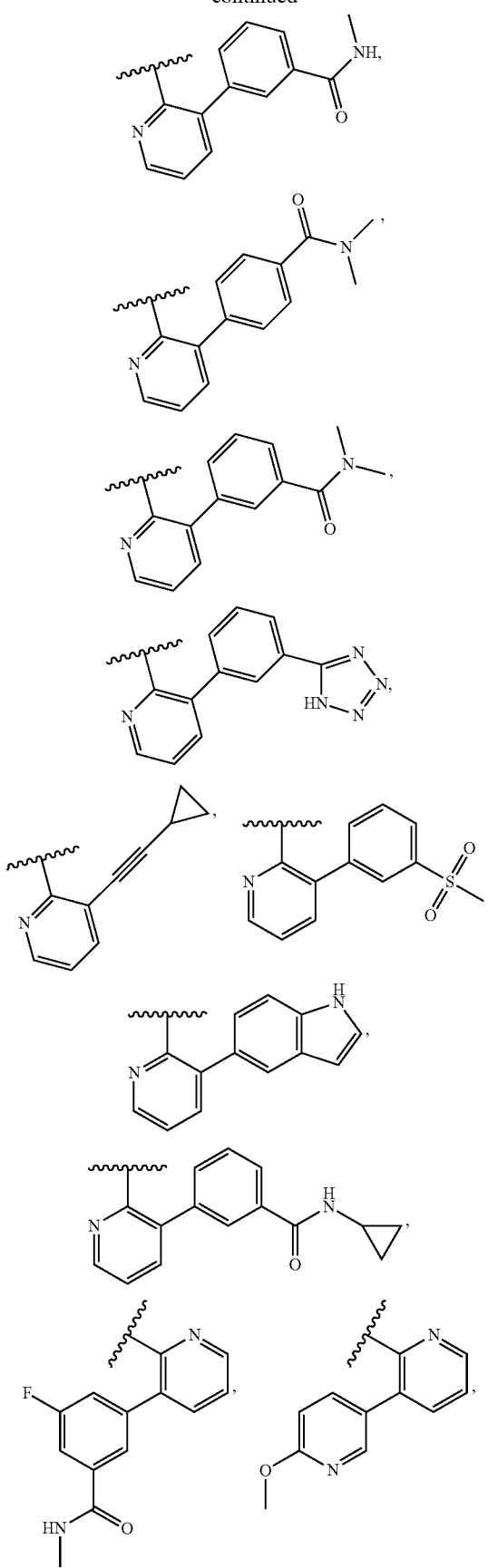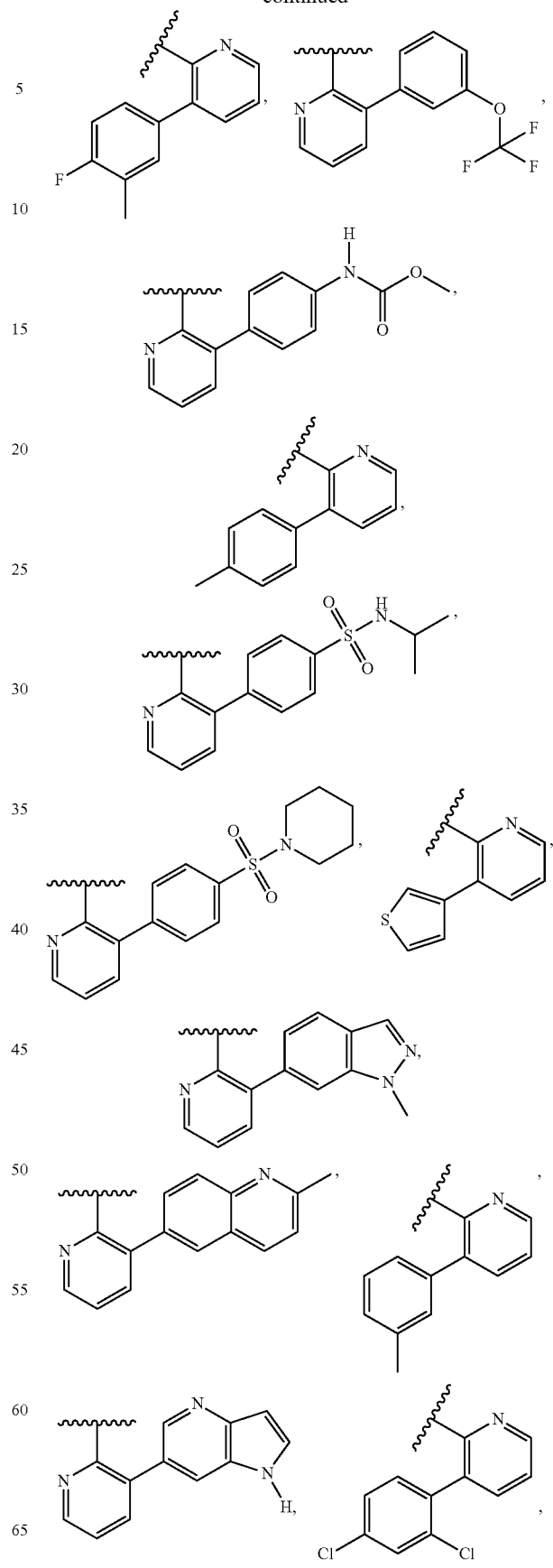

89
-continued
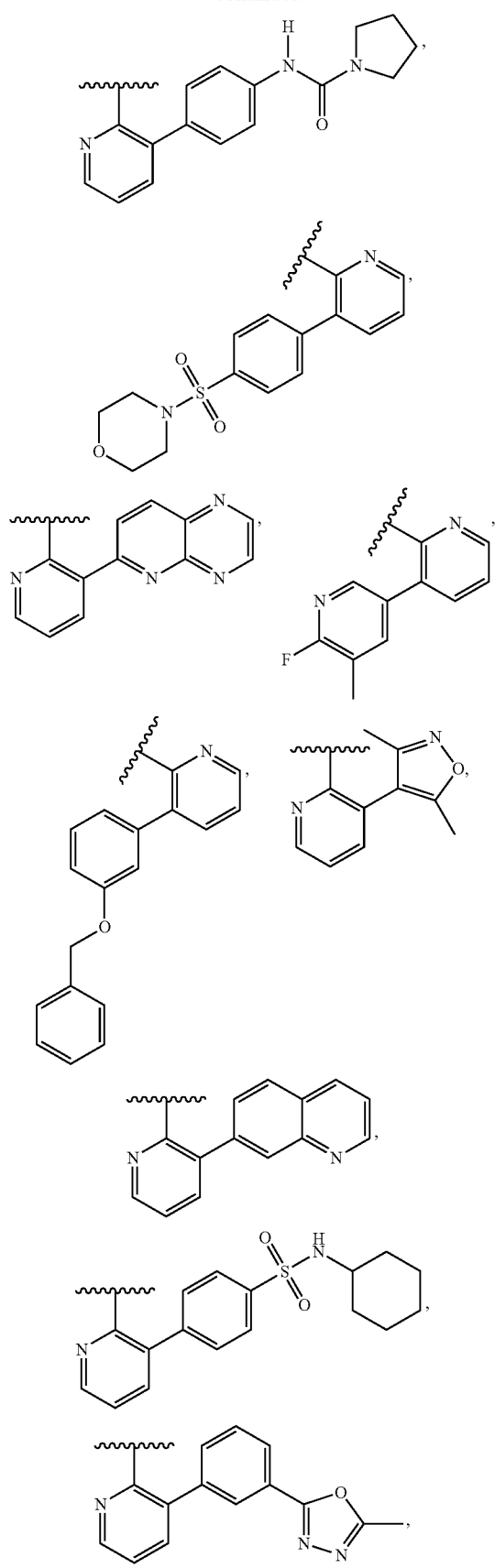
90
-continued
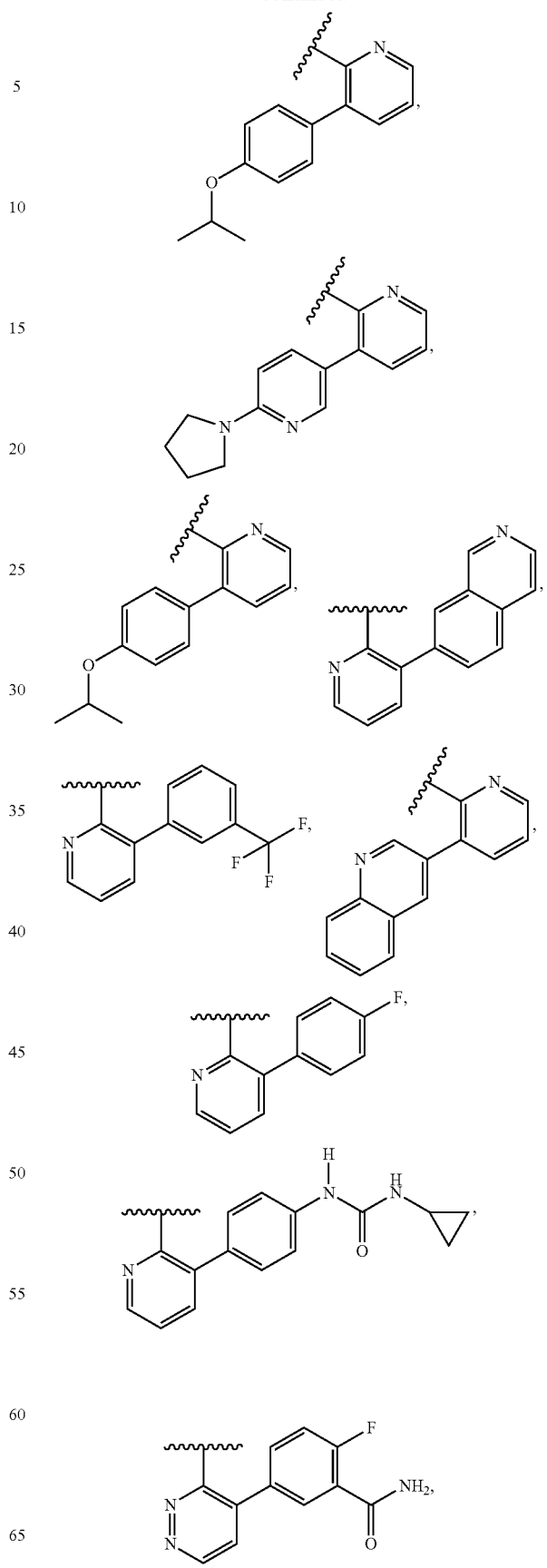

-continued
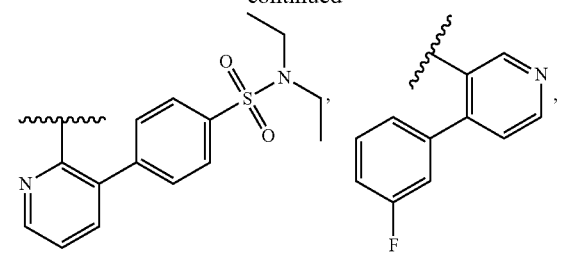
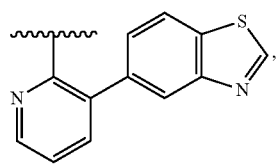
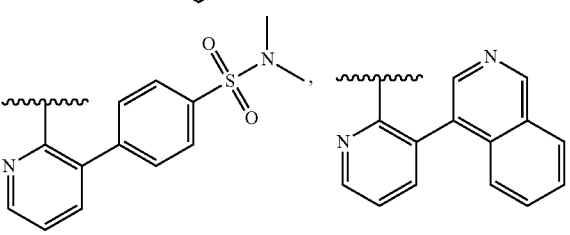
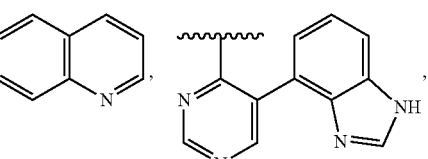
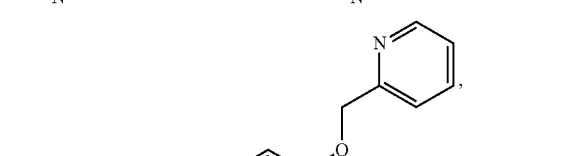
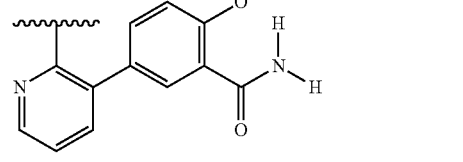
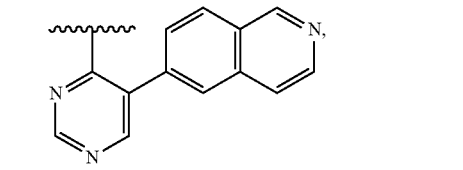
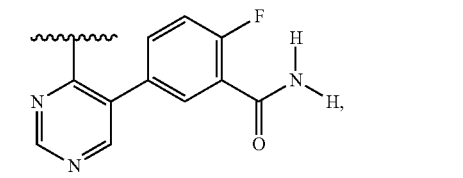
-continued
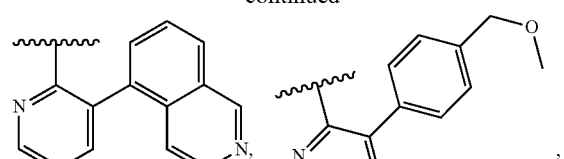
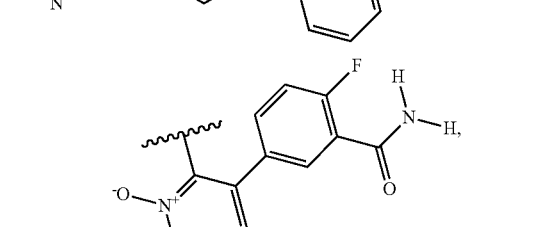
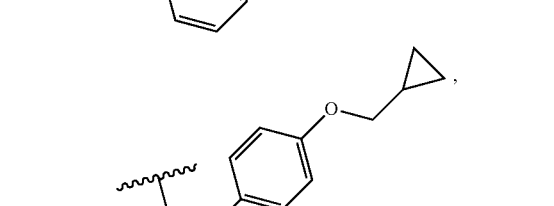
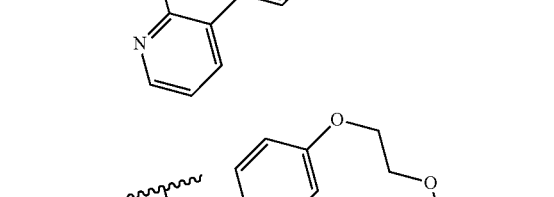
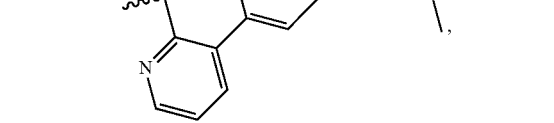
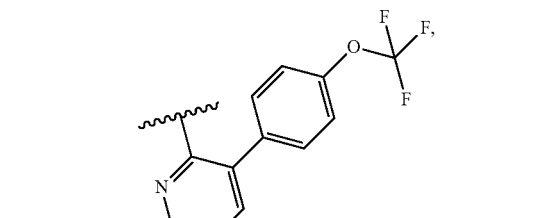
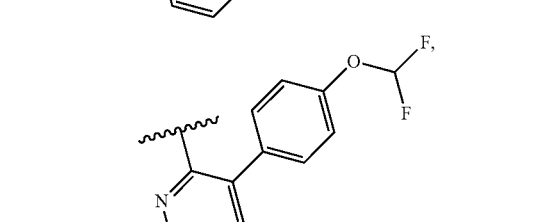
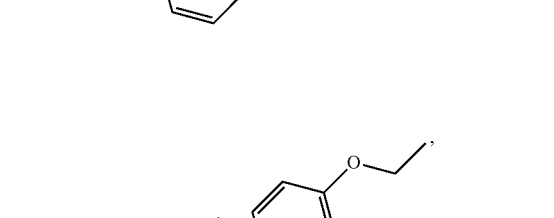
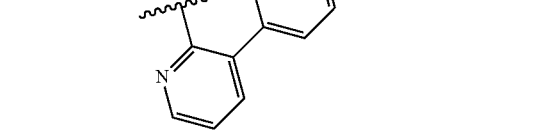

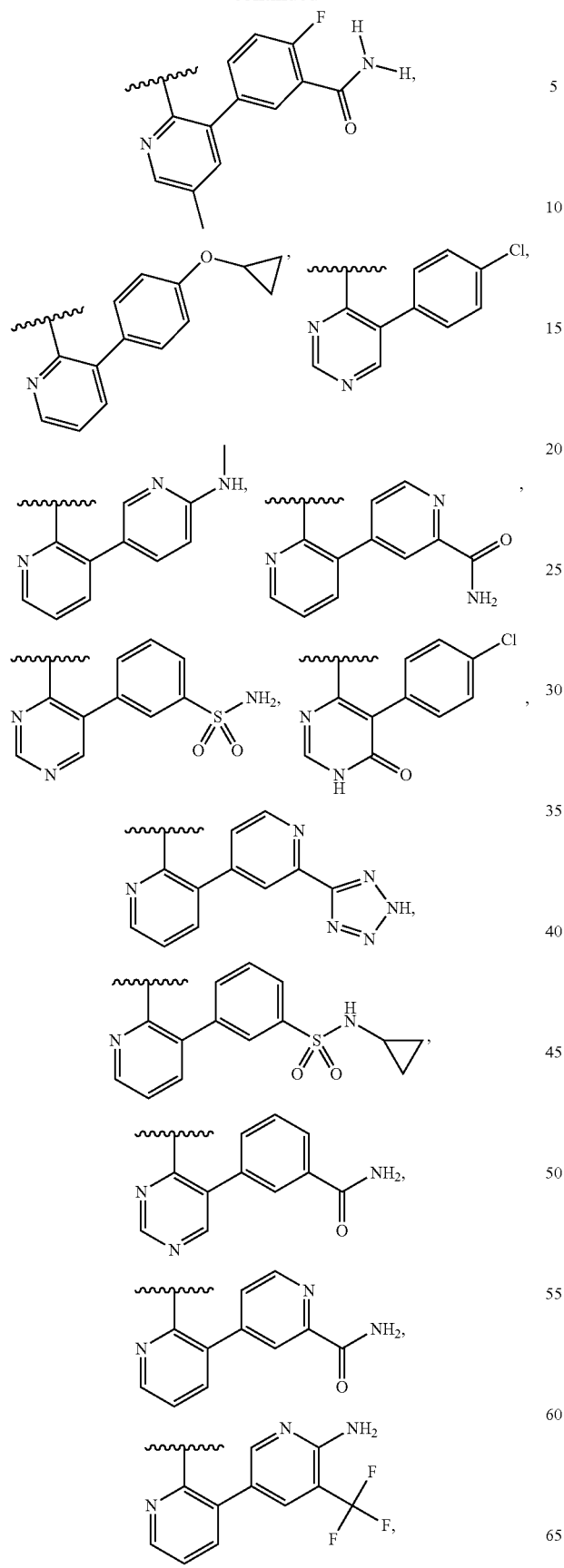
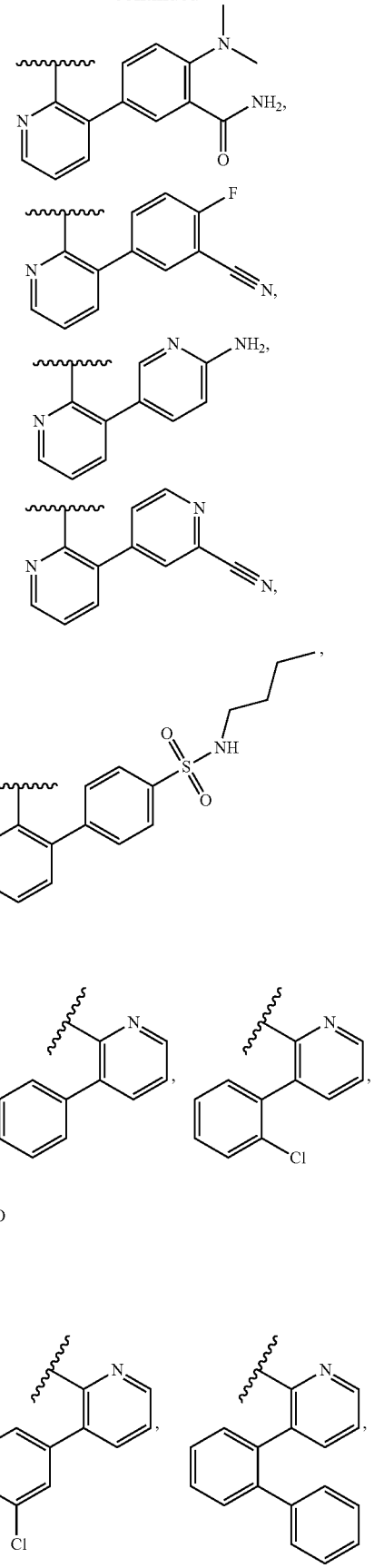

95
-continued
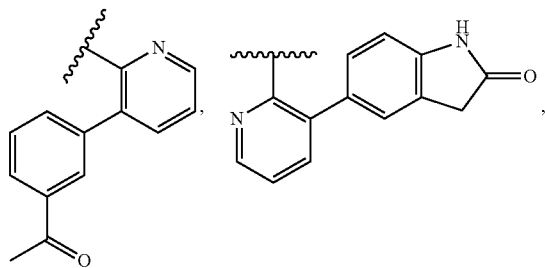
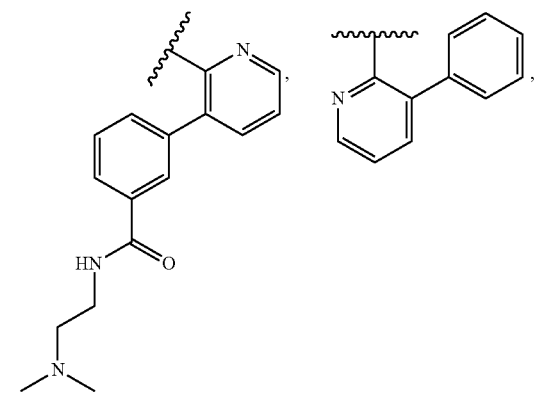
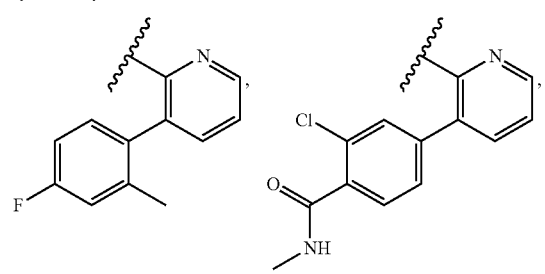
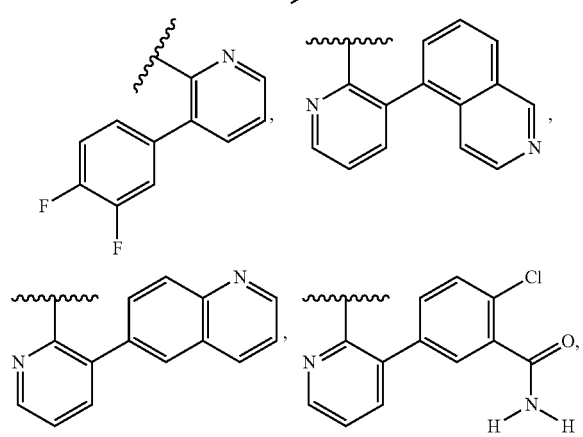
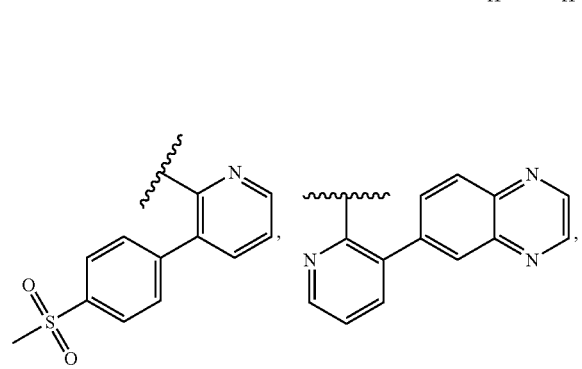
96
-continued
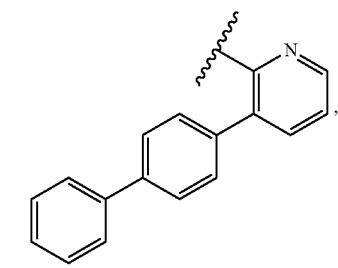
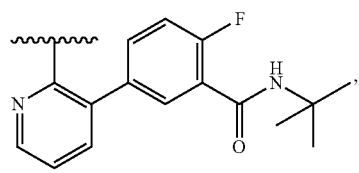
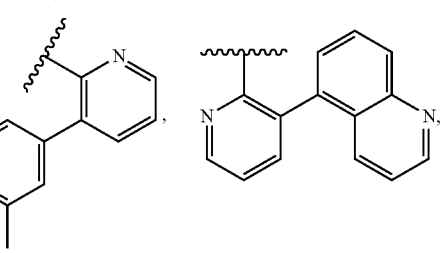
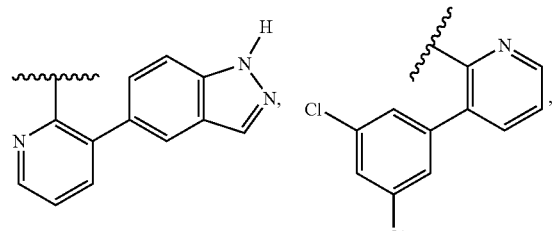
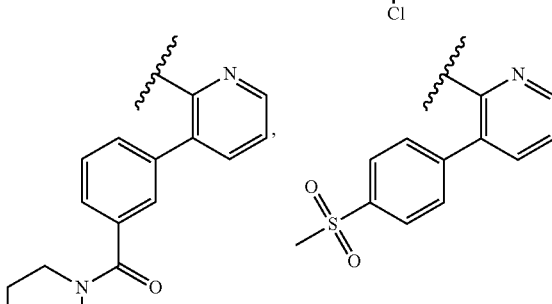
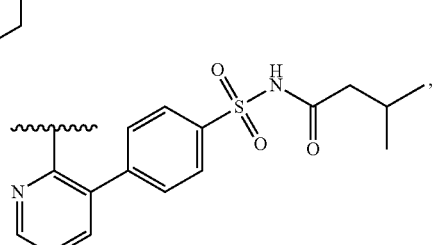
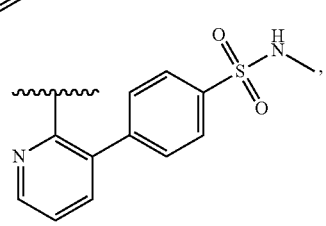

-continued

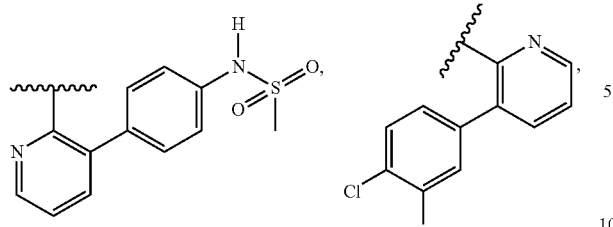

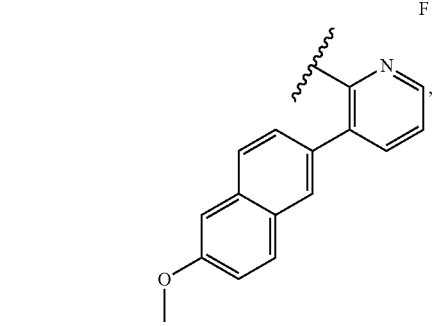

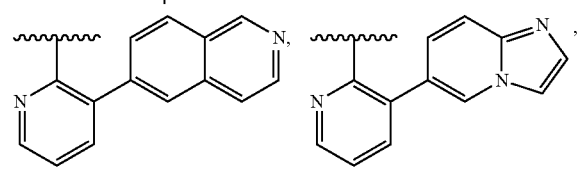

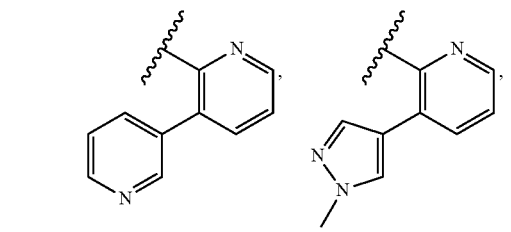

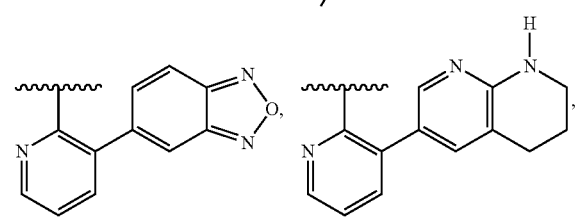

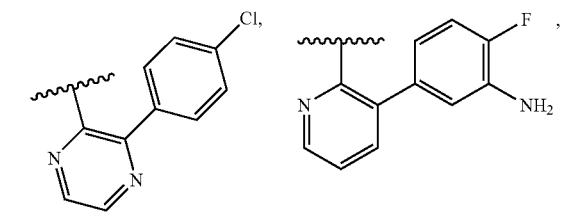

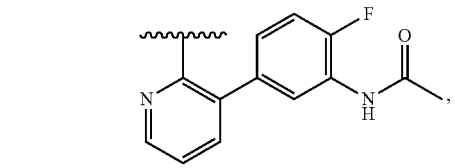

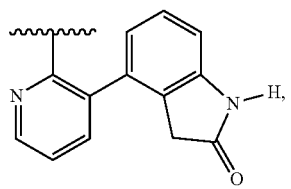

-continued

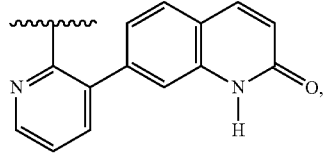

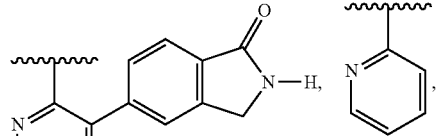

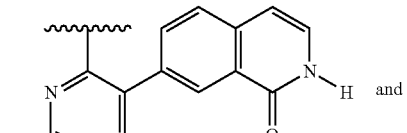 and

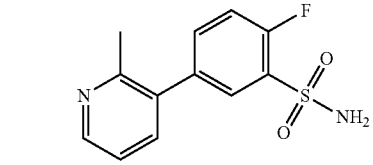

A specific value for $R^1$ is a value for $R^1$ as depicted in any or all of the examples as described herein below.

A specific value for $R^2$ is a value for $R^2$ as depicted in any or all of the examples as described herein below.

A specific value for W is a value for W as depicted in any or all of the examples as described herein below.

A specific value for A is a value for A as depicted in any or all of the examples as described herein below.

In one embodiment a compound of the invention is a compound of formula I as described in any or all of the examples as described herein below.

In one embodiment a compound of the invention is an isomer (e.g. stereoisomer such as an enantiomer or diastereomer) of a compound of formula I as described in any or all of the examples as described herein below.

In one embodiment a compound of the invention is a racemic mixture of a compound of formula I as described in any or all of the examples as described herein below.

In one embodiment a heteroaryl (multiple condensed ring system) is a ring system comprising 2, 3 or 4 rings.

In one embodiment a heteroaryl (multiple condensed ring system) is a ring system comprising 3 or 4 rings.

In one embodiment a heteroaryl (multiple condensed ring system) is a ring system comprising 2 or 3 rings.

In one embodiment a heteroaryl (multiple condensed ring system) is a ring system comprising 2 rings.

In one embodiment a heteroaryl (multiple condensed ring system) is a ring system comprising 3 rings.

In one embodiment a heteroaryl (multiple condensed ring system) is a ring system comprising 4 rings.

In one embodiment a heterocycle (multiple condensed ring system) is a ring system comprising 2, 3 or 4 rings.

In one embodiment a heterocycle (multiple condensed ring system) is a ring system comprising 3 or 4 rings.

In one embodiment a heterocycle (multiple condensed ring system) is a ring system comprising 2 or 3 rings.

In one embodiment a heterocycle (multiple condensed ring system) is a ring system comprising 2 rings.

In one embodiment a heterocycle (multiple condensed ring system) is a ring system comprising 3 rings.

In one embodiment a heterocycle (multiple condensed ring system) is a ring system comprising 4 rings.

In one embodiment the term "carbocycle" or "carbocyclyl" refers to a single saturated (i.e., cycloalkyl) or a single partially unsaturated (e.g., cycloalkenyl, cycloalkadienyl, etc.) ring having 3 to 7 carbon atoms (i.e. ($C_3$-$C_7$)carbocycle). The term "carbocycle" or "carbocyclyl" also includes multiple condensed ring systems (e.g. ring systems comprising 2, 3 or 4 carbocyclic rings). Accordingly, carbocycle includes multicyclic carbocyles having 7 to 12 carbon atoms as a bicycle, and up to about 20 carbon atoms as a polycycle. Multicyclic carbocyles can be connected to each other via a single carbon atom to form a spiro connection (e.g. spiropentane, spiro[4,5]decane, spiro[4.5]decane, etc), via two adjacent carbon atoms to form a fused connection such as a bicyclo [4,5], [5,5], [5,6] or [6,6] system, or 9 or 10 ring atoms arranged as a bicyclo [5,6] or [6,6] system (e.g. decahydronaphthalene, norsabinane, norcarane) or via two non-adjacent carbon atoms to form a bridged connection (e.g. norbornane, bicyclo[2.2.2]octane, etc). The "carbocycle" or "carbocyclyl" can also be optionally substituted with one or more (e.g. 1, 2 or 3) oxo groups. Non-limiting examples of monocyclic carbocycles include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl and 1-cyclohex-3-enyl.

In one embodiment the compounds of formula I do not include the compound:

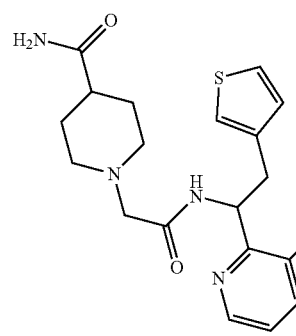

In one embodiment the compounds of formula I include:

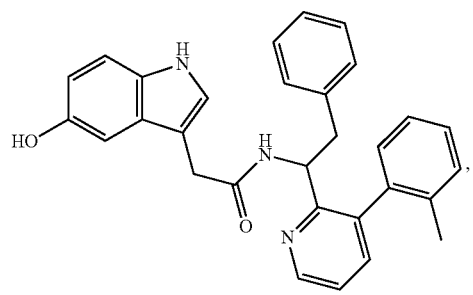

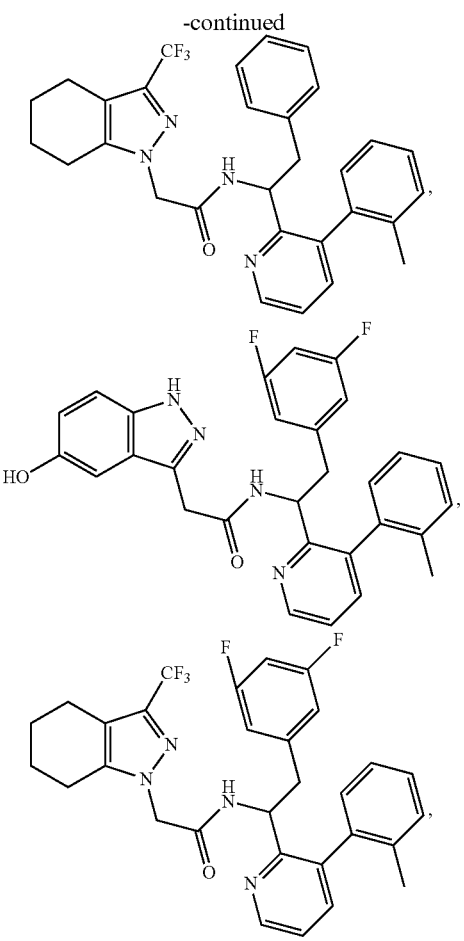

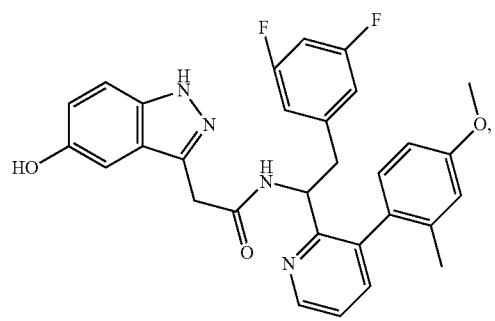

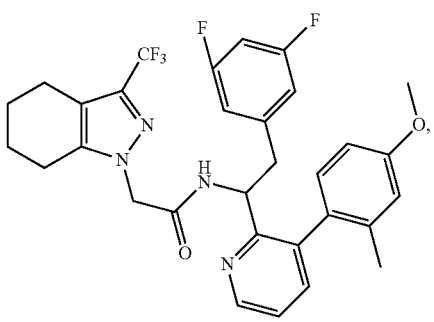

101
-continued
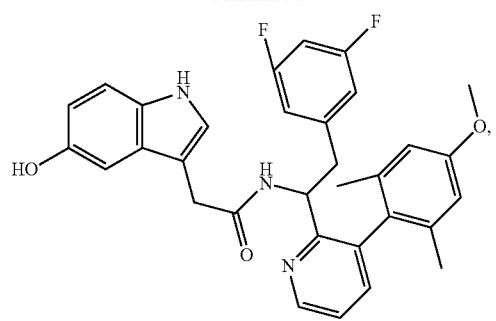
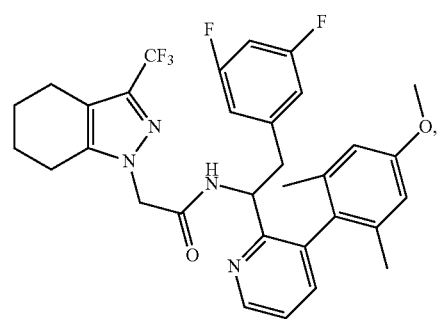
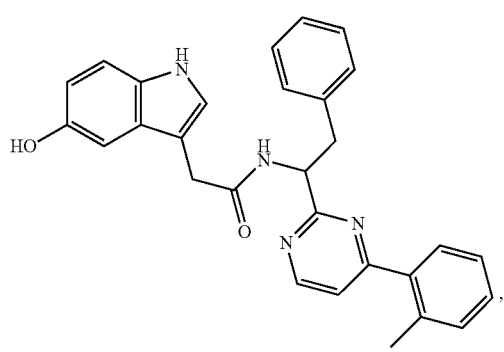
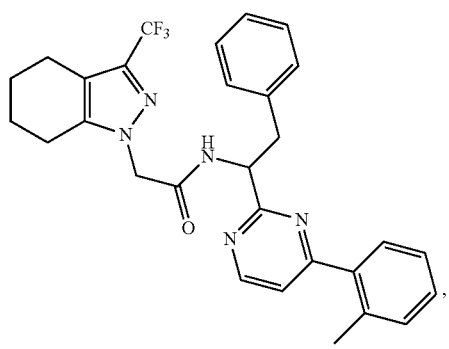
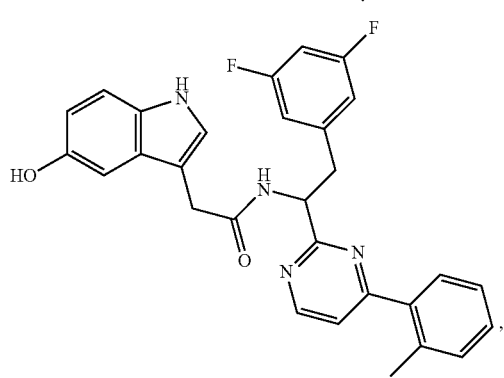
102
-continued
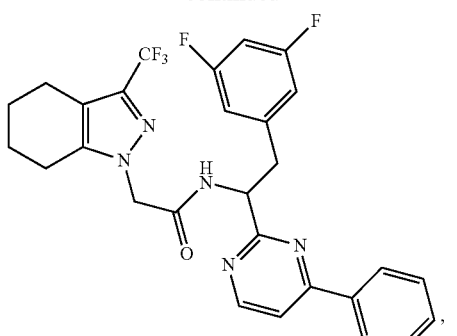
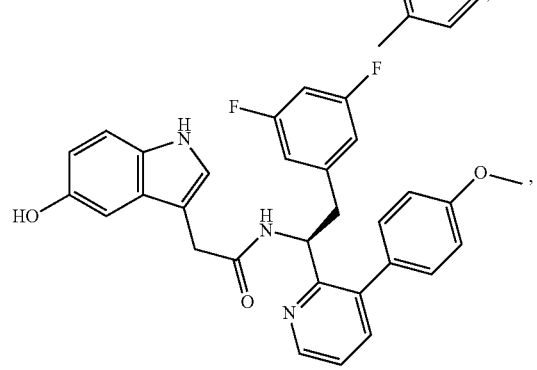
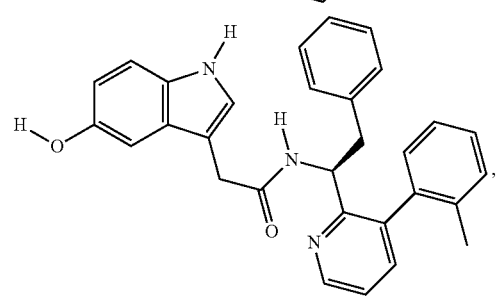
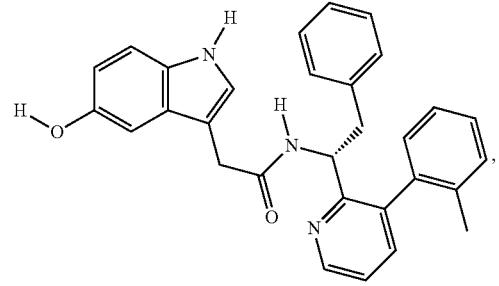
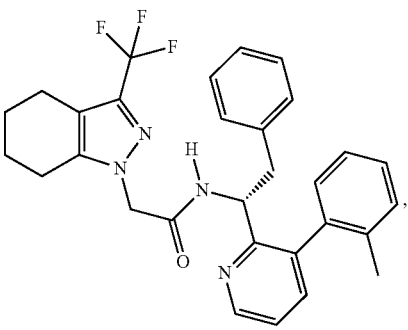

103
-continued
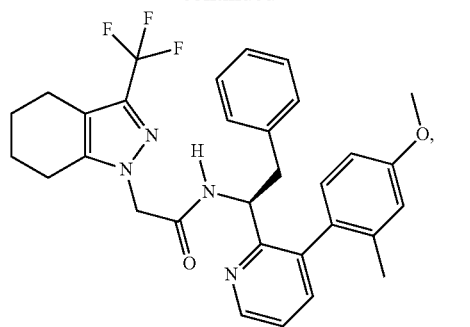
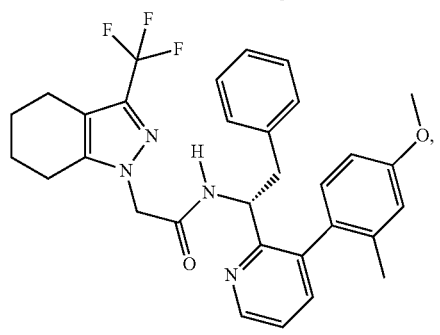
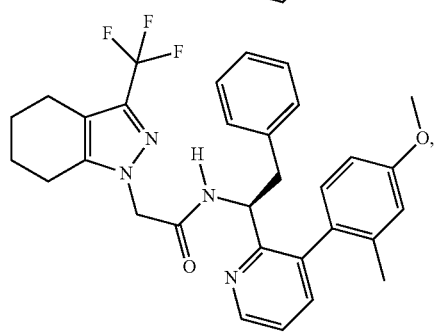
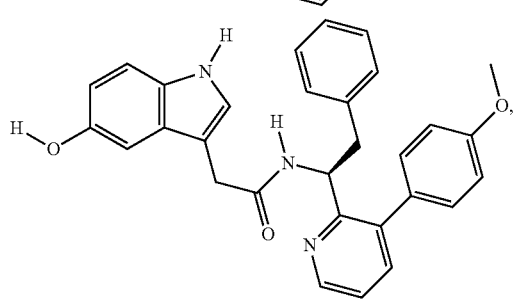
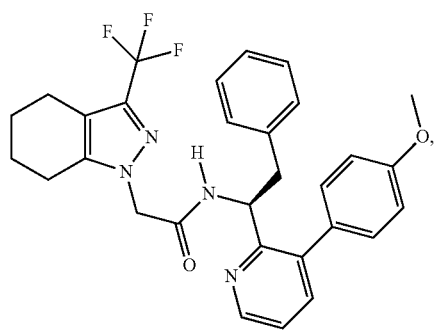
104
-continued
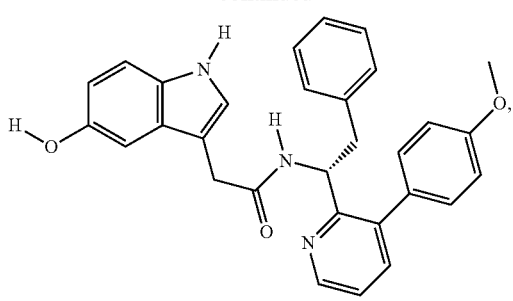
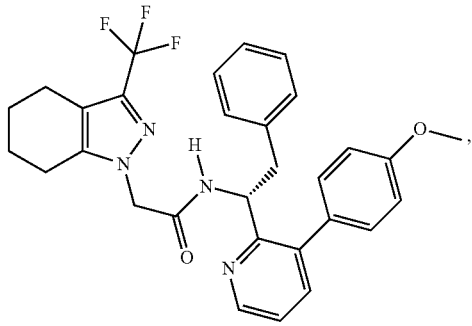
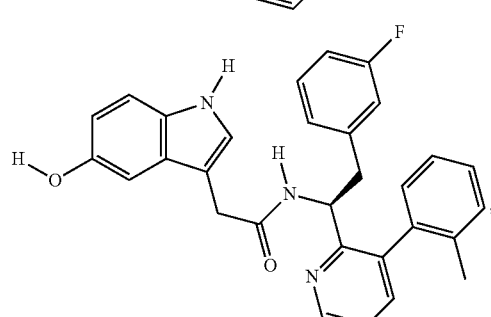
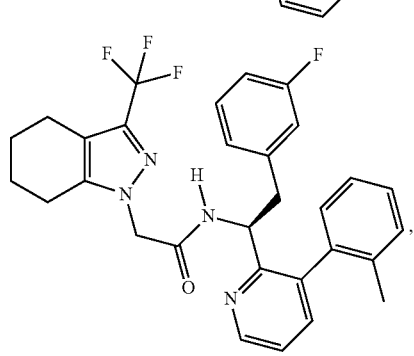
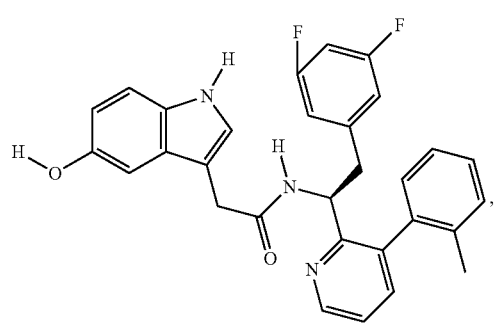

105
-continued
106
-continued
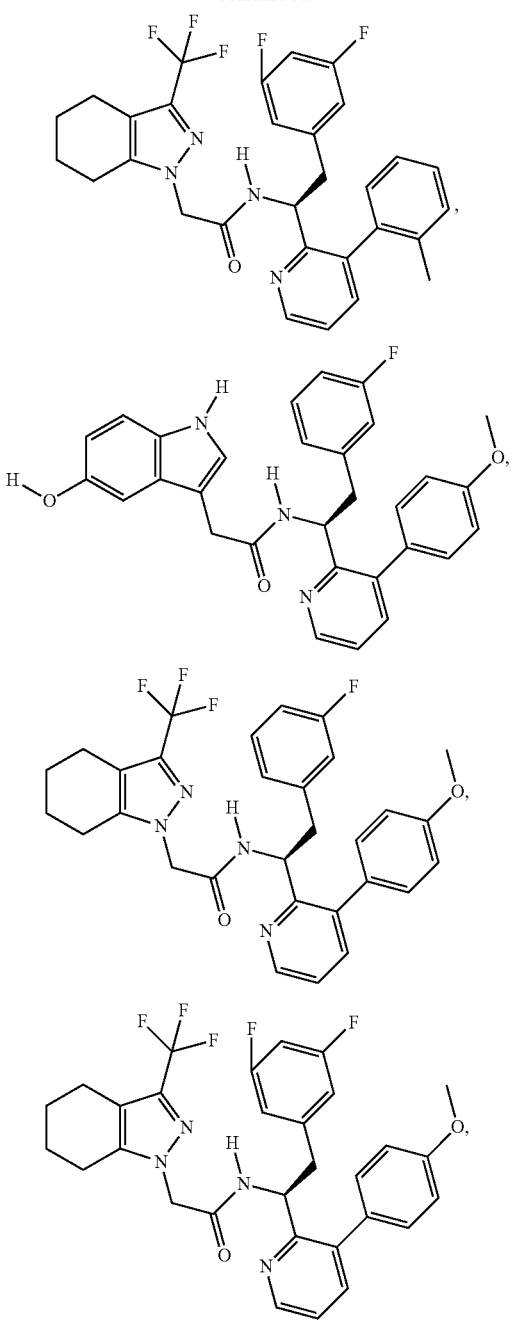
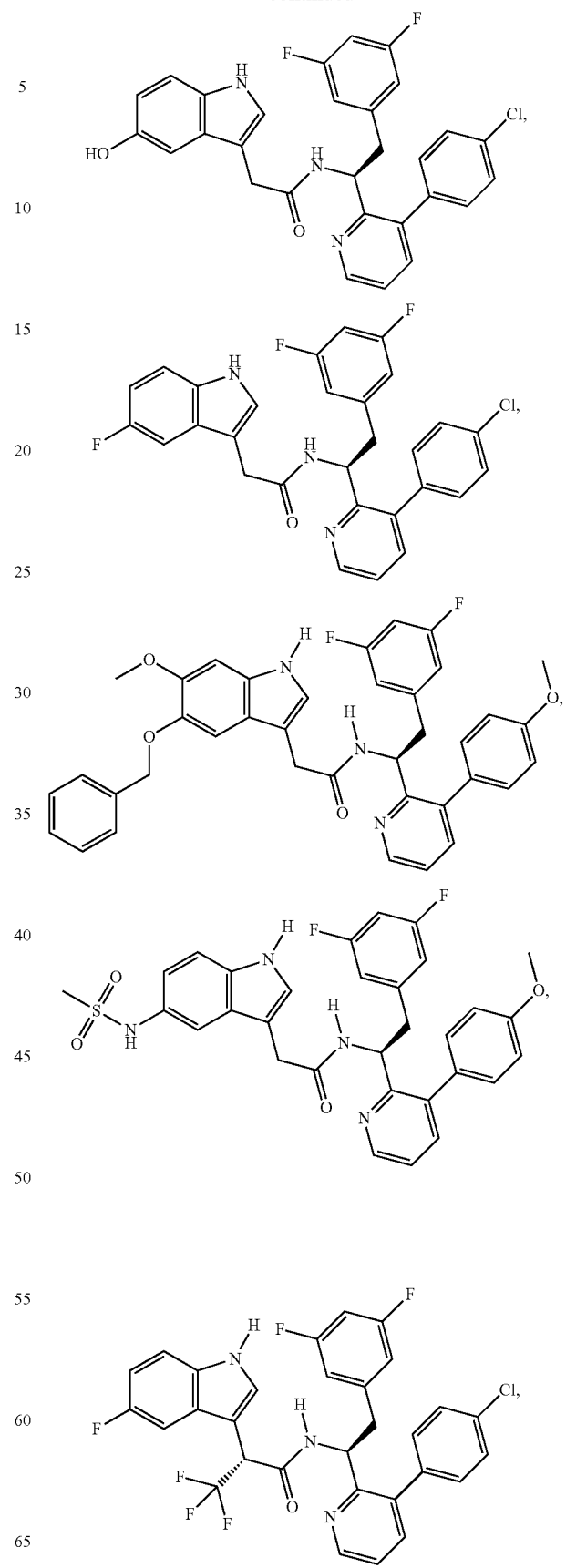

107
-continued
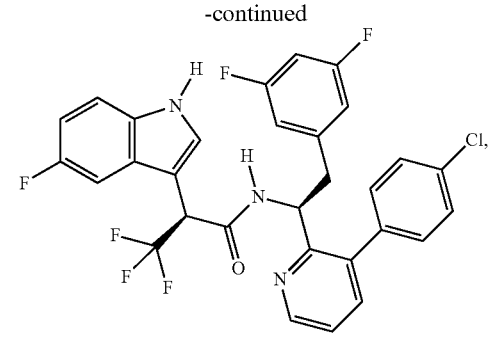
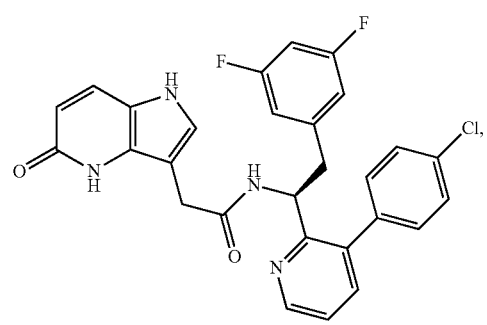
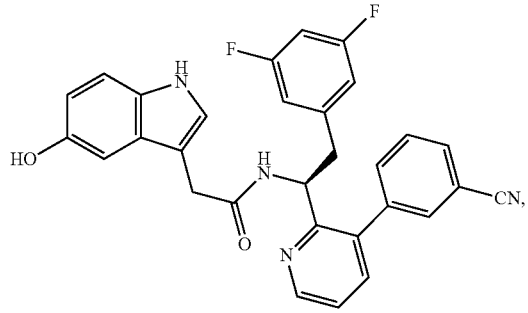
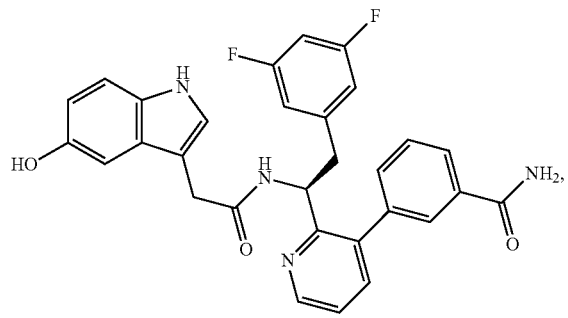
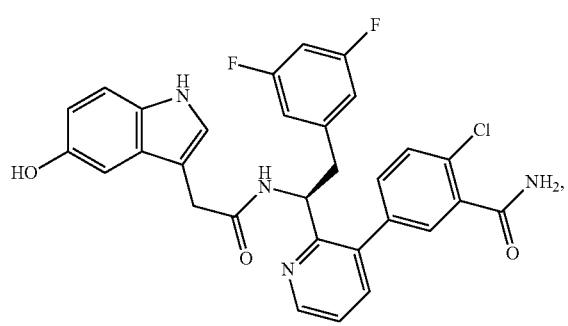
108
-continued
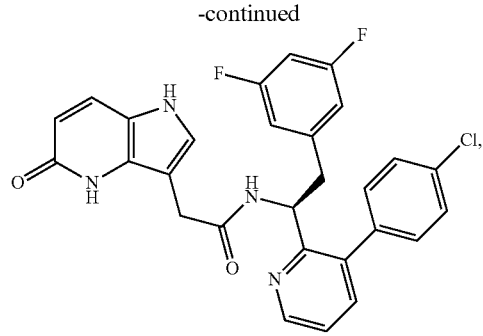
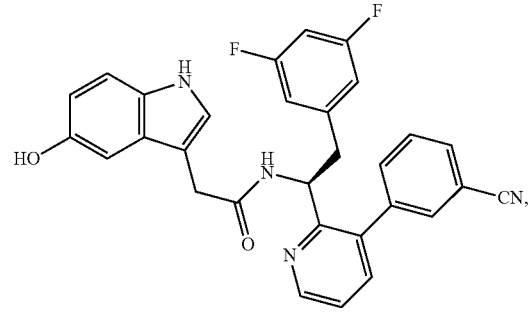
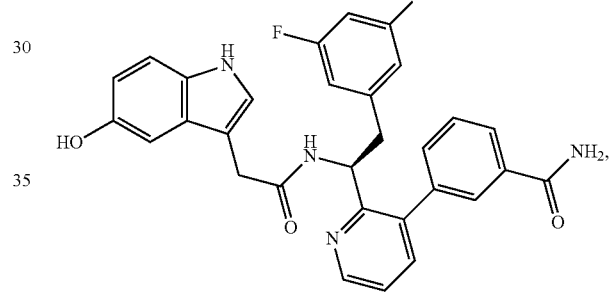
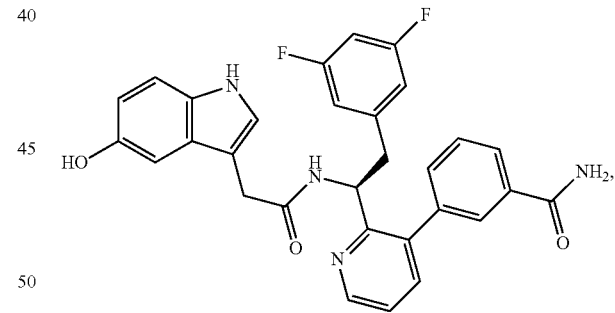
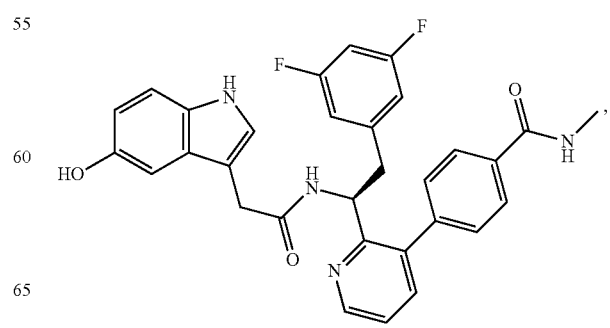

-continued
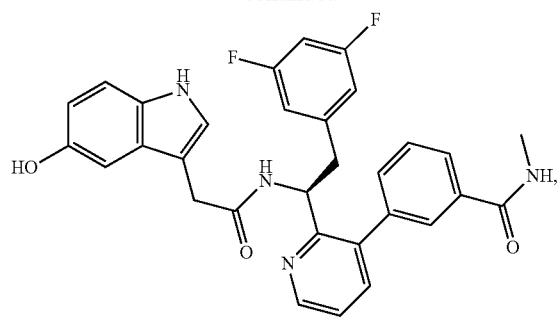
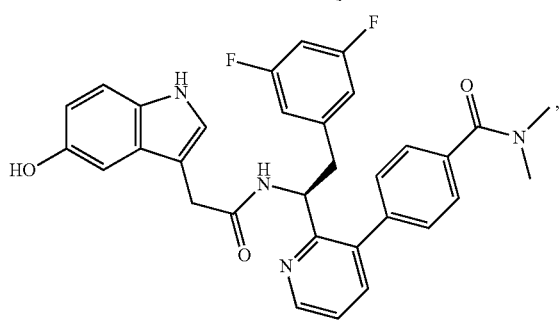
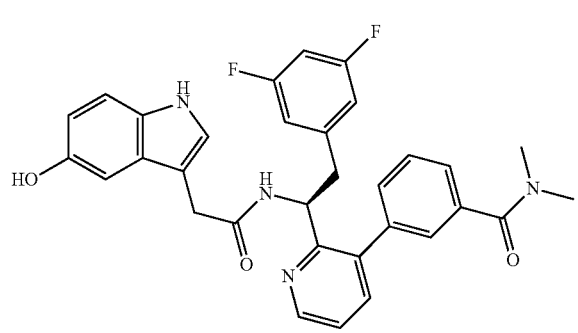
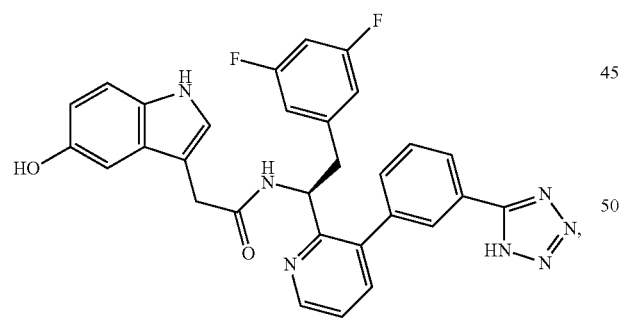

-continued
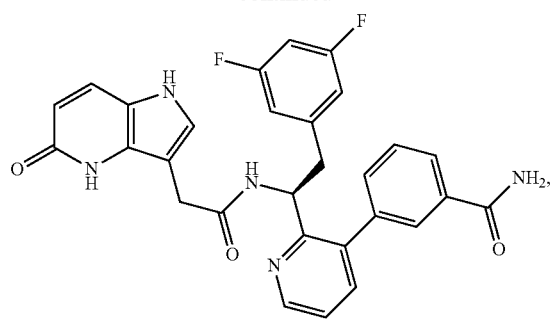
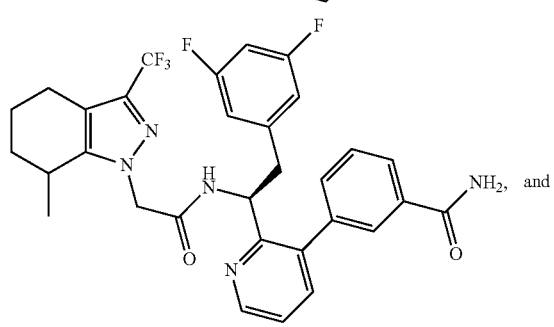
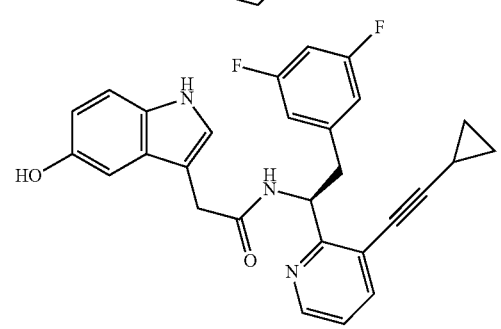
and salts thereof.
In one embodiment the compounds of formula I include:
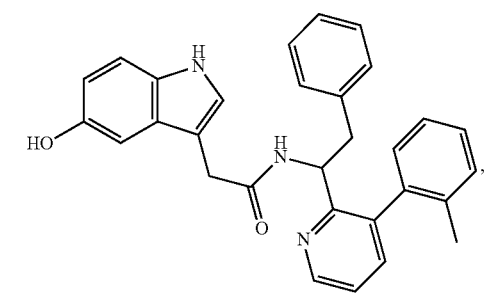
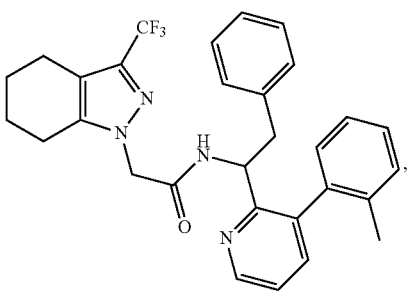

111
-continued
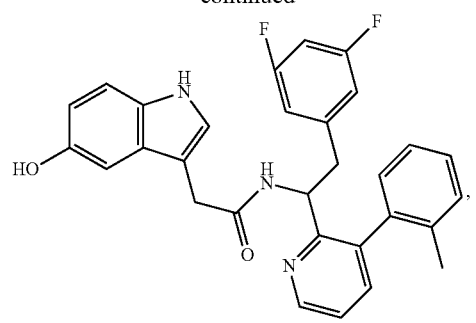
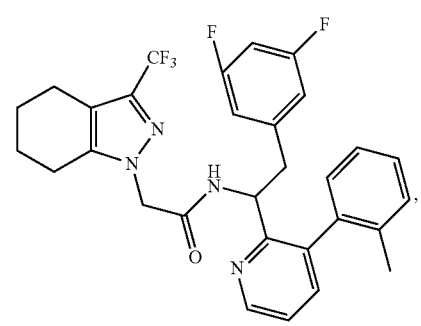
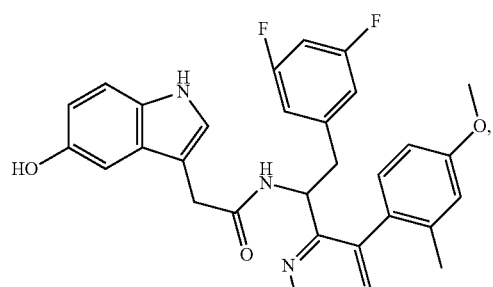
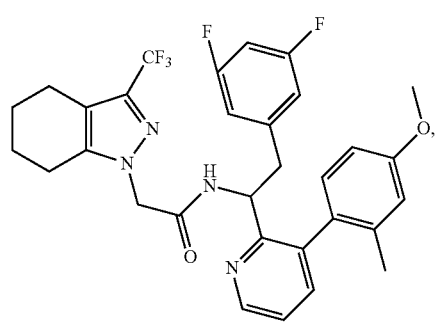
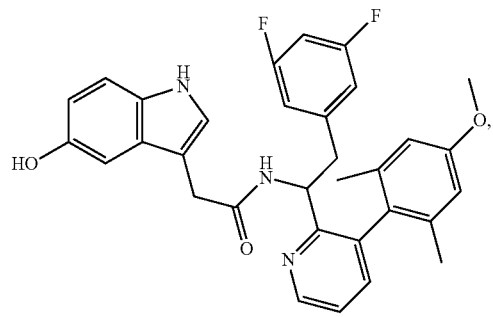
112
-continued
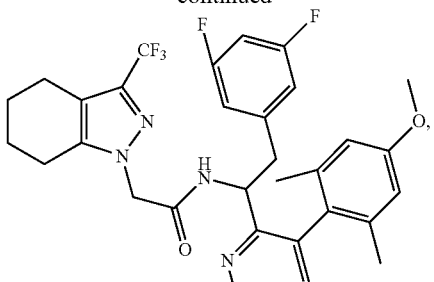
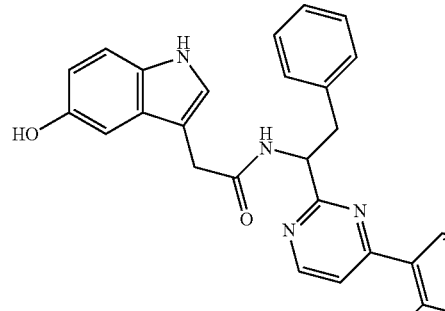
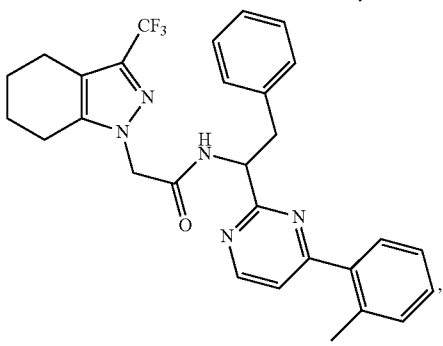
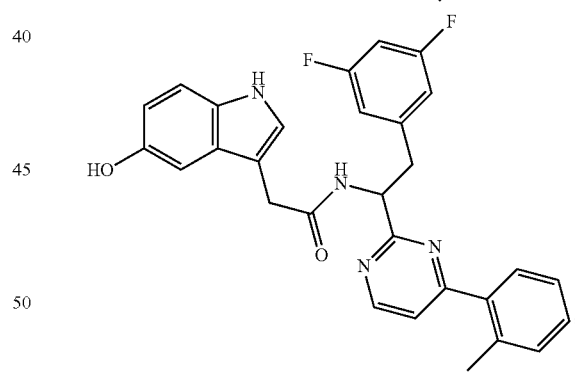
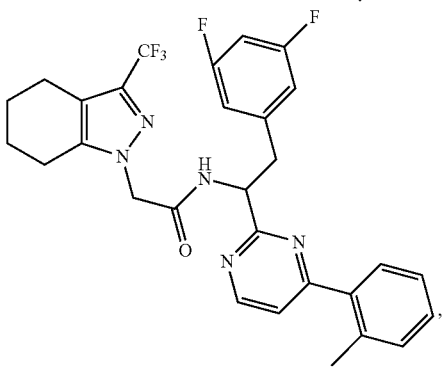

113
-continued
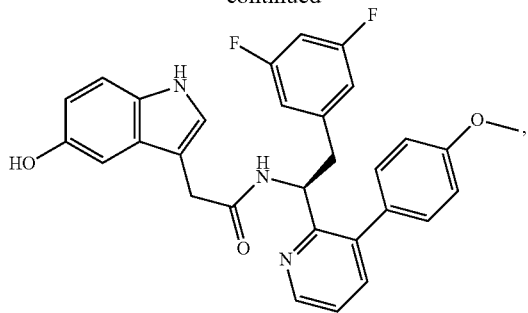
114
-continued
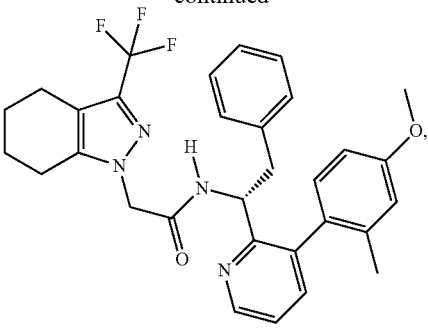
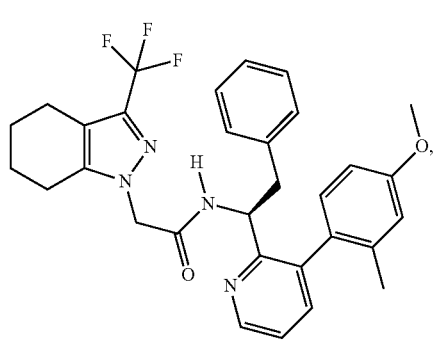
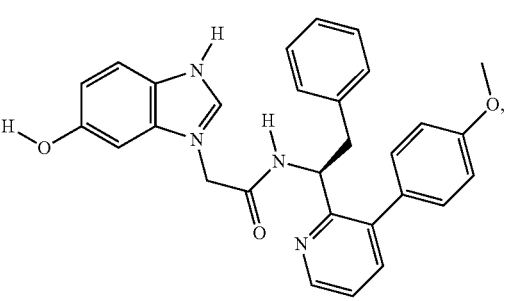
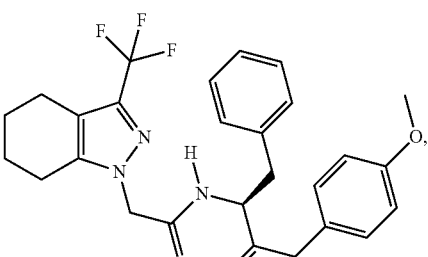
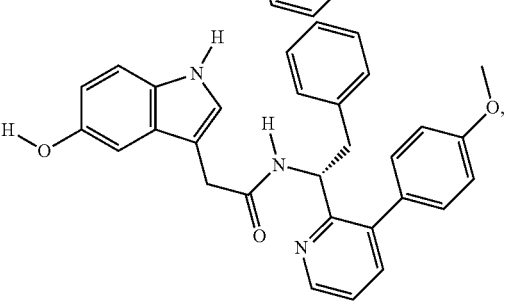

115
-continued
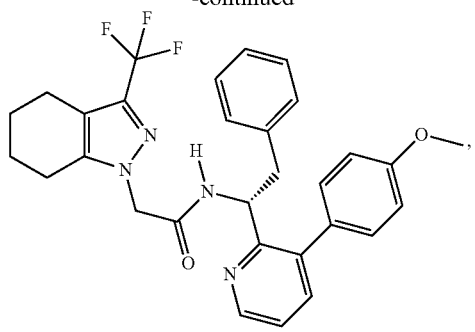
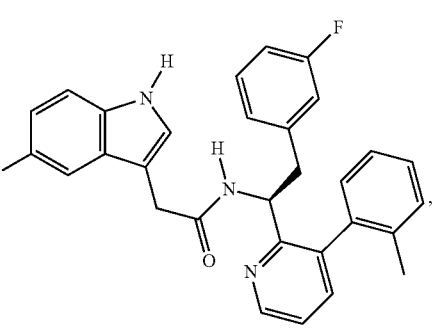
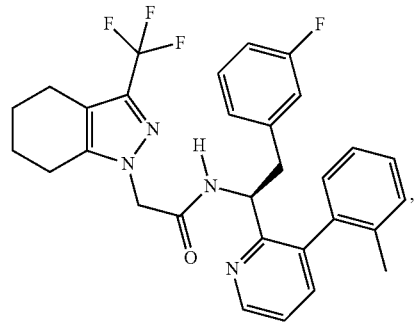
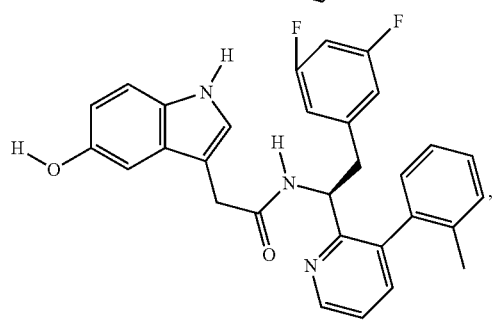
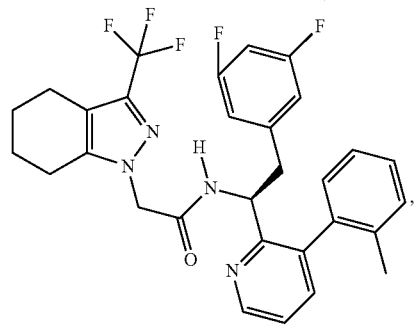
116
-continued
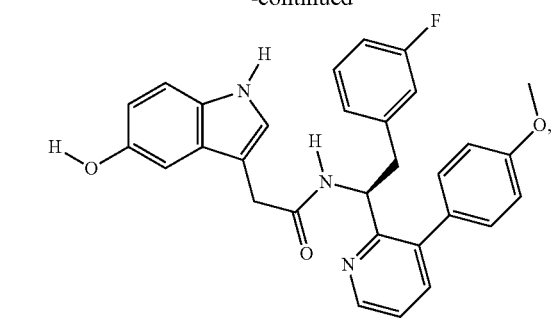
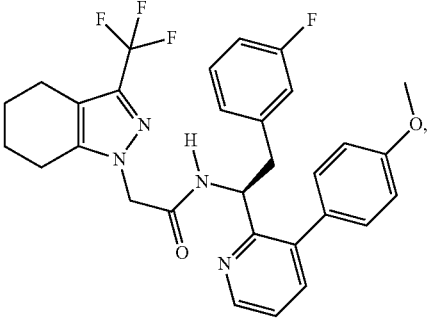
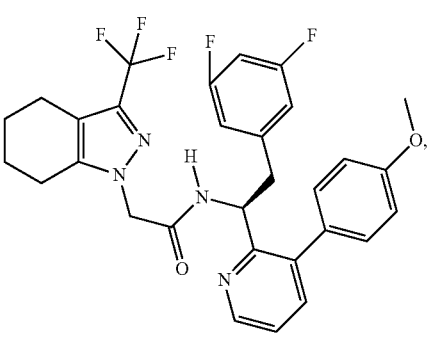
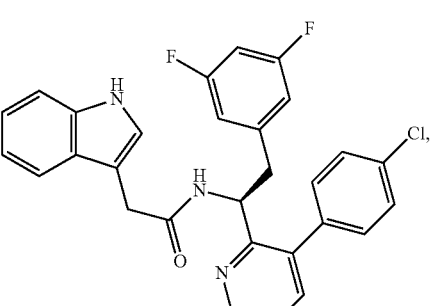
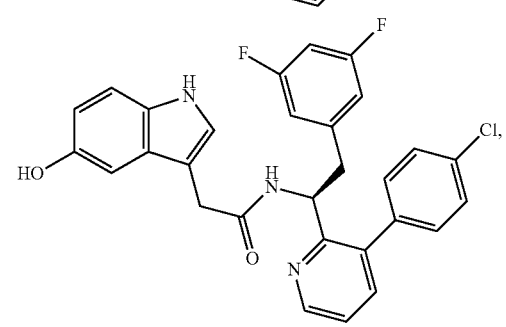

117
-continued
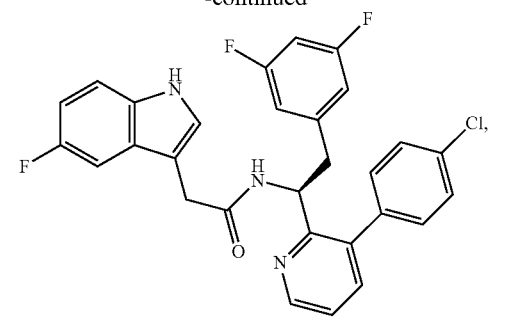
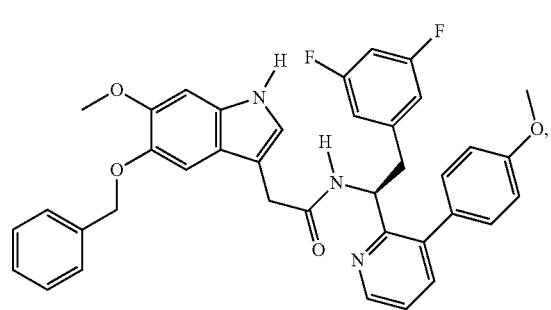
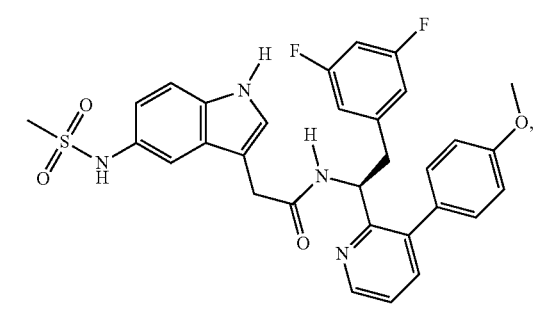
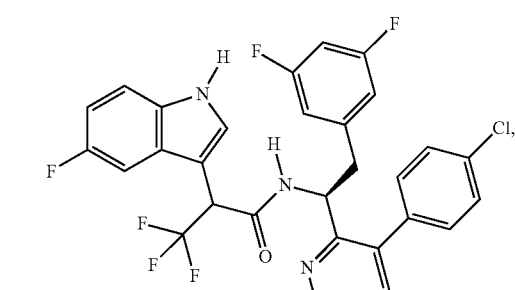
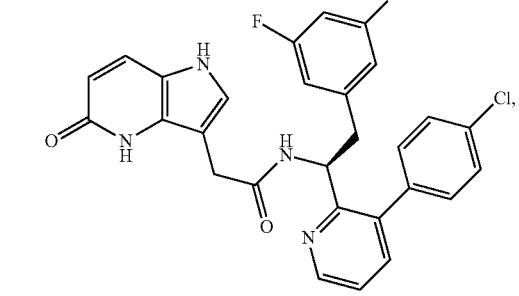
118
-continued
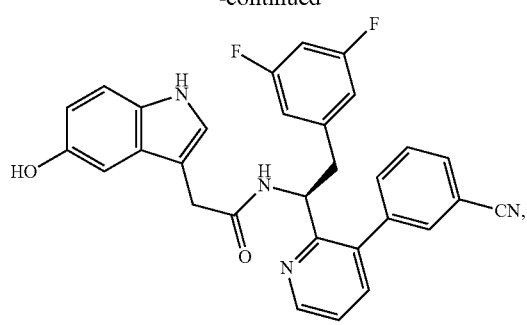
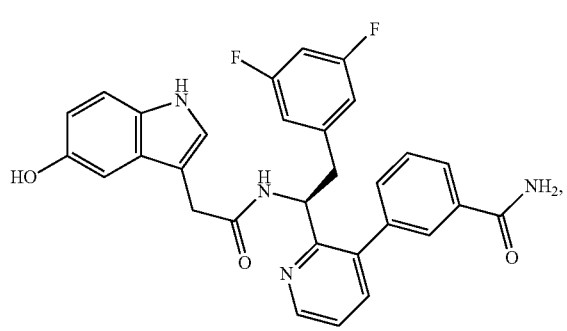
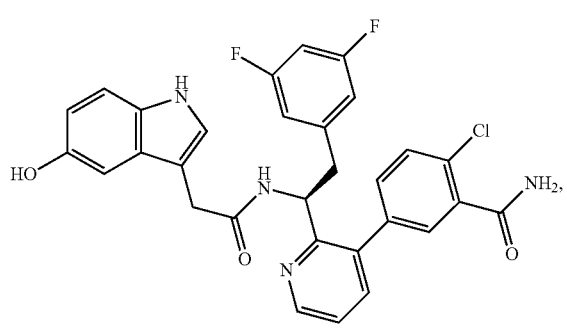
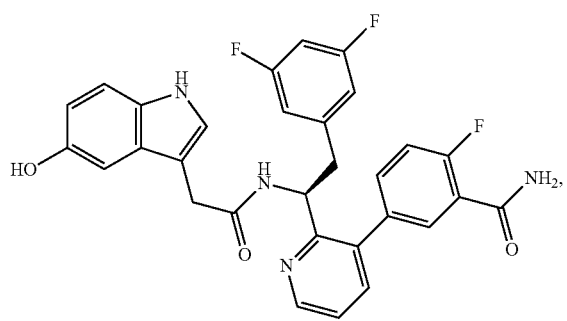
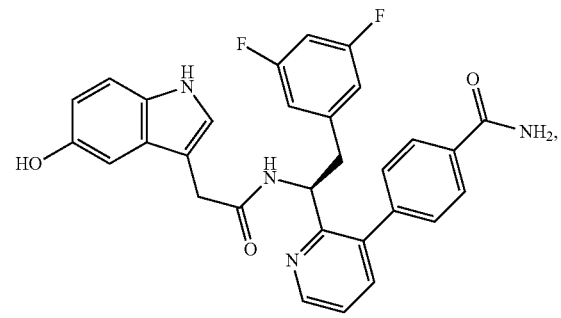

119
-continued
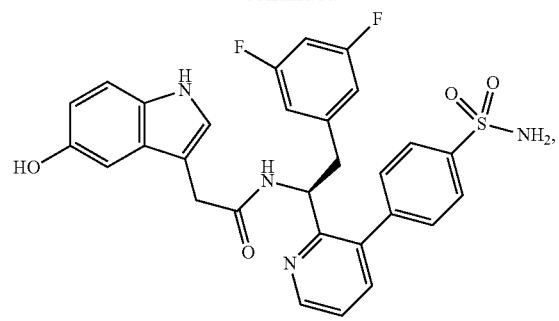
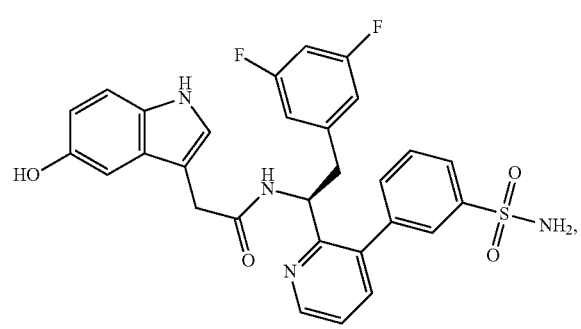
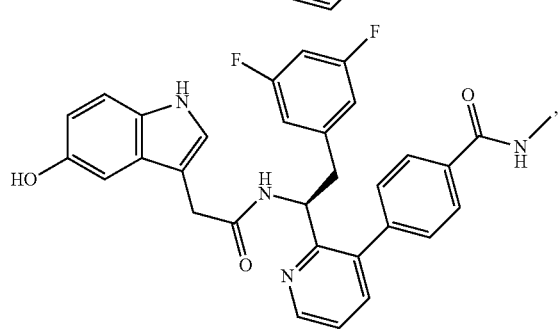
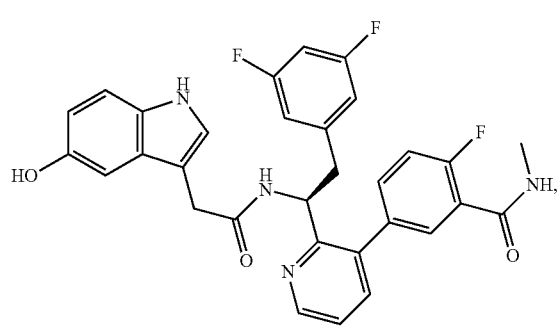
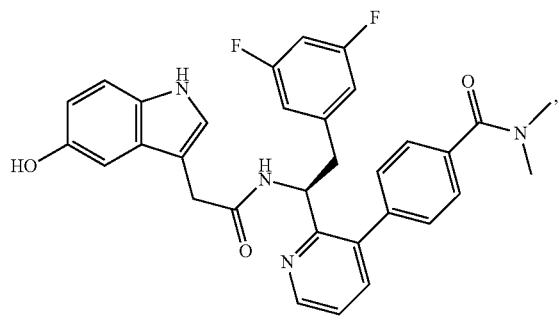
120
-continued
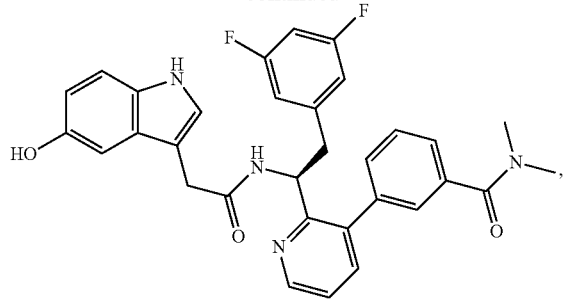
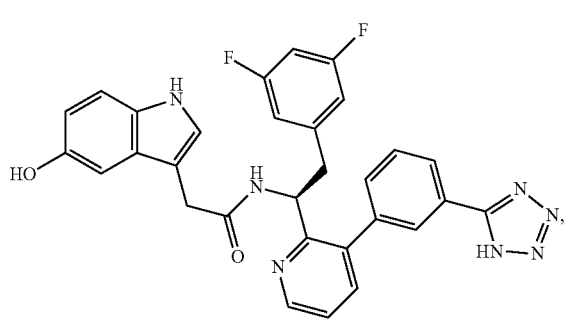
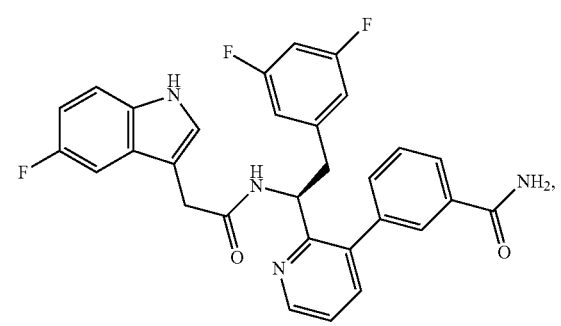
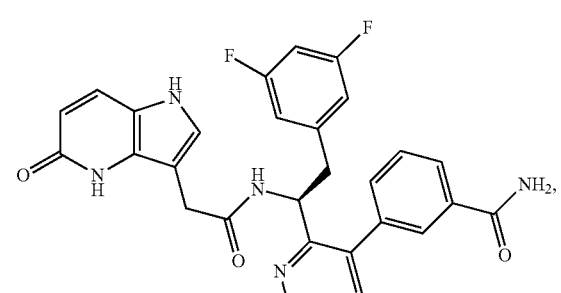
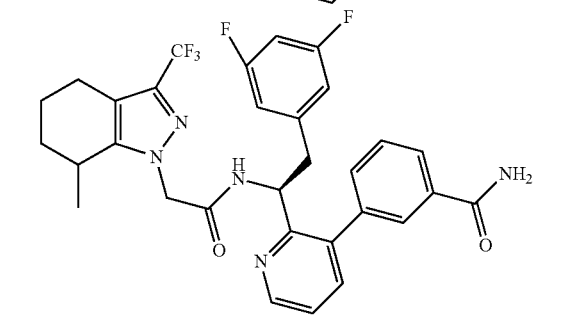

-continued
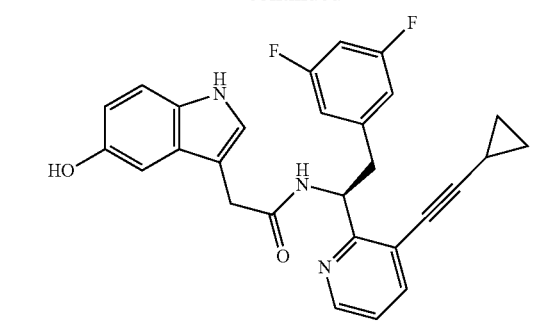
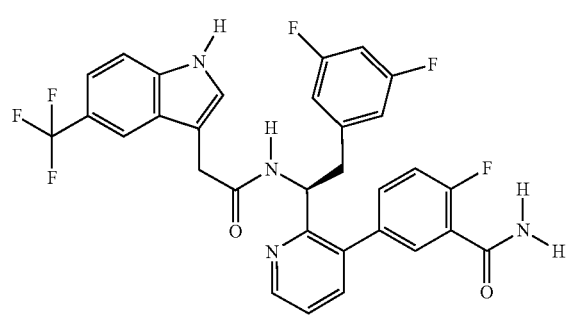
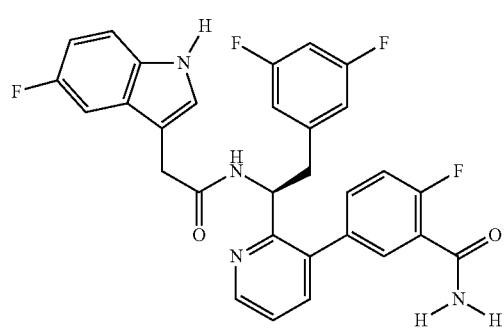
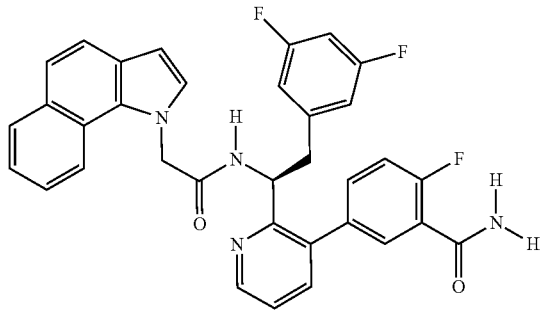
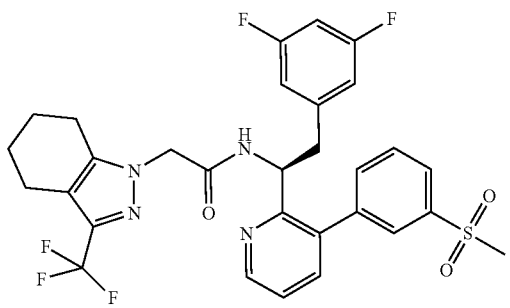
-continued
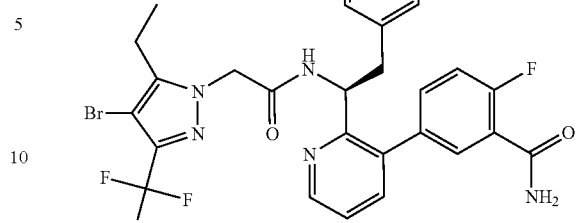
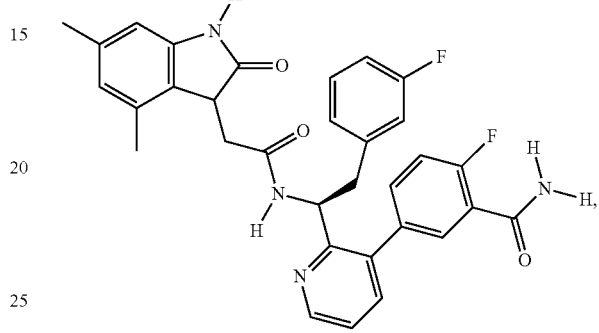
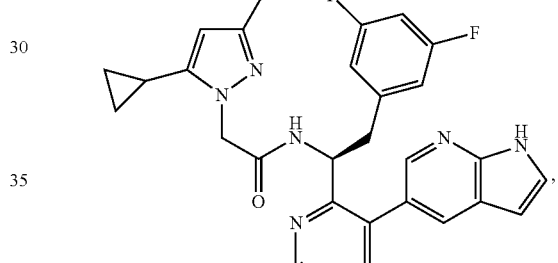
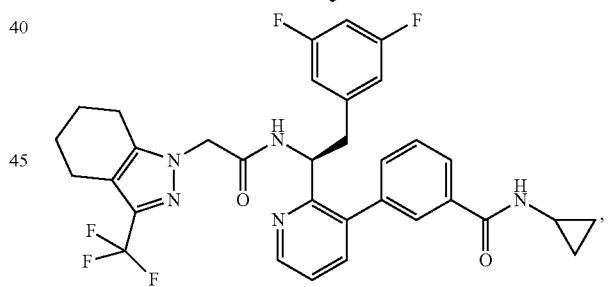
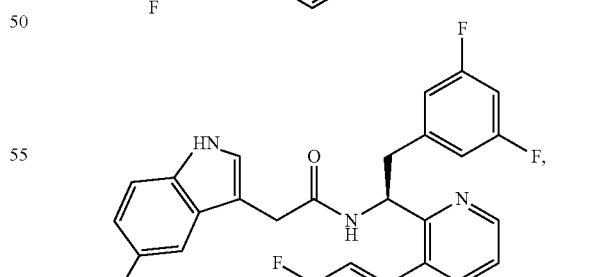
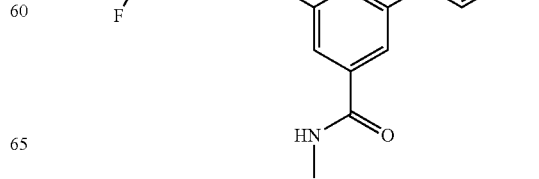

123
-continued
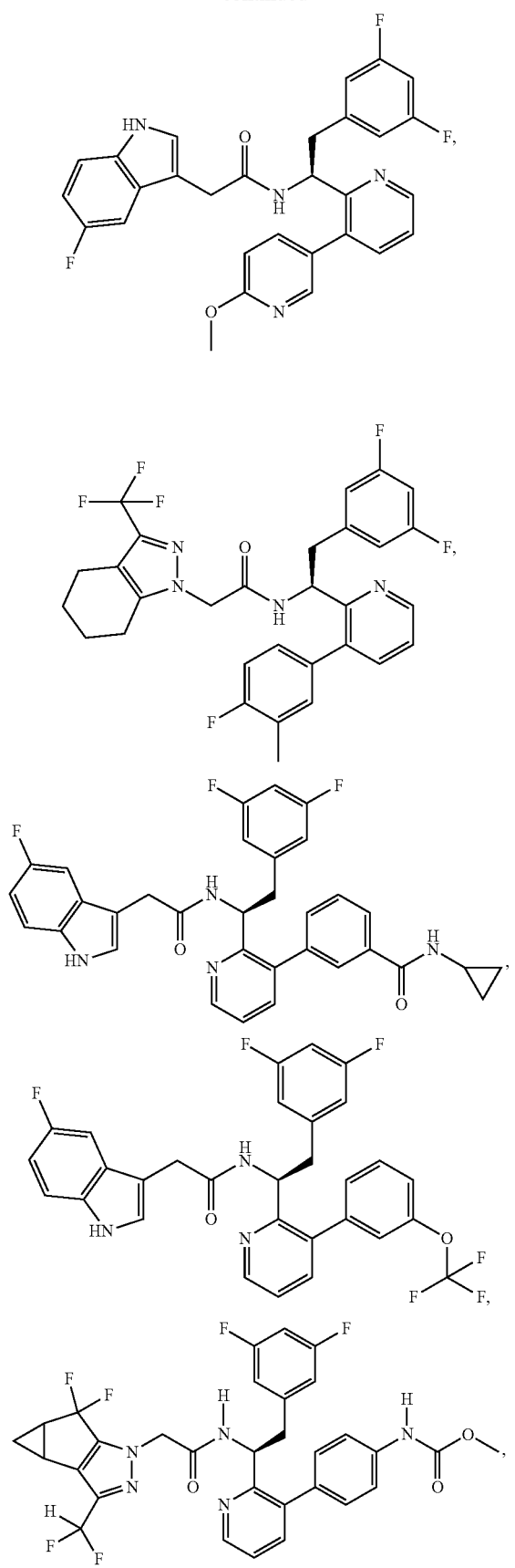
124
-continued
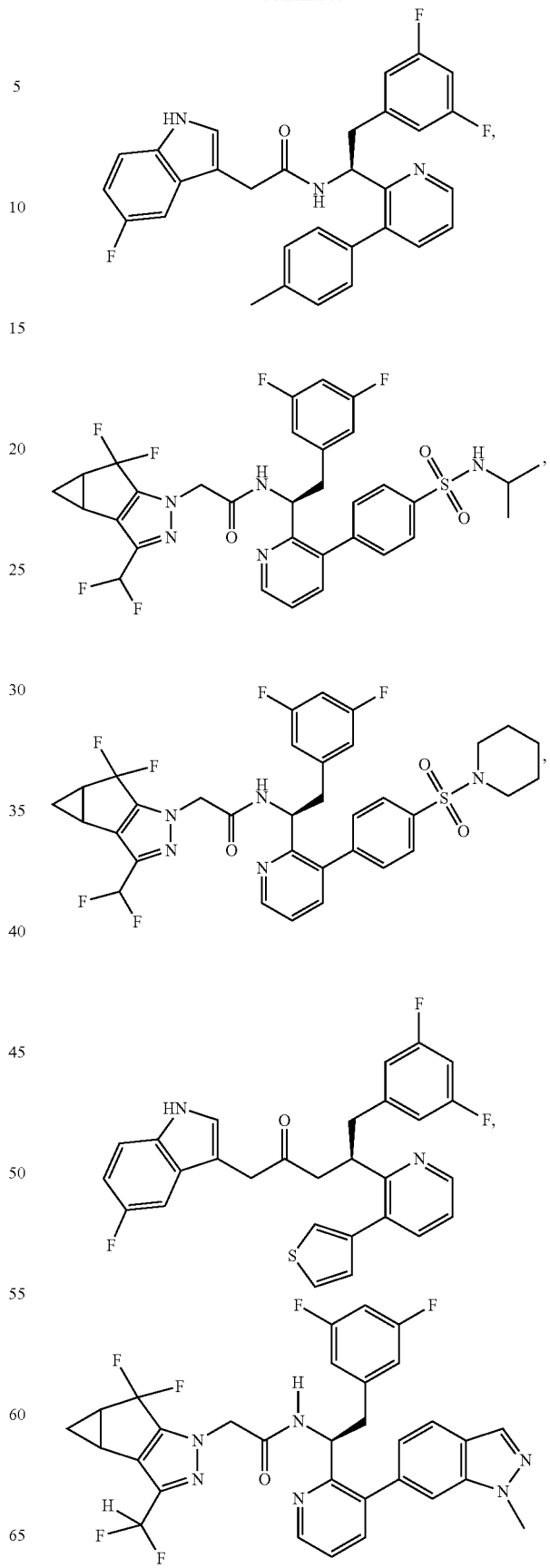

125
-continued
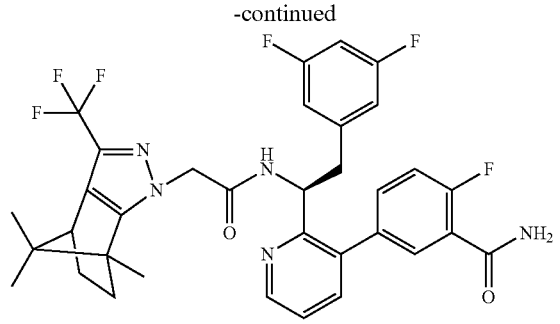
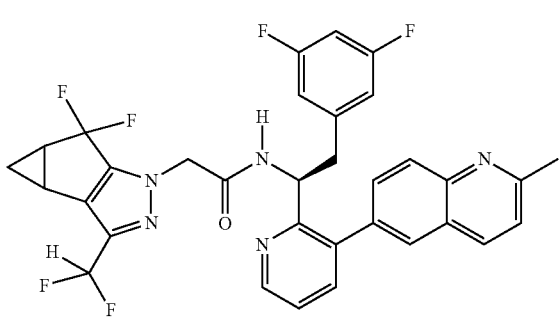
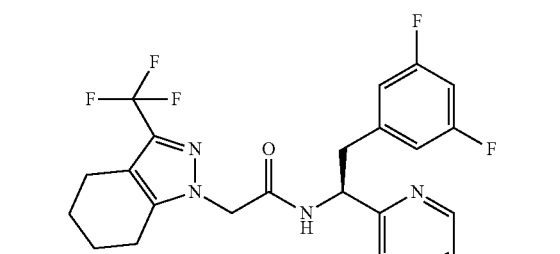
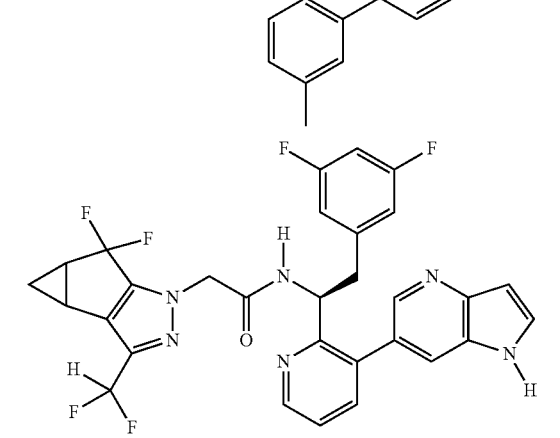
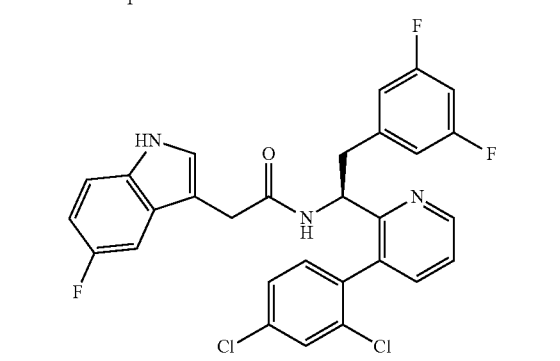
126
-continued
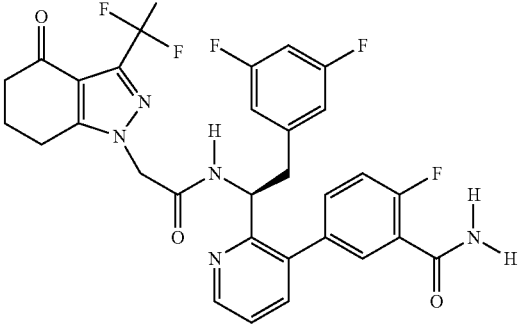
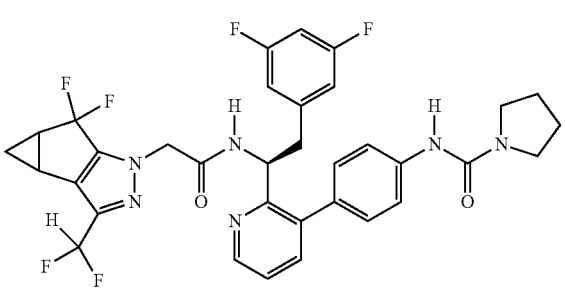
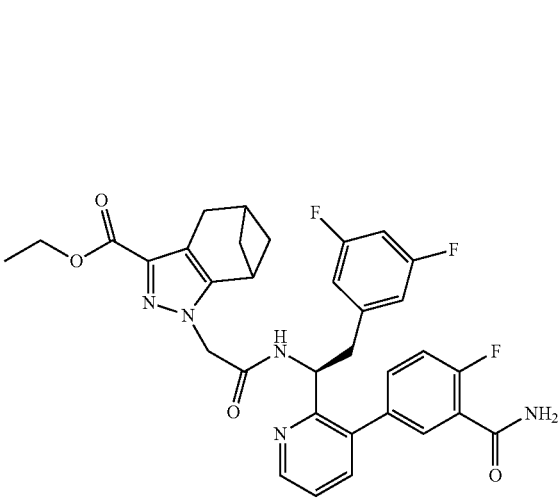
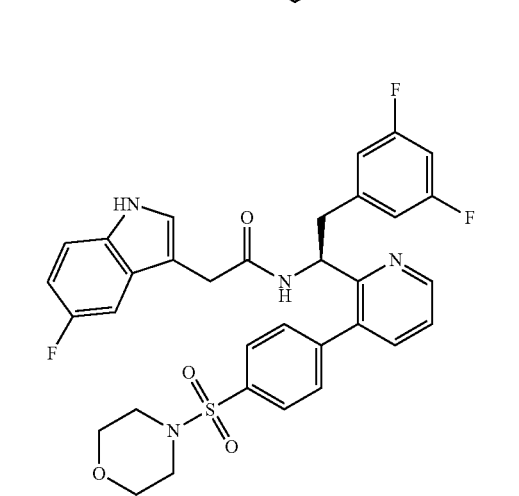

127
-continued
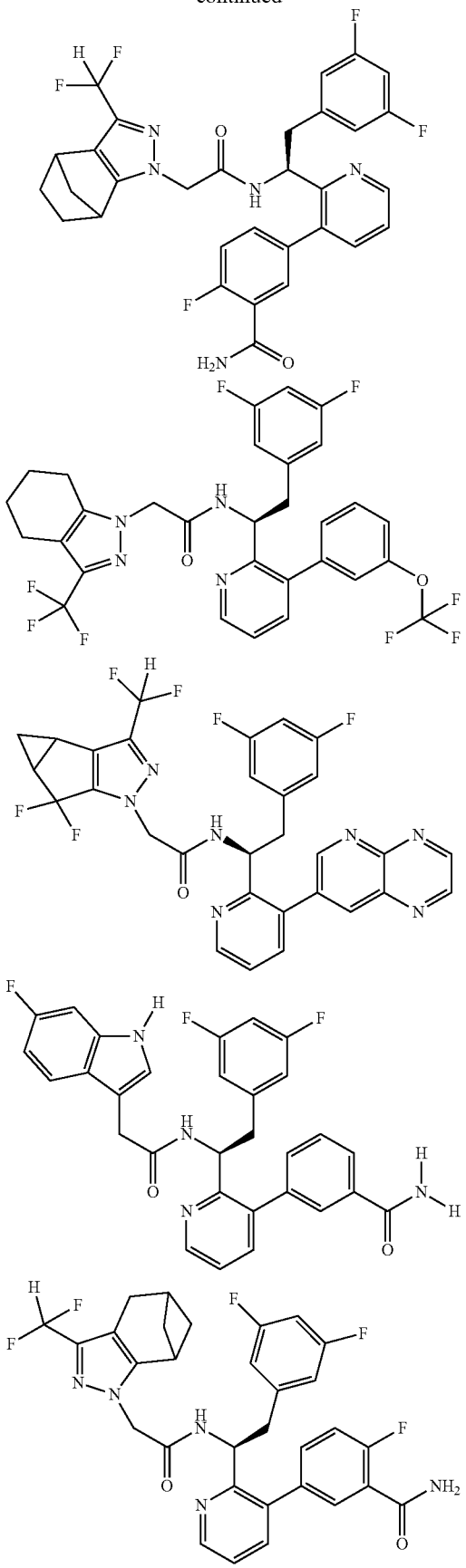
128
-continued
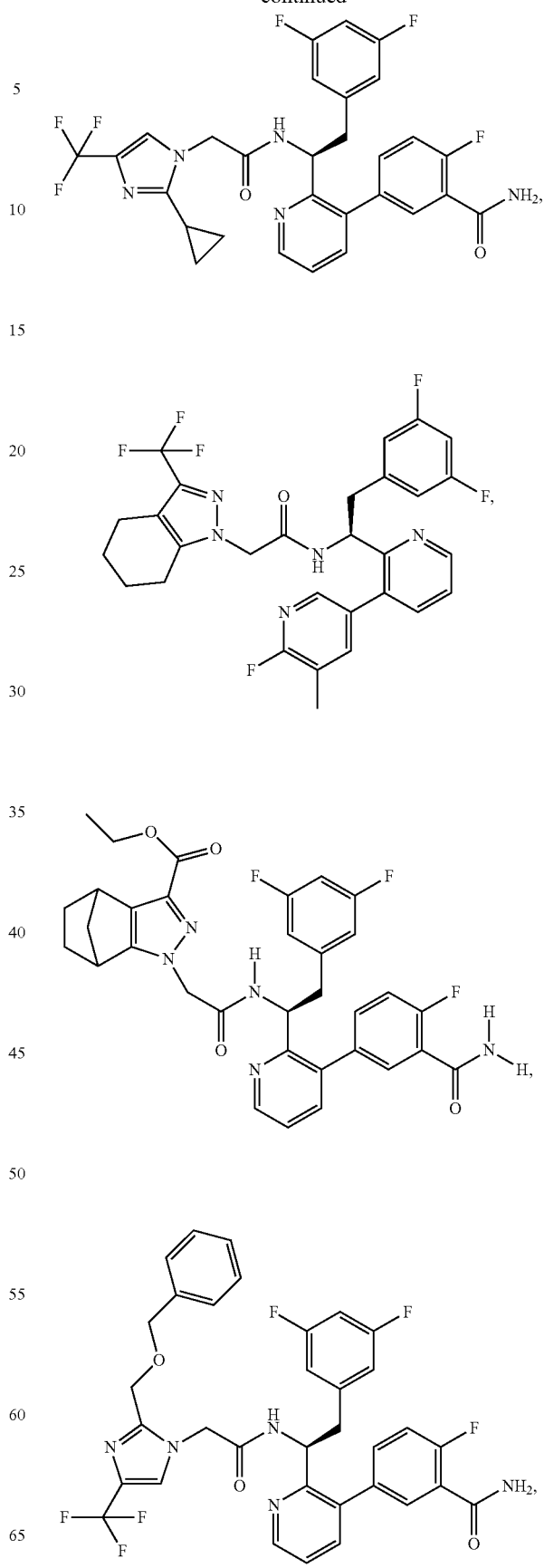

129
-continued
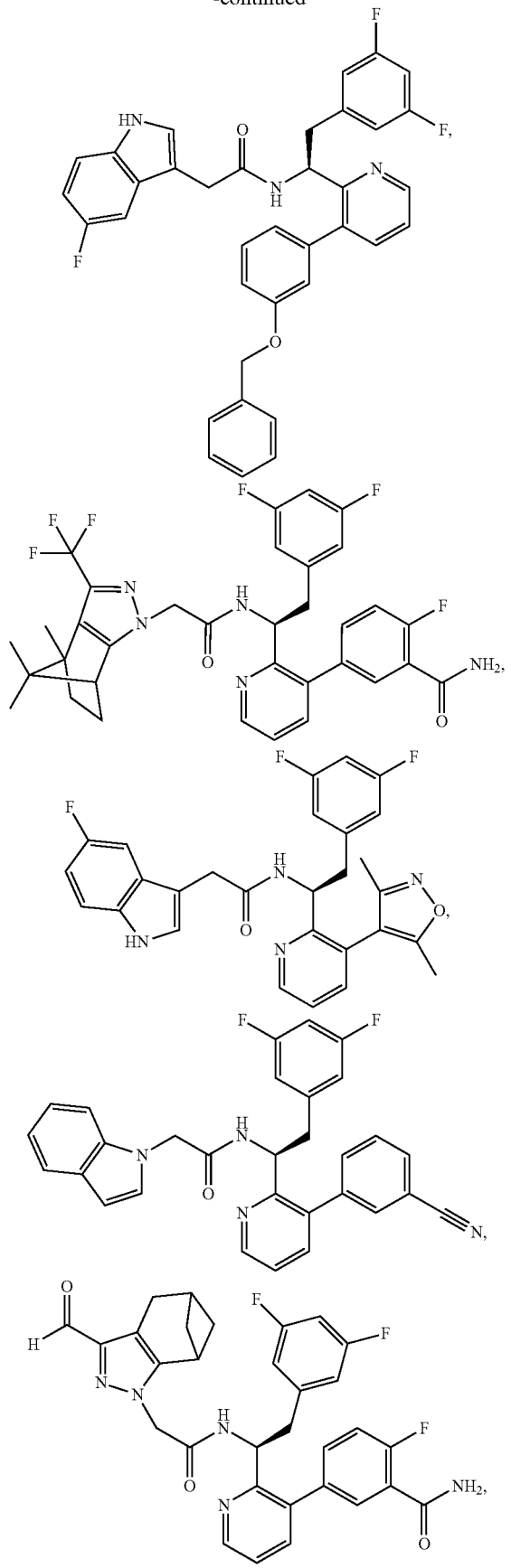
130
-continued
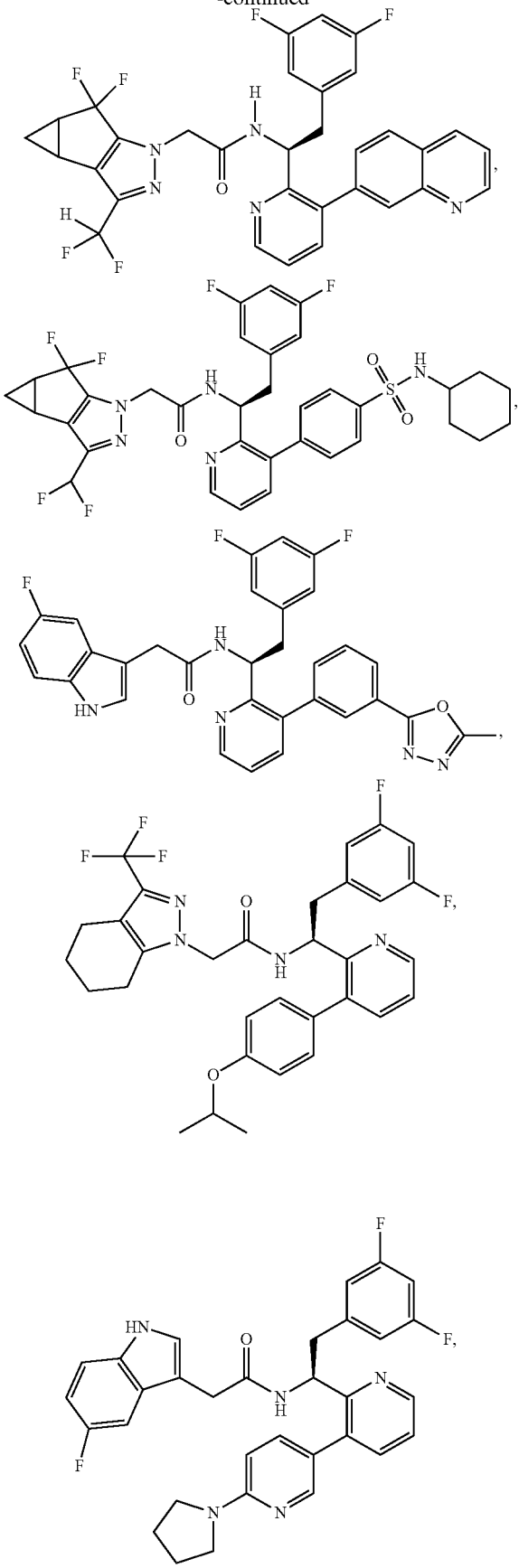

131
-continued
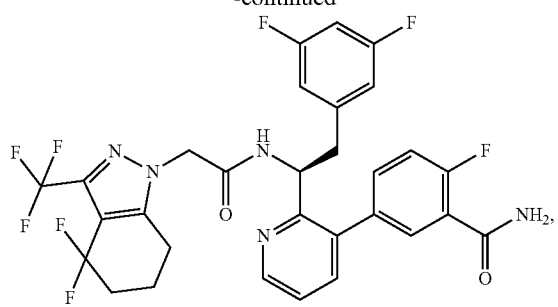
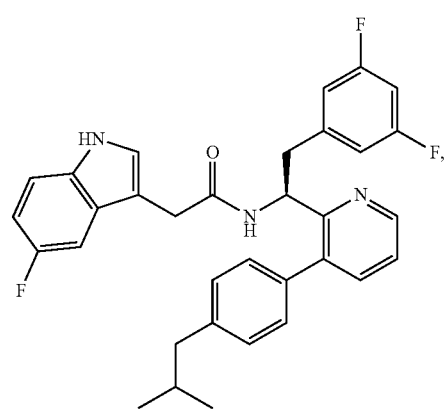
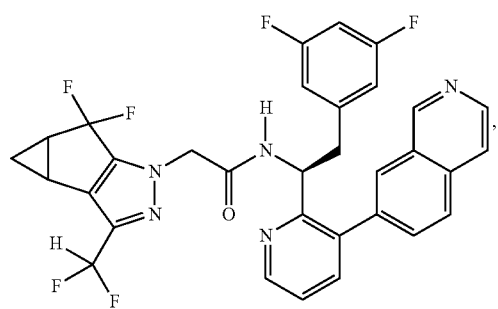
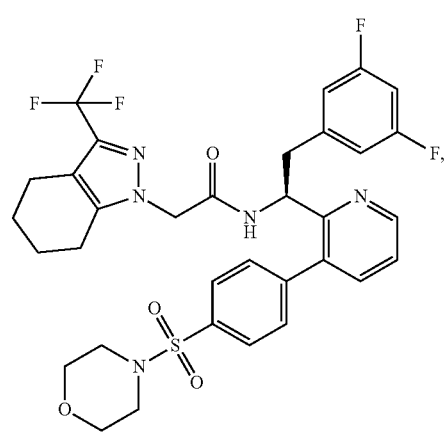
132
-continued
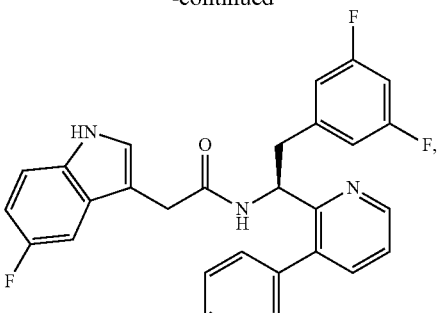
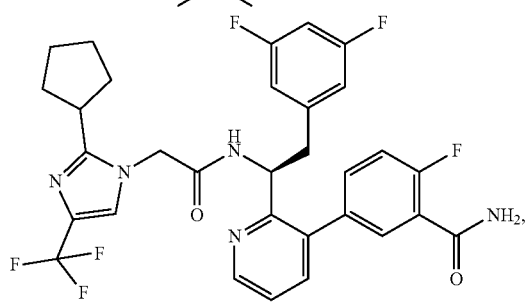
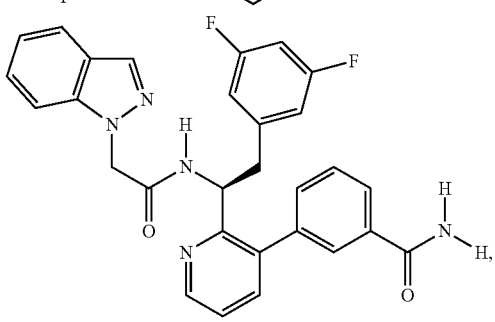
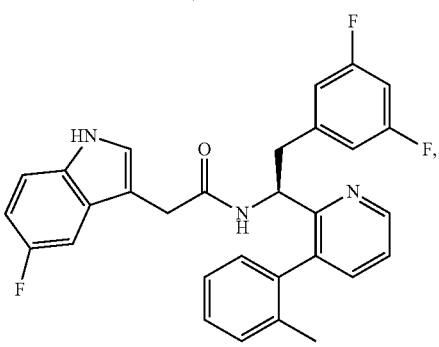
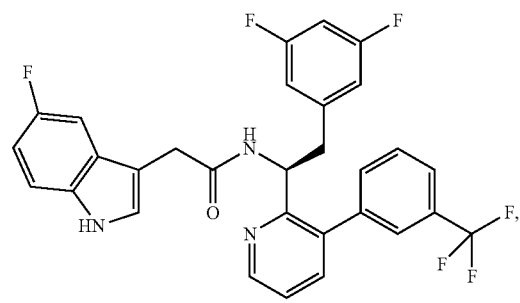

133
-continued
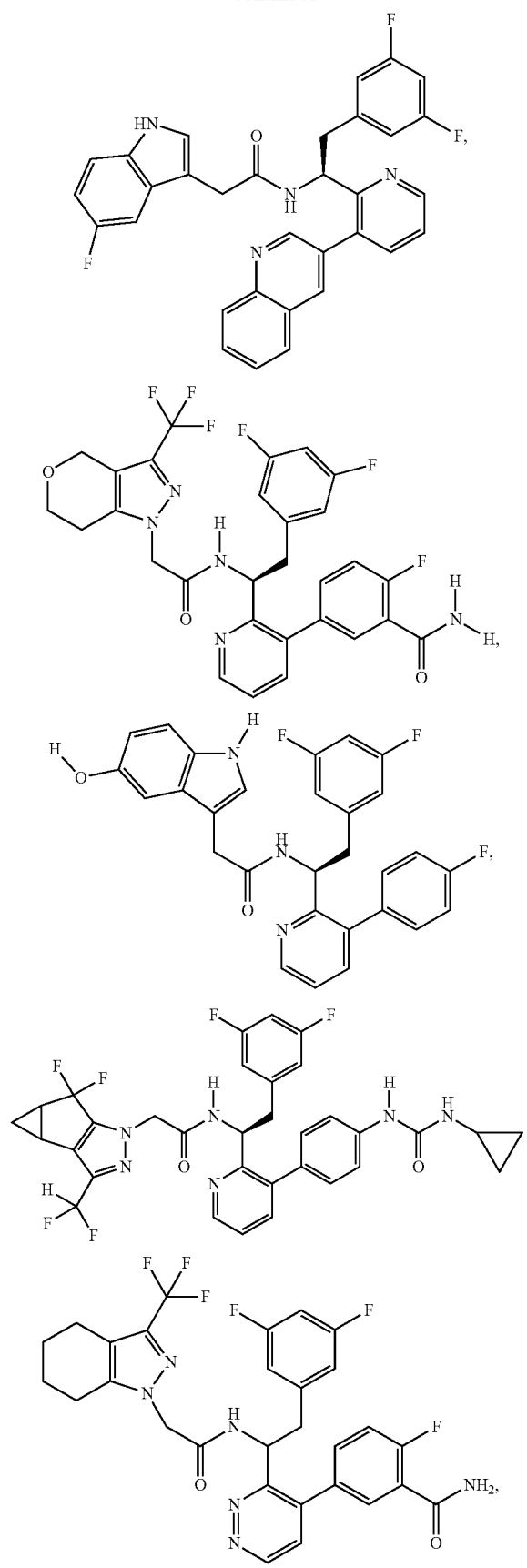
134
-continued
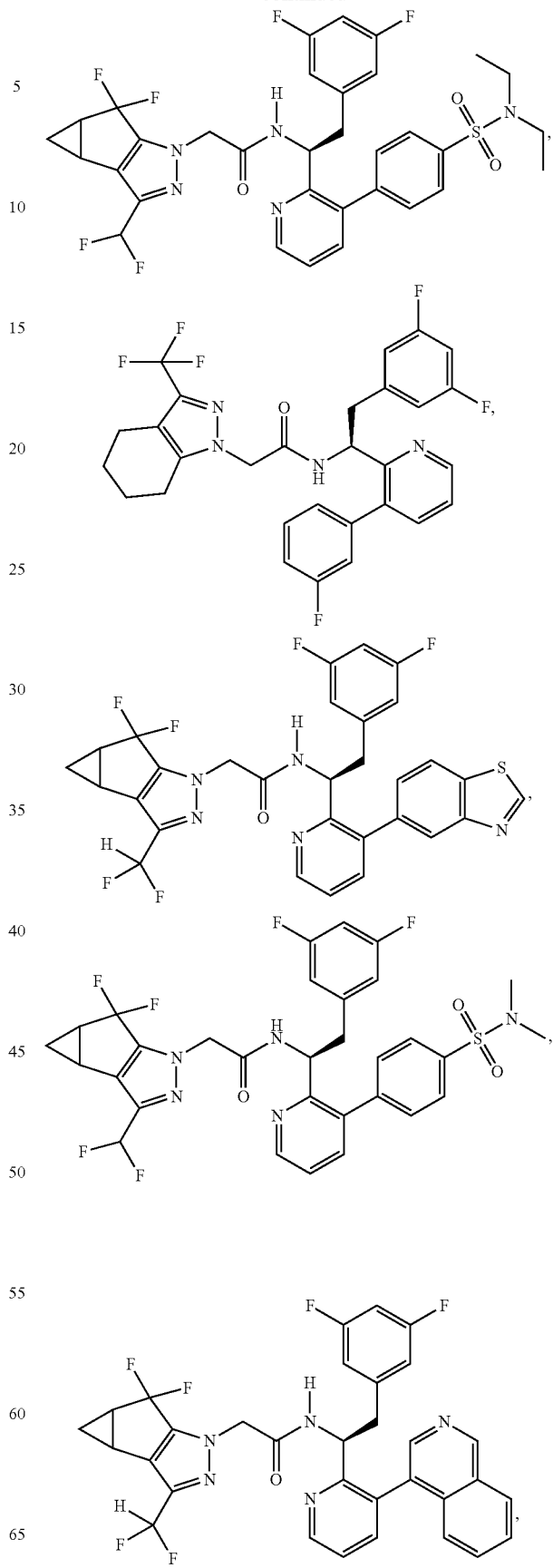

135
-continued
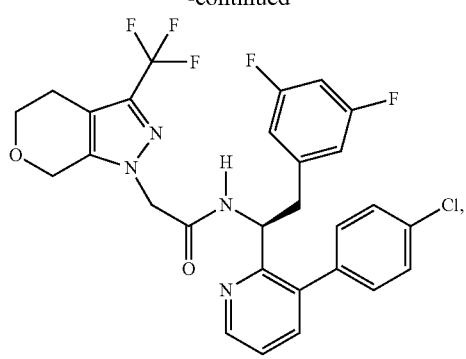
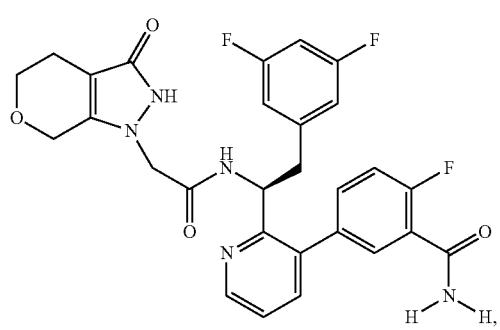
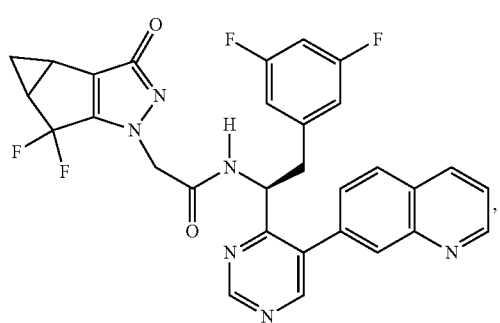
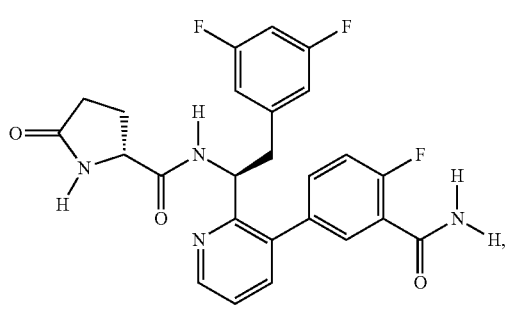
136
-continued
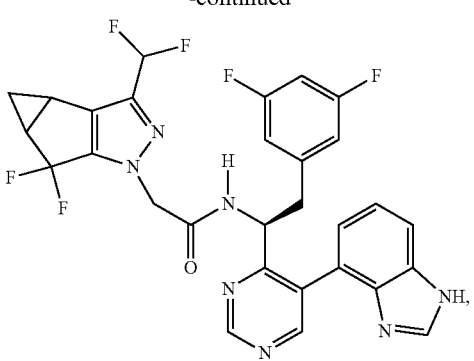
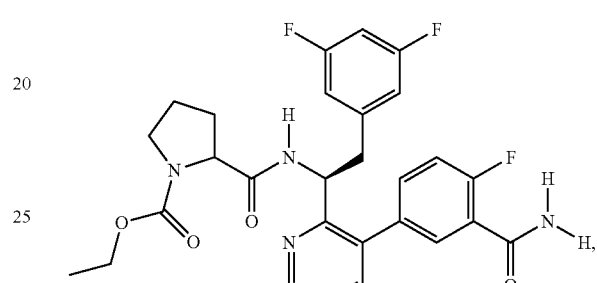
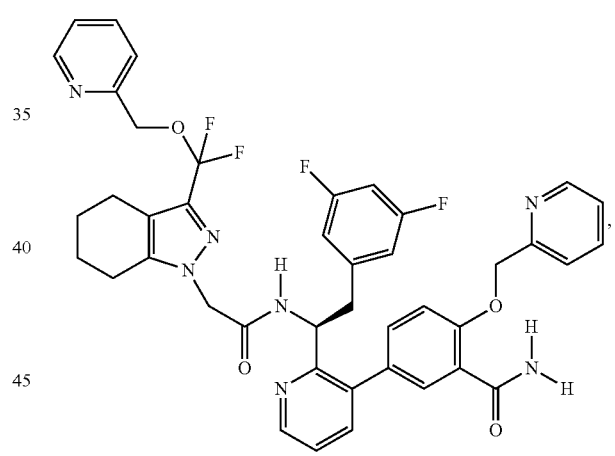
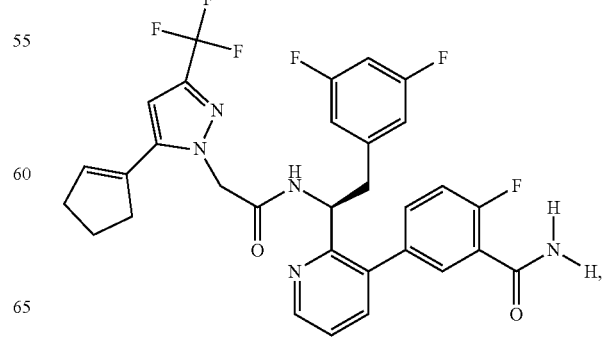

137
-continued
138
-continued
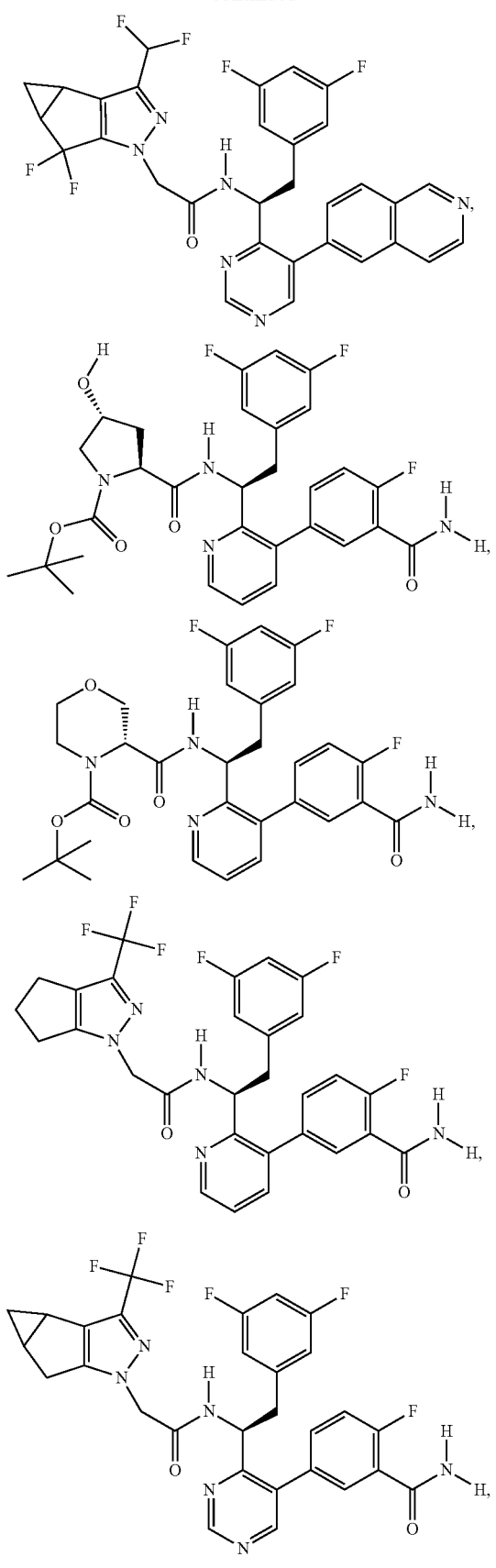
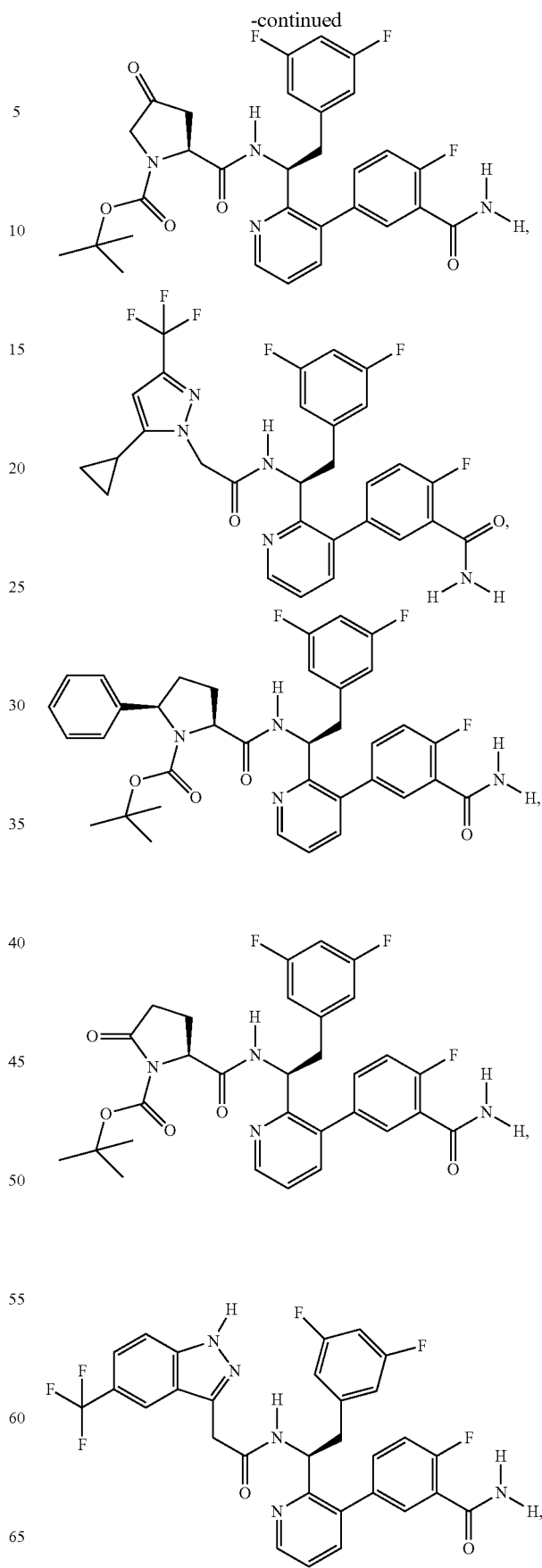

139
-continued
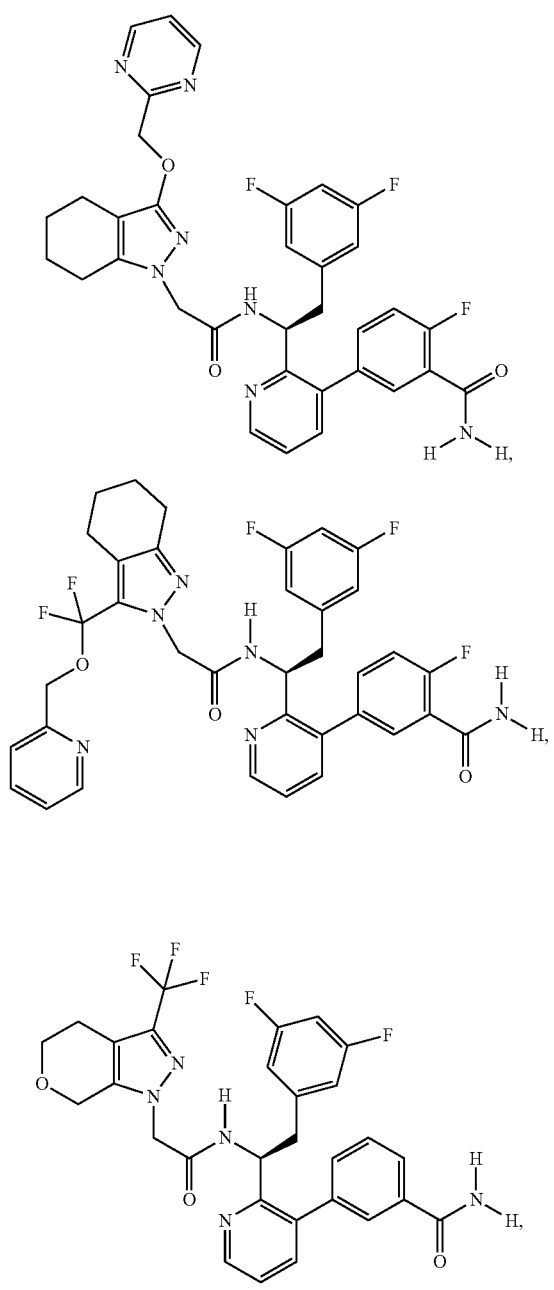
140
-continued
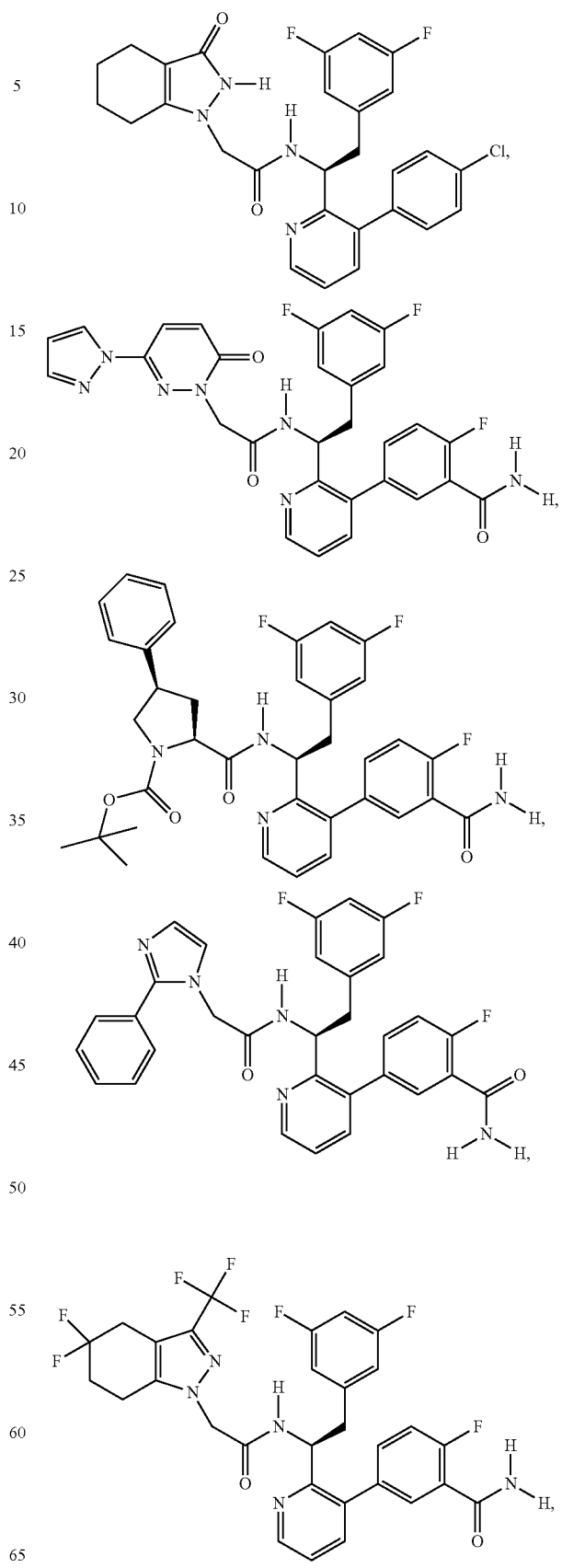

141
-continued
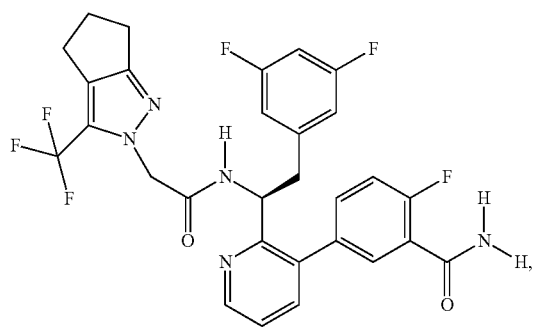
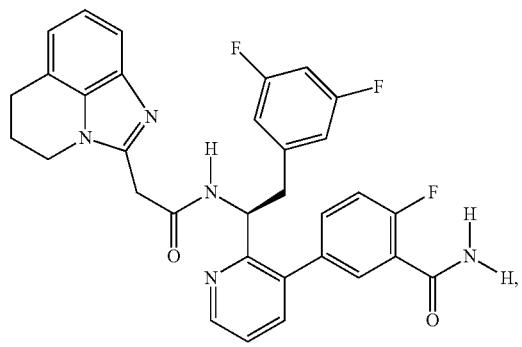
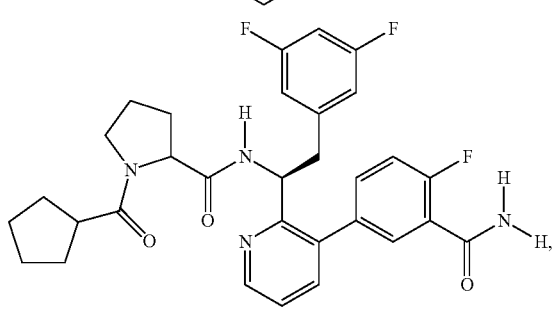
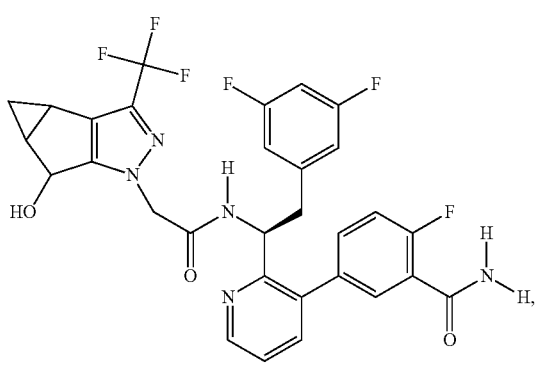
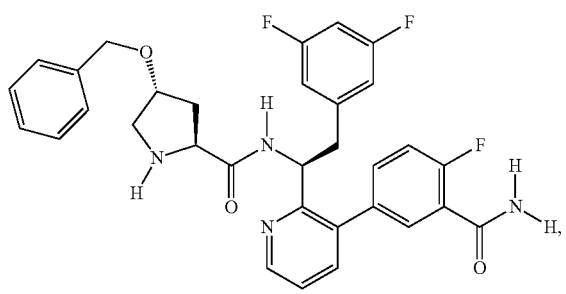
142
-continued
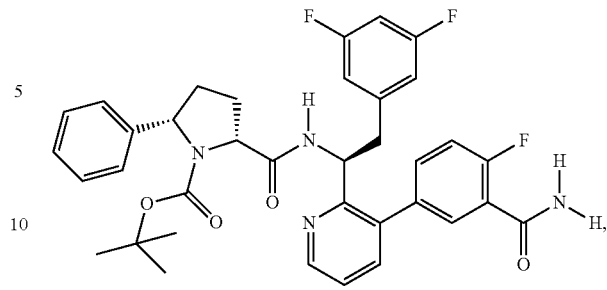
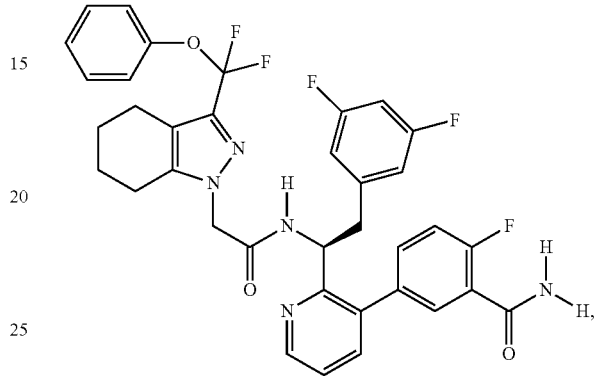
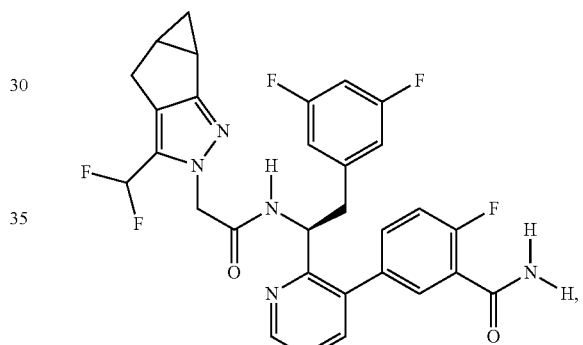
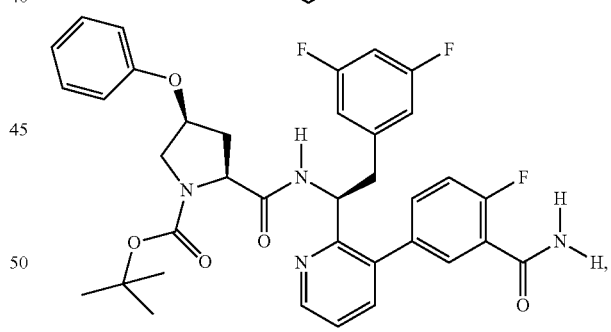
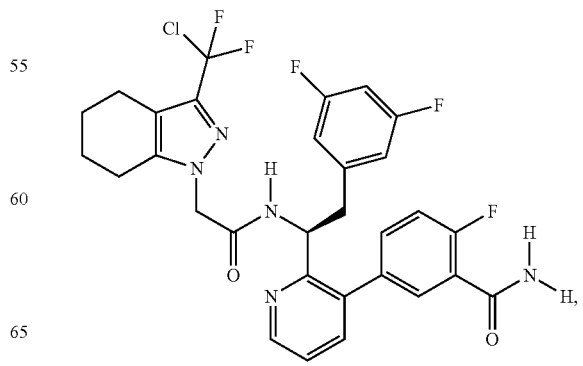

143
-continued
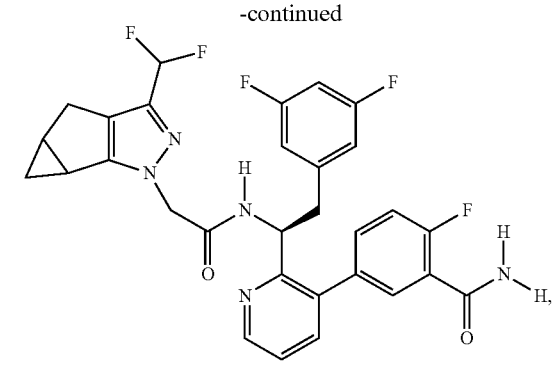
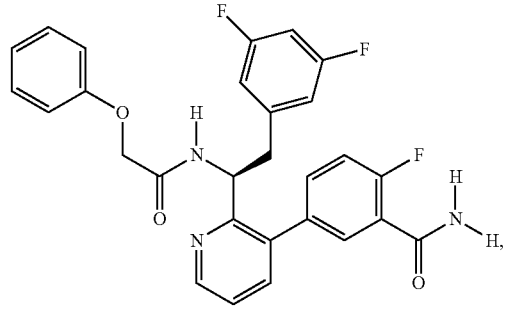
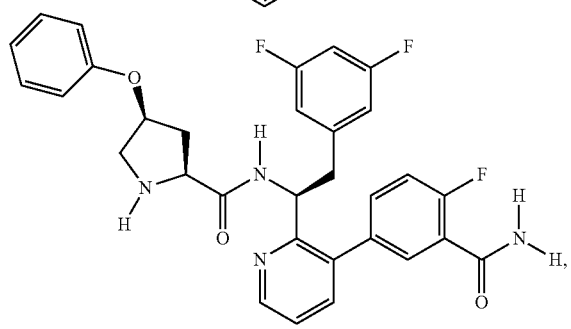
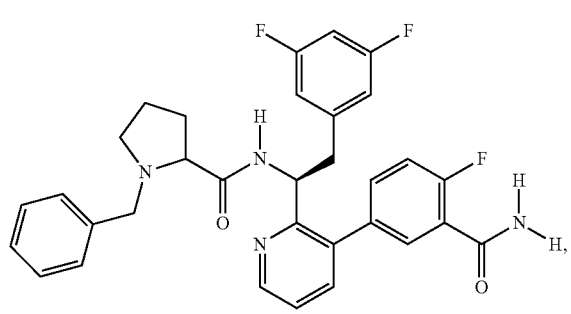
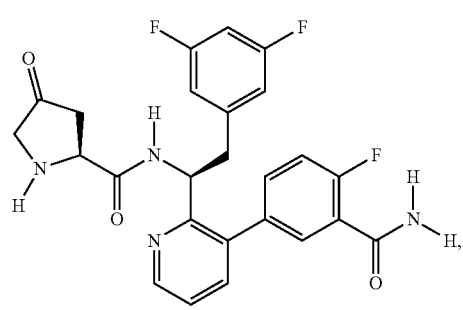
144
-continued
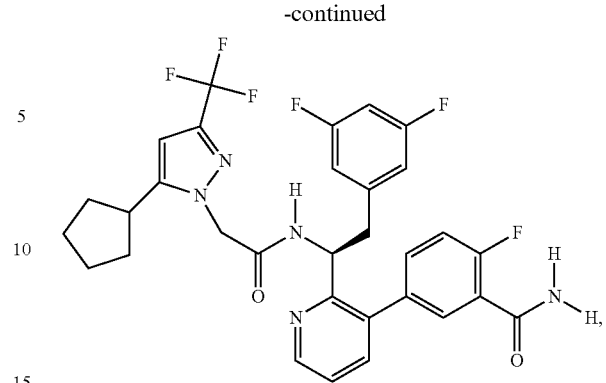
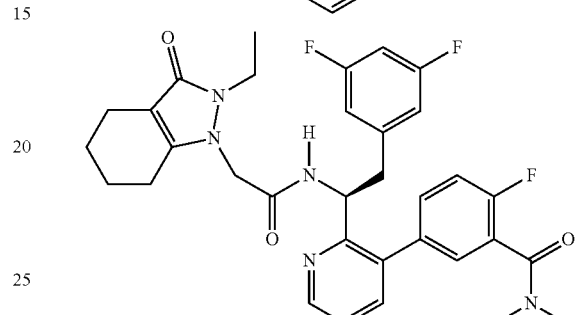
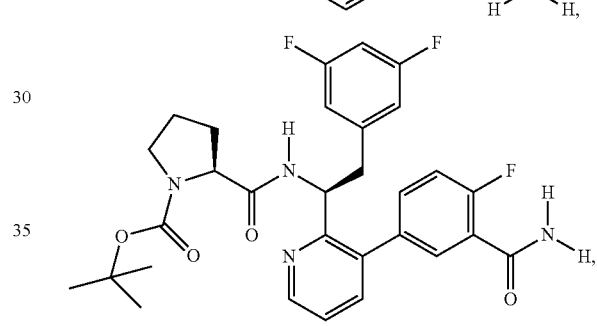
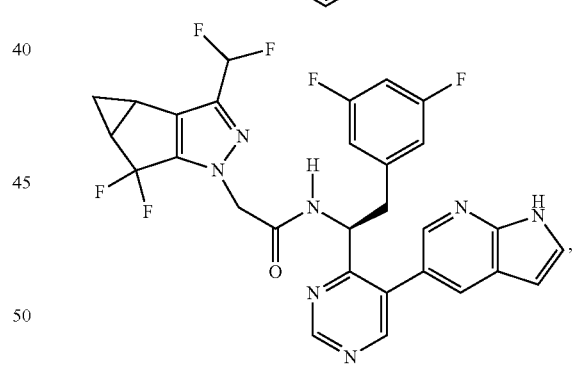
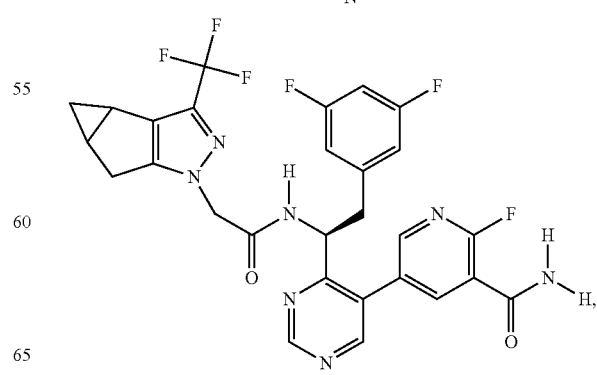

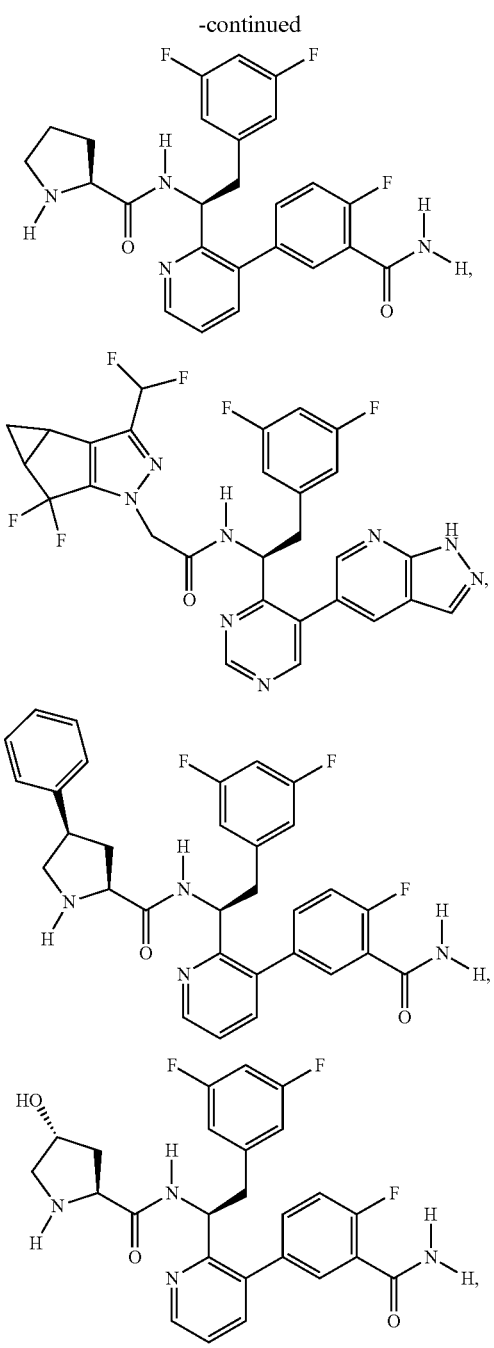
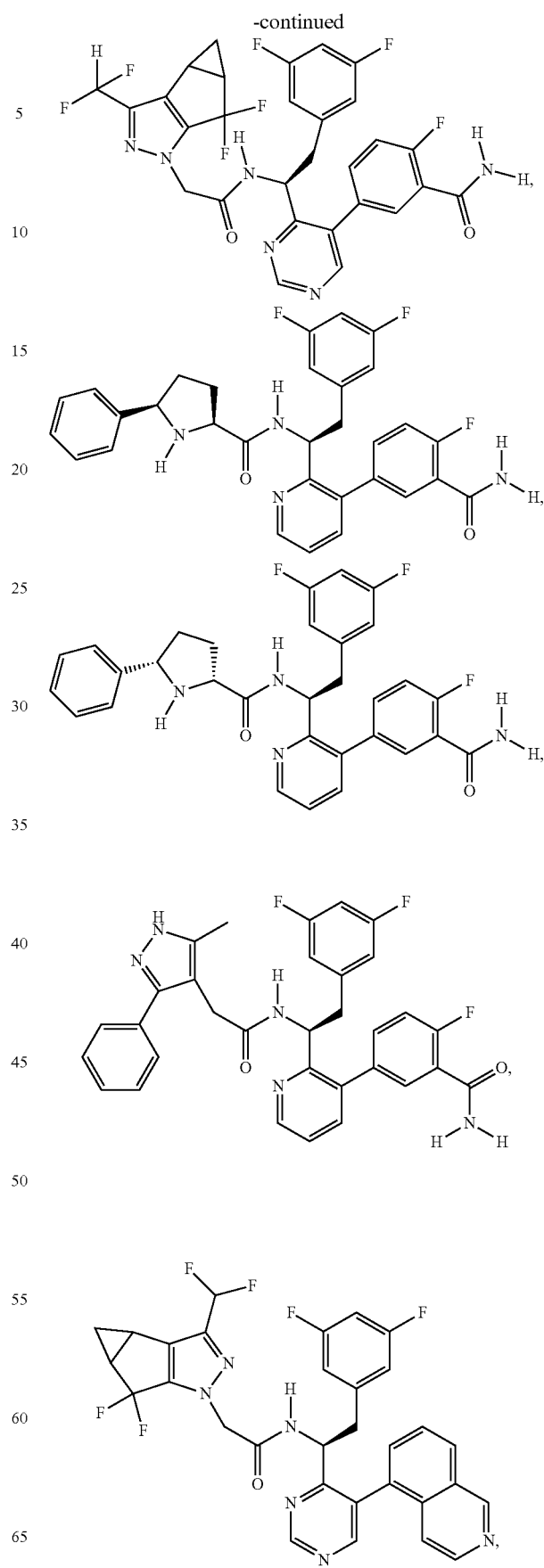

147
-continued
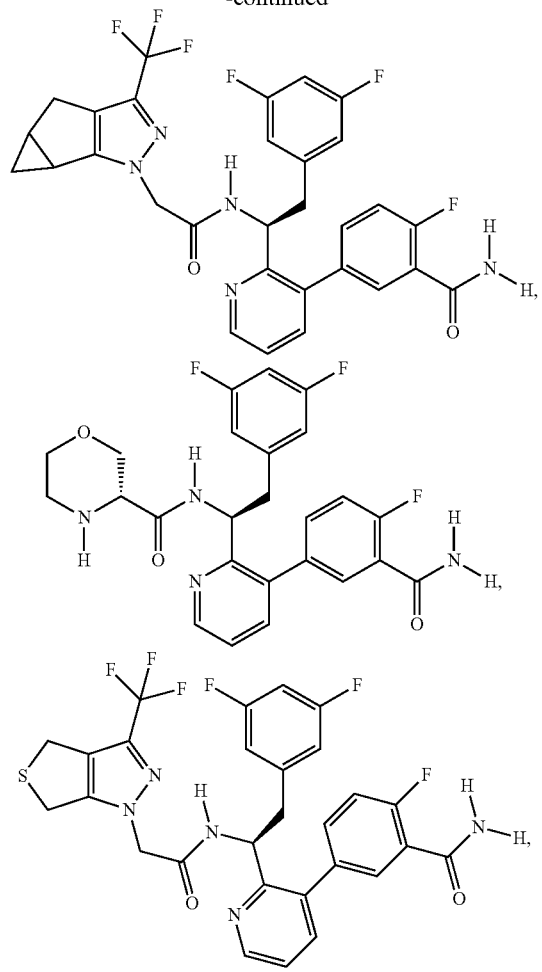
148
-continued
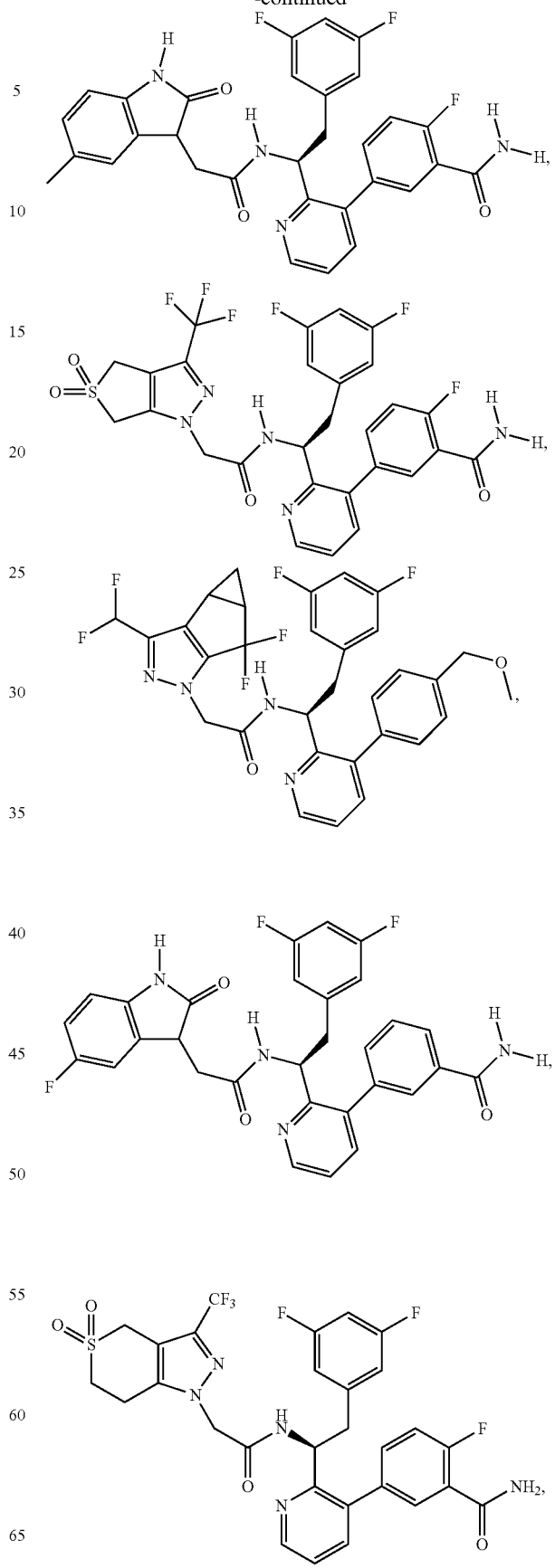

149
-continued
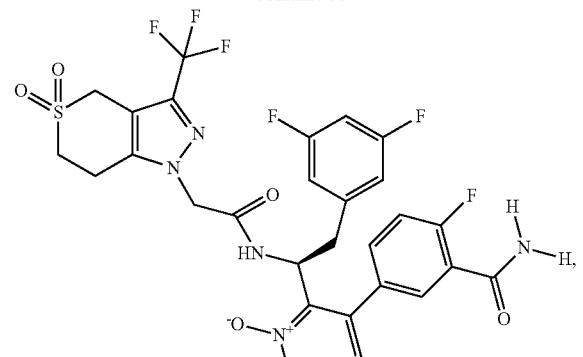
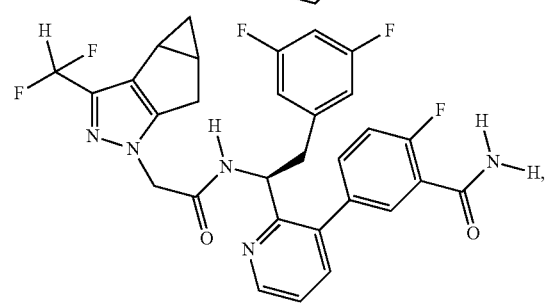
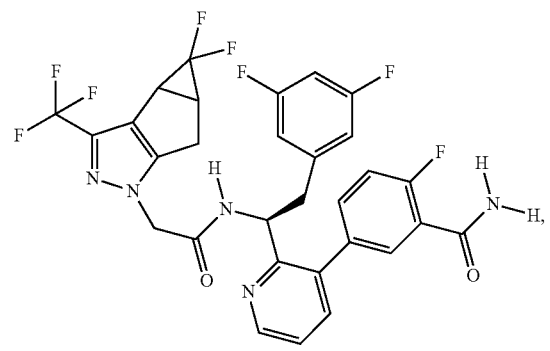
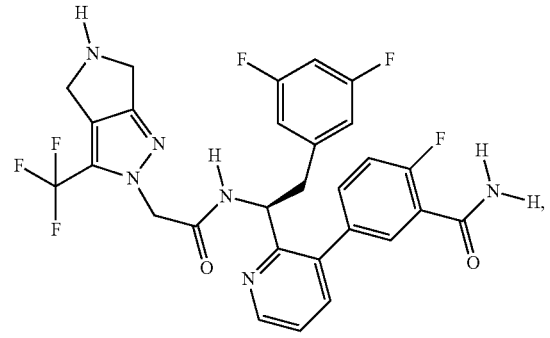
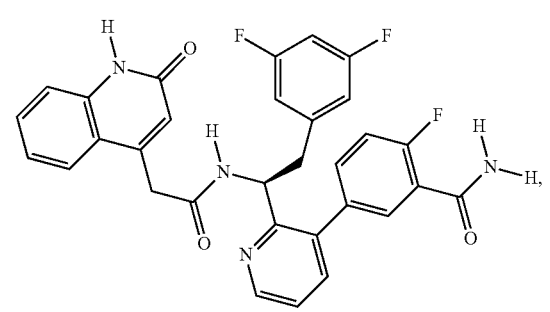
150
-continued
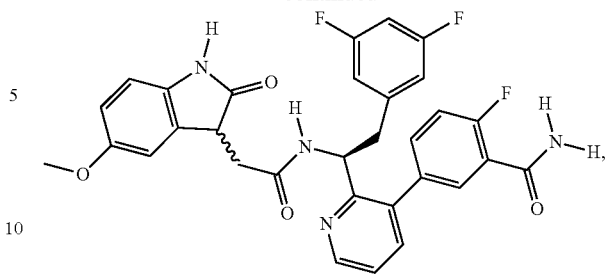
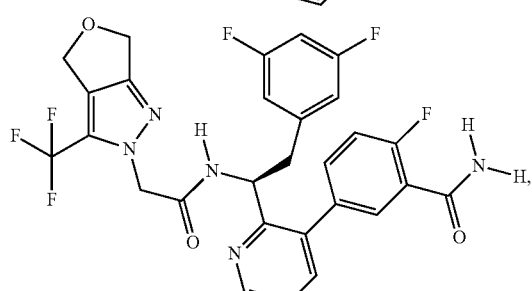
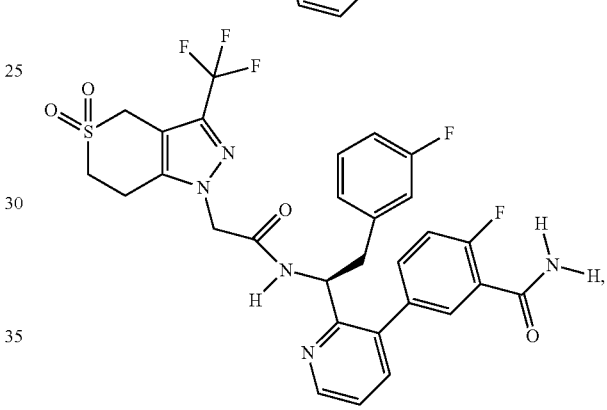
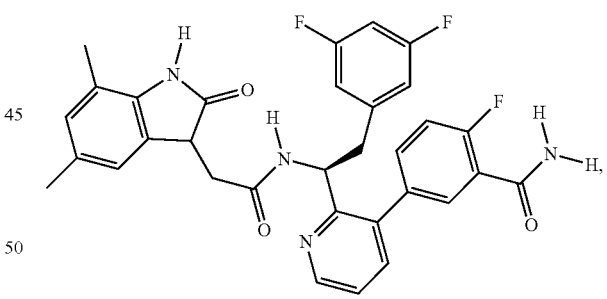
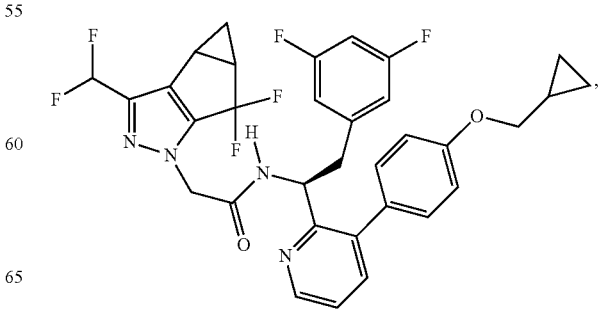

151
-continued
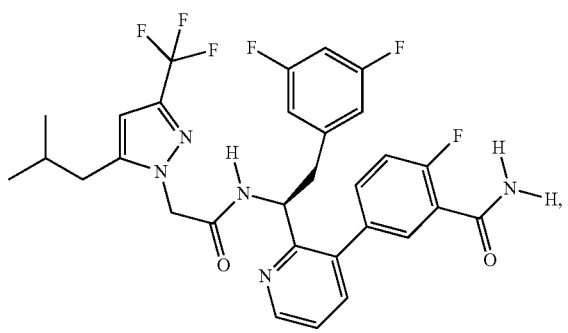
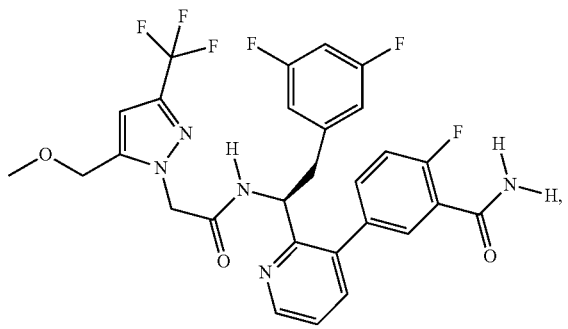
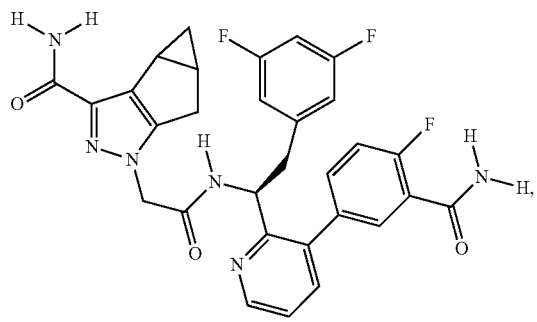
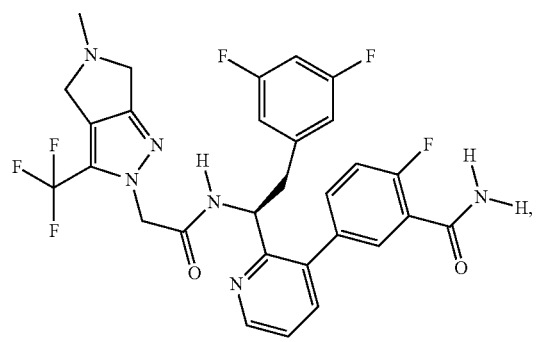
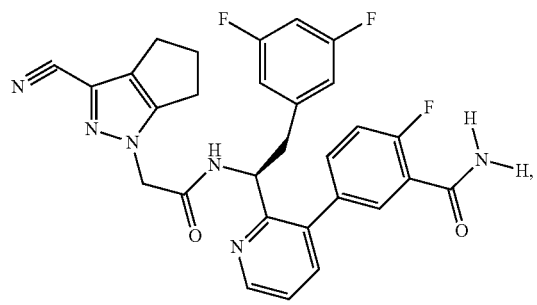
152
-continued
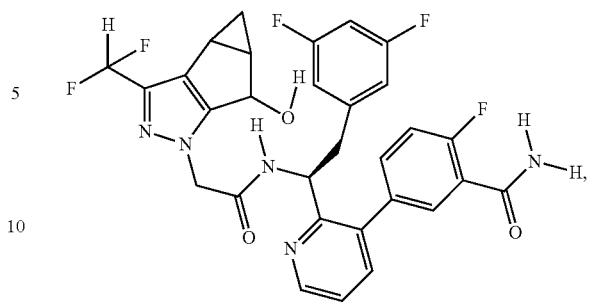
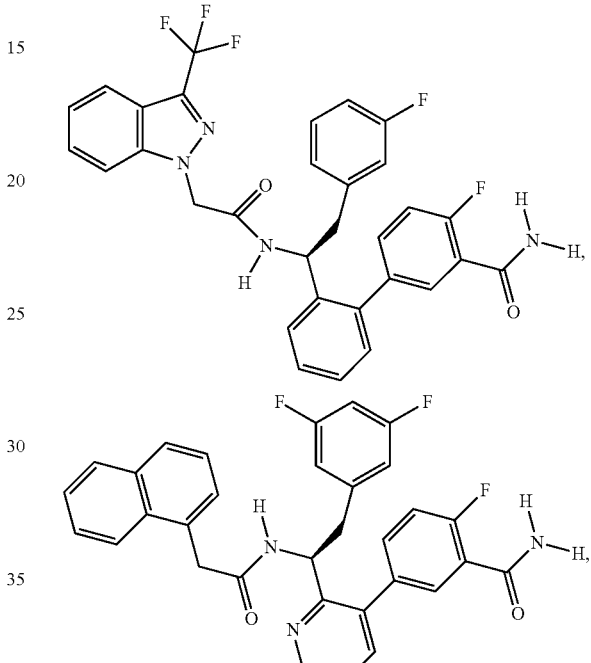
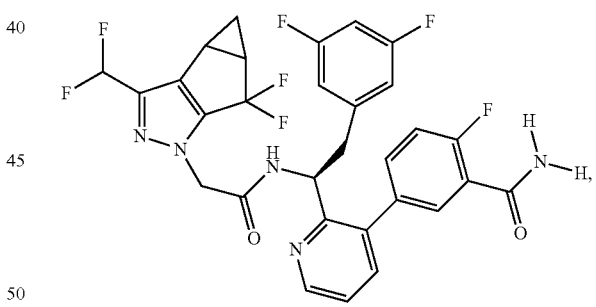

153
-continued
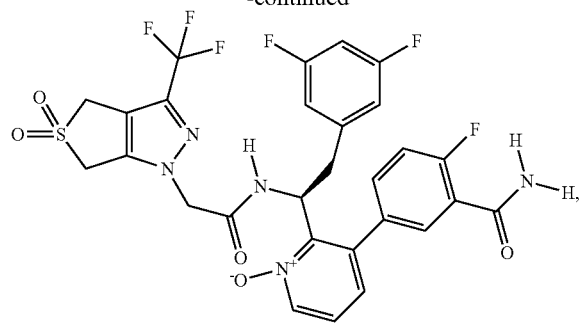
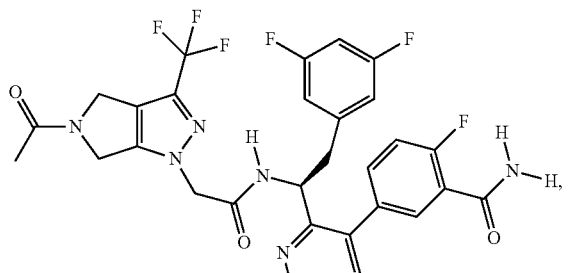
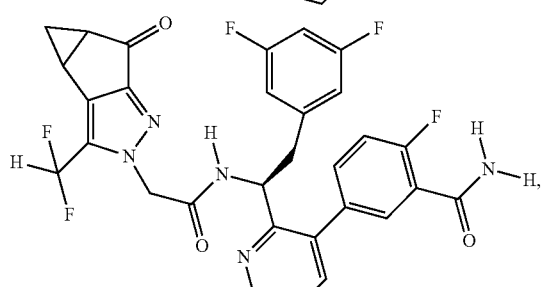
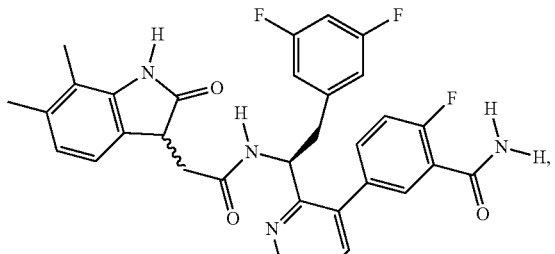
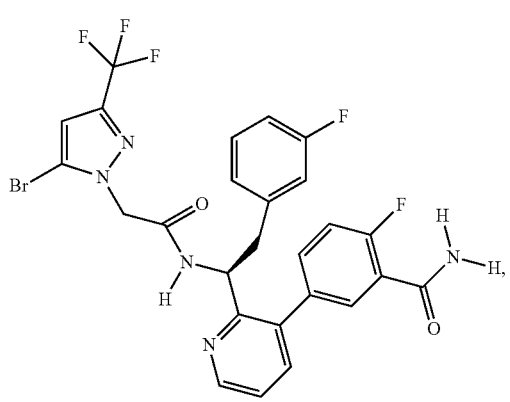
154
-continued
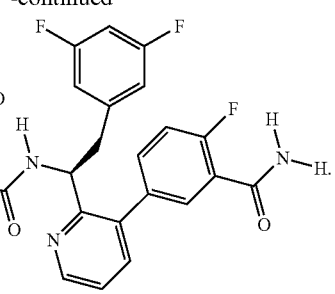
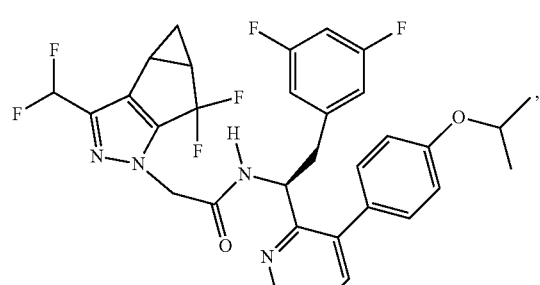
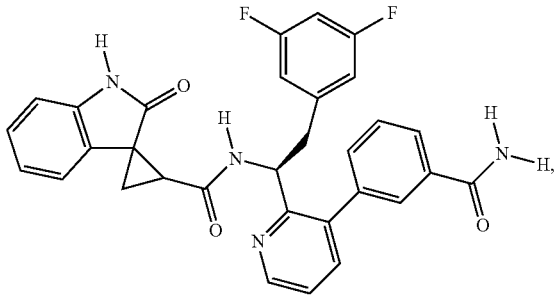
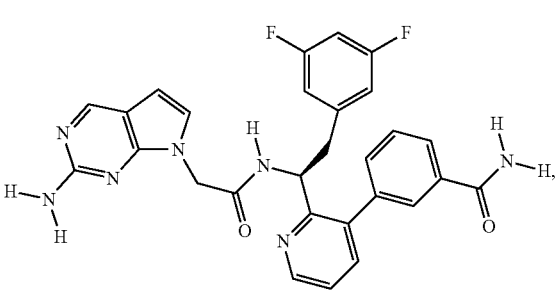
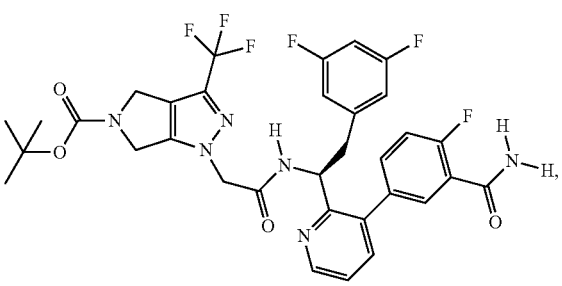

155
-continued
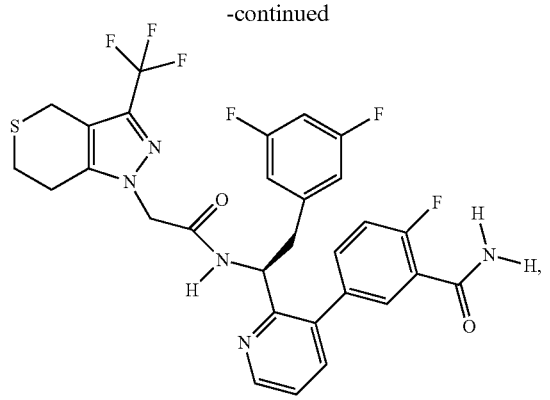
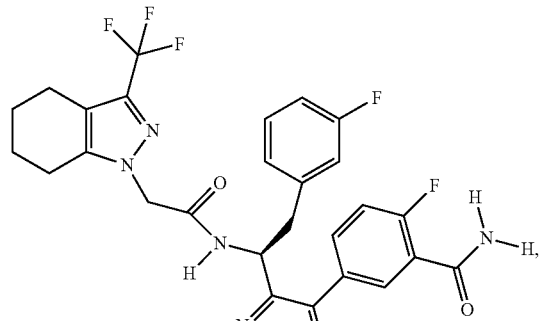
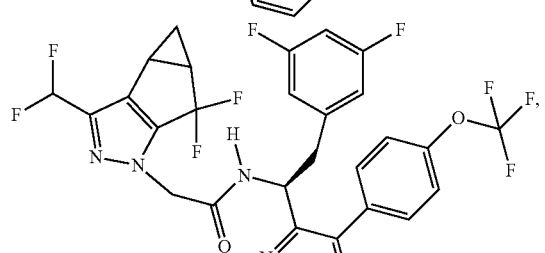
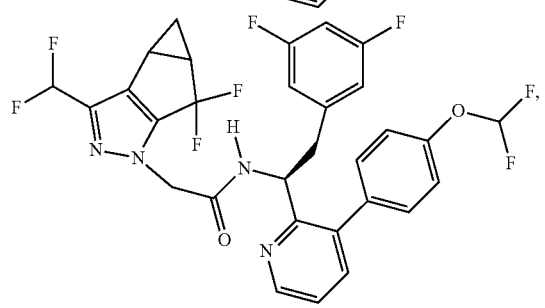
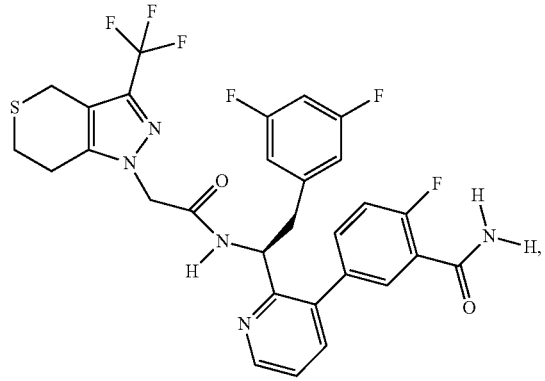
156
-continued
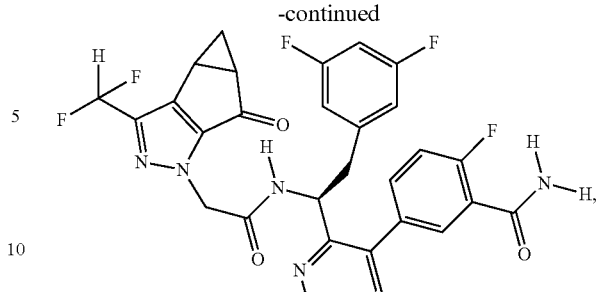
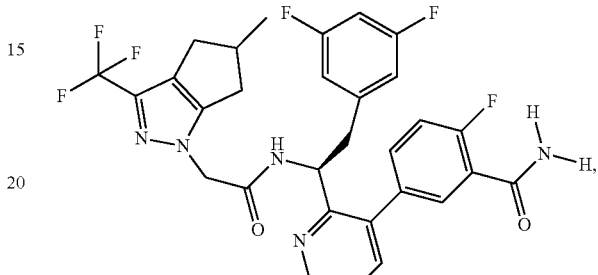
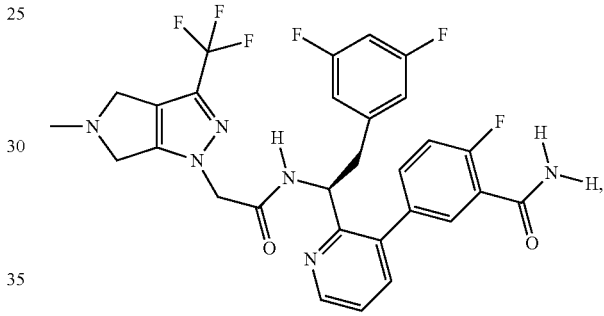
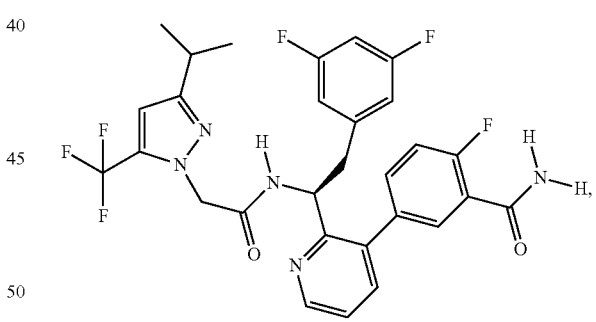
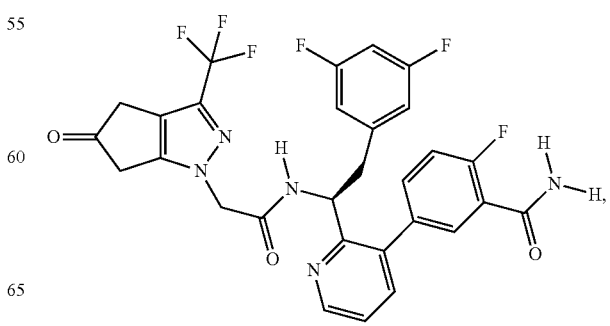

157
-continued
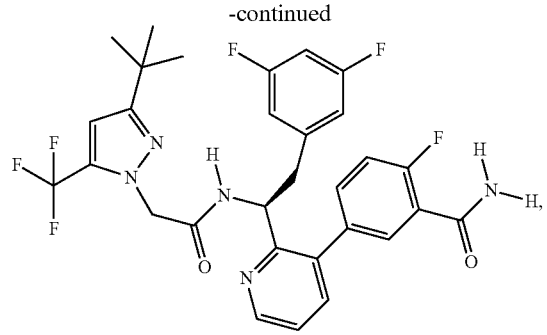
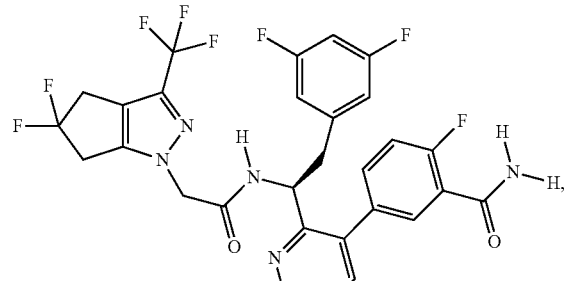
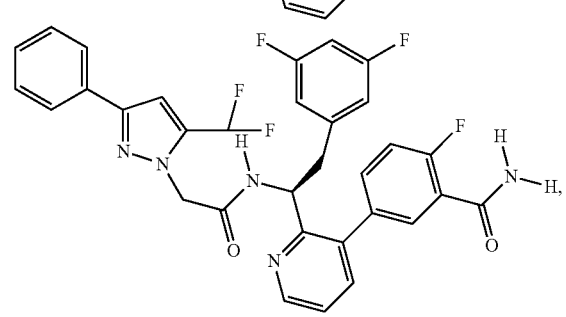
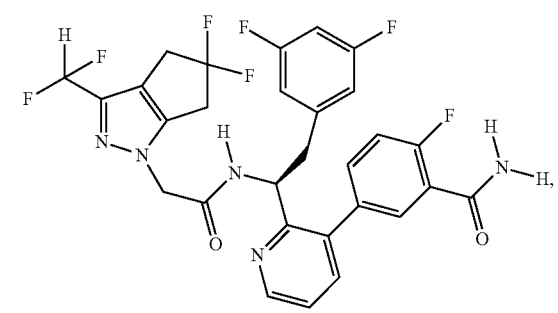
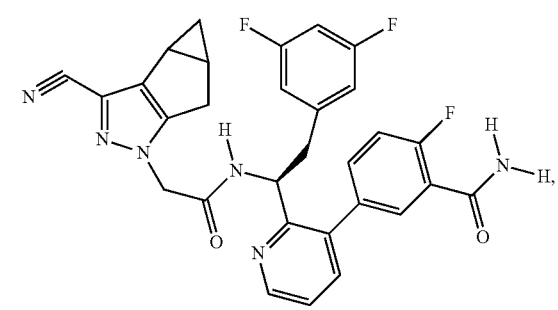
158
-continued
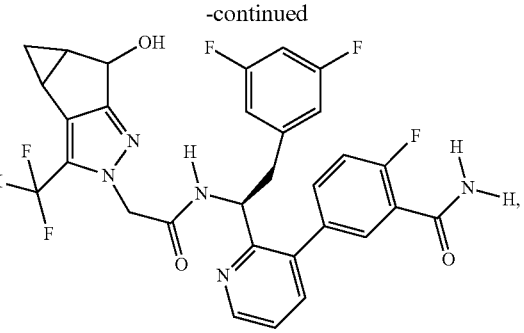
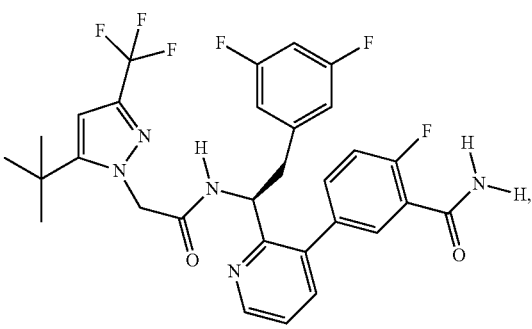
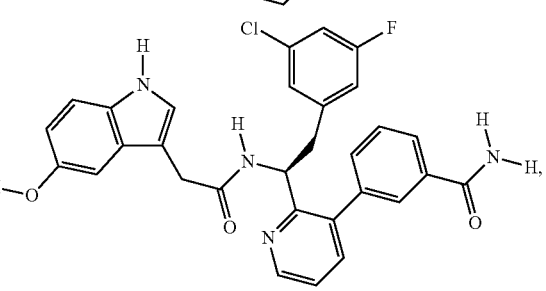
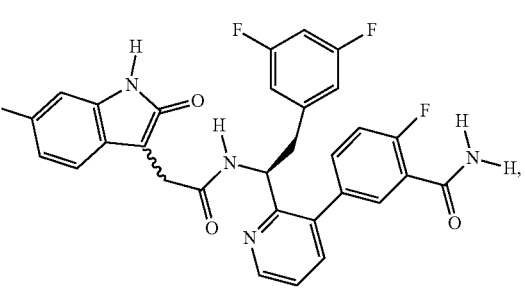
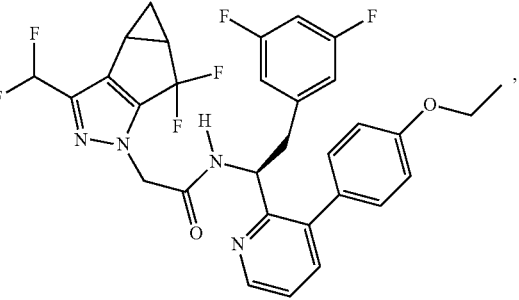

159
-continued
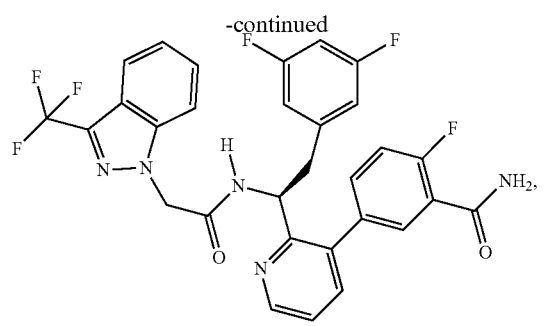
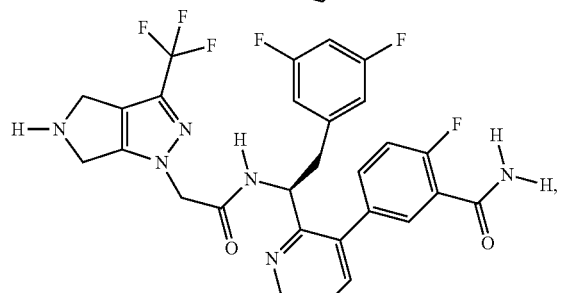
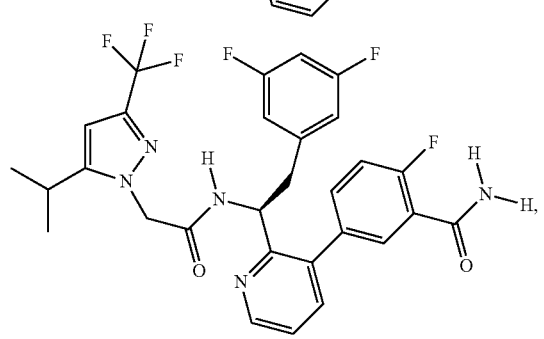
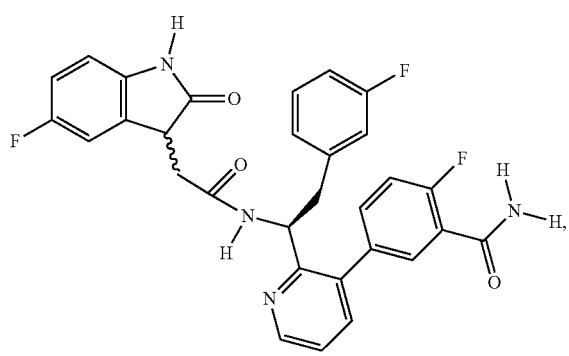
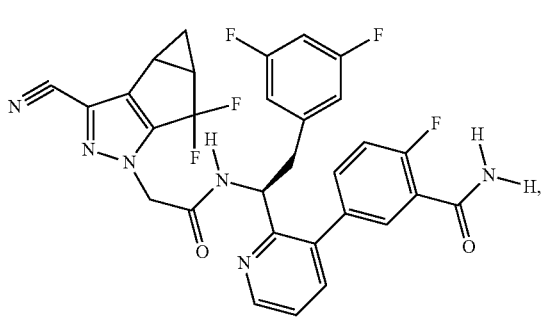
160
-continued
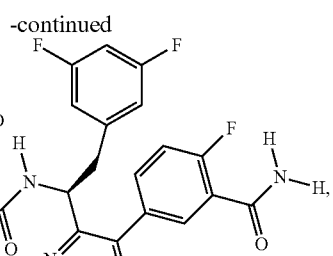
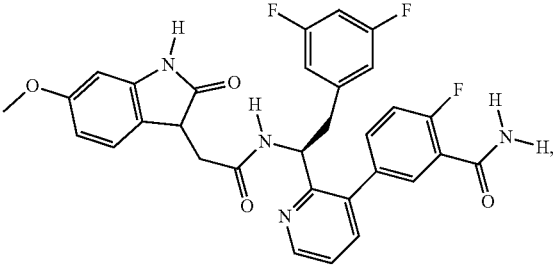
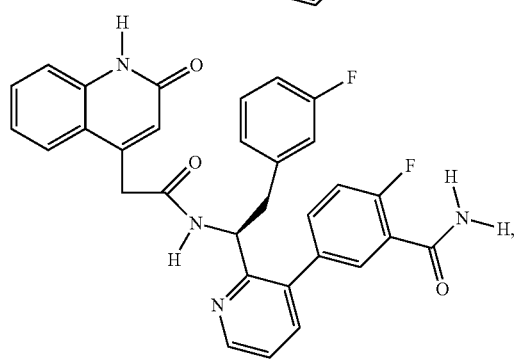
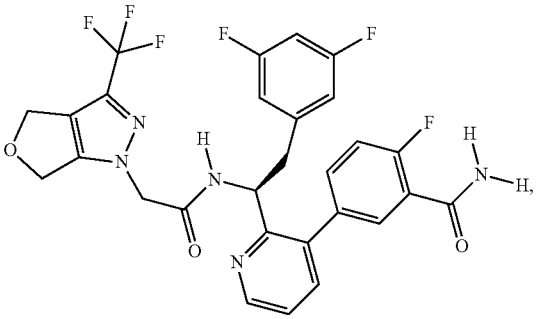
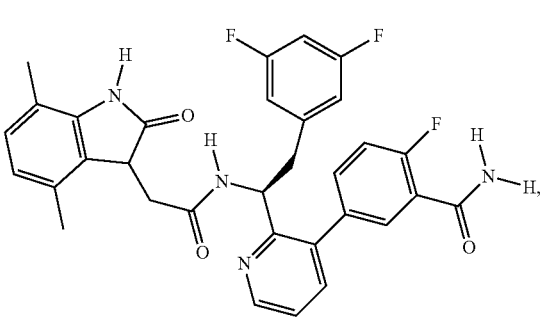

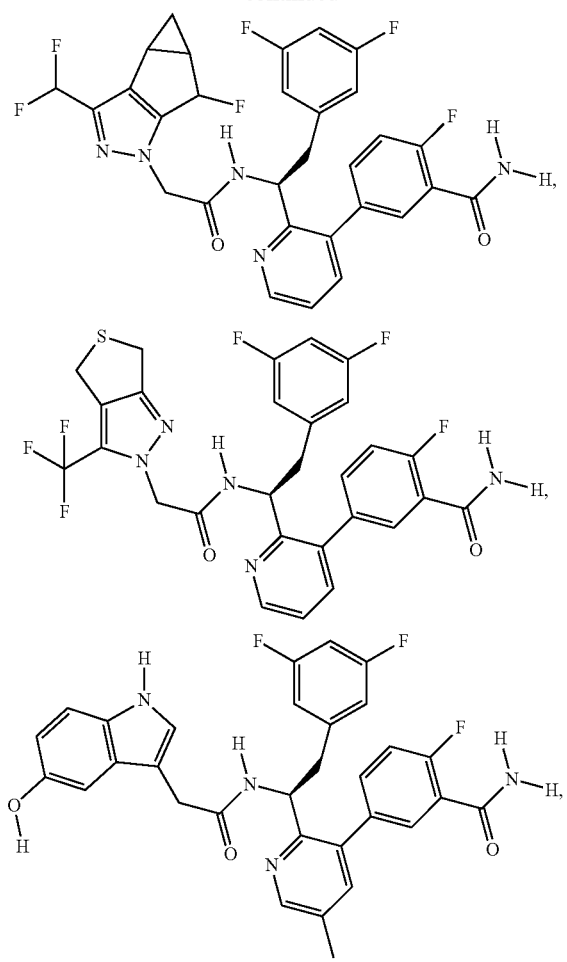
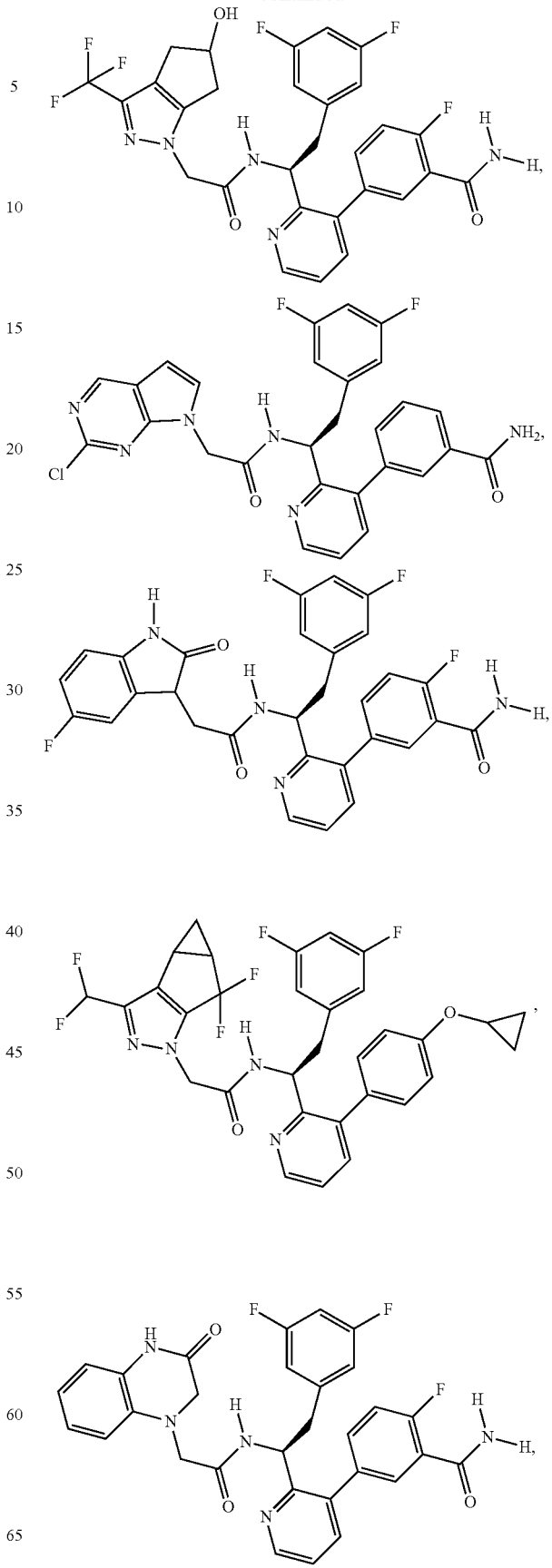

-continued
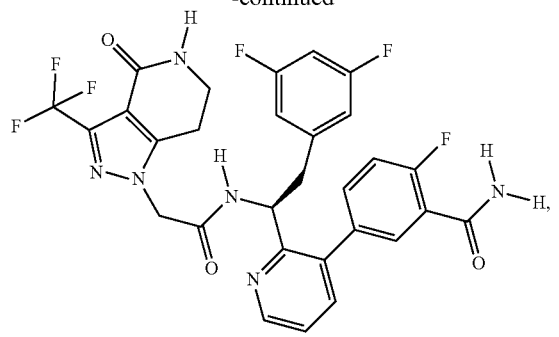
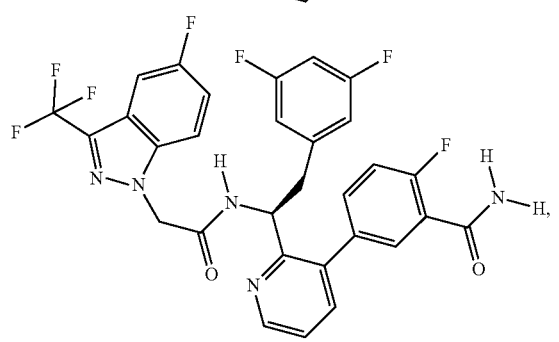
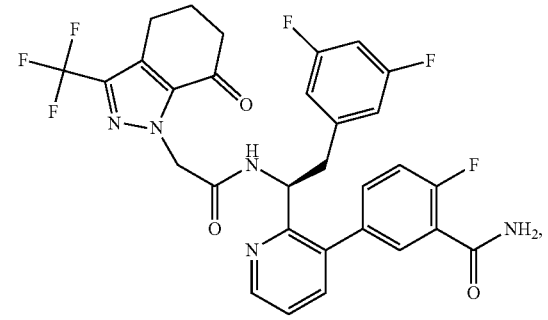
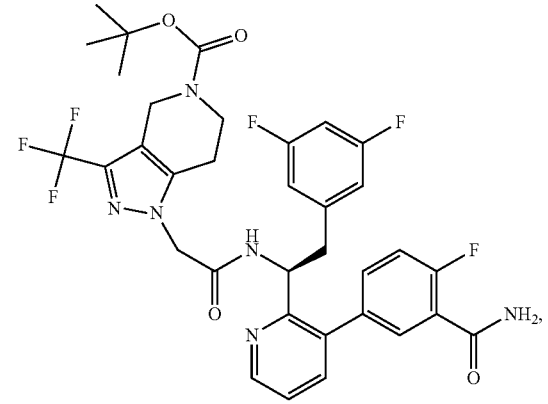
-continued
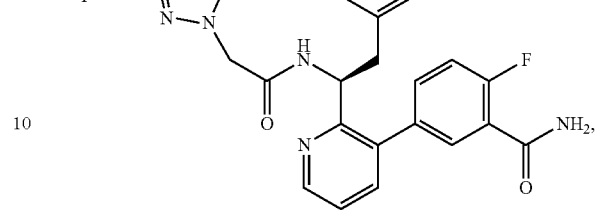
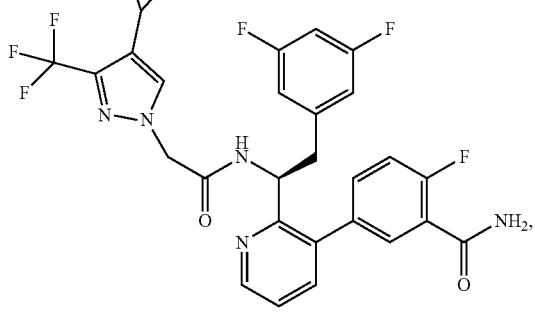
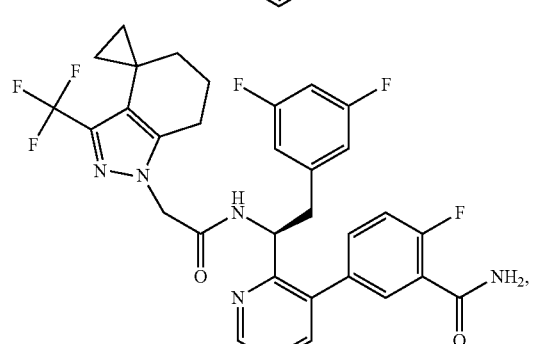
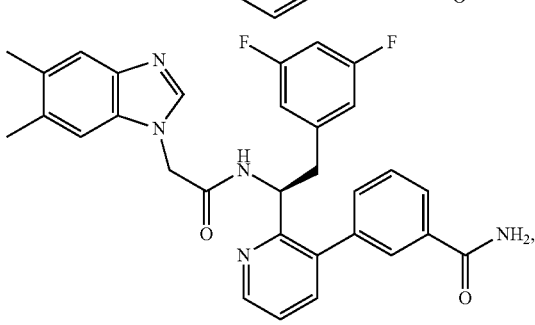
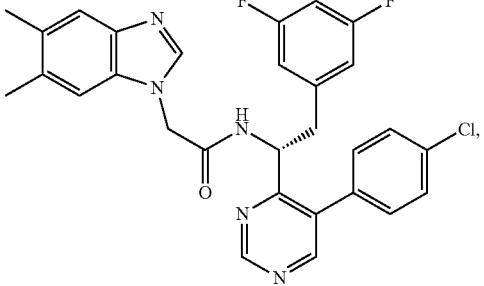

165
-continued
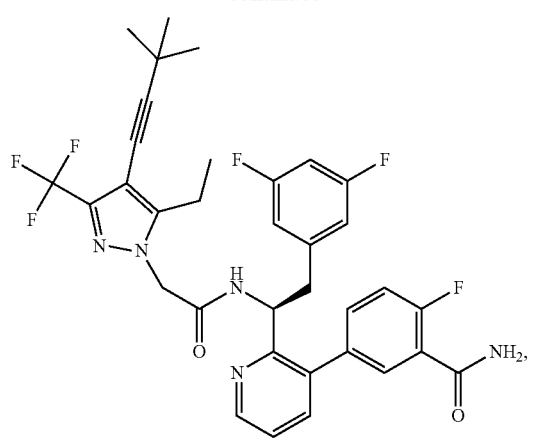
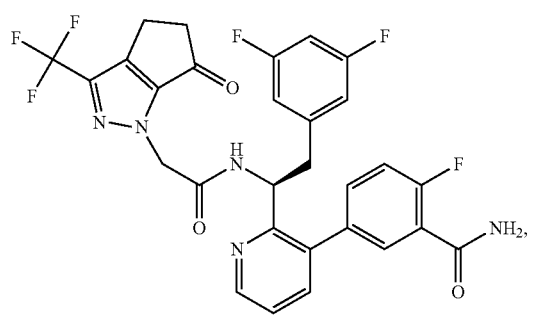
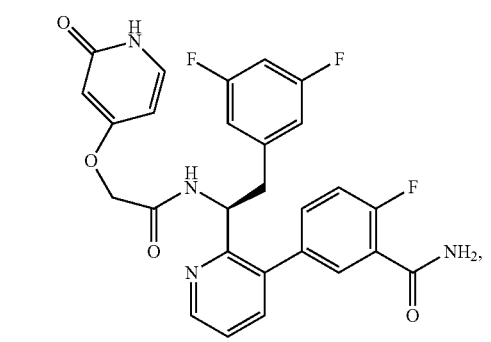
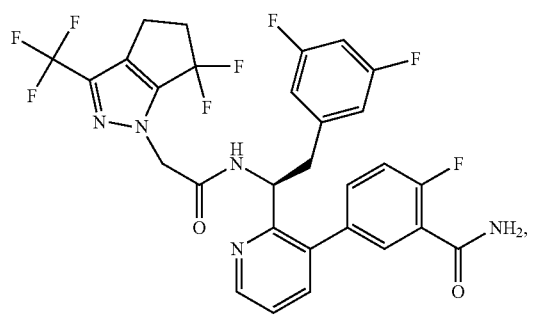
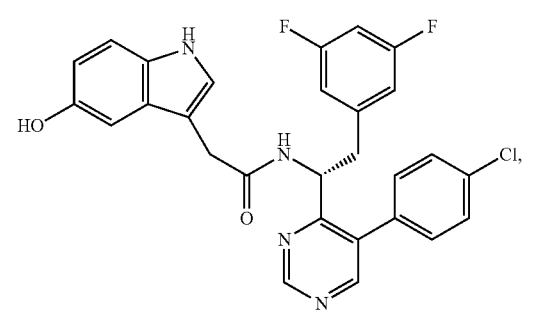
166
-continued
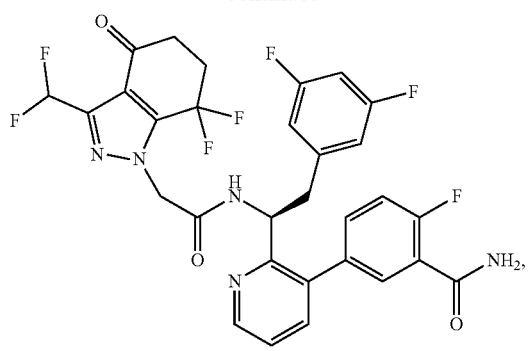
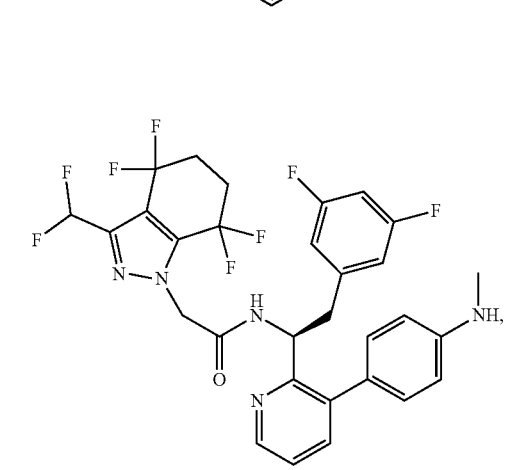
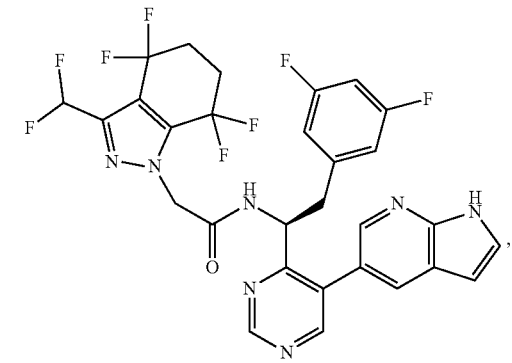
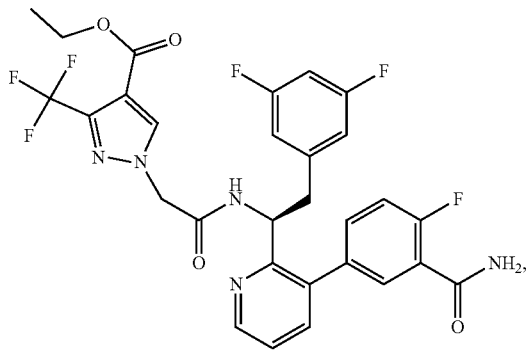

167
-continued
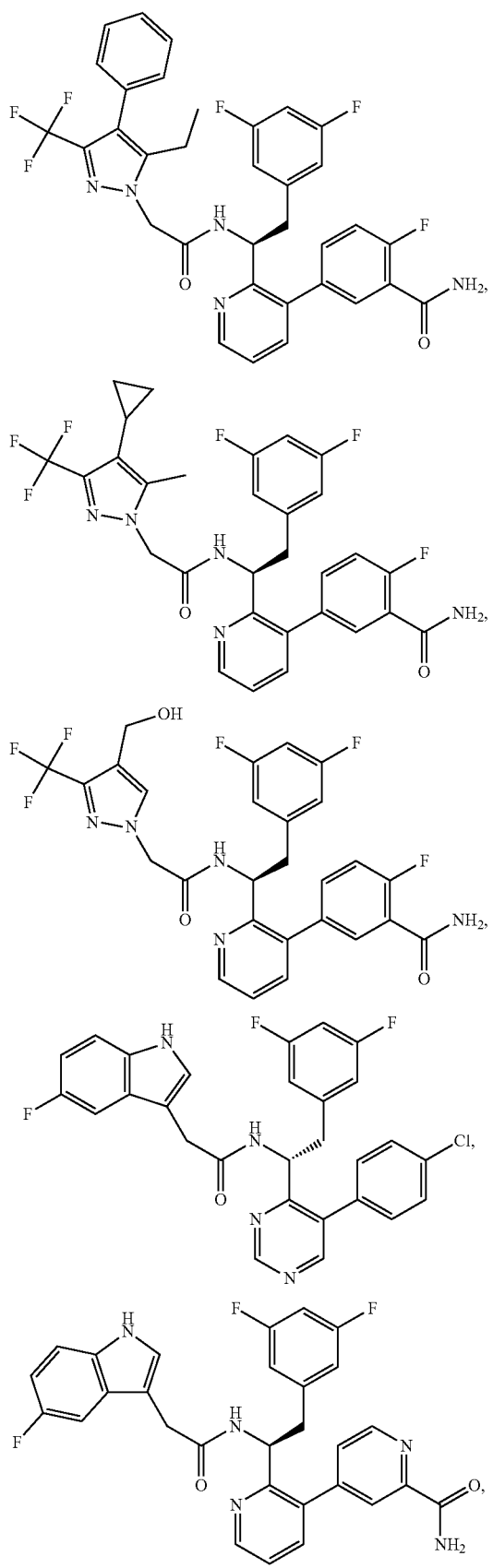
168
-continued
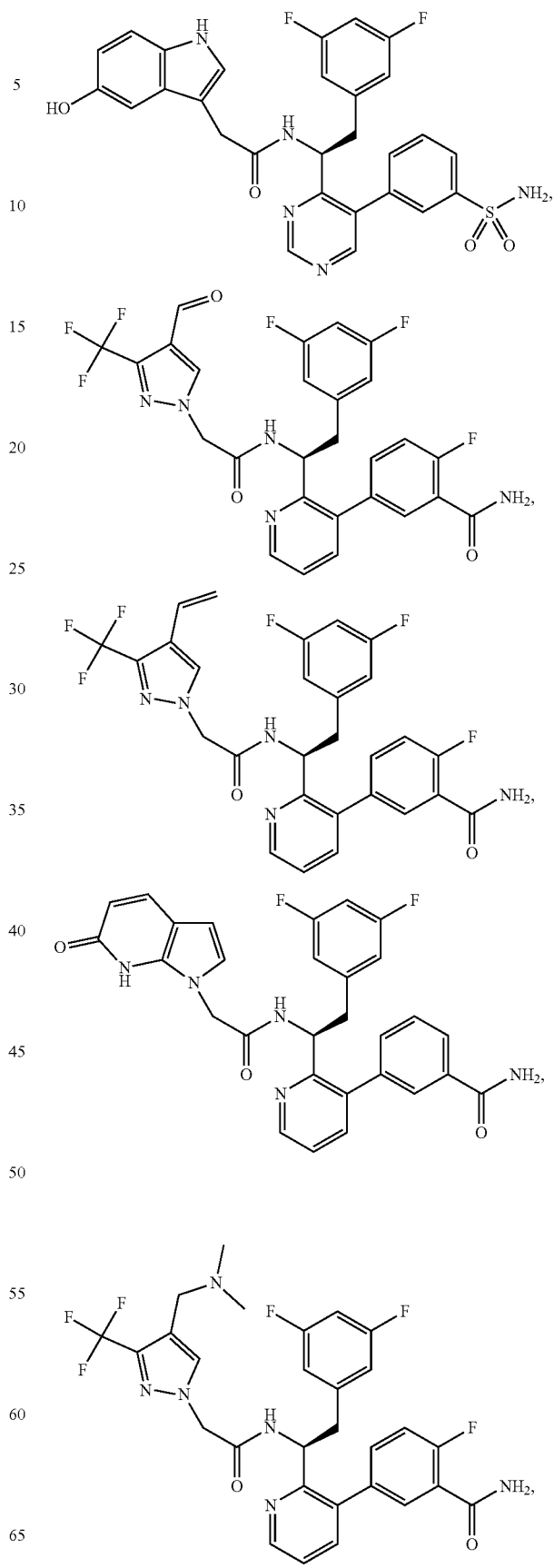

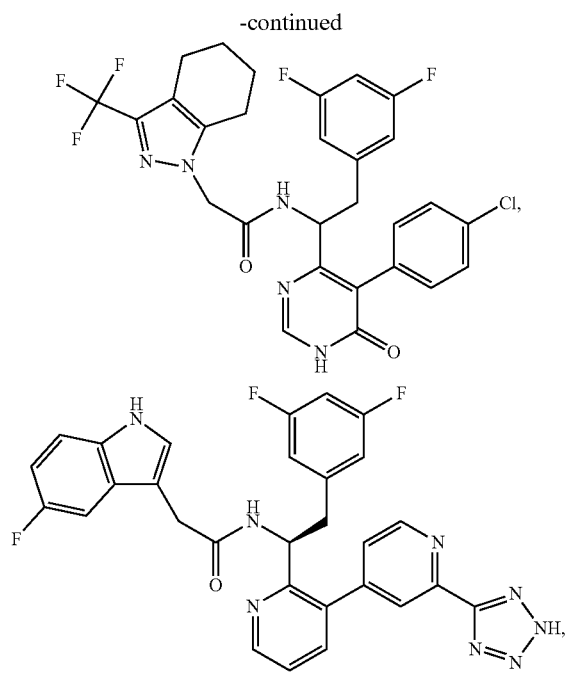
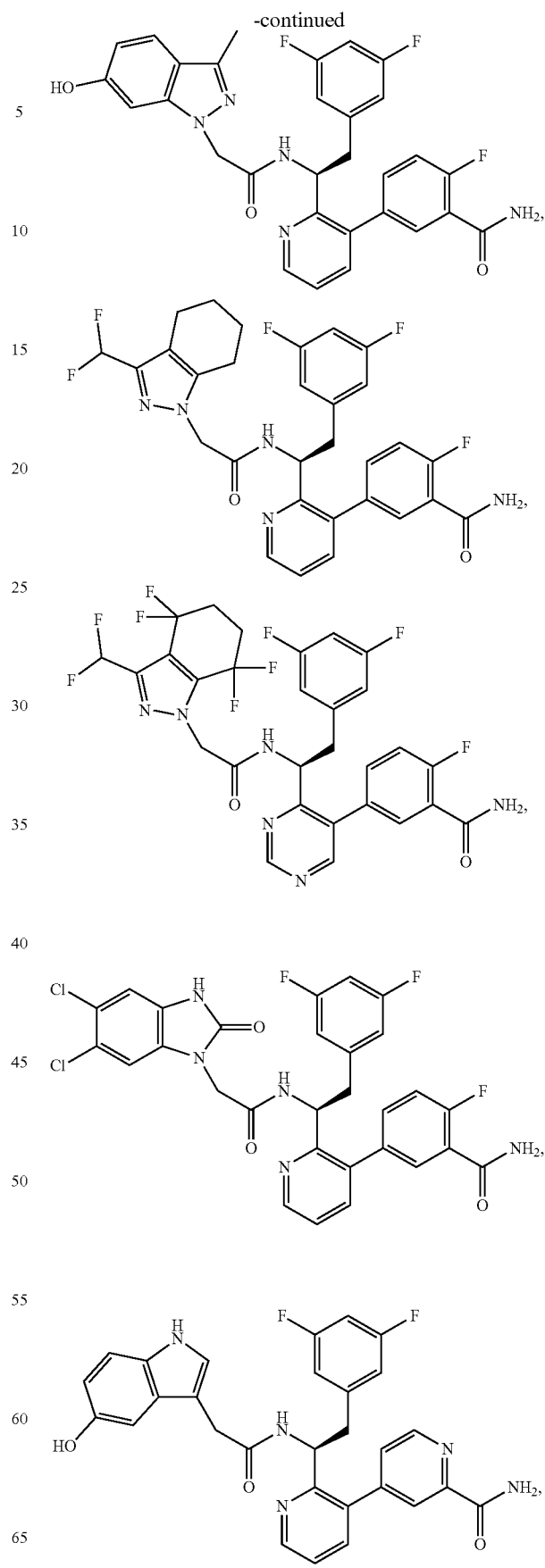

171
-continued
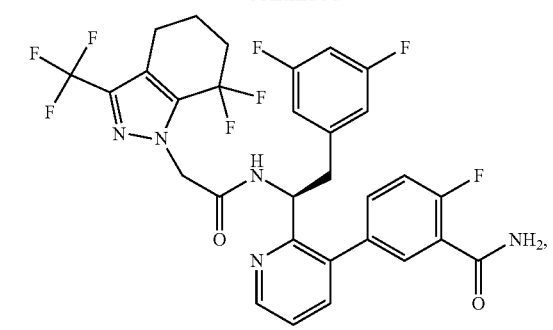
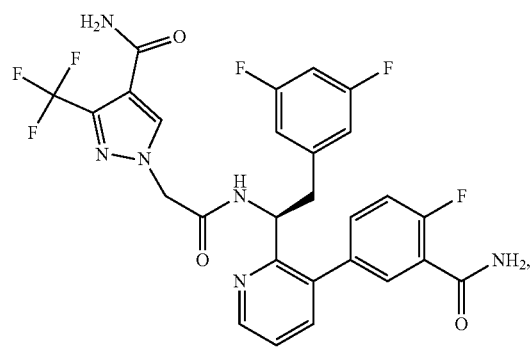
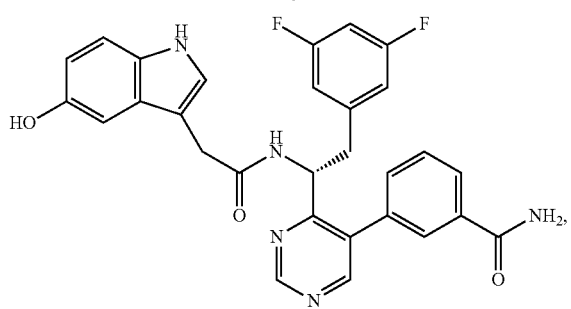
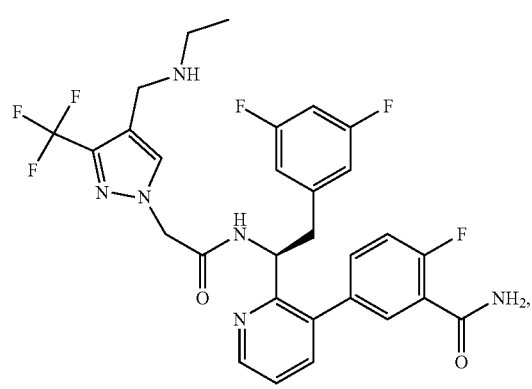
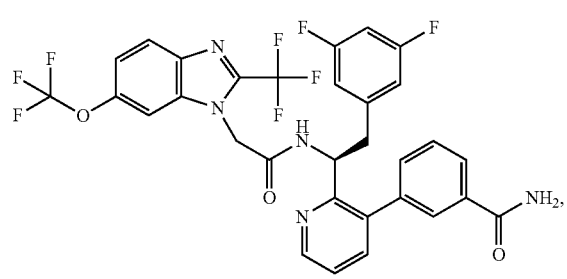
172
-continued
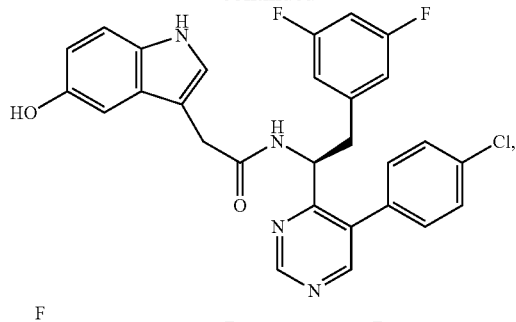
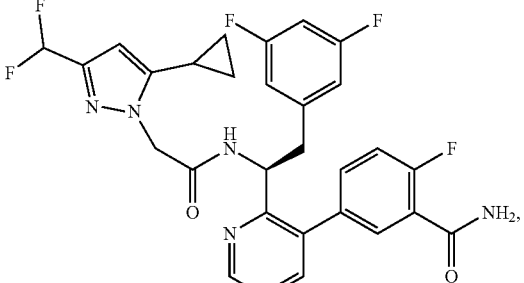
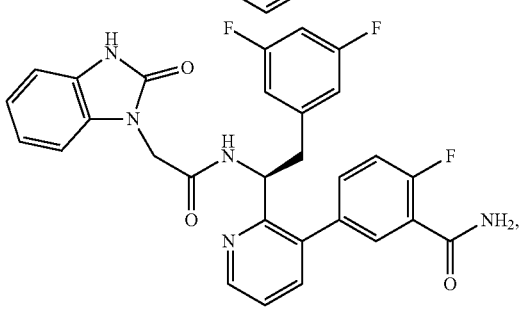
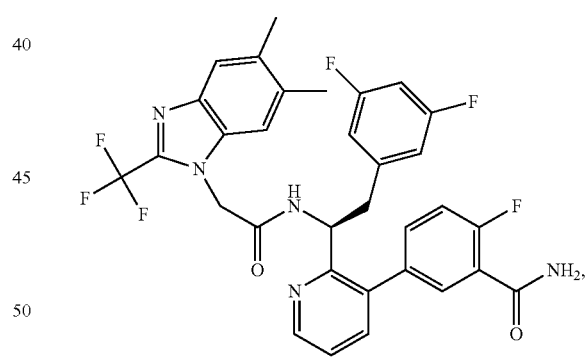
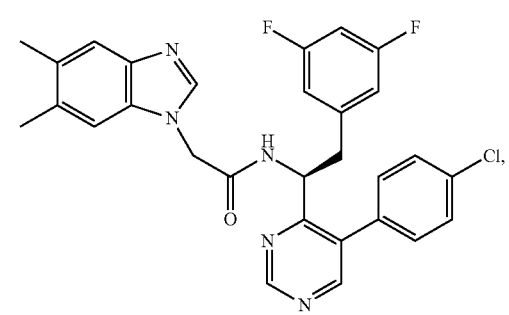

173
-continued
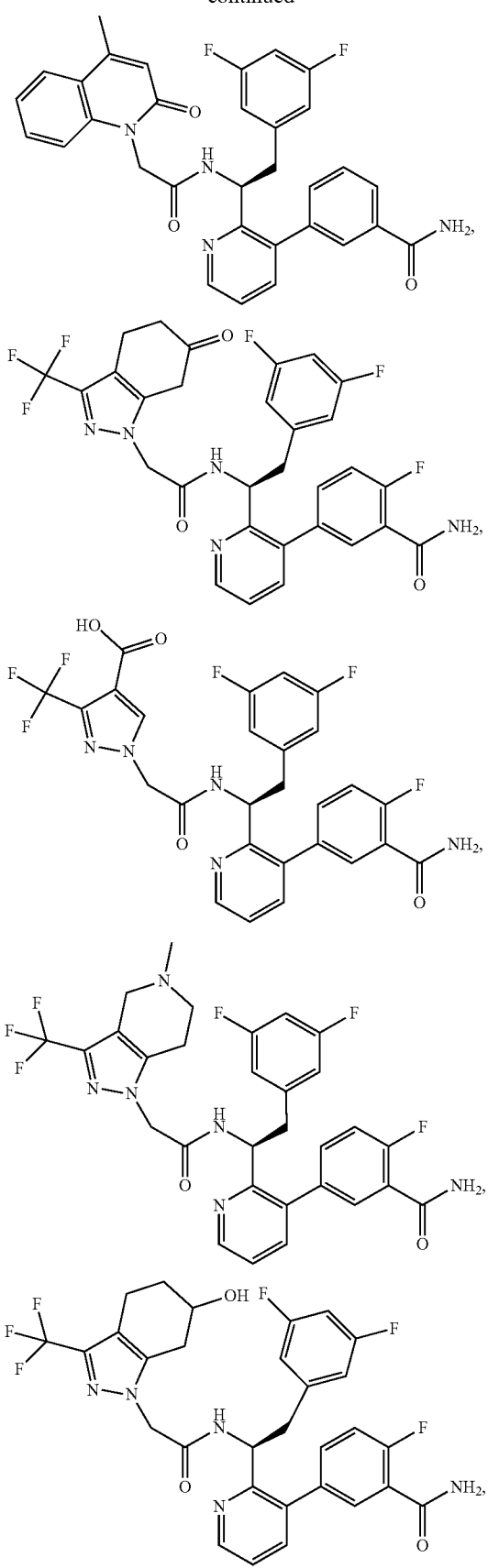
174
-continued
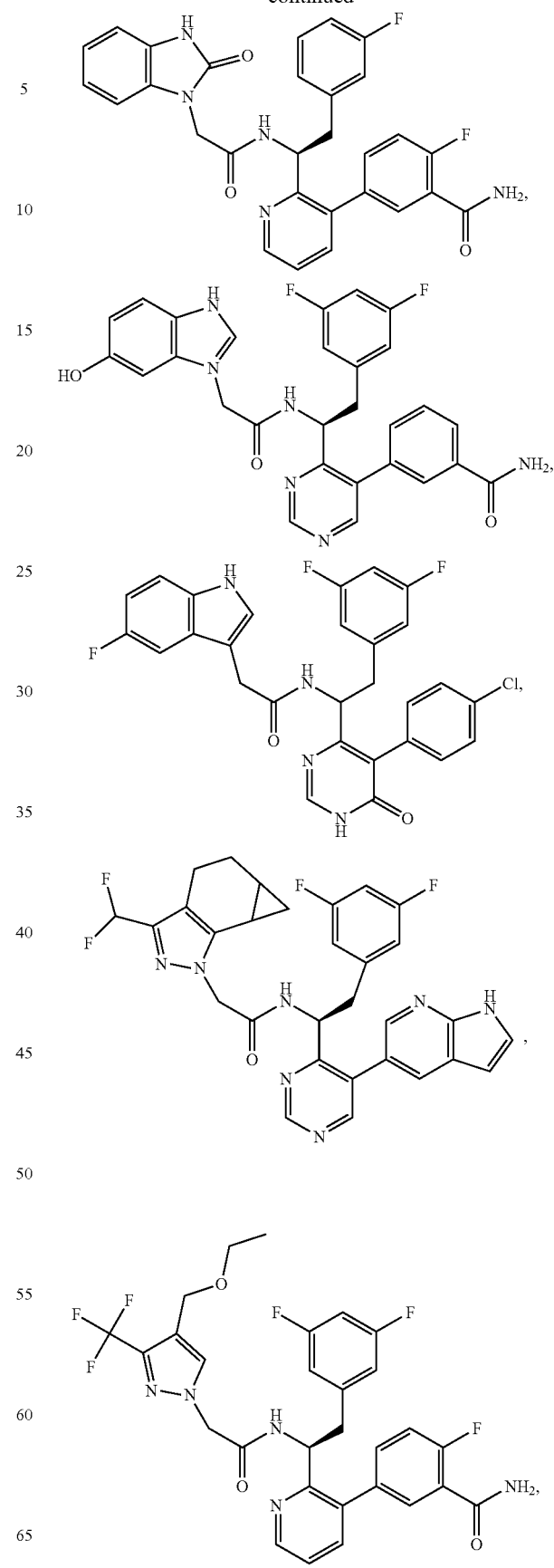

175
-continued
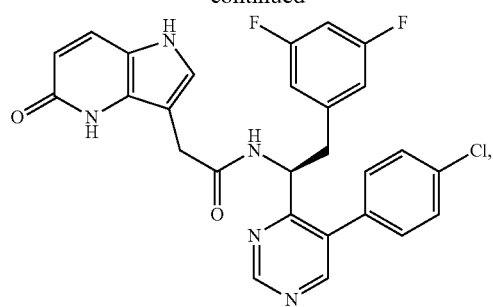
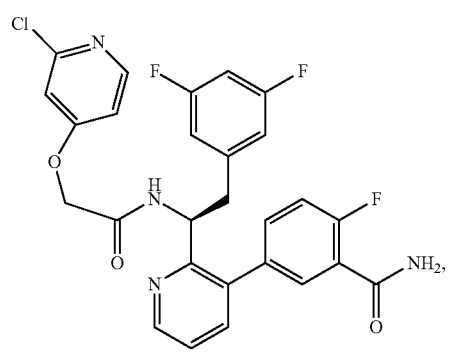
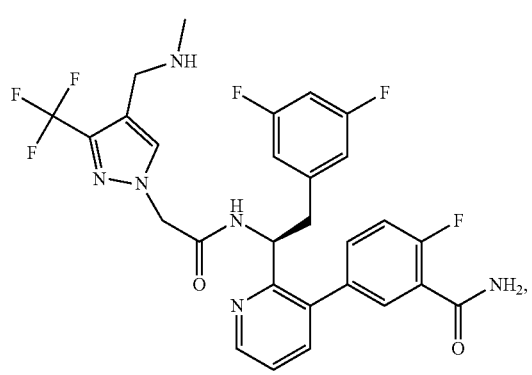
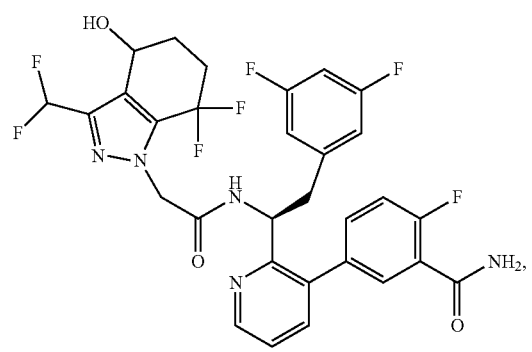
176
-continued
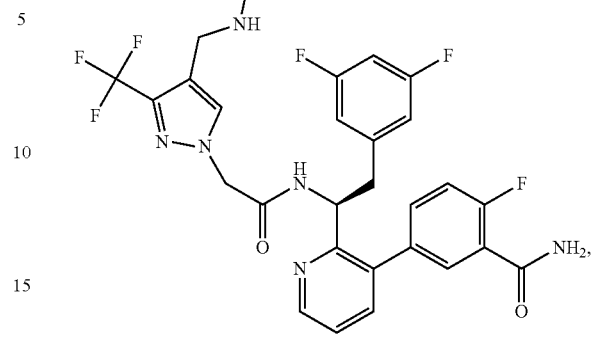
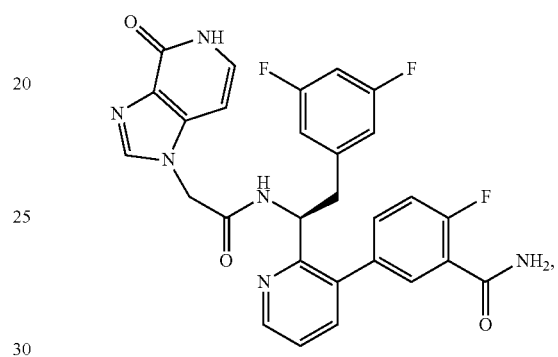
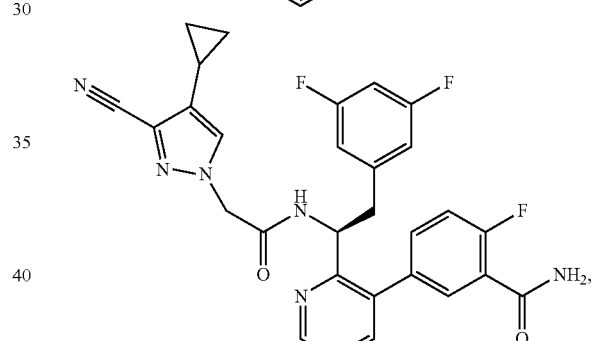
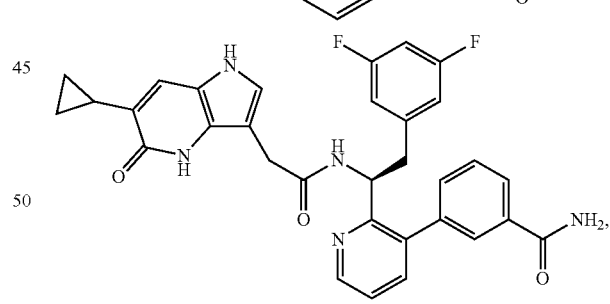
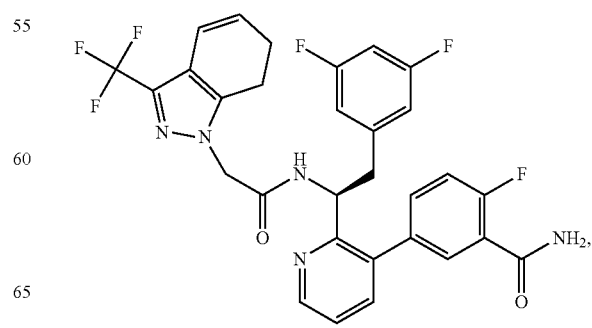

177
-continued
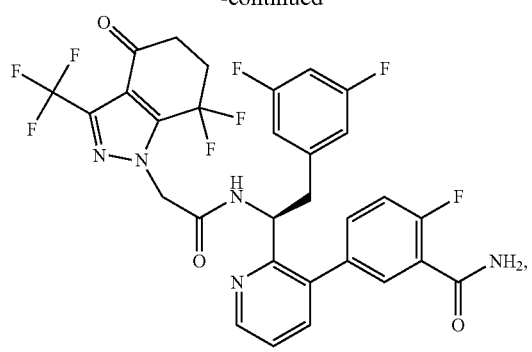
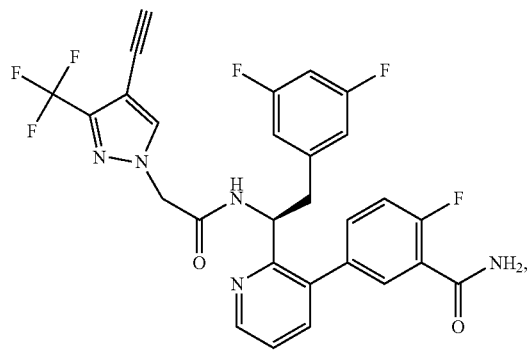
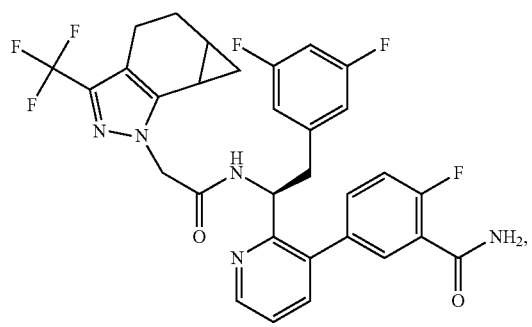
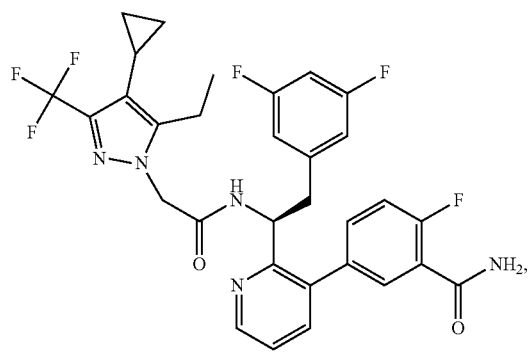
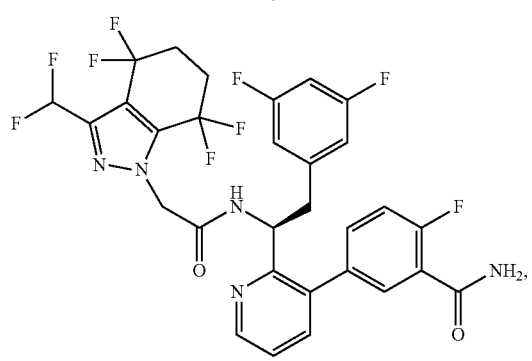
178
-continued
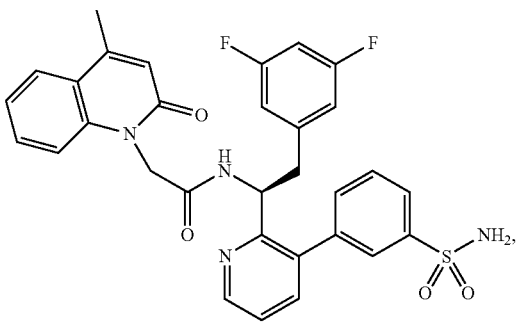
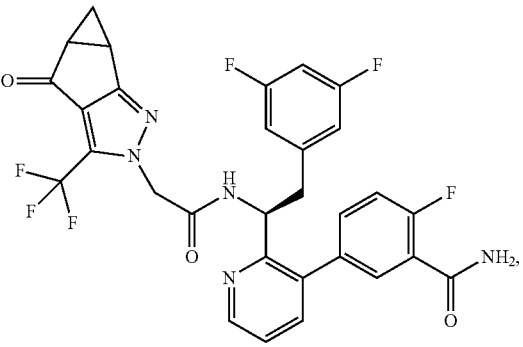
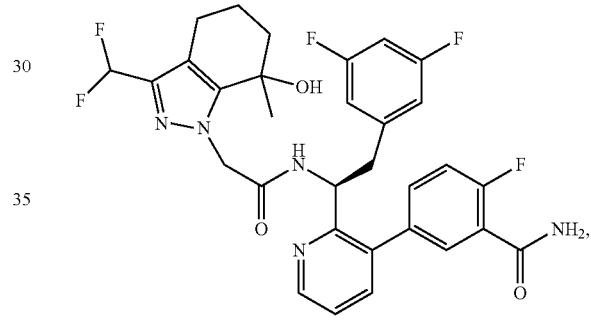
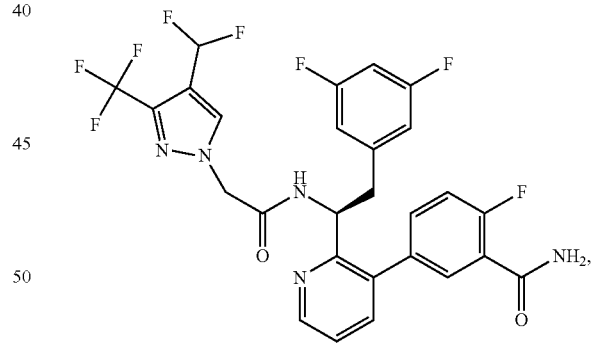
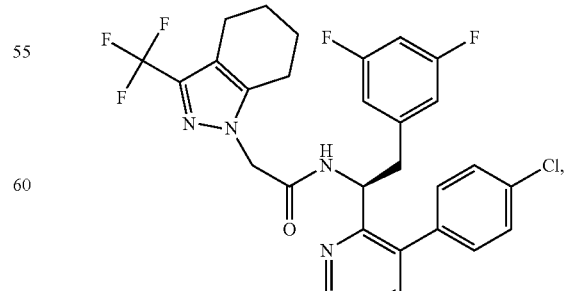

179
-continued
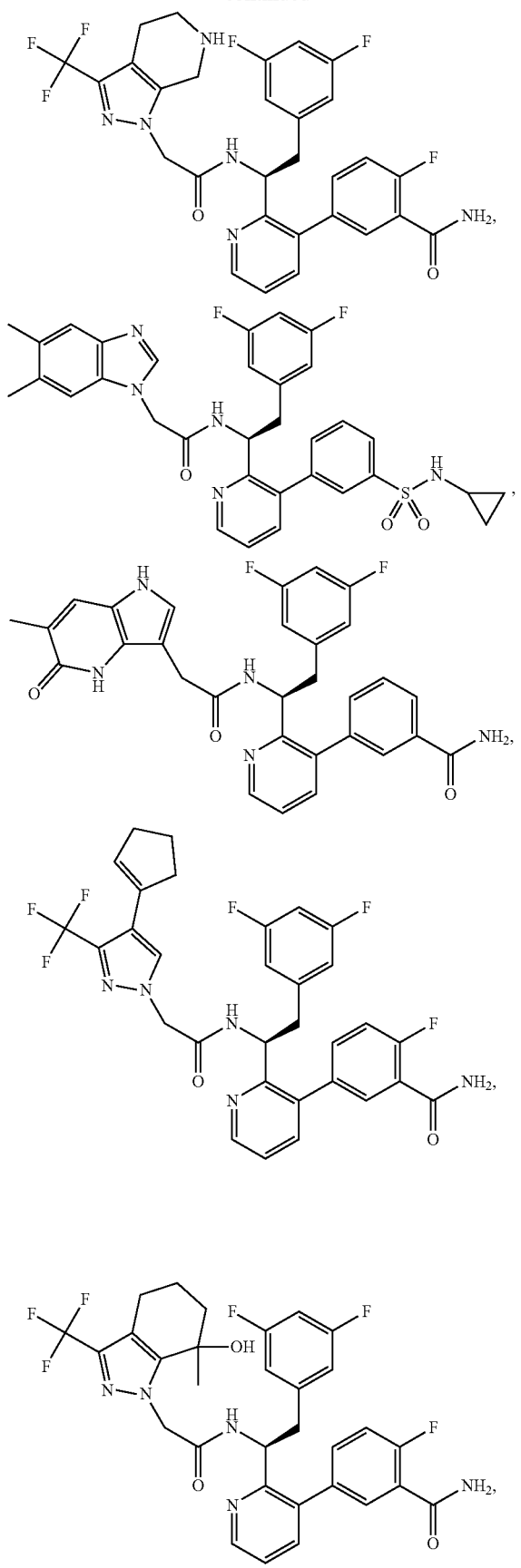
180
-continued
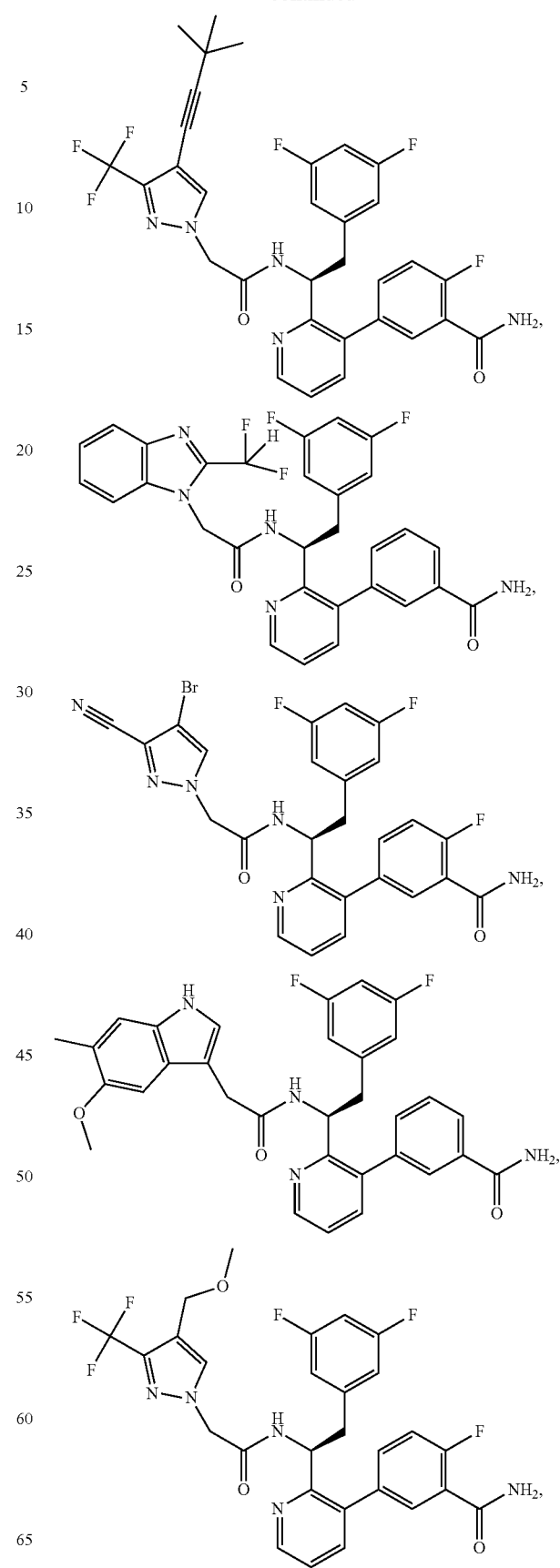

-continued
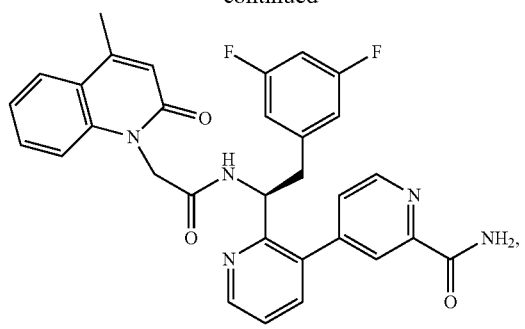
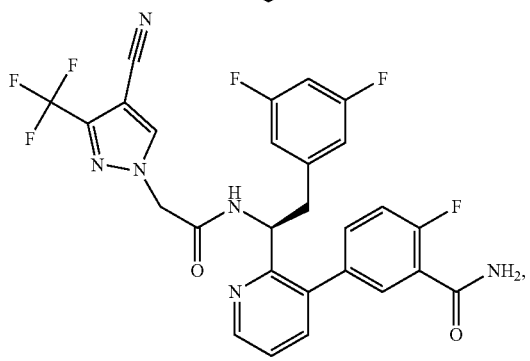
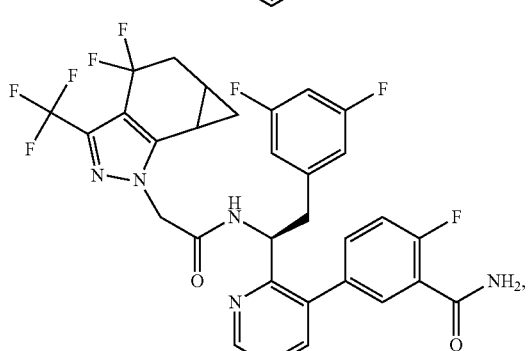
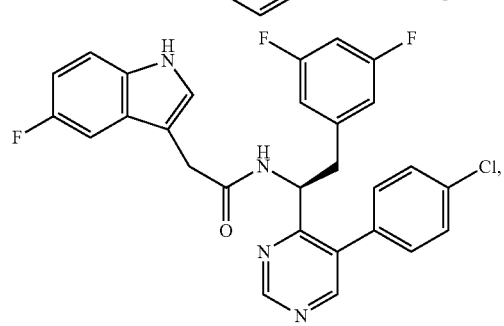
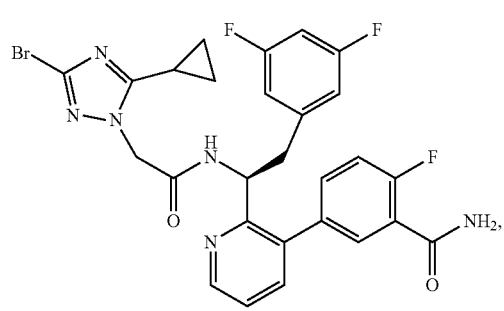
-continued
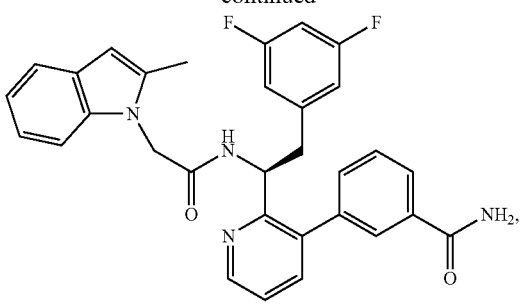
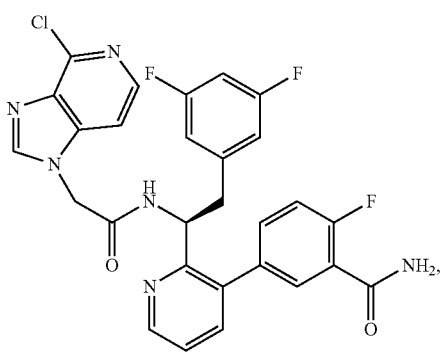
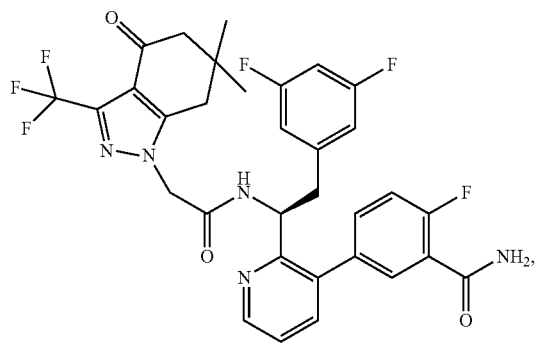
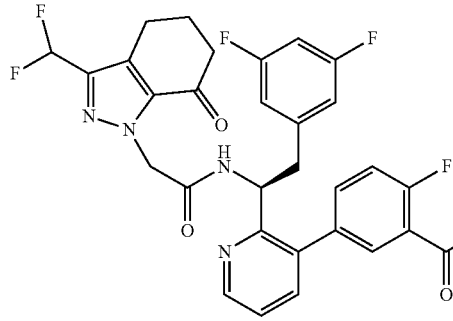
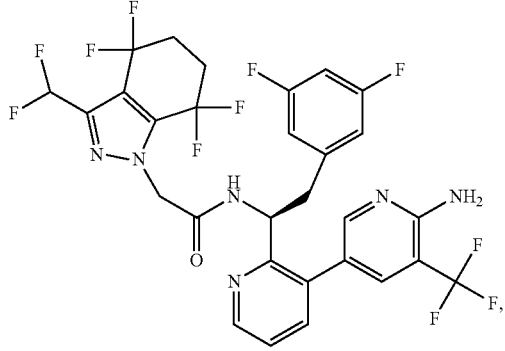

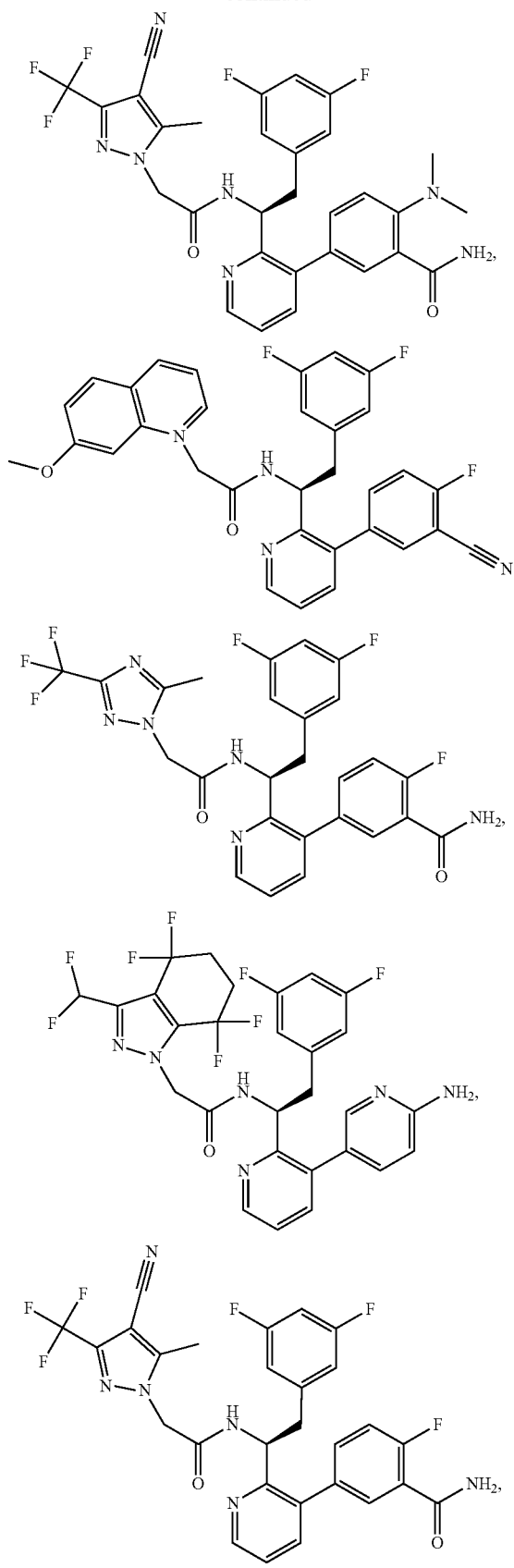
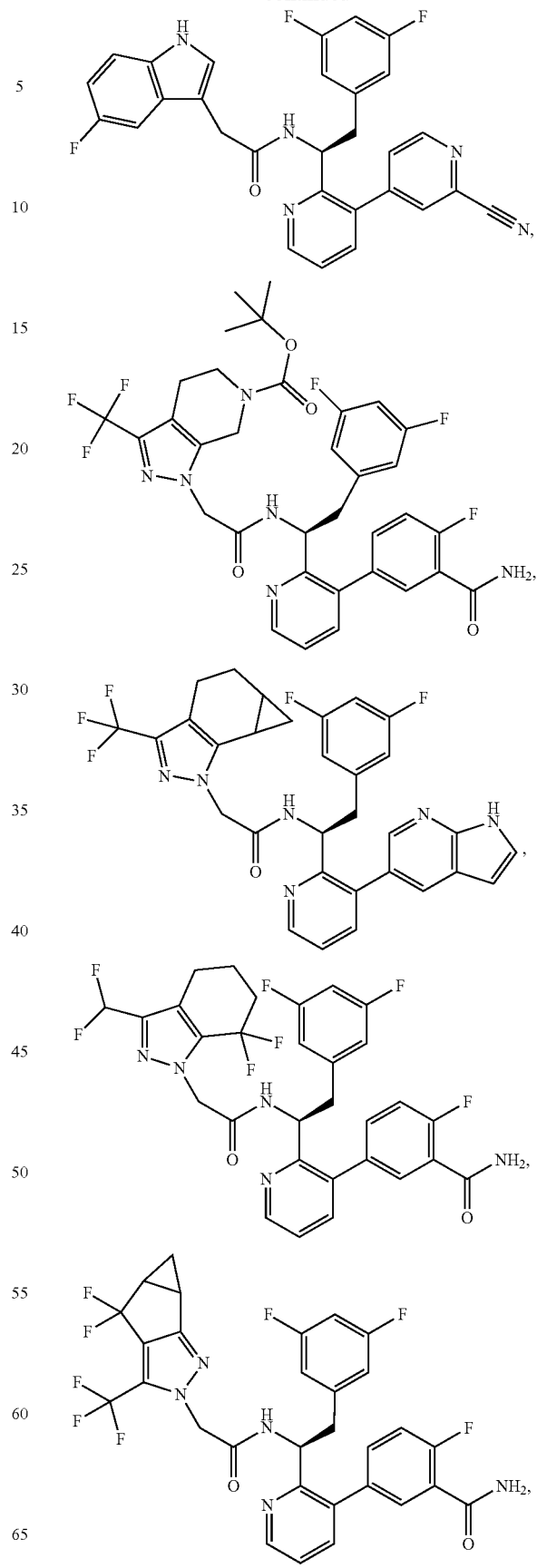

185
-continued
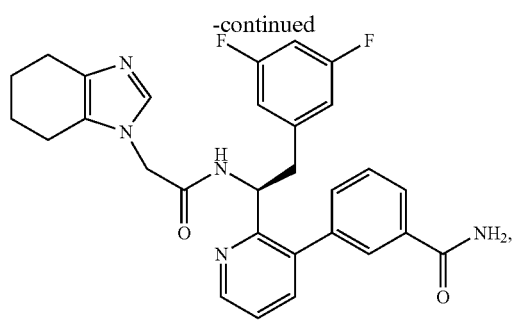
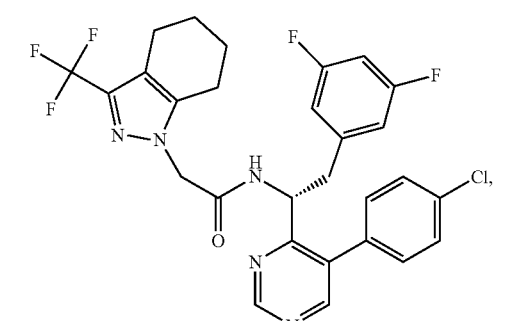
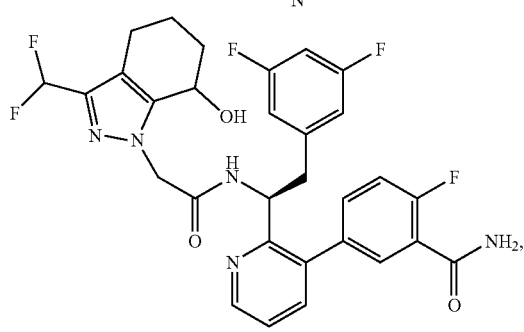
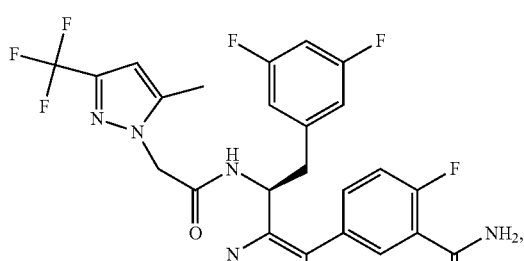
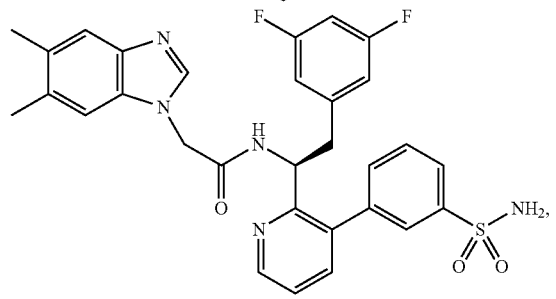
186
-continued
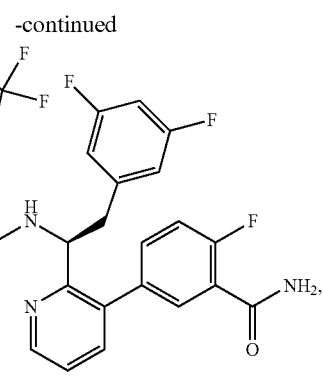
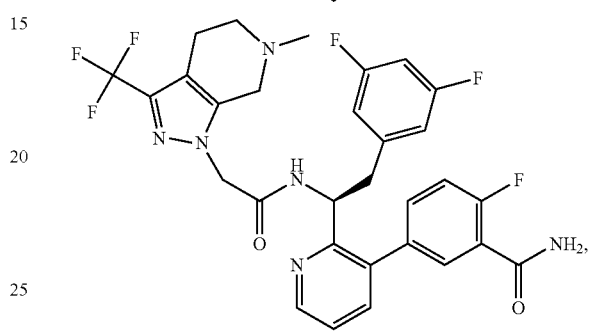
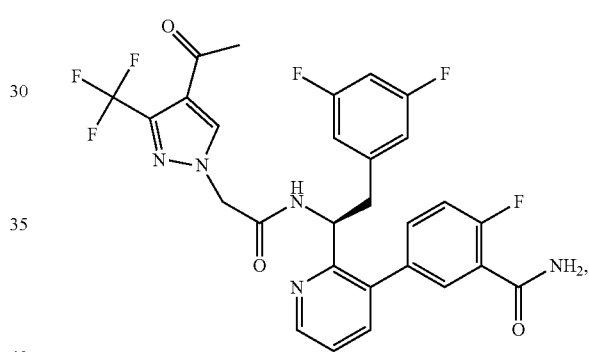
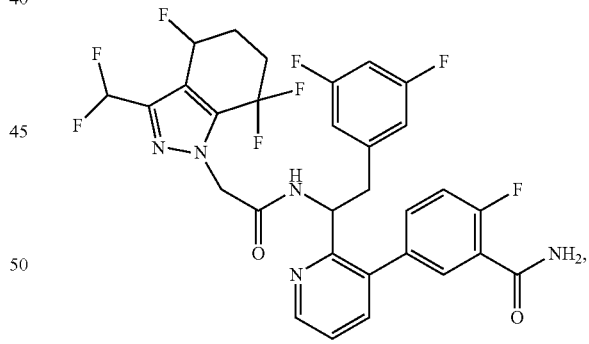
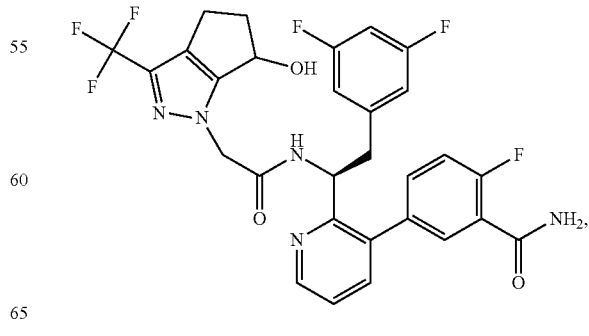

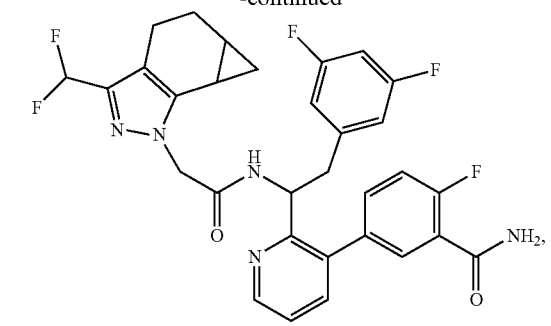
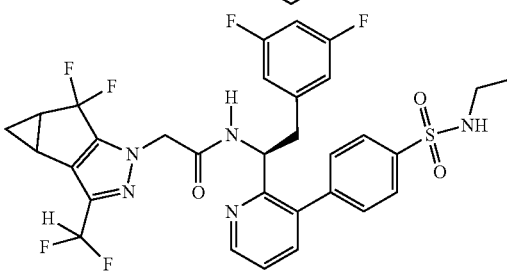
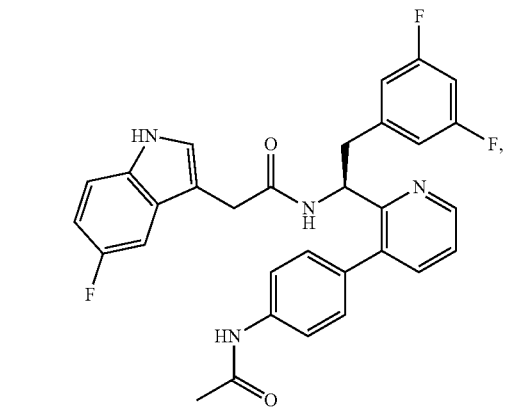
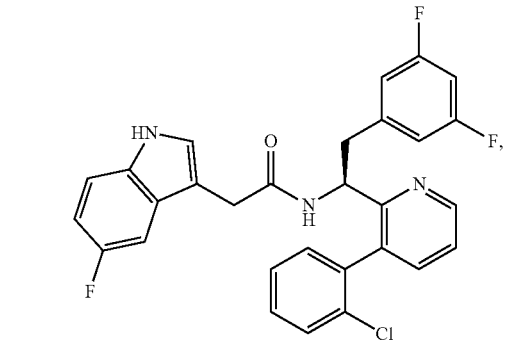
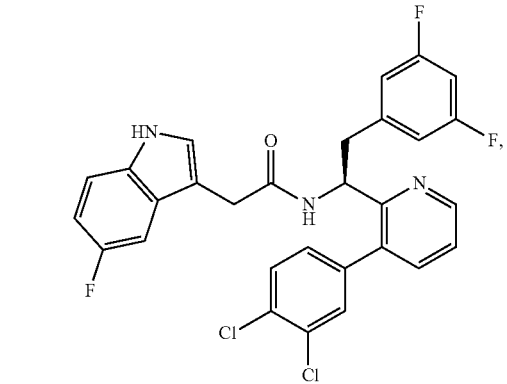

189
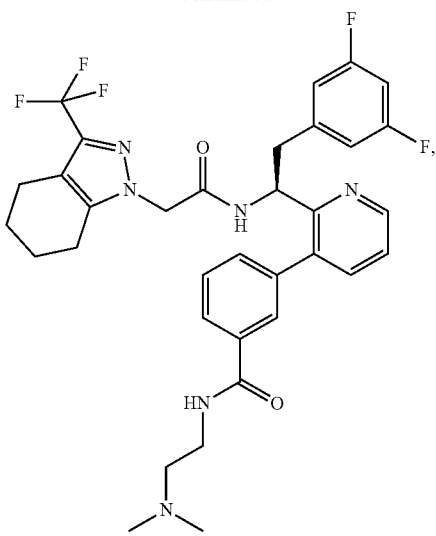
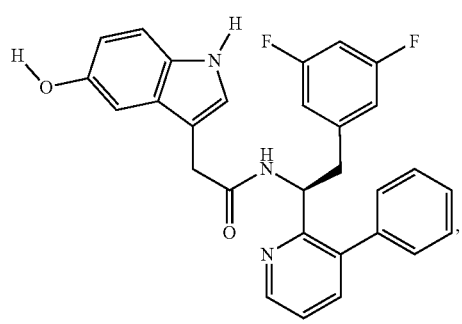
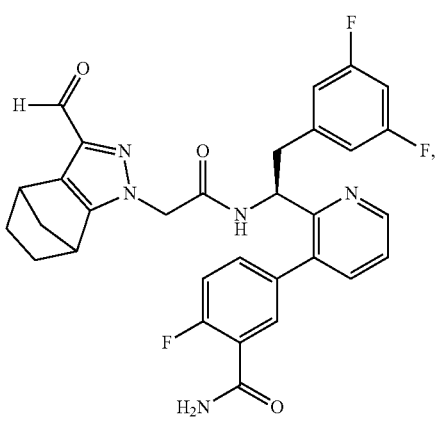
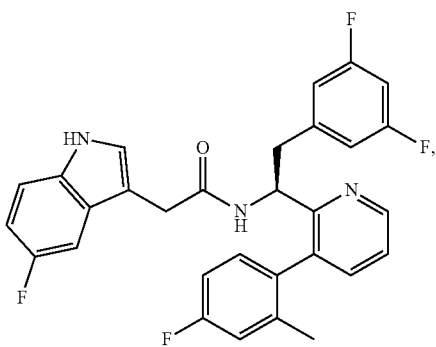
190
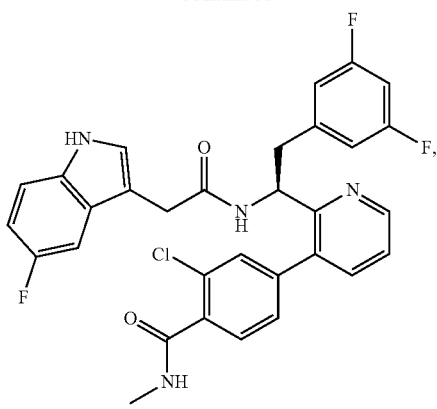
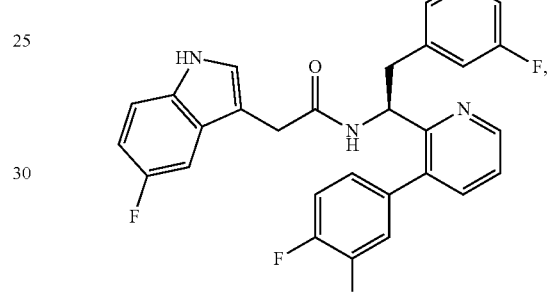
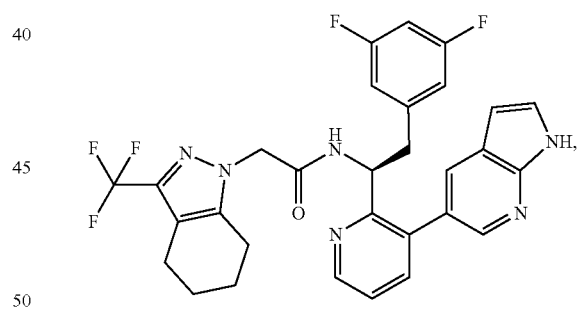
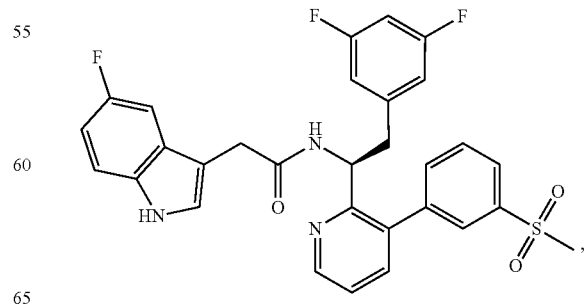

191
-continued
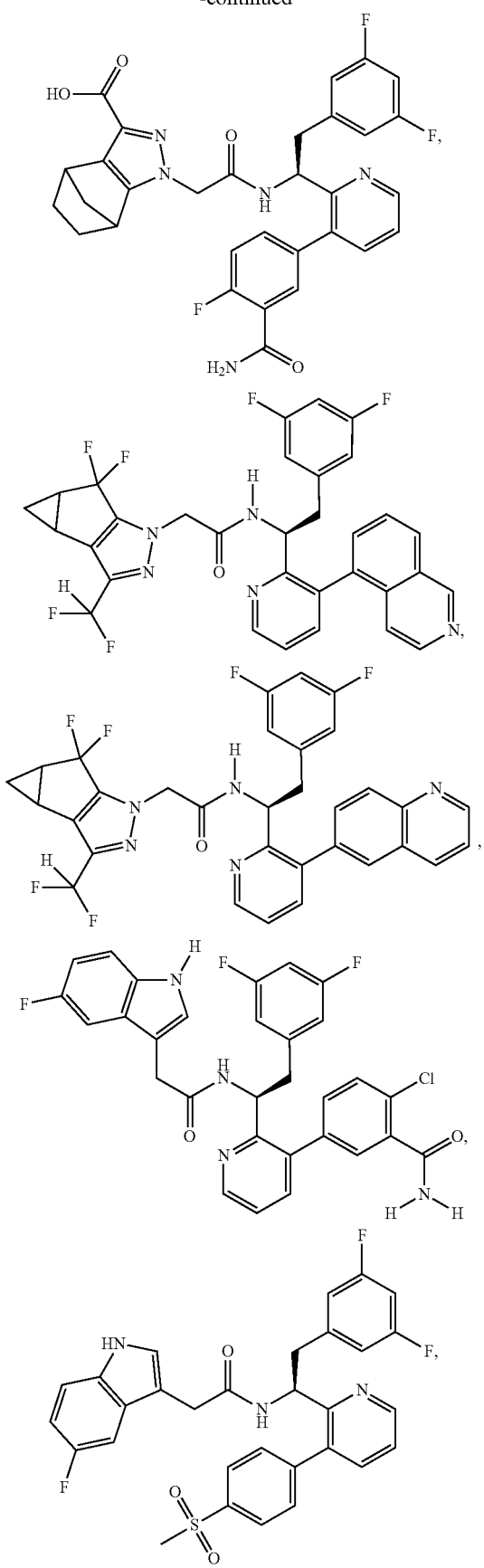
192
-continued
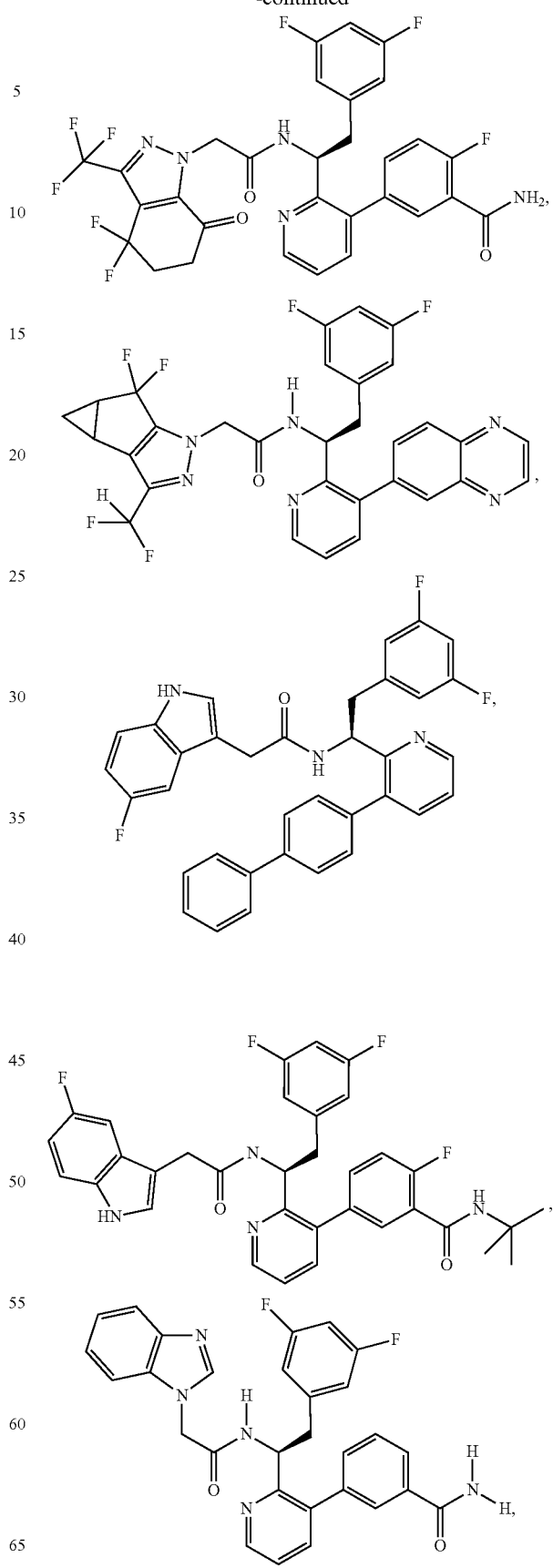

193
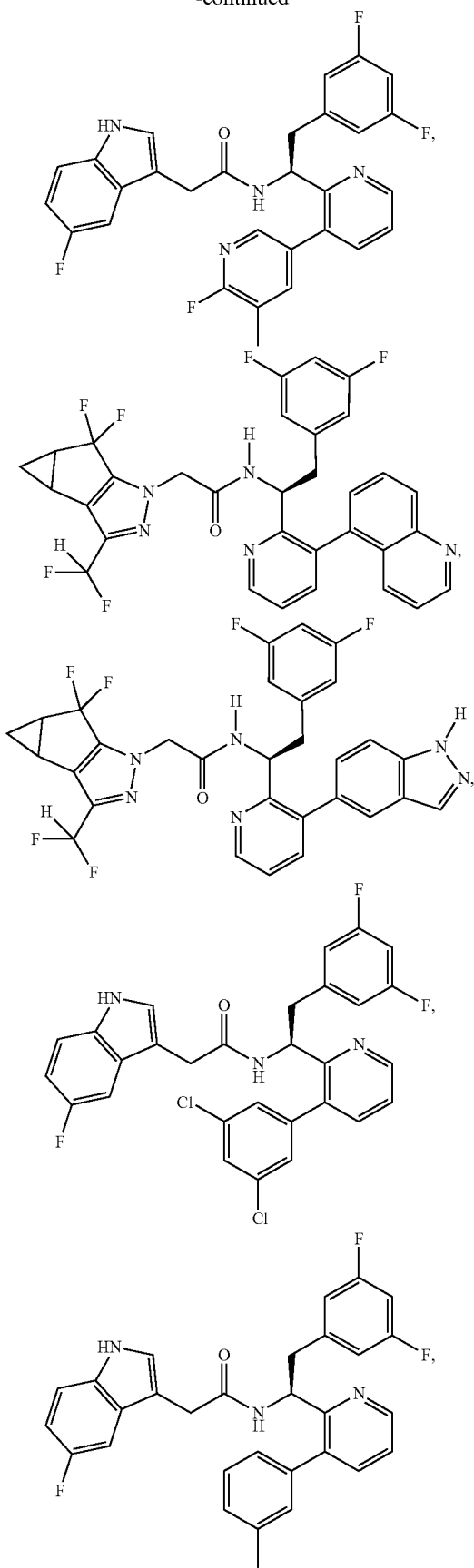
194
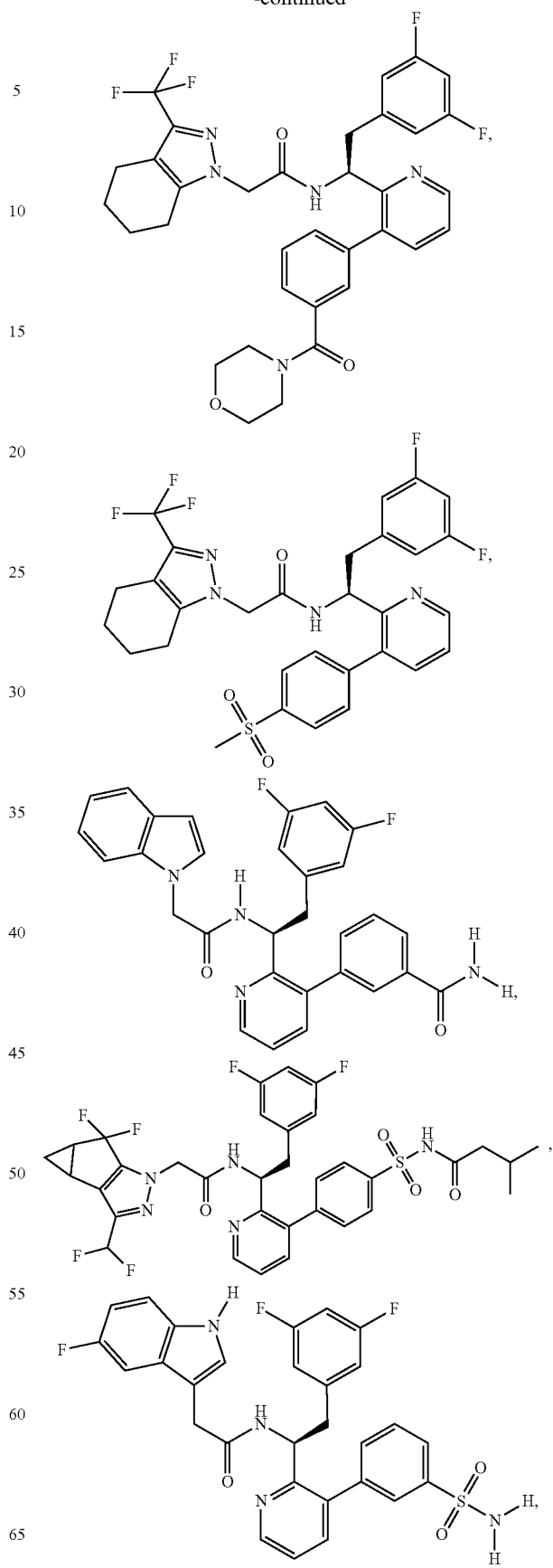

195
-continued
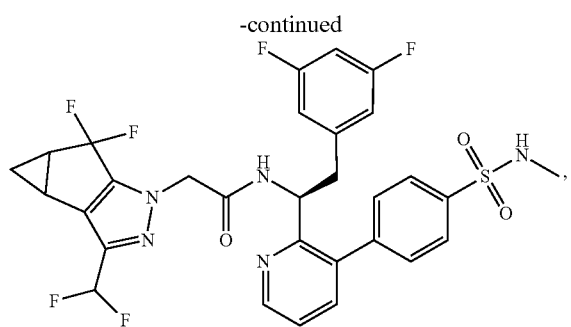
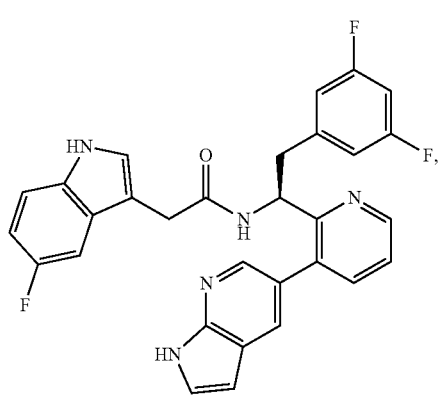
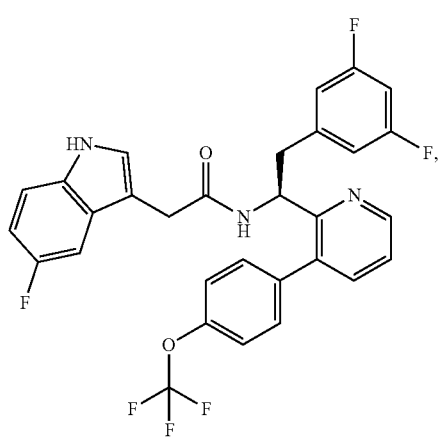
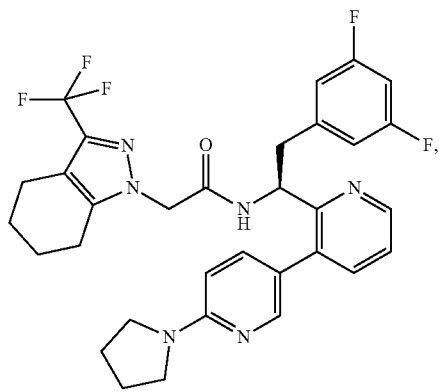
196
-continued
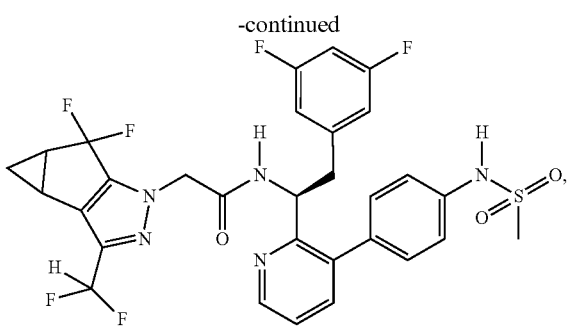
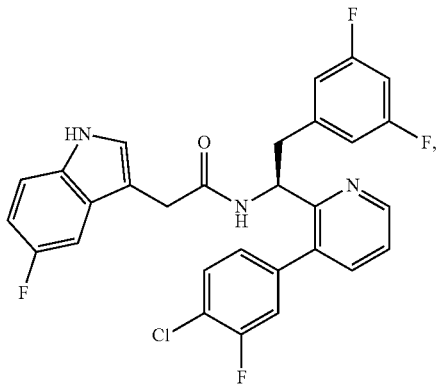
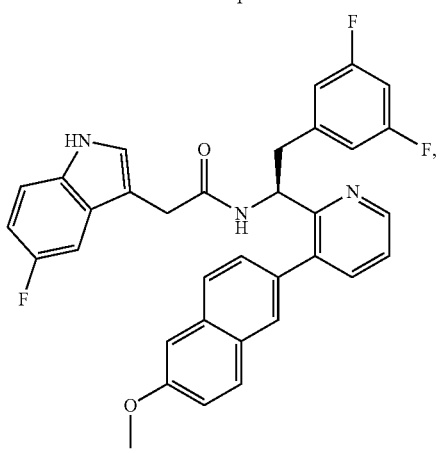
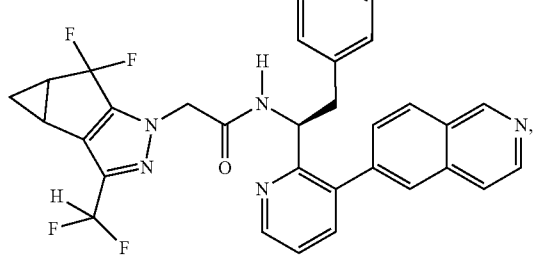
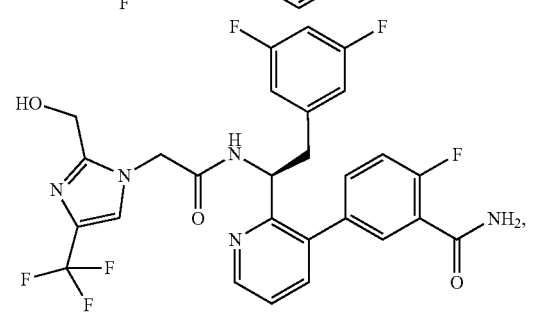

-continued
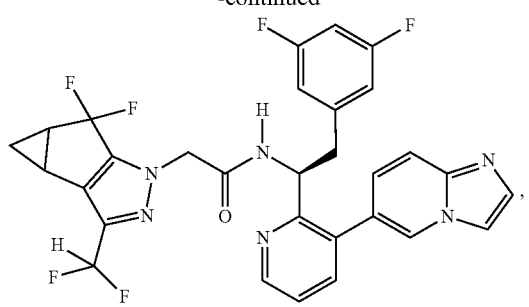
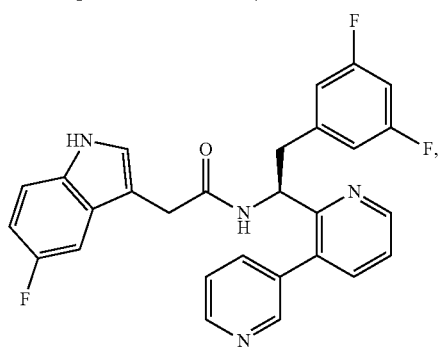
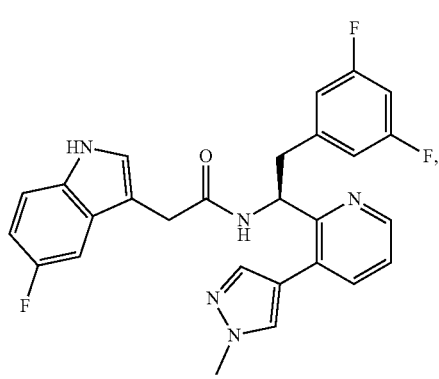
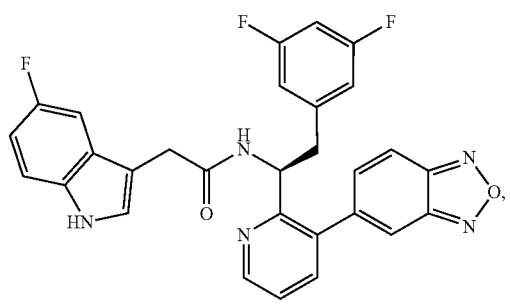
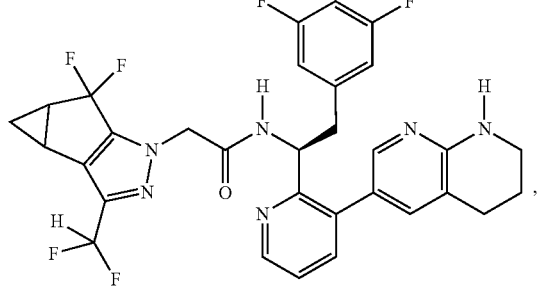
-continued
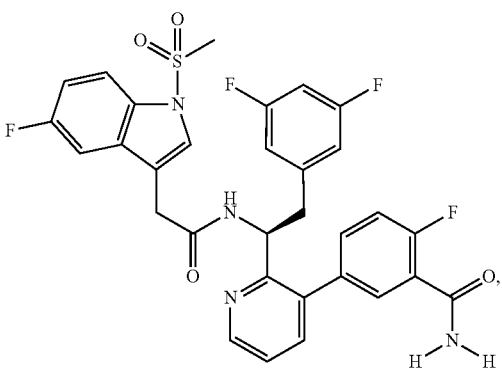
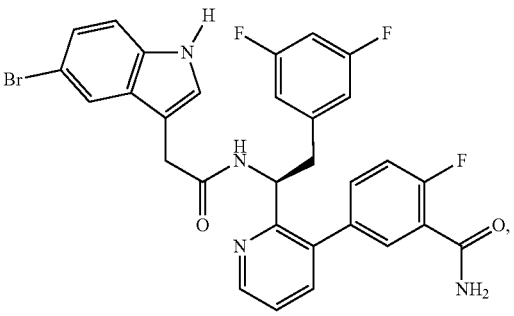
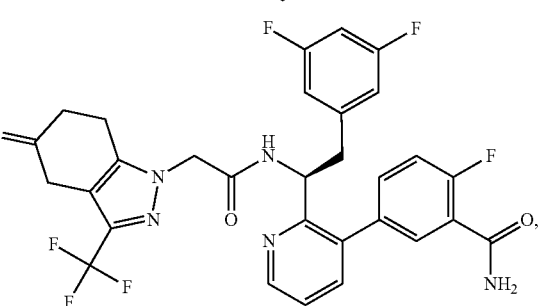
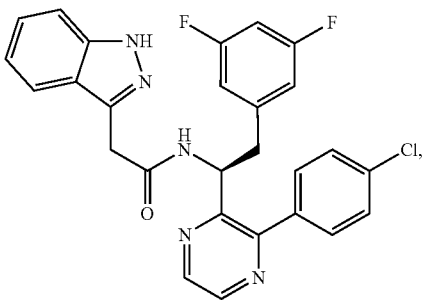

199
-continued
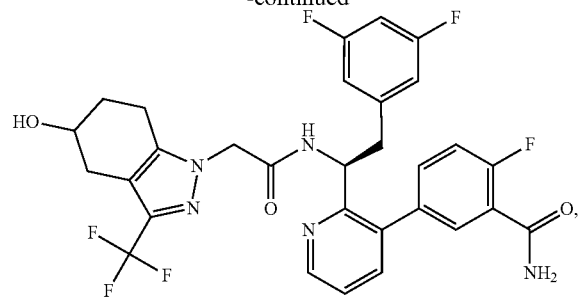
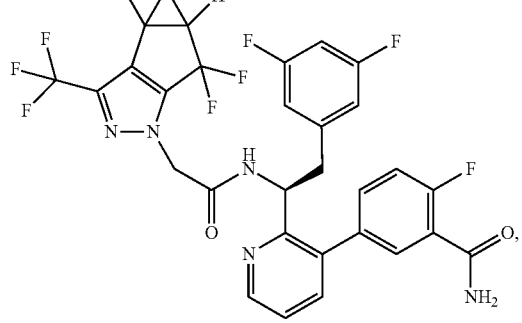
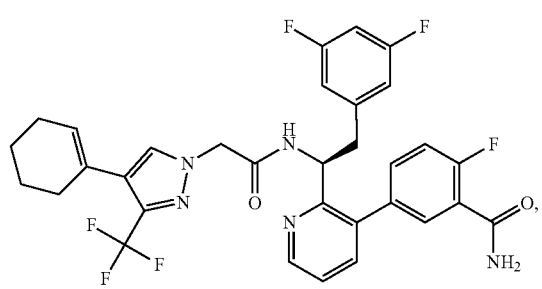
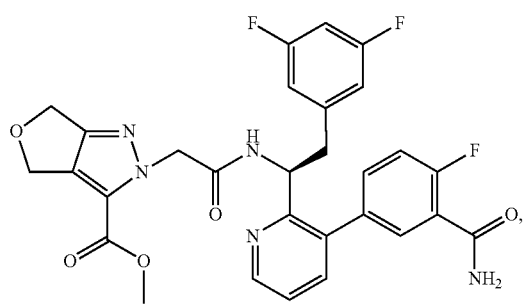
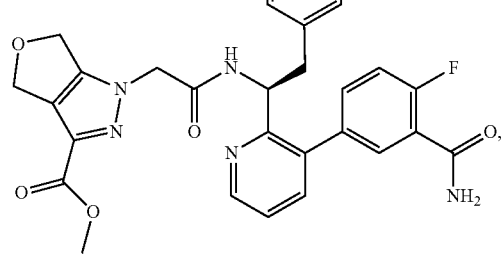
200
-continued
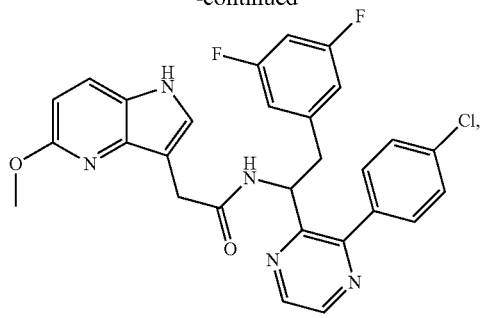
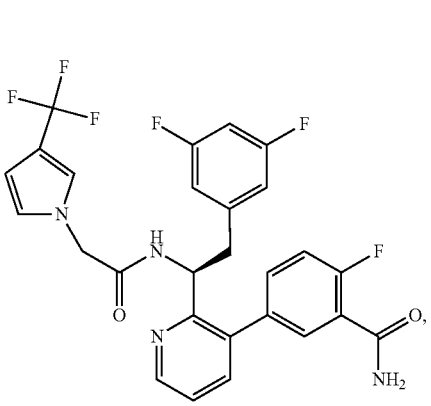
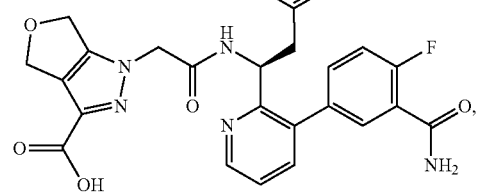
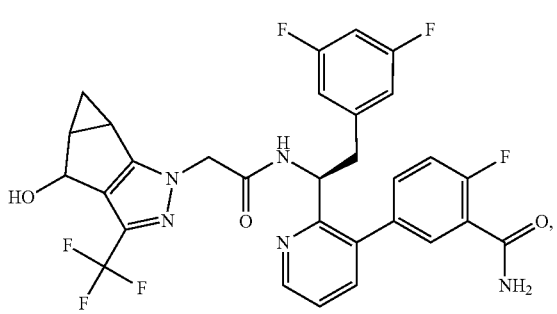
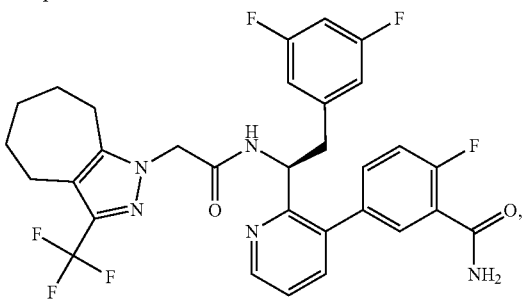

201
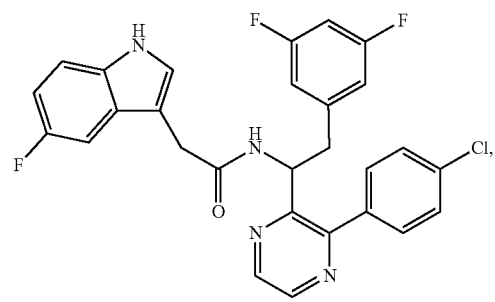
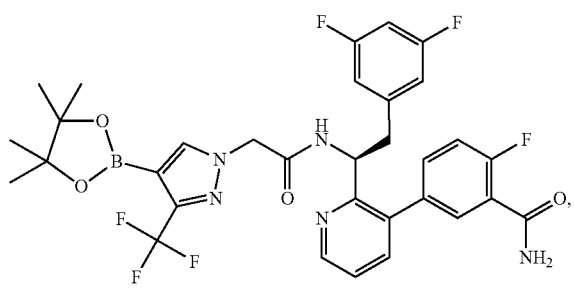
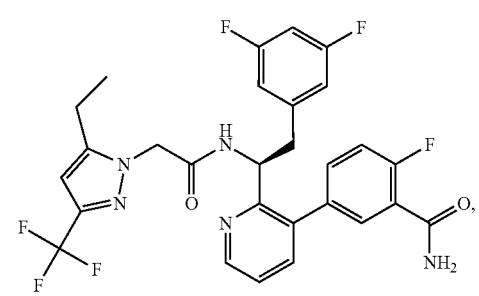
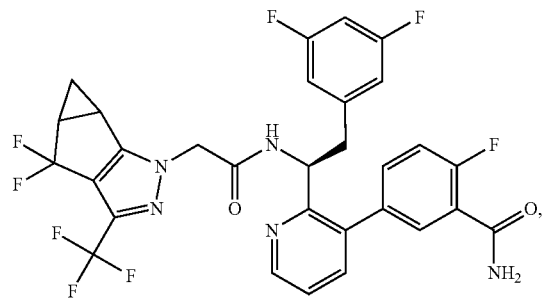
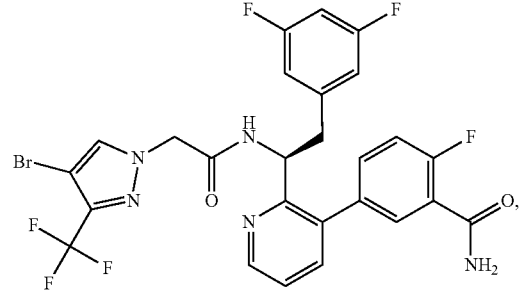
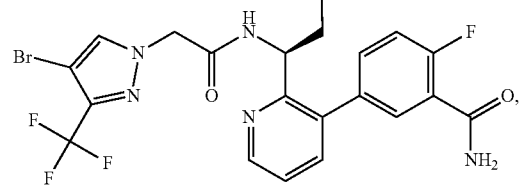
202
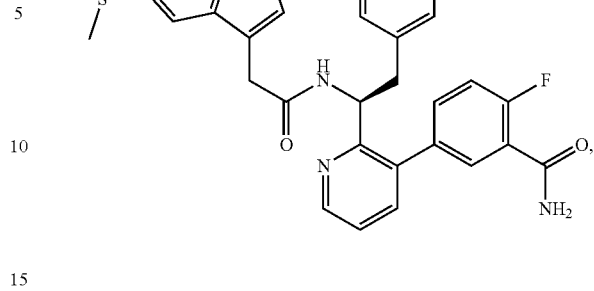
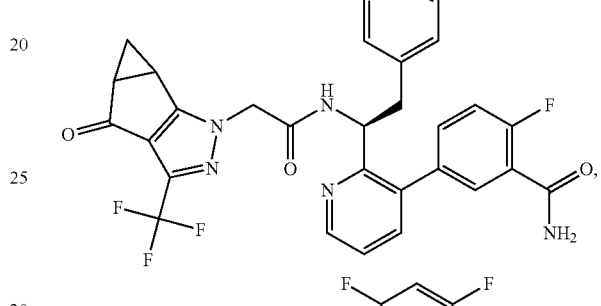
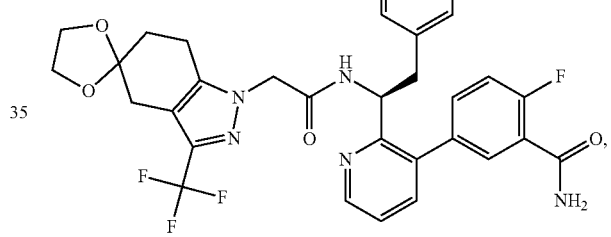
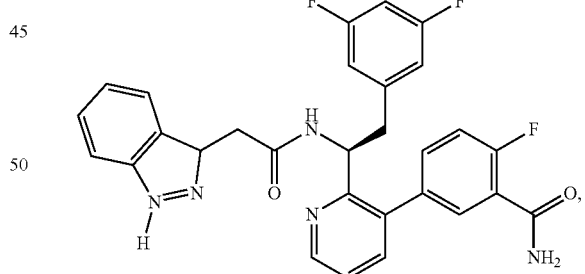
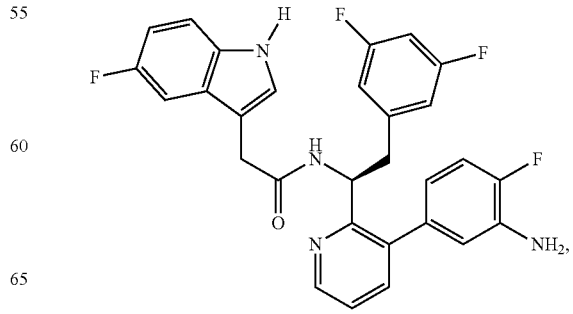
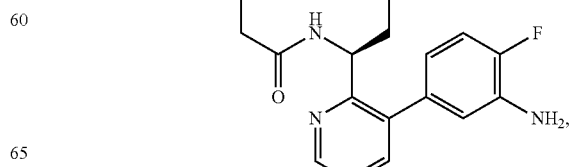

203
-continued
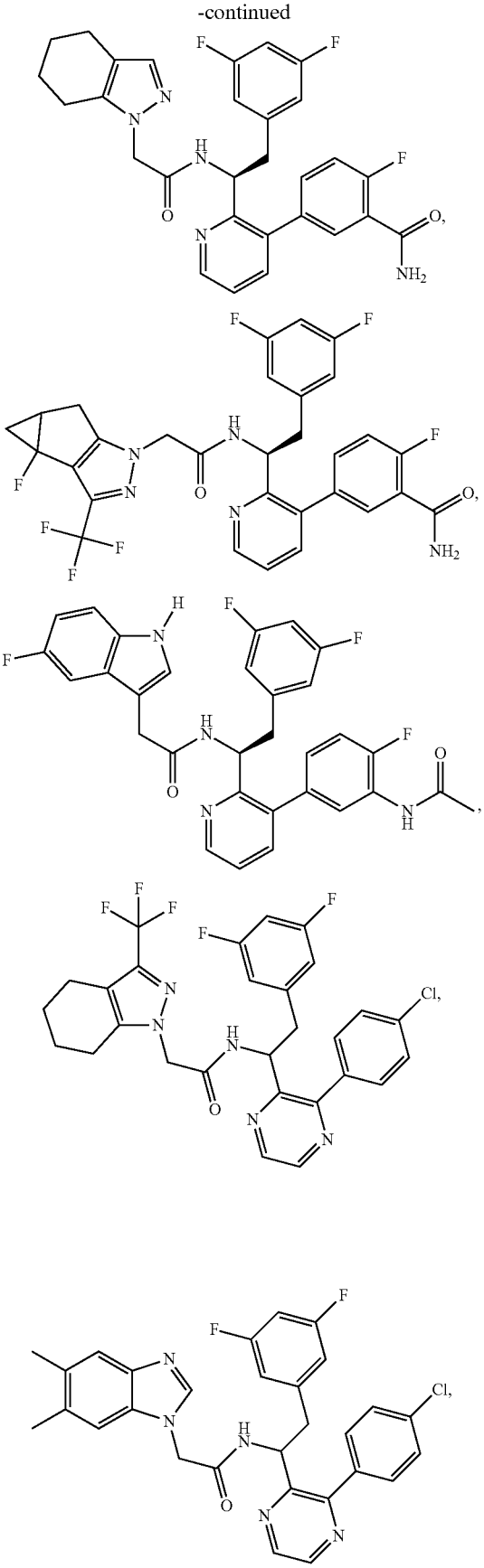
204
-continued
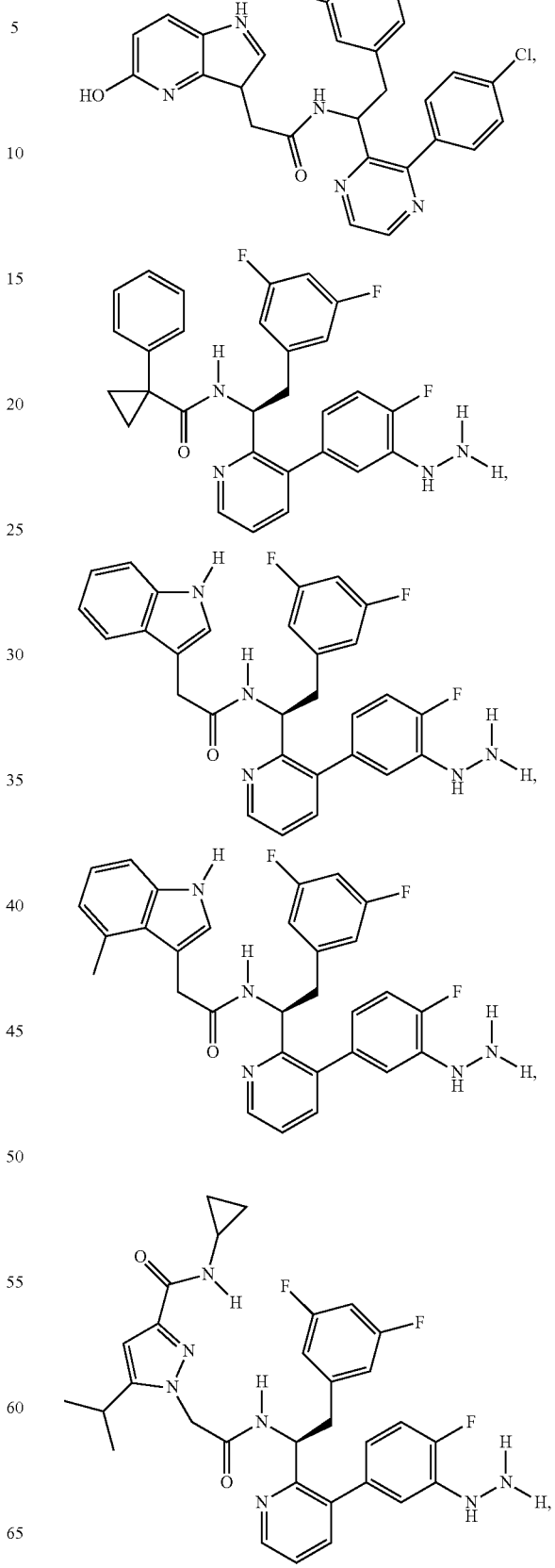

205
-continued
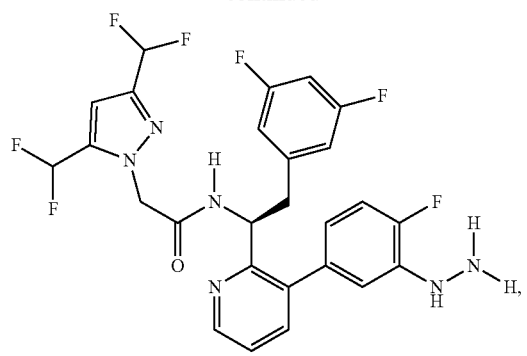
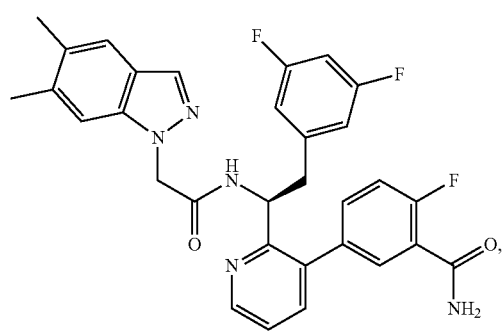
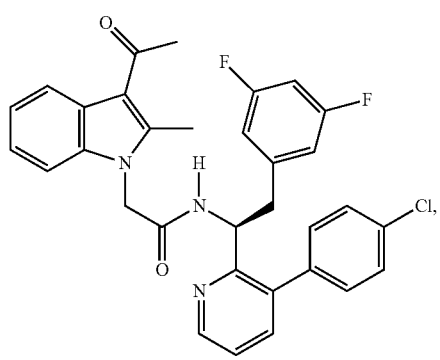
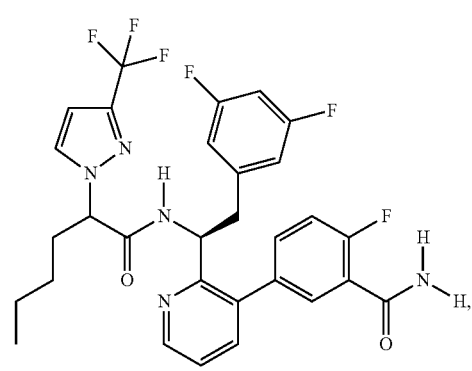
206
-continued
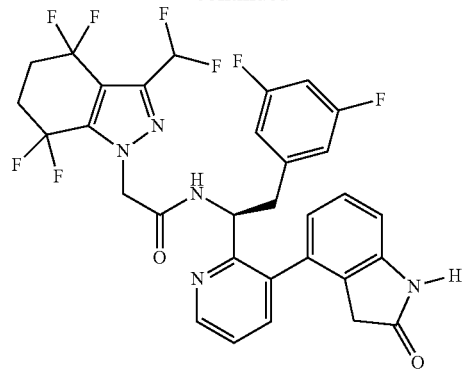
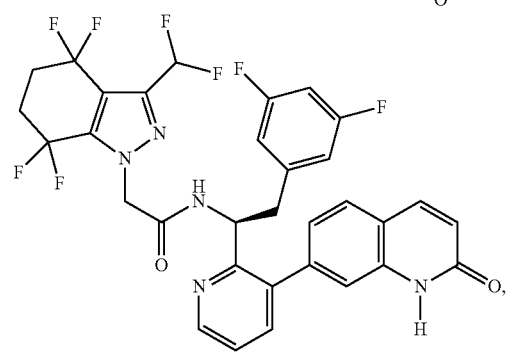
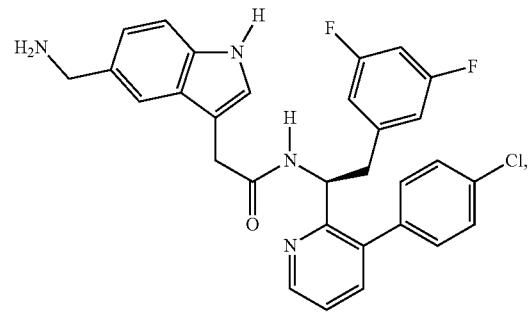
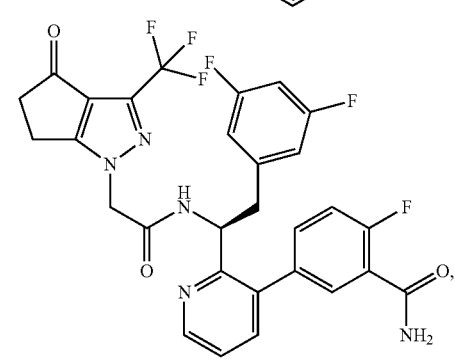
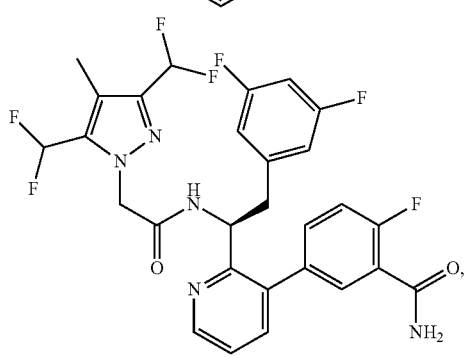

207
-continued
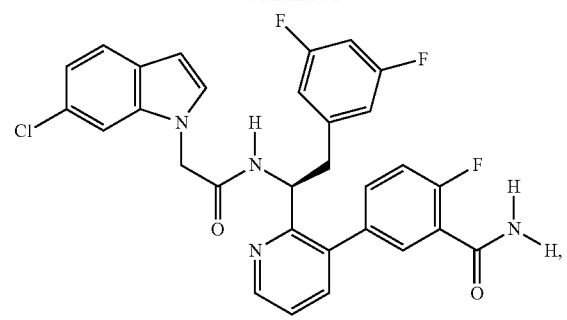
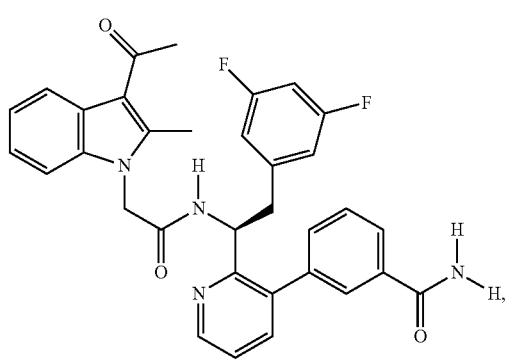
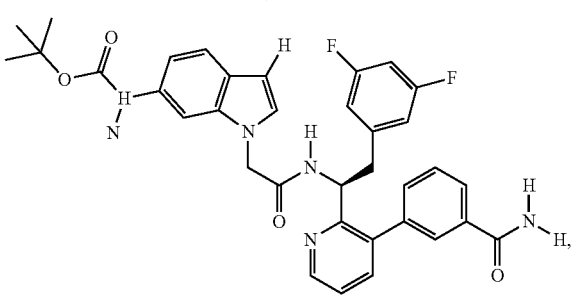
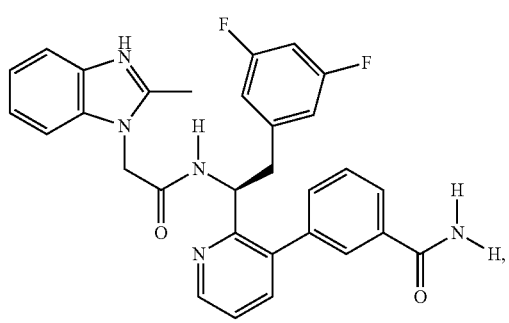
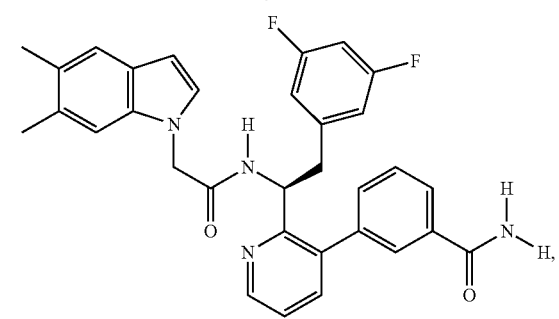
208
-continued
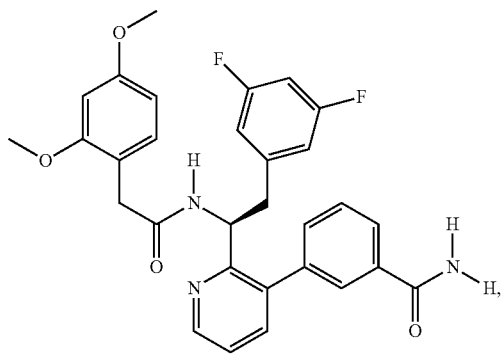
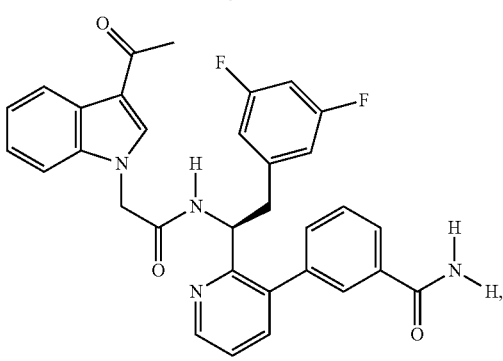
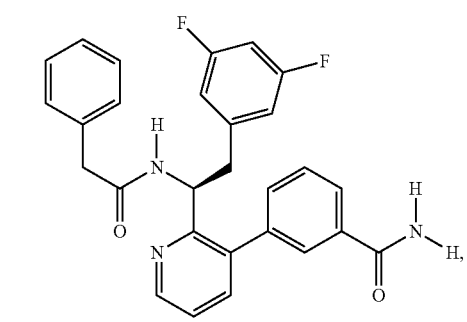
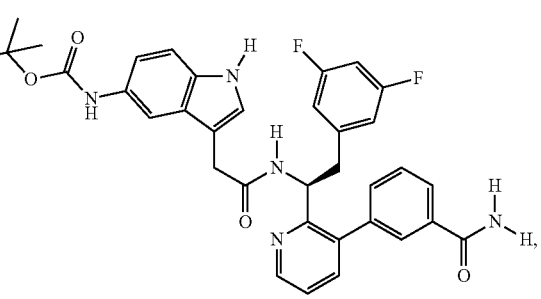
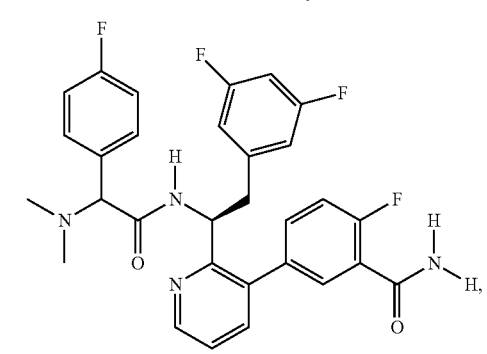

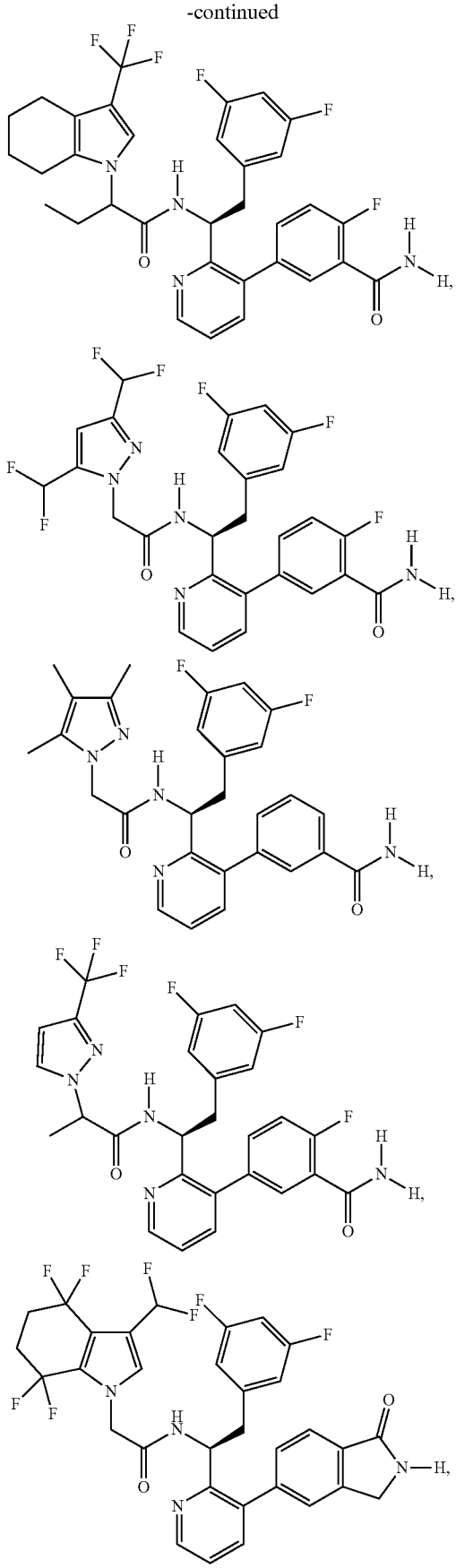
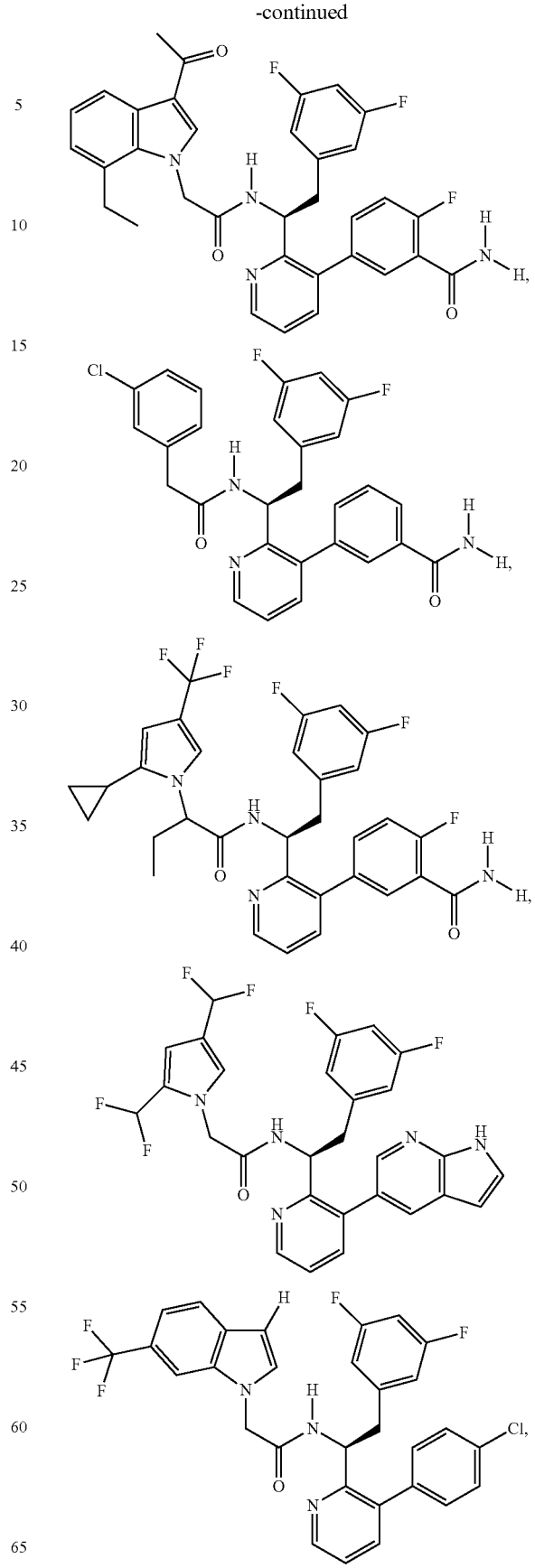

211
-continued
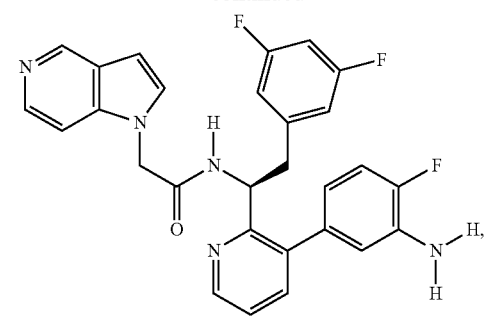
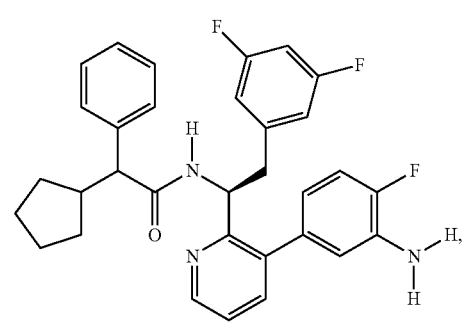
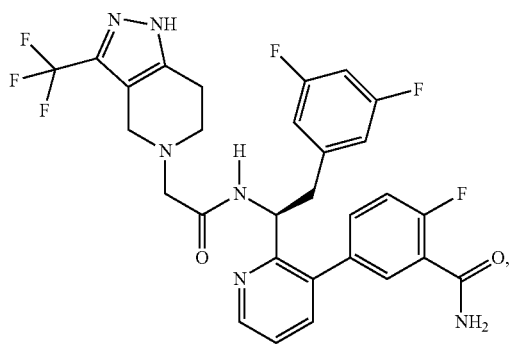
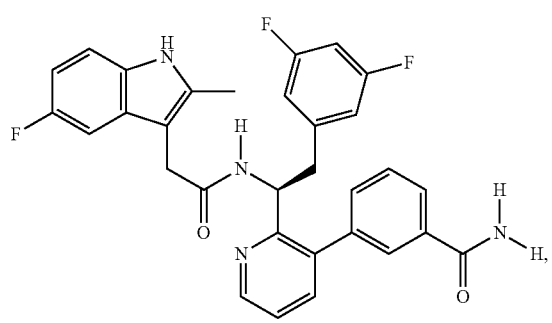
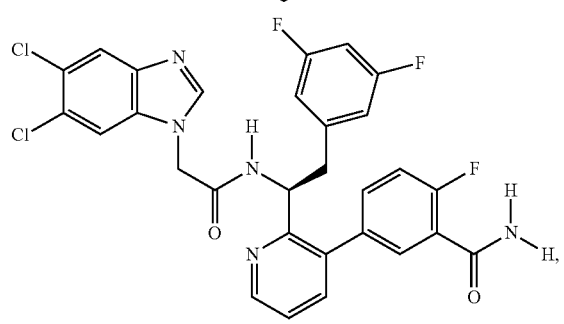
212
-continued
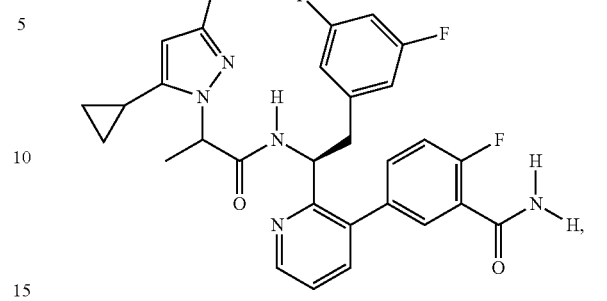
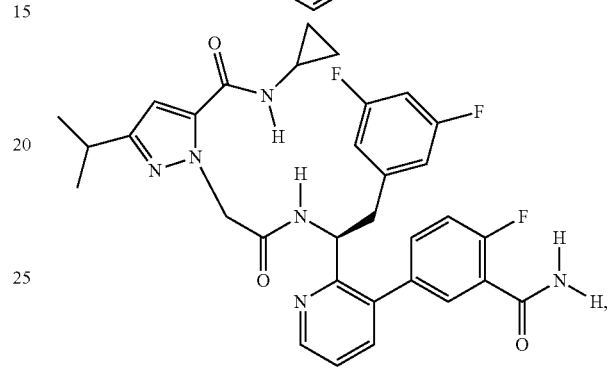
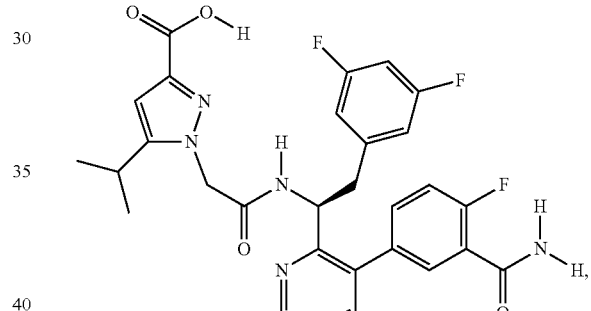
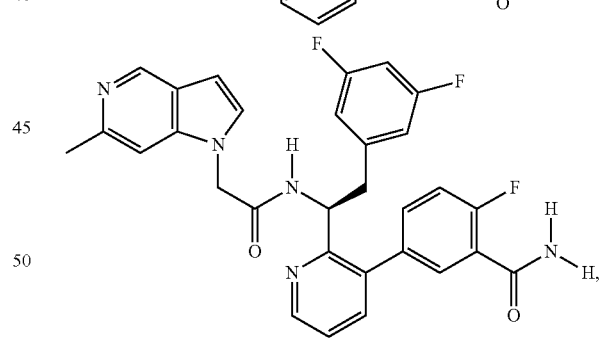
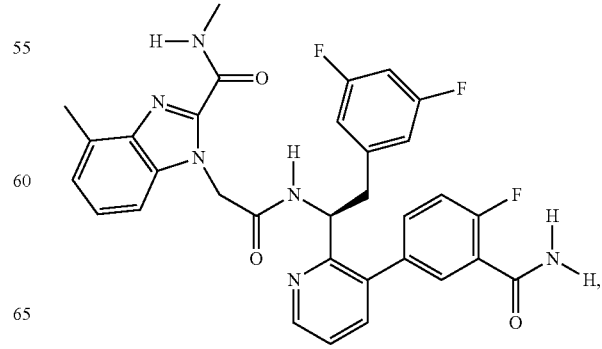

213
-continued
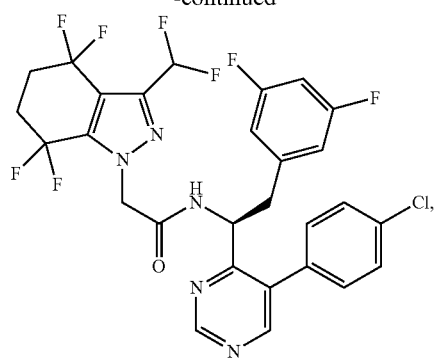
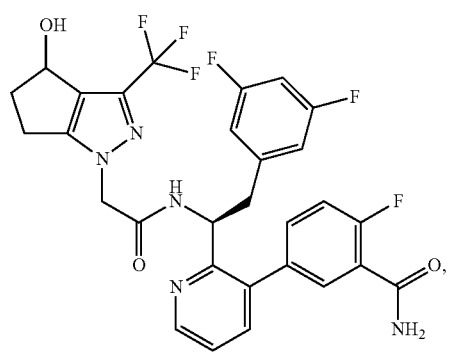
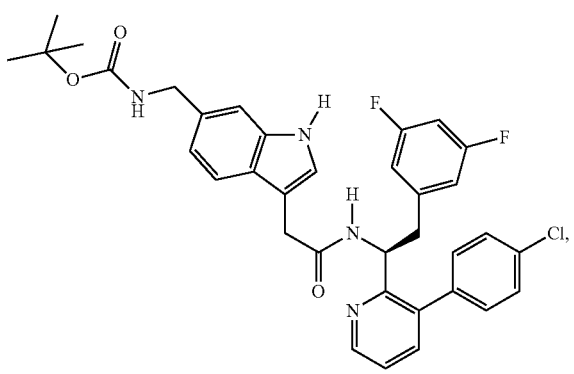
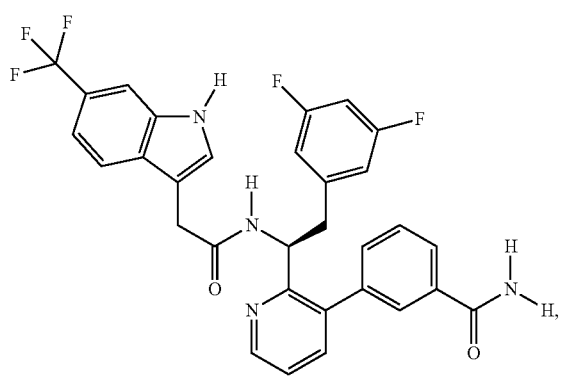
214
-continued
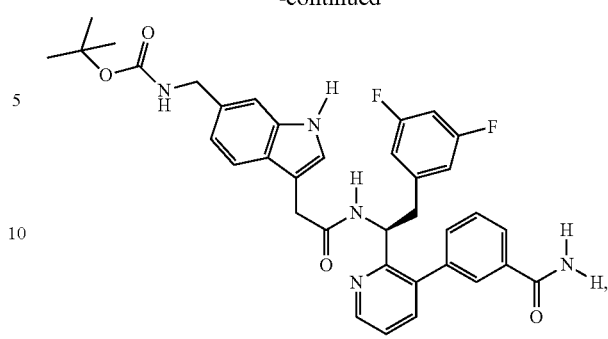
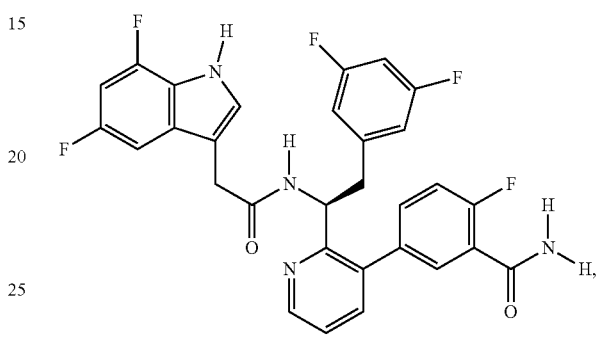
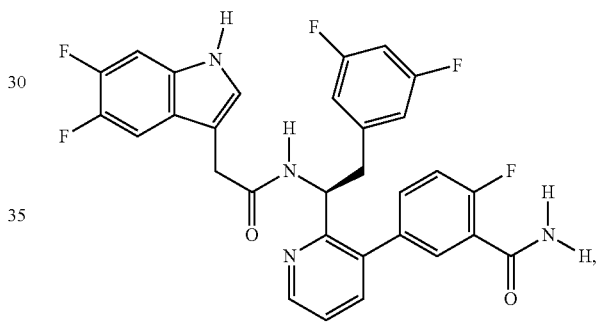
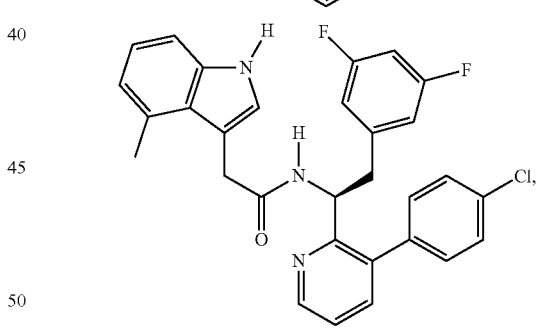
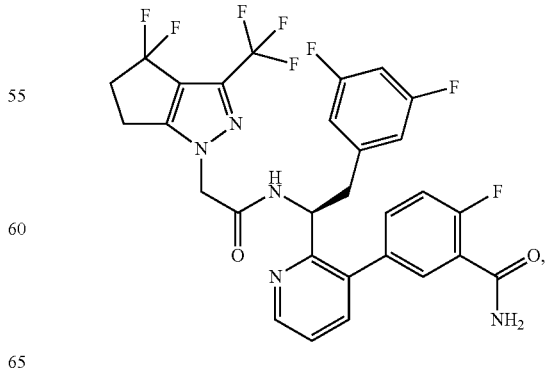

215
-continued
216
-continued
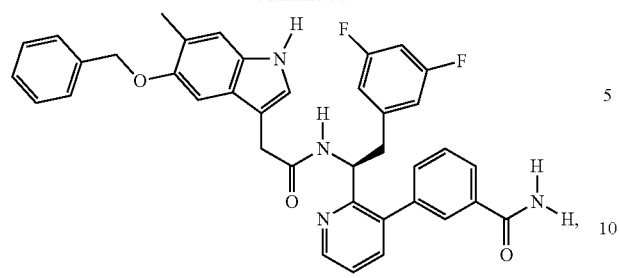
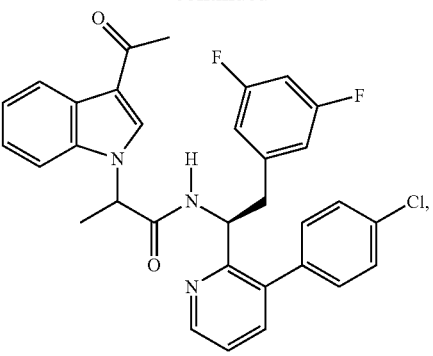
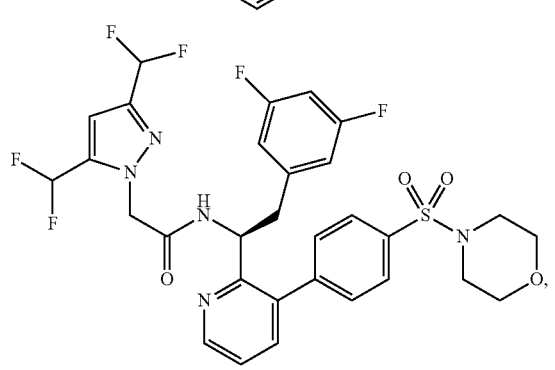
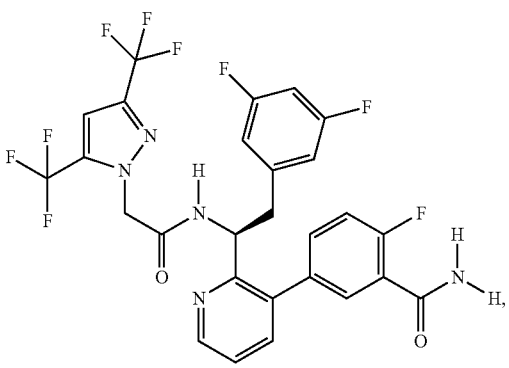
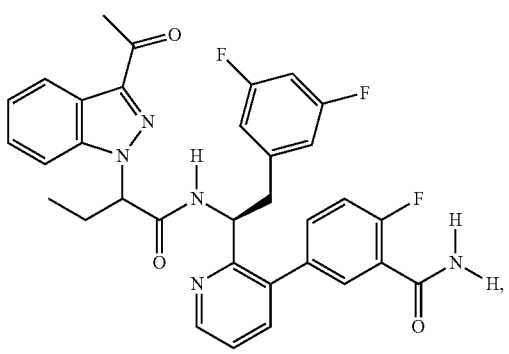
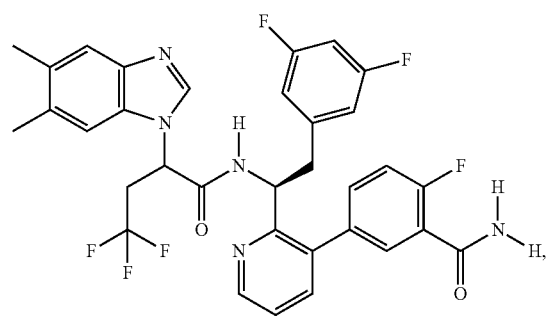
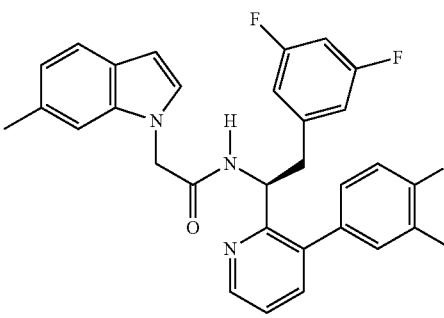

217
-continued
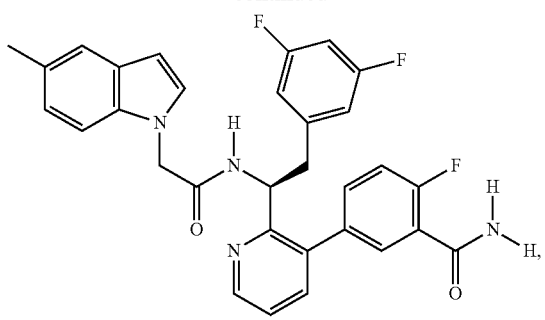
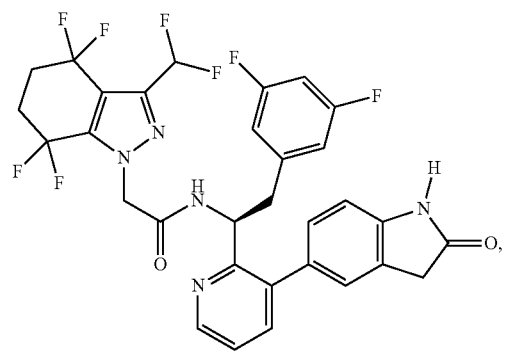
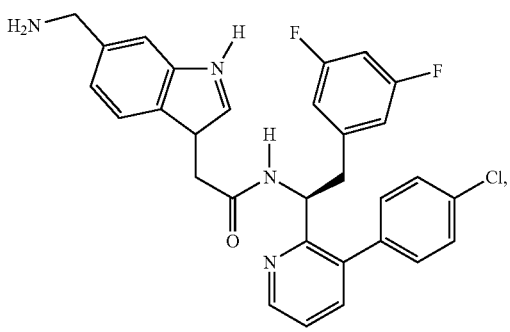
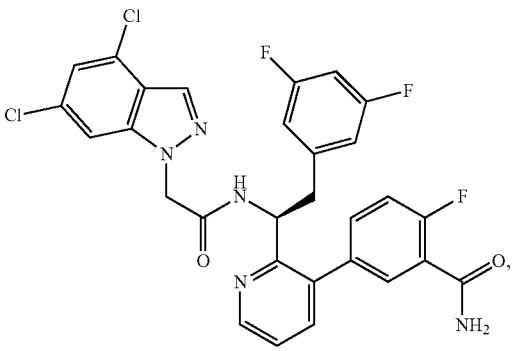
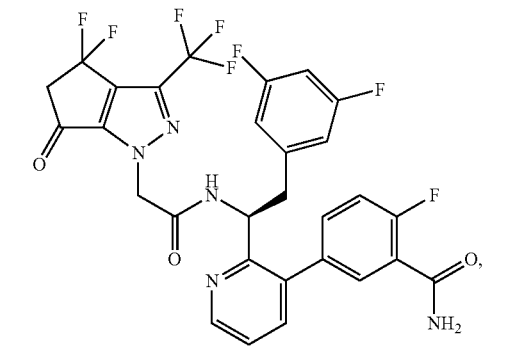
218
-continued
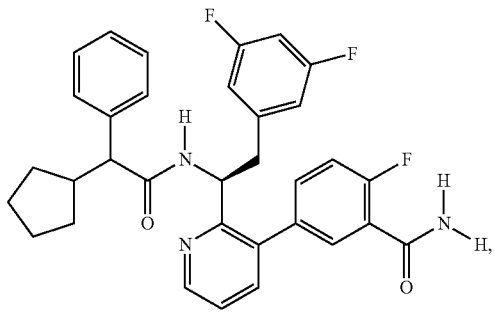
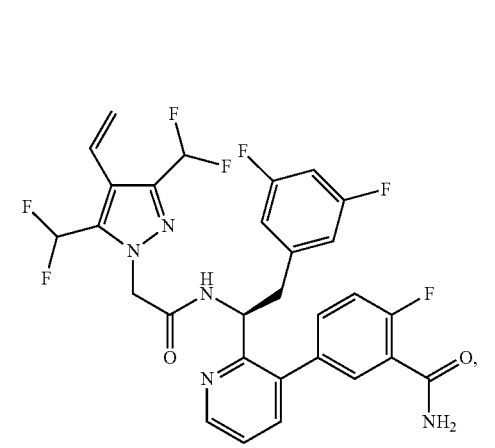
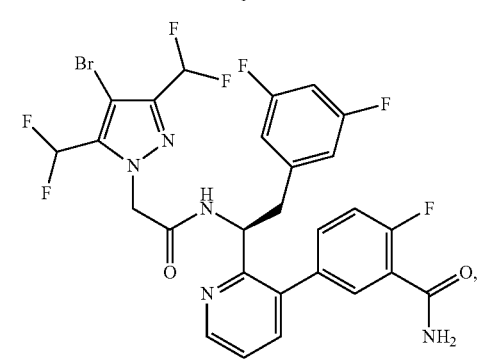
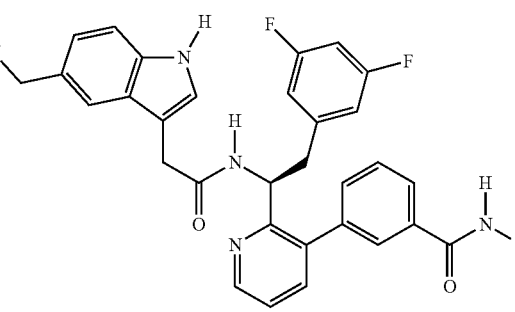
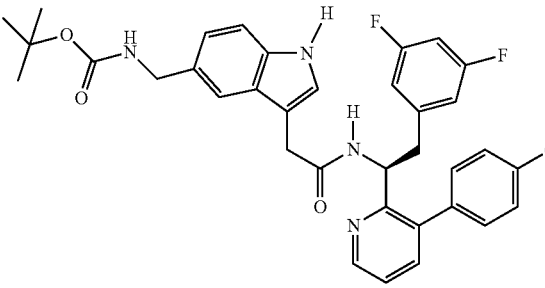

219
-continued
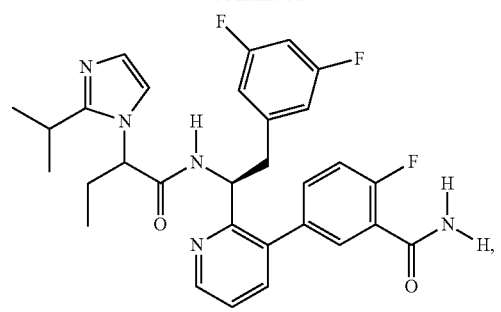
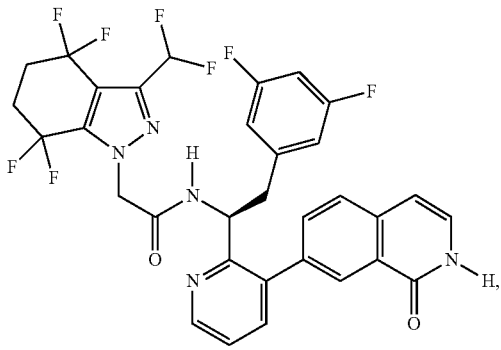
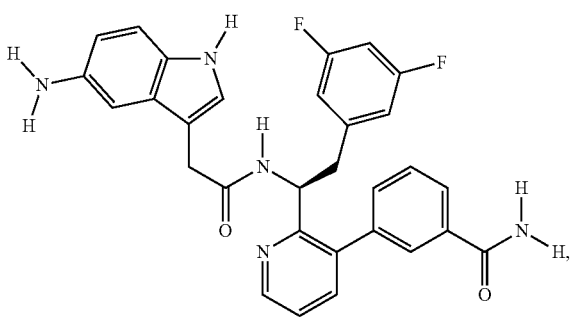
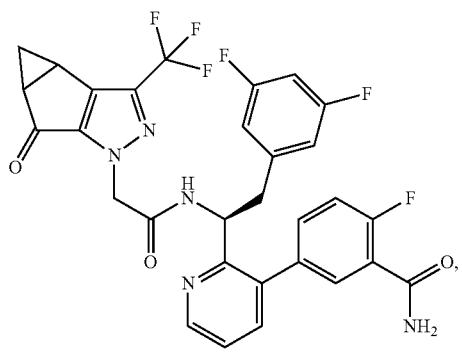
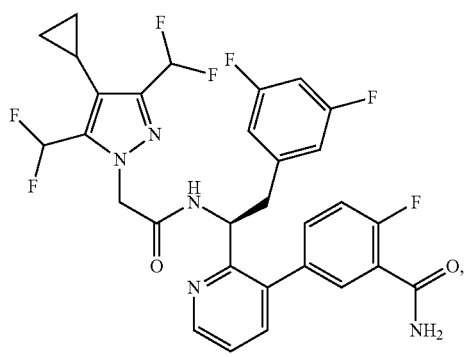
220
-continued
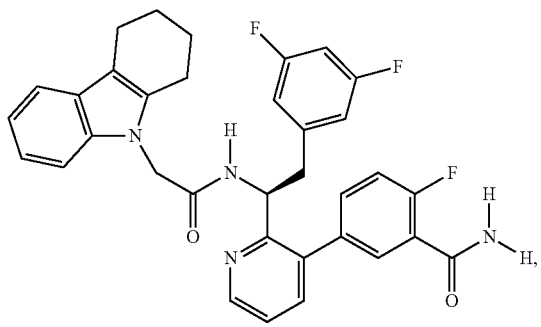
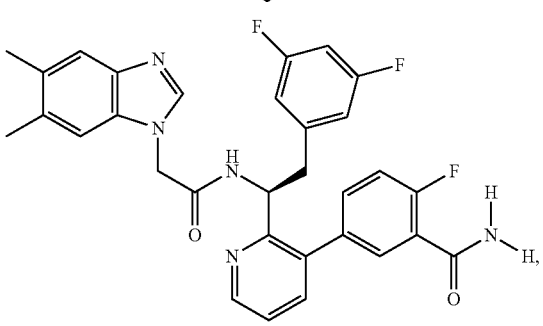
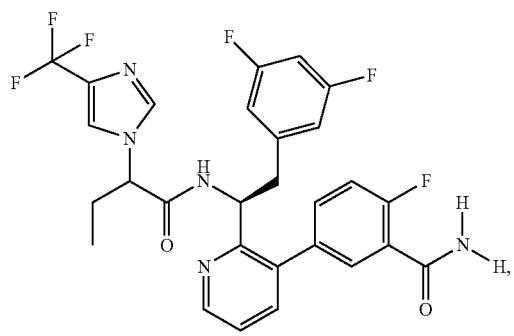
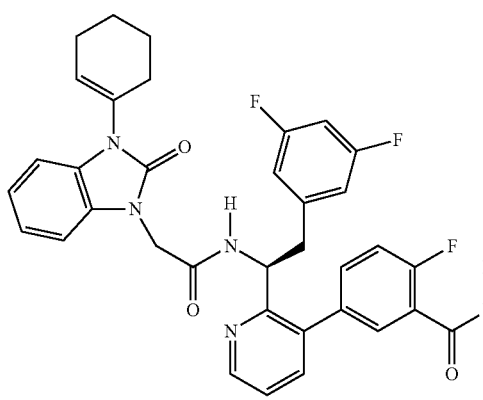
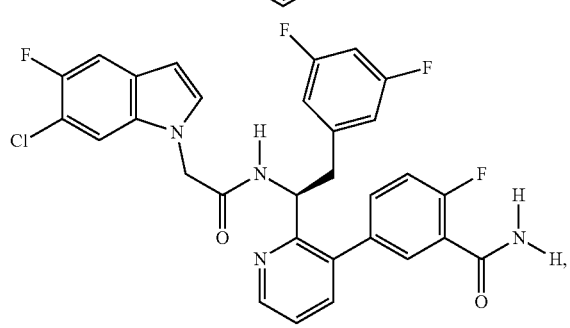

221
-continued
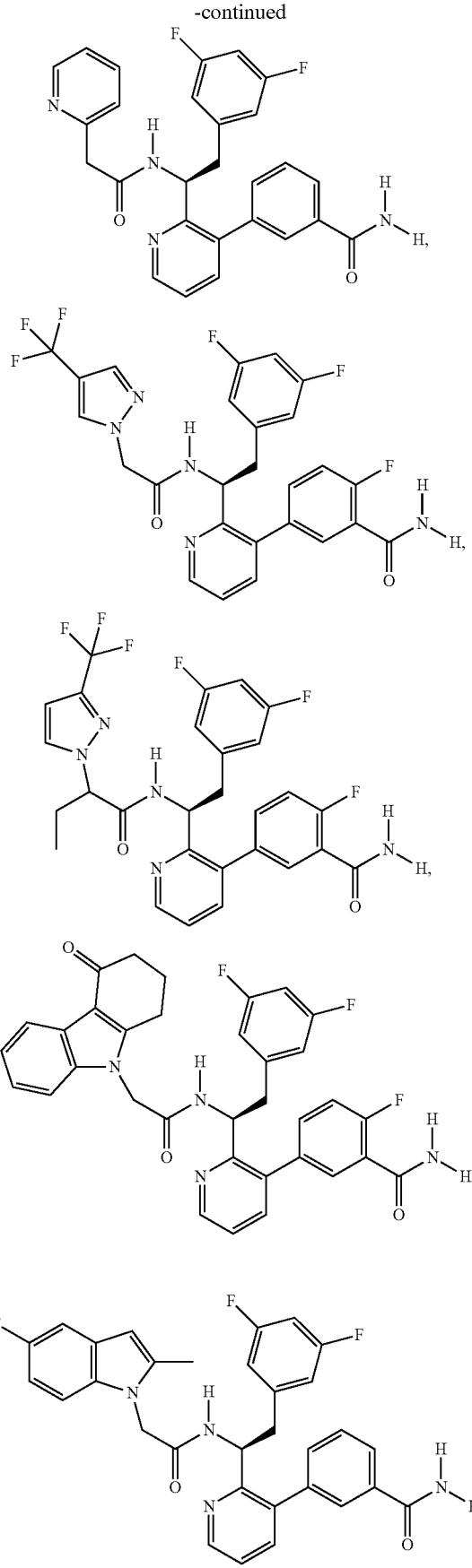
222
-continued
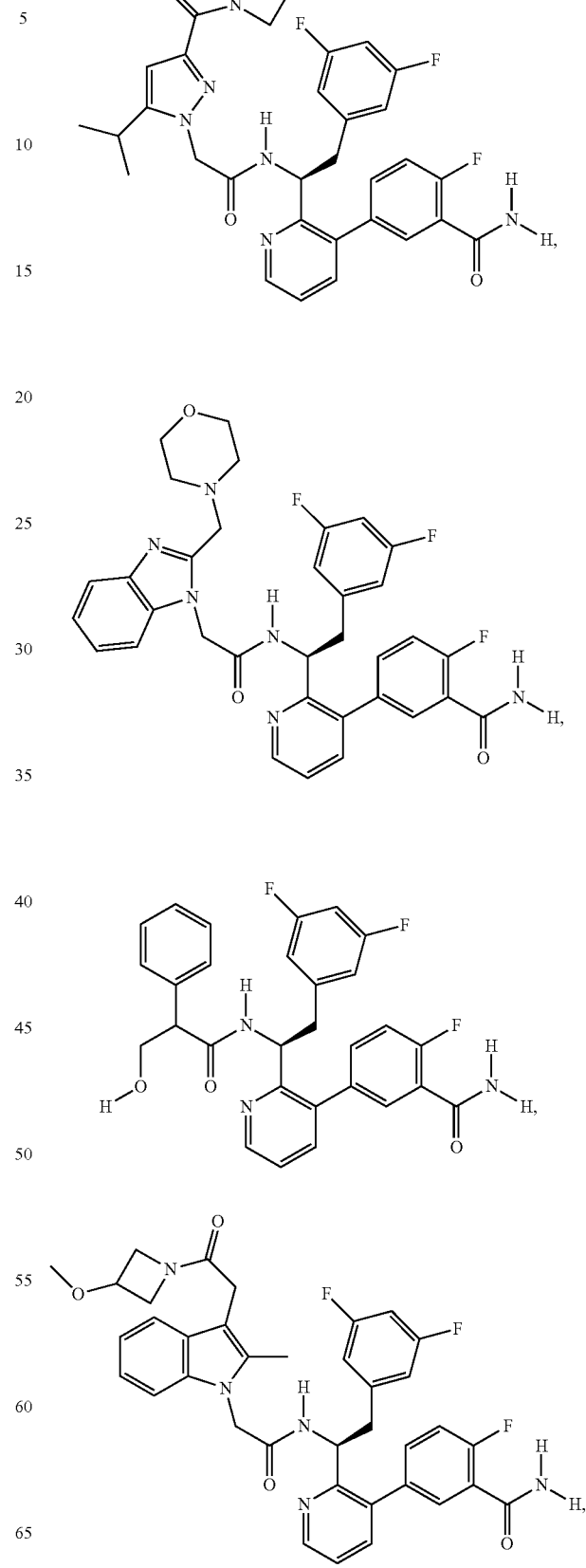

223
-continued
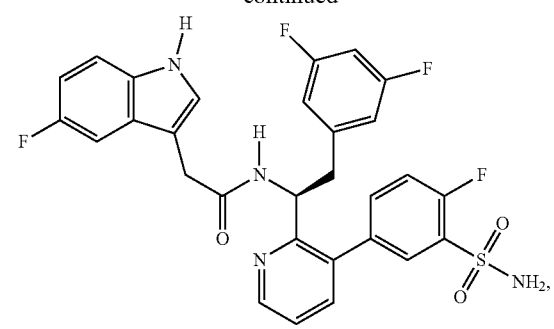
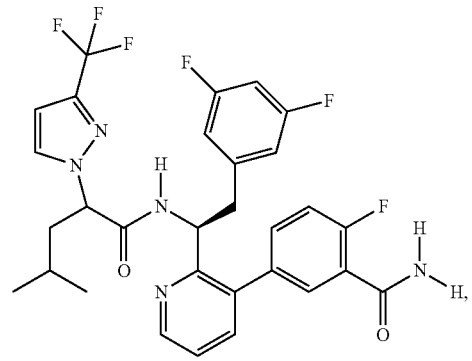
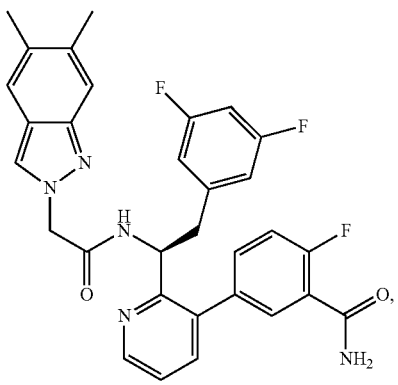
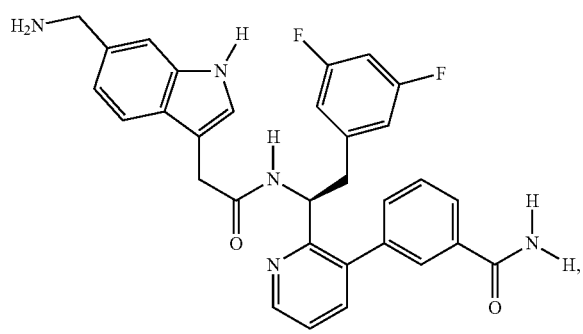
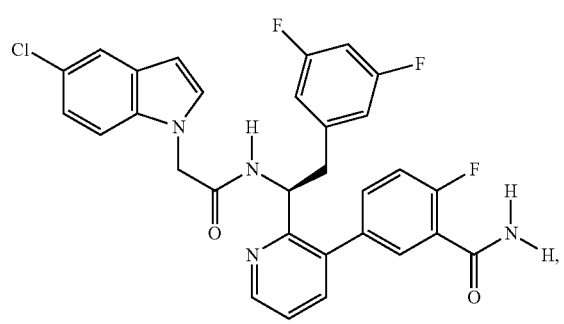
224
-continued
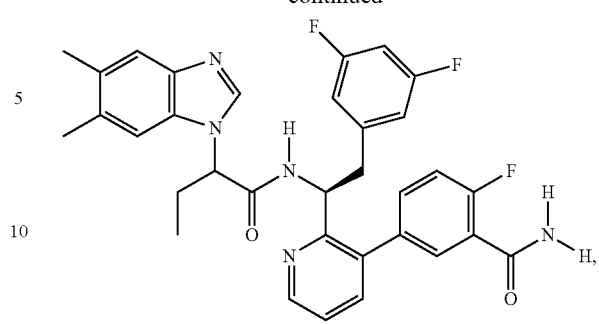
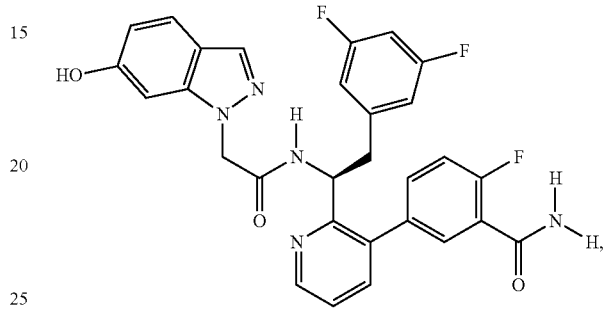
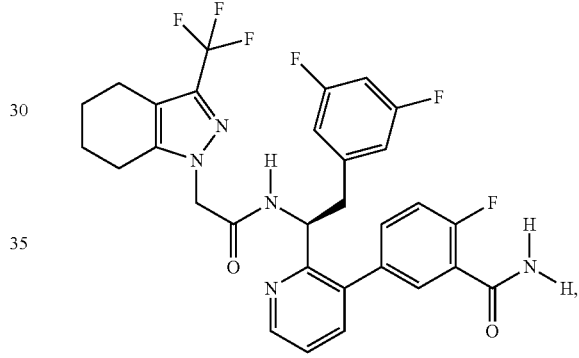
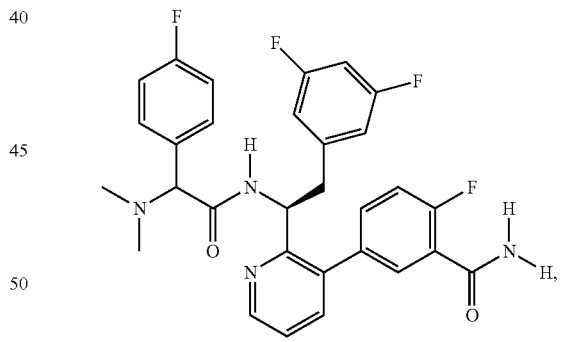
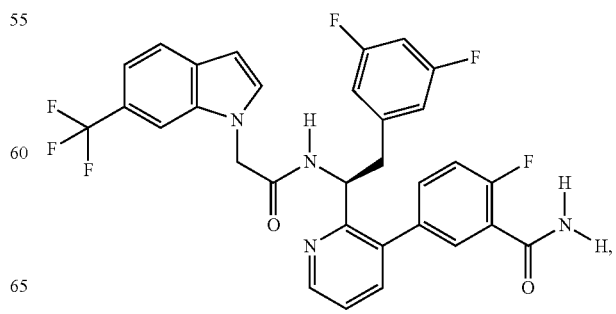

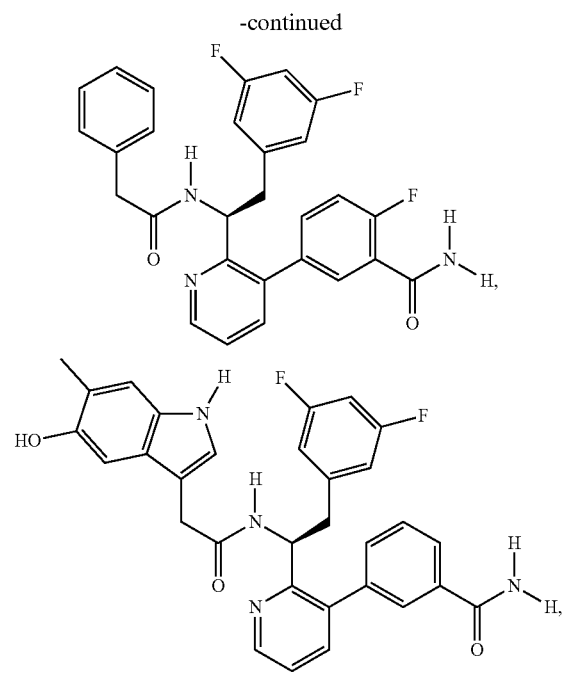
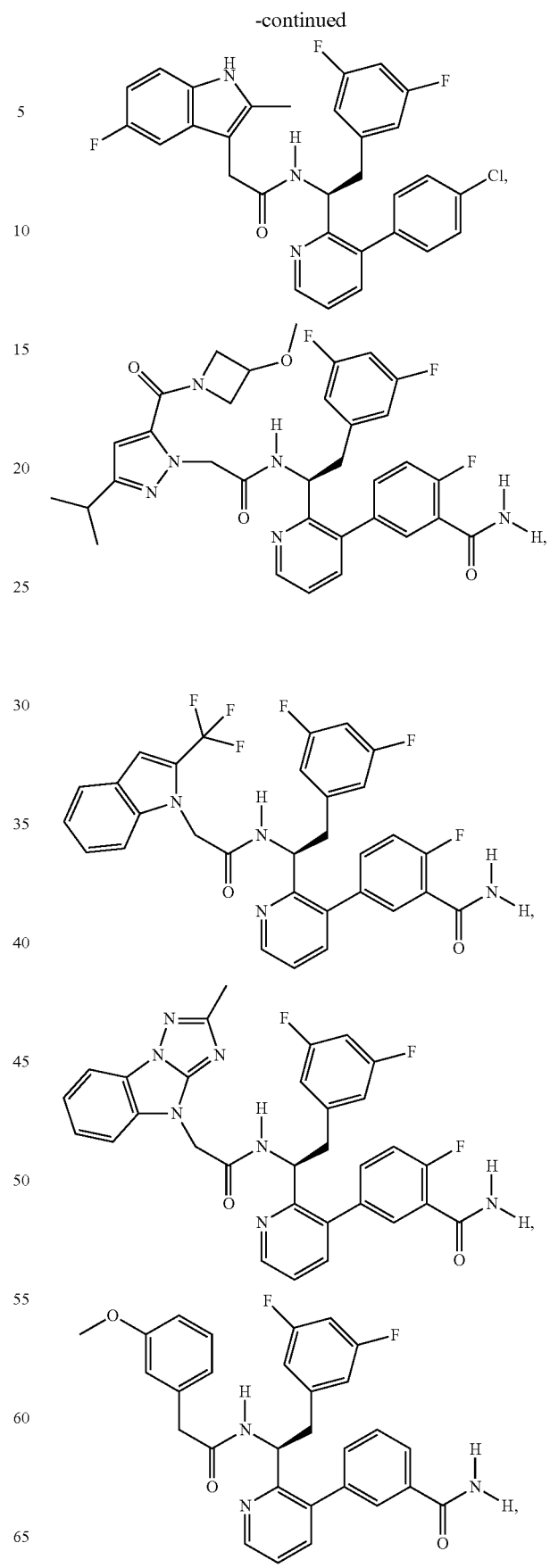

227
-continued
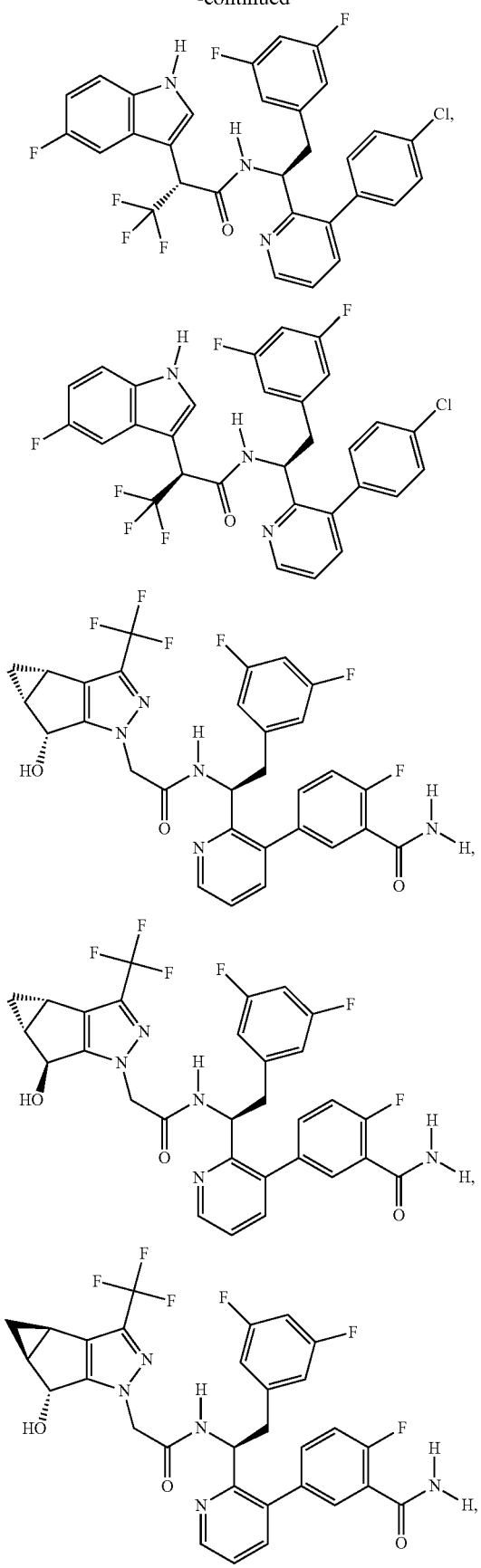
228
-continued
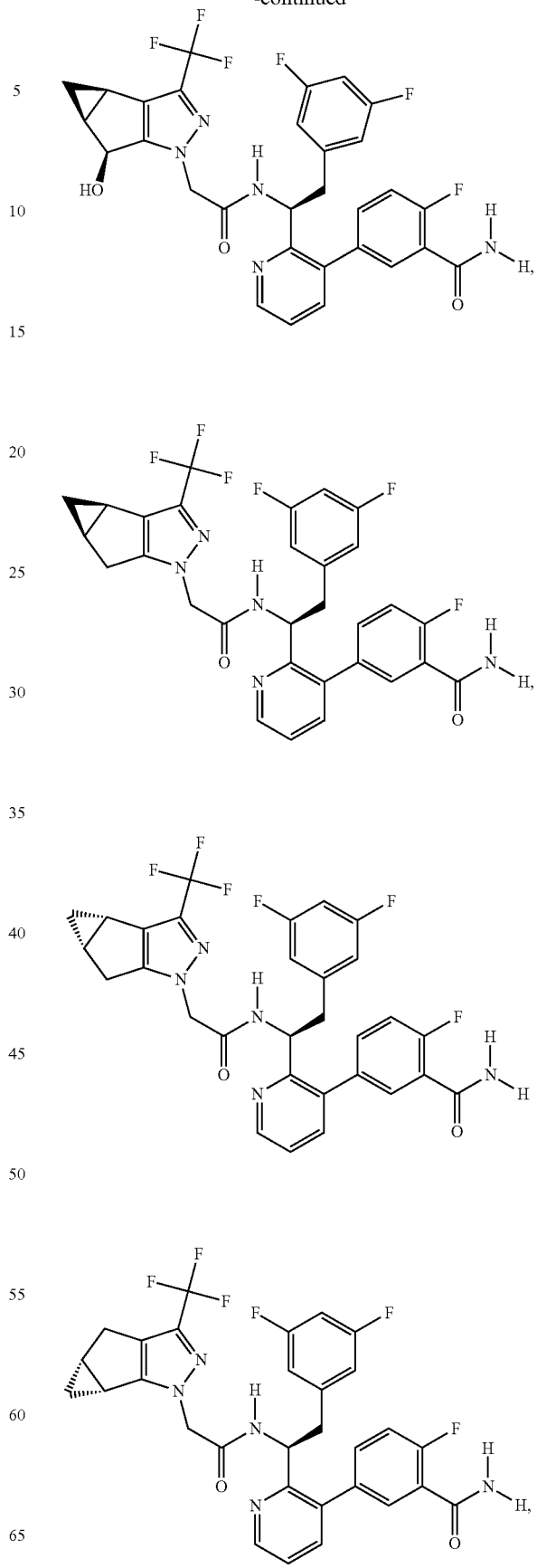

229
-continued
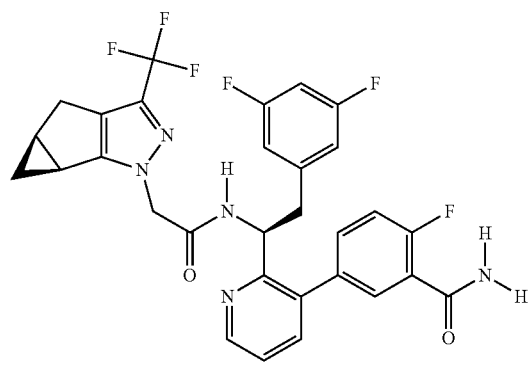
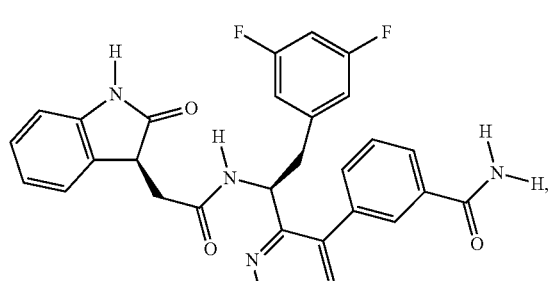
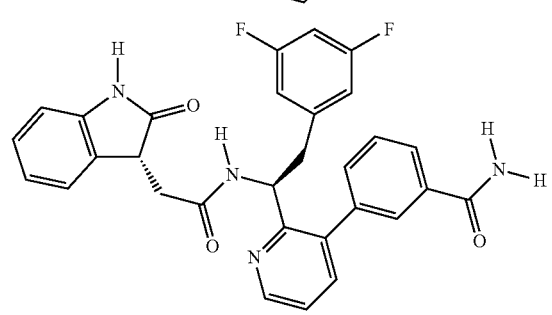
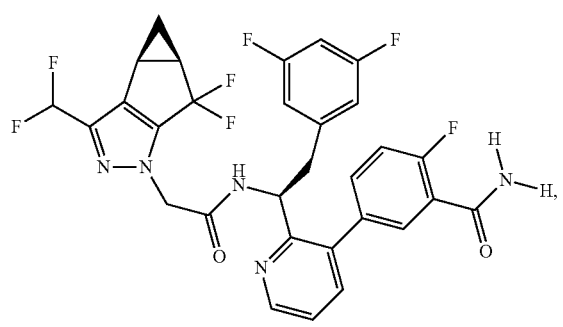
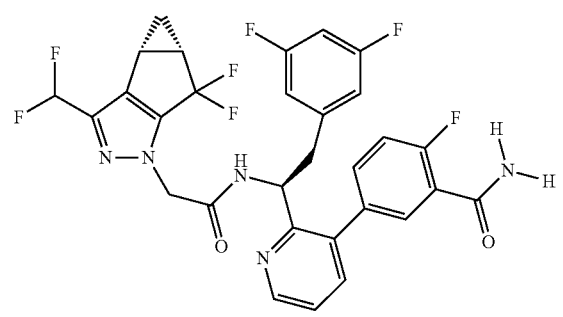
230
-continued
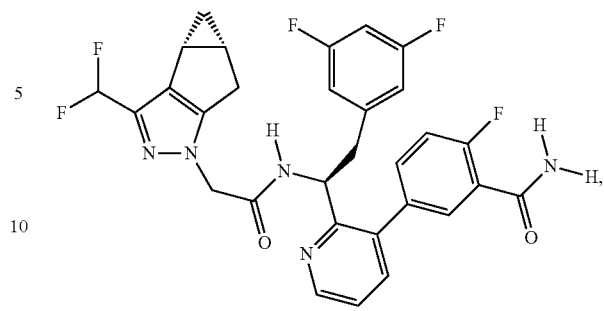
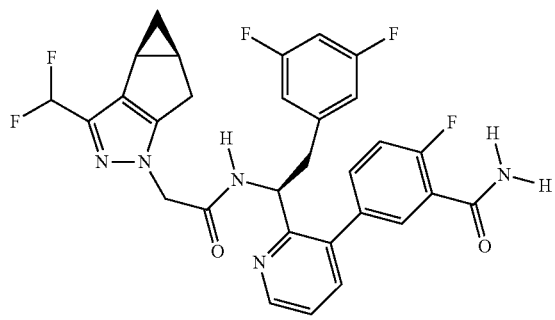
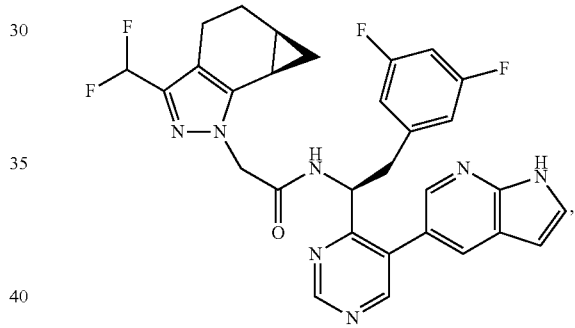
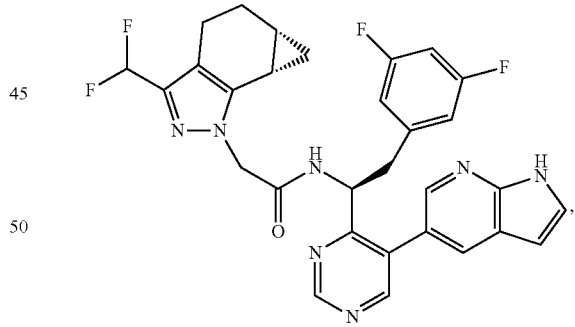
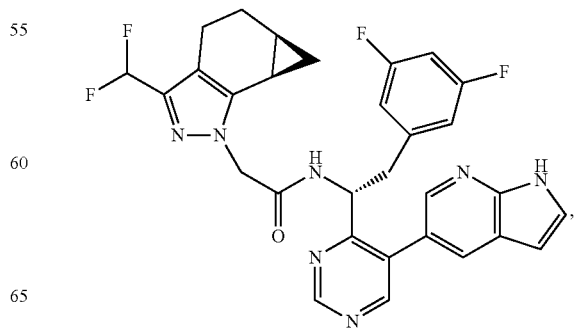

231
-continued
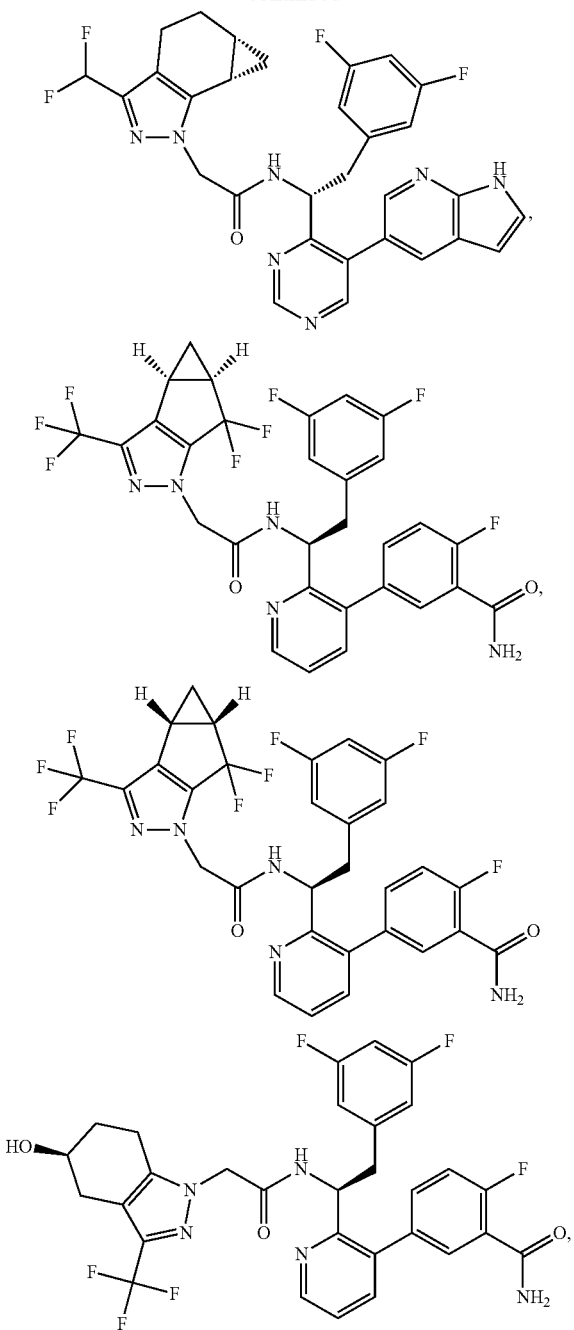
232
-continued
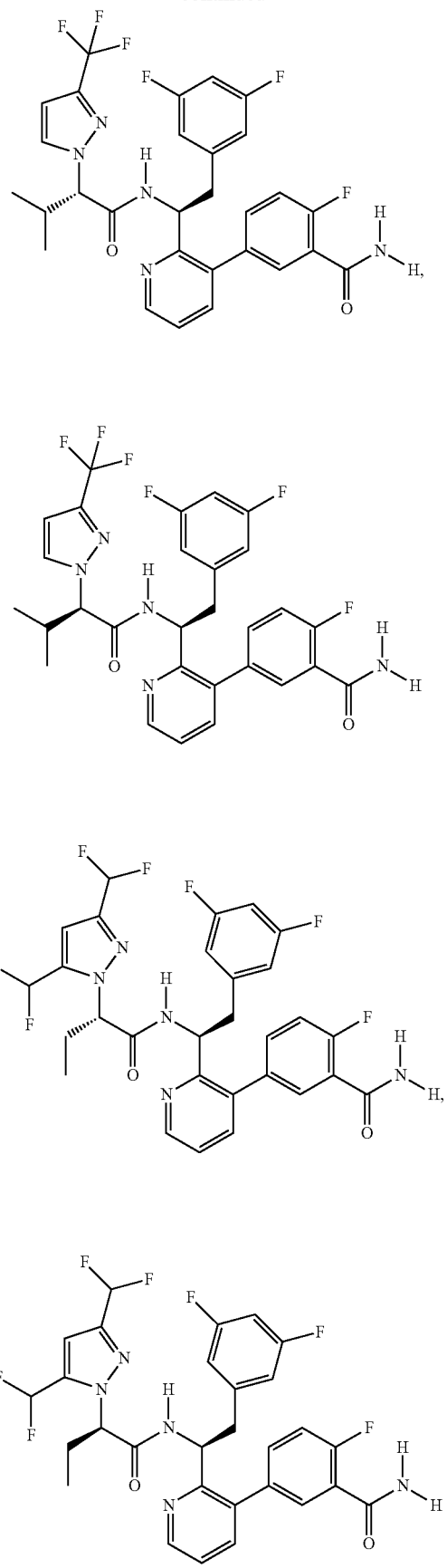

233
-continued
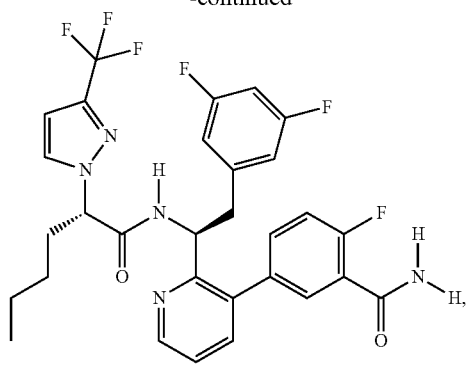
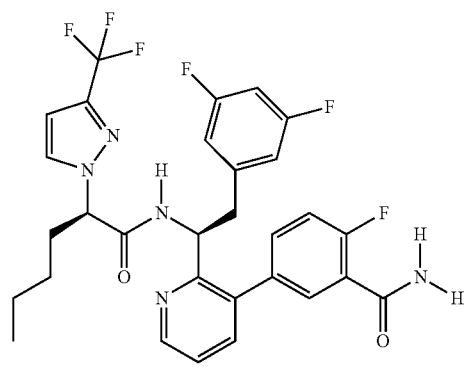
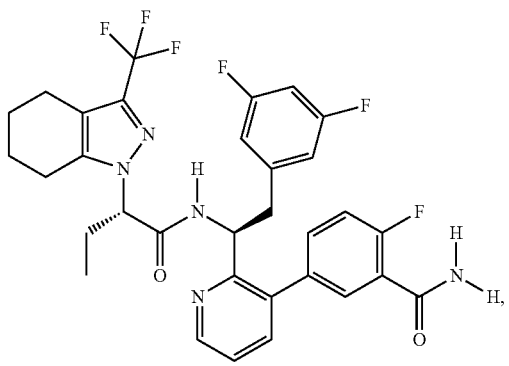
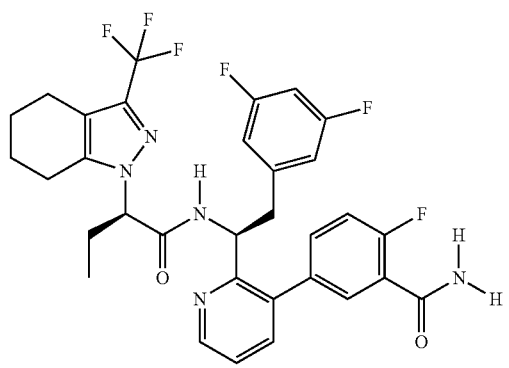
234
-continued

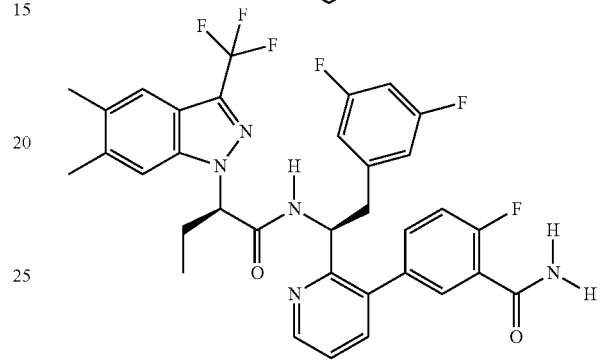
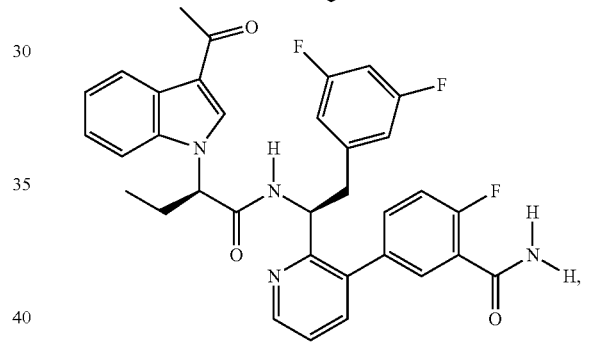
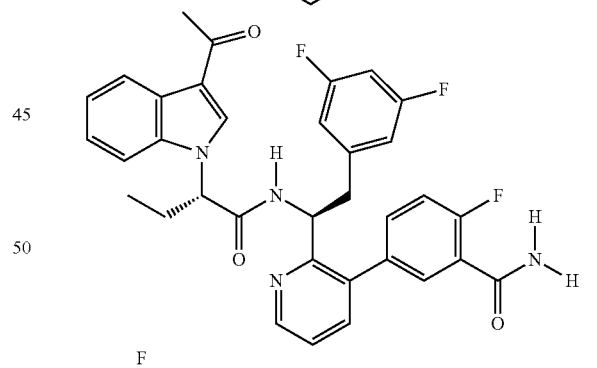
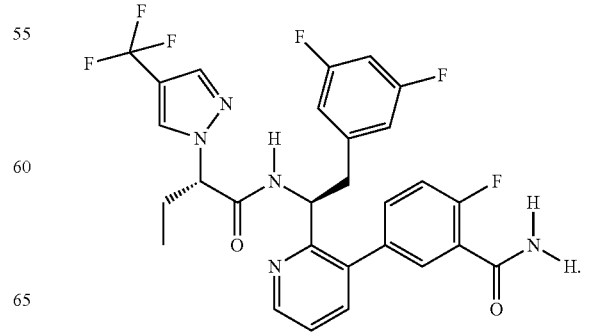

-continued

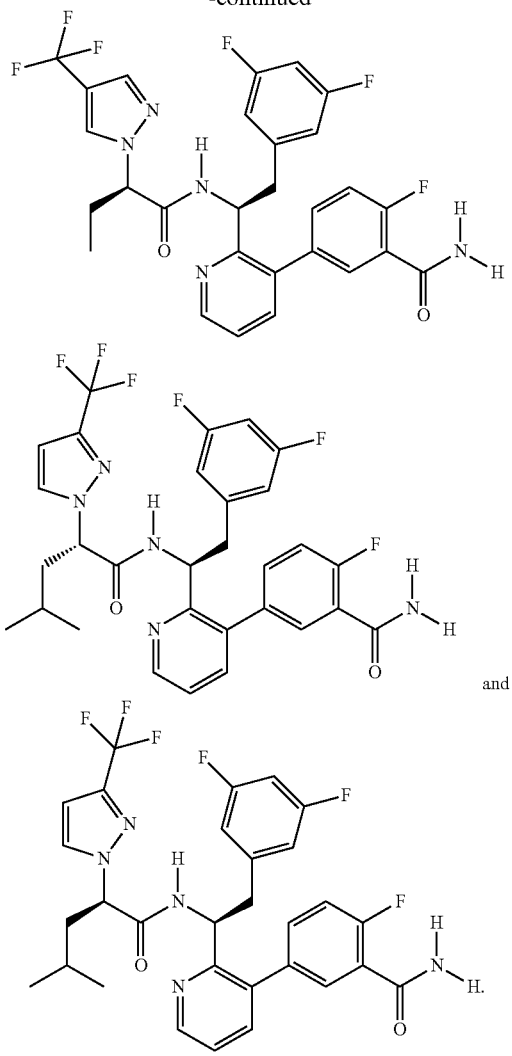

and salts thereof.

In one embodiment, the invention provides a compound of the invention which is a compound of formula I':

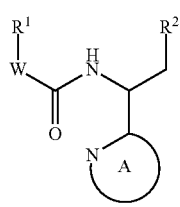

wherein:

A is a 6-membered heteroaryl comprising one or two nitrogens, wherein the 6-membered heteroaryl is substituted with one $Z^1$ group and optionally substituted with one or more (e.g. 1, 2, or 3) $Z^2$ groups;

W is $CR^{3a}R^{3b}$, O or $NR^4$;

$R^1$ is aryl, heteroaryl or heterocycle, wherein any aryl, heteroaryl or heterocycle of $R^1$ is optionally substituted with one or more (e.g. 1, 2, 3, 4 or 5) $Z^3$ groups;

$R^2$ is a 6-membered aryl, 5-membered heteroaryl or 6-membered heteroaryl, wherein any 6-membered aryl, 5-membered heteroaryl or 6-membered heteroaryl of $R^2$ is optionally substituted with one or more (e.g. 1, 2 or 3) $Z^4$ groups;

each $R^{3a}$ and $R^{3b}$ is independently selected from H, halogen, $(C_1-C_3)$alkyl, $(C_1-C_3)$haloalkyl, $(C_1-C_6)$heteroalkyl, heteroaryl$(C_1-C_6)$alkyl-, heterocyclyl$(C_1-C_6)$alkyl-, —$NR_aR_b$, and —$NR_cOR_d$; or $R^{3a}$ and $R^{3b}$ together with the carbon to which they are attached form a $(C_3-C_6)$ carbocycle;

$R^4$ is selected from H, $(C_1-C_6)$alkyl, $(C_3-C_6)$carbocycle, aryl$(C_1-C_6)$alkyl- and heteroaryl$(C_1-C_6)$alkyl-;

$R_a$ and $R_b$ are each independently selected from H, $(C_1-C_8)$alkyl, $(C_2-C_8)$alkenyl, $(C_2-C_8)$alkynyl, $(C_3-C_7)$carbocycle, heterocycle, heteroaryl, aryl, haloaryl, haloheteroaryl, haloheterocycle, $(C_1-C_8)$haloalkyl and $(C_1-C_8)$heteroalkyl, or $R_a$ and $R_b$ together with the nitrogen to which they are attached form a 5, 6 or 7-membered heterocycle;

each $R_c$ is independently selected from H, $(C_1-C_8)$alkyl, $(C_2-C_8)$alkenyl, $(C_2-C_8)$alkynyl, $(C_3-C_7)$carbocycle, heterocycle, heteroaryl, aryl, haloaryl, haloheteroaryl, haloheterocycle, $(C_1-C_8)$haloalkyl and $(C_1-C_8)$heteroalkyl;

each $R_d$ is independently selected from $(C_1-C_8)$alkyl, $(C_2-C_8)$alkenyl, $(C_2-C_8)$alkynyl, $(C_3-C_7)$carbocycle, heterocycle, heteroaryl, aryl, haloaryl, haloheteroaryl, haloheterocycle, $(C_1-C_8)$haloalkyl and $(C_1-C_8)$heteroalkyl;

each $Z^1$ is independently selected from $(C_2-C_8)$alkenyl, $(C_2-C_8)$alkynyl, $(C_3-C_7)$carbocycle, aryl, heteroaryl, heterocycle and —$OR_{n1}$, wherein any $(C_3-C_7)$carbocycle, aryl, heteroaryl and heterocycle of $Z^1$ is optionally substituted with one or more (e.g. 1, 2, 3, 4 or 5) $Z^{1a}$ or $Z^{1b}$ groups and wherein any $(C_1-C_8)$alkyl, $(C_2-C_8)$alkenyl and $(C_2-C_8)$alkynyl of Z is optionally substituted with one or more (e.g. 1, 2, 3, 4 or 5) $Z^{1a}$ groups;

each $Z^{1a}$ is independently selected from $(C_3-C_7)$carbocycle, aryl, heteroaryl, heterocycle, halogen, —CN, —$OR_{n2}$, —$OC(O)R_{p2}$, —$OC(O)NR_{q2}R_{r2}$, —$SR_{n2}$, —$S(O)R_{p2}$, —$S(O)_2OH$, —$S(O)_2R_{p2}$, —$S(O)_2NR_{q2}R_{r2}$, —$NR_{q2}R_{r2}$, —$NR_{n2}COR_{p2}$, —$NR_{n2}CO_2R_{p2}$, —$NR_{n2}CONR_{q2}R_{r2}$, —$NR_{n2}S(O)_2R_{p2}$, —$NR_{n2}S(O)_2OR_{p2}$, —$NR_{n2}S(O)_2NR_{q2}R_{r2}$, $NO_2$, —$C(O)R_{r2}$, —$C(O)OR_{n2}$, and, —$C(O)NR_{q2}R_{r2}$, wherein any $(C_3-C_7)$carbocycle, aryl, heteroaryl and heterocycle of $Z^{1a}$ is optionally substituted with one or more (e.g. 1, 2, 3, 4 or 5) $Z^{1c}$ or $Z^{1d}$ groups;

each $Z^{1b}$ is independently selected from $(C_1-C_8)$alkyl, $(C_2-C_8)$alkenyl and $(C_2-C_8)$alkynyl, wherein any $(C_1-C_8)$alkyl, $(C_2-C_8)$alkenyl and $(C_2-C_8)$alkynyl of $Z^{1b}$ is optionally substituted with one or more (e.g. 1, 2, 3, 4 or 5) $Z^{1c}$ groups;

each $Z^{1c}$ is independently selected from $(C_3-C_7)$carbocycle, aryl, heteroaryl, heterocycle, halogen, —CN, —$OR_{n3}$, —$OC(O)R_{p3}$, —$OC(O)NR_{q3}R_{r3}$, —$SR_{n3}$, —$S(O)R_{p3}$, —$S(O)_2OH$, —$S(O)_2R_{p3}$, —$S(O)_2NR_{q3}R_{r3}$, —$NR_{q3}R_{r3}$, —$NR_{n3}COR_{p3}$, —$NR_{n3}CO_2R_{r3}$, —$NR_{n3}CONR_{q3}R_{r3}$, —$NR_{n3}S(O)_2R_{p3}$, —$NR_{n3}S(O)_2OR_{p3}$, —$NR_{n3}S(O)_2NR_{q3}R_{r3}$, $NO_2$, —$C(O)R_{n3}$, —$C(O)OR_{n3}$, —$C(O)NR_{q3}R_{r3}$, haloaryl, haloheteroaryl, haloheterocycle and $(C_1-C_8)$heteroalkyl;

each $Z^{1d}$ is independently selected from $(C_1-C_8)$alkyl, $(C_2-C_8)$alkenyl, $(C_2-C_8)$alkynyl and $(C_1-C_8)$haloalkyl;

each $R_{n1}$ is independently selected from $(C_1-C_8)$alkyl, $(C_2-C_8)$alkenyl, $(C_2-C_8)$alkynyl, $(C_3-C_7)$carbocycle, heterocycle, heteroaryl and aryl, wherein any $(C_3-C_7)$carbocycle, aryl, heteroaryl and heterocycle of $R_{n1}$ is optionally substituted with one or more (e.g. 1, 2, 3, 4 or 5) $Z^{1a}$ or $Z^{1b}$ groups, and wherein any $(C_1-C_8)$alkyl, $(C_2-C_8)$alkenyl and $(C_2-C_8)$alkynyl of $R_{n1}$ is optionally substituted with one or more (e.g. 1, 2, 3, 4 or 5) $Z^{1a}$ groups;

each $R_{n2}$ is independently selected from H, $(C_1-C_8)$alkyl, $(C_2-C_8)$alkenyl, $(C_2-C_8)$alkynyl, $(C_3-C_7)$carbocycle, heterocycle, heteroaryl and aryl, wherein any $(C_3-C_7)$carbocycle, aryl, heteroaryl and heterocycle of $R_{n2}$ is optionally substituted with one or more (e.g. 1, 2, 3, 4 or 5) $Z^{1c}$ or $Z^{1d}$ groups, and wherein any $(C_1-C_8)$alkyl, $(C_2-C_8)$alkenyl and $(C_2-C_8)$alkynyl of $R_{n2}$ is optionally substituted with one or more (e.g. 1, 2, 3, 4 or 5) $Z^{1c}$ groups;

each $R_{p2}$ is independently selected from $(C_1-C_8)$alkyl, $(C_2-C_8)$alkenyl, $(C_2-C_8)$alkynyl, $(C_3-C_7)$carbocycle, heterocycle, heteroaryl and aryl, wherein any $(C_3-C_7)$carbocycle, aryl, heteroaryl and heterocycle of $R_{p2}$ is optionally substituted with one or more (e.g. 1, 2, 3, 4 or 5) $Z^{1c}$ or $Z^{1d}$ groups, and wherein any $(C_1-C_8)$alkyl, $(C_2-C_8)$alkenyl and $(C_2-C_8)$alkynyl of $R_{p2}$ is optionally substituted with one or more (e.g. 1, 2, 3, 4 or 5) $Z^{1c}$ groups;

$R_{q2}$ and $R_{r2}$ are each independently selected from H, $(C_1-C_8)$alkyl, $(C_2-C_8)$alkenyl, $(C_2-C_8)$alkynyl, $(C_3-C_7)$carbocycle, heterocycle, heteroaryl and aryl, wherein any $(C_3-C_7)$carbocycle, aryl, heteroaryl and heterocycle of $R_{q2}$ or $R_{r2}$ is optionally substituted with one or more (e.g. 1, 2, 3, 4 or 5) $Z^{1c}$ or $Z^{1d}$ groups, and wherein any $(C_1-C_8)$alkyl, $(C_2-C_8)$alkenyl and $(C_2-C_8)$alkynyl of $R_{q2}$ or $R_{r2}$ is optionally substituted with one or more (e.g. 1, 2, 3, 4 or 5) $Z^{1c}$ groups, or $R_{q2}$ and $R_{r2}$ together with the nitrogen to which they are attached form a 5, 6 or 7-membered heterocycle, wherein the 5, 6 or 7-membered heterocycle is optionally substituted with one or more (e.g. 1, 2, 3, 4 or 5) $Z^{1c}$ or $Z^{1d}$ groups;

each $R_{n3}$ is independently selected from H, $(C_1-C_8)$alkyl, $(C_2-C_8)$alkenyl, $(C_2-C_8)$alkynyl, $(C_3-C_7)$carbocycle, heterocycle, heteroaryl, aryl, haloaryl, haloheteroaryl, haloheterocycle, $(C_1-C_8)$haloalkyl and $(C_1-C_8)$heteroalkyl;

each $R_{p3}$ is independently selected from $(C_1-C_8)$alkyl, $(C_2-C_8)$alkenyl, $(C_2-C_8)$alkynyl, $(C_3-C_7)$carbocycle, heterocycle, heteroaryl, aryl, haloaryl, haloheteroaryl, haloheterocycle, $(C_1-C_8)$haloalkyl and $(C_1-C_8)$heteroalkyl;

$R_{q3}$ and $R_{r3}$ are each independently selected from H, $(C_1-C_8)$alkyl, $(C_2-C_8)$alkenyl, $(C_2-C_8)$alkynyl, $(C_3-C_7)$carbocycle, heterocycle, heteroaryl, aryl, haloaryl, haloheteroaryl, haloheterocycle, $(C_1-C_8)$haloalkyl and $(C_1-C_8)$heteroalkyl, or $R_{q3}$ and $R_{r3}$ together with the nitrogen to which they are attached form a 5, 6 or 7-membered heterocycle;

each $Z^2$ is independently selected from $(C_1-C_6)$alkyl, $(C_1-C_6)$haloalkyl, $(C_3-C_7)$carbocycle, halogen, CN, OH and —O$(C_1-C_6)$alkyl;

each $Z^3$ is independently selected from $(C_1-C_8)$alkyl, $(C_2-C_8)$alkenyl, $(C_2-C_8)$alkynyl, $(C_3-C_7)$carbocycle, aryl, heteroaryl, heterocycle, halogen, —CN, —OR$_{n4}$, —OC(O)R$_{p4}$, —OC(O)NR$_{q4}$R$_{r4}$, —SR$_{n4}$, —S(O)R$_{p4}$, —S(O)$_2$OH, —S(O)$_2$R$_{p4}$, —S(O)$_2$NR$_{q4}$R$_{r4}$, —NR$_{q4}$R$_{r4}$, —NR$_{n4}$COR$_{p4}$, —NR$_{n4}$CO$_2$R$_{p4}$, —NR$_{n4}$CONR$_{q4}$R$_{r4}$, —NR$_{n4}$S(O)$_2$R$_{p4}$, —NR$_{n4}$S(O)$_2$OR$_{p4}$, —NR$_{n4}$S(O)$_2$NR$_{q4}$R$_{r4}$, NO$_2$, —C(O)R$_{n4}$, —C(O)OR$_{n4}$, and —C(O)NR$_{q4}$R$_{r4}$, wherein any $(C_3-C_7)$carbocycle, aryl, heteroaryl and heterocycle of $Z^3$ is optionally substituted with one or more (e.g. 1, 2, 3, 4 or 5) $Z^{3a}$ or $Z^{3b}$ groups, and wherein any $(C_1-C_8)$alkyl, $(C_2-C_8)$alkenyl and $(C_2-C_8)$alkynyl of $Z^3$ is optionally substituted with one or more (e.g. 1, 2, 3, 4 or 5) $Z^{3a}$ groups;

each $Z^{3a}$ is independently selected from $(C_3-C_7)$carbocycle, aryl, heteroaryl, heterocycle, halogen, —CN, —OR$_{n5}$, —OC(O)R$_{p5}$, —OC(O)NR$_{q5}$R$_{r5}$, —SR$_{n5}$, —S(O)R$_{p5}$, —S(O)$_2$OH, —S(O)$_2$R$_{p5}$, —S(O)$_2$NR$_{q5}$R$_{r5}$, —NR$_{q5}$R$_{r5}$, —NR$_{n5}$COR$_{p5}$, —NR$_{n5}$CO$_2$R$_{p5}$, —NR$_{n5}$CONR$_{q5}$R$_{r5}$, —NR$_{n5}$S(O)$_2$R$_{p5}$, —NR$_{n5}$S(O)$_2$OR$_{p5}$, —NR$_{n5}$S(O)$_2$NR$_{q5}$R$_{r5}$, NO$_2$, —C(O)R$_{n5}$, —C(O)OR$_{n5}$, and —C(O)NR$_{q5}$R$_{r5}$, wherein any $(C_3-C_7)$carbocycle, aryl, heteroaryl and heterocycle of $Z^{3a}$ is optionally substituted with one or more (e.g. 1, 2, 3, 4 or 5) $Z^{3c}$ or $Z^{3d}$ groups;

each $Z^{3b}$ is independently selected from $(C_1-C_8)$alkyl, $(C_2-C_8)$alkenyl and $(C_2-C_8)$alkynyl, wherein any $(C_1-C_8)$alkyl, $(C_2-C_8)$alkenyl and $(C_2-C_8)$alkynyl of $Z^{3b}$ is optionally substituted with one or more (e.g. 1, 2, 3, 4 or 5) $Z^{3c}$ groups;

each $Z^{3c}$ is independently selected from $(C_3-C_7)$carbocycle, aryl, heteroaryl, heterocycle, halogen, —CN, —OR$_{n6}$, —OC(O)R$_{p6}$, —OC(O)NR$_{q6}$R$_{r6}$, —SR$_{n6}$, —S(O)R$_{p6}$, —S(O)$_2$OH, —S(O)$_2$R$_{p6}$, —S(O)$_2$NR$_{q6}$R$_{r6}$, —NR$_{q6}$R$_{r6}$, —NR$_{n6}$COR$_{p6}$, —NR$_{n6}$CO$_2$R$_{p6}$, —NR$_{n6}$CONR$_{q6}$R$_{r6}$, —NR$_{n6}$S(O)$_2$R$_{p6}$, —NR$_{n6}$S(O)$_2$OR$_{p6}$, —NR$_{n6}$S(O)$_2$NR$_{q6}$R$_{r6}$, NO$_2$, —C(O)R$_{n6}$, —C(O)OR$_{n6}$, —C(O)NR$_{q6}$R$_{r6}$, haloaryl, haloheteroaryl, haloheterocycle and $(C_1-C_8)$heteroalkyl;

each $Z^{3d}$ is independently selected from $(C_1-C_8)$alkyl, $(C_2-C_8)$alkenyl, $(C_2-C_8)$alkynyl, and $(C_1-C_8)$haloalkyl;

each $R_{n4}$ is independently selected from H, $(C_1-C_8)$alkyl, $(C_2-C_8)$alkenyl, $(C_2-C_8)$alkynyl, $(C_3-C_7)$carbocycle, heterocycle, heteroaryl and aryl, wherein any $(C_3-C_7)$carbocycle, aryl, heteroaryl and heterocycle of $R_{n4}$ is optionally substituted with one or more (e.g. 1, 2, 3, 4 or 5) $Z^{3a}$ or $Z^{3b}$ groups, and wherein any $(C_1-C_8)$alkyl, $(C_2-C_8)$alkenyl and $(C_2-C_8)$alkynyl of $R_{n4}$ is optionally substituted with one or more (e.g. 1, 2, 3, 4 or 5) $Z^{3a}$ groups;

each $R_{p4}$ is independently selected from $(C_1-C_8)$alkyl, $(C_2-C_8)$alkenyl, $(C_2-C_8)$alkynyl, $(C_3-C_7)$carbocycle, heterocycle, heteroaryl and aryl, wherein any $(C_3-C_7)$carbocycle, aryl, heteroaryl, or heterocycle of $R_{p4}$ is optionally substituted with one or more (e.g. 1, 2, 3, 4 or 5) $Z^{3a}$ or $Z^{3b}$ groups, and wherein any $(C_1-C_8)$alkyl, $(C_2-C_8)$alkenyl or $(C_2-C_8)$alkynyl of $R_{p4}$ is optionally substituted with one or more (e.g. 1, 2, 3, 4 or 5) $Z^{3a}$ groups;

$R_{q4}$ and $R_{r4}$ are each independently selected from H, $(C_1-C_8)$alkyl, $(C_2-C_8)$alkenyl, $(C_2-C_8)$alkynyl, $(C_3-C_7)$carbocycle, heterocycle, heteroaryl and aryl, wherein any $(C_3-C_7)$carbocycle, aryl, heteroaryl and heterocycle of $R_{q4}$ or $R_{r4}$ is optionally substituted with one or more (e.g. 1, 2, 3, 4 or 5) $Z^{3a}$ or $Z^{3b}$ groups, and wherein any $(C_1-C_8)$alkyl, $(C_2-C_8)$alkenyl and $(C_2-C_8)$alkynyl of $R_{q4}$ or $R_{r4}$ is optionally substituted with one or more (e.g. 1, 2, 3, 4 or 5) $Z^{3a}$ groups, or $R_{q4}$ and $R_{r4}$ together with the nitrogen to which they are attached form a 5, 6 or 7-membered heterocycle, wherein the 5, 6 or 7-membered heterocycle is optionally substituted with one or more (e.g. 1, 2, 3, 4 or 5) $Z^{3a}$ or $Z^{3b}$ groups;

each $R_{n5}$ is independently selected from H, $(C_1-C_8)$alkyl, $(C_2-C_8)$alkenyl, $(C_2-C_8)$alkynyl, $(C_3-C_7)$carbocycle, heterocycle, heteroaryl and aryl, wherein any $(C_3-C_7)$carbocycle, aryl, heteroaryl and heterocycle of $R_{n5}$ is optionally substituted with one or more (e.g. 1, 2, 3, 4 or 5) $Z^{3c}$ or $Z^{3d}$ groups, and wherein any $(C_1-C_8)$alkyl, $(C_2-C_8)$alkenyl and $(C_2-C_8)$alkynyl of $R_{n5}$ is optionally substituted with one or more (e.g. 1, 2, 3, 4 or 5) $Z^{3c}$ groups;

each $R_{p5}$ is independently selected from $(C_1-C_8)$alkyl, $(C_2-C_8)$alkenyl, $(C_2-C_8)$alkynyl, $(C_3-C_7)$carbocycle, heterocycle, heteroaryl and aryl, wherein any $(C_3-C_7)$carbocycle, aryl, heteroaryl and heterocycle of $R_{p5}$ is optionally substituted with one or more (e.g. 1, 2, 3, 4 or 5) $Z^{3c}$ or $Z^{3d}$ groups, and wherein any $(C_1-C_8)$alkyl, $(C_2-C_8)$alkenyl and $(C_2-C_8)$alkynyl of $R_{p5}$ is optionally substituted with one or more (e.g. 1, 2, 3, 4 or 5) $Z^{3c}$ groups;

$R_{q5}$ and $R_{r5}$ are each independently selected from H, $(C_1-C_8)$alkyl, $(C_2-C_8)$alkenyl, $(C_2-C_8)$alkynyl, $(C_3-C_7)$carbocycle, heterocycle, heteroaryl and aryl, wherein any $(C_3-C_7)$carbocycle, aryl, heteroaryl and heterocycle of $R_{q5}$ or $R_{r5}$ is optionally substituted with one or more (e.g. 1, 2, 3, 4 or 5) $Z^{3c}$ or $Z^{3d}$ groups, and wherein any $(C_1-C_8)$alkyl, $(C_2-C_8)$alkenyl and $(C_2-C_8)$alkynyl of $R_{q5}$ or $R_{r5}$ is optionally substituted with one or more (e.g. 1, 2, 3, 4 or 5) $Z^{3c}$ groups, or $R_{q5}$ and $R_{r5}$ together with the nitrogen to which they are attached form a 5, 6 or 7-membered heterocycle, wherein the 5, 6 or 7-membered heterocycle is optionally substituted with one or more (e.g. 1, 2, 3, 4 or 5) $Z^{3c}$ or $Z^{3d}$ groups;

each $R_{n6}$ is independently selected from H, $(C_1-C_8)$alkyl, $(C_2-C_8)$alkenyl, $(C_2-C_8)$alkynyl, $(C_3-C_7)$carbocycle, heterocycle, heteroaryl, aryl, haloaryl, haloheteroaryl, haloheterocycle, $(C_1-C_8)$haloalkyl and $(C_1-C_8)$heteroalkyl;

each $R_{p6}$ is independently selected from $(C_1-C_8)$alkyl, $(C_2-C_8)$alkenyl, $(C_2-C_8)$alkynyl, $(C_3-C_7)$carbocycle, heterocycle, heteroaryl, aryl, haloaryl, haloheteroaryl, haloheterocycle, $(C_1-C_8)$haloalkyl and $(C_1-C_8)$heteroalkyl;

$R_{q6}$ and $R_{r6}$ are each independently selected from H, $(C_1-C_8)$alkyl, $(C_2-C_8)$alkenyl, $(C_2-C_8)$alkynyl, $(C_3-C_7)$carbocycle, heterocycle, heteroaryl, aryl, haloaryl, haloheteroaryl, haloheterocycle, $(C_1-C_8)$haloalkyl and $(C_1-C_8)$heteroalkyl, or $R_{q6}$ and $R_{r6}$ together with the nitrogen to which they are attached form a 5, 6 or 7-membered heterocycle;

each $Z^4$ is independently selected from $(C_1-C_8)$alkyl, $(C_2-C_8)$alkenyl, $(C_2-C_8)$alkynyl, $(C_3-C_7)$carbocycle, aryl, heteroaryl, heterocycle, halogen, —CN, —$OR_{n8}$, —OC(O)$R_{p8}$, —OC(O)$NR_{q8}R_{r8}$, —$SR_{n8}$, —S(O)$R_{p8}$, —$S(O)_2$OH, —$S(O)_2R_{p8}$, —$S(O)_2NR_{q8}R_{r8}$, —$NR_{q8}R_{r8}$, —$NR_{n8}COR_{p8}$, —$NR_{n8}CO_2R_{p8}$, —$NR_{n8}CONR_{q8}R_{r8}$, —$NR_{n8}S(O)_2R_{p8}$, —$NR_{n8}S(O)_2OR_{p8}$, —$NR_{n8}S(O)_2$ $NR_{q8}R_{r8}$, $NO_2$, —C(O)$R_{n8}$, —C(O)$OR_{n8}$, and —C(O)$NR_{q8}R_{r8}$, wherein any $(C_3-C_7)$carbocycle, aryl, heteroaryl and heterocycle of $Z^4$ is optionally substituted with one or more (e.g. 1, 2, 3, 4 or 5) $Z^{4c}$ or $Z^{4d}$ groups and wherein any $(C_1-C_8)$alkyl, $(C_2-C_8)$alkenyl and $(C_2-C_8)$alkynyl of $Z^4$ is optionally substituted with one or more (e.g. 1, 2, 3, 4 or 5) $Z^{4c}$ groups;

each $Z^{4c}$ is independently selected from of $(C_3-C_7)$carbocycle, aryl, heteroaryl, heterocycle, halogen, —CN, —$OR_{n9}$, —OC(O)$R_{p9}$, —OC(O)$NR_{q9}R_{r9}$, —$SR_{n9}$, —S(O)$R_{p9}$, —$S(O)_2$OH, —$S(O)_2R_{p9}$, —$S(O)_2NR_{q9}R_{r9}$, —$NR_{q9}R_{r9}$, —$NR_{n9}COR_{p9}$, —$NR_{n9}CO_2R_{p9}$, —$NR_{n9}CONR_{q9}R_{r9}$, —$NR_{n9}S(O)_2R_{p9}$, —$NR_{n9}S(O)_2OR_{p9}$, —$NR_{n9}S(O)_2$ $NR_{q9}R_{r9}$, $NO_2$, —C(O)$R_{n9}$, —C(O)$OR_{n9}$, —C(O)$NR_{q9}R_{r9}$, haloaryl, haloheteroaryl, haloheterocycle and $(C_1-C_8)$heteroalkyl;

each $Z^{4d}$ is independently selected from of $(C_1-C_8)$alkyl, $(C_2-C_8)$alkenyl, $(C_2-C_8)$alkynyl and $(C_1-C_8)$haloalkyl;

each $R_{n8}$ is independently selected from H, $(C_1-C_8)$alkyl, $(C_2-C_8)$alkenyl, $(C_2-C_8)$alkynyl, $(C_3-C_7)$carbocycle, heterocycle, heteroaryl and aryl, wherein any $(C_3-C_7)$carbocycle, aryl, heteroaryl and heterocycle of $R_{n8}$ is optionally substituted with one or more (e.g. 1, 2, 3, 4 or 5) $Z^{4c}$ or $Z^{4d}$ groups, and wherein any $(C_1-C_8)$alkyl, $(C_2-C_8)$alkenyl or $(C_2-C_8)$alkynyl of $R_{n8}$ is optionally substituted with one or more (e.g. 1, 2, 3, 4 or 5) $Z^{4c}$ groups;

each $R_{p8}$ is independently selected from $(C_1-C_8)$alkyl, $(C_1-C_6)$haloalkyl, $(C_2-C_8)$alkenyl, $(C_2-C_8)$alkynyl, $(C_3-C_7)$carbocycle, heterocycle, heteroaryl and aryl, wherein any $(C_3-C_7)$carbocycle, aryl, heteroaryl and heterocycle of $R_{p8}$ is optionally substituted with one or more (e.g. 1, 2, 3, 4 or 5) $Z^{4c}$ or $Z^{4d}$ groups, and wherein any $(C_1-C_8)$alkyl, $(C_2-C_8)$alkenyl and $(C_2-C_8)$alkynyl of $R_{p8}$ is optionally substituted with one or more (e.g. 1, 2, 3, 4 or 5) $Z^{4c}$ groups;

$R_{q8}$ and $R_{r8}$ are each independently selected from H, $(C_1-C_8)$alkyl, $(C_2-C_8)$alkenyl, $(C_2-C_8)$alkynyl, $(C_3-C_7)$carbocycle, heterocycle, heteroaryl and aryl, wherein any $(C_3-C_7)$carbocycle, aryl, heteroaryl and heterocycle of $R_{q8}$ or $R_{r8}$ is optionally substituted with one or more (e.g. 1, 2, 3, 4 or 5) $Z^{4c}$ or $Z^{4d}$ groups, and wherein any $(C_1-C_8)$alkyl, $(C_2-C_8)$alkenyl and $(C_2-C_8)$alkynyl of $R_{q8}$ or $R_{r8}$ is optionally substituted with one or more (e.g. 1, 2, 3, 4 or 5) $Z^{4c}$ groups, or $R_{q8}$ and $R_{r8}$ together with the nitrogen to which they are attached form a 5, 6 or 7-membered heterocycle, wherein the 5, 6 or 7-membered heterocycle is optionally substituted with one or more (e.g. 1, 2, 3, 4 or 5) $Z^{4c}$ or $Z^{4d}$ groups;

each $R_{n9}$ is independently selected from H, $(C_1-C_8)$alkyl, $(C_2-C_8)$alkenyl, $(C_2-C_8)$alkynyl, $(C_3-C_7)$carbocycle, heterocycle, heteroaryl, aryl, haloaryl, haloheteroaryl, haloheterocycle, $(C_1-C_8)$haloalkyl and $(C_1-C_8)$heteroalkyl;

each $R_{p9}$ is independently selected from $(C_1-C_8)$alkyl, $(C_2-C_8)$alkenyl, $(C_2-C_8)$alkynyl, $(C_3-C_7)$carbocycle, heterocycle, heteroaryl, aryl, haloaryl, haloheteroaryl, haloheterocycle, $(C_1-C_8)$haloalkyl and $(C_1-C_8)$heteroalkyl; and $R_{q9}$ and $R_{r9}$ are each independently selected from H, $(C_1-C_8)$alkyl, $(C_2-C_8)$alkenyl, $(C_2-C_8)$alkynyl, $(C_3-C_7)$carbocycle, heterocycle, heteroaryl, aryl, haloaryl, haloheteroaryl, haloheterocycle, $(C_1-C_8)$haloalkyl and $(C_1-C_8)$heteroalkyl; or $R_{q9}$ and $R_{r9}$ together with the nitrogen to which they are attached form a 5, 6 or 7-membered heterocycle;

or a salt thereof.

In one embodiment, the invention provides a compound of the invention which is a compound of formula I':

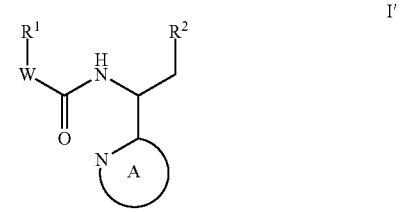

I' wherein:

A is a 6-membered heteroaryl comprising one or two nitrogens, wherein the 6-membered heteroaryl is substituted with one $Z^1$ group and optionally substituted with one or more (e.g. 1, 2, or 3) $Z^2$ groups;

W is $CR^{3a}R^{3b}$, O or $NR^4$;

$R^1$ is aryl, heteroaryl or heterocycle, wherein any aryl, heteroaryl or heterocycle of $R^1$ is optionally substituted with one or more (e.g. 1, 2, 3, 4 or 5) $Z^3$ groups;

$R^2$ is a 6-membered aryl, 5-membered heteroaryl or 6-membered heteroaryl, wherein any 6-membered aryl, 5-membered heteroaryl or 6-membered heteroaryl of $R^2$ is optionally substituted with one or more (e.g. 1, 2 or 3) $Z^4$ groups;

each $R^{3a}$ and $R^{3b}$ is independently selected from H, halogen, $(C_1-C_3)$alkyl, $(C_1-C_3)$haloalkyl, $(C_1-C_6)$heteroalkyl, —$(C_1-C_6)$alkylheteroaryl, —$(C_1-C_6)$alkylheterocyclyl, —$NR_aR_b$, and —$NR_cCOR_d$; or $R^{3a}$ and $R^{3b}$ together with the carbon to which they are attached form a $(C_3-C_6)$carbocycle;

$R^4$ is selected from H, $(C_1-C_6)$alkyl, $(C_3-C_6)$carbocycle, —$(C_1-C_6)$alkylaryl and —$(C_1-C_6)$alkylheteroaryl;

$R_a$ and $R_b$ are each independently selected from H, $(C_1-C_8)$alkyl, $(C_2-C_8)$alkenyl, $(C_2-C_8)$alkynyl, $(C_3-C_7)$carbocycle, heterocycle, heteroaryl, aryl, haloaryl, haloheteroaryl, haloheterocycle, $(C_1-C_8)$haloalkyl and $(C_1-C_8)$heteroalkyl, or $R_a$ and $R_b$ together with the nitrogen to which they are attached form a 5, 6 or 7-membered heterocycle;

each $R_c$ is independently selected from H, $(C_1-C_8)$alkyl, $(C_2-C_8)$alkenyl, $(C_2-C_8)$alkynyl, $(C_3-C_7)$carbocycle, heterocycle, heteroaryl, aryl, haloaryl, haloheteroaryl, haloheterocycle, $(C_1-C_8)$haloalkyl and $(C_1-C_8)$heteroalkyl;

each $R_d$ is independently selected from $(C_1-C_8)$alkyl, $(C_2-C_8)$alkenyl, $(C_2-C_8)$alkynyl, $(C_3-C_7)$carbocycle, heterocycle, heteroaryl, aryl, haloaryl, haloheteroaryl, haloheterocycle, $(C_1-C_8)$haloalkyl and $(C_1-C_8)$heteroalkyl;

each $Z^1$ is independently selected from $(C_1-C_8)$alkyl, $(C_2-C_8)$alkenyl, $(C_2-C_8)$alkynyl, $(C_3-C_7)$carbocycle, aryl, heteroaryl, heterocycle and $-OR_{n1}$, wherein any $(C_3-C_7)$carbocycle, aryl, heteroaryl and heterocycle of $Z^1$ is optionally substituted with one or more (e.g. 1, 2, 3, 4 or 5) $Z^{1a}$ or $Z^{1b}$ groups and wherein any $(C_1-C_8)$alkyl, $(C_2-C_8)$alkenyl and $(C_2-C_8)$alkynyl of $Z^1$ is optionally substituted with one or more (e.g. 1, 2, 3, 4 or 5) $Z^{1a}$ groups;

each $Z^{1a}$ is independently selected from $(C_3-C_7)$carbocycle, aryl, heteroaryl, heterocycle, halogen, $-CN$, $-OR_{n2}$, $-OC(O)R_{p2}$, $-OC(O)NR_{q2}R_{r2}$, $-SR_{n2}$, $-S(O)R_{p2}$, $-S(O)_2OH$, $-S(O)_2R_{p2}$, $-S(O)_2NR_{q2}R_{r2}$, $-NR_{q2}R_{r2}$, $-NR_{n2}COR_{p2}$, $-NR_{n2}CO_2R_{p2}$, $-NR_{n2}CONR_{q2}R_{r2}$, $-NR_{n2}S(O)_2R_{p2}$, $-NR_{n2}S(O)_2OR_{p2}$, $-NR_{n2}S(O)_2NR_{q2}R_{r2}$, $NO_2$, $-C(O)R_{n2}$, $-C(O)OR_{n2}$, and, $-C(O)NR_{p2}R_{q2}$, wherein any $(C_3-C_7)$carbocycle, aryl, heteroaryl and heterocycle of $Z^{1a}$ is optionally substituted with one or more (e.g. 1, 2, 3, 4 or 5) $Z^{1c}$ or $Z^{1d}$ groups;

each $Z^{1b}$ is independently selected from $(C_1-C_8)$alkyl, $(C_2-C_8)$alkenyl and $(C_2-C_8)$alkynyl, wherein any $(C_1-C_8)$alkyl, $(C_2-C_8)$alkenyl and $(C_2-C_8)$alkynyl of $Z^{1b}$ is optionally substituted with one or more (e.g. 1, 2, 3, 4 or 5) $Z^{1c}$ groups;

each $Z^{1c}$ is independently selected from $(C_3-C_7)$carbocycle, aryl, heteroaryl, heterocycle, halogen, $-CN$, $-OR_{n3}$, $-OC(O)R_{p3}$, $-OC(O)NR_{q3}R_{r3}$, $-SR_{n3}$, $-S(O)R_{p3}$, $-S(O)_2OH$, $-S(O)_2R_{p3}$, $-S(O)_2NR_{q3}R_{r3}$, $-NR_{q3}R_{r3}$, $-NR_{n3}COR_{p3}$, $-NR_{n3}CO_2R_{p3}$, $-NR_{n3}CONR_{q3}R_{r3}$, $-NR_{n3}S(O)_2R_{p3}$, $-NR_{n3}S(O)_2OR_{p3}$, $-NR_{n3}S(O)_2NR_{q3}R_{r3}$, $NO_2$, $-C(O)R_{n3}$, $-C(O)OR_{n3}$, $-C(O)NR_{q3}R_{r3}$, haloaryl, haloheteroaryl, haloheterocycle and $(C_1-C_8)$heteroalkyl;

each $Z^{1d}$ is independently selected from $(C_1-C_8)$alkyl, $(C_2-C_8)$alkenyl, $(C_2-C_8)$alkynyl and $(C_1-C_8)$haloalkyl;

each $R_{n1}$ is independently selected from $(C_1-C_8)$alkyl, $(C_2-C_8)$alkenyl, $(C_2-C_8)$alkynyl, $(C_3-C_7)$carbocycle, heterocycle, heteroaryl and aryl, wherein any $(C_3-C_7)$carbocycle, aryl, heteroaryl and heterocycle of $R_{n1}$ is optionally substituted with one or more (e.g. 1, 2, 3, 4 or 5) $Z^{1a}$ or $Z^{1b}$ groups, and wherein any $(C_1-C_8)$alkyl, $(C_2-C_8)$alkenyl and $(C_2-C_8)$alkynyl of $R_{n1}$ is optionally substituted with one or more (e.g. 1, 2, 3, 4 or 5) $Z^{1a}$ groups;

each $R_{n2}$ is independently selected from H, $(C_1-C_8)$alkyl, $(C_2-C_8)$alkenyl, $(C_2-C_8)$alkynyl, $(C_3-C_7)$carbocycle, heterocycle, heteroaryl and aryl, wherein any $(C_3-C_7)$carbocycle, aryl, heteroaryl and heterocycle of $R_{n2}$ is optionally substituted with one or more (e.g. 1, 2, 3, 4 or 5) $Z^{1c}$ or $Z^{1d}$ groups, and wherein any $(C_1-C_8)$alkyl, $(C_2-C_8)$alkenyl and $(C_2-C_8)$alkynyl of $R_{n2}$ is optionally substituted with one or more (e.g. 1, 2, 3, 4 or 5) $Z^{1c}$ groups;

each $R_{p2}$ is independently selected from $(C_1-C_8)$alkyl, $(C_2-C_8)$alkenyl, $(C_2-C_8)$alkynyl, $(C_3-C_7)$carbocycle, heterocycle, heteroaryl and aryl, wherein any $(C_3-C_7)$carbocycle, aryl, heteroaryl and heterocycle of $R_{p2}$ is optionally substituted with one or more (e.g. 1, 2, 3, 4 or 5) $Z^{1c}$ or $Z^{1d}$ groups, and wherein any $(C_1-C_8)$alkyl, $(C_2-C_8)$alkenyl and $(C_2-C_8)$alkynyl of $R_{p2}$ is optionally substituted with one or more (e.g. 1, 2, 3, 4 or 5) $Z^{1c}$ groups;

$R_{q2}$ and $R_{r2}$ are each independently selected from H, $(C_1-C_8)$alkyl, $(C_2-C_8)$alkenyl, $(C_2-C_8)$alkynyl, $(C_3-C_7)$carbocycle, heterocycle, heteroaryl and aryl, wherein any $(C_3-C_7)$carbocycle, aryl, heteroaryl and heterocycle of $R_{q2}$ or $R_{r2}$ is optionally substituted with one or more (e.g. 1, 2, 3, 4 or 5) $Z^{1c}$ or $Z^{1d}$ groups, and wherein any $(C_1-C_8)$alkyl, $(C_2-C_8)$alkenyl and $(C_2-C_8)$alkynyl of $R_{q2}$ or $R_{r2}$ is optionally substituted with one or more (e.g. 1, 2, 3, 4 or 5) $Z^{1c}$ groups, or $R_{q2}$ and $R_{r2}$ together with the nitrogen to which they are attached form a 5, 6 or 7-membered heterocycle, wherein the 5, 6 or 7-membered heterocycle is optionally substituted with one or more (e.g. 1, 2, 3, 4 or 5) $Z^{1c}$ or $Z^{1d}$ groups;

each $R_{n3}$ is independently selected from H, $(C_1-C_8)$alkyl, $(C_2-C_8)$alkenyl, $(C_2-C_8)$alkynyl, $(C_3-C_7)$carbocycle, heterocycle, heteroaryl, aryl, haloaryl, haloheteroaryl, haloheterocycle, $(C_1-C_8)$haloalkyl and $(C_1-C_8)$heteroalkyl;

each $R_{p3}$ is independently selected from $(C_1-C_8)$alkyl, $(C_2-C_8)$alkenyl, $(C_2-C_8)$alkynyl, $(C_3-C_7)$carbocycle, heterocycle, heteroaryl, aryl, haloaryl, haloheteroaryl, haloheterocycle, $(C_1-C_8)$haloalkyl and $(C_1-C_8)$heteroalkyl;

$R_{q3}$ and $R_{r3}$ are each independently selected from H, $(C_1-C_8)$alkyl, $(C_2-C_8)$alkenyl, $(C_2-C_8)$alkynyl, $(C_3-C_7)$carbocycle, heterocycle, heteroaryl, aryl, haloaryl, haloheteroaryl, haloheterocycle, $(C_1-C_8)$haloalkyl and $(C_1-C_8)$heteroalkyl, or $R_{q3}$ and $R_{r3}$ together with the nitrogen to which they are attached form a 5, 6 or 7-membered heterocycle;

each $Z^2$ is independently selected from $(C_1-C_6)$alkyl, $(C_1-C_6)$haloalkyl, $(C_3-C_7)$carbocycle, halogen, CN, OH and $-O(C_1-C_6)$alkyl;

each $Z^3$ is independently selected from $(C_1-C_8)$alkyl, $(C_2-C_8)$alkenyl, $(C_2-C_8)$alkynyl, $(C_3-C_7)$carbocycle, aryl, heteroaryl, heterocycle, halogen, $-CN$, $-OR_{n4}$, $-OC(O)R_{p4}$, $-OC(O)NR_{q4}R_{r4}$, $-SR_{n4}$, $-S(O)R_{p4}$, $-S(O)_2OH$, $-S(O)_2R_{p4}$, $-S(O)_2NR_{q4}R_{r4}$, $-NR_{q4}R_{r4}$, $-NR_{n4}COR_{p4}$, $-NR_{n4}CO_2R_{p4}$, $-NR_{n4}CONR_{q4}R_{r4}$, $-NR_{n4}S(O)_2R_{p4}$, $-NR_{n4}S(O)_2OR_{p4}$, $-NR_{n4}S(O)_2NR_{q4}R_{r4}$, $NO_2$, $-C(O)R_{n4}$, $-C(O)OR_{n4}$, and $-C(O)NR_{q4}R_{r4}$, wherein any $(C_3-C_7)$carbocycle, aryl, heteroaryl and heterocycle of $Z^3$ is optionally substituted with one or more (e.g. 1, 2, 3, 4 or 5) $Z^{3a}$ or $Z^{3b}$ groups, and wherein any $(C_1-C_8)$alkyl, $(C_2-C_8)$alkenyl and $(C_2-C_8)$alkynyl of $Z^3$ is optionally substituted with one or more (e.g. 1, 2, 3, 4 or 5) $Z^{3a}$ groups;

each $Z^{3a}$ is independently selected from $(C_3-C_7)$carbocycle, aryl, heteroaryl, heterocycle, halogen, $-CN$, $-OR_{n5}$, $-OC(O)R_{p5}$, $-OC(O)NR_{q5}R_{r5}$, $-SR_{n5}$, $-S(O)R_{p5}$, $-S(O)_2OH$, $-S(O)_2R_{p5}$, $-S(O)_2NR_{q5}R_{r5}$, $-NR_{q5}R_{r5}$, $-NR_{n5}COR_{p5}$, $-NR_{n5}CO_2R_{p5}$, $-NR_{n5}CONR_{q5}R_{r5}$, $-NR_{n5}S(O)_2R_{p5}$, $-NR_{n5}S(O)_2OR_{p5}$, $-NR_{n5}S(O)_2NR_{q5}R_{r5}$, $NO_2$, $-C(O)R_{n5}$, $-C(O)OR_{n5}$, and $-C(O)NR_{q5}R_{r5}$, wherein any $(C_3-C_7)$carbocycle, aryl, heteroaryl and heterocycle of $Z^{3a}$ is optionally substituted with one or more (e.g. 1, 2, 3, 4 or 5) $Z^{3c}$ or $Z^{3d}$ groups;

each $Z^{3b}$ is independently selected from $(C_1-C_8)$alkyl, $(C_2-C_8)$alkenyl and $(C_2-C_8)$alkynyl, wherein any $(C_1-C_8)$alkyl, $(C_2-C_8)$alkenyl and $(C_2-C_8)$alkynyl of $Z^{3b}$ is optionally substituted with one or more (e.g. 1, 2, 3, 4 or 5) $Z^{3c}$ groups;

each $Z^{3c}$ is independently selected from $(C_3-C_7)$carbocycle, aryl, heteroaryl, heterocycle, halogen, $-CN$, $-OR_{n6}$, $-OC(O)R_{p6}$, $-OC(O)NR_{q6}R_{r6}$, $-SR_{n6}$, $-S(O)R_{p6}$, $-S(O)_2OH$, $-S(O)_2R_{p6}$, $-S(O)_2NR_{q6}R_{r6}$, $-NR_{q6}R_{r6}$, $-NR_{n6}COR_{p6}$, $-NR_{n6}CO_2R_{p6}$, $-NR_{n6}CONR_{q6}R_{r6}$, $-NR_{n6}S(O)_2R_{p6}$, $-NR_{n6}S(O)_2OR_{p6}$, $-NR_{n6}S(O)_2NR_{q6}R_{r6}$, $NO_2$, $-C(O)R_{n6}$, $-C(O)OR_{n6}$, $-C(O)NR_{q6}R_{r6}$, haloaryl, haloheteroaryl, haloheterocycle and $(C_1-C_8)$heteroalkyl;

each $Z^{3d}$ is independently selected from of $(C_1-C_8)$alkyl, $(C_2-C_8)$alkenyl, $(C_2-C_8)$alkynyl, and $(C_1-C_8)$haloalkyl;

each $R_{n4}$ is independently selected from H, $(C_1-C_8)$alkyl, $(C_2-C_8)$alkenyl, $(C_2-C_8)$alkynyl, $(C_3-C_7)$carbocycle, heterocycle, heteroaryl and aryl, wherein any $(C_3-C_7)$carbocycle, aryl, heteroaryl and heterocycle of $R_{n4}$ is optionally substituted with one or more (e.g. 1, 2, 3, 4 or 5) $Z^{3a}$ or $Z^{3b}$ groups, and wherein any $(C_1-C_8)$alkyl, $(C_2-C_8)$alkenyl and $(C_2-C_8)$alkynyl of $R_{n4}$ is optionally substituted with one or more (e.g. 1, 2, 3, 4 or 5) $Z^{3a}$ groups;

each $R_{p4}$ is independently selected from $(C_1-C_8)$alkyl, $(C_2-C_8)$alkenyl, $(C_2-C_8)$alkynyl, $(C_3-C_7)$carbocycle, heterocycle, heteroaryl and aryl, wherein any $(C_3-C_7)$carbocycle, aryl, heteroaryl, or heterocycle of $R_{p4}$ is optionally substituted with one or more (e.g. 1, 2, 3, 4 or 5) $Z^{3a}$ or $Z^{3b}$ groups, and wherein any $(C_1-C_8)$alkyl, $(C_2-C_8)$alkenyl or $(C_2-C_8)$alkynyl of $R_{p4}$ is optionally substituted with one or more (e.g. 1, 2, 3, 4 or 5) $Z^{3a}$ groups;

$R_{q4}$ and $R_{r4}$ are each independently selected from H, $(C_1-C_8)$alkyl, $(C_2-C_8)$alkenyl, $(C_2-C_8)$alkynyl, $(C_3-C_7)$carbocycle, heterocycle, heteroaryl and aryl, wherein any $(C_3-C_7)$carbocycle, aryl, heteroaryl and heterocycle of $R_{q4}$ or $R_{r4}$ is optionally substituted with one or more (e.g. 1, 2, 3, 4 or 5) $Z^{3a}$ or $Z^{3b}$ groups, and wherein any $(C_1-C_8)$alkyl, $(C_2-C_8)$alkenyl and $(C_2-C_8)$alkynyl of $R_{q4}$ or $R_{r4}$ is optionally substituted with one or more (e.g. 1, 2, 3, 4 or 5) $Z^{3a}$ groups, or $R_{q4}$ and $R_{r4}$ together with the nitrogen to which they are attached form a 5, 6 or 7-membered heterocycle, wherein the 5, 6 or 7-membered heterocycle is optionally substituted with one or more (e.g. 1, 2, 3, 4 or 5) $Z^{3a}$ or $Z^{3b}$ groups;

each $R_{n5}$ is independently selected from H, $(C_1-C_8)$alkyl, $(C_2-C_8)$alkenyl, $(C_2-C_8)$alkynyl, $(C_3-C_7)$carbocycle, heterocycle, heteroaryl and aryl, wherein any $(C_3-C_7)$carbocycle, aryl, heteroaryl and heterocycle of $R_{n5}$ is optionally substituted with one or more (e.g. 1, 2, 3, 4 or 5) $Z^{3c}$ or $Z^{3d}$ groups, and wherein any $(C_1-C_8)$alkyl, $(C_2-C_8)$alkenyl and $(C_2-C_8)$alkynyl of $R_{n5}$ is optionally substituted with one or more (e.g. 1, 2, 3, 4 or 5) $Z^{3c}$ groups;

each $R_{p5}$ is independently selected from $(C_1-C_8)$alkyl, $(C_2-C_8)$alkenyl, $(C_2-C_8)$alkynyl, $(C_3-C_7)$carbocycle, heterocycle, heteroaryl and aryl, wherein any $(C_3-C_7)$carbocycle, aryl, heteroaryl and heterocycle of $R_{p5}$ is optionally substituted with one or more (e.g. 1, 2, 3, 4 or 5) $Z^{3c}$ or $Z^{3d}$ groups, and wherein any $(C_1-C_8)$alkyl, $(C_2-C_8)$alkenyl and $(C_2-C_8)$alkynyl of $R_{p5}$ is optionally substituted with one or more (e.g. 1, 2, 3, 4 or 5) $Z^{3c}$ groups;

$R_{q5}$ and $R_{r5}$ are each independently selected from H, $(C_1-C_8)$alkyl, $(C_2-C_8)$alkenyl, $(C_2-C_8)$alkynyl, $(C_3-C_7)$carbocycle, heterocycle, heteroaryl and aryl, wherein any $(C_3-C_7)$carbocycle, aryl, heteroaryl and heterocycle of $R_{q5}$ or $R_{r5}$ is optionally substituted with one or more (e.g. 1, 2, 3, 4 or 5) $Z^{3c}$ or $Z^{3d}$ groups, and wherein any $(C_1-C_8)$alkyl, $(C_2-C_8)$alkenyl and $(C_2-C_8)$alkynyl of $R_{q5}$ or $R_{r5}$ is optionally substituted with one or more (e.g. 1, 2, 3, 4 or 5) $Z^{3c}$ groups, or $R_{q5}$ and $R_{r5}$ together with the nitrogen to which they are attached form a 5, 6 or 7-membered heterocycle, wherein the 5, 6 or 7-membered heterocycle is optionally substituted with one or more (e.g. 1, 2, 3, 4 or 5) $Z^{3c}$ or $Z^{3d}$ groups;

each $R_{n6}$ is independently selected from H, $(C_1-C_8)$alkyl, $(C_2-C_8)$alkenyl, $(C_2-C_8)$alkynyl, $(C_3-C_7)$carbocycle, heterocycle, heteroaryl, aryl, haloaryl, haloheteroaryl, haloheterocycle, $(C_1-C_8)$haloalkyl and $(C_1-C_8)$heteroalkyl;

each $R_{p6}$ is independently selected from $(C_1-C_8)$alkyl, $(C_2-C_8)$alkenyl, $(C_2-C_8)$alkynyl, $(C_3-C_7)$carbocycle, heterocycle, heteroaryl, aryl, haloaryl, haloheteroaryl, haloheterocycle, $(C_1-C_8)$haloalkyl and $(C_1-C_8)$heteroalkyl;

$R_{q6}$ and $R_{r6}$ are each independently selected from H, $(C_1-C_8)$alkyl, $(C_2-C_8)$alkenyl, $(C_2-C_8)$alkynyl, $(C_3-C_7)$carbocycle, heterocycle, heteroaryl, aryl, haloaryl, haloheteroaryl, haloheterocycle, $(C_1-C_8)$haloalkyl and $(C_1-C_8)$heteroalkyl, or $R_{q6}$ and $R_{r6}$ together with the nitrogen to which they are attached form a 5, 6 or 7-membered heterocycle;

each $Z^4$ is independently selected from $(C_1-C_8)$alkyl, $(C_2-C_8)$alkenyl, $(C_2-C_8)$alkynyl, $(C_3-C_7)$carbocycle, aryl, heteroaryl, heterocycle, halogen, —CN, —OR$_{n8}$, —OC(O)R$_{p8}$, —OC(O)NR$_{q8}$R$_{r8}$, —SR$_{n8}$, —S(O)R$_{p8}$, —S(O)$_2$OH, —S(O)$_2$R$_{p8}$, —S(O)$_2$NR$_{q8}$R$_{r8}$, —NR$_{n8}$R$_{r8}$, —NR$_{n8}$COR$_{p8}$, —NR$_{n8}$CO$_2$R$_{p8}$, —NR$_{n8}$CONR$_{q8}$R$_{r8}$, —NR$_{n8}$S(O)$_2$R$_{p8}$, —NR$_{n8}$S(O)$_2$OR$_{p8}$, —NR$_{n8}$S(O)$_2$ NR$_{q8}$R$_{r8}$, NO$_2$, —C(O)R$_{n8}$, —C(O)OR$_{n5}$, and —C(O)NR$_{q8}$R$_{r8}$, wherein any $(C_3-C_7)$carbocycle, aryl, heteroaryl and heterocycle of $Z^4$ is optionally substituted with one or more (e.g. 1, 2, 3, 4 or 5) $Z^{4c}$ or $Z^{4d}$ groups and wherein any $(C_1-C_8)$alkyl, $(C_2-C_8)$alkenyl and $(C_2-C_8)$alkynyl of $Z^4$ is optionally substituted with one or more (e.g. 1, 2, 3, 4 or 5) $Z^{4c}$ groups;

each $Z^{4c}$ is independently selected from of $(C_3-C_7)$carbocycle, aryl, heteroaryl, heterocycle, halogen, —CN, —OR$_{n9}$, —OC(O)R$_{p9}$, —OC(O)NR$_{q9}$R$_{r9}$, —SR$_{n9}$, —S(O)R$_{p9}$, —S(O)$_2$OH, —S(O)$_2$R$_{p9}$, —S(O)$_2$NR$_{q9}$R$_{r9}$, —NR$_{q9}$R$_{r9}$, —NR$_{n9}$COR$_{p9}$, —NR$_{n9}$CO$_2$R$_{p9}$, —NR$_{n9}$CONR$_{q9}$R$_{r9}$, —NR$_{n9}$S(O)$_2$R$_{p9}$, —NR$_{n9}$S(O)$_2$OR$_{p9}$, —NR$_{n9}$S(O)$_2$NR$_{q9}$R$_{r9}$, NO$_2$, —C(O)R$_{n9}$, —C(O)OR$_{n9}$, —C(O)NR$_{q9}$R$_{r9}$, haloaryl, haloheteroaryl, haloheterocycle and $(C_1-C_8)$heteroalkyl;

each $Z^{4d}$ is independently selected from of $(C_1-C_8)$alkyl, $(C_2-C_8)$alkenyl, $(C_2-C_8)$alkynyl and $(C_1-C_8)$haloalkyl;

each $R_{n8}$ is independently selected from H, $(C_1-C_8)$alkyl, $(C_2-C_8)$alkenyl, $(C_2-C_8)$alkynyl, $(C_3-C_7)$carbocycle, heterocycle, heteroaryl and aryl, wherein any $(C_3-C_7)$carbocycle, aryl, heteroaryl and heterocycle of $R_{n8}$ is optionally substituted with one or more (e.g. 1, 2, 3, 4 or 5) $Z^{4c}$ or $Z^{4d}$ groups, and wherein any $(C_1-C_8)$alkyl, $(C_2-C_8)$alkenyl or $(C_2-C_8)$alkynyl of $R_{n8}$ is optionally substituted with one or more (e.g. 1, 2, 3, 4 or 5) $Z^{4c}$ groups;

each $R_{p8}$ is independently selected from $(C_1-C_8)$alkyl, $(C_1-C_6)$haloalkyl, $(C_2-C_8)$alkenyl, $(C_2-C_8)$alkynyl, $(C_3-C_7)$carbocycle, heterocycle, heteroaryl and aryl, wherein any $(C_3-C_7)$carbocycle, aryl, heteroaryl and heterocycle of $R_{p8}$ is optionally substituted with one or more (e.g. 1, 2, 3, 4 or 5) $Z^{4c}$ or $Z^{4d}$ groups, and wherein any $(C_1-C_8)$alkyl, $(C_2-C_8)$alkenyl and $(C_2-C_8)$alkynyl of $R_{p8}$ is optionally substituted with one or more (e.g. 1, 2, 3, 4 or 5) $Z^{4c}$ groups;

$R_{q8}$ and $R_{r8}$ are each independently selected from H, $(C_1-C_8)$alkyl, $(C_2-C_8)$alkenyl, $(C_2-C_8)$alkynyl, $(C_3-C_7)$carbocycle, heterocycle, heteroaryl and aryl, wherein any $(C_3-C_7)$carbocycle, aryl, heteroaryl and heterocycle of $R_{q8}$ or $R_{r8}$ is optionally substituted with one or more (e.g. 1, 2, 3, 4 or 5) $Z^{4c}$ or $Z^{4d}$ groups, and wherein any $(C_1-C_8)$alkyl, $(C_2-C_8)$alkenyl and $(C_2-C_8)$alkynyl of $R_{q8}$ or $R_{r8}$ is optionally substituted with one or more (e.g. 1, 2, 3, 4 or 5) $Z^{4c}$ groups, or $R_{q8}$ and $R_{r8}$ together with the nitrogen to which they are attached form a 5, 6 or 7-membered heterocycle, wherein the 5, 6 or 7-membered heterocycle is optionally substituted with one or more (e.g. 1, 2, 3, 4 or 5) $Z^{4c}$ or $Z^{4d}$ groups;

each $R_{n9}$ is independently selected from H, $(C_1-C_8)$alkyl, $(C_2-C_8)$alkenyl, $(C_2-C_8)$alkynyl, $(C_3-C_7)$carbocycle, heterocycle, heteroaryl, aryl, haloaryl, haloheteroaryl, haloheterocycle, $(C_1-C_8)$haloalkyl and $(C_1-C_8)$heteroalkyl;

each $R_{p9}$ is independently selected from $(C_1-C_8)$alkyl, $(C_2-C_8)$alkenyl, $(C_2-C_8)$alkynyl, $(C_3-C_7)$carbocycle, heterocycle, heteroaryl, aryl, haloaryl, haloheteroaryl, haloheterocycle, $(C_1-C_8)$haloalkyl and $(C_1-C_8)$heteroalkyl; and $R_{q9}$ and $R_{r9}$ are each independently selected from H, $(C_1-C_8)$alkyl, $(C_2-C_8)$alkenyl, $(C_2-C_8)$alkynyl, $(C_3-C_7)$carbocycle, heterocycle, heteroaryl, aryl, haloaryl, haloheteroaryl, haloheterocycle, $(C_1-C_8)$haloalkyl and $(C_1-C_8)$heteroalkyl; or $R_{q9}$ and $R_{r9}$ together with the nitrogen to which they are attached form a 5, 6 or 7-membered heterocycle;

or a salt thereof.

General Synthetic Procedures

Schemes 1, 2 and 3 describe methods that can be used to prepare compounds of formula I.

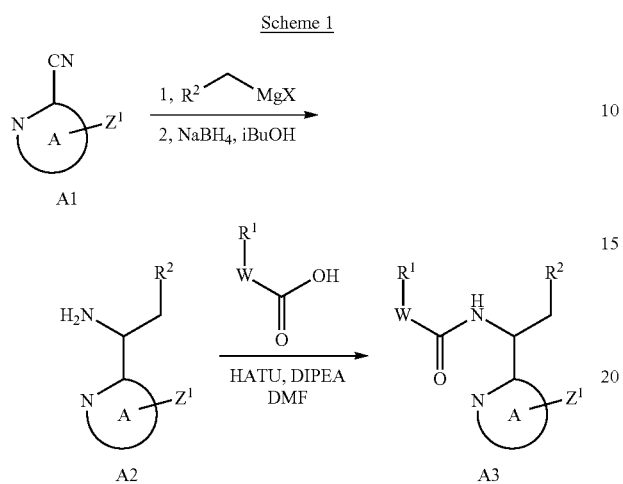

Scheme 1 describes a general synthetic route which can be used to prepare compounds of formula I. An appropriately substituted heteroaryl nitrile may be reacted with a Grignard reagent followed by reduction to provide compounds of formula A2. The amine can be coupled to a variety of carboxcyclic acid derivatives to provide compounds of formula A3.

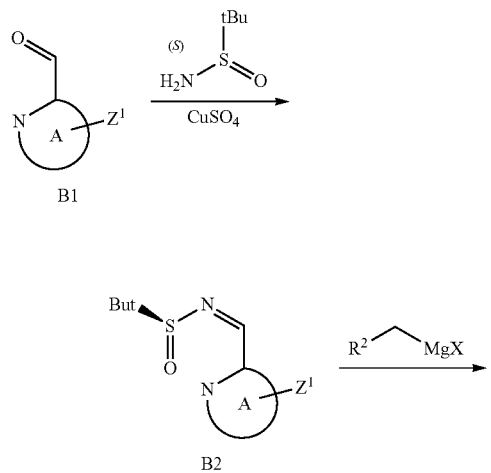

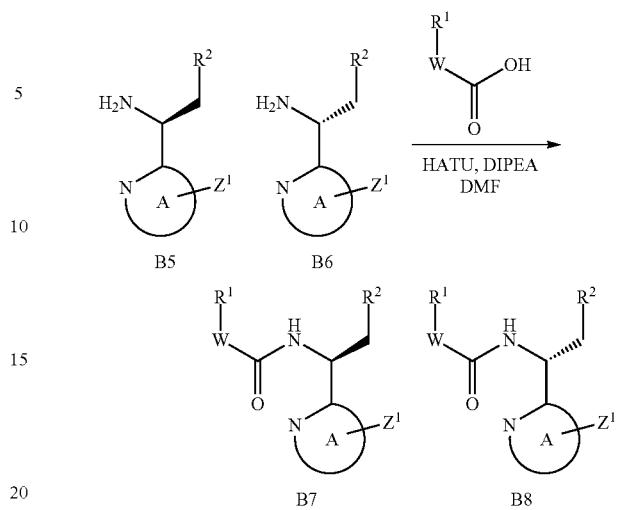

Scheme 2 describes a general stereoselective route which can be used to prepare compounds of formula I. Heteroaryl aldehydes of formula B1 can be condensed with a chiral auxiliary to provide a stereoselective addition of a nucleophilic reagent. Depicted in Scheme 2 is the condensation of an appropriately substituted heterocyclic aldehyde B1 with tert-butane sulfonamide and the addition of a Grignard reagent to provide a mixture of B3 and B4 enriched in B3. This mixture may be separated by column chromatography on silica gel to provide pure diastereomers. Removal of the auxiliary provides amines B5 and B6 which can be coupled to a variety of carboxylic acids to provide compounds of formula B7 and B8.

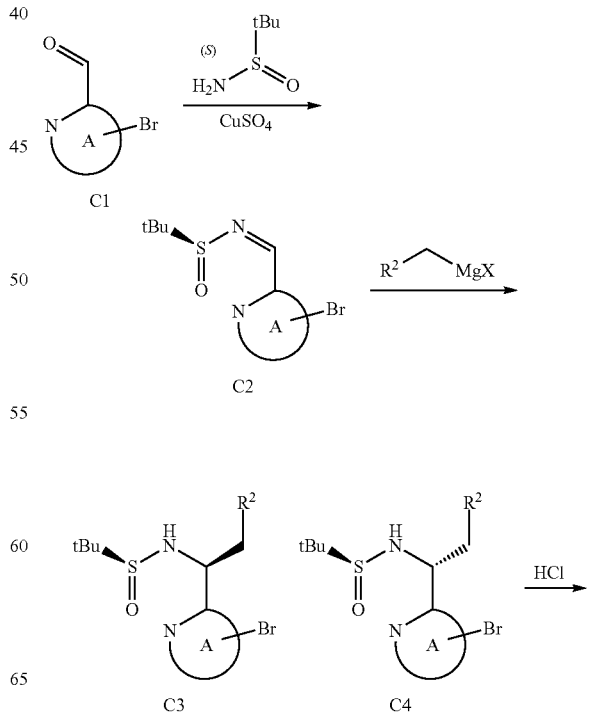

-continued

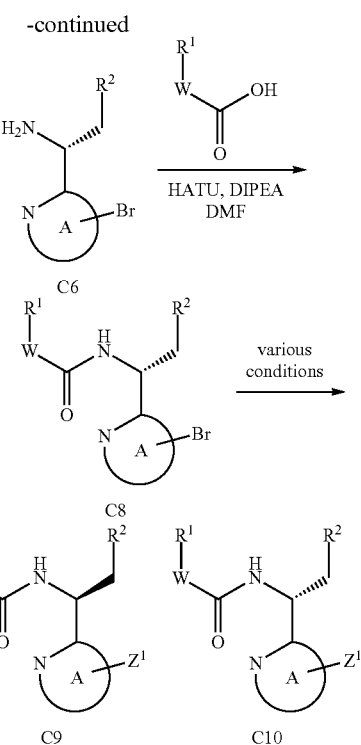

Scheme 3 describes a general stereoselective route which can be used to prepare compounds of formula I. Heteroaryl aldehydes of formula B1 can be condensed with a chiral auxiliary to provide a stereoselective addition of a nucleophilic reagent. Depicted in Scheme 3 is the condensation of an bromo-substituted heterocyclic aldehyde C1 with (S) tert-butane sulfonamide and the addition of a Grignard reagent to provide a mixture of C3 and C4 enriched in C3. This mixture may be separated by column chromatography on silica gel to provide pure diastereomers. Removal of the auxiliary provides amines C5 and C6 which can be coupled to a variety of carboxylic acids to provide heteroaryl compounds of formula C7 and C8. Diversification of C7 and C8 may be accomplished by a variety of methods including metal catalyzed cross coupling reactions such as Suzuki couplings and Sonogashira couplings.

Prodrugs

In one embodiment, the invention provides for a prodrug of a compound of the invention. The term "prodrug" as used herein refers to any compound that when administered to a biological system generates a compound of the invention that inhibits the replication of HIV ("the active inhibitory compound"). The compound may be formed from the prodrug as a result of: (i) spontaneous chemical reaction(s), (ii) enzyme catalyzed chemical reaction(s), (iii) photolysis, and/ or (iv) metabolic chemical reaction(s).

"Prodrug moiety" refers to a labile functional group which separates from the active inhibitory compound during metabolism, systemically, inside a cell, by hydrolysis, enzymatic cleavage, or by some other process (Bundgaard, Hans, "Design and Application of Prodrugs" in *A Textbook of Drug Design and Development* (1991), P. Krogsgaard-Larsen and H. Bundgaard, Eds. Harwood Academic Publishers, pp. 113-191). Enzymes which are capable of an enzymatic activation mechanism with the prodrug compounds of the invention include, but are not limited to, amidases, esterases, microbial enzymes, phospholipases, cholinesterases, and phosphases. Prodrug moieties can serve to enhance solubility, absorption and lipophilicity to optimize drug delivery, bioavailability and efficacy. A prodrug moiety may include an active metabolite or drug itself.

Exemplary prodrug moieties include the hydrolytically sensitive or labile acyloxymethyl esters —$CH_2OC(=O)R^{99}$ and acyloxymethyl carbonates —$CH_2OC(=O)OR^{99}$ where $R^{99}$ is $C_1$-$C_6$ alkyl, $C_1$-$C_6$ substituted alkyl, $C_6$-$C_{20}$ aryl or $C_6$-$C_{20}$ substituted aryl. The acyloxyalkyl ester was first used as a prodrug strategy for carboxylic acids and then applied to phosphates and phosphonates by Farquhar et al. (1983) *J. Pharm. Sci.* 72: 324; also U.S. Pat. Nos. 4,816,570, 4,968,788, 5,663,159 and 5,792,756. Subsequently, the acyloxyalkyl ester was used to deliver phosphonic acids across cell membranes and to enhance oral bioavailability. A close variant of the acyloxyalkyl ester, the alkoxycarbonyloxyalkyl ester (carbonate), may also enhance oral bioavailability as a prodrug moiety in the compounds of the combinations of the invention. An exemplary acyloxymethyl ester is pivaloyloxymethoxy, (POM) —$CH_2OC(=O)C(CH_3)_3$. An exemplary acyloxymethyl carbonate prodrug moiety is pivaloyloxymethylcarbonate (POC) —$CH_2OC(=O)OC(CH_3)_3$.

Aryl esters of phosphorus groups, especially phenyl esters, are reported to enhance oral bioavailability (De Lombaert et al. (1994) *J. Med. Chem.* 37: 498). Phenyl esters containing a carboxylic ester ortho to a phosphate have also been described (Khamnei and Torrence, (1996) *J. Med. Chem.* 39:4109-4115). Benzyl esters are reported to generate parent phosphonic acids. In some cases, substituents at the ortho- or para-position may accelerate the hydrolysis. Benzyl analogs with an acylated phenol or an alkylated phenol may generate the phenolic compound through the action of enzymes, e.g., esterases, oxidases, etc., which in turn undergoes cleavage at the benzylic C—O bond to generate phosphoric acid and a quinone methide intermediate. Examples of this class of prodrugs are described by Mitchell et al. (1992) *J. Chem. Soc. Perkin Trans. II* 2345; Glazier WO 91/19721. Still other benzylic prodrugs have been described containing a carboxylic ester-containing group attached to the benzylic methylene (Glazier WO 91/19721). Thio-containing prodrugs are reported to be useful for the intracellular delivery of phosphonate drugs. These proesters contain an ethylthio group in which the thiol group is either esterified with an acyl group or combined with another thiol group to form a disulfide. Deesterification or reduction of the disulfide generates the free thio intermediate which subsequently breaks down to the phosphoric acid and episulfide (Puech et al. (1993) *Antiviral Res.*, 22: 155-174; Benzaria et al. (1996) *J. Med. Chem.* 39: 4958).

Combination Therapy

In one embodiment, the invention provides for a method for treating an HIV infection, comprising administering to a patient in need thereof a therapeutically effective amount of a compound of the invention, or a pharmaceutically acceptable salt, thereof, in combination with a therapeutically effective amount of one or more additional therapeutic agents which are suitable for treating an HIV infection.

In one embodiment, the invention provides pharmaceutical compositions comprising a compound of the present invention, or a pharmaceutically acceptable salt thereof, in combination with at least one additional therapeutic agent, and a pharmaceutically acceptable carrier. For example, the therapeutic agent used in combination with the compound of the present invention can be any anti-HIV agent.

In one embodiment, the invention provides pharmaceutical compositions comprising a compound of the present invention, or a pharmaceutically acceptable salt thereof, in combination with at least one additional therapeutic agent selected from the group consisting of HIV protease inhibiting compounds, HIV non-nucleoside inhibitors of reverse transcriptase, HIV nucleoside inhibitors of reverse transcriptase, HIV nucleotide inhibitors of reverse transcriptase, HIV integrase inhibitors, gp41 inhibitors, CXCR4 inhibitors, gp120 inhibitors, CCR5 inhibitors, capsid polymerization inhibitors, and other drug for treating HIV, and combinations thereof, and a pharmaceutically acceptable carrier.

In another embodiment, the invention provides pharmaceutical compositions comprising a compound of the present invention, or a pharmaceutically acceptable salt thereof, in combination with at least one additional therapeutic agent selected from the group consisting of:

(1) HIV protease inhibiting compounds selected from the group consisting of amprenavir, atazanavir, fosamprenavir, indinavir, lopinavir, ritonavir, nelfinavir, saquinavir, tipranavir, brecanavir, darunavir, TMC-126, TMC-114, mozenavir (DMP-450), JE-2147 (AG1776), L-756423, RO0334649, KNI-272, DPC-681, DPC-684, GW640385X, DG17, PPL-100, DG35, and AG 1859;

(2) HIV non-nucleoside inhibitors of reverse transcriptase selected from the group consisting of capravirine, emivirine, delaviridine, efavirenz, nevirapine, (+) calanolide A, etravirine, GW5634, DPC-083, DPC-961, DPC-963, MIV-150, and TMC-120, rilpivirene, BILR 355 BS, VRX 840773, UK-453061, and RDEA806;

(3) HIV nucleoside inhibitors of reverse transcriptase selected from the group consisting of zidovudine, emtricitabine, didanosine, stavudine, zalcitabine, lamivudine, abacavir, amdoxovir, elvucitabine, alovudine, MIV-210, ±-FTC, D-d4FC, emtricitabine, phosphazide, fozivudine tidoxil, apricitibine (AVX754), amdoxovir, KP-1461, and fosalvudine tidoxil (formerly HDP 99.0003);

(4) HIV nucleotide inhibitors of reverse transcriptase selected from the group consisting of tenofovir, tenofovir disoproxil fumarate, GS-7340 (Gilead Sciences), adefovir, adefovir dipivoxil, CMX-001 (Chimerix) or CMX-157 (Chimerix)

(5) HIV integrase inhibitors selected from the group consisting of curcumin, derivatives of curcumin, chicoric acid, derivatives of chicoric acid, 3,5-dicaffeoylquinic acid, derivatives of 3,5-dicaffeoylquinic acid, aurintricarboxylic acid, derivatives of aurintricarboxylic acid, caffeic acid phenethyl ester, derivatives of caffeic acid phenethyl ester, tyrphostin, derivatives of tyrphostin, quercetin, derivatives of quercetin, S-1360, AR-177, L-870812, and L-870810, raltegravir, BMS-538158, GSK364735C, BMS-707035, MK-2048, BA 011 and dolutegravir;

(6) gp41 inhibitors selected from the group consisting of enfuvirtide, sifuvirtide, FB006M, and TRI-1144;

(7) the CXCR4 inhibitor AMD-070;

(8) the entry inhibitor SP01A;

(9) the gp120 inhibitor BMS-488043;

(10) the G6PD and NADH-oxidase inhibitor immunitin;

(11) CCR5 inhibitors selected from the group consisting of aplaviroc, vicriviroc, maraviroc, PRO-140, INCB15050, PF-232798 (Pfizer), and CCR5mAb004;

(12) other drugs for treating HIV selected from the group consisting of BAS-100, SPI-452, REP 9, SP-01A, TNX-355, DES6, ODN-93, ODN-112, VGV-1, PA-457 (bevirimat), HRG214, VGX-410, KD-247, AMZ 0026, CYT 99007A-221 HIV, DEBIO-025, BAY 50-4798, MDXO10 (ipilimumab), PBS 119, ALG 889, and PA-1050040 (PA-040).

In another embodiment, the invention provides pharmaceutical compositions comprising a compound of the present invention, or a pharmaceutically acceptable salt thereof, in combination with two, three, four or more additional therapeutic agents. For example, a compound of the present invention, or a pharmaceutically acceptable salt, thereof, is combined with two, three, four or more additional therapeutic agents selected from the classes of HIV protease inhibiting compounds, HIV non-nucleoside inhibitors of reverse transcriptase, HIV nucleoside inhibitors of reverse transcriptase, HIV nucleotide inhibitors of reverse transcriptase, HIV integrase inhibitors, gp41 inhibitors, CXCR4 inhibitors, gp120 inhibitors, CCR5 inhibitors, capsid polymerization inhibitors and other drug for treating HIV. The two, three four or more additional therapeutic agents can be different therapeutic agents selected from the same class of therapeutic agents, or they can be selected from different classes of therapeutic agents.

In one embodiment, the invention provides for a combination pharmaceutical agent comprising:

a) a compound of the invention (e.g. a compound of Formula I), or a pharmaceutically acceptable salt, thereof; and b) at least one additional active agent which is suitable for treating an HIV infection.

In another embodiment, the invention provides a combination pharmaceutical agent comprising:

a) a compound of the invention (e.g. a compound of Formula I), or a pharmaceutically acceptable salt thereof; and b) at least one additional therapeutic agent selected from the group consisting of HIV protease inhibiting compounds, HIV non-nucleoside inhibitors of reverse transcriptase, HIV nucleoside inhibitors of reverse transcriptase, HIV nucleotide inhibitors of reverse transcriptase, HIV integrase inhibitors, gp41 inhibitors, CXCR4 inhibitors, gp120 inhibitors, CCR5 inhibitors, capsid polymerization inhibitors and other drug for treating HIV.

It is also possible to combine any compound of the invention with one or more other active therapeutic agents in a unitary dosage form for simultaneous or sequential administration to a patient. The combination therapy may be administered as a simultaneous or sequential regimen. When administered sequentially, the combination may be administered in two or more administrations.

It is also possible to co-administer a compound of the invention with one or more other active therapeutic agents. Co-administration of a compound of the invention with one or more other active therapeutic agents generally refers to simultaneous or sequential administration of a compound of the invention and one or more other active therapeutic agents, such that therapeutically effective amounts of the compound of the invention and one or more other active therapeutic agents are both present in the body of the patient.

Co-administration includes administration of unit dosages of the compounds of the invention before or after administration of unit dosages of one or more other active therapeutic agents, for example, administration of the compounds of the invention within seconds, minutes, or hours of the administration of one or more other active therapeutic agents. For example, a unit dose of a compound of the invention can be administered first, followed within seconds or minutes by administration of a unit dose of one or more other active therapeutic agents. Alternatively, a unit dose of one or more other therapeutic agents can be administered first, followed by administration of a unit dose of a compound of the invention within seconds or minutes. In some cases, it may be desirable to administer a unit dose of a compound of the invention first, followed, after a period of hours (e.g., 1-12 hours), by administration of a unit dose of one or more other active therapeutic agents. In other cases, it may be desirable to administer a unit dose of one or more other active therapeutic agents first, followed, after a period of hours (e.g., 1-12 hours), by administration of a unit dose of a compound of the invention.

The combination therapy may provide "synergy" and "synergistic effect", i.e. the effect achieved when the active ingredients used together is greater than the sum of the effects that results from using the compounds separately. A synergistic effect may be attained when the active ingredients are: (1) co-formulated and administered or delivered simultaneously in a combined formulation; (2) delivered by alternation or in parallel as separate formulations; or (3) by some other regimen. When delivered in alternation therapy, a synergistic effect may be attained when the compounds are administered or delivered sequentially, e.g., in separate tablets, pills or capsules, or by different injections in separate syringes. In general, during alternation therapy, an effective dosage of each active ingredient is administered sequentially, i.e. serially, whereas in combination therapy, effective dosages of two or more active ingredients are administered together.

In yet another embodiment, the present application provides a method for treating an HIV infection comprising administering to a patient in need thereof a therapeutically effective amount of a compound of the present invention, or a pharmaceutically acceptable salt thereof, in combination with a therapeutically effective amount of one or more additional therapeutic agents selected from the group consisting of HIV protease inhibiting compounds, HIV non-nucleoside inhibitors of reverse transcriptase, HIV nucleoside inhibitors of reverse transcriptase, HIV nucleotide inhibitors of reverse transcriptase, HIV integrase inhibitors, gp41 inhibitors, CXCR4 inhibitors, gp120 inhibitors, CCR5 inhibitors, capsid polymerization inhibitors, and other drug for treating HIV.

In yet another embodiment, the present application provides a method for treating an HIV infection comprising administering to a patient in need thereof a therapeutically effective amount of a compound of the present invention, or a pharmaceutically acceptable salt, thereof, in combination with a therapeutically effective amount of one or more additional therapeutic agents selected from the group consisting of:

(1) HIV protease inhibiting compounds selected from the group consisting of amprenavir, atazanavir, fosamprenavir, indinavir, lopinavir, ritonavir, nelfinavir, saquinavir, tipranavir, brecanavir, darunavir, TMC-126, TMC-114, mozenavir (DMP-450), JE-2147 (AG1776), L-756423, RO0334649, KNI-272, DPC-681, DPC-684, GW640385X, DG17, PPL-100, DG35, and AG 1859;

(2) HIV non-nucleoside inhibitors of reverse transcriptase selected from the group consisting of capravirine, emivirine, delaviridine, efavirenz, nevirapine, (+) calanolide A, etravirine, GW5634, DPC-083, DPC-961, DPC-963, MIV-150, and TMC-120, rilpivirene, BILR 355 BS, VRX 840773, UK-453061, and RDEA806;

(3) HIV nucleoside inhibitors of reverse transcriptase selected from the group consisting of zidovudine, emtricitabine, didanosine, stavudine, zalcitabine, lamivudine, abacavir, amdoxovir, elvucitabine, alovudine, MIV-210, ±-FTC, D-d4FC, emtricitabine, phosphazide, fozivudine tidoxil, apricitibine (AVX754), amdoxovir, KP-1461, and fosalvudine tidoxil (formerly HDP 99.0003);

(4) HIV nucleotide inhibitors of reverse transcriptase selected from the group consisting of tenofovir, tenofovir disoproxil fumarate, GS-7340 (Gilead Sciences), adefovir, adefovir dipivoxil, CMX-001 (Chimerix) or CMX-157 (Chimerix)

(5) HIV integrase inhibitors selected from the group consisting of curcumin, derivatives of curcumin, chicoric acid, derivatives of chicoric acid, 3,5-dicaffeoylquinic acid, derivatives of 3,5-dicaffeoylquinic acid, aurintricarboxylic acid, derivatives of aurintricarboxylic acid, caffeic acid phenethyl ester, derivatives of caffeic acid phenethyl ester, tyrphostin, derivatives of tyrphostin, quercetin, derivatives of quercetin, S-1360, AR-177, L-870812, and L-870810, raltegravir, BMS-538158, GSK364735C, BMS-707035, MK-2048, BA 011 and dolutegravir;

(6) gp41 inhibitors selected from the group consisting of enfuvirtide, sifuvirtide, FB006M, and TRI-1144;

(7) the CXCR4 inhibitor AMD-070;

(8) the entry inhibitor SP01A;

(9) the gp120 inhibitor BMS-488043;

(10) the G6PD and NADH-oxidase inhibitor immunitin;

(11) CCR5 inhibitors selected from the group consisting of aplaviroc, vicriviroc, maraviroc, PRO-140, INCB15050, PF-232798 (Pfizer), and CCR5mAb004;

(12) other drugs for treating HIV selected from the group consisting of BAS-100, SPI-452, REP 9, SP-01A, TNX-355, DES6, ODN-93, ODN-112, VGV-1, PA-457 (bevirimat), HRG214, VGX-410, KD-247, AMZ 0026, CYT 99007A-221 HIV, DEBIO-025, BAY 50-4798, MDX010 (ipilimumab), PBS 119, ALG 889, and PA-1050040 (PA-040).

Pharmaceutical Formulations

The compounds of this invention are formulated with conventional carriers and excipients, which will be selected in accord with ordinary practice. Tablets will contain excipients, glidants, fillers, binders and the like. Aqueous formulations are prepared in sterile form, and when intended for delivery by other than oral administration generally will be isotonic. All formulations will optionally contain excipients such as those set forth in the *Handbook of Pharmaceutical Excipients* (1986). Excipients include ascorbic acid and other antioxidants, chelating agents such as EDTA, carbohydrates such as dextrin, hydroxyalkylcellulose, hydroxyalkylmethylcellulose, stearic acid and the like. The pH of the formulations ranges from about 3 to about 11, but is ordinarily about 7 to 10.

While it is possible for the active ingredients to be administered alone it may be preferable to present them as pharmaceutical formulations. The formulations, both for veterinary and for human use, of the invention comprise at least one active ingredient, as above defined, together with one or more acceptable carriers and optionally other therapeutic ingredients. The carrier(s) must be "acceptable" in the sense of being compatible with the other ingredients of the formulation and physiologically innocuous to the recipient thereof.

The formulations include those suitable for the foregoing administration routes. The formulations may conveniently be presented in unit dosage form and may be prepared by any of the methods well known in the art of pharmacy. Techniques and formulations generally are found in *Remington's Pharmaceutical Sciences* (Mack Publishing Co., Easton, Pa.). Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

Formulations of the present invention suitable for oral administration may be presented as discrete units such as capsules, cachets or tablets each containing a predetermined amount of the active ingredient; as a powder or granules; as a solution or a suspension in an aqueous or non-aqueous liquid; or as an oil-in-water liquid emulsion or a water-in-oil liquid emulsion. The active ingredient may also be administered as a bolus, electuary or paste.

A tablet is made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, preservative, surface active or dispersing agent. Molded tablets may be made by molding in a suitable machine a mixture of the powdered active ingredient moistened with an inert liquid diluent. The tablets may optionally be coated or scored and optionally are formulated so as to provide slow or controlled release of the active ingredient therefrom.

For administration to the eye or other external tissues e.g., mouth and skin, the formulations are preferably applied as a topical ointment or cream containing the active ingredient (s) in an amount of, for example, 0.075 to 20% w/w (including active ingredient(s) in a range between 0.1% and 20% in increments of 0.1% w/w such as 0.6% w/w, 0.7% w/w, etc.), preferably 0.2 to 15% w/w and most preferably 0.5 to 10% w/w. When formulated in an ointment, the active ingredients may be employed with either a paraffinic or a water-miscible ointment base. Alternatively, the active ingredients may be formulated in a cream with an oil-in-water cream base.

If desired, the aqueous phase of the cream base may include, for example, at least 30% w/w of a polyhydric alcohol, i.e. an alcohol having two or more hydroxyl groups such as propylene glycol, butane 1,3-diol, mannitol, sorbitol, glycerol and polyethylene glycol (including PEG 400) and mixtures thereof. The topical formulations may desirably include a compound which enhances absorption or penetration of the active ingredient through the skin or other affected areas. Examples of such dermal penetration enhancers include dimethyl sulphoxide and related analogs.

The oily phase of the emulsions of this invention may be constituted from known ingredients in a known manner. While the phase may comprise merely an emulsifier (otherwise known as an emulgent), it desirably comprises a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make up the so-called emulsifying wax, and the wax together with the oil and fat make up the so-called emulsifying ointment base which forms the oily dispersed phase of the cream formulations.

Emulgents and emulsion stabilizers suitable for use in the formulation of the invention include Tween® 60, Span® 80, cetostearyl alcohol, benzyl alcohol, myristyl alcohol, glyceryl mono-stearate and sodium lauryl sulfate.

The choice of suitable oils or fats for the formulation is based on achieving the desired cosmetic properties. The cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils are used.

Pharmaceutical formulations according to the present invention comprise one or more compounds of the invention together with one or more pharmaceutically acceptable carriers or excipients and optionally other therapeutic agents. Pharmaceutical formulations containing the active ingredient may be in any form suitable for the intended method of administration. When used for oral use for example, tablets, troches, lozenges, aqueous or oil suspensions, dispersible powders or granules, emulsions, hard or soft capsules, syrups or elixirs may be prepared. Compositions intended for oral use may be prepared according to any method known to the art for the manufacture of pharmaceutical compositions and such compositions may contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients may be, for example, inert diluents, such as calcium or sodium carbonate, lactose, lactose monohydrate, croscarmellose sodium, povidone, calcium or sodium phosphate; granulating and disintegrating agents, such as maize starch, or alginic acid; binding agents, such as cellulose, microcrystalline cellulose, starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

Formulations for oral use may be also presented as hard gelatin capsules where the active ingredient is mixed with an inert solid diluent, for example calcium phosphate or kaolin, or as soft gelatin capsules wherein the active ingredient is mixed with water or an oil medium, such as peanut oil, liquid paraffin or olive oil.

Aqueous suspensions of the invention contain the active materials in admixture with excipients suitable for the manufacture of aqueous suspensions. Such excipients include a suspending agent, such as sodium carboxymethylcellulose, methylcellulose, hydroxypropyl methylcellulose, sodium alginate, polyvinylpyrrolidone, gum tragacanth and gum acacia, and dispersing or wetting agents such as a naturally occurring phosphatide (e.g., lecithin), a condensation product of an alkyl oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl p-hydroxybenzoate, one or more coloring agents, one or more flavoring agents and one or more sweetening agents, such as sucrose or saccharin.

Oil suspensions may be formulated by suspending the active ingredient in a vegetable oil, such as *arachis* oil, olive oil, sesame oil or coconut oil, or in a mineral oil such as liquid paraffin. The oral suspensions may contain a thickening agent, such as beeswax, hard paraffin or cetyl alcohol. Sweetening agents, such as those set forth above, and flavoring agents may be added to provide a palatable oral preparation. These compositions may be preserved by the addition of an antioxidant such as ascorbic acid.

Dispersible powders and granules of the invention suitable for preparation of an aqueous suspension by the addition of water provide the active ingredient in admixture with a dispersing or wetting agent, a suspending agent, and one or more preservatives. Suitable dispersing or wetting agents and suspending agents are exemplified by those disclosed above. Additional excipients, for example sweetening, flavoring and coloring agents, may also be present.

The pharmaceutical compositions of the invention may also be in the form of oil-in-water emulsions. The oily phase may be a vegetable oil, such as olive oil or *arachis* oil, a mineral oil, such as liquid paraffin, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan monooleate, and condensation products of these partial esters with ethylene oxide, such as polyoxyethylene sorbitan monooleate. The emulsion may also contain sweetening and flavoring agents. Syrups and elixirs may be formulated with sweetening agents, such as glycerol, sorbitol or sucrose. Such formulations may also contain a demulcent, a preservative, a flavoring or a coloring agent.

The pharmaceutical compositions of the invention may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, such as a solution in 1,3-butane-diol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

The amount of active ingredient that may be combined with the carrier material to produce a single dosage form will vary depending upon the host treated and the particular mode of administration. For example, a time-release formulation intended for oral administration to humans may contain approximately 1 to 1000 mg of active material compounded with an appropriate and convenient amount of carrier material which may vary from about 5 to about 95% of the total compositions (weight:weight). The pharmaceutical composition can be prepared to provide easily measurable amounts for administration. For example, an aqueous solution intended for intravenous infusion may contain from about 3 to 500 μg of the active ingredient per milliliter of solution in order that infusion of a suitable volume at a rate of about 30 mL/hr can occur.

Formulations suitable for administration to the eye include eye drops wherein the active ingredient is dissolved or suspended in a suitable carrier, especially an aqueous solvent for the active ingredient. The active ingredient is preferably present in such formulations in a concentration of 0.5 to 20%, advantageously 0.5 to 10% particularly about 1.5% w/w.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate.

Formulations suitable for intrapulmonary or nasal administration have a particle size for example in the range of 0.1 to 500 microns (including particle sizes in a range between 0.1 and 500 microns in increments microns such as 0.5, 1, 30 microns, 35 microns, etc.), which is administered by rapid inhalation through the nasal passage or by inhalation through the mouth so as to reach the alveolar sacs. Suitable formulations include aqueous or oily solutions of the active ingredient. Formulations suitable for aerosol or dry powder administration may be prepared according to conventional methods and may be delivered with other therapeutic agents.

Formulations suitable for vaginal administration may be presented as pessaries, tampons, creams, gels, pastes, foams or spray formulations containing in addition to the active ingredient such carriers as are known in the art to be appropriate.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

The formulations are presented in unit-dose or multi-dose containers, for example sealed ampoules and vials, and may be stored in a freeze-dried (lyophilized) condition requiring only the addition of the sterile liquid carrier, for example water for injection, immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

It should be understood that in addition to the ingredients particularly mentioned above the formulations of this invention may include other agents conventional in the art having regard to the type of formulation in question, for example those suitable for oral administration may include flavoring agents.

The invention further provides veterinary compositions comprising at least one active ingredient as above defined together with a veterinary carrier.

Veterinary carriers are materials useful for the purpose of administering the composition and may be solid, liquid or gaseous materials which are otherwise inert or acceptable in the veterinary art and are compatible with the active ingredient. These veterinary compositions may be administered orally, parenterally or by any other desired route.

Compounds of the invention can also be formulated to provide controlled release of the active ingredient to allow less frequent dosing or to improve the pharmacokinetic or toxicity profile of the active ingredient. Accordingly, the invention also provides compositions comprising one or more compounds of the invention formulated for sustained or controlled release.

Effective dose of active ingredient depends at least on the nature of the condition being treated, toxicity, whether the compound is being used prophylactically (lower doses), the method of delivery, and the pharmaceutical formulation, and will be determined by the clinician using conventional dose escalation studies.

Routes of Administration

One or more compounds of the invention (herein referred to as the active ingredients) are administered by any route appropriate to the condition to be treated. Suitable routes include oral, rectal, nasal, topical (including buccal and sublingual), vaginal and parenteral (including subcutaneous, intramuscular, intravenous, intradermal, intrathecal and epidural), and the like. It will be appreciated that the preferred route may vary with for example the condition of the recipient. An advantage of the compounds of this invention is that they are orally bioavailable and can be dosed orally.

The antiviral properties of a compound of the invention may be determined using Test A described below.

Test A: Antiviral Assay in MT4 Cells

For the antiviral assay, 40 µL of 1× test concentration of 3-fold serially diluted compound in culture medium with 10% FBS was added to each well of a 384-well plate (10 concentrations) in quadruplicate. MT-4 cells were next mixed with HIV-IIIb at an m.o.i of 0.003 for 1 hour, after which time 35 µL of virus/cell mixture (2000 cells) was immediately added to each well containing 40 µL of diluted compound. The plates were then incubated at 37° C. for 5 days. After 5 days of incubation, 25 µl of 2× concentrated CellTiter-Glo™ Reagent (catalog # G7571, Promega Biosciences, Inc., Madison, Wis.) was added to each well containing MT-4 cells. Cell lysis was carried out by incubating at room temperature for 10 min and then chemiluminescence was read. EC50 values were defined as the compound concentration that caused a 50% decrease in luminescence signal, a measure of HIV-1 replication. Percent inhibition of virus-induced cell killing calculated from the dose response curve at 2 uM drug concentration is shown in the table below.

Test B: Cytotoxicity Assay

Compound cytotoxicity and the corresponding CC50 values was determined using the same protocol as described in the antiviral assay (Test A) except that uninfected cells were used.

Compounds of the present invention demonstrate antiviral activity as depicted in the table below. Accordingly, the compounds of the invention may be useful for treating an HIV virus infection, treating AIDS or for delaying the onset of AIDS or ARC symptoms. Shown below are the corresponding values for CC50 and percent inhibition of virus-induced cell killing in the presence of 2 uM drug concentration.

| Compound | % inhibition at 2 µM | CC50 (nM) |
| --- | --- | --- |
| 1D | 17 | 30766 |
| 2 | 29 | 14001 |
| 3 | 40 | 21900 |
| 4 | 69 | 10299 |
| 5 | 76 | 32736 |
| 6 | 45 | 11424 |
| 7 | 18 | 17620 |
| 8 | 20 | 15707 |
| 9E | 0 | 35914 |
| 10 | 0 | 12973 |
| 11 | 0 | 35671 |
| 12 | 0 | 8978 |
| 13G | 97 | 25557 |
| 14 | 76 | 25450 |
| 15 | 0 | 28235 |
| 16 | 0 | 14004 |
| 17 | 70 | 13779 |
| 18 | 0 | 14595 |
| 19 | 25 | 14241 |
| 20 | 84 | 48268 |
| 21 | 28 | 15531 |
| 22 | 0 | 45696 |
| 23 | 0 | 13820 |
| 24 | 39 | 24822 |
| 25 | 71 | 11920 |
| 26 | 70 | 24504 |
| 27 | 72 | 11952 |
| 28 | 93 | 25972 |
| 29 | 36 | 13232 |
| 30 | 76 | 11932 |
| 31 | 34 | 8633 |
| 32 | 94 | 19310 |
| 33 | 75 | 9750 |
| 34E | 0 | 27812 |
| 35G | 49 | 22398 |
| 36F | 15 | 7201 |
| 36G | 0 | 6931 |
| 37 | 84 | 34204 |
| 38D | 3 | 42570 |
| 38E | 86 | 28602 |
| 39 | 99 | >47993 |
| 40 | 99 | >48902 |
| 41 | 97 | >53000 |
| 42 | 96 | >53000 |
| 43 | 28 | >53000 |
| 44 | 96 | >52456 |
| 45 | 32 | >53000 |
| 46 | 87 | >53000 |
| 47 | 59 | >53000 |
| 48 | 74 | >53000 |
| 49 | 0 | 562 |
| 50D | 106 | 16937 |
| 51 | 52 | >53000 |
| 52 | 92 | 13348 |
| 53 | 33 | 28268 |
| 54G | 111 | 10343 |
| 55F | 101 | 21646 |
| 56B | 4 | 18889 |
| 57B | 98 | 13318 |
| 58D | 14 | 9996 |
| 59E | 75 | 45084 |
| 60H | 97 | 23982 |
| 61F | 74 | 17882 |
| 62 | 80 | 9984 |
| 63 | 22 | 14800 |
| 64 | 88 | 21071 |
| 65 | 33 | 11125 |
| 66 | −2 | 16799 |
| 67 | 0 | 6458 |
| 68B | 28 | >53192 |
| 69 | 84 | 6687 |
| 70 | 56 | 51249 |
| 71 | 64 | >53192 |
| 72 | 56 | 16153 |
| 73 | 15 | 9794 |
| 74D | 4 | 8470 |
| 75 | 17 | 10749 |
| 76 | 20 | 11515 |
| 77 | 65 | 12434 |
| 78 | 11 | 7890 |
| 79F | 19 | >50627 |
| 80 | 0 | >53192 |
| 81D | 75 | 16742 |
| 82 | 114 | 19283 |

| Compound | % inhibition at 2 μM | CC50 (nM) |
| --- | --- | --- |
| 83 | 92 | 25486 |
| 84 | 18 | 9046 |
| 85 | 9 | 43043 |
| 86 | 97 | 21450 |
| 87 | 101 | 21647 |
| 88E | 44 | >53192 |
| 89 | 73 | 10675 |
| 90F | 13 | 34585 |
| 91B | 17 | 22046 |
| 92 | 0 | 10286 |
| 93B | 0 | 8141 |
| 94 | 3 | 42048 |
| 95C | 14 | 14620 |
| 96 | 104 | 9625 |
| 97 | 27 | 33870 |
| 98 | 13 | 17954 |
| 99 | 0 | >53192 |
| 100 | 56 | 7828 |
| 101 | 29 | 12626 |
| 102D | 50 | 21484 |
| 103 | 0 | 5170 |
| 104 | 32 | 15722 |
| 105 | 99 | 9084 |
| 107E | 30 | 42789 |
| 108 | 13 | >53000 |
| 109 | 50 | 9085 |
| 110 | 6 | 7611 |
| 111 | 41 | 9946 |
| 112B | 28 | >53192 |
| 113 | 78 | 22275 |
| 114 | 32 | >53192 |
| 116 | 72 | >53192 |
| 117 | 89 | 8256 |
| 118 | 108 | 35951 |
| 119 | 48 | >53192 |
| 120 | 73 | 13828 |
| 121 | 68 | 9103 |
| 122G | 101 | 19919 |
| 123E | 84 | >53192 |
| 124C | 77 | 20162 |
| 125 | 0 | >53000 |
| 126 | 7 | >53000 |
| 127C | 97 | 31894 |
| 128 | 7 | 23549 |
| 129 | 0 | 10152 |
| 130D | 39 | 15764 |
| 131C | 47 | 10412 |
| 132 | 7 | 22253 |
| 133 | 1 | >53000 |
| 134 | 98 | 25170 |
| 135 | 53 | 21069 |
| 136D | 88 | 27842 |
| 137 | 1 | 21734 |
| 138 | 30 | 24507 |
| 139 | 8 | 13954 |
| 140 | 0 | >53000 |
| 141G | 4 | 21761 |
| 142C | 23 | >53192 |
| 143 | 10 | 19885 |
| 144 | 89 | >53000 |
| 145 | 0 | 22394 |
| 146 | 66 | 20592 |
| 147 | 10 | >53192 |
| 148 | 11 | 12278 |
| 149 | 2 | >53192 |
| 150 | 15 | 18420 |
| 151E | 11 | 20301 |
| 152D | 81 | 28392 |
| 153 | 10 | 17285 |
| 154 | 90 | 36786 |
| 155 | 97 | 36975 |
| 156 | 30 | 39244 |
| 157 | 10 | 38312 |
| 158 | 0 | 8496 |
| 159 | 84 | 19108 |
| 160 | 45 | 29334 |
| 161 | 0 | 9307 |
| 162E | 37 | >53192 |
| 163C | 105 | 27367 |
| 164 | 2 | 29860 |
| 165 | 0 | 52527 |
| 166 | 0 | 6358 |
| 167 | 0 | >53000 |
| 168B | 21 | 11089 |
| 169E | 94 | 19777 |
| 170C | 22 | >53192 |
| 171 | 4 | 11916 |
| 172D | 104 | 22084 |
| 173 | 94 | 25452 |
| 174 | 71 | 20003 |
| 175 | 1 | >53000 |
| 176C | 59 | 46532 |
| 177 | 0 | 51738 |
| 178 | 0 | >53000 |
| 179C | 52 | 22309 |
| 180 | 93 | >50359 |
| 181E | 99 | 27266 |
| 182 | 8 | 50969 |
| 183 | 0 | 35204 |
| 184 | 5 | 43151 |
| 185C | 94 | 26547 |
| 186 | 80 | 16844 |
| 187 | 31 | 18854 |
| 188 | 0 | >53000 |
| 189D | 48 | 23338 |
| 190E | 0 | 25337 |
| 191 | 19 | >50905 |
| 192 | 2 | 47551 |
| 193 | 2 | >53192 |
| 194 | 11 | >53192 |
| 195 | 85 | 23013 |
| 196 | 2 | 29560 |
| 197 | 0 | >53192 |
| 198 | 112 | 45902 |
| 199E | 18 | 9517 |
| 200B | 0 | >53192 |
| 201 | 8 | >53192 |
| 202 | 1 | >53192 |
| 203D | 0 | >53192 |
| 204 | 1 | >53192 |
| 205 | 12 | 13110 |
| 206 | 54 | 20028 |
| 207C | 16 | 13158 |
| 208D | 2 | >53192 |
| 209 | 51 | >53192 |
| 210 | 0 | >53192 |
| 211C | 83 | 36086 |
| 212 | 69 | >53192 |
| 213C | 14 | 15905 |
| 214 | 8 | 22180 |
| 215 | 80 | 19235 |
| 216 | 86 | 18650 |
| 217 | 92 | 29562 |
| 218 | 0 | >53192 |
| 219 | 1 | >53192 |
| 220B | 70 | 39195 |
| 221 | 1 | 40533 |
| 222B | 21 | 25598 |
| 223 | 76 | 41755 |
| 224 | 17 | 20360 |
| 225 | 15 | 23007 |
| 226C | 0 | >53000 |
| 227 | 1 | 14284 |
| 228B | 51 | 23388 |
| 229 | 95 | 18604 |
| 230 | 66 | 13981 |
| 231 | 79 | 43226 |
| 232 | 61 | 18655 |
| 233B | 5 | 32173 |
| 234 | 73 | 15892 |
| 235 | 12 | >53192 |
| 236D | 15 | 25638 |

| Compound | % inhibition at 2 μM | CC50 (nM) |
|---|---|---|
| 237 | 1 | 38182 |
| 238E | 12 | 16978 |
| 239 | 18 | 19379 |
| 240C | 0 | 34872 |
| 241D | 78 | 25386 |
| 242D | 97 | 25477 |
| 243 | 33 | >53192 |
| 244B | 0 | 16370 |
| 245F | 71 | 30316 |
| 246 | 1 | 47945 |
| 247 | 39 | 26251 |
| 248 | 88 | 26502 |
| 249 | 100 | 23353 |
| 250 | 19 | 18457 |
| 251 | 1 | >53192 |
| 252 | 18 | 19227 |
| 253 | 27 | >53192 |
| 254 | 91 | 16562 |
| 255 | 1 | >53192 |
| 256 | 15 | >53192 |
| 257 | 7 | >53192 |
| 258 | 8 | >53192 |
| 259 | 2 | 47617 |
| 260 | 54 | 28136 |
| 261 | 6 | 21226 |
| 262G | 109 | >51193 |
| 263 | 17 | >53192 |
| 264 | 24 | >53192 |
| 265 | 74 | >53192 |
| 266C | 0 | 51915 |
| 267 | 5 | >52894 |
| 268 | 27 | 27745 |
| 269 | 8 | >53192 |
| 270C | 1 | >53192 |
| 271B | 15 | 11411 |
| 272F | 92 | 14257 |
| 273 | 10 | 29555 |
| 274 | 0 | 11007 |
| 275 | 53 | 16906 |
| 276 | 29 | 16948 |
| 277B | 96 | 19304 |
| 278 | 121 | 8534 |
| 279G | 82 | 9300 |
| 280 | 0 | 4177 |
| 281C | 5 | 28296 |
| 282 | 0 | >53192 |
| 283C | 65 | 24368 |
| 284 | 50 | 16234 |
| 285G | 58 | 48534 |
| 286 | 0 | 25178 |
| 287E | 98 | 15976 |
| 288 | 108 | 16448 |
| 289 | 2 | 26418 |
| 290 | 4 | 11503 |
| 291 | 86 | 16519 |
| 292 | 1 | >53192 |
| 293 | 44 | 11190 |
| 294 | 114 | 20456 |
| 295B | 99 | >53192 |
| 296 | 96 | 10826 |
| 297 | 14 | 23313 |
| 298C | 61 | >53000 |
| 299D | 100 | 19498 |
| 300 | 0 | >53192 |
| 301B | 0 | 5652 |
| 302 | 0 | 16805 |
| 303 | 14 | 35540 |
| 304C | 94 | 1699 |
| 305 | 0 | >53192 |
| 306C | 10 | 41624 |
| 307 | 99 | 26681 |
| 308 | 102 | 39781 |
| 309 | 9 | 12000 |
| 310C | 97 | >53000 |
| 311B | 97 | 14846 |
| 312 | 2 | >53192 |
| 313 | 14 | >53192 |
| 314 | 3 | 23595 |
| 315 | 0 | 47185 |
| 316 | 100 | 21369 |
| 317 | 41 | >47618 |
| 318 | 27 | >53192 |
| 319 | 70 | >52484 |
| 320 | 110 | 12474 |
| 321 | 30 | 29687 |
| 322 | 10 | 37130 |
| 323 | 0 | >53192 |
| 324 | 31 | >53192 |
| 325 | 86 | 46137 |
| 326 | 27 | >53192 |
| 327 | 94 | >53192 |
| 328 | 0 | 10002 |
| 329 | 99 | 14697 |
| 330 | 3 | 29347 |
| 331B | 99 | 43107 |
| 332B | 2 | 39967 |
| 333 | 2 | >53192 |
| 334 | 63 | 26549 |
| 335 | 3 | 51148 |
| 336 | 0 | >53192 |
| 337 | 20 | 27878 |
| 338C | 35 | >53000 |
| 339B | 53 | 19437 |
| 340B | 32 | 32752 |
| 341 | 13 | 26585 |
| 342C | 119 | 13655 |
| 343 | 62 | 15548 |
| 344 | 93 | 17232 |
| 345 | 21 | 12409 |
| 346D | 1 | 39020 |
| 347 | 1 | 19378 |
| 348 | 103 | 14152 |
| 349B | 94 | 40798 |
| 350 | 10 | 28062 |
| 351 | 95 | 8601 |
| 352 | 16 | 32910 |
| 353B | 110 | 12655 |
| 354 | 82 | >53000 |
| 355 | 1 | 9465 |
| 356 | 76 | 20617 |
| 357 | 0 | 8824 |
| 358 | 20 | 47446 |
| 359 | 2 | 25272 |
| 360E | 55 | 13132 |
| 361 | 8 | >53192 |
| 362 | 23 | >53000 |
| 363 | 2 | 21873 |
| 364 | 38 | 3757 |
| 365 | 86 | 12470 |
| 366 | 6 | >53192 |
| 367 | 20 | 13404 |
| 368 | 2 | 47287 |
| 369 | 5 | >53000 |
| 370 | 33 | 22663 |
| 371 | 83 | 7589 |
| 372 | 0 | 24037 |
| 373 | 0 | 8142 |
| 374 | 5 | >53192 |
| 375 | 98 | 15176 |
| 376 | 2 | 29126 |
| 377 | 22 | 18646 |
| 378 | 5 | 17140 |
| 379 | 112 | 9237 |
| 380 | 97 | 18292 |
| 381 | 1 | 24923 |
| 382 | 85 | >39934 |
| 383 | 32 | 15504 |
| 384 | 97 | >53192 |
| 385 | 40 | >53192 |
| 386 | 114 | 11949 |
| 387 | 61 | 21235 |
| 388 | 54 | >53192 |

| Compound | % inhibition at 2 μM | CC50 (nM) |
|---|---|---|
| 389B | 2 | >53192 |
| 390 | 99 | 21565 |
| 391 | 60 | 44809 |
| 392 | 105 | 19144 |
| 393 | 54 | 26117 |
| 394 | 14 | 30759 |
| 395 | 41 | 11615 |
| 396 | 39 | 9999 |
| 397 | 26 | >53192 |
| 398 | 2 | 9831 |
| 399 | 31 | 12770 |
| 400 | 45 | 23303 |
| 401C | 87 | 9717 |
| 402 | 92 | 24761 |
| 403 | 112 | 10455 |
| 404 | 0 | 44624 |
| 405 | 11 | 21128 |
| 406 | 27 | 11432 |
| 407 | 102 | 11978 |
| 408 | 88 | 12745 |
| 409 | 0 | >53192 |
| 410 | 103 | 13729 |
| 411 | 53 | 8978 |
| 412 | 80 | 11140 |
| 413 | 61 | 14499 |
| 414 | 39 | 23433 |
| 415 | 39 | 38002 |
| 416 | 0 | 10281 |
| 417 | 8 | 12778 |
| 418 | 19 | >53192 |
| 419 | 42 | 27120 |
| 420 | 110 | 18698 |
| 421 | 70 | 10198 |
| 422 | 0 | 6763 |
| 423 | 14 | 8455 |
| 424 | 78 | 14163 |
| 425 | 85 | 15596 |
| 426 | 19 | >53000 |
| 427 | 0 | 32797 |
| 428 | 94 | 23043 |
| 429 | 57 | 41551 |
| 430 | 31 | 26293 |
| 431 | 7 | 6387 |
| 432 | 90 | 7993 |
| 433 | 16 | 20821 |
| 434 | 20 | 12326 |
| 435 | 7 | 13856 |
| 436 | 20 | 11275 |
| 437 | 3 | >53192 |
| 438 | 81 | 12103 |
| 439 | -2 | 21696 |
| 440 | 82 | 21699 |
| 441 | 35 | 8649 |
| 442 | 79 | 8876 |
| 443I | 82 | 16399 |
| 444 | 23 | 15522 |
| 445 | 114 | 10720 |
| 446 | 79 | >53192 |
| 447 | 0 | 12969 |
| 448 | 103 | >53192 |
| 449 | 94 | 21114 |
| 450 | 33 | 19264 |
| 451B | 1 | 37054 |
| 452C | 4 | 9069 |
| 453 | 3 | >53192 |
| 454 | 1 | 11111 |
| 455 | 4 | >53192 |
| 456 | 0 | >53192 |
| 457 | 64 | >53192 |
| 458 | 90 | 15703 |
| 459 | 28 | 14198 |
| 460 | 0 | 8970 |
| 461 | 25 | 32036 |
| 462J | 2 | 17992 |
| 463 | 11 | 14737 |
| 464 | 119 | >53192 |
| 465B | 3 | >53192 |
| 466 | 115 | >53192 |
| 467 | 103 | >53192 |
| 468D | 14 | >53000 |
| 469 | 17 | >53192 |
| 470 | 68 | 20769 |
| 471 | 62 | >53192 |
| 473 | 18 | 14644 |
| 474 | 17 | 9979 |
| 475 | 23 | 20371 |
| 476 | 30 | 53182 |
| 477 | 0 | 21395 |
| 478E | 0 | 21514 |
| 479 | 2 | 26449 |
| 480 | 93 | 27787 |
| 481 | 53 | 22927 |
| 482C | 2 | 51352 |
| 483D | 19 | 26191 |
| 484 | 25 | 27390 |
| 485 | 43 | 22202 |
| 486 | 76 | 7076 |
| 487C | 10 | 9712 |
| 488 | 8 | 12411 |
| 489D | 97 | 20784 |
| 490D | 87 | 38047 |
| 491F | 18 | 7849 |
| 492B | 2 | >53192 |
| 493 | 48 | 33923 |
| 494 | 17 | 10354 |
| 495 | 85 | 15531 |
| 496B | 17 | 18411 |
| 497 | 67 | 27052 |
| 498F | 60 | 13214 |
| 499 | 22 | >53000 |
| 500 | 59 | 24349 |
| 501 | 11 | 39631 |
| 502F | 50 | 3054 |
| 503 | 3 | 40356 |
| 504E | 142 | 12820 |
| 505 | 28 | >47368 |
| 506 | 32 | >53000 |
| 507B | 22 | >45266 |
| 508D | 96 | 5132 |
| 509 | 48 | 24601 |
| 510 | 3 | 35940 |
| 511C | 17 | 11777 |
| 512C | 60 | 19883 |
| 513 | 63 | 10682 |
| 514 | 3 | >46077 |
| 515 | 0 | 9461 |
| 517E | 87 | 19079 |
| 518 | 11 | 10548 |
| 519 | 65 | 20324 |
| 520 | 30 | >53192 |
| 521 | 0 | >53192 |
| 522 | 4 | 47889 |
| 523 | 24 | 48801 |
| 524D | 78 | 8533 |
| 525 | 83 | >53192 |
| 526 | 50 | 10031 |
| 527E | 66 | 10638 |
| 528 | 0 | >53192 |
| 529 | 53 | 13001 |
| 530E | 55 | 15251 |
| 531 | 98 | 7401 |
| 532 | 9 | 12162 |
| 533E | 142 | 19292 |
| 534 | 29 | 9824 |
| 535G | 9 | 25309 |
| 536I | 12 | 8605 |
| 537 | 2 | >53192 |
| 538 | 14 | 23328 |
| 539 | 10 | 20785 |
| 540E | -4 | >53192 |
| 541 | 37 | 8152 |
| 542 | 1 | 33639 |

-continued

| Compound | % inhibition at 2 μM | CC50 (nM) |
|---|---|---|
| 543 | 4 | 43954 |
| 544 | 75 | >53192 |
| 545 | 37 | 15894 |
| 546C | 15 | 16774 |
| 547 | 45 | 13332 |
| 548D | 54 | 10129 |
| 549 | 38 | 10166 |
| 550 | 1 | 16979 |
| 551 | 0 | >53192 |
| 552 | 8 | 11041 |
| 553 | 11 | 23837 |
| 554 | 63 | 48909 |
| 555C | 14 | 25510 |
| 556 | 83 | 47803 |
| 557 | 73 | 7859 |
| 558B | 3 | >53192 |
| 559D | 96 | 23060 |
| 560 | 112 | >53000 |
| 561B | 8 | 29040 |
| 562 | 42 | 17783 |
| 563 | 62 | 27019 |
| 564 | 100 | 10281 |
| 565 | 0 | 37625 |
| 566 | 3 | 23700 |
| 567 | 11 | 15782 |
| 568 | 42 | 11417 |
| 569 | 11 | >53000 |
| 570 | 5 | >53192 |
| 571 | 2 | 34848 |
| 572B | 11 | 36737 |
| 573 | 18 | 30054 |
| 574D | 24 | 52462 |
| 575B | 14 | 17450 |
| 576B | 2 | >53192 |
| 577 | 20 | >53192 |
| 578 | 15 | >53192 |
| 579D | 18 | >53192 |
| 580F | 95 | 32553 |
| 581D | 6 | 10563 |
| 582 | 5 | 14430 |
| 583 | 28 | 23239 |
| 584 | 93 | 7251 |
| 585 | 58 | 13736 |
| 586 | 1 | >53192 |
| 587C | 93 | 22970 |
| 588 | 2 | 21529 |
| 589 | 106 | 17933 |
| 590 | 13 | 38595 |
| 591 | 15 | 14237 |
| 592 | 8 | >53192 |
| 593 | 52 | >53000 |
| 594B | 12 | 13423 |
| 595 | 99 | 12699 |
| 596 | 96 | 10945 |
| 597 | 89 | 8650 |
| 598 | 3 | >53192 |
| 599 | 2 | 31550 |
| 600 | 9 | >53192 |
| 601 | 22 | 41944 |

The specific pharmacological responses observed may vary according to and depending on the particular active compound selected or whether there are present pharmaceutical carriers, as well as the type of formulation and mode of administration employed, and such expected variations or differences in the results are contemplated in accordance with practice of the present invention.

The invention has been described with reference to various specific and preferred embodiments and techniques. However, it should be understood that many variations and modifications may be made while remaining within the spirit and scope of the invention.

The invention will now be illustrated by the following non-limiting Examples. The Examples provided herein describe the synthesis of compounds of the invention (i.e. compounds of Formula I) as well as intermediates used to prepare compounds of the invention.

Example 1

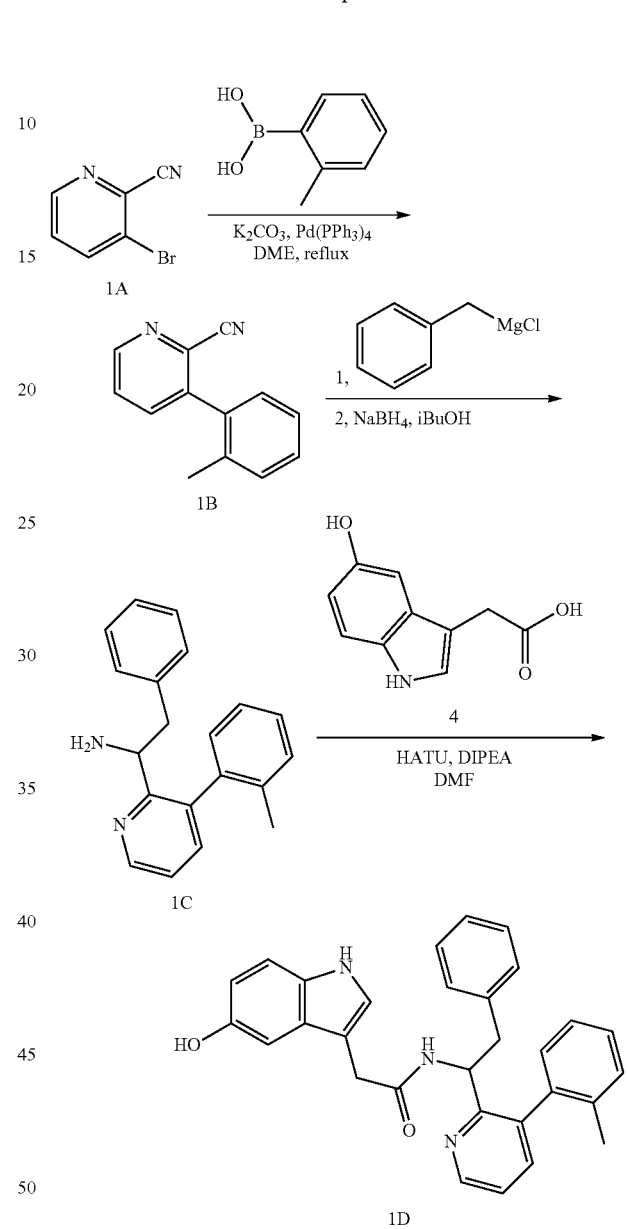

Synthesis of 3-o-tolylpicolinonitrile (1B)

To a suspension of 3-bromopicolinonitrile (1.0 g, 5.46 mmol), potassium carbonate (27 ml, 0.4M in water), o-tolylboronic acid (1A, 0.74 g, 5.46 mmol) and tetrakis(triphenylphosphine) palladium (310 mg, 0.27 mmol) in DME (40 ml), was degassed for 20 minutes. The mixture was then heated at reflux. After 2 hours the reaction was filtered through celite and the filtrate was extracted with EtOAc (30 ml) twice. The organic layer was dried over $Na_2SO_4$, filtered and concentrated. The crude product was purified by flash column (Rf: 0.3 EtOAc/Hexanes=20%). The yield was 94%. MS (m/z) 195 [M+H]$^+$ Synthesis of 2-phenyl-1-(3-o-tolylpyridin-2-yl)ethanamine (1C)

To a solution of 3-o-tolylpicolinonitrile (0.5 g, 2.56 mmol) in toluene cooled by an ice bath, benzylmagnesium chloride (2M in THF) (3.0 ml, 6.0 mmol) was added dropwise. After 30 minutes, the reaction was warmed up to room temperature and stirring was continued for 1 hr. The reaction was then cooled to 0° C. and 2-butanol (10 ml) was added. NaBH$_4$ (187 mg, 4.93 mmol) was then added to the solution and the reaction was stirred overnight (warmed up to r.t. slowly). The reaction was quenched with MeOH (3 ml) and extracted with EtOAc (2×30 ml). The organic layer was dried with Na$_2$SO$_4$, filtered and concentrated. The crude product was purified by flash column. The yield was (180 mg, 0.62 mmol) 24.2%. MS (m/z) 289 [M+H]$^+$ Synthesis of 2-(6-hydroxy-1H-indol-3-yl)-N-(2-phenyl-1-(3-o-tolylpyridin-2-yl)ethyl)acetamide (1D)

HATU (40 mg, 0.105 mmol) was added to a solution of 2-(5-hydroxy-1H-indol-3-yl)acetic acid (19.2 mg, 0.1 mmol) and DIPEA (0.02 ml, 0.12 mmol) in DMF (0.3 ml). After 10 minutes, 2-phenyl-1-(3-o-tolylpyridin-2-yl)ethanamine (29 mg, 0.1 mmol) in 0.2 ml of DMF was added to the reaction. The reaction was stirred for 2 hours. The DMF solution was filtered and purified by RP HPLC to provide the desired product. The yield was 24 mg. The product is a mixture of rotamers. The ratio is 3:2. NMR of the major rotamer is reported. $^1$H NMR (d-DMSO, 400 MHz) δ 10.22 (s, 1H), 8.6-8.62 (m, 1H), 8.05 (d, 1H), 7.45 (d, 1H), 7.34-7.4 (m, 1H), 7.2-7.31 (m, 2H), 7.0-7.18 (m, 5H), 6.88 (s, 1H), 6.75 (s, 1H), 6.0-6.64 (m, 2H), 6.5-6.58 (m, 2H), 4.75 (q, 1H), 3.3-3.41 (m, 2H), 2.7-2.9 (m, 2H), 1.92 (s, 3H); MS (m/z) 462 [M+H]$^+$.

Example 2

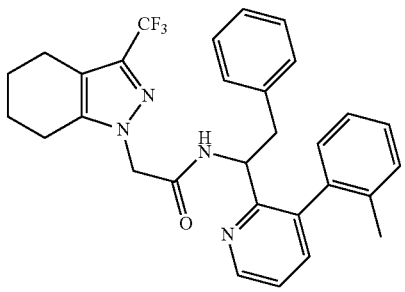

2

Synthesis of N-(2-phenyl-1-(3-(o-tolyl)pyridin-2-yl)ethyl)-2-(3-(trifluoromethyl)-4,5,6,7-tetrahydro-1H-indazol-1-yl)acetamide (2)

The title compound was prepared according to the method presented for the synthesis of Compound 1D of Example 1 substituting 2-(3-(trifluoromethyl)-4,5,6,7-tetrahydro-1H-indazol-1-yl)acetic acid for 2-(5-hydroxy-1H-indol-3-yl)acetic acid. MS (m/z) 519 [M+H]$^+$.

Example 3

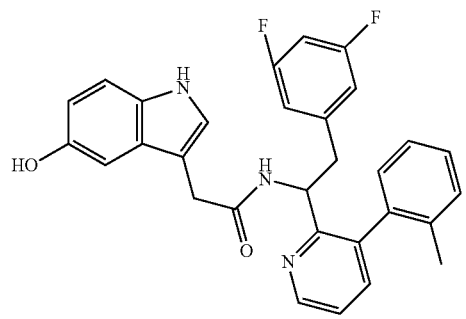

3

The Synthesis of N-(2-(3,5-difluorophenyl)-1-(3-o-tolylpyridin-2-yl)ethyl)-2-(5-hydroxy-1H-indol-3-yl)acetamide (3)

The title compound was prepared according to the method presented for the synthesis of Compound 1D of Example 1 substituting (3,5-difluorobenzyl)magnesium chloride for benzylmagnesium chloride. MS (m/z) 498 [M+H]$^+$.

Example 4

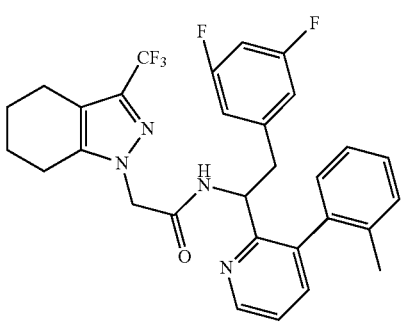

4

The Synthesis of N-(2-(3,5-difluorophenyl)-1-(3-o-tolylpyridin-2-yl)ethyl)-2-(3-(trifluoromethyl)-4,5,6,7-tetrahydro-1H-indazol-1-yl)acetamide (4)

The title compound was prepared according to the method presented for the synthesis of Compound 1D of Example 1 substituting (3,5-difluorobenzyl)magnesium chloride for benzylmagnesium chloride and 2-(3-(trifluoromethyl)-4,5,6,7-tetrahydro-1H-indazol-1-yl)acetic acid for 2-(5-hydroxy-1H-indol-3-yl)acetic acid. MS (m/z) 555 [M+H]$^+$.

Example 5

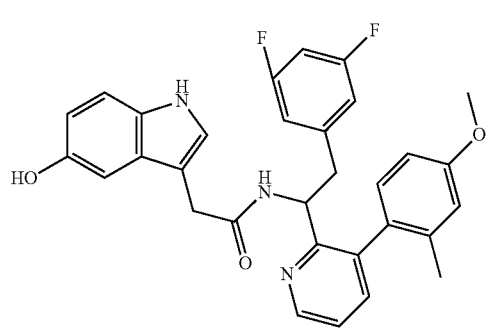

The Synthesis of N-(2-(3,5-difluorophenyl)-1-(3-(4-methoxy-2-methylphenyl)pyridin-2-yl)ethyl)-2-(5-hydroxy-1H-indol-3-yl)acetamide (5)

The title compound was prepared according to the method presented for the synthesis of Compound 1D of Example 1 substituting 4-methoxy-2-methylphenylboronic acid for o-tolylboronic acid and (3,5-difluorobenzyl)magnesium chloride for benzylmagnesium chloride to provide. MS (m/z) 528 [M+H]$^+$.

Example 6

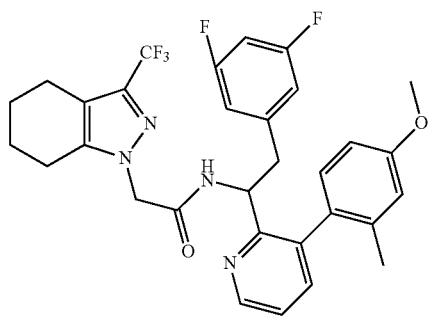

The Synthesis of N-(2-(3,5-difluorophenyl)-1-(3-(4-methoxy-2-methylphenyl)pyridin-2-yl)ethyl)-2-(3-(trifluoromethyl)-4,5,6,7-tetrahydro-1H-indazol-1-yl)acetamide (6)

The title compound was prepared according to the method presented for the synthesis of Compound 1D of Example 1 substituting 4-methoxy-2-methylphenylboronic acid for o-tolylboronic acid, (3,5-difluorobenzyl)magnesium chloride for benzylmagnesium chloride, and 2-(3-(trifluoromethyl)-4,5,6,7-tetrahydro-1H-indazol-1-yl)acetic acid for 2-(5-hydroxy-1H-indol-3-yl)acetic acid. MS (m/z) 585 [M+H]$^+$.

Example 7

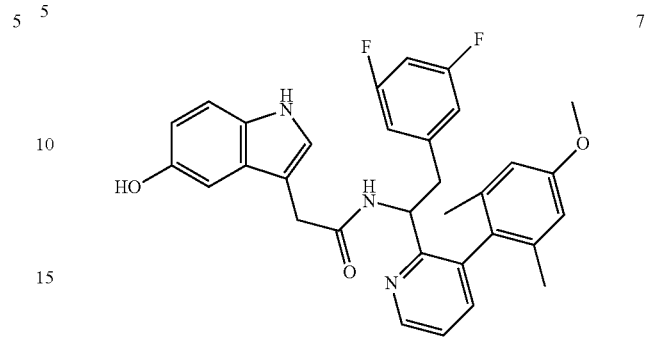

The Synthesis of N-(2-(3,5-difluorophenyl)-1-(3-(4-methoxy-2,6-dimethylphenyl)pyridin-2-yl)ethyl)-2-(5-hydroxy-1H-indol-3-yl)acetamide (7)

The title compound was prepared according to the method presented for the synthesis of Compound 1D of Example 1 substituting 4-methoxy-2,6-dimethylphenylboronic acid for o-tolylboronic acid and (3,5-difluorobenzyl)magnesium chloride for benzylmagnesium chloride. MS (m/z) 542 [M+H]$^+$.

Example 8

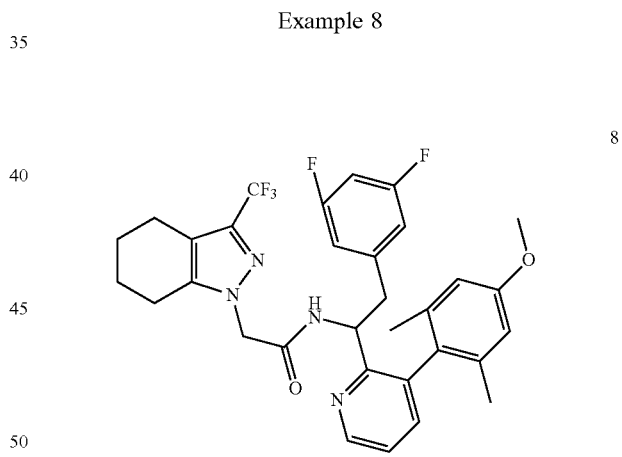

The Synthesis of N-(2-(3,5-difluorophenyl)-1-(3-(4-methoxy-2,6-dimethylphenyl)pyridin-2-yl)ethyl)-2-(3-(trifluoromethyl)-4,5,6,7-tetrahydro-1H-indazol-1-yl)acetamide (8)

The title compound was prepared according to the method presented for the synthesis of Compound 1D of Example 1 substituting 4-methoxy-2,6-dimethylphenylboronic acid for o-tolylboronic acid, (3,5-difluorobenzyl)magnesium chloride for benzylmagnesium chloride, and 2-(3-(trifluoromethyl)-4,5,6,7-tetrahydro-1H-indazol-1-yl)acetic acid for 2-(5-hydroxy-1H-indol-3-yl)acetic acid. MS (m/z) 599 [M+H]$^+$.

Example 9

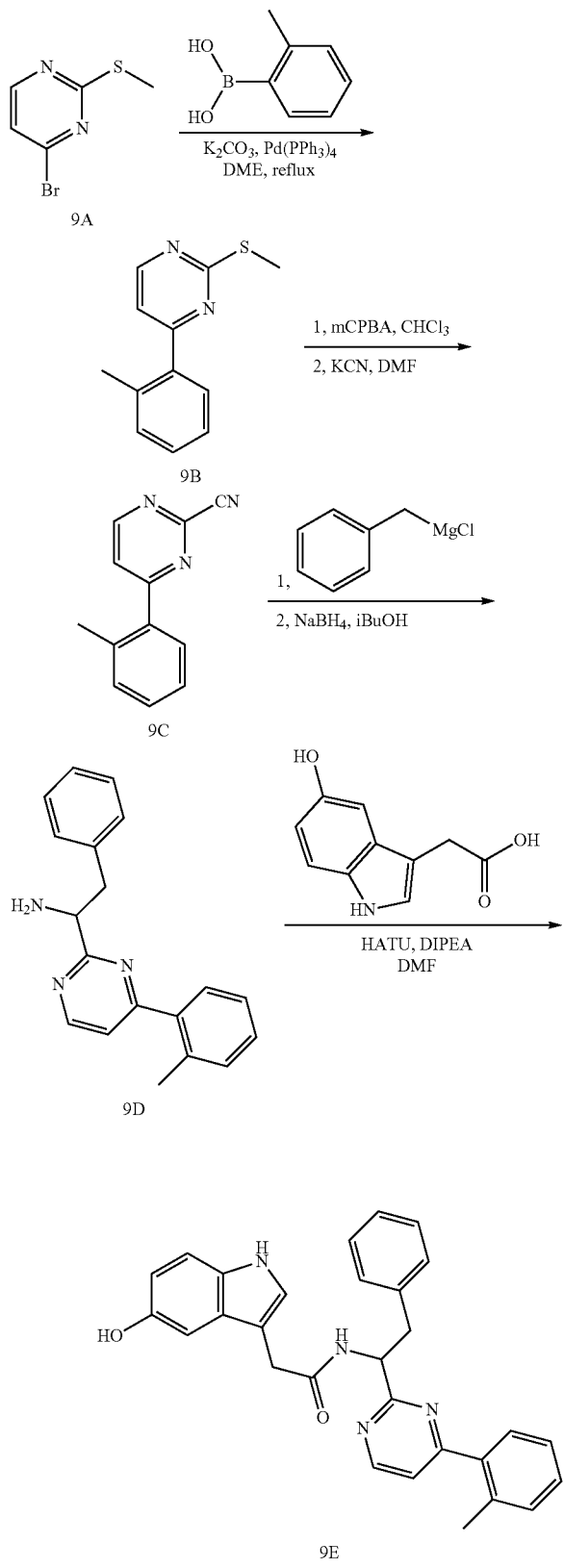

Synthesis of 2-(methylthio)-4-o-tolylpyrimidine (9B)

A suspension of 4-bromo-2-(methylthio)pyrimidine (9A, 1.18 g, 7.35 mmol), potassium carbonate (37 ml, 0.4 M in water), o-tolylboronic acid (1 g, 7.35 mmol) and tetrakis(triphenylphosphine)palladium(0) (425 mg, 0.37 mmol) in DME (40 ml) was degassed for 20 minutes. It was then heated at reflux for 2 hours. The reaction mixture was cooled and filtered through celite. The filtrate was extracted with EtOAc (2×30 ml). The organic layer was dried with $Na_2SO_4$, filtered and concentrated. The crude product was purified by flash column (Rf: 0.3 10% EtOAc/Hexanes). The yield was 98%. MS (m/z) 217 [M+H]$^+$

Synthesis of 4-o-tolylpyrimidine-2-carbonitrile (9C)

To a solution of 2-(methylthio)-4-o-tolylpyrimidine (1.55 g, 7.2 mmol) in DCM (10 ml) was added mCPBA (77% from Aldrich) (1.25 g, 5.6 mmol). The reaction mixture was stirred for 2 hours then diluted with DCM (50 ml) and washed with $NaHCO_3$(aq) (2×50 ml). The organic layer was dried over $Na_2SO_4$, filtered and concentrated. The crude product was dried under high vacuum then redissolved in DMF. KCN(s) (936 mg, 14.4 mmol) was added to the solution and the reaction was stirred overnight. The reaction was diluted with EtOAc (100 ml) and washed with $NaHCO_3$ (aq) (2×50 ml). The organic layer was dried over $Na_2SO_4$, filtered and concentrated. The crude product was purified by flash column (Rf: 0.3 EtOAc/Hexanes=15%). The yield was (690 mg, 3.53 mmol). 49% for two steps. MS (m/z) 196 [M+H]$^+$

Synthesis of 2-phenyl-1-(4-o-tolylpyrimidin-2-yl)ethanamine (9D)

Benzylmagnesium chloride (2M in THF) (2.11 ml, 4.22 mmol) was added dropwise to a solution of 4-o-tolylpyrimidine-2-carbonitrile (9C, 690 mg, 3.52 mmol) in toluene (10 ml) at 0° C. After 30 minutes, the reaction was warmed up to r.t. and stirred for 1 hr. The reaction was then cooled it to 0° C. and 2-butanol (10 ml) was added followed by $NaBH_4$ (s) (187 mg, 4.93 mmol). The reaction mixture was stirred overnight at room temperature. The reaction was quenched with MeOH (3 ml) and extracted with EtOAc (2×30 ml). The organic layer was dried with $Na_2SO_4$, filtered and concentrated. The crude product was purified by flash column (Rf: 0.4 10% MeOH/DCM). The yield was 380. MS (m/z) 290 [M+H]$^+$

Synthesis of 2-(5-hydroxy-1H-indol-3-yl)-N-(2-phenyl-1-(4-o-tolylpyrimidin-2-yl)ethyl)acetamide (9E)

HATU (40 mg, 0.105 mmol) was added to a solution of 2-(5-hydroxy-1H-indol-3-yl)acetic acid (19.2 mg, 0.1 mmol) and DIEPA (0.02 ml, 0.12 mmol) in DMF (0.3 ml). After 10 minutes, 2-phenyl-1-(4-o-tolylpyrimidin-2-yl)ethanamine (29 mg, 0.1 mmol) in 0.2 ml of DMF was added to the reaction. The reaction was stirred for 2 hours. The DMF solution was filtered and purified by RP HPLC using a C18 column and a gradient of 20% B to 85% B over 25 minutes (A=0.1% TFA/$H_2O$, B=0.1% TFA/acetonitrile) to provide the title compound. The yield was 30 mg. $^1$H NMR (d-DMSO, 400 MHz) δ 10.48 (s, 1H), 8.79 (d, 1H), 8.14 (d, 1H), 7.5 (d, 1H), 7.22-7.3 (m, 4H), 7.08-7.35 (m, 4H), 6.92-6.98 (m, 3H), 6.6 (s, 1H), 6.58 (d, 1H), 5.21 (q, 1H), 3.4-3.55 (m, 2H), 3.0-3.2 (m, 2H), 1.98 (s, 3H); MS (m/z) 463 [M+H]+

Example 10

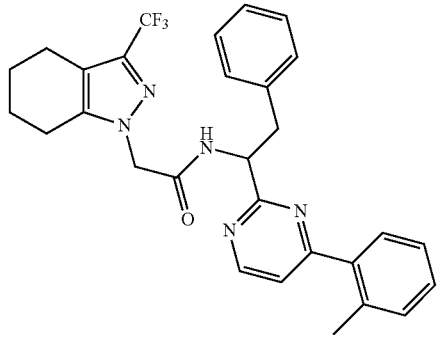

The Synthesis of N-(2-phenyl-1-(4-o-tolylpyrimidin-2-yl)ethyl)-2-(3-(trifluoromethyl)-4,5,6,7-tetrahydro-1H-indazol-1-yl)acetamide (10)

The title compound was prepared according to the method presented in the synthesis of Example 9 substituting 2-(3-(trifluoromethyl)-4,5,6,7-tetrahydro-1H-indazol-1-yl)acetic acid for 2-(5-hydroxy-1H-indol-3-yl)acetic acid. MS (m/z) 520 [M+H]+.

Examples 11

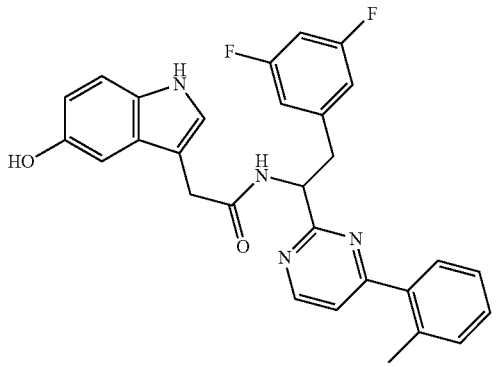

The Synthesis of N-(2-(3,5-difluorophenyl)-1-(4-o-tolylpyrimidin-2-yl)ethyl)-2-(5-hydroxy-1H-indol-3-yl)acetamide (11)

The title compound was prepared according to the method presented in the synthesis of Example 9 substituting (3,5-difluorobenzyl)magnesium chloride for benzylmagnesium chloride. MS (m/z) 499 [M+H]+.

Example 12

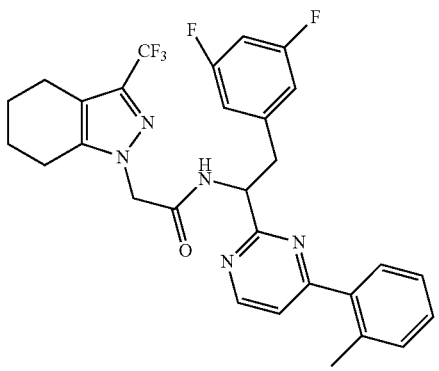

The Synthesis of N-(2-(3,5-difluorophenyl)-1-(4-o-tolylpyrimidin-2-yl)ethyl)-2-(3-(trifluoromethyl)-4,5,6,7-tetrahydro-1H-indazol-1-yl)acetamide (12)

The title compound was prepared according to the method presented in the synthesis of Example 9 substituting (3,5-difluorobenzyl)magnesium chloride for benzylmagnesium chloride and 2-(3-(trifluoromethyl)-4,5,6,7-tetrahydro-1H-indazol-1-yl)acetic acid for 2-(5-hydroxy-1H-indol-3-yl)acetic acid. MS (m/z) 556 [M+H]+.

Example 13

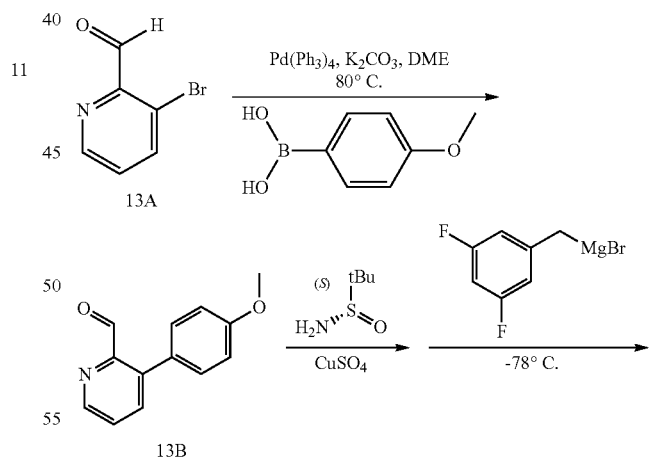

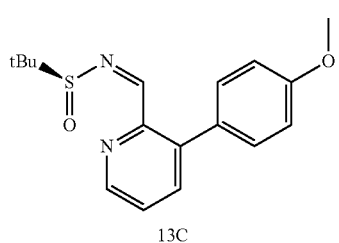

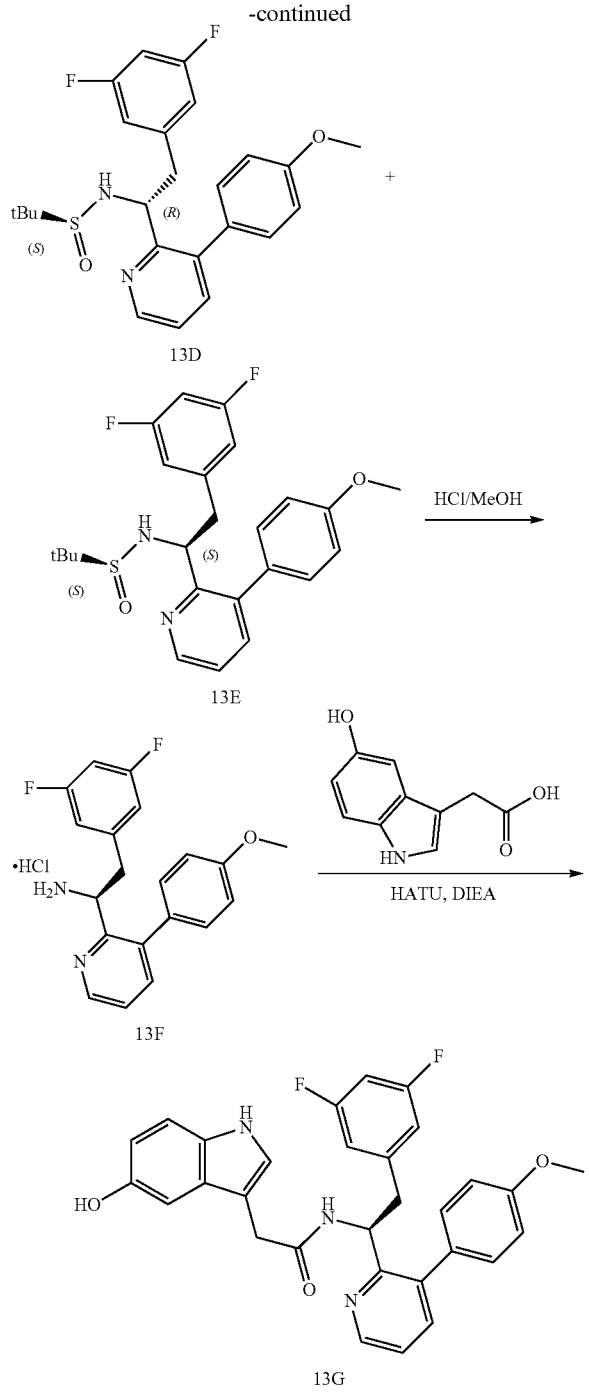

filtered and concentrated. The crude product was purified by flash column (Rf: 0.4 50% EtOAc/Hexanes). The yield was 2 g. MS (m/z) 214 [M+H]+

Synthesis of (S)—N-((3-(4-methoxyphenyl)pyridin-2-yl)methylene)-2-methylpropane-2-sulfinamide (13C)

Copper(II) sulfate (anhydrous 2.52 g, 17.2 mmol) was added to a solution of 3-(4-methoxyphenyl)picolinaldehyde (1.7 g, 8.6 mmol) and (S)-2-methylpropane-2-sulfinamide (1.06 g, 9.4 mmol) in DCM (20 ml). The suspension was stirred overnight at room temperature. The reaction was filtered and washed with DCM (3×20 ml). The filtrate was concentrated. The crude product was purified by flash column (Rf: 0.6, 60% EtOAc/Hexanes). The yield was (2.4 g, 7.7 mmol) 90%. MS (m/z) 195 [M+H]+

Synthesis of (S)—N—((R)-2-(3,5-difluorophenyl)-1-(3-(4-methoxyphenyl)pyridin-2-yl)ethyl)-2-methylpropane-2-sulfinamide (13D) and (S)—N—((S)-2-(3,5-difluorophenyl)-1-(3-(4-methoxyphenyl)pyridin-2-yl)ethyl)-2-methylpropane-2-sulfinamide (13E)

(3,5-difluorobenzyl)magnesium bromide (0.25 M in ether, 10 ml, 2.5 mmol) was added dropwise to a solution of (S)—N-((3-(4-methoxyphenyl)pyridin-2-yl)methylene)-2-methylpropane-2-sulfinamide (13C, 0.5 g, 1.67 mmol) in DCM (40 ml) at −78° C. The reaction was stirred for 3 hour at −78° C. Ammonium chloride (aq, 10 ml) was added to the reaction and the mixture was allowed to warm to r.t. The mixture was extracted with EtOAc (2×30 ml). The organic layer was dried over Na2SO4, filtered and concentrated. The crude product contained a mixture of diastereomers 13D ((S,R) sulfinamide intermediate) and 13E ((S,S) sulfinamide intermediate) separable by flash chromatography (Rf: 0.3 50% EtOAc/Hexanes). The yield was (220 mg, 30%). MS (m/z) 445 [M+H]+

(S)-2-(3,5-difluorophenyl)-1-(3-(4-methoxyphenyl)pyridin-2-yl)ethanamine hydrochloride Salt (13F)

(S)—N—((S)-2-(3,5-difluorophenyl)-1-(3-(4-methoxyphenyl)pyridin-2-yl)ethyl)-2-methylpropane-2-sulfinamide (13E, 220 mg, 0.5 mmol) was treated with a mixture of 2 ml of 1.25 M HCl in MeOH/1 ml of 4 M HCl in dioxane for 1 hour. The solvent was removed in vacuo. Used without further purification. MS (m/z) 341 [M+H]+

Synthesis of (S)—N-(2-(3,5-difluorophenyl)-1-(3-(4-methoxyphenyl)pyridin-2-yl)ethyl)-2-(5-hydroxy-1H-indol-3-yl)acetamide (13G)

HATU (40 mg, 0.105 mmol) was added to a solution of 2-(5-hydroxy-1H-indol-3-yl)acetic acid (19.2 mg, 0.1 mmol) and DIPEA (0.04 ml, 0.24 mmol) in DMF (0.3 ml). After 10 minutes, (S)-2-(3,5-difluorophenyl)-1-(3-(4-methoxyphenyl)pyridin-2-yl)ethanamine hydrochloride salt (34 mg, 0.1 mmol) in 0.2 ml of DMF was added. The reaction was stirred for 2 hours at room temperature. The DMF solution was filtered and purified by RP HPLC using a C18 column and a gradient of 20% B to 85% B over 25 minutes (A=0.1% TFA/H2O, B=0.1% TFA/acetonitrile) to provide the desired product. The yield was 39 mg. 1H NMR (d-DMSO, 400 MHz) δ 10.22 (s, 1H), 8.6 (d, 1H), 8.4 (d, 1H), 7.53 (d, 1H), 7.3-7.4 (m, 1H), 7.0-7.1 (m, 3H), 6.8-6.98

Synthesis of 3-(4-methoxyphenyl)picolinaldehyde (13B)

A suspension of 3-bromopicolinaldehyde (13A, 1.86 g, 10 mmol), potassium carbonate (50 ml, 2M in water), 4-methoxyphenylboronic acid (1.6 g, 10.5 mmol) and tetrakis(triphenylphosphine) palladium (580 mg, 0.5 mmol) in DME (70 ml) was degassed for 30 minutes. The mixture was heated at reflux for 2 hours. The reaction was cooled and filtered through celite. The filtrate was extracted with EtOAc (2×50 ml). The organic layer was dried over Na2SO4, (m, 4H), 6.78 (s, 1H), 6.56 (d, 1H), 6.3-6.4 (m, 2H), 5.21 (q, 1H), 3.75 (s, 3H), 3.4 (s, 2H), 2.9 (d, 2H); MS (m/z) 514 [M+H]⁺

Example 14

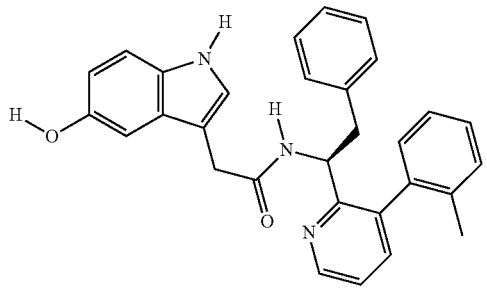

The Synthesis of (S)-2-(5-hydroxy-1H-indol-3-yl)-N-(2-phenyl-1-(3-o-tolylpyridin-2-yl)ethyl)acetamide (14)

The title compound was prepared according to the method presented in the synthesis of Example 13 substituting o-tolylboronic acid for 4-methoxyphenylboronic acid and benzylmagnesium chloride for (3,5-difluorobenzyl)magnesium chloride. MS (m/z) 462 [M+H]⁺.

Example 15

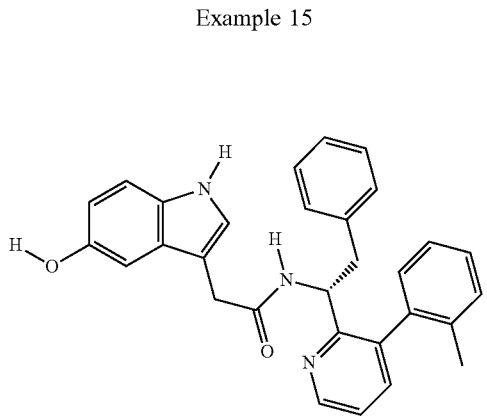

The Synthesis of (R)-2-(5-hydroxy-1H-indol-3-yl)-N-(2-phenyl-1-(3-o-tolylpyridin-2-yl)ethyl)acetamide (15)

The title compound was prepared according to the method presented in the synthesis of Example 13 substituting o-tolylboronic acid for 4-methoxyphenylboronic acid and benzylmagnesium chloride for (3,5-difluorobenzyl)magnesium chloride and carrying forward the (S,R) sulfinamide intermediate. MS (m/z) 462 [M+H]⁺.

Example 16

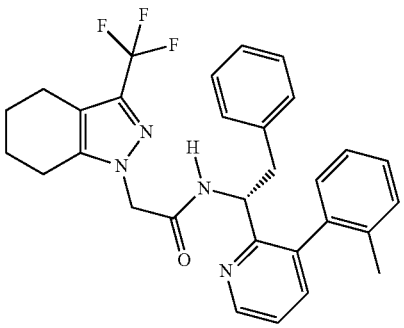

The Synthesis of (R)—N-(2-phenyl-1-(3-o-tolylpyridin-2-yl)ethyl)-2-(3-(trifluoromethyl)-4,5,6,7-tetrahydro-1H-indazol-1-yl)acetamide (16)

The title compound was prepared according to the method presented in the synthesis of Example 13 substituting o-tolylboronic acid for 4-methoxyphenylboronic acid, benzylmagnesium chloride for (3,5-difluorobenzyl)magnesium chloride, 2-(3-(trifluoromethyl)-4,5,6,7-tetrahydro-1H-indazol-1-yl)acetic acid for 2-(5-hydroxy-1H-indol-3-yl)acetic acid and carrying forward the (S,R) sulfinamide intermediate. MS (m/z) 519 [M+H]⁺.

Example 17

The Synthesis of (S)—N-(2-phenyl-1-(3-o-tolylpyridin-2-yl)ethyl)-2-(3-(trifluoromethyl)-4,5,6,7-tetrahydro-1H-indazol-1-yl)acetamide (17)

The title compound was prepared according to the method presented in the synthesis of Example 13 substituting o-tolylboronic acid for 4-methoxyphenylboronic acid, benzylmagnesium chloride for (3,5-difluorobenzyl)magnesium chloride, and 2-(3-(trifluoromethyl)-4,5,6,7-tetrahydro-1H-indazol-1-yl)acetic acid for 2-(5-hydroxy-1H-indol-3-yl)acetic acid. MS (m/z) 519 [M+H]⁺.

Example 18

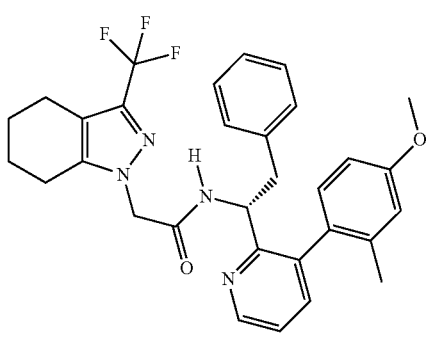

The Synthesis of (R)—N-(1-(3-(4-methoxy-2-methylphenyl)pyridin-2-yl)-2-phenylethyl)-2-(3-(trifluoromethyl)-4,5,6,7-tetrahydro-1H-indazol-1-yl)acetamide (18)

The title compound was prepared according to the method presented in the synthesis of Example 13 substituting 4-methoxy-2-methylphenylboronic acid for 4-methoxyphenylboronic acid, benzylmagnesium chloride for (3,5-difluorobenzyl)magnesium chloride, 2-(3-(trifluoromethyl)-4,5,6,7-tetrahydro-1H-indazol-1-yl)acetic acid for 2-(5-hydroxy-1H-indol-3-yl)acetic acid and carrying forward the (S,R) sulfinamide intermediate. MS (m/z) 549 [M+H]$^+$.

Example 19

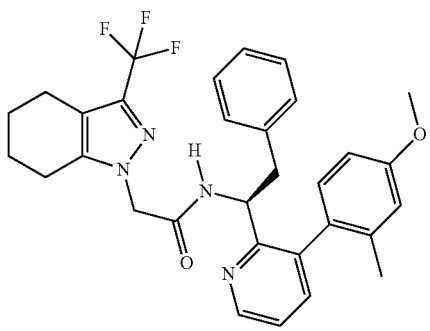

The Synthesis of (S)—N-(1-(3-(4-methoxy-2-methylphenyl)pyridin-2-yl)-2-phenylethyl)-2-(3-(trifluoromethyl)-4,5,6,7-tetrahydro-1H-indazol-1-yl)acetamide (19)

The title compound was prepared according to the method presented in the synthesis of Example 13 substituting 4-methoxy-2-methylphenylboronic acid for 4-methoxyphenylboronic acid, benzylmagnesium chloride for (3,5-difluorobenzyl)magnesium chloride, and 2-(3-(trifluoromethyl)-4,5,6,7-tetrahydro-1H-indazol-1-yl)acetic acid for 2-(5-hydroxy-1H-indol-3-yl)acetic acid. MS (m/z) 549 [M+H]$^+$.

Example 20

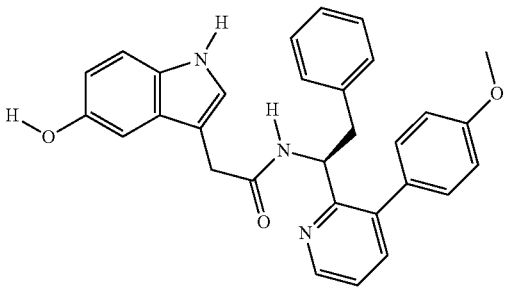

The Synthesis of (S)-2-(5-hydroxy-1H-indol-3-yl)-N-(1-(3-(4-methoxyphenyl)pyridin-2-yl)-2-phenylethyl)acetamide (20)

The title compound was prepared according to the method presented in the synthesis of Example 13 substituting benzylmagnesium chloride for (3,5-difluorobenzyl)magnesium chloride. MS (m/z) 478 [M+H]$^+$.

Example 21

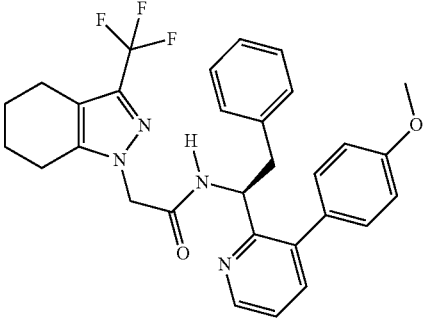

The Synthesis of (S)—N-(1-(3-(4-methoxyphenyl)pyridin-2-yl)-2-phenylethyl)-2-(3-(trifluoromethyl)-4,5,6,7-tetrahydro-1H-indazol-1-yl)acetamide (21)

The title compound was prepared according to the method presented in the synthesis of Example 13 substituting benzylmagnesium chloride for (3,5-difluorobenzyl)magnesium chloride, and 2-(3-(trifluoromethyl)-4,5,6,7-tetrahydro-1H-indazol-1-yl)acetic acid for 2-(5-hydroxy-1H-indol-3-yl)acetic acid. MS (m/z) 535 [M+H]$^+$.

Example 22

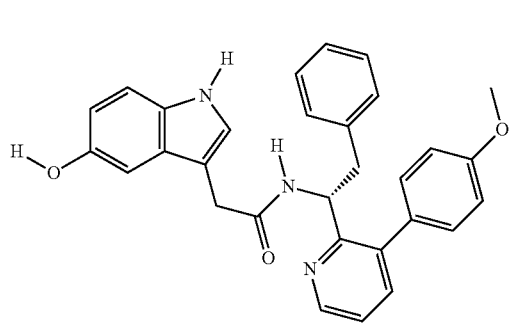

The Synthesis of (R)-2-(5-hydroxy-1H-indol-3-yl)-N-(1-(3-(4-methoxyphenyl)pyridin-2-yl)-2-phenylethyl)acetamide (22)

The title compound was prepared according to the method presented in the synthesis of Example 13 substituting benzylmagnesium chloride for (3,5-difluorobenzyl)magnesium chloride and carrying forward the (S,R) sulfinamide intermediate. MS (m/z) 478 [M+H]$^+$.

Example 23

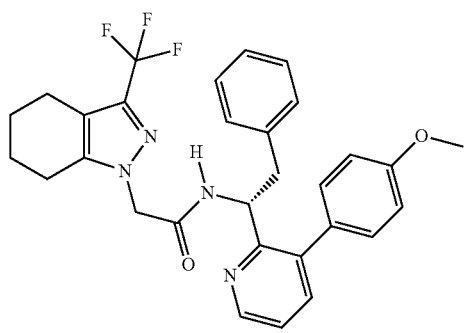

The Synthesis of (R)—N-(1-(3-(4-methoxyphenyl)pyridin-2-yl)-2-phenylethyl)-2-(3-(trifluoromethyl)-4,5,6,7-tetrahydro-1H-indazol-1-yl)acetamide (23)

The title compound was prepared according to the method presented in the synthesis of Example 13 substituting benzylmagnesium chloride for (3,5-difluorobenzyl)magnesium chloride, 2-(3-(trifluoromethyl)-4,5,6,7-tetrahydro-1H-indazol-1-yl)acetic acid for 2-(5-hydroxy-1H-indol-3-yl)acetic acid and carrying forward the (S,R) sulfinamide intermediate. MS (m/z) 535 [M+H]$^+$.

Example 24

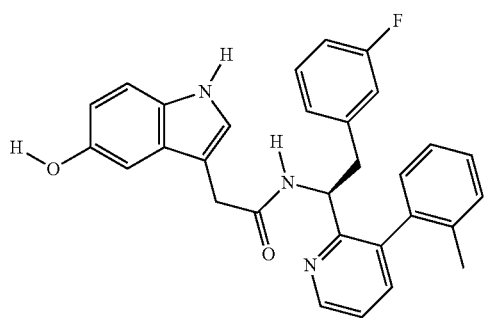

The Synthesis of (S)—N-(2-(3-fluorophenyl)-1-(3-o-tolylpyridin-2-yl)ethyl)-2-(5-hydroxy-1H-indol-3-yl)acetamide (24)

The title compound was prepared according to the method presented in the synthesis of Example 13 substituting o-tolylboronic acid for 4-methoxyphenylboronic acid and (3-fluorobenzyl)magnesium chloride for (3,5-difluorobenzyl)magnesium chloride. MS (m/z) 480 [M+H]$^+$.

Example 25

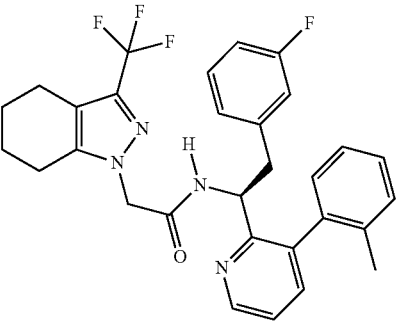

The Synthesis of (S)—N-(2-(3-fluorophenyl)-1-(3-o-tolylpyridin-2-yl)ethyl)-2-(3-(trifluoromethyl)-4,5,6,7-tetrahydro-1H-indazol-1-yl)acetamide (25)

The title compound was prepared according to the method presented in the synthesis of Example 13 substituting o-tolylboronic acid for 4-methoxyphenylboronic acid, (3-fluorobenzyl)magnesium chloride for (3,5-difluorobenzyl)magnesium chloride, and 2-(3-(trifluoromethyl)-4,5,6,7-tetrahydro-1H-indazol-1-yl)acetic acid for 2-(5-hydroxy-1H-indol-3-yl)acetic acid. MS (m/z) 537 [M+H]$^+$.

Example 26

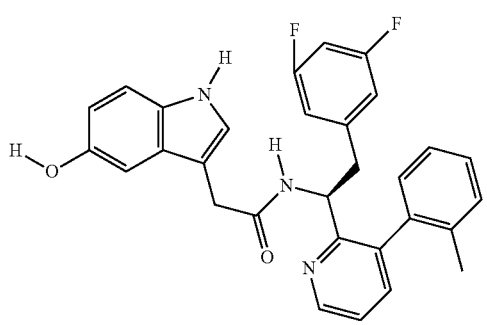

The Synthesis of (S)—N-(2-(3,5-difluorophenyl)-1-(3-o-tolylpyridin-2-yl)ethyl)-2-(5-hydroxy-1H-indol-3-yl)acetamide (26)

The title compound was prepared according to the method presented in the synthesis of Example 13 substituting o-tolylboronic acid for 4-methoxyphenylboronic acid. MS (m/z) 498 [M+H]$^+$.

Example 27

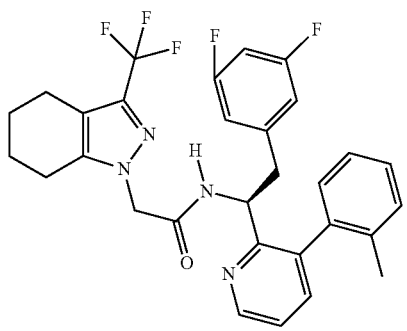

The Synthesis of (S)—N-(2-(3,5-difluorophenyl)-1-(3-o-tolylpyridin-2-yl)ethyl)-2-(3-(trifluoromethyl)-4,5,6,7-tetrahydro-1H-indazol-1-yl)acetamide (27)

The title compound was prepared according to the method presented in the synthesis of Example 13 substituting o-tolylboronic acid for 4-methoxyphenylboronic acid and 2-(3-(trifluoromethyl)-4,5,6,7-tetrahydro-1H-indazol-1-yl) acetic acid for 2-(5-hydroxy-1H-indol-3-yl)acetic acid. MS (m/z) 555 [M+H]$^+$.

Example 28

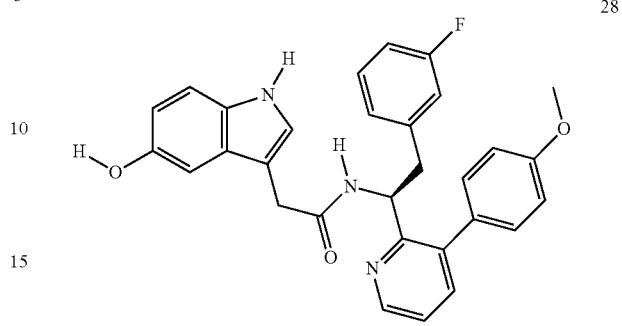

The Synthesis of (S)—N-(2-(3-fluorophenyl)-1-(3-(4-methoxyphenyl)pyridin-2-yl)ethyl)-2-(5-hydroxy-1H-indol-3-yl)acetamide (28)

The title compound was prepared according to the method presented in the synthesis of Example 13 substituting (3-fluorobenzyl)magnesium chloride for (3,5-difluorobenzyl)magnesium chloride. MS (m/z) 496 [M+H]$^+$.

Example 29

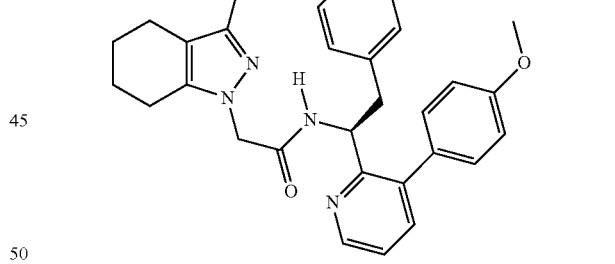

The Synthesis of (S)—N-(2-(3-fluorophenyl)-1-(3-(4-methoxyphenyl)pyridin-2-yl)ethyl)-2-(3-(trifluoromethyl)-4,5,6,7-tetrahydro-1H-indazol-1-yl)acetamide (29)

The title compound was prepared according to the method presented in the synthesis of Example 13 substituting (3-fluorobenzyl)magnesium chloride for (3,5-difluorobenzyl)magnesium chloride, and 2-(3-(trifluoromethyl)-4,5,6,7-tetrahydro-1H-indazol-1-yl)acetic acid for 2-(5-hydroxy-1H-indol-3-yl)acetic acid. MS (m/z) 553 [M+H]$^+$.

Example 30

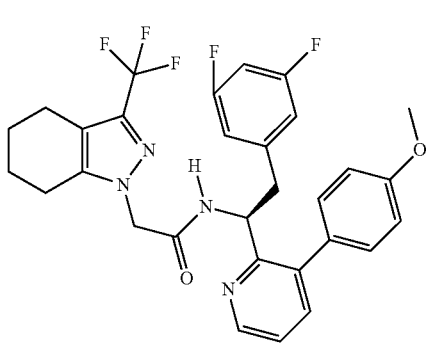

The Synthesis of (S)—N-(2-(3,5-difluorophenyl)-1-(3-(4-methoxyphenyl)pyridin-2-yl)ethyl)-2-(3-(trifluoromethyl)-4,5,6,7-tetrahydro-1H-indazol-1-yl)acetamide (30)

The title compound was prepared according to the method presented in the synthesis of Example 13 substituting 2-(3-(trifluoromethyl)-4,5,6,7-tetrahydro-1H-indazol-1-yl)acetic acid for 2-(5-hydroxy-1H-indol-3-yl)acetic acid. MS (m/z) 571 [M+H]+.

Example 31

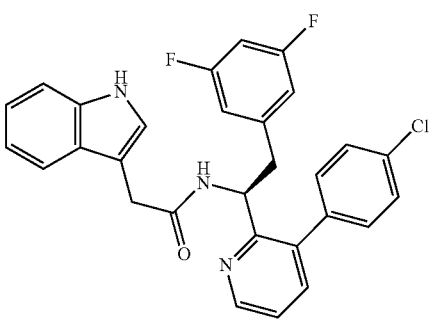

The Synthesis of (S)—N-(1-(3-(4-chlorophenyl)pyridin-2-yl)-2-(3,5-difluorophenyl)ethyl)-2-(1H-indol-3-yl)acetamide (31)

The title compound was prepared according to the method presented in the synthesis of Example 13 substituting 4-chlorophenylboronic acid for 4-methoxyphenylboronic acid and 2-(1H-indol-3-yl)acetic acid for 2-(5-hydroxy-1H-indol-3-yl)acetic acid. MS (m/z) 502 [M+H]+.

Example 32

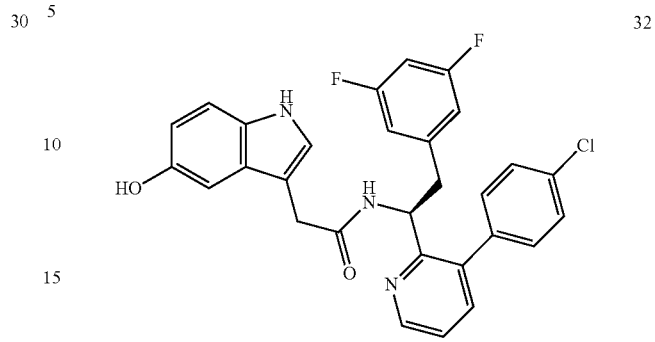

The Synthesis of (S)—N-(1-(3-(4-chlorophenyl)pyridin-2-yl)-2-(3,5-difluorophenyl)ethyl)-2-(5-hydroxy-1H-indol-3-yl)acetamide (32)

The title compound was prepared according to the method presented for the synthesis of Example 19 substituting 4-chlorophenylboronic acid for 4-methoxyphenylboronic acid. MS (m/z) 518 [M+H]+.

Example 33

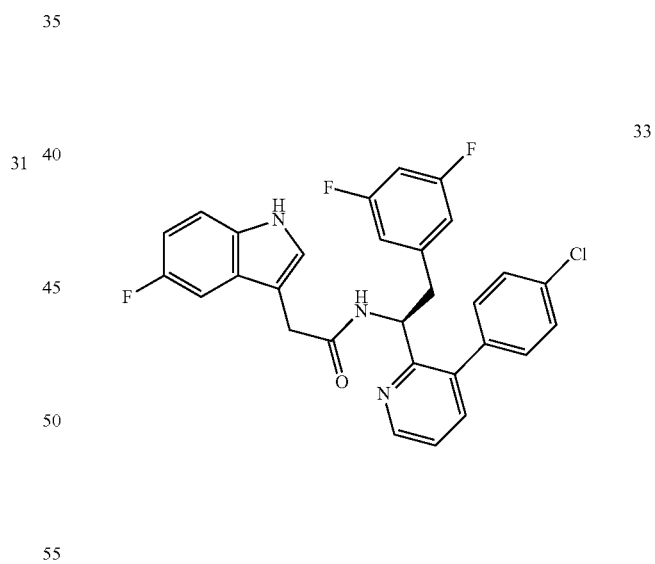

The Synthesis of(S)—N-(1-(3-(4-chlorophenyl)pyridin-2-yl)-2-(3,5-difluorophenyl)ethyl)-2-(5-fluoro-1H-indol-3-yl)acetamide (33)

The title compound was prepared according to the method presented in the synthesis of Example 13 substituting 4-chlorophenylboronic acid for 4-methoxyphenylboronic acid and 2-(5-fluoro-1H-indol-3-yl)acetic acid for 2-(5-hydroxy-1H-indol-3-yl)acetic acid. MS (m/z) 502 [M+H]+.

Example 34

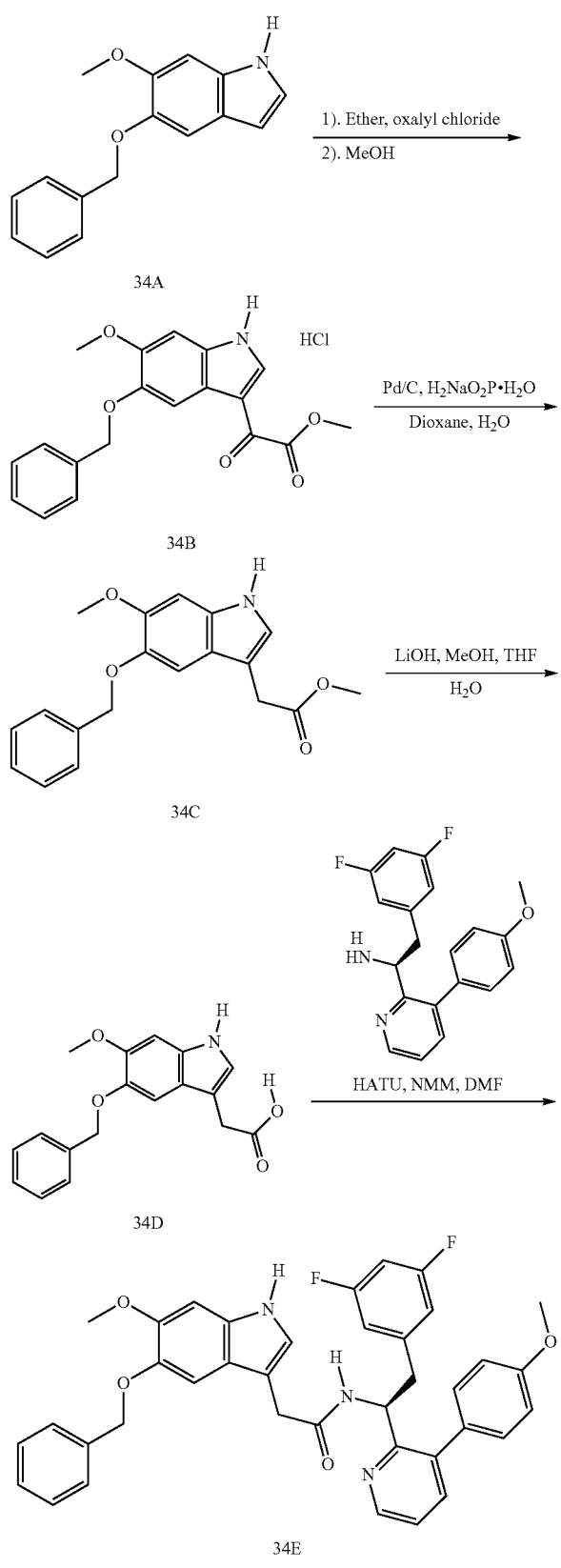

Synthesis of methyl 2-(5-(benzyloxy)-6-methoxy-1H-indol-3-yl)-2-oxoacetate (34B)

A round bottom flask was charged with ether (3 ml) and 5-(benzyloxy)-6-methoxy-1H-indole (34A, 1 g, 3.9 mmol) followed by slow addition of oxalyl chloride (0.34 ml, 3.9 mmol). The reaction was stirred for one minute after complete addition of all reagents then quickly filtered. The cake was soaked in 1 ml methanol after which the methanol was filtered off. This was repeated three times to give a 1200 mg of greenish/yellow colored solid which was used with no further purification. The yield was 82%. MS (m/z) 339.9 $[M+H]^+$.

Synthesis of methyl 2-(5-(benzyloxy)-6-methoxy-1H-indol-3-yl)acetate (34C)

A round bottom is charged with methyl 2-(5-(benzyloxy)-6-methoxy-1H-indol-3-yl)-2-oxoacetate (34B, 1200 mg, 3.2 mmol), dioxane (100 ml), Pd/C (300 mg), $H_2NaO_2P\cdot H_2O$ (3 mg, 28 mmol), and $H_2O$ (40 ml). The resulting mixture was stirred at 95° C. until done as indicated by LC/MS. The reaction mixture was cooled to RT and filtered over a plug of celite, rinsing with ethyl acetate. The layers were partitioned and the organic layer was dried over sodium sulfate, filtered and concentrated to give a solid mixture of benzyl and de-benzylated solid which was used with no further purification. MS (m/z) 325.98 $[M+H]^+$.

Synthesis of 2-(5-(benzyloxy)-6-methoxy-1H-indol-3-yl)acetic acid (34D)

A round bottom flask was charged with methyl 2-(5-(benzyloxy)-6-methoxy-1H-indol-3-yl)acetate (34C, 140 mg, mixture of benzyl and non benzyl), methanol (1 mil), and THF (1 ml). To the resulting mixture was added a solution of LiOH (60 mg, 2.5 mmol) dissolved in water (1 ml). The mixture was stirred until done after which the mixture was diluted with ethyl acetate and the layers separated, the aqueous layer was acidified and extracted 2× with ethyl acetate and the combined organic layers were dried over sodium sulfate, filtered and concentrated to give mixture of both benzyl and non-benzyl products as a solid which was used with no further purification. MS (m/z) 311.92 $[M+H]^+$

Synthesis of (S)-2-(5-(benzyloxy)-6-methoxy-1H-indol-3-yl)-N-(2-(3,5-difluorophenyl)-1-(3-(4-methoxyphenyl)pyridin-2-yl)ethyl)acetamide (34E)

A round bottom flask was charged with 2-(5-(benzyloxy)-6-methoxy-1H-indol-3-yl)acetic acid (66 mg, mixture of benzyl and non-benzyl), DMF (2 ml), N-methyl-morpholine (0.1 ml, 0.9 mmol), HATU (50 mg, 0.13 mmol), and (S)-2-(3,5-difluorophenyl)-1-(3-(4-methoxyphenyl)pyridin-2-yl)ethanamine (34 mg, 0.1 mmol). The mixture was stirred until done as indicated by LC/MS then filtered and purified by HPLC to afford the desired product (3.2 mg, $^1$H NMR ((CD$_3$)$_2$SO, 300 MHz) δ 10.50 (s, 1H), 8.53 (dd, 1H), 8.37 (d, 1H), 7.47 (dd, 1H), 7.41 (d, 2H), 7.35 (t, 2H), 7.30-7.27 (m, 2H), 7.11 (s, 1H), 7.07 (d, 2H), 6.88-6.85 (m, 5H), 6.33 (d, 2H), 5.25 (q, 1H), 4.89 (s, 2H), 3.74 (s, 3H), 3.39 (s, 2H), 2.88 (d, 2H), 2.78 (s, 3H); MS (m/z) 634.4 $[M+H]^+$.

Example 35

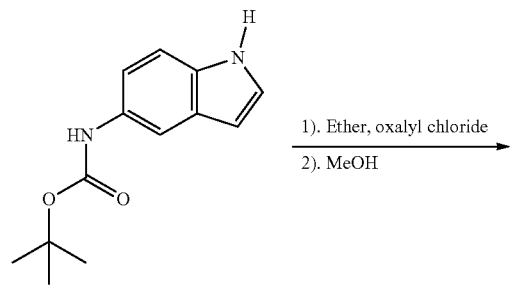

35A

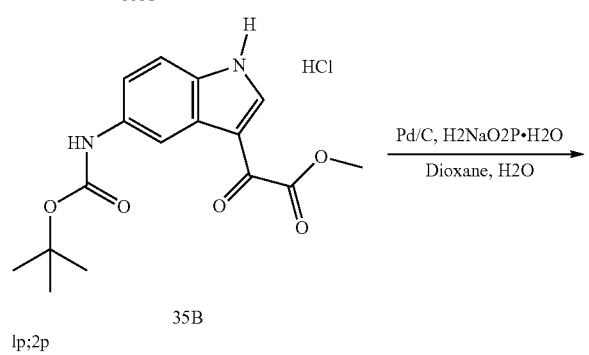

35B

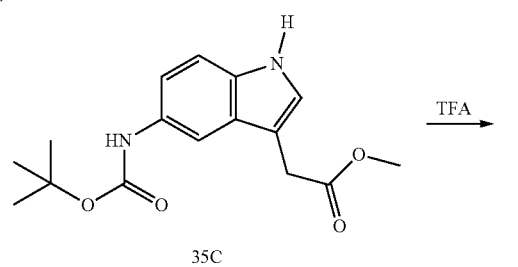

35C

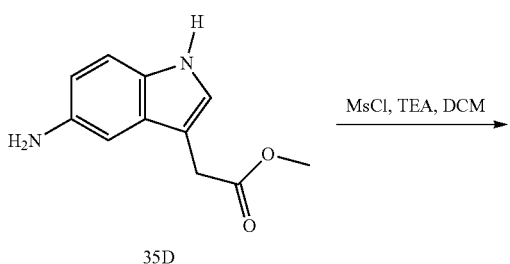

35D

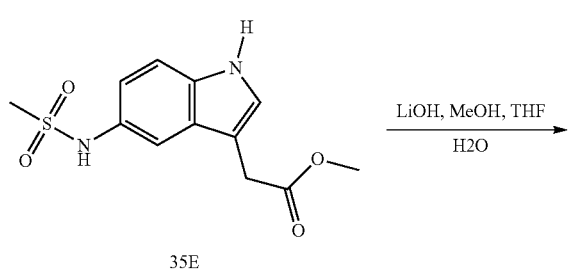

35E

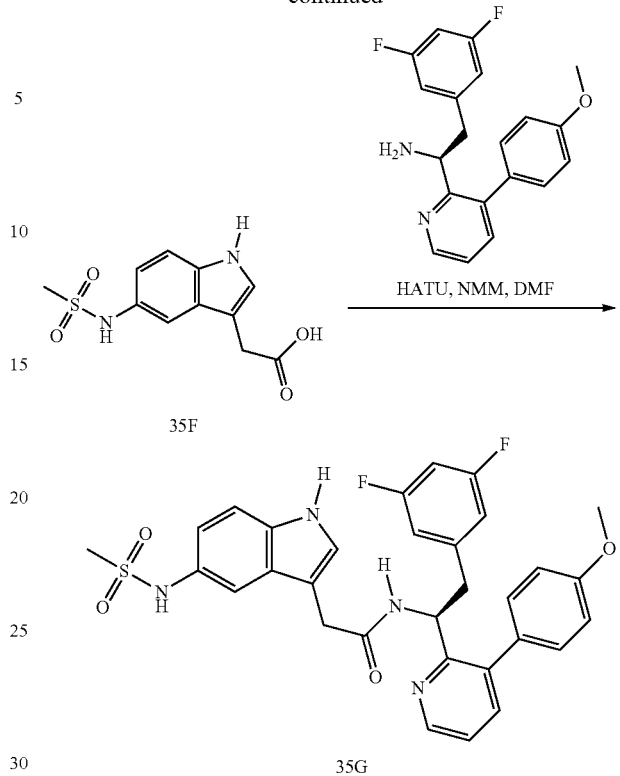

The Synthesis of methyl 2-(5-(tert-butoxycarbonylamino)-1H-indol-3-yl)-2-oxoacetate hydrochloride (35B)

The title compound was prepared according to the method presented in the synthesis of methyl 2-(5-(benzyloxy)-6-methoxy-1H-indol-3-yl)-2-oxoacetate. Treatment of tert-butyl 1H-indol-5-ylcarbamate (10.8 mmol) occurred under the same conditions, adjusted for scale, to afford the desired compound. The yield was 76% as HCl salt. MS (m/z) 319.0 [M+H]$^+$

The Synthesis of methyl 2-(5-(tert-butoxycarbonylamino)-1H-indol-3-yl)acetate (35C)

The title compound was prepared according to the method presented in the synthesis of methyl 2-(5-(benzyloxy)-6-methoxy-1H-indol-3-yl)acetate. Treatment of methyl 2-(5-(tert-butoxycarbonylamino)-1H-indol-3-yl)-2-oxoacetate (7.0 mmol) occurred under the same conditions, adjusted for scale, to afford the desired product. The yield was 69%. MS (m/z) 249.15 [M+H-t-Butyl]$^+$

Synthesis of methyl 2-(5-amino-1H-indol-3-yl)acetate (35D)

A round bottom flask was charged with methyl 2-(5-(tert-butoxycarbonylamino)-1H-indol-3-yl)acetate (1.35 g, 4.4 mmol) and TFA (4 ml). The mixture was stirred until done after which the mixture was concentrated to a light pink oil. The oil was diluted with DCM, sonicated, and filtered to give 1660 mg of white solid which was used with no further purification. The yield was 76%. MS (m/z) 205.15 [M+H]$^+$

Synthesis of methyl 2-(5-(methylsulfonamido)-1H-indol-3-yl)acetate (35E)

A round bottom flask was charged with methyl 2-(5-amino-1H-indol-3-yl)acetate (200 mg, 1 mmol), DCM (3 ml), and TEA (0.43 ml, 3.1 mmol) and cooled to 0° C. To the resulting mixture MsCl (0.04 ml, 0.5 mmol) dissolved in DCM (2 ml) was added drop wise. The mixture was stirred until done after which the mixture was washed with a solution of 10% aqueous citric acid followed by a saturated solution of NaHCO$_3$. The organic layer was dried over sodium sulfate, concentrated by flash chromatography to give 80 mg of solid. The yield was 29%. MS (m/z) 282.9 [M+H]$^+$.

The Synthesis of 2-(5-(methylsulfonamido)-1H-indol-3-yl)acetic acid (35F)

The title compound was prepared according to the method presented in the synthesis of 2-(5-(benzyloxy)-6-methoxy-1H-indol-3-yl)acetic acid. Treatment of methyl 2-(5-(methylsulfonamido)-1H-indol-3-yl)acetate (0.28 mmol) occurred under the same conditions, adjusted for scale, to afford the desired product. The yield was 95%. MS (m/z) 268.8 [M+H]$^+$.

The Synthesis of (S)—N-(2-(3,5-difluorophenyl)-1-(3-(4-methoxyphenyl)pyridin-2-yl)ethyl)-2-(5-(methylsulfonamido)-1H-indol-3-yl)acetamide (35G)

The title compound was prepared according to the method presented in the synthesis of (S)-2-(5-(benzyloxy)-6-methoxy-1H-indol-3-yl)-N-(2-(3,5-difluorophenyl)-1-(3-(4-methoxyphenyl)pyridin-2-yl)ethyl)acetamide. Treatment of 2-(5-(methylsulfonamido)-1H-indol-3-yl)acetic acid (0.14 mmol) occurred under the same conditions, adjusted for scale, to afford the desired product. The mixture was stirred until done by LC/MS then filtered and purified by HPLC to afford the desired product (3.7 mg, 4%): $^1$H NMR ((CD$_3$)$_2$SO, 300 MHz) δ 10.84 (s, 1H), 9.15 (s, 1H), 8.58 (dd, 1H), 8.42 (d, 1H), 7.48 (dd, 1H), 7.36-7.35 (m, 1H), 7.32 (dd, 1H), 7.25 (d, 1H), 7.07 (s, 1H), 7.05 (d, 2H), 6.92 (dd, 1H), 6.87 (d, 3H), 6.32 (d, 2H), 5.24 (q, 1H), 3.74 (s, 3H), 3.47 (s, 2H), 2.89 (d, 2H), 2.78 (s, 3H); MS (m/z) 591.37 [M+H]$^+$.

Examples 36

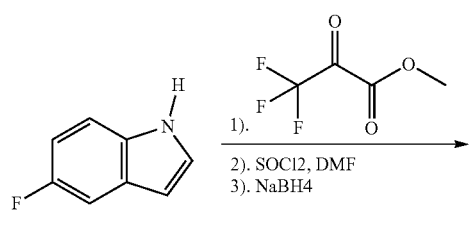

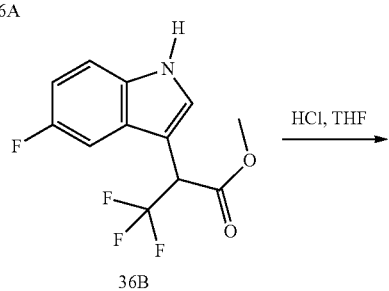

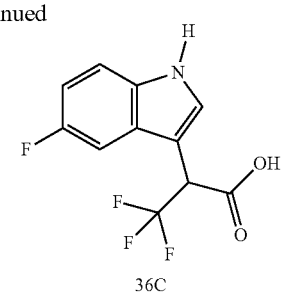

36C

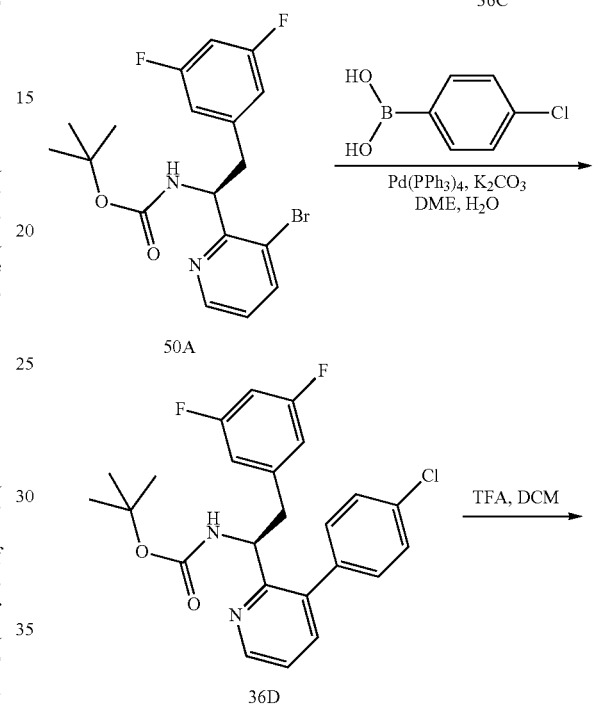

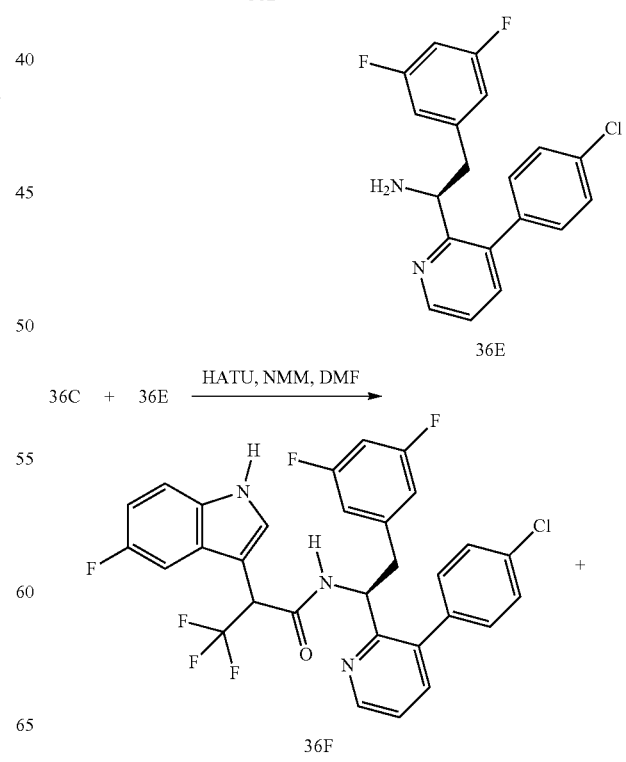

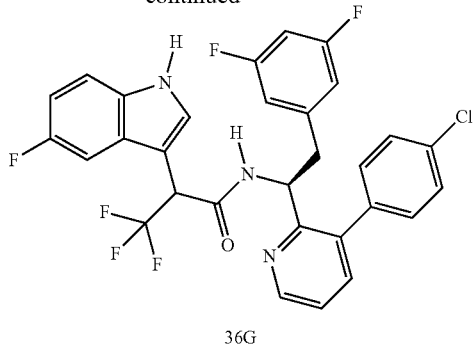

36G

Synthesis of methyl 3,3,3-trifluoro-2-(5-fluoro-1H-indol-3-yl)-2-hydroxypropanoate (36B)

A round bottom flask was charged with 5-fluoro-1H-indole (3000 mg, 22.2 mmol) and methyl 3,3,3-trifluoro-2-oxopropanoate (2.27 ml, 22.2 mmol). The mixture was stirred until done and then diluted with DMF (100 ml), cool to 0° C. and slowly add $SOCl_2$ (4 ml, 55.5 mmol) until peak has shifted by LC/MS. Slowly add $NaBH_4$ (2800 mg, 66.6 mmol) in portions and allow mixture to stir for 3 hours after which the mixture was dumped into stirring saturated $NH_4Cl$ and resulting solids were filtered off and the mother liquor was extracted 2× ethyl acetate. The organic layer was dried over sodium sulfate and concentrated and purified by flash chromatography to yield 2.98 g of the desired compound in a yield of 49%. MS (m/z) 275.9 [M+H]$^+$.

Synthesis of 3,3,3-trifluoro-2-(5-fluoro-1H-indol-3-yl)propanoic acid (36C)

A round bottom flask was charged with methyl 3,3,3-trifluoro-2-(5-fluoro-1H-indol-3-yl)-2-hydroxypropanoate (1000 mg, 3.6 mmol), HCl (4 ml), and THF (2 ml). The mixture was stirred at 95° C. for 3 days and then the cooled solution was extracted with ethyl acetate, the organic layer was extracted with saturated $NaHCO_3$, the aqueous layer was acidified and extract 2× with ethyl acetate and the combined organic layers were dried over sodium sulfate and concentrated to give 210 mg of solid which was used with no further purification. The yield was 22%. MS (m/z) 262.1 [M+H]$^+$.

Synthesis of (S)-tert-butyl 1-(3-(4-chlorophenyl)pyridin-2-yl)-2-(3,5-difluorophenyl)ethylcarbamate (36D)

A round bottom flask was charged with 50A (1 g, 2.4 mmol), DME (40 ml), 4-chlorophenylboronic acid (454 mg, 3 mmol), Pd(PPh$_3$)$_4$ (280 mg, 0.24 mmol) and $K_2CO_3$ (669 mg, 4.8 mmol) dissolved in water (5 ml). The mixture was heated overnight at 85° C. Allow the reaction to cool then dilute with $H_2O$ and extract 2× EtOAc. The combined organic layers were washed with brine then dried over sodium sulfate, concentrated, and purified by flash chromatography to give 692 mg of desired compound. The yield was 64%. MS (m/z) 445.3 [M+H]$^+$.

Synthesis of (S)-1-(3-(4-chlorophenyl)pyridin-2-yl)-2-(3,5-difluorophenyl)ethanamine trifluoroacetate (36E)

A round bottom flask was charged with (S)-tert-butyl 1-(3-(4-chlorophenyl)pyridin-2-yl)-2-(3,5-difluorophenyl)ethylcarbamate (690 mg, 1.6 mmol) and TFA:DCM 1:2.5 (7 ml). The reaction was stirred at room temperature until done by LC/MS then concentrated 2× from DCM. The crude solid was used as is in next reaction. MS (m/z) 345.3 [M+H]$^+$.

Synthesis of Compounds N—((S)-1-(3-(4-chlorophenyl)pyridin-2-yl)-2-(3,5-difluorophenyl)ethyl)-3,3,3-trifluoro-2-(5-fluoro-1H-indol-3-yl)propanamide (36F and 36G)

A 2 dram vial was charged with 36C (200 mg, 0.8 mmol), 36E (240 mg, 0.7 mmol), HATU (351 mg, 0.9 mmol), NMM (0.1 ml, 0.6 mmol) and DMF (6 ml). The mixture was stirred until done by LC/MS then diluted with a 1:1 mixture of TFA:water (0.5 ml), filtered and purified by HPLC to afford the separated diastereomeric products (36F, 52.9 mg, 12%; 36G, 166.1 mg, 37%): 36F $^1$H NMR ((CD$_3$)$_2$SO, 300 MHz) δ 11.27 (s, 1H), 8.98 (dd, 1H), 8.67 (dd, 1H), 7.59 (dd, 1H), 7.47 (d, 2H), 7.41 (dd, 1H), 7.35-7.31 (m, 3H), 7.21 (d, 2H), 6.90 (dt, 1H), 6.69 (dt, 1H), 6.21 (d, 2H), 5.17 (q, 1H), 4.95 (q, 1H), 2.83 (m, 2H); MS (m/z) 588.6 [M+H]$^+$. 36G $^1$H NMR ((CD$_3$)$_2$SO, 300 MHz) δ 11.27 (s, 1H), 8.98 (dd, 1H), 8.51 (dd, 1H), 7.50 (dd, 1H), 7.38-7.28 (m, 6H), 7.05 (d, 2H), 6.96 (dt, 1H), 6.90 (dt, 1H), 6.50 (d, 2H), 5.15 (q, 1H), 4.90 (q, 1H), 3.00-2.98 (m, 2H); MS (m/z) 588.6 [M+H]$^+$.

Example 37

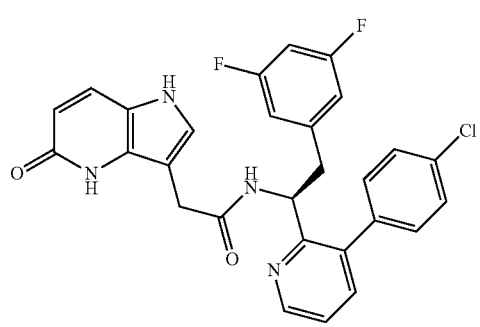

37

The Synthesis of (S)—N-(1-(3-(4-chlorophenyl)pyridin-2-yl)-2-(3,5-difluorophenyl)ethyl)-2-(5-oxo-4,5-dihydro-1H-pyrrolo[3,2-b]pyridin-3-yl)acetamide (37)

The title compound was prepared according to the method presented in the synthesis of Example 13 substituting 4-chlorophenylboronic acid for 4-methoxyphenylboronic acid and 2-(5-oxo-4,5-dihydro-1H-pyrrolo[3,2-b]pyridin-3-yl)acetic acid for 2-(5-hydroxy-1H-indol-3-yl)acetic acid. MS (m/z) 519 [M+H]$^+$.

Example 38

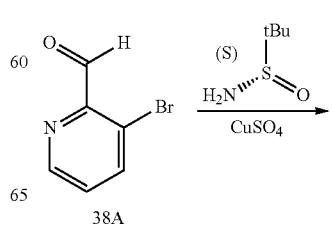

38A

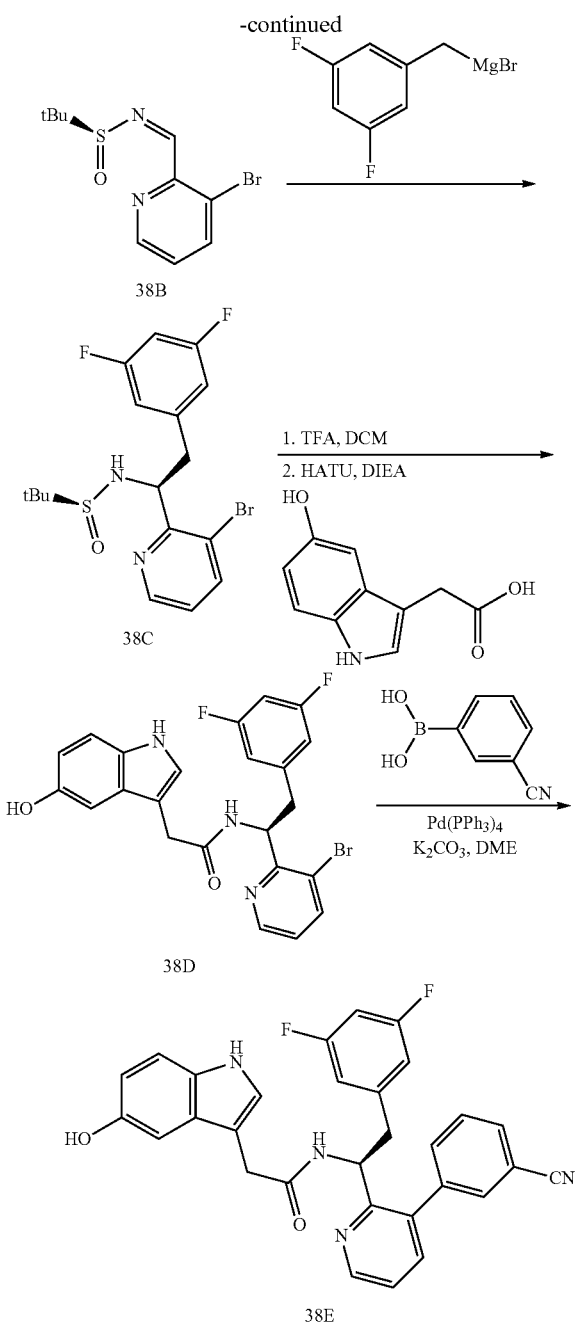

Synthesis of (S)—N-((3-bromopyridin-2-yl)methylene)-2-methylpropane-2-sulfinamide (38B)

The title compound was prepared according to the procedure described in the synthesis of 13C in Example 13 utilizing 3-bromopicolinaldehyde. MS (m/z) 288.9 [M+H]⁺.

Synthesis of (S)—N—((S)-1-(3-bromopyridin-2-yl)-2-(3,5-difluorophenyl)ethyl)-2-methylpropane-2-sulfinamide (38C)

The title compound was prepared according to the procedure described in the synthesis of 13E in Example 13 utilizing 38B. MS (m/z) 417.1 [M+H]⁺.

Synthesis of (S)—N-(1-(3-bromopyridin-2-yl)-2-(3,5-difluorophenyl)ethyl)-2-(5-hydroxy-1H-indol-3-yl)acetamide (38D)

A solution of (S)—N—((S)-1-(3-bromopyridin-2-yl)-2-(3,5-difluorophenyl)ethyl)-2-methylpropane-2-sulfinamide (1 g, 2.4 mmol) in 6 ml of HCl (2N/4 ml of MeOH and 2 ml of 1,4-dioxane) was stirred for 3 hours. The solvent was removed and the crude product was dried by high vacuum. Used without further purification. To a solution of 2-(5-hydroxy-1H-indol-3-yl)acetic acid (304 mg, 1.58 mmol) and DIEA (0.6 ml, 3.32 mmol) in DMF (5 ml), was added HATU (630 mg, 1.66 mmol). After 20 minutes, the crude product from last step in 5 ml of DMF was added to the solution. It was stirred for 2 hours. The DMF solution was removed. Redissolved in 100 ml of EtOAc and washed with NaHCO₃ (aq) and brine. The organic layer was dried over Na₂SO₄, filtered and concentrated. Purified the crude product by flash column (Rf: 0.3 MeOH/DCM=5%). The yield was (486 mg, 1.15 mmol). 48% for two steps. ¹H NMR (d-CD₃OD, 400 MHz) δ 8.36 (d, 1H), 7.9 (d, 1H), 7.11-7.17 (m, 2H), 7.035 (s, 1H), 6.8 (s, 1H), 6.6-6.7 (m, 2H), 6.51-6.53 (m, 2H), 5.73 (t, 1H), 3.57 (s, 2H), 3.0-3.1 (m, 1H), 2.9-39 (m, 1H); MS (m/z) 486 [M+H]⁺.

Synthesis of (S)—N-(1-(3-(3-cyanophenyl)pyridin-2-yl)-2-(3,5-difluorophenyl)ethyl)-2-(5-hydroxy-1H-indol-3-yl)acetamide (38E)

A mixture of (S)—N-(1-(3-bromopyridin-2-yl)-2-(3,5-difluorophenyl)ethyl)-2-(5-hydroxy-1H-indol-3-yl)acetamide (48.7 mg, 0.1 mmol), potassium carbonate (27 mg, 0.2 mmol) in 0.5 ml of water, tetrakis(triphenylphosphine)palladium(0) (8 mg, 0.007 mmol) and 3-cyanophenylboronic acid (0.12 mmol) in DME (1.5 mL) was heated at 120° C. for 30 minutes under microwave irradiation. Solvents were concentrated in vacuo and the residue was purified by RP HPLC using a C18 column to provide the title product: ¹H NMR (d-DMSO, 400 MHz) δ 10.46 (s, 1H), 8.68 (d, 1H), 8.53 (d, 1H), 7.81 (d, 1H), 7.51-7.55 (m, 4H), 7.46 (s, 1H), 7.36-7.38 (m, 1H), 7.05 (s, 1H), 6.89-6.94 (m, 2H), 6.8 (s, 1H), 6.53 (d, 1H), 6.34 (d, 1H), 5.09 (q, 1H), 3.41 (q, 2H), 2.8-3.0 (m, 2H); MS (m/z) 509 [M+H]⁺.

Example 39

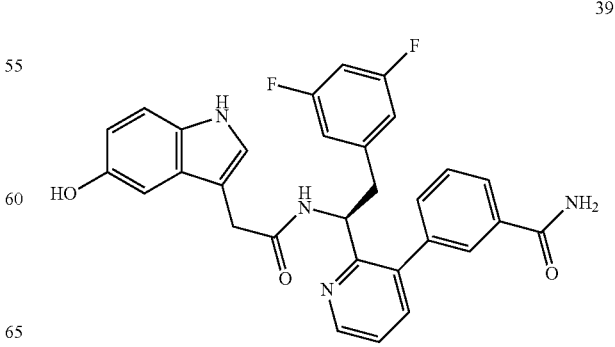

39

The Synthesis of (S)-3-(2-(2-(3,5-difluorophenyl)-1-(2-(5-hydroxy-1H-indol-3-yl)acetamido)ethyl)pyridin-3-yl)benzamide (39)

The title compound was prepared according to the method presented in the synthesis of Example 38 substituting 3-carbamoylphenylboronic acid for 3-cyanophenylboronic acid. MS (m/z) 527 [M+H]$^+$.

Example 40

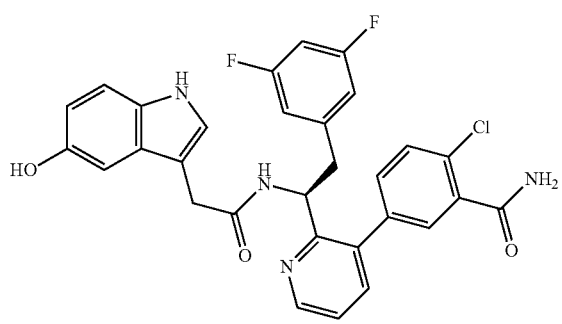

The Synthesis of (S)-2-chloro-5-(2-(2-(3,5-difluorophenyl)-1-(2-(5-hydroxy-1H-indol-3-yl)acetamido)ethyl)pyridin-3-yl)benzamide (40)

The title compound was prepared according to the method presented in the synthesis of Example 38 substituting 3-carbamoyl-4-chlorophenylboronic acid for 3-cyanophenylboronic acid. MS (m/z) 561 [M+H]$^+$.

Example 41

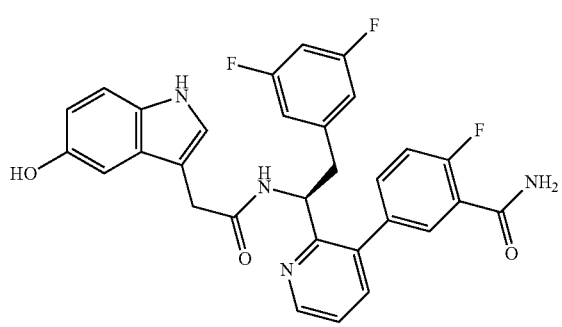

The Synthesis of (S)-5-(2-(2-(3,5-difluorophenyl)-1-(2-(5-hydroxy-1H-indol-3-yl)acetamido)ethyl)pyridin-3-yl)-2-fluorobenzamide (41)

The title compound was prepared according to the method presented in the synthesis of Example 38 substituting 3-carbamoyl-4-fluorophenylboronic acid for 3-cyanophenylboronic acid. MS (m/z) 545 [M+H]$^+$.

Example 42

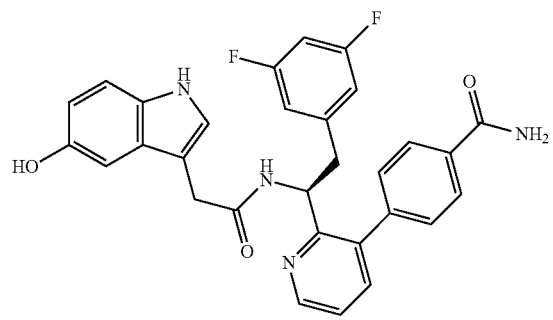

The Synthesis of (S)-4-(2-(2-(3,5-difluorophenyl)-1-(2-(5-hydroxy-1H-indol-3-yl)acetamido)ethyl)pyridin-3-yl)benzamide (42)

The title compound was prepared according to the method presented in the synthesis of Example 38 substituting 4-carbamoylphenylboronic acid for 3-cyanophenylboronic acid. MS (m/z) 527 [M+H]$^+$.

Example 43

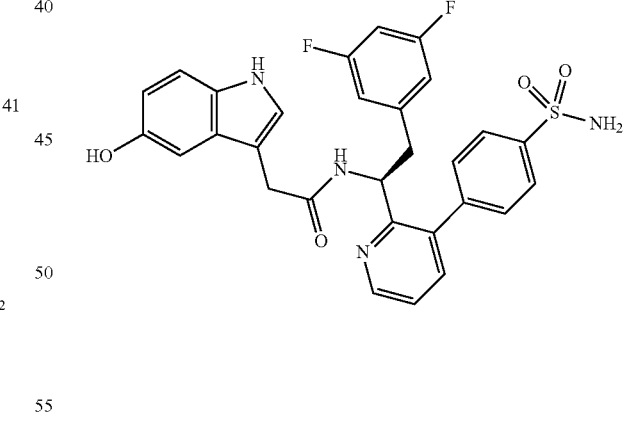

The Synthesis of (S)—N-(2-(3,5-difluorophenyl)-1-(3-(4-sulfamoylphenyl)pyridin-2-yl)ethyl)-2-(5-hydroxy-1H-indol-3-yl)acetamide (43)

The title compound was prepared according to the method presented in the synthesis of Example 38 substituting 4-sulfamoylphenylboronic acid for 3-cyanophenylboronic acid. MS (m/z) 563 [M+H]$^+$.

Example 44

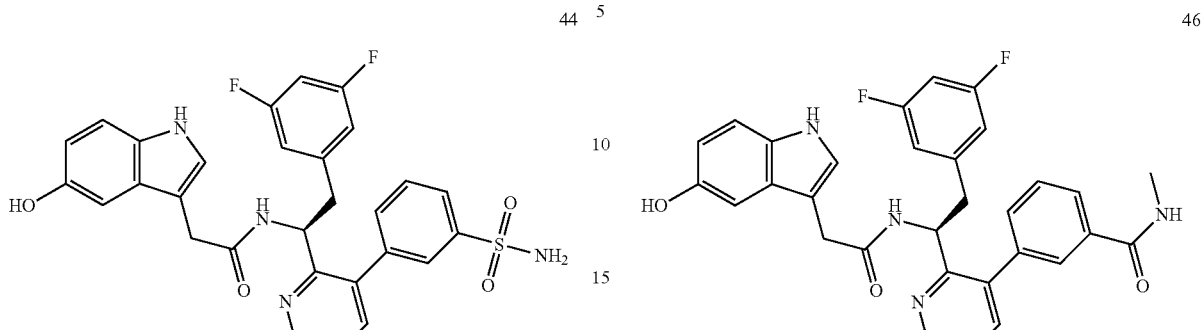

The Synthesis of (S)—N-(2-(3,5-difluorophenyl)-1-(3-(3-sulfamoylphenyl)pyridin-2-yl)ethyl)-2-(5-hydroxy-1H-indol-3-yl)acetamide (44)

The title compound was prepared according to the method presented in the synthesis of Example 38 substituting 3-sulfamoylphenylboronic acid for 3-cyanophenylboronic acid. MS (m/z) 563 [M+H]$^+$.

Example 45

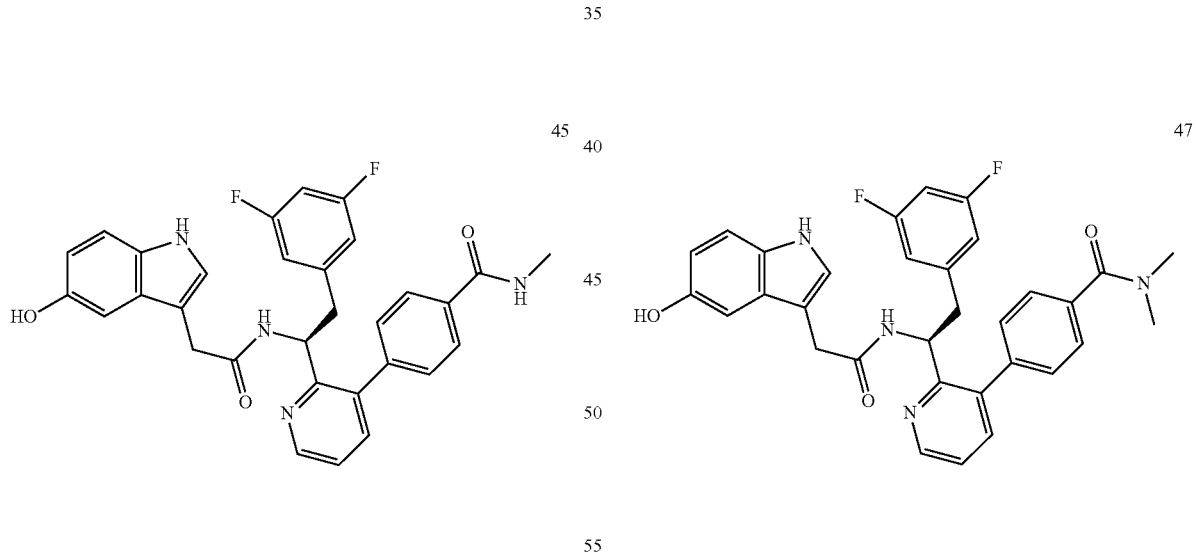

The Synthesis of (S)-4-(2-(2-(3,5-difluorophenyl)-1-(2-(5-hydroxy-1H-indol-3-yl)acetamido)ethyl)pyridin-3-yl)-N-methylbenzamide (45)

The title compound was prepared according to the method presented in the synthesis of Example 38 substituting 4-(methylcarbamoyl)phenylboronic acid for 3-cyanophenylboronic acid. MS (m/z) 540 [M+H]$^+$.

Example 46

The Synthesis of (S)-3-(2-(2-(3,5-difluorophenyl)-1-(2-(5-hydroxy-1H-indol-3-yl)acetamido)ethyl)pyridin-3-yl)-N-methylbenzamide (46)

The title compound was prepared according to the method presented in the synthesis of Example 38 substituting 3-(methylcarbamoyl)phenylboronic acid for 3-cyanophenylboronic acid. MS (m/z) 540 [M+H]$^+$.

Example 47

The Synthesis of (S)-4-(2-(2-(3,5-difluorophenyl)-1-(2-(5-hydroxy-1H-indol-3-yl)acetamido)ethyl)pyridin-3-yl)-N,N-dimethylbenzamide (47)

The title compound was prepared according to the method presented in the synthesis of Example 38 substituting 4-(dimethylcarbamoyl)phenylboronic acid for 3-cyanophenylboronic acid. MS (m/z) 555 [M+H]$^+$.

Example 48

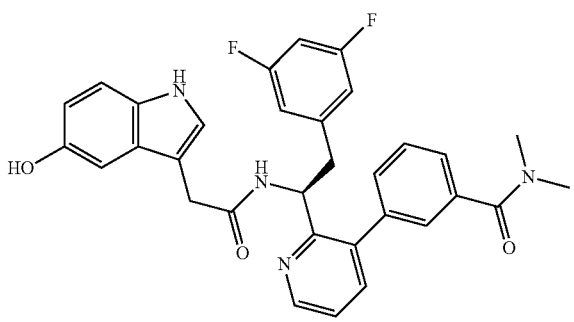

The Synthesis of (S)-3-(2-(2-(3,5-difluorophenyl)-1-(2-(5-hydroxy-1H-indol-3-yl)acetamido)ethyl)pyridin-3-yl)-N,N-dimethylbenzamide (48)

The title compound was prepared according to the method presented in the synthesis of Example 38 substituting 3-(dimethylcarbamoyl)phenylboronic acid for 3-cyanophenylboronic acid. MS (m/z) 555 [M+H]+.

Example 49

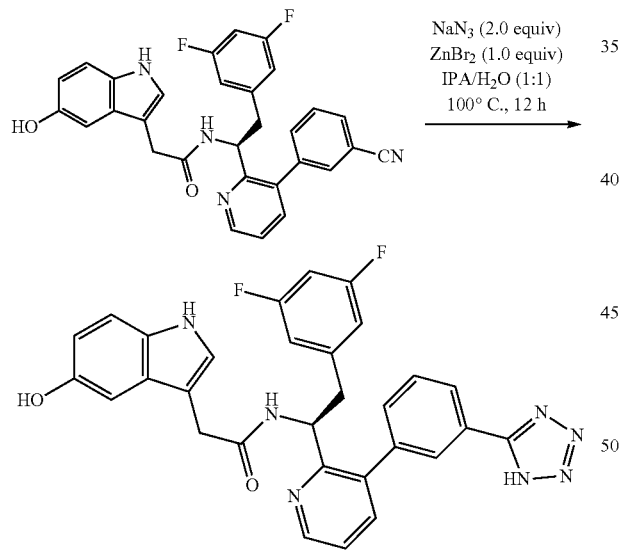

The Synthesis of S)—N-(1-(3-(3-(1H-tetrazol-5-yl)phenyl)pyridin-2-yl)-2-(3,5-difluorophenyl)ethyl)-2-(5-hydroxy-1H-indol-3-yl)acetamide (49)

To a solution of (S)—N-(1-(3-(3-cyanophenyl)pyridin-2-yl)-2-(3,5-difluorophenyl)ethyl)-2-(5-hydroxy-1H-indol-3-yl)acetamide (10 mg, 0.02 mmol) in a mixture of 1 mL isopropanol and 1 mL water in a 5 mL microwave tube was added ZnBr2 (4.5 mg, 0.02 mmol) and NaN3 (2.6 mg, 0.04 mmol) at room temperature. The tube was sealed and the mixture was heated at 100° C. overnight. After the completion of the reaction, the mixture was purified by reverse phase HPLC to afford the desired product (3.4 mg, 0.006 mmol); MS (m/z): 552.1 [M+H]+.

Example 50

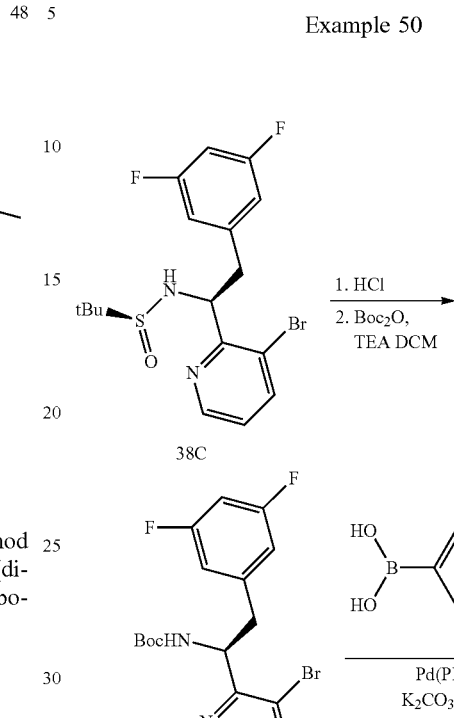

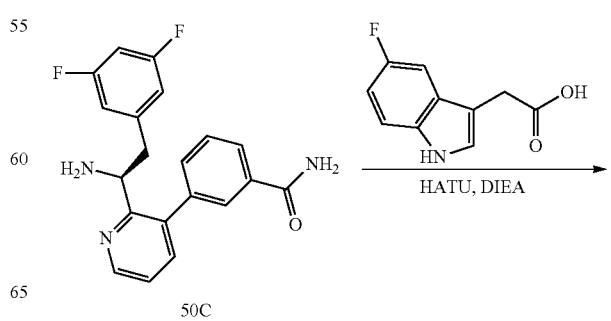

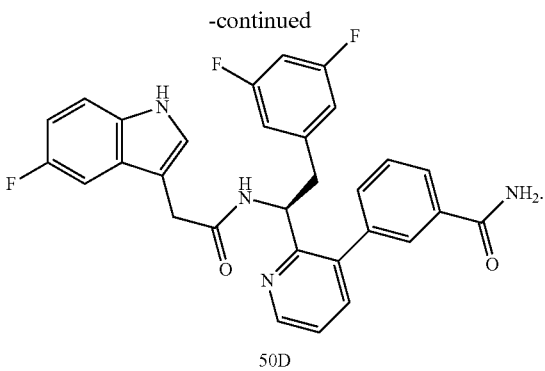

50D

Synthesis of (S)-tert-butyl 1-(3-bromopyridin-2-yl)-2-(3,5-difluorophenyl)ethylcarbamate (50A)

Mixed 1.5M HCl/MeOH (2 ml) and 4N HCl/1,4-dioxane (1.0 ml) together. Added the resulting solution to the N—((S)-1-(3-bromopyridin-2-yl)-2-(3,5-difluorophenyl) ethyl)-2-methylpropane-2-sulfinamide (1.02 g, 2.44 mmol). After 10 min, concentrated reaction mixture in vacuo. Co-evaporated residue with Et₂O until material became a solid. Collected solid by filtration. Suspended solids (702 mg, 2.01 mmol) in CH₂Cl₂. Di-tert-butyl dicarbonate (482 mg, 2.21 mmol) was added to the suspension followed by triethylamine (560 µl, 4.02 mmol). Stirred reaction at room temperature for 30 min. Concentrated reaction in vacuo. Partitioned residue between EtOAc and H₂O. Extracted aqueous layer 2× with EtOAc. Washed combined organics with brine. Dried organics over MgSO₄, filtered and concentrated. Purified residue on 40 g SiO₂ column using EtOAc/hex (rf=0.47 in 20% EtOAc/hex.). Combined pure fractions and concentrated. Dried solid on high vacuum for 3 hrs. The yield was 736 mg.

Synthesis of (S)-tert-butyl 1-(3-(3-carbamoylphenyl)pyridin-2-yl)-2-(3,5-difluorophenyl)ethylcarbamate (50B)

Dissolved (S)-tert-butyl 1-(3-bromopyridin-2-yl)-2-(3,5-difluorophenyl)ethylcarbamate (736 mg, 1.78 mmol) and 3-carbamoylphenylboronic (352 mg, 2.14 mmol) in 1,2-dimethoxyethane. Added 0.4N aq. K₂CO₃ (515 µl, 3.56 mmol) and degassed reaction by evacuation and purge with N₂ (3×). Added Pd(PPh₃)₄ (206 mg, 0.178 mmol) and degassed again. Heated reaction at 80° C. overnight. LC/MS of reaction mixture shows complete conversion to product. Filtered cooled reaction mixture through celite, washing with EtOAc. Partitioned filtrate between EtOAc and H₂O. Extracted aqueous layer 2× with EtOAc. Washed combined organics with brine. Dried organics over MgSO₄, filtered and concentrated. Purified residue on 40 g SiO₂ column using EtOAc/hex (rf=0.25 in 50% EtOAc/hex.) Combined pure fractions and concentrated. Dried solid on high vacuum for 3 hrs. The yield was 750 mg. $^1$H NMR (400 MHz, CDCl₃) δ 8.64 (dd, J=4.7, 1.5 Hz, 1H), 7.96 (d, J=7.7 Hz, 1H), 7.72 (s, 2H), 7.43 (dd, J=16.4, 8.6 Hz, 2H), 7.24 (s, 1H), 6.83 (d, J=7.4 Hz, 1H), 6.50 (t, J=9.0 Hz, 1H), 6.06 (d, J=6.2 Hz, 2H), 5.79 (s, 1H), 5.67 (s, 1H), 5.39 (m, 1H), 2.93 (m, 2H), 1.42 (s, 9H).

Synthesis of (S)-3-(2-(1-amino-2-(3,5-difluorophenyl)ethyl)pyridin-3-yl)benzamide trifluoroacetate (50C)

(S)-tert-butyl 1-(3-(3-carbamoylphenyl)pyridin-2-yl)-2-(3,5-difluorophenyl)ethylcarbamate (750 mg, 1.65 mmol) was dissolved in 5 ml CH₂Cl₂. To the solution was added 5 ml of trifluoroacetic acid. The reaction was stirred at room temperature for 30 min. Concentrated reaction mixture in vacuo. Dried resulting solid on high vacuum overnight. The yield was 759 mg.

Synthesis of (S)-3-(2-(2-(3,5-difluorophenyl)-1-(2-(5-fluoro-1H-indol-3-yl)acetamido)ethyl)pyridin-3-yl)benzamide (50D)

Combined (S)-3-(2-(1-amino-2-(3,5-difluorophenyl) ethyl)pyridin-3-yl)benzamide trifluoroacetate (133 mg, 0.285 mmol) 2-(5-fluoro-1H-indol-3-yl)acetic acid (50 mg, 0.259 mmol), and HATU (108 mg, 0.285 mmol) in 20 ml vial. Added DMF and stirred to dissolve the solids. Added diisopropylethylamine (135 µl, 0.77 mmol) and stirred reaction at room temperature for 90 min. Purified reaction mixture on prep reverse phase HPLC using 20-80% B (A=0.1% TFA/H₂O; B=0.1% TFA/ACN). Combined pure fractions as determined by LC/MS and lyophilized. The yield was 98 mg. $^1$H NMR (400 MHz, d-DMSO) δ 10.89 (s, 1H), 8.66 (m, 2H), 7.95 (s, 1H), 7.86 (d, 1H), 7.73 (s, 1H), 7.62 (dd, 1H), 7.44 (m, 4H), 7.22 (dd, 1H), 7.10 (m, 2H), 6.84 (m, 2H), 6.47 (d, 2H), 5.73 (broad), 5.19 (m, 1H), 3.44 (d, 2H), 2.94 (m, 2H); MS (m/z) 529 [M+H]⁺.

Example 51

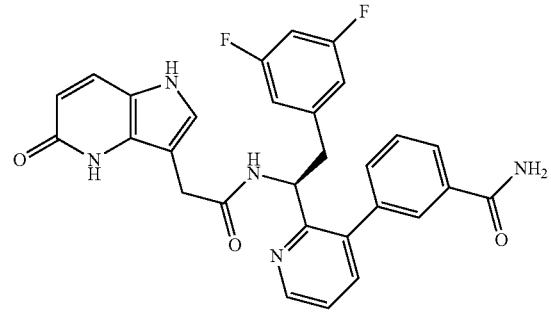

51

The Synthesis of (S)-3-(2-(2-(3,5-difluorophenyl)-1-(2-(5-oxo-4,5-dihydro-1H-pyrrolo[3,2-b]pyridin-3-yl)acetamido)ethyl)pyridin-3-yl)benzamide (51)

The title compound was prepared according to the method presented for the synthesis of Example 50 substituting 2-(5-oxo-4,5-dihydro-1H-pyrrolo[3,2-b]pyridin-3-yl)acetic acid for 2-(5-fluoro-1H-indol-3-yl)acetic acid. MS (m/z) 528 [M+H]⁺.

Example 52

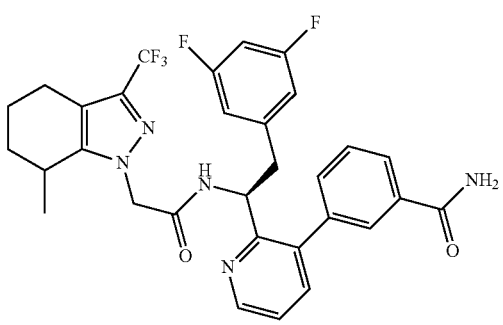

52

The Synthesis of 3-(2-((1S)-2-(3,5-difluorophenyl)-1-(2-(7-methyl-3-(trifluoromethyl)-4,5,6,7-tetrahydro-1H-indazol-1-yl)acetamido)ethyl)pyridin-3-yl)benzamide (52)

The title compound was prepared according to the method presented for the synthesis of Example 50 substituting 2-(7-methyl-3-(trifluoromethyl)-4,5,6,7-tetrahydro-1H-indazol-1-yl)acetic acid for 2-(5-fluoro-1H-indol-3-yl)acetic acid. MS (m/z) 598 [M+H]$^+$.

Example 53

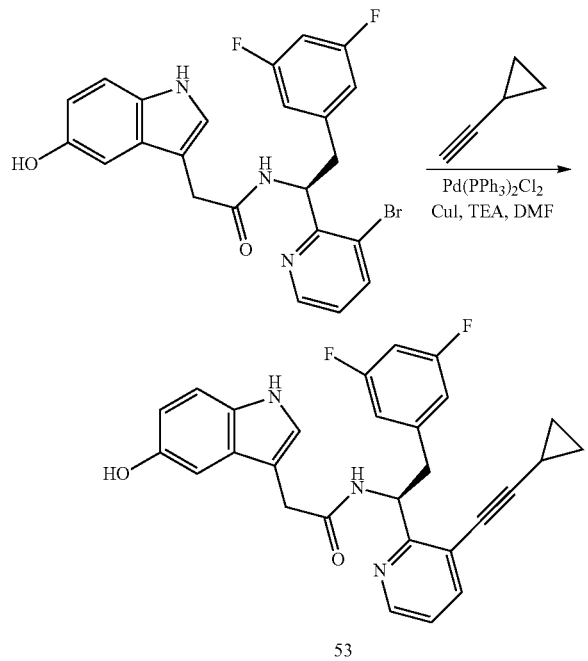

53

Synthesis of (S)—N-(1-(3-(cyclopropylethynyl)pyridin-2-yl)-2-(3,5-difluorophenyl)ethyl)-2-(5-hydroxy-1H-indol-3-yl)acetamide (53)

To a solution of (S)—N-(1-(3-bromopyridin-2-yl)-2-(3,5-difluorophenyl)ethyl)-2-(5-hydroxy-1H-indol-3-yl)acetamide (97.4 mg, 0.2 mmol), bis(triphenylphosphine)dichloro palladium (15 mg, 0.021 mmol), copper(I) iodide (4 mg, 0.o21 mmol) in DMF (0.36 ml) and triethylamine (0.6 ml), ethynylcyclopropane (20.8 mg, 0.315 mmol) was added to the solution. It was heated at 120° C. for 120 minutes under microwave irradiation. Solvents were concentrated in vacuo and the residue was purified by RP HPLC using a C18 column with a gradient of H$_2$O, 0.1% TFA-acetonitrile, to provide the desired product. $^1$H NMR (d-DMSO, 400 MHz) δ 10.46 (s, 1H), 8.48 (d, 1H), 8.25 (d, 1H), 7.66 (d, 1H), 7.2-7.3 (m, 1H), 7.1-7.2 (d, 1H), 6.9-7.0 (m, 2H), 6.78 (s, 1H), 6.65-6.75 (m, 2H), 6.53 (d, 1H), 5.56 (q, 1H), 3.41 (q, 2H), 2.8-3.0 (m, 2H), 1.5-1.6 (m, 1H), 1.8-1.9 (m, 2H), 1.6-1.7 (m, 2H); MS (m/z) 472 [M+H]$^+$

Example 54

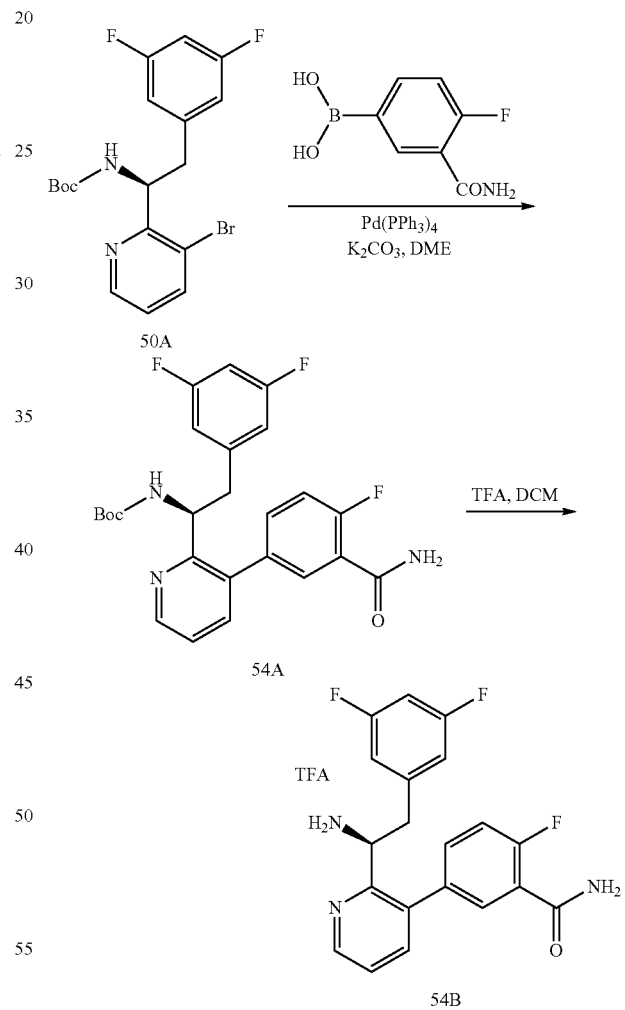

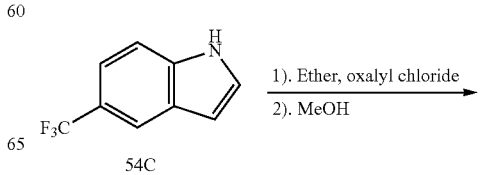

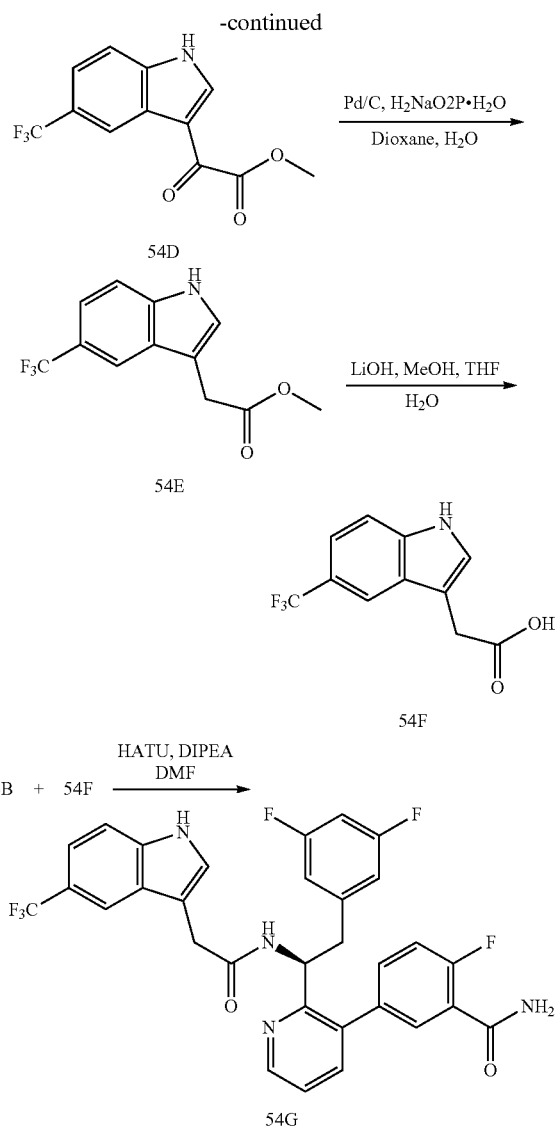

Synthesis of (S)-tert-butyl 1-(3-(3-carbamoyl-4-fluorophenyl)pyridin-2-yl)-2-(3,5-difluorophenyl)ethylcarbamate (54A)

A round bottom flask was charged with 50A (3 g, 7.3 mmol), DME (100 ml), 3-carbamoyl-4-fluorophenylboronic acid (1.6 g, 8.7 mmol), Pd(PPh$_3$)$_4$ (419 mg, 0.36 mmol) and K$_2$CO$_3$ (2 g, 14.5 mmol) dissolved in water (12 ml). Heat the stirring mixture overnight at 85° C. Allow the reaction to cool then dilute with H$_2$O and extract 2× EtOAc. The combined organic layers were washed with brine then dried over sodium sulfate, concentrated, and purified by flash chromatography to give the title compound (1.8 g, 53%): MS (m/z) 472.6 [M+H]$^+$.

Synthesis of (S)-5-(2-(1-amino-2-(3,5-difluorophenyl)ethyl)pyridin-3-yl)-2-fluorobenzamide triflouroacetate (54B)

A round bottom flask was charged with (S)-tert-butyl 1-(3-(3-carbamoyl-4-fluorophenyl)pyridin-2-yl)-2-(3,5-difluorophenyl)ethylcarbamate (1 g, 2.2 mmol) and TFA:DCM 1:1 (4 ml). The reaction was stirred at room temperature until complete disappearance of starting materials then concentrated 2× from DCM. The crude solid was used as is in next reaction: MS (m/z) 372.4 [M+H]$^+$.

Synthesis of methyl 2-oxo-2-(5-(trifluoromethyl)-1H-indol-3-yl)acetate (54D)

A round bottom flask was charged with ether (2 ml) and 5-(trifluoromethyl)-1H-indole (3 g, 16.2 mmol) followed by slow addition of oxalyl chloride (3 ml, 34 mmol). The reaction was stirred for 15 minutes after complete addition of all reagents then filtered. The cake was rinsed with ether then soaked in 6 ml methanol after which the methanol was filtered off (repeated 3 times). Drying under vacuum gave 3 g of the desired compound as the HCl salt which was used with no further purification. The yield was 60%. MS (m/z) 272.1 [M+H]$^+$.

Synthesis of methyl 2-(5-(trifluoromethyl)-1H-indol-3-yl)acetate (54E)

A round bottom is charged with methyl 2-oxo-2-(5-(trifluoromethyl)-1H-indol-3-yl)acetate (3 g, 9.8 mmol), dioxane (200 ml), Pd/C (1 g), H$_2$NaO$_2$P—H$_2$O (6 g, 57 mmol), and H$_2$O (18 ml). The resulting mixture was stirred at 125° C. until complete disappearance of starting material. The reaction mixture was cooled to RT and filtered over a plug of celite, rinsing with ethyl acetate. The layers were partitioned and the organic layer was dried over sodium sulfate, filtered, concentrated and purified by flash chromatography to give the desired compound (1.3 g, 50%): MS (m/z) 258.1 [M+H]$^+$.

Synthesis of 2-(5-(trifluoromethyl)-1H-indol-3-yl)acetic acid (54F)

A round bottom flask was charged with methyl 2-(5-(trifluoromethyl)-1H-indol-3-yl)acetate (1.4 g, 5.3 mmol), methanol (2 ml), and THF (6 ml). To the resulting mixture was added a solution of LiOH (638 mg, 27 mmol) dissolved in water (2 ml). The mixture was stirred until done after which the mixture was diluted with ethyl acetate and the layers separated, the aqueous layer was acidified and extracted 2× with ethyl acetate and the combined organic layers were dried over sodium sulfate, filtered and concentrated to give the desired compound (1.3 g. 99%): MS (m/z) 244.1 [M+H]$^+$.

Synthesis of (S)-5-(2-(2-(3,5-difluorophenyl)-1-(2-(5-(trifluoromethyl)-1H-indol-3-yl)acetamido)ethyl)pyridin-3-yl)-2-fluorobenzamide (54G)

A 2 dram vial was charged with 54F (25 mg, 0.13 mmol), 54B (50 mg, 0.13 mmol), HATU (50 mg, 0.13 mmol), DiPEA (0.1 ml, 0.6 mmol) and DMF (1.5 ml). The mixture was stirred until done by LC/MS then diluted with a 1:1 mixture of TFA:water (0.5 ml), filtered and purified by HPLC to afford the desired compound (16.8 mg, 28%): $^1$H NMR (400 MHz, dmso) δ 11.24 (s, 1H), 8.70 (d, 1H), 8.63 (dd, 1H), 7.80 (s, 1H), 7.63 (d, 2H), 7.56 (dd, 1H), 7.50-7.42 (m, 2H), 7.37 (dd, 2H), 7.31-7.17 (m, 3H), 6.82 (t, 1H), 6.48 (d, 2H), 5.14 (dd, 1H), 3.52 (s, 2H), 2.96 (d, 2H); MS (m/z) 597.6 [M+H]$^+$.

Example 55

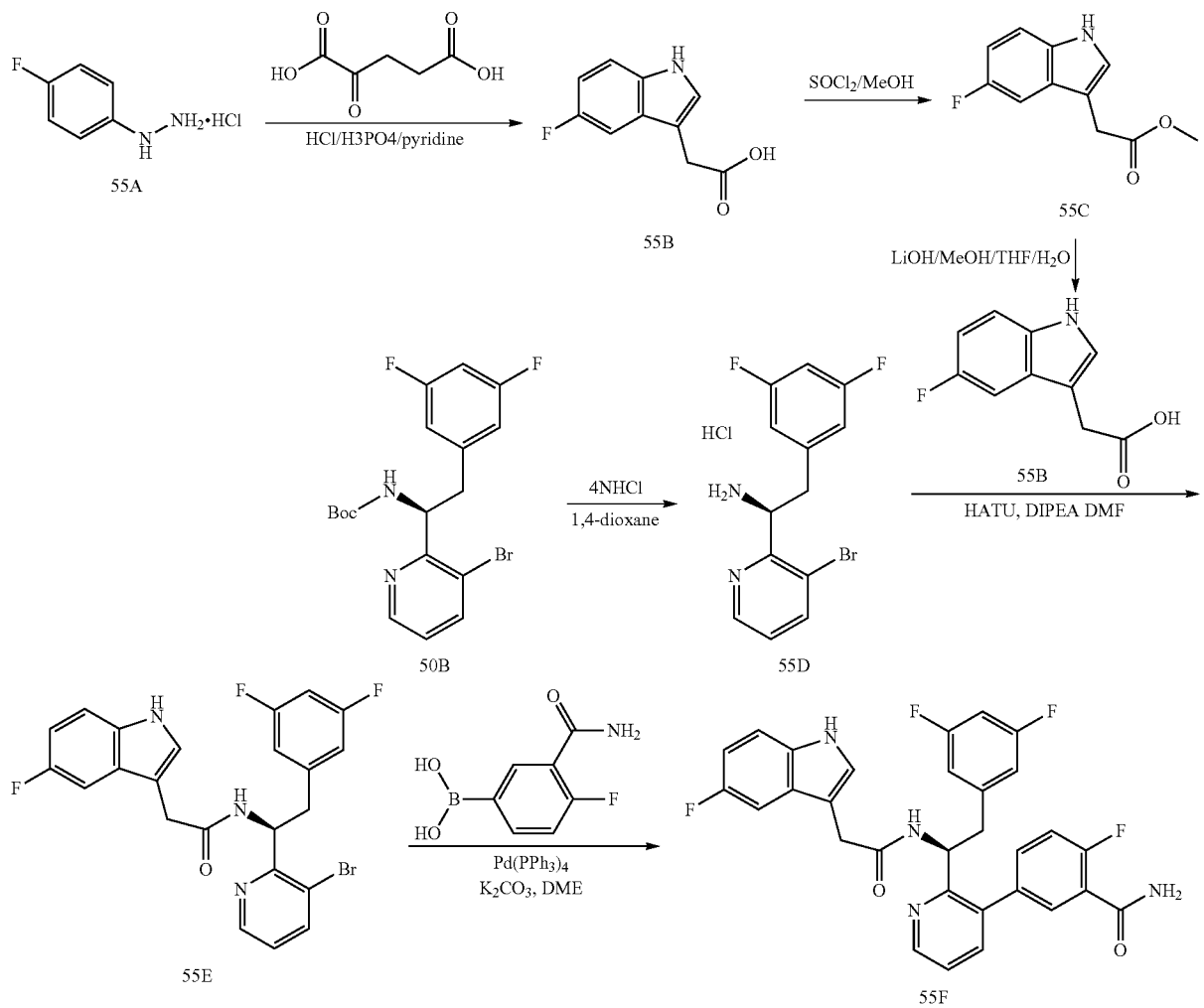

Synthesis of 2-(5-fluoro-1H-indol-3-yl)acetic acid (55B)

To a suspension of 55A (140 g, 861 mmol, 1.0 eq), alpha-ketoglutaric acid (151 g, 1.03 mol) in conc. HCl (1500 mL) and H$_3$PO$_4$ (600 mL) was added dropwise pyridine (450 mL) while keeping the temperature below 10° C. After addition, the suspension was refluxed for 4 hours. Upon cooling, the mixture was extracted with ether (1000 mL 5). The combined organic layer was dried with anhydrous Na$_2$SO$_4$, concentrated to afford 120 g of crude title compound as a blackish green solid, which was used for the next step without any further purification.

Synthesis of Methyl 2-(5-fluoro-1H-indol-3-yl)acetate (55C)

To a suspension of 55B (130 g, crude) in MeOH (1000 mL) was added dropwise SOCl$_2$ (120 g, 1.00 mol) while keeping the temperature below 10° C. After addition, the suspension was refluxed for 3 hours. After cooling and concentration, the residue was diluted with DCM (1000 mL) and H$_2$O (500 mL). The organic layer was washed with saturated NaHCO$_3$ solution, dried and concentrated. The residue was purified by silica chromatography (PE/EtOAc from 50/1 to 10/1) to afford 20.5 g of the title compound as a pale solid.

Synthesis of 2-(5-fluoro-1H-indol-3-yl)acetic acid (55B) by Saponification

Compound 55B was saponified by a method analogous to Example 74C.

Synthesis of(S)-1-(3-bromopyridin-2-yl)-2-(3,5-difluorophenyl)ethanamine hydrochloride (55D)

Dissolved 50B (4.4 g, 10.7 mmol) in 20 ml 4N HCl/1,4-dioxane. The reaction was stirred for 1 hr at room temperature then concentrated in vacuo. Azeotroped residue 3× with Et$_2$O, then dried under vacuum to give 3.7 g of the title compound as an off white solid.

Synthesis of (S)—N-(1-(3-bromopyridin-2-yl)-2-(3,5-difluorophenyl)ethyl)-2-(5-fluoro-1H-indol-3-yl)acetamide (55E)

Dissolved 55B (151 mg, 0.780 mmol) and 55E (300 mg, 0.858 mmol) in DMF (8 ml) Diisoproplyethylamine (791 ul, 2.57 mmol) and HATU (326 mg, 0.858 mmol) were added and the reaction was stirred at room temperature overnight. The reaction was partitioned between EtOAc and H₂O. The aqueous layer was extracted 2×EtOAc. The combined organics were washed 2× brine, dried and concentrated. Purified crude product on SiO₂ eluting with EtOAc/hexanes. Concentration of the purified fractions gave 373 mg of the title compound. MS (m/z) 488.7 [M+H]⁺.

Synthesis of (S)-5-(2-(2-(3,5-difluorophenyl)-1-(2-(5-fluoro-1H-indol-3-yl)acetamido)ethyl)pyridin-3-yl)-2-fluorobenzamide (55)

To a solution of 55E (50 mg, 0.102 mmol) and 4-fluoro-3carbamoyl phenylboronic acid (21 mg, 0.113 mmol) in DME (1 ml) was added 0.4N aq. K₂CO₃ (515 ul) and Pd(PPh₃)₄ (11.9 mg, 0.0010 mmol). The resulting mixture was heated at 110° C. for 10 min. in a microwave. The reaction mixture was filtered, washed 1× with DMF and the solution was purified by RP HPLC using a C18 column with a gradient of 0.1%/H₂O, 0.1% TFA-acetonitrile, to provide 37 mg of the title compound. ¹H NMR (400 MHz, dmso) δ 10.87 (s, 1H), 8.81-8.53 (m, 2H), 7.66 (d, 2H), 7.56 (d, 1H), 7.47 (dd, 1H), 7.39-7.32 (m, 1H), 7.30-7.17 (m, 2H), 7.15-7.04 (m, 2H), 6.83 (ddd, 2H), 6.51 (d, 2H), 5.12 (dd, 1H), 3.51-3.31 (m, 2H), 2.98 (dd, 2H). MS (m/z) 547 [M+H]⁺.

Example 56

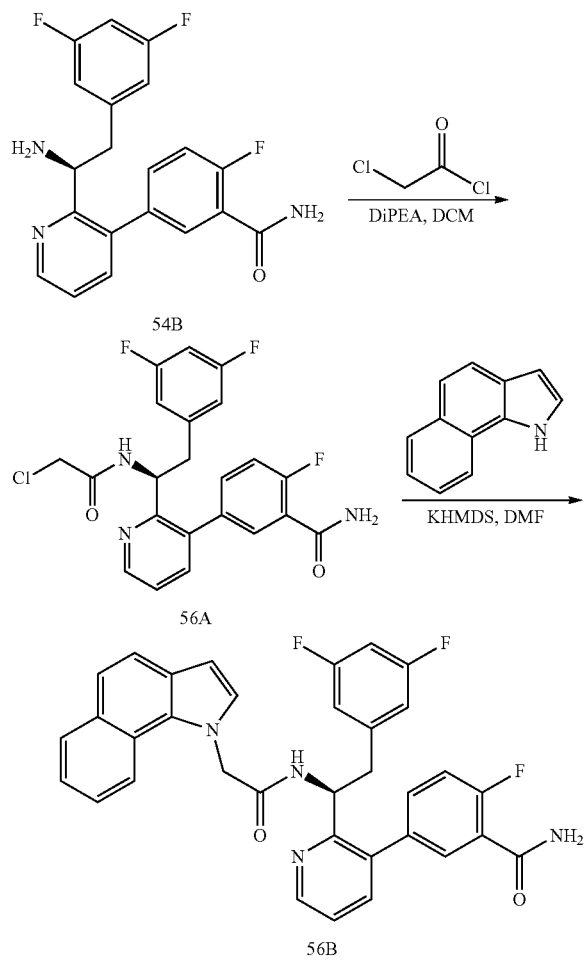

Synthesis of (S)-5-(2-(1-(2-chloroacetamido)-2-(3,5-difluorophenyl)ethyl)pyridin-3-yl)-2-fluorobenzamide (56A)

A round bottom flask was charged with (S)-5-(2-(1-amino-2-(3,5-difluorophenyl)ethyl)pyridin-3-yl)-2-fluorobenzamide (800 mg, 7.7 mmol), DCM (20 ml), and DiPEA (0.8 ml, 4.6 mmol). To the stirring mixture slowly add 2-chloroacetyl chloride (0.16 ml, 2 mmol) and allow to stir 30 minutes then quench with H₂O. Extract 2×DCM The combined organic layers were dried over sodium sulfate, concentrated, and purified by flash chromatography to give the desired compound (460 mg, 61%): MS (m/z) 448.5 [M+H]⁺.

Synthesis of (S)-5-(2-(1-(2-(1H-benzo[g]indol-1-yl)acetamido)-2-(3,5-difluorophenyl)ethyl)pyridin-3-yl)-2-fluorobenzamide (56B)

A 2 dram vial was charged with 1H-benzo[g]indole (11.7 mg, 0.07 mmol), KHMDS (13.9 mg, 0.07 mmol), and DMF (1.5 ml). The resulting mixture was stirred for 10 minutes then (S)-5-(2-(1-(2-chloroacetamido)-2-(3,5-difluorophenyl)ethyl)pyridin-3-yl)-2-fluorobenzamide (30 mg, 0.07 mmol) was added. The mixture was stirred until done by LC/MS then diluted with a 1:1 mixture of TFA:water (0.5 ml), filtered and purified by HPLC to afford the desired compound (5.4 mg, 13%): ¹H NMR (400 MHz, dmso) δ 9.09 (d, 1H), 8.73 (d, 1H), 7.91 (d, 1H), 7.85 (d, 1H), 7.57 (dd, 4H), 7.40 (dd, 3H), 7.29 (d, 3H), 7.19 (dd, 2H), 6.93 (s, 1H), 6.51 (d, 3H), 5.25 (s, 2H), 5.16 (d, 1H), 3.02 (d, 2H); MS (m/z) 579.8 [M+H]⁺.

Example 57

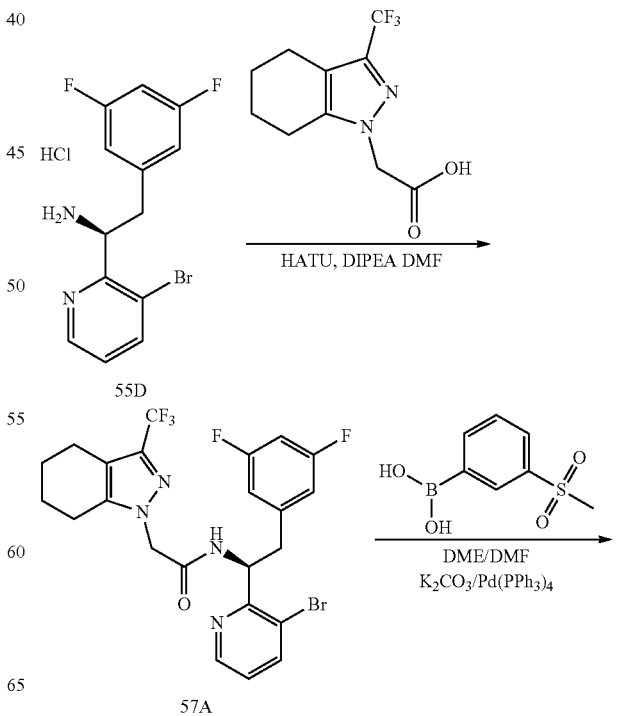

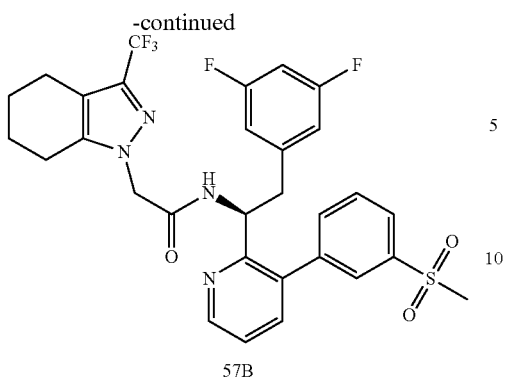

57B

Synthesis of(S)—N-(1-(3-bromopyridin-2-yl)-2-(3,5-difluorophenyl)ethyl)-2-(3-(trifluoromethyl)-4,5,6,7-tetrahydro-1H-indazol-1-yl)acetamide (57A)

To a solution of 55D (3.73 g, 10.7 mmol) and diisopropylethylamine (5.07 ml, 29.1 mmol) was added 2-(3-(trifluoromethyl)-4,5,6,7-tetrahydro-1H-indazol-1-yl)acetic acid (2.41 g, 9.71 mmol) and 2-(1H-7-Azabenzotriazol-1-yl)-1,1,3,3-tetramethyl uronium hexafluorophosphate (HATU, 3.69 g, 9.71 mmol). The reaction mixture was stirred 16 hrs at room temperature and then concentrated under reduce pressure. The residue was dissolved in hot $CH_2Cl_2$ and filtered to remove insoluble material. The filtrate was reheated and allowed to cool. The solid that formed was collected by filtration, washed with hexanes and air dried. The mother liquors were concentrated and the residue was recyrstallized from EtOAc/hexanes. Recovered a total of 4.2 g of the title compound. MS (m/z) 544.7 $[M+H]^+$.

Synthesis of (S)—N-(2-(3,5-difluorophenyl)-1-(3-(3-(methylsulfonyl)phenyl)pyridin-2-yl)ethyl)-2-(3-(trifluoromethyl)-4,5,6,7-tetrahydro-1H-indazol-1-yl)acetamide (57B)

Dissolved 57A (49.4 mg, 0.091 mmol) and 3-methylsulfonylphenyl boronic acid (20 mg, 0.1 mmol) in 4:1 DMEDMF (1 ml). Added 2N aq. $K_2CO_3$ (100 ul) and $Pd(PPh_3)_4$ (12 mg, 0.01 mmol) and then heated the reaction at 100° C. under $N_2$ for 16 hrs. The reactions were cooled, diluted with $H_2O$ and extracted with EtOAc (2×). The organic layer was concentrated under reduced pressure. The residue was purified by RP HPLC using a C18 column with a gradient of 0.1%/$H_2O$, 0.1% TFA-acetonitrile to give 2.6 mg of the title compound. MS (m/z) 619 $[M+H]^+$.

Example 58

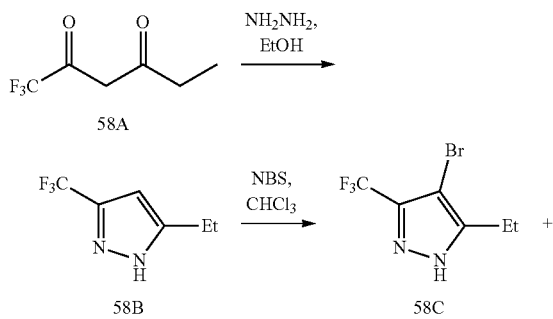

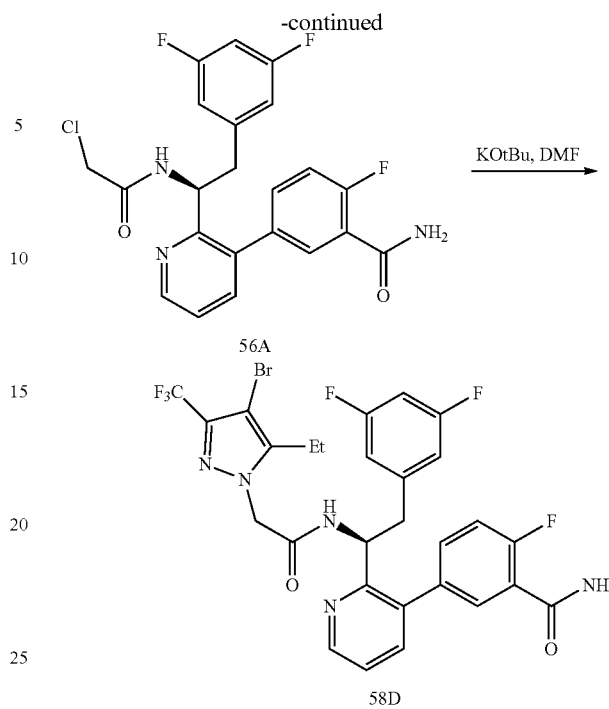

Synthesis of 5-ethyl-3-(trifluoromethyl)-1H-pyrazole (58B)

To a solution of 1,1,1-trifluorohexane-2,4-dione (8.4 g, 50 mmol) in EtOH (100 mL) was slowly added hydrazine hydrate (5.0 g, 50 mmol). The reaction was stirred at room temperature for 1 h and then heated to reflux for 1 h. The reaction was cooled to room temperature and the solvent was removed in vacuo to give 8 g of the title compound. MS (m/z): 165.0 $[M+H]^+$; HPLC retention time 0.77 min (2-98% acetonitrile:water with 0.05% trifluoroacetic acid).

Synthesis of 4-bromo-5-ethyl-3-(trifluoromethyl)-1H-pyrazole (58C)

To a solution of 5-ethyl-3-(trifluoromethyl)-1H-pyrazole (3.3 g, 20 mmol) in $CHCl_3$ (100 mL) was added NBS (4.3 g, 24 mmol). The reaction was stirred at room temperature overnight and was then poured into ethyl acetate and washed with saturated $Na_2S_2O_3$ solution and brine. The organic layer was dried over sodium sulfate, filtered and concentrated. The resulting residue was purified by silica gel chromatography eluting with EtOAc/hexanes to afford 4.8 g of the title product. MS (m/z): 243.1 $[M+H]^+$; HPLC retention time 0.98 min (2-98% acetonitrile:water with 0.05% trifluoroacetic acid).

Synthesis of (S)-5-(2-(1-(2-(4-bromo-5-ethyl-3-(trifluoromethyl)-1H-pyrazol-1-yl)acetamido)-2-(3,5-difluorophenyl)ethyl)pyridin-3-yl)-2-fluorobenzamide (58D)

To a solution of 4-bromo-5-ethyl-3-(trifluoromethyl)-1H-pyrazole (290 mg, 1.2 mmol) in DMF (5 mL) was added potassium tert-butoxide (168 mg, 1.5 mmol) at room temperature. After stirred at rt for 10 min, (S)-5-(2-(1-(2-chloroacetamido)-2-(3,5-difluorophenyl)ethyl)pyridin-3-yl)-2-fluorobenzamide (447 mg, 1 mmol) was added in one portion. The reaction was stirred at room temperature for 1 h and was then poured into ethyl acetate and washed with saturated NH₄Cl solution and brine. The organic layer was dried over sodium sulfate, filtered and concentrated. The resulting residue was purified by silica gel chromatography eluting with EtOAc/hexanes to afford 430 mg of the title product. MS (m/z): 656.1 [M+H]⁺; HPLC retention time 1.22 min (2-98% acetonitrile:water with 0.05% trifluoroacetic acid). ¹H NMR (400 MHz, cdcl₃) δ 8.56 (s, 1H), 7.61 (d, J=5.1 Hz, 1H), 7.50 (s, 1H), 7.31 (s, 1H), 7.29-7.13 (m, 3H), 6.75 (s, 1H), 6.55 (s, 1H), 6.12 (d, J=6.4 Hz, 2H), 5.79 (s, 1H), 5.43 (d, J=7.4 Hz, 1H), 4.79 (d, J=3.5 Hz, 2H), 2.87 (m, 2H), 2.65 (q, J=7.6 Hz, 2H), 1.09 (t, J=7.6 Hz, 3H).

Example 59

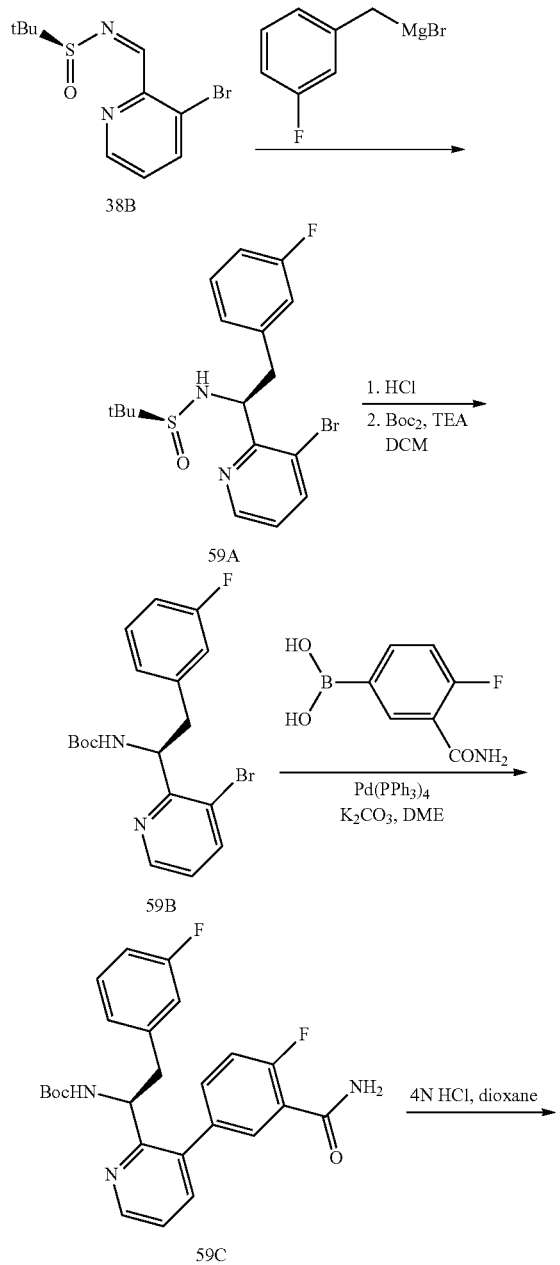

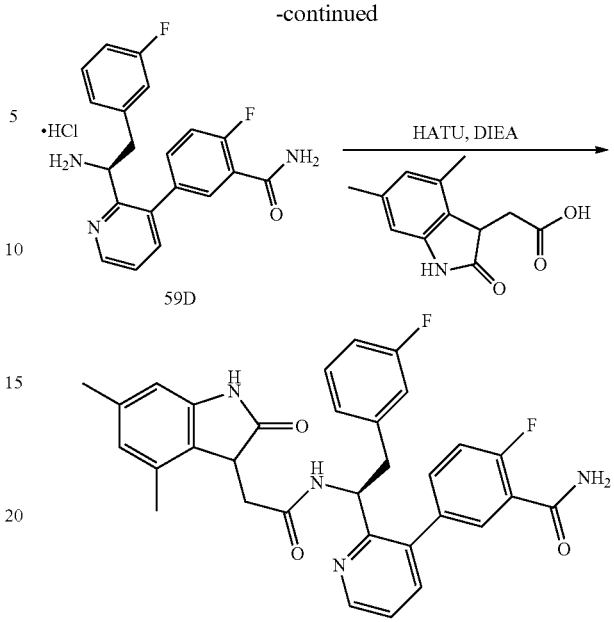

Synthesis of (S)—N—((S)-1-(3-bromopyridin-2-yl)-2-(3-fluorophenyl)ethyl)-2-methylpropane-2-sulfinamide (59A)

Compound 59A was prepared according to the method presented for the synthesis of Example 38 substituting (3-fluorobenzyl)magnesium chloride for (3,5-difluorobenzyl)magnesium bromide and 38B to provide of 1.2 g of title compound. MS (m/z) 399 [M+H]⁺.

Synthesis of (S)-tert-butyl (1-(3-bromopyridin-2-yl)-2-(3-fluorophenyl)ethyl) carbamate (59B)

Compound 59B was prepared according to the method presented for the synthesis of Example 50 substituting 59A for 38C to provide 0.5 g of title compound: MS (m/z) 395 [M+H]⁺.

Synthesis of (S)-tert-butyl (1-(3-(3-carbamoyl-4-fluorophenyl)pyridin-2-yl)-2-(3-fluorophenyl)ethyl) carbamate (59C)

Compound 59C was prepared according to the method presented for the synthesis of Example 50 utilizing 59B for 50A and (3-carbamoyl-4-fluorophenyl)boronic acid to provide 450 mg of title compound: MS (m/z) 454 [M+H]⁺.

Synthesis of (S)-5-(2-(1-amino-2-(3-fluorophenyl) ethyl)pyridin-3-yl)-2-fluorobenzamide hydrochloride (59D)

4N HCl/1,4-dioxane (5.0 ml) was added to 59C (0.45 g, 10 mmol). LC/Mass showed completion of reaction after 10 min. Concentrated reaction mixture in vacuo to give 360 mg of title compound: MS (m/z) 354 [M+H]⁺.

Synthesis of 5-(2-((1S)-1-(2-(4,6-dimethyl-2-oxoindolin-3-yl)acetamido)-2-(3-fluorophenyl)ethyl)pyridin-3-yl)-2-fluorobenzamide (59E)

Combined 59D (36 mg, 0.1 mmol), 2-(4,6-dimethyl-2-oxoindolin-3-yl)acetic acid (22 mg, 0.1 mmol) and HATU (38 mg, 0.1 mmol) in 1 ml vial. Added DMF and stirred to dissolve the solids. Added diisopropylethylamine (45 ul, 0.26 mmol) and stirred reaction at room temperature for 90 min. LC/MS shows desired product with a small amount of acid. Purified reaction mixture on prep reverse phase HPLC using 20-80% B over 20 min. (A=0.1% TFA/H$_2$O; B=0.1% TFA/Acetonitrile). Combined pure fractions as determined by LC/MS and lyophilized to provide 35 mg of title compound. $^1$H NMR (400 MHz, cd$_3$od) δ 8.63 (ddd, 2H), 7.67 (dd, 1H), 7.58 (dd, 1H), 7.51-7.09 (m, 8H), 7.14 (s, 1H), 7.16-6.95 (m, 3H), 6.81 (dd, 2H), 6.69 (d, 2H), 6.57 (d, 2H), 6.53-6.32 (m, 4H), 5.27 (dd, 2H), 3.95 (d, 2H), 3.05-2.76 (m, 6H), 2.76-2.59 (m, 3H), 2.34 (s, 1H), 2.24 (d, 51H), 2.14 (d, 5H); MS (m/z) 555 [M+H]$^+$.

Example 60

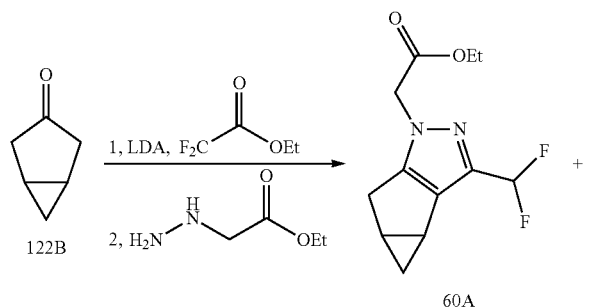

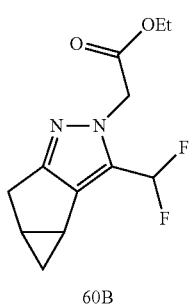

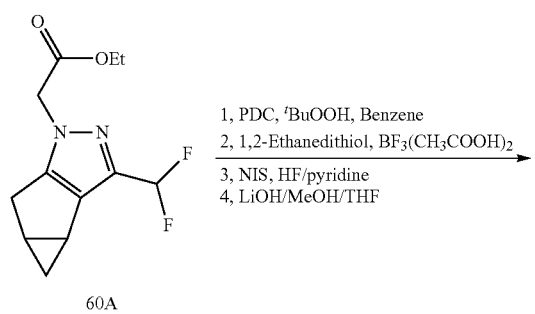

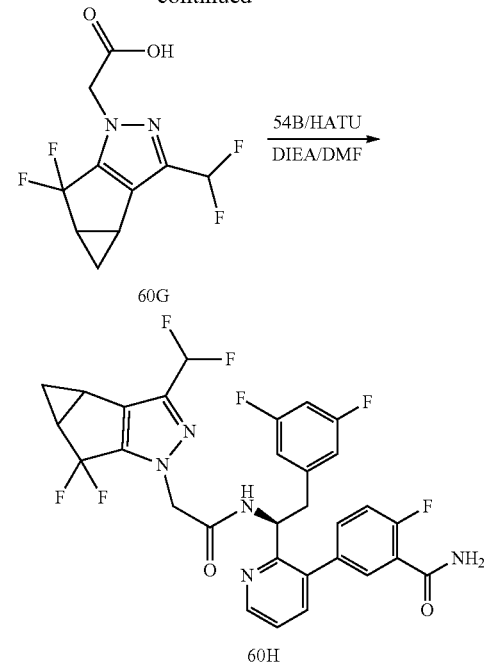

Synthesis of ethyl 2-(3-(difluoromethyl)-3b,4,4a,5-tetrahydro-1H-cyclopropa[3,4]cyclopenta[1,2-c] pyrazol-1-yl)acetate (60A) and ethyl 2-(3-(difluoromethyl)-3b,4,4a,5-tetrahydro-2H-cyclopropa[3,4] cyclopenta[1,2-c]pyrazol-2-yl)acetate (60B)

Compound 60A and 60B were prepared according to the method presented for the synthesis of Example 122 substituting ethyl 2,2-difluoroacetate for ethyl 2,2,2-trifluoroacetate to provide 1.7 g of 60A and 0.33 g of 60B. 60A: MS (m/z) 257 [M+H]$^+$ and 60B: MS (m/z) 257 [M+H]$^+$.

Synthesis of 2-(3-(difluoromethyl)-5,5-difluoro-3 b,4,4a,5-tetrahydro-1H-cyclopropa[3,4]cyclopenta[1, 2-c]pyrazol-1-yl)acetic acid (60G)

Compound 60G was prepared according to the method presented for the synthesis of Example 181 substituting 60A for 122D to provide 140 mg of title compound. MS (m/z) 265 [M+H]$^+$.

Synthesis of 5-(2-((1S)-1-(2-(3-(difluoromethyl)-5, 5-difluoro-3b,4,4a,5-tetrahydro-1H-cyclopropa[3,4] cyclopenta[1,2-c]pyrazol-1-yl)acetamido)-2-(3,5-difluorophenyl)ethyl)pyridin-3-yl)-2-fluorobenzamide (60H)

Compound 60H was prepared according to the method presented for the synthesis of Example 54 utilizing 54B and 60G to provide 254 mg of title compound: $^1$H NMR (400 MHz, cd$_3$od) δ 8.66 (dd, 1H), 7.54 (ddd, 1.7 Hz, 1H), 7.27 (dddd, 4H), 6.82 (d, 1H), 6.73-6.57 (m, 2H), 6.54 (d, 1H), 6.37-6.19 (m, 2H), 5.42-5.27 (m, 1H), 4.39-4.22 (m, 1H), 4.07 (q, 1H), 3.23-2.91 (m, 2H), 2.51-2.38 (m, 2H), 1.98 (s, 1H), 1.82 (s, 1H), 1.97-1.17 (m, 4H), 1.15-0.97 (m, 1H), 0.89 (t, 1H). MS (m/z) 618 [M+H]$^+$.

Example 61

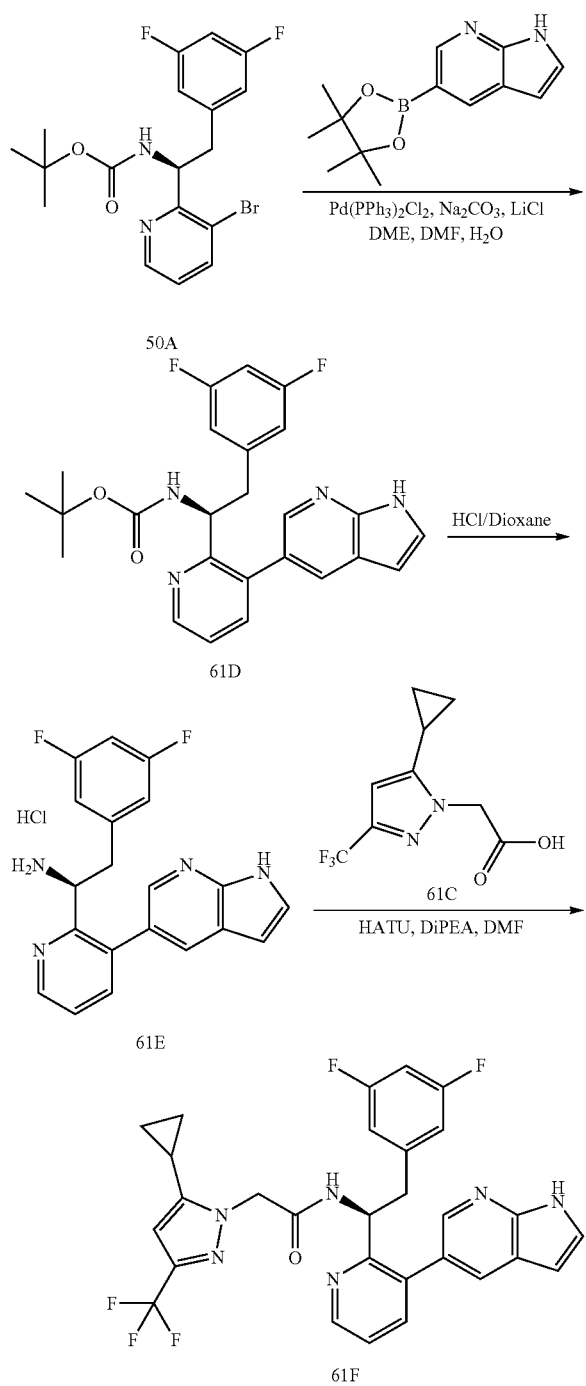

Synthesis of (S)-tert-butyl 1-(3-(1H-pyrrolo[2,3-b]pyridin-5-yl)pyridin-2-yl)-2-(3,5-difluorophenyl)ethylcarbamate (61D)

A round bottom flask was charged with 50A (1 g, 2.4 mmol), DME (8 ml), DMF (2 ml), 5-(4,4,5,5-tetramethyl-1,3,2-dioxaborolan-2-yl)-1H-pyrrolo[2,3-b]pyridine (886 mg, 3.6 mmol), LiCl (308 mg, 7.2 mmol), Pd(PPh$_3$)$_2$Cl$_2$ (85 mg, 0.12 mmol) and Na$_2$CO$_3$ (513 mg, 4.8 mmol) dissolved in water (2 ml). Microwave the reaction at 150° C. for 20 minutes. Allow the reaction to cool then dilute with H$_2$O and extract 2× EtOAc. The combined organic layers were washed with brine then dried over sodium sulfate, concentrated, and purified by flash chromatography to give the desired compound (785 mg, 72%): MS (m/z) 451.3 [M+H]$^+$.

Synthesis of (S)-1-(3-(1H-pyrrolo[2,3-b]pyridin-5-yl)pyridin-2-yl)-2-(3,5-difluorophenyl)ethanamine hydrochloride (61E)

A round bottom flask was charged with (S)-tert-butyl 1-(3-(1H-pyrrolo[2,3-b]pyridin-5-yl)pyridin-2-yl)-2-(3,5-difluorophenyl)ethylcarbamate (549 mg, 1.2 mmol) and 4 N HCl/dioxane (3 ml). The reaction was stirred at room temperature until done by LC/MS then concentrated 2× from DCM. The crude solid was used as is in next reaction: MS (m/z) 351.2 [M+H]$^+$.

Synthesis of (S)—N-(1-(3-(1H-pyrrolo[2,3-b]pyridin-5-yl)pyridin-2-yl)-2-(3,5-difluorophenyl)ethyl)-2-(5-cyclopropyl-3-(trifluoromethyl)-1H-pyrazol-1-yl)acetamide (61F)

The title compound was prepared according to the method presented in the synthesis of 34E substituting 61C for 34D and 61E for (S)-2-(3,5-difluorophenyl)-1-(3-(4-methoxyphenyl)pyridin-2-yl)ethanamine to provide the desired compound (16.8 mg, 33%): $^1$H NMR (400 MHz, cd$_3$od) δ 8.72 (d, 1H), 8.01 (s, 1H), 7.85 (s, 1H), 7.66 (d, 1H), 7.56 (d, 1H), 7.44 (dd, 4.8 Hz, 1H), 6.70 (s, 1H), 6.62 (d, 1H), 6.28 (d, 2H), 6.23 (s, 1H), 5.42-5.20 (m, 1H), 4.99 (s, 2H), 4.82-4.88 (m, 1H), 3.46 (s, 1H), 3.12-2.99 (m, 2H), 1.63 (s, 1H), 0.94-0.84 (m, 2H), 0.63 (s, 2H); MS (m/z) 567.5 [M+H]$^+$.

Example 62

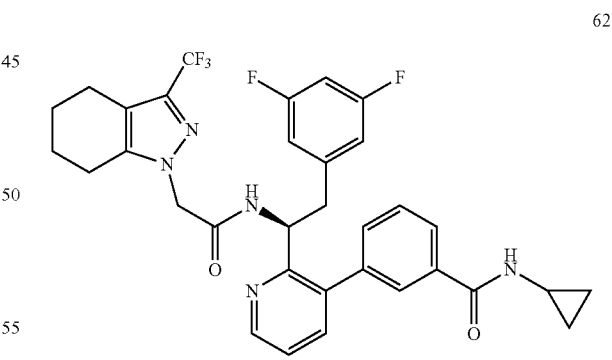

Synthesis of (S)—N-cyclopropyl-3-(2-(2-(3,5-difluorophenyl)-1-(2-(3-(trifluoromethyl)-4,5,6,7-tetrahydro-1H-indazol-1-yl)acetamido)ethyl)pyridin-3-yl)benzamide (62)

Prepared 29 mg of the title compound by a method analogous to compound 57B using 57A and 3-(cyclopropylcarbamoyl)phenylboronic acid. MS (m/z) 624 [M+H]$^+$.

Example 63

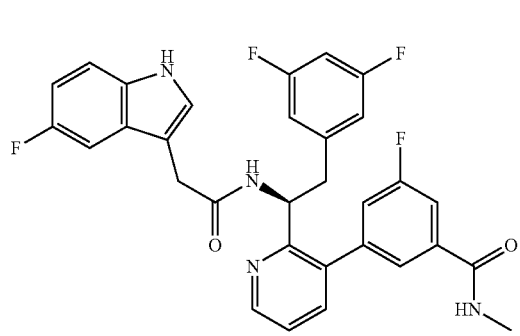

Synthesis of (S)-3-(2-(2-(3,5-difluorophenyl)-1-(2-(5-fluoro-1H-indol-3-yl)acetamido)ethyl)pyridin-3-yl)-5-fluoro-N-methylbenzamide (63)

Prepared 16 mg of the title compound by a method analogous to 55F using 3-fluoro-5-(methylcarbamoyl)phenylboronic acid and 55E. MS (m/z) 561 [M+H]$^+$.

Example 64

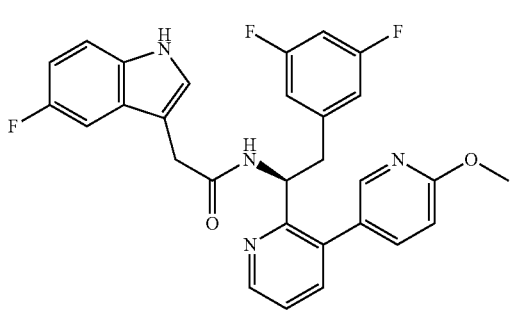

Synthesis of (S)—N-(2-(3,5-difluorophenyl)-1-(6'-methoxy-3,3'-bipyridin-2-yl)ethyl)-2-(5-fluoro-1H-indol-3-yl)acetamide (64)

Prepared 22 mg of the title compound by a method analogous to 55F using 6-methoxypyridin-3-ylboronic acid and 55E. MS (m/z) 544 [M+H]$^+$.

Example 65

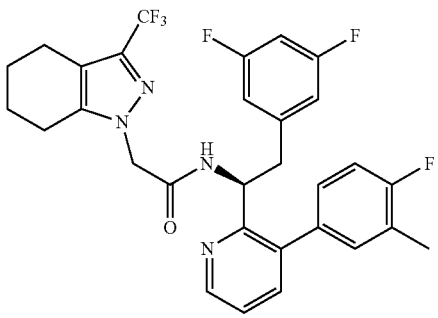

Synthesis of (S)—N-(2-(3,5-difluorophenyl)-1-(3-(4-fluoro-3-methylphenyl)pyridin-2-yl)ethyl)-2-(3-(trifluoromethyl)-4,5,6,7-tetrahydro-1H-indazol-1-yl)acetamide (65)

Prepared 33.5 mg of the title compound by a method analogous to compound 57B using 57A and 3-methyl-4-fluorophenyl boronic acid. MS (m/z) 573 [M+H]$^+$.

Example 66

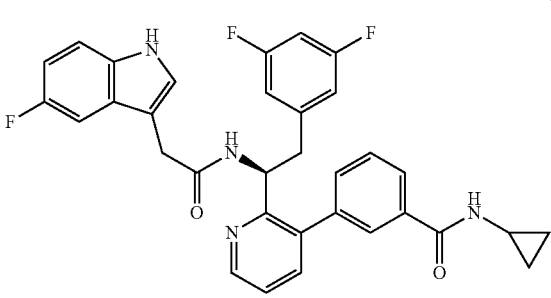

Synthesis of (S)—N-cyclopropyl-3-(2-(2-(3,5-difluorophenyl)-1-(2-(5-fluoro-1H-indol-3-yl)acetamido)ethyl)pyridin-3-yl)benzamide (66)

Prepared 1.5 mg of the title compound by a method analogous to 55F using [3-(cyclopropylaminocarbonyl)phenyl] boronic acid and 55E. MS (m/z) 569 [M+H]$^+$.

Example 67

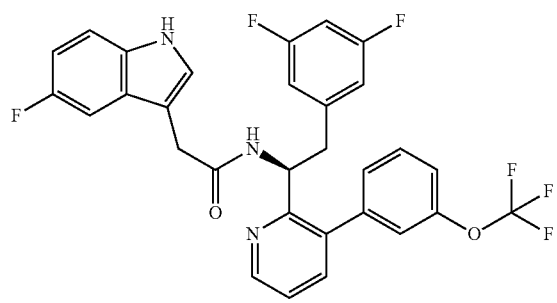

67

Synthesis of (S)—N-(2-(3,5-difluorophenyl)-1-(3-(3-(trifluoromethoxy)phenyl)pyridin-2-yl)ethyl)-2-(5-fluoro-1H-indol-3-yl)acetamide (67)

Prepared 34.9 mg of the title compound by a method analogous to 55F using 3-trifluoromethoxy-phenylboronic acid and 55E. MS (m/z) 570 [M+H]$^+$.

Example 68

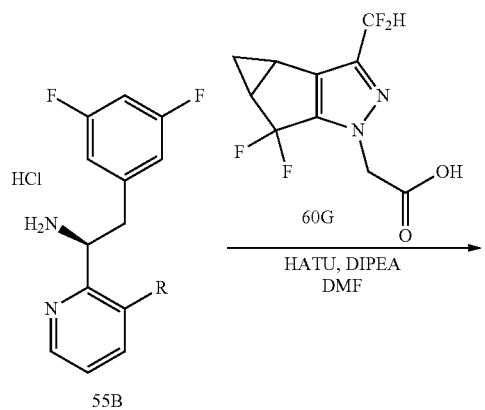

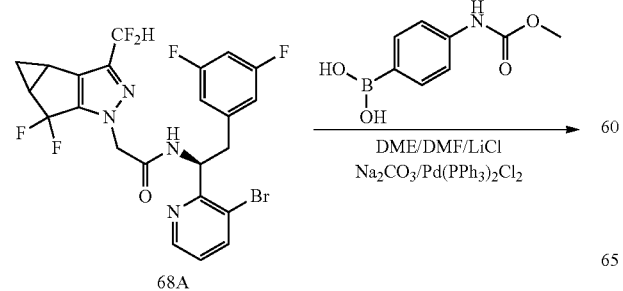

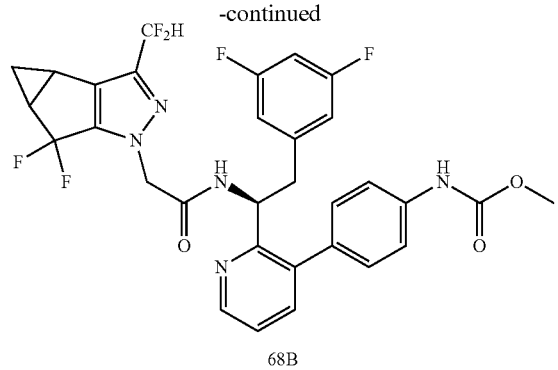

68B

Synthesis of (S)—N-(1-(3-bromo-pyridin-2-yl)-2-(3,5-difluorophenyl)ethyl)-2-(3-(difluoromethyl)-5,6-dihydro-4,5-(methano)-6,6-difluoro-cyclopenta[c]pyrazol-1(4H)-yl)acetamide (68A)

Prepared 1.5 g of the title compound by a method analogous to 55E using 60G and 55B. MS (m/z) 560 [M+H]$^+$.

Synthesis of (S)-methyl 4-(2-(1-(3-(difluoromethyl)-5,6-dihydro-4,5-(methano)-6,6-difluoro-cyclopenta[c]pyrazol-1 (4H)-ylacetamido)-2-(3,5-difluorophenyl)ethyl)pyridin-3-yl)phenylcarbamate (68B)

To a solution of 68A (28 mg, 0.05 mmol) and (4-(methoxycarbonylamino)phenylboronic acid (19.5 mg, 0.1 mmol) in 4:1 DME/DMF (500 ul) was added LiCl (6.4 mg, 0.15 mmol), 1N aq. Na$_2$CO$_3$ (125 ul, 0.125 mmol), and Pd(PPh$_3$)$_2$Cl$_2$ (7 mg, 0.01 mmol). The reaction was heated in a microwave synthesizer at 150° C. for 15 min. The cooled suspension was filtered and the filtrate was purified by RP HPLC using a C18 column with a gradient of 0.1%/H$_2$O, 0.1% TFA-acetonitrile to give 18.5 mg of the title compound. MS (m/z) 630 [M+H]$^+$.

Example 69

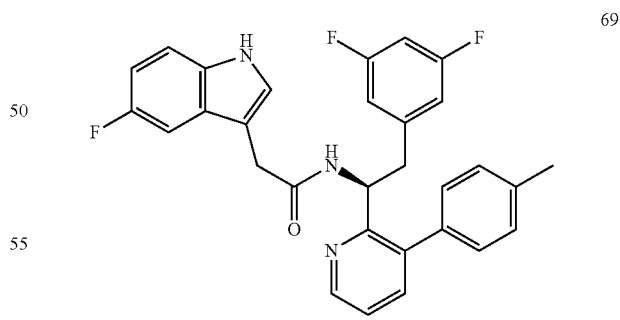

69

Synthesis of (S)—N-(2-(3,5-difluorophenyl)-1-(3-p-tolylpyridin-2-yl)ethyl)-2-(5-fluoro-1H-indol-3-yl)acetamide (69)

Prepared 36.3 mg of the title compound by a method analogous to 55F using 4-methylphenylboronic acid and 55E. MS (m/z) 500 [M+H]$^+$.

Example 70

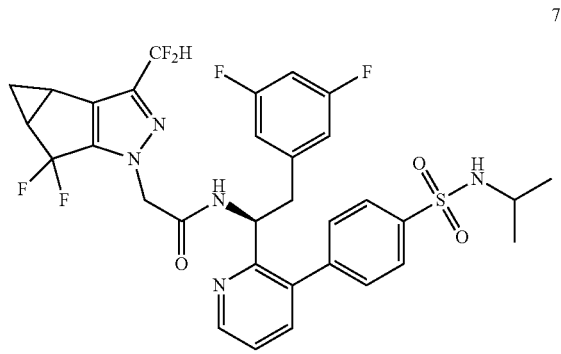

Synthesis of (S)—N-(1-(3-(4-(N-isopropylsulfamoyl)phenyl)-pyridin-2-yl)-2-(3,5-difluorophenyl)ethyl)-2-(3-(difluoromethyl)-5,6-dihydro-4,5-(methano)-6,6-difluoro-cyclopenta[c]pyrazol-1(4H)-yl)acetamide (70)

Prepared 8.4 mg of the title compound by a method analogous to 68B using 68A and N-isopropyl 4-boronobenzenesulfonamide. MS (m/z) 678 [M+H]+.

Example 71

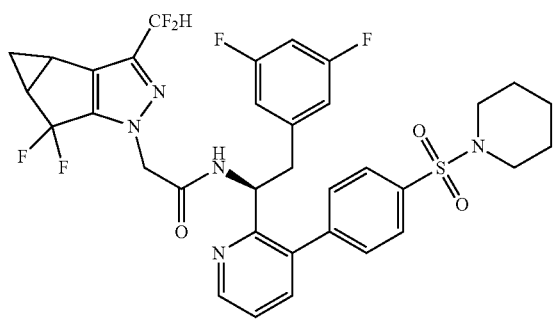

Synthesis of (S)—N-(1-(3-(4-((piperidin-1-yl)sulfonyl)phenyl)-pyridin-2-yl)-2-(3,5-difluorophenyl)ethyl)-2-(3-(difluoromethyl)-5,6-dihydro-4,5-(methano)-6,6-difluoro-cyclopenta[c]pyrazol-1(4H)-yl)acetamide (71)

Prepared 14.8 mg of the title compound by a method analogous to 68B using 68A and 4-(piperidin-1-ylsulfonyl)phenylboronic acid. MS (m/z) 704 [M+H]+.

Example 72

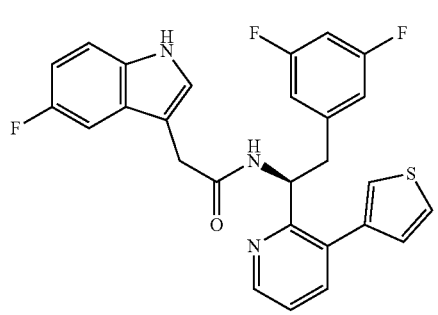

Synthesis of (S)—N-(2-(3,5-difluorophenyl)-1-(3-(thiophen-3-yl)pyridin-2-yl)ethyl)-2-(5-fluoro-1H-indol-3-yl)acetamide (72)

Prepared 29 mg of the title compound by analogous method to 55F using thiophen-3-yl-boronic acid and 55E. MS (m/z) 492 [M+H]+.

Example 73

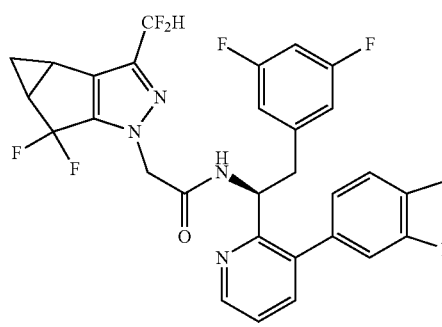

Synthesis of (S)—N-(1-(3-(1-methylindazole-6-yl)-pyridin-2-yl)-2-(3,5-difluorophenyl)ethyl)-2-(3-(difluoromethyl)-5,6-dihydro-4,5-(methano)-6,6-difluoro-cyclopenta[c]pyrazol-1(4H)-yl)acetamide (73)

Prepared 21.1 mg of the title compound by a method analogous to 68B using 68A and 1-methylindazole-6-boronic acid. MS (m/z) 611 [M+H]+.

Example 74

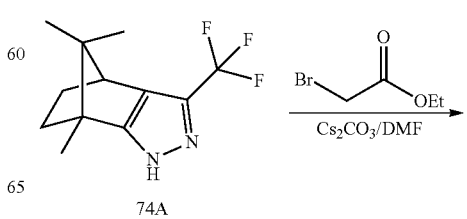

74A

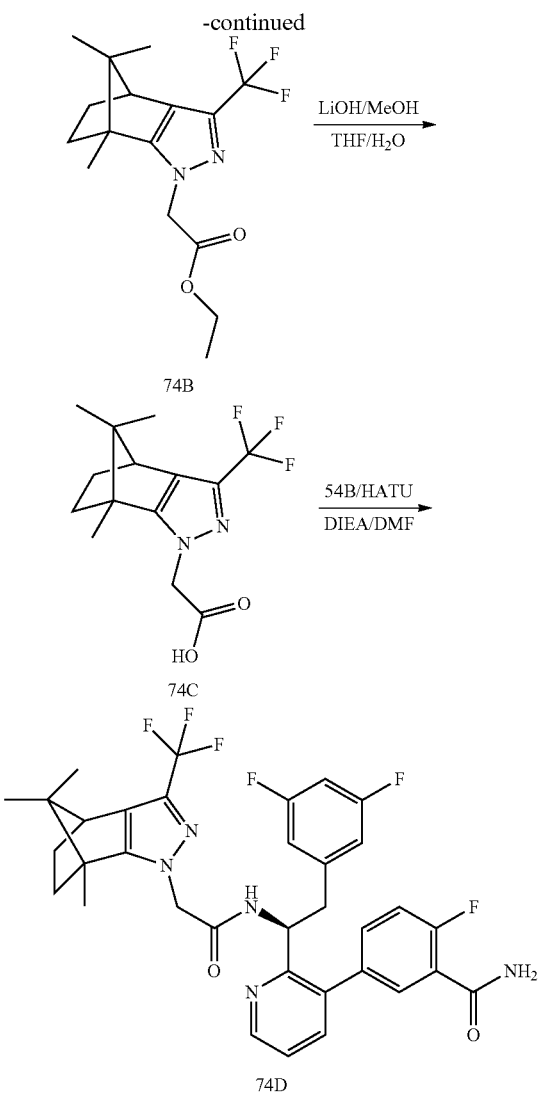

was then acidified to pH=3 with 1N aq. HCl and extracted 3× with EtOAc. The combined organics were washed with brine, dried over MgSO$_4$, filtered and concentrated. Obtained 265 mg of the title compound after drying overnight under vacuum.

Synthesis of (S)-5-(2-(2-(3,5-difluorophenyl)-1-(2-(L-4,5,6,7-Tetrahydro-3-trifluoromethyl-7,8,8-trimethyl-1H-4,7-(methano)indazol-1-yl)acetamido)ethyl)pyridin-3-yl)-2-fluorobenzamide (74D)

Prepared 60 mg of the title compound by a method analogous to 54G using 74C and 54B. $^1$H NMR (400 MHz, CD$_3$OD) δ 8.71 (dd, 1H), 7.67 (dd, 1H), 7.49-7.40 (m, 2H), 7.30 (s, 1H), 7.27-7.20 (m, 1H), 6.69 (t, 1H), 6.36 (d, 2H), 5.37 (t, 1H), 3.08 (d, 2H), 2.86 (d, 1H), 2.10 (d, 1H), 1.78 (t, 1H), 1.30 (t, 1H), 1.20 (s, 3H), 1.07 (s, 1H), 0.92 (s, 3H), 0.71 (s, 3H). MS (m/z) 656 [M+H]$^+$.

Example 75

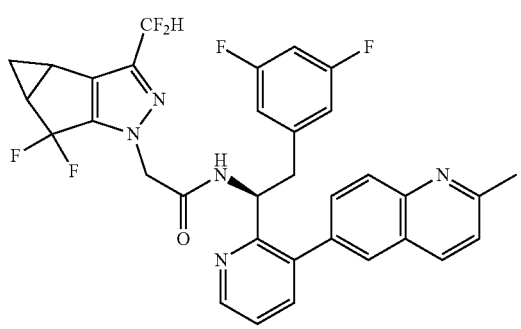

Synthesis of (S)—N-(1-(3-(2-methylquinoline-6-yl)-pyridin-2-yl)-2-(3,5-difluorophenyl)ethyl)-2-(3-(difluoromethyl)-5,6-dihydro-4,5-(methano)-6,6-difluoro-cyclopenta[c]pyrazol-1(4H)-yl)acetamide (75)

Prepared 16.1 mg of the title compound by a method analogous to 68B using 68A and 2-methylquinoline-6-boronic acid pinacol ester. MS (m/z) 622 [M+H]$^+$.

Synthesis of ethyl 2-(L-4,5,6,7-Tetrahydro-3-trifluoromethyl-7,8,8-trimethyl-1H-4,7-(methano)indazol-1-yl)acetate (74B)

To a suspension of L-4,5,6,7-tetrahydro-3-trifluoromethyl-7,8,8-trimethyl-1H-4,7-(methano)indazole (977 mg, 4 mmol), Cs$_2$CO$_3$ (1.6 g, 8.3 mmol) in DMF (6 ml) was added ethyl bromoacetate as a solution in 5 ml of DMF. The reaction was stirred at room temperature for 5 hrs, then diluted with water. The mixture was extracted with EtOAc. The organics were dried over Na$_2$SO$_4$, filtered and concentrated. The crude product was purified by SiO$_2$ chromatography eluting with a gradient of EtOAc in hexanes. Concentrated pure fractions to give 300 mg of the title compound.

Synthesis of L-4,5,6,7-Tetrahydro-3-trifluoromethyl-7,8,8-trimethyl-1H-4,7-(methano)indazol-1-yl) acetic acid (74C)

Dissolved 74B (300 mg, 0.908 mmol) in THF (5 ml) and MeOH (2.5 ml). Added 2.5 ml of 2.5N aq. LiOH and stirred the reaction for 30 min. at room temperature. The mixture Example 76

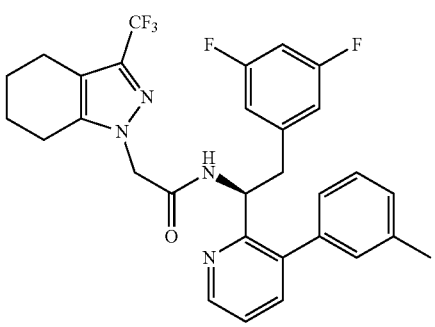

329

Synthesis of (S)—N-(2-(3,5-difluorophenyl)-1-(3-m-tolylpyridin-2-yl)ethyl)-2-(3-(trifluoromethyl)-4,5,6,7-tetrahydro-1H-indazol-1-yl)acetamide (76)

Prepared 11.4 mg of the title compound by a method analogous to compound 57B using 57A and 3-methylphenyl boronic acid. MS (m/z) 555 [M+H]⁺.

Example 77

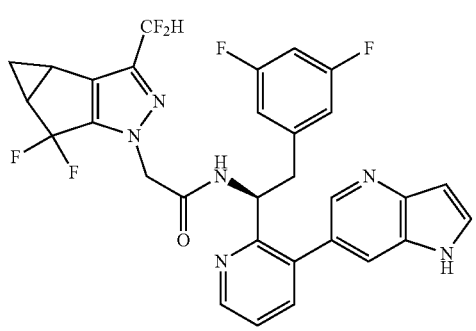

77

Synthesis of (S)—N-(1-(3-(1H-pyrrolo[3,2-b]pyridine-6-yl)-pyridin-2-yl)-2-(3,5-difluorophenyl)ethyl)-2-(3-(difluoromethyl)-5,6-dihydro-4,5-(methano)-6,6-difluoro-cyclopenta[c]pyrazol-1(4H)-yl)acetamide (77)

Prepared 17.4 mg of the title compound by a method analogous to 68B using 68A and 6-(4,4,5,5-tetramethyl-1,3,2-dioxaborolan-2-yl)-1H-pyrrolo[3,2-b]pyridine. MS (m/z) 597 [M+H]⁺.

Example 78

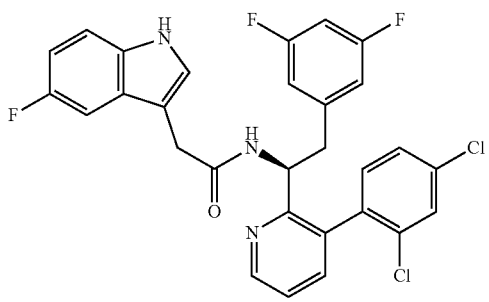

78

Synthesis of (S)—N-(1-(3-(2,4-dichlorophenyl)pyridin-2-yl)-2-(3,5-difluorophenyl)ethyl)-2-(5-fluoro-1H-indol-3-yl)acetamide (78)

Prepared 19.8 mg of the title compound by a method analogous to 55F using (2,4-dichlorophenyl)-boronic acid and 55E. MS (m/z) 555 [M+H]⁺.

330

Example 79

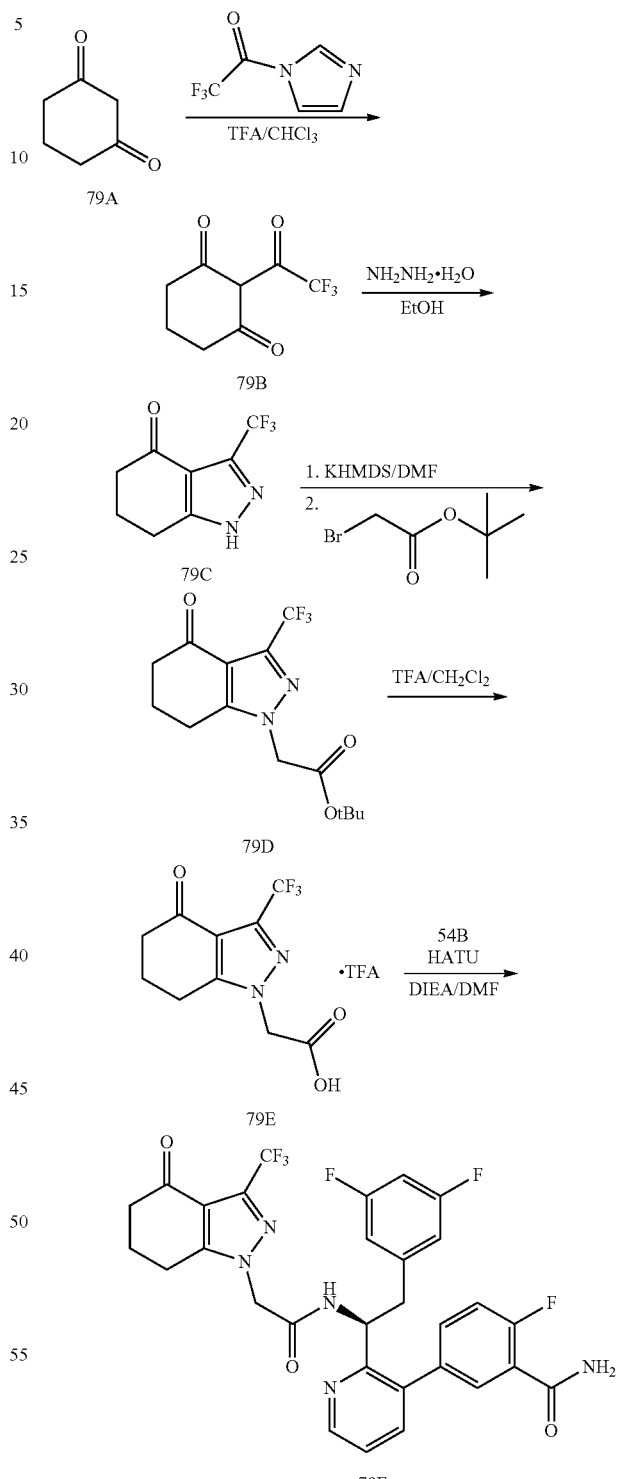

Synthesis of 2-(2,2,2-trifluoroacetyl)cyclohexane-1,3-dione (79B)

To a solution of 1,3-cyclohexanedione (561 mg, 5.0 mmol) and imidazole (340 mg, 5.0 mmol) in CH₂Cl₂ (50 mil) was added neat N-trifluoroacetyl imidazole (2.27 ml, 20 mmol). The reaction mixture was stirred at room temperature for 45 min. The reaction was diluted with 4N aq. HCl and the layers were separated. The aqueous layer was extracted 2× $CH_2Cl_2$. The combined organics were washed with $H_2O$ and brine. The organics were dried over $MgSO_4$, filtered and concentrated. The crude product was used directly for the next step.

Synthesis of 3-(trifluoromethyl)-6,7-dihydro-1H-indazol-4(5H)-one (79C)

To a solution of crude 79B in EtOH (5 ml) was added hydrazine hydrate (500 ul, 7.8 mmol). The reaction was heated at 70° C. for 2.5 hrs and then concentrated under reduced pressure. The crude product was used directly for the next step.

Synthesis of tert-butyl 2-(4-oxo-3-(trifluoromethyl)-4,5,6,7-tetrahydro-1H-indazol-1-yl)acetate (79D)

To a solution of crude 79C in DMF (25 ml) was added potassium hexamethyldisilazane (997 mg, 5 mmol). The reaction mixture was stirred for 2 min. at room temperature and then neat alpha-bromo-t-butylacetate was added. The reaction was stirred 1 hr at room temperature and then concentrated under reduced pressure. The residue was portioned between EtOAc and $H_2O$. The aqueous was extracted 2× EtOAc. The combined organics were washed with brine, dried over MgSO4, filtered and concentrated. Purified crude product on $SiO_2$ eluting with a gradient of EtOAc in hexanes to give 458 mg of the title compound. MS (m/z) 319 $[M+H]^+$.

Synthesis of 2-(4-oxo-3-(trifluoromethyl)-4,5,6,7-tetrahydro-1H-indazol-1-yl)acetic acid (79E)

Prepared 508 mg of the title compound using a method analogous to 83E using 79D. MS (m/z) 263 $[M+H]^+$.

Synthesis of (S)-5-(2-(2-(3,5-difluorophenyl)-1-(2-(4-oxo-3-(trifluoromethyl)-4,5,6,7-tetrahydro-1H-indazol-1-yl)acetamido)ethyl)pyridin-3-yl)-2-fluorobenzamide (79F)

Prepared 9.1 mg of the title compound by a method analogous to 54F using 54B and 79E. MS (m/z) 616 $[M+H]^+$.

Example 80

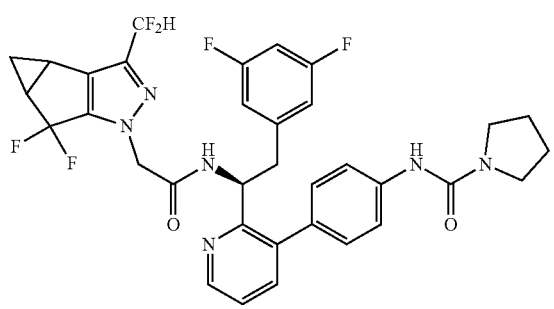

Synthesis of (S)—N-(1-(3-(4-(pyrrolidinylcarbonylamino)phenyl)-pyridin-2-yl)-2-(3,5-difluorophenyl)ethyl)-2-(3-(difluoromethyl)-5,6-dihydro-4,5-(methano)-6,6-difluoro-cyclopenta[c]pyrazol-1(4H)-yl)acetamide (80)

Prepared 9.3 mg of the title compound by a method analogous to 68B using 68A and 4-(pyrrolidinylcarbonylamino)phenylboronic acid, pinacol ester. MS (m/z) 655 $[M+H]^+$.

Example 81

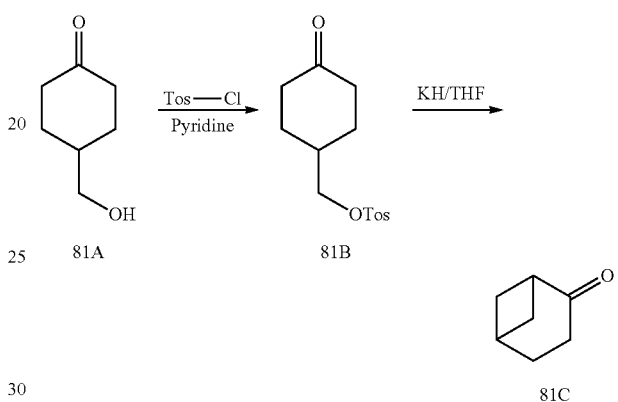

Synthesis of (4-oxocyclohexyl)methyl 4-methylbenzenesulfonate (81B)

To a 0° C. solution of Compound 81A (10 g, 78 mmol) in pyridine (78 ml) was added 4-toluenesulfonyl chloride (16.7 g, 87.8 mmol) in portions of 5 min. The reaction was stirred at 16 hrs at room temperature. The reaction was poured into 400 ml of a 1:1 mixture of $Et_2O/H_2O$. The layers were separated and the organic layer was extracted 2× with $Et_2O$. The combined organics were washed with $H_2O$ (5×) and brine (2×). The organics were dried over $MgSO_4$, filtered and concentrated. Purified the crude product on $SiO_2$ eluting with a gradient of EtOAc in hexanes to give 18.5 g of the title compound after drying under reduced pressure. MS (m/z) 283 $[M+H]^+$.

Synthesis of bicyclo[3.1.1]heptan-2-one (81C)

Potassium hydride (30% oil dispersion, 9.49 g, 71 mmol) was washed 3× with pentane and the dried under a stream of $N_2$. The solid was then suspended in THF (259 ml). Compound 81B (10 g, 35.5 mmol) was dissolved in THF (43 ml) and the resulting solution was added to the potassium hydride suspension over 5 min. The resulting mixture was heated at 50° C. for 16 hrs. The cooled reaction mixture was filtered through a sintered glass funnel to remove gelatinous precipitate. The filtrate was concentrated to a small volume (150 ml) and poured into an ice water/ether mixture. The layers were separated and the aqueous layer was extracted 3× with $Et_2O$. The combined organics were washed with $H_2O$ (3×), brine (1×), dried over $MgSO_4$, filtered and concentrated to a small volume. The crude material was used without further purification (assumed 40% yield).

81D

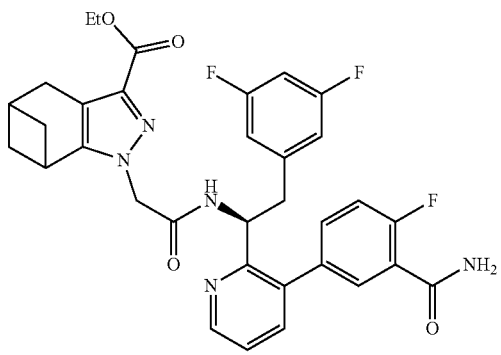

Synthesis of (S)-5-(2-(2-(3,5-difluorophenyl)-1-(2-(4,5,6,7-tetrahydro-3-carboethoxy-5,7-(methano)indazol-1-yl)acetamido)ethyl)pyridin-3-yl)-2-fluorobenzamide (81D)

Prepared 2.01 g of the title compound by method analogous to Compound 90 starting with compound 81C. MS (m/z) 618 [M+H]$^+$.

Example 82

82

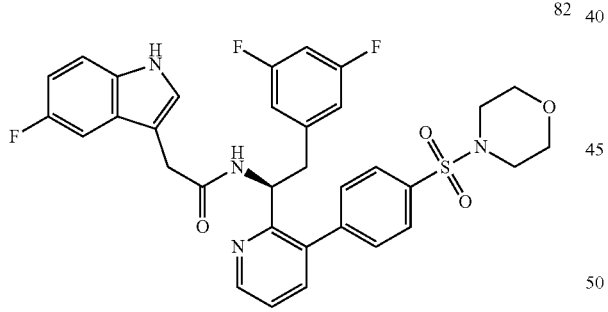

Synthesis of (S)—N-(2-(3,5-difluorophenyl)-1-(3-(4-(morpholinosulfonyl)phenyl)pyridin-2-yl)ethyl)-2-(5-fluoro-1H-indol-3-yl)acetamide (82)

Prepared 25.2 mg of the title compound by a method analogous to 55F using 4-(morpholinosulfonyl)phenyl boronic acid and 55E. MS (m/z) 635 [M+H]$^+$.

Example 83

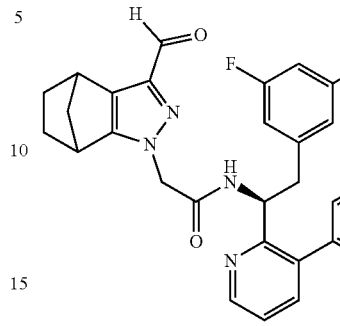

403

DAST/CH$_2$Cl$_2$
→

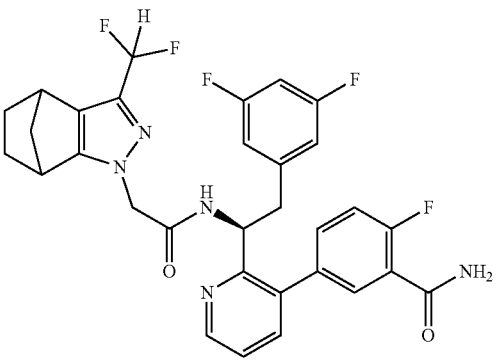

83

Synthesis of (S)-5-(2-(2-(3,5-difluorophenyl)-1-(2-(4,5,6,7-tetrahydro-3-difluoromethyl-4,7-(methano)indazol-1-yl)acetamido)ethyl)pyridin-3-yl)-2-fluorobenzamide (83)

The crude Compound 403 (100 mg, 0.174 mmol) was dissolved in CH$_2$Cl$_2$ (2 ml). The resulting solution was treated with diethylaminosulfur trifluoride (DAST) (49 ul, 0.376 mmol) at room temperature for 5 hrs. The reaction mixture was poured into sat. aqueous NaHCO$_3$. The layers were separated and the organic layer was washed 2× H$_2$O and 1× brine. The organics were dried over MgSO$_4$, filtered and concentrated. The residue was purified by RP HPLC using a C18 column with a gradient of 0.1%/H$_2$O, 0.1% TFA-acetonitrile to give 13.7 mg of the title compound. MS (m/z) 596 [M+H]$^+$.

Example 84

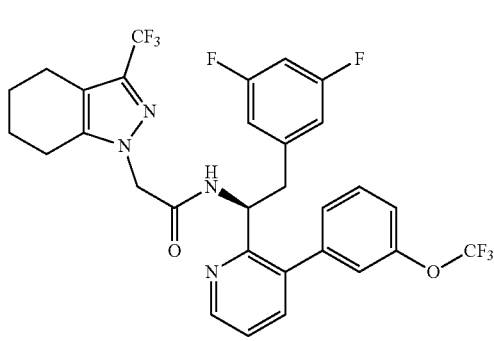

Synthesis of (S)—N-(2-(3,5-difluorophenyl)-1-(3-(3-(trifluoromethoxy)phenyl)pyridin-2-yl)ethyl)-2-(3-(trifluoromethyl)-4,5,6,7-tetrahydro-1H-indazol-1-yl)acetamide (84)

Prepared 28.1 mg of the title compound by a method analogous to compound 57B using 57A and 3-trifluoromethoxyphenyl boronic acid. MS (m/z) 625 [M+H]⁺.

Example 85

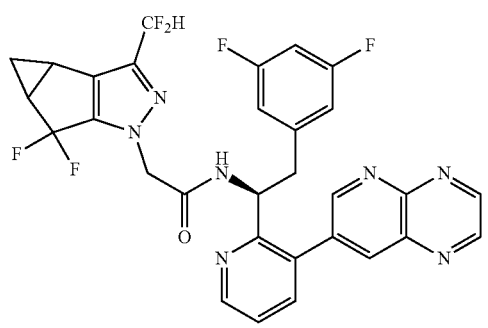

Synthesis of (S)—N-(1-(3-(pyrido[2,3-b]pyrazin-7-yl)-pyridin-2-yl)-2-(3,5-difluorophenyl)ethyl)-2-(3-(difluoromethyl)-5,6-dihydro-4,5-(methano)-6,6-difluoro-cyclopenta[c]pyrazol-1(4H)-yl)acetamide (85)

Prepared 2.5 mg of the title compound by a method analogous to 68B using 68A and pyrido[2,3-b]pyrazin-7-ylboronic acid, pinacol ester. MS (m/z) 610 [M+H]⁺.

Example 86

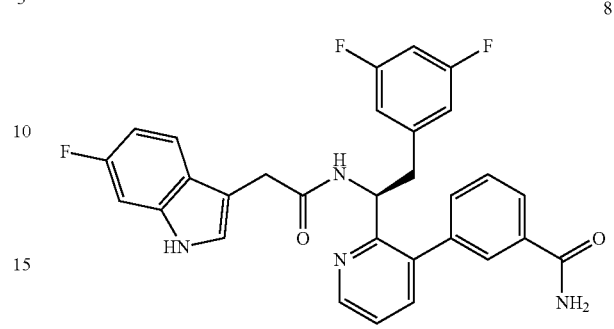

Synthesis of (S)-3-(2-(2-(3,5-difluorophenyl)-1-(2-(6-fluoro-1H-indol-3-yl)acetamido)ethyl)pyridin-3-yl)benzamide (86)

Prepared 49 mg of the title compound by a method analogous to 50D using 6-fluoro-3-indole acetic acid. ¹H NMR (400 MHz, d6-DMSO) δ 10.82 (s, 1H), 8.66 (dd, 2H), 7.92 (d, 1H), 7.86 (s, 1H), 7.75 (s, 1H), 7.61 (dd, 1H), 7.49-7.35 (m, 4H), 7.26 (dd, 1H), 7.05-6.98 (m, 2H), 6.91 (t, 1H), 6.74-6.61 (m, 1H), 6.49 (d, 2H), 5.17 (dd, 3H), 4.70-4.65 (m, 1H), 3.44 (q, 2H), 2.95 (d, 2H). MS (m/z) 529 [M+H]⁺.

Example 87

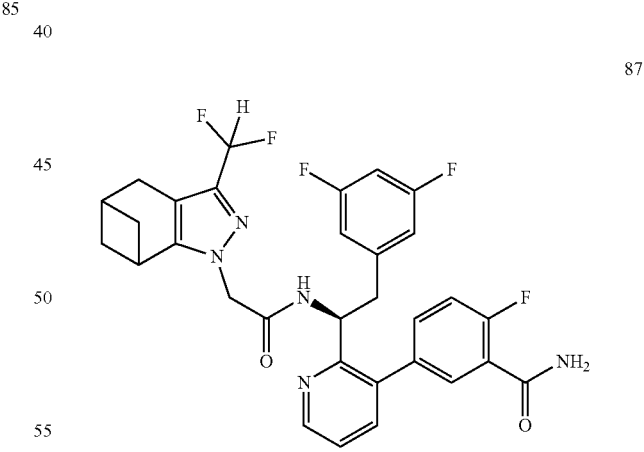

Synthesis of (S)-5-(2-(2-(3,5-difluorophenyl)-1-(2-(4,5,6,7-tetrahydro-3-difluoromethyl-5,7-(methano)indazol-1-yl)acetamido)ethyl)pyridin-3-yl)-2-fluorobenzamide (87)

Prepared 41.6 mg of the title compound by method analogous to compound 83 starting with compound 96. MS (m/z) 596 [M+H]⁺.

Example 88

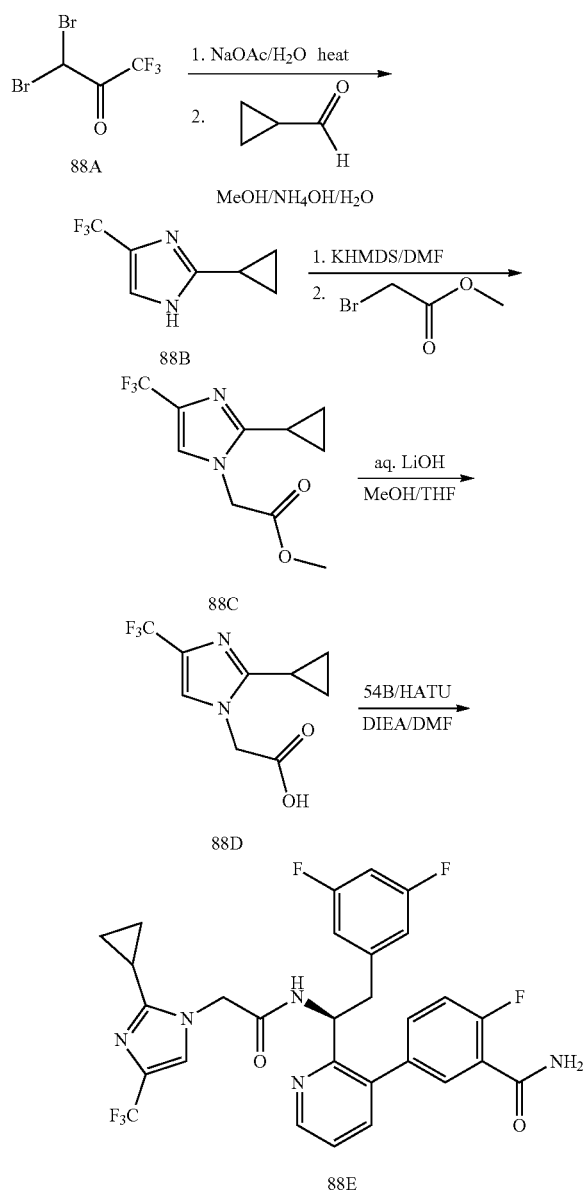

Synthesis of 2-cyclopropyl-4-(trifluoromethyl)-1H-imidazole (88B)

To a suspension of 3,3-dibromo-1-trifluoromethyl-propane (2.0 g, 7.41 mmol) in H₂O (10 ml) was added sodium acetate (1.33 g, 16.2 mmol). The mixture was heated at 100° C. for 30 min and then cooled to room temperature. A solution of cyclopropylcarboxaldehyde (646 ul, 8.64 mmol) in of MeOH (4 ml) was added to the reaction mixture followed by NH₄OH (2.8 ml, 20% in H₂O). The reaction was stirred at room temperature overnight. The mixture was extracted 3× with EtOAc. The combined organics were washed with brine, dried over MgSO₄, filtered and concentrated to give 1.07 g of crude title product which was used directly for the next step.

Synthesis of methyl-2-(2-cyclopentyl-4-(trifluoromethyl)-1H-imidazol-1-yl)acetate (88C)

The crude product 88B was dissolved in DMF (60 ml). Solid KHMDS (1.45 g, 7.29 mmol) was added and the reaction was stirred 5 min. at room temperature. Added methyl bromoacetate (690 ul, 7.29 mmol) and then stirred the reaction for 1 hr at room temperature. The mixture was concentrated under reduced pressure to a small volume then partitioned between EtOAc and H₂O. Extracted the aqueous layer 2× EtOAc. The combined organics were washed with brine, dried over MgSO₄, filtered and concentrated. The crude product was purified by column chromatography on SiO₂ to give 630 mg of the title compound.

Synthesis of 2-(2-cyclopentyl-4-(trifluoromethyl)-1H-imidazol-1-yl) acetic acid (88D)

Prepared 83 mg of the title compound by a method analogous to 74C using 88C.

Synthesis of (S)-5-(2-(1-(2-(2-cyclopropyl-4-(trifluoromethyl)-1H-imidazol-1-yl)acetamido)-2-(3,5-difluorophenyl)ethyl)pyridin-3-yl)-2-fluorobenzamide (88E)

Prepared 29.4 mg of the title compound by a method analogous to 54G using 88D and 54B. MS (m/z) 588 [M+H]⁺.

Example 89

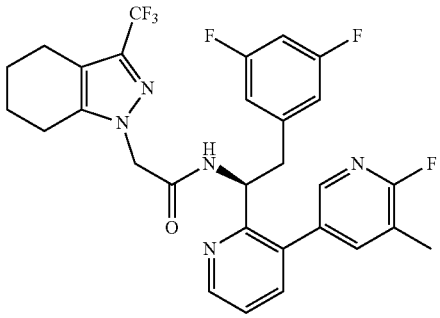

89

Synthesis of (S)—N-(2-(3,5-difluorophenyl)-1-(6'-fluoro-5'-methyl-3,3'-bipyridin-2-yl)ethyl)-2-(3-(trifluoromethyl)-4,5,6,7-tetrahydro-1H-indazol-1-yl)acetamide (89)

Prepared 28.2 mg of the title compound by a method analogous to compound 57B using 57A and 6-fluoro-5-methylpyridin-3-ylboronic acid. MS (m/z) 574 [M+H]⁺.

Example 90

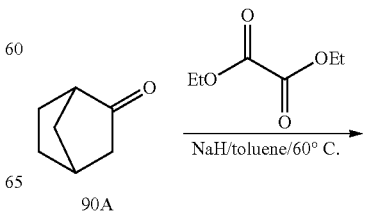

90A

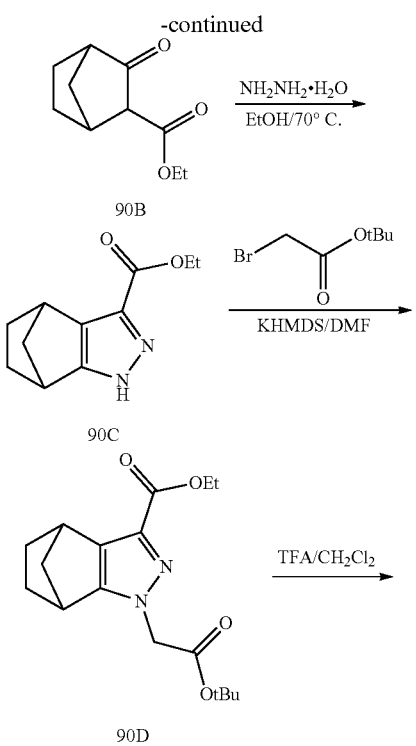

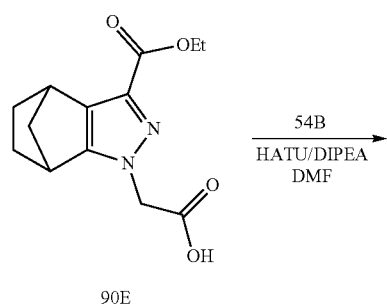

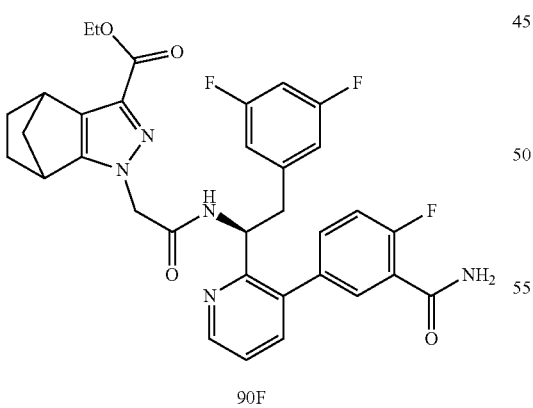

Synthesis of ethyl 3-oxobicyclo[2.2.1]heptane-2-carboxylate (90B)

Suspended NaH (400 mg, 10 mmol) in toluene (8 ml). Added diethyl oxalyate (1.26 ml, 9.2 mmol) and heated mixture to 60° C. Added a solution of norboranone (850 mg, 7.7 mmol) in toluene (4 ml). Stirred reaction mixture for 1 hr. Cooled reaction to room temperature and the poured into ice. Neutralized aqueous layer to pH=2 with 1N aq. HCl. Extracted mixture 3× with EtOAc. The combined organics were washed with brine, dried over MgSO$_4$, filtered and concentrated. Purified residue on SiO$_2$ column using a gradient of EtOAc and hexanes to give 1.33 g of the title compound.

Synthesis of 4,5,6,7-tetrahydro-3-carboethoxy-4,7-(methano)indazole (90C)

Dissolved 90B (1.33 g, 6.33 mmol) in EtOH (13 ml). Added hydrazine hydrate (405 ul, 6.33 mmol) and heated reaction to 70° C. Stirred reaction for 72 hrs at 70° C. Cooled reaction to room temperature, then partition mixture between EtOAc and H$_2$O. Extracted aqueous layer 1× EtOAc. Dried combined organic over MgSO$_4$, filtered and concentrated. Purified the residue on SiO$_2$ column using a gradient of EtOAc and hexanes to give 497 mg of the title compound. MS (m/z) 206 [M+H]$^+$.

Synthesis of t-butyl 2-(4,5,6,7-tetrahydro-3-carboethoxy-4,7-(methano)indazol-1-yl)acetate (90D)

Prepared 542 mg of the title compound by a method analogous to 107C using 90C. MS (m/z) 321 [M+H]$^+$.

Synthesis of 2-(4,5,6,7-tetrahydro-3-carboethoxy-4,7-(methano)indazol-1-yl)acetic acid (90E)

Prepared 455 mg of the title compound by a method analogous to 107D using 90D. MS (m/z) 265 [M+H]$^+$.

Synthesis of (S)-5-(2-(2-(3,5-difluorophenyl)-1-(2-(4,5,6,7-tetrahydro-3-carboethoxy-4,7-(methano) indazol-1-yl)acetamido)ethyl)pyridin-3-yl)-2-fluorobenzamide (90F)

Prepared 236 mg of the title compound using a method analogous to 107E using 90E and 54B $^1$H NMR (400 MHz, CD$_3$OD) δ 8.69 (s, 1H), 7.65 (t, 1H), 7.44 (s, 2H), 7.31 (s, 1H), 7.26-7.17 (m, 1H), 6.66 (d, 1H), 6.35 (d, 2H), 5.35 (d, 1H), 4.30 (q, 2H), 3.50 (s, 1H), 3.05 (d, 2H), 1.87 (d, 4H), 1.66 (s, 1H), 1.34 (t, 3H), 1.09 (s, 2H). MS (m/z) 618 [M+H]$^+$.

Example 91

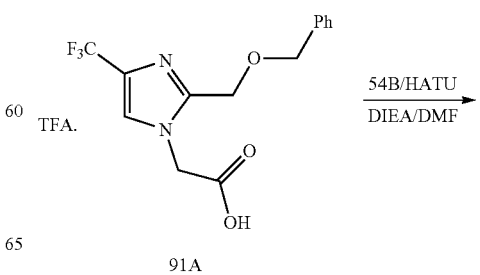

91A

-continued

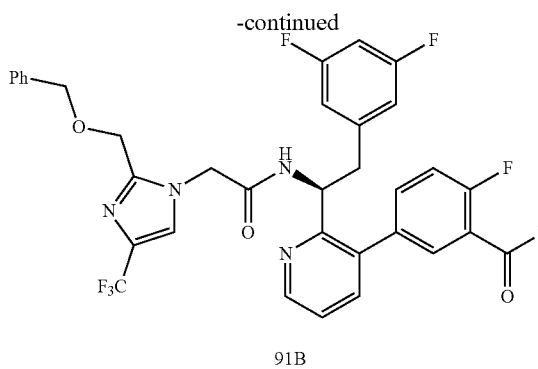

91B

Synthesis of 2-(2-(benzyloxymethyl)-4-(trifluoromethyl)-1H-imidazol-1-yl)acetic acid (91A)

Prepared 115 mg of the title compound by a method analogous to 107D using benzyloxyacetaldehyde.

Synthesis of (S)-5-(2-(1-(2-(2-(benzyloxymethyl)-4-(trifluoromethyl)-1H-imidazol-1-yl)acetamido)-2-(3,5-difluorophenyl)ethyl)pyridin-3-yl)-2-fluorobenzamide (91B)

Prepared 81.2 mg of the title compound by a method analogous to 107E using 107D and 54B $^1$H NMR (400 MHz, CD$_3$OD) δ 8.69 (s, 1H), 7.57 (d, 2H), 7.39 (s, 2H), 7.22 (d, 6H), 6.64 (s, 1H), 6.24 (s, 2H), 5.28 (s, 1H), 4.54 (d, 2H), 4.40 (s, 2H), 2.95 (d, 2H). MS (m/z) 668 [M+H]$^+$.

Example 92

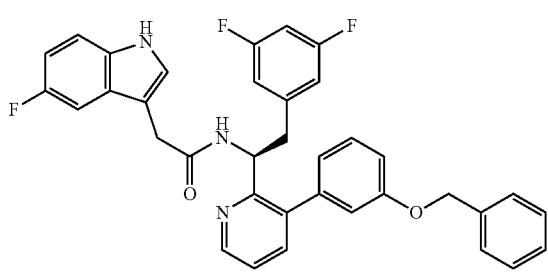

92

Synthesis of (S)—N-(1-(3-(3-(benzyloxy)phenyl)pyridin-2-yl)-2-(3,5-difluorophenyl)ethyl)-2-(5-fluoro-1H-indol-3-yl)acetamide (92)

Prepared 25 mg of the title compound by a method analogous to 55F using 3-phenoxy-phenylboronic acid and 55E. MS (m/z) 592 [M+H]$^+$.

Example 93

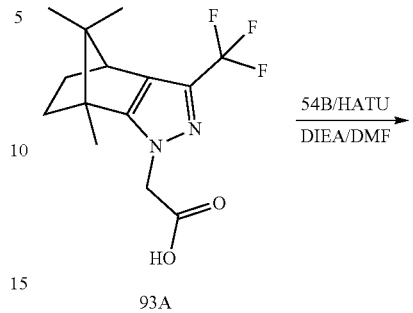

93A

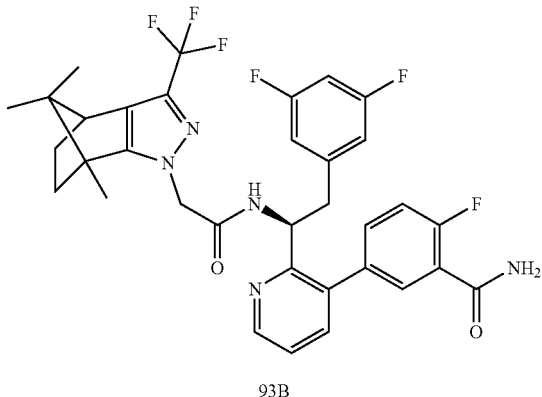

93B

Synthesis of (S)-5-(2-(2-(3,5-difluorophenyl)-1-(2-(D-4,5,6,7-Tetrahydro-3-trifluoromethyl-7,8,8-trimethyl-1H-4,7-(methano)indazol-1-yl)acetamido)ethyl)pyridin-3-yl)-2-fluorobenzamide (93B)

Prepared 60.9 mg of the title compound by a method analogous to 74D using 93A, obtained by a method analogous to 74C, and 54B. $^1$H NMR (400 MHz, CD$_3$OD) δ 8.69 (dd, 1H), 7.66 (dd, 1H), 7.46 (dd, 2H), 7.28 (s, 1H), 7.24-7.18 (m, 1H), 6.68 (t, 1H), 6.36 (d, 2H), 5.37 (t, 1H), 3.06 (d, 2H), 2.84 (d, 1H), 2.06 (d, 1H), 1.76 (t, 1H), 1.24 (d, 1H), 1.16 (s, 3H), 1.07-0.94 (m, 1H), 0.90 (s, 3H), 0.73 (s, 3H). MS (m/z) 656 [M+H]$^+$.

Example 94

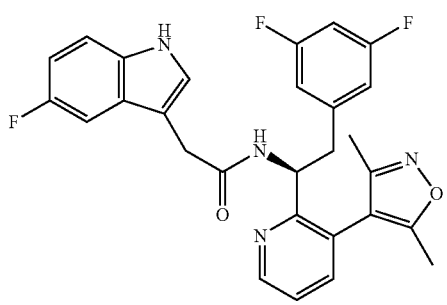

94

Synthesis of N-((1S)-2-(3,5-difluorophenyl)-1-(3-(3,
5-dimethylisoxazol-4-yl)pyridin-2-yl)ethyl)-2-(5-
fluoro-1H-indol-3-yl)acetamide (94)

Prepared 2 mg of the title compound by a method analogous to 55F using 3,5-dimethyl-1,2-oxazolyl-4-boronic acid and 55E. MS (m/z) 505 [M+H]⁺.

Example 95

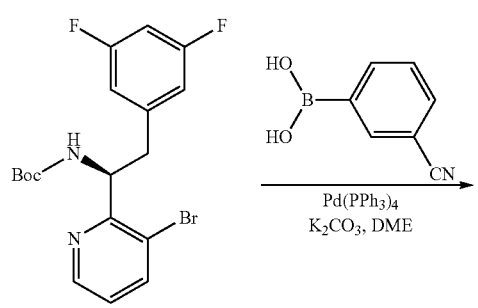

50B

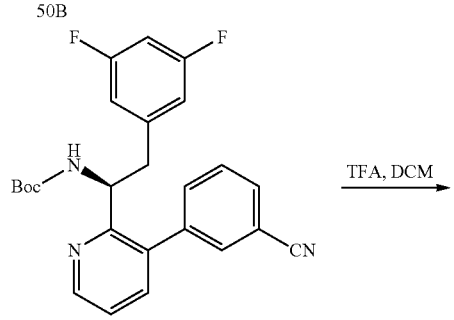

95A

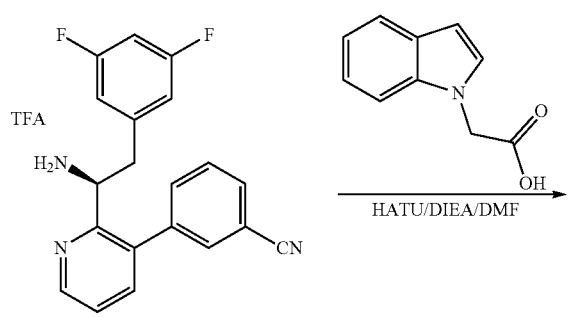

95B

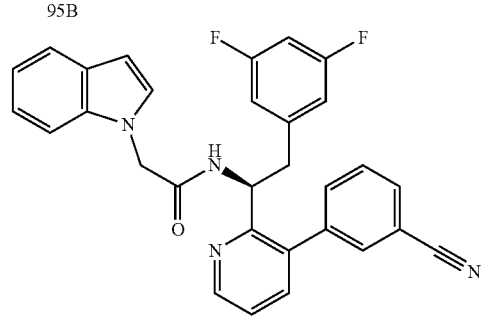

95C

Synthesis of (S)-tert-butyl 1-(3-(3-cyanophenyl)
pyridin-2-yl)-2-(3,5-difluorophenyl)ethylcarbamate
(95A)

Prepared 60 mg of the title compound by a method analogous to 54A using 3-cyanophenyl boronic acid.

Synthesis of (S)-3-(2-(1-amino-2-(3,5-difluorophe-
nyl)ethyl)pyridin-3-yl)benzonitrile trifluoroacetate
(95B)

Prepared 61.9 mg of the title compound by a method analogous to 54B.

Synthesis of (S)—N-(1-(3-(3-cyanophenyl)pyridin-
2-yl)-2-(3,5-difluorophenyl)ethyl)-2-(1H-indol-1-yl)
acetamide (95C)

Prepared 33 mg of the title compound by a method analogous to 74D using compound 95B and indole-1-acetic acid. MS (m/z) 493 [M+H]⁺.

Example 96

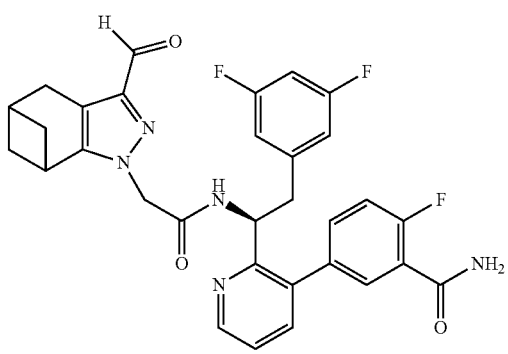

96

Synthesis of (S)-5-(2-(2-(3,5-difluorophenyl)-1-(2-
(4,5,6,7-tetrahydro-3-formyl-5,7-(methano)indazol-
1-yl)acetamido)ethyl)pyridin-3-yl)-2-fluorobenz-
amide (96)

Prepared 256 mg of the title compound by a method analogous to compound 403 starting with compound 81D. MS (m/z) 574 [M+H]⁺.

Example 97

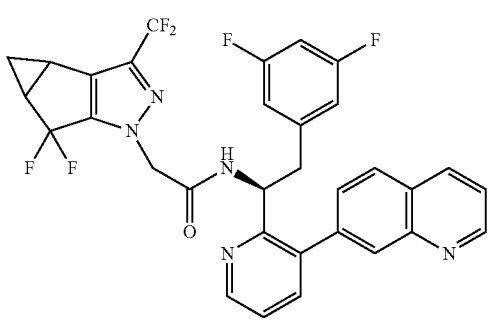

97

Synthesis of (S)—N-(1-(3-(quinoline-7-yl)-pyridin-2-yl)-2-(3,5-difluorophenyl)ethyl)-2-(3-(difluoromethyl)-5,6-dihydro-4,5-(methano)-6,6-difluoro-cyclopenta[c]pyrazol-1(4H)-yl)acetamide (97)

Prepared 6.1 mg of the title compound by a method analogous to 68B using 68A and quinolin-7-yl-7-boronic acid. MS (m/z) 608 [M+H]⁺.

Example 98

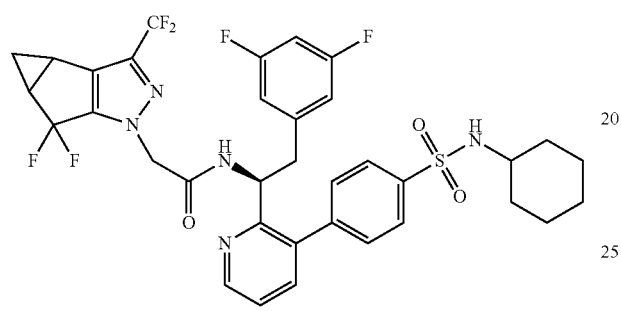

98

Synthesis of (S)—N-(1-(3-(4-(N-cyclohexylsulfamoyl)phenyl)-pyridin-2-yl)-2-(3,5-difluorophenyl)ethyl)-2-(3-(difluoromethyl)-5,6-dihydro-4,5-(methano)-6,6-difluoro-cyclopenta[c]pyrazol-1(4H)-yl)acetamide (98)

Prepared 17.3 mg of the title compound by a method analogous to 68B using 68A and 4-(N-cyclohexylsulfamoyl)phenylboronic acid. MS (m/z) 718 [M+H]⁺.

Example 99

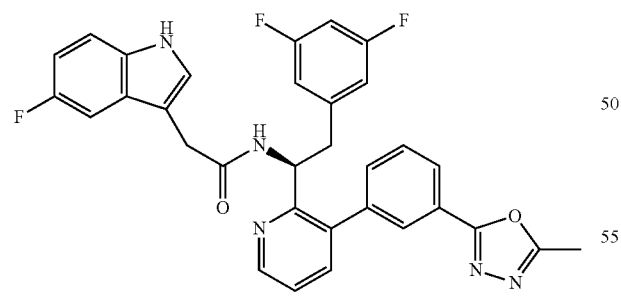

99

Synthesis of (S)—N-(2-(3,5-difluorophenyl)-1-(3-(3-(5-methyl-1,3,4-oxadiazol-2-yl)phenyl)pyridin-2-yl)ethyl)-2-(5-fluoro-1H-indol-3-yl)acetamide (99)

Prepared 9.5 mg of the title compound by a method analogous to 55F using 3-(5-methyl-1,3,4-oxadiazol-2-yl)phenylboronic acid and 55E. MS (m/z) 569 [M+H]⁺.

Example 100

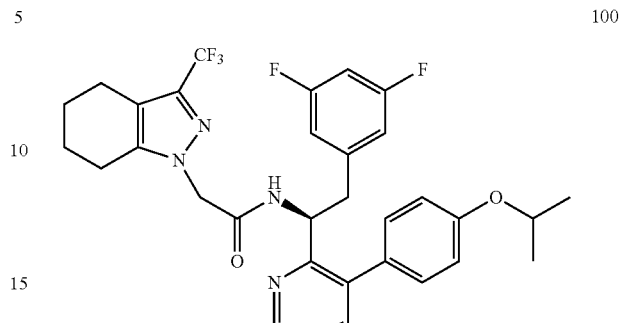

100

Synthesis of (S)—N-(2-(3,5-difluorophenyl)-1-(3-(4-isopropoxyphenyl)pyridin-2-yl)ethyl)-2-(3-(trifluoromethyl)-4,5,6,7-tetrahydro-1H-indazol-1-yl)acetamide (100)

Prepared 4.7 mg of the title compound by a method analogous to compound 57B using 57A and 4-isoproxyphenyl boronic acid. MS (m/z) 599 [M+H]⁺.

Example 101

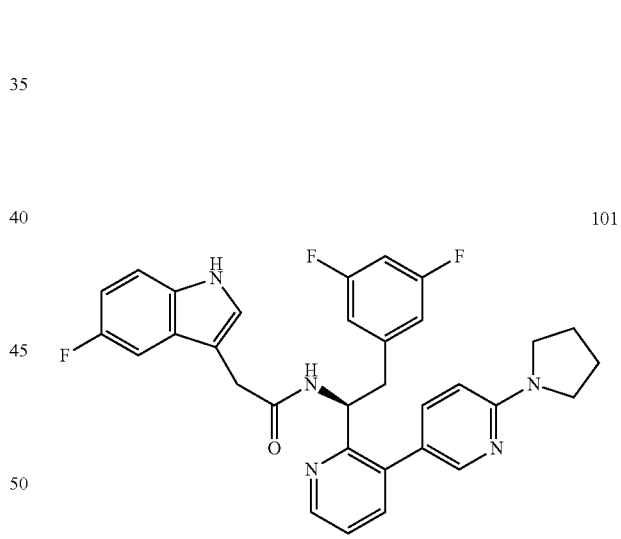

101

Synthesis of (S)—N-(2-(3,5-difluorophenyl)-1-(6'-(pyrrolidin-1-yl)-3,3'-bipyridin-2-yl)ethyl)-2-(5-fluoro-1H-indol-3-yl)acetamide (101)

Prepared 35.5 mg of the title compound by a method analogous to 55F using 6-(pyrrolidin-1-yl)pyridin-3-ylboronic acid and 55E. MS (m/z) 566 [M+H]⁺.

Example 102

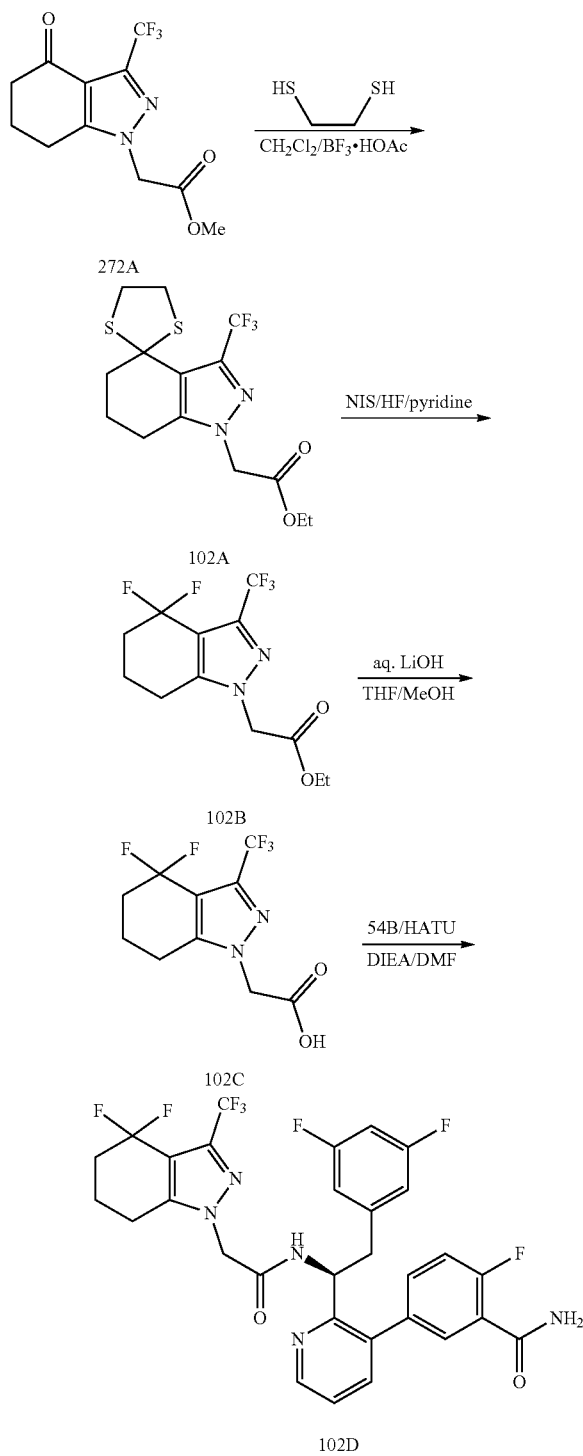

Synthesis of ethyl 2-(3'-(trifluoromethyl)-6',7'-dihydrospiro[[1,3]dithiolane-2,4'-indazole]-1'(5'H)-yl)acetate (102A)

To a solution of 272A (290 mg, 1.0 mmol) in CH$_2$Cl$_2$ was add 1,2-ethanedithiol (126 ul, 1.5 mmol) and BF$_3$·2HOAc (210 ul, 1.5 mmol). The reaction mixture was stirred at room temperature for 16 hrs then partitioned between CH$_2$Cl$_2$ and water. Extracted the aqueous layer 1×CH$_2$Cl$_2$. Washed the combined organics 1× with sat. aq. NaHCO$_3$, H$_2$O and brine. Dried the organics over MgSO$_4$, filtered and concentrated. Purified the crude product on SiO$_2$ eluting with a gradient of EtOAc in hexanes to give 334 mg of the title compound.

Synthesis of ethyl 2-(4,4-difluoro-3-(trifluoromethyl)-4,5,6,7-tetrahydro-1H-indazol-1-yl)acetate (102B)

A solution of N-iodosuccinimide (423 mg, 1.88 mmol) and HF/pyridine (2.6 ml) in CH$_2$Cl$_2$ (2.6 ml) in a Teflon reaction vessel was cooled to −70° C. under N$_2$. A solution of Compound 102A (334 mg, 0.91 mmol) in CH$_2$Cl$_2$ (2.6 ml) was added to the cooled reaction mixture over 5 min. The resulting mixture was stirred at −70° C. for 45 min. then warmed to −50° C. for 20 min. The reaction vessel was placed in an ice bath and the reaction was quenched with sat. aq. NaHCO$_3$. The mixture was diluted with CH$_2$Cl$_2$ and the layers were separated. Extracted the aqueous layer 2× CH$_2$Cl$_2$. Washed the combined organics 1× with brine. Dried the organics over MgSO$_4$, filtered and concentrated. Purified the crude product on SiO$_2$ eluting with a gradient of EtOAc in hexanes to give 112 mg of the title compound.

Synthesis of Ethyl 2-(4,4-difluoro-3-(trifluoromethyl)-4,5,6,7-tetrahydro-1H-indazol-1-yl)acetate (102C)

Prepared 79.2 mg of the title compound by a method analogous to compound 401B using compound 102B.

Synthesis of (S)-5-(2-(1-(2-(4,4-difluoro-3-(trifluoromethyl)-4,5,6,7-tetrahydro-1H-indazol-1-yl)acetamido)-2-(3,5-difluorophenyl)ethyl)pyridin-3-yl)-2-fluorobenzamide (102D)

Prepared 130 mg of the title compound by a method analogous to 54F using 102C and 54B. $^1$H NMR (400 MHz, CD$_3$OD) δ 8.70 (dd, 1H), 7.65 (d, 1H), 7.45 (dd, 2H), 7.33 (s, 1H), 7.22 (dd, 1H), 6.67 (t, 1H), 6.34 (d, 2H), 5.36 (t, 1H), 4.86 (d, 2H), 3.07 (d, 2H), 2.57 (d, 2H), 2.17 (d, 2H), 2.00 (d, 2H). MS (m/z) 638 [M+H]$^+$.

Example 103

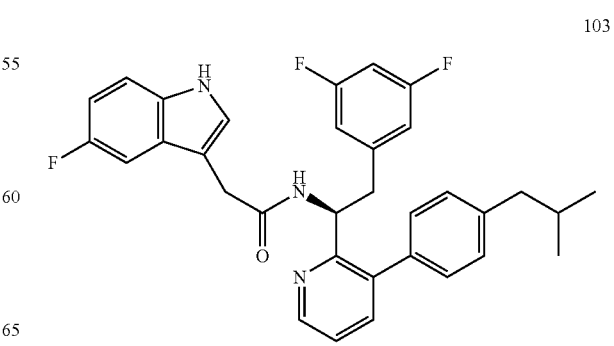

103

Synthesis of (S)—N-(2-(3,5-difluorophenyl)-1-(3-(4-isobutylphenyl)pyridin-2-yl)ethyl)-2-(5-fluoro-1H-indol-3-yl)acetamide (103)

Prepared 37 mg of the title compound by a method analogous to 55F using 4-isobutylphenylboronic acid and 55E. MS (m/z) 542 [M+H]$^+$.

Example 104

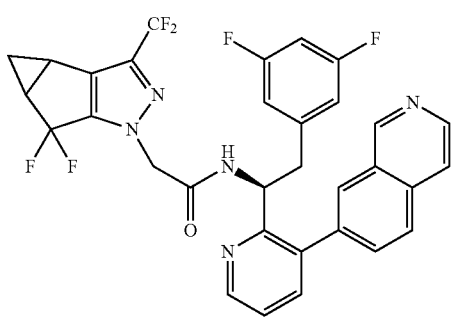

104

Synthesis of (S)—N-(1-(3-(isoquinolin-7-yl)-pyridin-2-yl)-2-(3,5-difluorophenyl)ethyl)-2-(3-(difluoromethyl)-5,6-dihydro-4,5-(methano)-6,6-difluorocyclopenta[c]pyrazol-1(4H)-yl)acetamide (104)

Prepared 11.7 mg of the title compound by a method analogous to 68B using 68A and isoquinolin-7-ylboronic acid. MS (m/z) 608 [M+H]$^+$.

Example 105

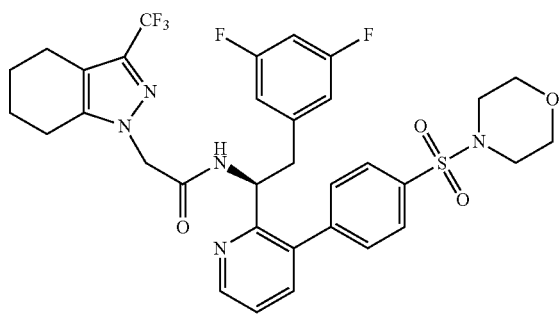

105

Synthesis of (S)—N-(2-(3,5-difluorophenyl)-1-(3-(4-(morpholinosulfonyl)phenyl)pyridin-2-yl)ethyl)-2-(3-(trifluoromethyl)-4,5,6,7-tetrahydro-1H-indazol-1-yl)acetamide (105)

Prepared 38.6 mg of the title compound by a method analogous to compound 57B using 57A and 4-(morpholinosulfonyl)phenylboronic acid. MS (m/z) 690 [M+H]$^+$.

Example 106

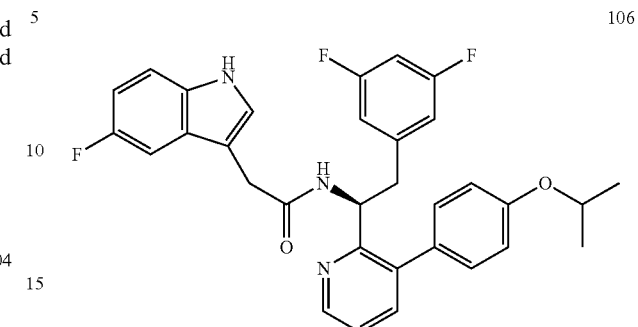

106

Synthesis of (S)—N-(2-(3,5-difluorophenyl)-1-(3-(4-isopropoxyphenyl)pyridin-2-yl)ethyl)-2-(5-fluoro-1H-indol-3-yl)acetamide (106)

Prepared 25.4 mg of the title compound by a method analogous to 55F using 4-isopropoxyphenylboronic acid and 55E. MS (m/z) 544 [M+H]$^+$.

Example 107

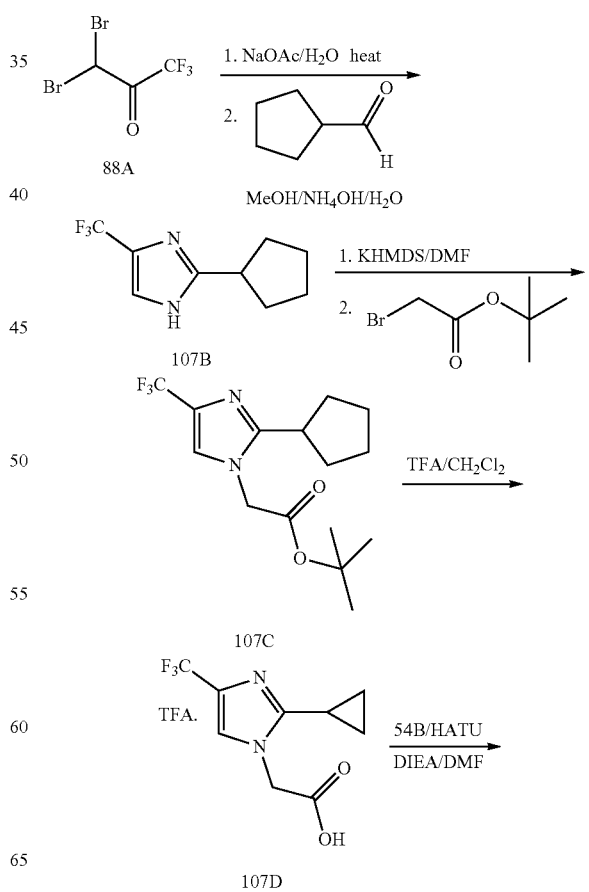

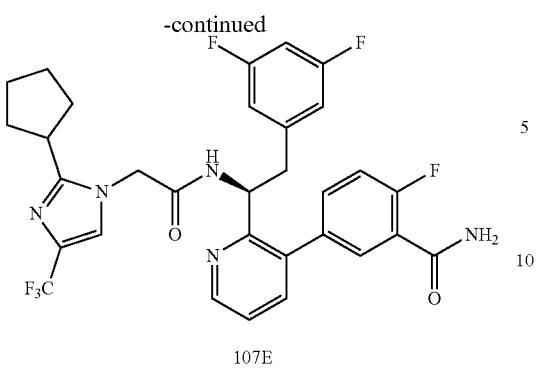

107E

Synthesis of 2-cyclopentyl-4-(trifluoromethyl)-1H-imidazole (107B)

To a suspension of 3,3-dibromo-1-trifluoromethyl-propane (2.35 g, 8.72 mmol) in $H_2O$ was added sodium acetate (1.67 g, 20.4 mmol). The mixture was heated at 100° C. for 30 min. and then cooled to room temperature. A solution of cyclopentanecarboxaldehyde (1 g, 10.2 mmol) in 4.8 ml of MeOH was added to the reaction mixture followed by $NH_4OH$ (4.8 ml, 20% in $H_2O$). The reaction was stirred at room temperature overnight. The mixture was extracted 3× with EtOAc. The combined organics were washed with brine, dried over $MgSO_4$, filtered and concentrated. The crude product was used directly for the next step.

Synthesis of tert-butyl 2-(2-cyclopentyl-4-(trifluoromethyl)-1H-imidazol-1-yl)acetate (107C)

The crude product from 107B (8.72 mmol) was dissolved in 86 ml DMF. Solid KHMDS (2.09 g, 10.5 mmol) was added and the reaction was stirred 5 min. at room temperature. Added t-butyl bromoacetate (1.52 ml, 10.5 mmol) and then stirred the reaction for 30 min. at room temperature. The mixture was concentrated under reduced pressure to a small volume then partitioned between EtOAc and $H_2O$. Extracted the aqueous layer 2× EtOAc. The combined organics were washed with brine, dried over $MgSO_4$, filtered and concentrated. The crude product was purified by column chromatography on $SiO_2$ to give 279 mg of the title compound.

Synthesis of 2-(2-cyclopentyl-4-(trifluoromethyl)-1H-imidazol-1-yl)acetic acid (107D)

Dissolved 107C (84 mg, 0.264 mmol) in 1:1 $TFA/CH_2Cl_2$ (2 ml). Added 2 drops of $H_2O$ and stirred reaction at room temperature for 4 hrs. The reaction mixture was concentrated in vacuo. The residue was azeotroped 2× with $Et_2O$ and then dried under reduced pressure to give 105 mg of the title compound.

Synthesis of (S)-5-(2-(1-(2-(2-cyclopentyl-4-(trifluoromethyl)-1H-imidazol-1-yl)acetamido)-2-(3,5-difluorophenyl)ethyl)pyridin-3-yl)-2-fluorobenzamide (107E)

Prepared 58.5 mg of the title compound by a method analogous to 54G using 107D and 54B. $^1H$ NMR (400 MHz, $CD_3OD$) δ 8.62 (d, 1H), 7.51 (d, 1H), 7.39 (s, 2H), 7.32 (dd, 1H), 7.29-7.22 (m, 1H), 7.18-7.11 (m, 1H), 6.60 (s, 1H), 6.29 (d, 2H), 5.26 (t, 1H), 4.71 (d, 2H), 3.05-2.92 (m, 2H), 2.87 (s, 1H), 1.69 (s, 8H). MS (m/z) 616 $[M+H]^+$.

Example 108

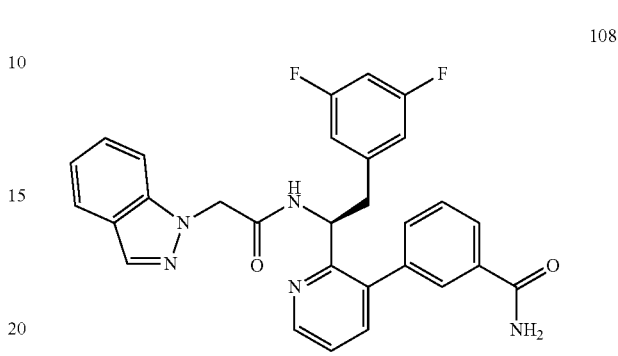

108

Synthesis of (S)-3-(2-(1-(2-(1H-indazol-1-yl)acetamido)-2-(3,5-difluorophenyl)ethyl)pyridin-3-yl) benzamide (108)

Prepared 22 mg of the title compound by a method analogous to 50C using benzimidazole-1-acetic acid. $^1H$ NMR (400 MHz, dmso) δ 8.91 (d, 1H), 8.69 (dd, 1H), 7.96 (s, 1H), 7.96-7.81 (m, 2H), 7.75-7.59 (m, 3H), 7.53-7.36 (m, 3H), 7.27 (q, 2H), 7.07 (t, 1H), 6.93 (t, 1H), 6.51 (d, 2H), 5.18 (dd, 2H), 5.04 (s, 2H), 4.59-4.54 (m, 1H), 3.08-2.53 (m, 3H). MS (m/z) 512 $[M+H]^+$.

Example 109

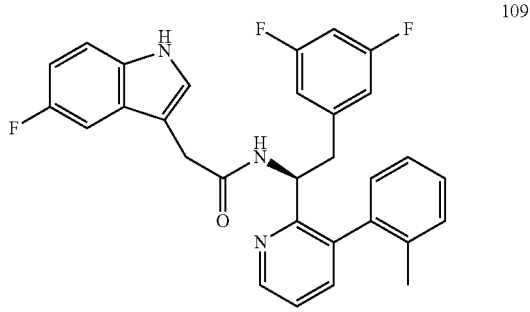 [SMILES: Cc1ccccc1-c1cccnc1[C@H](Cc1cc(F)cc(F)c1)NC(=O)Cc1c[nH]c2ccc(F)cc12]

109

Synthesis of (S)—N-(2-(3,5-difluorophenyl)-1-(3-o-tolylpyridin-2-yl)ethyl)-2-(5-fluoro-1H-indol-3-yl) acetamide (109)

Prepared 16.7 mg of the title compound by a method analogous to 55F using 2-methylphenylboronic acid and 55E. MS (m/z) 500 $[M+H]^+$.

Example 110

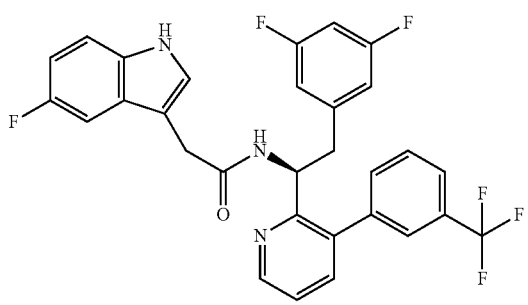

Synthesis of (S)—N-(2-(3,5-difluorophenyl)-1-(3-(3-(trifluoromethyl)phenyl)pyridin-2-yl)ethyl)-2-(5-fluoro-1H-indol-3-yl)acetamide (110)

Prepared 34 mg of the title compound by a method analogous to 55F using 3-trifluormethylphenyl boronic acid and 55E. MS (m/z) 554 [M+H]+.

Example 111

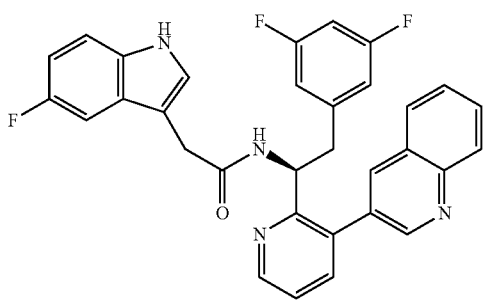

Synthesis of (S)—N-(2-(3,5-difluorophenyl)-1-(3-(quinolin-3-yl)pyridin-2-yl)ethyl)-2-(5-fluoro-1H-indol-3-yl)acetamide (111)

Prepared 22.7 mg of the title compound by analogous method to 55F using quinoline-3-ylboronic acid and 55E. MS (m/z) 537 [M+H]+.

Example 112

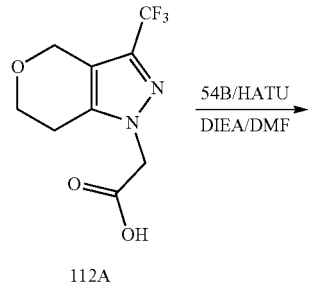

112A

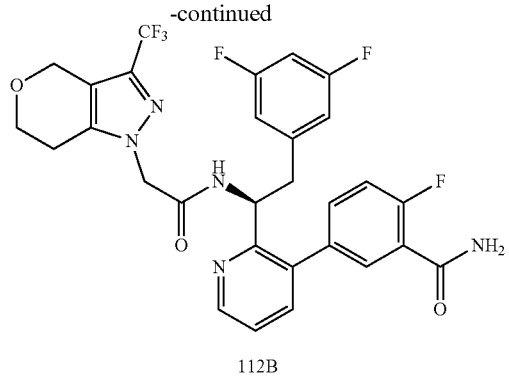

112B

Synthesis of (S)-5-(2-(2-(3,5-difluorophenyl)-1-(2-(3-(trifluoromethyl)-6,7-dihydropyrano[4,3-c]pyrazol-1(4H)-yl)acetamido)ethyl)pyridin-3-yl)-2-fluorobenzamide (112B)

Prepared 58.5 mg of the title compound by a method analogous to 54G using 112A (prepared by analogous method to 107D) and 54B. ¹H NMR (400 MHz, CD₃OD) δ 8.62 (d, 1H), 7.56 (dd, 1H), 7.27 (ddd, 4H), 6.59 (t, 1H), 6.26 (d, 2H), 5.28 (t, 1H), 4.56 (s, 2H), 3.79 (t, 2H), 3.08-2.90 (m, 2H), 2.78-2.27 (m, 3H). MS (m/z) 605 [M+H]+.

Example 113

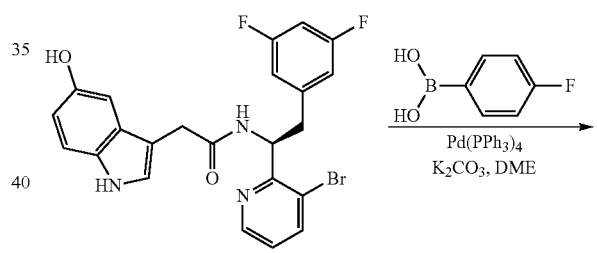

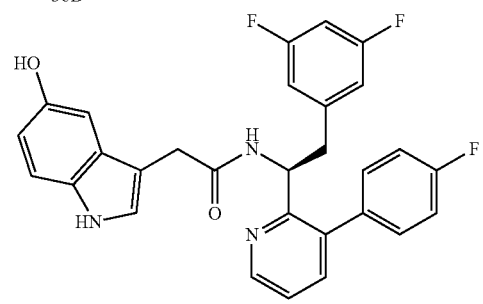

113

Synthesis of (S)—N-(2-(3,5-difluorophenyl)-1-(3-(4-fluorophenyl)pyridin-2-yl)ethyl)-2-(5-hydroxy-1H-indol-3-yl)acetamide (113)

To a solution of 38D (50 mg, 0.103 mmol) and 4-fluorophenyl boronic acid (15.7 mg, 0.113 mmol) in 1 ml DME was added 0.4N aq. K₂CO₃ (515 ul) and Pd(PPh₃)₄ (11.9 mg, 0.0010 mmol). The resulting mixture was heated at 120° C.

for 10 min. under microwave irradiation. Solvents were concentrated in vacuo and the residue was purified by RP HPLC using a C18 column with a gradient of 0.1%/H$_2$O, 0.1% TFA-acetonitrile, to provide 31 mg of the title compound. $^1$H NMR (400 MHz, dmso) δ 10.47 (s, 1H), 8.62 (dd, 1H), 8.46 (d, 1H), 7.51 (dd, 1H), 7.34 (dd, 1H), 7.15 (dd, 4H), 7.05 (d, 1H), 6.91 (dd, 2H), 6.77 (d, 2H), 6.53 (dd, 1H), 6.34 (d, 2H), 5.15 (q, 2H), 4.27-4.22 (m, 1H), 3.39 (s, 2H), 2.90 (d, 2H). MS (m/z) 501 [M+H]$^+$.

Example 114

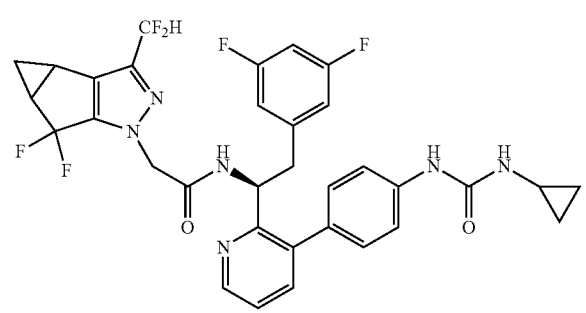

114

Synthesis of (S)—N-(1-(3-(4-(3-cyclopropylureido)phenyl)-pyridin-2-yl)-2-(3,5-difluorophenyl)ethyl)-2-(3-(difluoromethyl)-5,6-dihydro-4,5-(methano)-6,6-difluoro-cyclopenta[c]pyrazol-1(4H)-yl)acetamide (114)

Prepared 12.2 mg of the title compound by a method analogous to 68B using 68A and 4-(3-cyclopropylureido)phenylboronic acid, pinacol ester. MS (m/z) 655 [M+H]$^+$.

Example 115

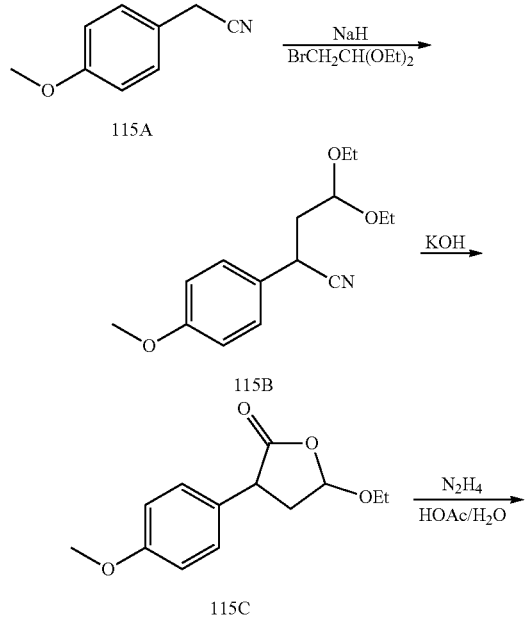

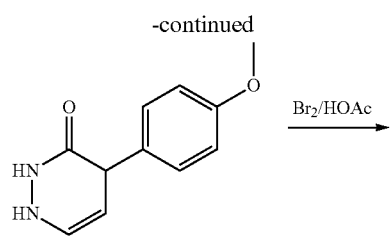

115D

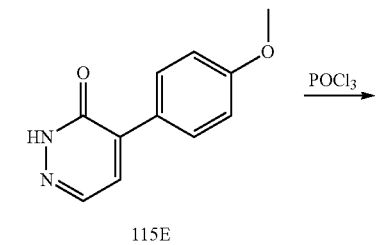

115E

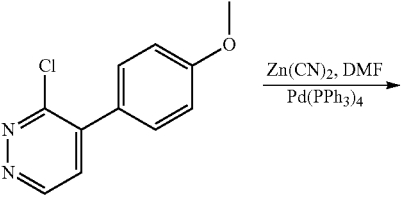

115F

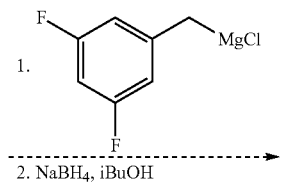

115G

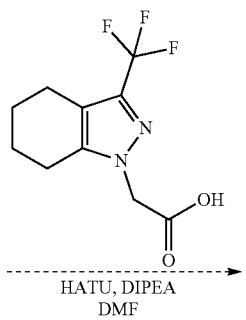

115H

Synthesis of 4,4-diethoxy-2-(4-methoxyphenyl)butanenitrile (115B)

Compound 115A (21.0 g, 143 mmol) was added to a suspension of NaH (8.9 g, 215 mmol) in THF (250 ml), and stirred at 50° C. for 1.5 hr. Ethyl bromoacetate (33.82 g, 172 mmol) was added to the mixture which was then boiled under reflux for 2 hr. The mixture was diluted with water, extracted with EtOAc (400 ml 3) and washed with brine (1000 ml). The combined extracts are dried with anhydrous Na$_2$SO$_4$, filtered and concentrated. The residue was purified by column chromatography on silica gel to afford the title compound (29.2 g, 78% yield) as a pale yellow oil.

Synthesis of 5-ethoxy-3-(4-methoxyphenyl)dihydrofuran-2(3H)-one (115C)

Compound 115B (29.0 g, 110 mmol) and KOH (30.9 g, 550 mmol) are dissolved in EtOH (300 ml) and water (100 ml). The solution was boiled under reflux for 3 days, acidified with 10 N HCl and evaporated, extracted with EtOAc (400 ml 4) and washed with brine (1500 ml). The combined extracts are dried with anhydrous Na$_2$SO$_4$, filtered and concentrated. The residue was purified by column chromatography on silica gel (PE/EtOAc=8/1) to afford the title compound (14.0 g, 54% yield) as a pale yellow oil.

Synthesis of 4-(4-methoxyphenyl)-1,2-dihydropyridazin-3(4H)-one (115D)

Compound 115C (3.54 g, 15 mmol) and N$_2$H$_4$.H$_2$O (2 ml, 30 mmol) are dissolved in AcOH (15 ml) and water (10 ml). The solution was boiled under reflux for 1.5 hr, and poured into aqueous NaHCO$_3$, extracted with EtOAc (100 ml 4) and wash with brine (300 ml). The combined extracts are dried with anhydrous Na$_2$SO$_4$, filtered and concentrated. The residue was purified by column chromatography on silica gel (PE/EtOAc=5/1) to afford the title compound (2.32 g, 72% yield) as a pale yellow solid.

Synthesis of 4-(4-methoxyphenyl)pyridazin-3(2H)-one (115E)

A solution of Br$_2$ (0.4 ml) in AcOH (1 ml) was added during 2 min to a stirred solution of Compound 115D (1.22 g, 6 mmol) in AcOH (7 ml) at 70° C., which was then poured into aqueous NaHCO$_3$, extracted with DCM (100 ml 4) and wash with brine (400 ml). The combined extracts are dried with anhydrous Na$_2$SO$_4$, filtered and concentrated. The residue was purified by column chromatography on silica gel (PE/EtOAc=2/1) to afford the title compound (0.89 g, 74% yield) as a yellow solid.

Synthesis of 3-chloro-4-(4-methoxyphenyl)pyridazine (115F)

A solution of Compound 115E (0.89 g, 4.4 mmol, 1.0 eq) in POCl$_3$ (15 ml) and 3 drops pyridine was boiled under reflux for 3 h. After cooling, the solution was poured onto ice and extracted with DCM (100 ml 4) and wash with aqueous NaHCO$_3$ (500 ml) and brine (500 ml). The combined extracts are dried with anhydrous Na$_2$SO$_4$, filtered and concentrated. The residue was purified by column chromatography on silica gel (PE/EtOAc=3/1) to afford the title compound (0.69 g, 71% yield) as a pale yellow solid. $^1$H NMR (300 MHz, CDCl$_3$): δ 3.89 (3H, s), 7.05 (2H, d), 7.45 (1H, d), 7.50 (2H, d), 9.13 (1H, d); MS (m/z) 613 [M+H]$^+$.

Synthesis of 4-(4-methoxyphenyl)pyridazine-3-carbonitrile (115G)

To 115F (395 mg, 1.8 mmol) dissolved in DMF (18 mL) was added Zn(CN)$_2$ (388 mg, 3.3 mmol) and Pd(PPh$_3$)$_4$ (50 mg, 0.44 mmol). The mixture was degassed by alternating vacuum/N$_2$ purge (3×) and the reaction heated to 100° C. After 2 h, the reaction was cooled to ambient temperature, filtered over celite, and the eluent was concentrated. The residue was partitioned between EtOAc and H$_2$O. The organics separated, washed with saturated aqueous NaCl, and dried. After removal of solvent in vacuo, the residue was purified by column chromatography on silica to provide 350 mg of the title compound: $^1$H NMR (400 MHz, cdcl$_3$) δ 9.30 (d, J=5.6 Hz, 1H), 7.66-7.57 (m, 3H), 7.24 (s, 1H), 7.12-7.05 (m, 2H), 3.89 (s, 3H). MS (m/z) 212.2 [M+H]$^+$.

Synthesis of 5-(3-(1-amino-2-(3,5-difluorophenyl)ethyl)pyridazin-4-yl)-2-fluorobenzamide (115H)

We envision Compound 115G may be further elaborated to the amine compound 115H in the manner described for an analogous pyridine compound 1B in Example 1. Alternatively, we envision Compound 115G may be further elaborated to the amine compound 115H in the manner described for an analogous pyrazine compound 443B in Example 443

Synthesis of 5-(3-(2-(3,5-difluorophenyl)-1-(2-(3-(trifluoromethyl)-4,5,6,7-tetrahydro-1H-indazol-1-yl)acetamido)ethyl)pyridazin-4-yl)-2-fluorobenzamide (115I)

In a manner analogous to the synthesis of Example 589, we envision the title compound may be synthesized utilizing 2-(3-(trifluoromethyl)-4,5,6,7-tetrahydro-1H-indazol-1-yl) acetic acid and substituting 115H for 54B.

Example 116

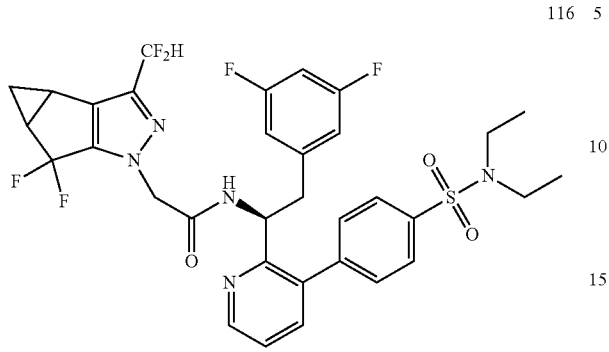

Synthesis of (S)—N-(1-(3-(4-(N,N-diethylsulfamoyl)phenyl)-pyridin-2-yl)-2-(3,5-difluorophenyl)ethyl)-2-(3-(difluoromethyl)-5,6-dihydro-4,5-(methano)-6,6-difluoro-cyclopenta[c]pyrazol-1(4H)-yl)acetamide (116)

Prepared 14 mg of the title compound by a method analogous to 68B using 68A and 4-(N,N-diethylsulfamoyl)phenylboronic acid. MS (m/z) 692 [M+H]$^+$.

Example 117

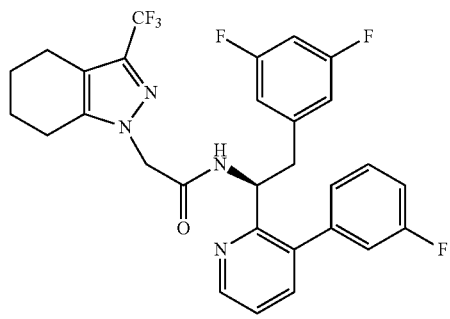

Synthesis of (S)—N-(2-(3,5-difluorophenyl)-1-(3-(3-fluorophenyl)pyridin-2-yl)ethyl)-2-(3-(trifluoromethyl)-4,5,6,7-tetrahydro-1H-indazol-1-yl)acetamide (117)

Prepared 11.2 mg of the title compound by a method analogous to compound 57B using 57A and 3-fluorophenyl boronic acid. MS (m/z) 559 [M+H]$^+$.

Example 118

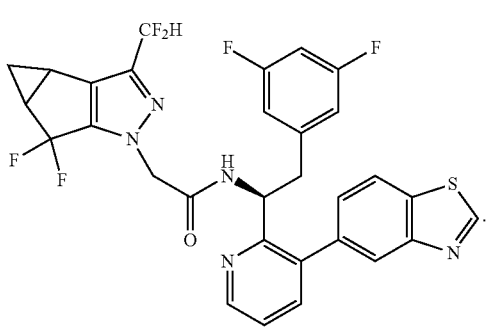

Synthesis of (S)—N-(1-(3-(benzo[d]thiazole-5-yl)-pyridin-2-yl)-2-(3,5-difluorophenyl)ethyl)-2-(3-(difluoromethyl)-5,6-dihydro-4,5-(methano)-6,6-difluoro-cyclopenta[c]pyrazol-1(4H)-yl)acetamide (118)

Prepared 11.1 mg of the title compound by a method analogous to 68B using 68A and 5-(4,4,5,5-tetramethyl-1,3,2-dioxaborolan-2-yl)benzo[d]thiazole. MS (m/z) 612 [M+H]$^+$.

Example 119

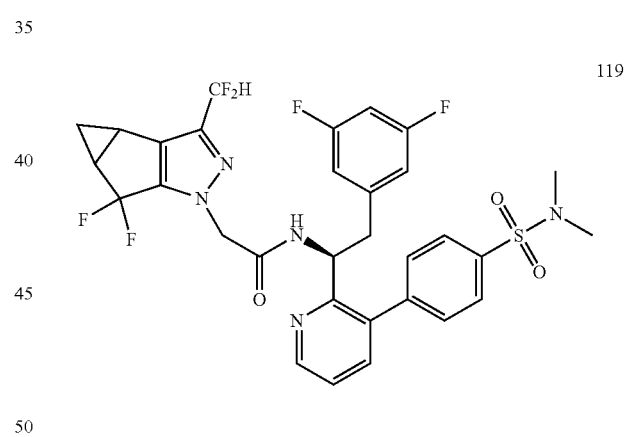

Synthesis of (S)—N-(1-(3-(4-(N,N-dimethylsulfamoyl)phenyl)-pyridin-2-yl)-2-(3,5-difluorophenyl)ethyl)-2-(3-(difluoromethyl)-5,6-dihydro-4,5-(methano)-6,6-difluoro-cyclopenta[c]pyrazol-1(4H)-yl)acetamide (119)

Prepared 17.3 mg of the title compound by a method analogous to 68B using 68A and 4-(N,N-dimethylsulfamoyl)phenylboronic acid. MS (m/z) 664 [M+H]$^+$.

Example 120

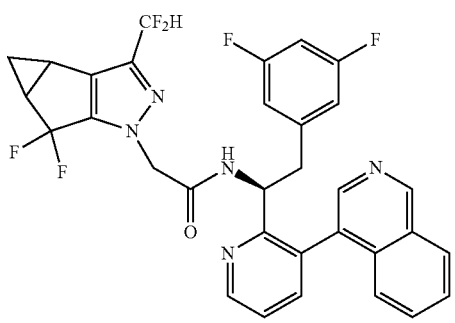

Synthesis of 2-(3-(difluoromethyl)-5,5-difluoro-3b,4,4a,5-tetrahydro-1H-cyclopropa[3,4]cyclopenta[1,2-c]pyrazol-1-yl)-N—((S)-2-(3,5-difluorophenyl)-1-(3-(isoquinolin-4-yl)pyridin-2-yl)ethyl)acetamide (120)

Prepared 6.1 mg of the title compound by a method analogous to 68B using 68A and 4-(4,4,5,5-tetramethyl-1,3,2-dioxaborolan-2-yl)isoquinoline. MS (m/z) 608 [M+H]$^+$.

Example 121

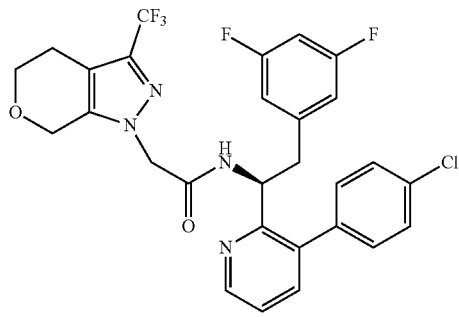

Synthesis of (S)—N-(1-(3-(4-chlorophenyl)pyridin-2-yl)-2-(3,5-difluorophenyl)ethyl)-2-(3-(trifluoromethyl)-4,5-dihydropyrano[3,4-c]pyrazol-1(7H)-yl)acetamide (121)

The title compound was prepared (22 mg) according to the method presented in the synthesis of Example 36 utilizing 36E and 2-(3-(trifluoromethyl)-4,5-dihydropyrano[3,4-c]pyrazol-1 (7H)-yl)acetic acid. $^1$H NMR (400 MHz, dmso) δ 8.95 (s, 1H), 8.61 (s, 1H), 7.50 (s, 1H), 7.44-7.28 (m, 3H), 7.19-7.03 (m, 2H), 6.89 (s, 1H), 6.44-6.31 (m, 2H), 5.10 (s, 1H), 4.74-4.64 (m, 3H), 4.51-4.30 (m, 4H), 3.72-3.59 (m, 4H), 2.95-2.85 (m, 2H), 2.62-2.47 (m, 3H), 2.24 (s, 1H), 1.87-1.76 (m, 1H). MS (m/z) 577.5 [M+H]$^+$.

Example 122

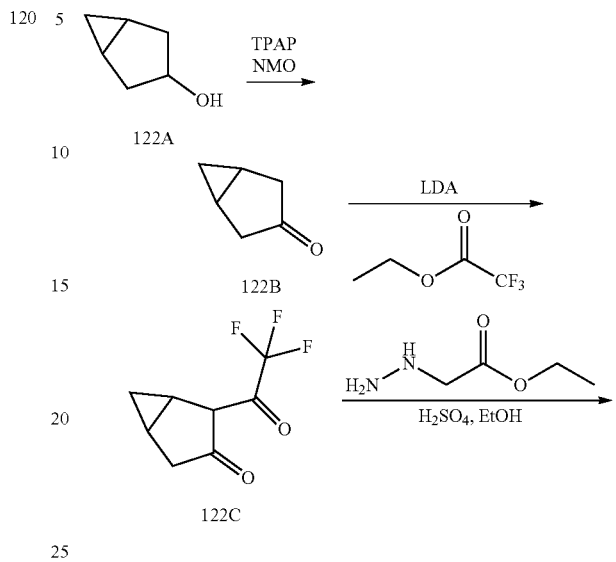

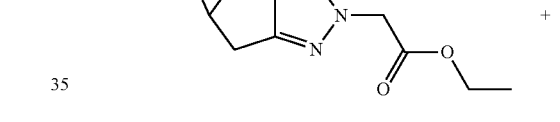

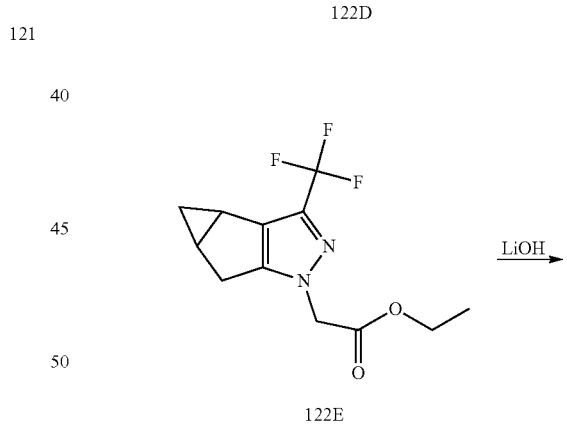

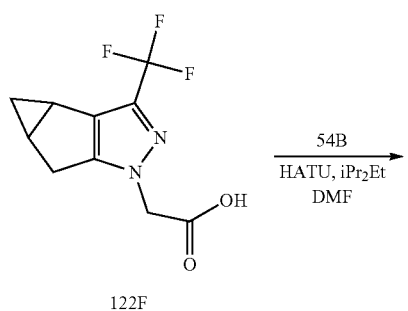

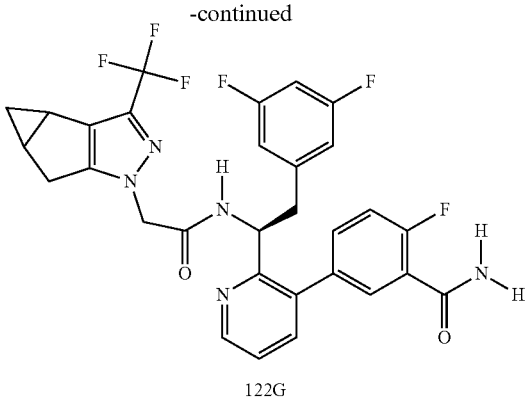

122G

Synthesis of bicyclo[3.1.0]hexan-3-one (122B)

To bicyclo[3.1.0]hexan-3-ol (2 g, 20.4 mmol) dissolved in DCM (40 mL) was added NMO (2.99 g, 25.5 mmol) and 4 Å molecular sieves (~4 g). The reaction mixture was cooled to 0° C. and TPAP (144 mg, 2 mol %) added. After 10 min, the reaction was let warm to ambient temperature and stirred for 3 h. The reaction was filtered over celite, eluted with DCM and the eluent purified by column chromatography on silica. The desired fractions were combined, washed with aqueous 1 N HCl (3×), dried with sodium sulfate, and solvents removed in vacuo to provide the title compound.

Synthesis of 2-(2,2,2-trifluoroacetyl)bicyclo[3.1.0] hexan-3-one (122C)

Bicyclo[3.1.0]hexan-3-one (2.18 g, 22.7 mmol) was dissolved in THF (150 mL) and cooled to −78° C. upon which LDA (2.0 M, 11.5 mL) was added and stirred 15 min at −78° C. Ethyl 2,2,2-trifluoroacetate (2.96 mL, 25 mmol) was added dropwise and the reaction stirred 30 at −78° C. and then let warm to room temperature. After 3 h at room temperature, the reaction was judged complete by LCMS. The reaction was quenched with aqueous 1 N HCl and then partitioned between EtOAc and aqueous citric acid. The organics were separated and dried with saturated aqueous NaCl. Solvents were removed in vacuo to provide the title compound (3.74 g).

Synthesis of ethyl 2-(3-(trifluoromethyl)-3b,4,4a,5-tetrahydro-1H-cyclopropa[3,4]cyclopenta[1,2-c]pyrazol-2-yl)acetate (122D) and ethyl 2-(3-(trifluoromethyl)-3b,4,4a,5-tetrahydro-1H-cyclopropa[3,4]cyclopenta[1,2-c]pyrazol-1-yl)acetate (122E)

2-(2,2,2-trifluoroacetyl)bicyclo[3.1.0]hexan-3-one (1 g, 5.2 mmol) was dissolved in EtOH (10 mL) to which sulfuric acid (0.1 mL) was added. 2-hydrazinyl acetic acid ethyl ester hydrochloride (0.805 g, 5.2 mmol) was added and the reaction mixture was heated to 85° C. After 30 min, LCMS shows complete conversion to pyrazole product. After cooling to room temperature, the reaction was neutralized by the addition of 2N aqueous NaOH. The reaction was concentrated in vacuo and the residue was partitioned between EtOAc and water. The organics were separated, washed with saturated aqueous NaHCO₃, dried with saturated aqueous NaCl, and solvents removed in vacuo. NMR indicated the crude product was a mixture of 122D and the title compound 122E as a ratio of 1:5.5. The regioisomers were separable by column chromatography on silica to provide 122D (MS (m/z) 275.1 [M+H]⁺) and the title compound 122E (720 mg, MS (m/z) 275.1 [M+H]⁺).

Synthesis of 2-(3-(trifluoromethyl)-3b,4,4a,5-tetrahydro-1H-cyclopropa[3,4]cyclopenta[1,2-c]pyrazol-1-yl)acetic acid (122F)

Ethyl 2-(3-(trifluoromethyl)-3b,4,4a,5-tetrahydro-1H-cyclopropa[3,4]cyclopenta[1,2-c]pyrazol-1-yl)acetate (145 mg, 0.53 mmol) was dissolved in a mixture of THF (3 mL) and MeOH (1 mL) and treated with LiOH (19 mg, 0.8 mmol) dissolved in H₂O (1 mL). After stirring 3 h at ambient temperature, the mixture was partitioned between EtOAc and 20% aqueous KH₂PO₄. The organics were separated, dried, and removed in vacuo to provide the title compound.

Synthesis of 5-(2-((1S)-2-(3,5-difluorophenyl)-1-(2-(3-(trifluoromethyl)-3b,4,4a,5-tetrahydro-1H-cyclopropa[3,4]cyclopenta[1,2-c]pyrazol-1-yl)acetamido)ethyl)pyridin-3-yl)-2-fluorobenzamide (122G)

Compound 122G was prepared according to the method presented in the synthesis of Example 54 utilizing 54B and 122F to provide the title compound (46 mg): ¹H NMR (400 MHz, dmso) δ 8.91 (d, 1H), 8.66 (s, 1H), 7.75-7.56 (m, 3H), 7.49-7.37 (m, 3H), 7.36-7.25 (m, 1H), 6.91 (d, 1H), 6.64-6.41 (m, 3H), 5.15 (d, 2H), 4.66 (dd, 3H), 2.99 (t, 2H), 2.64 (s, 1H), 2.55 (d, 2H), 2.49-2.42 (m), 2.29 (s, 1H), 2.00 (s, 2H), 1.02 (d, 1H), 0.12 (s, 1H). MS (m/z) 600.4 [M+H]⁺.

Example 123

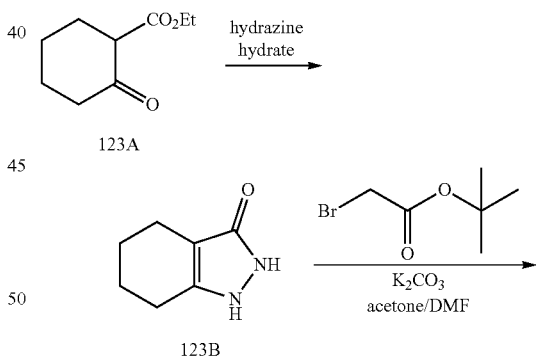

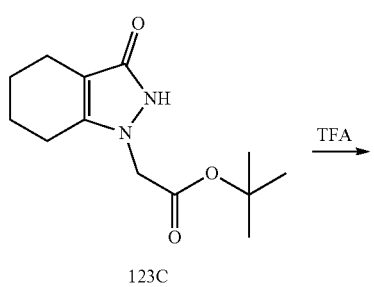

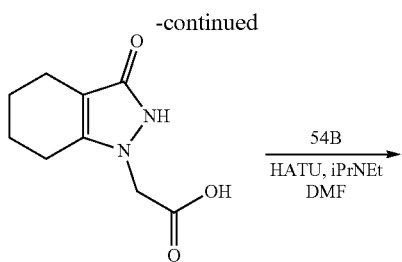

123D

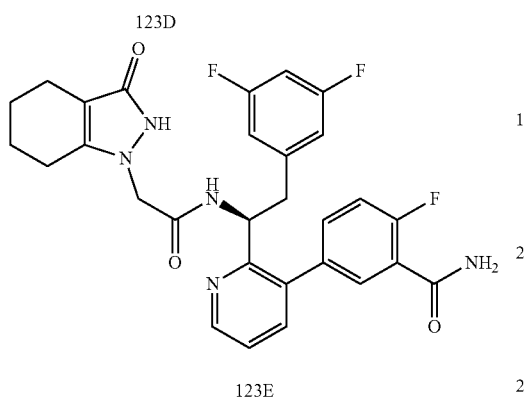

123E

Synthesis of 4,5,6,7-tetrahydro-1H-indazol-3(2H)-one (123B)

Ethyl 2-oxocyclohexanecarboxylate (5 mL, 29.4 mmol) was combined with hydrazine hydrate (1.47 mL, 29.4 mmol) in EtOH (60 mL) and heated to reflux. After 6 h, the reaction was cooled to ambient temperature and white precipitate was filtered to obtain pure title compound. MS (m/z) 139.13 [M+H]$^+$.

Synthesis of tert-butyl 2-(3-oxo-2,3,4,5,6,7-hexahydro-1H-indazol-1-yl)acetate (123C)

4,5,6,7-Tetrahydro-1H-indazol-3(2H)-one (300 mg, 2.17 mmol) was combined with tert-butyl 2-bromoacetate (0.29 mL, 1.96 mmol) and K$_2$CO$_3$ (300 mg, 2.17 mmol) in acetone/DMF (25 mL, 4:1). The reaction mixture was stirred at 25° C. for 14 h. Multiple isomers were formed in the reaction mixture and desired product was isolated by column chromatography on silica (yield: 200 mg): MS (m/z) 253.34 [M+H]$^+$.

Synthesis of 2-(3-oxo-2,3,4,5,6,7-hexahydro-1H-indazol-1-yl)acetic acid (123D)

tert-Butyl 2-(3-oxo-2,3,4,5,6,7-hexahydro-1H-indazol-1-yl)acetate (30 mg, 0.119 mmol) was dissolved in DCM (0.6 mL) and treated with TFA (0.6 mL). The reaction was stirred for 1.5 h at ambient temperature at which time solvents were removed in vacuo to provide the desired product: MS (m/z) 197.16 [M+H]$^+$.

Synthesis of (S)-5-(2-(2-(3,5-difluorophenyl)-1-(2-(3-oxo-2,3,4,5,6,7-hexahydro-1H-indazol-1-yl)acetamido)ethyl)pyridin-3-yl)-2-fluorobenzamide (123E)

The title compound was prepared (24 mg) according to the method presented in the synthesis of Example 54G utilizing 54B and 2-(3-oxo-2,3,4,5,6,7-hexahydro-1H-indazol-1-yl)acetic acid. $^1$H NMR (400 MHz, cd$_3$od) δ 8.69 (dd, 1H), 7.62 (dd, 1H), 7.50 (d, 1H), 7.42 (dd, 1H), 7.38-7.17 (m, 2H), 6.75-6.61 (m, 1H), 6.33 (d, 2H), 5.34 (t, 1H), 4.85 (s, 11H), 4.66 (d, 2H), 3.29 (dt, 8H), 3.16-2.98 (m, 2H), 2.39 (dt, Hz, 3H), 1.99-1.51 (m, 4H), 1.45 (s, 1H). MS (m/z) 550.5 [M+H]$^+$.

Example 124

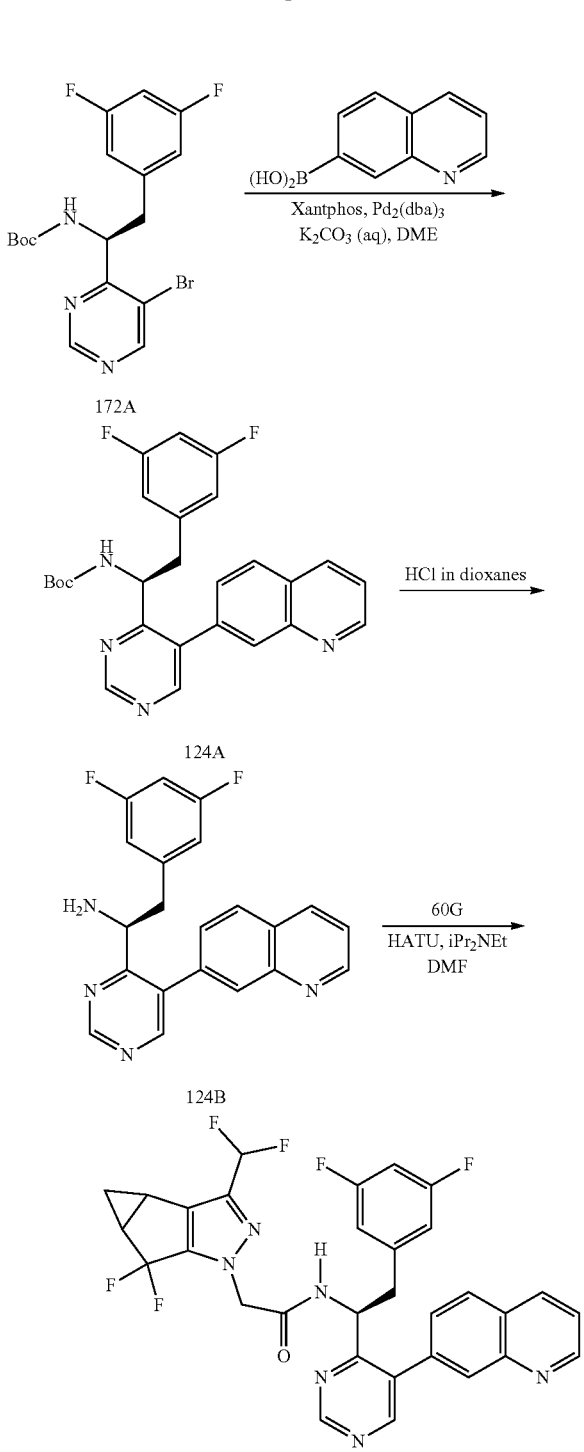

Synthesis of (S)-tert-butyl 2-(3,5-difluorophenyl)-1-(5-(quinolin-7-yl)pyrimidin-4-yl)ethylcarbamate (124A)

The title compound as prepared according to the method presented in the synthesis of 136B in Example 136 utilizing 172A and quinolin-7-ylboronic acid to provide the title compound. MS (m/z) 463.1 [M+H]⁺.

Synthesis of (S)-2-(3,5-difluorophenyl)-1-(5-(quinolin-7-yl)pyrimidin-4-yl)ethanamine (124B)

The title compound as prepared according to the method presented in the synthesis of 136C in Example 136 utilizing (S)-tert-butyl 2-(3,5-difluorophenyl)-1-(5-(quinolin-7-yl)pyrimidin-4-yl)ethylcarbamate to provide the title compound.

Synthesis of 2-(3-(difluoromethyl)-5,5-difluoro-3b,4,4a,5-tetrahydro-1H-cyclopropa[3,4]cyclopenta[1,2-c]pyrazol-1-yl)-N—((S)-2-(3,5-difluorophenyl)-1-(5-(quinolin-7-yl)pyrimidin-4-yl)ethyl)acetamide (124C)

The title compound as prepared (20 mg) according to the method presented in the synthesis of Example 54 utilizing 60G and 124B. ¹H NMR (400 MHz, dmso) δ 9.31 (s, 1H), 9.13 (d, 1H), 8.97 (s, 1H), 8.74 (s, 1H), 8.48 (s, 1H), 8.06 (d, 1H), 7.86 (s, 1H), 7.62 (s, 1H), 7.55 (d, 1H), 6.95-6.85 (m, 2H), 6.44 (d, 2H), 5.21 (d, 1H), 4.84-4.61 (m, 3H), 3.73 (s, 1H), 3.02 (s, 3H), 2.50-2.42 (m), 1.35 (s, 1H), 0.87 (s, 1H). MS (m/z) 609.4 [M+H]⁺.

Example 125

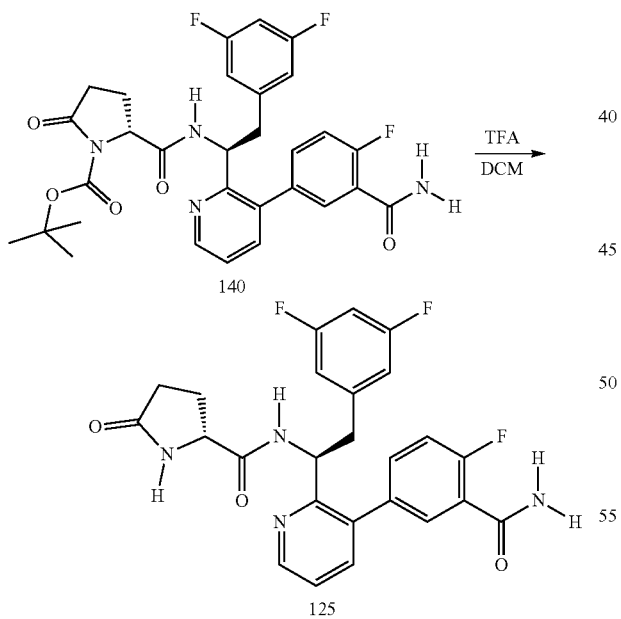

Synthesis of (R)—N—((S)-1-(3-(3-carbamoyl-4-fluorophenyl)pyridin-2-yl)-2-(3,5-difluorophenyl)ethyl)-5-oxopyrrolidine-2-carboxamide (125)

Compound 140 (6 mg) was dissolved in DCM (3 mL) and treated with TFA (2 mL). The reaction was stirred for 3 h at ambient temperature at which time solvents were removed in vacuo to provide the title compound (5 mg). MS (m/z) 483.4 [M+H]⁺.

Example 126

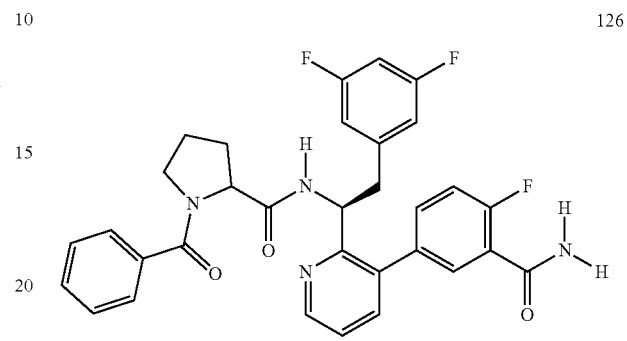

Synthesis of 1-benzoyl-N—((S)-1-(3-(3-carbamoyl-4-fluorophenyl)pyridin-2-yl)-2-(3,5-difluorophenyl)ethyl)pyrrolidine-2-carboxamide (126)

The title compound was prepared (19 mg) according to the method presented in the synthesis of Example 54 utilizing 54B and 1-benzoylpyrrolidine-2-carboxylic acid. MS (m/z) 573.4 [M+H]⁺.

Example 127

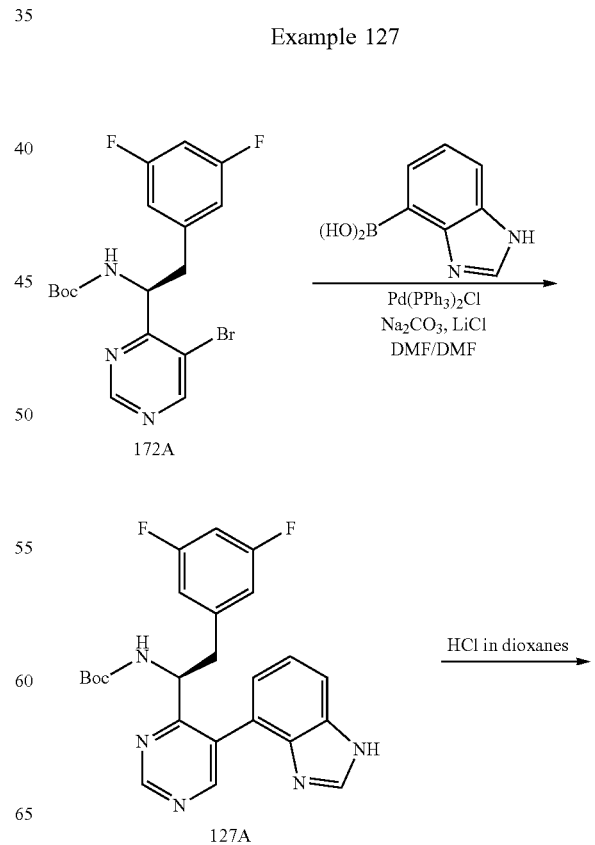

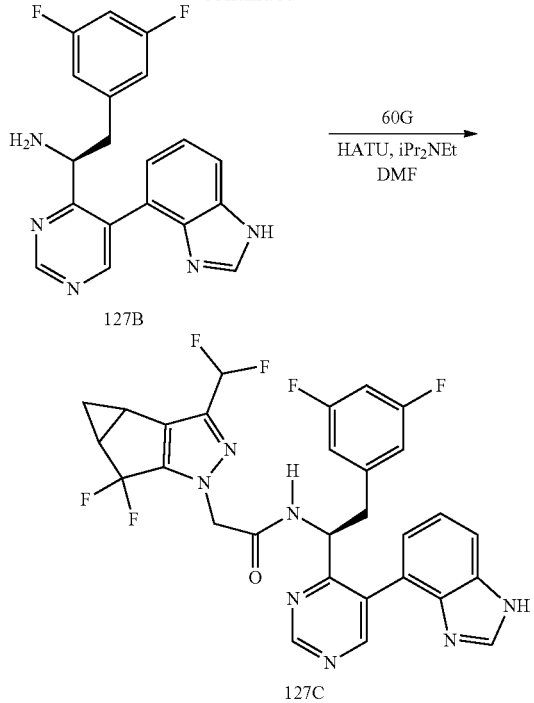

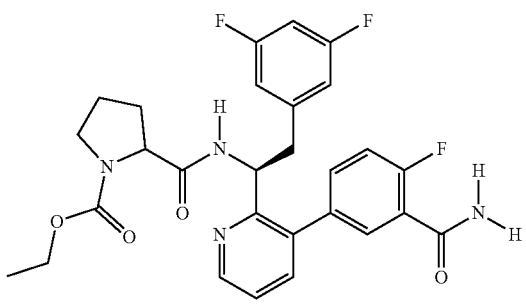

Synthesis of ethyl 2-((S)-1-(3-(3-carbamoyl-4-fluorophenyl)pyridin-2-yl)-2-(3,5-difluorophenyl)ethylcarbamoyl)pyrrolidine-1-carboxylate (128)

The title compound was prepared (9 mg) according to the method presented in the synthesis of Example 54 utilizing 54B and 1-(ethoxycarbonyl)pyrrolidine-2-carboxylic acid.

Example 129

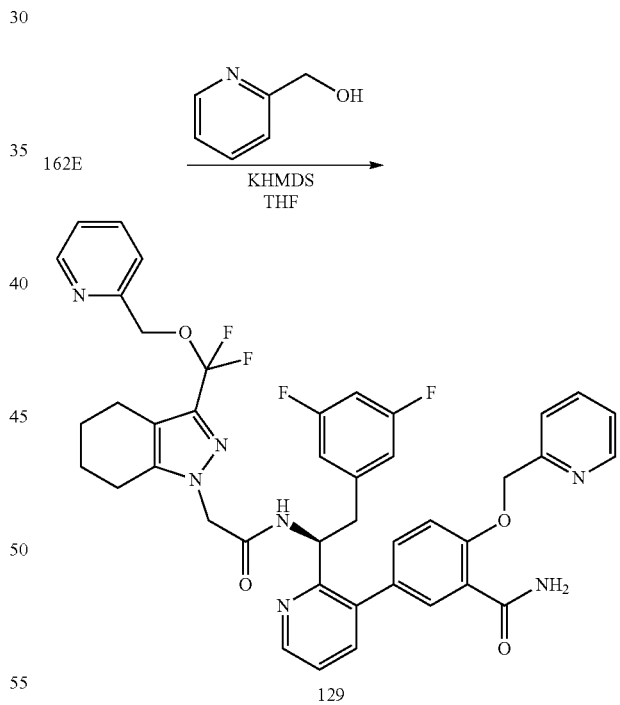

Synthesis of (S)-tert-butyl 1-(5-(1H-benzo[d]imidazol-4-yl)pyrimidin-4-yl)-2-(3,5-difluorophenyl)ethylcarbamate (127A)

The title compound as prepared according to the method presented in the synthesis of 68B in Example 68 utilizing 172A and 1H-benzo[d]imidazol-4-ylboronic acid to provide the title compound. MS (m/z) 452.2 [M+H]+.

Synthesis of (S)-1-(5-(1H-benzo[d]imidazol-4-yl)pyrimidin-4-yl)-2-(3,5-difluorophenyl)ethanamine (127B)

The title compound as prepared according to the method presented in the synthesis of 136C in Example 136 utilizing (S)-tert-butyl 1-(5-(1H-benzo[d]imidazol-4-yl)pyrimidin-4-yl)-2-(3,5-difluorophenyl)ethylcarbamate to provide the title compound.

Synthesis of N—((S)-1-(5-(1H-benzo[d]imidazol-4-yl)pyrimidin-4-yl)-2-(3,5-difluorophenyl)ethyl)-2-(3-(difluoromethyl)-5,5-difluoro-3b,4,4a,5-tetrahydro-1H-cyclopropa[3,4]cyclopenta[1,2-c]pyrazol-1-yl)acetamide (127C)

The title compound as prepared (9 mg) according to the method presented in the synthesis of Example 54 utilizing 60G and 127B. $^1$H NMR (400 MHz, cd$_3$od) δ 9.36 (s, 1H), 9.20 (s, 1H), 8.72 (s, 1H), 7.90 (d, 1H), 7.65 (s, 1H), 6.82 (s, 1H), 6.68 (s, 2H), 6.54 (s, 1H), 6.31 (s, 3H), 4.86 (s), 4.77 (s, 3H), 3.29 (dt), 3.06 (d, 3H), 2.97 (s, 1H), 2.84 (s, 1H), 2.44 (s, 3H), 1.35 (s, 1H), 1.01 (s, 2H), 0.08 (s, 1H). MS (m/z) 598.3 [M+H]+.

Synthesis of (S)-5-(2-(1-(2-(3-(difluoro(pyridin-2-ylmethoxy)methyl)-4,5,6,7-tetrahydro-1H-indazol-1-yl)acetamido)-2-(3,5-difluorophenyl)ethyl)pyridin-3-yl)-2-(pyridin-2-ylmethoxy)benzamide (129)

The title compound was prepared (2 mg) according to the method presented in the synthesis of Example 159 utilizing 162E and pyridin-2-ylmethanol. $^1$H NMR (400 MHz, dmso) δ 8.80 (d, J=8.6 Hz, 1H), 8.60 (dd, J=26.7, 10.9 Hz, 2H), 8.03 (s, 1H), 7.85 (dd, J=15.6, 7.9 Hz, 1H), 7.71-7.56 (m, 2H), 7.50-7.32 (m, 3H), 7.25 (d, J=8.5 Hz, 1H), 6.91 (s, 1H), 6.61 (d, J=6.5 Hz, 2H), 5.39 (s, 1H), 5.22 (d, J=6.7 Hz, 1H), 5.00 (s, 1H), 4.63 (d, J=3.4 Hz, 2H), 3.87 (s, 2H), 3.00 (s, 2H), 2.63 (s, 1H), 2.51-2.28 (m, 20H), 2.12 (s, 1H), 1.56 (s, 3H). MS (m/z) 780.3 [M+H]$^+$.

Example 130

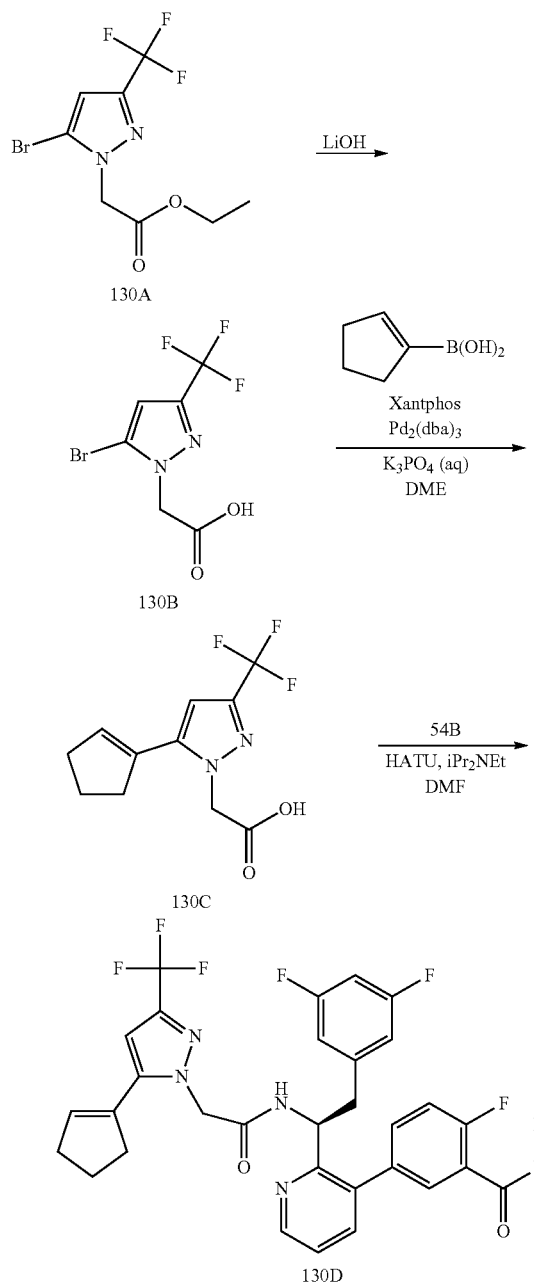

Synthesis of 2-(5-bromo-3-(trifluoromethyl)-1H-pyrazol-1-yl)acetic acid (130B)

The title compound was prepared according to the method presented in the synthesis of 122F in Example 122 utilizing ethyl 2-(5-bromo-3-(trifluoromethyl)-1H-pyrazol-1-yl)acetate (synthesized as described in WO 2008/13622).

Synthesis of 2-(5-cyclopentenyl-3-(trifluoromethyl)-1H-pyrazol-1-yl)acetic acid (130C)

In a microwave vial, 2-(5-bromo-3-(trifluoromethyl)-1H-pyrazol-1-yl)acetic acid (60 mg, 0.22 mmol), cyclopentenylboronic acid (49 mg, 0.44 mmol), Xantphos (13 mg), Pd$_2$(dba)$_3$ (10 mg), and 2M aq K$_3$PO$_4$ (0.24 mL) were combined in DME (2.2 mL). The reaction was heated in a microwave reactor at 180° C. for 40 min. The reaction mixture was filtered and solvents removed in vacuo. The residue was partitioned between aqueous saturated NaHCO$_3$ and EtOAc. The aqueous layer was then acidified with 1N aq HCl and extracted with EtOAc. The organics were washed, dried, and removed in vacuo to provide the title compound. MS (m/z) 573.4 [M+H]$^+$.

Synthesis of (S)-5-(2-(1-(2-(5-cyclopentenyl-3-(trifluoromethyl)-1H-pyrazol-1-yl)acetamido)-2-(3,5-difluorophenyl)ethyl)pyridin-3-yl)-2-fluorobenzamide (130D)

The title compound was prepared (7 mg) according to the method presented in the synthesis of Example 54 utilizing 54B and 130C. MS (m/z) 614.4 [M+H]$^+$.

Example 131

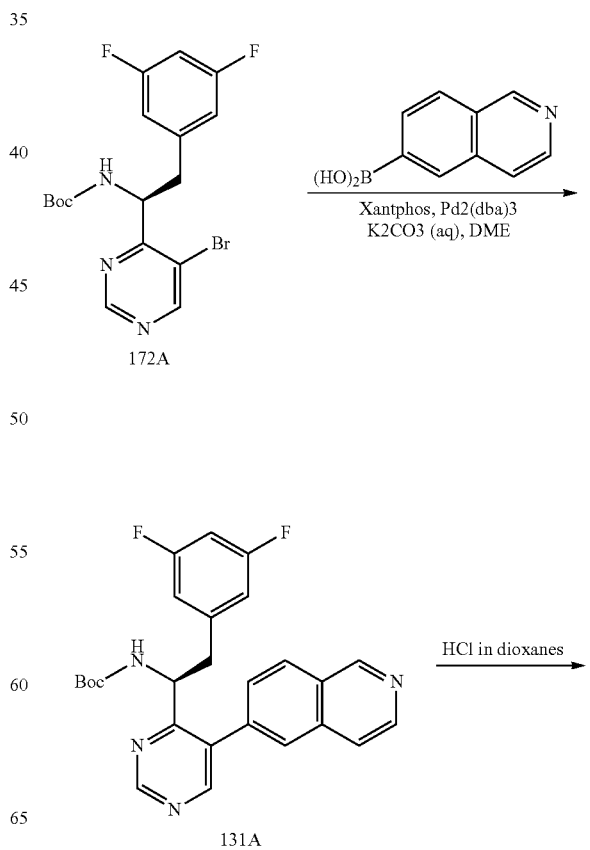

373

-continued

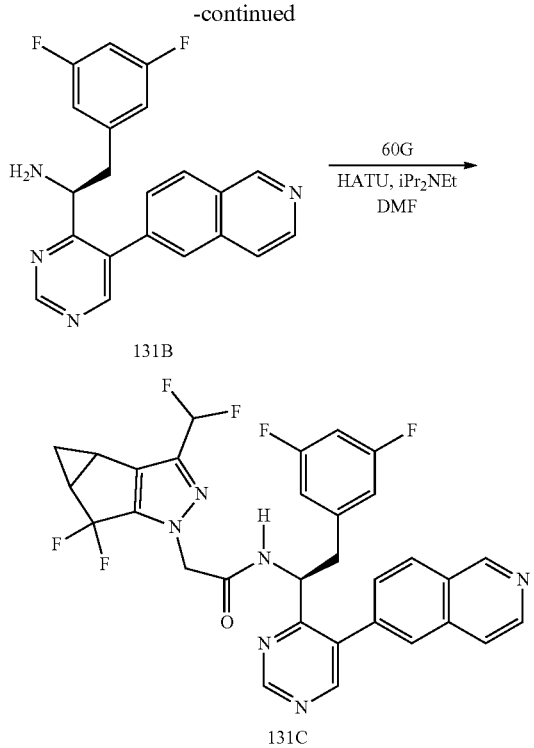

Synthesis of (S)-tert-butyl 2-(3,5-difluorophenyl)-1-(5-(isoquinolin-6-yl)pyrimidin-4-yl)ethylcarbamate (131A)

The title compound as prepared according to the method presented in the synthesis of 136B in Example 136 utilizing 172A and isoquinolin-6-ylboronic acid to provide the title compound. MS (m/z) 463.1 [M+H]$^+$.

Synthesis of (S)-2-(3,5-difluorophenyl)-1-(5-(isoquinolin-6-yl)pyrimidin-4-yl)ethanamine (131B)

The title compound as prepared according to the method presented in the synthesis of 136C in Example 136 utilizing (S)-tert-butyl 2-(3,5-difluorophenyl)-1-(5-(isoquinolin-6-yl)pyrimidin-4-yl)ethylcarbamate to provide the title compound.

Synthesis of 2-(3-(difluoromethyl)-5,5-difluoro-3b,4,4a,5-tetrahydro-1H-cyclopropa[3,4]cyclopenta[1,2-c]pyrazol-1-yl)-N—((S)-2-(3,5-difluorophenyl)-1-(5-(isoquinolin-6-yl)pyrimidin-4-yl)ethyl)acetamide (131C)

The title compound as prepared (26 mg) according to the method presented in the synthesis of Example 54 utilizing 60G and 131B. $^1$H NMR (400 MHz, dmso) δ 9.60 (s, 1H), 9.35 (s, 1H), 9.15 (s, 1H), 8.75 (d, 1H), 8.62 (d, 1H), 8.35 (d, 1H), 8.02 (s, 1H), 7.80 (s, 2H), 6.98-6.88 (m, 2H), 6.79 (s, 1H), 6.47 (d, 2H), 5.25-5.05 (m, 2H), 4.83-4.63 (m, 4H), 3.05 (d, 2H), 2.50-2.41 (m), 1.34 (s, 1H), 0.87 (s, 1H). MS (m/z) 609.4 [M+H]$^+$.

374

Example 132

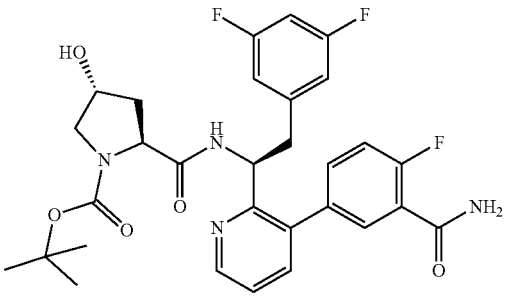

Synthesis of (2S,4R)-tert-butyl 2-((S)-1-(3-(3-carbamoyl-4-fluorophenyl)pyridin-2-yl)-2-(3,5-difluorophenyl)ethylcarbamoyl)-4-hydroxypyrrolidine-1-carboxylate (132)

The title compound was prepared (13 mg) according to the method presented in the synthesis of Example 54 utilizing 54B and (2S,4R)-1-(tert-butoxycarbonyl)-4-hydroxypyrrolidine-2-carboxylic acid. MS (m/z) 585.1 [M+H]$^+$.

Example 133

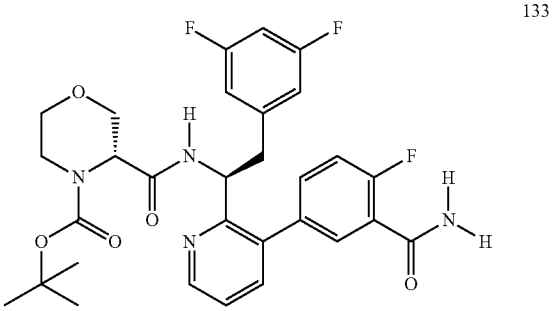 [SMILES: CC(C)(C)OC(=O)N1CCOC[C@@H]1C(=O)N[C@@H](Cc1cc(F)cc(F)c1)c1ncccc1-c1ccc(F)c(C(N)=O)c1]

Synthesis of (R)-tert-butyl 3-((S)-1-(3-(3-carbamoyl-4-fluorophenyl)pyridin-2-yl)-2-(3,5-difluorophenyl)ethylcarbamoyl)morpholine-4-carboxylate (133)

The title compound was prepared (13 mg) according to the method presented in the synthesis of Example 54 utilizing 54B and (R)-4-(tert-butoxycarbonyl)morpholine-3-carboxylic acid. $^1$H NMR (400 MHz, cdcl$_3$) δ 8.80 (s, 2H), 7.97 (s, 1H), 7.83 (s, 1H), 7.74 (s, 1H), 7.54 (s, 1H), 7.37-7.22 (m, 11H), 6.98 (s, 1H), 6.59 (s, 1H), 6.19 (s, 4H), 5.57 (s, 1H), 4.55 (s, 1H), 4.39 (s, 1H), 3.71 (d, 3H), 3.63-3.62 (m, 1H), 3.45 (s, 1H), 3.24 (s, 2H), 2.50 (s, 1H), 1.46 (s, 5H).

Example 134

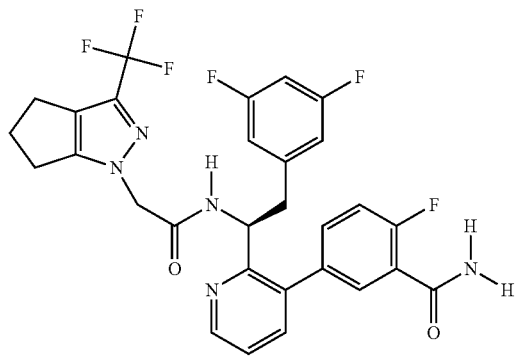

134

Synthesis of (S)-5-(2-(2-(3,5-difluorophenyl)-1-(2-(3-(trifluoromethyl)-5,6-dihydrocyclopenta[c]pyrazol-1(4H)-yl)acetamido)ethyl)pyridin-3-yl)-2-fluorobenzamide (134)

The title compound was prepared (7 mg) according to the method presented in the synthesis of Example 56 utilizing 56A and 3-(trifluoromethyl)-1,4,5,6-tetrahydrocyclopenta[c]pyrazole. $^1$H NMR (400 MHz, dmso) δ 8.94 (d, 1H), 8.67 (s, 1H), 7.72-7.56 (m, 3H), 7.48 (s, 1H), 7.45-7.15 (m, 4H), 6.90 (s, 1H), 6.53 (d, 2H), 5.15 (s, 1H), 4.70 (s, 2H), 3.00 (s, 2H), 2.55 (s, 2H), 2.51-2.41 (m). MS (m/z) 588.3 [M+H]$^+$.

Example 135

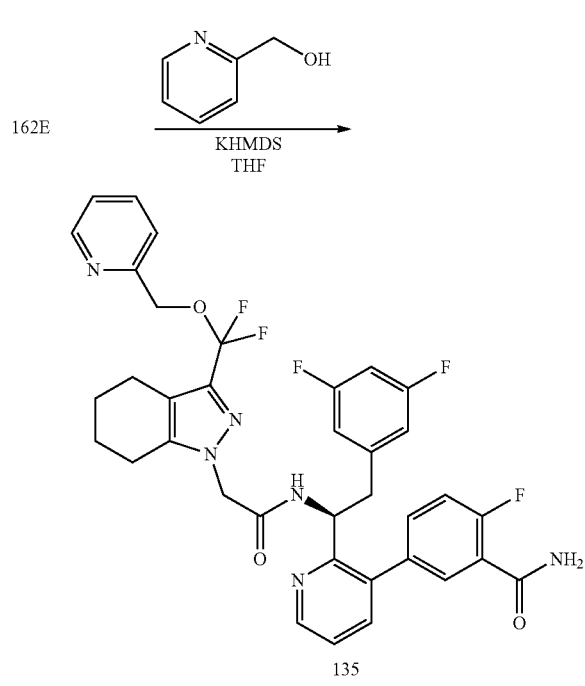

Synthesis (S)-5-(2-(1-(2-(3-(difluoro(pyridin-2-yl-methoxy)methyl)-4,5,6,7-tetrahydro-1H-indazol-1-yl)acetamido)-2-(3,5-difluorophenyl)ethyl)pyridin-3-yl)-2-fluorobenzamide (135)

The title compound was prepared (2 mg) according to the method presented in the synthesis of Example 159 utilizing 162E and pyridin-2-ylmethanol. The title compound exhibited a shorter retention time on HPLC relative to its regioisomer (Compound 143). $^1$H NMR (400 MHz, dmso) δ 8.86 (d, J=8.3 Hz, 1H), 8.66 (d, J=3.0 Hz, 1H), 8.53 (d, J=5.2 Hz, 1H), 7.83 (d, J=8.2 Hz, 1H), 7.76-7.56 (m, 2H), 7.52-7.21 (m, 4H), 6.91 (s, 1H), 6.55 (d, J=6.6 Hz, 2H), 5.17 (d, J=6.6 Hz, 1H), 4.98-4.87 (m, 1H), 4.65 (s, 2H), 4.06 (s, 2H), 2.99 (d, J=7.9 Hz, 2H), 2.52-2.41 (m, 18H), 2.39 (s, 1H), 2.37-2.30 (m, 1H), 2.22 (d, J=43.0 Hz, 2H), 1.57 (s, 3H). MS (m/z) 691.3 [M+H]$^+$.

Example 136

377

-continued

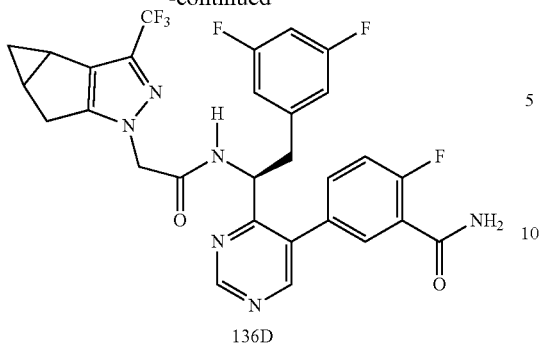

136D

Synthesis of (S)-tert-butyl 1-(5-(3-carbamoyl-4-fluorophenyl)pyrimidin-4-yl)-2-(3,5-difluorophenyl)ethylcarbamate (136B)

To (S)-tert-butyl 1-(5-bromopyrimidin-4-yl)-2-(3,5-difluorophenyl)ethylcarbamate (250 mg, 0.6 mmol) in DME (3 mL) was added 3-carbamoyl-4-fluorophenylboronic acid (110 mg, 0.6 mmol), Xantphos (35 mg), $Pd_2(dba)_3$ (28 mg), and aqueous 2M $K_2CO_3$ (0.45 mL). The reaction was heated to 65° C. for 2 d at which time it was diluted with aqueous 1N HCl and extracted with EtOAc. The organics were separated, washed, dried and removed in vacuo. The crude product was purified by column chromatography on silica to provide 130 mg of the title compound. MS (m/z) 473.0 $[M+H]^+$.

Synthesis of (S)-5-(4-(1-amino-2-(3,5-difluorophenyl)ethyl)pyrimidin-5-yl)-2-fluorobenzamide (136C)

(S)-tert-butyl 1-(5-(3-carbamoyl-4-fluorophenyl)pyrimidin-4-yl)-2-(3,5-difluorophenyl)ethylcarbamate (130 mg, 0.28 mmol) was dissolved in DCM (2 mL) and treated with HCl (4 N in dioxanes, 3 mL). After 3 h at ambient temperature, the solvents were removed in vacuo to provide the title compound.

Synthesis of 5-(4-((1S)-2-(3,5-difluorophenyl)-1-(2-(3-(trifluoromethyl)-3b,4,4a,5-tetrahydro-1H-cyclopropa[3,4]cyclopenta[1,2-c]pyrazol-1-yl)acetamido)ethyl)pyrimidin-5-yl)-2-fluorobenzamide (136D)

The title compound as prepared (16 mg) according to the method presented in the synthesis of Example 54 utilizing 122F and 136C. $^1$H NMR (400 MHz, dmso) δ 9.15 (d, 1H), 8.97 (d, 1H), 8.52 (s, 1H), 7.58 (s, 2H), 7.45 (dd, 1H), 7.36 (s, 1H), 7.28-7.20 (m, 1H), 6.83 (d, 1H), 6.48 (t, 2H), 5.03 (d, 3H), 4.74-4.40 (m, 4H), 2.50 (ddd, 2H), 2.42-2.20 (m), 1.91 (s, 2H), 0.99-0.73 (m, 1H), 0.01 (s, 1H). MS (m/z) 601.2 $[M+H]^+$.

378

Example 137

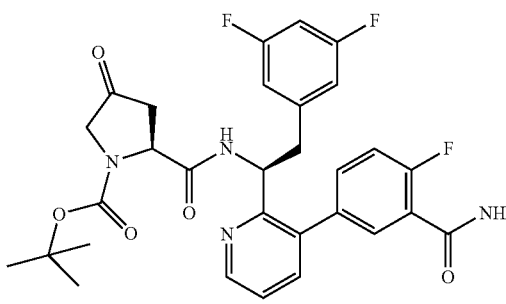

137

Synthesis of (S)-tert-butyl 2-((S)-1-(3-(3-carbamoyl-4-fluorophenyl)pyridin-2-yl)-2-(3,5-difluorophenyl)ethylcarbamoyl)-4-oxopyrrolidine-1-carboxylate (137)

The title compound was prepared (12 mg) according to the method presented in the synthesis of Example 54 utilizing 54B and (S)-1-(tert-butoxycarbonyl)-4-oxopyrrolidine-2-carboxylic acid. MS (m/z) 583.2 $[M+H]^+$.

Example 138

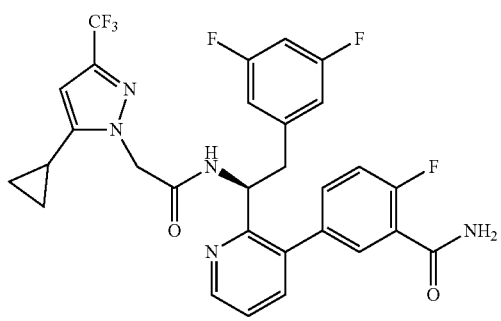

138

Synthesis of (S)-5-(2-(1-(2-(5-cyclopropyl-3-(trifluoromethyl)-1H-pyrazol-1-yl)acetamido)-2-(3,5-difluorophenyl)ethyl)pyridin-3-yl)-2-fluorobenzamide (138)

The title compound was prepared (43 mg) according to the method presented in the synthesis of Example 54 utilizing 54B and 61C. $^1$H NMR (400 MHz, dmso) δ 8.96 (d, 1H), 8.71-8.64 (m, 1H), 7.77-7.57 (m, 3H), 7.55-7.32 (m, 3H), 7.29 (d, 1H), 6.91 (t, 1H), 6.56 (d, 2H), 6.28 (s, 1H), 5.19 (d, 2H), 4.86 (s, 2H), 3.11-2.81 (m, 3H), 2.52-2.42 (m, 20H), 1.87 (s, 1H), 1.47 (t, 1H), 0.74 (d, 2H), 0.59 (s, 1H), 0.53 (s, 1H). MS (m/z) 588.6 $[M+H]^+$.

Example 139

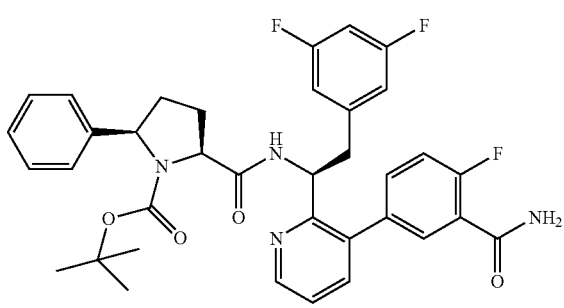 [SMILES: CC(C)(C)OC(=O)N1[C@@H](c2ccccc2)CC[C@H]1C(=O)N[C@@H](Cc1cc(F)cc(F)c1)c1ncccc1-c1ccc(F)c(C(N)=O)c1]

Synthesis of (2S,5R)-tert-butyl 2-((S)-1-(3-(3-carbamoyl-4-fluorophenyl)pyridin-2-yl)-2-(3,5-difluorophenyl)ethylcarbamoyl)-5-phenylpyrrolidine-1-carboxylate (139)

The title compound was prepared (9 mg) according to the method presented in the synthesis of Example 54 utilizing 54B and (2S,5R)-1-(tert-butoxycarbonyl)-5-phenylpyrrolidine-2-carboxylic acid. MS (m/z) 645.1 [M+H]+.

Example 140

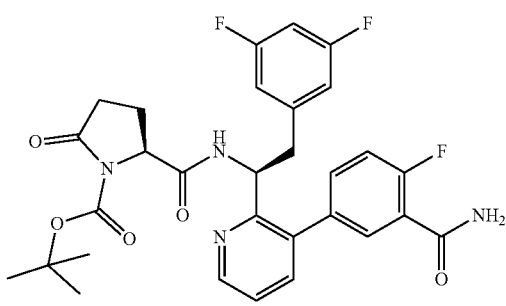

Synthesis of (S)-tert-butyl 2-((S)-1-(3-(3-carbamoyl-4-fluorophenyl)pyridin-2-yl)-2-(3,5-difluorophenyl)ethylcarbamoyl)-5-oxopyrrolidine-1-carboxylate (140)

The title compound as prepared (4 mg) according to the method presented in the synthesis of Example 54 utilizing 54B and (S)-1-(tert-butoxycarbonyl)-5-oxopyrrolidine-2-carboxylic acid. MS (m/z) 583.0 [M+H]+.

Example 141

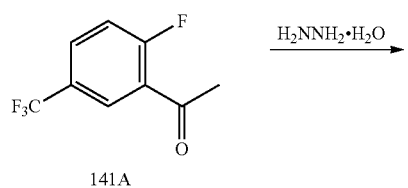

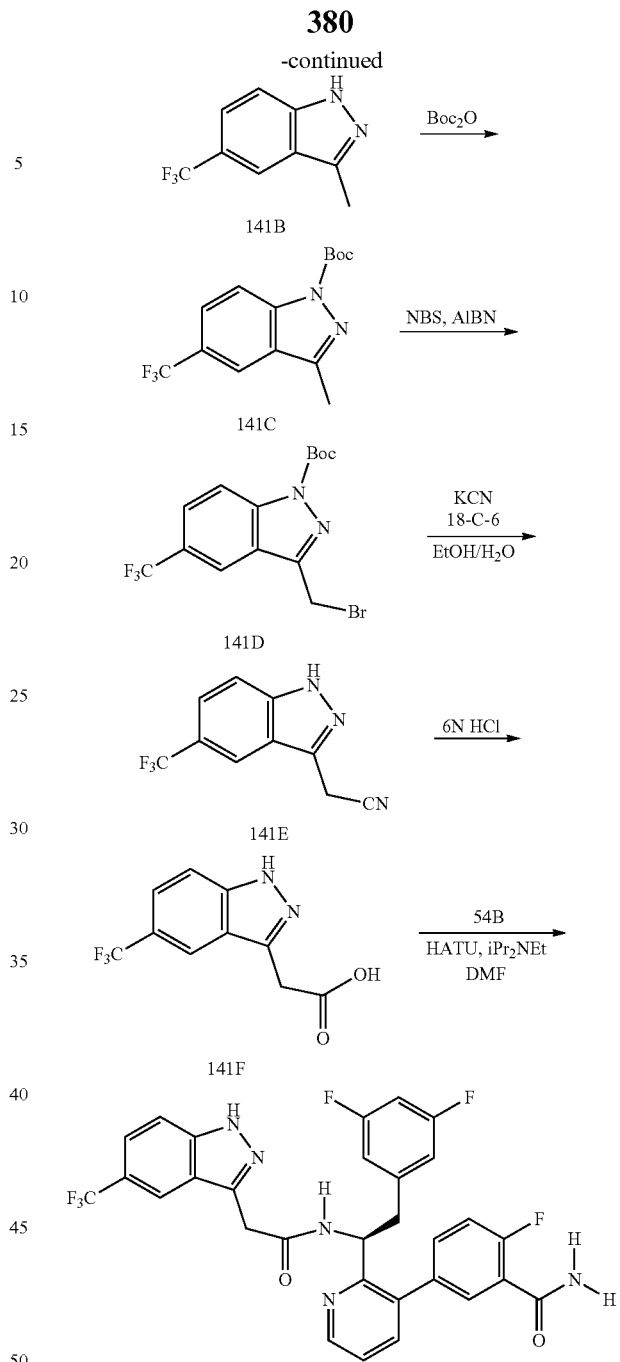

Synthesis of 3-methyl-5-(trifluoromethyl)-1H-indazole (141B)

To 1-(2-fluoro-5-(trifluoromethyl)phenyl)ethanone (12.95 g, 62.9 mmol) in ethylene glycol (33 mL) was added hydrazine hydrate (3.1 mL, 100 mmol). The reaction was heated at 165° C. for 16 h. After cooling to ambient temperature, the reaction solidifies and the solids filtered. The cake was dissolved in DCM, washed with H2O, and dried over sodium sulfate. Solvents were removed in vacuo to provide 6.75 g of the title compound. MS (m/z) 201.0 [M+H]+.

381

Synthesis of tert-butyl 3-methyl-5-(trifluoromethyl)-1H-indazole-1-carboxylate (141C)

To 3-methyl-5-(trifluoromethyl)-1H-indazole (3 g, 15 mmol) in THF (100 mL) was added Boc$_2$O (3.27 g, 15 mmol), TEA (2.1 mL, 15 mmol), and DMAP (367 mg, 3 mmol). The reaction was stirred for 2 h then partitioned between EtOAc and saturated aqueous NH$_4$Cl. Organics were separated, dried, and removed in vacuo to provide 3.8 g of the title compound.

Synthesis of tert-butyl 3-(bromomethyl)-5-(trifluoromethyl)-1H-indazole-1-carboxylate (141D)

To tert-butyl 3-methyl-5-(trifluoromethyl)-1H-indazole-1-carboxylate (1.9 g) in carbon tetrachloride (20 mL) was added NBS (1.28 g, 7.2 mmol). The reaction was heated to 90° C. then AIBN (115 mg, 0.7 mmol) was added. After 16 h, additional aliquots of NBS (500 mg) and AIBN (115 mg) were added and the temperature was raised to 110° C. After 16 h, the reaction was cooled to ambient temperature and solvents removed in vacuo. The crude residue was partitioned between EtOAc and H$_2$O. The organics were separated, washed with saturated aqueous NaHCO$_3$, dried, removed in vacuo. The crude product was purified by column chromatography on silica to provide title compound. MS (m/z) 279.0 [M+H]$^+$.

Synthesis of 2-(5-(trifluoromethyl)-1H-indazol-3-yl)acetonitrile (141E)

To tert-butyl 3-(bromomethyl)-5-(trifluoromethyl)-1H-indazole-1-carboxylate (300 mg, 0.79 mmol) dissolved in EtOH (3.5 mL) and H$_2$O (0.5 mL) was added catalytic 18-C-6 and KCN (51 mg, 0.79 mmol). The reaction was stirred 2 h then the reaction was partitioned between EtOAc and saturated aqueous NaHCO$_3$. The organics were separated, washed with, saturated aqueous NaHCO$_3$ dried and removed in vacuo to provide the title compound. MS (m/z) 226.0 [M+H]$^+$.

Synthesis of 2-(5-(trifluoromethyl)-1H-indazol-3-yl)acetic acid (141F)

2-(5-(trifluoromethyl)-1H-indazol-3-yl)acetonitrile (60 mg) was treated with 6N aqueous HCl (2 mL) and heated to 105° C. for 5 h. The reaction was extracted with EtOAc, organics washed with 20% aqueous KH$_2$PO$_4$, dried and solvents removed in vacuo to provide 55 mg of the title compound. MS (m/z) 245.0 [M+H]$^+$.

Synthesis of (S)-5-(2-(2-(3,5-difluorophenyl)-1-(2-(5-(trifluoromethyl)-1H-indazol-3-yl)acetamido)ethyl)pyridin-3-yl)-2-fluorobenzamide (141G)

The title compound was prepared (13 mg) according to the method presented in the synthesis of Example 54 utilizing 54B and 141F. $^1$H NMR (400 MHz, dmso) δ 8.93 (d, 1H), 8.64 (d, 1H), 8.03 (s, 1H), 7.56 (dt, 5H), 7.48-7.28 (m, 3H), 7.28-7.17 (m, 1H), 6.82 (s, 1H), 6.47 (d, 2H), 5.15 (d, 1H), 3.82 (s, 2H), 2.98 (d, 2H), 2.52-2.41 (m). MS (m/z) 598.4 [M+H]$^+$.

382

Example 142

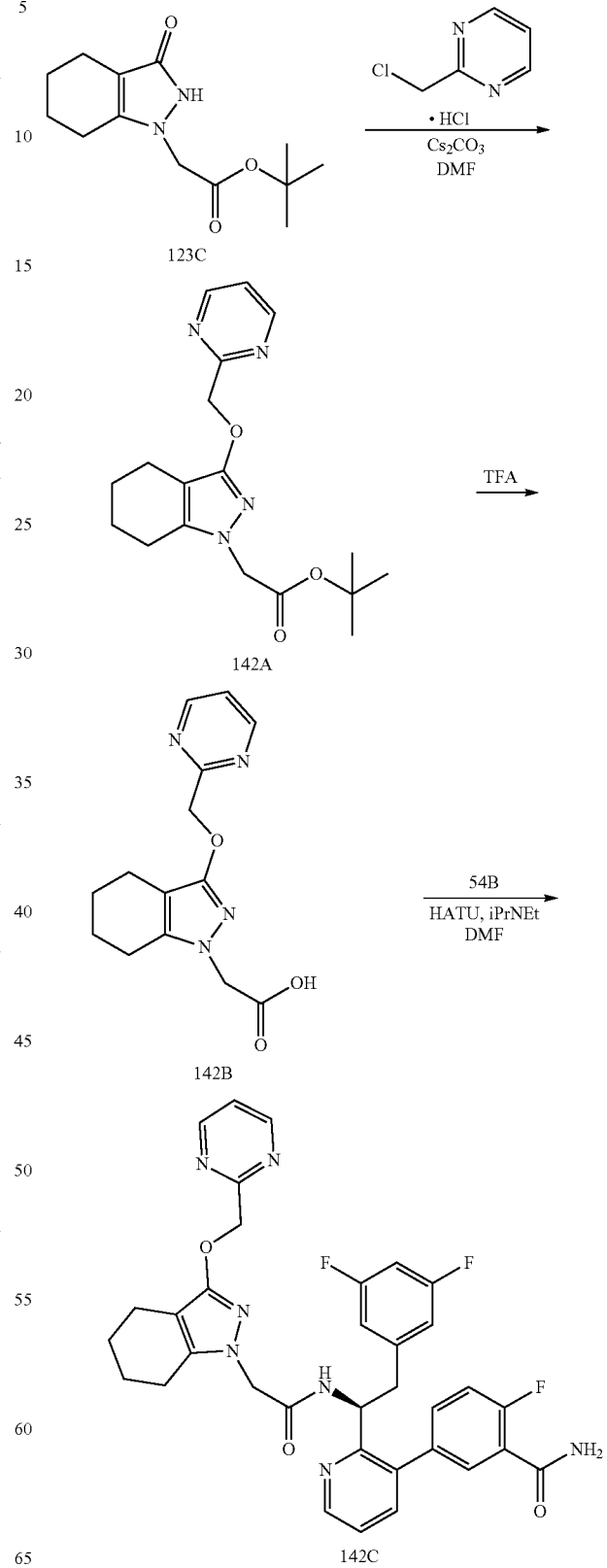

Synthesis of tert-butyl 2-(3-(pyrimidin-2-yl-
methoxy)-4,5,6,7-tetrahydro-1H-indazol-1-yl)acetate
(142A)

tert-Butyl 2-(3-oxo-2,3,4,5,6,7-hexahydro-1H-indazol-1-yl)acetate (38 mg, 0.15 mmol) was dissolved in DMF (1.5 mL) and treated with 2-(chloromethyl)pyrimidine hydrochloride (27 mg, 0.17 mmol) and Cs$_2$CO$_3$ (196 mg, 0.6 mmol). The reaction mixture was stirred 3 hr. The solids were filtered and the filtrate partitioned between EtOAc and H$_2$O. The organics were dried over saturated aqueous NaCl and removed in vacuo. The crude residue was purified by column chromatography on silica to provide a mixture of N1 and N2 regioisomers that were carried onto the next step: MS (m/z) 345.2 [M+H]$^+$.

Synthesis of 2-(3-(pyrimidin-2-ylmethoxy)-4,5,6,7-
tetrahydro-1H-indazol-1-yl)acetic acid (142B)

The title compound was prepared according to the method presented in the synthesis of 170B in Example 170: MS (m/z) 289.2 [M+H]$^+$.

Synthesis of (S)-5-(2-(2-(3,5-difluorophenyl)-1-(2-
(3-(pyrimidin-2-ylmethoxy)-4,5,6,7-tetrahydro-1H-
indazol-1-yl)acetamido)ethyl)pyridin-3-yl)-2-fluo-
robenzamide (142C)

The title compound was prepared (29 mg) according to the method presented in the synthesis of Example 54 utilizing 54B and 2-(3-(pyrimidin-2-ylmethoxy)-4,5,6,7-tetrahydro-1H-indazol-1-yl)acetic acid. The undesired N2 isomer observed in the synthesis of 142A was removed during purification: $^1$H NMR (400 MHz, dmso) δ 8.76 (d, 2H), 8.64 (d, 1H), 8.45 (d, 1H), 7.77-7.58 (m, 3H), 7.58-7.27 (m, 5H), 6.90 (s, 1H), 6.52 (d, 2H), 5.23-5.12 (m, 3H), 4.34 (s, 2H), 2.94 (dd, 2H), 2.53-2.41 (m, 20H), 2.22 (s, 3H), 1.87 (s, 1H), 1.56 (s, 5H). MS (m/z) 642.7 [M+H]$^+$.

Example 143

162E and pyridin-2-ylmethanol. The title compound exhibited a longer retention time on HPLC relative to its regioisomer (Compound 135). MS (m/z) 691.3 [M+H]$^+$.

Example 144

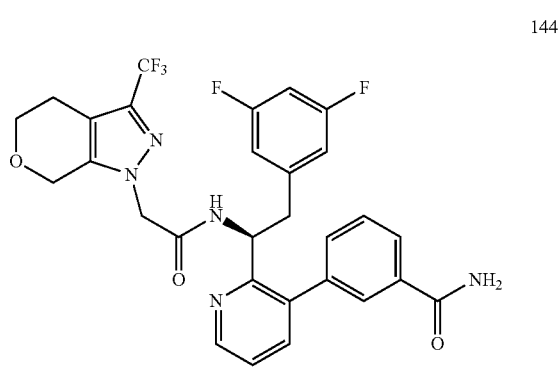 [SMILES: NC(=O)c1cccc(-c2cccnc2[C@H](Cc2cc(F)cc(F)c2)NC(=O)Cn2nc(C(F)(F)F)c3c2COCC3)c1]

144

Synthesis of (S)-3-(2-(2-(3,5-difluorophenyl)-1-(2-
(3-(trifluoromethyl)-4,5-dihydropyrano[3,4-c]pyra-
zol-1 (7H)-yl)acetamido)ethyl)pyridin-3-yl)benz-
amide (144)

The title compound was prepared (31 mg) according to the method presented in the synthesis of Example 50 utilizing 50C and 2-(3-(trifluoromethyl)-4,5-dihydropyrano[3,4-c]pyrazol-1 (7H)-yl)acetic acid. $^1$H NMR (400 MHz, dmso) δ 8.99 (d, 1H), 8.68 (s, 1H), 8.01-7.84 (m, 2H), 7.71 (s, 1H), 7.64 (d, 1H), 7.45 (dd, 10.1 Hz, 5H), 6.90 (s, 1H), 6.48 (d, 2H), 5.19 (s, 1H), 4.75 (s, 2H), 4.48 (d, 2H), 4.39 (d, 2H), 3.71 (s, 2H), 3.00 (s, 1H), 2.54 (s, 2H), 2.52-2.42 (m, 68H), 2.29 (s, 1H). MS (m/z) 586.4 [M+H]$^+$.

Example 145

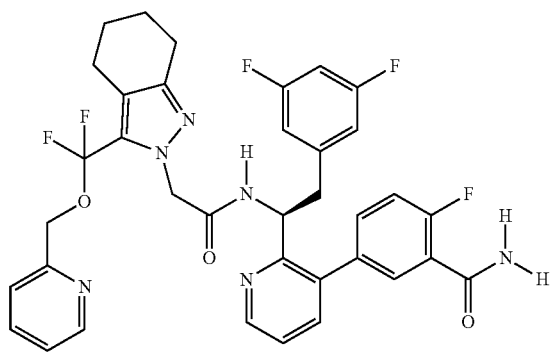

143

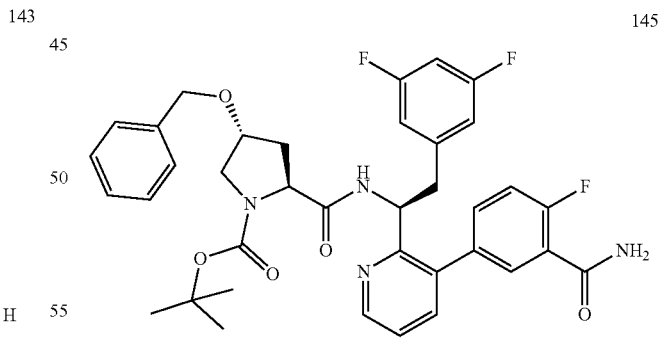

145

Synthesis of (S)-5-(2-(1-(2-(3-(difluoro(pyridin-2-
ylmethoxy)methyl)-4,5,6,7-tetrahydro-2H-indazol-2-
yl)acetamido)-2-(3,5-difluorophenyl)ethyl)pyridin-3-
yl)-2-fluorobenzamide (143)

The title compound was prepared (1 mg) according to the method presented in the synthesis of Example 159 utilizing Synthesis of (2S,4R)-tert-butyl 4-(benzyloxy)-2-
((S)-1-(3-(3-carbamoyl-4-fluorophenyl)pyridin-2-
yl)-2-(3,5-difluorophenyl)ethylcarbamoyl)pyrroli-
dine-1-carboxylate (145)

The title compound was prepared (19 mg) according to the method presented in the synthesis of Example 54 utilizing 54B and (2S,4R)-4-(benzyloxy)-1-(tert-butoxycarbonyl)pyrrolidine-2-carboxylic acid. $^1$H NMR (400 MHz, cdcl₃) δ 9.08 (s, 1H), 8.75 (s, 1H), 7.94 (s, 1H), 7.85-7.71 (m, 1H), 7.64 (d, 4H), 7.33-7.23 (m, 1H), 7.23-7.21 (m, 1H), 7.08 (s, 1H), 6.59 (s, 1H), 6.33 (s, 1H), 6.28 (d, 3H), 5.54 (s, 1H), 4.47 (d, 3H), 4.32 (t, 2H), 4.11 (s, 1H), 3.78 (s, 1H), 3.67 (s, 1H), 3.58 (s, 1H), 3.20 (s, 1H), 3.09 (s, 1H), 2.36 (s, 1H), 1.90 (s, 1H), 1.41 (s, 8H), 1.23 (s, 4H).

Example 146

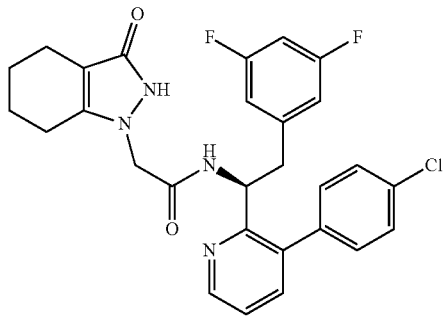

Synthesis of (S)—N-(1-(3-(4-chlorophenyl)pyridin-2-yl)-2-(3,5-difluorophenyl)ethyl)-2-(3-oxo-2,3,4,5,6,7-hexahydro-1H-indazol-1-yl)acetamide (146)

The title compound was prepared (14 mg) according to the method presented in the synthesis of Example 36 utilizing 36E and 123D. ¹H NMR (400 MHz, cd₃od) δ 8.76-8.36 (m, 1H), 7.61 (dd, 1H), 7.50-7.25 (m, 1H), 7.09 (d, 1H), 6.70 (d, 1H), 6.29 (d, 1H), 5.40 (t, 1H), 5.10 (s, 1H), 4.84 (s, 8H), 4.72-4.54 (m, 1H), 3.29 (dt, 8H), 3.10 (d, 1H), 2.99 (d, 1H), 2.61 (s, 1H), 2.60-2.16 (m, 2H), 2.24-2.16 (m, 1H), 2.01 (s, 1H), 1.76 (d, 2H). MS (m/z) 523.9 [M+H]⁺.

Example 147

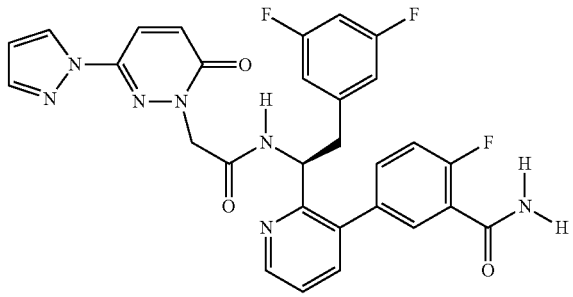

Synthesis of (S)-5-(2-(2-(3,5-difluorophenyl)-1-(2-(6-oxo-3-(1H-pyrazol-1-yl)pyridazin-1(6H)-yl)acetamido)ethyl)pyridin-3-yl)-2-fluorobenzamide (147)

The title compound was prepared (21 mg) according to the method presented in the synthesis of Example 54 utilizing 54B and 2-(6-oxo-3-(1H-pyrazol-1-yl)pyridazin-1(6H)-yl)acetic acid. ¹H NMR (400 MHz, dmso) δ 8.94 (d, 1H), 8.71-8.64 (m, 1H), 8.15 (d, 1H), 8.02 (d, 1H), 7.80 (d, 1H), 7.71-7.55 (m, 3H), 7.47-7.36 (m, 3H), 7.34-7.20 (m, 1H), 7.11 (d, 1H), 6.89 (t, 1H), 6.60-6.42 (m, 3H), 5.16 (d, 1H), 4.63 (q, 2H), 3.00 (d, 2H), 2.52-2.41 (m). MS (m/z) 574.3 [M+H]⁺.

Example 148

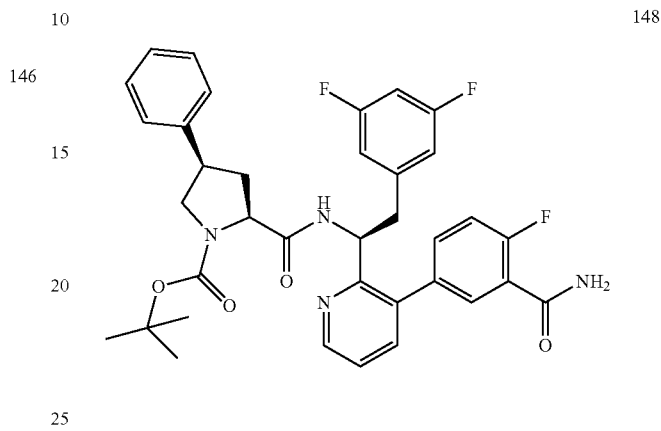

Synthesis of (2 S,4R)-tert-butyl 2-((S)-1-(3-(3-carbamoyl-4-fluorophenyl)pyridin-2-yl)-2-(3,5-difluorophenyl)ethylcarbamoyl)-4-phenylpyrrolidine-1-carboxylate (148)

The title compound was prepared (16 mg) according to the method presented in the synthesis of Example 54 utilizing 54B and (2S,4R)-1-(tert-butoxycarbonyl)-4-phenylpyrrolidine-2-carboxylic acid. ¹H NMR (400 MHz, cdcl₃) δ 9.06 (s, 1H), 8.76 (s, 1H), 7.98 (s, 1H), 7.72 (s, 2H), 7.63 (s, 1H), 7.44-7.14 (m, 3H), 6.58 (s, 1H), 6.27 (d, J=22.0 Hz, 3H), 5.64 (s, 1H), 4.40 (s, 1H), 4.01 (s, 1H), 3.32 (s, 3H), 3.21 (s, 2H), 2.25 (s, 3H), 1.45 (s, 7H), 1.28 (s, 3H). MS (m/z) 645.1 [M+H]⁺.

Example 149

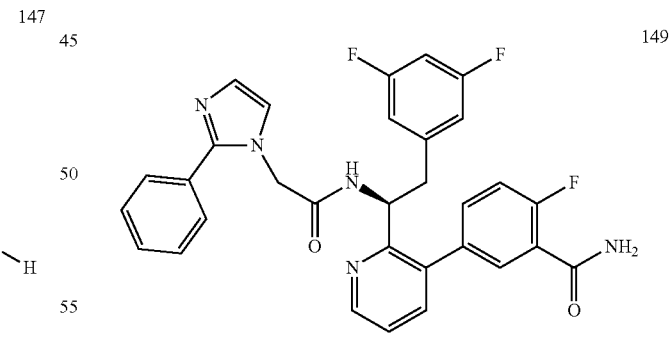

Synthesis of (S)-5-(2-(2-(3,5-difluorophenyl)-1-(2-(2-phenyl-1H-imidazol-1-yl)acetamido)ethyl)pyridin-3-yl)-2-fluorobenzamide (149)

The title compound was prepared (7 mg) according to the method presented in the synthesis of Example 54 utilizing 54B and 2-(2-phenyl-1H-imidazol-1-yl)acetic acid. ¹H NMR (400 MHz, dmso) δ 9.13 (d, 1H), 8.69 (d, 1H), 7.74 (s, 1H), 7.72-7.49 (m, 6H), 7.50 (s, 1H), 7.56-7.39 (m, 6H), 7.31 (d, 2H), 6.95 (s, 1H), 6.51 (d, 2H), 5.11 (d, 1H), 4.85 (s, 3H), 2.95 (dd, 2H), 2.52-2.41 (m, 38H). MS (m/z) 556.6 [M+H]⁺.

Example 150

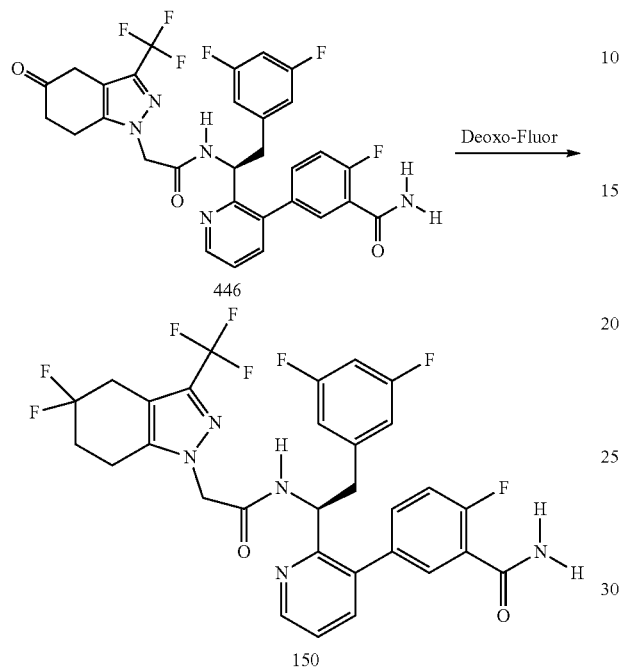

Synthesis of (S)-5-(2-(1-(2-(5,5-difluoro-3-(trifluoromethyl)-4,5,6,7-tetrahydro-1H-indazol-1-yl)acetamido)-2-(3,5-difluorophenyl)ethyl)pyridin-3-yl)-2-fluorobenzamide (150)

In a plastic bottle, 446 (15 mg, 0.024 mmol) was dissolved in DCM (0.10 mL) and treated with Deoxo-Fluor (25 µL). After 15 min at ambient temperature, the reaction was quenched with aqueous saturated NaHCO₃ and extracted with DCM. The organics evaporated and the residue was purified by RP HPLC to provide the desired compound (3 mg). ¹⁹F NMR (376 MHz, cdcl₃) δ −62.32, −76.30, −98.50, −109.31. MS (m/z) 638.2 [M+H]⁺.

Example 151

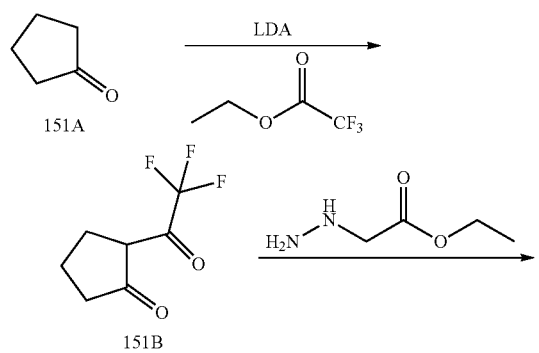

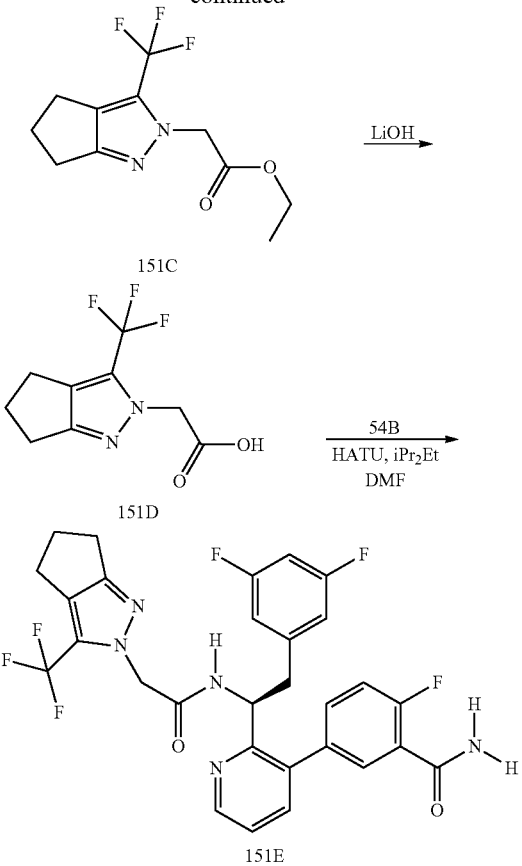

Synthesis of 2-(2,2,2-trifluoroacetyl)cyclopentanone (151B)

The title compound was prepared according to the method presented in the synthesis of 122C in Example 122 utilizing cyclopentanone Synthesis of ethyl 2-(3-(trifluoromethyl)-5,6-dihydrocyclopenta[c]pyrazol-2(4H)-yl)acetate (151C)

The title compound was prepared according to the method presented in the synthesis of 122D in Example 122 utilizing 2-(2,2,2-trifluoroacetyl)cyclopentanone. The title compound was the exclusive product of this reaction. MS (m/z) 263.1 [M+H]⁺.

Synthesis of 2-(3-(trifluoromethyl)-5,6-dihydrocyclopenta[c]pyrazol-2(4H)-yl)acetic acid (151D)

The title compound was prepared according to the method presented in the synthesis of 122F in Example 122 utilizing ethyl 2-(3-(trifluoromethyl)-5,6-dihydrocyclopenta[c]pyrazol-2(4H)-yl)acetate. MS (m/z) 235.0 [M+H]⁺.

Synthesis of (S)-5-(2-(2-(3,5-difluorophenyl)-1-(2-(3-(trifluoromethyl)-5,6-dihydrocyclopenta[c]pyrazol-2(4H)-yl)acetamido)ethyl)pyridin-3-yl)-2-fluorobenzamide (151E)

The title compound was prepared (8 mg) according to the method presented in the synthesis of Example 54 utilizing 54B and 151D. ¹H NMR (400 MHz, dmso) δ 8.79 (d, 1H), 8.67 (d, 1H), 7.73-7.57 (m, 3H), 7.40 (dt, 3H), 7.30 (s, 1H), 6.91 (s, 1H), 6.54 (d, 2H), 5.14 (s, 1H), 4.72 (s, 2H), 2.98 (s, 2H), 2.63-2.52 (m, 4H), 2.52-2.41 (m), 2.30 (s, 2H). MS (m/z) 588.3 [M+H]⁺.

Example 152

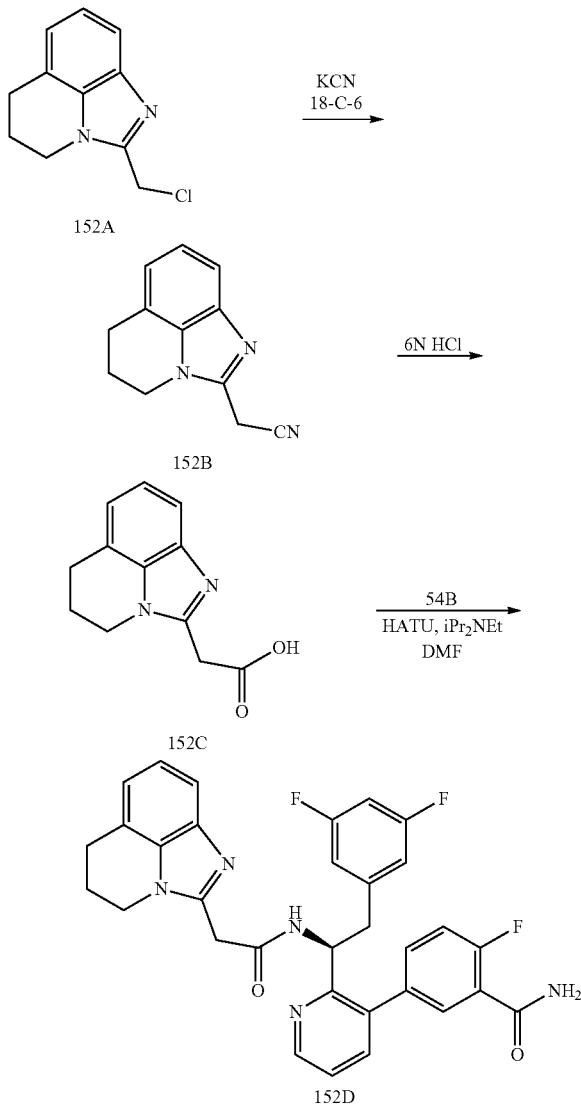

Synthesis of 2-(5,6-dihydro-4H-imidazo[4,5,1-ij]quinolin-2-yl)acetonitrile (152B)

To 2-(chloromethyl)-5,6-dihydro-4H-imidazo[4,5,1-ij]quinoline (synthesized as described in US 2007/0032469) (700 mg, 3.39 mmol) dissolved in EtOH (12 mL)/H₂O (1.2 mL) was added 18-C-6 (catalytic amount) and KCN (220 mg, 3.39 mmol). The reaction was heated to 50° C. for 3 h. Solvents were removed in vacuo and the residue was purified by column chromatography on silica to provide the title compound. MS (m/z) 198.1 [M+H]⁺.

Synthesis of 2-(5,6-dihydro-4H-imidazo[4,5,1-ij]quinolin-2-yl)acetic acid (152C)

2-(5,6-dihydro-4H-imidazo[4,5,1-ij]quinolin-2-yl)acetonitrile (90 mg, 0.45 mmol) was dissolved in 6 N HCl (3 mL) and heated to 70° C. After 1 h, the reaction temperature was raised to 105° C. After 2 h, the reaction was cooled to 0° C., neutralized with 20% aqueous NaOH, and buffered with 20% aqueous KH₂PO₄. The product was water soluble and unable to extract into organic solvents. The aqueous solution was removed in vacuo and crude product was directly used in the next reaction. MS (m/z) 217.1 [M+H]⁺.

Synthesis of (S)-5-(2-(2-(3,5-difluorophenyl)-1-(2-(5,6-dihydro-4H-imidazo[4,5,1-ij]quinolin-2-yl)acetamido)ethyl)pyridin-3-yl)-2-fluorobenzamide (152D)

The title compound (4 mg) was prepared according to the method presented in the synthesis of Example 54G utilizing 54B and 2-(5,6-dihydro-4H-imidazo[4,5,1-ij]quinolin-2-yl)acetic acid. ¹H NMR (400 MHz, cd₃od) δ 8.60 (d, 1H), 7.52-7.45 (m, 1H), 7.37 (d, 1H), 7.31-7.23 (m, 1H), 7.21 (s, 1H), 7.15-6.98 (m, 2H), 6.91 (d, 1H), 6.54 (t, 1H), 6.26 (d, 2H), 5.28 (t, 1H), 4.75 (s, 19H), 3.98 (s, 2H), 3.83 (s, 1H), 3.24 (s, 1H), 3.38-2.92 (m, 23H), 2.86 (t, 2H), 2.30-1.90 (m, 2H). MS (m/z) 570.4 [M+H]⁺.

Example 153

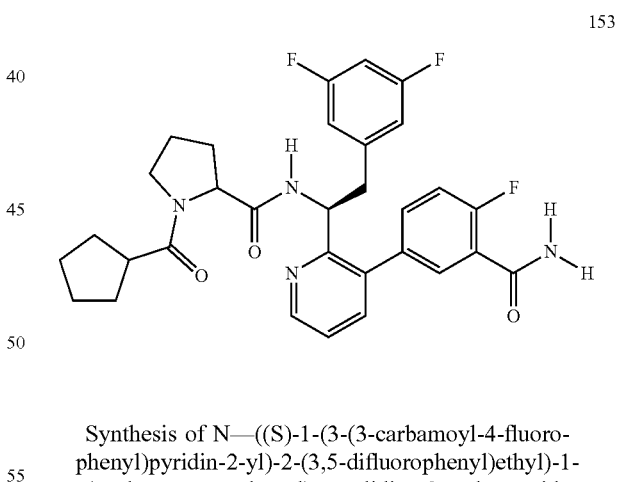

153

Synthesis of N—((S)-1-(3-(3-carbamoyl-4-fluorophenyl)pyridin-2-yl)-2-(3,5-difluorophenyl)ethyl)-1-(cyclopentanecarbonyl)pyrrolidine-2-carboxamide (153)

The title compound was prepared (6 mg) according to the method presented in the synthesis of Example 54 utilizing 54B and 1-(cyclopentanecarbonyl)pyrrolidine-2-carboxylic acid. ¹H NMR (400 MHz, cdcl₃) δ 8.78 (s, 1H), 8.71 (s, 1H), 8.02 (s, 1H), 7.75 (s, 2H), 7.61 (s, 1H), 7.31 (s, 1H), 6.59 (s, 1H), 6.28 (d, J=6.2 Hz, 2H), 6.06 (s, 1H), 5.61 (s, 1H), 4.33 (s, 1H), 3.95 (s, 1H), 3.55 (s, 1H), 3.28 (d, J=28.6 Hz, 2H), 3.03 (s, 1H), 2.13 (s, 6H), 1.93 (s, 6H), 1.61 (d, J=43.1 Hz, 6H).

Example 154, 155, and 156

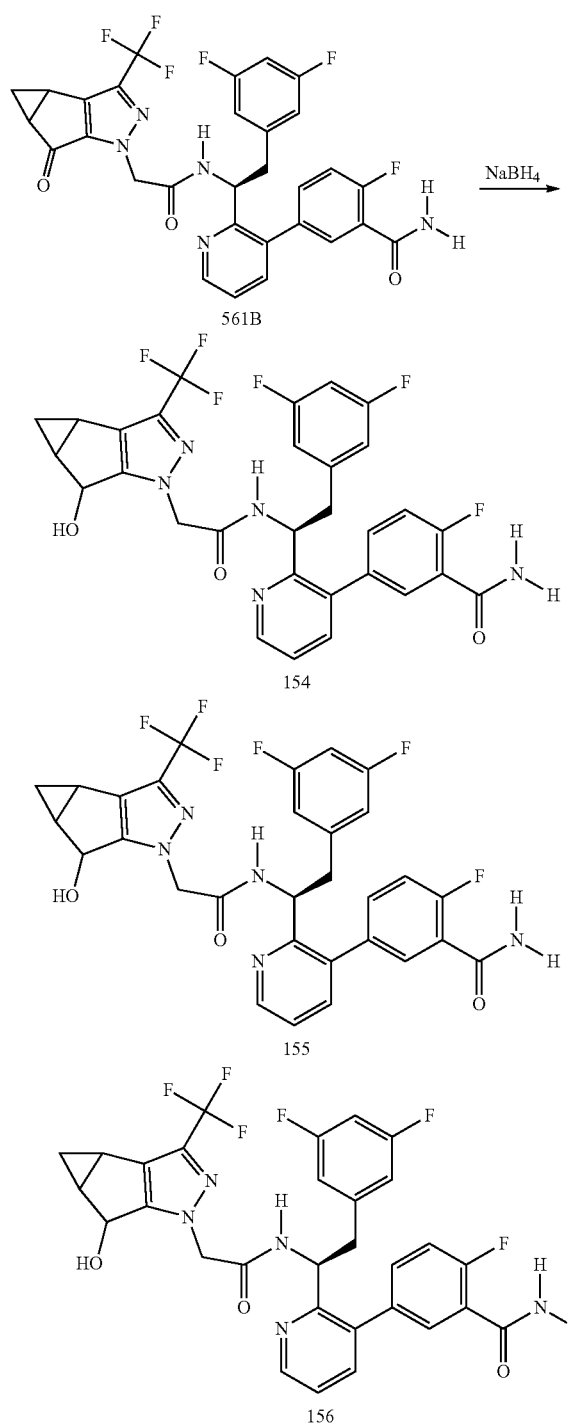

Synthesis of 5-(2-((1S)-2-(3,5-difluorophenyl)-1-(2-(5-hydroxy-3-(trifluoromethyl)-3b,4,4a,5-tetrahydro-1H-cyclopropa[3,4]cyclopenta[1,2-c]pyrazol-1-yl)acetamido)ethyl)pyridin-3-yl)-2-fluorobenzamide (154)

The title compound was prepared according to the method presented in the synthesis of 325B in Example 325 utilizing 561B. Purification of the crude mixture by RP HPLC resulted in isolation of three peaks. Compound 154 (3.5 mg) is the peak with the shortest retention time. $^1$H NMR (400 MHz, cd$_3$cn) δ 8.58 (dd, 1H), 8.17 (s, 1H), 7.70 (dd, 1H), 7.65-7.43 (m, 2H), 7.26 (s, 1H), 7.17 (dd, 1H), 6.77 (s, 1H), 6.61 (t, 1H), 6.27 (t, 3H), 5.34-5.21 (m, 2H), 4.61 (q, 2H), 3.32 (s, 2H), 2.94 (qd, 3H), 2.30-1.90 (m, 3H), 1.85 (dt), 0.89 (td, 1H), 0.72 (dd, 1H). MS (m/z) 616.1 [M+H]$^+$.

Synthesis of 5-(2-((1S)-2-(3,5-difluorophenyl)-1-(2-(5-hydroxy-3-(trifluoromethyl)-3 b,4,4a,5-tetrahydro-1H-cyclopropa[3,4]cyclopenta[1,2-c]pyrazol-1-yl)acetamido)ethyl)pyridin-3-yl)-2-fluorobenzamide (155)

The title compound was prepared according to the method presented in the synthesis of 325B in Example 325 utilizing 561B. Purification of the crude mixture by RP HPLC resulted in isolation of three peaks. Compound 155 (5 mg) is the peak with second shortest retention time and is a mixture of diastereomers. $^1$H NMR (400 MHz, cd$_3$cn) δ 8.57-8.45 (m, 1H), 7.68 (dd, 1H), 7.66-7.41 (m, 2H), 7.41-7.06 (m, 3H), 7.06-7.03 (m, 1H), 6.61 (d, 2H), 6.50 (d, 1H), 6.33-5.90 (m, 4H), 5.27-5.06 (m, 2H), 4.64-4.47 (m, 2H), 3.62 (s, 6H), 3.17-2.66 (m, 3H), 1.96 (ddd, 3H), 1.75 (dt), 1.09-0.87 (m, 1H), 0.78 (dd, 1H), 0.61 (d, 1H), 0.02 (dd, J=8.3, 4.7 Hz, 1H). MS (m/z) 616.1 [M+H]$^+$.

Synthesis of 5-(2-((1S)-2-(3,5-difluorophenyl)-1-(2-(5-hydroxy-3-(trifluoromethyl)-3b,4,4a,5-tetrahydro-1H-cyclopropa[3,4]cyclopenta[1,2-c]pyrazol-1-yl)acetamido)ethyl)pyridin-3-yl)-2-fluorobenzamide (156)

The title compound was prepared according to the method presented in the synthesis of 325B in Example 325 utilizing 561B. Purification of the crude mixture by RP HPLC resulted in isolation of three peaks. Compound 156 (4 mg) is the peak with longest retention time and is a mixture of diastereomers. $^1$H NMR (400 MHz, cd$_3$cn) δ 8.68 (d, 1H), 7.73 (s, 1H), 7.63 (s, 1H), 7.51 (s, 1H), 7.36-7.23 (m, 2H), 6.90 (s, 1H), 6.69 (s, 1H), 6.34 (d, 4H), 5.34 (d, 2H), 4.74 (dd, 2H), 3.00 (d, 3H), 2.16 (s, 1H), 1.95 (dt), 1.20 (s, 1H), 0.97 (d, 1H), 0.75 (d, 1H), 0.22 (s, 1H). MS (m/z) 616.1 [M+H]$^+$.

Example 157

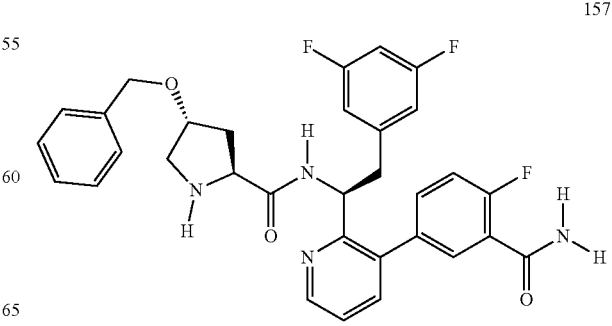

157

393

Synthesis of (2S,4R)-4-(benzyloxy)-N—((S)-1-(3-(3-carbamoyl-4-fluorophenyl)pyridin-2-yl)-2-(3,5-difluorophenyl)ethyl)pyrrolidine-2-carboxamide (157)

The title compound was prepared (9 mg) according to the method presented in the synthesis of Example 125 utilizing 145. MS (m/z) 575.4 [M+H]⁺.

Example 158

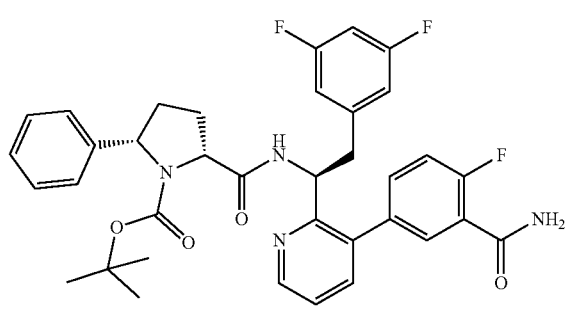

158

Synthesis of (2R,5S)-tert-butyl 2-((S)-1-(3-(3-carbamoyl-4-fluorophenyl)pyridin-2-yl)-2-(3,5-difluorophenyl)ethylcarbamoyl)-5-phenylpyrrolidine-1-carboxylate (158)

The title compound was prepared (6 mg) according to the method presented in the synthesis of Example 54 utilizing 54B and (2R,5S)-1-(tert-butoxycarbonyl)-5-phenylpyrrolidine-2-carboxylic acid. ¹H NMR (400 MHz, cdcl₃) δ 8.74 (d, 1H), 8.6 (m, 1H) 7.86 (s, 1H), 7.62 (d, 2H), 7.33-7.22 (m, 10H), 6.59 (s, 1H), 6.19 (d, 2H), 6.06 (s, 1H), 5.48 (s, 1H), 4.59 (d, 1H), 3.11 (s, 1H), 3.02 (s, 1H), 2.53 (s, 2H), 2.43 (s, 2H), 1.86 (s, 1H), 1.41 (s, 10H). MS (m/z) 645.1 [M+H]⁺.

Example 159

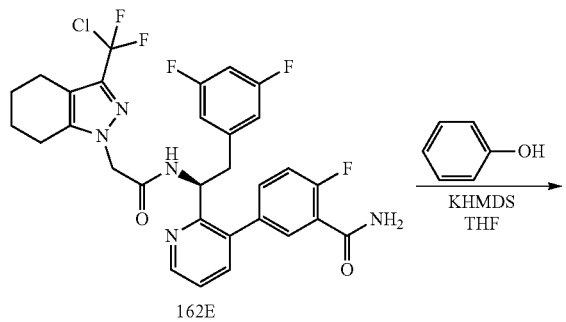

162E

394

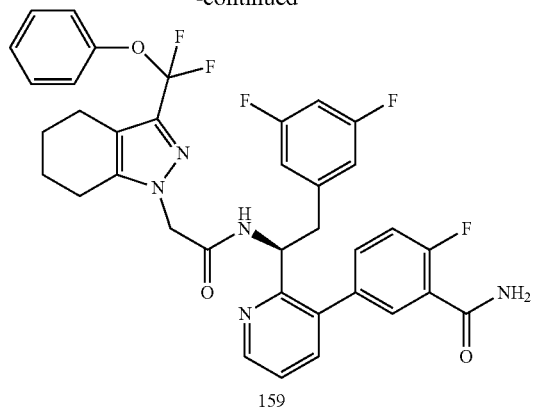

159

Synthesis of(S)-5-(2-(1-(2-(3-(difluoro(phenoxy)methyl)-4,5,6,7-tetrahydro-1H-indazol-1-yl)acetamido)-2-(3,5-difluorophenyl)ethyl)pyridin-3-yl)-2-fluorobenzamide (159)

(S)-5-(2-(1-(2-(3-(chlorodifluoromethyl)-4,5,6,7-tetrahydro-1H-indazol-1-yl)acetamido)-2-(3,5-difluorophenyl)ethyl)pyridin-3-yl)-2-fluorobenzamide (36 mg, 0.06 mmol) was dissolved in THF (0.6 mL) and treated with KHMDS (2.7 mg, 0.14 mmol). Phenol (14 mg, 0.15 mmol) was added to the reaction mixture the temperature was raised to 45° C. After stirring for 16 h, solvent were removed in vacuo. The residue was purified by RP HPLC to provide the title compound (7 mg) as a mixture with its regioisomer ((S)-5-(2-(1-(2-(3-(difluoro(phenoxy)methyl)-4,5,6,7-tetrahydro-2H-indazol-2-yl)acetamido)-2-(3,5-difluorophenyl)ethyl)pyridin-3-yl)-2-fluorobenzamide: ¹H NMR (400 MHz, dmso) δ 8.88 (d, 1H), 8.81-8.59 (m, 2H), 7.84-7.55 (m, 4H), 7.55-7.14 (m, 8H), 7.10 (d, 1H), 7.05-6.81 (m, 1H), 6.56 (d, 2H), 6.47 (d, 1H), 5.22-5.12 (m, 1H), 4.84 (s, 2H), 4.74 (d, 16H), 3.18-2.72 (m, 3H), 2.52-2.42 (m, 12H), 2.25 (d, 1H), 1.60 (s, 6H). MS (m/z) 676.2 [M+H]⁺.

Example 160

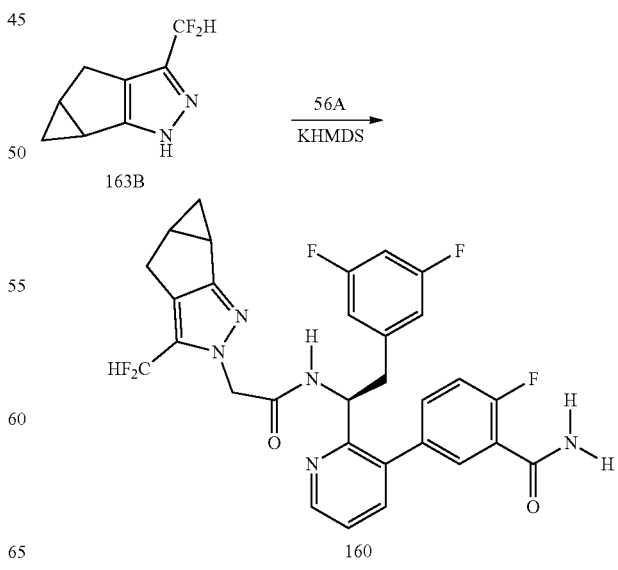

160

395

Synthesis of 5-(2-((1S)-1-(2-(3-(difluoromethyl)-4,4a,5,5a-tetrahydro-2H-cyclopropa[4,5]cyclopenta[1,2-c]pyrazol-2-yl)acetamido)-2-(3,5-difluorophenyl)ethyl)pyridin-3-yl)-2-fluorobenzamide (160)

The title compound was prepared (8 mg) according to the method presented in the synthesis of Example 56 utilizing 56A and 163B to provide to regioisomeric products. The title compound was the minor product (8 mg): $^1$H NMR (400 MHz, dmso) δ 8.63 (t, 1H), 8.53 (d, 1H), 7.47 (dd, 3H), 7.41-7.19 (m, 3H), 7.19-7.09 (m, 1H), 6.85 (s, 1H), 6.80-6.69 (m, 1H), 6.58 (d, 1H), 6.36 (d, 2H), 5.00 (d, 1H), 4.55 (s, 2H), 2.84 (t, 2H), 2.62 (d, 2H), 2.44 (d, 1H), 2.34 (s, 3H), 2.34-1.72 (m), 0.93 (d, 1H), 0.00 (d, J=4.0 Hz, 2H). MS (m/z) 582.2 [M+H]$^+$.

Example 161

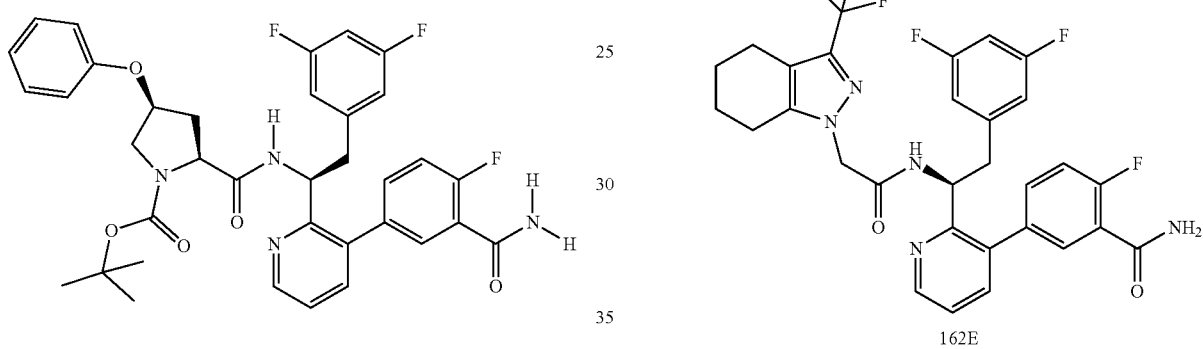

161

Synthesis of (2S,4S)-tert-butyl 2-((S)-1-(3-(3-carbamoyl-4-fluorophenyl)pyridin-2-yl)-2-(3,5-difluorophenyl)ethylcarbamoyl)-4-phenoxypyrrolidine-1-carboxylate (161)

The title compound as prepared (12 mg) according to the method presented in the synthesis of Example 54 utilizing 54B and (2S,4S)-1-(tert-butoxycarbonyl)-4-phenoxypyrrolidine-2-carboxylic acid. MS (m/z) 661.3 [M+H]$^+$.

Example 162

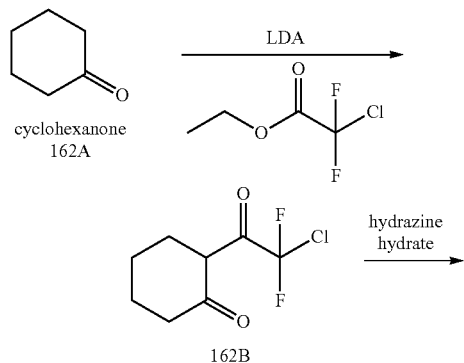

396

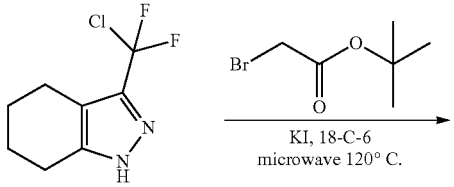

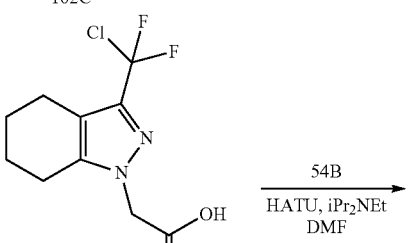

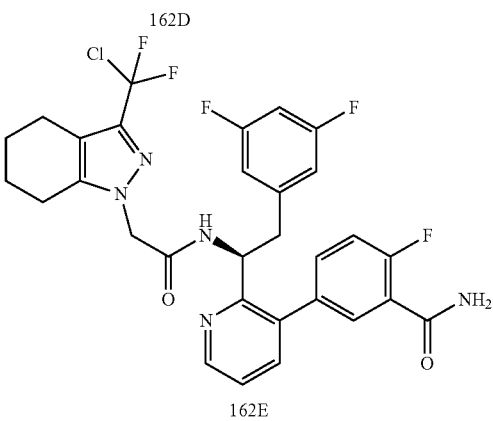

Synthesis of 2-(2-chloro-2,2-difluoroacetyl)cyclohexanone (162B)

The title compound was prepared according to the method presented in the synthesis of 122C in Example 122 utilizing cyclohexanone and ethyl 2-chloro-2,2-difluoroacetate Synthesis of 3-(chlorodifluoromethyl)-4,5,6,7-tetrahydro-1H-indazole (162C)

The title compound was prepared according to the method presented in the synthesis of 169D in Example 169 utilizing 2-(2-chloro-2,2-difluoroacetyl)cyclohexanone. MS (m/z) 207.4 [M+H]$^+$.

Synthesis of 2-(3-(chlorodifluoromethyl)-4,5,6,7-tetrahydro-1H-indazol-1-yl)acetic acid (162D)

In a microwave vial, 3-(chlorodifluoromethyl)-4,5,6,7-tetrahydro-1H-indazole (580 mg, 2.81 mmol) was combined with tert-butyl 2-bromoacetate (2.5 mL, 17 mmol), KI (166 mg), and 18-C-6 (catalytic) in NMP (2.8 mL). The reaction mixture was heated in a microwave reactor at 120° C. for 90 min. The reaction was partitioned between EtOAc and saturated aqueous NaCl. The organics were separated, dried and removed in vacuo. The residue was purified by column chromatography on silica to provide the title compound as a 1.5:1 mixture with its regioisomer 2-(3-(chlorodifluoromethyl)-4,5,6,7-tetrahydro-2H-indazol-2-yl)acetic acid. MS (m/z) 265.1 [M+H]+.

Synthesis of (S)-5-(2-(1-(2-(3-(chlorodifluoromethyl)-4,5,6,7-tetrahydro-1H-indazol-1-yl)acetamido)-2-(3,5-difluorophenyl)ethyl)pyridin-3-yl)-2-fluorobenzamide (162E)

The title compound was prepared according to the method presented in the synthesis of Example 54 utilizing 162D. The title compound (5 mg) was not able to be purified from the regioisomer ((S)-5-(2-(1-(2-(3-(chlorodifluoromethyl)-4,5,6,7-tetrahydro-2H-indazol-2-yl)acetamido)-2-(3,5-difluorophenyl)ethyl)pyridin-3-yl)-2-fluorobenzamide) and was tested as a mixture. $^1$H NMR (400 MHz, cd$_3$od) δ 8.68 (s, 1H), 7.60 (s, 1H), 7.36 (d, J=22.1 Hz, 3H), 7.21 (s, 1H), 6.66 (s, 1H), 6.32 (s, 2H), 5.36 (s, 2H), 3.03 (s, 2H), 2.62 (s, 3H), 2.44 (s, 2H), 1.76 (s, 4H). MS (m/z) 618.7 [M+H]+.

Example 163

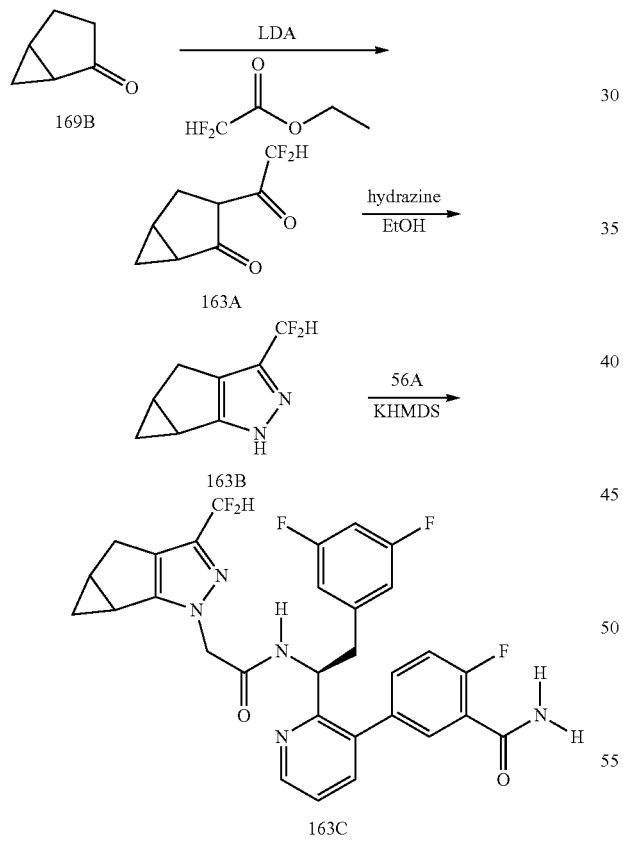

Synthesis of 3-(2,2-difluoroacetyl)bicyclo[3.1.0]hexan-2-one (163A)

The title compound was prepared according to the method presented in the synthesis of 122C in Example 122 utilizing 169B and ethyl 2,2-difluoroacetate Synthesis of 3-(difluoromethyl)-4,4a,5,5a-tetrahydro-1H-cyclopropa[4,5]cyclopenta[1,2-c]pyrazole (163B)

The title compound was prepared according to the method presented in the synthesis of 169D in Example 169 utilizing 163A. MS (m/z) 171.0 [M+H]+.

Synthesis of 5-(2-((1S)-1-(2-(3-(difluoromethyl)-4,4a,5,5a-tetrahydro-1H-cyclopropa[4,5]cyclopenta[1,2-c]pyrazol-1-yl) acetamido)-2-(3,5-difluorophenyl)ethyl)pyridin-3-yl)-2-fluorobenzamide (163C)

The title compound was prepared according to the method presented in the synthesis of Example 56 utilizing 56A and 163B to provide to regioisomeric products. The title compound was the major product (6 mg): $^1$H NMR (400 MHz, dmso) δ 8.67 (d, 1H), 8.47 (d, 1H), 7.57-7.35 (m, 3H), 7.35-7.16 (m, 3H), 7.16-7.01 (m, 1H), 6.69 (dd, 2H), 6.48 (s, 1H), 6.35 (d, 3H), 5.23-4.92 (m, 2H), 4.74-4.39 (m, 4H), 3.90 (s, 1H), 2.80 (d, 3H), 2.65-2.33 (m, 3H), 2.32 (s, 1H), 2.30-2.22 (m), 1.81 (d, 5H), 0.77 (dd, 2H), 0.00 (d, 1H). MS (m/z) 582.2 [M+H]+.

Example 164

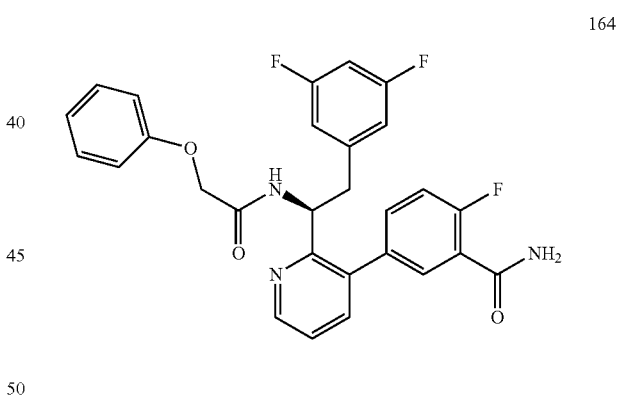

Synthesis of (S)-5-(2-(2-(3,5-difluorophenyl)-1-(2-phenoxyacetamido)ethyl)pyridin-3-yl)-2-fluorobenzamide (164)

Under the conditions described in Example 159, the title compound was isolated as side product (2 mg): $^1$H NMR (400 MHz, dmso) δ 8.66 (dd, 1H), 8.57 (d, 1H), 7.87-7.58 (m, 4H), 7.54 (s, 1H), 7.54-7.28 (m, 4H), 7.28-7.15 (m, 2H), 6.90 (dd, 2H), 6.78 (d, 2H), 6.55 (d, 2H), 5.21 (d, 2H), 4.41 (s, 3H), 3.79 (bs), 3.17-2.90 (m, 3H), 2.52-2.41 (m, 14H). MS (m/z) 506.4 [M+H]+.

Example 165

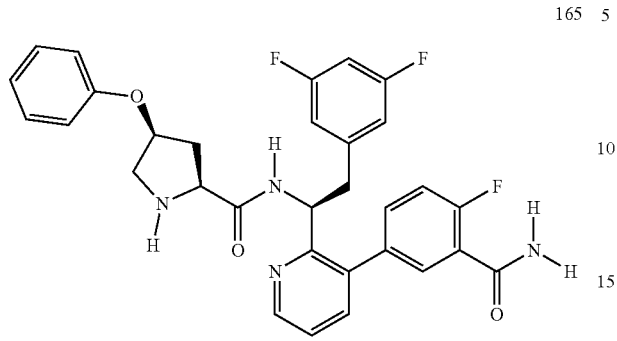

Synthesis of (2S,4S)—N—((S)-1-(3-(3-carbamoyl-4-fluorophenyl)pyridin-2-yl)-2-(3,5-difluorophenyl)ethyl)-4-phenoxypyrrolidine-2-carboxamide (165)

The title compound was prepared (3 mg) according to the method presented in the synthesis of Example 125 utilizing 161.

Example 166

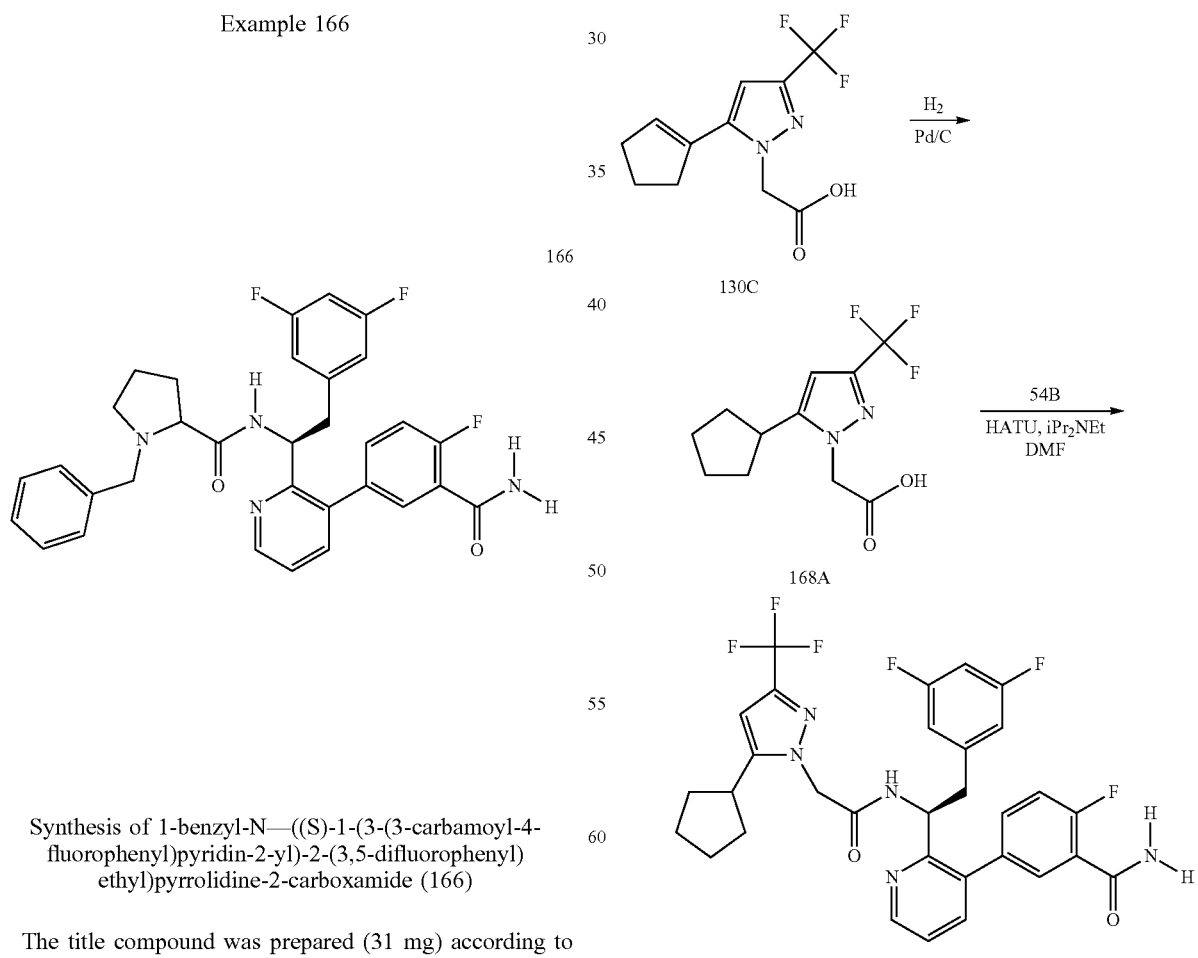

Synthesis of 1-benzyl-N—((S)-1-(3-(3-carbamoyl-4-fluorophenyl)pyridin-2-yl)-2-(3,5-difluorophenyl)ethyl)pyrrolidine-2-carboxamide (166)

The title compound was prepared (31 mg) according to the method presented in the synthesis of Example 54 utilizing 54B and 1-benzylpyrrolidine-2-carboxylic acid. MS (m/z) 559.4 [M+H]$^+$.

Example 167

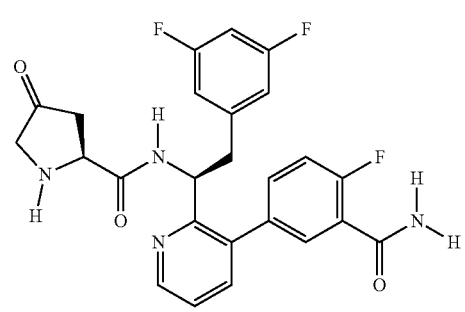

Synthesis of (S)—N—((S)-1-(3-(3-carbamoyl-4-fluorophenyl)pyridin-2-yl)-2-(3,5-difluorophenyl)ethyl)-4-oxopyrrolidine-2-carboxamide (167)

The title compound was prepared (5 mg) according to the method presented in the synthesis of Example 125 utilizing 137. MS (m/z) 483.4 [M+H]$^+$.

Example 168

Synthesis of 2-(5-cyclopentyl-3-(trifluoromethyl)-1H-pyrazol-1-yl)acetic acid (168A)

To 130C (30 mg, 0.11 mmol) dissolved in EtOH (4 mL) was added Pd/C (5 mg) and placed under an atmosphere of H$_2$. The reaction was stirred for 16 h then filtered over celite. The eluent was removed in vacuo. MS (m/z) 263.1 [M+H]$^+$.

Synthesis of (S)-5-(2-(1-(2-(5-cyclopentyl-3-(trifluoromethyl)-1H-pyrazol-1-yl)acetamido)-2-(3,5-difluorophenyl)ethyl)pyridin-3-yl)-2-fluorobenzamide (168B)

The title compound was prepared (5 mg) according to the method presented in the synthesis of Example 54 utilizing 54B and 168A. $^1$H NMR (400 MHz, dmso) δ 8.92 (d, 1H), 8.67 (d, 1H), 7.67-7.58 (m, 3H), 7.53-7.31 (m, 4H), 7.29 (d, 1H), 6.92 (s, 1H), 6.57 (d, 2H), 6.44 (s, 1H), 5.17 (d, 2H), 4.80 (q, 4H), 3.01 (t, 2H), 2.72 (t, 1H), 2.52-2.41 (m), 1.77 (s, 1H), 1.77-1.66 (m, 1H), 1.54 (d, 4H), 1.37 (d, 1H). MS (m/z) 616.4 [M+H]$^+$.

Example 169

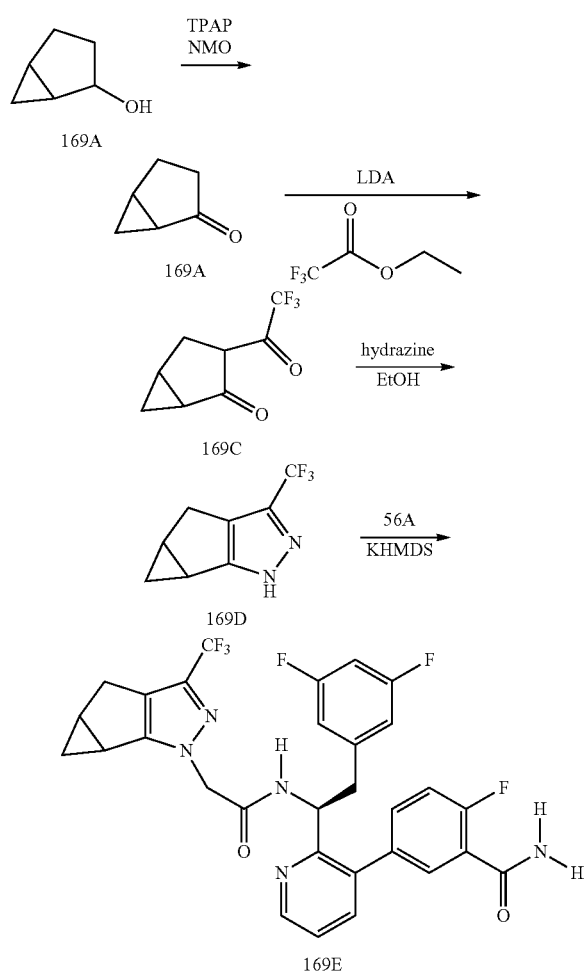

Synthesis of bicyclo[3.1.0]hexan-2-one (169B)

The title compound was prepared according to the method presented in the synthesis of 122B in Example 122 utilizing bicyclo[3.1.0]hexan-2-ol (synthesized as described in *J. Am. Chem. Soc.* 2004, 126, 8664-8665).

Synthesis of 3-(2,2,2-trifluoroacetyl)bicyclo[3.1.0]hexan-2-one (169C)

The title compound was prepared according to the method presented in the synthesis of 122C in Example 122 utilizing bicyclo[3.1.0]hexan-2-one Synthesis of 3-(trifluoromethyl)-4,4a,5,5a-tetrahydro-1H-cyclopropa[4,5]cyclopenta[1,2-c]pyrazole (169D)

To 3-(2,2,2-trifluoroacetyl)bicyclo[3.1.0]hexan-2-one (290 mg, 1.5 mmol) dissolved in EtOH (14 mL) was added hydrazine hydrate (2 mmol) and heated to 85° C. After 16 hours, the reaction was cooled to ambient temperature and solvents removed in vacuo. The residue was partitioned between EtOAc and H$_2$O. The organics were separated, dried and removed in vacuo. The crude product was purified by column chromatography on silica to provide the title compound. MS (m/z) 189.0 [M+H]$^+$.

Synthesis of 5-(2-((1S)-2-(3,5-difluorophenyl)-1-(2-(3-(trifluoromethyl)-4,4a,5,5a-tetrahydro-1H-cyclopropa[4,5]cyclopenta[1,2-c]pyrazol-1-yl)acetamido)ethyl)pyridin-3-yl)-2-fluorobenzamide (169E)

The title compound was prepared (14 mg) according to the method presented in the synthesis of Example 56 utilizing 56A and 169D. MS (m/z) 600.3 [M+H]$^+$.

Example 170

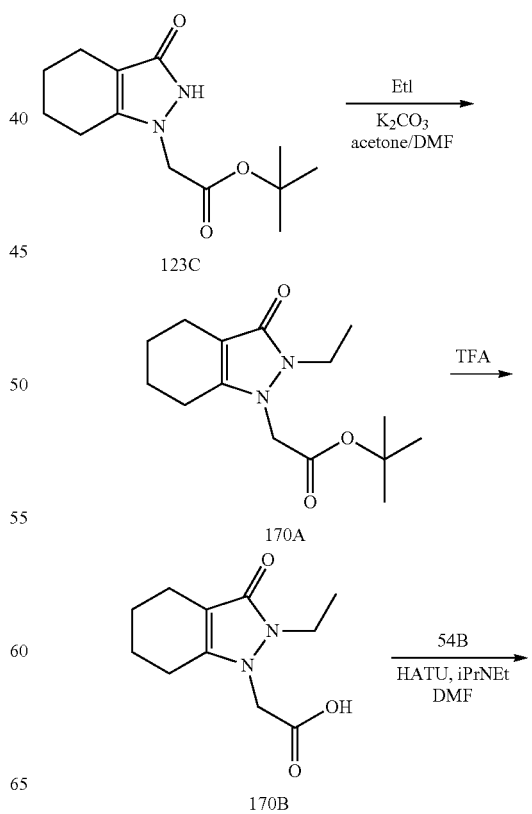

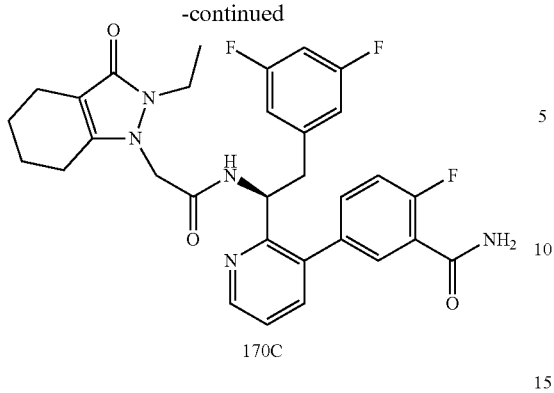

170C

Synthesis of tert-butyl 2-(2-ethyl-3-oxo-2,3,4,5,6,7-hexahydro-1H-indazol-1-yl)acetate (170A)

tert-Butyl 2-(3-oxo-2,3,4,5,6,7-hexahydro-1H-indazol-1-yl)acetate (52 mg, 0.21 mmol) was dissolved in acetone (2 mL) and treated with EtI (18 μL, 0.23 mmol) and K₂CO₃ (34 mg, 0.23 mmol). DMF (1 mL) was added to aid solubility and the reaction was heated to 50° C. for 14 hr. Two alkylation regioisomers were obtained. The title compound was the minor regioisomer exhibiting a longer retention time on HPLC: MS (m/z) 281.1 [M+H]⁺.

Synthesis of 2-(2-ethyl-3-oxo-2,3,4,5,6,7-hexahydro-1H-indazol-1-yl)acetic acid (170B)

tert-Butyl 2-(2-ethyl-3-oxo-2,3,4,5,6,7-hexahydro-1H-indazol-1-yl)acetate (0.1 mmol) was dissolved in DCM (1 mL) and treated with TFA (1 mL). The reaction was stirred for 2 h at ambient temperature at which time solvents were removed in vacuo to provide the desired product: MS (m/z) 225.2 [M+H]⁺.

Synthesis of (S)-5-(2-(2-(3,5-difluorophenyl)-1-(2-(2-ethyl-3-oxo-2,3,4,5,6,7-hexahydro-1H-indazol-1-yl)acetamido)ethyl)pyridin-3-yl)-2-fluorobenzamide (170C)

The title compound was prepared (14 mg) according to the method presented in the synthesis of Example 54 utilizing 54B and 2-(2-ethyl-3-oxo-2,3,4,5,6,7-hexahydro-1H-indazol-1-yl)acetic acid. ¹H NMR (400 MHz, cd₃od) δ 8.73-8.66 (m, 1H), 7.63-7.55 (m, 1H), 7.50 (d, 1H), 7.32 (ddd, 3H), 6.69 (s, 1H), 6.37 (d, 2H), 5.31 (t, 1H), 4.83 (s, 20H), 4.72-4.58 (m, 3H), 4.12 (d, 1H), 4.01-3.67 (m, 3H), 3.29 (dt, 29H), 3.04 (t, 4H), 2.79 (s, 1H), 2.45 (d, 2H), 2.35 (d, 4H), 1.78 (s, 3H), 1.71 (s, 3H), 1.31 (t, 1H), 1.12 (t, 3H). MS (m/z) 578.5 [M+H]⁺.

Example 171

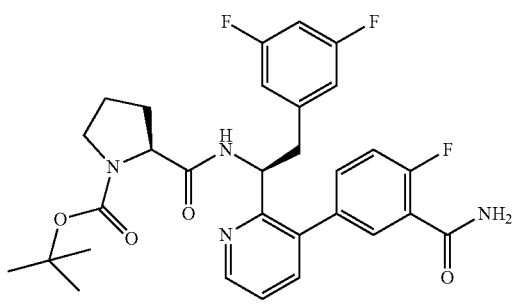

171

Synthesis of (S)-tert-butyl 2-((S)-1-(3-(3-carbamoyl-4-fluorophenyl)pyridin-2-yl)-2-(3,5-difluorophenyl)ethylcarbamoyl)pyrrolidine-1-carboxylate (171)

The title compound was prepared (6 mg) according to the method presented in the synthesis of Example 54 utilizing 54B and (S)-1-(tert-butoxycarbonyl)pyrrolidine-2-carboxylic acid. MS (m/z) 569.2 [M+H]⁺.

Example 172

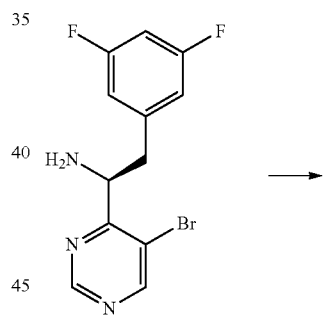

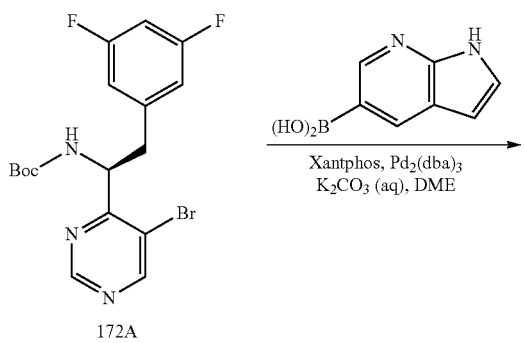

172A

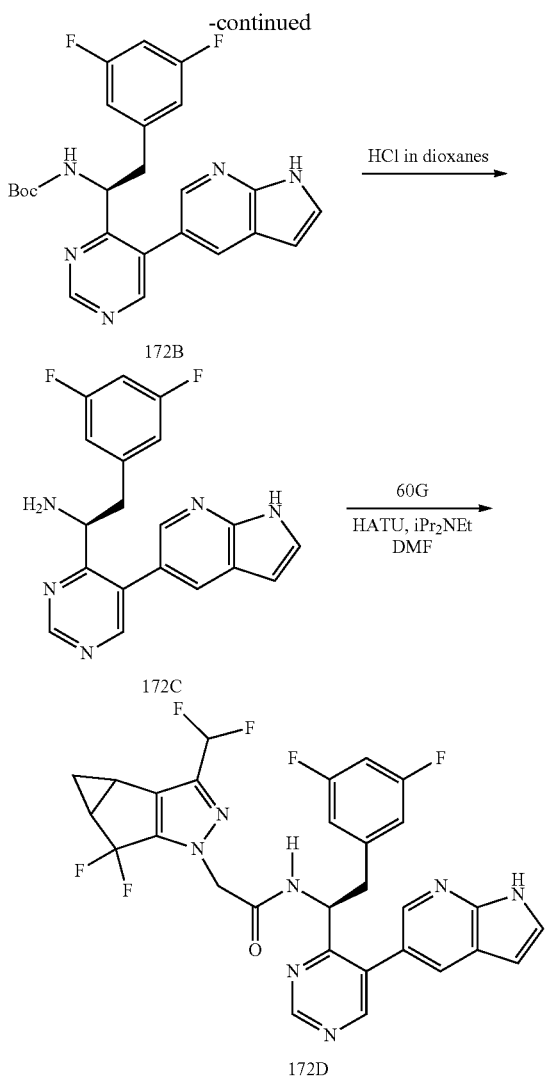

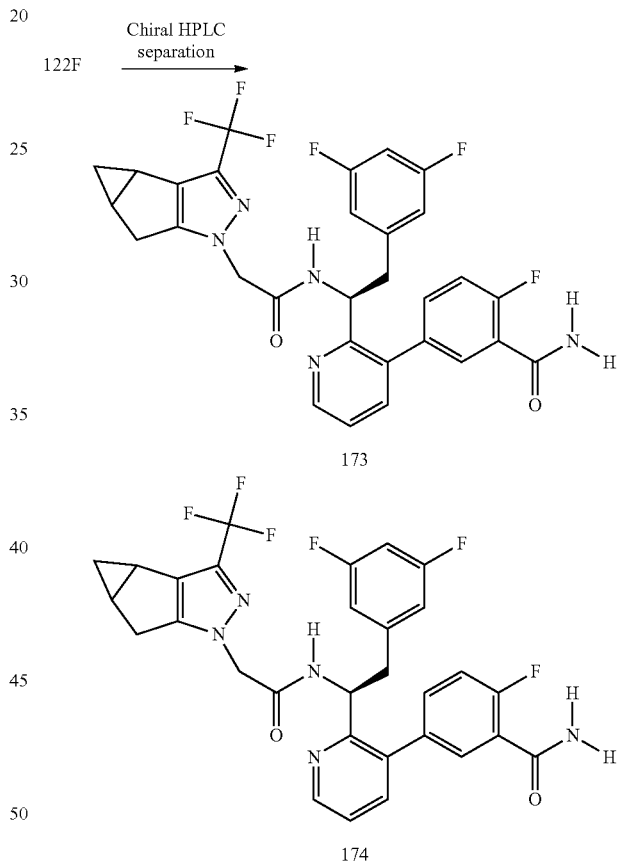

Synthesis of N—((S)-1-(5-(1H-pyrrolo[2,3-b]pyridin-5-yl)pyrimidin-4-yl)-2-(3,5-difluorophenyl)ethyl)-2-(3-(difluoromethyl)-5,5-difluoro-3b,4,4a,5-tetrahydro-1H-cyclopropa[3,4]cyclopenta[1,2-c]pyrazol-1-yl)acetamide (172D)

The title compound as prepared (4 mg) according to the method presented in the synthesis of Example 54 utilizing 60G and 172C. $^1$H NMR (400 MHz, cd$_3$cn) δ 12.37 (s, 1H), 9.26 (s, 1H), 8.59 (s, 1H), 8.20 (d, 1H), 8.08 (d, 1H), 7.70 (s, 1H), 7.42 (s, 3H), 6.89 (d, 1H), 6.74 (dd, 2H), 6.62 (d, 1H), 6.37 (d, 2H), 5.30 (d, 1H), 4.74 (p, 2H), 3.02 (t, 2H), 2.48 (s, 2H), 1.95 (dt), 1.39 (dd, 1H), 1.01 (s, 1H). MS (m/z) 598.1 [M+H]$^+$.

Examples 173 and 174

Synthesis of (S)-tert-butyl 1-(5-bromopyrimidin-4-yl)-2-(3,5-difluorophenyl)ethylcarbamate (172A)

Synthesis of (S)-tert-butyl 1-(5-(1 H-pyrrolo[2,3-b]pyridin-5-yl)pyrimidin-4-yl)-2-(3,5-difluorophenyl)ethylcarbamate (172B)

The title compound as prepared according to the method presented in the synthesis of 136B in Example 136 utilizing 172A and 1H-pyrrolo[2,3-b]pyridin-5-ylboronic acid to provide the title compound. MS (m/z) 451.8 [M+H]$^+$.

Synthesis of (S)-1-(5-(1H-pyrrolo[2,3-b]pyridin-5-yl)pyrimidin-4-yl)-2-(3,5-difluorophenyl)ethanamine (172C)

The title compound as prepared according to the method presented in the synthesis of 136C in Example 136 utilizing (S)-tert-butyl 1-(5-(1H-pyrrolo[2,3-b]pyridin-5-yl)pyrimidin-4-yl)-2-(3,5-difluorophenyl)ethylcarbamate to provide the title compound.

Synthesis of 5-(2-((S)-2-(3,5-difluorophenyl)-1-(2-((3bR,4aR)-3-(trifluoromethyl)-3b,4,4a,5-tetrahydro-1H-cyclopropa[3,4]cyclopenta[1,2-c]pyrazol-1-yl)acetamido)ethyl)pyridin-3-yl)-2-fluorobenzamide and 5-(2-((S)-2-(3,5-difluorophenyl)-1-(2-((3bS,4aS)-3-(trifluoromethyl)-3b,4,4a,5-tetrahydro-1H-cyclopropa[3,4]cyclopenta[1,2-c]pyrazol-1-yl)acetamido)ethyl)pyridin-3-yl)-2-fluorobenzamide (173 and 174)

The title compounds were separated from the diastereomeric mixture 122F by semi-preparative chiral HPLC fitted with a Chiralpak IC column running a 70:30 mixture of Hep:IPA to obtain the desired compounds as pure diastereomers: 173 (14 mg): HPLC rt=11.5 min; MS (m/z) 600.4 [M+H]+. 174 (12 mg): HPLC rt=13.5 min; MS (m/z) 600.4 [M+H]+. Absolute stereochemistry is unknown.

Example 175

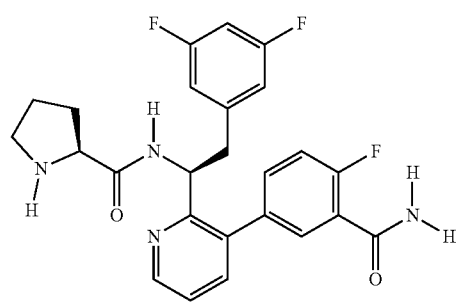

Synthesis of (S)—N—((S)-1-(3-(3-carbamoyl-4-fluorophenyl)pyridin-2-yl)-2-(3,5-difluorophenyl)ethyl)pyrrolidine-2-carboxamide (175)

The title compound was prepared (4 mg) according to the method presented in the synthesis of Example 125 utilizing 171. MS (m/z) 469.4 [M+H]+.

Example 176

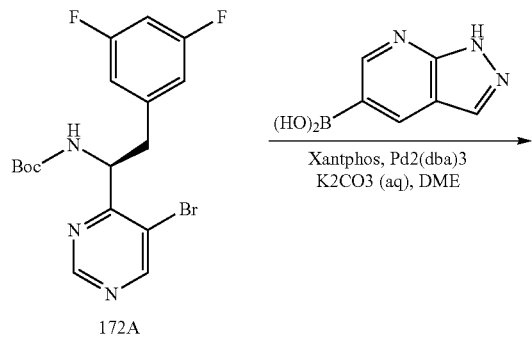

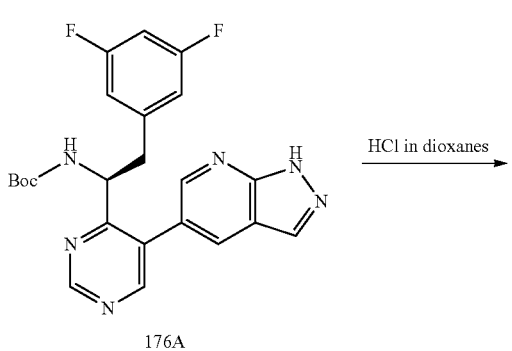

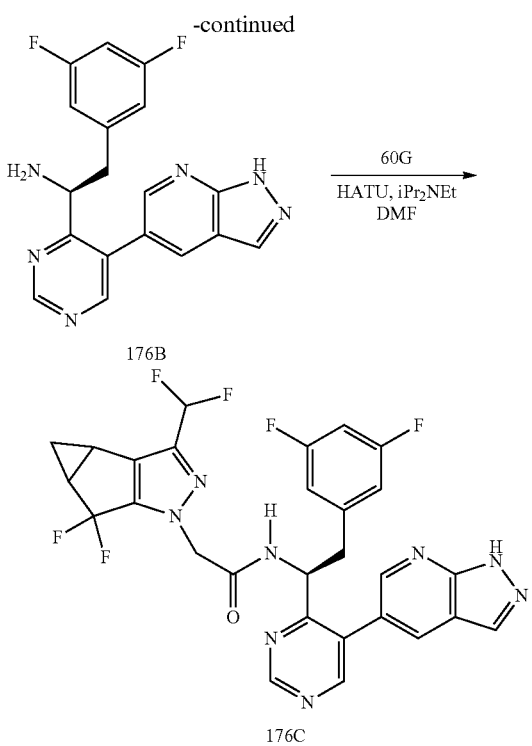

Synthesis of (S)-tert-butyl 1-(5-(1H-pyrazolo[3,4-b]pyridin-5-yl)pyrimidin-4-yl)-2-(3,5-difluorophenyl)ethylcarbamate (176A)

The title compound as prepared according to the method presented in the synthesis of 136B in Example 136 utilizing 172A and 1H-pyrazolo[3,4-b]pyridin-5-ylboronic acid to provide the title compound. MS (m/z) 452.8 [M+H]+.

Synthesis of (S)-1-(5-(1H-pyrazolo[3,4-b]pyridin-5-yl)pyrimidin-4-yl)-2-(3,5-difluorophenyl)ethanamine (176B)

The title compound as prepared according to the method presented in the synthesis of 136C in Example 136 utilizing (S)-tert-butyl 1-(5-(1H-pyrazolo[3,4-b]pyridin-5-yl)pyrimidin-4-yl)-2-(3,5-difluorophenyl)ethyl carbamate to provide the title compound.

Synthesis of N—((S)-1-(5-(1H-pyrazolo[3,4-b]pyridin-5-yl)pyrimidin-4-yl)-2-(3,5-difluorophenyl)ethyl)-2-(3-(difluoromethyl)-5,5-difluoro-3b,4,4a,5-tetrahydro-1H-cyclopropa[3,4]cyclopenta[1,2-c]pyrazol-1-yl)acetamide (176C)

The title compound as prepared (2 mg) according to the method presented in the synthesis of Example 54 utilizing 60G and 176B. $^1$H NMR (400 MHz, cd$_3$cn) δ 9.23 (s, 1H), 8.58 (d, 1H), 8.29 (s, 1H), 8.10 (d, 1H), 7.88 (d, 1H), 7.37 (d, 1H), 6.89 (d, —1H), 6.73 (dd, 2H), 6.62 (d, 1H), 6.33 (d, 2H), 5.33 (q, 1H), 4.87-4.65 (m, 3H), 2.99 (dd, 3H), 2.48 (s, 2H), 1.95 (dt), 1.39 (dd, 1H), 1.01 (s, 1H). MS (m/z) 599.0 [M+H]+.

Example 177

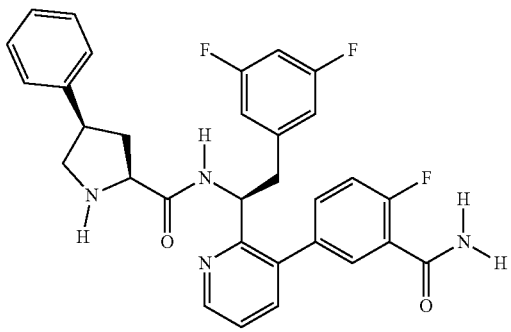

177

Synthesis of (2 S,4R)—N—((S)-1-(3-(3-carbamoyl-4-fluorophenyl)pyridin-2-yl)-2-(3,5-difluorophenyl)ethyl)-4-phenylpyrrolidine-2-carboxamide (177)

The title compound was prepared (11 mg) according to the method presented in the synthesis of Example 125 utilizing 148. MS (m/z) 545.2 [M+H]$^+$.

Example 178

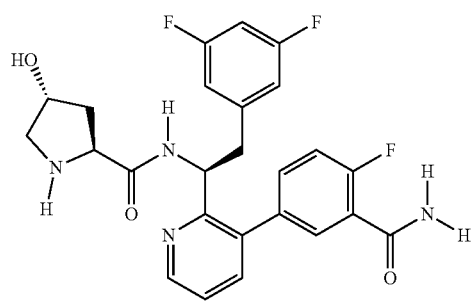

178

Synthesis of (2S,4R)—N—((S)-1-(3-(3-carbamoyl-4-fluorophenyl)pyridin-2-yl)-2-(3,5-difluorophenyl)ethyl)-4-hydroxypyrrolidine-2-carboxamide (178)

The title compound was prepared (10 mg) according to the method presented in the synthesis of Example 125 utilizing 132. MS (m/z) 485.4 [M+H]$^+$.

Example 179

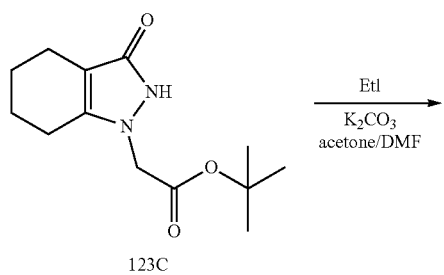

123C

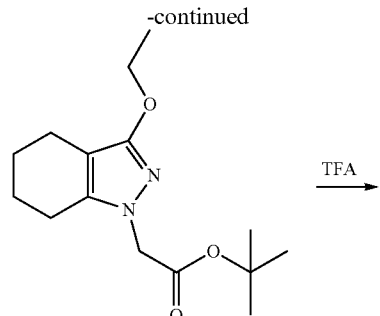

179A

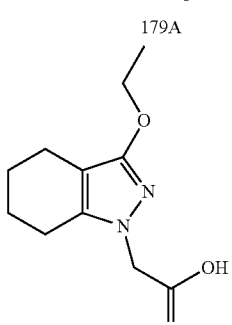

179B

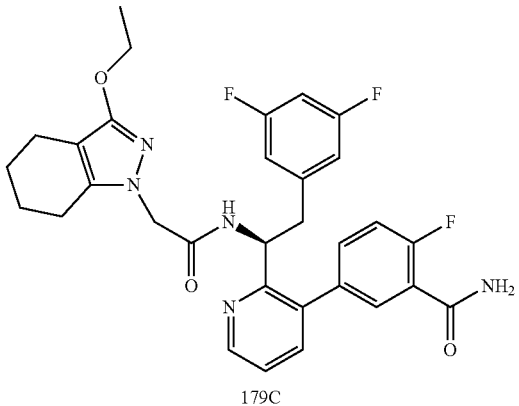

179C

Synthesis of tert-butyl 2-(3-ethoxy-4,5,6,7-tetrahydro-1H-indazol-1-yl)acetate (179A)

Under the conditions described for the synthesis of 170A in Example 170, the title compound was synthesized as the major regioisomer exhibiting a shorter retention time on HPLC: MS (m/z) 281.1 [M+H]$^+$.

Synthesis of 2-(3-ethoxy-4,5,6,7-tetrahydro-1H-indazol-1-yl)acetic acid (179B)

The title compound was prepared according to the method presented in the synthesis of 170B in Example 170: MS (m/z) 225.2 [M+H]$^+$.

Synthesis of (S)-5-(2-(2-(3,5-difluorophenyl)-1-(2-(3-ethoxy-4,5,6,7-tetrahydro-1H-indazol-1-yl)acetamido)ethyl)pyridin-3-yl)-2-fluorobenzamide (179C)

The title compound was prepared (70 mg) according to the method presented in the synthesis of Example 54 utilizing 54B and 2-(3-ethoxy-4,5,6,7-tetrahydro-1H-indazol- 1-yl)acetic acid. ¹H NMR (400 MHz, cd₃od) δ 8.66 (dd, 1H), 7.68 (dd, 1H), 7.56-7.43 (m, 2H), 7.34 (s, 1H), 7.25 (dd, 1H), 6.67 (t, 1H), 6.32 (d, 2H), 5.38 (t, 1H), 4.84 (s, 10H), 4.52 (s, 2H), 4.14 (q, 2H), 3.29 (dt, 9H), 2.99 (d, 2H), 2.34 (dt, 4H), 1.78-1.64 (m, 4H), 1.33 (t, 3H). MS (m/z) 578.7 [M+H]⁺.

Example 180

Example 181

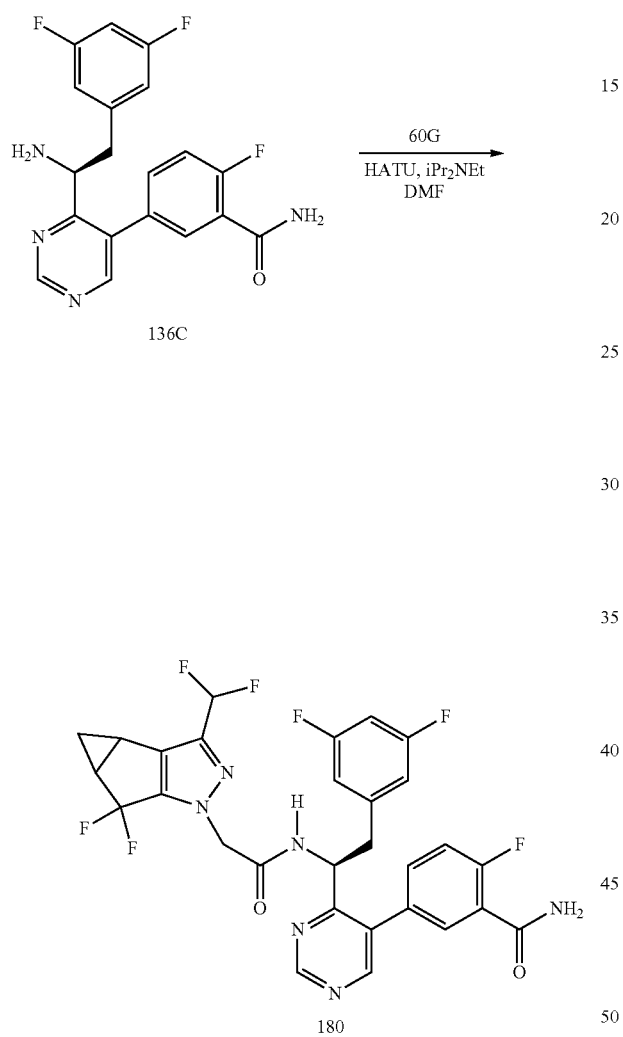

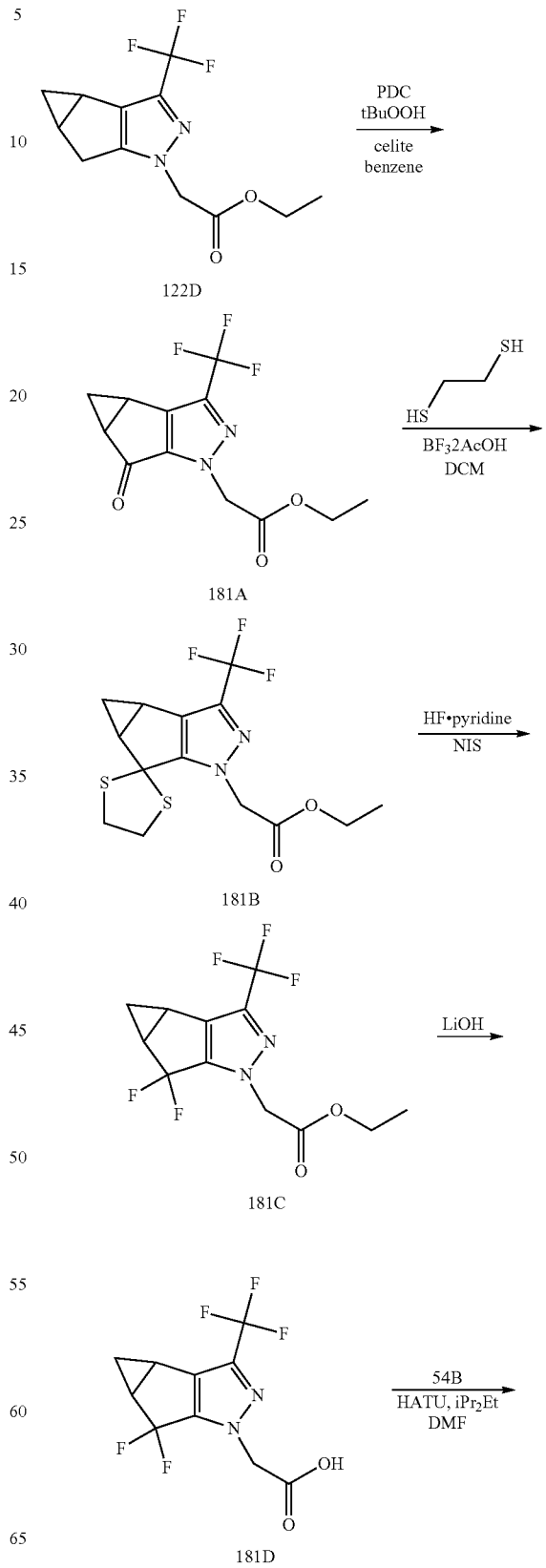

Synthesis of 5-(4-((1S)-1-(2-(3-(difluoromethyl)-5,5-difluoro-3b,4,4a,5-tetrahydro-1H-cyclopropa[3,4]cyclopenta[1,2-c]pyrazol-1-yl)acetamido)-2-(3,5-difluorophenyl)ethyl)pyrimidin-5-yl)-2-fluorobenzamide (180)

The title compound as prepared (51 mg) according to the method presented in the synthesis of Example 54 utilizing 60G and 136C. ¹H NMR (400 MHz, dmso) δ 9.25 (s, 1H), 9.11 (s, 1H), 8.62 (s, 1H), 7.66 (s, 2H), 7.52 (s, 1H), 7.36 (d, 1H), 6.92 (s, 2H), 6.59 (s, 2H), 5.11 (s, 1H), 4.70 (d, 3H), 3.37 (bs), 3.00 (d, 3H), 2.51-2.42 (m), 1.33 (s, 1H), 0.87 (s, 1H). MS (m/z) 619.3 [M+H]⁺.

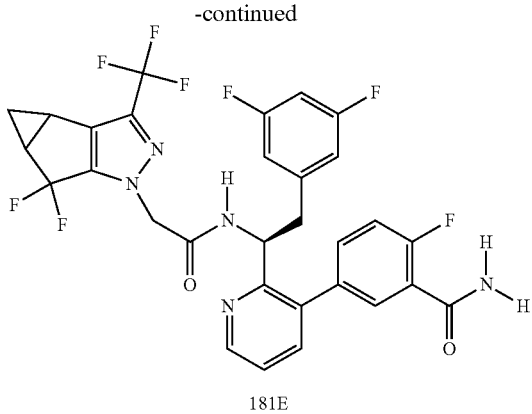

181E

Synthesis of ethyl 2-(5-oxo-3-(trifluoromethyl)-3b,4,4a,5-tetrahydro-1H-cyclopropa[3,4]cyclopenta[1,2-c]pyrazol-1-yl)acetate (181A)

Ethyl 2-(3-(trifluoromethyl)-3b,4,4a,5-tetrahydro-1H-cyclopropa[3,4]cyclopenta[1,2-c]pyrazol-1-yl)acetate (1.92 g, 7 mmol) and celite 545 (1 g/mmol) was combined in benzene (50 mL) and cooled to 5° C. (just above freezing). PDC (10.5 g, 28 mmol) was added followed by tert-butylhydroperoxide (5-6 M solution in decane, 5.1 mL, 28 mmol). The solution was let warm to ambient temperature, then stirred for 3 days. The reaction is filtered over celite, eluted with EtOAc, and the solvents removed in vacuo. Crude residue is resubjected to the same reaction conditions and let stir for 1 day. The reaction is again filtered over celite, eluted with EtOAc, and the solvents removed in vacuo to provide the title compound (1.1 g) as a mixture with 122D (ratio determined by 19F NMR): MS (m/z) 289.0 [M+H]$^+$.

Synthesis of ethyl 2-(3-(trifluoromethyl)-4,4a-dihydrospiro[cyclopropa[3,4]cyclopenta[1,2-c]pyrazole-5,2'-[1,3]dithiolane]-1 (3bH)-yl)acetate (181B)

Ethyl 2-(5-oxo-3-(trifluoromethyl)-3b,4,4a,5-tetrahydro-1H-cyclopropa[3,4]cyclopenta[1,2-c]pyrazol-1-yl)acetate (1.1 g, 3.8 mmol) and ethanediol (0.54 mL, 6.4 mmol) were combined in DCM (12 mL) to which BF$_3$ acetic acid complex (0.88 mL, 6.4 mmol) was added. The reaction was stirred at ambient temperature for 3 h. LCMS shows complete conversion of keto-starting material to product. The reaction was cooled to 0° C. and quenched with saturated aqueous NaHCO$_3$. The organics were separated and dried with saturated aqueous NaCl. Solvents were removed in vacuo and the residue purified by column chromatography on silica to provide 900 mg of the title compound product as a mixture with compound 122D. MS (m/z) 365.1 [M+H]$^+$.

Synthesis of ethyl 2-(5,5-difluoro-3-(trifluoromethyl)-3b,4,4a,5-tetrahydro-1H-cyclopropa[3,4]cyclopenta[1,2-c]pyrazol-1-yl)acetate (181C)

In a teflon bottle, NIS (1.34 g, 5.93 mmol) was suspended in DCM (1.5 mL) and cooled to −78° C. HF pyridine (4 mL) added. Ethyl 2-(3-(trifluoromethyl)-4,4a-dihydrospiro[cyclopropa[3,4]cyclopenta[1,2-c]pyrazole-5,2'-[1,3]dithiolane]-1 (3bH)-yl)acetate was dissolved in DCM (2.5 mL) and added dropwise. The reaction was stirred 30 min at −78° C. then let slowly warm to −30° C. The reaction was held at −30 OC for 3 h. To a 1 L beaker charged with saturated aqueous NaHCO$_3$ (100 mL), ice was added to increase volume to 250 ml and stirred vigorously. The reaction was poured into the basic quench solution. The solution was extracted with EtOAc (3×), organics separated and dried with saturated aqueous NaCl. Solvents were removed in vacuo and the residue purified by column chromatography on silica to provide the title compound (320 mg): MS (m/z) 311.0 [M+H]$^+$.

Synthesis of 2-(5,5-difluoro-3-(trifluoromethyl)-3b,4,4a,5-tetrahydro-1H-cyclopropa[3,4]cyclopenta[1,2-c]pyrazol-1-yl)acetic acid (181D)

The title compound was prepared according to the method presented in the synthesis of 122F in Example 122 utilizing 181C. MS (m/z) 283.0 [M+H]$^+$.

Synthesis of 5-(2-(((1S)-1-(2-(5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)pyridin-3-yl)-2-fluorobenzamide (181E)

The title compound (10 mg) was prepared according to the method presented in the synthesis of Example 54 utilizing 54B and 181D. $^1$H NMR (400 MHz, dmso) δ 8.97 (s, 1H), 8.67 (d, 1H), 7.75-7.57 (m, 3H), 7.41 (dd, 2H), 7.35-7.24 (m, 1H), 6.88 (s, 1H), 6.53 (s, 2H), 5.14 (s, 1H), 4.77 (dt, 4H), 3.88 (bs), 2.98 (d, 2H), 2.51-2.42 (m), 1.36 (s, 1H), 0.96 (s, 1H). MS (m/z) 636.1 [M+H]$^+$.

Example 182

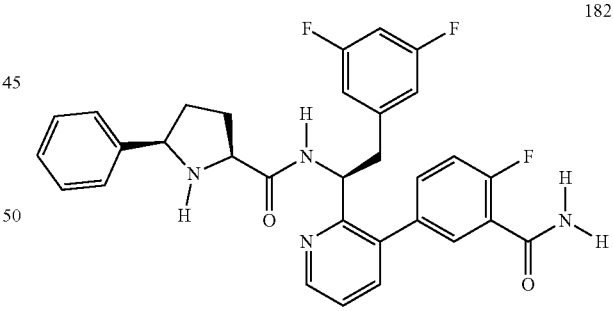

182

Synthesis of (2S,5R)—N—((S)-1-(3-(3-carbamoyl-4-fluorophenyl)pyridin-2-yl)-2-(3,5-difluorophenyl)ethyl)-5-phenylpyrrolidine-2-carboxamide (182)

The title compound was prepared (3 mg) according to the method presented in the synthesis of Example 125 utilizing 139. MS (m/z) 545.3 [M+H]$^+$.

415

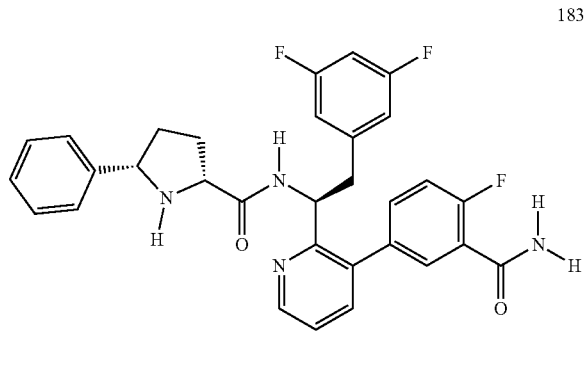

Example 183

Synthesis of (2R,5S)—N—((S)-1-(3-(3-carbamoyl-4-fluorophenyl)pyridin-2-yl)-2-(3,5-difluorophenyl)ethyl)-5-phenylpyrrolidine-2-carboxamide (183)

The title compound was prepared (3 mg) according to the method presented in the synthesis of Example 125 utilizing 158. MS (m/z) 545.3 [M+H]+.

Example 184

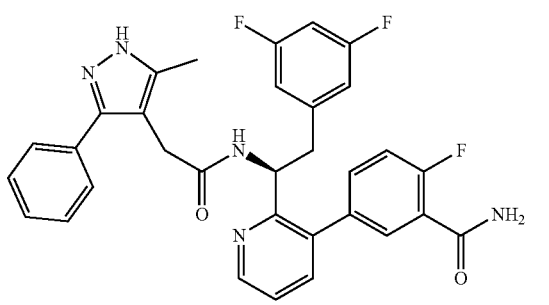

Synthesis of (S)-5-(2-(2-(3,5-difluorophenyl)-1-(2-(5-methyl-3-phenyl-1H-pyrazol-4-yl)acetamido)ethyl)pyridin-3-yl)-2-fluorobenzamide (184)

The title compound was prepared (9 mg) according to the method presented in the synthesis of Example 54 utilizing 54B and 2-(5-methyl-3-phenyl-1H-pyrazol-4-yl)acetic acid. $^1$H NMR (400 MHz, dmso) δ 8.66 (d, 1H), 8.51 (d, 1H), 7.62 (dd, 2H), 7.54-7.36 (m, 4H), 7.36-7.02 (m, 3H), 6.92 (t, 1H), 6.53 (d, 2H), 5.17 (d, 1H), 3.26 (s, 2H), 2.95 (d, 2H), 2.52-2.42 (m, 13H), 1.99 (s, 2H), 1.87 (s, 1H). MS (m/z) 570.8 [M+H]+.

416

Example 185

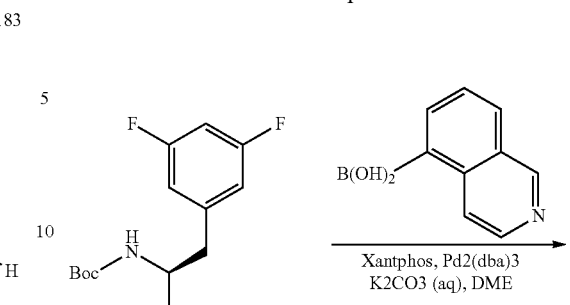

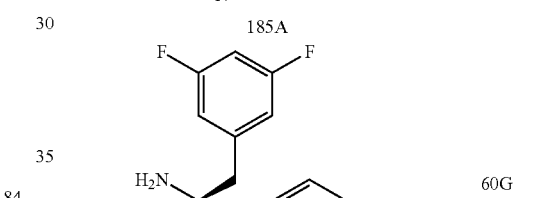

Synthesis of (S)-tert-butyl 2-(3,5-difluorophenyl)-1-(5-(isoquinolin-5-yl)pyrimidin-4-yl)ethylcarbamate (185A)

The title compound as prepared according to the method presented in the synthesis of 136B in Example 136 utilizing 172A and isoquinolin-6-ylboronic acid to provide the title compound. MS (m/z) 463.3 [M+H]+.

Synthesis of (S)-2-(3,5-difluorophenyl)-1-(5-(isoquinolin-5-yl)pyrimidin-4-yl)ethanamine (185B)

The title compound as prepared according to the method presented in the synthesis of 136C in Example 136 utilizing (S)-tert-butyl 2-(3,5-difluorophenyl)-1-(5-(isoquinolin-5-yl)pyrimidin-4-yl)ethylcarbamate to provide the title compound.

Synthesis of 2-(3-(difluoromethyl)-5,5-difluoro-3b,4,4a,5-tetrahydro-1H-cyclopropa[3,4]cyclopenta[1,2-c]pyrazol-1-yl)-N—((S)-2-(3,5-difluorophenyl)-1-(5-(isoquinolin-5-yl)pyrimidin-4-yl)ethyl)acetamide (185C)

The title compound as prepared (4 mg) according to the method presented in the synthesis of Example 54 utilizing 60G and 185B. The title compound exists as a mixture of rotational isomers which was confirmed by a high temperature NMR experiment. ¹H NMR (400 MHz, dmso) δ 9.62 (s, 1H), 9.56 (s, 1H), 9.44-9.38 (m, 1H), 9.05 (d, 1H), 8.88 (t, 1H), 8.75-8.67 (m, 2H), 8.46-8.29 (m, 3H), 8.01-7.60 (m, 3H), 7.58 (d, 1H), 7.36 (s, 1H), 7.10-6.92 (m, 3H), 6.92-6.68 (m, 2H), 6.44 (s, 2H), 6.21 (d, 2H), 4.90 (d, 2H), 4.78-4.45 (m, 8H), 2.97 (t, 3H), 2.91-2.82 (m, 1H), 2.50-2.41 (m), 1.34 (d, 2H), 0.88 (s, 1H), 0.81 (s, 1H). MS (m/z) 609.4 [M+H]+.

Examples 186 and 187

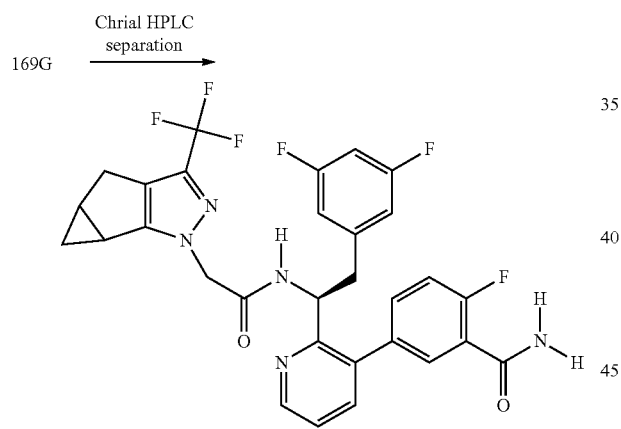

186

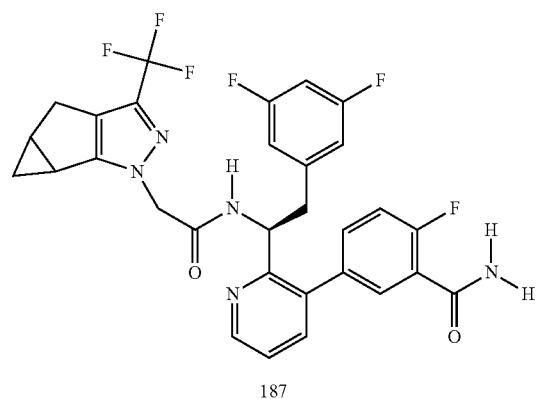 [SMILES: NC(=O)c1cc(-c2cccnc2[C@H](Cc2cc(F)cc(F)c2)NC(=O)Cn2nc(C(F)(F)F)c3c2C(F)(F)C2CC32)ccc1F]

187

Synthesis of 5-(2-(((S)-2-(3,5-difluorophenyl)-1-(2-((4aS,5aS)-3-(trifluoromethyl)-4,4a,5,5a-tetrahydro-1H-cyclopropa[4,5]cyclopenta[1,2-c]pyrazol-1-yl)acetamido)ethyl)pyridin-3-yl)-2-fluorobenzamide and 5-(2-(((S)-2-(3,5-difluorophenyl)-1-(2-((4aR,5aR)-3-(trifluoromethyl)-4,4a,5,5a-tetrahydro-1H-cyclopropa[4,5]cyclopenta[1,2-c]pyrazol-1-yl)acetamido)ethyl)pyridin-3-yl)-2-fluorobenzamide (186 and 187)

The title compounds were separated from the diastereomeric mixture 169G by semi-preparative chiral HPLC fitted with a Chiralpak IC column running a 70:30 mixture of Hep:IPA to obtain the desired compounds as pure diastereomers: 186 (4 mg): HPLC rt=12.4 min; MS (m/z) 600.4 [M+H]+. 187 (3 mg): HPLC rt=14.0 min; MS (m/z) 600.4 [M+H]+. Absolute stereochemistry is unknown.

Example 188

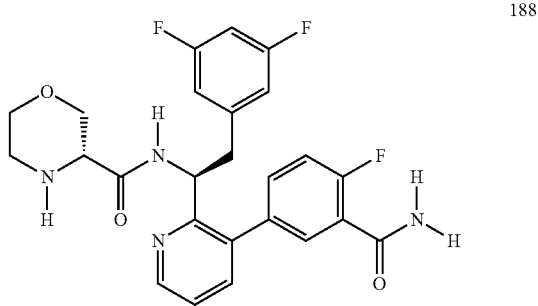 [SMILES: NC(=O)c1cc(-c2cccnc2[C@H](Cc2cc(F)cc(F)c2)NC(=O)[C@H]2COCCN2)ccc1F]

188

Synthesis of (R)—N—((S)-1-(3-(3-carbamoyl-4-fluorophenyl)pyridin-2-yl)-2-(3,5-difluorophenyl)ethyl)morpholine-3-carboxamide (188)

The title compound was prepared (6 mg) according to the method presented in the synthesis of Example 125 utilizing 133.

Example 189

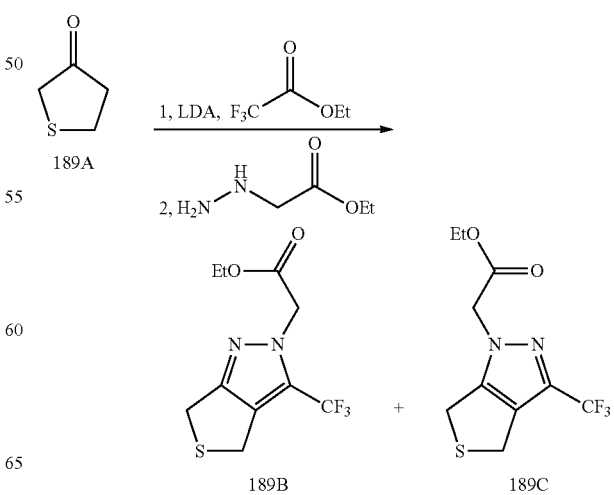

-continued

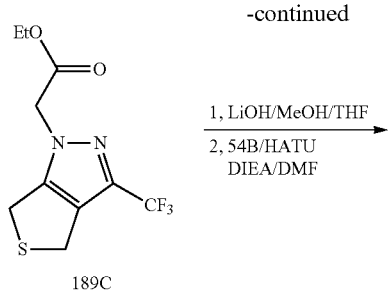
189C

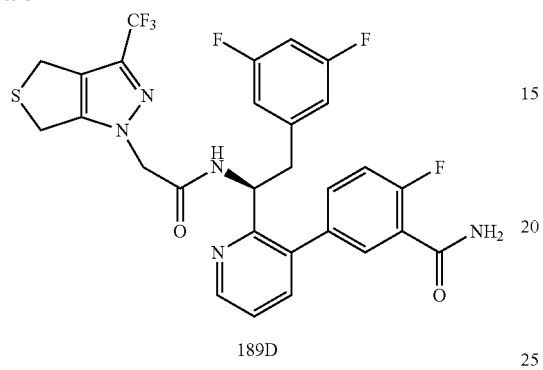
189D

Synthesis of ethyl 2-(3-(trifluoromethyl)-4,6-dihydro-2H-thieno[3,4-c]pyrazol-2-yl)acetate (189B) and 300 mg of ethyl 2-(3-(trifluoromethyl)-4,6-dihydro-1H-thieno[3,4-c]pyrazol-1-yl)acetate (189C)

Compound 189B and 189C were prepared according to the method presented for the synthesis of Example 122 substituting dihydrothiophen-3(2H)-one for 122B to provide 80 mg of 189B and 300 mg of 189C. 189B: MS (m/z) 281 [M+H]+ and 189C: MS (m/z) 281 [M+H]+.

Synthesis of (S)-5-(2-(2-(3,5-difluorophenyl)-1-(2-(3-(trifluoromethyl)-4,6-dihydro-1H-thieno[3,4-c]pyrazol-1-yl)acetamido)ethyl)pyridin-3-yl)-2-fluorobenzamide (189D)

Compound 189D was prepared according to the method presented for the synthesis of Example 122 substituting 189C for 122D to provide 18 mg of title compound: ¹H NMR (400 MHz, cd₃od) δ 8.76-8.68 (m, 1H), 7.72-7.63 (m, 1H), 7.52-7.42 (m, 1H), 7.42-7.25 (m, 2H), 7.25-7.17 (m, 1H), 6.67 (t, 1H), 6.32 (d, 2H), 5.35 (t, 1H), 4.91 (s, 2H), 3.94 (d, 4H), 3.05 (d, 2H). MS (m/z) 606 [M+H]+.

Example 190

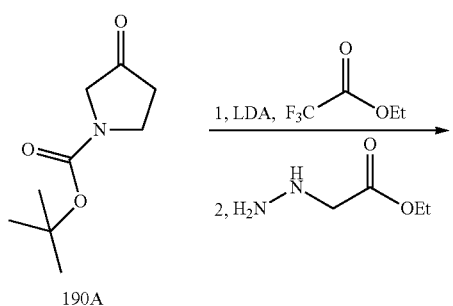
190A

-continued

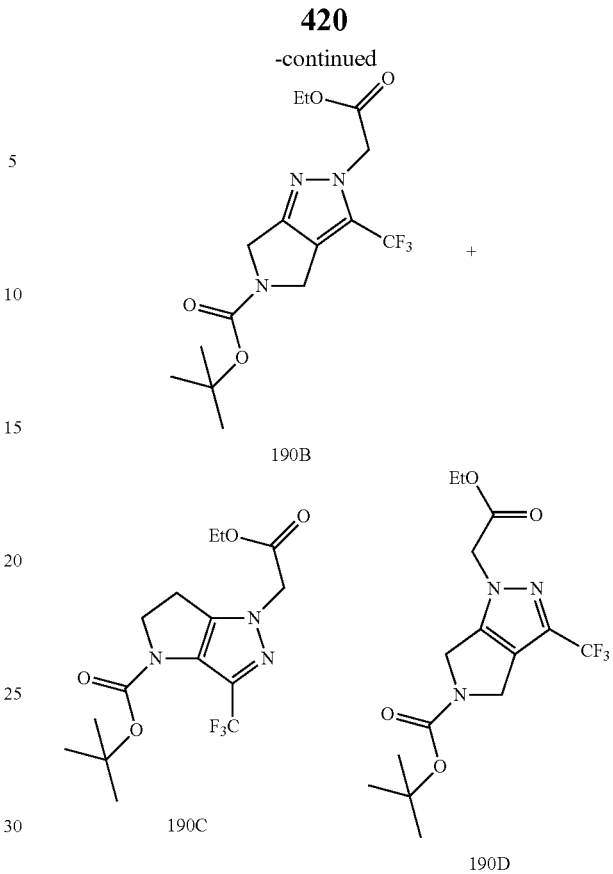

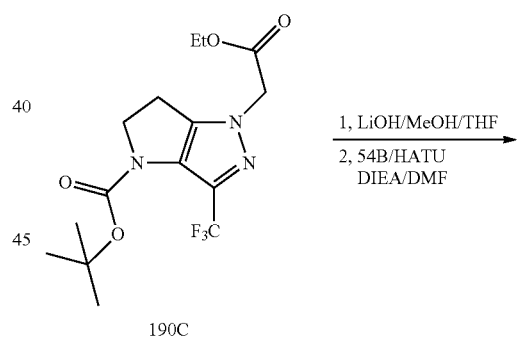
190C

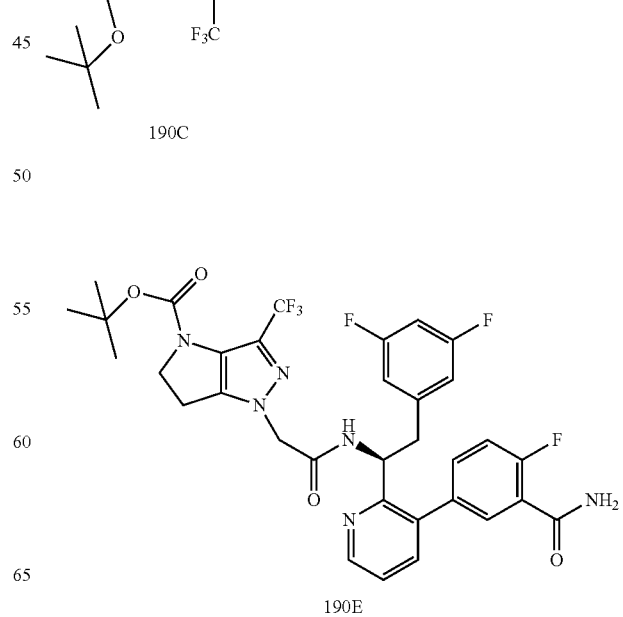
190E

421

Synthesis of tert-butyl 2-(2-ethoxy-2-oxoethyl)-3-(trifluoromethyl)-4,6-dihydropyrrolo[3,4-c]pyrazole-5(2H)-carboxylate (190B), tert-butyl 1-(2-ethoxy-2-oxoethyl)-3-(trifluoromethyl)-5,6-dihydropyrrolo[3,2-c]pyrazole-4(1H)-carboxylate (190C) and tert-butyl 1-(2-ethoxy-2-oxoethyl)-3-(trifluoromethyl)-4,6-dihydropyrrolo[3,4-c]pyrazole-5(1H)-carboxylate (190D)

Compound 190B, 190C and 190D were prepared according to the method presented for the synthesis of Example 122 substituting tert-butyl 3-oxopyrrolidine-1-carboxylate for 122B to provide 60 mg of 190B, 35 mg of 190C and 60 mg of 190D. 190B: MS (m/z) 364 [M+H]$^+$, 190C: MS (m/z) 364 [M+H]$^+$ and 190D: MS (m/z) 364 [M+H]$^+$.

Synthesis of (S)-tert-butyl 1-(2-((1-(3-(3-carbamoyl-4-fluorophenyl)pyridin-2-yl)-2-(3,5-difluorophenyl)ethyl)amino)-2-oxoethyl)-3-(trifluoromethyl)-5,6-dihydropyrrolo[3,2-c]pyrazole-4(1H)-carboxylate (190E)

Compound 190E was prepared according to the method presented for the synthesis of Example 122 substituting 190C for 122D to provide 46 mg of title compound: $^1$H NMR (400 MHz, cd$_3$od) δ 8.70 (d, 1H), 7.61 (d, 1H), 7.42 (d, 2H), 7.31 (s, 1H), 7.27-7.16 (m, 1H), 6.66 (t, 1H), 6.32 (d, 2H), 5.34 (t, 1H), 4.96 (s, 2H), 4.46 (dd, 4H), 3.06 (dd, 3H), 1.50 (s, 9H). MS (m/z) 689 [M+H]$^+$.

Example 191

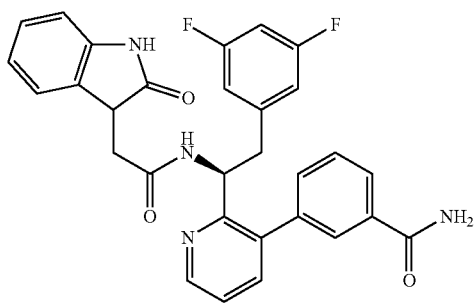

Synthesis of 3-(2-(((1S)-2-(3,5-difluorophenyl)-1-(2-(2-oxoindolin-3-yl)acetamido)ethyl)pyridin-3-yl)benzamide (191)

Compound 191 was prepared according to the method presented for the synthesis of Example 50 utilizing 50C and 2-(2-oxoindolin-3-yl)acetic acid to provide 44 mg of title compound: $^1$H NMR (400 MHz, dmso) δ 9.83 (d, 1H), 9.03-8.72 (m, 1H), 8.64 (d, 1H), 8.01-7.70 (m, 2H), 7.67-7.45 (m, 2H), 7.44-7.25 (m, 2H), 7.02 (dt, 1H), 6.86 (t, 1H), 6.71 (ddd, 2H), 6.47 (d, 2H), 5.19-4.96 (m, 1H), 3.82 (dt, 1H), 2.93 (dd, 2H), 2.40-2.16 (m, 2H); MS (m/z) 527 [M+H]$^+$.

Example 192

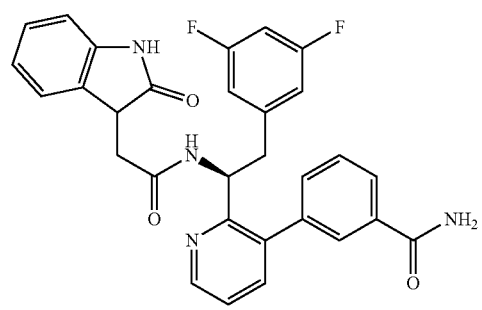

Synthesis of 3-(2-((1S)-2-(3,5-difluorophenyl)-1-(2-(2-oxoindolin-3-yl)acetamido)ethyl)pyridin-3-yl)benzamide (192)

Compound 192 was purified from compound 191 by RP HPLC using a C18 column with a gradient of H$_2$O, 0.1% TFA-acetonitrile. The fast eluent was collected and concentrated to provide 18 mg of title compound: $^1$H NMR (400 MHz, dmso) δ 9.89 (s, 1H), 8.82 (d, 1H), 8.69-8.61 (m, 1H), 8.02-7.81 (m, 2H), 7.70-7.56 (m, 2H), 7.48-7.27 (m, 4H), 7.06 (t, 2H), 6.92 (t, 1H), 6.85-6.70 (m, 2H), 6.51 (d, 2H), 5.14 (d, 1H), 3.88 (t, 2H), 2.99 (d, 2H), 2.44-2.20 (m, 2H). MS (m/z) 527 [M+H]$^+$.

Example 193

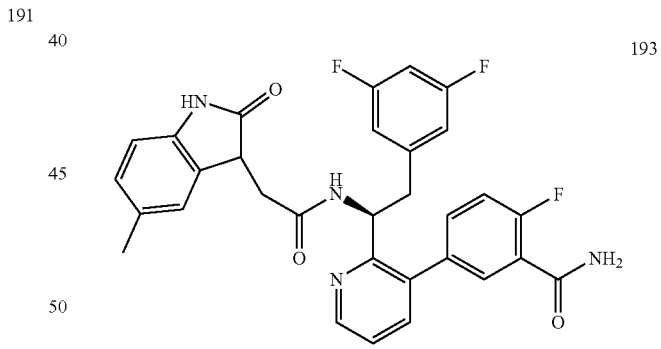

Synthesis of 5-(2-((1S)-2-(3,5)-difluorophenyl)-1-(5-methyl-2-oxoindolin-3-yl)acetamido)ethyl)pyridin-3-yl)-2-fluorobenzamide (193)

Compound 193 was prepared according to the method presented for the synthesis of Example 54 utilizing 54B and 2-(5-methyl-2-oxoindolin-3-yl)acetic acid to provide 18 mg of title compound: $^1$H NMR (400 MHz, cd$_3$od) δ 8.71 (s, 1H), 7.69 (dd, 1H), 7.49 (ddd, 1H), 7.45-7.07 (m, 3H), 7.07-6.57 (m, 511), 6.27 (t, 2H), 5.34 (dd, 1H), 3.71 (t, 1H), 3.04-2.85 (m, 3H), 2.75-2.62 (m, 1H). MS (m/z) 559 [M+H]$^+$.

Example 194

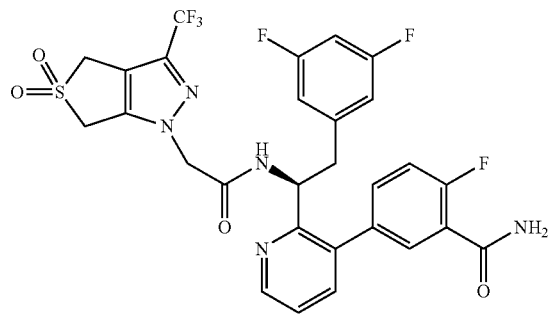

Synthesis of (S)-5-(2-(2-(3,5-difluorophenyl)-1-(2-(5,5-dioxido-3-(trifluoromethyl)-4,6-dihydro-1H-thieno[3,4-c]pyrazol-1-yl)acetamido)ethyl)pyridin-3-yl)-2-fluorobenzamide (194)

Compound 194 was prepared according to the method presented for the synthesis of Example 197 utilizing 189 (60 mg, 0.1 mmol), 3-Chloroperbenzoic acid (87 mg, 77% max., 0.2 mmol) in DCM (3 mL) at 0° C. to provide 20 mg of title compound: $^1$H NMR (400 MHz, cd$_3$od) δ 8.61 (dd, 1H), 7.93-7.80 (m, 1H), 7.61 (s, 1H), 7.58-7.44 (m, 2H), 7.44-7.30 (m, 2H), 7.19 (ddd, 3H), 6.56 (tt, 1H), 6.23 (dd, 2H), 5.38 (s, 1H), 5.25 (dd, 1H), 4.91 (d, 2H), 4.75 (s, 5H), 4.45-4.18 (m, 4H), 4.00 (dd, 1H), 3.21 (dt, 3H), 3.09-2.86 (m, 2H), 2.22-2.03 (m, 1H), 1.91 (s, 1H), 1.17 (dd, 2H), 1.13-0.97 (m, 1H), 0.80 (dd, 1H). MS (m/z) 638 [M+H]$^+$

Example 195

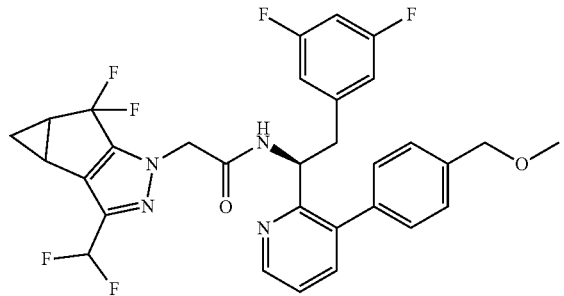

Synthesis of 2-(3-(difluoromethyl)-5,5-difluoro-3b,4,4a,5-tetrahydro-1H-cyclopropa[3,4]cyclopenta[1,2-c]pyrazol-1-yl)-N—((S)-2-(3,5-difluorophenyl)-1-(3-(4-(methoxymethyl)phenyl)pyridin-2-yl)ethyl)acetamide (195)

Compound 195 was prepared according to the method presented for the synthesis of Example 68 utilizing 68A and (4-(methoxymethyl)phenyl)boronic acid to provide 13 mg of title compound: $^1$H NMR (400 MHz, cd$_3$od) δ 8.65 (d, 1H), 7.63 (dd, 8.0 Hz, 2H), 7.45 (dd, 2H), 7.35 (dd, 3H), 7.14-7.01 (m, 2H), 6.68 (ddd, 3H), 6.24 (d, 2H), 5.44 (dd, 1H), 4.48 (d, 2H), 3.38 (s, 3H), 2.97 (dd, 2H), 2.56-2.34 (m, 2H), 1.37 (s, 1H), 1.04 (d, 1H). MS (m/z) 601 [M+H]$^+$.

Example 196

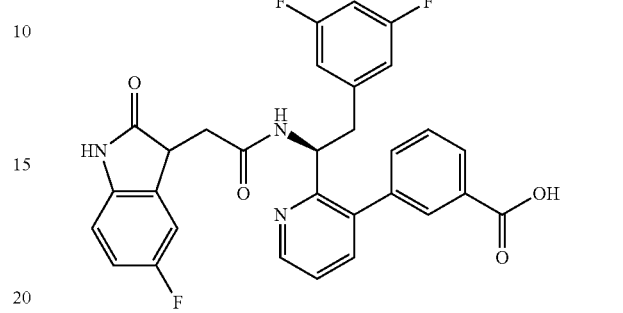

Synthesis of 3-(2-(((1S)-2-(3,5-difluorophenyl)-1-(2-(5-fluoro-2-oxoindolin-3-yl)acetamido)ethyl)pyridin-3-yl)benzamide (196)

Compound 196 was prepared according to the method presented for the synthesis of Example 50 utilizing 50C and 2-(5-fluoro-2-oxoindolin-3-yl)acetic acid to provide 27 mg of title compound: $^1$H NMR (400 MHz, dmso) δ 9.89 (d, 1H), 8.89 (dd, 1H), 8.66 (dd, 1H), 8.07-7.72 (m, 2H), 7.72-7.50 (m, 2H), 7.50-7.23 (m, 3H), 7.13-6.59 (m, 4H), 6.47 (d, 2H), 5.22-5.02 (m, 1H), 3.92-3.79 (m, 1H), 2.95 (dd, 2H), 2.34 (ddd, 1H). MS (m/z) 545 [M+H]$^+$.

Example 197

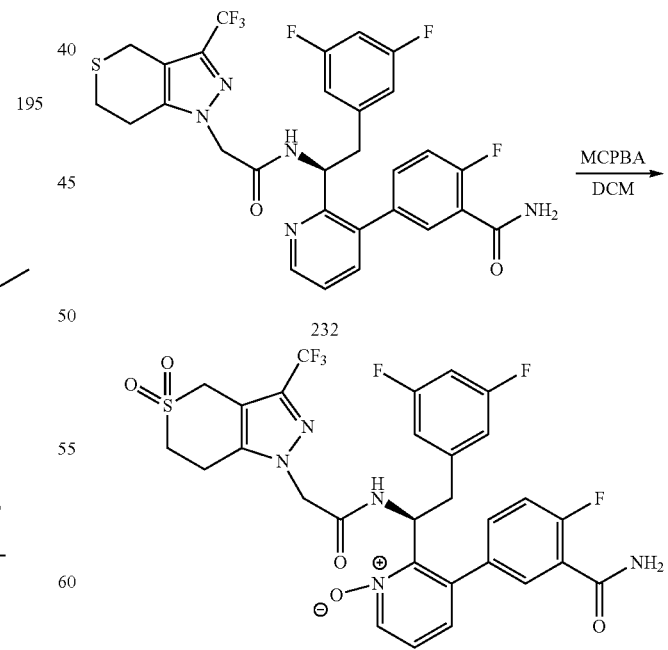

+

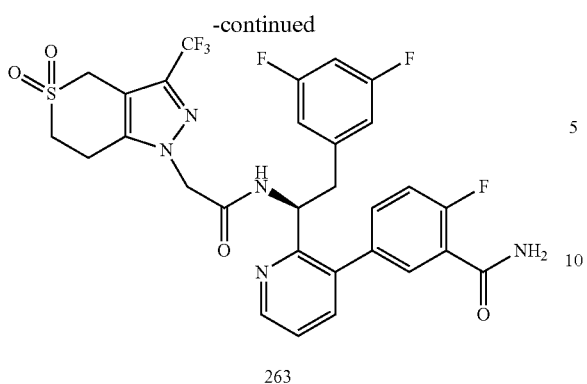

263

Synthesis of (S)-3-(3-carbamoyl-4-fluorophenyl)-2-(2-(3,5-difluorophenyl)-1-(2-(5,5-dioxido-3-(trifluoromethyl)-6,7-dihydrothiopyrano[4,3-c]pyrazol-1(4H)-yl)acetamido)ethyl)pyridine-1-oxide (197) and (S)-5-(2-(2-(3,5-difluorophenyl)-1-(2-(5,5-dioxido-3-(trifluoromethyl)-6,7-dihydrothiopyrano[4,3-c]pyrazol-1(4H)-yl)acetamido)ethyl)pyridin-3-yl)-2-fluorobenzamide (263)

232 (120 mg, 0.194 mmol) and 3-Chloroperbenzoic acid (87 mg, 77% max., 0.2 mmol) in DCM (5 mL) at 0° C., was stirred for 2 hours. Solvents were concentrated in vacuo and the residue was purified by RP HPLC using a C18 column with a gradient of $H_2O$, 0.1% TFA-acetonitrile, to provide 25 mg of 197 and 27 mg of 263: 1H NMR (400 MHz, cd3od) δ 8.94 (d, 1H), 8.33 (d, 1H), 7.92-7.79 (m, 1H), 7.51-7.30 (m, 3H), 7.19-7.09 (m, 1H), 6.65 (t, 1H), 6.34 (d, 2H), 5.46-5.29 (m, 1H), 4.85 (d, 2H), 4.19 (s, 2H), 3.18-2.94 (m, 4H), 0.02-3.24 (m, 6H), 3.57-3.44 (m, 1H), 3.31 (d, 2H); MS (m/z) 668 [M+H]$^+$.

Example 198

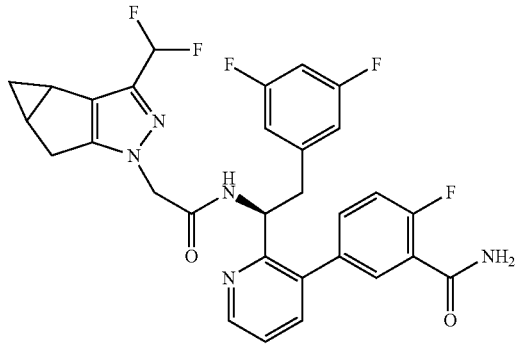

198

Synthesis of 5-(2-((1S)-1-(2-(3-(difluoromethyl)-3b,4,4a,5-tetrahydro-1H-cyclopropa[3,4]cyclopenta[1,2-c]pyrazol-1-yl)acetamido)-2-(3,5-difluorophenyl)ethyl)pyridin-3-yl)-2-fluorobenzamide (198)

Compound 198 was prepared according to the method presented for the synthesis of Example 122 substituting ethyl 2,2-difluoroacetate for ethyl 2,2,2-trifluoroacetate to provide 48 mg of title compound: $^1$H NMR (400 MHz, cd$_3$od) δ 8.48 (d, 1H), 7.45 (d, 1H), 7.33-7.17 (m, 2H), 7.12 (s, 1H), 7.08-6.95 (m, 1H), 6.57-6.22 (m, 2H), 6.12 (d, 2H), 5.14 (t, 1H), 4.57-4.38 (m, 2H), 2.93-2.77 (m, 2H), 2.58 (dd, 1H), 2.44 (dd, 1H), 1.89 (d, 2H), 0.86 (d, 1H), 0.01 (dd, 1H). MS (m/z) 582 [M+H]$^+$.

Example 199

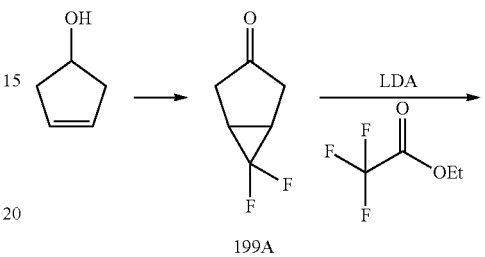

199A

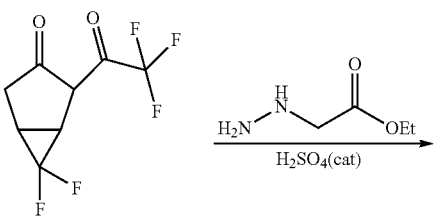

199B 199C 199D

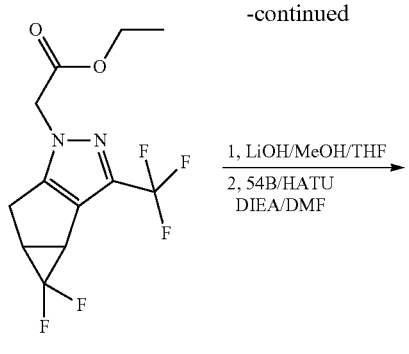

199C

1, LiOH/MeOH/THF
2, 54B/HATU
DIEA/DMF
→

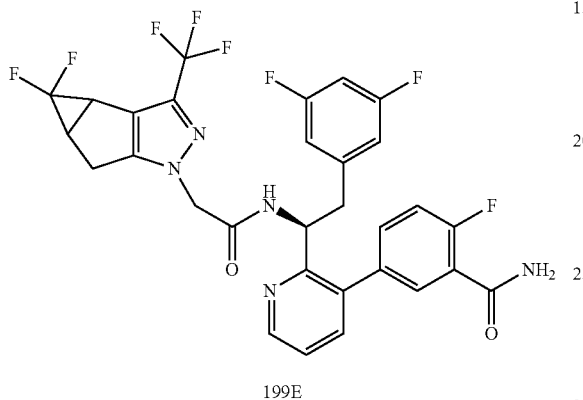

199E

Synthesis of 6,6-difluorobicyclo[3.1.0]hexan-3-one (199A)

Compound 199A was prepared according to the method presented in the page 153 of WO 2011/059887 to provide 2.77 g of crude title compound. MS (m/z) 133 [M+H]$^+$.

Synthesis of ethyl 2-(4,4-difluoro-3-(trifluoromethyl)-3b,4,4a,5-tetrahydro-1H-cyclopropa[3,4]cyclopenta[1,2-c]pyrazol-1-yl)acetate (199C) and ethyl 2-(5-fluoro-3-(trifluoromethyl)-1H-indazol-1-yl)acetate (199D)

Compound 199C and 199D were prepared according to the method presented for the synthesis of Example 122 substituting 199A for 122B to provide 0.4 g of 199C and 2 g of 199D. 199C: MS (m/z) 311 [M+H]$^+$ and 199D: MS (m/z) 291 [M+H]$^+$.

Synthesis of 5-(2-((1S)-1-(2-(4,4-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)pyridin-3-yl)-2-fluorobenzamide (199E)

Compound 199E was prepared according to the method presented for the synthesis of Example 122 substituting 199C for 122D to provide 23 mg of title compound: $^1$H NMR (400 MHz, cd$_3$od) δ 8.70 (d, 1H), 7.65 (dd, 1H), 7.45 (dt, 2H), 7.30 (s, 1H), 7.27-7.15 (m, 1H), 6.66 (dd, 1H), 6.32 (t, 2H), 5.34 (t, 1H), 4.82-4.70 (m, 2H), 3.15-2.93 (m, 5H), 2.85 (dd, 1H). MS (m/z) 636 [M+H]$^+$.

Example 200

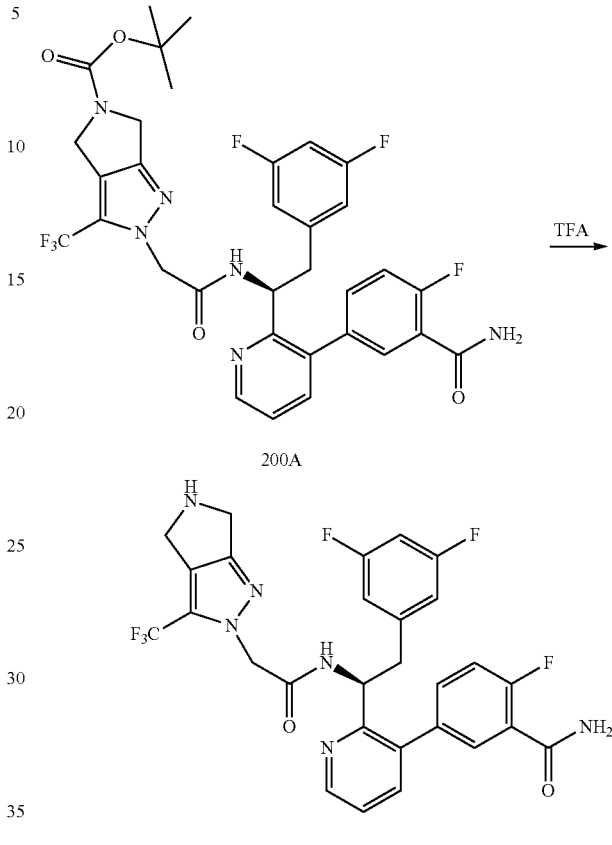

Synthesis of (S)-tert-butyl 2-(2-((1-(3-(3-carbamoyl-4-fluorophenyl)pyridin-2-yl)-2-(3,5-difluorophenyl)ethyl)amino)-2-oxoethyl)-3-(trifluoromethyl)-4,6-dihydropyrrolo[3,4-c]pyrazole-5(2H)-carboxylate (200A)

Compound 200A was prepared according to the method presented for the synthesis of Example 122 substituting 60 mg 190B for 122D to provide 35 mg of title compound: MS (m/z) 689 [M+H]$^+$.

Synthesis of (S)-5-(2-(2-(3,5-difluorophenyl)-1-(2-(3-(trifluoromethyl)-5,6-dihydropyrrolo[3,4-c]pyrazol-2(4H)-yl)acetamido)ethyl)pyridin-3-yl)-2-fluorobenzamide (200B)

200A (35 mg, 0.05 mmol) and trifluoroacetic acid (1 mL) was stirred for 1 hours. Solvents were concentrated in vacuo and the residue was purified by RP HPLC using a C18 column with a gradient of H$_2$O, 0.1% TFA-acetonitrile, to provide 5 mg of title product: $^1$H NMR (400 MHz, cd$_3$od) δ 8.76-8.65 (m, 1H), 7.59 (dd, 1H), 7.49-7.35 (m, 2H), 7.29 (s, 1H), 7.20 (dd, 1H), 6.67 (t, 1H), 6.35 (d, 2H), 5.34 (t, 1H), 5.00 (s, 2H), 4.51 (s, 2H), 4.43 (s, 2H), 3.06 (ddd, 2H); MS (m/z) 589 [M+H]$^+$

Example 201

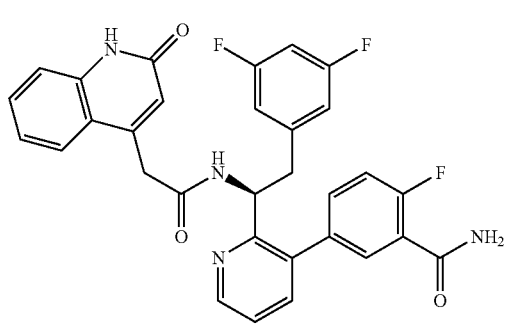

Synthesis of (S)-5-(2-(2-(3,5-difluorophenyl)-1-(2-(2-oxo-1,2-dihydroquinolin-4-yl)acetamido)ethyl)pyridin-3-yl)-2-fluorobenzamide (201)

Compound 201 was prepared according to the method presented for the synthesis of Example 54 utilizing 54B and 2-(2-oxo-1,2-dihydroquinolin-4-yl)acetic acid to provide 83 mg of title compound: $^1$H NMR (400 MHz, cd$_3$od) δ 8.61 (dd, 1H), 7.57 (d, 1H), 7.50-7.37 (m, 2H), 7.37-7.18 (m, 4H), 7.16-7.01 (m, 2H), 6.65-6.48 (m, 1H), 6.45 (s, 1H), 6.25 (d, 2H), 5.26 (t, 1H), 3.75 (s, 2H), 3.07-2.86 (m, 2H); MS (m/z) 557 [M+H]$^+$.

Example 202

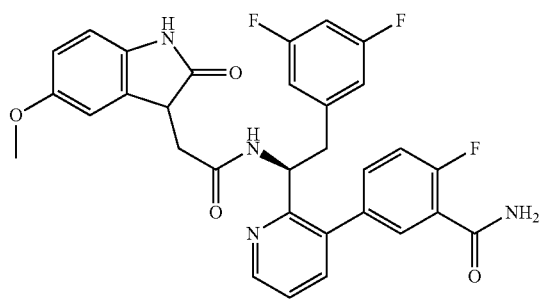

Synthesis of 5-(2-((1S)-2-(3,5-difluorophenyl)-1-(2-(5-methoxy-2-oxoindolin-3-yl)acetamido)ethyl)pyridin-3-yl)-2-fluorobenzamide (202)

Compound 202 was prepared according to the method presented for the synthesis of Example 54 utilizing 54B and 2-(5-methoxy-2-oxoindolin-3-yl)acetic acid to provide 17 mg of title compound: $^1$H NMR (400 MHz, cd$_3$od) δ 8.61 (dd, 1H), 7.53 (dd, 1H), 7.43-7.34 (m, 1H), 7.29 (dd, 1H), 7.25-6.96 (m, 2H), 6.77-6.41 (m, 4H), 6.21 (dd, 2H), 5.37-5.15 (m, 1H), 3.79 (dt, 1H), 3.61 (d, 3H), 3.10-2.81 (m, 2H), 2.69-2.48 (m, 2H). MS (m/z) 575 [M+H]$^+$.

Example 203

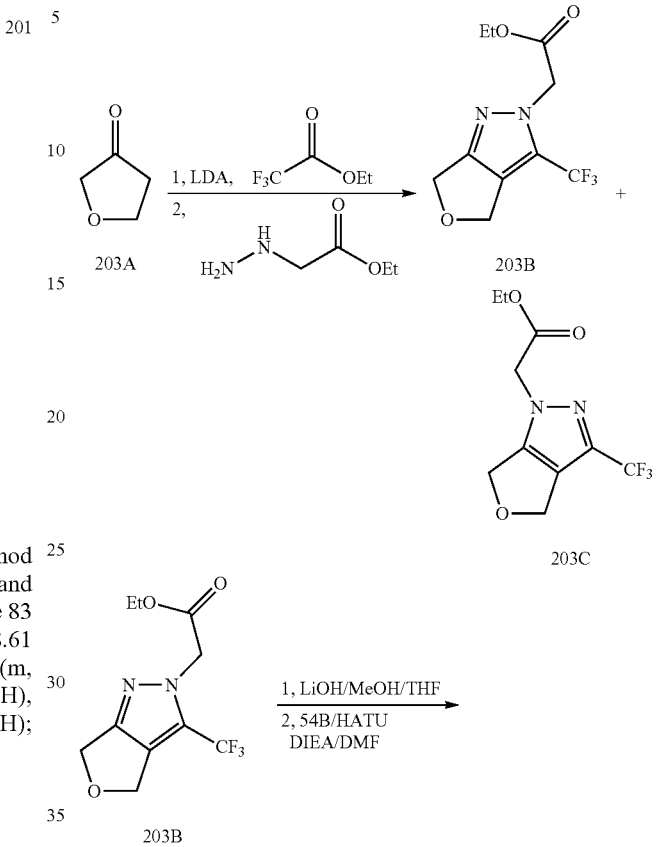

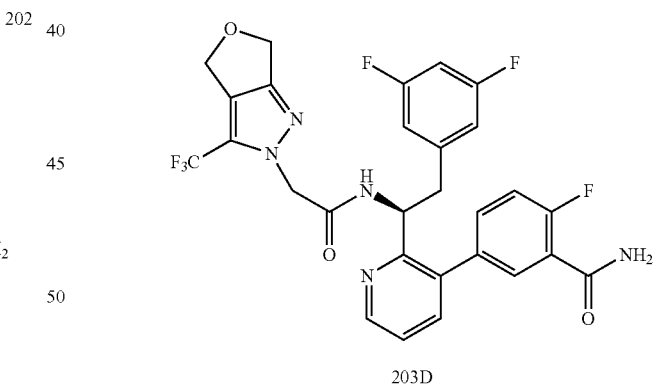

Synthesis of ethyl 2-(3-(trifluoromethyl)-4,6-dihydro-2H-furo[3,4-c]pyrazol-2-yl)acetate (203B) and ethyl 2-(3-(trifluoromethyl)-4,6-dihydro-1H-furo[3,4-c]pyrazol-1-yl)acetate (20° C.)

Compound 203B and 203C were prepared according to the method presented for the synthesis of Example 122 substituting dihydrofuran-3(2H)-one for 122B to provide 82 mg of 203B and 500 mg of 203C: 203B: MS (m/z) 265 [M+H]$^+$ and 203C: MS (m/z) 265 [M+H]$^+$.

Synthesis of (S)-5-(2-(2-(3,5-difluorophenyl)-1-(2-(3-(trifluoromethyl)-4,6-dihydro-2H-furo[3,4-c]pyrazol-2-yl)acetamido)ethyl)pyridin-3-yl)-2-fluorobenzamide (203D)

Compound 203D was prepared according to the method presented for the synthesis of Example 122 substituting 203B for 122D to provide 33 mg of title compound: $^1$H NMR (400 MHz, cd$_3$od) δ 8.75-8.67 (m, 1H), 7.63 (dd, 1H), 7.49-7.37 (m, 2H), 7.32 (s, 1H), 7.26-7.16 (m, 1H), 6.66 (t, 1H), 6.32 (d, 2H), 5.35 (t, 11-H), 4.92 (d, 4H), 4.79 (s, 2H), 3.05 (dd, 2H). MS (m/z) 590 [M+H]$^+$.

Example 204

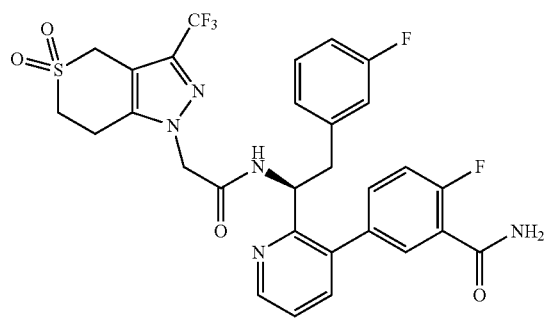

204

Synthesis of (S)-5-(2-(1-(2-(5,5-dioxido-3-(trifluoromethyl)-6,7-dihydrothiopyrano[4,3-c]pyrazol-1(4H)-yl)acetamido)-2-(3-fluorophenyl)ethyl)pyridin-3-yl)-2-fluorobenzamide (204)

Compound 204 was prepared according to the method presented for the synthesis of Example 197 utilizing 228 (62 mg, 0.1 mmol), 3-Chloroperbenzoic acid (87 mg, 77% max., 0.2 mmol) in DCM (3 mL) at 0° C. to provide 39 mg of title compound: $^1$H NMR (400 MHz, cd$_3$od) δ 8.68 (dd, 1H), 7.51 (dd, 1H), 7.42-7.31 (m, 2H), 7.15 (t, 2H), 7.05 (td, 1H), 6.81 (td, 1H), 6.52 (d, 1H), 6.43 (d, 1H), 5.40-5.28 (m, 1H), 4.87 (d, 2H), 4.32-4.17 (m, 2H), 3.44-3.24 (m, 4H), 3.24-2.95 (m, 4H). MS (m/z) 634 [M+H]$^+$ Example 205

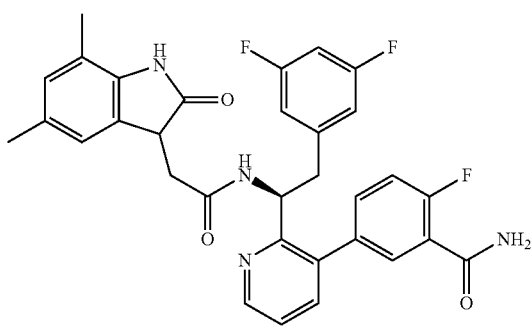

205

Synthesis of 5-(2-((1S)-2-(3,5-difluorophenyl)-1-(2-(5,7-dimethyl-2-oxoindolin-3-yl)acetamido)ethyl)pyridin-3-yl)-2-fluorobenzamide (205)

Compound 205 was prepared according to the method presented for the synthesis of Example 54 utilizing 54B and 2-(5,7-dimethylindolin-3-yl)acetic acid to provide 19 mg of title compound: $^1$H NMR (400 MHz, cd$_3$od) δ 8.68 (t, 1H), 7.61 (dd, 1H), 7.54-7.34 (m, 2H), 7.34-7.09 (m, 2H), 6.97-6.54 (m, 3H), 6.30 (dd, 2H), 5.37-5.24 (m, 1H), 3.83 (dd, 1H), 3.15-2.89 (m, 3H), 2.76-2.54 (m, 2H), 2.17 (dd, 6H). MS (m/z) 573 [M+H]$^+$.

Example 206

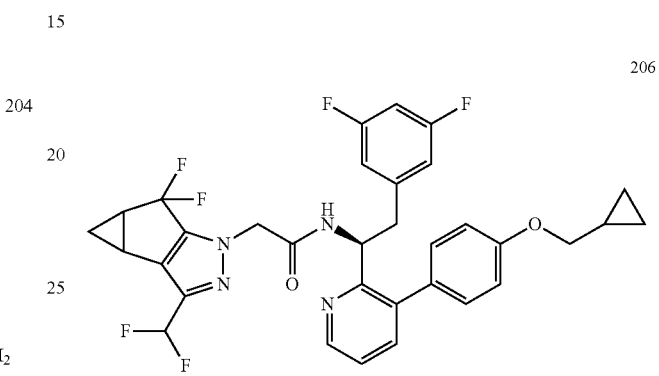

206

Synthesis of N—((S)-1-(3-(4-(cyclopropylmethoxy)phenyl)pyridin-2-yl)-2-(3,5-difluorophenyl)ethyl)-2-(3-(difluoromethyl)-5,5-difluoro-3b,4,4a,5-tetrahydro-1H-cyclopropa[3,4]cyclopenta[1,2-c]pyrazol-1-yl)acetamide (206)

Compound 206 was prepared according to the method presented for the synthesis of Example 68 utilizing 68A and (4-(cyclopropylmethoxy)phenyl)boronic acid to provide 5 mg of title compound: $^1$H NMR (400 MHz, cd$_3$od) δ 8.26 (s, 1H), 7.24 (d, 1H), 7.11-7.00 (m, 1H), 6.68-6.18 (m, 6H), 5.91 (s, 2H), 5.13 (s, 1H), 3.49 (d, 2H), 2.63 (s, 2H), 2.12 (s, 2H), 1.03 (s, 3H), 0.80-0.63 (m, 2H), 0.27 (d, 2H), 0.01 (d, 2H). MS (m/z) 627 [M+H]$^+$.

Example 207

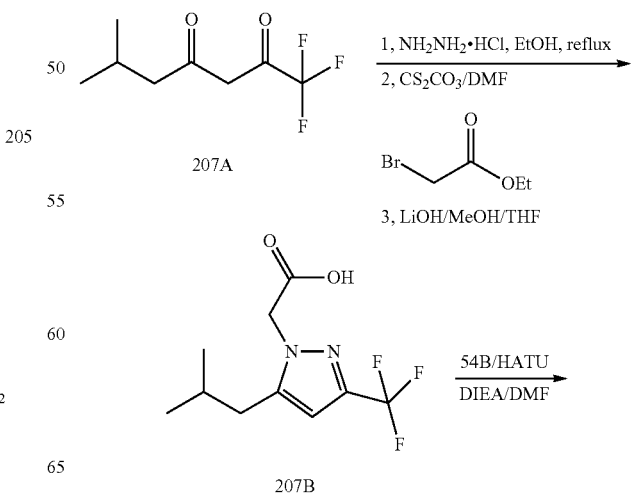

-continued

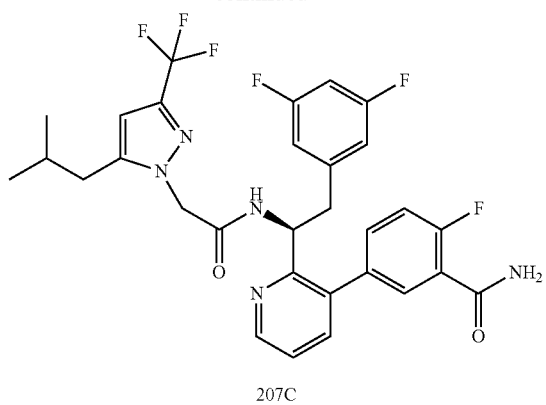

207C

Synthesis of 2-(5-isobutyl-3-(trifluoromethyl)-1H-pyrazol-1-yl)acetic acid (207B)

Compound 207B was prepared according to the method presented for the synthesis of Example 238 substituting 1,1,1-trifluoro-6-methylheptane-2,4-dione for 238A to provide 650 mg of title compound. MS (m/z) 251 [M+H]$^+$.

Synthesis of (S)-5-(2-(2-(3,5-difluorophenyl)-1-(2-(5-isobutyl-3-(trifluoromethyl)-1H-pyrazol-1-yl)acetamido)ethyl)pyridin-3-yl)-2-fluorobenzamide (207C)

Compound 207 was prepared according to the method presented for the synthesis of Example 54 utilizing 54B and 2-(5-isobutyl-3-(trifluoromethyl)-1H-pyrazol-1-yl)acetic acid to provide 20 mg of title compound: $^1$H NMR (400 MHz, cd$_3$od) δ 8.69 (dd, 1H), 7.63 (dd, 1H), 7.48-7.38 (m, 2H), 7.32 (s, 1H), 7.21 (dd, 1H), 6.67 (dd, 1H), 6.39 (s, 1H), 6.32 (d, 2H), 5.36 (t, 1H), 4.88 (s, 2H), 3.05 (d, 2H), 2.42 (dd, 2H), 1.84 (dt, 1H), 0.88 (dd, 6H). MS (m/z) 604 [M+H]$^+$.

Example 208

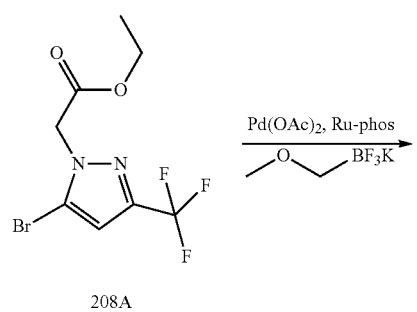

208A

-continued

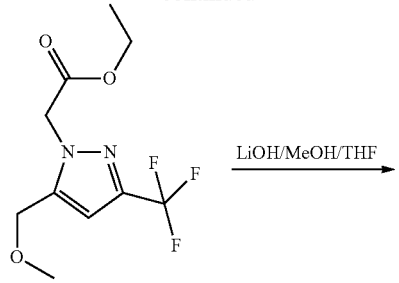

208B

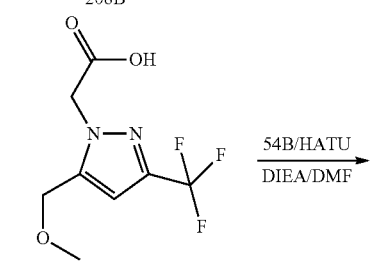

208C

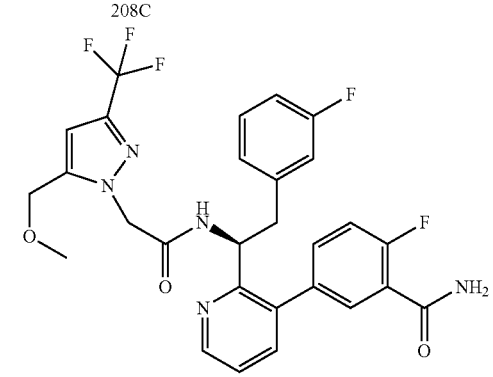

208D

Synthesis of ethyl 2-(5-bromo-3-(trifluoromethyl)-1H-pyrazol-1-yl)acetate (208A)

Compound 208A was prepared according to the method presented for the synthesis of Example 74 substituting 5-bromo-3-(trifluoromethyl)-1H-pyrazole for 74B to provide 300 mg of title compound. MS (m/z) 300 [M+H]$^+$.

Synthesis of ethyl 2-(5-(methoxymethyl)-3-(trifluoromethyl)-1H-pyrazol-1-yl)acetate (208B)

To a solution of 208A (300 mg, 0.1 mmol) and potassium trifluoro(methoxymethyl)borate (304 mg, 0.2 mmol) in 3 ml dioxane/water (10:1) was added 3 aq. Cs$_2$CO$_3$ and 2-dicyclohexylphosphino-2',6'-diisopropoxybiphenyl (Ruphos) (93.4 mg, 0.2 mmol) and Palladium(II)acetate (22.5 mg, 0.1 mmol). The resulting mixture was heated at reflux for overnight. The reaction mixture was filtered and the mixture was extracted with EtOAc. The organics were dried over Na$_2$SO$_4$, filtered and concentrated. The crude product was purified by SiO$_2$ chromatography eluting with a gradient of EtOAc in hexanes to provide 12 mg of title compound. MS (m/z) 267 [M+H]$^+$.

Synthesis of 2-(5-(methoxymethyl)-3-(trifluoromethyl)-1H-pyrazol-1-yl)acetic acid (208C)

Compound 208C was prepared according to the method presented for the synthesis of Example 74 substituting 208B for 74B to provide 10 mg of title compound. MS (m/z) 239 [M+H]$^+$.

Synthesis of (S)-2-fluoro-5-(2-(2-(3-fluorophenyl)-1-(2-(5-(methoxymethyl)-3-(trifluoromethyl)-1H-pyrazol-1-yl)acetamido)ethyl)pyridin-3-yl)benzamide (208D)

Compound 208D was prepared according to the method presented for the synthesis of Example 54 utilizing 54B and 208D to provide 3 mg of title compound: $^1$H NMR (400 MHz, cd$_3$od) δ 8.68 (dd, 1H), 7.59 (dd, 1H), 7.40 (dd, 2H), 7.29 (s, 1H), 7.21 (dd, 1H), 6.73-6.62 (m, 1H), 6.59 (s, 1H), 6.31 (d, 2H), 5.35 (t, 1H), 4.95 (s, 2H), 4.47-4.36 (m, 2H), 3.23 (s, 3H), 3.07-3.01 (m, 2H). MS (m/z) 592 [M+H]$^+$.

Example 209

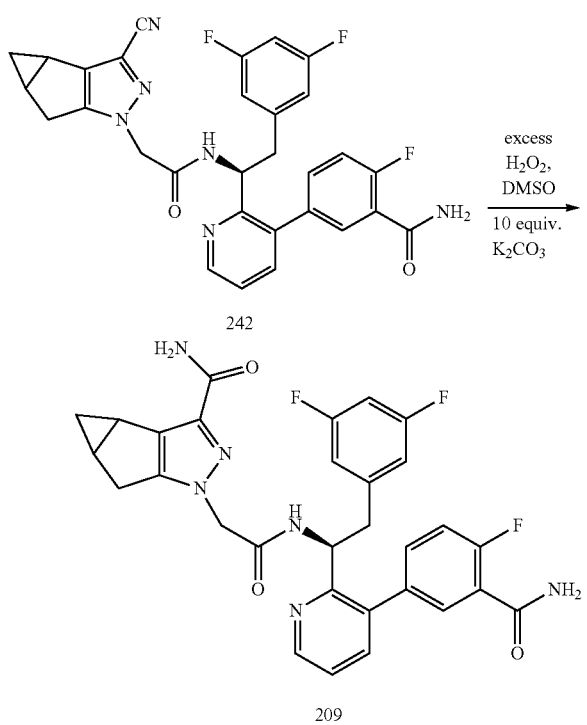

Synthesis of 1-(2-(((S)-1-(3-(3-carbamoyl-4-fluorophenyl)pyridin-2-yl)-2-(3,5-difluorophenyl)ethyl)amino)-2-oxoethyl)-3b,4,4a,5-tetrahydro-1H-cyclopropa[3,4]cyclopenta[1,2-c]pyrazole-3-carboxamide (209)

H$_2$O$_2$ (30 wt %, excess) was added to a suspension of 242 (30 mg, 0.054 mmol) and potassium carbonate (74.5 mg, 0.54 mmol) in DMSO (1 mL) at 0° C. and then stirred for 1 hour. The suspension was filtered and the filtrate was purified by RP HPLC using a C18 column with a gradient of H$_2$O, 0.1% TFA-acetonitrile, to provide 18 mg of the title compound; $^1$H NMR (400 MHz, cd$_3$od) δ 8.51 (dd, 1H), 7.51 (d, 1H), 7.37-7.24 (m, 2H), 7.15 (s, 1H), 7.11-6.99 (m, 1H), 6.49 (t, 1H), 6.13 (d, 2H), 5.22-5.08 (m, 1H), 4.59-4.43 (m, 2H), 2.85 (dd, 2H), 2.66-2.53 (m, 1H), 2.50-2.39 (m, 1H), 2.04 (s, 1H), 1.87 (s, 1H), 0.88 (dd, 1H), 0.01 (dt, 1H). MS (m/z) 575 [M+H]$^+$ Example 210

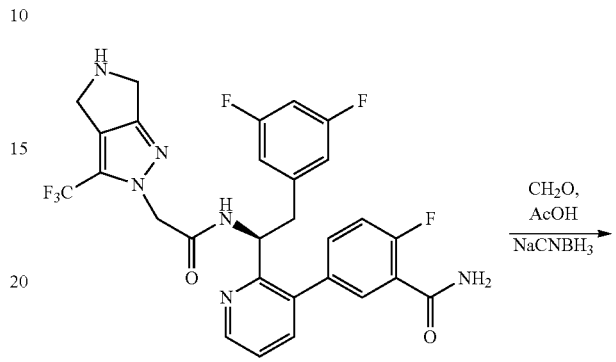

Synthesis of (S)-5-(2-(2-(3,5-difluorophenyl)-1-(2-(5-methyl-3-(trifluoromethyl)-5,6-dihydropyrrolo[3,4-c]pyrazol-2(4H)-yl)acetamido)ethyl)pyridin-3-yl)-2-fluorobenzamide (210)

A mixture of 200B (30 mg, 0.05 mmol) and formaldehyde (15.3 mg, 0.5 mmol) in acetic acid (1 mL) was stirred for 30 minutes. Sodium cyanoborohydride (4.8 mg, 0.076 mmol) was added to the suspension and stirred for 1 hour. Solvents were concentrated in vacuo and the residue was purified by RP HPLC using a C18 column with a gradient of H$_2$O, 0.1% TFA-acetonitrile, to provide 18 mg of the title compound: $^1$H NMR (400 MHz, cd$_3$od) δ 8.71 (dd, 1H), 7.59 (dd, 1H), 7.50-7.37 (m, 2H), 7.29 (s, 1H), 7.20 (dd, 1H), 6.67 (t, 1H), 6.35 (d, 2H), 5.34 (t, 1H), 5.01 (s, 2H), 4.64 (s, 4H), 3.16 (s, 3H), 3.07 (ddd, 2H); MS (m/z) 603 [M+H]$^+$

Example 211

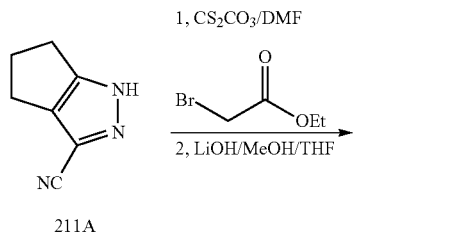

211A

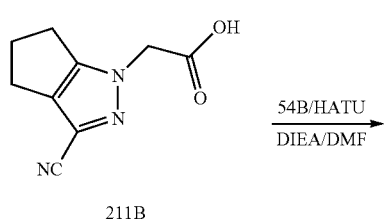

211B

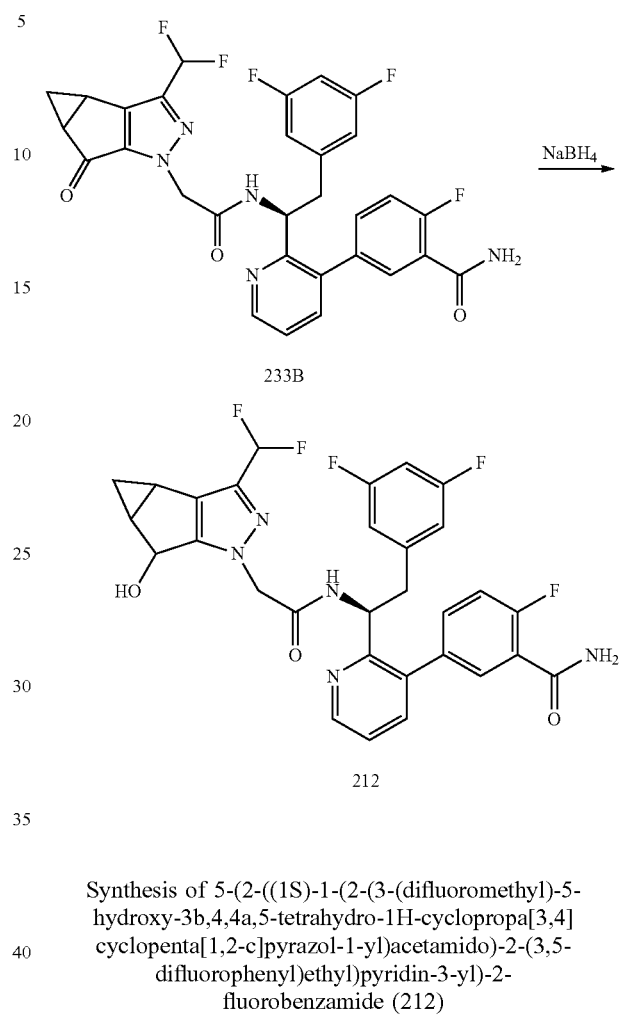

211C

Synthesis of 2-(3-cyano-5,6-dihydrocyclopenta[c]pyrazol-1(4H)-yl)acetic acid (211B)

Compound 211B was prepared according to the method presented for the synthesis of Example 74 substituting 1,4,5,6-tetrahydrocyclopenta[c]pyrazole-3-carbonitrile (211A) for 1-7,8,8-trimethyl-3-(trifluoromethyl)-4,5,6,7-tetrahydro-1H-4,7-methanoindazole (74A) to provide 300 mg of title compound: MS (m/z) 192 [M+H]$^+$.

Synthesis of (S)-5-(2-(1-(2-(3-cyano-5,6-dihydrocyclopenta[c]pyrazol-1(4H)-yl)acetamido)-2-(3,5-difluorophenyl)ethyl)pyridin-3-yl)-2-fluorobenzamide (211C)

Compound 211C was prepared according to the method presented for the synthesis of Example 54 utilizing 54B and 2-(3-cyano-5,6-dihydrocyclopenta[c]pyrazol-1(4H)-yl)acetic acid (211B) to provide 42 mg of title compound: $^1$H NMR (400 MHz, cd$_3$od) δ 8.71 (dd, 1H), 7.67 (dd, 1H), 7.47 (dd, 2H), 7.33 (s, 1H), 7.23 (dd, 1H), 6.67 (t, 1H), 6.33 (d, 2H), 5.35 (t, 1H), 4.81 (s, 2H), 3.06 (d, 2H), 2.77-2.48 (m, 6H). MS (m/z) 545 [M+H]$^+$.

Example 212

Synthesis of 5-(2-((1S)-1-(2-(3-(difluoromethyl)-5-hydroxy-3b,4,4a,5-tetrahydro-1H-cyclopropa[3,4]cyclopenta[1,2-c]pyrazol-1-yl)acetamido)-2-(3,5-difluorophenyl)ethyl)pyridin-3-yl)-2-fluorobenzamide (212)

Compound 212 was prepared according to the method presented for the synthesis of Example 154 substituting 233B for 154B to provide 12 mg of title compound: $^1$H NMR (400 MHz, cd$_3$od) δ 8.61 (dd, 1H), 7.57 (d, 1H), 7.37 (dd, 2H), 7.28-7.08 (m, 2H), 6.78-6.34 (m, 2H), 6.32-6.14 (m, 2H), 5.39-5.17 (m, 2H), 4.66 (ddd, 2H), 3.04-2.88 (m, 2H), 2.19-1.99 (m, 2H), 0.95-0.65 (m, 2H). MS (m/z) 598 [M+H]$^+$.

Example 213

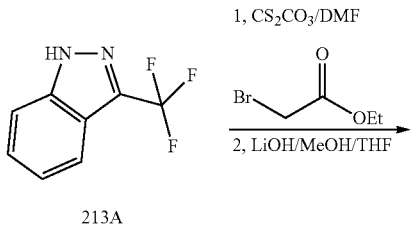

213A

-continued

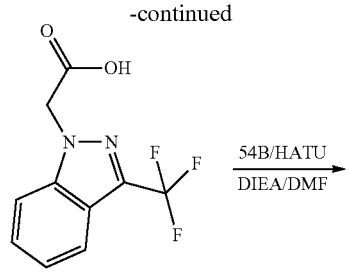

213B

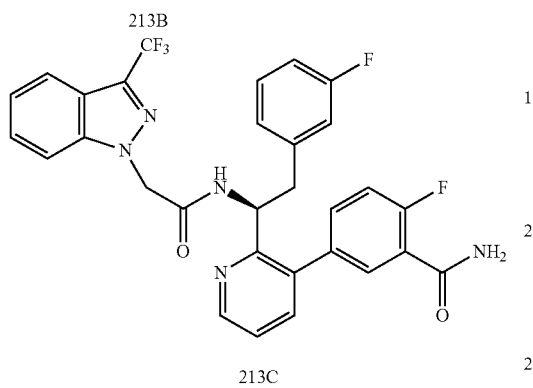

213C

Synthesis of 2-(3-(trifluoromethyl)-1H-indazol-1-yl) acetic acid (213B)

Compound 213B was prepared according to the method presented for the synthesis of Example 74 substituting 3-(trifluoromethyl)-1H-indazole (213A) for 1-7,8,8-trimethyl-3-(trifluoromethyl)-4,5,6,7-tetrahydro-1H-4,7-methanoindazole (74A) to provide 155 mg of title compound. MS (m/z) 245 [M+H]⁺.

Synthesis of(S)-2-fluoro-5-(2-(2-(3-fluorophenyl)-1-(2-(3-(trifluoromethyl)-1H-indazol-1-yl)acetamido) ethyl)pyridin-3-yl)benzamide (213B)

Compound 213 was prepared according to the method presented for the synthesis of Example 59 utilizing 59D and 2-(3-(trifluoromethyl)-1H-indazol-1-yl)acetic acid (213B) to provide 25 mg of title compound: ¹H NMR (400 MHz, cd₃od) δ 8.70 (dd, 1H), 7.78 (d, 1H), 7.63 (dd, 1H), 7.59-7.41 (m, 3H), 7.38-7.11 (m, 4H), 7.04 (dd, 1H), 6.82 (t, 1H), 6.47 (dd, 2H), 5.34 (t, 1H), 5.23 (s, 2H), 3.07 (d, 2H). MS (m/z) 580 [M+H]⁺.

Example 214

Synthesis of (S)-5-(2-(2-(3,5-difluorophenyl)-1-(2-(naphthalen-1-yl)acetamido)ethyl)pyridin-3-yl)-2-fluorobenzamide (214)

Compound 214 was prepared according to the method presented for the synthesis of Example 54 utilizing 54B and 2-(naphthalen-1-yl)acetic acid to provide: ¹H NMR (400 MHz, cdcl₃) δ 8.76 (d, 1H), 8.69 (d, 1H), 7.94 (d, 1H), 7.80 (dd, 3H), 7.72-7.66 (m, 1H), 7.61 (d, 1H), 7.49-7.34 (m, 3H), 7.34-7.25 (m, 1H), 6.99 (d, 1H), 6.10 (d, 2H), 5.39 (dd, 1H), 4.01 (p, 2H), 2.99 (ddd, 2H). MS (m/z) 540 [M+H]⁺.

Example 215

215

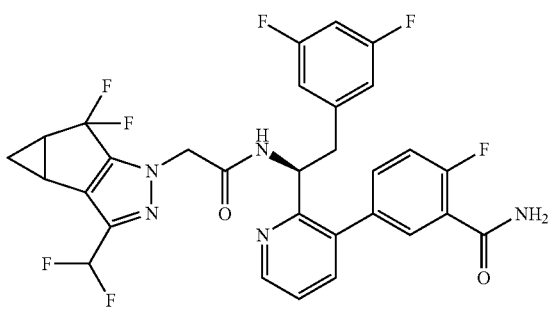

Synthesis of 5-(2-((1S)-1-(2-(3-(difluoromethyl)-5,5-difluoro-3b,4,4a,5-tetrahydro-1H-cyclopropa[3,4] cyclopenta[1,2-c]pyrazol-1-yl)acetamido)-2-(3,5-difluorophenyl)ethyl)pyridin-3-yl)-2-fluorobenzamide (215)

215 was separated from the diastereomeric mixture of 60 by semi-preparative chiral HPLC fitted with a Chiralcel AZ-H column running a 70:30 mixture of Hep:IPA. The fast eluent was collected to obtain 58 mg of the single diastereomer: ¹H NMR (400 MHz, cd₃od) δ 8.65 (dd, 1H), 7.53 (dd, 1H), 7.35 (dd, 2H), 7.33-7.12 (m, 2H), 6.87-6.48 (m, 2H), 6.26 (d, 2H), 5.40-5.28 (m, 1H), 4.79 (s, 2H), 3.00 (qd, 2H), 2.51-2.36 (m, 2H), 1.16-1.08 (m, 1H), 1.02 (d, 1H). MS (m/z) 618 [M+H]⁺.

Example 216

214

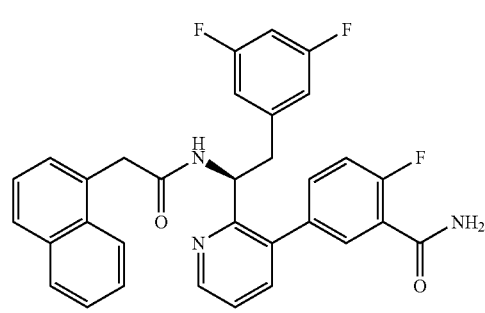

216

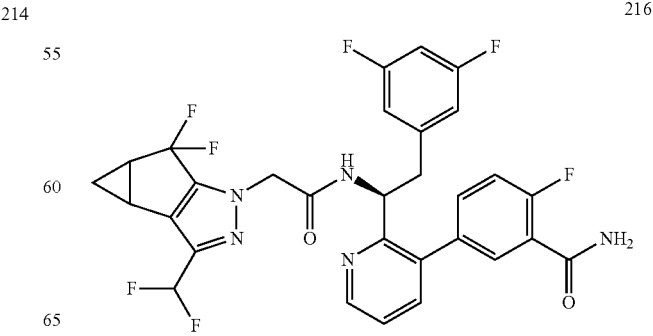

441

Synthesis of 5-(2-((1S)-1-(2-(3-(difluoromethyl)-5,5-difluoro-3b,4,4a,5-tetrahydro-1H-cyclopropa[3,4]cyclopenta[1,2-c]pyrazol-1-yl)acetamido)-2-(3,5-difluorophenyl)ethyl)pyridin-3-yl)-2-fluorobenzamide (216)

216 was separated from the diastereomeric mixture of 60 by semi-preparative chiral HPLC fitted with a Chiralcel AZ-H column running a 70:30 mixture of Hep:IPA. The slow eluent was collected to obtain 58 mg of the single diastereomer: $^1$H NMR (400 MHz, cd$_3$od) δ 8.66 (dd, 1H), 7.52 (dd, 1H), 7.35 (dd, 2H), 7.31-7.13 (m, 2H), 6.83-6.48 (m, 2H), 6.26 (d, 2H), 5.40-5.26 (m, 1H), 4.79 (s, 2H), 3.12-2.93 (m, 2H), 2.44 (ddd, 2H), 1.18-1.10 (m, 1H), 1.10-1.00 (m, 1H). MS (m/z) 618 [M+H]$^+$.

Example 217

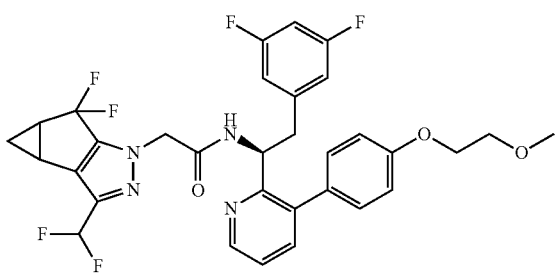

217

Synthesis of 2-(3-(difluoromethyl)-5,5-difluoro-3b,4,4a,5-tetrahydro-1H-cyclopropa[3,4]cyclopenta[1,2-c]pyrazol-1-yl)-N—((S)-2-(3,5-difluorophenyl)-1-(3-(4-(2-methoxyethoxy)phenyl)pyridin-2-yl)ethyl)acetamide (217)

Compound 217 was prepared according to the method presented for the synthesis of Example 68 utilizing 68A and (4-(2-methoxyethoxy)phenyl)boronic acid to provide 8 mg of title compound: $^1$H NMR (400 MHz, cd$_3$od) δ 8.61 (d, 1H), 7.61 (d, 1H), 7.41 (dd, 1H), 7.07-6.87 (m, 4H), 6.68 (ddd, 2H), 6.25 (d, 2H), 5.48 (d, 1H), 4.13 (d, 2H), 3.81-3.70 (m, 2H), 3.42 (s, 3H), 2.96 (dd, 2H), 2.46 (s, 2H), 1.37 (s, 1H), 1.07 (s, 1H). MS (m/z) 631 [M+H]$^+$.

Example 218

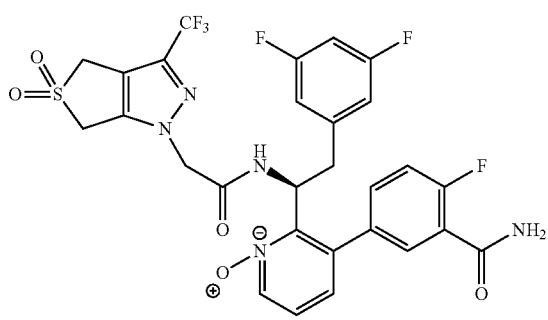

218

442

Synthesis of (S)-3-(3-carbamoyl-4-fluorophenyl)-2-(2-(3,5-difluorophenyl)-1-(2-(5,5-dioxido-3-(trifluoromethyl)-4,6-dihydro-1H-thieno[3,4-c]pyrazol-1-yl)acetamido)ethyl)pyridine 1-oxide (218)

Compound 218 was prepared according to the method presented for the synthesis of Example 197 utilizing 189 to provide 25 mg of title compound: $^1$H NMR (400 MHz, cd$_3$od) δ 8.32 (d, 1H), 7.85 (dd, 1H), 7.54-7.44 (m, 1H), 7.44-7.28 (m, 2H), 7.21 (d, 1H), 7.18-7.07 (m, 1H), 6.62 (t, 1H), 6.33 (d, 2H), 5.48-5.31 (m, 1H), 5.03-4.85 (m, 2H), 4.42-4.17 (m, 3H), 3.51 (dd, 1H), 3.04 (dd, 1H). MS ((m/z) 654 [M+H]$^+$

Example 219

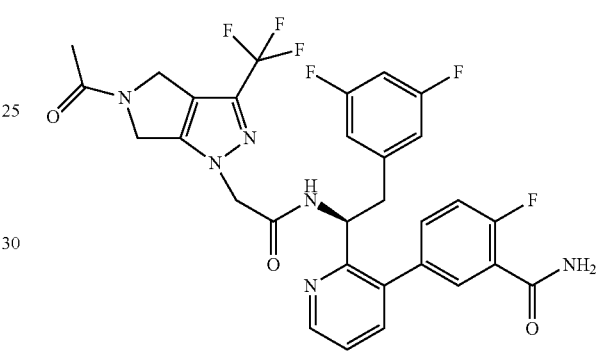

219

Synthesis of(S)-5-(2-(1-(2-(5-acetyl-3-(trifluoromethyl)-5,6-dihydropyrrolo[3,4-c]pyrazol-1(4H)-yl)acetamido)-2-(3,5-difluorophenyl)ethyl)pyridin-3-yl)-2-fluorobenzamide (219)

Compound 219 was prepared according to the method presented for the synthesis of Example 54 substituting 251 for 54B to provide 32 mg of title compound: $^1$H NMR (400 MHz, cd$_3$od) δ 8.75-8.67 (m, 1H), 7.64 (d, 1H), 7.58-7.40 (m, 2H), 7.25 (dd, 2H), 6.66 (t, 1H), 6.32 (d, 2H), 5.35 (dd, 1H), 4.92 (d, 2H), 4.69 (d, 2H), 4.51 (d, 2H), 3.16-3.01 (m, 2H), 2.11 (d, 3H). MS (m/z) 631 [M+H]$^+$.

Example 220

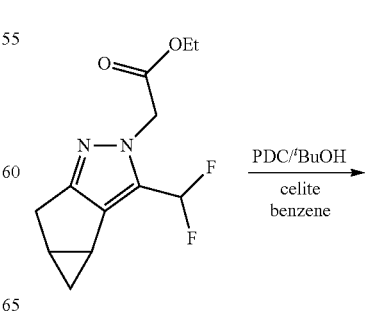

60B

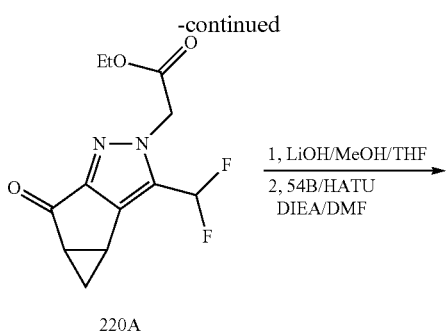

220A

1, LiOH/MeOH/THF
2, 54B/HATU
DIEA/DMF

Example 221

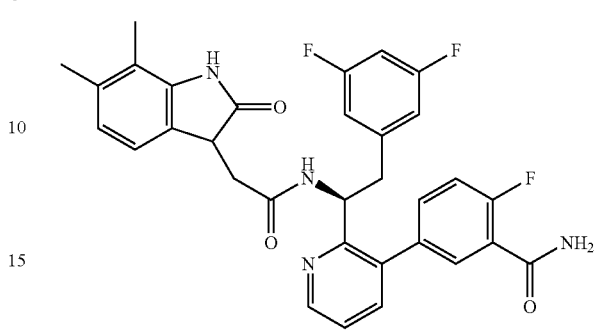

221

Synthesis of 5-(2-(((1S)-2-(3,5-difluorophenyl)-1-(2-(6,7-dimethyl-2-oxoindolin-3-yl)acetamido)ethyl)pyridin-3-yl)-2-fluorobenzamide (221)

Compound 221 was prepared according to the method presented for the synthesis of Example 54 utilizing 54B and 2-(6,7-dimethylindolin-3-yl)acetic acid to provide 15 mg of title compound: $^1$H NMR (400 MHz, cd$_3$od) δ 8.64 (td, 1H), 7.71-7.56 (m, 1H), 7.49-7.40 (m, 1H), 7.40-6.91 (m, 3H), 6.76 (dd, 1H), 6.66-6.49 (m, 2H), 6.49-6.10 (m, 3H), 5.22 (dd, 1H), 3.61 (dd, 1H), 2.99-2.47 (m, 5H), 2.22-1.94 (m, 6H). MS (m/z) 573 [M+H]$^+$.

Example 222

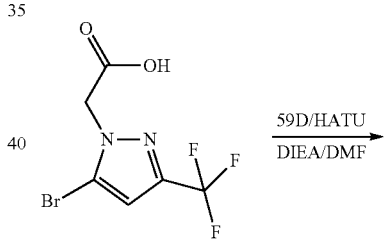

222A

59D/HATU
DIEA/DMF

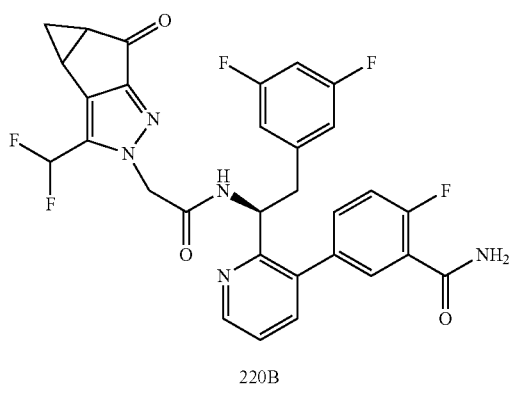

220B

Synthesis of 2-(3-(difluoromethyl)-5-oxo-3b,4,4a,5-tetrahydro-2H-cyclopropa[3,4]cyclopenta[1,2-c]pyrazol-2-yl)acetic acid (220A)

Compound 220A was prepared according to the method presented for the synthesis of Example 181 substituting 60B for 122D to provide 8 mg of title compound. MS (m/z) 271 [M+H]$^+$.

Synthesis of 5-(2-(((1S)-1-(2-(3-(difluoromethyl)-5-oxo-3b,4,4a,5-tetrahydro-2H-cyclopropa[3,4]cyclopenta[1,2-c]pyrazol-2-yl)acetamido)-2-(3,5-difluorophenyl)ethyl)pyridin-3-yl)-2-fluorobenzamide (220B)

Compound 220B was prepared according to the method presented for the synthesis of Example 154 substituting 220A for 181A to provide 6 mg of title compound: $^1$H NMR (400 MHz, cd$_3$od) δ 8.62 (dd, 1H), 7.54 (dd, 1H), 7.35 (dd, 2H), 7.15 (dd, 2H), 6.90 (td, 1H), 6.58 (t, 1H), 6.22 (d, 2H), 5.26 (t, 1H), 4.94 (s, 2H), 3.05-2.89 (m, 2H), 2.78-2.67 (m, 1H), 2.50-2.38 (m, 1H), 1.58 (dd, 1H), 1.40 (dd, 1H). MS (m/z) 596 [M+H]$^+$.

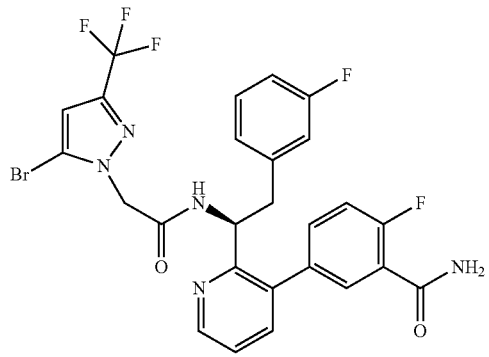

222B

Synthesis of 2-(5-bromo-3-(trifluoromethyl)-1H-pyrazol-1-yl)acetic acid (222A)

Compound 222A was prepared according to the method presented for the synthesis of Example 74 substituting 5-bromo-3-(trifluoromethyl)-1H-pyrazole for 74B to provide 270 mg of title compound. MS (m/z) 273 [M+H]+.

Synthesis of (S)-5-(2-(1-(2-(5-bromo-3-(trifluoromethyl)-1H-pyrazol-1-yl)acetamido)-2-(3-fluorophenyl)ethyl)pyridin-3-yl)-2-fluorobenzamide (222B)

Compound 222B was prepared according to the method presented for the synthesis of Example 59 utilizing 59D and 2-(5-bromo-3-(trifluoromethyl)-1H-pyrazol-1-yl)acetic acid (222A) to provide 490 mg of title compound: $^1$H NMR (400 MHz, cd$_3$od) δ 8.62 (dd, 1H), 7.54 (dd, 1H), 7.35 (dd, 2H), 7.15 (dd, 2H), 6.90 (td, 1H), 6.58 (t, 1H), 6.22 (d, 2H), 5.26 (t, 1H), 4.94 (s, 2H), 3.05-2.89 (m, 2H), 2.78-2.67 (m, 1H), 2.50-2.38 (m, 1H), 1.58 (dd, 1H), 1.40 (dd, 1H). MS (m/z) 608 [M+H]+.

Example 223

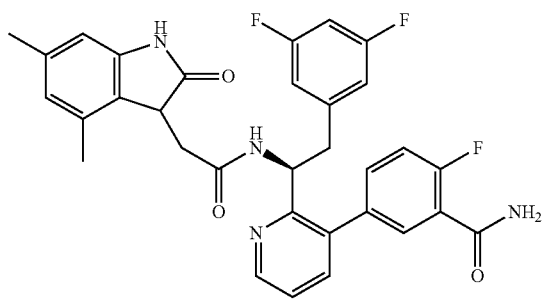

Synthesis of 5-(2-((1S)-2-(3,5-difluorophenyl)-1-(2-(5,7-dimethyl-2-oxoindolin-3-yl)acetamido)ethyl)pyridin-3-yl)-2-fluorobenzamide (223)

Compound 223 was prepared according to the method presented for the synthesis of Example 54 utilizing 54B and 2-(5,7-dimethylindolin-3-yl)acetic acid to provide 19 mg of title compound: $^1$H NMR (400 MHz, cd$_3$od) δ 8.70-8.54 (m, 1H), 7.76-7.52 (m, 1H), 7.33 (dddd, 4H), 6.79-6.46 (m, 3H), 6.27 (dd, 2H), 5.39-5.21 (m, 1H), 4.04 (dd, 2H), 3.07-2.56 (m, 5H), 2.31-2.09 (m, 6H). MS (m/z) 573 [M+H]+.

Example 224

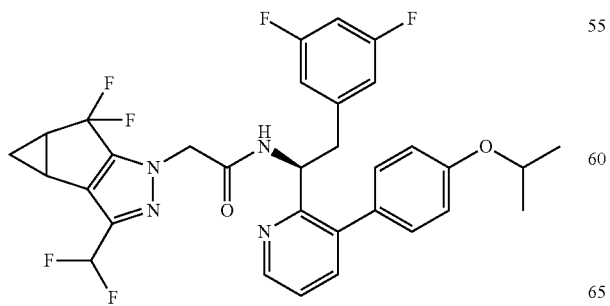

Synthesis of 2-(3-(difluoromethyl)-5,5-difluoro-3b,4,4a,5-tetrahydro-1H-cyclopropa[3,4]cyclopenta[1,2-c]pyrazol-1-yl)-N—((S)-2-(3,5-difluorophenyl)-1-(3-(4-isopropoxyphenyl)pyridin-2-yl)ethyl) acetamide (224)

Compound 224 was prepared according to the method presented for the synthesis of Example 68 utilizing 68A and (4-isopropoxyphenyl)boronic acid to provide 14 mg of title compound: $^1$H NMR (400 MHz, cd$_3$od) δ 8.61 (d, 1H), 7.64 (d, 1H), 7.43 (dd, 1H), 7.04-6.95 (m, 2H), 6.89 (dd, 2H), 6.68 (ddd, 2H), 6.26 (s, 2H), 5.50 (d, 1H), 4.69-4.56 (m, 1H), 2.96 (t, 2H), 2.46 (s, 2H), 1.46-1.21 (m, 7H), 1.02 (s, 1H). MS (m/z) 615 [M+H]+.

Example 225

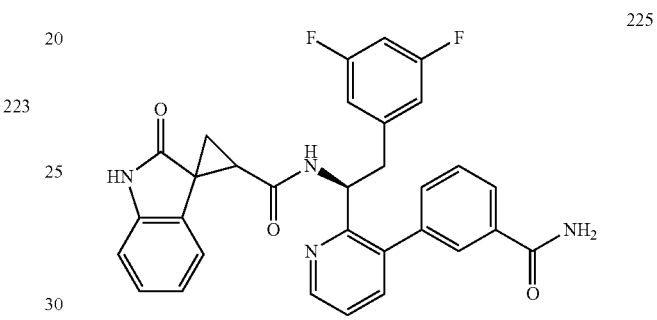

Synthesis of N—((S)-1-(3-(3-carbamoylphenyl)pyridin-2-yl)-2-(3,5-difluorophenyl)ethyl)-2'-oxospiro[cyclopropane-1,3'-indoline]-2-carboxamide (225)

Compound 225 was prepared according to the method presented for the synthesis of Example 50 utilizing 50C and 2'-oxospiro[cyclopropane-1,3'-indoline]-2-carboxylic acid to provide 46 mg of title compound: $^1$H NMR (400 MHz, dmso) δ 10.56 (d, 1H), 8.91 (dd, 1H), 8.50 (dd, 1H), 8.06-7.85 (m, 2H), 7.78-7.21 (m, 6H), 7.12-6.56 (m, 5H), 6.50 (d, 1H), 6.18 (d, 1H), 5.17 (dd, 1H), 2.94 (d, 1H), 2.86-2.71 (m, 1H), 2.63 (t, 1H), 1.88-1.76 (m, 1H), 1.61-1.50 (m, 1H). MS (m/z) 539 [M+H]+.

Example 226

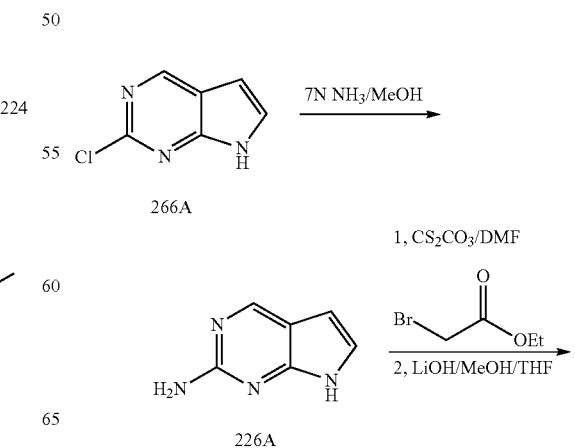

447
-continued

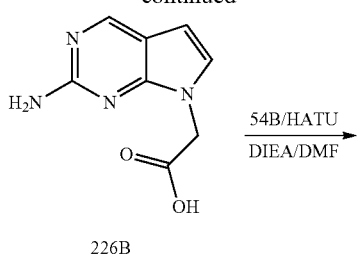

226B

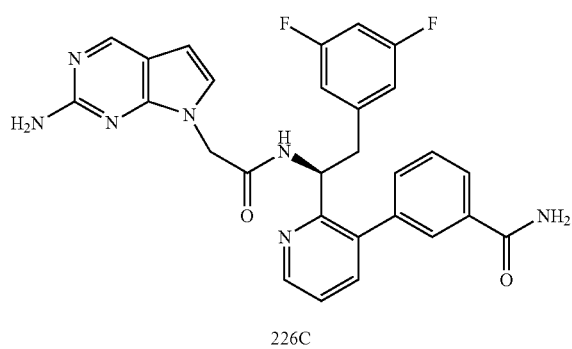

226C

Synthesis of 7H-pyrrolo[2,3-d]pyrimidin-2-amine (226A)

A solution of 266A in 10 mL of NH$_3$ (7N in MeOH) was heated at 130° C. in sealed tube overnight. The reaction was monitored by LC/Mass until completion. Remove the solvent and used as crude. MS (m/z) 135 [M+H]$^+$.

Synthesis of 2 ethyl 2-(2-amino-7H-pyrrolo[2,3-d]pyrimidin-7-yl)acetate (226B)

Compound 266B was prepared according to the method presented for the synthesis of Example 74 substituting 7H-pyrrolo[2,3-d]pyrimidin-2-amine (226A) for 1 7,8,8-trimethyl-3-(trifluoromethyl)-4,5,6,7-tetrahydro-1H-4,7-methanoindazole (74A) to provide 20 mg of title compound. MS (m/z) 221 [M+H]$^+$.

Synthesis of (S)-3-(2-(1-(2-(2-amino-7H-pyrrolo[2,3-d]pyrimidin-7-yl)acetamido)-2-(3,5-difluorophenyl)ethyl)pyridin-3-yl)benzamide (226C)

Compound 226C was prepared according to the method presented for the synthesis of Example 50 utilizing 50C and 2-(2-amino-7H-pyrrolo[2,3-d]pyrimidin-7-yl)acetic (226B) to provide 15 mg of title compound: $^1$H NMR (400 MHz, cd$_3$od) δ 8.64-8.54 (m, 1H), 8.40 (s, 1H), 7.77 (d, 1H), 7.56-7.45 (m, 2H), 7.37 (t, 1H), 7.30 (dd, 1H), 7.15 (d, 1H), 7.06 (d, 1H), 6.55 (t, 1H), 6.43 (d, 1H), 6.15 (d, 2H), 5.44-5.31 (m, 3H), 2.93 (ddd, 2H). MS (m/z) 528 [M+H]$^+$.

448

Example 227

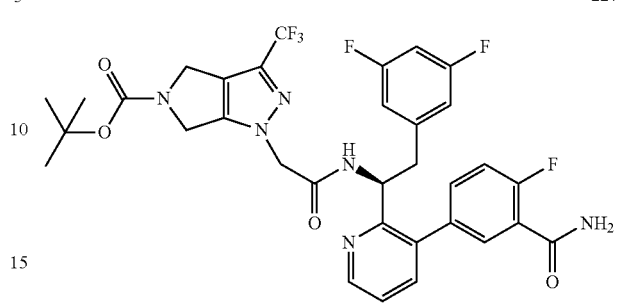

227

Synthesis of (S)-tert-butyl 1-(2-((1-(3-(3-carbamoyl-4-fluorophenyl)pyridin-2-yl)-2-(3,5-difluorophenyl)ethyl)amino)-2-oxoethyl)-3-(trifluoromethyl)-4,6-dihydropyrrolo[3,4-c]pyrazole-5(1H)-carboxylate (227)

Compound 227 was prepared according to the method presented for the synthesis of Example 122 substituting 190D for 122D to provide 40 mg of title compound: $^1$H NMR (400 MHz, cd$_3$od) δ 8.70 (s, 1H), 7.65 (d, 1H), 7.51-7.18 (m, 4H), 6.65 (s, 1H), 6.32 (s, 2H), 5.35 (d, 1H), 4.89 (d, 2H), 4.43 (d, 4H), 3.06 (d, 2H), 1.49 (d, 9H). MS (m/z) 689 [M+H]$^+$.

Example 228

228A

228B

Synthesis of 2-(3-(trifluoromethyl)-6,7-dihydrothiopyrano[4,3-c]pyrazol-1 (4H)-yl)acetic acid (228A)

Compound 228A was prepared according to the method presented for the synthesis of Example 122 substituting dihydro-2H-thiopyran-4(3H)-one for 122B to provide 1 g of title compound. MS (m/z) 267 [M+H]+.

Synthesis of (S)-2-fluoro-5-(2-(2-(3-fluorophenyl)-1-(2-(3-(trifluoromethyl)-6,7-dihydrothiopyrano[4,3-c]pyrazol-1(4H)-yl)acetamido)ethyl)pyridin-3-yl)benzamide (228B)

Compound 228B was prepared according to the method presented for the synthesis of Example 59 utilizing 59D and 228A to provide 27 mg of title compound: $^1$H NMR (400 MHz, cd$_3$od) δ 8.72 (dd, 1H), 7.70 (dd, 1H), 7.50 (dd, 1H), 7.38 (d, 1H), 7.28 (s, 1H), 7.20 (dd, 1H), 7.07 (dd, 1H), 6.84 (td, 1H), 6.50 (dd, 2H), 5.33 (dd, 1H), 3.65 (d, 2H), 3.12-3.01 (m, 2H), 2.87 (dd, 2H), 2.77-2.66 (m, 2H). MS (m/z) 602 [M+H]+.

Example 229

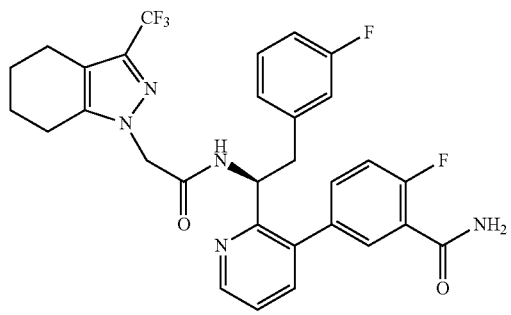

Synthesis of (S)-2-fluoro-5-(2-(2-(3-fluorophenyl)-1-(2-(3-(trifluoromethyl)-4,5,6,7-tetrahydro-1H-indazol-1-yl)acetamido)ethyl)pyridin-3-yl)benzamide (229)

Compound 229 was prepared according to the method presented for the synthesis of Example 59 utilizing 59D and 2-(3-(trifluoromethyl)-4,5,6,7-tetrahydro-1H-indazol-1-yl)acetic acid to provide 37 mg of title compound: $^1$H NMR (400 MHz, cd$_3$od) δ 8.70 (dd, 1H), 7.66 (dd, 1H), 7.47 (dd, 1H), 7.36 (d, 1H), 7.25 (d, 1H), 7.20-7.14 (m, 1H), 7.07 (dd, 1H), 6.83 (dd, 1H), 6.49 (dd, 2H), 5.35 (t, 1H), 4.78 (s, 2H), 3.05 (d, 2H), 2.54 (t, 2H), 2.44 (s, 2H), 1.75 (dd, 4H). MS (m/z) 584 [M+H]+.

Example 230

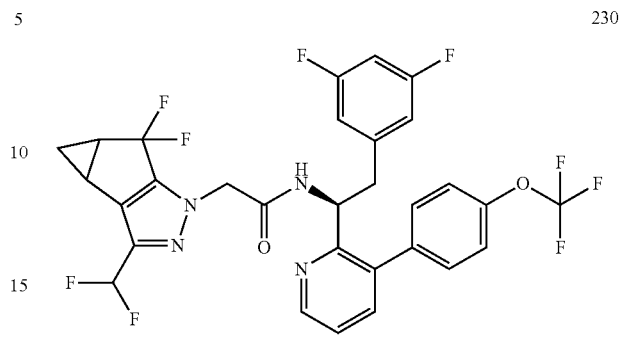

Synthesis of 2-(3-(difluoromethyl)-5,5-difluoro-3b,4,4a,5-tetrahydro-1H-cyclopropa[3,4]cyclopenta[1,2-c]pyrazol-1-yl)-N—((S)-2-(3,5-difluorophenyl)-1-(3-(4-(trifluoromethoxy)phenyl)pyridin-2-yl)ethyl) acetamide (230)

Compound 230 was prepared according to the method presented for the synthesis of Example 68 utilizing 68A and (4-(trifluoromethoxy)phenyl)boronic acid to provide 13 mg of title compound: $^1$H NMR (400 MHz, cd$_3$od) δ 8.67 (d, 1H), 7.58 (d, 1H), 7.40 (dd, 1H), 7.24 (s, 2H), 7.18-7.08 (m, 2H), 6.68 (ddd, 2H), 6.23 (d, 2H), 5.38 (d, 1H), 2.99 (t, 2H), 2.46 (s, 2H), 1.37 (s, 1H), 1.03 (s, 1H). MS (m/z) 641 [M+H]+.

Example 231

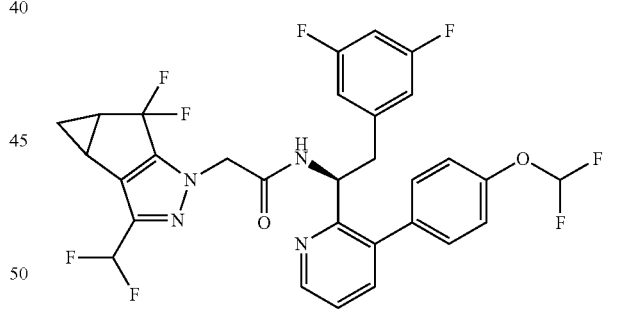

Synthesis of N—((S)-1-(3-(4-(difluoromethoxy)phenyl)pyridin-2-yl)-2-(3,5-difluorophenyl)ethyl)-2-(3-(difluoromethyl)-5,5-difluoro-3b,4,4a,5-tetrahydro-1H-cyclopropa[3,4]cyclopenta[1,2-c]pyrazol-1-yl)acetamide (231)

Compound 231 was prepared according to the method presented for the synthesis of Example 68 utilizing 68A and (4-(difluoromethoxy)phenyl)boronic acid to provide 4 mg of title compound: $^1$H NMR (400 MHz, cd$_3$od) δ 8.65 (d, 1H), 7.58 (d, 1H), 7.39 (dd, 1H), 7.09 (dd, 4H), 7.04-6.50 (m, 4H), 6.27 (s, 2H), 5.40 (s, 1H), 2.99 (d, 2H), 2.46 (s, 2H), 1.37 (s, 1H), 1.10-1.02 (m, 1H). MS (m/z) 641 [M+H]+.

Example 232

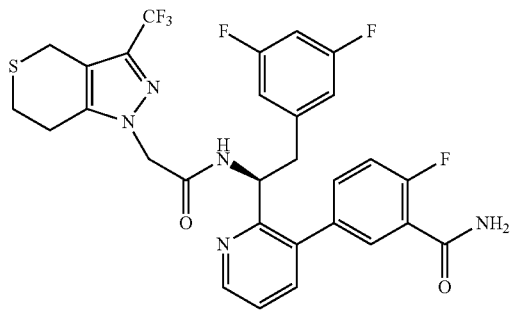

232

Synthesis of (S)-5-(2-(2-(3,5-difluorophenyl)-1-(2-(3-(trifluoromethyl)-6,7-dihydrothiopyrano[4,3-c]pyrazol-1(4H)-yl)acetamido)ethyl)pyridin-3-yl)-2-fluorobenzamide (232)

Compound 232 was prepared according to the method presented for the synthesis of Example 122 substituting dihydro-2H-thiopyran-4(3H)-one for 122B to provide 130 mg of title compound: $^1$H NMR (400 MHz, cdcl$_3$) δ 8.53 (dd, 1H), 7.69-7.55 (m, 2H), 7.45 (dd, 1H), 7.30-7.07 (m, 3H), 6.88 (d, 1H), 6.72 (d, 1H), 6.51 (ddd, 1H), 6.13 (d, 2H), 5.41 (dd, 1H), 3.68 (d, 2H), 2.93-2.64 (m, 6H). MS (m/z) 620 [M+H]$^+$.

Example 233

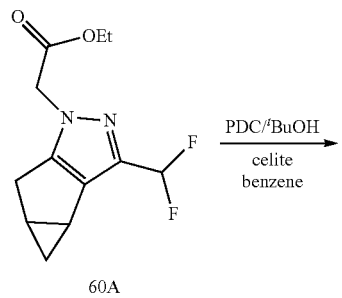

60A

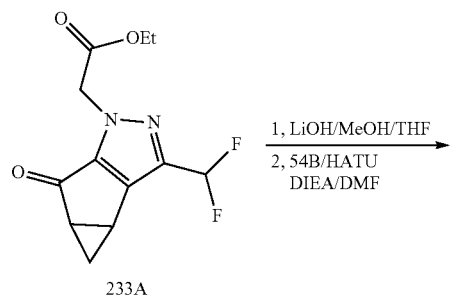

233A

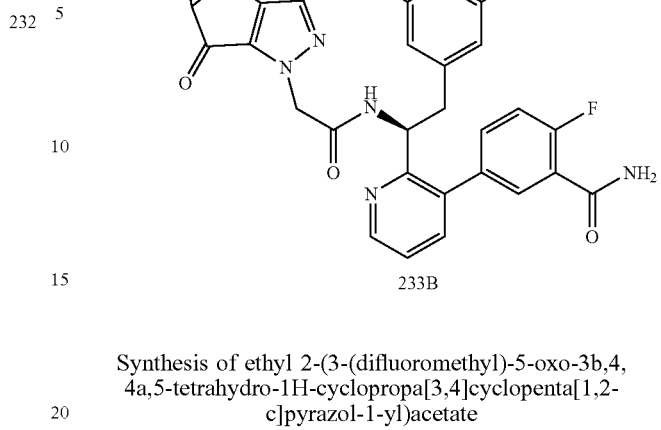

233B

Synthesis of ethyl 2-(3-(difluoromethyl)-5-oxo-3b,4,4a,5-tetrahydro-1H-cyclopropa[3,4]cyclopenta[1,2-c]pyrazol-1-yl)acetate Compound 233A was prepared according to the method presented for the synthesis of Example 181 substituting 60A for 122D to provide 450 mg of title compound. MS (m/z) 271 [M+H]$^+$.

Synthesis of 5-(2-((1S)-1-(2-(3-(difluoromethyl)-5-oxo-3b,4,4a,5-tetrahydro-1H-cyclopropa[3,4]cyclopenta[1,2-c]pyrazol-1-yl)acetamido)-2-(3,5-difluorophenyl)ethyl)pyridin-3-yl)-2-fluorobenzamide (233B)

Compound 233B was prepared according to the method presented for the synthesis of Example 154 substituting 233A for 181A to provide 38 mg of title compound: $^1$H NMR (400 MHz, cd$_3$od) δ 8.70 (dd, 1H), 7.79-7.68 (m, 1H), 7.57-7.48 (m, 1H), 7.42-7.24 (m, 2H), 7.16 (dd, 1H), 6.81-6.52 (m, 2H), 6.25 (d, 2H), 5.30 (dd, 1H), 3.12-2.93 (m, 2H), 2.76-2.63 (m, 1H), 2.46 (dt, 1H), 1.65-1.48 (m, 2H). MS (m/z) 596 [M+H]$^+$.

Example 234

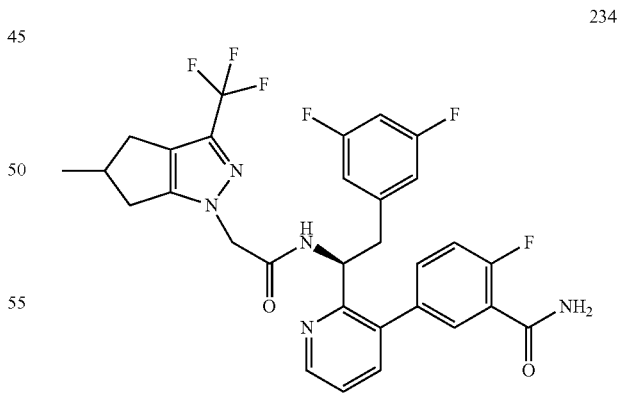

234

Synthesis of 5-(2-((1S)-2-(3,5-difluorophenyl)-1-(2-(5-methyl-3-(trifluoromethyl)-5,6-dihydrocyclopenta[c]pyrazol-1(4H)-yl)acetamido)ethyl)pyridin-3-yl)-2-fluorobenzamide (234)

Compound 234 was prepared according to the method presented for the synthesis of Example 122 substituting 3-methylcyclopentanone for 122B to provide 42 mg of title compound: ¹H NMR (400 MHz, cd₃od) δ 8.70 (d, 1H), 7.68 (dd, 1H), 7.47 (dd, 2H), 7.35 (s, 1H), 7.29-7.16 (m, 1H), 6.75-6.61 (m, 1H), 6.33 (d, 2H), 5.44-5.30 (m, 1H), 4.77 (s, 2H), 3.07 (t, 3H), 2.84 (dddd, 2H), 2.34-2.19 (m, 2H), 1.25-1.12 (m, 3H). MS (m/z) 602 [M+H]$^+$.

Example 235

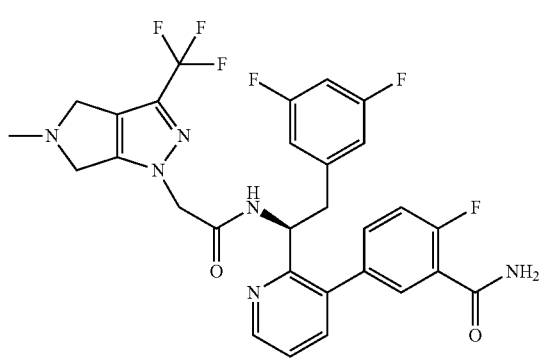

235

Synthesis of (S)-5-(2-(2-(3,5-difluorophenyl)-1-(2-(5-methyl-3-(trifluoromethyl)-5,6-dihydropyrrolo[3,4-c]pyrazol-1(4H)-yl)acetamido)ethyl)pyridin-3-yl)-2-fluorobenzamide (235)

Compound 235 was prepared according to the method presented for the synthesis of Example 210 substituting 251 for 200B to provide 22 mg of title compound: ¹H NMR (400 MHz, cd₃od) δ 8.71 (dd, 1H), 7.62 (ddd, 1.6 Hz, 1H), 7.53 (d, 1H), 7.43 (ddd, 1H), 7.23 (dd, 2H), 6.67 (dd, 1H), 6.33 (t, 2H), 5.38-5.27 (m, 1H), 4.95 (d, 2H), 4.53-4.39 (m, 2H), 4.30-4.14 (m, 2H), 3.16-3.04 (m, 2H), 3.01 (d, 3H). MS (m/z) 603 [M+H]$^+$.

Example 236

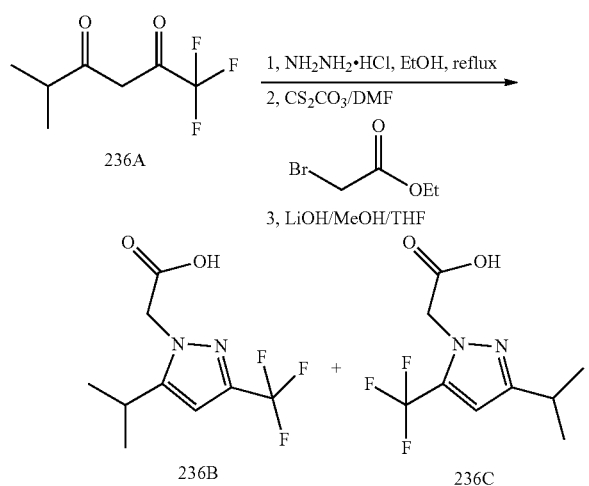

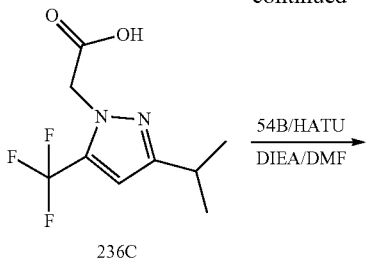

236C

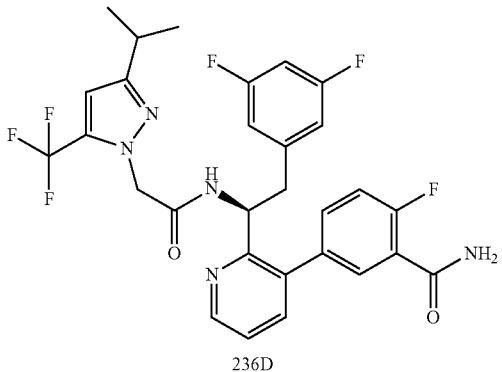

236D

Synthesis of 2-(5-isopropyl-3-(trifluoromethyl)-1H-pyrazol-1-yl)acetic acid (236B) and 2-(3-isopropyl-5-(trifluoromethyl)-1H-pyrazol-1-yl)acetic acid (236C)

Compound 236B and 236C were prepared according to the method presented for the synthesis of Example 238 substituting 1,1,1-trifluoro-5-methylhexane-2,4-dione for 1,1,1-trifluoro-5,5-dimethylhexane-2,4-dione (238A) to provide 420 mg of 236B and 400 mg of 236C. 236B: MS (m/z) 237 [M+H]$^+$. 236C: MS (m/z) 237 [M+H]$^+$.

Synthesis of (S)-5-(2-(2-(3,5-difluorophenyl)-1-(2-(3-isopropyl-5-(trifluoromethyl)-1H-pyrazol-1-yl)acetamido)ethyl)pyridin-3-yl)-2-fluorobenzamide (236D)

Compound 236D was prepared according to the method presented for the synthesis of Example 54 utilizing 54B and 2-(3-isopropyl-5-(trifluoromethyl)-1H-pyrazol-1-yl)acetic acid (236C) to provide 22 mg of title compound: ¹H NMR (400 MHz, cd₃od) δ 8.70 (dd, 1H), 7.67 (dd, 1H), 7.55-7.40 (m, 2H), 7.33 (s, 1H), 7.22 (dd, 1H), 6.75-6.61 (m, 1H), 6.49-6.27 (m, 3H), 5.36 (t, 1H), 4.90 (s, 2H), 3.06 (d, 2H), 2.83 (dt, 1H), 1.24-1.09 (m, 6H). MS (m/z) 590 [M+H]$^+$.

Example 237

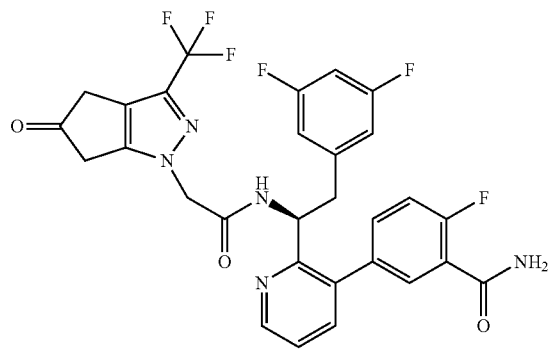

Synthesis of (S)-5-(2-(2-(3,5-difluorophenyl)-1-(2-(5-oxo-3-(trifluoromethyl)-5,6-dihydrocyclopenta[c]pyrazol-1(4H)-yl)acetamido)ethyl)pyridin-3-yl)-2-fluorobenzamide (237)

Compound 237 was prepared according to the method presented for the synthesis of Example 122 substituting 3-ethoxycyclopent-2-enone for 122B to provide 3 mg of title compound: $^1$H NMR (400 MHz, cd$_3$od) δ 8.65 (dt, 1H), 7.54 (dd, 1H), 7.46 (dd, 1H), 7.42-7.26 (m, 2H), 7.19 (dd, 1H), 6.63 (t, 1H), 6.30 (d, 2H), 5.35 (t, 1H), 4.92 (s, 2H), 3.44-3.22 (m, 4H), 3.05 (qd, 2H). MS (m/z) 602 [M+H]$^+$.

Example 238

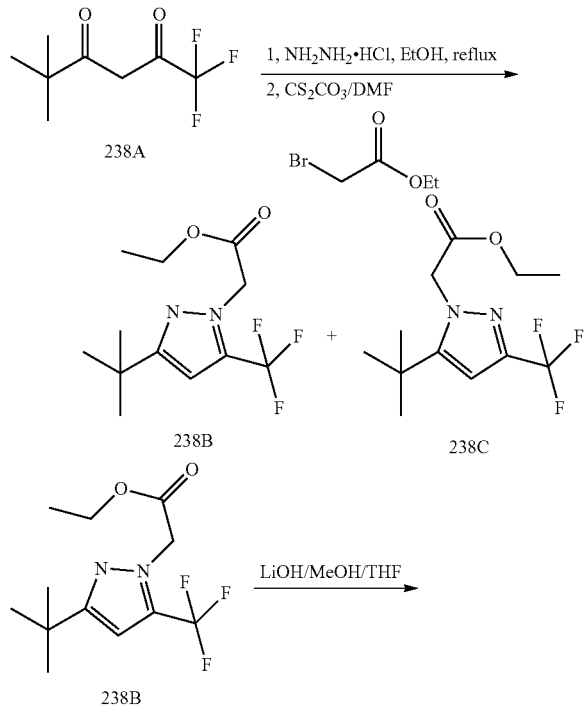

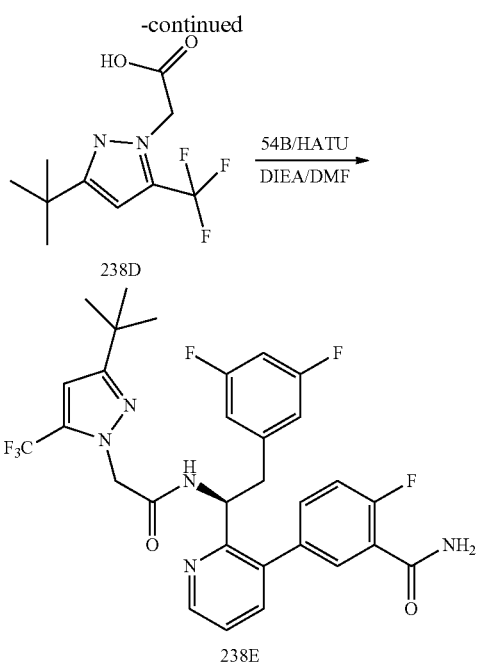

Synthesis of ethyl 2-(3-(tert-butyl)-5-(trifluoromethyl)-1H-pyrazol-1-yl)acetate (238B) and ethyl 2-(5-(tert-butyl)-3-(trifluoromethyl)-1H-pyrazol-1-yl)acetate (238C)

A solution of 1,1,1-trifluoro-5,5-dimethylhexane-2,4-dione (1 g, 5.1 mmol) and hydrazine (280 mg, 5.6 mmol) in ethanol, was heated at reflux for 1 hour. Removed the solvent and used without further purification. To a suspension of crude product and Cs$_2$CO$_3$ (1.6 g, 8.3 mmol) in DMF (6 mL) was added ethyl bromoacetate as a solution in DMF (5 mL). The reaction was stirred at room temperature for 5 hrs and then diluted with water. The mixture was extracted with EtOAc. The organics were dried over Na$_2$SO$_4$, filtered and concentrated. The crude product was purified by SiO$_2$ chromatography eluting with a gradient of EtOAc in hexanes to provide 500 mg of 238B and 750 mg of 238C. 238B: MS (m/z) 279 [M+H]$^+$. 238C: MS (m/z) 279 [M+H]$^+$.

Synthesis of provide 2-(3-(tert-butyl)-5-(trifluoromethyl)-1H-pyrazol-1-yl)acetic acid (238D)

Compound 238D was prepared according to the method presented for the synthesis of Example 74 substituting 238B for 74B to provide 460 mg of title compound. MS (m/z) 251 [M+H]$^+$.

Synthesis of(S)-5-(2-(1-(2-(3-(tert-butyl)-5-(trifluoromethyl)-1H-pyrazol-1-yl)acetamido)-2-(3,5-difluorophenyl)ethyl)pyridin-3-yl)-2-fluorobenzamide (238E)

Compound 238E was prepared according to the method presented for the synthesis of Example 54 utilizing 54B and 2-(3-(tert-butyl)-5-(trifluoromethyl)-1H-pyrazol-1-yl)acetic acid (238D) to provide 23 mg of title compound: $^1$H NMR (400 MHz, cd$_3$od) δ 8.68 (dd, 1H), 7.64 (dd, 1H), 7.49-7.37 (m, 2H), 7.32 (s, 1H), 7.22 (dd, 1H), 6.67 (t, 1H), 6.40 (s, 1H), 6.32 (d, 2H), 5.35 (t, 1H), 5.03 (s, 2H), 3.03 (d, 2H), 1.27 (s, 9H). MS (m/z) 604 [M+H]⁺.

Example 239

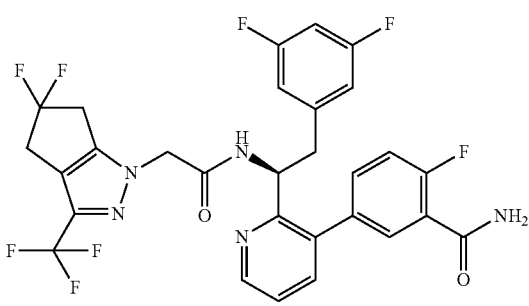 [SMILES: NC(=O)c1cc(-c2cccnc2[C@H](Cc2cc(F)cc(F)c2)NC(=O)Cn2nc(C(F)(F)F)c3c2CC(F)(F)C3)ccc1F]

Synthesis of (S)-5-(2-(1-(2-(5,5-difluoro-3-(trifluoromethyl)-5,6-dihydrocyclopenta[c]pyrazol-1(4H)-yl)acetamido)-2-(3,5-difluorophenyl)ethyl)pyridin-3-yl)-2-fluorobenzamide (239)

Compound 239 was prepared according to the method presented for the synthesis of Example 150 utilizing 237 and 2-(5,5-difluoro-3-(trifluoromethyl)-5,6-dihydrocyclopenta[c]pyrazol-1(4H)-yl)acetic acid to provide 22 mg of title compound: ¹H NMR (400 MHz, cd₃od) δ 8.71 (dd, 1H), 7.66 (dd, 1H), 7.46 (dd, 2H), 7.34 (s, 1H), 7.22 (dd, 1H), 6.74-6.60 (m, 1H), 6.33 (d, 2H), 5.35 (t, 1H), 4.88 (s, 2H), 3.07 (d, 2H). MS (m/z) 624 [M+H]⁺.

Example 240

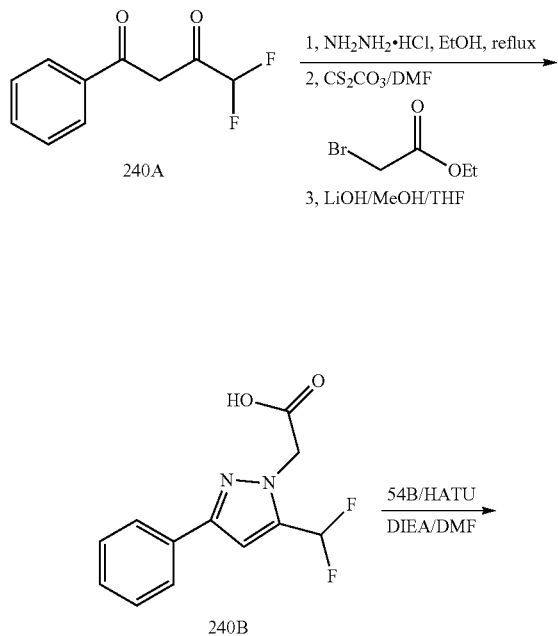

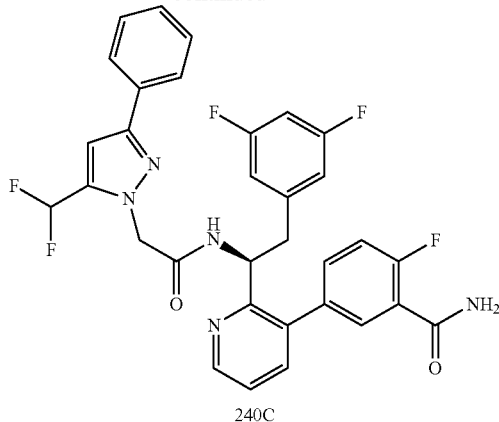

Synthesis of 22-(5-(difluoromethyl)-3-phenyl-1H-pyrazol-1-yl)acetic acid (240B)

Compound 240B was prepared according to the method presented for the synthesis of Example 238 substituting 4,4-difluoro-1-phenylbutane-1,3-dione for 238A to provide 1.4 g of title compound. MS (m/z) 253 [M+H]⁺.

Synthesis of (S)-5-(2-(1-(2-(5-(difluoromethyl)-3-phenyl-1H-pyrazol-1-yl)acetamido)-2-(3,5-difluorophenyl)ethyl)pyridin-3-yl)-2-fluorobenzamide (240C)

Compound 240C was prepared according to the method presented for the synthesis of Example 54 utilizing 54B and 2-(5-(difluoromethyl)-3-phenyl-1H-pyrazol-1-yl)acetic acid (240B) to provide 20 mg of title compound: ¹H NMR (400 MHz, cd₃od) δ 8.69 (dd, 1H), 7.63 (dd, 1H), 7.44 (dd, 1H), 7.41-7.34 (m, 5H), 7.22 (dd, 2H), 6.92-6.53 (m, 3H), 6.28 (d, 2H), 5.32 (t, 1H), 4.85 (s, 2H), 3.08-2.91 (m, 2H). MS (m/z) 606 [M+H]⁺.

Example 241

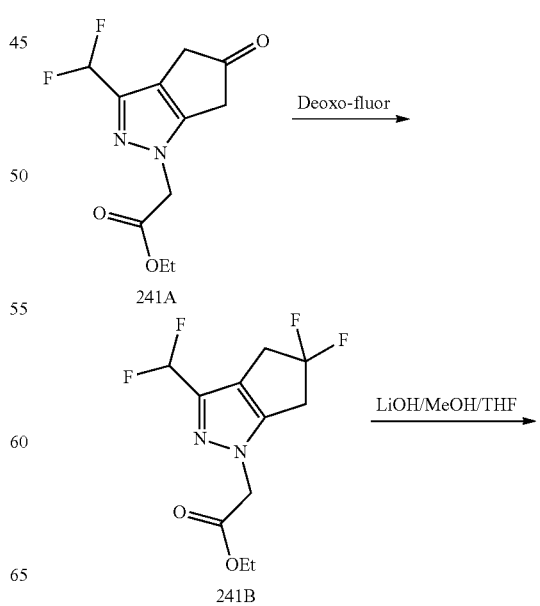

7.68-7.57 (m, 1H), 7.52-7.39 (m, 2H), 7.32 (s, 1H), 7.27-7.16 (m, 1H), 6.65 (dd, 2H), 6.33 (d, 2H), 5.34 (t, 1H), 3.22 (d, 2H), 3.05 (dd, 2H). MS (m/z) 606 [M+H]+.

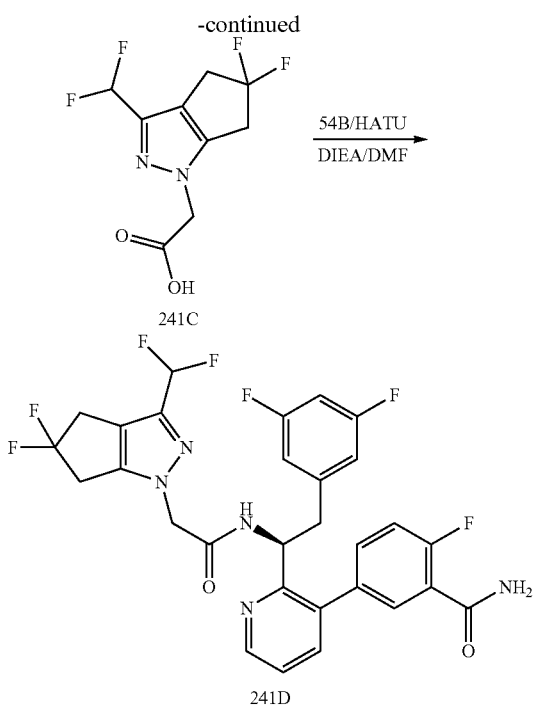

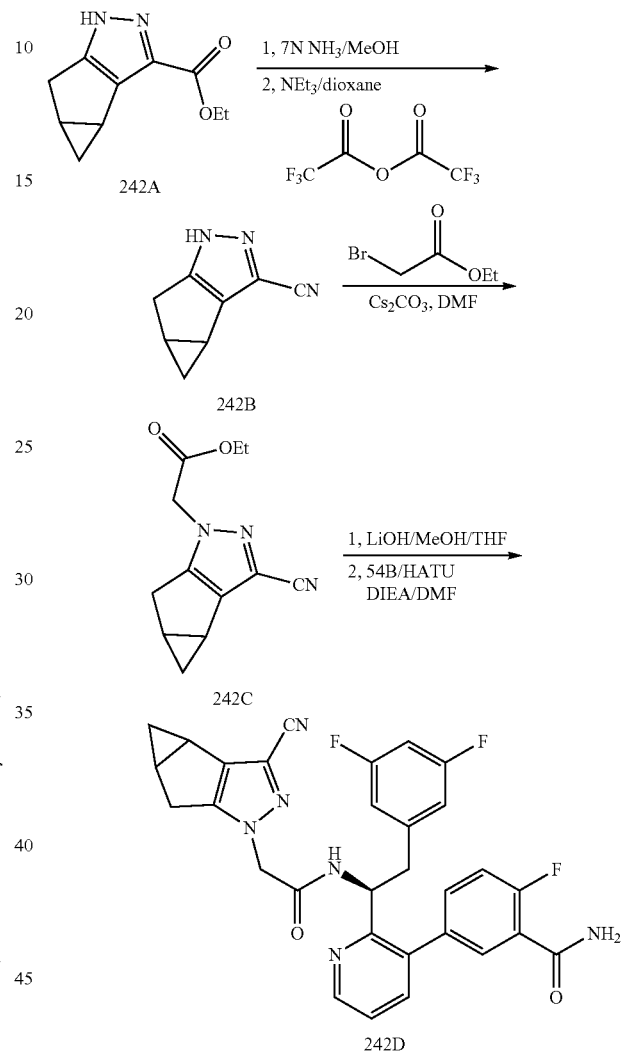

Example 242

Synthesis of Provide ethyl 2-(3-(difluoromethyl)-5-oxo-5,6-dihydrocyclopenta[c]pyrazol-1(4H)-yl)acetate (241A)

Compound 241A was prepared according to the method presented for the synthesis of Example 122 substituting 3-ethoxycyclopent-2-enone for 122B and ethyl 2,2-difluoroacetate for ethyl 2,2,2-trifluoroacetate to provide 1.6 g of title compound. MS (m/z) 259 [M+H]+.

Synthesis of ethyl 2-(3-(difluoromethyl)-5,5-difluoro-5,6-dihydrocyclopenta[c]pyrazol-1(4H)-yl) acetate (241B)

Compound 241B was prepared according to the method presented for the synthesis of Example 150 substituting 241A for 446 to provide 250 mg of title compound. MS (m/z) 281 [M+H]+.

Synthesis of 2-(3-(difluoromethyl)-5,5-difluoro-5,6-dihydrocyclopenta[c]pyrazol-1(4H)-yl)acetic acid (241C)

Compound 241C was prepared according to the method presented for the synthesis of Example 74 substituting 241B for 74B to provide 238 mg of title compound. MS (m/z) 253 [M+H]+.

Synthesis of (S)-5-(2-(1-(2-(3-(difluoromethyl)-5,5-difluoro-5,6-dihydrocyclopenta[c]pyrazol-1(4H)-yl)acetamido)-2-(3,5-difluorophenyl)ethyl)pyridin-3-yl)-2-fluorobenzamide (241D)

Compound 241D was prepared according to the method presented for the synthesis of Example 54 utilizing 54B and 2-(3-(difluoromethyl)-5,5-difluoro-5,6-dihydrocyclopenta[c]pyrazol-1 (4H)-yl)acetic acid (241C) to provide 7 mg of title compound: 1H NMR (400 MHz, cd3od) δ 8.69 (d, 1H),

Synthesis of ethyl 3b,4,4a,5-tetrahydro-1H-cyclopropa[3,4]cyclopenta[1,2-c]pyrazole-3-carboxylate (242A)

Compound 242A was prepared according to the method presented for the synthesis of Example 90 substituting bicyclo[3.1.0]hexan-3-one (122B) for 90A to provide 19.4 g of title compound. MS (m/z) 193 [M+H]+.

Synthesis of 3b,4,4a,5-tetrahydro-1H-cyclopropa[3,4]cyclopenta[1,2-c]pyrazole-3-carbonitrile (242B)

A suspension of 242A (1 g, 5.62 mmol) in 5 mL of NH3 (7N in MeOH) was heated at 130° C. in sealed tube overnight. The reaction was monitored by LC/Mass until complete. Removed the solvent and used as crude. Dissolved the crude product in dioxane (5 mL) and added triethyl amine (4 mL). Trifluoromethanesulfonic anhydride (3.54 g, 16.8 mmol) was added to the mixture dropwise. The reaction was stirred for 2 hours. Diluted mixture with EtOAc (100 mL) and washed with aqueous NaHCO$_3$ twice. The layers were separated and the organic layer was washed 2× H$_2$O and 1× brine. The organics were dried over MgSO$_4$, filtered and concentrated. The crude product was purified by column chromatography on SiO$_2$ to provide 560 mg of title compound. MS (m/z) 146 [M+H]$^+$.

Synthesis of ethyl 2-(3-cyano-3b,4,4a,5-tetrahydro-1H-cyclopropa[3,4]cyclopenta[1,2-c]pyrazol-1-yl)acetate (242C)

Compound 242C was prepared according to the method presented for the synthesis of Example 74 substituting 560 mg of 242B for 74A to provide 463 mg of title compound. MS (m/z) 232 [M+H]$^+$.

Synthesis of 5-(2-((1S)-1-(2-(3-cyano-3b,4,4a,5-tetrahydro-1H-cyclopropa[3,4]cyclopenta[1,2-c]pyrazol-1-yl)acetamido)-2-(3,5-difluorophenyl)ethyl)pyridin-3-yl)-2-fluorobenzamide (242D)

Compound 242D was prepared according to the method presented for the synthesis of Example 122 substituting 242C for 122D to provide 41 mg of title compound: $^1$H NMR (400 MHz, cd$_3$od) δ 8.63 (dd, 1H), 7.57 (d, 1H), 7.48-7.33 (m, 2H), 7.25 (s, 1H), 7.15 (ddd, 1H), 6.68-6.53 (m, 1H), 6.25 (d, 2H), 5.26 (td, 1H), 4.75-4.56 (m, 2H), 2.98 (d, 2H), 2.83-2.69 (m, 1H), 2.61 (dd, 1H), 2.13-1.99 (m, 2H), 1.05 (dd, 1H), 0.26-0.14 (m, 1H). MS (m/z) 557 [M+H]$^+$.

Example 243

Synthesis of 5-(2-((1 S)-1-(2-(3-(difluoromethyl)-5-hydroxy-3b,4,4a,5-tetrahydro-2H-cyclopropa[3,4]cyclopenta[1,2-c]pyrazol-2-yl)acetamido)-2-(3,5-difluorophenyl)ethyl)pyridin-3-yl)-2-fluorobenzamide (243)

Compound 243 was prepared according to the method presented for the synthesis of Example 154 substituting 220B for 154B to provide 4 mg: $^1$H NMR (400 MHz, cd$_3$od) δ 8.68 (d, 1H), 7.59 (dd, 1H), 7.48-7.32 (m, 2H), 7.32-7.13 (m, 2H), 6.87 (dd, 1H), 6.65 (t, 1H), 6.29 (d, 2H), 5.45-5.28 (m, 2H), 3.13-2.92 (m, 2H), 2.19 (d, 2H), 1.27 (s, 2H), 1.03 (dd, 1H), 0.83 (s, 1H). MS (m/z) 598 [M+H]$^+$.

Example 244

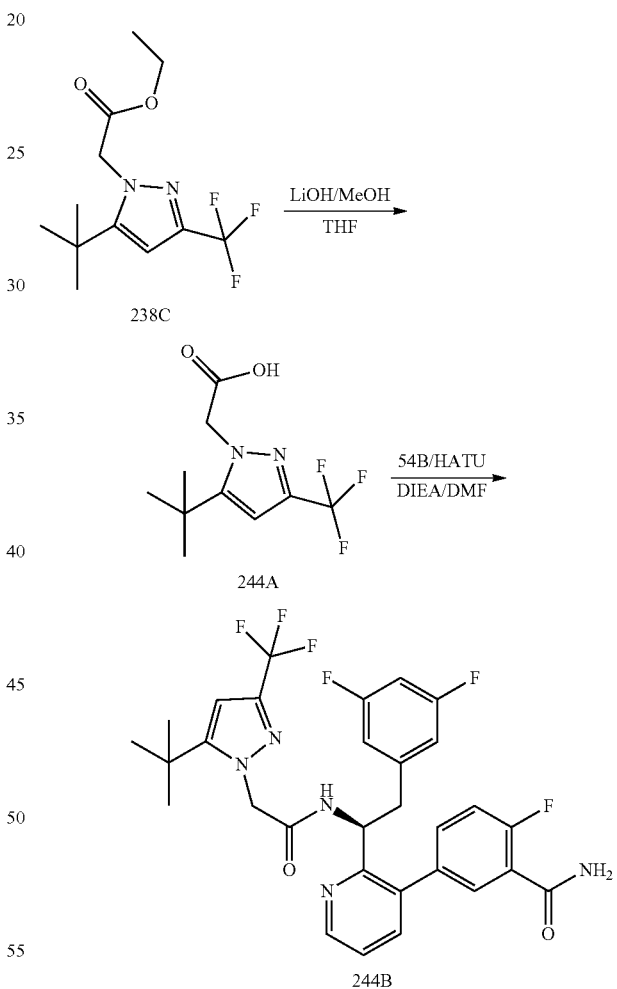

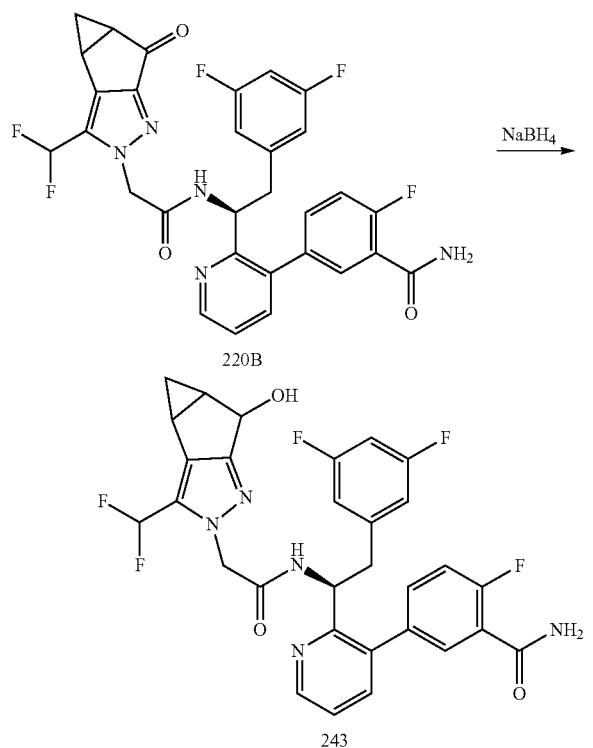

Synthesis of 2-(5-(tert-butyl)-3-(trifluoromethyl)-1H-pyrazol-1-yl)acetic acid (244A)

Compound 244A was prepared according to the method presented for the synthesis of Example 74 substituting 238C for 74B to provide 450 mg of title compound. MS (m/z) 251 [M+H]$^+$.

Synthesis of (S)-5-(2-(1-(2-(5-(tert-butyl)-3-(trifluoromethyl)-1H-pyrazol-1-yl)acetamido)-2-(3,5-difluorophenyl)ethyl)pyridin-3-yl)-2-fluorobenzamide (244B)

Compound 244B was prepared according to the method presented for the synthesis of Example 54 utilizing 54B and 2-(5-(tert-butyl)-3-(trifluoromethyl)-1H-pyrazol-1-yl)acetic acid (244A) to provide 22 mg of title compound: $^1$H NMR (400 MHz, cd$_3$od) δ 8.67 (dd, 1H), 7.65 (dd, 1H), 7.45 (dd, 1H), 7.39 (d, 1H), 7.31 (s, 1H), 7.23 (dd, 1H), 6.71-6.59 (m, 2H), 6.28 (d, 2H), 5.37 (t, 1H), 4.91 (d, 2H), 3.00 (d, 2H), 1.29 (s, 9H). MS (m/z) 604 [M+H]$^+$.

Example 245F

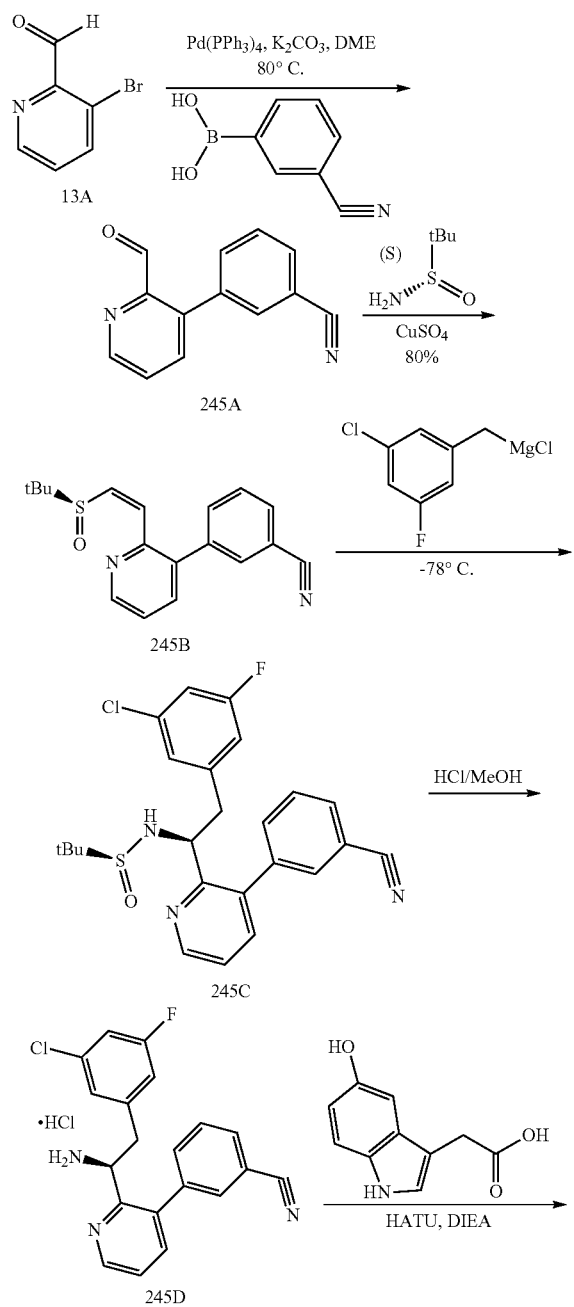

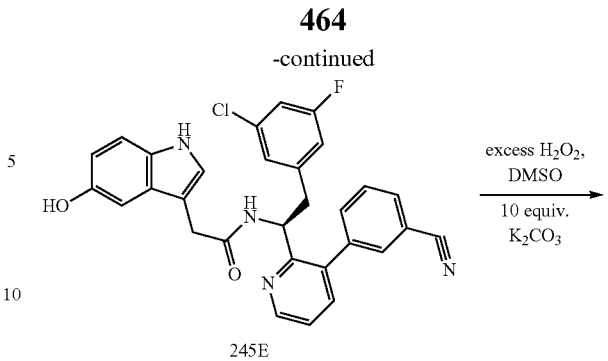

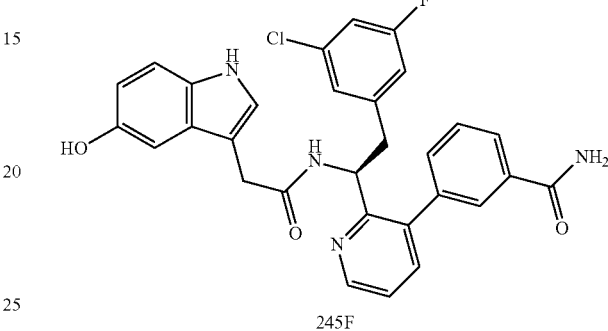

Synthesis of 3-(2-formylpyridin-3-yl)benzonitrile (245A)

Compound 245A was prepared according to the method presented for the synthesis of Example 13 utilizing 13A and (3-cyanophenyl)boronic acid to provide 3.8 g of title compound: MS (m/z) 209 [M+H]$^+$.

Synthesis of (S,Z)—N-((3-(3-cyanophenyl)pyridin-2-yl)methylene)-2-methylpropane-2-sulfinamide (245B)

Compound 245B was prepared according to the method presented for the synthesis of Example 13 substituting 245A for 13B to provide 4 g of title compound: MS (m/z) 312 [M+H]$^+$.

Synthesis of (S)—N—((S)-2-(3-chloro-5-fluorophenyl)-1-(3-(3-cyanophenyl)pyridin-2-yl)ethyl)-2-methylpropane-2-sulfinamide (245C)

Compound 245C was prepared according to the method presented for the synthesis of Example 13 substituting 245B for 13C and (3-chloro-5-fluorobenzyl)magnesium chloride to provide 1.9 g of title compound: MS (m/z) 456 [M+H]$^+$.

Synthesis of (S)-3-(2-(1-amino-2-(3-chloro-5-fluorophenyl)ethyl)pyridin-3-yl)benzonitrile hydrochloride (245D)

Compound 245D was prepared according to the method presented for the synthesis of Example 13 substituting 245C for 13E to provide 70 mg of title compound: MS (m/z) 352 [M+H]$^+$.

Synthesis of (S)—N-(2-(3-chloro-5-fluorophenyl)-1-(3-(3-cyanophenyl)pyridin-2-yl)ethyl)-2-(5-hydroxy-1H-indol-3-yl)acetamide (245E)

Compound 245E was prepared according to the method presented for the synthesis of Example 13 substituting 245D for 13F to provide 120 mg of title compound: MS (m/z) 525 [M+H]⁺.

Synthesis of (S)-3-(2-(2-(3-chloro-5-fluorophenyl)-1-(2-(5-hydroxy-1H-indol-3-yl)acetamido)ethyl)pyridin-3-yl)benzamide (245F)

H$_2$O$_2$ (30 wt %, excess) was added to a suspension of 245E (120 mg, 0.19 mmol) and potassium carbonate (210 mg, 1.52 mmol) in DMSO (1 mL) at 0° C. The suspension and stirred for 1 hour, filtered and the filtrate was purified by RP HPLC using a C18 column with a gradient of H$_2$O, 0.1% TFA-acetonitrile, to provide 80 mg of the title product. ¹H NMR (400 MHz, dmso) δ 10.42 (s, 1H), 8.61 (dd, 1H), 8.44 (d, 1H), 7.91 (s, 1H), 7.83 (d, 1H), 7.66 (s, 1H), 7.56 (dd, 1H), 7.47-7.25 (m, 4H), 7.02 (d, 2H), 6.88 (s, 1H), 6.73 (d, 1H), 6.55 (s, 1H), 6.54-6.43 (m, 2H), 5.16 (dd, 2H), 3.36 (s, 2H), 2.88 (d, 2H). MS (m/z) 543 [M+H]⁺.

Example 246

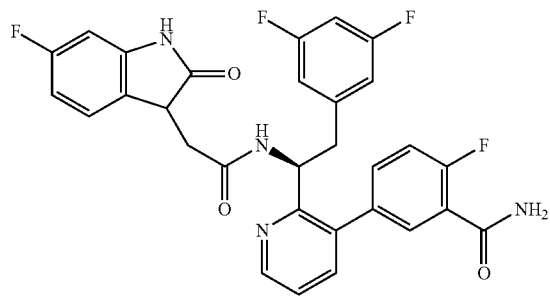

246

Synthesis of 5-(2-((1S)-2-(3,5-difluorophenyl)-1-(2-(6-fluoro-2-oxoindolin-3-yl)acetamido)ethyl)pyridin-3-yl)-2-fluorobenzamide (246)

Compound 246 was prepared according to the method presented for the synthesis of Example 54 utilizing 54B and 2-(6-fluoro-2-oxoindolin-3-yl)acetic acid to provide 13 mg of title compound: ¹H NMR (400 MHz, cd$_3$od) δ 8.62 (d, 1H), 7.64-7.53 (m, 1H), 7.43-7.33 (m, 1H), 7.31-7.00 (m, 3H), 6.95-6.79 (m, 1H), 6.68-6.35 (m, 3H), 6.30-6.12 (m, 2H), 5.24 (dd, 1H), 3.62 (s, 1H), 3.01-2.72 (m, 3H), 2.65-2.49 (m, 1H). MS (m/z) 563 [M+H]⁺.

Example 247

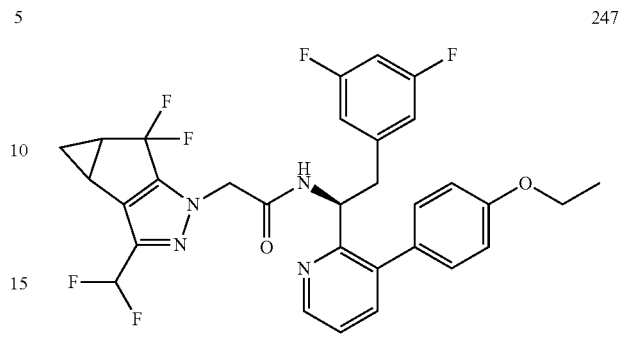

247

Synthesis of 2-(3-(difluoromethyl)-5,5-difluoro-3b,4,4a,5-tetrahydro-1H-cyclopropa[3,4]cyclopenta[1,2-c]pyrazol-1-yl)-N—((S)-2-(3,5-difluorophenyl)-1-(3-(4-ethoxyphenyl)pyridin-2-yl)ethyl)acetamide (247)

Compound 247 was prepared according to the method presented for the synthesis of Example 68 utilizing 68A and (4-ethoxyphenyl)boronic acid to provide 8 mg of title compound: ¹H NMR (400 MHz, cd$_3$od) δ 8.61 (d, 1H), 7.61 (d, 1H), 7.40 (dd, 4.9 Hz, 1H), 7.03-6.94 (m, 2H), 6.90 (dd, 2H), 6.86-6.51 (m, 3H), 6.25 (d, 2H), 5.48 (d, 1H), 4.05 (q, 2H), 2.96 (t, 2H), 2.46 (s, 2H), 1.39 (t, 4H), 1.07 (s, 1H). MS (m/z) 601 [M+H]⁺.

Example 248

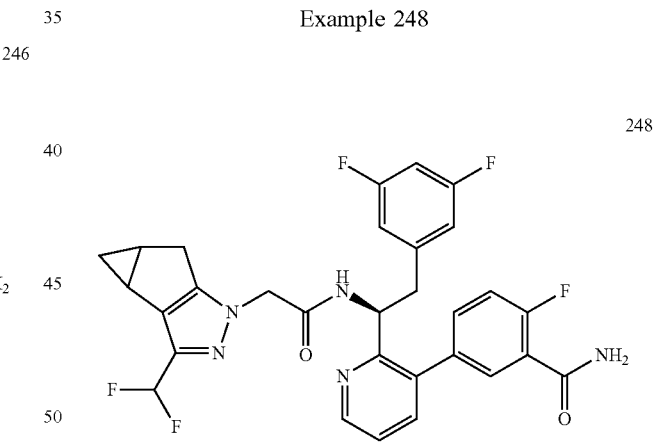

248

Synthesis of 5-(2-((1S)-1-(2-(3-(difluoromethyl)-3b,4,4a,5-tetrahydro-1H-cyclopropa[3,4]cyclopenta[1,2-c]pyrazol-1-yl)acetamido)-2-(3,5-difluorophenyl)ethyl)pyridin-3-yl)-2-fluorobenzamide (248)

248 was separated from the diastereomeric mixture of 198 by semi-preparative chiral HPLC fitted with a Chiralcel AZ-H column running a 70:30 mixture of Hep:IPA. The fast eluent was collected to obtain 3 mg of the single diastereomer: ¹H NMR (400 MHz, cd$_3$od) δ 8.50 (dd, 1H), 7.46 (dd, 1H), 7.34-7.10 (m, 3H), 7.04 (dd, 8.5 Hz, 1H), 6.58-6.23 (m, 2H), 6.11 (t, 2H), 5.15 (t, 1H), 4.57-4.38 (m, 2H), 2.93-2.79 (m, 2H), 2.59 (dd, 1H), 2.43 (d, 1H), 1.99-1.77 (m, 2H), 0.86 (td, 1H), 0.01 (dd, 1H). MS (m/z) 582 [M+H]⁺.

Example 249

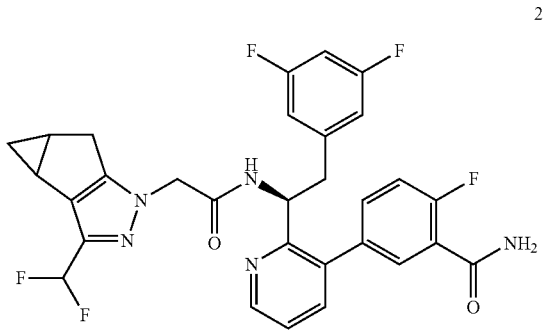

249

Synthesis of 5-(2-((1S)-1-(2-(3-(difluoromethyl)-3b,4,4a,5-tetrahydro-1H-cyclopropa[3,4]cyclopenta[1,2-c]pyrazol-1-yl)acetamido)-2-(3,5-difluorophenyl)ethyl)pyridin-3-yl)-2-fluorobenzamide (249)

249 was separated from the diastereomeric mixture of 198 by semi-preparative chiral HPLC fitted with a Chiralcel AZ-H column running a 70:30 mixture of Hep:IPA. The slow eluent was collected to obtain 3 mg of the single diastereomer: $^1$H NMR (400 MHz, cd$_3$od) δ 8.47 (dd, 1H), 7.40 (dd, 1H), 7.21 (dd, 2H), 7.10 (s, 1H), 7.01 (dd, 1H), 6.54-6.20 (m, 2H), 6.11 (d, 2H), 5.12 (t, 1H), 4.54-4.37 (m, 2H), 2.93-2.72 (m, 2H), 2.58 (dd, 1H), 2.44 (d, 1H), 1.86 (dd, 2H), 0.85 (td, 1H), 0.02 (dd, 1H). MS (m/z) 582 [M+H]$^+$.

Example 250

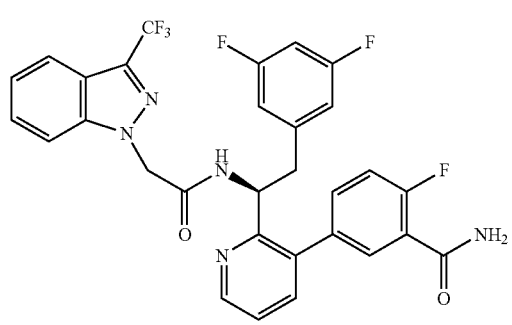

250

Synthesis of (S)-5-(2-(2-(3,5-difluorophenyl)-1-(2-(3-(trifluoromethyl)-1H-indazol-1-yl)acetamido)ethyl)pyridin-3-yl)-2-fluorobenzamide (250)

Compound 250 was prepared according to the method presented for the synthesis of Example 54 utilizing 54B and 2-(3-(trifluoromethyl)-1H-indazol-1-yl)acetic acid to provide 36 mg of title compound: $^1$H NMR (400 MHz, dmso) δ 9.13 (d, 1H), 8.71 (dd, 1H), 7.73 (d, 1H), 7.67-7.55 (m, 3H), 7.52-7.35 (m, 4H), 7.28 (ddd, 2H), 6.92 (t, 1H), 6.57 (d, 2H), 5.27-5.09 (m, 3H), 3.03 (d, 2H). MS (m/z) 598 [M+H]$^+$.

Example 251

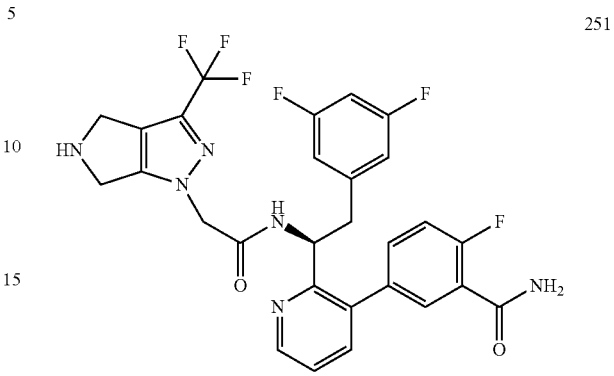

251

Synthesis of (S)-5-(2-(2-(3,5-difluorophenyl)-1-(2-(3-(trifluoromethyl)-5,6-dihydropyrrolo[3,4-c]pyrazol-1(4H)-yl)acetamido)ethyl)pyridin-3-yl)-2-fluorobenzamide (251)

Compound 251 was prepared according to the method presented for the synthesis of Example 200 substituting 227 for 200A to provide 7 mg of title compound: $^1$H NMR (400 MHz, cd$_3$od) δ 8.70 (dd, 1H), 7.58 (dd, 2H), 7.40 (dd, 1H), 7.19 (t, 2H), 6.66 (tt, 1H), 6.33 (t, 2H), 5.32 (dd, 1H), 4.96 (s, 2H), 4.51 (s, 2H), 4.46 (s, 2H), 3.08 (qd, 2H). MS (m/z) 589 [M+H]$^+$.

Example 252

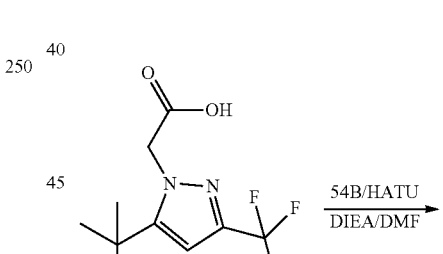

236B

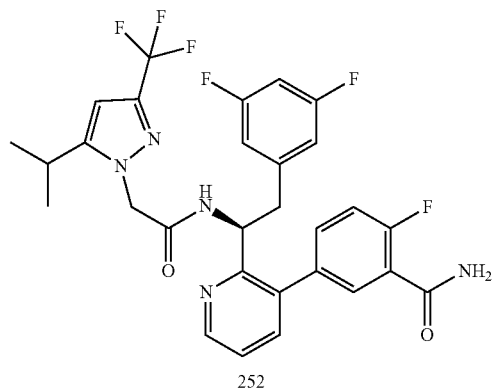

252

Synthesis of (S)-5-(2-(2-(3,5-difluorophenyl)-1-(2-(5-isopropyl-3-(trifluoromethyl)-1H-pyrazol-1-yl)acetamido)ethyl)pyridin-3-yl)-2-fluorobenzamide (252)

Compound 252 was prepared according to the method presented for the synthesis of Example 54 utilizing 54B and 2-(5-isopropyl-3-(trifluoromethyl)-1H-pyrazol-1-yl)acetic acid (236B) to provide 18 mg of title compound: ¹H NMR (400 MHz, cd₃od) δ 8.70 (dd, 1H), 7.65 (dd, 1H), 7.45 (dd, 2H), 7.33 (s, 1H), 7.22 (dd, 1H), 6.67 (t, 1H), 6.40 (s, 1H), 6.34 (d, 2H), 5.36 (t, 1H), 4.90 (s, 2H), 3.06 (d, 2H), 2.83 (dt, 1H), 1.17 (t, 6H). MS (m/z) 590 [M+H]⁺.

Example 253

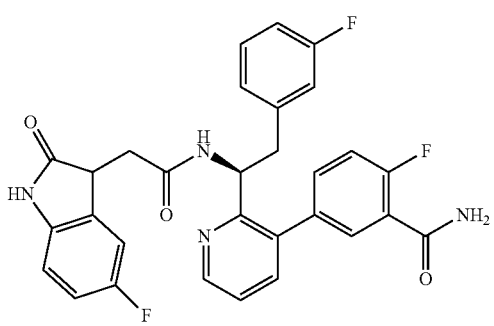

Synthesis of 2-fluoro-5-(2-((1S)-1-(2-(5-fluoro-2-oxoindolin-3-yl)acetamido)-2-(3-fluorophenyl)ethyl)pyridin-3-yl)benzamide (253)

Compound 253 was prepared according to the method presented for the synthesis of Example 59 utilizing 59D and 2-(5-fluoro-2-oxoindolin-3-yl)acetic acid to provide 21 mg of title compound: ¹H NMR (400 MHz, cd₃od) δ 8.62 (ddd, 1H), 7.56 (ddd, 1H), 7.45-7.24 (m, 2H), 7.22-6.80 (m, 51H), 6.73 (ddd, 2H), 6.43 (t, 1H), 6.40-6.32 (m, 1H), 5.23 (dt, 1H), 3.89-3.74 (m, 1H), 3.03-2.88 (m, 2H), 2.66-2.54 (m, 2H). MS (m/z) 545 [M+H]⁺.

Example 254

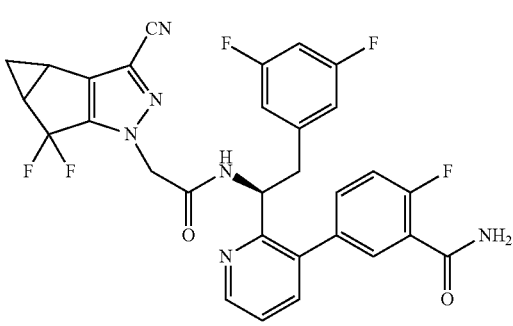

Synthesis of 5-(2-((1S)-1-(2-(3-cyano-5,5-difluoro-3b,4,4a,5-tetrahydro-1H-cyclopropa[3,4]cyclopenta[1,2-c]pyrazol-1-yl)acetamido)-2-(3,5-difluorophenyl)ethyl)pyridin-3-yl)-2-fluorobenzamide (254)

Compound 254 was prepared according to the method presented for the synthesis of Example 181 substituting 242C for 122D to provide 28 mg of title compound: ¹H NMR (400 MHz, cd₃od) δ 8.72 (dd, 1H), 7.67 (d, 1H), 7.48 (dd, 1H), 7.34 (d, 2H), 7.27-7.16 (m, 1H), 6.67 (t, 1H), 6.31 (d, 2H), 5.34 (t, 1H), 4.90 (s, 2H), 3.06 (dd, 2H), 2.52 (d, 2H), 1.42 (dd, 1H), 1.11 (s, 1H). MS (m/z) 593 [M+H]⁺.

Example 255

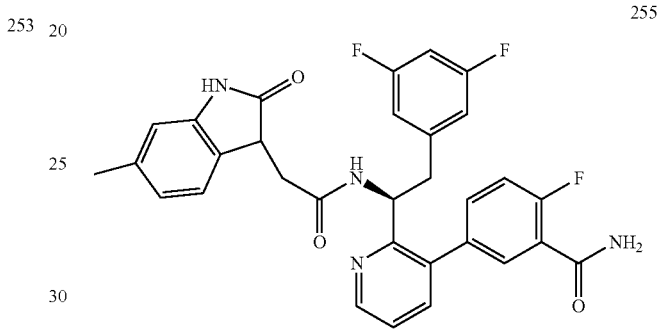

Synthesis of 5-(2-((1S)-2-(3,5-difluorophenyl)-1-(2-(6-methyl-2-oxoindolin-3-yl)acetamido)ethyl)pyridin-3-yl)-2-fluorobenzamide (255)

Compound 225 was prepared according to the method presented for the synthesis of Example 54 utilizing 54B and 2-(6-methyl-2-oxoindolin-3-yl)acetic acid to provide 7 mg of title compound: ¹H NMR (400 MHz, cd₃od) δ 8.71 (t, 1H), 7.75-7.66 (m, 1H), 7.50 (td, 1H), 7.46-7.09 (m, 3H), 7.08-6.52 (m, 5H), 6.29 (t, 2H), 5.32 (dd, 1H), 3.66 (d, 1H), 3.06-2.93 (m, 2H), 2.93-2.56 (m, 3H), 2.23 (d, 3H). MS (m/z) 559 [M+H]⁺.

Example 256

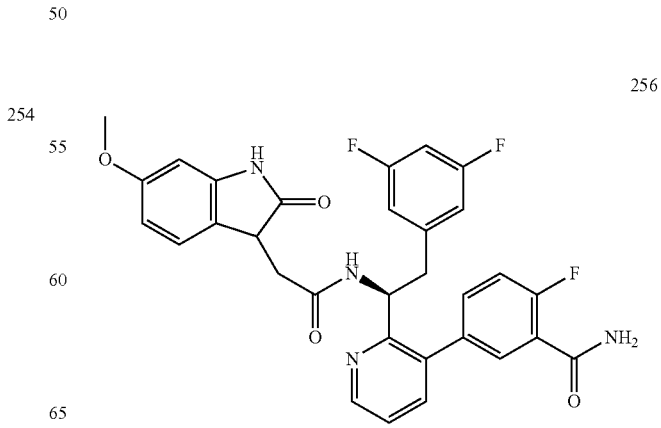

471

Synthesis of 5-(2-((1S)-2-(3,5-difluorophenyl)-1-(2-(6-methoxy-2-oxoindolin-3-yl)acetamido)ethyl)pyridin-3-yl)-2-fluorobenzamide (256)

Compound 256 was prepared according to the method presented for the synthesis of Example 54 utilizing 54B and 2-(6-methoxy-2-oxoindolin-3-yl)acetic acid to provide 19 mg of title compound: $^1$H NMR (400 MHz, cd$_3$od) δ 8.68 (dd, 1H), 7.61 (dd, 1H), 7.53-7.34 (m, 2H), 7.34-7.08 (m, 2H), 7.03 (d, 1H), 6.74-6.57 (m, 1H), 6.56-6.22 (m, 4H), 5.31 (dt, 1H), 3.91-3.70 (m, 4H), 3.13-2.89 (m, 2H), 2.76-2.58 (m, 2H). MS (m/z) 575 [M+H]$^+$.

Example 257

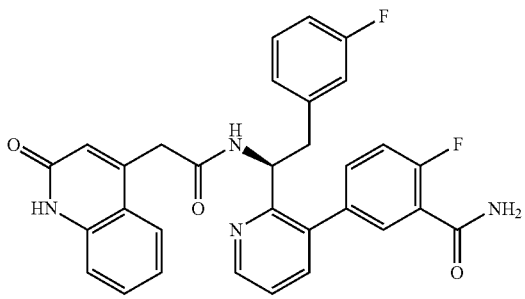

257

Synthesis of (S)-2-fluoro-5-(2-(2-(3-fluorophenyl)-1-(2-(2-oxo-1,2-dihydroquinolin-4-yl)acetamido)ethyl)pyridin-3-yl)benzamide (257)

Compound 257 was prepared according to the method presented for the synthesis of Example 59 utilizing 59D and 2-(2-oxo-1,2-dihydroquinolin-4-yl)acetic acid to provide 15 mg of title compound: $^1$H NMR (400 MHz, cd$_3$od) δ 8.73 (dd, 1H), 7.67 (dd, 2H), 7.56-7.45 (m, 2H), 7.40-7.24 (m, 3H), 7.23-7.10 (m, 2H), 7.04 (dd, 1H), 6.81 (dd, 1H), 6.60-6.41 (m, 3H), 5.33 (t, 1H), 3.85 (s, 2H), 3.13-3.02 (m, 2H). MS (m/z) 539 [M+H]$^+$.

Example 258

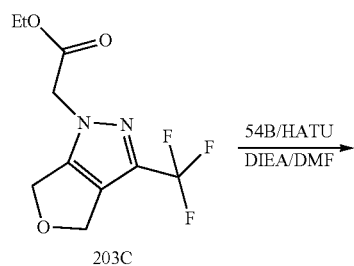

203C

472

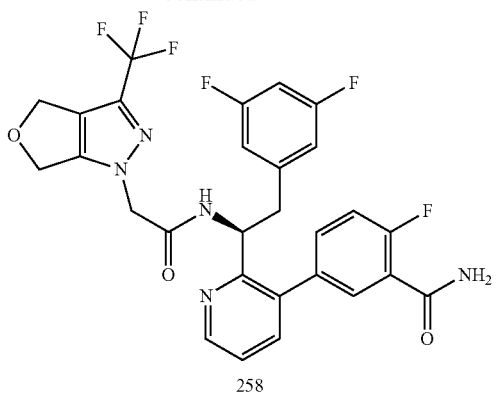

258

Synthesis of (S)-5-(2-(2-(3,5-difluorophenyl)-1-(2-(3-(trifluoromethyl)-4,6-dihydro-1H-furo[3,4-c]pyrazol-1-yl)acetamido)ethyl)pyridin-3-yl)-2-fluorobenzamide (258)

Compound 258 was prepared according to the method presented for the synthesis of Example 122 substituting 203C for 122D to provide 42 mg of title compound: $^1$H NMR (400 MHz, cd$_3$od) δ 8.70 (dd, 1H), 7.63 (dd, 1H), 7.54-7.39 (m, 2H), 7.31 (s, 1H), 7.22 (dd, 1H), 6.66 (t, 1H), 6.32 (d, 2H), 5.34 (t, 1H), 4.90-4.84 (m, 4H), 4.78 (d, 2H), 3.16-2.97 (m, 2H). MS (m/z) 590 [M+H]$^+$.

Example 259

259

Synthesis of 5-(2-((1S)-2-(3,5-difluorophenyl)-1-(2-(4,7-dimethyl-2-oxoindolin-3-yl)acetamido)ethyl)pyridin-3-yl)-2-fluorobenzamide (259)

Compound 259 was prepared according to the method presented for the synthesis of Example 54 utilizing 54B and 2-(4,7-dimethylindolin-3-yl)acetic acid to provide 21 mg of title compound: $^1$H NMR (400 MHz, cd$_3$od) δ 8.76-8.65 (m, 1H), 7.62 (dd, 1H), 7.46 (dd, 1H), 7.12 (ddd, 3H), 6.93-6.57 (m, 4H), 6.29 (dd, 3H), 5.30-5.15 (m, 1H), 3.69 (d, 1H), 3.14-2.82 (m, 5H), 2.15 (d, 6H). MS (m/z) 573 [M+H]$^+$.

Example 260

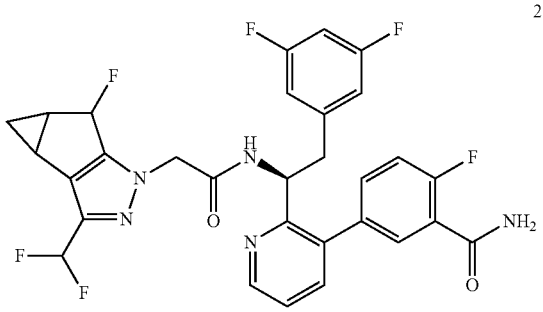

Synthesis of 5-(2-((1S)-1-(2-(3-(difluoromethyl)-5-fluoro-3b,4,4a,5-tetrahydro-1H-cyclopropa[3,4]cyclopenta[1,2-c]pyrazol-1-yl)acetamido)-2-(3,5-difluorophenyl)ethyl)pyridin-3-yl)-2-fluorobenzamide (260)

Compound 260 was prepared according to the method presented for the synthesis of Example 390 substituting 212 for 334 to provide 18 mg of title compound: $^1$H NMR (400 MHz, cd$_3$od) δ 8.73-8.55 (m, 1H), 7.67-7.53 (m, 1H), 7.50-7.08 (m, 4H), 6.78-6.37 (m, 2H), 6.22 (td, 2H), 6.14-5.86 (m, 1H), 5.46 (dd, 1H), 5.25 (ddd, 1H), 3.03-2.85 (m, 2H), 2.36-2.10 (m, 2H), 1.21 (dd, 1H), 1.12-0.84 (m, 1H), 0.39-0.15 (m, 1H). MS (m/z) 600 [M+H]$^+$.

Example 261

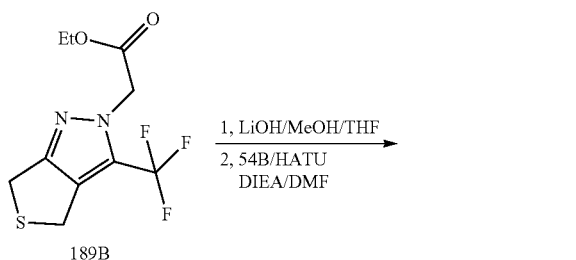

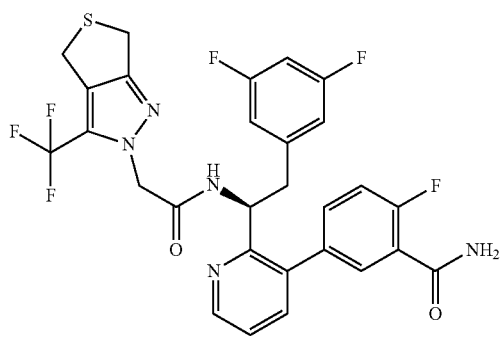

Synthesis of (S)-5-(2-(2-(3,5-difluorophenyl)-1-(2-(3-(trifluoromethyl)-4,6-dihydro-2H-thieno[3,4-c]pyrazol-2-yl)acetamido)ethyl)pyridin-3-yl)-2-fluorobenzamide (261)

Compound 261 was prepared according to the method presented for the synthesis of Example 122 substituting 189B for 122D to provide to provide 31 mg of title compound: $^1$H NMR (400 MHz, cd$_3$od) δ 8.73-8.59 (m, 1H), 7.53 (dd, 1H), 7.49-7.26 (m, 3H), 7.26-7.15 (m, 1H), 6.63 (t, 1H), 6.37-6.23 (m, 2H), 5.35 (t, 1H), 4.88 (d, 1H), 4.00-3.78 (m, 4H), 3.15-2.89 (m, 2H). MS (m/z) 606 [M+H]$^+$.

Example 262

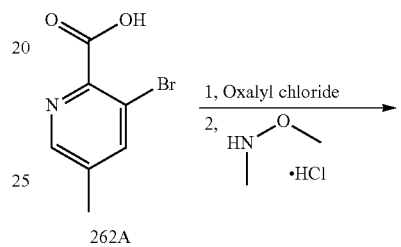

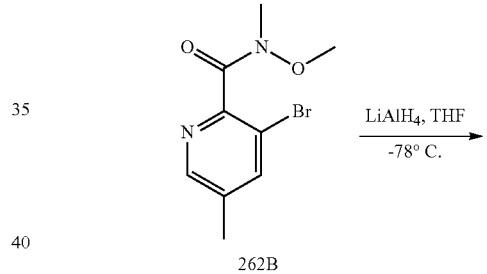

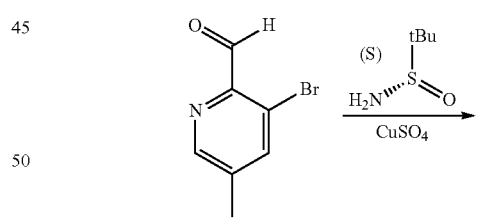

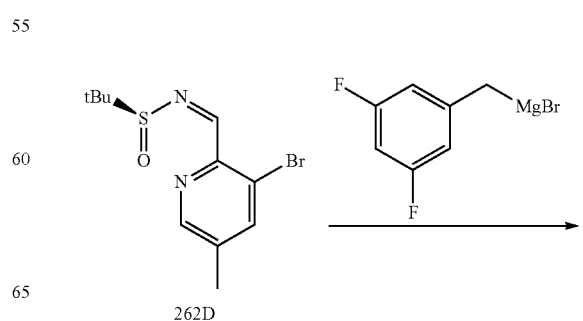

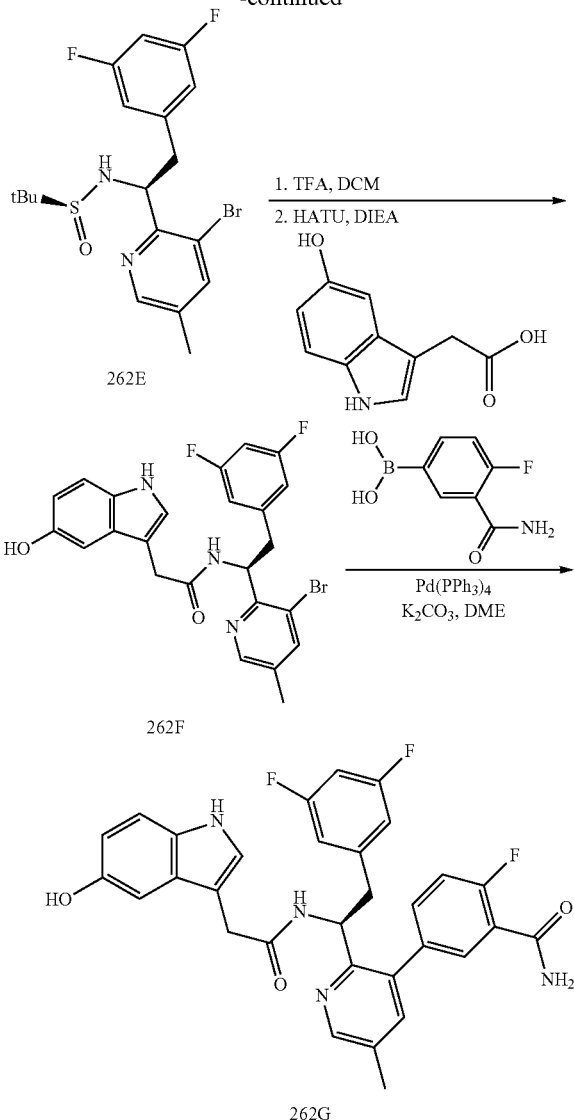

Synthesis of 3-bromo-N-methoxy-N,5-dimethylpicolinamide (262B)

A solution of 262A (1 g, 4.63 mmol) in oxalyl chloride (5 mL) was heated at 60° C. for 30 minutes. Removed the solvent and dissolved in DCM (10 mL). Cooled mixture to 0° C. N,O-Dimethylhydroxylamine hydrochloride (0.57 g, 5.84 mmol) and DIEA (1.61 mL, 9.26 mmol) were added to the mixture slowly. After 1 hour, diluted the reaction with EtOAc (50 mL) and washed with brine (20 mL) twice. The organic layer was dried with Na$_2$SO$_4$, concentrated and purified by flash column (Rf: 0.3 EtOAc/Hexanes=40%) to provide 1.07 g of title compound. MS (m/z) 259 [M+H]$^+$.

Synthesis of 3-bromo-5-methylpicolinaldehyde (262C)

A solution of 262B (1.7 g, 3.7 mmol) in tetrahydrofuran (20 mL) at −78° C., LiAlH4 (5.55 mL, 1M in THF) was added to a solution dropwise. The mixture was stirred for 3 hours at −78° C. Acidified by 1N_hydrochloride in methanol at −78° C. and warmed up to r.t. The mixture was extracted with EtOAc (50 mL) twice. The organic layer was dried with Na$_2$SO$_4$, concentrated and purified by flash column (Rf: 0.3 EtOAc/Hexanes=5%) to provide 0.83 g of title compound. MS (m/z) 200 [M+H]$^+$.

Synthesis of (S)—N-(1-(3-bromo-5-methylpyridin-2-yl)-2-(3,5-difluorophenyl)ethyl)-2-(5-hydroxy-1H-indol-3-yl)acetamide (262F)

Compound 262F was prepared according to the method presented for the synthesis of Example 38 substituting 262C (0.83, 3.7 mmol) for 38A to provide 360 mg of title compound: MS (m/z) 500 [M+H]$^+$.

Synthesis of (S)-5-(2-(2-(3,5-difluorophenyl)-1-(2-(5-hydroxy-1H-indol-3-yl)acetamido)ethyl)-5-methylpyridin-3-yl)-2-fluorobenzamide (262G)

262F (48.7 mg, 0.1 mmol), potassium carbonate (27 mg, 0.2 mmol) in 0.5 ml of water, tetrakis(triphenylphosphine)palladium(0) (8 mg, 0.007 mmol) and 3-cyanophenylboronic acid (0.12 mmol) in DME (1.5 mL) was heated to 120° C. for 30 minutes under microwave irradiation. Solvents were concentrated in vacuo and the residue was purified by RP HPLC using a C18 column with a gradient of 0.1% TFA-acetonitrile in 0.1% TFA/H$_2$O to provide 7.5 mg of title compound: $^1$H NMR (400 MHz, cd$_3$od) δ 8.38 (s, 1H), 7.56 (s, 1H), 7.43 (s, 1H), 7.33-7.11 (m, 3H), 7.06 (s, 1H), 6.72 (d, 1H), 6.66 (d, 2H), 6.26 (d, 2H), 5.47 (s, 2H), 5.36-5.22 (m, 1H), 3.59 (d, 2H), 3.05-2.85 (m, 2H), 2.38 (s, 3H); MS (m/z) 559 [M+H]$^+$

Example 263

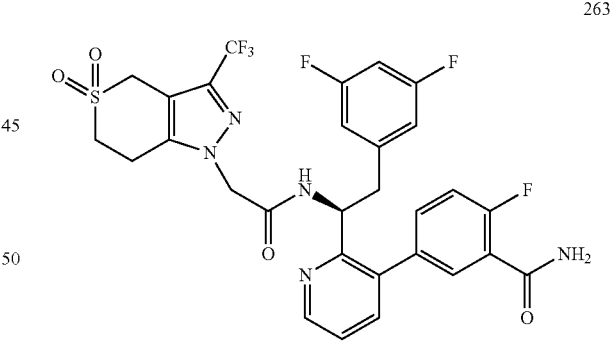

263

Synthesis of (S)-5-(2-(2-(3,5-difluorophenyl)-1-(2-(5,5-dioxido-3-(trifluoromethyl)-6,7-dihydrothiopyrano[4,3-c]pyrazol-1(4H)-yl)acetamido)ethyl)pyridin-3-yl)-2-fluorobenzamide (263)

Compound 263 was prepared according to the method presented for the synthesis of Example 197 to provide 25 mg of title compound: $^1$H NMR (400 MHz, cd$_3$od) δ 8.33 (d, 1H), 7.51-7.08 (m, 5H), 6.64 (t, 1H), 6.34 (d, 2H), 5.38 (dd, 1H), 4.95-4.81 (m, 2H), 4.19 (s, 2H), 3.57-3.43 (m, 1H), 3.31 (d, 2H), 3.17-2.94 (m, 3H). MS (m/z) 652 [M+H]$^+$.

Example 264

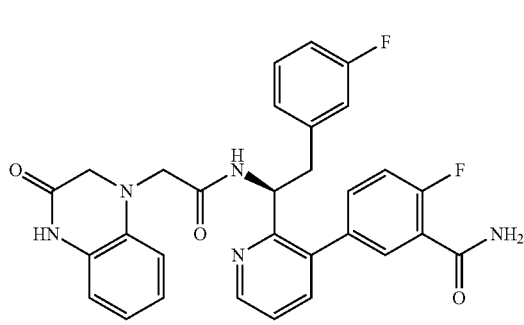

264

Synthesis of (S)-2-fluoro-5-(2-(2-(3-fluorophenyl)-1-(2-(3-oxo-3,4-dihydroquinoxalin-1(2H)-yl)acetamido)ethyl)pyridin-3-yl)benzamide (264)

Compound 264 was prepared according to the method presented for the synthesis of Example 59 utilizing 59D and 2-(3-oxo-3,4-dihydroquinoxalin-1(2H)-yl)acetic acid to provide 18 mg of title compound: ¹H NMR (400 MHz, cd₃od) δ 8.73-8.59 (m, 1H), 7.63 (dd, 1H), 7.44 (ddd, 1H), 7.36-7.16 (m, 2H), 7.17-6.95 (m, 2H), 6.77 (t, 2H), 6.70-6.50 (m, 2H), 6.43 (dd, 2H), 5.29 (dd, 1H), 4.49 (d, 1H), 3.78 (s, 1H), 3.08-2.89 (m, 2H). MS (m/z) 542 [M+H]⁺.

Example 265

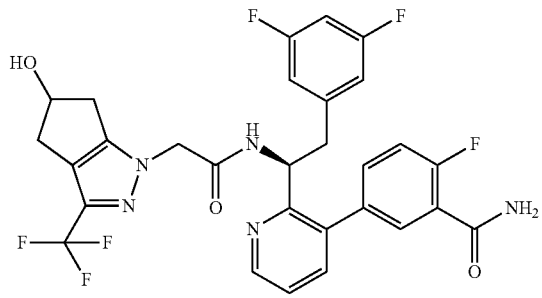

265

Synthesis of 5-(2-((1S)-2-(3,5-difluorophenyl)-1-(2-(5-hydroxy-3-(trifluoromethyl)-5,6-dihydrocyclopenta[c]pyrazol-1(4H)-yl)acetamido)ethyl)pyridin-3-yl)-2-fluorobenzamide (265)

Compound 265 was prepared according to the method presented for the synthesis of Example 325 substituting 237 for 325 to provide 19 mg of title compound: ¹H NMR (400 MHz, cd₃od) δ 8.71 (dd, 1H), 7.75-7.62 (m, 1H), 7.55-7.40 (m, 2H), 7.31 (s, 1H), 7.27-7.15 (m, 1H), 6.67 (td, 1H), 6.42-6.23 (m, 2H), 5.36 (td, 1H), 4.95 (ddd, 1H), 4.81 (d, 2H), 3.15-2.94 (m, 4H), 2.65-2.50 (m, 2H). MS (m/z) 604 [M+H]⁺.

Example 266

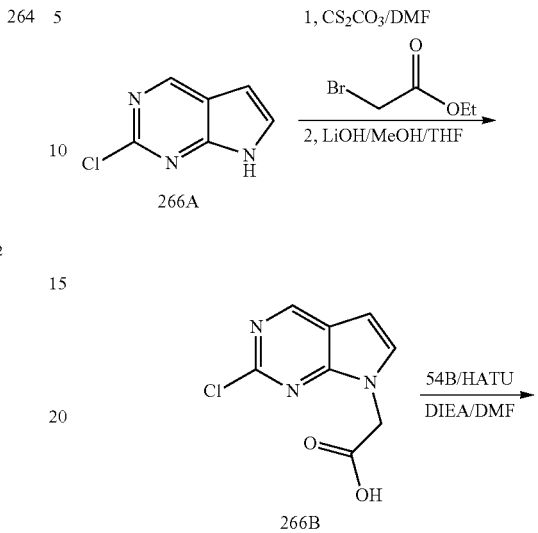

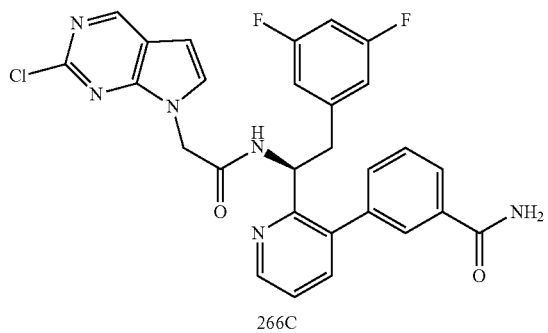

Synthesis of 2ethyl 2-(2-chloro-7H-pyrrolo[2,3-d]pyrimidin-7-yl)acetate (266B)

Compound 266B was prepared according to the method presented for the synthesis of Example 74 substituting 2-chloro-7H-pyrrolo[2,3-d]pyrimidine (266A) for 1-7,8,8-trimethyl-3-(trifluoromethyl)-4,5,6,7-tetrahydro-1H-4,7-methanoindazole (74A) to provide 480 mg of title compound. MS (m/z) 240 [M+H]⁺.

Synthesis of (S)-3-(2-(1-(2-(2-chloro-7H-pyrrolo[2,3-d]pyrimidin-7-yl)acetamido)-2-(3,5-difluorophenyl)ethyl)pyridin-3-yl)benzamide (266C)

Compound 266C was prepared according to the method presented for the synthesis of Example 50 utilizing 50C and 2-(2-chloro-7H-pyrrolo[2,3-d]pyrimidin-7-yl)acetic acid (266B) to provide 5 mg of title compound: ¹H NMR (400 MHz, cd₃od) δ 8.72 (d, 1H), 8.66 (dd, 1H), 7.78 (d, 1H), 7.68 (dd, 1H), 7.51 (s, 1H), 7.45 (dd, 1H), 7.41-7.30 (m, 2H), 7.22 (d, 1H), 6.67-6.50 (m, 2H), 6.18 (d, 2H), 5.36 (dd, 1H), 5.04-4.86 (m, 2H), 2.98 (d, 2H). MS (m/z) 547 [M+H]⁺.

Example 267

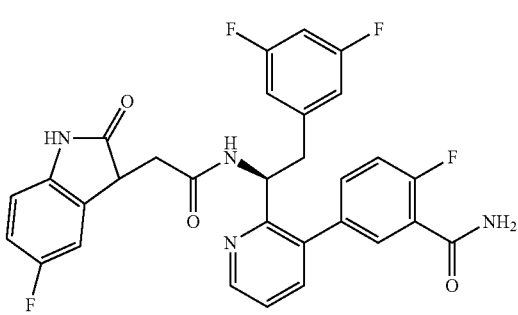

Synthesis of 5-(2-((1S)-2-(3,5-difluorophenyl)-1-(2-(5-fluoro-2-oxoindolin-3-yl)acetamido)ethyl)pyridin-3-yl)-2-fluorobenzamide (267)

Compound 267 was prepared according to the method presented for the synthesis of Example 54 utilizing 54B and 2-(5-fluorol-2-oxoindolin-3-yl)acetic acid to provide 19 mg of title compound: $^1$H NMR (400 MHz, cd$_3$od) δ 8.77-8.62 (m, 1H), 7.60 (dd, 1H), 7.53-7.31 (m, 2H), 7.31-7.21 (m, 1H), 7.20-6.97 (m, 1H), 6.96-6.77 (m, 2H), 6.65 (dd, 1H), 6.31 (t, 2H), 5.33 (dt, 1H), 3.90 (dt, 1H), 3.15-2.88 (m, 2H), 2.67 (dd, 2H); MS (m/z) 563 [M+H]$^+$

Example 268

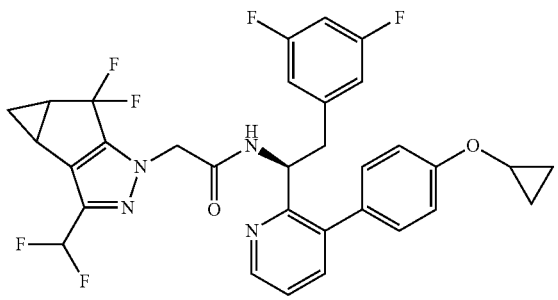

Synthesis of N—((S)-1-(3-(4-cyclopropoxyphenyl)pyridin-2-yl)-2-(3,5-difluorophenyl)ethyl)-2-(3-(difluoromethyl)-5,5-difluoro-3b,4,4a,5-tetrahydro-1H-cyclopropa[3,4]cyclopenta[1,2-c]pyrazol-1-yl)acetamide (268)

Compound 268 was prepared according to the method presented for the synthesis of Example 68 utilizing 68A and (4-cyclopropoxyphenyl)boronic acid to provide 14 mg of title compound: $^1$H NMR (400 MHz, cd$_3$od) δ 8.62 (d, 1H), 7.73-7.61 (m, 1H), 7.45 (dd, 1H), 7.10-6.95 (m, 4H), 6.68 (ddd, 2H), 6.25 (d, 2H), 5.49 (d, 1H), 3.79 (s, 1H), 2.97 (t, 2H), 2.46 (d, 2H), 1.36 (s, 1H), 1.07 (s, 1H), 0.86-0.65 (m, 4H). MS (m/z) 613 [M+H]$^+$.

Example 269

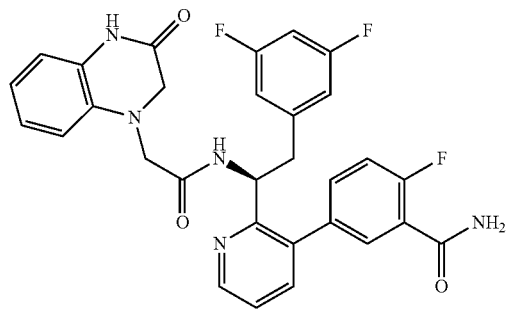

Synthesis of (S)-5-(2-(2-(3,5-difluorophenyl)-1-(2-(3-oxo-3,4-dihydroquinoxalin-1(2H)-yl)acetamido)ethyl)pyridin-3-yl)-2-fluorobenzamide (269)

Compound 269 was prepared according to the method presented for the synthesis of Example 54 utilizing 54B and 2-(3-oxo-3,4-dihydroquinoxalin-1(2H)-yl)acetic acid to provide 14 mg of title compound: $^1$H NMR (400 MHz, cd$_3$od) δ 8.79-8.70 (m, 1H), 7.89-7.68 (m, 2H), 7.63-7.33 (m, 4H), 7.30-7.13 (m, 2H), 6.85 (dd, 1H), 6.80-6.55 (m, 3H), 6.36 (d, 2H), 5.39 (dd, 1H), 4.60 (s, 1H), 3.87 (d, 1H), 3.19-2.99 (m, 2H). MS (m/z) 560 [M+H]$^+$.

Example 270

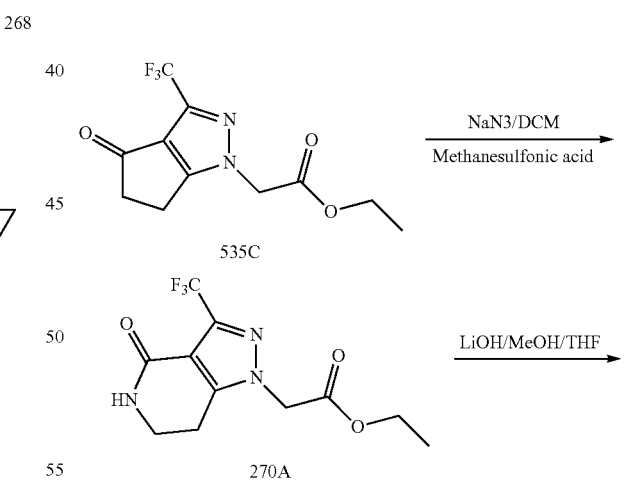

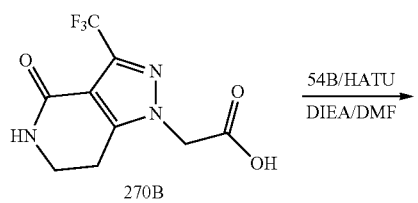

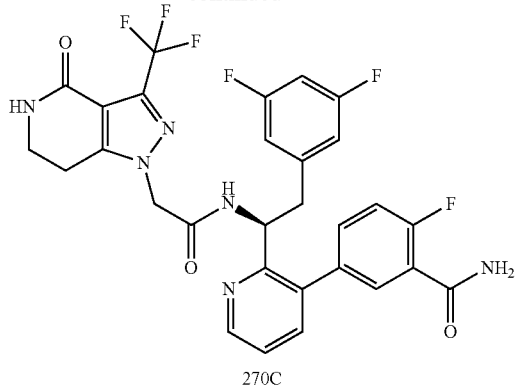

270C

Synthesis of ethyl 2-(4-oxo-3-(trifluoromethyl)-4,5,6,7-tetrahydro-1H-pyrazolo[4,3-c]pyridin-1-yl)acetate (270A)

To a mixture of 535C (200 mg, 0.72 mmol) in methanesulfonic acid (0.86 mL) and DCM (1.2 mL), sodium azide (65 mg, 1 mmol) was added and the mixture was stirred overnight. Diluted with DCM (30 mL) and washed with NaHCO$_3$(aq) twice. The organics were dried over Na$_2$SO$_4$, filtered and concentrated. The crude product was purified by SiO$_2$ chromatography eluting with a gradient of EtOAc in hexanes to provide 40 mg of title compound. MS (m/z) 292 [M+H]$^+$.

Synthesis of 2-(4-oxo-3-(trifluoromethyl)-4,5,6,7-tetrahydro-1H-pyrazolo[4,3-c]pyridin-1-yl)acetic acid (270B)

Compound 270B was prepared according to the method presented for the synthesis of Example 74 substituting 270A for 74B to provide 30 mg of title compound. MS (m/z) 264 [M+H]$^+$.

Synthesis of (S)-5-(2-(2-(3,5-difluorophenyl)-1-(2-(4-oxo-3-(trifluoromethyl)-4,5,6,7-tetrahydro-1H-pyrazolo[4,3-c]pyridin-1-yl)acetamido)ethyl)pyridin-3-yl)-2-fluorobenzamide (270C)

Compound 270C was prepared according to the method presented for the synthesis of Example 54 utilizing 54B and 2-(4-oxo-3-(trifluoromethyl)-4,5,6,7-tetrahydro-1H-pyrazolo[4,3-c]pyridin-1-yl)acetic acid to provide 42 mg of title compound: $^1$H NMR (400 MHz, cd$_3$od) δ 8.72 (dd, 1H), 7.67 (dd, 1H), 7.47 (dd, 2H), 7.31 (s, 1H), 7.22 (dd, 1H), 6.76-6.60 (m, 1H), 6.34 (d, 2H), 5.36 (t, 1H), 4.95 (s, 2H), 3.52 (t, 2H), 3.10 (t, 2H), 2.96-2.77 (m, 2H). MS (m/z) 617 [M+H]$^+$.

Example 271

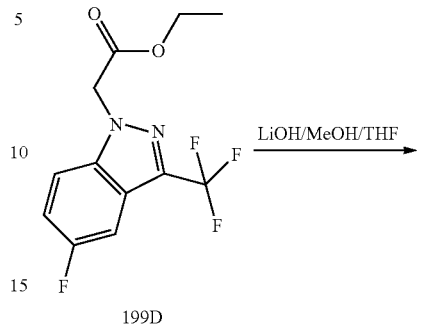

199D

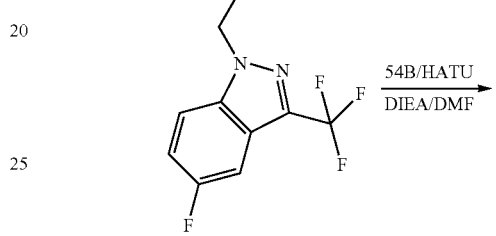

271A

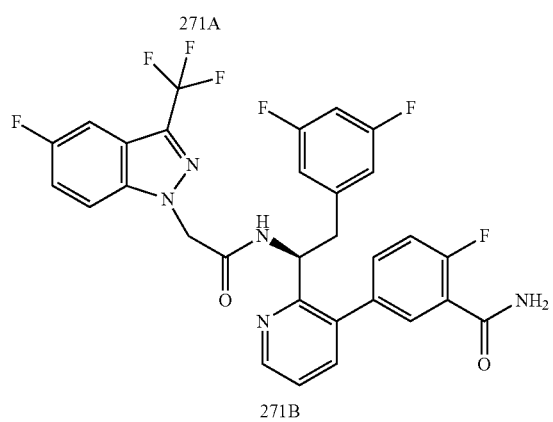

271B

Synthesis of 2-(5-fluoro-3-(trifluoromethyl)-1H-indazol-1-yl)acetic acid (271A)

Compound 271A was prepared according to the method presented for the synthesis of Example 74 substituting 199D for 74B to provide 52.6 mg of title compound. MS (m/z) 263 [M+H]$^+$.

Synthesis of (S)-5-(2-(2-(3,5-difluorophenyl)-1-(2-(5-fluoro-3-(trifluoromethyl)-1H-indazol-1-yl)acetamido)ethyl)pyridin-3-yl)-2-fluorobenzamide (271B)

Compound 271B was prepared according to the method presented for the synthesis of Example 54 utilizing 54B and 271A to provide 76 mg of title compound: $^1$H NMR (400 MHz, cd$_3$od) δ 8.72 (dd, 1H), 7.67 (dd, 1H), 7.55 (dd, 1H), 7.52-7.38 (m, 3H), 7.38-7.24 (m, 2H), 7.19 (dd, 1H), 6.66 (ddd, 1H), 6.33 (t, 2H), 5.36 (t, 1H), 5.24 (s, 2H), 3.08 (d, 2H). MS (m/z) 616 [M+H]$^+$.

Example 272

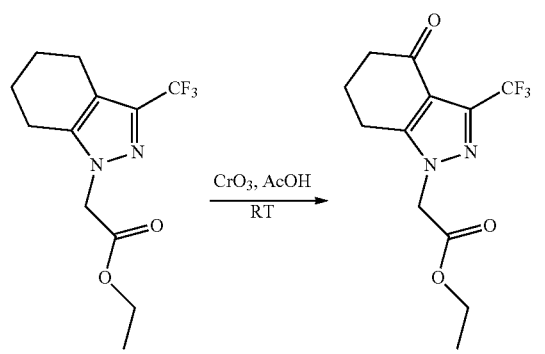

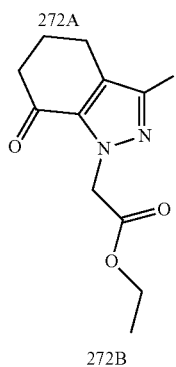

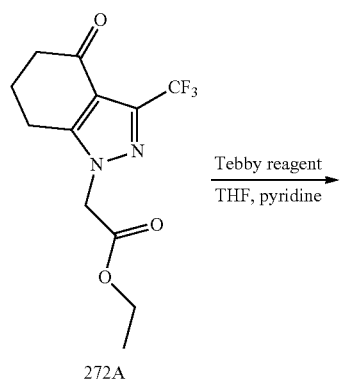

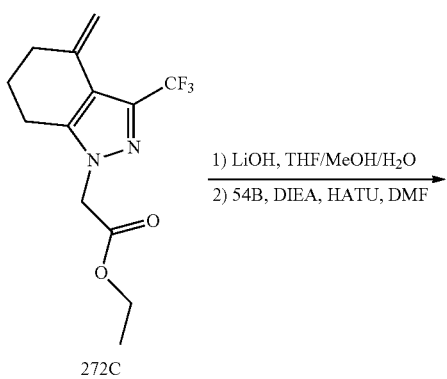

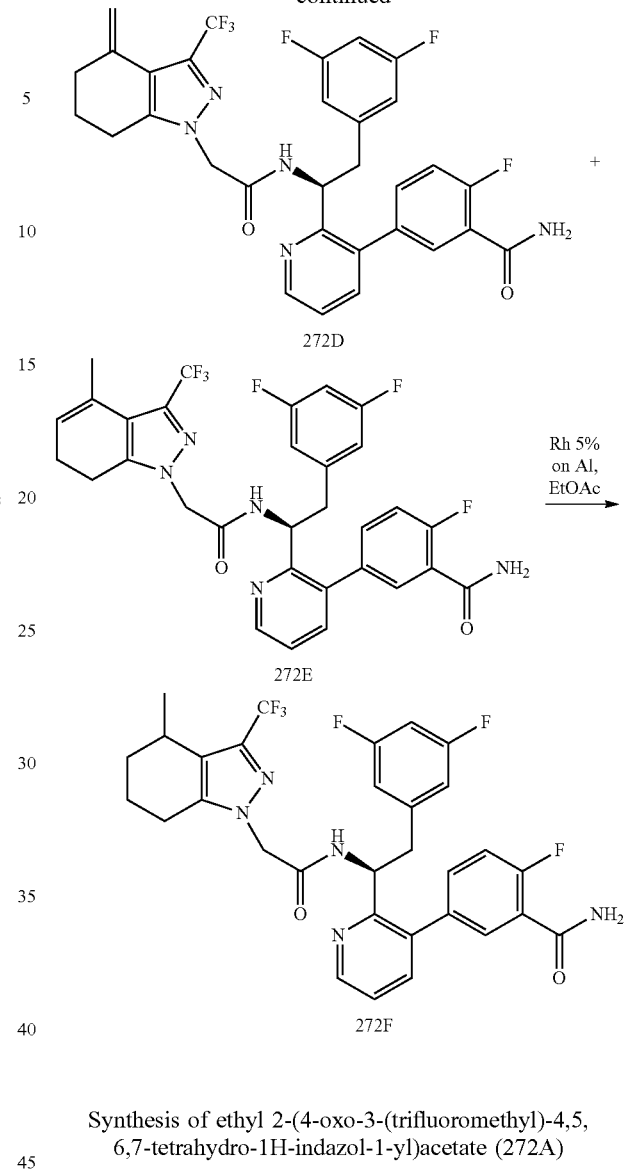

Synthesis of ethyl 2-(4-oxo-3-(trifluoromethyl)-4,5,6,7-tetrahydro-1H-indazol-1-yl)acetate (272A)

Ethyl 2-(3-(trifluoromethyl)-4,5,6,7-tetrahydro-1H-indazol-1-yl)acetate (4.9 g. 17.7 mmol) was dissolved in 170 mL of acetic acid. To it was added chromium trioxide (2.65 g, 26.5 mmol) and the resulting mixture was stirred at ambient temperature for 3 days. To it was added more chromium trioxide (885 mg, 8.85 mmol) and the reaction was allowed to stir for one day. It was then quenched with 2-propanol at 0° C. and the solvent was removed in vacuo. The residue was partitioned between EtOAc and water. The organic layer was separated, washed with half brine, dried over MgSO$_4$ and filtered. The filtrate was concentrated and purified by silica gel chromatography eluting with EtOAc and hexanes to afford 1.78 g of 272B and 1.94 g of the title compound. MS (m/z) 291.16 [M+H]$^+$.

Synthesis of ethyl 2-(4-methylene-3-(trifluoromethyl)-4,5,6,7-tetrahydro-1H-indazol-1-yl)acetate (272C)

Ethyl 2-(4-oxo-3-(trifluoromethyl)-4,5,6,7-tetrahydro-1H-indazol-1-yl)acetate (600 mg, 2 mmol) was dissolved in 20 mL of THF and 4 mL of pyridine. To it at 0° C. was slowly added 2 mL of Tebbe reagent (0.5 M in toluene, 3 mmol) and the reaction mixture was stirred at ambient temperature for 3 hours. More Tebbe reagent (0.5 M in toluene, 3 mmol) was added and the reaction was allowed to stir for 3 days. It was quenched at 0° C. with NaHCO₃ (saturated aqueous solution), and filtered through a pad of celite. The filtrate was partitioned between EtOAc and water. The organic layer was separated, washed with half brine, dried over MgSO₄ and filtered. The filtrate was concentrated and purified by silica gel chromatography eluting with EtOAc and hexanes to afford 45 mg of the title compound. MS (m/z) 289.10 [M+H]$^+$.

Synthesis of (S)-5-(2-(2-(3,5-difluorophenyl)-1-(2-(4-methylene-3-(trifluoromethyl)-4,5,6,7-tetrahydro-1H-indazol-1-yl)acetamido)ethyl)pyridin-3-yl)-2-fluorobenzamide (272D) and (S)-5-(2-(2-(3,5-difluorophenyl)-1-(2-(4-methyl-3-(trifluoromethyl)-6,7-dihydro-1H-indazol-1-yl)acetamido)ethyl)pyridin-3-yl)-2-fluorobenzamide (272E)

The mixture of Compound 272D and Compound 272E was prepared according to the method presented in the synthesis of Example 60 utilizing Compound 54B and ethyl 2-(4-methylene-3-(trifluoromethyl)-4,5,6,7-tetrahydro-1H-indazol-1-yl)acetate to afford the title compounds. MS (m/z) 614.22 [M+H]$^+$.

Synthesis of 5-(2-((1S)-2-(3,5-difluorophenyl)-1-(2-(4-methyl-3-(trifluoromethyl)-4,5,6,7-tetrahydro-1H-indazol-1-yl)acetamido)ethyl)pyridin-3-yl)-2-fluorobenzamide (272F)

The mixture of 272D and 272E (7.2 mg) was dissolved in 10 mL of EtOAc. The system was purged with argon, and then Rh/Al (5%, 5 mg) was added. The reaction was stirred under 1 atm H₂ at ambient temperature for 16 hours. Upon completion of the reaction, it was filtered through a pad of celite and washed with EtOAc. The filtrate was collected and the volatiles were removed in vacuo. The residue was purified by reverse phase HPLC eluting with acetonitrile/water (with 0.1% TFA) to afford 3.4 mg of the title compound. MS (m/z) 616.19 [M+H]$^+$. $^1$H NMR (400 MHz, cd₃od) δ 8.61 (dd, J=4.8, 1.5 Hz, 1H), 7.55 (dd, J=7.8, 1.5 Hz, 1H), 7.42-7.33 (m, 2H), 7.27 (s, 1H), 7.15 (dd, J=10.7, 8.5 Hz, 1H), 6.59 (t, J=9.1 Hz, 1H), 6.27 (d, J=8.1 Hz, 2H), 5.29 (t, J=7.5 Hz, 1H), 4.70 (s, 2H), 2.98 (d, J=8.1 Hz, 2H), 2.85 (d, J=5.8 Hz, 1H), 2.47-2.14 (m, 2H), 1.92-1.63 (m, 3H), 1.54-1.43 (m, 1H), 1.10 (d, J=6.9 Hz, 3H).

Example 273

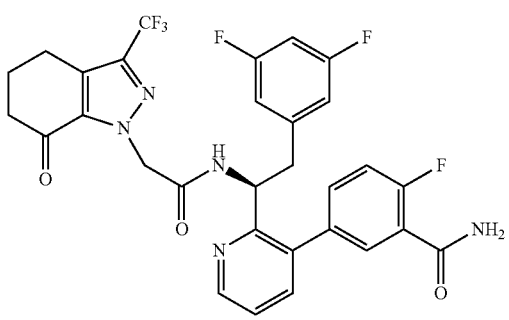

273

Synthesis of (S)-5-(2-(2-(3,5-difluorophenyl)-1-(2-(7-oxo-3-(trifluoromethyl)-4,5,6,7-tetrahydro-1H-indazol-1-yl)acetamido)ethyl)pyridin-3-yl)-2-fluorobenzamide (273)

Compound 273 was prepared (11 mg) according to the method presented in the synthesis of Example 60 utilizing Compound 54B and Compound 272B to provide the title compound: MS (m/z) 616.43 [M+H]$^+$. $^1$H NMR (400 MHz, cd₃od) δ 8.75 (dd, J=5.0, 1.6 Hz, 1H), 7.73 (dd, J=7.8, 1.6 Hz, 1H), 7.53 (dd, J=7.8, 5.0 Hz, 1H), 7.45-7.28 (m, 2H), 7.20 (dd, J=10.7, 8.6 Hz, 1H), 6.66 (tt, J=9.2, 2.3 Hz, 1H), 6.31 (d, J=6.1 Hz, 2H), 5.36 (dd, J=8.4, 6.7 Hz, 1H), 5.24 (s, 2H), 3.18-3.02 (m, 2H), 2.85 (t, J=5.9 Hz, 2H), 2.60-2.47 (m, 2H), 2.25-2.03 (m, 2H).

Example 274

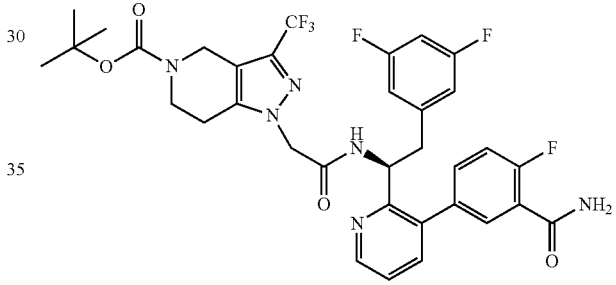

274

Synthesis of (S)-tert-butyl 1-(2-(1-(3-(3-carbamoyl-4-fluorophenyl)pyridin-2-yl)-2-(3,5-difluorophenyl)ethylamino)-2-oxoethyl)-3-(trifluoromethyl)-6,7-dihydro-1H-pyrazolo[4,3-c]pyridine-5(4H)-carboxylate (274)

Compound 274 was prepared (7 mg) according to the method presented in the synthesis of Example 56 utilizing 56A and tert-butyl 3-(trifluoromethyl)-6,7-dihydro-1H-pyrazolo[4,3-c]pyridine-5(4H)-carboxylate to provide the title compound. MS (m/z) 703.16 [M+H]$^+$. $^1$H NMR (400 MHz, cdcl₃) δ 8.56 (d, J=4.8 Hz, 1H), 7.64 (d, J=5.7 Hz, 1H), 7.48 (d, J=7.0 Hz, 1H), 7.38 (s, 1H), 7.33-7.28 (m, 1H), 7.18 (dd, J=11.1, 8.5 Hz, 1H), 6.77 (s, 1H), 6.54 (t, J=9.1 Hz, 1H), 6.11 (d, J=6.1 Hz, 2H), 5.86 (s, 1H), 5.42 (dd, J=14.9, 7.7 Hz, 1H), 4.70 (s, 2H), 4.51 (s, 2H), 3.69 (s, 2H), 2.85 (dd, J=16.0, 8.2 Hz, 2H), 2.61 (d, J=5.3 Hz, 2H), 1.48 (d, J=7.8 Hz, 9H).

Example 275

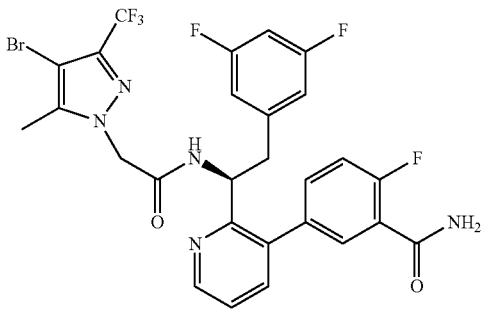

Synthesis of (S)-5-(2-(1-(2-(4-bromo-5-methyl-3-(trifluoromethyl)-1H-pyrazol-1-yl)acetamido)-2-(3,5-difluorophenyl)ethyl)pyridin-3-yl)-2-fluorobenzamide (275)

Compound 275 was prepared (6 mg) according to the method presented in the synthesis of Example 56 utilizing Compound 56A and 4-bromo-5-methyl-3-(trifluoromethyl)-1H-pyrazole to provide the title compound. MS (m/z) 641.32 [M+H]$^+$. $^1$H NMR (400 MHz, cd$_3$od) δ 8.69 (dd, J=4.7, 1.6 Hz, 1H), 7.56 (dd, J=7.8, 1.7 Hz, 1H), 7.46-7.27 (m, 3H), 7.21 (dd, J=10.7, 8.5 Hz, 1H), 6.65 (t, J=9.2 Hz, 1H), 6.32 (d, J=6.3 Hz, 2H), 5.40-5.25 (m, 1H), 4.92 (s, 2H), 3.06 (qd, J=13.3, 7.8 Hz, 2H), 2.17 (s, 3H).

Example 276

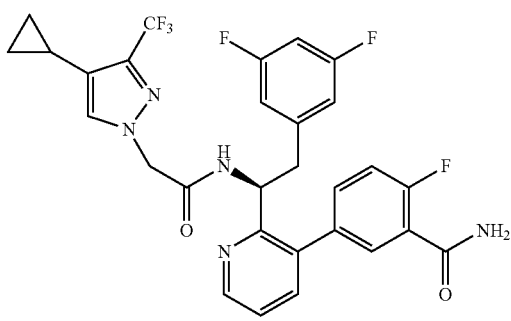

Synthesis of (S)-5-(2-(1-(2-(4-cyclopropyl-3-(trifluoromethyl)-1H-pyrazol-1-yl)acetamido)-2-(3,5-difluorophenyl)ethyl)pyridin-3-yl)-2-fluorobenzamide (276)

To the mixture of (S)-5-(2-(1-(2-(4-bromo-3-(trifluoromethyl)-1H-pyrazol-1-yl)acetamido)-2-(3,5-difluorophenyl)ethyl)pyridin-3-yl)-2-fluorobenzamide (463, 20 mg, 0.03 mmol), cyclopropane boronic acid (8.2 mg, 0.09 mmol) and potassium phosphate tribasic (25 mg, 0.12 mmol) were added 1 mL of toluene and 2 drops of water. After the system was purged with argon, palladium (II) acetate (2 mg, 0.003 mmol) and tricyclohexylphosphine (2 mg, 0.006 mmol) was added and the reaction mixture was heated up to 120° C. for 3 hours. The solvent was removed and the residue was purified by reverse phase HPLC eluting with acetonitrile/water (with 0.1% TFA) to afford 6.5 mg of the title compound. MS (m/z) 588.35 [M+H]$^+$. $^1$H NMR (400 MHz, cd$_3$od) δ 8.68 (dd, J=4.8, 1.6 Hz, 1H), 7.64 (dd, J=7.8, 1.6 Hz, 1H), 7.49-7.29 (m, 4H), 7.22 (dd, J=10.7, 8.5 Hz, 1H), 6.65 (t, J=9.2 Hz, 1H), 6.30 (d, J=6.3 Hz, 2H), 5.33 (t, J=7.5 Hz, 1H), 4.83 (s, 1H), 3.04 (d, J=7.7 Hz, 2H), 1.72 (m, 1H), 1.01-0.76 (m, 2H), 0.62-0.45 (m, 2H).

Example 277

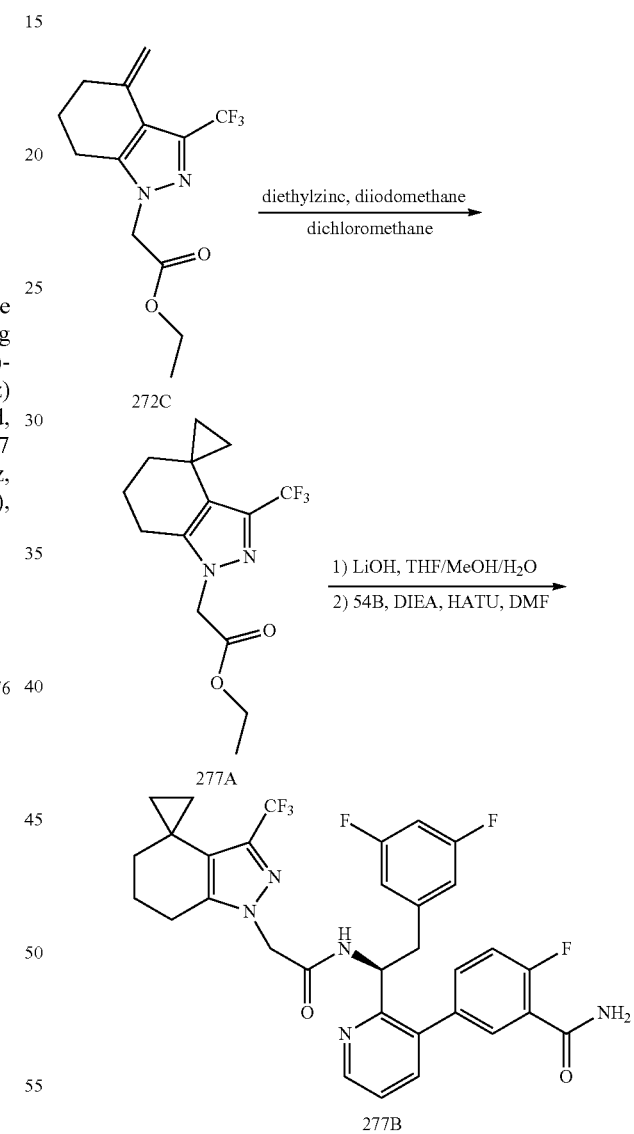

Synthesis of ethyl 2-(3'-(trifluoromethyl)-6',7'-dihydrospiro[cyclopropane-1,4'-indazole]-1'(5'H)-yl)acetate (277A)

Dichloromethane (3 mL) was added to diethylzinc (1.0 M hexane solution, 1.56 mL, 1.56 mmol), and then a solution of TFA (48 μL, 0.6 mmol) in dichloromethane (2 mL) was slowly added at 0° C. The reaction mixture was stirred for 20 min, and then a solution of diiodomethane (125 µL, 1.5 mmol) in dichloromethane (2 mL) was added dropwise. The reaction mixture was stirred for 20 min, and then a solution of ethyl 2-(4-methylene-3-(trifluoromethyl)-4,5,6,7-tetrahydro-1H-indazol-1-yl)acetate (272, 45 mg, 0.15 mmol) in dichloromethane (1.5 mL) was added and the reaction was allowed to stir at ambient temperature for 16 hours. Dichloromethane and saturated aqueous ammonium chloride solution were added to the reaction mixture and the organic layer was separated and the aqueous layer was extracted by dichloromethane one more time. The combined organic layer was dried over sodium sulfate anhydrous, filtered and concentrated. The residue was purified by silica gel chromatography eluting with EtOAc and hexane to afford 21 mg of the title compound. MS (m/z) 303.20 [M+H]$^+$.

Synthesis of (S)-5-(2-(2-(3,5-difluorophenyl)-1-(2-(3'-(trifluoromethyl)-6',7'-dihydrospiro[cyclopropane-1,4'-indazole]-1'(5'H)-yl)acetamido)ethyl)pyridin-3-yl)-2-fluorobenzamide (277B)

Compound 277B was prepared (27 mg) according to the method presented in the synthesis of Example 60 utilizing Compound 54B and ethyl 2-(3'-(trifluoromethyl)-6',7'-dihydrospiro[cyclopropane-1,4'-indazole]-1'(5'H)-yl)acetate to provide the title compound. MS (m/z) 628.5 [M+H]$^+$. $^1$H NMR (400 MHz, cd$_3$od) δ 8.71 (dd, J=4.9, 1.6 Hz, 1H), 7.71 (dd, J=7.8, 1.6 Hz, 1H), 7.48 (ddd, J=9.2, 7.3, 3.6 Hz, 2H), 7.37 (s, 1H), 7.24 (dd, J=10.7, 8.5 Hz, 1H), 6.68 (tt, J=9.2, 2.2 Hz, 1H), 6.36 (t, J=6.2 Hz, 2H), 5.38 (t, J=7.6 Hz, 1H), 4.79 (s, 2H), 3.21-2.94 (m, 2H), 2.63-2.39 (m, 2H), 2.02-1.76 (m, 2H), 1.64-1.42 (m, 2H), 1.08-0.87 (m, 2H), 0.63 (t, J=5.2 Hz, 2H).

Example 278

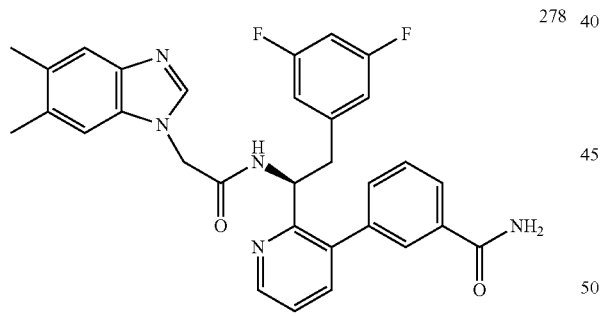

278

Synthesis of (S)-3-(2-(2-(3,5-difluorophenyl)-1-(2-(5,6-dimethyl-1H-benzo[d]imidazol-1-yl)acetamido)ethyl)pyridin-3-yl)benzamide (278)

Compound 278 was prepared (13 mg) according to the method presented in the synthesis of Example 55 utilizing Compound 55D and 2-(5,6-dimethyl-1H-benzo[d]imidazol-1-yl)acetic acid, and then Suzuki coupling with 3-carbamoylphenylboronic acid to afford the title compound. MS (m/z) 540.2 [M+H]$^+$. $^1$H NMR (400 MHz, cd$_3$od) δ 9.23 (s, 1H), 8.74 (d, J=4.8 Hz, 1H), 7.87 (d, J=7.7 Hz, 1H), 7.71-7.55 (m, 3H), 7.53-7.39 (m, 3H), 7.29 (d, J=7.7 Hz, 1H), 6.66 (m, 1H), 6.30 (d, J=6.4 Hz, 2H), 5.45 (t, J=7.5 Hz, 1H), 5.26 (s, 2H), 3.18-2.96 (m, 2H), 2.44 (d, J=6.9 Hz, 6H).

Example 279

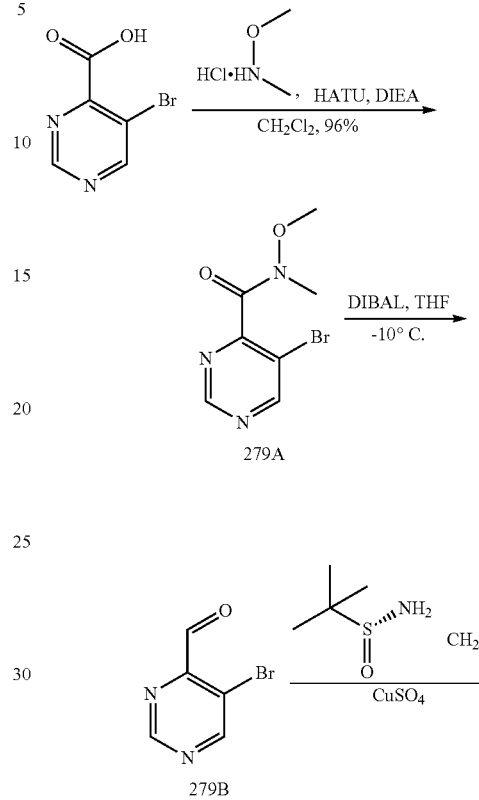

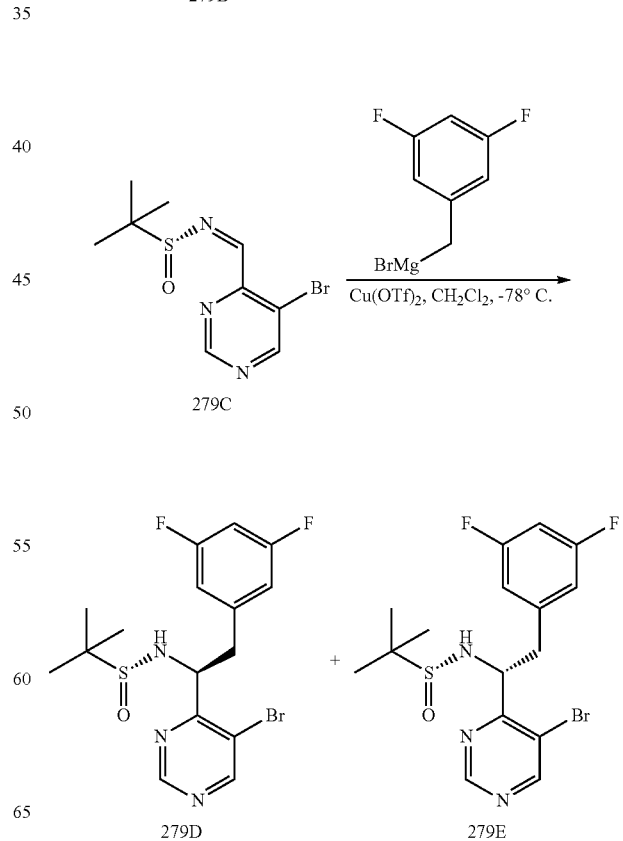

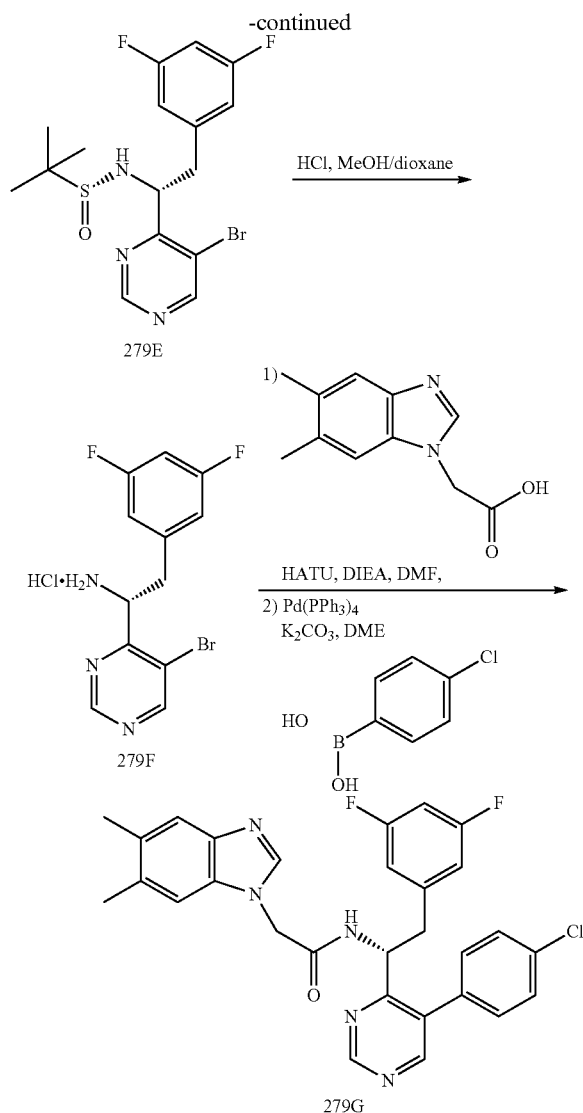

Synthesis of 5-bromo-N-methoxy-N-methylpyrimidine-4-carboxamide (279A)

5-bromopyrimidine-4-carboxylic acid (5 g, 24.6 mmol) and N,O-dimethylhydroxylamine hydrochloride (3.6 g, 36.9 mmol) were dissolved in 100 mL of $CH_2Cl_2$ and to it was added N,N-diisopropylethylamine (21 mL, 123 mmol). The reaction mixture was cooled down to 0° C. and to it was added HATU (11.2 g, 29.5 mmol). The reaction mixture was allowed to stir at 0° C. for 30 min. it was then diluted with $CH_2Cl_2$ and washed with half brine. The organic layer was separated, dried over $MgSO_4$, filtered and concentrated. The crude product was purified by silica gel chromatography eluting with EtOAc/hexanes to afford 5.84 g of the title compound. MS (m/z): 248.1 [M+H]+.

Synthesis of 5-bromopyrimidine-4-carbaldehyde (279B)

5-bromo-N-methoxy-N-methylpyrimidine-4-carboxamide (2.45 g, 10 mmol) was dissolved in 50 mL of THF and cooled down to −10° C. DIBAL (1.0 M in toluene, 15 mL, and 15 mmol) was added slowly to keep internal temperature at −10° C. After addition, the reaction was quenched with iPrOH and 1N HCl. The mixture was partitioned between EtOAc and brine. The organic layer was separated, dried over $MgSO_4$, filtered and concentrated to afford 1.19 g of the title compound. MS (m/z): 187.2 [M+H]+.

Synthesis of N-((5-bromopyrimidin-4-yl)methylene)-2-methylpropane-2-sulfinamide (279C)

Compound 279C was prepared according to the method presented for the synthesis of Example 13C substituting Compound 279B for 3-(4-methoxyphenyl)picolinaldehyde to provide the title compound: MS (m/z) 292.0 [M+H]+.

Synthesis of (R)—N—((R)-1-(5-bromopyrimidin-4-yl)-2-(3,5-difluorophenyl)ethyl)-2-methylpropane-2-sulfinamide (279E)

(3,5-difluorobenzyl)magnesium bromide (0.25 M in ether, 20 mL, 5 mmol) was added dropwise to a solution of N-((5-bromopyrimidin-4-yl)methylene)-2-methylpropane-2-sulfinamide (730 mg, 2.5 mmol) and copper (II) triflate (45 mg, 0.125 mmol) in $CH_2Cl_2$ (15 mL) at −78° C. After addition, ammonium chloride (aq, 10 ml) was added to the reaction and the mixture was allowed to warm up to ambient temperature. It was extracted with EtOAc (2×30 mL). The organic layer was dried over $Na_2SO_4$, filtered and concentrated. The crude product was purified by flash column to afford 136 mg of (R)—N—((S)-1-(5-bromopyrimidin-4-yl)-2-(3,5-difluorophenyl)ethyl)-2-methylpropane-2-sulfinamide (279D) and 355 mg of the title compound: MS (m/z) 419.8 [M+H]+

Synthesis of (R)-1-(5-bromopyrimidin-4-yl)-2-(3,5-difluorophenyl)ethanamine hydrochloride (279F)

(R)—N—((R)-1-(5-bromopyrimidin-4-yl)-2-(3,5-difluorophenyl)ethyl)-2-methylpropane-2-sulfinamide (766 mg, 1.8 mmol) was dissolved in 5 mL of methanol and to it was added HCl solution (4N in dioxane, 1.8 mL). After stirring at ambient temperature for 10 min, diethyl ether was added and the mixture was allowed to stir for 1 hour. The resulting precipitate was collected by vacuum filtration and then dried under high vacuum to provide 554 mg of the title compound: MS (m/z) 316.2 [M+H]+.

Synthesis (R)—N-(1-(5-(4-chlorophenyl)pyrimidin-4-yl)-2-(3,5-difluorophenyl)ethyl)-2-(5,6-dimethyl-1H-benzo[d]imidazol-1-yl)acetamide (279G)

Compound 279G was prepared (11 mg) according to the method presented in the synthesis of Example 57 utilizing Compound 279F and 2-(5,6-dimethyl-1H-benzo[d]imidazol-1-yl)acetic acid, and then Suzuki coupling with 4-chlorophenylboronic acid to afford the title compound. MS (m/z) 532.3 [M+H]+. $^1$H NMR (400 MHz, $cd_3od$) δ 9.23 (d, J=15.1 Hz, 2H), 8.54 (s, 1H), 7.59 (s, 1H), 7.51-7.35 (m, 3H), 7.18 (d, J=8.1 Hz, 2H), 6.74 (m, 1H), 6.38 (d, J=6.8 Hz, 2H), 5.45 (d, J=7.5 Hz, 1H), 5.25 (s, 2H), 3.08 (t, J=7.1 Hz, 2H), 2.45 (s, 6H).

Example 280

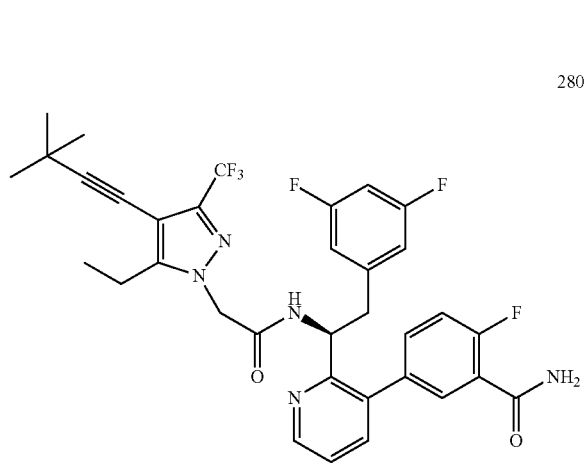 [SMILES: CCc1c(C#CC(C)(C)C)c(C(F)(F)F)nn1CC(=O)N[C@@H](Cc1cc(F)cc(F)c1)c1ncccc1-c1ccc(F)c(C(N)=O)c1]

280

Synthesis of (S)-5-(2-(2-(3,5-difluorophenyl)-1-(2-(4-(3,3-dimethylbut-1-ynyl)-5-ethyl-3-(trifluoromethyl)-1H-pyrazol-1-yl)acetamido)ethyl)pyridin-3-yl)-2-fluorobenzamide (280)

(S)-5-(2-(1-(2-(4-bromo-5-ethyl-3-(trifluoromethyl)-1H-pyrazol-1-yl)acetamido)-2-(3,5-difluorophenyl)ethyl)pyridin-3-yl)-2-fluorobenzamide (58, 40 mg, 0.06 mmol) was dissolved in 2 mL of DMF and 0.4 mL of triethylamine. The system was degassed and purged with argon. To it was added copper(I) iodide (2.2 mg, 0.012 mmol) and bis(triphenylphosphine)palladium(II) chloride (4.2 mg, 0.006 mmol). The system was purged with argon again. 3,3-dimethylbut-1-yne (37 µL, 0.3 mmol) was added and the mixture was heated up to 85° C. for 16 hours and then added more 3,3-dimethylbut-1-yne (74 µL, 0.6 mmol), copper(I) iodide (2.2 mg, 0.012 mmol) and bis(triphenylphosphine)palladium(II) chloride (4.2 mg, 0.006 mmol). The mixture was heated up to 180° C. for 16 hours. It was cooled down and filtered through a pad of celite and washed with EtOAc. The filtrate was washed with 5% LiCl aqueous solution, water (20 mL with 1 mL of ammonia) and brine. The organic layer was separated, washed with half brine, dried over MgSO$_4$ and filtered. The filtrate was concentrated and purified by reverse phase HPLC eluting with acetonitrile/water (with 0.1% TFA) to afford 6 mg of the title compound. MS (m/z) 657.10 [M+H]$^+$. $^1$H NMR (400 MHz, cd$_3$od) δ 8.69 (dd, J=4.8, 1.6 Hz, 1H), 7.60 (dd, J=7.8, 1.6 Hz, 1H), 7.41 (dd, J=7.8, 4.8 Hz, 2H), 7.31 (s, 1H), 7.21 (dd, J=10.7, 8.5 Hz, 1H), 6.66 (t, J=9.2 Hz, 1H), 6.33 (d, J=6.3 Hz, 2H), 5.34 (t, J=7.5 Hz, 1H), 4.86 (s, 2H), 3.13-2.96 (m, 2H), 2.60 (q, J=7.6 Hz, 2H), 1.27 (s, 9H), 1.13 (t, J=7.6 Hz, 3H).

Example 281

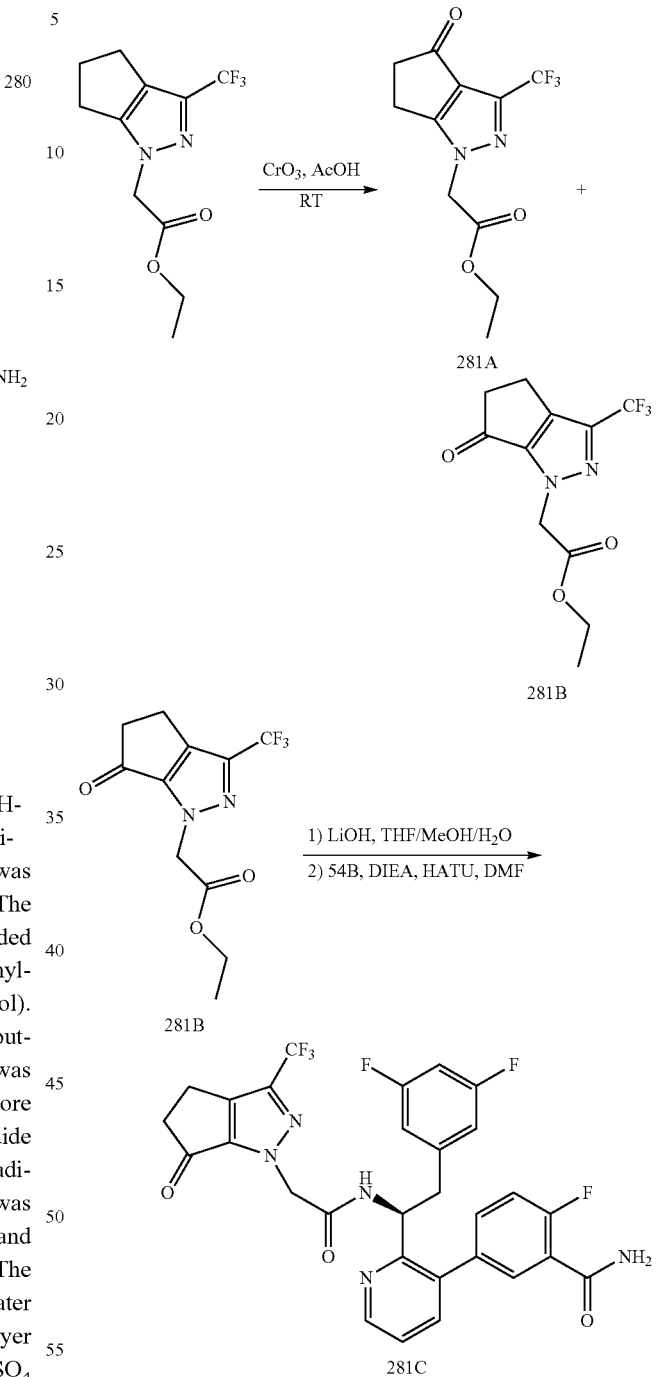

Synthesis of ethyl 2-(6-oxo-3-(trifluoromethyl)-5,6-dihydrocyclopenta[c]pyrazol-1(4H)-yl)acetate (281B)

Compound 281B was prepared according to the method presented in the synthesis of Example 272B utilizing ethyl 2-(3-(trifluoromethyl)-5,6-dihydrocyclopenta[c]pyrazol-1(4H)-yl)acetate to afford the title compound; MS (m/z) 277.06 [M+H]$^+$.

Synthesis of (S)-5-(2-(2-(3,5-difluorophenyl)-1-(2-(6-oxo-3-(trifluoromethyl)-5,6-dihydrocyclopenta[c]pyrazol-1(4H)-yl)acetamido)ethyl)pyridin-3-yl)-2-fluorobenzamide (281C)

Compound 281C was prepared (12 mg) according to the method presented in the synthesis of Example 54 utilizing Compound 54B and ethyl 2-(6-oxo-3-(trifluoromethyl)-5,6-dihydrocyclopenta[c]pyrazol-1(4H)-yl)acetate to provide the title compound; MS (m/z) 602.49 [M+H]$^+$. $^1$H NMR (400 MHz, cd$_3$od) δ 8.73 (dd, J=4.9, 1.6 Hz, 1H), 7.67 (dd, J=7.8, 1.6 Hz, 1H), 7.48 (dd, J=7.8, 4.9 Hz, 1H), 7.38 (d, J=6.8 Hz, 1H), 7.31 (s, 1H), 7.20 (dd, J=10.7, 8.5 Hz, 1H), 6.73-6.57 (m, 1H), 6.30 (d, J=6.1 Hz, 2H), 5.36 (t, J=7.6 Hz, 1H), 5.12-4.98 (m, 2H), 3.08 (d, J=7.6 Hz, 2H), 3.03 (dd, J=6.3, 3.4 Hz, 2H), 2.99-2.89 (m, 2H).

Example 282

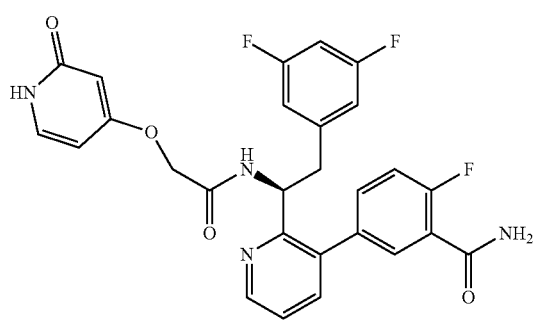

282

Synthesis of (S)-5-(2-(2-(3,5-difluorophenyl)-1-(2-(2-oxo-1,2-dihydropyridin-4-yloxy)acetamido)ethyl)pyridin-3-yl)-2-fluorobenzamide (282)

(S)-5-(2-(1-(2-(2-chloropyridin-4-yloxy)acetamido)-2-(3,5-difluorophenyl)ethyl)pyridin-3-yl)-2-fluorobenzamide (332, 25 mg) was dissolved in 1 mL of acetic acid and heated up to 150° C. in a Biotage® Initiator Microwave Synthesizer for 75 min. It was cooled down and the solvent was removed. The residue was purified by reverse phase HPLC eluting with acetonitrile/water (with 0.1% TFA) to afford 5 mg of the title compound. MS (m/z) 523.27 [M+H]$^+$. $^1$H NMR (400 MHz, cd$_3$od) δ 8.61 (dd, J=4.8, 1.6 Hz, 1H), 7.56 (dd, J=7.8, 1.6 Hz, 1H), 7.46-7.29 (m, 3H), 7.26 (s, 1H), 7.17 (dd, J=10.7, 8.6 Hz, 1H), 6.59 (t, J=9.2 Hz, 1H), 6.23 (dd, J=9.5, 4.5 Hz, 3H), 5.85 (d, J=2.4 Hz, 1H), 5.34 (t, J=7.5 Hz, 1H), 4.52 (s, 2H), 2.96 (t, J=21.2 Hz, 2H).

Example 283

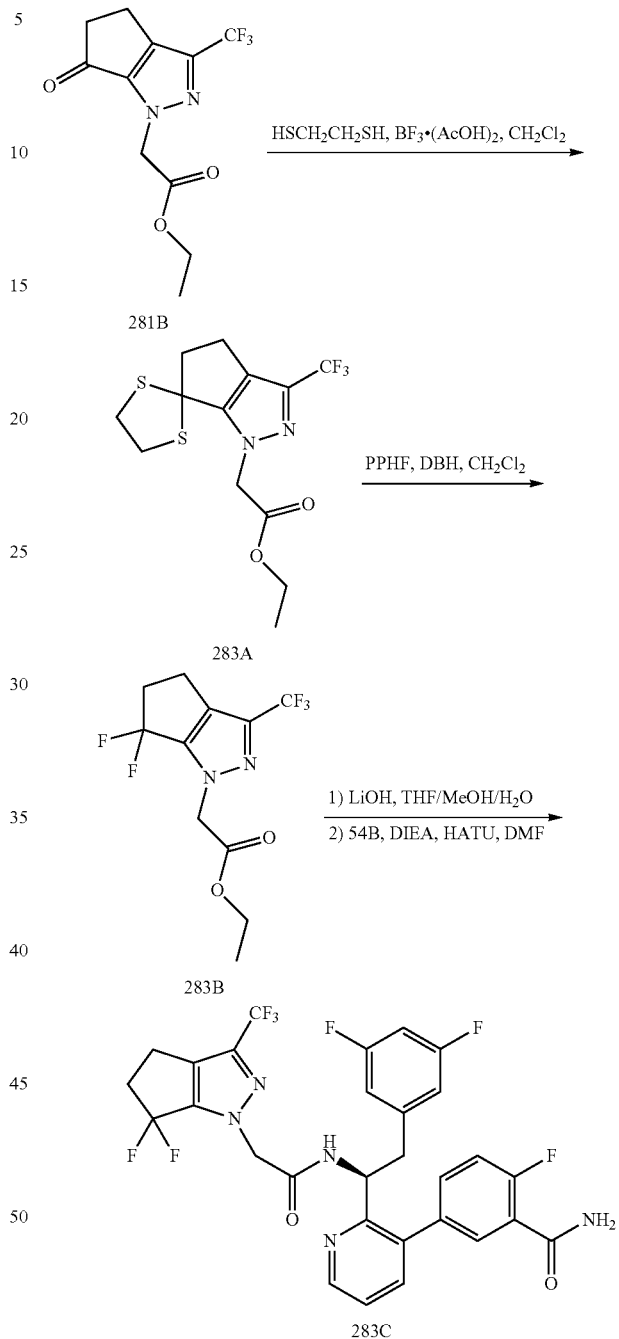

Synthesis of ethyl 2-(3-(trifluoromethyl)-4,5-dihydro-1H-spiro[cyclopenta[c]pyrazole-6,2'-[1,3]dithiolane]-1-yl)acetate (283A)

To a solution of ethyl 2-(6-oxo-3-(trifluoromethyl)-5,6-dihydrocyclopenta[c]pyrazol-1 (4H)-yl)acetate (281B, 219 mg, 0.79 mmol) in CH$_2$C$_2$ (2 mL) was added 1,2-ethanedithiol (100 μL, 1.2 mmol) and BF$_3$.2AcOH (165 μL, 1.2 mmol) under N$_2$. The mixture was stirred at ambient temperature for 16 hours. The reaction was quenched with saturated NaHCO₃ aqueous solution at 0° C.; and then extracted with EtOAc. The organic layer was separated, dried over MgSO₄, filtered and concentrated. The residue was purified by silica gel chromatography eluting with EtOAc/Hexanes to afford 253 mg of the title compound: MS (m/z) 353.17 [M+H]⁺.

Synthesis of ethyl 2-(6,6-difluoro-3-(trifluoromethyl)-5,6-dihydrocyclopenta[c]pyrazol-1(4H)-yl)acetate (283B)

In a Teflon vessel was added 1,3-dibromo-5,5-dimethylhydantoin (114 mg, 0.4 mmol) and CH₂Cl₂ (1 mL). The mixture was allowed to stir under N₂ and cooled down to −78° C. To it was added 1 mL of hydrogen fluoride pyridine (pyridine ~30%, hydrogen fluoride ~70%) followed by dropwise addition of a solution of ethyl 2-(3-(trifluoromethyl)-4,5-dihydro-1H-spiro[cyclopenta[c]pyrazole-6,2'-[1,3]dithiolane]-1-yl)acetate (141 mg, 0.4 mmol) in CH₂Cl₂ (1 mL). The reaction was kept at −78° C. for 30 min, and then warmed up to −30° C. The reaction was carefully poured to cold (0° C.) saturated NaHCO₃, and added more NaHCO₃ if pH was less than 7. Then it was extracted with CH₂Cl₂. The organic layer was separated, dried over MgSO₄, filtered and concentrated. The residue was purified by silica gel chromatography eluting with EtOAc/Hexanes to afford 40 mg of the title compound: MS (m/z) 298.97, [M+H]⁺.

Synthesis of (S)-5-(2-(1-(2-(6,6-difluoro-3-(trifluoromethyl)-5,6-dihydrocyclopenta[c]pyrazol-1(4H)-yl)acetamido)-2-(3,5-difluorophenyl)ethyl)pyridin-3-yl)-2-fluorobenzamide (283C)

Compound 283C was prepared (30 mg) according to the method presented in the synthesis of Example 54 utilizing Compound 54B and ethyl 2-(6,6-difluoro-3-(trifluoromethyl)-5,6-dihydrocyclopenta[c]pyrazol-1 (4H)-yl)acetate to provide the title compound; MS (m/z) 624.48 [M+H]⁺. ¹H NMR (400 MHz, cd₃od) δ 8.72 (dd, J=4.9, 1.6 Hz, 1H), 7.68 (dd, J=7.8, 1.6 Hz, 1H), 7.48 (dd, J=7.8, 4.9 Hz, 1H), 7.38 (d, J=6.9 Hz, 1H), 7.32 (s, 1H), 7.21 (dd, J=10.7, 8.5 Hz, 1H), 6.76-6.57 (m, 1H), 6.30 (d, J=6.2 Hz, 2H), 5.36 (t, J=7.6 Hz, 1H), 4.96 (d, J=16.8 Hz, 2H), 3.17-2.90 (m, 4H), 2.83 (dd, J=7.5, 4.4 Hz, 2H).

Example 284

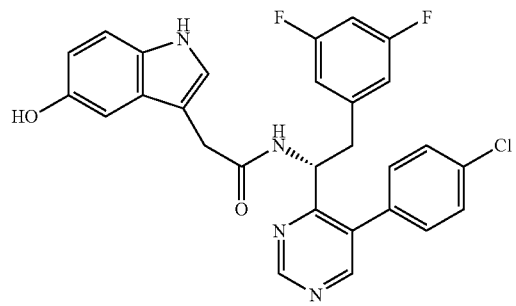

284

Synthesis of (R)—N-(1-(5-(4-chlorophenyl)pyrimidin-4-yl)-2-(3,5-difluorophenyl)ethyl)-2-(5-hydroxy-1H-indol-3-yl)acetamide (284)

Compound 284 was prepared (21 mg) according to the method presented for the synthesis of Example 279G substituting 2-(5-hydroxy-1H-indol-3-yl)acetic acid for 2-(5,6-dimethyl-1H-benzo[d]imidazol-1-yl)acetic acid to afford the title compound: MS (m/z) 518.8 [M+H]⁺. ¹H NMR (400 MHz, cd₃od) δ 9.10 (s, 1H), 8.48 (s, 1H), 7.39 (d, J=8.3 Hz, 2H), 7.15 (dd, J=17.6, 8.5 Hz, 3H), 7.06 (s, 1H), 6.83 (d, J=2.1 Hz, 1H), 6.68 (dd, J=12.7, 5.8 Hz, 2H), 6.30 (d, J=6.5 Hz, 2H), 5.40 (t, J=7.5 Hz, 1H), 3.71-3.50 (m, 2H), 3.06-2.84 (m, 2H).

Example 285

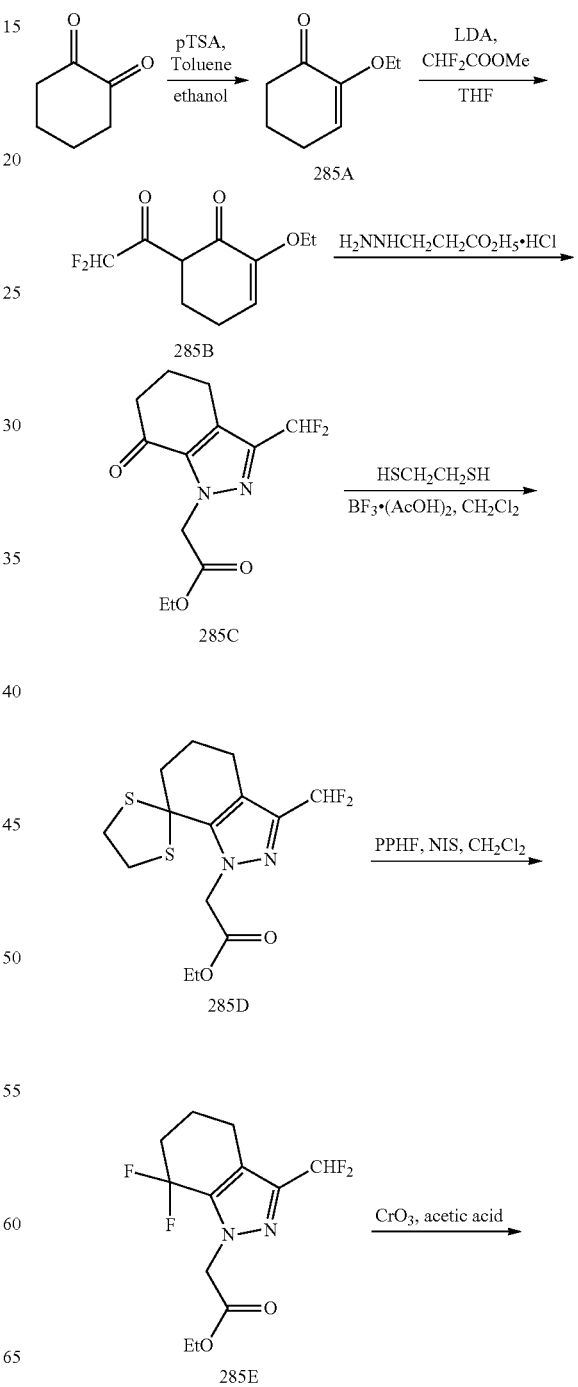

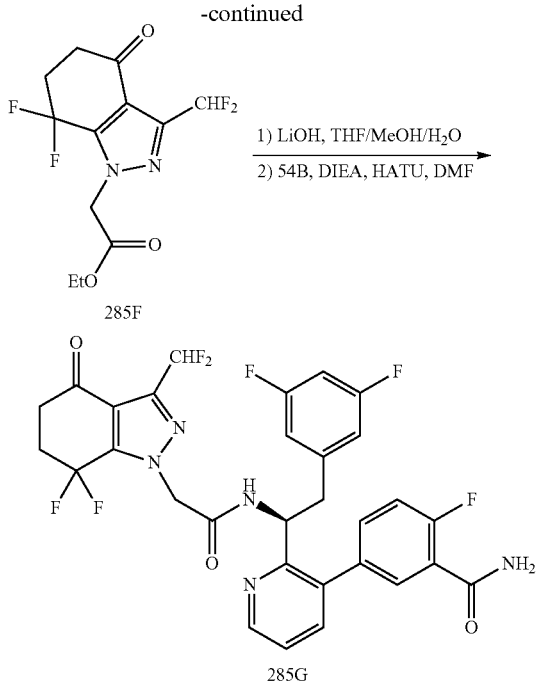

Synthesis of 2-ethoxycyclohex-2-enone (285A)

5 gram of cyclohexane-1,2-dione was dissolved in a mixture of 100 mL of toluene and 50 mL of ethanol. To it was added 1 gram of p-Toluenesulfonic acid and the solution was heated at reflux for one day; then cooled down and removed the solvent. The residue was dissolved in $CH_2Cl_2$ and washed with $NaHCO_3$ (sat'd aqueous solution) and half brine. The organic layer was separated, dried over $MgSO_4$, filtered and concentrated. The residue was purified by silica gel chromatography eluting with EtOAc/Hexanes to afford 4.6 gram of the title compound. MS (m/z) 141.08 $[M+H]^+$.

Synthesis of 6-(2,2-difluoroacetyl)-2-ethoxycyclohex-2-enone (285B)

Compound 285B was prepared according to the method presented in the synthesis of Example 60B utilizing 2-ethoxycyclohex-2-enone to provide the title compound. MS (m/z) 219.12 $[M+H]^+$.

Synthesis of ethyl 2-(3-(difluoromethyl)-7-oxo-4,5,6,7-tetrahydro-1H-indazol-1-yl)acetate (285C)

Compound 285C was prepared according to the method presented in the synthesis of Example 60C utilizing 6-(2,2-difluoroacetyl)-2-ethoxycyclohex-2-enone to provide the title compound. MS (m/z) 273.11 $[M+H]^+$.

Synthesis of ethyl 2-(3'-(difluoromethyl)-5',6'-dihydrospiro[[1,3]dithiolane-2,7'-indazole]-1'(4'H)-yl)acetate (285D)

Compound 285D was prepared according to the method presented in the synthesis of Example 283A utilizing ethyl 2-(3-(difluoromethyl)-7-oxo-4,5,6,7-tetrahydro-1H-indazol-1-yl)acetate to provide the title compound. MS (m/z) 349.28 $[M+H]^+$.

Synthesis of ethyl 2-(3-(difluoromethyl)-7,7-difluoro-4,5,6,7-tetrahydro-1H-indazol-1-yl)acetate (285E)

Compound 285E was prepared according to the method presented in the synthesis of Example 283B utilizing ethyl 2-(3'-(difluoromethyl)-5',6'-dihydrospiro[[1,3]dithiolane-2,7'-indazole]-1'(4'H)-yl)acetate to provide the title compound. MS (m/z) 295.02 $[M+H]^+$.

Synthesis of ethyl 2-(3-(difluoromethyl)-7,7-difluoro-4-oxo-4,5,6,7-tetrahydro-1H-indazol-1-yl)acetate (285F)

Compound 285F was prepared according to the method presented in the synthesis of Example 272A utilizing ethyl 2-(3-(difluoromethyl)-7,7-difluoro-4,5,6,7-tetrahydro-1H-indazol-1-yl)acetate to provide the title compound. MS (m/z) 309.01 $[M+H]^+$.

Synthesis of (S)-5-(2-(1-(2-(3-(difluoromethyl)-7,7-difluoro-4-oxo-4,5,6,7-tetrahydro-1H-indazol-1-yl)acetamido)-2-(3,5-difluorophenyl)ethyl)pyridin-3-yl)-2-fluorobenzamide (285G)

Compound 285G was prepared (6 mg) according to the method presented in the synthesis of Example 54 utilizing Compound 54B and ethyl 2-(3-(difluoromethyl)-7,7-difluoro-4-oxo-4,5,6,7-tetrahydro-1H-indazol-1-yl)acetic acid to provide the title compound; MS (m/z) 634.43 $[M+H]^+$. $^1$H NMR (400 MHz, cd$_3$od) δ 8.72 (dd, J=4.9, 1.6 Hz, 1H), 7.63 (dd, J=7.8, 1.6 Hz, 1H), 7.44 (dd, J=7.8, 4.9 Hz, 1H), 7.39 (d, J=7.0 Hz, 1H), 7.29 (s, 1H), 7.20 (t, J=5.3 Hz, 1H), 6.99 (t, J=53.5 Hz, 1H), 6.66 (t, J=9.2 Hz, 1H), 6.32 (d, J=6.2 Hz, 2H), 5.36 (t, J=7.5 Hz, 1H), 5.12 (s, 2H), 3.17-3.00 (m, 2H), 2.85-2.56 (m, 4H).

Example 286

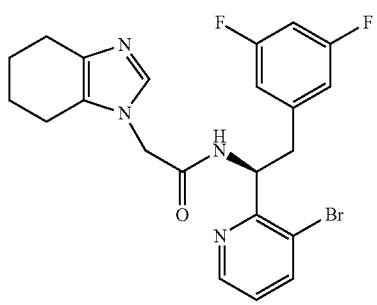

Synthesis of (S)—N-(1-(3-bromopyridin-2-yl)-2-(3,5-difluorophenyl)ethyl)-2-(4,5,6,7-tetrahydro-1H-benzo[d]imidazol-1-yl)acetamide (286)

Compound 286 was prepared (8 mg) according to the method presented in the synthesis of Example 57 utilizing Compound 55D and 2-(4,5,6,7-tetrahydro-1H-benzo[d]imidazol-1-yl)acetic acid to afford the title compound. MS (m/z) 475.1 [M+H]⁺. ¹H NMR (400 MHz, cdcl₃) δ 8.72 (s, 1H), 8.52 (s, 1H), 8.11 (m, 1H), 7.98 (d, J=8.0 Hz, 1H), 6.73-6.54 (m, 3H), 5.78 (d, J=5.5 Hz, 1H), 4.78 (d, J=22.5 Hz, 2H), 3.18 (dd, J=13.6, 5.2 Hz, 1H), 3.00 (dd, J=13.5, 8.2 Hz, 1H), 2.66 (s, 2H), 2.42 (s, 2H), 1.84 (s, 4H).

Example 287

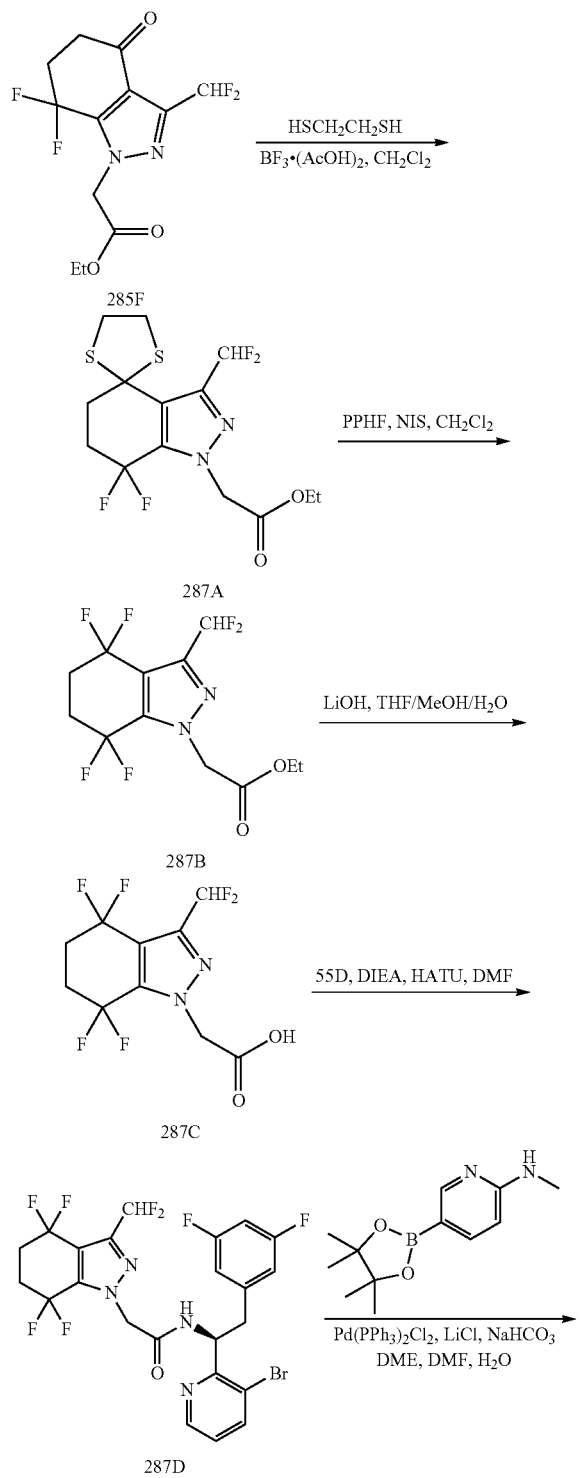

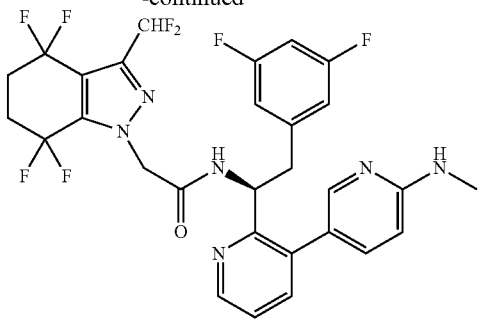

287E

Synthesis of ethyl 2-(3'-(difluoromethyl)-7',7'-difluoro-6',7'-dihydrospiro[[1,3]dithiolane-2,4'-indazole]-1'(5'H)-yl)acetate (287A)

Compound 287A was prepared according to the method presented in the synthesis of Example 283A utilizing ethyl 2-(3-(difluoromethyl)-7,7-difluoro-4-oxo-4,5,6,7-tetrahydro-1H-indazol-1-yl)acetate. MS (m/z) 385.26 [M+H]⁺.

Synthesis of ethyl 2-(3-(difluoromethyl)-4,4,7,7-tetrafluoro-4,5,6,7-tetrahydro-1H-indazol-1-yl)acetate (287B)

Compound 287B was prepared according to the method presented in the synthesis of Example 283B utilizing ethyl 2-(3'-(difluoromethyl)-7',7'-difluoro-6',7'-dihydrospiro[[1,3]dithiolane-2,4'-indazole]-1'(5'H)-yl)acetate and substituting 2 mol equivalent of N-iodosuccinimide for 1,3-dibromo-5,5-dimethylhydantoin to afford the title compound. MS (m/z) 330.98 [M+H]⁺.

Synthesis of 2-(3-(difluoromethyl)-4,4,7,7-tetrafluoro-4,5,6,7-tetrahydro-1H-indazol-1-yl)acetic acid (287C)

Compound 287C was prepared according to the method presented in the synthesis of Example 60G utilizing ethyl 2-(3-(difluoromethyl)-4,4,7,7-tetrafluoro-4,5,6,7-tetrahydro-1H-indazol-1-yl)acetate to afford the title compound. MS (m/z) 303.08 [M+H]⁺.

Synthesis of (S)—N-(1-(3-bromopyridin-2-yl)-2-(3,5-difluorophenyl)ethyl)-2-(3-(difluoromethyl)-4,4,7,7-tetrafluoro-4,5,6,7-tetrahydro-1H-indazol-1-yl)acetamide (287D)

Compound 287D was prepared according to the method presented in the synthesis of Example 55E utilizing Compound 55D and 2-(3-(difluoromethyl)-4,4,7,7-tetrafluoro-4,5,6,7-tetrahydro-1H-indazol-1-yl)acetic acid to afford the title compound. MS (m/z) 597.88 [M+H]⁺.

Synthesis of (S)-2-(3-(difluoromethyl)-4,4,7,7-tetrafluoro-4,5,6,7-tetrahydro-1H-indazol-1-yl)-N-(2-(3,5-difluorophenyl)-1-(6'-(methylamino)-3,3'-bipyridin-2-yl)ethyl)acetamide (287E)

Compound 287E was prepared (9 mg) according to the method presented in the synthesis of Example 61D substituting N-methyl-5-(4,4,5,5-tetramethyl-1,3,2-dioxaborolan- 2-yl)pyridin-2-amine for 5-(4,4,5,5-tetramethyl-1,3,2-di-oxaborolan-2-yl)-1H-pyrrolo[2,3-b]pyridine to provide the title compound. MS (m/z) 625.22 [M+H]⁺. ¹H NMR (400 MHz, cd₃od) δ 8.74 (dd, J=4.7, 1.6 Hz, 1H), 7.64-7.53 (m, 2H), 7.47 (s, 1H), 7.39 (dd, J=7.8, 4.8 Hz, 1H), 6.98 (d, J=9.2 Hz, 1H), 6.92-6.62 (m, 2H), 6.42 (d, J=6.3 Hz, 2H), 5.28 (t, J=7.6 Hz, 1H), 5.13-4.96 (m, 2H), 3.13 (d, J=7.7 Hz, 2H), 3.02 (s, 3H), 2.50 (d, J=12.1 Hz, 4H).

Example 288

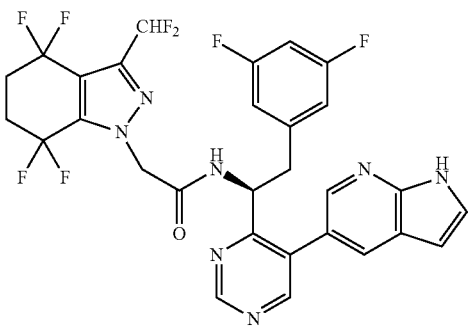

288

Synthesis of (S)—N-(1-(5-(1H-pyrrolo[2,3-b]pyridin-5-yl)pyrimidin-4-yl)-2-(3,5-difluorophenyl)ethyl)-2-(3-(difluoromethyl)-4,4,7,7-tetrafluoro-4,5,6,7-tetrahydro-1H-indazol-1-yl)acetamide (288)

Compound 288 was prepared (35 mg) according to the method presented in the synthesis of Example 13 utilizing Compound 172C and 2-(3-(difluoromethyl)-4,4,7,7-tetra-fluoro-4,5,6,7-tetrahydro-1H-indazol-1-yl)acetic acid to provide the title compound. MS (m/z) 636.29 [M+H]⁺. ¹H NMR (400 MHz, cd₃od) δ 9.28 (s, 1H), 9.16 (d, J=7.8 Hz, 1H), 8.62 (s, 1H), 8.10 (s, 1H), 7.98 (s, 1H), 7.60 (d, J=3.5 Hz, 1H), 6.99-6.57 (m, 3H), 6.35 (d, J=6.1 Hz, 2H), 5.47-5.25 (m, 1H), 5.06 (s, 2H), 3.12 (t, J=10.7 Hz, 2H), 2.65-2.34 (m, 4H).

Example 289

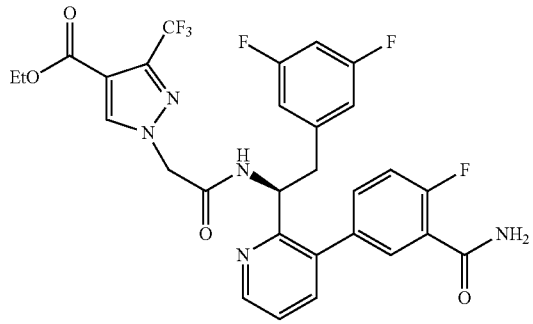

289

Synthesis of (S)-ethyl 1-(2-(1-(3-(3-carbamoyl-4-fluorophenyl)pyridin-2-yl)-2-(3,5-difluorophenyl)ethylamino)-2-oxoethyl)-3-(trifluoromethyl)-1H-pyrazole-4-carboxylate (289)

Compound 289 was prepared (10 mg) according to the method presented in the synthesis of Example 56B utilizing Compound 56A and ethyl 3-(trifluoromethyl)-1H-pyrazole-4-carboxylate to provide the title compound. MS (m/z) 620.21 [M+H]⁺. ¹H NMR (400 MHz, cd₃od) δ 8.68 (dd, J=4.8, 1.6 Hz, 1H), 8.28 (s, 1H), 7.55 (dd, J=7.8, 1.6 Hz, 1H), 7.45-7.34 (m, 2H), 7.31 (s, 1H), 7.20 (dd, J=10.8, 8.5 Hz, 1H), 6.64 (m, 1H), 6.29 (d, J=6.2 Hz, 2H), 5.33 (dd, J=8.6, 6.5 Hz, 1H), 4.97 (s, 2H), 4.28 (q, J=7.1 Hz, 2H), 3.06 (qd, J=12.9, 7.6 Hz, 2H), 1.32 (t, J=7.1 Hz, 3H).

Example 290

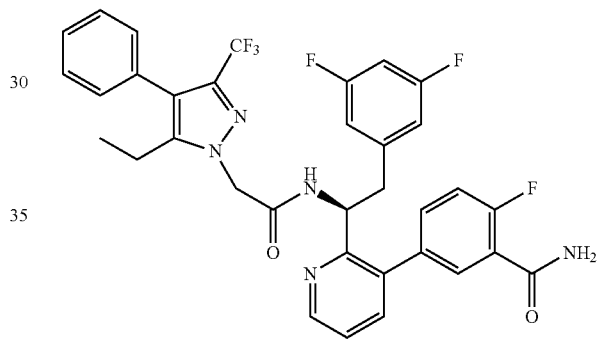

290

Synthesis of(S)-5-(2-(2-(3,5-difluorophenyl)-1-(2-(5-ethyl-4-phenyl-3-(trifluoromethyl)-1H-pyrazol-1-yl)acetamido)ethyl)pyridin-3-yl)-2-fluorobenzamide (290)

Compound 290 was prepared (4 mg) according to the method presented in the synthesis of Example 276 substituting (S)-5-(2-(1-(2-(4-bromo-5-ethyl-3-(trifluoromethyl)-1H-pyrazol-1-yl)acetamido)-2-(3,5-difluorophenyl)ethyl)pyridin-3-yl)-2-fluorobenzamide (58) and phenylboronic acid for (S)-5-(2-(1-(2-(4-bromo-3-(trifluoromethyl)-1H-pyrazol-1-yl)acetamido)-2-(3,5-difluorophenyl)ethyl)pyridin-3-yl)-2-fluorobenzamide and cyclopropane boronic acid to provide the title compound. MS (m/z) 652.43 [M+H]⁺. ¹H NMR (400 MHz, cd₃od) δ 8.70 (dd, J=4.9, 1.6 Hz, 1H), 7.64 (dd, J=7.8, 1.6 Hz, 1H), 7.56-7.34 (m, 6H), 7.28-7.16 (m, 3H), 6.67 (t, J=9.3 Hz, 1H), 6.35 (d, J=6.2 Hz, 2H), 5.39 (t, J 7.5 Hz, 1H), 4.95 (s, 2H), 3.08 (d, J=7.5 Hz, 2H), 2.50 (dt, J=10.4, 7.6 Hz, 2H), 0.94 (t, J=7.6 Hz, 3H).

Example 291

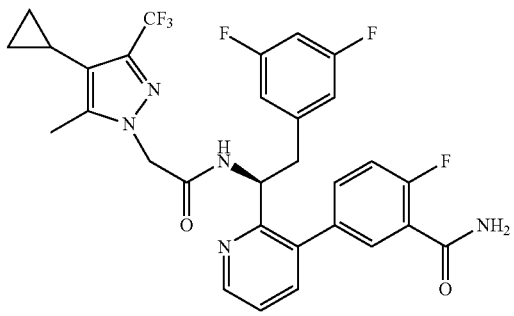

Synthesis of (S)-5-(2-(1-(2-(4-cyclopropyl-5-methyl-3-(trifluoromethyl)-1H-pyrazol-1-yl)acetamido)-2-(3,5-difluorophenyl)ethyl)pyridin-3-yl)-2-fluorobenzamide (291)

Compound 291 was prepared (25 mg) according to the method presented for the synthesis of Example 276 substituting (S)-5-(2-(1-(2-(4-bromo-5-methyl-3-(trifluoromethyl)-1H-pyrazol-1-yl)acetamido)-2-(3,5-difluorophenyl)ethyl)pyridin-3-yl)-2-fluorobenzamide (275) for (S)-5-(2-(1-(2-(4-bromo-3-(trifluoromethyl)-1H-pyrazol-1-yl)acetamido)-2-(3,5-difluorophenyl)ethyl)pyridin-3-yl)-2-fluorobenzamide to provide the title compound: MS (m/z) 602.32 [M+H]+. 1H NMR (400 MHz, cd3od) δ 8.70 (dd, J=4.9, 1.6 Hz, 1H), 7.68 (dd, J=7.8, 1.6 Hz, 1H), 7.56-7.42 (m, 2H), 7.35 (s, 1H), 7.22 (dd, J=10.7, 8.5 Hz, 1H), 6.79-6.60 (m, 1H), 6.33 (d, J=6.2 Hz, 2H), 5.36 (t, J=7.6 Hz, 1H), 4.83 (s, 2H), 3.05 (d, J=7.6 Hz, 2H), 2.16 (s, 3H), 1.53 (m, 1H), 0.93-0.73 (m, 2H), 0.51 (q, J=5.7 Hz, 2H).

Example 292

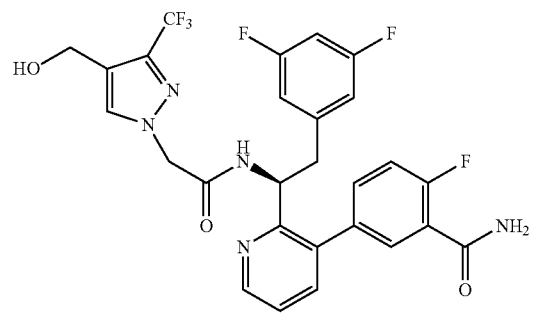

(S)-5-(2-(2-(3,5-difluorophenyl)-1-(2-(4-(hydroxymethyl)-3-(trifluoromethyl)-1H-pyrazol-1-yl)acetamido)ethyl)pyridin-3-yl)-2-fluorobenzamide (292)

Compound 292 was prepared (10 mg) according to the method presented for the synthesis of Example 333 to afford the title compound as a side product. MS (m/z) 578.20 [M+H]+. 1H NMR (400 MHz, cd3od) δ 8.70 (dd, J=4.9, 1.6 Hz, 1H), 7.71 (s, 1H), 7.63 (dd, J=7.8, 1.7 Hz, 1H), 7.47-7.38 (m, 2H), 7.30 (s, 1H), 7.21 (dd, J=10.7, 8.5 Hz, 1H), 6.73-6.55 (m, 1H), 6.30 (d, J=6.2 Hz, 2H), 5.35 (dd, J=13.2, 6.4 Hz, 1H), 4.92 (s, 2H), 4.55 (s, 2H), 3.15-2.94 (m, 2H).

Example 293

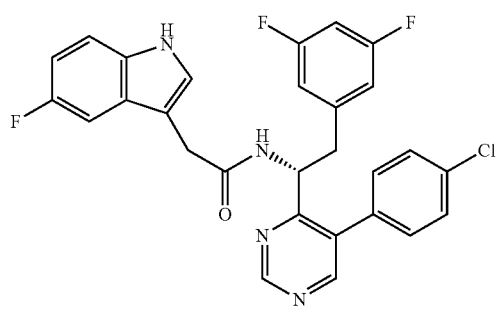

Synthesis of (R)—N-(1-(5-(4-chlorophenyl)pyrimidin-4-yl)-2-(3,5-difluorophenyl)ethyl)-2-(5-fluoro-1H-indol-3-yl)acetamide (293)

Compound 293 was prepared (24 mg) according to the method presented for the synthesis of Example 279G substituting 2-(5-fluoro-1H-indol-3-yl)acetic acid for 2-(5,6-dimethyl-1H-benzo[d]imidazol-1-yl)acetic acid to afford the title compound: MS (m/z) 521.2 [M+H]+. 1H NMR (400 MHz, cdcl3) δ 9.04 (s, 1H), 8.55 (s, 1H), 8.24 (s, 1H), 7.46 (d, J=8.2 Hz, 2H), 7.35 (dd, J=8.6, 4.2 Hz, 1H), 7.19 (s, 1H), 7.12 (d, J=8.2 Hz, 2H), 7.01 (t, J=9.2 Hz, 2H), 6.82 (d, J=7.9 Hz, 1H), 6.56 (t, J=8.8 Hz, 1H), 6.07 (d, J=5.9 Hz, 2H), 5.52 (q, J=7.5 Hz, 1H), 3.81-3.61 (m, 2H), 2.83-2.65 (m, 2H).

Example 294

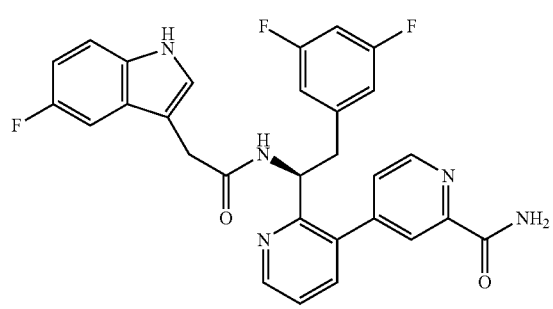

Synthesis of (S)-2-(2-(3,5-difluorophenyl)-1-(2-(5-fluoro-1H-indol-3-yl)acetamido)ethyl)-3,4'-bipyridine-2'-carboxamide (294)

(S)—N-(1-(2'-cyano-3,4'-bipyridin-2-yl)-2-(3,5-difluorophenyl)ethyl)-2-(5-fluoro-1H-indol-3-yl)acetamide (377, 10 mg) was dissolved in 1 mL of THF and cooled down to 0° C. with ice-water bath. To it was added 0.05 mL of KOH solution (50% in H2O) and 0.1 mL of hydrogen peroxide solution [30% (w/w) in water]. The reaction was allowed to warm to ambient temperature and stirred for 16 hours and then concentrated. The residue was purified by reverse phase HPLC eluting with acetonitrile/water (with 0.1% TFA) to afford 5.9 mg of the title compound. MS (m/z) 529.9 [M+H]+. 1H NMR (400 MHz, cdcl3) δ 8.68 (d, J=5.0 Hz, 1H), 8.52 (d, J=4.5 Hz, 1H), 8.19-8.09 (m, 2H), 7.97 (s, 1H), 7.86 (s, 1H), 7.80 (d, J=7.9 Hz, 1H), 7.67-7.50 (m, 2H), 7.26-7.20 (m, 1H), 7.13 (s, 1H), 6.92-6.75 (m, 2H), 6.51 (m, 2H), 6.03 (d, J=5.8 Hz, 2H), 5.28 (dd, J=15.9, 7.6 Hz, 1H), 3.74-3.49 (m, 2H), 2.97 (dd, J=13.6, 7.2 Hz, 1H), 2.87-2.78 (m, 1H).

Example 295

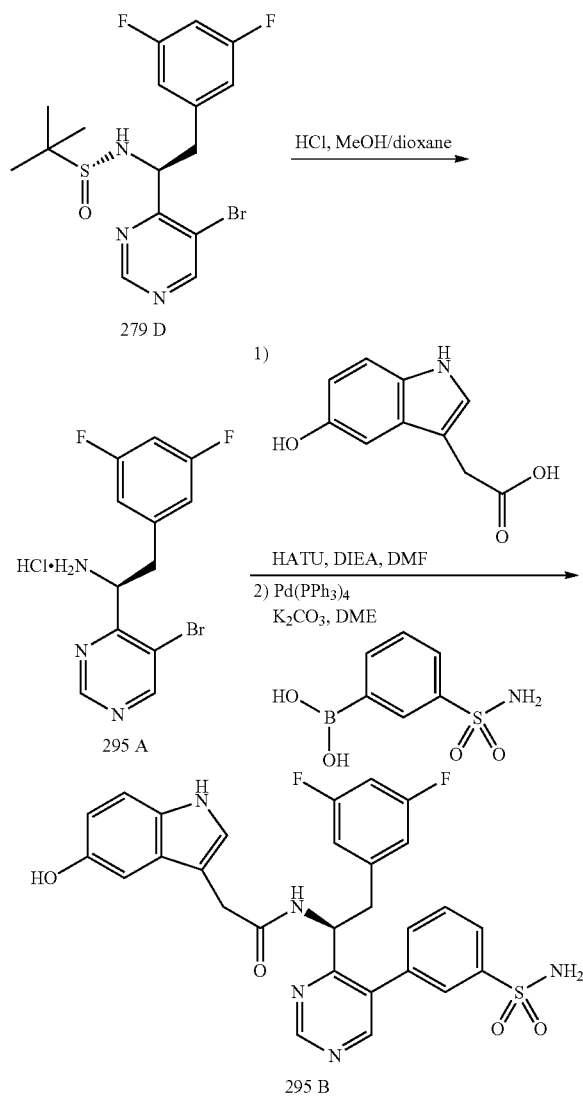

Synthesis of (S)-1-(5-bromopyrimidin-4-yl)-2-(3,5-difluorophenyl)ethanamine hydrochloride (295A)

Compound 295A was prepared according to the method presented for the synthesis of Example 279F substituting Compound 279D for Compound 279E to afford the title compound: MS (m/z) 316.2 [M+H]+.

Synthesis of (S)—N-(2-(3,5-difluorophenyl)-1-(5-(3-sulfamoylphenyl)pyrimidin-4-yl)ethyl)-2-(5-hydroxy-1H-indol-3-yl)acetamide (295B)

Compound 295B was prepared (19 mg) according to the method presented in the synthesis of Example 57 utilizing Compound 295A and 2-(5-hydroxy-1H-indol-3-yl)acetic acid, then Suzuki coupling with 3-sulfamoylphenylboronic acid to afford the title compound. MS (m/z) 564.2 [M+H]+. 1H NMR (400 MHz, cd3od) δ 9.05 (s, 1H), 8.45 (s, 1H), 7.87 (d, J=8.0 Hz, 1H), 7.72 (s, 1H), 7.49 (t, J=7.8 Hz, 1H), 7.27 (d, J=7.6 Hz, 1H), 7.07 (d, J=8.7 Hz, 1H), 6.96 (s, 1H), 6.73 (s, 1H), 6.57 (d, J=8.6 Hz, 2H), 6.23 (d, J=6.8 Hz, 2H), 5.29 (t, J=7.5 Hz, 1H), 3.66-3.40 (m, 2H), 2.90 (d, J=7.5 Hz, 2H).

Example 296

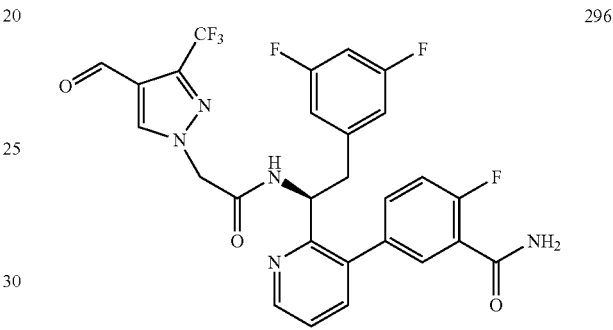

Synthesis of (S)-5-(2-(2-(3,5-difluorophenyl)-1-(2-(4-formyl-3-(trifluoromethyl)-1H-pyrazol-1-yl)acetamido)ethyl)pyridin-3-yl)-2-fluorobenzamide (296)

Compound 296 was prepared (4 mg) according to the method presented in the synthesis of Example 56B utilizing compound 56A and 3-(trifluoromethyl)-1H-pyrazole-4-carbaldehyde to provide the title compound. MS (m/z) 620.21 [M+H]+. 1H NMR (400 MHz, cdcl3) δ 9.97 (s, 1H), 8.59 (d, J=3.3 Hz, 1H), 8.14 (s, 1H), 7.64 (d, J=7.0 Hz, 1H), 7.52 (d, J=7.9 Hz, 1H), 7.48-7.37 (m, 1H), 7.33 (m, 1H), 7.22-7.09 (m, 2H), 6.73 (m, 1H), 6.56 (d, J=9.1 Hz, 1H), 6.12 (d, J=6.6 Hz, 2H), 5.87 (s, 1H), 5.44 (d, J=6.3 Hz, 1H), 4.89 (s, 2H), 2.93 (s, 2H).

Example 297

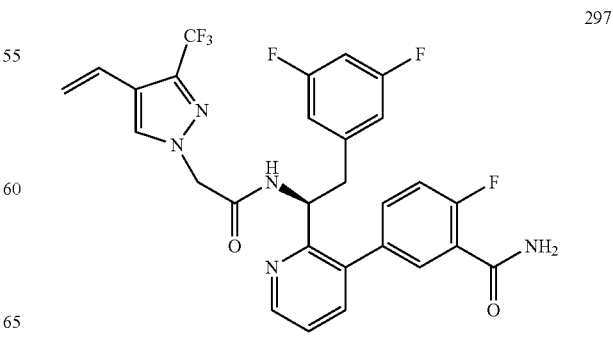

Synthesis of (S)-5-(2-(2-(3,5-difluorophenyl)-1-(2-(3-(trifluoromethyl)-4-vinyl-1H-pyrazol-1-yl)acetamido)ethyl)pyridin-3-yl)-2-fluorobenzamide (297)

(S)-5-(2-(2-(3,5-difluorophenyl)-1-(2-(4-ethynyl-3-(trifluoromethyl)-1H-pyrazol-1-yl)acetamido)ethyl)pyridin-3-yl)-2-fluorobenzamide (341, 40 mg) was dissolved in 10 mL of EtOAc. The system was purged with argon and then 30 mg of Lindlar Catalyst was added. The reaction was stirred for 20 hours under 1 atm H$_2$ at ambient temperature. Upon completion of the reaction, it was filtered through a pad of celite and washed with EtOAc. The filtrate was collected and the volatiles were removed in vacuo. The residue was purified by reverse phase HPLC eluting with acetonitrile/water (with 0.1% TFA) to afford 15 mg of the title compound. MS (m/z) 574.40 [M+H]$^+$. $^1$H NMR (400 MHz, cd$_3$od) δ 8.69 (dd, J=4.9, 1.6 Hz, 1H), 7.93 (s, 1H), 7.64 (dd, J=7.8, 1.6 Hz, 1H), 7.49-7.40 (m, 2H), 7.33 (s, 1H), 7.21 (dd, J=10.7, 8.6 Hz, 1H), 6.65 (t, J=9.2 Hz, 1H), 6.60-6.48 (m, 1H), 6.30 (d, J=6.2 Hz, 2H), 5.58 (d, J=17.7 Hz, 1H), 5.35 (t, J=7.5 Hz, 1H), 5.22 (dd, J=11.2, 1.2 Hz, 1H), 4.91 (s, 2H), 3.06 (d, J=7.8 Hz, 2H).

Example 298

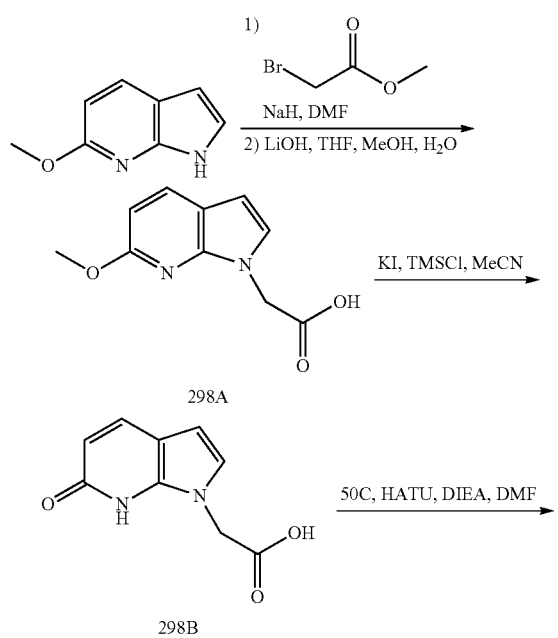

Synthesis of 2-(6-methoxy-1H-pyrrolo[2,3-b]pyridin-1-yl)acetic acid (298A)

6-methoxy-1H-pyrrolo[2,3-b]pyridine (250 mg, 1.69 mmol) was dissolved in 2 mL of DMF and cooled down to 0° C. To it was added NaH (60% in oil dispersion, 68 mg, 1.69 mmol) portionwise. The mixture was stirred at ambient temperature for 20 min, a solution of methyl 2-bromoacetate (192 µL, 2 mmol) in 0.5 mL of DMF was added dropwise. It was stirred for 2 hours and quenched with saturated aqueous NH$_4$Cl solution. The mixture was partitioned between EtOAc and water. The organic layer was separated, dried over MgSO$_4$, filtered and concentrated to afford crude methyl 2-(6-methoxy-1H-pyrrolo[2,3-b]pyridin-1-yl)acetate which was dissolved in 5 mL of THF/MeOH/H$_2$O (3/2/1) and to it was added LiOH.H$_2$O (355 mg, 8.45 mmol). The mixture was stirred at ambient temperature for 20 min and concentrated to small volume. It was filtered and purified by reverse phase HPLC eluting with acetonitrile/water (with 0.1% TFA) to afford 186 mg of the title compound. MS (m/z) 205.1 [M–H]$^-$ Synthesis of 2-(6-oxo-6,7-dihydro-1H-pyrrolo[2,3-b]pyridin-1-yl)acetic acid (298B)

2-(6-methoxy-1H-pyrrolo[2,3-b]pyridin-1-yl)acetic acid (100 mg, 0.48 mmol) was dissolved in 5 mL of acetonitrile. To it was added KI (161 mg, 0.96 mmol) and TMSCl (122 µL, 0.96 mmol) The reaction mixture was heated up to 80° C. for 4 hours and cooled down to ambient temperature. It was filtered and purified by reverse phase HPLC eluting with acetonitrile/water (with 0.1% TFA) to afford 30 mg of the title compound. MS (m/z) 193.3 [M+H]$^+$.

Synthesis of (S)-3-(2-(2-(3,5-difluorophenyl)-1-(2-(6-oxo-6,7-dihydro-1H-pyrrolo[2,3-b]pyridin-1-yl)acetamido)ethyl)pyridin-3-yl)benzamide (298C)

Compound 298C was prepared (6 mg) according to the method presented in the synthesis of Example 50D utilizing compound 50C and 2-(6-oxo-6,7-dihydro-1H-pyrrolo[2,3-b]pyridin-1-yl)acetic acid to provide the title compound. MS (m/z) 528.0 [M+H]$^+$. $^1$H NMR (400 MHz, cd$_3$od) δ 8.69 (d, J=4.9 Hz, 1H), 7.95 (d, J=8.6 Hz, 1H), 7.89 (d, J=7.8 Hz, 1H), 7.70 (d, J=7.8 Hz, 1H), 7.64 (s, 1H), 7.48 (dd, J=10.2, 5.0 Hz, 2H), 7.28 (d, J=7.1 Hz, 1H), 7.03 (d, J=3.5 Hz, 1H), 6.64 (t, J=9.2 Hz, 1H), 6.51 (d, J=8.5 Hz, 1H), 6.46 (d, J=3.5 Hz, 1H), 6.23 (d, J=6.2 Hz, 2H), 5.42 (t, J=7.5 Hz, 1H), 4.93 (s, 2H), 3.10-2.96 (m, 2H).

Example 299

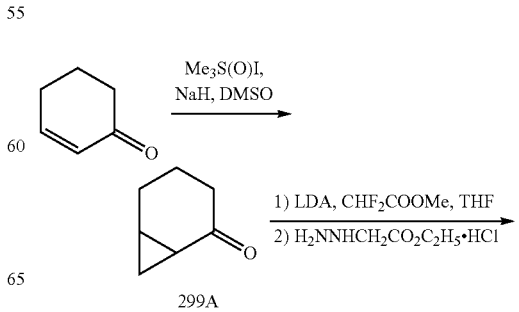

511

-continued

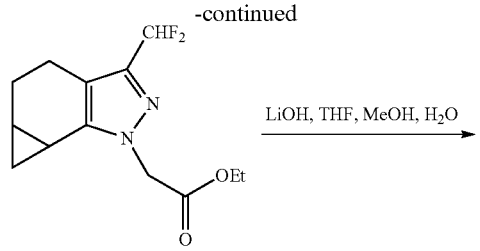

299B

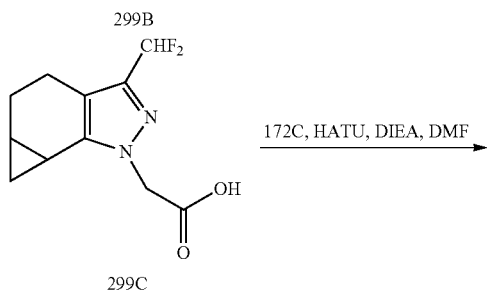

299C

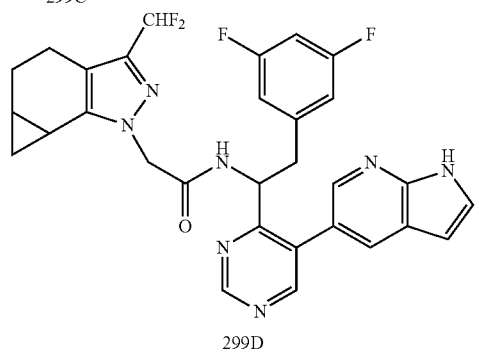

299D

Synthesis of bicyclo[4.1.0]heptan-2-one (299A)

Compound 299A was prepared according to the method presented in Tetrahedron, Vol. 51. No. 43, p. 11757, 1995.
$^1$H NMR (400 MHz, cdcl3) δ 2.27-2.18 (m, 1H), 2.05-1.79 (m, 4H), 1.72-1.47 (m, 3H), 1.14 (m, 1H), 1.08-0.92 (m, 1H).

Synthesis of ethyl 2-(3-(difluoromethyl)-5,5a,6,6a-tetrahydrocyclopropa[g]indazol-1(4H)-yl)acetate (299B)

Compound 299B was prepared according to the method presented in the synthesis of Example 60C utilizing bicyclo[4.1.0]heptan-2-one to provide the title compound as a mixture of diastereomers. MS (m/z) 271.17 [M+H]$^+$.

Synthesis of 2-(3-(difluoromethyl)-5,5a,6,6a-tetrahydrocyclopropa[g]indazol-1(4H)-yl)acetic acid (299C)

Ethyl 2-(3-(difluoromethyl)-5,5a,6,6a-tetrahydrocyclopropa[g]indazol-1(4H)-yl)acetate (27 mg, 0.1 mmol) was dissolved in 2 mL of THF/MeOH/H$_2$O (3/2/1) and to it was added LiOH.H$_2$O (13 mg, 0.3 mmol). The mixture was stirred at ambient temperature for 10 min and cooled down to 0° C. It was acidified with 1N HCl and extracted with EtOAc. The organic layer was separated, dried over MgSO$_4$, filtered and concentrated to afford the title compound. MS (m/z) 243.12 [M+H]$^+$.

512

Synthesis of N-(1-(5-(1H-pyrrolo[2,3-b]pyridin-5-yl)pyrimidin-4-yl)-2-(3,5-difluorophenyl)ethyl)-2-(3-(difluoromethyl)-5,5a,6,6a-tetrahydrocyclopropa[g]indazol-1(4H)-yl)acetamide (299D)

Compound 299D was prepared (30 mg) according to the method presented in the synthesis of Example 13 utilizing Compound 172C and 2-(3-(difluoromethyl)-5,5a,6,6a-tetrahydrocyclopropa[g]indazol-1 (4H)-yl)acetic acid to provide the title compound as mixture of diastereomers. MS (m/z) 576.38 [M+H]$^+$. $^1$H NMR (400 MHz, cd$_3$od) δ 9.20 (d, J=2.1 Hz, 1H), 8.60 (s, 1H), 7.95 (s, 1H), 7.81 (d, J=1.9 Hz, 1H), 7.46 (d, J=3.5 Hz, 1H), 6.76-6.66 (m, 1H), 6.60-6.41 (m, 2H), 6.31 (t, J=5.7 Hz, 2H), 5.48 (td, J=7.5, 3.3 Hz, 1H), 4.87 (s, 2H), 3.12-2.94 (m, 2H), 2.70 (dd, J=15.7, 5.7 Hz, 1H), 2.11 (ddt, J=41.1, 27.6, 14.0 Hz, 2H), 1.88-1.69 (m, 2H), 1.60 (m, 1H), 0.94 (dtd, J=13.2, 8.2, 4.9 Hz, 1H), 0.65 (m, 1H).

Example 300

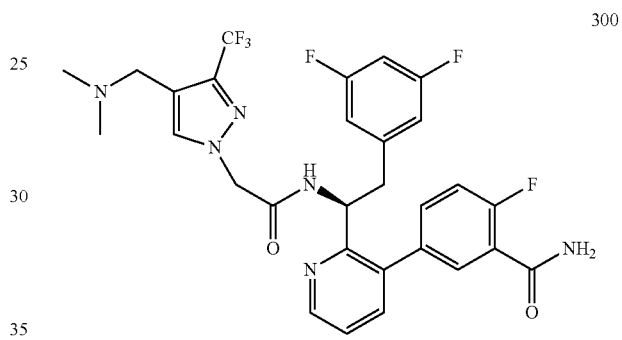

300

Synthesis of (S)-5-(2-(2-(3,5-difluorophenyl)-1-(2-(4-((dimethylamino)methyl)-3-(trifluoromethyl)-1H-pyrazol-1-yl)acetamido)ethyl)pyridin-3-yl)-2-fluorobenzamide (300)

Compound 300 was prepared (8 mg) according to the method presented for the synthesis of Example 333 substituting dimethylamine hydrochloride for methylamine hydrochloride to afford the title compound: MS (m/z) 605.29 [M+H]$^+$. $^1$H NMR (400 MHz, cd$_3$od) δ 8.70 (dd, J=4.8, 1.6 Hz, 1H), 8.02 (s, 1H), 7.59 (dd, J=7.8, 1.6 Hz, 1H), 7.49 (d, J=5.0 Hz, 1H), 7.41 (dd, J=7.8, 4.8 Hz, 1H), 7.31-7.14 (m, 2H), 6.66 (m, 1H), 6.33 (d, J=6.2 Hz, 2H), 5.41-5.26 (m, 1H), 5.02 (s, 2H), 4.31 (s, 2H), 3.09 (qd, J=13.0, 7.6 Hz, 2H), 2.86 (s, 6H).

Example 301

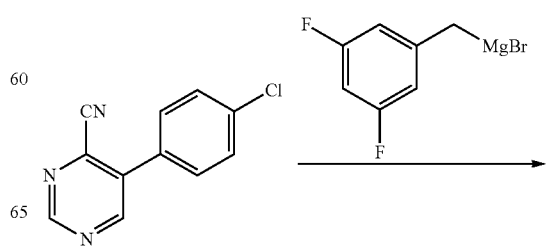

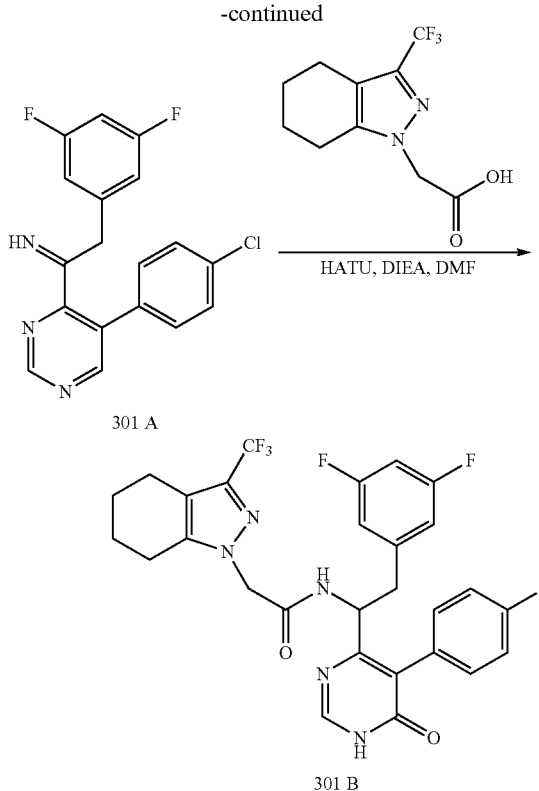

301 A

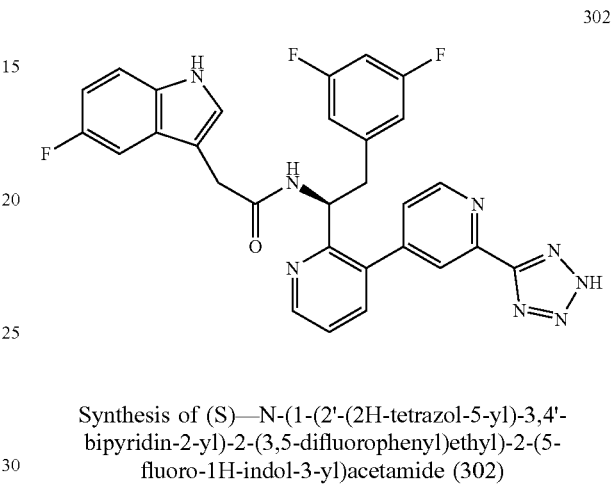

301 B

Synthesis of 1-(5-(4-chlorophenyl)pyrimidin-4-yl)-2-(3,5-difluorophenyl)ethanimine (301A)

5-(4-chlorophenyl)pyrimidine-4-carbonitrile (215 mg, 1 mmol) was dissolved in toluene and cooled down to 0° C. To it was added (3,5-difluorobenzyl)magnesium bromide (0.25 M in ether, 4.8 ml, 1.2 mmol) dropwise. After stirring for 30 min the reaction was allowed to warm to ambient temperature and stirred for 1 hour. It was cooled down to 0° C. again and 3 mL of 2-butanol was added followed by NaBH$_4$ (76 mg, 2 mmol) and the reaction was stirred at ambient temperature for 16 hours. The reaction was quenched with water at 0° C. and extracted with EtOAc. The organic layer was separated, dried over MgSO$_4$, filtered and concentrated. The residue was purified by silica gel chromatography eluting with EtOAc/Hexanes to afford 100 mg of the title compound. MS (m/z) 344.2 [M+H]$^+$.

Synthesis of (S)—N-(1-(5-(4-chlorophenyl)-6-oxo-1,6-dihydropyrimidin-4-yl)-2-(3,5-difluorophenyl)ethyl)-2-(3-(trifluoromethyl)-4,5,6,7-tetrahydro-1H-indazol-1-yl)acetamide (301B)

2-(3-(trifluoromethyl)-4,5,6,7-tetrahydro-1H-indazol-1-yl)acetic acid (25 mg, 0.1 mmol) and 1-(5-(4-chlorophenyl)pyrimidin-4-yl)-2-(3,5-difluorophenyl)ethanimine (35 mg, 0.1 mmol) was dissolved in 1 mL of DMF and cooled down to 0° C. To it was added N,N-Diisopropylethylamine (52 µL, 0.3 mmol) followed by HATU (46 mg, 0.12 mmol). The reaction was allowed to stir at 0° C. for 20 min and then purified by reverse phase HPLC eluting with acetonitrile/water (with 0.1% TFA). The fractions were combined and heated up to 60° C. for 20 min. After cooled down to room temperature it was purified by reverse phase HPLC again eluting with acetonitrile/water (with 0.1% TFA) to afford 5 mg of the title compound. MS (m/z) 592.1 [M+H]$^+$. $^1$H NMR (400 MHz, cdcl$_3$) δ 9.54 (s, 1H), 8.41 (s, 1H), 7.49-7.34 (m, 3H), 7.11 (t, J=8.8 Hz, 2H), 6.68 (t, J=8.8 Hz, 1H), 6.44 (d, J=5.6 Hz, 2H), 4.99 (m, 1H), 4.68 (q, J=16.8 Hz, 2H), 2.79-2.50 (m, 4H), 2.47-2.23 (m, 2H), 1.97-1.70 (m, 4H).

Example 302

302

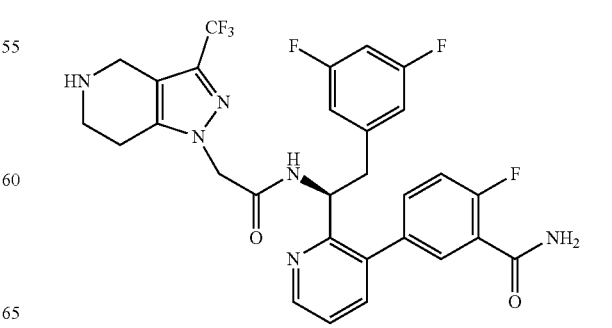

Synthesis of (S)—N-(1-(2'-(2H-tetrazol-5-yl)-3,4'-bipyridin-2-yl)-2-(3,5-difluorophenyl)ethyl)-2-(5-fluoro-1H-indol-3-yl)acetamide (302)

(S)—N-(1-(2'-cyano-3,4'-bipyridin-2-yl)-2-(3,5-difluorophenyl)ethyl)-2-(5-fluoro-1H-indol-3-yl)acetamide (377, 8 mg, 0.016 mmol) was dissolved in 1 mL of isopropanol and 1 mL of water. To it was added zinc bromide (3.5 mg, 0.016 mmol) and sodium azide (3 mg, 0.048 mmol). The reaction mixture was heated up to 100° C. for 16 hours. It was cooled down and filtered. The residue was purified by reverse phase HPLC twice eluting with acetonitrile/water (with 0.1% TFA) to afford 3.5 mg of the title compound. MS (m/z) 555.2 [M+H]$^+$. $^1$H NMR (400 MHz, cd$_3$od) δ 8.61 (d, J=4.4 Hz, 2H), 7.62 (s, 1H), 7.55 (d, J=6.2 Hz, 1H), 7.41-7.28 (m, 2H), 7.19 (dd, J=8.8, 4.4 Hz, 1H), 7.09 (s, 1H), 7.01 (d, J=2.3 Hz, 1H), 6.79-6.69 (m, 1H), 6.43 (t, J=9.2 Hz, 1H), 6.18 (d, J=6.2 Hz, 2H), 5.27 (t, J=7.6 Hz, 1H), 3.54 (s, 2H), 2.94 (d, J=7.6 Hz, 2H).

Example 303

303

Synthesis of (S)-5-(2-(2-(3,5-difluorophenyl)-1-(2-(3-(trifluoromethyl)-4,5,6,7-tetrahydro-1H-pyrazolo[4,3-c]pyridin-1-yl)acetamido)ethyl)pyridin-3-yl)-2-fluorobenzamide (303)

(S)-tert-butyl 1-(2-(1-(3-(3-carbamoyl-4-fluorophenyl)pyridin-2-yl)-2-(3,5-difluorophenyl)ethylamino)-2-oxoethyl)-3-(trifluoromethyl)-6,7-dihydro-1H-pyrazolo[4,3-c]pyridine-5(4H)-carboxylate (274, 269 mg, 0.38 mmol) was dissolved in 3 mL of 1,4-dioxane and to it was added 1 mL of HCl solution (4 N in 1,4-dioxane). The mixture was allowed to stir at ambient temperature for 1 day. To it was added diethyl ether and the resulting precipitate was collected by vacuum filtration and further high vacuum drying to afford 210 mg of the title compound. MS (m/z) 603.30 [M+H]$^+$. $^1$H NMR (400 MHz, cd$_3$od) δ 8.82 (dd, J=5.4, 1.5 Hz, 1H), 8.03 (d, J=7.9 Hz, 1H), 7.77 (dd, J=7.9, 5.4 Hz, 1H), 7.67 (m, 1H), 7.32 (s, 1H), 7.28-7.19 (m, 1H), 6.73 (t, J=9.2 Hz, 1H), 6.38 (d, J=6.2 Hz, 2H), 5.41 (dd, J=9.0, 6.5 Hz, 1H), 5.11-4.94 (m, 2H), 3.59-3.49 (m, 2H), 3.23 (dd, J=13.3, 6.5 Hz, 1H), 3.12-3.06 (m, 1H), 3.02 (d, J=5.8 Hz, 2H).

Example 304

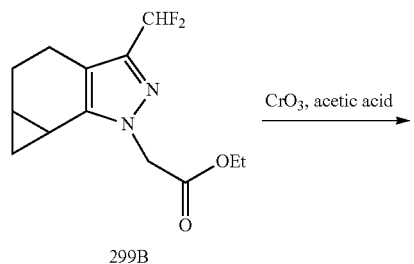

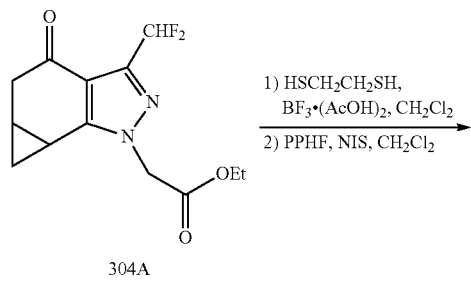

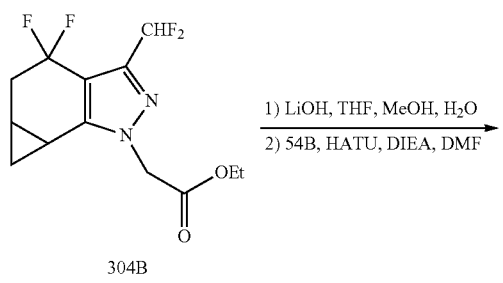

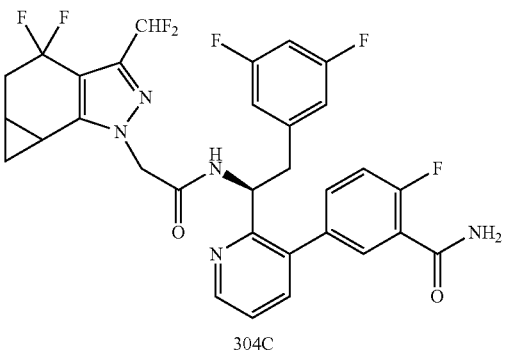

Synthesis of ethyl 2-(3-(difluoromethyl)-4-oxo-5,5a,6,6a-tetrahydrocyclopropa[g]indazol-1 (4H)-yl)acetate (304A)

Compound 304A was prepared according to the method presented in the synthesis of Example 272A substituting Compound 299B for ethyl 2-(3-(trifluoromethyl)-4,5,6,7-tetrahydro-1H-indazol-1-yl)acetate to afford the title compound; MS (m/z) 303.16 [M+H]$^+$.

Synthesis of ethyl 2-(3-(difluoromethyl)-4,4-difluoro-5,5a,6,6a-tetrahydrocyclopropa[g]indazol-1 (4H)-yl)acetate (304B)

Compound 304B was prepared according to the method presented in the synthesis of Example 285E substituting Compound 304A for Compound 285C to afford the title compound. MS (m/z) 307.19 [M+H]$^+$.

Synthesis of 5-(2-((1S)-1-(2-(3-(difluoromethyl)-4,4-difluoro-5,5a,6,6a-tetrahydrocyclopropa[g]indazol-1 (4H)-yl)acetamido)-2-(3,5-difluorophenyl)ethyl)pyridin-3-yl)-2-fluorobenzamide (304C)

Compound 304C was prepared according to the method presented in the synthesis of Example 54 utilizing Compound 54B and 2-(4,4-difluoro-3-(trifluoromethyl)-5,5a,6,6a-tetrahydrocyclopropa[g]indazol-1(4H)-yl)acetic acid to provide 6 mg of the title compound. MS (m/z) 632.09 [M+H]$^+$. $^1$H NMR (400 MHz, cd$_3$od) δ 8.69 (t, J=3.3 Hz, 1H), 7.68-7.55 (m, 1H), 7.51-7.40 (m, 2H), 7.31 (m, 1H), 7.22 (t, J=9.6 Hz, 1H), 6.90-6.45 (m, 2H), 6.34 (dd, J=13.1, 6.4 Hz, 2H), 5.36 (q, J=7.6 Hz, 1H), 5.06-4.91 (m, 2H), 3.17-2.92 (m, 2H), 2.62 (t, J=16.4 Hz, 1H), 2.39-2.17 (m, 1H), 2.04 (m, 1H), 1.77 (m, 1H), 1.17 (dd, J=14.2, 5.7 Hz, 1H), 0.46 (m, 1H).

Example 305

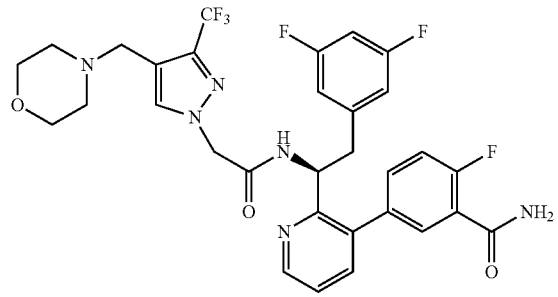

Synthesis of (S)-5-(2-(2-(3,5-difluorophenyl)-1-(2-(4-(morpholinomethyl)-3-(trifluoromethyl)-1H-pyrazol-1-yl)acetamido)ethyl)pyridin-3-yl)-2-fluorobenzamide (305)

Compound 305 was prepared according to the method presented for the synthesis of Example 333 substituting morpholine for methylamine hydrochloride to afford 7 mg of the title compound: MS (m/z) 647.27 [M+H]$^+$. $^1$H NMR (400 MHz, cd$_3$od) δ 8.70 (dd, J=4.8, 1.6 Hz, 1H), 8.02 (s, 1H), 7.68-7.58 (m, 1H), 7.52 (d, J=6.8 Hz, 1H), 7.41 (dd, J=7.8, 4.8 Hz, 1H), 7.30-7.10 (m, 2H), 6.66 (dd, J=10.4, 8.1 Hz, 1H), 6.34 (d, J=6.2 Hz, 2H), 5.38-5.28 (m, 1H), 5.02 (s, 2H), 4.35 (s, 2H), 4.04 (bs, 2H), 3.73 (bs, 2H), 3.40 (bs, 2H), 3.09 (m, 4H).

Example 306

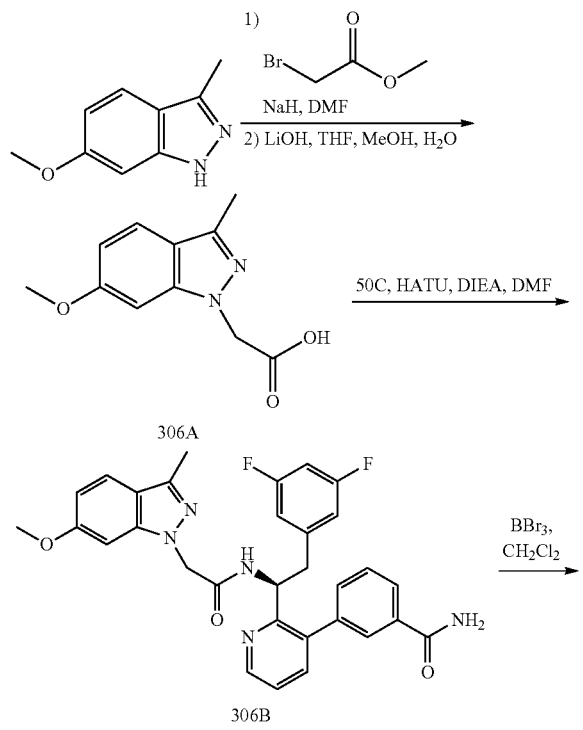

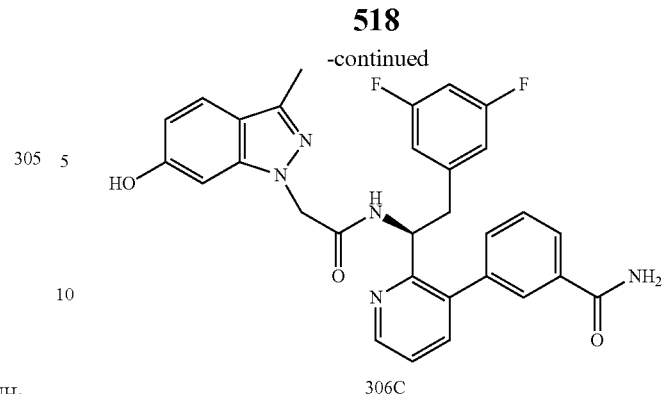

Synthesis of 2-(6-methoxy-3-methyl-1H-indazol-1-yl)acetic acid (306A)

Compound 306A was prepared according to the method presented for the synthesis of Example 298A substituting 6-methoxy-3-methyl-1H-indazole for 6-methoxy-1H-pyrrolo[2,3-b]pyridine to afford the title compound: MS (m/z) 221.3 [M+H]$^+$.

Synthesis of (S)-3-(2-(2-(3,5-difluorophenyl)-1-(2-(6-methoxy-3-methyl-1H-indazol-1-yl)acetamido)ethyl)pyridin-3-yl)benzamide (306B)

Compound 306B was prepared according to the method presented in the synthesis of Example 50D utilizing Compound 50C and 2-(6-methoxy-3-methyl-1H-indazol-1-yl)acetic acid to provide the title compound. MS (m/z) 556.2 [M+H]$^+$.

Synthesis of (S)-3-(2-(2-(3,5-difluorophenyl)-1-(2-(6-hydroxy-3-methyl-1H-indazol-1-yl)acetamido)ethyl)pyridin-3-yl)benzamide (306C)

(S)-3-(2-(2-(3,5-difluorophenyl)-1-(2-(6-methoxy-3-methyl-1H-indazol-1-yl)acetamido)ethyl)pyridin-3-yl)benzamide (21 mg, 0.038 mmol) was dissolved in 1 mL of CH$_2$Cl$_2$ and cooled down to −78° C. with dry ice-acetone bath. To it was added BBr$_3$ (1 M in CH$_2$Cl$_2$) and the reaction mixture was allowed to warm to ambient temperature and stirred for 16 hours. It was quenched with NaHCO$_3$ (sat'd aqueous solution) and extracted with EtOAc. The organic layer was separated, washed with brine, dried over MgSO$_4$, filtered and concentrated. The residue was purified by reverse phase HPLC eluting with acetonitrile/water (with 0.1% TFA) to afford 9.3 mg of the title compound. MS (m/z) 542.0 [M+H]$^+$. $^1$H NMR (400 MHz, cd$_3$od) δ 8.56 (d, J=4.9 Hz, 1H), 7.79 (d, J=7.7 Hz, 1H), 7.58 (d, J=7.7 Hz, 1H), 7.49 (s, 1H), 7.46-7.32 (m, 3H), 7.16 (d, J=7.2 Hz, 1H), 6.62 (d, J=8.8 Hz, 1H), 6.56 (d, J=10.1 Hz, 2H), 6.12 (d, J=6.5 Hz, 2H), 5.35 (t, J=7.5 Hz, 1H), 4.83 (s, 2H), 2.88 (d, J=7.6 Hz, 2H), 2.39 (s, 3H).

Example 307

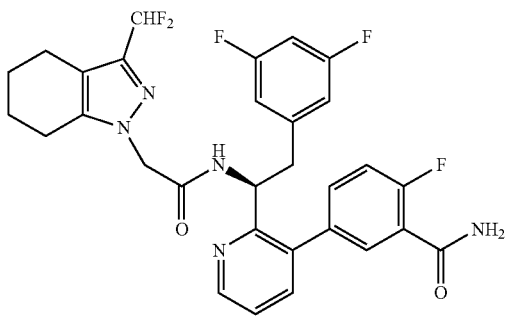

307

Synthesis of (S)-5-(2-(1-(2-(3-(difluoromethyl)-4,5,6,7-tetrahydro-1H-indazol-1-yl)acetamido)-2-(3,5-difluorophenyl)ethyl)pyridin-3-yl)-2-fluorobenzamide (307)

Compound 307 was prepared according to the method presented in the synthesis of Example 56B utilizing Compound 56A and 3-(difluoromethyl)-4,5,6,7-tetrahydro-1H-indazole to provide 6 mg of the title compound. MS (m/z) 584.36 [M+H]$^+$.

$^1$H NMR (400 MHz, cdcl$_3$) δ 9.59-9.33 (m, 3H), 8.79 (dd, J=5.5, 1.4 Hz, 1H), 7.97 (dd, J=7.9, 1.5 Hz, 1H), 7.82-7.58 (m, 2H), 7.34-7.26 (m, 1H), 6.99 (d, J=9.8 Hz, 1H), 6.76 (m, 1H), 6.67-6.53 (m, 1H), 6.19 (d, J=5.7 Hz, 2H), 5.47 (dd, J=16.1, 7.2 Hz, 1H), 4.84-4.57 (m, 2H), 3.17 (dd, J=13.6, 7.1 Hz, 1H), 3.01 (dd, J=13.6, 9.1 Hz, 1H), 2.59 (t, J=5.6 Hz, 2H), 2.42 (t, J=10.4 Hz, 2H), 1.75 (dd, J=30.7, 5.7 Hz, 4H).

Example 308

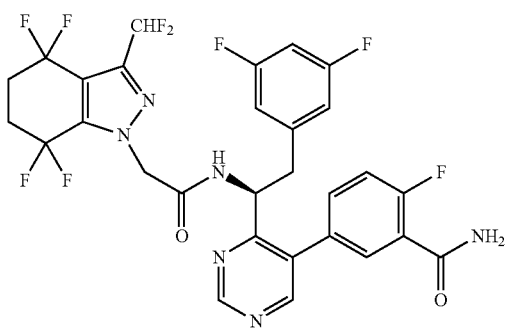

308

Synthesis of (S)-5-(4-(1-(2-(3-(difluoromethyl)-4,4,7,7-tetrafluoro-4,5,6,7-tetrahydro-1H-indazol-1-yl)acetamido)-2-(3,5-difluorophenyl)ethyl)pyrimidin-5-yl)-2-fluorobenzamide (308)

Compound 308 was prepared according to the method presented in the synthesis of Example 54G utilizing Compound 136C and 2-(3-(difluoromethyl)-4,4,7,7-tetrafluoro-4,5,6,7-tetrahydro-1H-indazol-1-yl)acetic acid to provide 11 mg of the title compound. MS (m/z) 636.29 [M+H]$^+$. $^1$H NMR (400 MHz, cd$_3$od) δ 9.23 (s, 1H), 9.12 (d, J=7.9 Hz, 1H), 8.55 (s, 1H), 7.46 (d, J=5.8 Hz, 2H), 7.33-7.20 (m, 1H), 6.96-6.58 (m, 2H), 6.40 (d, J=6.1 Hz, 2H), 5.36 (q, J=7.7 Hz, 1H), 5.04 (s, 2H), 3.08 (d, J=7.6 Hz, 2H), 2.63-2.33 (m, 4H).

Example 309

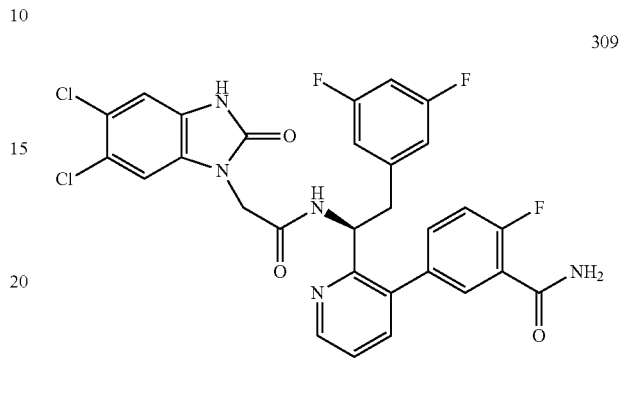

309

Synthesis of (S)-5-(2-(1-(2-(5,6-dichloro-2-oxo-2,3-dihydro-1H-benzo[d]imidazol-1-yl)acetamido)-2-(3,5-difluorophenyl)ethyl)pyridin-3-yl)-2-fluorobenzamide (309)

Compound 309 was prepared according to the method presented in the synthesis of Example 56B utilizing Compound 56A and 5,6-dichloro-1H-benzo[d]imidazol-2(3H)-one to provide 25 mg of the title compound. MS (m/z) 614.72 [M+H]$^+$. $^1$H NMR (400 MHz, cd$_3$od) δ 8.72 (d, J=4.7 Hz, 1H), 7.65 (d, J=7.7 Hz, 1H), 7.53-7.30 (m, 3H), 7.27-7.14 (m, 2H), 7.07 (s, 1H), 6.66 (t, J=9.2 Hz, 1H), 6.32 (d, J=6.2 Hz, 2H), 5.36 (t, J=7.7 Hz, 2H), 4.64-4.44 (m, 2H), 3.07 (d, J=7.4 Hz, 2H).

Example 310

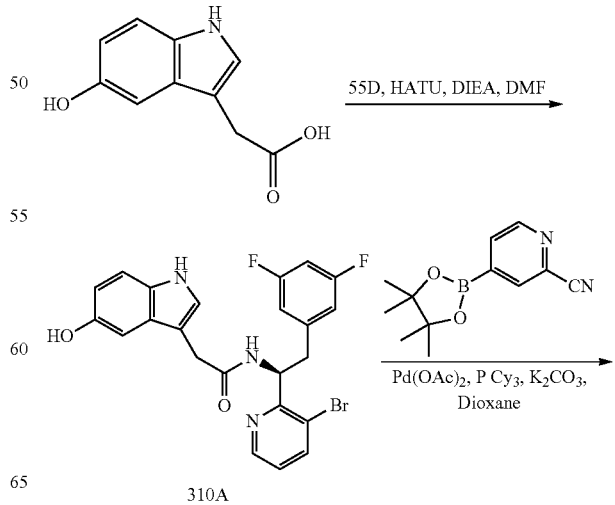

310A

521

-continued

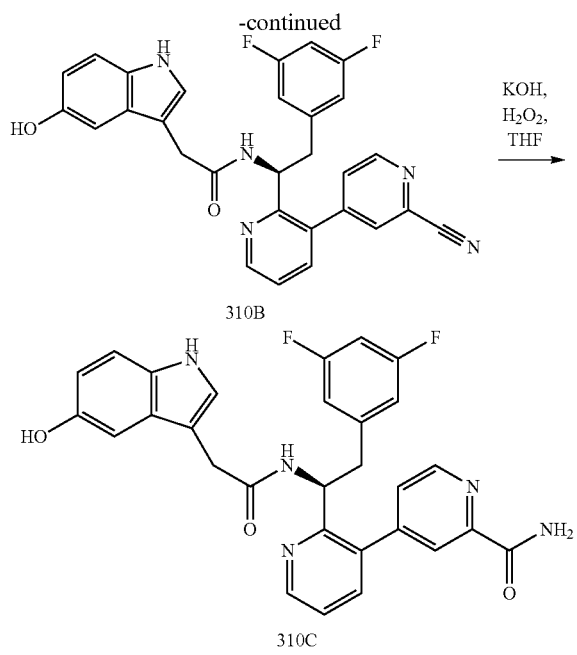

Synthesis of (S)—N-(1-(3-bromopyridin-2-yl)-2-(3,5-difluorophenyl)ethyl)-2-(5-hydroxy-1H-indol-3-yl)acetamide (310A)

Compound 310A was prepared according to the method presented in the synthesis of Example 55E utilizing compound 55D and 2-(5-hydroxy-1H-indol-3-yl)acetic acid to provide the title compound. MS (m/z) 486.00 [M+H]$^+$.

Synthesis of (S)—N-(1-(2'-cyano-3,4'-bipyridin-2-yl)-2-(3,5-difluorophenyl)ethyl)-2-(5-hydroxy-1H-indol-3-yl)acetamide (310B)

To a mixture of Compound 310A (49 mg, 0.1 mmol), 4-(4,4,5,5-tetramethyl-1,3,2-dioxaborolan-2-yl)picolinonitrile (35 mg, 0.15 mmol) and potassium carbonate (41 mg, 0.3 mmol) was added 1 mL of 1,4-dioxane. After the system was purged with argon, palladium (II) acetate (2.2 mg, 0.01 mmol) and tricyclohexylphosphine (5.6 mg, 0.02 mmol) was added and the reaction mixture was heated up to 100° C. for 16 hours. It was cooled down and partitioned between EtOAc and water. The organic layer was separated, washed with brine, dried over MgSO$_4$, filtered and concentrated. The residue was purified by reverse phase HPLC eluting with acetonitrile/water (with 0.1% TFA) to afford the title compound. MS (m/z) 509.8 [M+H]$^+$.

Synthesis of (S)-2-(2-(3,5-difluorophenyl)-1-(2-(5-hydroxy-1H-indol-3-yl)acetamido)ethyl)-3,4'-bipyridine-2'-carboxamide (310C)

Compound 310C was prepared according to the method presented for the synthesis of Example 294 substituting Compound 310B for Compound 377 to afford 4 mg of the title compound: MS (m/z) 528.2 [M+H]$^+$. $^1$H NMR (400 MHz, cd$_3$od) δ 8.51 (dd, J=14.7, 4.9 Hz, 2H), 7.61-7.47 (m, 2H), 7.32 (dd, J=7.9, 4.8 Hz, 2H), 7.08 (d, J=8.6 Hz, 1H), 6.98 (s, 1H), 6.73 (d, J=2.0 Hz, 1H), 6.62-6.47 (m, 2H), 6.13 (d, J=6.2 Hz, 2H), 5.30-5.11 (m, 1H), 3.51 (s, 2H), 2.97-2.75 (m, 2H).

522

Example 311

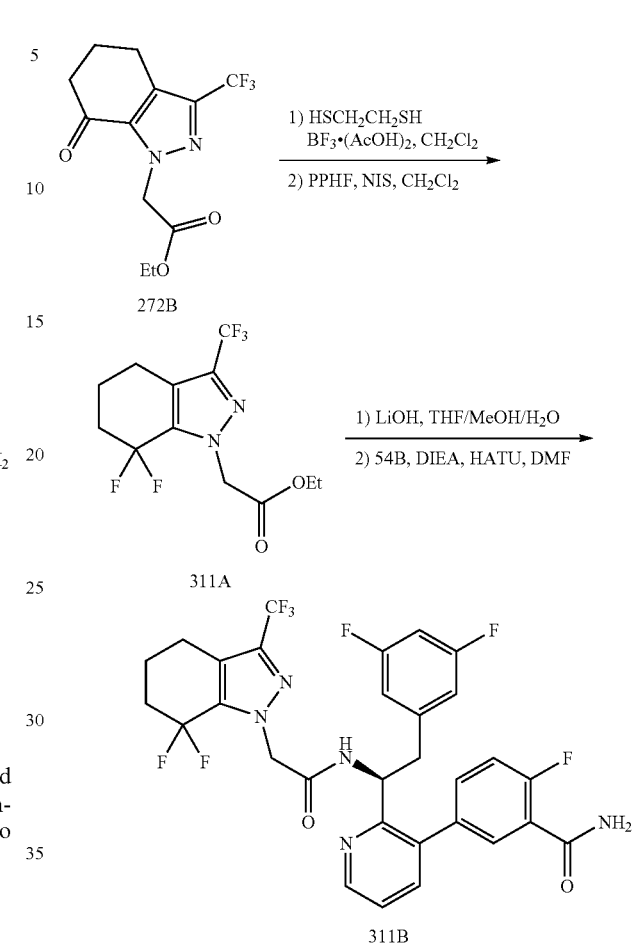

Synthesis of ethyl 2-(7,7-difluoro-3-(trifluoromethyl)-4,5,6,7-tetrahydro-1H-indazol-1-yl)acetate (311A)

Compound 311A was prepared according to the method presented in the synthesis of Example 285E substituting Compound 272B for Compound 285C to afford the title compound. MS (m/z) 313.05 [M+H]$^+$.

Synthesis of (S)-5-(2-(1-(2-(7,7-difluoro-3-(trifluoromethyl)-4,5,6,7-tetrahydro-1H-indazol-1-yl)acetamido)-2-(3,5-difluorophenyl)ethyl)pyridin-3-yl)-2-fluorobenzamide (311B)

Compound 311B was prepared according to the method presented in the synthesis of Example 54 utilizing Compound 54B and ethyl ethyl 2-(7,7-difluoro-3-(trifluoromethyl)-4,5,6,7-tetrahydro-1H-indazol-1-yl)acetate to provide 43 mg of the title compound; MS (m/z) 638.46 [M+H]$^+$. $^1$H NMR (400 MHz, cd$_3$od) δ 8.72 (dd, J=5.0, 1.6 Hz, 1H), 7.71 (dd, J=7.8, 1.6 Hz, 1H), 7.51 (dd, J=7.8, 5.0 Hz, 1H), 7.44-7.27 (m, 2H), 7.22 (dd, J=10.7, 8.6 Hz, 1H), 6.66 (tt, J=9.2, 2.3 Hz, 1H), 6.31 (t, J=6.3 Hz, 2H), 5.36 (t, J=7.6 Hz, 1H), 5.15-4.97 (m, 2H), 3.05 (t, J=10.6 Hz, 2H), 2.65 (s, 2H), 2.32-2.16 (m, 2H), 2.06-1.85 (m, 2H).

Example 312

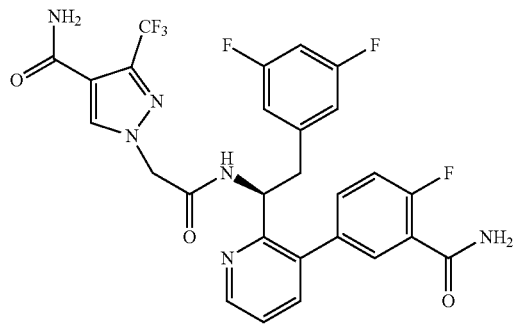

Synthesis of (S)-1-(2-(1-(3-(3-carbamoyl-4-fluoro-phenyl)pyridin-2-yl)-2-(3,5-difluorophenyl)ethyl-amino)-2-oxoethyl)-3-(trifluoromethyl)-1H-pyrazole-4-carboxamide (312)

To a solution of (S)-1-(2-(1-(3-(3-carbamoyl-4-fluorophenyl)pyridin-2-yl)-2-(3,5-difluorophenyl)ethylamino)-2-oxoethyl)-3-(trifluoromethyl)-1H-pyrazole-4-carboxylic acid (323, 30 mg, 0.05 mmol) in 0.5 mL of DMF were added HOBt (10 mg, 0.075 mmol), 0.5 M ammonia solution in 1,4-dioxane (0.5 mL, 0.25 mmol), N,N-diisopropylethylamine (26 µL, 0.15 mmol), and HATU (29 mg, 0.075 mmol). After stirring for 2 hours at room temperature, It was partitioned between EtOAc and saturated NaHCO$_3$ aqueous solution. The organic layer was separated, washed with brine, dried over MgSO$_4$, filtered and concentrated. The residue was purified by reverse phase HPLC eluting with acetonitrile/water (with 0.1% TFA) to afford 10 mg of the title compound. MS (m/z) 591.34 [M+H]$^+$. $^1$H NMR (400 MHz, cd$_3$od) δ 8.70-8.56 (m, 1H), 8.09 (s, 1H), 7.47 (dd, J=7.8, 1.7 Hz, 1H), 7.37-7.25 (m, 2H), 7.14 (m, 2H), 6.56 (t, J=9.3 Hz, 1H), 6.22 (d, J=6.3 Hz, 2H), 5.36-5.18 (m, 1H), 4.88 (s, 2H), 2.99 (m, 2H).

Example 313

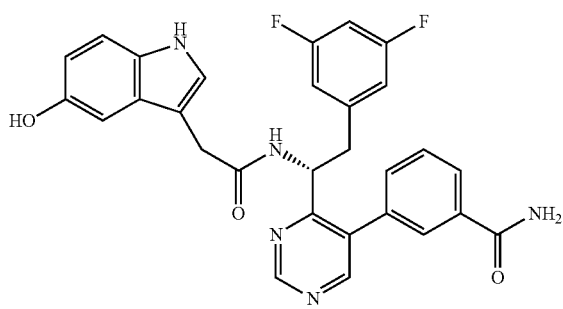

Synthesis of (R)-3-(4-(2-(3,5-difluorophenyl)-1-(2-(5-hydroxy-1H-indol-3-yl)acetamido)ethyl)pyrimidin-5-yl)benzamide (313)

Compound 313 was prepared according to the method presented for the synthesis of Example 295B substituting Compound 279F and 3-carbamoylphenylboronic acid for Compound 295A and 3-sulfamoylphenylboronic acid to afford 19 mg of the title compound: MS (m/z) 528.4 [M+H]$^+$. $^1$H NMR (400 MHz, cd$_3$od) δ 9.13 (s, 1H), 8.54 (s, 1H), 7.94 (d, J=8.1 Hz, 1H), 7.65 (s, 1H), 7.52 (t, J=7.6 Hz, 1H), 7.37 (d, J=7.2 Hz, 1H), 7.17 (d, J=8.8 Hz, 1H), 7.06 (s, 1H), 6.83 (s, 1H), 6.65 (t, J=10.3 Hz, 2H), 6.27 (d, J=6.5 Hz, 2H), 5.45 (t, J=7.4 Hz, 1H), 3.71-3.50 (m, 2H), 2.97 (d, J=7.5 Hz, 2H).

Example 314

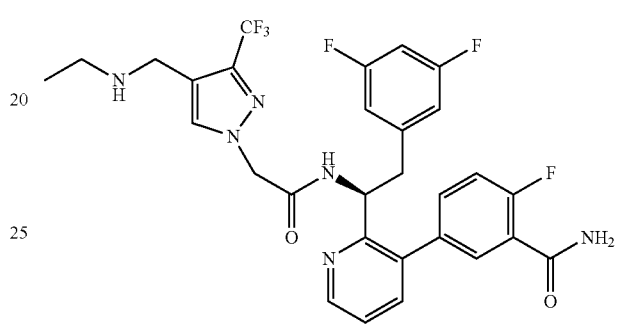

Synthesis of (S)-5-(2-(2-(3,5-difluorophenyl)-1-(2-(4-((ethylamino)methyl)-3-(trifluoromethyl)-1H-pyrazol-1-yl)acetamido)ethyl)pyridin-3-yl)-2-fluorobenzamide (314)

Compound 314 was prepared according to the method presented for the synthesis of Example 333 substituting ethylamine hydrochloride for methylamine hydrochloride to afford 5 mg of the title compound: MS (m/z) 605.32 [M+H]$^+$. $^1$H NMR (400 MHz, cd$_3$od) δ 8.70 (dd, J=4.8, 1.6 Hz, 1H), 7.94 (s, 1H), 7.57 (dd, J=7.8, 1.7 Hz, 1H), 7.48 (d, J=5.0 Hz, 1H), 7.39 (dd, J=7.8, 4.8 Hz, 1H), 7.30-7.12 (m, 2H), 6.66 (dd, J=10.4, 8.1 Hz, 1H), 6.33 (d, J=6.2 Hz, 2H), 5.46-5.22 (m, 1H), 4.99 (s, 2H), 4.18 (s, 2H), 3.16-3.00 (m, 4H), 1.31 (t, J=7.3 Hz, 3H).

Example 315

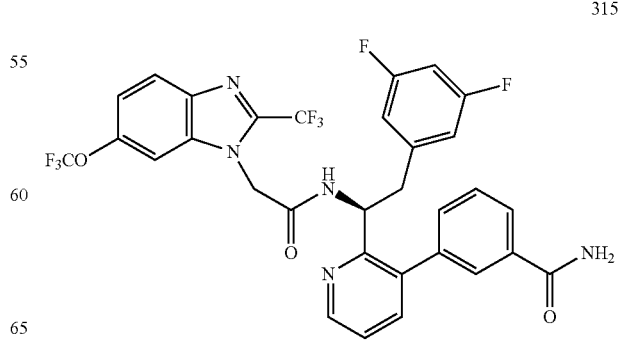

525

Synthesis of (S)-3-(2-(2-(3,5-difluorophenyl)-1-(2-(6-(trifluoromethoxy)-2-(trifluoromethyl)-1H-benzo[d]imidazol-1-yl)acetamido)ethyl)pyridin-3-yl)benzamide (315)

Compound 315 was prepared according to the method presented in the synthesis of Example 55F utilizing Compound 55D and 2-(6-(trifluoromethoxy)-2-(trifluoromethyl)-1H-benzo[d]imidazol-1-yl)acetic acid to afford (S)—N-(1-(3-bromopyridin-2-yl)-2-(3,5-difluorophenyl)ethyl)-2-(6-(trifluoromethoxy)-2-(trifluoromethyl)-1H-benzo[d]imidazol-1-yl)acetamide and then Suzuki coupling with 3-carbamoylphenylboronic acid to provide 17 mg of the title compound. MS (m/z) 663.7 [M+H]$^+$. $^1$H NMR (400 MHz, cd$_3$od) δ 8.75 (d, J=4.9 Hz, 1H), 7.86 (d, J=8.8 Hz, 2H), 7.67 (d, J=7.8 Hz, 1H), 7.55 (d, J=6.8 Hz, 2H), 7.50-7.41 (m, 2H), 7.31 (dd, J=19.6, 8.3 Hz, 2H), 6.67 (t, J=9.2 Hz, 1H), 6.29 (d, J=6.3 Hz, 2H), 5.44 (t, J=7.6 Hz, 1H), 5.22 (s, 2H), 3.10-3.03 (m, 2H).

Example 316

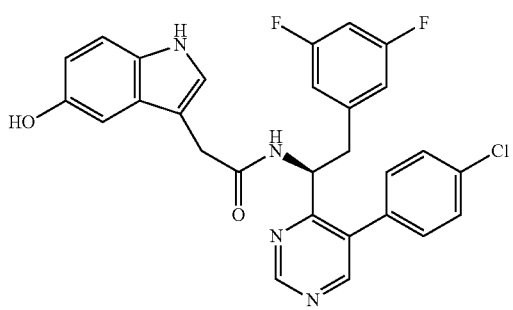

316

Synthesis of (S)—N-(1-(5-(4-chlorophenyl)pyrimidin-4-yl)-2-(3,5-difluorophenyl)ethyl)-2-(5-hydroxy-1H-indol-3-yl)acetamide (316)

Compound 316 was prepared according to the method presented for the synthesis of Example 279G substituting Compound 279D and 2-(5-hydroxy-1H-indol-3-yl)acetic acid for Compound 279E and 2-(5,6-dimethyl-1H-benzo[d]imidazol-1-yl)acetic acid to afford 12 mg of the title compound: MS (m/z) 519.3 [M+H]$^+$. $^1$H NMR (400 MHz, cd$_3$od) δ 9.10 (s, 1H), 8.48 (s, 1H), 7.40 (d, J=8.2 Hz, 2H), 7.15 (dd, J=17.5, 8.5 Hz, 3H), 7.06 (s, 1H), 6.83 (s, 1H), 6.67 (d, J=9.2 Hz, 2H), 6.30 (d, J=6.8 Hz, 2H), 5.40 (t, J=7.6 Hz, 1H), 3.68-3.51 (m, 2H), 2.96 (d, J=7.8 Hz, 2H).

526

Example 317

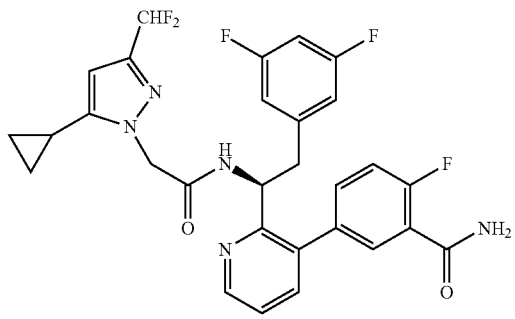

317

Synthesis of (S)-5-(2-(1-(2-(5-cyclopropyl-3-(difluoromethyl)-1H-pyrazol-1-yl)acetamido)-2-(3,5-difluorophenyl)ethyl)pyridin-3-yl)-2-fluorobenzamide (317)

Compound 317 was prepared according to the method presented in the synthesis of Example 56 utilizing Compound 56A and 5-cyclopropyl-3-(difluoromethyl)-1H-pyrazole to provide 36 mg of the title compound. MS (m/z) 570.34 [M+H]$^+$. $^1$H NMR (400 MHz, cd$_3$od) δ 8.70 (dd, J=4.9, 1.7 Hz, 1H), 7.79-7.65 (m, 1H), 7.57-7.46 (m, 1H), 7.34 (s, 1H), 7.23 (dt, J=10.9, 4.3 Hz, 1H), 6.73-6.42 (m, 2H), 6.32 (dd, J=18.4, 5.2 Hz, 2H), 6.11 (s, 1H), 5.37 (dd, J=16.3, 8.8 Hz, 1H), 4.95 (s, 2H), 3.10-2.93 (m, 2H), 1.71-1.57 (m, 1H), 0.97-0.80 (m, 2H), 0.72-0.55 (m, 2H).

Example 318

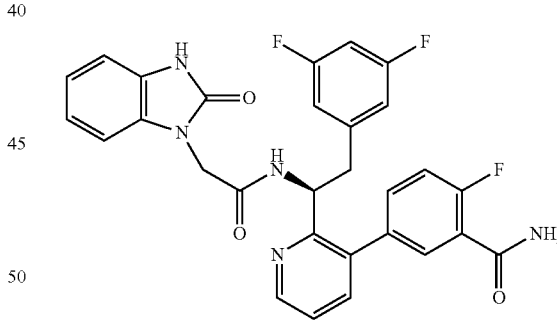

318

Synthesis of (S)-5-(2-(2-(3,5-difluorophenyl)-1-(2-(2-oxo-2,3-dihydro-1H-benzo[d]imidazol-1-yl)acetamido)ethyl)pyridin-3-yl)-2-fluorobenzamide (318)

Compound 318 was prepared according to the method presented for the synthesis of Example 332 substituting 1H-benzo[d]imidazol-2(3H)-one for 2-chloropyridin-4-ol to afford 10 mg of the title compound: MS (m/z) 546.37 [M+H]$^+$. $^1$H NMR (400 MHz, cd3od) δ 8.63 (dd, J=5.0, 1.6 Hz, 1H), 7.63 (dd, J=7.8, 1.6 Hz, 1H), 7.46-7.20 (m, 3H), 7.13 (dd, J=10.7, 8.5 Hz, 1H), 7.02-6.87 (m, 3H), 6.77 (d, J=7.0 Hz, 1H), 6.64-6.52 (m, 1H), 6.26 (d, J=6.1 Hz, 2H), 5.31 (t, J=7.6 Hz, 1H), 4.76 (s, 12H), 3.12-2.83 (m, 2H).

Example 319

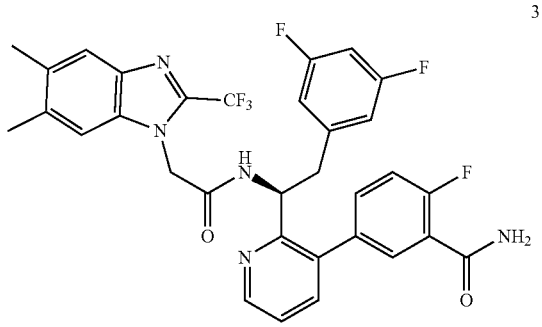

Synthesis of (S)-5-(2-(2-(3,5-difluorophenyl)-1-(2-(5,6-dimethyl-2-(trifluoromethyl)-1H-benzo[d]imidazol-1-yl)acetamido)ethyl)pyridin-3-yl)-2-fluorobenzamide (319)

Compound 319 was prepared according to the method presented in the synthesis of Example 54 utilizing Compound 54B and 2-(5,6-dimethyl-2-(trifluoromethyl)-1H-benzo[d]imidazol-1-yl)acetic acid to provide 11 mg of the title compound. MS (m/z) 625.5 [M+H]$^+$. $^1$H NMR (400 MHz, cd$_3$od) δ 8.73 (d, J=4.7 Hz, 1H), 7.57 (d, J=7.8 Hz, 1H), 7.52 (s, 1H), 7.40 (dd, J=7.7, 4.9 Hz, 2H), 7.30 (s, 1H), 7.23 (s, 1H), 7.21-7.11 (m, 1H), 6.68 (t, J=9.3 Hz, 1H), 6.35 (d, J=6.4 Hz, 2H), 5.35 (t, J=7.5 Hz, 1H), 5.19-5.00 (m, 2H), 3.15-2.98 (m, 2H), 2.38 (s, 6H).

Example 320

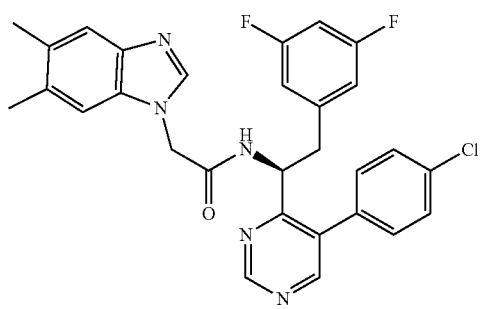

Synthesis of (S)—N-(1-(5-(4-chlorophenyl)pyrimidin-4-yl)-2-(3,5-difluorophenyl)ethyl)-2-(5,6-dimethyl-1H-benzo[d]imidazol-1-yl)acetamide (320)

Compound 320 was prepared according to the method presented for the synthesis of Example 316 substituting 2-(5,6-dimethyl-1H-benzo[d]imidazol-1-yl)acetic acid for 2-(5-hydroxy-1H-indol-3-yl)acetic acid to afford 11 mg of the title compound: MS (m/z) 531.9 [M+H]$^+$. $^1$H NMR (400 MHz, cd$_3$od) δ 9.23 (d, J=13.3 Hz, 2H), 8.54 (s, 1H), 7.59 (s, 1H), 7.46-7.36 (m, 3H), 7.18 (d, J=8.0 Hz, 2H), 6.74 (t, J=9.1 Hz, 1H), 6.38 (d, J=6.8 Hz, 2H), 5.45 (d, J=7.2 Hz, 1H), 5.25 (s, 2H), 3.08 (m, 2H), 2.45 (s, 6H).

Example 321

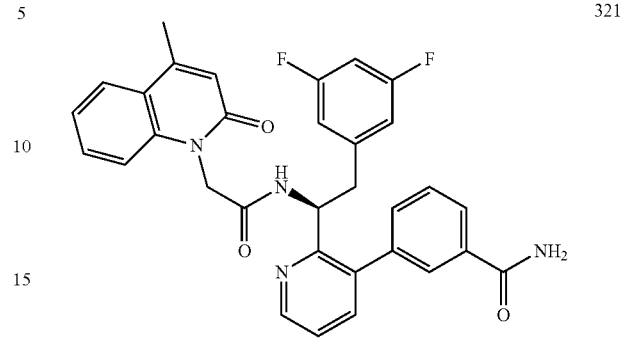

Synthesis of (S)-3-(2-(2-(3,5-difluorophenyl)-1-(2-(4-methyl-2-oxoquinolin-1(2H)-yl)acetamido)ethyl)pyridin-3-yl)benzamide (321)

Compound 321 was prepared according to the method presented in the synthesis of Example 55 utilizing Compound 55D and 2-(4-methyl-2-oxoquinolin-1(2H)-yl)acetic acid to afford (S)—N-(1-(3-bromopyridin-2-yl)-2-(3,5-difluorophenyl)ethyl)-2-(4-methyl-2-oxoquinolin-1(2H)-yl)acetamide, and then Suzuki coupling with 3-carbamoylphenylboronic acid to provide 18 mg of the title compound. MS (m/z) 553.0 [M+H]$^+$. $^1$H NMR (400 MHz, cd$_3$od) δ 8.83-8.68 (m, 1H), 7.87 (dd, J=12.7, 7.9 Hz, 2H), 7.80-7.69 (m, 1H), 7.62 (s, 1H), 7.59-7.41 (m, 3H), 7.38-7.15 (m, 3H), 6.67 (t, J=9.3 Hz, 1H), 6.60 (s, 1H), 6.30 (d, J=6.2 Hz, 2H), 5.48 (t, J=7.6 Hz, 1H), 5.21-5.02 (m, 2H), 3.12-2.97 (m, 2H), 2.51 (s, 3H).

Example 322

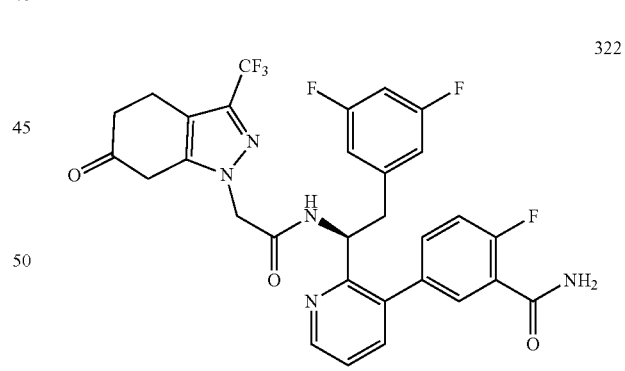

Synthesis of (S)-5-(2-(2-(3,5-difluorophenyl)-1-(2-(6-oxo-3-(trifluoromethyl)-4,5,6,7-tetrahydro-1H-indazol-1-yl)acetamido)ethyl)pyridin-3-yl)-2-fluorobenzamide (322)

Compound 322 was prepared according to the method presented for the synthesis of Example 60H substituting 3-ethoxycyclohex-2-enone for bicyclo[3.1.0]hexan-3-one to afford 8 mg of the title compound: MS (m/z) 616.02 [M+H]$^+$. $^1$H NMR (400 MHz, cdcl$_3$) δ 9.99 (d, J=7.2 Hz, 1H), 8.81 (d, J=5.6 Hz, 1H), 8.13-8.01 (m, 1H), 7.83 (dd, J=7.9, 5.6 Hz, 2H), 7.60 (m, 1H), 7.30 (dd, J=11.2, 8.6 Hz, 1H), 6.98 (s, 2H), 6.62 (t, J=8.9 Hz, 1H), 6.20 (d, J=5.6 Hz, 2H), 5.48 (dd, J=16.4, 7.2 Hz, 1H), 4.80 (q, J=16.7 Hz, 2H), 3.37 (q, J=20.3 Hz, 2H), 3.22 (dd, J=13.6, 6.8 Hz, 1H), 3.07-2.86 (m, 3H), 2.66 (t, J=6.8 Hz, 2H).

Example 323

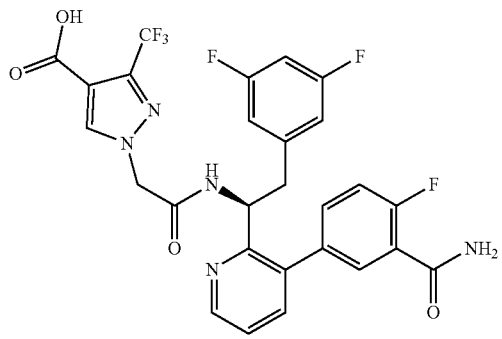

323

Synthesis of (S)-1-(2-(1-(3-(3-carbamoyl-4-fluoro-phenyl)pyridin-2-yl)-2-(3,5-difluorophenyl)ethyl-amino)-2-oxoethyl)-3-(trifluoromethyl)-1H-pyra-zole-4-carboxylic acid (323)

Compound 289 (352 mg, 0.57 mmol) was dissolved in 10 mL of THF/MeOH/H₂O (3/2/1) and to it was added LiOH.H₂O (119 mg, 2.8 mmol). The mixture was stirred at ambient temperature for 16 hours. It was acidified at 0° C. with 1N HCl and extracted with EtOAc. The organic layer was separated, dried over MgSO₄, filtered and concentrated. The residue was purified by reverse phase HPLC eluting with acetonitrile/water (with 0.1% TFA) to afford 256 mg of the title compound. MS (m/z) 592.25 [M+H]⁺. ¹H NMR (400 MHz, cd₃od) δ 8.71 (dd, J=4.9, 1.6 Hz, 1H), 8.26 (s, 1H), 7.66 (dd, J=7.8, 1.6 Hz, 1H), 7.51-7.40 (m, 2H), 7.34 (s, 1H), 7.22 (dd, J=10.7, 8.6 Hz, 1H), 6.65 (dd, J=10.3, 8.1 Hz, 1H), 6.31 (d, J=6.2 Hz, 2H), 5.35 (t, J=7.6 Hz, 1H), 4.99 (s, 2H), 3.08 (d, J=7.6 Hz, 2H).

Example 324

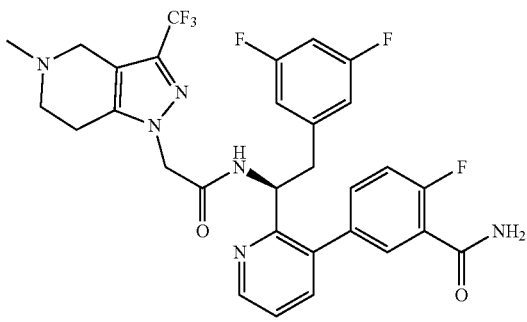

324

Synthesis of (S)-5-(2-(2-(3,5-difluorophenyl)-1-(2-(5-methyl-3-(trifluoromethyl)-4,5,6,7-tetrahydro-1H-pyrazolo[4,3-c]pyridin-1-yl)acetamido)ethyl)pyridin-3-yl)-2-fluorobenzamide (324)

Compound 303 (30 mg, 0.05 mmol) was dissolved in 1 mL of 1,2-dichloroethane. To it was added formic acid solution (40% in water, 15 mg, 0.5 mmol) and acetic acid (29 μL, 0.5 mmol). After stirring at ambient temperature for 20 min, NaBH(OAc)₃ (16 mg, 0.15 mmol) was added, and the reaction mixture was stirred for 10 min. The reaction was quenched by adding NaHCO₃ (saturated aqueous solution), and extracted by EtOAc. The organic layer was separated, washed with half brine, dried over MgSO₄ and filtered. The filtrate was concentrated and purified by reverse phase HPLC eluting with acetonitrile/water (with 0.1% TFA) to afford 19.1 mg of the title compound. MS (m/z) 617.39 [M+H]⁺. ¹H NMR (400 MHz, cd₃od) δ 8.71 (dd, J=4.8, 1.6 Hz, 1H), 7.64-7.58 (m, 1H), 7.53 (d, J=6.4 Hz, 1H), 7.41 (dd, J=7.8, 4.8 Hz, 1H), 7.27-7.12 (m, 2H), 6.67 (t, J=9.2 Hz, 1H), 6.34 (d, J=6.2 Hz, 2H), 5.42-5.25 (m, 1H), 4.94 (s, 2H), 4.29 (bs, 2H), 3.52 (bs, 2H), 3.20-2.93 (m, 7H).

Example 325

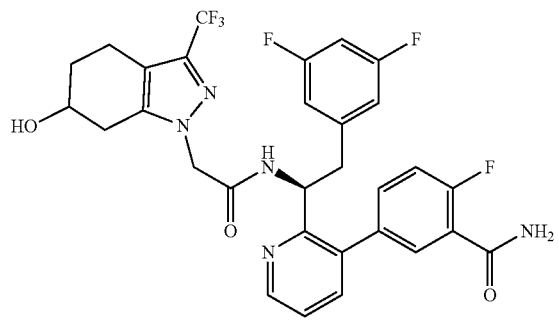

325

Synthesis of 5-(2-((1S)-2-(3,5-difluorophenyl)-1-(2-(6-hydroxy-3-(trifluoromethyl)-4,5,6,7-tetrahydro-1H-indazol-1-yl)acetamido)ethyl)pyridin-3-yl)-2-fluorobenzamide (325)

Compound 322 (30 mg, 0.049 mmol) was dissolved in 2 mL of CH₂Cl₂ and 1 mL of isopropanol. To it was added NaBH₄ (36 mg, 0.98 mmol) and the resulting mixture was stirred at ambient temperature for 4 hours. The reaction was quenched by adding NaHCO₃ (saturated aqueous solution), and extracted by EtOAc. The organic layer was separated, washed with half brine, dried over MgSO₄ and filtered. The filtrate was concentrated and purified by reverse phase HPLC eluting with acetonitrile/water (with 0.1% TFA) to afford 19.1 mg of the title compound. MS (m/z) 618.51 [M+H]⁺. ¹H NMR (400 MHz, cd₃od) δ 8.71 (dd, J=4.9, 1.6 Hz, 1H), 7.68 (m, 1H), 7.47 (m, 2H), 7.32 (s, 1H), 7.26-7.07 (m, 1H), 6.79-6.58 (m, 1H), 6.32 (t, J=7.1 Hz, 2H), 5.36 (q, J=7.4 Hz, 1H), 4.81 (s, 2H), 4.13 (d, J=5.7 Hz, 1H), 3.06 (d, J=7.7 Hz, 2H), 2.87-2.64 (m, 2H), 2.65-2.37 (m, 2H), 1.82 (m, 2H).

Example 326

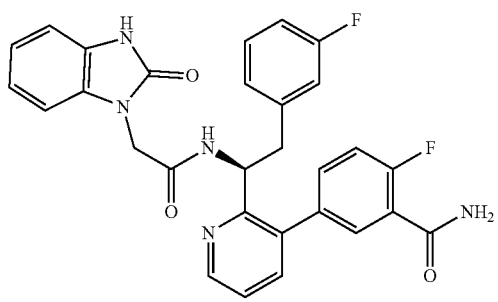

Synthesis of (S)-2-fluoro-5-(2-(2-(3-fluorophenyl)-1-(2-(2-oxo-2,3-dihydro-1H-benzo[d]imidazol-1-yl)acetamido)ethyl)pyridin-3-yl)benzamide (326)

Compound 326 was prepared according to the method presented in the synthesis of Example 59 utilizing Compound 59D and 2-(2-oxo-2,3-dihydro-1H-benzo[d]imidazol-1-yl)acetic acid to provide 21 mg of the title compound. MS (m/z) 528.35 [M+H]$^+$. $^1$H NMR (400 MHz, cd$_3$od) δ 8.72 (dd, J=5.0, 1.5 Hz, 1H), 7.71 (dd, J=7.8, 1.6 Hz, 1H), 7.52 (dd, J=7.8, 5.0 Hz, 1H), 7.32 (d, J=6.3 Hz, 2H), 7.17 (dd, J=10.6, 8.7 Hz, 1H), 7.11-6.94 (m, 4H), 6.91-6.79 (m, 2H), 6.48 (dd, J=22.6, 8.5 Hz, 2H), 5.40-5.31 (m, 1H), 4.56 (s, 2H), 3.17-2.95 (m, 2H).

Example 327

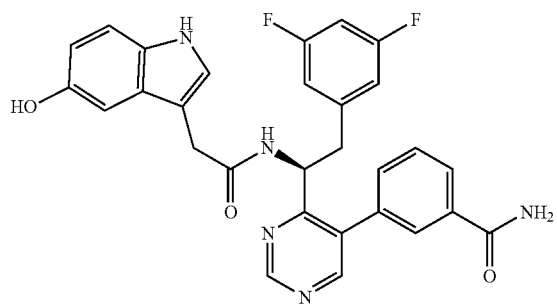

Synthesis of (S)-3-(4-(2-(3,5-difluorophenyl)-1-(2-(5-hydroxy-1H-indol-3-yl)acetamido)ethyl)pyrimidin-5-yl)benzamide (327)

Compound 327 was prepared according to the method presented for the synthesis of Example 295B substituting 3-carbamoylphenylboronic acid for 3-sulfamoylphenylboronic acid to afford 20 mg of the title compound: MS (m/z) 528.1 [M+H]$^+$. $^1$H NMR (400 MHz, cd$_3$od) δ 9.13 (s, 1H), 8.54 (s, 1H), 7.94 (d, J=7.5 Hz, 1H), 7.65 (s, 1H), 7.52 (t, J=7.9 Hz, 1H), 7.37 (d, J=7.7 Hz, 1H), 7.17 (d, J=8.6 Hz, 1H), 7.06 (s, 1H), 6.83 (s, 1H), 6.65 (t, J=10.4 Hz, 2H), 6.27 (d, J=6.8 Hz, 2H), 5.45 (t, J=7.7 Hz, 1H), 3.71-3.51 (m, 2H), 2.97 (d, J=7.5 Hz, 2H).

Example 328

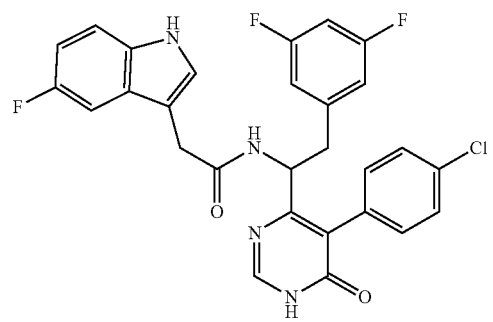

Synthesis of N-(1-(5-(4-chlorophenyl)-6-oxo-1,6-dihydropyrimidin-4-yl)-2-(3,5-difluorophenyl)ethyl)-2-(5-fluoro-1H-indol-3-yl)acetamide (328)

Compound 328 was prepared according to the method presented for the synthesis of Example 301B substituting 2-(5-fluoro-1H-indol-3-yl)acetic acid for 2-(3-(trifluoromethyl)-4,5,6,7-tetrahydro-1H-indazol-1-yl)acetic acid to afford 4 mg of the title compound: MS (m/z) 537.1 [M+H]$^+$. $^1$H NMR (400 MHz, cdcl$_3$) δ 9.77 (s, 1H), 8.33 (s, 2H), 7.30 (dt, J=9.8, 5.0 Hz, 1H), 7.24-7.11 (m, 2H), 7.07-6.89 (m, 3H), 6.84 (dd, J=14.5, 8.3 Hz, 2H), 6.58 (d, J=8.8 Hz, 1H), 6.82 (d, J=8.2 Hz, 2H), 5.83 (d, J=6.9 Hz, 1H), 4.93-4.76 (m, 1H), 3.72-3.46 (m, 2H), 2.58 (dd, J=14.4, 4.7 Hz, 1H), 1.97 (dd, J=14.4, 10.9 Hz, 1H).

Example 329

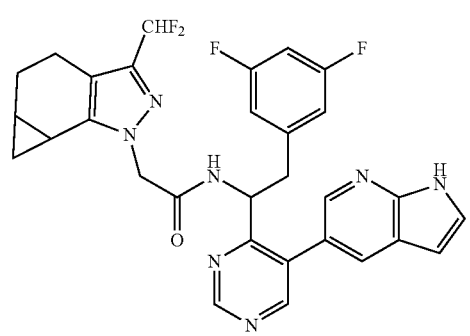

Compound 299D was purified by chiral column chromatography using a CHIRALPAK IC column eluting with heptane:ethanol (80:20). The slowest eluent (3$^{rd}$ peak) was collected, concentrated and high vacuum dried to provide 10 mg of the title compound as a single diastereomer. MS (m/z) 576.07 [M+H]$^+$. $^1$H NMR (400 MHz, cd$_3$od) δ 9.20 (s, 1H), 8.60 (s, 1H), 7.95 (d, J=2.0 Hz, 1H), 7.81 (d, J=1.9 Hz, 1H), 7.46 (d, J=3.5 Hz, 1H), 6.69 (m, 1H), 6.51 (dd, J=29.0, 25.6 Hz, 2H), 6.32 (d, J=6.2 Hz, 2H), 5.48 (t, J=7.4 Hz, 1H), 4.87 (s, 2H), 3.14-2.93 (m, 2H), 2.70 (dd, J=15.5, 5.5 Hz, 1H), 2.23-1.96 (m, 2H), 1.81-1.67 (m, 2H), 1.60 (m, 1H), 0.90 (m, 1H), 0.65 (dd, J=10.4, 4.9 Hz, 1H).

Example 330

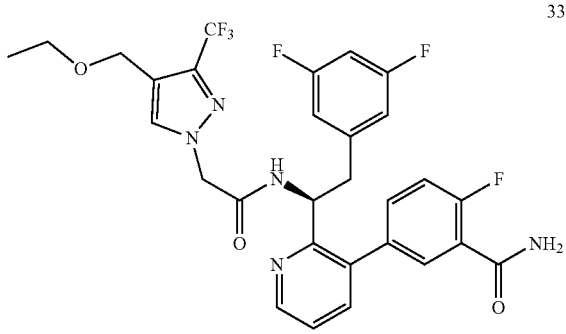

Synthesis of (S)-5-(2-(2-(3,5-difluorophenyl)-1-(2-(4-(ethoxymethyl)-3-(trifluoromethyl)-1H-pyrazol-1-yl)acetamido)ethyl)pyridin-3-yl)-2-fluorobenzamide (330)

Compound 330 was prepared according to the method presented for the synthesis of Example 361 substituting ethanol for methanol to afford 14 mg of the title compound: MS (m/z) 606.31 [M+H]+. $^1$H NMR (400 MHz, cd$_3$od) δ 8.70 (dd, J=4.9, 1.6 Hz, 1H), 7.74 (s, 1H), 7.66 (dd, J=7.8, 1.6 Hz, 1H), 7.51-7.38 (m, 2H), 7.37-7.10 (m, 2H), 6.66 (dd, J=10.3, 8.1 Hz, 1H), 6.31 (d, J=6.2 Hz, 2H), 5.35 (t, J=7.6 Hz, 1H), 4.92 (s, 2H), 4.44 (s, 2H), 3.58-3.42 (m, 2H), 3.16-3.02 (m, 2H), 1.17 (t, J=7.0 Hz, 3H).

Example 331

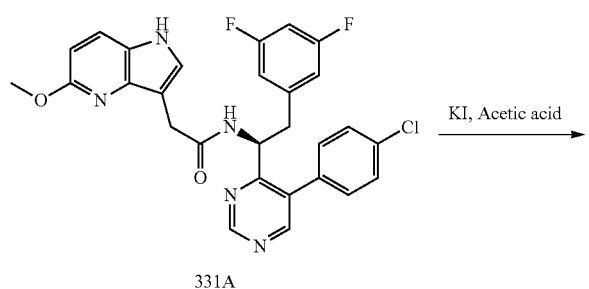

331A

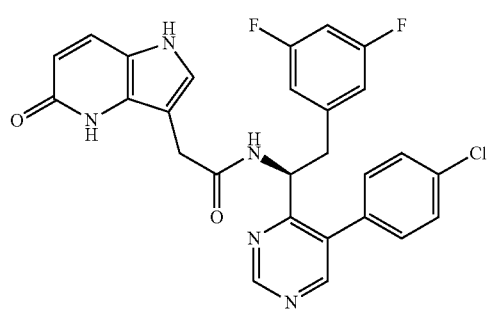

331B

Synthesis of (S)—N-(1-(5-(4-chlorophenyl)pyrimidin-4-yl)-2-(3,5-difluorophenyl)ethyl)-2-(5-methoxy-1H-pyrrolo[3,2-b]pyridin-3-yl)acetamide (331A)

Compound 331A was prepared according to the method presented for the synthesis of Example 316 substituting 2-(5-methoxy-1H-pyrrolo[3,2-b]pyridin-3-yl)acetic acid for 2-(5-hydroxy-1H-indol-3-yl)acetic acid to afford the title compound. MS (m/z) 534.1 [M+H]+.

Synthesis of (S)—N-(1-(5-(4-chlorophenyl)pyrimidin-4-yl)-2-(3,5-difluorophenyl)ethyl)-2-(5-oxo-4,5-dihydro-1H-pyrrolo[3,2-b]pyridin-3-yl)acetamide (331B)

Compound 331A (18 mg, 0.034 mmol) was dissolved in 1 mL of acetic acid and to it was added KI (22 mg, 0.14 mmol). The reaction mixture was heated up to 160° C. in a Biotage® Initiator Microwave Synthesizer for 10 min. It was cooled down and the solvent was removed. The residue was purified by reverse phase HPLC eluting with acetonitrile/water (with 0.1% TFA) to afford 4.1 mg of the title compound. MS (m/z) 520.1 [M+H]+. $^1$H NMR (300 MHz, cd$_3$od) δ 9.09 (s, 1H), 8.44 (s, 1H), 8.01 (d, J=9.0 Hz, 1H), 7.34 (d, J=8.7 Hz, 3H), 7.13 (d, J=8.5 Hz, 2H), 6.64-6.47 (m, 2H), 6.32-6.15 (m, 2H), 5.36 (t, J=7.5 Hz, 1H), 3.65-3.51 (m, 2H), 2.91 (d, J=7.6 Hz, 2H).

Example 332

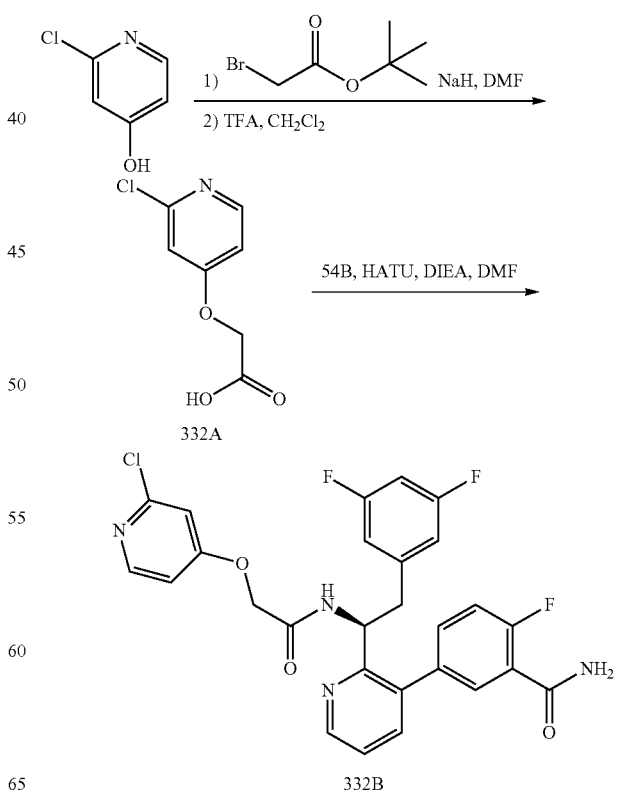

332A

332B

535

Synthesis of 2-(2-chloropyridin-4-yloxy)acetic acid (332A)

2-chloropyridin-4-ol (500 mg, 3.9 mmol) was dissolved in 10 mL of DMF and cooled down to 0° C. To it was added NaH (60% in oil dispersion, 187 mg, 4.68 mmol) portionwise. The mixture was stirred at ambient temperature for 20 min, a solution of tert-butyl 2-bromoacetate (683 μL, 4.68 mmol) was added dropwise. It was stirred for 20 min and quenched with saturated aqueous NH$_4$Cl solution. The mixture was partitioned between EtOAc and water. The organic layer was separated, dried over MgSO$_4$, filtered and concentrated. The residue was purified by silica gel chromatography eluting with EtOAc/Hexanes to afford 742 mg of tert-butyl 2-(2-chloropyridin-4-yloxy)acetate which was dissolved in 4 mL of 40% of TFA/CH$_2$Cl$_2$ and a drop of water. The reaction mixture was stirred at ambient temperature for 16 hours. The solvent was removed to provide the title compound. MS (m/z) 188.15 [M+H]$^+$.

Synthesis of (S)-5-(2-(1-(2-(2-chloropyridin-4-yloxy)acetamido)-2-(3,5-difluorophenyl)ethyl)pyridin-3-yl)-2-fluorobenzamide (332B)

Compound 332B was prepared according to the method presented in the synthesis of Example 54 utilizing Compound 54B and 2-(2-chloropyridin-4-yloxy)acetic acid to provide 7 mg of the title compound. MS (m/z) 541.75 [M+H]$^+$. $^1$H NMR (400 MHz, cd$_3$od) δ 8.70 (dd, J=4.9, 1.6 Hz, 1H), 8.16 (d, J=5.9 Hz, 1H), 7.69 (dd, J=7.8, 1.6 Hz, 1H), 7.55-7.44 (m, 2H), 7.36 (s, 1H), 7.25 (dd, J=10.7, 8.5 Hz, 1H), 7.04 (d, J=2.3 Hz, 1H), 6.95 (dd, J=5.9, 2.3 Hz, 1H), 6.74-6.60 (m, 1H), 6.34 (d, J=6.2 Hz, 2H), 5.43 (t, J=7.6 Hz, 1H), 4.67 (s, 2H), 3.13-2.97 (m, 2H).

Example 333

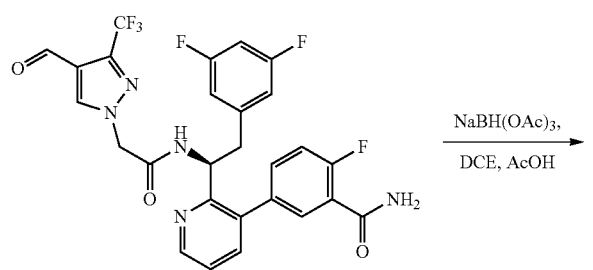

296

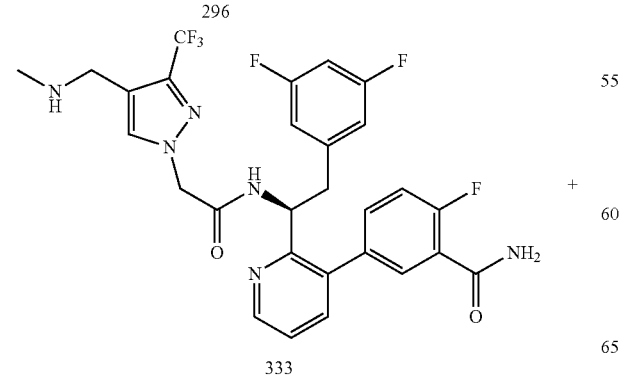

333

536

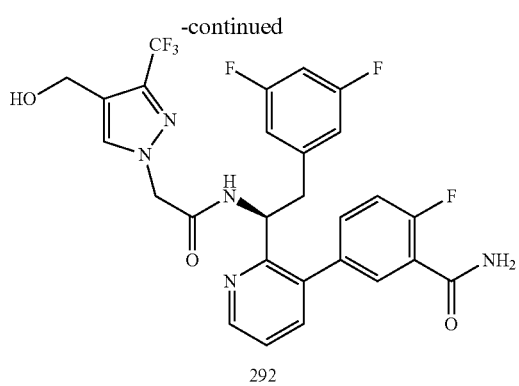

292

Synthesis of (S)-5-(2-(2-(3,5-difluorophenyl)-1-(2-(4-((methylamino)methyl)-3-(trifluoromethyl)-1H-pyrazol-1-yl)acetamido)ethyl)pyridin-3-yl)-2-fluorobenzamide (333)

To a mixture of (S)-5-(2-(2-(3,5-difluorophenyl)-1-(2-(4-formyl-3-(trifluoromethyl)-1H-pyrazol-1-yl)acetamido)ethyl)pyridin-3-yl)-2-fluorobenzamide (296, 20 mg, 0.035 mmol) and methylamine hydrochloride (5 mg, 0.07 mmol) was added 1 mL of 1,2-dichloroethane followed by 10 μL of acetic acid. After the reaction mixture was stirred at ambient temperature for 10 min, NaBH(OAc)$_3$ (9 mg, 0.042 mmol) was added, and the reaction mixture was stirred for 16 hours. The reaction was quenched by adding NaHCO$_3$ (saturated aqueous solution), and extracted by EtOAc. The organic layer was separated, washed with half brine, dried over MgSO$_4$ and filtered. The filtrate was concentrated and purified by reverse phase HPLC eluting with acetonitrile/water (with 0.1% TFA) to afford 9 mg of (S)-5-(2-(2-(3,5-difluorophenyl)-1-(2-(4-(hydroxymethyl)-3-(trifluoromethyl)-1H-pyrazol-1-yl)acetamido)ethyl)pyridin-3-yl)-2-fluorobenzamide as a side product and 6 mg of the title compound. MS (m/z) 591.32 [M+H]$^+$. $^1$H NMR (400 MHz, cd$_3$od) δ 8.70 (dd, J=4.7, 1.6 Hz, 1H), 7.94 (s, 1H), 7.57 (dd, J=7.8, 1.7 Hz, 1H), 7.48 (d, J=7.0 Hz, 1H), 7.39 (dd, J=7.8, 4.8 Hz, 1H), 7.26 (s, 1H), 7.24-7.14 (m, 1H), 6.66 (t, J=9.2 Hz, 1H), 6.32 (d, J=6.1 Hz, 2H), 5.40-5.21 (m, 1H), 4.99 (s, 2H), 4.19 (s, 2H), 3.08 (qd, J=13.2, 7.7 Hz, 2H), 2.70 (s, 3H).

Example 334

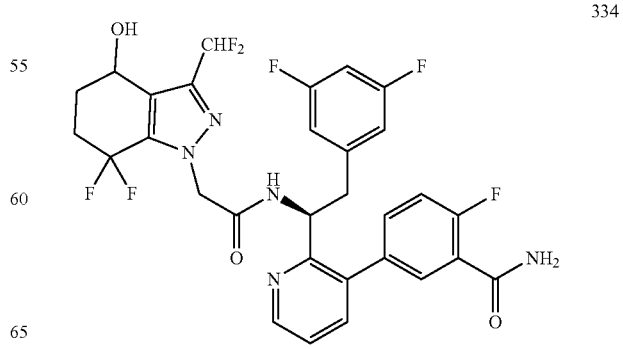

334

537

Synthesis of 5-(2-((1S)-1-(2-(3-(difluoromethyl)-7,7-difluoro-4-hydroxy-4,5,6,7-tetrahydro-1H-indazol-1-yl)acetamido)-2-(3,5-difluorophenyl)ethyl)pyridin-3-yl)-2-fluorobenzamide (334)

Compound 334 was prepared according to the method presented for the synthesis of Example 325 substituting Compound 285G for Compound 322 to afford 12 mg of the title compound: MS (m/z) 636.41 [M+H]$^+$. $^1$H NMR (400 MHz, cd$_3$od) δ 8.71 (d, J=4.8 Hz, 1H), 7.74-7.59 (m, 1H), 7.52-7.43 (m, 1H), 7.40-7.14 (m, 3H), 7.04-6.60 (m, 2H), 6.30 (d, J=7.7 Hz, 2H), 5.35 (t, J=7.5 Hz, 1H), 5.01 (s, 2H), 4.90 (s, 1H), 3.07 (m, 2H), 2.52 (m, 1H), 2.18 (m, 2H), 1.95 (m, 1H).

Example 335

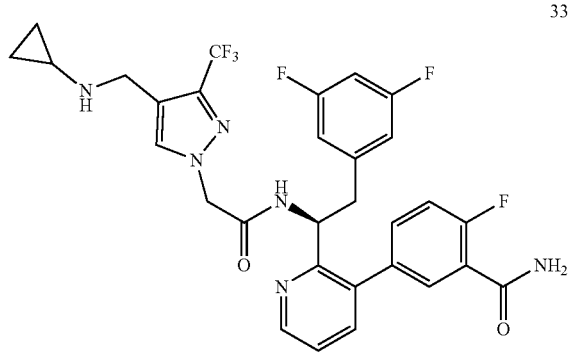

335

Synthesis of (S)-5-(2-(1-(2-(4-((cyclopropylamino)methyl)-3-(trifluoromethyl)-1H-pyrazol-1-yl)acetamido)-2-(3,5-difluorophenyl)ethyl)pyridin-3-yl)-2-fluorobenzamide (335)

Compound 335 was prepared according to the method presented for the synthesis of Example 333 substituting cyclopropanamine for methylamine hydrochloride to afford 10 mg of the title compound: MS (m/z) 617.30 [M+H]$^+$. $^1$H NMR (400 MHz, cd$_3$od) δ 8.70 (dd, J=4.8, 1.6 Hz, 1H), 7.94 (s, 1H), 7.58 (dd, J=7.8, 1.7 Hz, 1H), 7.48 (d, J=4.9 Hz, 1H), 7.40 (dd, J=7.8, 4.8 Hz, 1H), 7.33-7.10 (m, 2H), 6.72-6.55 (m, 1H), 6.33 (d, J=6.1 Hz, 2H), 5.32 (dd, J=8.4, 6.6 Hz, 1H), 4.99 (s, 2H), 4.30 (s, 2H), 3.08 (qd, J=13.0, 7.6 Hz, 2H), 2.85-2.68 (m, 1H), 0.99-0.73 (m, 4H).

Example 336

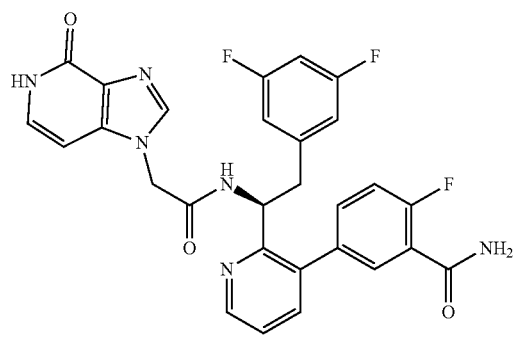

336

538

Synthesis of (S)-5-(2-(2-(3,5-difluorophenyl)-1-(2-(4-oxo-4,5-dihydro-1H-imidazo[4,5-c]pyridin-1-yl)acetamido)ethyl)pyridin-3-yl)-2-fluorobenzamide (336)

Compound 336 was prepared according to the method presented for the synthesis of Example 282 substituting Compound 368 for Compound 332 to afford 6 mg of the title compound: MS (m/z) 547.26 [M+H]$^+$. $^1$H NMR (400 MHz, cd$_3$od) δ 8.71 (dd, J=4.8, 1.6 Hz, 1H), 8.56 (s, 1H), 7.64-7.56 (m, 1H), 7.50 (d, J=5.2 Hz, 1H), 7.45-7.38 (m, 1H), 7.36-7.12 (m, 3H), 6.80-6.54 (m, 2H), 6.32 (dd, J=18.2, 6.3 Hz, 2H), 5.38-5.30 (m, 1H), 5.07 (s, 2H), 3.17-2.99 (m, 2H).

Example 337

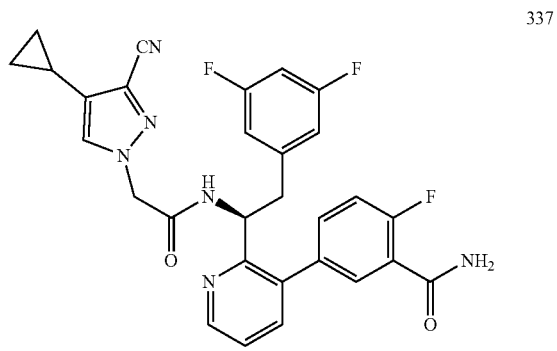 [SMILES: N#Cc1nn(CC(=O)N[C@@H](Cc2cc(F)cc(F)c2)c2ncccc2-c2ccc(F)c(C(N)=O)c2)cc1C1CC1]

337

Synthesis of (S)-5-(2-(1-(2-(3-cyano-4-cyclopropyl-1H-pyrazol-1-yl)acetamido)-2-(3,5-difluorophenyl)ethyl)pyridin-3-yl)-2-fluorobenzamide (337)

Compound 337 was prepared according to the method presented for the synthesis of Example 276 substituting Compound 359 for Compound 463 to afford 5 mg of the title compound: MS (m/z) 545.29 [M+H]$^+$. $^1$H NMR (400 MHz, cd$_3$od) δ 8.69 (dd, J=4.8, 1.6 Hz, 1H), 7.59 (dd, J=7.8, 1.7 Hz, 1H), 7.47-7.37 (m, 3H), 7.35-7.10 (m, 2H), 6.65 (t, J=9.2 Hz, 1H), 6.30 (d, J=6.1 Hz, 2H), 5.36-5.21 (m, 1H), 4.88-4.84 (m, 2H), 3.13-2.85 (m, 2H), 1.88-1.49 (m, 1H), 1.00-0.88 (m, 2H), 0.72-0.61 (m, 2H).

Example 338

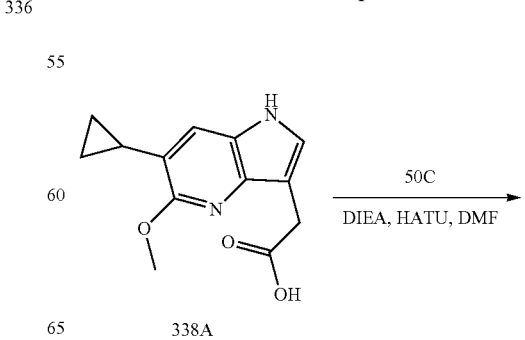

338A

539

-continued

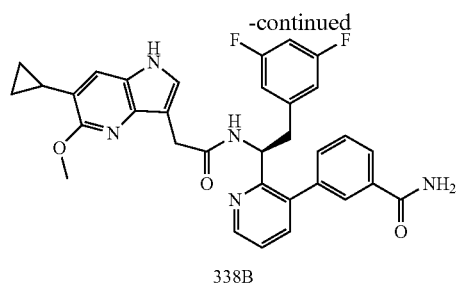

338B

KI, acetic acid →

540

Example 339

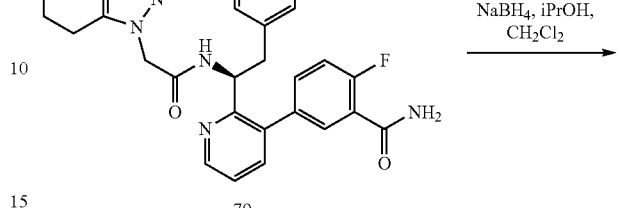

79

NaBH₄, iPrOH, CH₂Cl₂ →

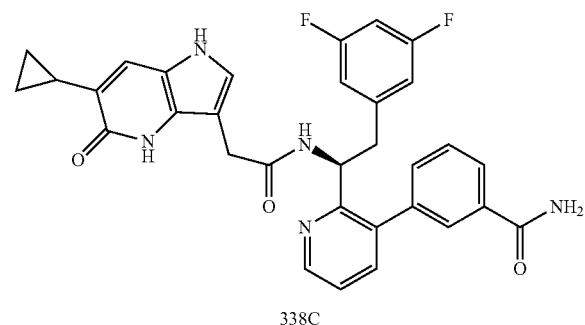

338C

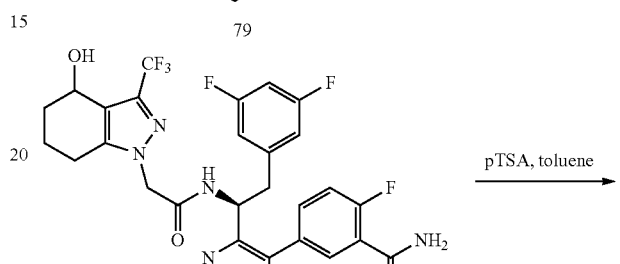

339A pTSA, toluene →

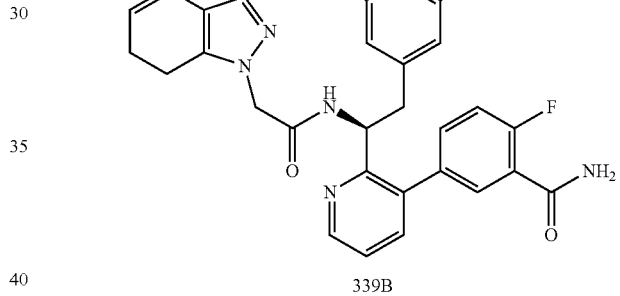

339B

Synthesis of 2-(6-cyclopropyl-5-methoxy-1H-pyrrolo[3,2-b]pyridin-3-yl)acetic acid (338A)

Compound 338A was prepared according to the method presented for the synthesis of Example 360D substituting cyclopropylboronic acid for methyl boronic acid to afford the title compound MS (m/z) 245.0 [M−H]⁻.

Synthesis of (S)-3-(2-(1-(2-(6-cyclopropyl-5-methoxy-1H-pyrrolo[3,2-b]pyridin-3-yl)acetamido)-2-(3,5-difluorophenyl)ethyl)pyridin-3-yl)benzamide (338B)

Compound 338B was prepared according to the method presented in the synthesis of Example 50 utilizing Compound 50C and Compound 338A to provide the title compound. MS (m/z) 582.1 [M+H]⁺.

Synthesis of (S)-3-(2-(1-(2-(6-cyclopropyl-5-oxo-4,5-dihydro-1H-pyrrolo[3,2-b]pyridin-3-yl)acetamido)-2-(3,5-difluorophenyl)ethyl)pyridin-3-yl)benzamide (338C)

Compound 338C was prepared according to the method presented for the synthesis of Example 331 substituting Compound 338B for Compound 331A to afford 4 mg of the title compound: MS (m/z) 568.1 [M+H]⁺. 1H NMR (400 MHz, cd₃od) δ 8.64 (d, J=3.7 Hz, 1H), 7.89 (d, J=7.8 Hz, 1H), 7.70 (s, 1H), 7.58 (d, J=6.7 Hz, 1H), 7.47 (t, J=7.7 Hz, 1H), 7.42-7.17 (m, 3H), 7.00 (s, 1H), 6.55 (t, J=9.1 Hz, 1H), 6.21 (d, J=6.5 Hz, 2H), 5.46 (dd, J=13.6, 6.2 Hz, 1H), 3.57 (s, 2H), 2.97 (ddd, J=19.9, 13.0, 7.5 Hz, 2H), 2.20-1.96 (m, 1H), 1.05-0.81 (m, 2H), 0.59 (q, J=5.5 Hz, 2H).

Synthesis of 5-(2-(((1S)-2-(3,5-difluorophenyl)-1-(2-(4-hydroxy-3-(trifluoromethyl)-4,5,6,7-tetrahydro-1H-indazol-1-yl)acetamido)ethyl)pyridin-3-yl)-2-fluorobenzamide (339A)

Compound 339A was prepared according to the method presented for the synthesis of Example 325 substituting Compound 79 for Compound 322 to afford the title compound. MS (m/z) 618.48 [M+H]⁺.

Synthesis of (S)-5-(2-(2-(3,5-difluorophenyl)-1-(2-(3-(trifluoromethyl)-6,7-dihydro-1H-indazol-1-yl)acetamido)ethyl)pyridin-3-yl)-2-fluorobenzamide (339B)

Compound 339A (160 mg) was dissolved in 10 mL of toluene, to it was added 20 mg of p-toluenesulfonic acid. The reaction mixture was stirred at ambient temperature for 16 hours then was heated up to 100° C. for 2 hours. It was cooled down, and the solvent was removed. The residue was purified by silica gel chromatography eluting with EtOAc/Hexanes to afford 108 mg of the title compound. MS (m/z) 600.46 [M+H]⁺. ¹H NMR (400 MHz, cdcl₃) δ 8.50 (dd, J=4.7, 1.4 Hz, 1H), 7.57 (dd, J=7.2, 2.1 Hz, 1H), 7.49-7.29

(m, 2H), 7.17 (ddd, J=32.2, 13.6, 6.6 Hz, 3H), 6.76 (d, J=9.0 Hz, 1H), 6.51-6.34 (m, 2H), 6.08 (d, J=5.8 Hz, 3H), 5.85-5.54 (m, 1H), 5.37 (dd, J=14.8, 7.9 Hz, 1H), 4.67 (s, 2H), 2.94-2.73 (m, 2H), 2.72-2.56 (m, 2H), 2.48-2.31 (m, 2H).

Example 340

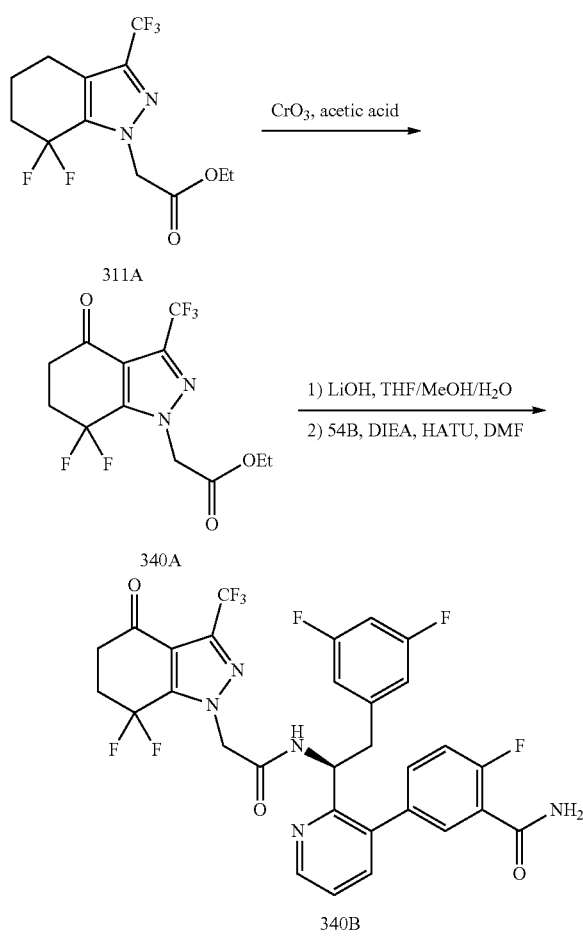

Synthesis of ethyl 2-(7,7-difluoro-4-oxo-3-(trifluoromethyl)-4,5,6,7-tetrahydro-1H-indazol-1-yl)acetate (340A)

Compound 340A was prepared according to the method presented for the synthesis of Example 285F substituting Compound 311A for Compound 285E to afford the title compound. MS (m/z) 326.96 [M+H]+.

Synthesis of (S)-5-(2-(1-(2-(7,7-difluoro-4-oxo-3-(trifluoromethyl)-4,5,6,7-tetrahydro-1H-indazol-1-yl)acetamido)-2-(3,5-difluorophenyl)ethyl)pyridin-3-yl)-2-fluorobenzamide (340B)

Compound 340B was prepared according to the method presented for the synthesis of Example 285G substituting Compound 340A for Compound 285F to afford 9 mg of the title compound. MS (m/z) 652.32 [M+H]+. 1H NMR (400 MHz, cd3od) δ 8.74 (dd, J=4.9, 1.6 Hz, 1H), 7.70 (dd, J=7.8, 1.6 Hz, 1H), 7.50 (dd, J=7.8, 5.0 Hz, 1H), 7.41 (d, J=4.9 Hz, 1H), 7.31 (s, 1H), 7.21 (dd, J=10.7, 8.5 Hz, 1H), 6.67 (ddd, J=9.3, 7.0, 2.3 Hz, 1H), 6.33 (d, J=6.1 Hz, 2H), 5.37 (t, J=7.6 Hz, 1H), 5.17 (s, 2H), 3.09 (d, J=7.6 Hz, 2H), 2.84-2.61 (m, 4H).

Example 341

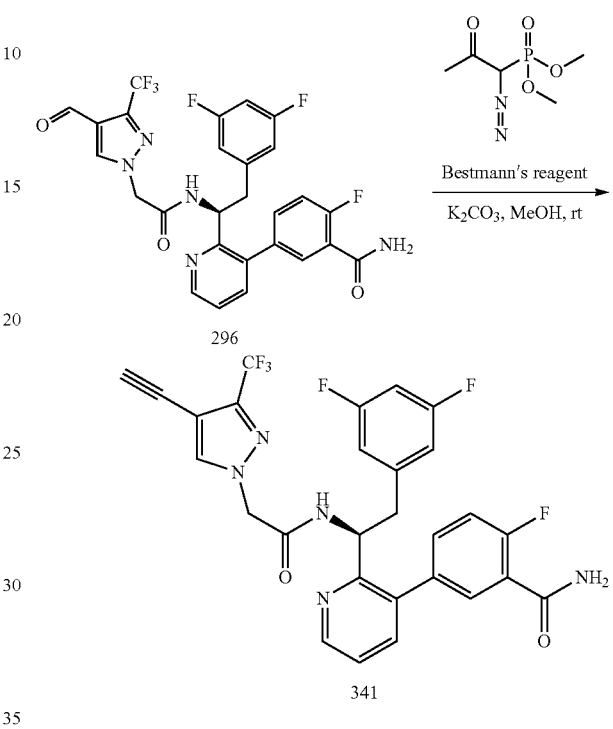

Synthesis of (S)-5-(2-(2-(3,5-difluorophenyl)-1-(2-(4-ethynyl-3-(trifluoromethyl)-1H-pyrazol-1-yl)acetamido)ethyl)pyridin-3-yl)-2-fluorobenzamide (341)

To a solution of Compound 296 (57 mg, 0.1 mmol) and dimethyl 1-diazo-2-oxopropylphosphonate (31 mg, 0.16 mmol) in MeOH (0.5 mL) was added K2CO3 (34.5 mg, 0.25 mmol). The resulting solution was stirred for 1 hour at ambient temperature. The reaction was then partitioned between EtOAc and 0.5 N HCl. The organic was dried over MgSO4 and then concentrated. The crude was purified by reverse phase preparative HPLC to afford 22 mg of the product. MS (m/z) 572.29 [M+H]+. 1H NMR (400 MHz, cd3od) δ 8.70 (dd, J=4.9, 1.6 Hz, 1H), 7.94 (s, 1H), 7.64 (dd, J=7.8, 1.6 Hz, 1H), 7.52-7.40 (m, 2H), 7.33 (s, 1H), 7.22 (dd, J=10.7, 8.6 Hz, 1H), 6.65 (t, J=9.1 Hz, 1H), 6.30 (d, J=6.2 Hz, 2H), 5.34 (t, J=7.5 Hz, 1H), 4.94 (s, 2H), 3.60 (d, J=13.7 Hz, 1H), 3.14-2.96 (m, 2H).

Example 342

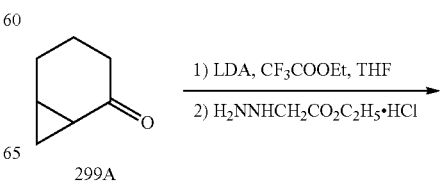

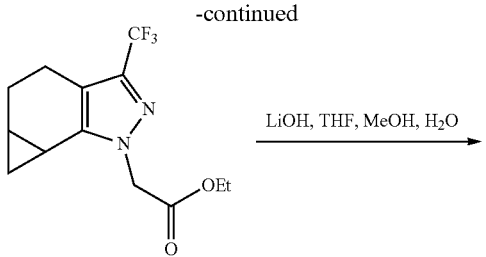

342A

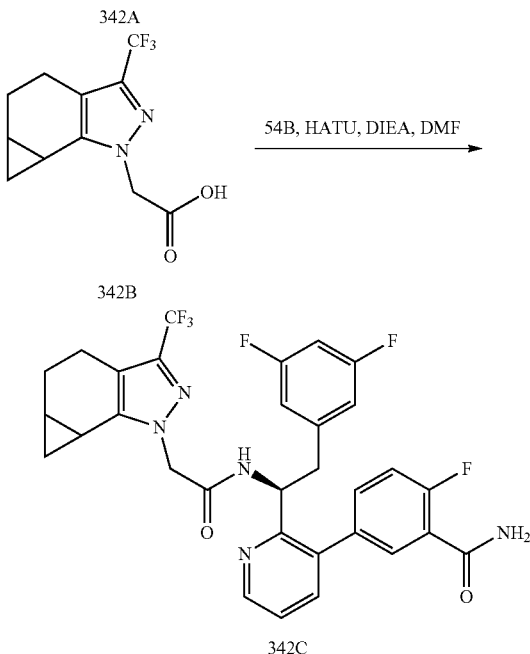

342B

342C

Synthesis of ethyl 2-(3-(trifluoromethyl)-5,5a,6,6a-tetrahydrocyclopropa[g]indazol-1(4H)-yl)acetate (342A)

Compound 342 was prepared according to the method presented for the synthesis of Example 299B substituting ethyltrifluoroacetate for methyldifluoroacetate to afford the title compound. MS (m/z) 289.26 [M+H]$^+$.

Synthesis of 2-(3-(trifluoromethyl)-5,5a,6,6a-tetrahydrocyclopropa[g]indazol-1 (4H)-yl)acetic acid (342B)

Compound 342B was prepared according to the method presented in the synthesis of Example 60G utilizing ethyl 2-(3-(trifluoromethyl)-5,5a,6,6a-tetrahydrocyclopropa[g]indazol-1(4H)-yl)acetate to afford the title compound. MS (m/z) 261.11 [M+H]$^+$.

Synthesis of 5-(2-((1S)-2-(3,5-difluorophenyl)-1-(2-(3-(trifluoromethyl)-5,5a,6,6a-tetrahydrocyclopropa[g]indazol-(4H)-yl)acetamido)ethyl)pyridin-3-yl)-2-fluorobenzamide (342C)

Compound 342C was prepared according to the method presented in the synthesis of Example 54 utilizing Compound 54B and 2-(3-(trifluoromethyl)-5,5a,6,6a-tetrahydrocyclopropa[g]indazol-1(4H)-yl)acetic acid to provide 68 mg of the title compound. MS (m/z) 614.50 [M+H]$^+$. $^1$H NMR (400 MHz, cd$_3$od) δ 8.77-8.64 (m, 1H), 7.70 (t, J=6.7 Hz, 1H), 7.47 (ddd, J=14.9, 7.6, 3.9 Hz, 2H), 7.35 (s, 1H), 7.23 (dd, J=10.7, 8.5 Hz, 1H), 6.68 (ddd, J=7.4, 6.0, 3.4 Hz, 1H), 6.34 (dd, J=9.7, 7.4 Hz, 2H), 5.38 (q, J=7.1 Hz, 1H), 4.96-4.91 (m, 2H), 3.13-2.95 (m, 2H), 2.65 (d, J=18.0 Hz, 1H), 2.25-1.98 (m, 2H), 1.94-1.52 (m, 3H), 0.96 (ddd, J=23.2, 8.3, 5.2 Hz, 1H), 0.66 (td, J=10.1, 5.0 Hz, 1H).

Example 343

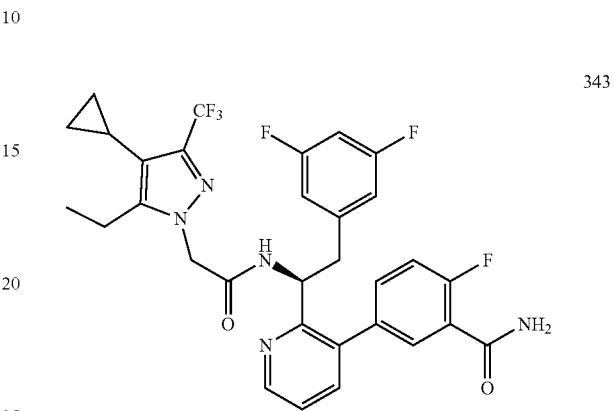

Synthesis of (S)-5-(2-(1-(2-(4-cyclopropyl-5-ethyl-3-(trifluoromethyl)-1H-pyrazol-1-yl)acetamido)-2-(3,5-difluorophenyl)ethyl)pyridin-3-yl)-2-fluorobenzamide (343)

Compound 343 was prepared according to the method presented for the synthesis of Example 276 substituting (S)-5-(2-(1-(2-(4-bromo-5-ethyl-3-(trifluoromethyl)-1H-pyrazol-1-yl)acetamido)-2-(3,5-difluorophenyl)ethyl)pyridin-3-yl)-2-fluorobenzamide (Compound 58) for (S)-5-(2-(1-(2-(4-bromo-3-(trifluoromethyl)-1H-pyrazol-1-yl)acetamido)-2-(3,5-difluorophenyl)ethyl)pyridin-3-yl)-2-fluorobenzamide (Compound 463) to afford 10 mg of the title compound: MS (m/z) 616.36 [M+H]$^+$. $^1$H NMR (400 MHz, cd$_3$od) δ 8.70 (dd, J=4.9, 1.5 Hz, 1H), 7.69 (dd, J=7.8, 1.6 Hz, 1H), 7.53-7.40 (m, 2H), 7.35 (s, 1H), 7.22 (dd, J=10.7, 8.5 Hz, 1H), 6.67 (t, J=9.2 Hz, 1H), 6.33 (d, J=6.2 Hz, 2H), 5.35 (t, J=7.6 Hz, 1H), 4.84 (s, 2H), 3.05 (d, J=7.6 Hz, 2H), 2.76-2.46 (m, 2H), 1.54 (dd, J=12.2, 6.8 Hz, 1H), 1.07 (t, J=7.6 Hz, 3H), 0.92-0.80 (m, 2H), 0.53 (q, J=5.7 Hz, 2H).

Example 344

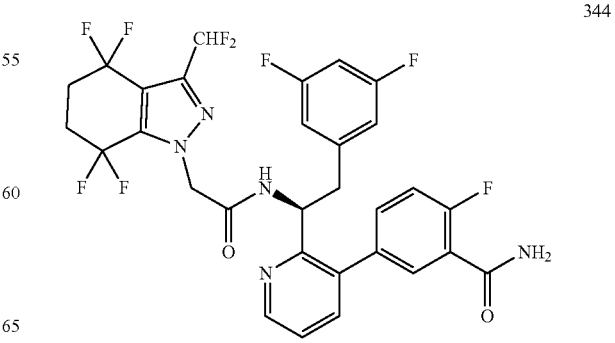

545

Synthesis of (S)-5-(2-(1-(2-(3-(difluoromethyl)-4,4,7,7-tetrafluoro-4,5,6,7-tetrahydro-1H-indazol-1-yl)acetamido)-2-(3,5-difluorophenyl)ethyl)pyridin-3-yl)-2-fluorobenzamide (344)

Compound 344 was prepared according to the method presented in the synthesis of Example 54 utilizing Compound 54B and 2-(3-(difluoromethyl)-4,4,7,7-tetrafluoro-4,5,6,7-tetrahydro-1H-indazol-1-yl)acetic acid (Compound 287C) to provide 155 mg of the title compound. MS (m/z) 656.52 [M+H]⁺. ¹H NMR (400 MHz, cd₃od) δ 8.70 (dd, J=4.8, 1.6 Hz, 1H), 7.62 (dd, J=7.8, 1.6 Hz, 1H), 7.43 (dd, J=7.8, 4.9 Hz, 1H), 7.37 (d, J=4.7 Hz, 1H), 7.30 (bs, 1H), 7.21 (dd, J=10.7, 8.5 Hz, 1H), 6.98-6.54 (m, 2H), 6.31 (d, J=6.3 Hz, 2H), 5.34 (t, J=7.6 Hz, 1H), 5.06 (s, 2H), 3.14-2.97 (m, 2H), 2.61-2.34 (m, 4H).

Example 345

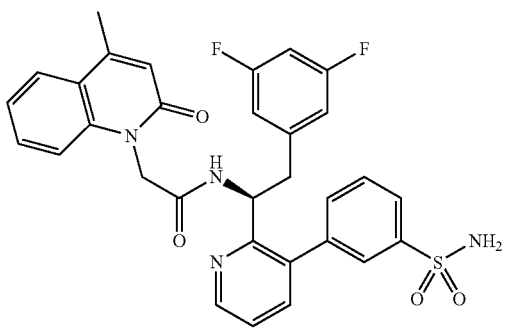

345

Synthesis of (S)—N-(2-(3,5-difluorophenyl)-1-(3-(3-sulfamoylphenyl)pyridin-2-yl)ethyl)-2-(4-methyl-2-oxoquinolin-1(2H)-yl)acetamide (345)

Compound 345 was prepared according to the method presented in the synthesis of Example 55 utilizing Compound 55D and 2-(4-methyl-2-oxoquinolin-1(2H)-yl)acetic acid to afford (S)—N-(1-(3-bromopyridin-2-yl)-2-(3,5-difluorophenyl)ethyl)-2-(4-methyl-2-oxoquinolin-1(2H)-yl)acetamide, and then Suzuki coupling with 3-sulfamoylphenylboronic acid to provide 8 mg of the title compound. MS (m/z) 589.2 [M+H]⁺. ¹H NMR (400 MHz, cd₃od) δ 8.63 (d, J=4.5 Hz, 1H), 7.78 (dd, J=20.9, 7.6 Hz, 2H), 7.63 (s, 1H), 7.54 (d, J=7.8 Hz, 1H), 7.44 (dd, J=14.9, 7.2 Hz, 2H), 7.34 (dd, J=7.7, 4.7 Hz, 1H), 7.22 (t, J=7.6 Hz, 2H), 7.11 (d, J=8.5 Hz, 1H), 6.58 (t, J=9.2 Hz, 1H), 6.50 (s, 1H), 6.26 (d, J=6.2 Hz, 2H), 5.31 (t, J=7.5 Hz, 1H), 4.96 (s, 2H), 3.06-2.92 (m, 2H), 2.43 (d, J=5.0 Hz, 3H).

Example 346

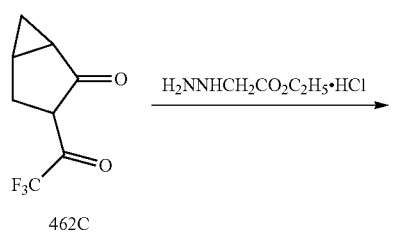

462C

→ H₂NNHCH₂CO₂C₂H₅·HCl

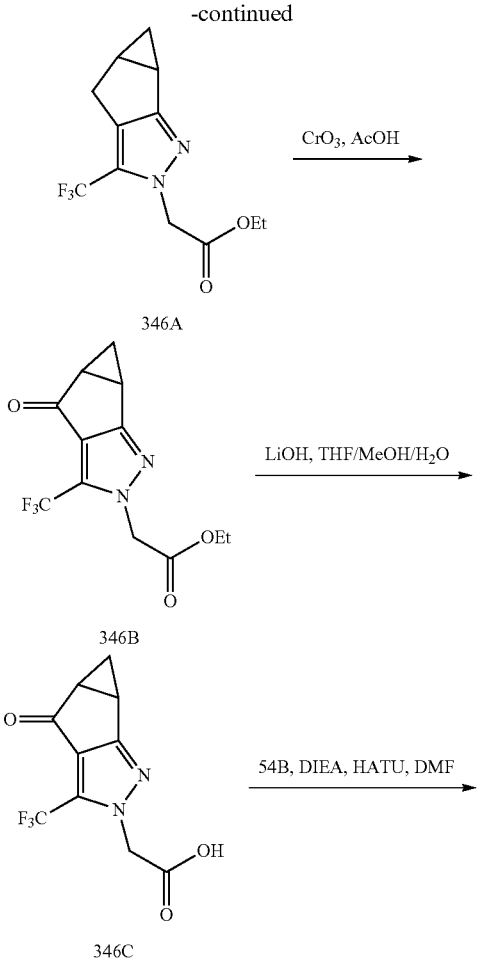

346A

→ CrO₃, AcOH

346B

→ LiOH, THF/MeOH/H₂O

346C

→ 54B, DIEA, HATU, DMF

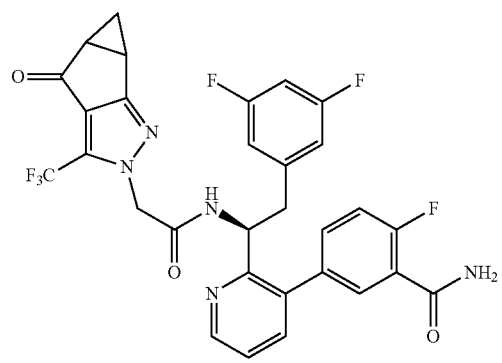

346D

Synthesis of ethyl 2-(3-(trifluoromethyl)-4,4a,5,5a-tetrahydro-2H-cyclopropa[4,5]cyclopenta[1,2-c]pyrazol-2-yl)acetate (346A)

Compound 346A was prepared according to the method presented for the synthesis of Compound 122D substituting 3-(2,2,2-trifluoroacetyl)bicyclo[3.1.0]hexan-2-one for Compound 122C afford the title compound: MS (m/z) 275.21 [M+H]⁺.

547

Synthesis of ethyl 2-(4-oxo-3-(trifluoromethyl)-4,4a,5,5a-tetrahydro-2H-cyclopropa[4,5]cyclopenta[1,2-c]pyrazol-2-yl)acetate (346B)

Compound 346B was prepared according to the method presented in the synthesis of Example 272A utilizing Compound 346A to provide the title compound. MS (m/z) 289.08 [M+H]$^+$.

Synthesis of 2-(4-oxo-3-(trifluoromethyl)-4,4a,5,5a-tetrahydro-2H-cyclopropa[4,5]cyclopenta[1,2-c]pyrazol-2-yl)acetic acid (346C)

Compound 346C was prepared according to the method presented for the synthesis of Compound 60G substituting Compound 346B for Compound 60F to afford the title compound. MS (m/z) 261.08 [M+H]$^+$.

Synthesis of 5-(2-((1S)-2-(3,5-difluorophenyl)-1-(2-(4-oxo-3-(trifluoromethyl)-4,4a,5,5a-tetrahydro-2H-cyclopropa[4,5]cyclopenta[1,2-c]pyrazol-2-yl)acetamido)ethyl)pyridin-3-yl)-2-fluorobenzamide (346D)

Compound 346D was prepared according to the method presented in the synthesis of Example 54 utilizing Compound 54B and Compound 346C to provide 16 mg of the title compound. MS (m/z) 614.18 [M+H]$^+$. $^1$H NMR (400 MHz, cd$_3$od) δ 8.71 (dd, J=4.9, 1.5 Hz, 1H), 7.74-7.55 (m, 1H), 7.44 (ddd, J=12.7, 7.2, 4.8 Hz, 2H), 7.32 (s, 1H), 7.22 (dd, J=14.2, 5.0 Hz, 1H), 6.67 (t, J=9.2 Hz, 1H), 6.33 (d, J=7.5 Hz, 2H), 5.35 (t, J=7.5 Hz, 1H), 4.99 (s, 2H), 3.17-3.00 (m, 2H), 2.81 (m, 1H), 2.61 (dt, J=8.7, 4.2 Hz, 1H), 1.64 (dd, J=12.7, 8.1 Hz, 1H), 1.54-1.44 (m, 1H).

Example 347

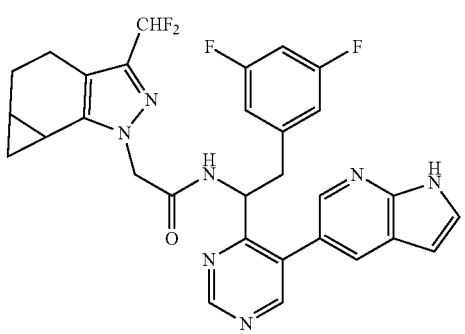

347

Compound 299D was purified by Chiral column chromatography using CHIRALPAK IC column eluting with Heptane:ethanol (80:20). The fastest eluent (1st peak) was collected, concentrated and high vacuum dried to provide 5 mg of the title compound as a mixture of diastereomers. MS (m/z) 576.07 [M+H]$^+$. $^1$H NMR (400 MHz, cd$_3$od) δ 9.20 (d, J=2.1 Hz, 1H), 8.60 (s, 1H), 7.95 (s, 1H), 7.81 (d, J=1.9 Hz, 1H), 7.46 (d, J=3.5 Hz, 1H), 6.69 (ddd, J=11.3, 8.5, 1.9 Hz, 1H), 6.61-6.42 (m, 2H), 6.31 (t, J=5.7 Hz, 2H), 5.48 (td, J=7.4, 3.3 Hz, 1H), 4.90 (d, J=17.7 Hz, 2H), 3.13-2.87 (m, 2H), 2.70 (dd, J=15.6, 5.7 Hz, 1H), 2.26-1.98 (m, 2H), 1.92-1.51 (m, 3H), 1.07-0.80 (m, 1H), 0.66 (d, J=6.6 Hz, 1H).

Example 348

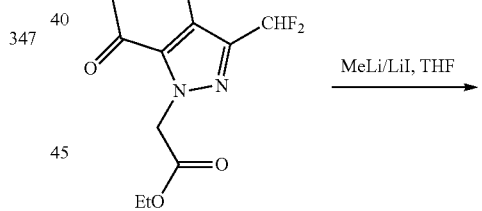

348

Compound 299D was purified by Chiral column chromatography using CHIRALPAK IC column eluting with Heptane:ethanol (80:20). The middle (2$^{nd}$ peak) was collected, concentrated and high vacuum dried to provide 10 mg of the title compound as a single diastereomer. MS (m/z) 576.07 [M+H]$^+$. $^1$H NMR (400 MHz, cd$_3$od) δ 9.20 (s, 1H), 8.60 (s, 1H), 7.94 (d, J=2.0 Hz, 1H), 7.81 (d, J=1.9 Hz, 1H), 7.46 (d, J=3.5 Hz, 1H), 6.69 (m, 1H), 6.52 (dd, J=29.1, 25.6 Hz, 2H), 6.31 (d, J=6.2 Hz, 2H), 5.47 (t, J=7.4 Hz, 1H), 4.91 (s, 2H), 3.11-2.87 (m, 2H), 2.71 (dd, J=15.7, 5.6 Hz, 1H), 2.32-1.96 (m, 2H), 1.76 (ddd, J=75.6, 39.8, 26.6 Hz, 3H), 0.94 (m, 1H), 0.64 (dd, J=10.4, 4.9 Hz, 1H).

Example 349

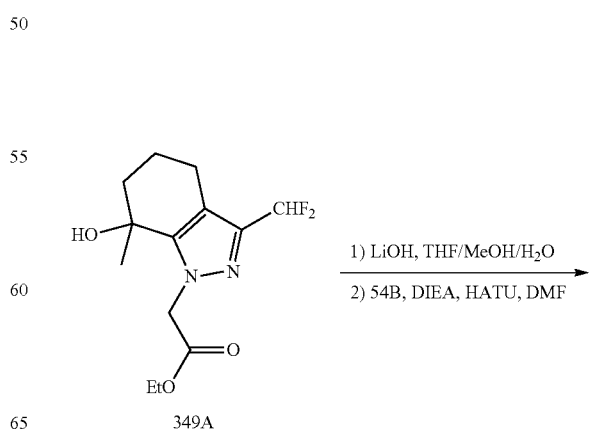

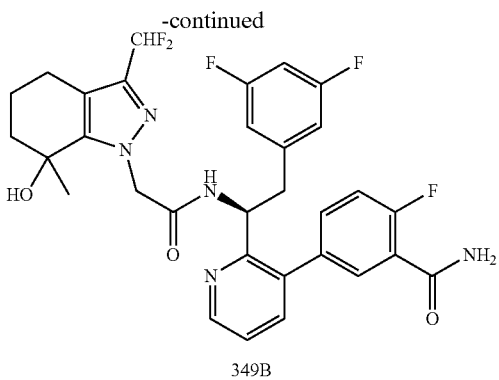

349B

Synthesis of ethyl 2-(3-(difluoromethyl)-7-hydroxy-7-methyl-4,5,6,7-tetrahydro-1H-indazol-1-yl)acetate (349A)

Ethyl 2-(3-(difluoromethyl)-7-oxo-4,5,6,7-tetrahydro-1H-indazol-1-yl)acetate (Compound 285C, 100 mg, 0.37 mmol) was dissolved in 5 mL of THF and cooled down to 0° C. To it was added a solution of methyllithium lithium iodide complex (1.0 M in diethyl ether, 1.8 mL, 1.8 mmol). After stirring at 0° C. for 5 min, It was quenched with NH₄Cl (sat'd aqueous solution) and extracted with EtOAc. The organic layer was separated, washed with brine, dried over MgSO₄, filtered and concentrated. The residue was purified by silica gel chromatography eluting with EtOAc/Hexanes to afford 27 mg of the title compound. MS (m/z) 288.03 [M+H]⁺.

Synthesis of 5-(2-((1S)-1-(2-(3-(difluoromethyl)-7-hydroxy-7-methyl-4,5,6,7-tetrahydro-1H-indazol-1-yl)acetamido)-2-(3,5-difluorophenyl)ethyl)pyridin-3-yl)-2-fluorobenzamide (349B)

Compound 349B was prepared according to the method presented in the synthesis of Example 54 utilizing Compound 54B and 2-(3-(difluoromethyl)-7-hydroxy-7-methyl-4,5,6,7-tetrahydro-1H-indazol-1-yl)acetic acid to provide 31 mg of the title compound. MS (m/z) 614.02 [M+H]⁺. ¹H NMR (400 MHz, cd₃od) δ 8.74-8.64 (m, 1H), 7.78-7.59 (m, 1H), 7.53-7.41 (m, 2H), 7.33 (s, 1H), 7.27-7.17 (m, 1H), 6.84-6.40 (m, 2H), 6.31 (dd, J=20.7, 6.1 Hz, 2H), 5.36 (dt, J=15.4, 7.8 Hz, 1H), 5.19 (m, 1H), 5.01-4.89 (m, 1H), 3.14-2.93 (m, 2H), 2.67-2.39 (m, 2H), 2.01-1.63 (m, 4H), 1.37 (d, J=5.3 Hz, 3H).

Example 350

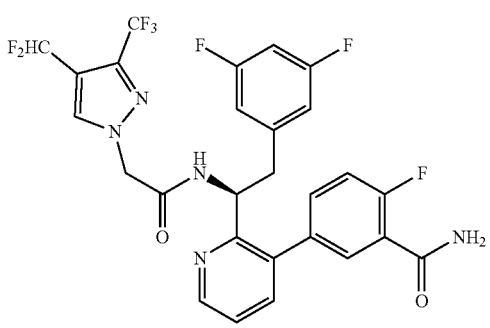

350

Synthesis of (S)-5-(2-(1-(2-(4-(difluoromethyl)-3-(trifluoromethyl)-1H-pyrazol-1-yl)acetamido)-2-(3,5-difluorophenyl)ethyl)pyridin-3-yl)-2-fluorobenzamide (350)

Compound 350 was prepared according to the method presented for the synthesis of Example 150 substituting (S)-5-(2-(2-(3,5-difluorophenyl)-1-(2-(4-formyl-3-(trifluoromethyl)-1H-pyrazol-1-yl)acetamido)ethyl)pyridin-3-yl)-2-fluorobenzamide (Compound 296) for (S)-5-(2-(2-(3,5-difluorophenyl)-1-(2-(5-oxo-3-(trifluoromethyl)-4,5,6,7-tetrahydro-1H-indazol-1-yl)acetamido)ethyl)pyridin-3-yl)-2-fluorobenzamide (Compound 446) to afford 26 mg of the title compound: MS (m/z) 598.10 [M+H]⁺. ¹H NMR (400 MHz, cd₃od) δ 8.71 (dd, J=4.9, 1.6 Hz, 1H), 8.05 (s, 1H), 7.66 (dd, J=7.8, 1.6 Hz, 1H), 7.55-7.38 (m, 2H), 7.34 (s, 1H), 7.22 (dd, J=10.7, 8.5 Hz, 1H), 6.86 (t, J=55.2 Hz, 1H), 6.66 (dd, J=10.4, 8.1 Hz, 1H), 6.31 (d, J=6.2 Hz, 2H), 5.35 (t, J=7.5 Hz, 1H), 4.99 (s, 2H), 3.07 (d, J=7.6 Hz, 2H).

Example 351

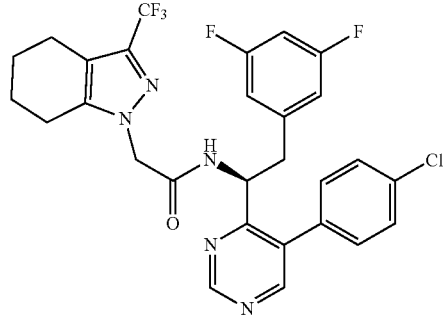

351

Synthesis of (S)—N-(1-(5-(4-chlorophenyl)pyrimidin-4-yl)-2-(3,5-difluorophenyl)ethyl)-2-(3-(trifluoromethyl)-4,5,6,7-tetrahydro-1H-indazol-1-yl)acetamide (351)

Compound 351 was prepared according to the method presented for the synthesis of Example 316 substituting 2-(3-(trifluoromethyl)-4,5,6,7-tetrahydro-1H-indazol-1-yl) acetic acid for 2-(5-hydroxy-1H-indol-3-yl)acetic acid to afford 20 mg of the title compound: MS (m/z) 576.1 [M+H]⁺. ¹H NMR (400 MHz, cd₃od) δ 9.22 (s, 1H), 8.55 (s, 1H), 7.44 (d, J=8.1 Hz, 2H), 7.20 (d, J=8.1 Hz, 2H), 6.74 (t, J=9.1 Hz, 1H), 6.38 (d, J=6.9 Hz, 2H), 5.45 (q, J=7.1 Hz, 1H), 4.79 (s, 2H), 3.20-2.85 (m, 2H), 2.55 (t, J=5.5 Hz, 2H), 2.51-2.31 (m, 2H), 1.85-1.65 (m, 4H).

Example 352

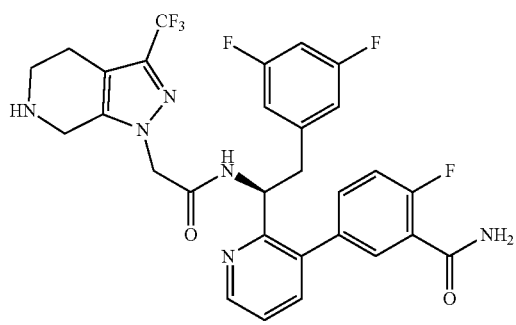

Synthesis of (S)-5-(2-(2-(3,5-difluorophenyl)-1-(2-(3-(trifluoromethyl)-4,5,6,7-tetrahydro-1H-pyrazolo[3,4-c]pyridin-1-yl)acetamido)ethyl)pyridin-3-yl)-2-fluorobenzamide (352)

Compound 352 was prepared according to the method presented in the synthesis of Example 303 utilizing Compound 378 to provide 10 mg of the title compound. MS (m/z) 603.13 [M+H]⁺. ¹H NMR (400 MHz, cd₃od) δ 8.70 (dd, J=5.2, 1.5 Hz, 1H), 7.85 (d, J=7.9 Hz, 1H), 7.61 (dd, J=7.8, 5.2 Hz, 2H), 7.15 (d, J=9.2 Hz, 2H), 6.63 (t, J=9.2 Hz, 1H), 6.26 (d, J=6.1 Hz, 2H), 5.29 (dd, J=9.2, 6.1 Hz, 1H), 4.94 (s, 2H), 4.33 (s, 2H), 3.39 (t, J=6.3 Hz, 2H), 3.10 (dd, J=13.1, 6.3 Hz, 1H), 2.98 (dd, J=13.2, 9.3 Hz, 1H), 2.86 (t, J=6.0 Hz, 2H).

Example 353

Synthesis of (S)—N-(1-(3-bromopyridin-2-yl)-2-(3,5-difluorophenyl)ethyl)-2-(5,6-dimethyl-1H-benzo[d]imidazol-1-yl)acetamide (353A)

Compound 353A was prepared according to the method presented in the synthesis of Example 55 utilizing Compound 55D and 2-(5,6-dimethyl-1H-benzo[d]imidazol-1-yl)acetic acid to provide the title compound. MS (m/z) 499.1 [M+H]⁺.

Synthesis of (S)—N-(1-(3-(3-(N-cyclopropylsulfamoyl)phenyl)pyridin-2-yl)-2-(3,5-difluorophenyl)ethyl)-2-(5,6-dimethyl-1H-benzo[d]imidazol-1-yl)acetamide (353B)

Compound 353B was prepared according to the method presented in the synthesis of Example 55 utilizing 3-(N-cyclopropylsulfamoyl)phenylboronic acid to provide 5 mg of the title compound. MS (m/z) 616.2 [M+H]⁺. ¹H NMR (400 MHz, cd₃od) δ 9.00 (s, 1H), 8.57 (d, J=4.7 Hz, 1H), 7.67 (d, J=7.8 Hz, 1H), 7.47 (dd, J=17.8, 9.1 Hz, 2H), 7.39 (t, J=7.8 Hz, 2H), 7.31-7.19 (m, 2H), 7.13 (d, J=7.6 Hz, 1H), 6.48 (t, J=9.2 Hz, 1H), 6.17 (d, J=6.4 Hz, 2H), 5.15 (t, J=7.5 Hz, 1H), 5.05 (s, 2H), 3.00-2.86 (m, 2H), 2.24 (d, J=5.9 Hz, 6H), 1.98-1.77 (m, 1H), 0.40--0.11 (m, 4H).

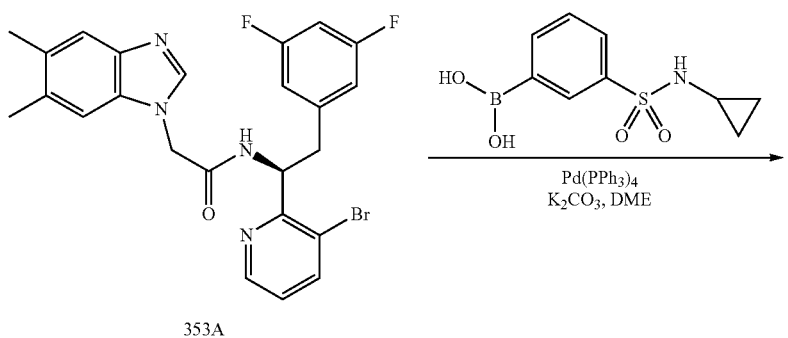

353A

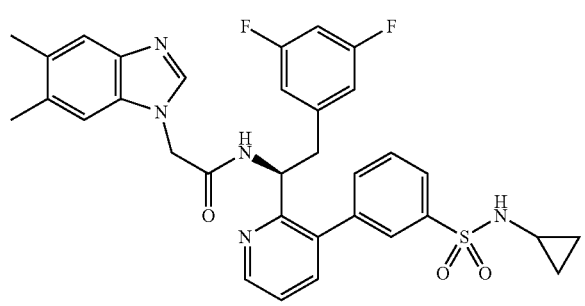

353B

Example 354

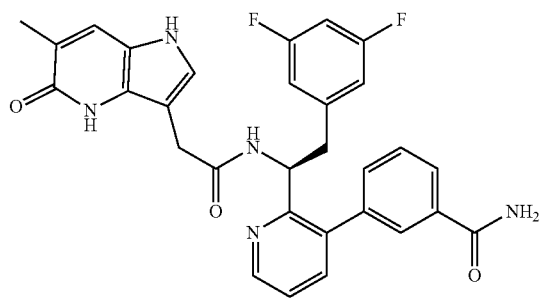

Synthesis of (S)-3-(2-(2-(3,5-difluorophenyl)-1-(2-(6-methyl-5-oxo-4,5-dihydro-1H-pyrrolo[3,2-b]pyridin-3-yl)acetamido)ethyl)pyridin-3-yl)benzamide (354)

Compound 354 was prepared according to the method presented for the synthesis of Example 331B utilizing Compound 360E to afford 5 mg of the title compound: MS (m/z) 542.1 [M+H]$^+$. $^1$H NMR (400 MHz, cdcl$_3$) δ 8.71 (m, 3H), 7.96 (d, J=7.8 Hz, 2H), 7.88 (s, 1H), 7.74 (m, 2H), 7.56-7.48 (m, 1H), 7.41 (t, J=7.8 Hz, 1H), 7.25 (s, 1H), 6.83 (d, J=7.7 Hz, 1H), 6.44 (m, 2H), 6.01 (d, J=5.8 Hz, 2H), 5.66 (dd, J=16.3, 8.9 Hz, 1H), 3.70 (s, 2H), 3.09-2.78 (m, 2H), 2.25 (s, 3H).

Example 355

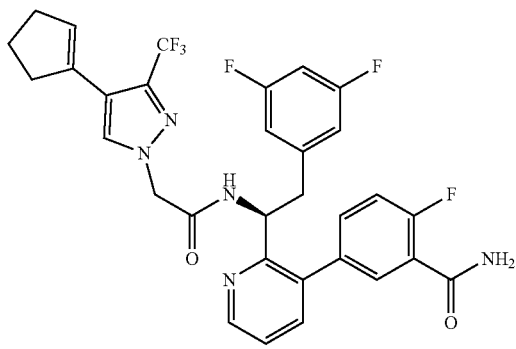

Synthesis of (S)-5-(2-(1-(2-(4-cyclopentenyl-3-(trifluoromethyl)-1H-pyrazol-1-yl)acetamido)-2-(3,5-difluorophenyl)ethyl)pyridin-3-yl)-2-fluorobenzamide (355)

Compound 355 was prepared according to the method presented in the synthesis of Example 276 utilizing Compound 463 and cyclopentenylboronic acid to provide 19 mg of the title compound. MS (m/z) 614.35 [M+H]$^+$. $^1$H NMR (400 MHz, cd$_3$od) δ 8.69 (dd, J=4.9, 1.6 Hz, 1H), 7.74-7.55 (m, 2H), 7.52-7.39 (m, 2H), 7.34 (s, 1H), 7.21 (dd, J=10.8, 8.5 Hz, 1H), 6.65 (t, J=9.2 Hz, 1H), 6.30 (d, J=6.3 Hz, 2H), 5.96 (s, 1H), 5.35 (t, J=7.5 Hz, 1H), 4.89 (s, 2H), 3.06 (d, J=7.6 Hz, 2H), 2.59 (m, 2H), 2.47 (m, 2H), 2.06-1.82 (m, 2H).

Example 356

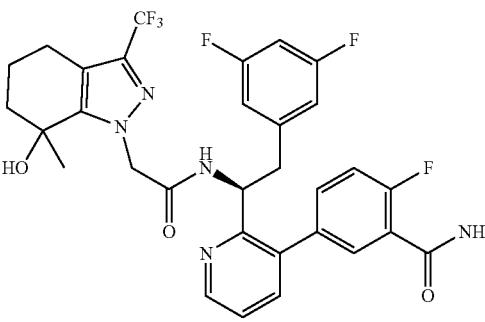

Synthesis of 5-(2-((1S)-2-(3,5-difluorophenyl)-1-(2-(7-hydroxy-7-methyl-3-(trifluoromethyl)-4,5,6,7-tetrahydro-1H-indazol-1-yl)acetamido)ethyl)pyridin-3-yl)-2-fluorobenzamide (356)

Compound 356 was prepared according to the method presented in the synthesis of Example 349B utilizing Compound 272B to provide 24 mg of the title compound. MS (m/z) 631.96 [M+H]$^+$. $^1$H NMR (400 MHz, cd$_3$od) δ 8.62-8.49 (m, 1H), 7.47 (ddd, J=7.7, 4.4, 1.7 Hz, 1H), 7.34-7.27 (m, 2H), 7.20 (s, 1H), 7.16-7.07 (m, 1H), 6.57 (t, J=9.3 Hz, 1H), 6.21 (dd, J=24.2, 6.2 Hz, 2H), 5.37-5.22 (m, 1H), 5.16 (dd, J=16.7, 4.3 Hz, 1H), 4.90 (dd, J=16.6, 2.6 Hz, 1H), 2.96 (td, J=13.0, 8.2 Hz, 2H), 2.46 (m, 2H), 1.90-1.51 (m, 4H), 1.29 (d, J=2.1 Hz, 3H).

Example 357

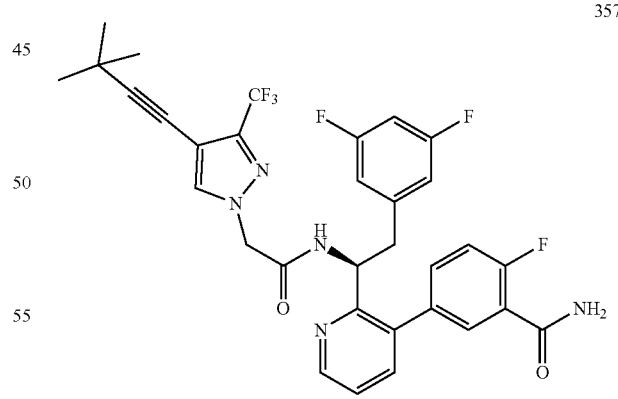

Synthesis of (S)-5-(2-(2-(3,5-difluorophenyl)-1-(2-(4-(3,3-dimethylbut-1-ynyl)-3-(trifluoromethyl)-1H-pyrazol-1-yl)acetamido)ethyl)pyridin-3-yl)-2-fluorobenzamide (357)

Compound 357 was prepared according to the method presented in the synthesis of Example 280 utilizing Compound 463 to provide 3 mg of the title compound. MS (m/z) 628.83 [M+H]+. 1H NMR (400 MHz, cd3od) δ 8.69 (dd, J=4.8, 1.6 Hz, 1H), 7.76 (s, 1H), 7.59 (dd, J=7.8, 1.6 Hz, 1H), 7.40 (dd, J=7.8, 4.8 Hz, 2H), 7.31 (s, 1H), 7.21 (dd, J=10.7, 8.6 Hz, 1H), 6.65 (t, J=9.3 Hz, 1H), 6.29 (d, J=6.4 Hz, 2H), 5.40-5.28 (m, 1H), 4.90 (s, 2H), 3.15-2.89 (m, 2H), 1.32-1.20 (m, 9H).

Example 358

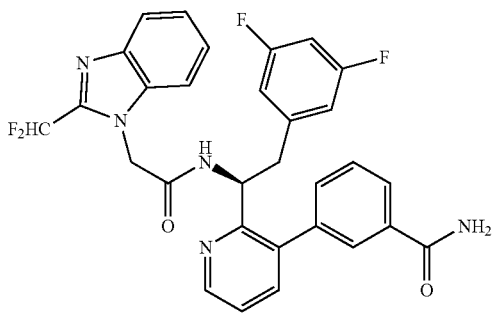

Synthesis of (S)-3-(2-(1-(2-(2-(difluoromethyl)-1H-benzo[d]imidazol-1-yl)acetamido)-2-(3,5-difluorophenyl)ethyl)pyridin-3-yl)benzamide (358)

Compound 358 was prepared according to the method presented in the synthesis of Example 55 utilizing Compound 55D and 2 2-(2-(difluoromethyl)-1H-benzo[d]imidazol-1-yl)acetic acid, and then Suzuki coupling with 3-carbamoylphenylboronic acid to afford 29 mg of the title compound. MS (m/z) 561.8 [M+H]+. 1H NMR (400 MHz, cdcl3) δ 10.08 (d, J=7.7 Hz, 1H), 8.78 (d, J=4.7 Hz, 1H), 8.12-7.96 (m, 2H), 7.93-7.69 (m, 3H), 7.53 (t, J=7.7 Hz, 1H), 7.32 (m, 1H), 7.03 (m, 3H), 6.63 (t, J=8.8 Hz, 1H), 6.15 (d, J=5.7 Hz, 1H), 6.05 (s, 1-), 5.65 (dd, J=16.2, 8.7 Hz, 1H), 5.15 (dd, J=39.0, 17.2 Hz, 2H), 3.17 (dd, J=13.4, 6.8 Hz, 1H), 3.05 (dd, J=13.4, 9.6 Hz, 1H).

Example 359

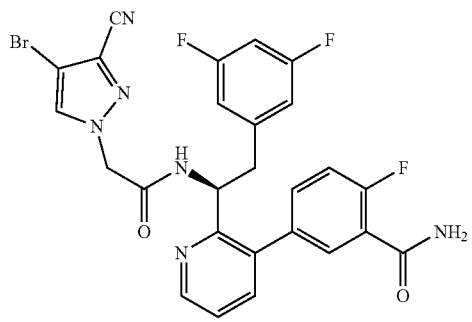

Synthesis of (S)-5-(2-(1-(2-(4-bromo-3-cyano-1H-pyrazol-1-yl)acetamido)-2-(3,5-difluorophenyl)ethyl)pyridin-3-yl)-2-fluorobenzamide (359)

Compound 359 was prepared according to the method presented in the synthesis of Example 56 utilizing Compound 56A and 4-bromo-1H-pyrazole-3-carbonitrile to provide 6 mg of the title compound. MS (m/z) 585.03 [M+H]+. 1H NMR (400 MHz, cd3od) δ 8.69 (dd, J=4.8, 1.6 Hz, 1H), 7.92 (s, 1H), 7.55 (dd, J=7.8, 1.6 Hz, 1H), 7.45-7.14 (m, 4H), 6.65 (t, J=9.2 Hz, 1H), 6.30 (d, J=6.3 Hz, 2H), 5.40-5.28 (m, 1H), 4.97 (s, 2H), 3.15-2.95 (m, 2H).

Example 360

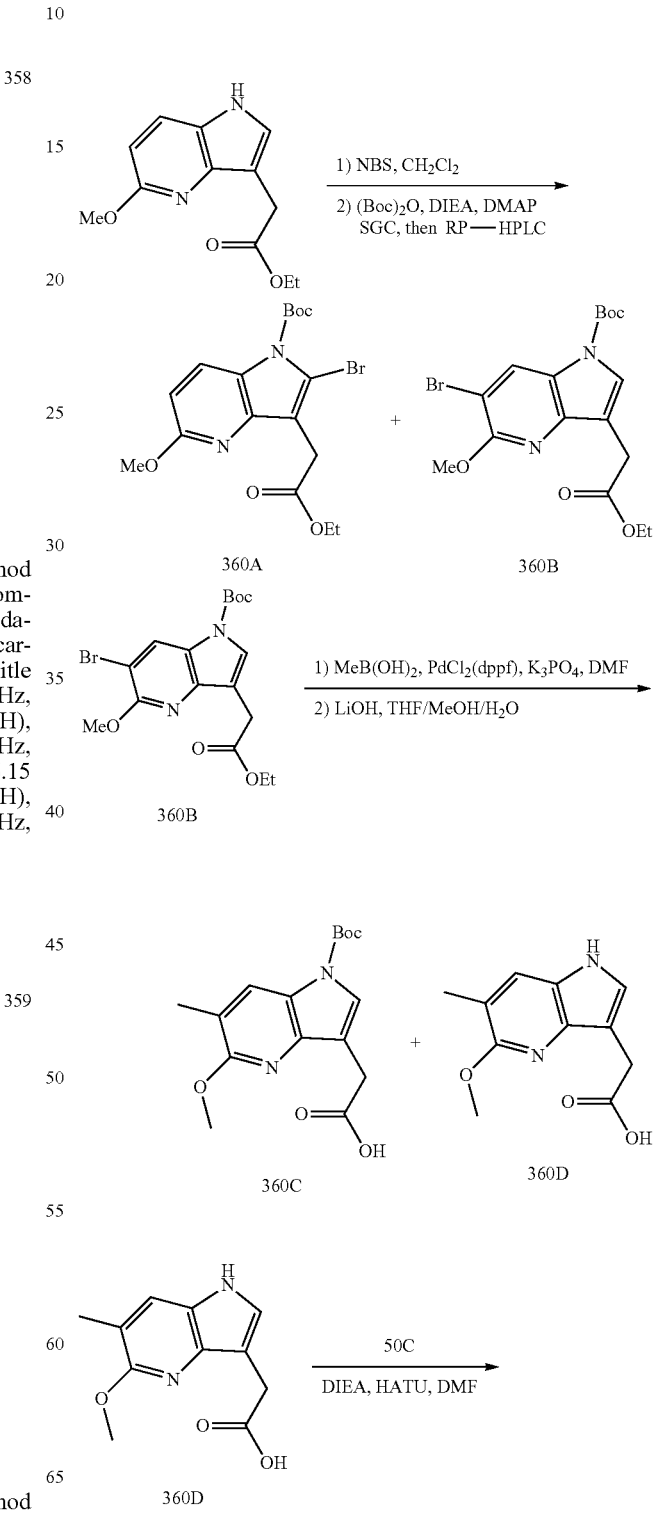

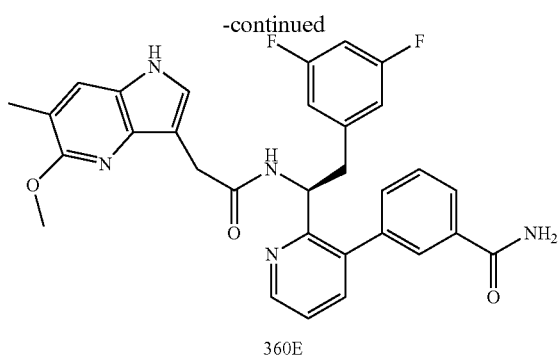

360E

Synthesis of tert-butyl 6-bromo-3-(2-ethoxy-2-oxo-ethyl)-5-methoxy-1H-pyrrolo[3,2-b]pyridine-1-carboxylate (360B)

Ethyl 2-(5-methoxy-1H-pyrrolo[3,2-b]pyridin-3-yl)acetate (1.0 g, 4.26 mmol) was dissolved in methylene chloride (40 mL) and cooled down to 0° C. with ice-water bath. NBS (760 mg, 4.26 mmol) was added in small portions over 1 hour. The reaction mixture was allowed to stir at 0° C. for two more hours. Then to it were added N,N-diisopropylethylamine (1.86 mL, 8.52 mmol), di-tert-butyl carbonate (1.86 G, 8.52 mmol) and 4-dimethylaminopyridine (52 mg, 0.42 mmol). The resulting mixture was allowed to stir for overnight at ambient temperature. The reaction mixture was partitioned between methylene chloride and water. The organic layer was separated and dried over MgSO$_4$, filtered and the filtrate was concentrated to dryness. The residue was purified by silica gel chromatography eluting with EtOAc/hexanes, and then RP-HPLC eluting with acetonitrile/water to afford 455 mg of 360A and 131 mg of the title compound. MS (m/z) 414.9 [M+H]+.

Synthesis of 2-(5-methoxy-6-methyl-1H-pyrrolo[3,2-b]pyridin-3-yl)acetic acid (360D)

Compound 360B (120 mg, 0.29 mmol) and methyl boronic acid (35 mg, 0.58 mmol) were dissolved in 3 mL of DMF. To it was added potassium phosphate tribasic (185 mg, 0.87 mmol) The system was degassed and purged with argon and then to it was added [1,1'-bis(diphenylphosphino)ferrocene]dichloropalladium(II) (11 mg, 0.015 mmol). The mixture was heated up to 85° C. for 16 hours. After cooling down to ambient temperature the DMF solution was filtered and purified by RP HPLC eluting with acetonitrile and water to afford 28 mg of tert-butyl 3-(2-ethoxy-2-oxoethyl)-5-methoxy-6-methyl-1H-pyrrolo[3,2-b]pyridine-1-carboxylate and 38 mg of ethyl 2-(5-methoxy-6-methyl-1H-pyrrolo[3,2-b]pyridin-3-yl)acetate which was dissolved in 1.5 mL of THF/MeOH/H$_2$O (3/2/1), and to it was added LiOH.H$_2$O (30 mg). The reaction mixture was allowed to stir at ambient temperature for 20 min and purified by RP-HPLC eluting with acetonitrile and water to afford 15 mg of the title compound. MS (m/z) 221.2 [M+H]+.

Synthesis of (S)-3-(2-(2-(3,5-difluorophenyl)-1-(2-(5-methoxy-6-methyl-1H-pyrrolo[3,2-b]pyridin-3-yl)acetamido)ethyl)pyridin-3-yl)benzamide (360E)

Compound 360E was prepared according to the method presented in the synthesis of Example 50 utilizing Compound 50C and 2-(5-methoxy-6-methyl-1H-pyrrolo[3,2-b] pyridin-3-yl)acetic acid to provide 4 mg of the title compound. MS (m/z) 556.1 [M+H]+. $^1$H NMR (400 MHz, cdcl$_3$) δ 9.77 (s, 1H), 8.81 (s, 1H), 8.62 (s, 1H), 7.93 (d, J=7.6 Hz, 2H), 7.76 (s, 3H), 7.53 (s, 1H), 7.44 (t, J=7.8 Hz, 1H), 7.23 (s, 1H), 6.96 (d, J=7.7 Hz, 1H), 6.41 (d, J=9.5 Hz, 2H), 6.02 (d, J=6.3 Hz, 2H), 5.61 (d, J=8.1 Hz, 1H), 4.08 (s, 3H), 3.76 (s, 2H), 2.94 (s, 2H), 2.23 (s, 3H).

Example 361

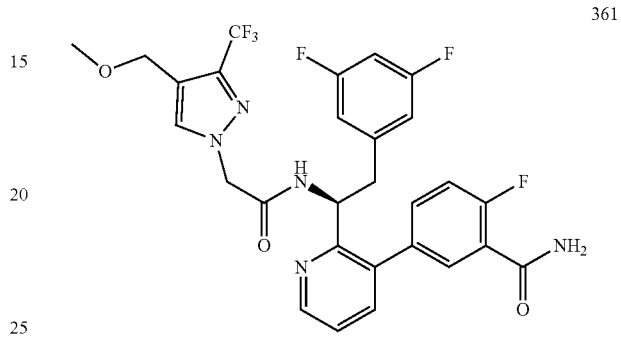

361

Synthesis of (S)-5-(2-(2-(3,5-difluorophenyl)-1-(2-(4-(methoxymethyl)-3-(trifluoromethyl)-1H-pyrazol-1-yl)acetamido)ethyl)pyridin-3-yl)-2-fluorobenzamide (361)

Compound 296 (20 mg, 0.03 mmol) was dissolved in 1 mL of methanol and to it was added decaborane (8.5 mg, 0.06 mmol). The reaction mixture was stirred at ambient temperature for 3 days. It was quenched with NaHCO$_3$ (sat'd aqueous solution) and extracted with EtOAc. The organic layer was separated, washed with brine, dried over MgSO$_4$, filtered and concentrated. The residue was purified by reverse phase HPLC eluting with acetonitrile/water (with 0.1% TFA) to afford 9.1 mg of the title compound. MS (m/z) 592.23 [M+H]+. $^1$H NMR (400 MHz, cd$_3$od) δ 8.69 (dd, J=4.8, 1.6 Hz, 1H), 7.74 (s, 1H), 7.64 (dd, J=7.8, 1.6 Hz, 1H), 7.49-7.36 (m, 2H), 7.30 (bs, 1H), 7.21 (dd, J=10.7, 8.5 Hz, 1H), 6.65 (dd, J=10.4, 8.1 Hz, 1H), 6.30 (d, J=6.2 Hz, 2H), 5.34 (t, J=7.5 Hz, 1H), 4.92 (s, 2H), 4.39 (s, 2H), 3.33 (s, 2H), 3.12-3.00 (m, 2H).

Example 362

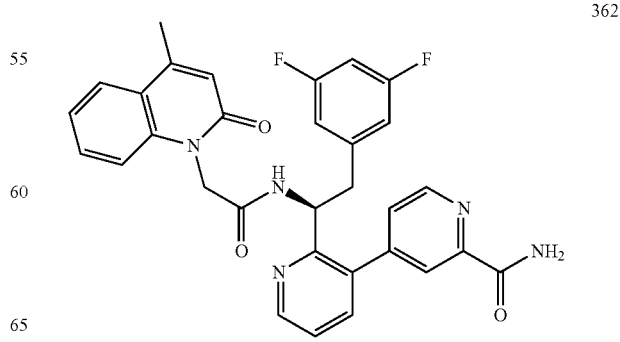

362

Synthesis of (S)-2-(2-(3,5-difluorophenyl)-1-(2-(4-methyl-2-oxoquinolin-1(2H)-yl)acetamido)ethyl)-3,4'-bipyridine-2'-carboxamide (362)

Compound 362 was prepared according to the method presented in the synthesis of Example 310 utilizing 2-(4-methyl-2-oxoquinolin-1 (2H)-yl)acetic acid to provide 9 mg of the title compound. MS (m/z) 554.5 [M+H]$^+$. $^1$H NMR (400 MHz, cd3od) δ 8.79 (d, J=4.7 Hz, 1H), 8.59 (d, J=5.0 Hz, 1H), 7.84 (d, J=8.0 Hz, 1H), 7.73-7.61 (m, 2H), 7.51 (ddd, J=12.7, 10.7, 5.1 Hz, 3H), 7.31 (t, J=7.5 Hz, 1H), 7.21 (d, J=8.5 Hz, 1H), 6.66 (t, J=9.3 Hz, 1H), 6.59 (s, 1H), 6.32 (d, J=6.4 Hz, 2H), 5.35 (t, J=7.6 Hz, 1H), 5.07 (q, J=16.7 Hz, 2H), 3.19-3.04 (m, 2H), 2.52 (s, 3H).

Example 363

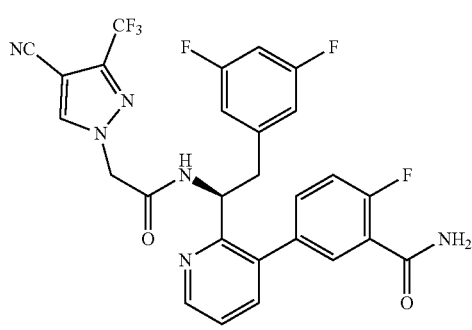

Synthesis of (S)-5-(2-(1-(2-(4-cyano-3-(trifluoromethyl)-1H-pyrazol-1-yl)acetamido)-2-(3,5-difluorophenyl)ethyl)pyridin-3-yl)-2-fluorobenzamide (363)

(S)-5-(2-(1-(2-(4-bromo-3-(trifluoromethyl)-1H-pyrazol-1-yl)acetamido)-2-(3,5-difluorophenyl)ethyl)pyridin-3-yl)-2-fluorobenzamide (Compound 463, 20 mg, 0.03 mmol) was dissolved in 0.5 mL of DMF. To it was added CuCN (5.7 mg, 0.06 mmol) and the reaction mixture was heated up to 200° C. for 16 hours. It was cooled down and partitioned between EtOAc and 5% LiCl aqueous solution. The organic layer was separated, washed with brine, dried over MgSO$_4$, filtered and concentrated. The residue was purified by reverse phase HPLC eluting with acetonitrile/water (with 0.1% TFA) to afford 6.5 mg of the title compound. MS (m/z) 573.22 [M+H]$^+$. $^1$H NMR (400 MHz, cd$_3$od) δ 8.70 (dd, J=4.8, 1.6 Hz, 1H), 8.43 (s, 1H), 7.61 (dd, J=7.8, 1.7 Hz, 1H), 7.42 (dd, J=7.8, 4.9 Hz, 2H), 7.31 (s, 1H), 7.21 (dd, J=10.7, 8.5 Hz, 1H), 6.65 (t, J=9.2 Hz, 1H), 6.31 (d, J=6.2 Hz, 2H), 5.41-5.23 (m, 1H), 5.04 (s, 2H), 3.09 (dd, J=16.5, 9.7 Hz, 2H).

Example 364

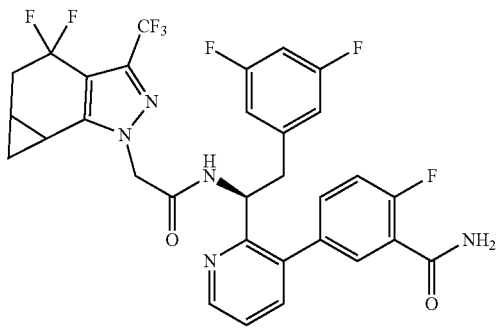

Synthesis of 5-(2-((1S)-1-(2-(4,4-difluoro-3-(trifluoromethyl)-5,5a,6,6a-tetrahydrocyclopropa[g]indazol-1(4H)-yl)acetamido)-2-(3,5-difluorophenyl)ethyl)pyridin-3-yl)-2-fluorobenzamide (364)

Compound 364 was prepared according to the method presented in the synthesis of Example 304 utilizing Compound 342A to provide 2 mg of the title compound. MS (m/z) 650.00 [M+H]$^+$. $^1$H NMR (400 MHz, cd$_3$od) δ 8.78-8.62 (m, 1H), 7.58 (dd, J=7.8, 1.7 Hz, 1H), 7.49-7.13 (m, 4H), 6.66 (d, J=6.8 Hz, 1H), 6.34 (dd, J=12.9, 6.6 Hz, 2H), 5.37 (t, J=7.4 Hz, 1H), 5.11-4.92 (m, 2H), 3.07 (m, 2H), 2.63 (t, J=16.6 Hz, 1H), 2.28 (m, 1H), 1.94-1.77 (m, 2H), 1.16 (m, 1H), 0.46 (m, 1H).

Example 365

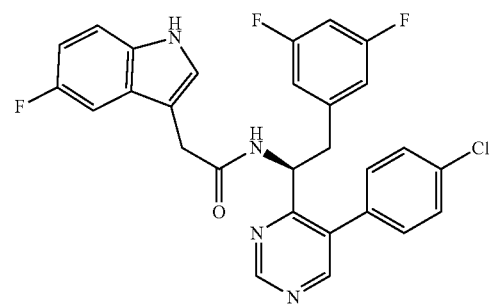

Synthesis of (S)—N-(1-(5-(4-chlorophenyl)pyrimidin-4-yl)-2-(3,5-difluorophenyl)ethyl)-2-(5-fluoro-1H-indol-3-yl)acetamide (365)

Compound 365 was prepared according to the method presented for the synthesis of Example 279G substituting Compound 279D and 2-(5-fluoro-1H-indol-3-yl)acetic acid for Compound 279E and 2-(5,6-dimethyl-1H-benzo[d]imidazol-1-yl)acetic acid to afford 22 mg of the title compound: MS (m/z) 521.1 [M+H]$^+$. $^1$H NMR (400 MHz, cd$_3$od) δ 9.13 (s, 1H), 8.48 (s, 1H), 7.39 (d, J=8.0 Hz, 2H), 7.28 (dd, J=8.8, 4.3 Hz, 1H), 7.19-7.10 (m, 4H), 6.84 (t, J=8.9 Hz, 1H), 6.68 (t, J=9.2 Hz, 1H), 6.33 (d, J=6.6 Hz, 2H), 5.42 (q, J=7.1 Hz, 1H), 3.69-3.44 (m, 2H), 2.99 (d, J=7.5 Hz, 2H).

Example 366

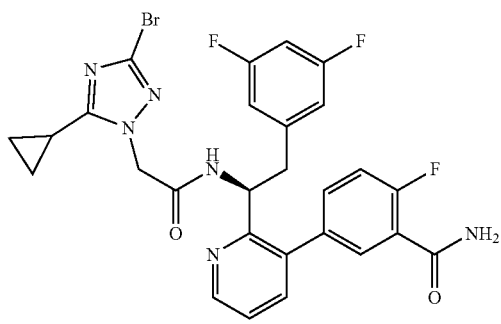

Synthesis of (S)-5-(2-(1-(2-(3-bromo-5-cyclopropyl-1H-1,2,4-triazol-1-yl)acetamido)-2-(3,5-difluorophenyl)ethyl)pyridin-3-yl)-2-fluorobenzamide (366)

Compound 366 was prepared according to the method presented in the synthesis of Example 56 utilizing Compound 56A and 3-bromo-5-cyclopropyl-1H-1,2,4-triazole to provide 6 mg of the title compound. MS (m/z) 599.90 [M+H]$^+$. H NMR (400 MHz, cd$_3$od) δ 8.71 (dd, J=4.9, 1.6 Hz, 1H), 7.66 (dd, J=7.8, 1.6 Hz, 1H), 7.46 (dd, J=7.8, 4.9 Hz, 2H), 7.33 (s, 1H), 7.23 (dd, J=10.7, 8.5 Hz, 1H), 6.67 (dd, J=10.4, 8.0 Hz, 1H), 6.34 (d, J=6.1 Hz, 2H), 5.36 (t, J=7.6 Hz, 1H), 4.97 (s, 2H), 3.08 (d, J=7.6 Hz, 2H), 1.88 (m, 1H), 1.12-0.74 (m, 4H).

Example 367

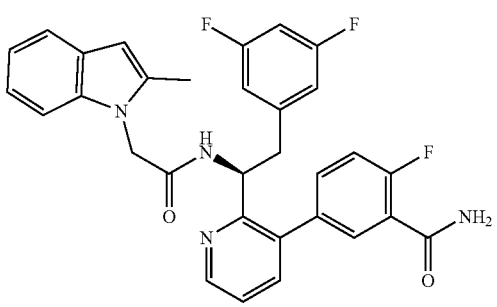

Synthesis of (S)-5-(2-(2-(3,5-difluorophenyl)-1-(2-(2-methyl-1H-indol-1-yl)acetamido)ethyl)pyridin-3-yl)-2-fluorobenzamide (367)

Compound 367 was prepared according to the method presented in the synthesis of Example 54 utilizing Compound 54B and 3 2-(2-methyl-1H-indol-1-yl)acetic acid to provide 20 mg of the title compound. MS (m/z) 525.2 [M+H]$^+$. $^1$H NMR (400 MHz, cd$_3$od) δ 8.60 (d, J=4.8 Hz, 1H), 7.88 (d, J=8.0 Hz, 1H), 7.65-7.55 (m, 2H), 7.53-7.33 (m, 3H), 7.28 (d, J=7.8 Hz, 1H), 7.12 (d, J=7.9 Hz, 1H), 7.06-6.94 (m, 2H), 6.66 (t, J=9.2 Hz, 1H), 6.25 (s, 3H), 5.46 (t, J=7.4 Hz, 1H), 4.80 (s, 2H), 2.93 (qd, J=13.0, 7.3 Hz, 2H), 2.30 (s, 3H).

Example 368

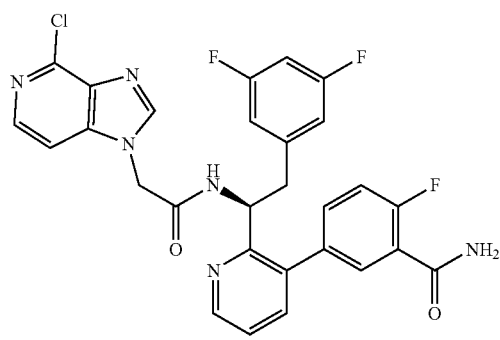

Synthesis of (S)-5-(2-(1-(2-(4-chloro-1H-imidazo[4,5-c]pyridin-1-yl)acetamido)-2-(3,5-difluorophenyl)ethyl)pyridin-3-yl)-2-fluorobenzamide (368)

Compound 368 was prepared according to the method presented for the synthesis of Example 332 substituting 4-chloro-1H-imidazo[4,5-c]pyridine for 2-chloropyridin-4-ol to afford 6 mg of the title compound: MS (m/z) 565.60 [M+H]$^+$. $^1$H NMR (400 MHz, cd$_3$od) δ 8.65 (dd, J=4.8, 1.6 Hz, 1H), 8.31 (s, 1H), 8.07 (t, J=6.2 Hz, 1H), 7.65-7.49 (m, 1H), 7.50-7.35 (m, 3H), 7.22 (s, 1H), 7.12 (dd, J=10.8, 8.5 Hz, 1H), 6.59 (dd, J=10.4, 8.0 Hz, 1H), 6.28 (t, J=9.0 Hz, 2H), 5.33-5.16 (m, 1H), 5.05 (s, 2H), 3.03 (m, 2H).

Example 369

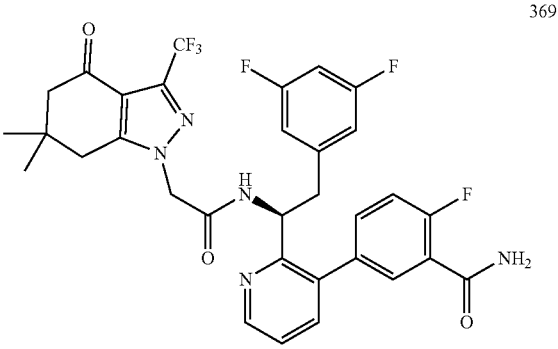 [SMILES: CC1(C)CC(=O)c2c(C(F)(F)F)nn(CC(=O)N[C@@H](Cc3cc(F)cc(F)c3)c3ncccc3-c3ccc(F)c(C(N)=O)c3)c2C1]

Synthesis of (S)-5-(2-(2-(3,5-difluorophenyl)-1-(2-(6,6-dimethyl-4-oxo-3-(trifluoromethyl)-4,5,6,7-tetrahydro-1H-indazol-1-yl)acetamido)ethyl)pyridin-3-yl)-2-fluorobenzamide (369)

Compound 369 was prepared according to the method presented in the synthesis of Example 56 utilizing Compound 56A and 6,6-dimethyl-3-(trifluoromethyl)-6,7-dihydro-1H-indazol-4(5H)-one to provide 4 mg of the title compound. MS (m/z) 644.36 [M+H]$^+$. $^1$H NMR (400 MHz, cd$_3$od) δ 8.70 (d, J=3.2 Hz, 1H), 7.56 (d, J=6.1 Hz, 1H), 7.46-7.30 (m, 3H), 7.21 (d, J=10.7 Hz, 1H), 6.66 (m, 1H), 6.35 (d, J=6.0 Hz, 2H), 5.34 (m, 1H), 4.93 (s, 2H), 3.18-2.93 (m, 2H), 2.65 (s, 2H), 2.37 (s, 2H), 1.06 (d, J=2.9 Hz, 6H).

Example 370

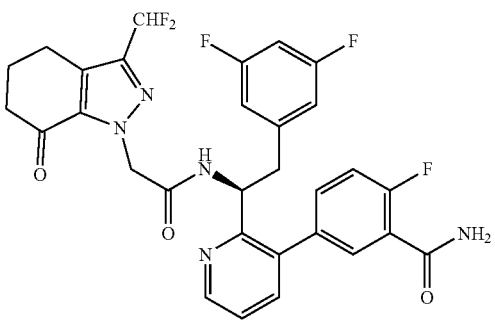

Synthesis of (S)-5-(2-(1-(2-(3-(difluoromethyl)-7-oxo-4,5,6,7-tetrahydro-1H-indazol-1-yl)acetamido)-2-(3,5-difluorophenyl)ethyl)pyridin-3-yl)-2-fluorobenzamide (370)

Compound 370 was prepared according to the method presented in the synthesis of Example 54 utilizing Compound 54B and Compound 285C to provide 11 mg of the title compound. MS (m/z) 598.36 [M+H]⁺. ¹H NMR (400 MHz, cd₃od) δ 8.74 (dd, J=5.0, 1.6 Hz, 1H), 7.72 (dd, J=7.8, 1.6 Hz, 1H), 7.51 (dd, J=7.8, 5.0 Hz, 1H), 7.45-7.26 (m, 2H), 7.20 (dd, J=10.7, 8.6 Hz, 1H), 6.98-6.51 (m, 2H), 6.31 (d, J=6.1 Hz, 2H), 5.35 (t, J=7.6 Hz, 1H), 5.25-5.09 (m, 2H), 3.06 (dd, J=11.7, 10.1 Hz, 2H), 2.87 (t, J=6.0 Hz, 2H), 2.61-2.38 (m, 2H), 2.23-2.03 (m, 2H).

Example 371

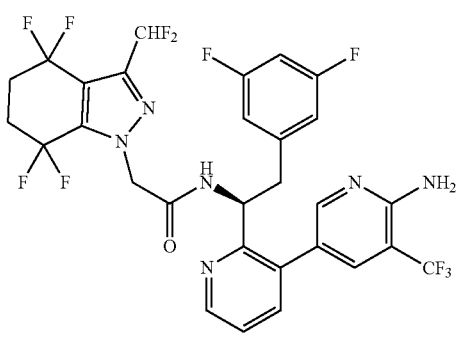

Synthesis of (S)—N-(1-(6'-amino-5'-(trifluoromethyl)-3,3'-bipyridin-2-yl)-2-(3,5-difluorophenyl)ethyl)-2-(3-(difluoromethyl)-4,4,7,7-tetrafluoro-4,5,6,7-tetrahydro-1H-indazol-1-yl)acetamide (371)

Compound 371 was prepared according to the method presented in the synthesis of Example 287E utilizing Compound 287D and 5-(4,4,5,5-tetramethyl-1,3,2-dioxaborolan-2-yl)-3-(trifluoromethyl)pyridin-2-amine to provide 15 mg of the title compound. MS (m/z) 679.35 [M+H]⁺. ¹H NMR (400 MHz, cd₃od) δ 8.74 (dd, J=4.8, 1.6 Hz, 1H), 7.99 (s, 1H), 7.63-7.50 (m, 2H), 7.42 (dd, J=7.8, 4.8 Hz, 1H), 7.03-6.56 (m, 2H), 6.37 (d, J=6.2 Hz, 2H), 5.25 (t, J=7.6 Hz, 1H), 5.16-4.94 (m, 2H), 3.12 (d, J=7.7 Hz, 2H), 2.75-2.30 (m, 4H).

Example 372

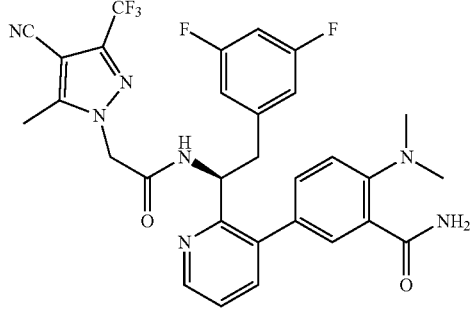

Synthesis of (S)-5-(2-(1-(2-(4-cyano-5-methyl-3-(trifluoromethyl)-1H-pyrazol-1-yl)acetamido)-2-(3,5-difluorophenyl)ethyl)pyridin-3-yl)-2-(dimethylamino)benzamide (372)

Compound 372 was prepared according to the method presented in the synthesis of Example 363 utilizing Compound 275 to provide Compound 376 and 12 mg of the title compound as a side product. MS (m/z) 612.31 [M+H]⁺. ¹H NMR (400 MHz, cd3cn) δ 8.76 (dd, J=4.8, 1.5 Hz, 1H), 7.92 (s, 1H), 7.73 (d, J=8.4 Hz, 1H), 7.64 (d, J=7.8 Hz, 1H), 7.46 (dd, J=7.8, 4.8 Hz, 1H), 7.33 (d, J=7.8 Hz, 1H), 6.79-6.60 (m, 1H), 6.28 (d, J=6.5 Hz, 2H), 5.53 (m, 1H), 5.07-4.83 (m, 2H), 3.18 (s, 6H), 3.02 (ddd, J=22.0, 13.0, 7.7 Hz, 2H), 2.38 (s, 3H).

Example 373

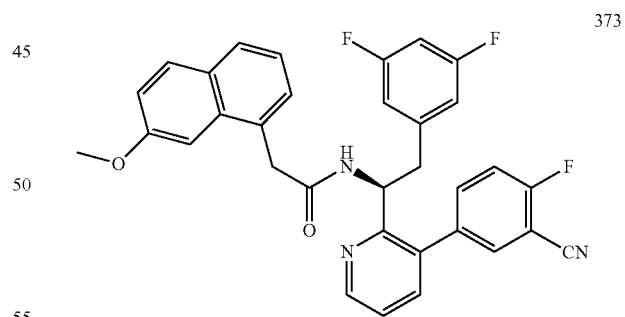

Synthesis of (S)—N-(1-(3-(3-cyano-4-fluorophenyl)pyridin-2-yl)-2-(3,5-difluorophenyl)ethyl)-2-(7-methoxynaphthalen-1-yl)acetamide (373)

Compound 373 was prepared according to the method presented in the synthesis of Example 55 utilizing Compound 55D and 2-(7-methoxynaphthalen-1-yl)acetic acid to afford (S)—N-(1-(3-bromopyridin-2-yl)-2-(3,5-difluorophenyl)ethyl)-2-(7-methoxynaphthalen-1-yl)acetamide, and then Suzuki coupling with 3-cyano-4-fluorophenylboronic acid to provide 6 mg of the title compound. MS (m/z) 552.2 [M+H]⁺. ¹H NMR (400 MHz, cd₃od) δ 8.64 (d, J=4.9 Hz, 1H), 7.74 (dd, J=17.6, 8.5 Hz, 2H), 7.58 (d, J=7.8 Hz, 1H), 7.42 (dd, J=7.8, 4.9 Hz, 2H), 7.34 (s, 1H), 7.32-7.24 (m, 3H), 7.21 (d, J=2.1 Hz, 1H), 7.11 (dd, J=9.0, 2.4 Hz, 1H), 6.70 (t, J=9.1 Hz, 1H), 6.25 (d, J=6.3 Hz, 2H), 5.35-5.16 (m, 1H), 3.98 (q, J=15.5 Hz, 2H), 3.79 (s, 3H), 3.09-2.87 (m, 2H).

Example 374

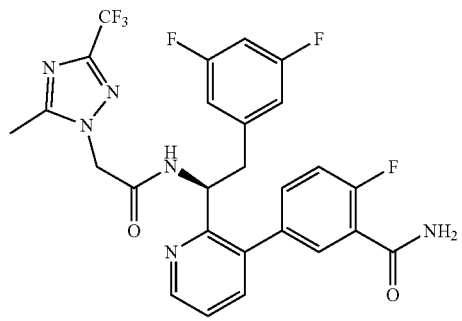

Synthesis of (S)-5-(2-(2-(3,5-difluorophenyl)-1-(2-(5-methyl-3-(trifluoromethyl)-1H-1,2,4-triazol-1-yl)acetamido)ethyl)pyridin-3-yl)-2-fluorobenzamide (374)

Compound 374 was prepared according to the method presented in the synthesis of Example 56 utilizing Compound 56A and 5-methyl-3-(trifluoromethyl)-1H-1,2,4-triazole to provide 40 mg of the title compound. MS (m/z) 563.32 [M+H]⁺. ¹H NMR (400 MHz, cd₃od) δ 8.72 (dd, J=4.9, 1.5 Hz, 1H), 7.67 (dd, J=7.8, 1.6 Hz, 1H), 7.47 (dd, J=7.8, 4.9 Hz, 2H), 7.32 (s, 1H), 7.22 (dd, J=10.7, 8.6 Hz, 1H), 6.78-6.49 (m, 1H), 6.34 (d, J=6.2 Hz, 2H), 5.36 (t, J=7.6 Hz, 1H), 5.02 (d, J=17.1 Hz, 2H), 3.09 (d, J=7.6 Hz, 2H), 2.39 (s, 3H).

Example 375

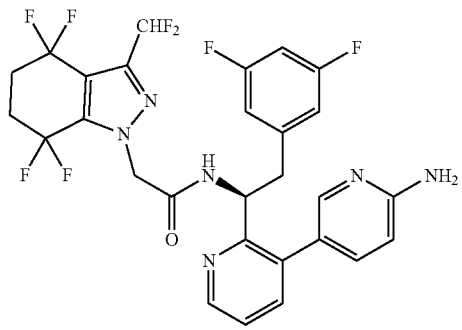

Synthesis of (S)—N-(1-(6'-amino-3,3'-bipyridin-2-yl)-2-(3,5-difluorophenyl)ethyl)-2-(3-(difluoromethyl)-4,4,7,7-tetrafluoro-4,5,6,7-tetrahydro-1H-indazol-1-yl)acetamide (375)

Compound 375 was prepared according to the method presented in the synthesis of Example 287E utilizing 287D and 5-(4,4,5,5-tetramethyl-1,3,2-dioxaborolan-2-yl)pyridin-2-amine to provide 11 mg of the title compound. MS (m/z) 611.34 [M+H]⁺. ¹H NMR (400 MHz, cd₃od) δ 8.74 (dd, J=4.7, 1.6 Hz, 1H), 7.64-7.50 (m, 3H), 7.39 (dd, J=7.8, 4.8 Hz, 1H), 7.03-6.88 (m, 1H), 6.81-6.61 (m, 2H), 6.42 (d, J=6.3 Hz, 2H), 5.27 (t, J=7.6 Hz, 1H), 5.14-4.99 (m, 2H), 3.12 (d, J=7.7 Hz, 2H), 2.70-2.34 (m, 4H).

Example 376

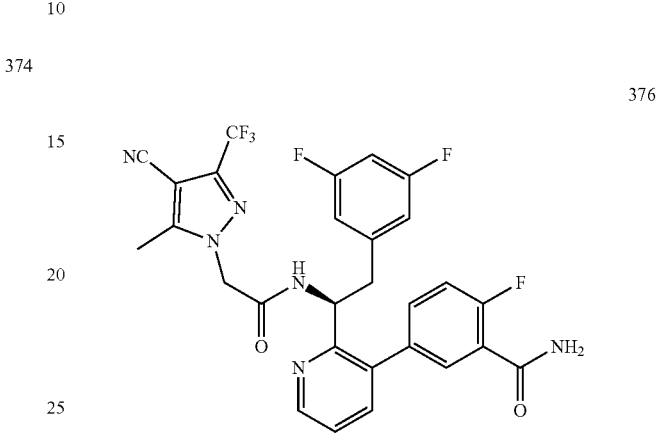

Synthesis of (S)-5-(2-(1-(2-(4-cyano-5-methyl-3-(trifluoromethyl)-1H-pyrazol-1-yl)acetamido)-2-(3,5-difluorophenyl)ethyl)pyridin-3-yl)-2-fluorobenzamide (376)

Compound 376 was prepared according to the method presented in the synthesis of Example 363 utilizing Compound 275 to provide 7 mg of the title compound. MS (m/z) 587.28 [M+H]⁺. ¹H NMR (400 MHz, cd₃od) δ 8.71 (dd, J=4.9, 1.6 Hz, 1H), 7.65 (dd, J=7.8, 1.6 Hz, 1H), 7.45 (dd, J=7.8, 4.9 Hz, 2H), 7.32 (s, 1H), 7.22 (dd, J=10.7, 8.6 Hz, 1H), 6.67 (t, J=9.2 Hz, 1H), 6.33 (d, J=6.2 Hz, 2H), 5.35 (t, J=7.6 Hz, 1H), 4.99 (s, 2H), 3.08 (d, J=7.7 Hz, 2H), 2.36 (s, 3H).

Example 377

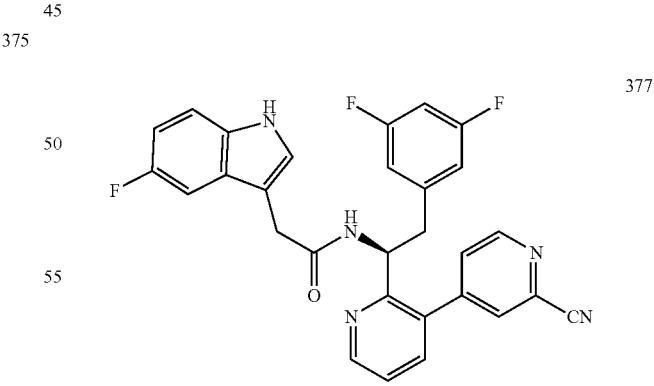

Synthesis of(S)—N-(1-(2'-cyano-3,4'-bipyridin-2-yl)-2-(3,5-difluorophenyl)ethyl)-2-(5-fluoro-1H-indol-3-yl)acetamide (377)

Compound 377 was prepared according to the method presented in the synthesis of Example 55 utilizing Compound 55E and 4-(4,4,5,5-tetramethyl-1,3,2-dioxaborolan-2-yl)picolinonitrile to provide 5 mg of the title compound. MS (m/z) 512.1 [M+H]⁺. ¹H NMR (400 MHz, cdcl₃) δ 8.83 (d, J=5.0 Hz, 1H), 8.62 (d, J=4.2 Hz, 1H), 8.24 (s, 1H), 8.09 (d, J=7.1 Hz, 1H), 7.91-7.79 (m, 1H), 7.69 (m, 2H), 7.30 (m, 1H), 7.22 (d, J=2.2 Hz, 1H), 6.94 (m, 1H), 6.84 (dd, J=9.4, 2.3 Hz, 1H), 6.69 (t, J=8.7 Hz, 1H), 6.11 (m, 2H), 5.36-5.12 (m, 1H), 3.70 (q, J=16.3 Hz, 2H), 3.06 (dd, J=13.5, 6.3 Hz, 1H), 2.94 (dd, J=13.4, 9.9 Hz, 1H).

Example 378

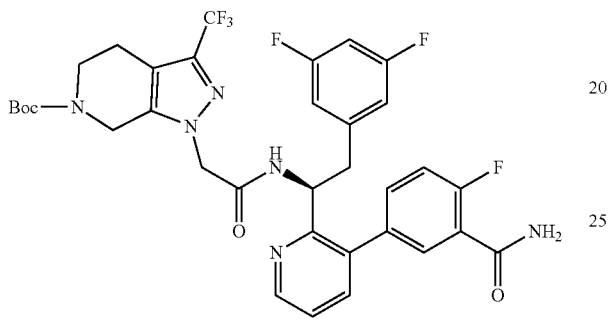

378

Synthesis of (S)-tert-butyl 1-(2-(1-(3-(3-carbamoyl-4-fluorophenyl)pyridin-2-yl)-2-(3,5-difluorophenyl)ethylamino)-2-oxoethyl)-3-(trifluoromethyl)-4,5-dihydro-1H-pyrazolo[3,4-c]pyridine-6(7H)-carboxylate (378)

Compound 378 was prepared according to the method presented in the synthesis of Example 56 utilizing 56A and tert-butyl 3-(trifluoromethyl)-4,5-dihydro-1H-pyrazolo[3,4-c]pyridine-6(7H)-carboxylate to provide 6 mg of the title compound. MS (m/z) 703.14 [M+H]⁺. ¹H NMR (400 MHz, cd₃od) δ 8.69 (d, J=4.8 Hz, 1H), 7.64-7.50 (m, 1H), 7.37 (m, 3H), 7.25-7.15 (m, 1H), 6.64 (m, 1H), 6.30 (d, J=6.3 Hz, 2H), 5.33 (m, 1H), 4.85 (s, 2H), 4.46 (s, 2H), 3.18-2.93 (m, 4H), 2.63 (m, 2H), 1.45 (s, 9H).

Example 379

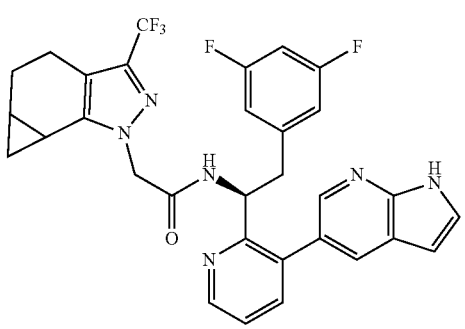

379

Synthesis of N—((S)-1-(3-(1H-pyrrolo[2,3-b]pyridin-5-yl)pyridin-2-yl)-2-(3,5-difluorophenyl)ethyl)-2-(3-(trifluoromethyl)-5,5a,6,6a-tetrahydrocyclopropa[g]indazol-1(4H)-yl)acetamide (379)

Compound 379 was prepared according to the method presented in the synthesis of Example 61F utilizing Compound 342B and Compound 61E to provide 19 mg of the title compound. MS (m/z) 593.42 [M+H]⁺. ¹H NMR (400 MHz, cd₃od) δ 8.86-8.64 (m, 1H), 8.09 (s, 1H), 7.96 (m, 1H), 7.70 (m, 1H), 7.63 (d, J=3.5 Hz, 1H), 7.54-7.38 (m, 1H), 6.81-6.58 (m, 2H), 6.30 (m, 2H), 5.33 (m, 1H), 4.93 (m, 2H), 3.23-2.96 (m, 2H), 2.65 (m, 1H), 2.15 (m, 2H), 1.88-1.47 (m, 3H), 1.09-0.76 (m, 1H), 0.66 (m, 1H).

Example 380

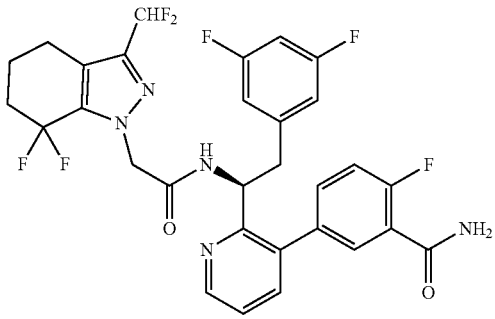

380

Synthesis of (S)-5-(2-(1-(2-(3-(difluoromethyl)-7,7-difluoro-4,5,6,7-tetrahydro-1H-indazol-1-yl)acetamido)-2-(3,5-difluorophenyl)ethyl)pyridin-3-yl)-2-fluorobenzamide (380)

Compound 380 was prepared according to the method presented in the synthesis of Example 54 utilizing Compound 54B and Compound 285E to provide 40 mg of the title compound. MS (m/z) 620.40 [M+H]⁺. ¹H NMR (400 MHz, cd₃od) δ 8.71 (dd, J=5.0, 1.6 Hz, 1H), 7.71 (dd, J=7.8, 1.6 Hz, 1H), 7.50 (dd, J=7.8, 5.0 Hz, 1H), 7.44-7.28 (m, 2H), 7.22 (dd, J=10.7, 8.5 Hz, 1H), 6.94-6.53 (m, 2H), 6.32 (m, 2H), 5.35 (t, J=7.6 Hz, 1H), 5.01 (m, 2H), 3.05 (d, J=7.6 Hz, 2H), 2.67 (m, 2H), 2.35-2.04 (m, 2H), 2.05-1.80 (m, 2H).

Example 381

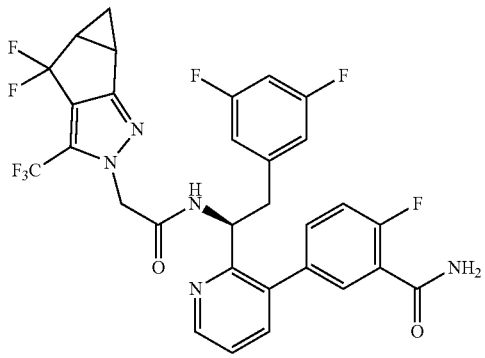

Synthesis of 5-(2-((1S)-1-(2-(4,4-difluoro-3-(trifluoromethyl)-4,4a,5,5a-tetrahydro-2H-cyclopropa[4,5]cyclopenta[1,2-c]pyrazol-2-yl)acetamido)-2-(3,5-difluorophenyl)ethyl)pyridin-3-yl)-2-fluorobenzamide (381)

Compound 381 was prepared according to the method presented in the synthesis of Example 304 utilizing Compound 346B to provide 41 mg of the title compound. MS (m/z) 636.38 [M+H]⁺. ¹H NMR (400 MHz, cd₃od) δ 8.71 (dd, J=4.9, 1.6 Hz, 1H), 7.74-7.60 (m, 1H), 7.49-7.29 (m, 3H), 7.27-7.15 (m, 1H), 6.67 (t, J=9.2 Hz, 1H), 6.32 (d, J=8.1 Hz, 2H), 5.35 (t, J=7.5 Hz, 1H), 4.94 (s, 2H), 3.05 (d, J=7.6 Hz, 2H), 2.72-2.41 (m, 2H), 1.41 (dd, J=14.1, 7.6 Hz, 1H), 1.06 (m, 1H).

Example 382

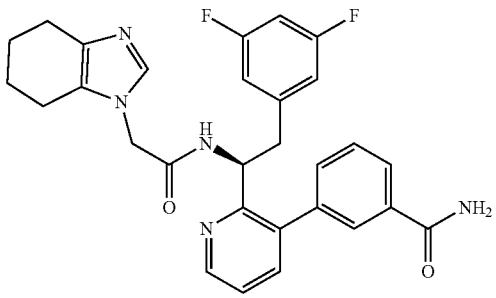

Synthesis of (S)-3-(2-(2-(3,5-difluorophenyl)-1-(2-(4,5,6,7-tetrahydro-1H-benzo[d]imidazol-1-yl)acetamido)ethyl)pyridin-3-yl)benzamide (382)

Compound 382 was prepared according to the method presented in the synthesis of Example 56 utilizing Compound 286 and 3-carbamoylphenylboronic acid to provide 8 mg of the title compound. MS (m/z) 516.2 [M+H]⁺. ¹H NMR (400 MHz, cdcl₃) δ 9.97 (d, J=8.3 Hz, 1H), 8.67 (m, 2H), 7.98-7.71 (m, 3H), 7.61 (m, 1H), 7.46-7.21 (m, 2H), 6.92 (m, 1H), 6.51 (t, J=8.8 Hz, 2H), 6.13 (d, J=6.0 Hz, 2H), 5.53 (d, J=8.2 Hz, 1H), 4.78 (m, 2H), 3.15-2.86 (m, 2H), 2.51 (m, 2H), 2.30 (m, 2H), 1.73 (m, 4H).

Example 383

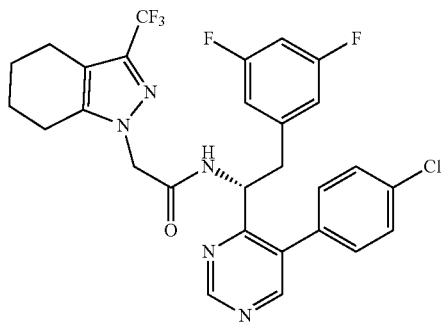

Synthesis (R)—N-(1-(5-(4-chlorophenyl)pyrimidin-4-yl)-2-(3,5-difluorophenyl)ethyl)-2-(3-(trifluoromethyl)-4,5,6,7-tetrahydro-1H-indazol-1-yl)acetamide (383)

Compound 383 was prepared according to the method presented for the synthesis of Example 279G substituting 2-(3-(trifluoromethyl)-4,5,6,7-tetrahydro-1H-indazol-1-yl) acetic acid for 2-(5,6-dimethyl-1H-benzo[d]imidazol-1-yl) acetic acid to afford 20 mg of the title compound: MS (m/z) 576.1 [M+H]⁺. ¹H NMR (400 MHz, cdcl₃) δ 9.17 (s, 1H), 8.57 (s, 1H), 7.48 (m, 3H), 7.09 (d, J=8.2 Hz, 2H), 6.60 (t, J=8.8 Hz, 1H), 6.17 (d, J=6.1 Hz, 2H), 5.53 (dd, J=15.1, 7.5 Hz, 1H), 4.72 (s, 2H), 2.83 (d, J=7.2 Hz, 2H), 2.68-2.42 (m, 4H), 1.80 (dd, J=26.2, 5.4 Hz, 4H).

Example 384

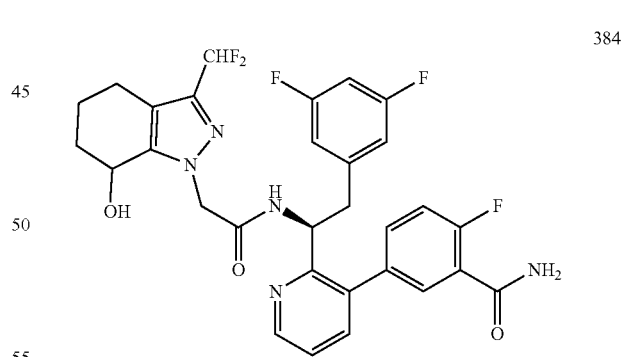

Synthesis of 5-(2-((1S)-1-(2-(3-(difluoromethyl)-7-hydroxy-4,5,6,7-tetrahydro-H-indazol-1-yl)acetamido)-2-(3,5-difluorophenyl)ethyl)pyridin-3-yl)-2-fluorobenzamide (384)

Compound 384 was prepared according to the method presented for the synthesis of Example 325 utilizing Compound 370 to afford 15 mg of the title compound. MS (m/z) 600.20 [M+H]⁺. ¹H NMR (400 MHz, cd₃od) δ 8.70 (d, J=5.0 Hz, 1H), 7.71 (td, J=8.5, 1.6 Hz, 1H), 7.49 (m, 2H), 7.34 (s, 1H), 7.22 (m, 1H), 6.81-6.47 (m, 2H), 6.31 (dd, J=9.5, 7.3 Hz, 2H), 5.47-5.20 (m, 1H), 5.07-4.86 (m, 2H), 4.70 (m, 1H), 3.12-2.95 (m, 2H), 2.82-2.26 (m, 2H), 1.99-1.55 (m, 4H).

Example 385

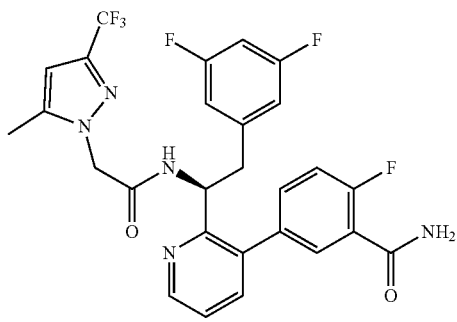

Synthesis of (S)-5-(2-(2-(3,5-difluorophenyl)-1-(2-(5-methyl-3-(trifluoromethyl)-1H-pyrazol-1-yl)acetamido)ethyl)pyridin-3-yl)-2-fluorobenzamide (385)

Compound 385 was prepared according to the method presented in the synthesis of Example 56 utilizing Compound 56A and 5-methyl-3-(trifluoromethyl)-1H-pyrazole to provide 33 mg of the title compound. MS (m/z) 599.90 [M+H]$^+$. $^1$H NMR (400 MHz, cd$_3$od) δ 8.71 (dd, J=4.9, 1.6 Hz, 1H), 7.68 (dd, J=7.8, 1.6 Hz, 1H), 7.54-7.43 (m, 2H), 7.34 (s, 1H), 7.22 (dd, J=10.7, 8.5 Hz, 1H), 6.67 (tt, J=9.2, 2.3 Hz, 1H), 6.43-6.18 (m, 3H), 5.37 (t, J=7.5 Hz, 1H), 4.88 (s, 2H), 3.07 (d, J=7.6 Hz, 2H), 2.20 (s, 3H).

Example 386

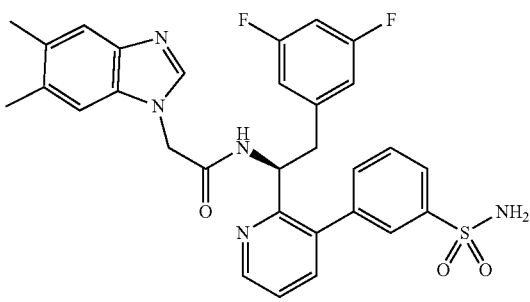

Synthesis of (S)—N-(2-(3,5-difluorophenyl)-1-(3-(3-sulfamoylphenyl)pyridin-2-yl)ethyl)-2-(5,6-dimethyl-1H-benzo[d]imidazol-1-yl)acetamide (386)

Compound 386 was prepared according to the method presented in the synthesis of Example 353 substituting 3-sulfamoylphenylboronic acid for 3-(N-cyclopropylsulfamoyl)phenylboronic acid to provide 10 mg of the title compound. MS (m/z) 616.2 [M+H]$^+$. $^1$H NMR (400 MHz, cd$_3$od) δ 9.23 (s, 1H), 8.77 (d, J=4.8 Hz, 1H), 7.90 (d, J=8.0 Hz, 1H), 7.76-7.51 (m, 4H), 7.49-7.38 (m, 2H), 7.29 (d, J=7.8 Hz, 1H), 6.66 (t, J=9.2 Hz, 1H), 6.36 (d, J=6.5 Hz, 2H), 5.37 (t, J=7.6 Hz, 1H), 5.27 (s, 2H), 3.15 (m, 2H), 2.45 (d, J=3.0 Hz, 6H).

Example 387

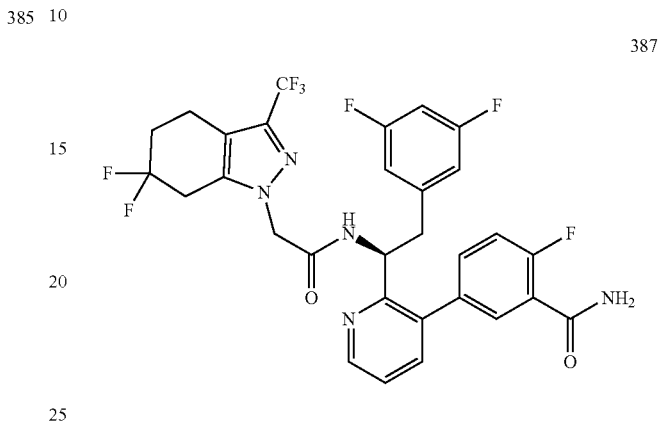

Synthesis of (S)-5-(2-(1-(2-(6,6-difluoro-3-(trifluoromethyl)-4,5,6,7-tetrahydro-1H-indazol-1-yl)acetamido)-2-(3,5-difluorophenyl)ethyl)pyridin-3-yl)-2-fluorobenzamide (387)

Compound 387 was prepared according to the method presented in the synthesis of Example 150 utilizing Compound 322 to provide 2 mg of the title compound. MS (m/z) 638.06 [M+H]$^+$. $^1$H NMR (400 MHz, cd$_3$od) δ 8.70 (dd, J=4.9, 1.6 Hz, 1H), 7.74-7.61 (m, 1H), 7.46 (m, 2H), 7.35 (s, 1H), 7.22 (m, 1H), 6.72-6.56 (m, 1H), 6.34 (d, J=6.2 Hz, 2H), 5.36 (t, J=7.6 Hz, 1H), 4.84 (s, 2H), 3.15-2.96 (m, 4H), 2.75 (t, J=6.5 Hz, 2H), 2.20 (tt, J=13.4, 6.5 Hz, 2H).

Example 388

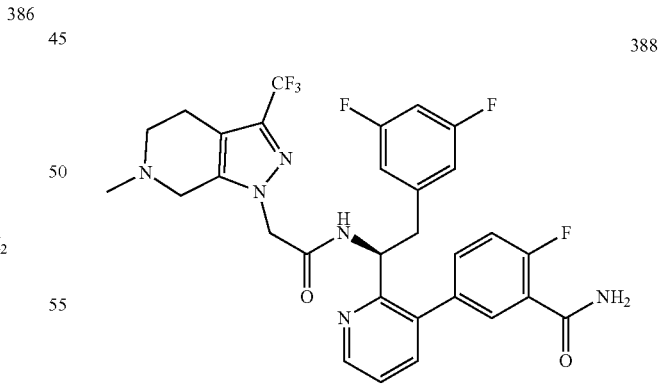

Synthesis of (S)-5-(2-(2-(3,5-difluorophenyl)-1-(2-(6-methyl-3-(trifluoromethyl)-4,5,6,7-tetrahydro-1H-pyrazolo[3,4-c]pyridin-1-yl)acetamido)ethyl)pyridin-3-yl)-2-fluorobenzamide (388)

Compound 388 was prepared according to the method presented in the synthesis of Example 324 utilizing Compound 352 to provide 22 mg of the title compound. MS (m/z) 617.37 [M+H]+. 1H NMR (400 MHz, cd3od) δ 8.71 (dd, J=4.8, 1.3 Hz, 1H), 7.61 (m, 2H), 7.49-7.33 (m, 1H), 7.30-6.98 (m, 2H), 6.77-6.52 (m, 1H), 6.31 (d, J=6.2 Hz, 2H), 5.31 (m, 1H), 5.00-4.89 (m, 2H), 4.48 (bs, 2H), 3.58 (bs, 2H), 3.23-2.93 (m, 7H).

Example 389

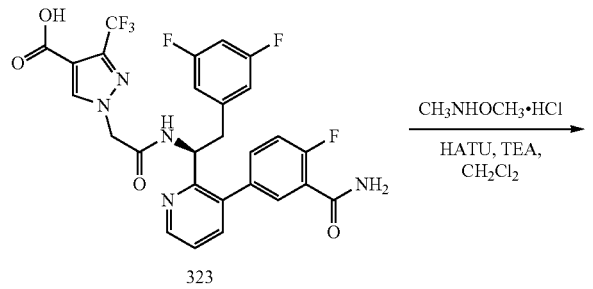

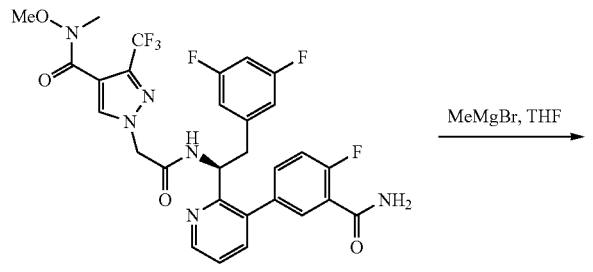

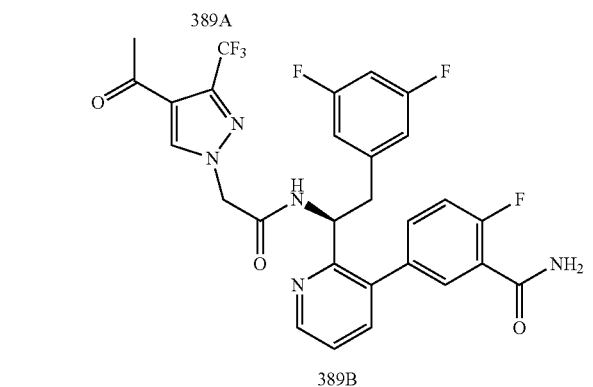

Synthesis of (S)-1-(2-(1-(3-(3-carbamoyl-4-fluoro-phenyl)pyridin-2-yl)-2-(3,5-difluorophenyl)ethyl-amino)-2-oxoethyl)-N-methoxy-N-methyl-3-(trifluoromethyl)-1H-pyrazole-4-carboxamide (389A)

To a mixture of Compound 323 (222 mg, 0.38 mmol) and N,O-dimethylhydroxylamine hydrochloride (73 mg, 0.75 mmol) were added triethylamine (159 µL, 1.1 mmol) and HATU (217 mg, 0.57 mmol). The reaction was allowed to stir at ambient temperature for 1 hour, and then partitioned between CH2Cl2 and 5% LiCl aqueous solution. The organic layer was separated, washed with brine, dried over MgSO4, filtered and concentrated. The residue was dissolved in CH2Cl2 and to it was added hexanes. The resulting precipitate was collected by vacuum filtration and then high vacuum dried to afford 220 mg of the title compound. MS (m/z) 635.36 [M+H]+.

Synthesis of (S)-5-(2-(1-(2-(4-acetyl-3-(trifluorom-ethyl)-1H-pyrazol-1-yl)acetamido)-2-(3,5-difluoro-phenyl)ethyl)pyridin-3-yl)-2-fluorobenzamide (389B)

Compound 389 A (120 mg, 0.19 mmol) was dissolved in 5 mL of THF and to it was added MeMgBr (3.0 M in diethyl ether, 0.67 mL, 2 mmol) and the reaction mixture was stirred at ambient temperature for 20 min. It was quenched with ice and 1 N HCl and extracted with EtOAc. The organic layer was separated, washed with brine, dried over MgSO4, filtered and concentrated. The residue was purified by reverse phase HPLC eluting with acetonitrile/water (with 0.1% TFA) to afford 25 mg of the title compound. MS (m/z) 590.09 [M+H]+. 1H NMR (400 MHz, cdcl3) δ 10.00 (d, J=7.3 Hz, 1H), 8.91-8.67 (m, 1H), 8.10-7.96 (m, 2H), 7.80 (m, 2H), 7.61 (d, J=6.1 Hz, 1H), 7.31 (dd, J=11.2, 8.6 Hz, 1H), 6.90 (m, 1H), 6.61 (m, 2H), 6.21 (d, J=5.7 Hz, 2H), 5.47 (dd, J=16.0, 7.4 Hz, 1H), 4.91 (q, J=16.2 Hz, 2H), 3.20 (dd, J=13.6, 7.1 Hz, 1H), 3.03 (dd, J=13.5, 9.0 Hz, 1H), 2.45 (s, 3H).

Example 390

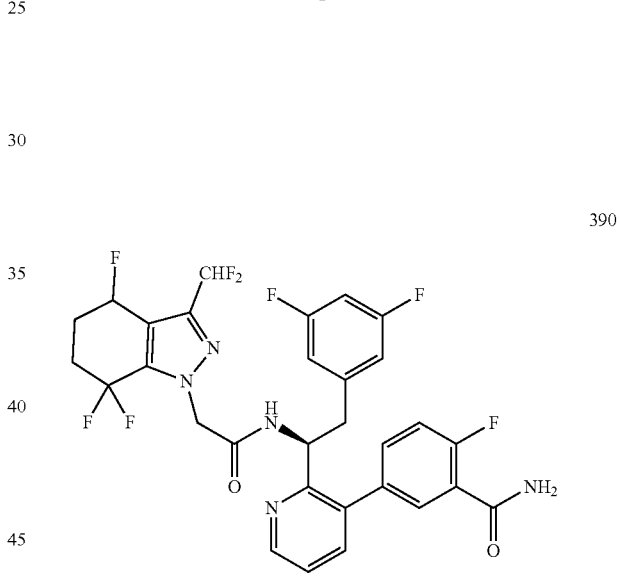

Synthesis of 5-(2-(1-(2-(3-(difluoromethyl)-4,7,7-trifluoro-4,5,6,7-tetrahydro-1H-indazol-1-yl)acet-amido)-2-(3,5-difluorophenyl)ethyl)pyridin-3-yl)-2-fluorobenzamide (390)

Compound 390 was prepared according to the method presented in the synthesis of Example 150 utilizing Compound 334 to provide 17 mg of the title compound. MS (m/z) 638.19 [M+H]+. 1H NMR (400 MHz, cd3od) δ 8.71 (d, J=4.9 Hz, 1H), 7.65 (d, J=7.8 Hz, 1H), 7.51-7.41 (m, 1H), 7.39-7.26 (m, 2H), 7.21 (dd, J=10.7, 8.6 Hz, 1H), 6.98-6.55 (m, 2H), 6.31 (d, J=6.7 Hz, 2H), 5.72 (d, 1H), 5.35 (t, J=6.7 Hz, 1H), 5.13-4.97 (m, 2H), 3.07 (m, 2H), 2.68-2.05 (m, 4H).

Example 391

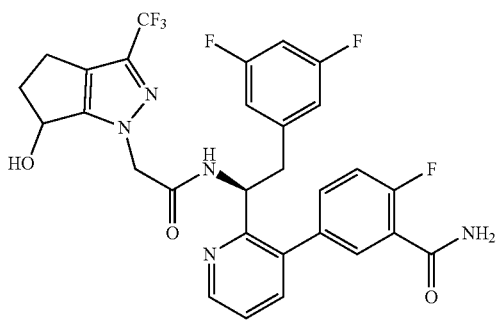

Synthesis of 5-(2-((1S)-2-(3,5-difluorophenyl)-1-(2-(6-hydroxy-3-(trifluoromethyl)-5,6-dihydrocyclopenta[c]pyrazol-1(4H)-yl)acetamido)ethyl)pyridin-3-yl)-2-fluorobenzamide (391)

Compound 391 was prepared according to the method presented for the synthesis of Example 325 utilizing Compound 281C to afford 15 mg of the title compound: MS (m/z) 604.36 [M+H]$^+$. $^1$H NMR (400 MHz, cd$_3$od) δ 8.71 (dt, J=4.9, 1.6 Hz, 1H), 7.70 (td, J=8.5, 1.6 Hz, 1H), 7.48 (m, 2H), 7.33 (bs, 1H), 7.22 (m, 1H), 6.66 (td, J=9.3, 7.0 Hz, 1H), 6.30 (dd, J=8.3, 6.3 Hz, 2H), 5.36 (dd, J=15.6, 8.1 Hz, 1H), 5.07 (dt, J=7.2, 3.5 Hz, 1H), 4.95-4.76 (m, 2H), 3.15-2.98 (m, 2H), 2.97-2.70 (m, 2H), 2.68-2.46 (m, 1H), 2.36 (m, 1H).

Example 392

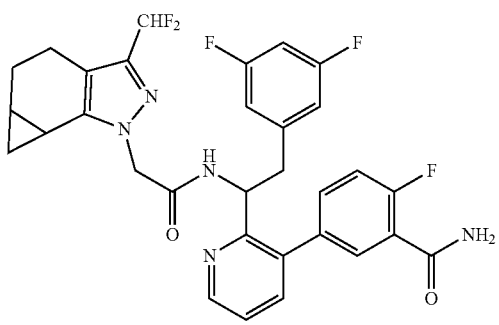

Synthesis of 5-(2-(1-(2-(3-(difluoromethyl)-5,5a,6,6a-tetrahydrocyclopropa[g]indazol-1(4H)-yl)acetamido)-2-(3,5-difluorophenyl)ethyl)pyridin-3-yl)-2-fluorobenzamide (392)

Compound 392 was prepared according to the method presented in the synthesis of Example 54 utilizing Compound 54B and 2-(3-(difluoromethyl)-5,5a,6,6a-tetrahydrocyclopropa[g]indazol-1(4H)-yl)acetic acid (Compound 299C) to provide 22 mg of the title compound. MS (m/z) 596.43 [M+H]$^+$. $^1$H NMR (400 MHz, cd$_3$od) δ 8.82-8.57 (m, 1H), 7.68 (dd, J=8.9, 3.8 Hz, 1H), 7.54-7.41 (m, 2H), 7.34 (bs, 1H), 7.30-7.13 (m, 1H), 6.83-6.42 (m, 2H), 6.33 (m, 2H), 5.37 (dd, J=13.4, 7.6 Hz, 1H), 4.97-4.73 (m, 2H), 3.14-2.98 (m, 2H), 2.70 (d, J=14.7 Hz, 1H), 2.24-1.93 (m, 2H), 1.94-1.48 (m, 3H), 0.93 (m, 1H), 0.64 (m, 1H).

Example 393

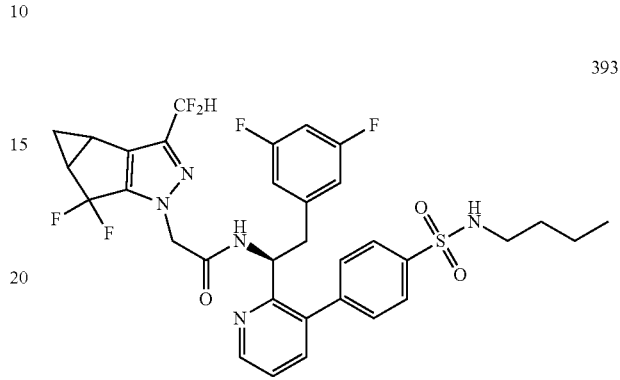

Synthesis of (S)—N-(1-(3-(4-(N-butylsulfamoyl)phenyl)-pyridin-2-yl)-2-(3,5-difluorophenyl)ethyl)-2-(3-(difluoromethyl)-5,6-dihydro-4,5-(methano)-6,6-difluoro-cyclopenta[c]pyrazol-1(4H)-yl)acetamide (393)

Prepared 2.5 mg of the title compound by a method analogous to 68B using 68A and 4-(N-butylsulfamoyl)phenylboronic acid. MS (m/z) 692 [M+H]$^+$.

Example 394

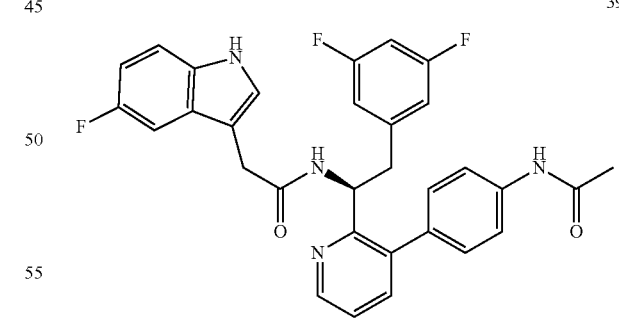

Synthesis of ((S)—N-(1-(3-(4-acetamidophenyl)pyridin-2-yl)-2-(3,5-difluorophenyl)ethyl)-2-(5-fluoro-1H-indol-3-yl)acetamide (394)

Prepared 37.1 mg of the title compound by a method analogous to 55F using 4-(acetamidophenyl)boronic acid and 55E. MS (m/z) 543 [M+H]$^+$.

Example 395

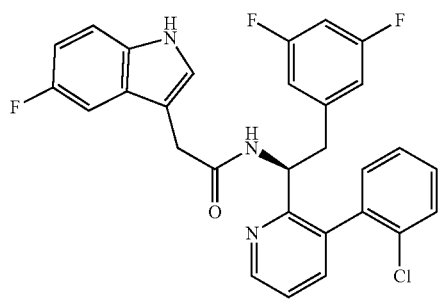

Synthesis of (S)—N-(1-(3-(2-chlorophenyl)pyridin-2-yl)-2-(3,5-difluorophenyl)ethyl)-2-(5-fluoro-1H-indol-3-yl)acetamide (395)

Prepared 37.1 mg of the title compound by a method analogous to 55F using 2-chlorophenylboronic acid and 55E. MS (m/z) 520 [M+H]⁺.

Example 396

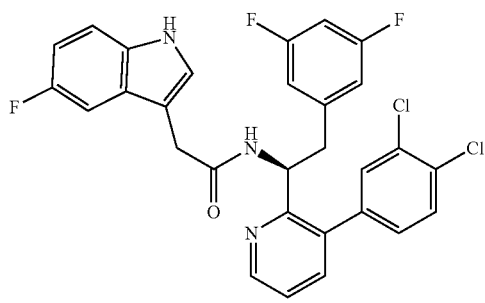

Synthesis of (S)—N-(1-(3-(3,4-dichlorophenyl)pyridin-2-yl)-2-(3,5-difluorophenyl)ethyl)-2-(5-fluoro-1H-indol-3-yl)acetamide (396)

Prepared 15.4 mg of the title compound by a method analogous to 55F using 3,4-dichloro-phenylboronic acid and 55E. MS (m/z) 554 [M+H]⁺.

Example 397

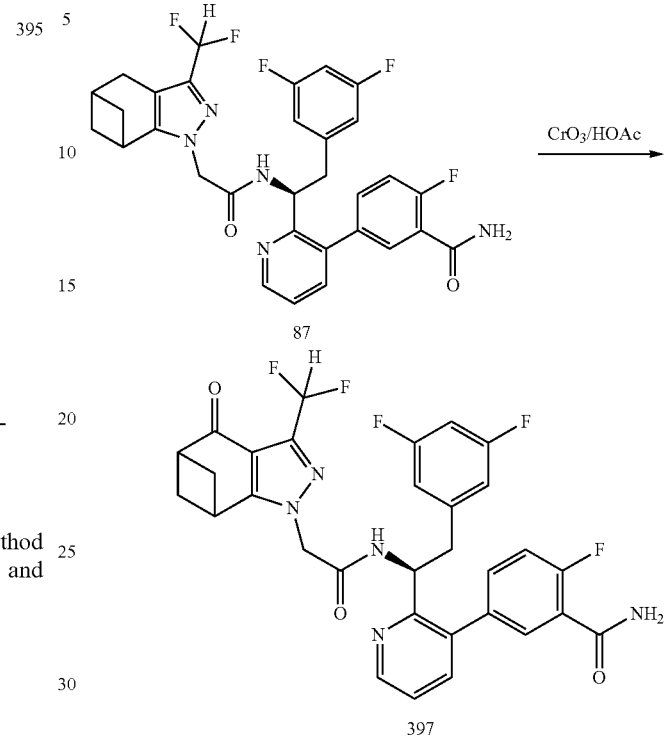

Synthesis of (S)-5-(2-(2-(3,5-difluorophenyl)-1-(2-(4,5,6,7-tetrahydro-3-difluoromethyl-4-oxo-5,7-(methano)indazol-1-yl)acetamido)ethyl)pyridin-3-yl)-2-fluorobenzamide (397)

To a solution of Compound 87 (20.7 mg, 0.029 mmol) in acetic acid (1 ml) was added CrO₃ (8.7 mg, 0.087 mmol). The reaction mixture was stirred at room temperature for 7 days and then filtered. The filtrate was purified by RP HPLC using a C18 column with a gradient of 0.1% TFA-acetonitrile/0.1%/H₂O to give 10.3 mg of the title compound. MS (m/z) 610 [M+H]⁺.

Example 398

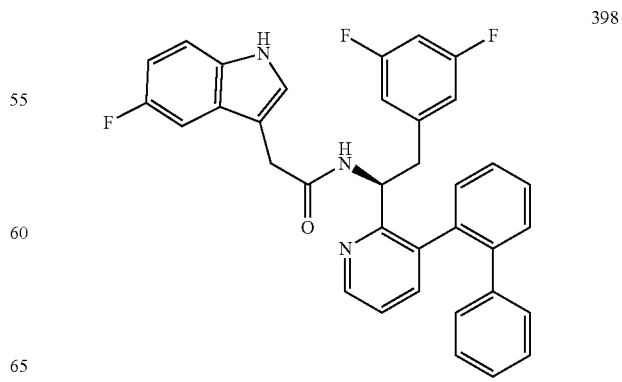

Synthesis of (S)—N-(1-(3-(biphenyl-2-yl)pyridin-2-yl)-2-(3,5-difluorophenyl)ethyl)-2-(5-fluoro-1H-indol-3-yl)acetamide (398)

Prepared 36.3 mg of the title compound by a method analogous to 55F using 2-phenyl-phenylboronic acid and 55E. MS (m/z) 562 [M+H]$^+$.

Example 399

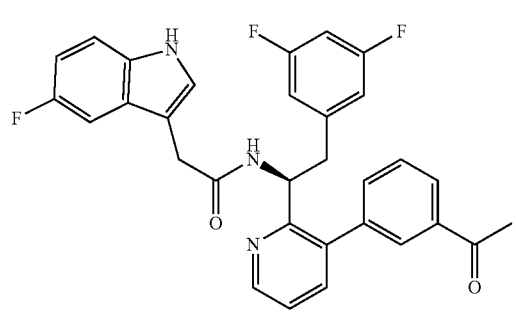

399

Synthesis of ((S)—N-(2-(3,5-difluorophenyl)-1-(6'-fluoro-5'-methyl-3,3'-bipyridin-2-yl)ethyl)-2-(5-fluoro-1H-indol-3-yl)acetamide (399)

Prepared 31.9 mg of the title compound by analogous method to 55F using 3-acetylphenylboronic acid and 55E. MS (m/z) 519 [M+H]$^+$.

Example 400

400

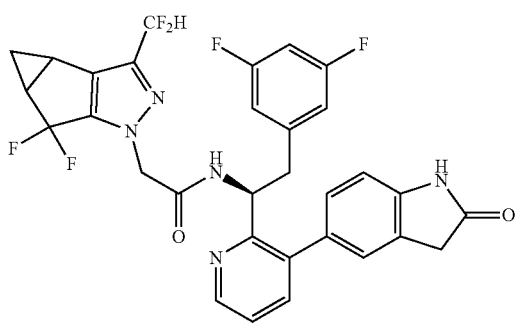

Synthesis of (S)—N-(1-(3-(oxindole-5-yl)-pyridin-2-yl)-2-(3,5-difluorophenyl)ethyl)-2-(3-(difluoromethyl)-5,6-dihydro-4,5-(methano)-6,6-difluoro-cyclopenta[e]pyrazol-1(4H)-yl)acetamide (400)

Prepared 4.8 mg of the title compound by a method analogous to 68B using 68A and oxindole-5-boronic acid, pinacol ester. MS (m/z) 612 [M+H]$^+$.

Example 401

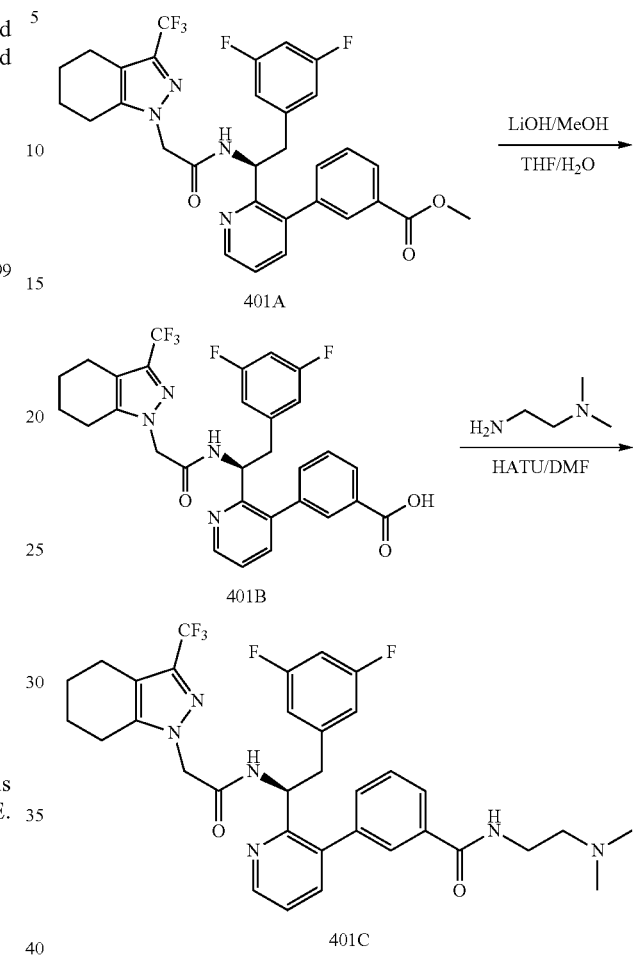

Synthesis of (S)-methyl 3-(2-(2-(3,5-difluorophenyl)-1-(2-(3-(trifluoromethyl)-4,5,6,7-tetrahydro-1H-indazol-1-yl)acetamido)ethyl)pyridin-3-yl)benzoate (401A)

Prepared 480 mg of the title compound by a method analogous to 57B using 3-carbomethoxy-phenylboronic acid and 57A. MS (m/z) 599 [M+H]$^+$.

Synthesis of (S)-3-(2-(2-(3,5-difluorophenyl)-1-(2-(3-(trifluoromethyl)-4,5,6,7-tetrahydro-1H-indazol-1-yl)acetamido)ethyl)pyridin-3-yl)benzoic acid (401B)

Dissolved 410A (480 mg, 0.803 mmol) in THF (4 ml) and MeOH (2 ml). Added 2.5N aq LiOH and stirred for 45 min. at room temperature. The reaction was acidified to pH=6 with 20 mM KH$_2$PO$_4$. The mixture was extracted 3× EtOAc. The combined organics were washed with brine, dried over MgSO$_4$, filtered and concentrated. The residue was dried under reduced pressure to give 348 mg of the title compound. MS (m/z) 585 [M+H]$^+$.

581

Synthesis of (S)-3-(2-(2-(3,5-difluorophenyl)-1-(2-(3-(trifluoromethyl)-4,5,6,7-tetrahydro-1H-indazol-1-yl)acetamido)ethyl)pyridin-3-yl)-N-(2-(dimethylamino)ethyl)benzamide (401C)

Dissolved 401B (30 mg, 0.051 mmol) in 1 ml of DMF. Added N,N-dimethylaminoethylamine (16.8 uL, 0.153 mmol) followed by HATU (21 mg, 0.056 mmol). Stirred the reaction for 1 hr at room temperature. Filtered reaction and purified filtrate by RP HPLC using a C18 column with a gradient of 0.1%/H$_2$O, 0.1% TFA-acetonitrile to give 24.1 mg of the title compound. $^1$H NMR (400 MHz, CD$_3$OD) δ 8.71 (d, 1H), 7.89 (d, 1H), 7.72 (s, 1H), 7.62 (d, 1H), 7.52 (t, 1H), 7.40 (dd, 1H), 7.23 (d, 1H), 6.68 (t, 1H), 6.26 (d, 2H), 5.52 (t, 1H), 3.66 (d, 2H), 3.01 (dd, 2H), 2.89 (d, 5H), 2.55 (s, 2H), 2.42 (d, 2H), 1.76 (s, 4H). MS (m/z) 655 [M+H]$^+$.

Example 402

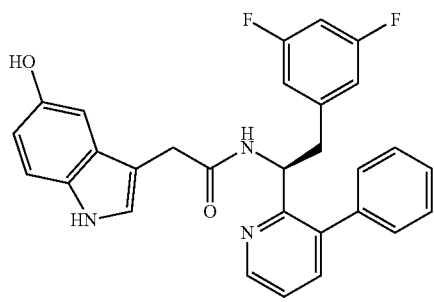

Synthesis of (S)—N-(2-(3,5-difluorophenyl)-1-(3-phenylpyridin-2-yl)ethyl)-2-(5-hydroxy-1H-indol-3-yl)acetamide (402)

Prepared 44 mg of the title compound by a method analogous to 113 using phenylboronic acid $^1$H NMR (d-DMSO, 400 MHz) δ 10.47 (1H. s), 8.615 (1H, dd), 8.40 (1H, d), 7.53 (1H, dd), 7.35 (3H, m), 7.15 (2H, m), 7.05 (1H, d), 6.91 (2H, mm), 6.76 (1H, d), 6.53 (1H, dd), 6.31 (2H, d), 5.22 (2H, q), 4.34 (1H, b), 3.39 (1H, s), 2.87 (2H, d). MS (m/z) 484 [M+H]$^+$.

Example 403

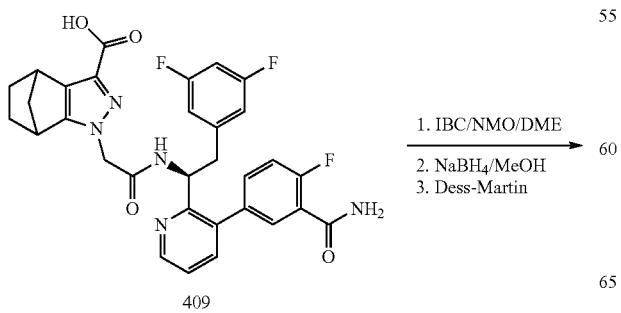

582

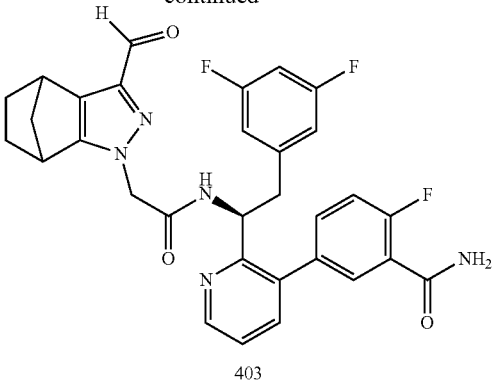

Synthesis of (S)-5-(2-(2-(3,5-difluorophenyl)-1-(2-(4,5,6,7-tetrahydro-3-formyl-4,7-(methano)indazol-1-yl)acetamido)ethyl)pyridin-3-yl)-2-fluorobenzamide (403)

To a 0° C. solution of Compound 409 (200 mg, 0.34 mmol) in DME (680 ul) was added N-methylmorpholine (37 ul, 0.34 mmol) and isobutylchloroformate (45 ul, 0.34 mmol). The reaction was stirred at 0° C. for 5 min. then filtered to remove the precipitate. Washed the precipitate 3×DME (2 ml total). To the combined filtrates was added NaBH$_4$ (19.3 mg, 0.51 mmol) in H$_2$O. The reaction was stirred 5 min. at room temperature. An additional 5.8 mg of NaBH$_4$ was added to drive the reaction to completion. The reaction mixture was partitioned between EtOAc and H$_2$O. Extracted the aqueous layer 2× EtOAc. The combined organics were washed with brine, dried over MgSO$_4$, filtered and concentrated. The residue on purified on SiO$_2$ using MeOH/CH$_2$Cl$_2$ to give 108 mg of (S)-5-(2-(2-(3,5-difluorophenyl)-1-(2-(4,5,6,7-tetrahydro-3-hydroxymethyl-4,7-(methano)indazol-1-yl)acetamido)ethyl)pyridin-3-yl)-2-fluorobenzamide. This material was dissolved in CH$_2$Cl$_2$ and treated with Dess-Martin periodinane (85.8 mg, 0.20 mmol) at room temperature for 1 hr. The reaction mixture was filtered and concentrated. The residue was re-dissolved in EtOAc and extracted 2× H$_2$O and 1× brine, dried over MgSO4, filtered and concentrated. Purified 7 mg of crude by RP HPLC using a C18 column with a gradient of 0.1%/H$_2$O, 0.1% TFA-acetonitrile to give 3.2 mg of the title compound. MS (m/z) 574 [M+H]$^+$. The 100 mg remaining was used crude.

Example 404

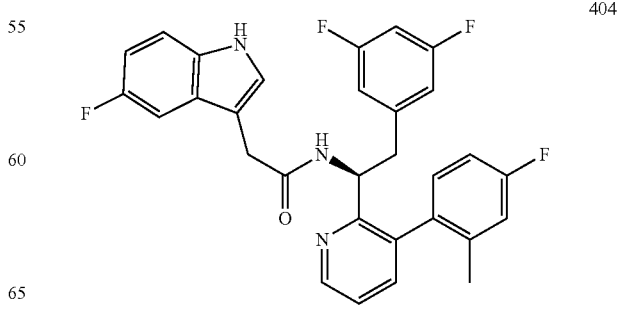

Synthesis of (S)—N-(2-(3,5-difluorophenyl)-1-(3-(4-fluoro-2-methylphenyl)pyridin-2-yl)ethyl)-2-(5-fluoro-1H-indol-3-yl)acetamide (404)

Prepared 2 mg the title compound by a method analogous to 55F using (4-fluoro-2-methylphenyl)-boronic acid (15.3 mg, 0.10 mmol) and 55E (40.7 mg, 0.83 mmol). MS (m/z) 518 [M+H]$^+$.

Example 405

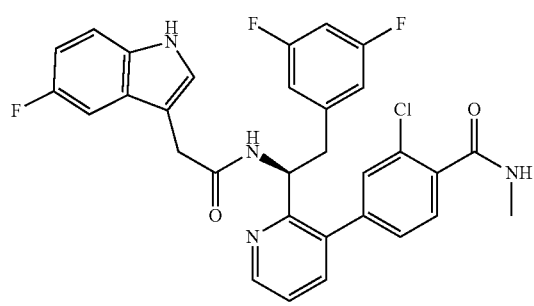

Synthesis of (S)-2-chloro-4-(2-(2-(3,5-difluorophenyl)-1-(2-(5-fluoro-1H-indol-3-yl)acetamido)ethyl)pyridin-3-yl)-N-methylbenzamide (405)

Prepared 8 mg of the title compound by a method analogous to 55F using 3-chloro-4-(methylcarbamoyl)phenylboronic acid and 55E. MS (m/z) 578 [M+H]$^+$.

Example 406

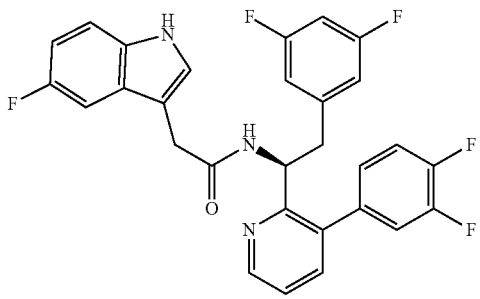

Synthesis of (S)—N-(2-(3,5-difluorophenyl)-1-(3-(3,4-difluorophenyl)pyridin-2-yl)ethyl)-2-(5-fluoro-1H-indol-3-yl)acetamide (406)

Prepared 28.1 mg of the title compound by a method analogous to 55F using 3,4-difluorophenylboronic acid and 55E. MS (m/z) 522 [M+H]$^+$.

Example 407

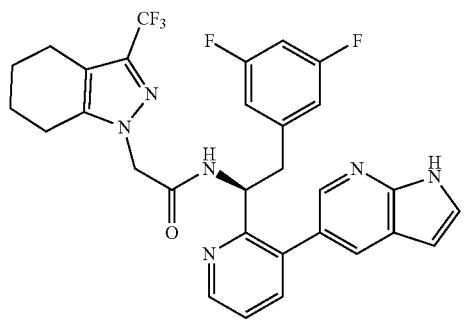

Synthesis of (S)—N-(1-(3-(1H-pyrrolo[2,3-b]pyridin-5-yl)pyridin-2-yl)-2-(3,5-difluorophenyl)ethyl)-2-(3-(trifluoromethyl)-4,5,6,7-tetrahydro-1H-indazol-1-yl)acetamide (407)

Prepared 1.4 mg of the title compound by a method analogous to 57B using 57A and 1H-pyrrolo[2,3-b]pyridin-5-ylboronic acid. MS (m/z) 583 [M+H]$^+$.

Example 408

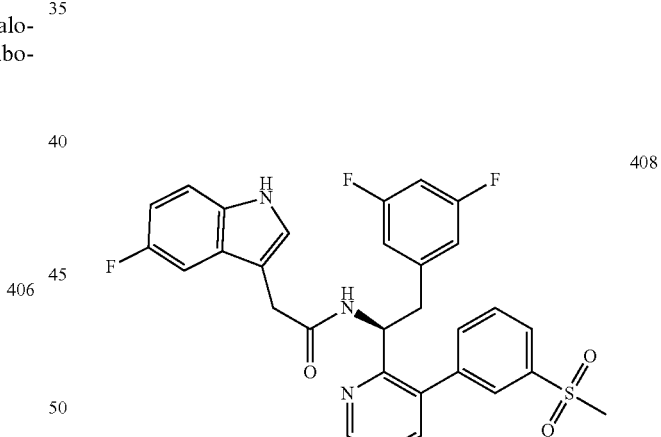

Synthesis of (S)—N-(2-(3,5-difluorophenyl)-1-(3-(4-(methylsulfonyl)phenyl)pyridin-2-yl)ethyl)-2-(5-fluoro-1H-indol-3-yl)acetamide (408)

Prepared 24 mg of the title compound by analogous method to 55F using 3-(methylsulfonyl)boronic acid and 55E. MS (m/z) 564 [M+H]$^+$.

Example 409

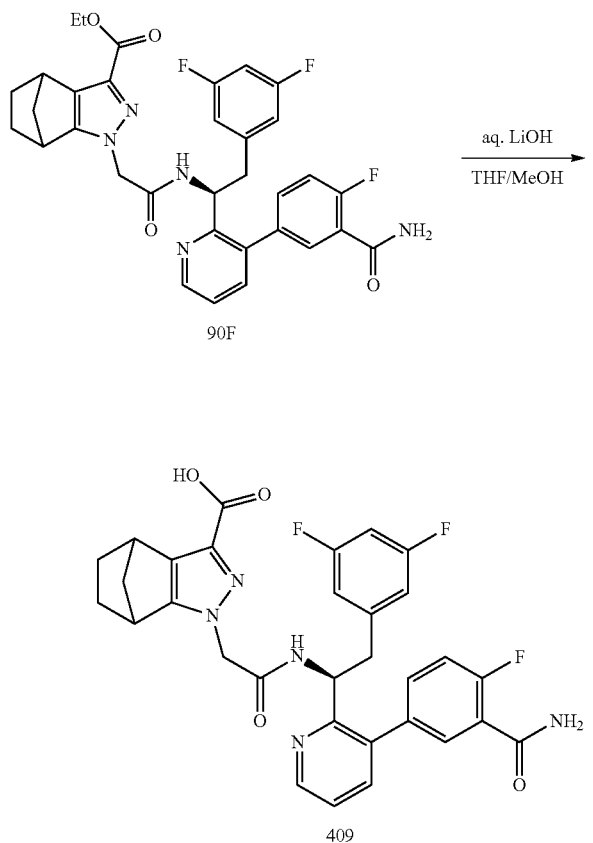

Synthesis of (S)-5-(2-(2-(3,5-difluorophenyl)-1-(2-(4,5,6,7-tetrahydro-3-carboxy-4,7-(methano)indazol-1-yl)acetamido)ethyl)pyridin-3-yl)-2-fluorobenzamide (409)

Prepared 209 mg of the title compound by a method analogous to 74C using compound 90F MS (m/z) 590 [M+H]+.

Example 410

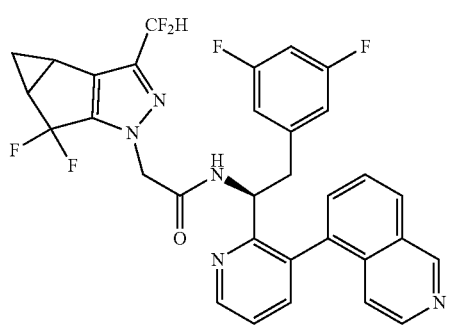

Synthesis of (S)—N-(1-(3-(quinole-5-yl)-pyridin-2-yl)-2-(3,5-difluorophenyl)ethyl)-2-(3-(difluoromethyl)-5,6-dihydro-4,5-(methano)-6,6-difluoro-cyclopenta[c]pyrazol-1 (4H)-yl)acetamide (410)

Prepared 19.8 mg of the title compound by a method analogous to 68B using 68A and quinoline-5-boronic acid. MS (m/z) 608 [M+H]+.

Example 411

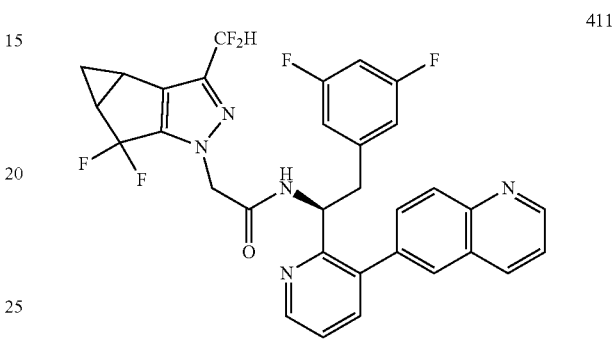

Synthesis of (S)—N-(1-(3-(quinoline-6-yl)-pyridin-2-yl)-2-(3,5-difluorophenyl)ethyl)-2-(3-(difluoromethyl)-5,6-dihydro-4,5-(methano)-6,6-difluoro-cyclopenta[c]pyrazol-1(4H)-yl)acetamide (411)

Prepared 6.1 mg of the title compound by a method analogous to 68B using 68A and quinoline-6-boronic acid. MS (m/z) 608 [M+H]+.

Example 412

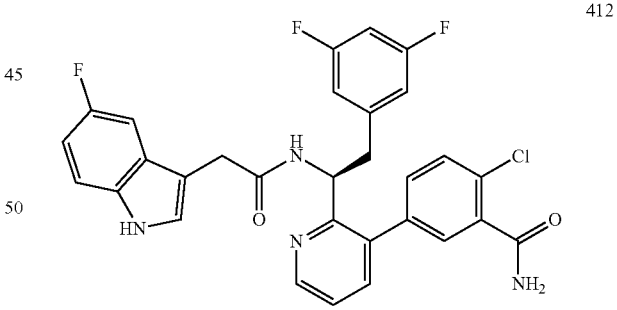

Synthesis of (S)-2-chloro-5-(2-(2-(3,5-difluorophenyl)-1-(2-(5-fluoro-1H-indol-3-yl)acetamido)ethyl)pyridin-3-yl)benzamide (412)

Prepared 37 mg of the title compound by a method analogous to 55F using 4-chloro-3-carbamoylphenyl boronic acid. ¹H NMR (400 MHz, d6-DMSO) δ 10.87 (s, 1H), 8.79-8.55 (m, 2H), 7.81 (s, 1H), 7.56 (dd, 2H), 7.46-7.31 (m, 3H), 7.28-7.00 (m, 4H), 6.96-6.74 (m, 3H), 6.51 (d, 2H), 5.14 (q, 1H), 3.42 (s, 2H), 2.98 (d, 2H). MS (m/z) 563 [M+H]+.

Example 413

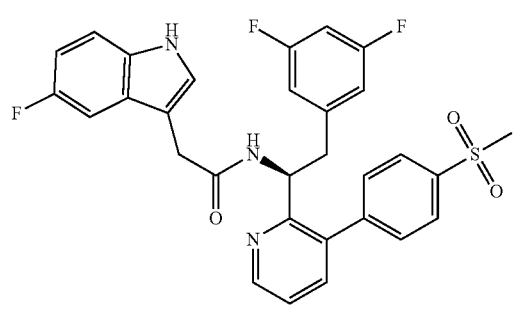

Synthesis of (S)—N-(2-(3,5-difluorophenyl)-1-(3-(4-(methylsulfonyl)phenyl)pyridin-2-yl)ethyl)-2-(5-fluoro-1H-indol-3-yl)acetamide (413)

Prepared 16.1 mg of the title compound by a method analogous to 55F using 4-(methylsulfonyl)boronic acid and 55E. MS (m/z) 564 [M+H]+.

Example 414

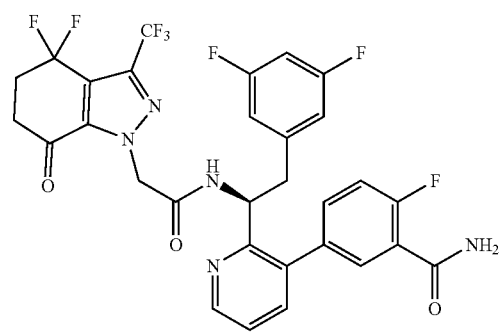 [SMILES: NC(=O)c1cc(-c2cccnc2[C@H](Cc2cc(F)cc(F)c2)NC(=O)Cn2nc(C(F)(F)F)c3c2C(=O)CCC3(F)F)ccc1F]

Synthesis of (S)-5-(2-(1-(2-(3-(difluoromethyl)-4,4-difluoro-7-oxo-4,5,6,7-tetrahydro-1H-indazol-1-yl)acetamido)-2-(3,5-difluorophenyl)ethyl)pyridin-3-yl)-2-fluorobenzamide (414)

Prepared 6 mg of the title compound by a method analogous to 397 using compound 102D. MS (m/z) 652.4 [M+H]+.

Example 415

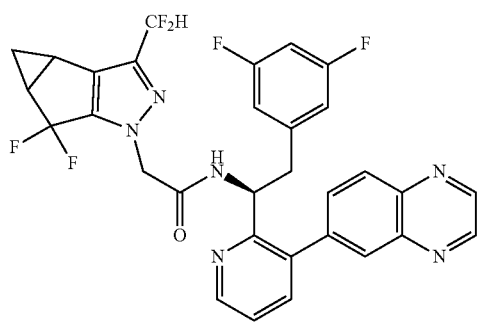

Synthesis of (S)—N-(1-(3-(quinoxalin-6-yl)-pyridin-2-yl)-2-(3,5-difluorophenyl)ethyl)-2-(3-(difluoromethyl)-5,6-dihydro-4,5-(methano)-6,6-difluoro-cyclopenta[c]pyrazol-1(4H)-yl)acetamide (415)

Prepared 5.1 mg of the title compound by a method analogous to 68B using 68A and 6-(4,4,5,5-Tetramethyl-1,3,2-dioxaborolan-2-yl)quinoxaline. MS (m/z) 609 [M+H]+.

Example 416

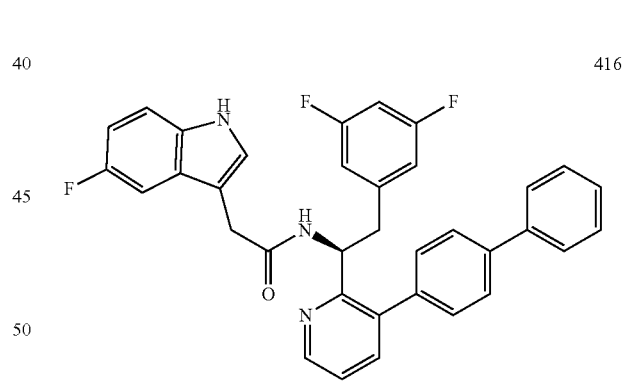

Synthesis of (S)—N-(1-(3-(biphenyl-4-yl)pyridin-2-yl)-2-(3,5-difluorophenyl)ethyl)-2-(5-fluoro-1H-indol-3-yl)acetamide (416)

Prepared 27 mg of the title compound by a method analogous to 55F using 4-phenyl-phenylboronic acid and 55E. MS (m/z) 562 [M+H]+.

Example 417

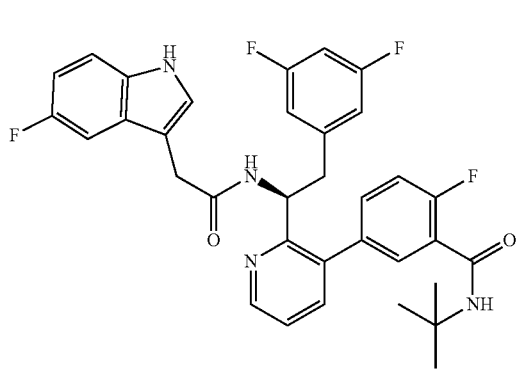

Synthesis of (S)—N-tert-butyl-5-(2-(2-(3,5-difluorophenyl)-1-(2-(5-fluoro-1H-indol-3-yl)acetamido)ethyl)pyridin-3-yl)-2-fluorobenzamide (417)

Prepared 34.9 mg of the title compound by a method analogous to 55F using 3-(tert-butylcarbamoyl)-4-fluorophenylboronic acid and 55E. MS (m/z) 603 [M+H]+.

Example 418

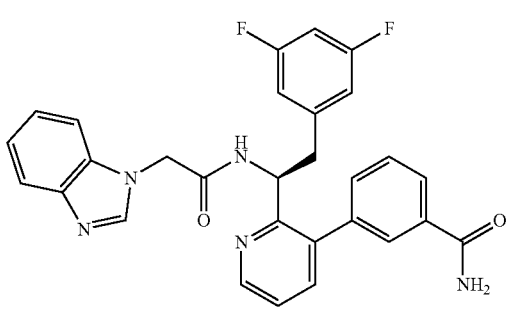

Synthesis of (S)-3-(2-(1-(2-(1H-benzo[d]imidazol-1-yl)acetamido)-2-(3,5-difluorophenyl)ethyl)pyridin-3-yl)benzamide (418)

Prepared 30 mg of the title compound by a method analogous to 50D using benzimidazole-1-acetic acid and 50C. ¹H NMR (400 MHz, dmso) δ 9.28 (d, 1H), 9.19 (s, 1H), 8.73 (dd, 1H), 8.03-7.81 (m, 2H), 7.80-7.59 (m, 3H), 7.53-7.29 (m, 6H), 6.94 (t, 1H), 6.57 (d, 2H), 5.24-5.07 (m, 3H), 3.05 (ddd, 2H). MS (m/z) 512 [M+H]+.

Example 419

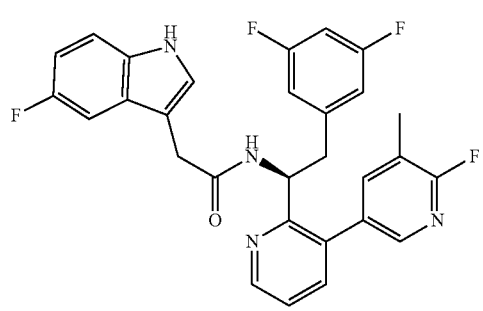

Synthesis of ((S)—N-(2-(3,5-difluorophenyl)-1-(6'-fluoro-5'-methyl-3,3'-bipyridin-2-yl)ethyl)-2-(5-fluoro-1H-indol-3-yl)acetamide (419)

Prepared 26.7 mg of the title compound by a method analogous to 55F using 2-Fluoro-3-methylpyridine-5-boronic acid and 55E. MS (m/z) 519 [M+H]+.

Example 420

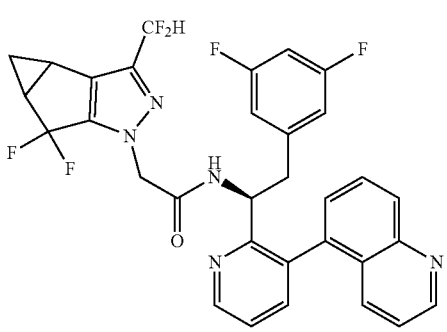

Synthesis of (S)—N-(1-(3-(isoquinole-5-yl)-pyridin-2-yl)-2-(3,5-difluorophenyl)ethyl)-2-(3-(difluoromethyl)-5,6-dihydro-4,5-(methano)-6,6-difluoro-cyclopenta[c]pyrazol-1(4H)-yl)acetamide (420)

Prepared 17.4 mg of the title compound by a method analogous to 68B using 68A and isoquinoline-5-boronic acid. MS (m/z) 608 [M+H]+.

Example 421

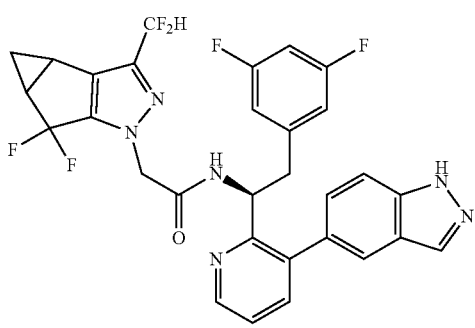

Synthesis of (S)—N-(1-(3-(indozol-5-yl)-pyridin-2-yl)-2-(3,5-difluorophenyl)ethyl)-2-(3-(difluoromethyl)-5,6-dihydro-4,5-(methano)-6,6-difluoro-cyclopenta[c]pyrazol-1 (4H)-yl)acetamide (421)

Prepared 3 mg of the title compound by a method analogous to 68B using 68A and indazole-5-boronic acid. MS (m/z) 597 [M+H]$^+$.

Example 422

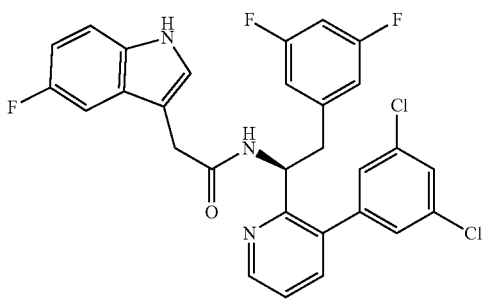

Synthesis of ((S)—N-(1-(3-(3,5-dichlorophenyl)pyridin-2-yl)-2-(3,5-difluorophenyl)ethyl)-2-(5-fluoro-1H-indol-3-yl)acetamide (422)

Prepared 25.2 mg of the title compound by a method analogous to 55F using 3,5-dichloro-phenylboronic acid and 55E. MS (m/z) 554 [M+H]$^+$.

Example 423

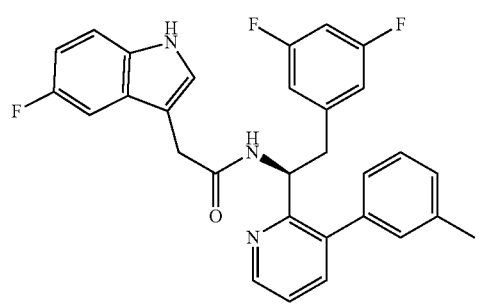

Synthesis of (S)—N-(2-(3,5-difluorophenyl)-1-(3-p-tolylpyridin-2-yl)ethyl)-2-(5-fluoro-1H-indol-3-yl)acetamide (423)

Prepared 34 mg of the title compound by a method analogous to 55F using 4-methylphenylboronic acid and 55E. MS (m/z) 500 [M+H]$^+$.

Example 424

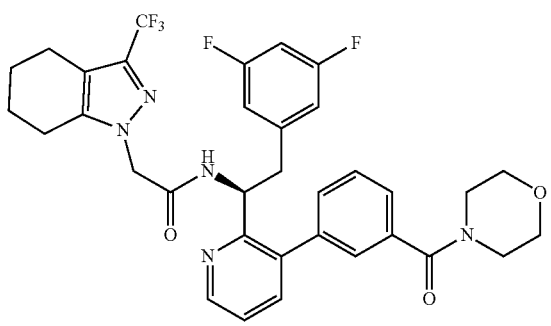

Synthesis of (S)—N-(2-(3,5-difluorophenyl)-1-(3-(3-(morpholine-4-carbonyl)phenyl)pyridin-2-yl)ethyl)-2-(3-(trifluoromethyl)-4,5,6,7-tetrahydro-1H-indazol-1-yl)acetamide (424)

Prepared 20.9 mg of the title compound by a method analogous to 401C using 401B and morpholine. $^1$H NMR (400 MHz, CD$_3$OD) δ 8.71 (d, 1H), 7.89 (d, 1H), 7.72 (s, 1H), 7.62 (d, 1H), 7.52 (t, 1H), 7.40 (dd, 1H), 7.23 (d, 1H), 6.68 (t, 1H), 6.26 (d, 2H), 5.52 (t, 1H), 3.66 (d, 2H), 3.01 (dd, 2H), 2.89 (d, 5H), 2.55 (s, 2H), 2.42 (d, 2H), 1.76 (s, 4H). MS (m/z) 654 [M+H]$^+$.

Example 435

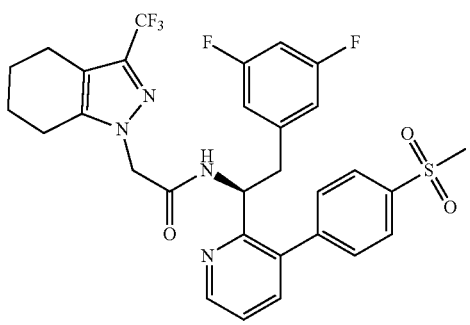

Synthesis of (S)—N-(2-(3,5-difluorophenyl)-1-(3-(4-(methylsulfonyl)phenyl)pyridin-2-yl)ethyl)-2-(3-(trifluoromethyl)-4,5,6,7-tetrahydro-1H-indazol-1-yl)acetamide (425)

Prepared 11.9 mg of the title compound by a method analogous to compound 57B using 57A and 4-methylsulfonylphenyl boronic acid. MS (m/z) 619 [M+H]$^+$.

Example 426

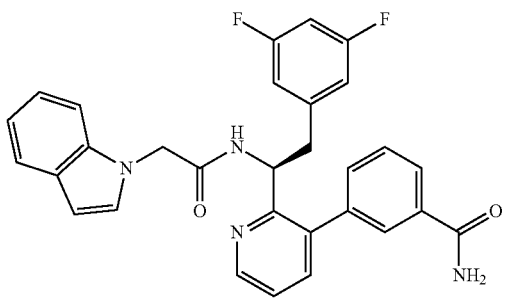

Synthesis of (S)-3-(2-(1-(2-(1H-indol-1-yl)acetamido)-2-(3,5-difluorophenyl)ethyl)pyridin-3-yl)benzamide (426)

Prepared 35 mg of the title compound by a method analogous to 50D using indole-1-acetic acid $^1$H NMR (400 MHz, dmso) δ 10.82 (s, 1H), 8.66 (dd, 2H), 7.92 (d, 1H), 7.86 (s, 1H), 7.75 (s, 1H), 7.61 (d, 1H), 7.49-7.35 (m, 4H), 7.26 (dd, 1H), 7.05-6.98 (m, 2H), 6.91 (t, 1H), 6.74-6.61 (m, 1H), 6.49 (d, 2H), 5.17 (dd, 3H), 4.70-4.65 (m, 1H), 3.44 (q, 2H), 2.95 (d, 2H). MS (m/z) 529 [M+H]$^+$.

Example 427

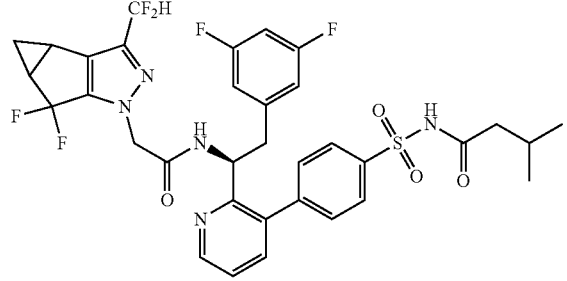

Synthesis of (S)—N-(1-(3-(4-(N-(3-methylbutanoyl)sulfamoyl)phenyl)-pyridin-2-yl)-2-(3,5-difluorophenyl)ethyl)-2-(3-(difluoromethyl)-5,6-dihydro-4,5-(methano)-6,6-difluoro-cyclopenta[c]pyrazol-1(4H)-yl)acetamide (427)

Prepared 11.6 mg of the title compound by a method analogous to 68B using 68A and 4-(N-(3-methylbutanoyl)sulfamoyl)phenylboronic acid. MS (m/z) 720 [M+H]$^+$.

Example 428

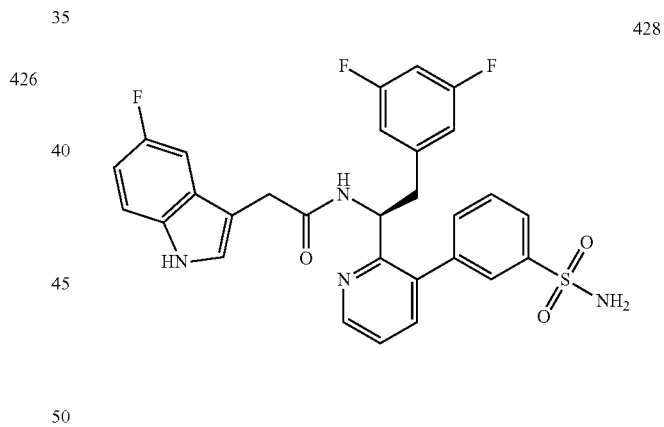

Synthesis of (S)—N-(2-(3,5-difluorophenyl)-1-(3-(3-sulfamoylphenyl)pyridin-2-yl)ethyl)-2-(5-fluoro-1H-indol-3-yl)acetamide (428)

Prepared 43 mg of the title compound by analogous method to 55F using 3-(4,4,5,5-tetramethyl-1,3,2-dioxaborolan-2-yl)benzenesulfonamide. $^1$H NMR (400 MHz, D6-DMSO) δ 10.87 (s, 9H), 8.69 (dd, J=9.5, 4.9 Hz, 19H), 7.82 (d, J=7.7 Hz, 10H), 7.68 (s, 11H), 7.61-7.16 (m, 69H), 7.13-7.02 (m, 19H), 6.93-6.78 (m, 22H), 6.52 (d, J=6.4 Hz, 31H), 5.13 (dd, J=14.9, 7.9 Hz, 13H), 3.50-3.33 (m, 20H), 3.10-2.86 (m, 21H), 2.05 (s, 6H), 1.26-0.77 (m, 19H). MS (m/z) 565 [M+H]$^+$.

Example 429

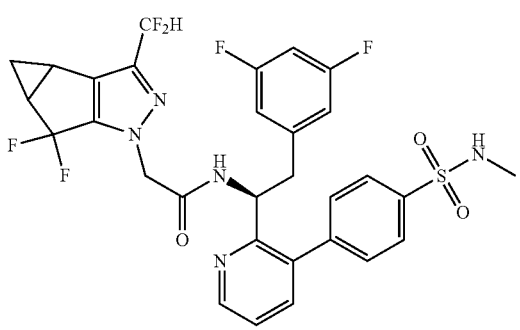

Synthesis of (S)—N-(1-(3-(4-(N-methylsulfamoyl)phenyl)-pyridin-2-yl)-2-(3,5-difluorophenyl)ethyl)-2-(3-(difluoromethyl)-5,6-dihydro-4,5-(methano)-6,6-difluoro-cyclopenta[c]pyrazol-1(4H)-yl)acetamide (429)

Prepared 17.3 mg of the title compound by a method analogous to 68B using 68A and 4-(N-methylsulfamoyl) phenylboronic acid pinacol ester. MS (m/z) 650 [M+H]$^+$.

Example 430

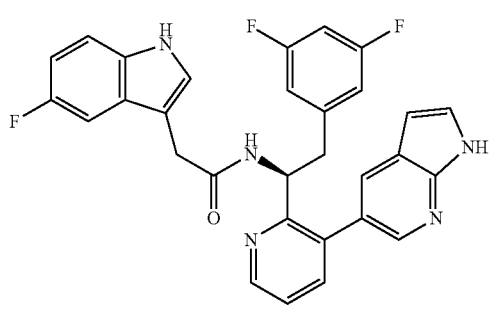

Synthesis of (S)—N-(1-(3-(1H-pyrrolo[2,3-b]pyridin-5-yl)pyridin-2-yl)-2-(3,5-difluorophenyl)ethyl)-2-(5-fluoro-1H-indol-3-yl)acetamide (430)

Prepared 26.7 mg of the title compound by analogous method to 55F using 5-(4,4,5,5-tetramethyl-1,3,2-dioxaborolan-2-yl)-1H-pyrrolo[2,3-b]pyridine and 55E. MS (m/z) 526 [M+H]$^+$.

Example 431

Synthesis of (S)—N-(2-(3,5-difluorophenyl)-1-(3-(4-(trifluoromethoxy)phenyl)pyridin-2-yl)ethyl)-2-(5-fluoro-1H-indol-3-yl)acetamide (431)

Prepared 38 mg of the title compound by a method analogous to 55F using 3-trifluoromethoxyphenyl boronic acid and 55E. MS (m/z) 570 [M+H]$^+$.

Example 432

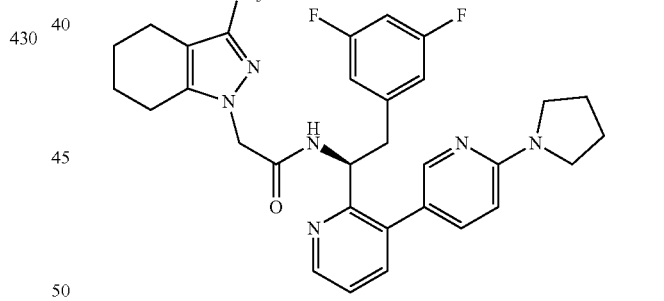

Synthesis of (S)—N-(2-(3,5-difluorophenyl)-1-(6'-(pyrrolidin-1-yl)-3,3'-bipyridin-2-yl)ethyl)-2-(3-(trifluoromethyl)-4,5,6,7-tetrahydro-1H-indazol-1-yl)acetamide (432)

Prepared 16.3 mg of the title compound by a method analogous to compound 57B using 57A and 6-(pyrrolidin-1-yl)pyridin-3-ylboronic acid. MS (m/z) 611 [M+H]$^+$.

Example 433

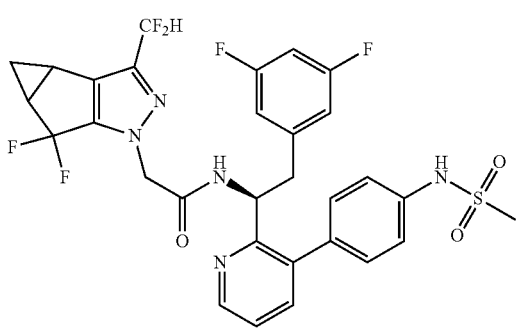

433

Synthesis of (S)—N-(1-(3-(4-(methylsulfonamido)phenyl)-pyridin-2-yl)-2-(3,5-difluorophenyl)ethyl)-2-(3-(difluoromethyl)-5,6-dihydro-4,5-(methano)-6,6-difluoro-cyclopenta[c]pyrazol-1 (4H)-yl)acetamide (433)

Prepared 20.6 mg of the title compound by a method analogous to 68B using 68A and N-4-methanesulfonamide-phenylboronic acid. MS (m/z) 650 [M+H]$^+$.

Example 434

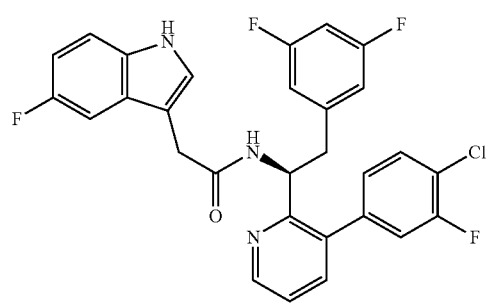

434

Synthesis of (S)—N-(2-(3,5-difluorophenyl)-1-(3-(1-methyl-1H-pyrazol-4-yl)pyridin-2-yl)ethyl)-2-(5-fluoro-1H-indol-3-yl)acetamide (434)

Prepared 1.5 mg of the title compound by a method analogous to 55F using 3-fluoro-4-chlorophenylboronic acid and 55E. MS (m/z) 538 [M+H]$^+$.

Example 435

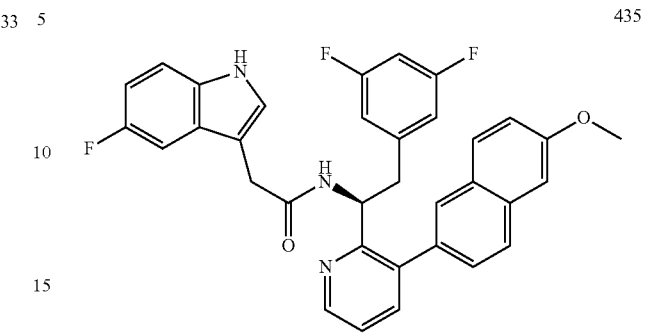

435

Synthesis of (S)—N-(2-(3,5-difluorophenyl)-1-(3-(6-methoxynaphthalen-2-yl)pyridin-2-yl)ethyl)-2-(5-fluoro-1H-indol-3-yl)acetamide (435)

Prepared 37.1 mg of the title compound by a method analogous to 55F using 6-methoxy-2-naphthaleneboronic acid and 55E. MS (m/z) 566 [M+H]$^+$.

Example 436

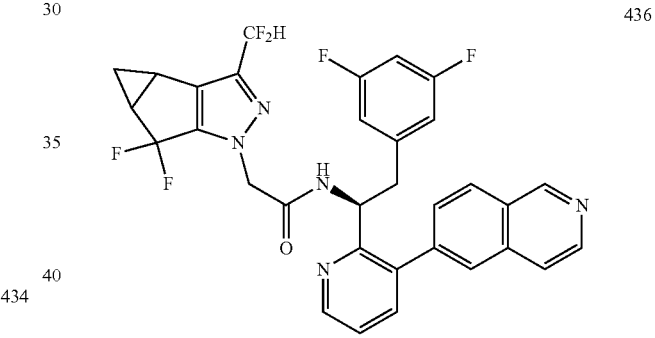

436

Synthesis of (S)—N-(1-(3-(isoquinolin-6-yl)-pyridin-2-yl)-2-(3,5-difluorophenyl)ethyl)-2-(3-(difluoromethyl)-5,6-dihydro-4,5-(methano)-6,6-difluoro-cyclopenta[c]pyrazol-1(4H)-yl)acetamide (436)

Prepared 15.1 mg of the title compound by a method analogous to 68B using 68A and isoquinoline-6-ylboronic acid. MS (m/z) 608 [M+H]$^+$.

Example 437

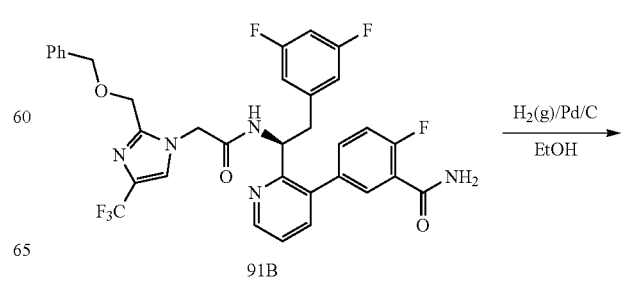

91B

Example 439

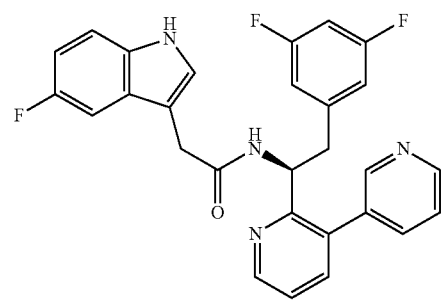

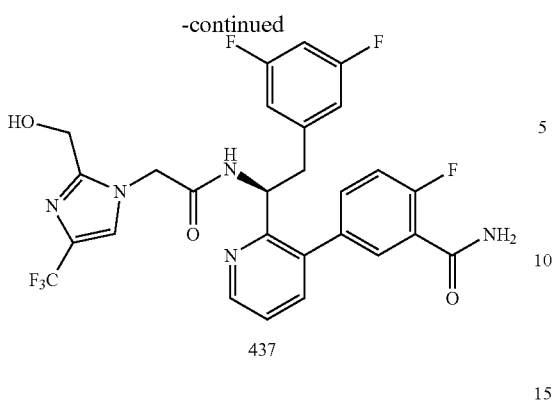

Synthesis of (S)-5-(2-(2-(3,5-difluorophenyl)-1-(2-(2-(hydroxymethyl)-4-(trifluoromethyl)-1H-imidazol-1-yl)acetamido)ethyl)pyridin-3-yl)-2-fluorobenzamide (437)

Dissolved 21.8 mg of 91B in 1 ml EtOH. Added 10 mg of 10% Pd/C. Stirred at RT under 1 atm $H_2$ for 72 hrs. Filtered reaction and purified filtrate by RP HPLC using a C18 column with a gradient of 0.1%/$H_2O$, 0.1% TFA-acetonitrile to give 10.8 mg of the title compound. MS (m/z) 578 $[M+H]^+$.

Example 428

Synthesis of (S)—N-(1-(3,3'-bipyridin-2-yl)-2-(3,5-difluorophenyl)ethyl)-2-(5-fluoro-1H-indol-3-yl)acetamide (439)

Prepared 20.8 mg of the title compound by a method analogous to 55F using (pyridin-3-yl)boronic acid and 55E. MS (m/z) 487 $[M+H]^+$.

Example 440

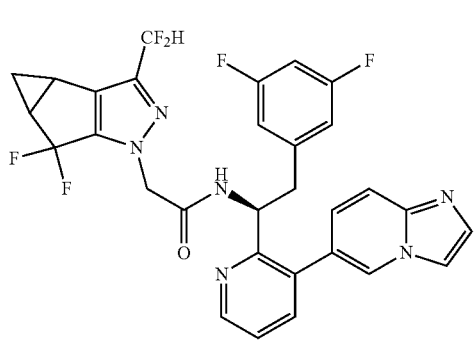

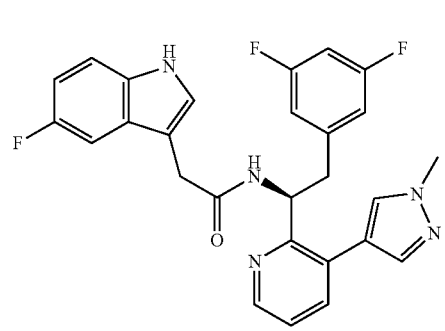

Synthesis of (S)—N-(1-(3-(imidazo[1,2-a]pyridine-6-yl)-pyridin-2-yl)-2-(3,5-difluorophenyl)ethyl)-2-(3-(difluoromethyl)-5,6-dihydro-4,5-(methano)-6,6-difluoro-cyclopenta[c]pyrazol-1(4H)-yl)acetamide (438)

Prepared 4.3 mg of the title compound by a method analogous to 68B using 68A and imidazo[1,2-a]pyridine-6-boronic acid. MS (m/z) 597 $[M+H]^+$.

Synthesis of (S)—N-(2-(3,5-difluorophenyl)-1-(3-(1-methyl-1H-pyrazol-4-yl)pyridin-2-yl)ethyl)-2-(5-fluoro-1H-indol-3-yl)acetamide (440)

Prepared 8.9 mg of the title compound by a method analogous to 55F using 1-methyl-4-(4,4,5,5-tetramethyl-1,3,2-dioxaborolan-2-yl)-1H-pyrazole and 55E. MS (m/z) 490 $[M+H]^+$.

601

Example 441

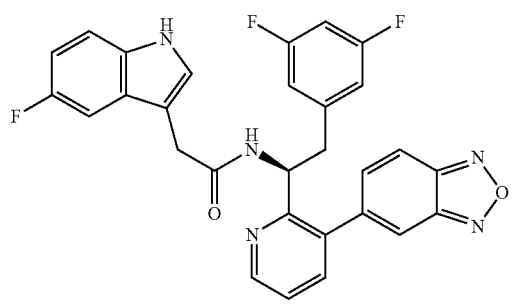

441

Synthesis of (S)—N-(1-(3-(benzo[c][1,2,5]oxadiazol-5-yl)pyridin-2-yl)-2-(3,5-difluorophenyl)ethyl)-2-(5-fluoro-1H-indol-3-yl)acetamide (441)

Prepared 16 mg of the title compound by a method analogous to 55F using benzo[c][1,2,5]oxadiazol-5-ylboronic acid and 55E. MS (m/z) 528 [M+H]$^+$.

Example 442

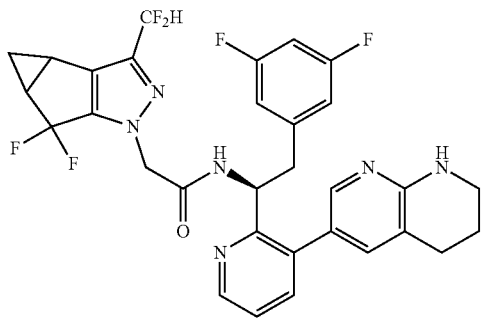

442

Synthesis of (S)—N-(1-(3-(5,6,7,8-tetrahydro-1,8-naphthyridin-3-yl)-pyridin-2-yl)-2-(3,5-difluorophenyl)ethyl)-2-(3-(difluoromethyl)-5,6-dihydro-4,5-(methano)-6,6-difluoro-cyclopenta[c]pyrazol-1(4H)-yl)acetamide (442)

Prepared 1.2 mg of the title compound by a method analogous to 68B using 68A and (8-Pivaloyl-5,6,7,8-tetrahydro-1,8-naphthyridin-3-yl)boronic acid pinacol ester. MS (m/z) 613 [M+H]$^+$.

Example 443

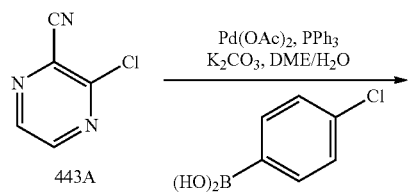

443A

602

-continued

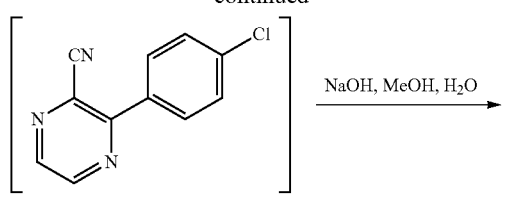

443B

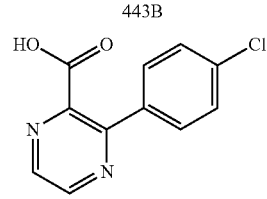

443C

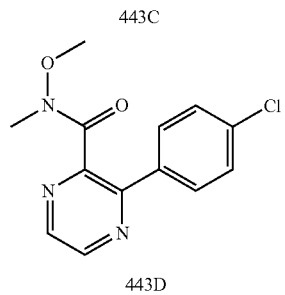

443D

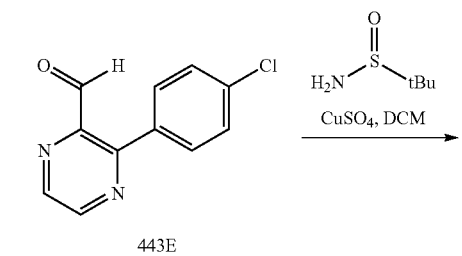

443E

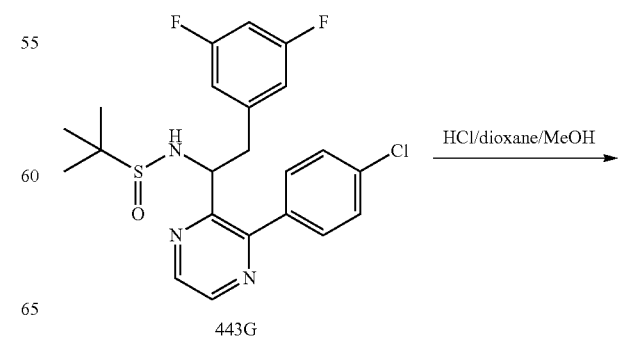

443F

443G

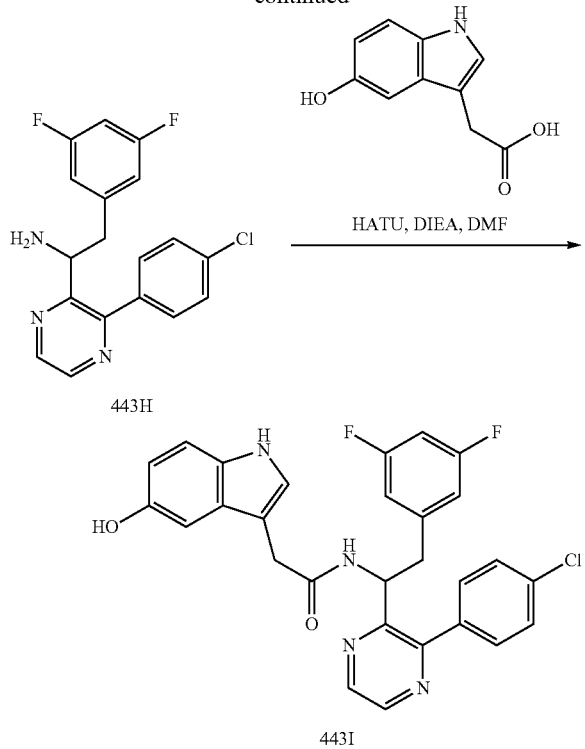

Synthesis of 3-(4-chlorophenyl)pyrazine-2-carboxylic acid (443C)

To a solution of 3-chloropyrazine-2-carbonitrile (1.39 g, 10 mmol) in a mixture of DME (30 mL) and H$_2$O (15 mL) was added 4-chlorophenylboronic acid (1.56 g, 10 mmol) and K$_2$CO$_3$ (4.13 g, 30 mmol), Pd(OAc)$_2$ (112 mg, 0.5 mmol) and triphenylphosphine (polymer-bound, 3.0 mmol). The reaction tube was sealed and heated at 95° C. overnight. After cooled to room temperature, the reaction mixture was poured into ethyl acetate and filtered through a pad of celite. The filtrate was concentrated to dryness and dissolved in 50 mL MeOH and 80 mL 4 N NaOH. The reaction was heated at 80° C. overnight. After cooled to room temperature, the mixture was acidified with concentrated HCl to pH=1. After removing the volatile, the crude was used in the next step without further purification.

Synthesis of 3-(4-chlorophenyl)-N-methoxy-N-methylpyrazine-2-carboxamide (443D)

Example 443D was prepared according to the method presented for the synthesis of Example 13G utilizing crude of 443C and N,O-dimethyl hydroxyamine hydrochloride to provide 3-(4-chlorophenyl)-N-methoxy-N-methylpyrazine-2-carboxamide: MS (m/z): 278.2 [M+H]$^+$; $^1$H NMR (400 MHz, cdcl$_3$) δ 8.69 (s, 1H), 8.55 (d, J=2.1 Hz, 1H), 7.69 (d, J=8.3 Hz, 2H), 7.44 (d, J=8.4 Hz, 2H), 3.48 (s, 3H), 3.28 (s, 3H).

Synthesis of 3-(4-chlorophenyl)pyrazine-2-carbaldehyde (443E)

To a solution of 3-(4-chlorophenyl)-N-methoxy-N-methylpyrazine-2-carboxamide (670 mg, 2.4 mmol) in THF (5 mL) was added DIBAL-H (1.0 M/toluene, 4.8 mmol) at −10° C. After stirred at −10° C. for 10 min, the reaction was poured into ethyl acetate and saturated NH$_4$Cl solution. The organic layer was separated and dried over sodium sulfate, filtered and concentrated. After removing the volatile, the crude was used in the next step without further purification. MS (m/z): 219.2 [M+H]$^+$.

Synthesis of N-((3-(4-chlorophenyl)pyrazin-2-yl)methylene)-2-methylpropane-2-sulfinamide (443F)

To a solution of 3-(4-chlorophenyl)pyrazine-2-carbaldehyde (crude from above reaction) in DCM (5 mL) was added (S)-2-methylpropane-2-sulfinamide (320 mg, 2.64 mmol) and CuSO$_4$ (766 mg, 4.8 mmol) at room temperature. After stirred at room temperature for 3 h, the reaction was filtered through a pad of celite and washed with DCM. The organic was dried over sodium sulfate, filtered and concentrated. After removing the volatile, the resulting residue was purified by silica gel chromatography eluting with EtOAc/hexanes to afford 0.48 g of the title product. MS (m/z): 321.8 [M+H]$^+$.

Synthesis of N-(1-(3-(4-chlorophenyl)pyrazin-2-yl)-2-(3,5-difluorophenyl)ethyl)-2-methylpropane-2-sulfinamide (443G)

To a solution of N-((3-(4-chlorophenyl)pyrazin-2-yl)methylene)-2-methylpropane-2-sulfinamide (480 mg, 1.5 mmol) and Cu(OTf) (27 mg, 0.075 mmol) in DCM (5 mL) was added (3,5-difluorobenzyl)magnesium bromide (0.5 M in ether, 3.0 mmol) at room temperature. After stirred at room temperature for 1 h, the reaction was poured into ethyl acetate and saturated NH$_4$Cl solution. The organic layer was separated and dried over sodium sulfate, filtered and concentrated. After removing the volatile, the crude was used in the next step without further purification. MS (m/z): 449.8 [M+H]$^+$.

Synthesis of 1-(3-(4-chlorophenyl)pyrazin-2-yl)-2-(3,5-difluorophenyl)ethanamine (443H)

To a solution of N-(1-(3-(4-chlorophenyl)pyrazin-2-yl)-2-(3,5-difluorophenyl)ethyl)-2-methylpropane-2-sulfinamide (crude from above reaction) in MeOH (5 mL) was added 2 mL 4 N HCl in dioxane at room temperature. After stirred at room temperature overnight, the volatile was removed in vacuo and the crude was used in the next step without further purification. MS (m/z): 346.1 [M+H]$^+$.

Synthesis of N-(1-(3-(4-chlorophenyl)pyrazin-2-yl)-2-(3,5-difluorophenyl)ethyl)-2-(5-hydroxy-1H-indol-3-yl)acetamide (443I)

Example 443I was prepared (10.3 mg) according to the method presented for the synthesis of Example 13G utilizing 443H and 2-(5-hydroxy-1H-indol-3-yl)acetic acid to provide (S)-5-(2-(1-(2-(5-bromo-1H-indol-3-yl)acetamido)-2-(3,5-difluorophenyl)ethyl)pyridin-3-yl)-2-fluorobenzamide: MS (m/z): 520.0 [M+H]$^+$; $^1$H NMR (400 MHz, dmso) δ 10.47 (s, 1H), 8.74-8.63 (m, 2H), 8.59 (s, 1H), 7.40 (s, 4H), 7.07 (d, J=8.6 Hz, 1H), 6.92 (d, J=15.6 Hz, 2H), 6.78 (s, 1H), 6.55 (d, J=8.3 Hz, 1H), 6.41 (d, J=7.1 Hz, 2H), 5.25 (q, J=7.5 Hz, 1H), 3.41 (s, 2H), 3.04 (dd, J=12.9, 6.9 Hz, 1H), 3.01-2.87 (m, 1H).

Example 444

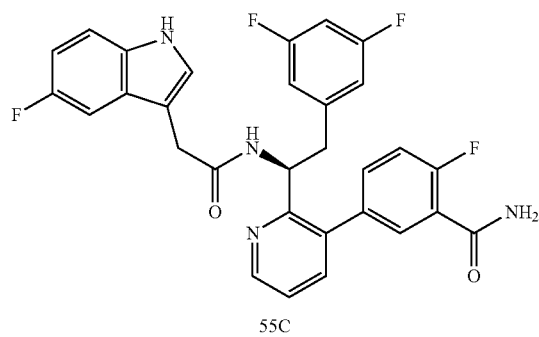

55C

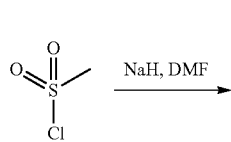

NaH, DMF →

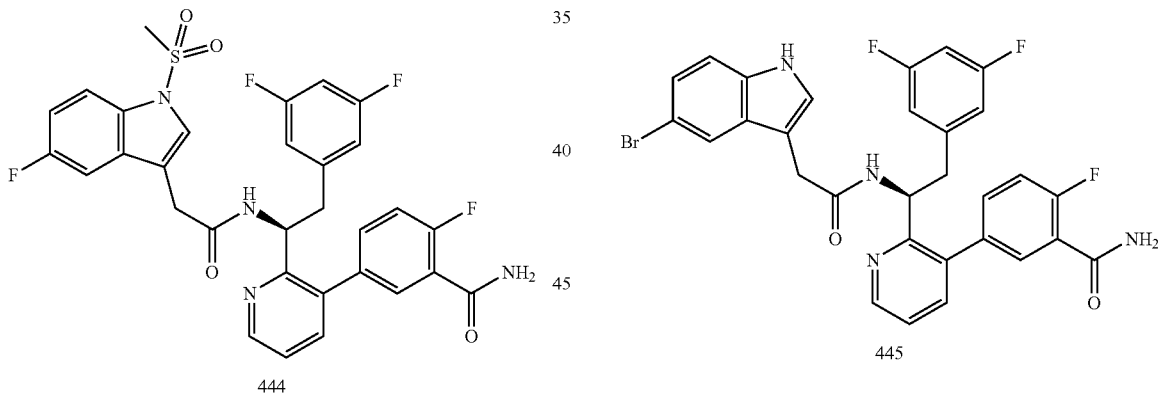

444

Synthesis of(S)-5-(2-(2-(3,5-difluorophenyl)-1-(2-(5-fluoro-1-(methylsulfonyl)-1H-indol-3-yl)acetamido)ethyl)pyridin-3-yl)-2-fluorobenzamide (444)

To a solution of (S)-5-(2-(2-(3,5-difluorophenyl)-1-(2-(5-fluoro-1H-indol-3-yl)acetamido)ethyl)pyridin-3-yl)-2-fluorobenzamide (10 mg, 0.02 mmol) in DMF (1 mL) was added NaH (1.6 mg, 0.04 mmol) and methylsulfonyl chloride (23 mg, 0.2 mmol). The reaction was stirred at room temperature overnight and was then purified by reverse phase HPLC eluting with acetonitrile/water to afford 1.0 mg of the title compound. MS (m/z): 625.1 [M+H]$^+$; HPLC retention time 3.74 min (2-98% acetonitrile:water with 0.05% trifluoroacetic acid).

Example 445

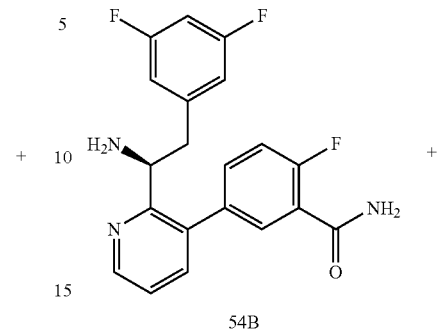

54B

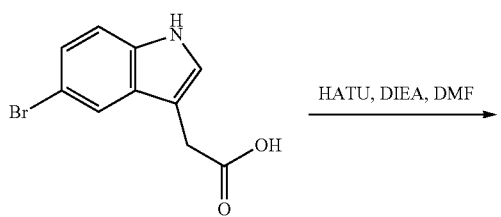

HATU, DIEA, DMF →

445

Synthesis of (S)-5-(2-(1-(2-(5-bromo-1H-indol-3-yl)acetamido)-2-(3,5-difluorophenyl)ethyl)pyridin-3-yl)-2-fluorobenzamide (445)

Example 445 was prepared (5.7 mg) according to the method presented for the synthesis of Example 13G utilizing 54B and 2-(5-bromo-1H-indol-3-yl)acetic acid to provide (S)-5-(2-(1-(2-(5-bromo-1H-indol-3-yl)acetamido)-2-(3,5-difluorophenyl)ethyl)pyridin-3-yl)-2-fluorobenzamide: MS (m/z): 607.2 [M+H]$^+$; HPLC retention time 3.62 min (2-98% acetonitrile:water with 0.05% trifluoroacetic acid). $^1$H NMR (400 MHz, cdcl$_3$) δ 8.51 (d, J=7.4 Hz, 1H), 8.40 (d, J=5.5 Hz, 1H), 8.26 (s, 1H), 7.90 (t, J=29.1 Hz, 1H), 7.81 (s, 1H), 7.61 (dd, J=17.6, 9.9 Hz, 2H), 7.34-7.21 (m, 1H), 7.21-7.06 (m, 3H), 6.93 (d, J=8.6 Hz, 1H), 6.49 (t, J=7.7 Hz, 2H), 6.11 (d, J=5.9 Hz, 2H), 5.33 (q, J=7.9 Hz, 1H), 3.65 (dd, J=22.0, 14.7 Hz, 1H), 3.53 (d, J=15.8 Hz, 1H), 3.03 (dd, J=13.6, 7.7 Hz, 1H), 2.96-2.82 (m, 1H).

Example 446

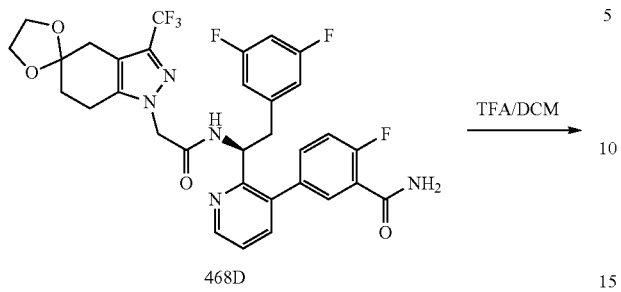

468D

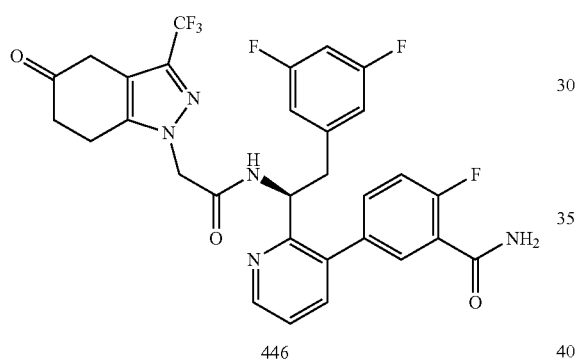

446

Synthesis of (S)-5-(2-(2-(3,5-difluorophenyl)-1-(2-(5-oxo-3-(trifluoromethyl)-4,5,6,7-tetrahydro-1H-indazol-1-yl)acetamido)ethyl)pyridin-3-yl)-2-fluorobenzamide (446)

A solution of (S)-5-(2-(2-(3,5-difluorophenyl)-1-(2-(3'-(trifluoromethyl)-6',7'-dihydrospiro[[1,3]dioxolane-2,5'-indazole]-1'(4'H)-yl)acetamido)ethyl)pyridin-3-yl)-2-fluorobenzamide (320 mg, 0.48 mmol) in 3 mL DCM and 1 mL TFA was stirred at room temperature overnight. The volatile was removed in vacuo and the residue was then purified by reverse phase HPLC eluting with acetonitrile/water to afford 11.8 mg of the title compound: MS (m/z): 616.7 [M+H]$^+$; HPLC retention time 0.94 min (2-98% acetonitrile:water with 0.05% trifluoroacetic acid). $^1$H NMR (400 MHz, cd$_3$od) δ 8.76-8.67 (m, 1H), 7.68 (dd, J=7.8, 1.6 Hz, 1H), 7.57-7.46 (m, 2H), 7.32 (s, 1H), 7.22 (m, 1H), 6.68 (t, J=9.2 Hz, 1H), 6.34 (d, J=6.2 Hz, 2H), 5.36 (t, J=7.6 Hz, 1H), 4.93-4.76 (m, 2H), 3.29 (dt, J=3.2, 1.6 Hz, 1H), 3.06 (d, J=7.5 Hz, 1H), 2.85 (d, J=46.2 Hz, 2H), 2.77-2.62 (m, 2H), 2.60-2.42 (m, 2H), 1.98 (dt, J=31.8, 11.5 Hz, 2H).

Example 447

447

Synthesis of N-(1-(3-(4-chlorophenyl)pyrazin-2-yl)-2-(3,5-difluorophenyl)ethyl)-2-(1H-indazol-3-yl)acetamide (447)

Example 447 was prepared (5.4 mg) according to the method presented for the synthesis of Example 13G utilizing 443H and 2-(1H-indazol-3-yl)acetic acid to provide N-(1-(3-(4-chlorophenyl)pyrazin-2-yl)-2-(3,5-difluorophenyl)ethyl)-2-(1H-indazol-3-yl)acetamide: MS (m/z): 505.1 [M+H]$^+$; $^1$H NMR (400 MHz, dmso) δ 9.06 (d, J=7.4 Hz, 1H), 8.75 (s, 1H), 8.62 (s, 1H), 7.50-7.36 (m, 5H), 7.26 (t, J=7.6 Hz, 1H), 6.99 (dt, J=14.9, 7.8 Hz, 3H), 6.51 (d, J=6.9 Hz, 2H), 5.26 (d, J=7.2 Hz, 1H), 3.83-3.68 (m, 2H), 3.15-2.93 (m, 2H).

Example 448

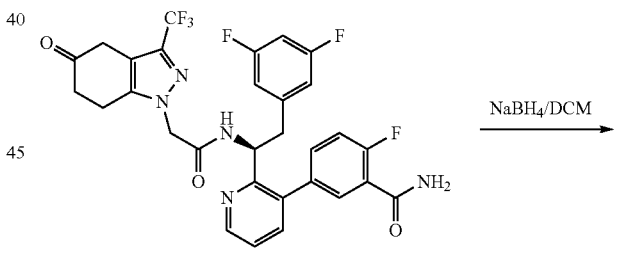

446

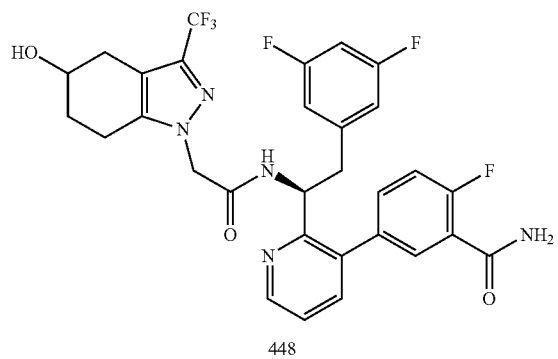

448

Synthesis of 5-(2-((1S)-2-(3,5-difluorophenyl)-1-(2-(5-hydroxy-3-(trifluoromethyl)-4,5,6,7-tetrahydro-1H-indazol-1-yl)acetamido)ethyl)pyridin-3-yl)-2-fluorobenzamide (448)

To solution of (S)-5-(2-(2-(3,5-difluorophenyl)-1-(2-(5-oxo-3-(trifluoromethyl)-4,5,6,7-tetrahydro-1H-indazol-1-yl)acetamido)ethyl)pyridin-3-yl)-2-fluorobenzamide (24 mg, 0.04 mmol) in 1 mL DCM was added NaBH$_4$ (200 mg, 5.3 mmol) and the resulting solution was stirred at room temperature overnight. The reaction was poured into ethyl acetate and washed with saturated NH$_4$Cl solution and brine. The organic layer was dried over sodium sulfate, filtered and concentrated. The resulting residue was purified by reverse phase HPLC eluting with acetonitrile/water to afford 10.8 mg of the title compound: MS (m/z): 618.3 [M+H]$^+$; $^1$H NMR of mixture of diastereomers (400 MHz, cdcl$_3$) δ 9.31 (d, J=7.3 Hz, 1H), 8.75 (s, 1H), 7.99-7.88 (m, 1H), 7.80-7.58 (m, 2H), 7.50 (s, 1H), 7.34-7.22 (m, 1H), 6.98 (m, 1H), 6.61 (t, J=8.6 Hz, 1H), 6.45 (s, 1H), 6.21 (s, 2H), 5.57-5.40 (m, 1H), 4.89-4.61 (m, 2H), 3.15 (dd, J=13.5, 7.0 Hz, 1H), 3.10-2.95 (m, 1H), 2.88 (d, J=12.2 Hz, 1H), 2.70 (m, 2H), 2.55 (dd, J=38.9, 32.9 Hz, 1H), 2.01 (m, 1H), 1.91 (m, 1H).

Example 449 and 450

Synthesis of 5-(2-((1S)-1-(2-(5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)pyridin-3-yl)-2-fluorobenzamide (449) and 5-(2-((1S)-1-(2-(5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)pyridin-3-yl)-2-fluorobenzamide (450)

The two diastereomers of 181E were separated by chiral HPLC (Chiralpak AD-H, Heptane:IPA 70:30) to provide 449 (18 mg, fast eluting peak) and 450 (18 mg, slow eluting peak). MS (m/z): 636.4 [M+H]$^+$.

Example 451

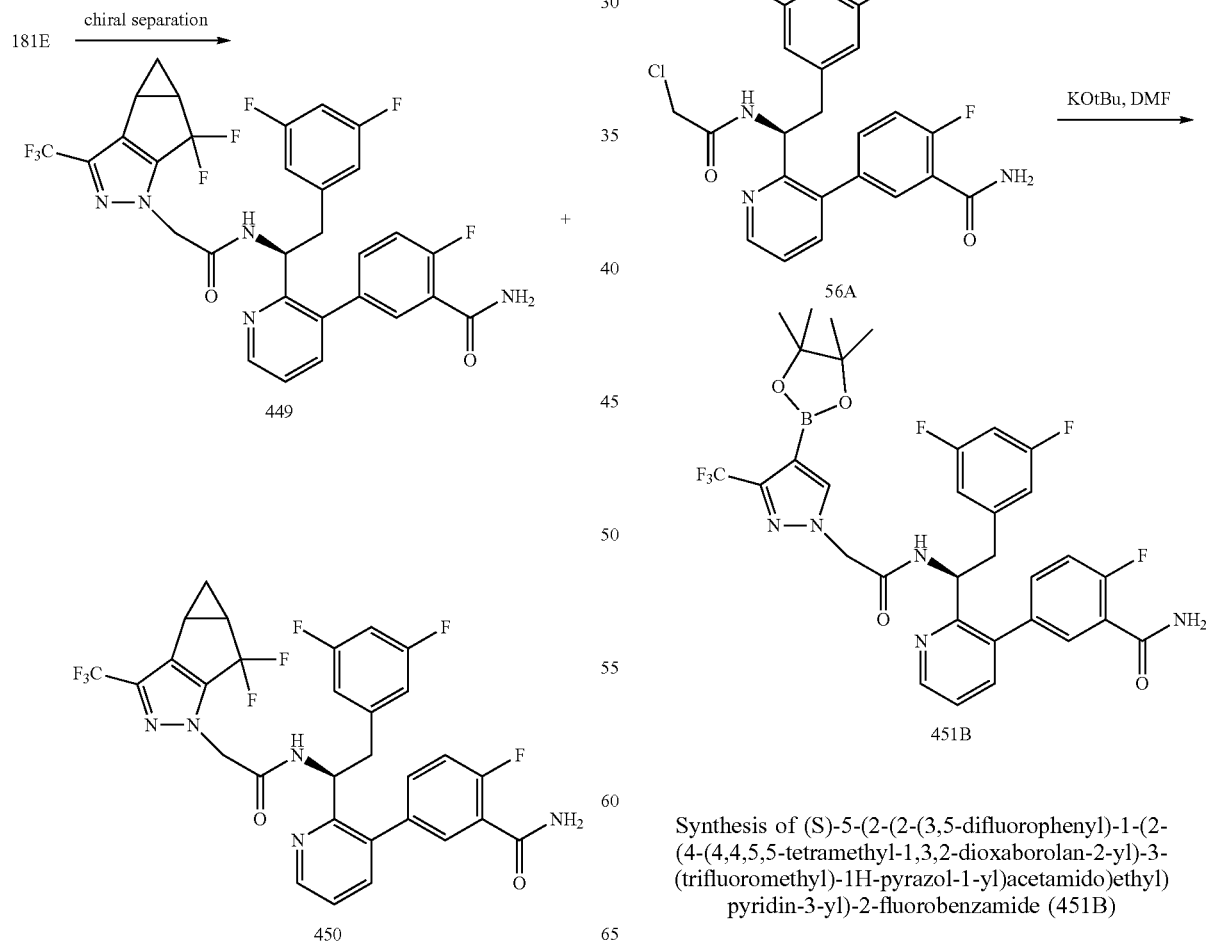

Synthesis of (S)-5-(2-(2-(3,5-difluorophenyl)-1-(2-(4-(4,4,5,5-tetramethyl-1,3,2-dioxaborolan-2-yl)-3-(trifluoromethyl)-1H-pyrazol-1-yl)acetamido)ethyl)pyridin-3-yl)-2-fluorobenzamide (451B)

Example 451B was prepared (6.6 mg) according to the method presented for the synthesis of Example 58D utilizing 56A and 4-(4,4,5,5-tetramethyl-1,3,2-dioxaborolan-2-yl)-3-(trifluoromethyl)-1H-pyrazole to provide (S)-5-(2-(2-(3,5-difluorophenyl)-1-(2-(4-(4,4,5,5-tetramethyl-1,3,2-dioxaborolan-2-yl)-3-(trifluoromethyl)-1H-pyrazol-1-yl)acetamido)ethyl)pyridin-3-yl)-2-fluorobenzamide: MS (m/z): 674.1 [M+H]+; 1H NMR (400 MHz, cdcl3) δ 8.57 (d, J=4.9 Hz, 1H), 7.79 (s, 1H), 7.56 (d, J=7.3 Hz, 1H), 7.47 (d, J=8.0 Hz, 1H), 7.38-7.22 (m, 1H), 7.21-7.11 (m, 1H), 6.78 (s, 1H), 6.53 (t, J=9.0 Hz, 1H), 6.09 (d, J=6.0 Hz, 2H), 5.82 (s, 1H), 5.42 (dd, J=14.3, 8.4 Hz, 1H), 4.83 (s, 2H), 2.95-2.72 (m, 2H), 1.35-1.20 (m, 12H).

Example 452 and 453

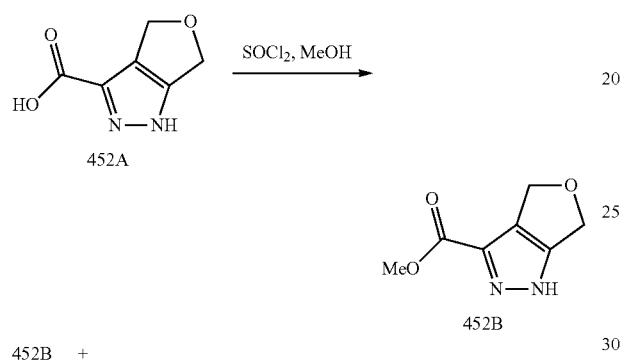

Synthesis of methyl 4,6-dihydro-1H-furo[3,4-c]pyrazole-3-carboxylate (452B)

Example 452B was prepared according to the method presented for the synthesis of Example 55C utilizing 4,6-dihydro-1H-furo[3,4-c]pyrazole-3-carboxylic acid to provide the title compound: MS (m/z): 169.1 [M+H]+.

Synthesis of (S)-methyl 1-(2-((1-(3-(3-carbamoyl-4-fluorophenyl)pyridin-2-yl)-2-(3,5-difluorophenyl)ethyl)amino)-2-oxoethyl)-4,6-dihydro-1H-furo[3,4-c]pyrazole-3-carboxylate (452C) and (S)-methyl 2-(2-((1-(3-(3-carbamoyl-4-fluorophenyl)pyridin-2-yl)-2-(3,5-difluorophenyl)ethyl)amino)-2-oxoethyl)-4,6-dihydro-2H-furo[3,4-c]pyrazole-3-carboxylate (453)

Example 452C (2.4 mg) and 453 (2.7 mg) were prepared according to the method presented for the synthesis of Example 58D utilizing 56A and methyl 4,6-dihydro-1H-furo[3,4-c]pyrazole-3-carboxylate to provide (S)-methyl 1-(2-(1-(3-(3-carbamoyl-4-fluorophenyl)pyridin-2-yl)-2-(3,5-difluorophenyl)ethylamino)-2-oxoethyl)-4,6-dihydro-1H-furo[3,4-c]pyrazole-3-carboxylate: MS (m/z): 580.4 [M+H]+; 1H NMR (400 MHz, cdcl3) δ 9.58 (s, 1H), 8.78 (d, J=4.8 Hz, 1H), 7.93 (d, J=6.7 Hz, 1H), 7.79-7.62 (m, 2H), 7.58 (s, 1H), 7.33-7.22 (m, 2H), 6.86 (s, 1H), 6.61 (s, 1H), 6.35 (s, 1H), 6.18 (d, J=5.9 Hz, 2H), 5.46 (s, 1H), 5.00 (s, 2H), 4.92-4.69 (m, 4H), 3.87 (s, 3H), 3.07-2.80 (m, 1H), 3.07-2.81 (m, 1H) and (S)-methyl 2-(2-(1-(3-(3-carbamoyl-4-fluorophenyl)pyridin-2-yl)-2-(3,5-difluorophenyl)ethylamino)-2-oxoethyl)-4,6-dihydro-2H-furo[3,4-c]pyrazole-3-carboxylate: MS (m/z): 580.7 [M+H]+.

Example 454

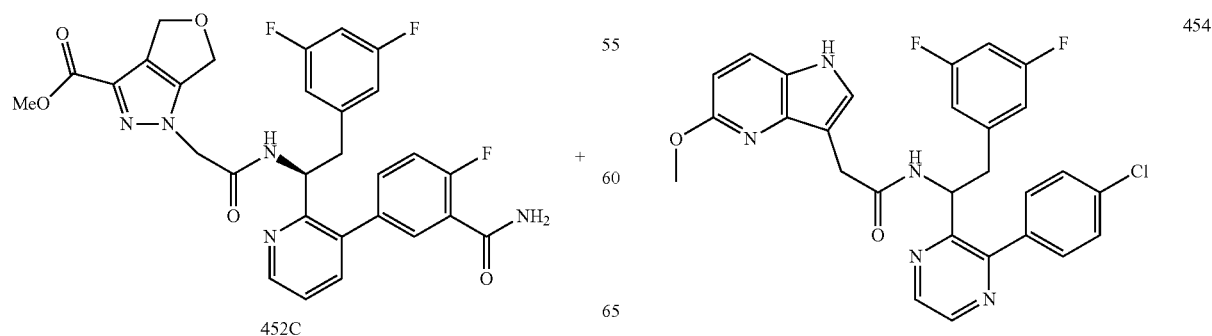

Synthesis of N-(1-(3-(4-chlorophenyl)pyrazin-2-yl)-2-(3,5-difluorophenyl)ethyl)-2-(5-methoxy-1H-pyrrolo[3,2-b]pyridin-3-yl)acetamide (454)

Example 454 was prepared (4.2 mg) according to the method presented for the synthesis of Example 13G utilizing 443H and 2-(5-methoxy-1H-pyrrolo[3,2-b]pyridin-3-yl)acetic acid to provide N-(1-(3-(4-chlorophenyl)pyrazin-2-yl)-2-(3,5-difluorophenyl)ethyl)-2-(5-methoxy-1H-pyrrolo[3,2-b]pyridin-3-yl)acetamide: MS (m/z): 535.1 [M+H]$^+$; $^1$H NMR (400 MHz, dmso) δ 11.08 (s, 1H), 8.68 (d, J=8.2 Hz, 2H), 8.62 (s, 1H), 7.73 (s, 1H), 7.50-7.39 (m, 4H), 7.28 (s, 1H), 6.91 (t, J=9.1 Hz, 1H), 6.59 (d, J=8.8 Hz, 1H), 6.38 (d, J=6.6 Hz, 2H), 5.32 (d, J=7.5 Hz, 1H), 3.86 (s, 3H), 3.58-3.31 (m, 2H), 2.97 (m, 2H).

Example 455

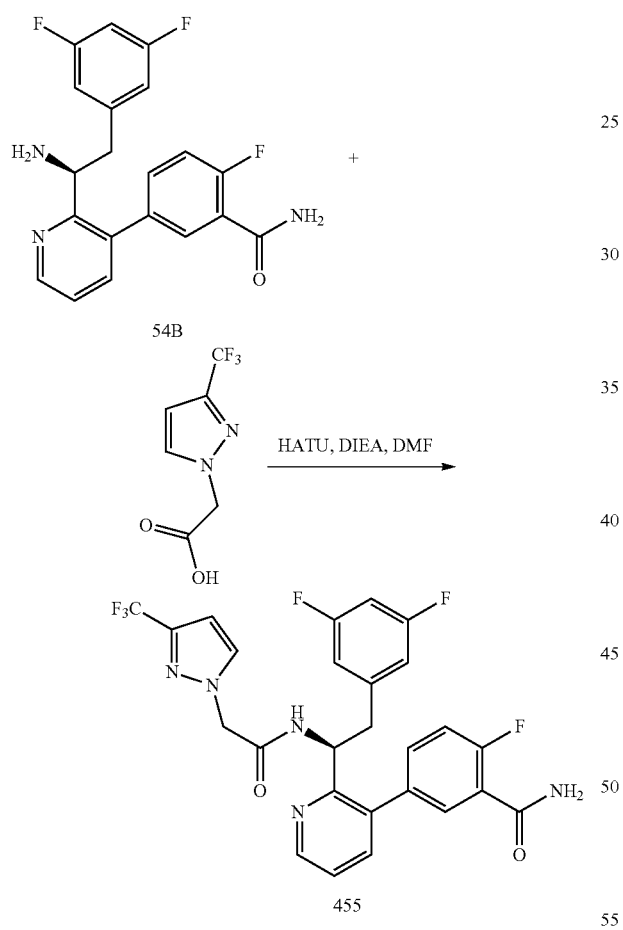

Synthesis of (S)-5-(2-(2-(3,5-difluorophenyl)-1-(2-(3-(trifluoromethyl)-1H-pyrazol-1-yl)acetamido)ethyl)pyridin-3-yl)-2-fluorobenzamide (455)

Example 455 was prepared (55 mg) according to the method presented for the synthesis of Example 13G utilizing 54B and 2-(3-(trifluoromethyl)-1H-pyrazol-1-yl)acetic acid to provide (S)-5-(2-(2-(3,5-difluorophenyl)-1-(2-(3-(trifluoromethyl)-1H-pyrazol-1-yl)acetamido)ethyl)pyridin-3-yl)-2-fluorobenzamide: MS (m/z): 548.1 [M+H]$^+$; HPLC retention time 3.56 min (2-98% acetonitrile:water with 0.05% trifluoroacetic acid). $^1$H NMR (400 MHz, cdcl$_3$) δ 9.53 (d, J=7.1 Hz, 1H), 8.79 (d, J=5.5 Hz, 1H), 7.98 (d, J=7.9 Hz, 1H), 7.93-7.70 (m, 2H), 7.62 (s, 1H), 7.60 (d, J=6.5 Hz, 1H), 7.62-7.23 (m, 2H), 6.95 (d, J=10.2 Hz, 1H), 6.61 (dd, J=19.8, 11.5 Hz, 3H), 6.20 (d, J=6.1 Hz, 2H), 5.48 (q, J=7.6 Hz, 1H), 5.00-4.84 (m, 2H), 3.18 (dd, J=13.5, 6.8 Hz, 1H), 3.02 (dd, J=13.6, 9.0 Hz, 1H).

Example 456

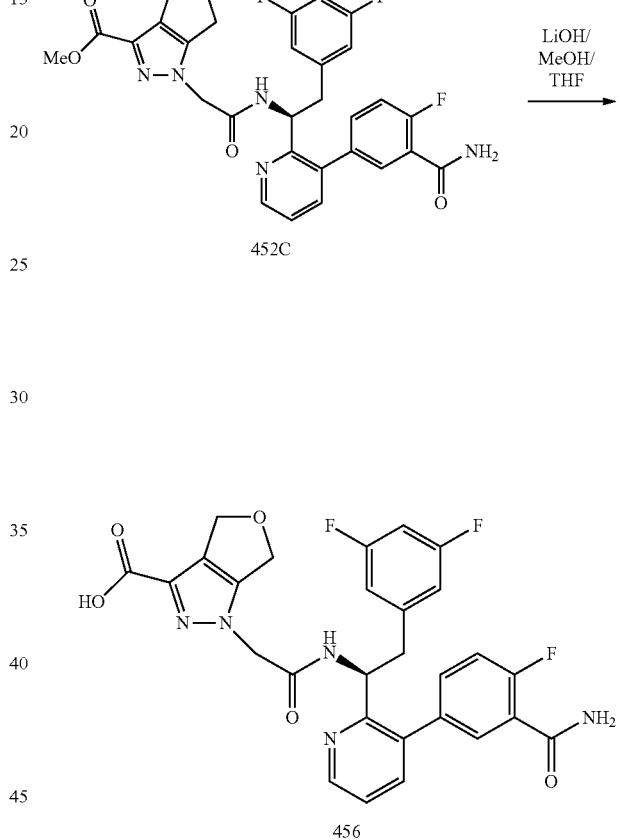

Synthesis of (S)-1-(2-(1-(3-(3-carbamoyl-4-fluorophenyl)pyridin-2-yl)-2-(3,5-difluorophenyl)ethylamino)-2-oxoethyl)-4,6-dihydro-1H-furo[3,4-c]pyrazole-3-carboxylic acid (456)

The carboxylic acid 456 was prepared (4.6 mg) according to the method presented for the synthesis of Example 60G utilizing 452C as starting material to provide (S)-1-(2-(1-(3-(3-carbamoyl-4-fluorophenyl)pyridin-2-yl)-2-(3,5-difluorophenyl)ethylamino)-2-oxoethyl)-4,6-dihydro-1H-furo[3,4-c]pyrazole-3-carboxylic acid: MS (m/z): 566.3 [M+H]$^+$. $^1$H NMR (400 MHz, cdcl$_3$) δ 8.83 (d, J=4.0 Hz, 1H), 7.88 (d, J=6.9 Hz, 1H), 7.66 (dd, J=21.3, 15.7 Hz, 1H), 7.60-7.58 (m, 1H), 7.24 (m, 2H), 6.98 (m, 1H), 6.68 (s, 1H), 6.57 (s, 1H), 6.16 (d, J=5.7 Hz, 3H), 5.45 (s, 1H), 5.25 (d, J=4.3 Hz, 2H), 4.97 (s, 2H), 4.85 (s, 2H), 3.13 (d, J=46.3 Hz, 1H), 3.05 (m, 1H).

Example 457

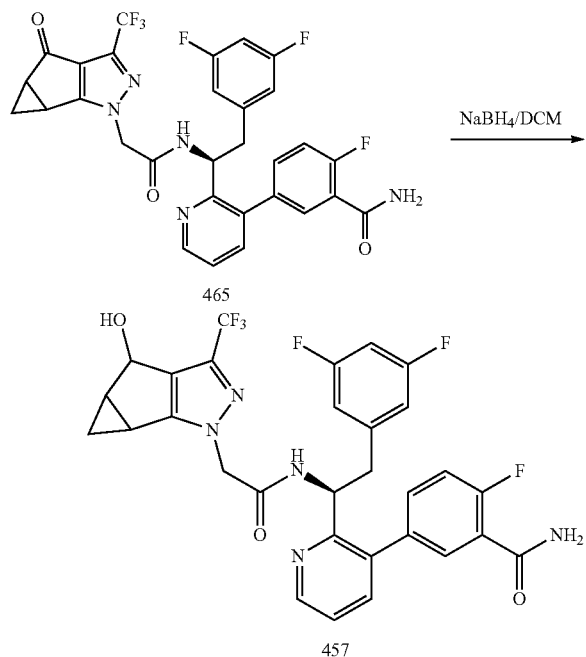

465

457

Synthesis of 5-(2-((1 S)-2-(3,5-difluorophenyl)-1-(2-(4-hydroxy-3-(trifluoromethyl)-4,4a,5,5a-tetrahydro-1H-cyclopropa[4,5]cyclopenta[1,2-c]pyrazol-1-yl)acetamido)ethyl)pyridin-3-yl)-2-fluorobenzamide (457)

The example 457 was prepared (2.6 mg) according to the method presented for the synthesis of Example 448 utilizing 465 as starting material: MS (m/z): 616.1 [M+H]⁺.

Example 458

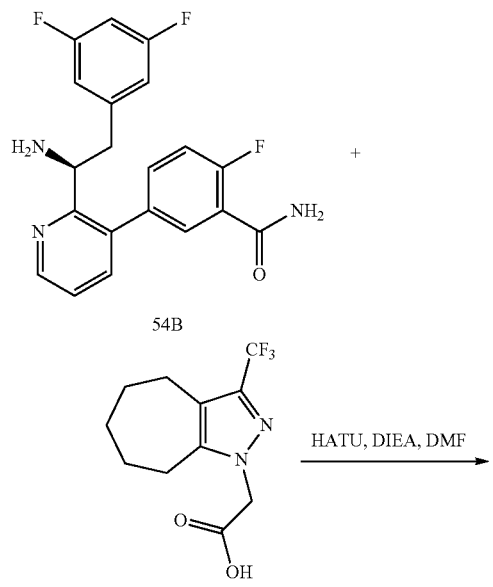

54B

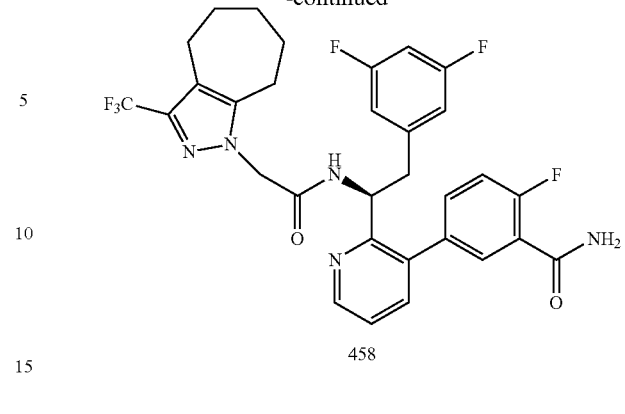

458

Synthesis of (S)-5-(2-(2-(3,5-difluorophenyl)-1-(2-(3-(trifluoromethyl)-5,6,7,8-tetrahydrocyclohepta[c]pyrazol-1(4H)-yl)acetamido)ethyl)pyridin-3-yl)-2-fluorobenzamide (458)

Example 458 was prepared (22 mg) according to the method presented for the synthesis of Example 13G utilizing 54B and 2-(3-(trifluoromethyl)-5,6,7,8-tetrahydrocyclohepta[c]pyrazol-1(4H)-yl)acetic acid to provide (S)-5-(2-(2-(3,5-difluorophenyl)-1-(2-(3-(trifluoromethyl)-5,6,7,8-tetrahydrocyclohepta[c]pyrazol-1(4H)-yl)acetamido)ethyl)pyridin-3-yl)-2-fluorobenzamide: MS (m/z): 616.6 [M+H]⁺; HPLC retention time 1.31 min (2-98% acetonitrile:water with 0.05% trifluoroacetic acid). $^1$H NMR (400 MHz, cdcl$_3$) δ 9.37 (d, J=7.5 Hz, 1H), 8.79-8.70 (m, 1H), 7.96-7.90 (m, 1H), 7.90-7.32 (m, 3H), 7.33-7.22 (m, 1H), 6.96 (d, J=10.7 Hz, 1H), 6.61 (t, J=5.6 Hz, 2H), 6.19 (d, J=5.7 Hz, 2H), 5.47 (dd, J=16.0, 7.5 Hz, 1H), 4.92-4.70 (m, 2H), 3.15 (dd, J=13.5, 6.9 Hz, 1H), 3.06-2.91 (m, 1H), 2.91-2.86 (m, 1H), 2.69-2.40 (m, 4H), 1.80 (d, J=5.1 Hz, 2H), 1.71-1.43 (m, 4H), 1.39 (dd, J=13.0, 6.7 Hz, 1H).

Example 459

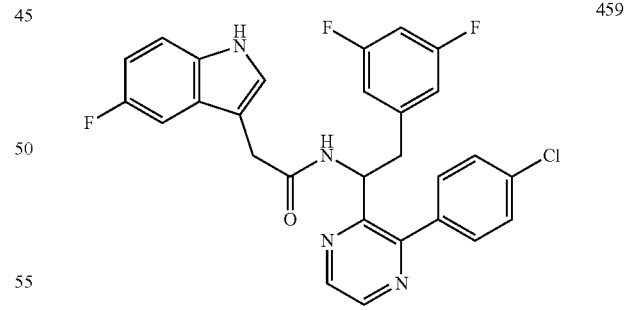

459

Synthesis of N-(1-(3-(4-chlorophenyl)pyrazin-2-yl)-2-(3,5-difluorophenyl)ethyl)-2-(5-fluoro-1H-indol-3-yl)acetamide (459)

Example 459 was prepared (11.3 mg) according to the method presented for the synthesis of Example 13G utilizing 443H and 2-(5-fluoro-1H-indol-3-yl)acetic acid to provide N-(1-(3-(4-chlorophenyl)pyrazin-2-yl)-2-(3,5-difluorophenyl)ethyl)-2-(5-fluoro-1H-indol-3-yl)acetamide: MS (m/z):

522.2 [M+H]⁺; ¹H NMR (400 MHz, dmso) δ 10.89 (s, 1H), 8.84 (d, J=7.8 Hz, 1H), 8.70 (s, 1H), 8.61 (s, 1H), 7.43 (s, 4H), 7.26 (dd, J=8.9, 4.5 Hz, 1H), 7.13 (d, J=10.9 Hz, 2H), 6.88 (dt, J=17.2, 9.0 Hz, 2H), 6.47 (d, J=7.2 Hz, 2H), 5.25 (d, J=7.6 Hz, 1H), 3.46 (s, 2H), 3.13-2.90 (m, 2H).

Example 460

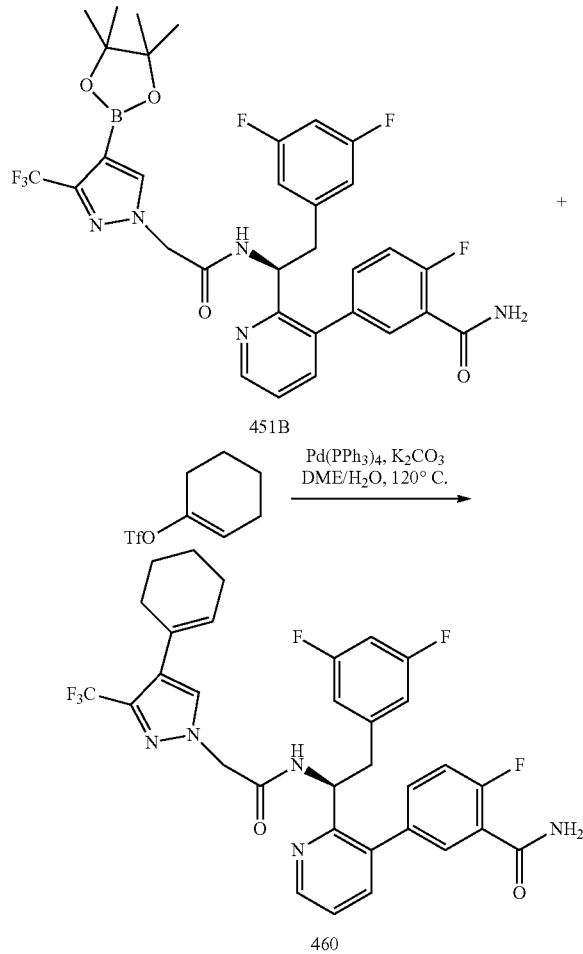

Synthesis of (S)-5-(2-(1-(2-(4-cyclohexenyl-3-(trifluoromethyl)-1H-pyrazol-1-yl)acetamido)-2-(3,5-difluorophenyl)ethyl)pyridin-3-yl)-2-fluorobenzamide (460)

Example 460 was prepared (4.9 mg) according to the method presented for the synthesis of Example 55F utilizing 451B and cyclohexenyl trifluoromethanesulfonate to provide (S)-5-(2-(1-(2-(4-cyclohexenyl-3-(trifluoromethyl)-1H-pyrazol-1-yl)acetamido)-2-(3,5-difluorophenyl)ethyl)pyridin-3-yl)-2-fluorobenzamide: MS (m/z): 628.3 [M+H]⁺; HPLC retention time 1.26 min (2-98% acetonitrile:water with 0.05% trifluoroacetic acid). ¹H NMR (400 MHz, cdcl₃) δ 9.25 (s, 1H), 8.77 (s, 1H), 8.02 (d, J=8.3 Hz, 1H), 7.80 (m, 2H), 7.51 (d, J=10.6 Hz, 1H), 7.41-7.22 (m, 2H), 6.93 (s, 1H), 6.66-6.63 (m, 1H), 6.59 (d, J=22.3 Hz, 1H), 6.18 (d, J=5.4 Hz, 2H), 5.88 (s, 1H), 5.51 (s, 1H), 4.88 (d, J=9.5 Hz, 2H), 3.22 (m, 1H), 3.14 (m, 1H), 2.16 (m, 4H), 1.73-1.58 (m, 4H).

Example 461

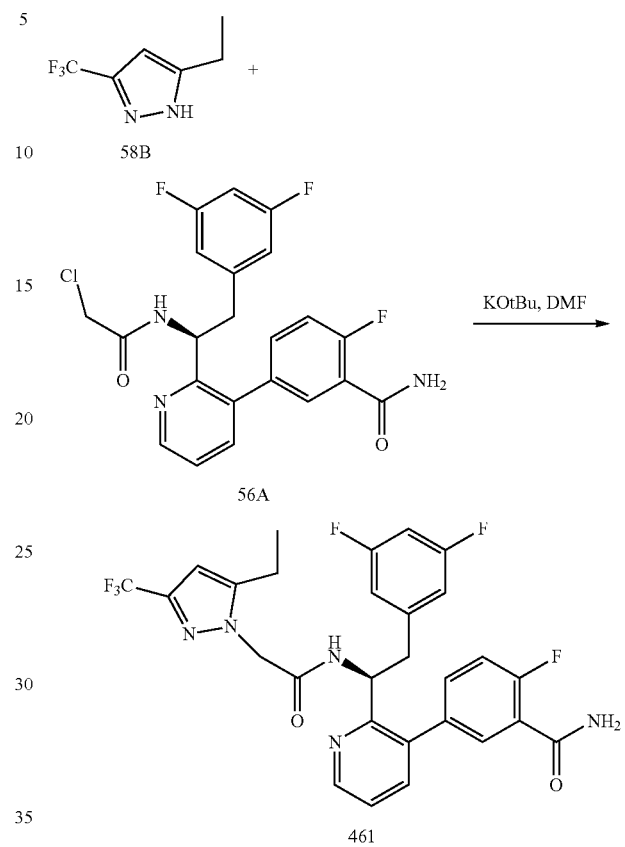

Synthesis of 5-(2-(2-(3,5-difluorophenyl)-1-(2-(5-ethyl-3-(trifluoromethyl)-1H-pyrazol-1-yl)acetamido)ethyl)pyridin-3-yl)-2-fluorobenzamide (461)

Example 461 was prepared (24 mg) according to the method presented for the synthesis of Example 58D utilizing 56A and 58B to provide (S)-5-(2-(2-(3,5-difluorophenyl)-1-(2-(5-ethyl-3-(trifluoromethyl)-1H-pyrazol-1-yl)acetamido)ethyl)pyridin-3-yl)-2-fluorobenzamide: MS (m/z): 576.2 [M+H]⁺; ¹H NMR (400 MHz, cdcl₃) δ 9.39 (d, J=7.6 Hz, 1H), 8.76 (d, J=5.4 Hz, 1H), 7.88 (m, 1H), 7.79 (s, 1H), 7.84-7.57 (m, 2H), 7.29 (d, J=8.5 Hz, 1H), 7.27-7.21 (m, 1H), 6.95 (d, J=9.6 Hz, 1H), 6.67-6.38 (m, 2H), 6.33 (s, 1H), 6.19 (d, J=5.8 Hz, 2H), 5.48 (dd, J=16.2, 7.6 Hz, 1H), 4.82 (q, J=16.7 Hz, 2H), 3.23-3.02 (m, 1H), 3.02-2.78 (m, 1H), 2.50 (dd, J=14.9, 7.5 Hz, 2H), 1.23 (t, J=7.5 Hz, 3H).

Example 462

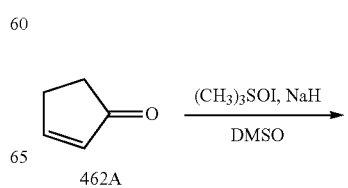

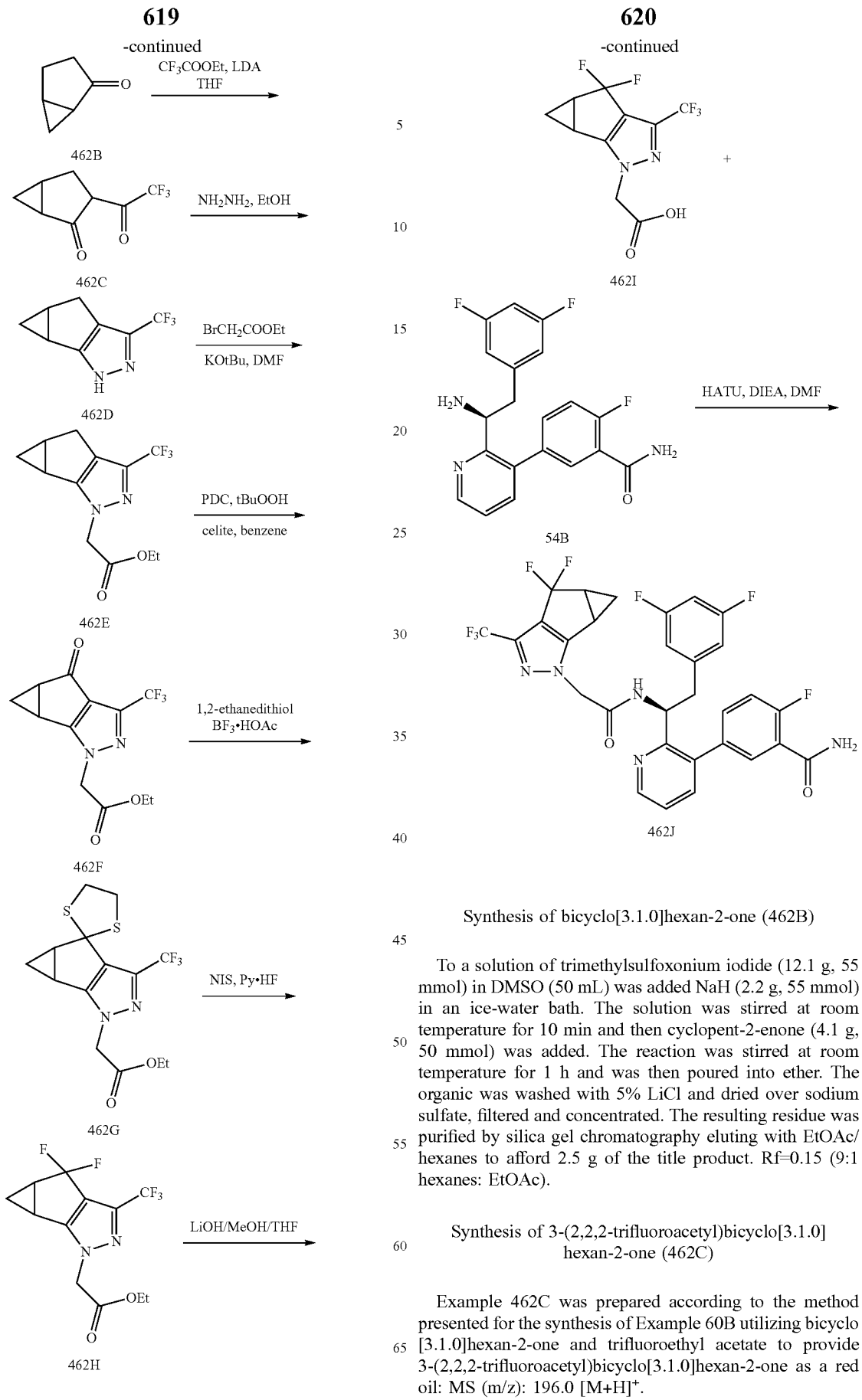

Synthesis of bicyclo[3.1.0]hexan-2-one (462B)

To a solution of trimethylsulfoxonium iodide (12.1 g, 55 mmol) in DMSO (50 mL) was added NaH (2.2 g, 55 mmol) in an ice-water bath. The solution was stirred at room temperature for 10 min and then cyclopent-2-enone (4.1 g, 50 mmol) was added. The reaction was stirred at room temperature for 1 h and was then poured into ether. The organic was washed with 5% LiCl and dried over sodium sulfate, filtered and concentrated. The resulting residue was purified by silica gel chromatography eluting with EtOAc/hexanes to afford 2.5 g of the title product. Rf=0.15 (9:1 hexanes: EtOAc).

Synthesis of 3-(2,2,2-trifluoroacetyl)bicyclo[3.1.0] hexan-2-one (462C)

Example 462C was prepared according to the method presented for the synthesis of Example 60B utilizing bicyclo[3.1.0]hexan-2-one and trifluoroethyl acetate to provide 3-(2,2,2-trifluoroacetyl)bicyclo[3.1.0]hexan-2-one as a red oil: MS (m/z): 196.0 [M+H]$^+$.

Synthesis of 3-(trifluoromethyl)-4,4a,5,5a-tetra-hydro-1H-cyclopropa[4,5]cyclopenta[1,2-c]pyrazole (462D)

Example 462D was prepared according to the method presented for the synthesis of Example 58B utilizing 3-(2,2,2-trifluoroacetyl)bicyclo[3.1.0]hexan-2-one and hydrazine hydrate to provide the title compound: MS (m/z): 189.1 [M+H]+.

Synthesis of ethyl 2-(3-(trifluoromethyl)-4,4a,5,5a-tetrahydro-1H-cyclopropa[4,5]cyclopenta[1,2-c]pyrazol-1-yl)acetate (462E)

Example 462E was prepared according to the method presented for the synthesis of Example 58D utilizing 462D and ethyl 2-bromoacetate to provide the title compound: MS (m/z): 275.1 [M+H]+.

Synthesis of ethyl 2-(4-oxo-3-(trifluoromethyl)-4,4a,5,5a-tetrahydro-1H-cyclopropa[4,5]cyclopenta[1,2-c]pyrazol-1-yl)acetate (462F)

Example 462F was prepared according to the method presented for the synthesis of Example 60D utilizing 462E to provide the title compound: MS (m/z): 275.1 [M+H]+.

Synthesis of ethyl 2-(3-(trifluoromethyl)-5,5a-dihydrospiro[cyclopropa[4,5]cyclopenta[1,2-c]pyrazole-4,2'-[1,3]dithiolan]-1(4aH)-yl)acetate (462G)

Example 462G was prepared according to the method presented for the synthesis of Example 60E utilizing 462F to provide the title compound: MS (m/z): 364.1 [M+H]+.

Synthesis of ethyl 2-(4,4-difluoro-3-(trifluoromethyl)-4,4a,5,5a-tetrahydro-1H-cyclopropa[4,5]cyclopenta[1,2-c]pyrazol-1-yl)acetate (462H)

Example 462H was prepared according to the method presented for the synthesis of Example 60F utilizing 462G to provide the title compound: MS (m/z): 311.2 [M+H]+.

Synthesis of 2-(4,4-difluoro-3-(trifluoromethyl)-4,4a,5,5a-tetrahydro-1H-cyclopropa[4,5]cyclopenta[1,2-c]pyrazol-1-yl)acetic acid (462I)

Example 462I was prepared according to the method presented for the synthesis of Example 60G utilizing 462H to provide the title compound: MS (m/z): 283.0 [M+H]+.

Synthesis of 5-(2-((1S)-1-(2-(4,4-difluoro-3-(trifluoromethyl)-4,4a,5,5a-tetrahydro-1H-cyclopropa[4,5]cyclopenta[1,2-c]pyrazol-1-yl)acetamido)-2-(3,5-difluorophenyl)ethyl)pyridin-3-yl)-2-fluorobenzamide (462J)

Example 462J was prepared (7.9 mg) according to the method presented for the synthesis of Example 13G utilizing 462I and 54B to provide the title compound: MS (m/z): 636.4 [M+H]+. 1H NMR of the mixture of diastereomers (400 MHz, cdcl3) δ 10.07 (d, J=7.2 Hz, 1H), 9.93 (d, J=6.6 Hz, 1H), 8.78 (d, J=5.4 Hz, 2H), 8.02 (d, J=4.6 Hz, 2H), 7.74 (dd, J=45.4, 39.5 Hz, 4H), 7.60 (m, 2H), 7.32 (t, J=9.8 Hz, 2H), 6.94 (s, 2H), 6.80-6.60 (m, 4H), 6.15 (dd, J=50.7, 43.2 Hz, 4H), 5.49 (dd, J=15.6, 7.5 Hz, 2H), 4.95-4.72 (m, 4H), 3.31-3.13 (m, 2H), 3.13-2.94 (m, 2H), 2.63 (m, 2H), 2.36 (m, 2H), 1.37 (dd, J=14.2, 7.3 Hz, 2H), 1.25 (s, 2H).

Example 463

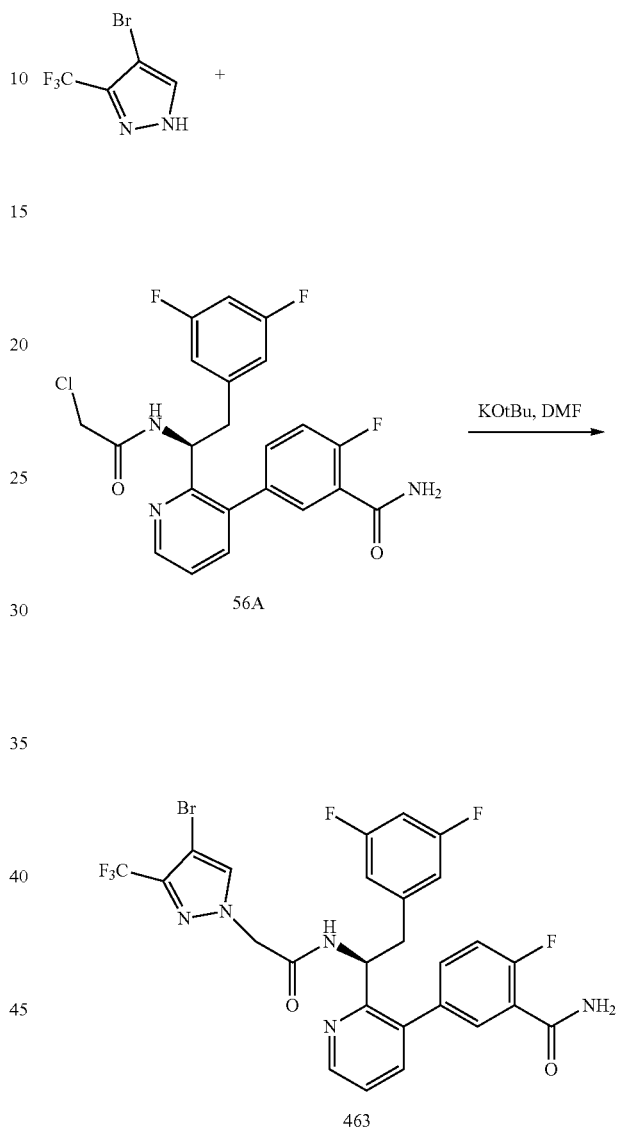

Synthesis of (S)-5-(2-(1-(2-(4-bromo-3-(trifluoromethyl)-1H-pyrazol-1-yl)acetamido)-2-(3,5-difluorophenyl)ethyl)pyridin-3-yl)-2-fluorobenzamide (463)

Example 463 was prepared (5.2 mg) according to the method presented for the synthesis of Example 58D utilizing 56A and 4-bromo-3-(trifluoromethyl)-1H-pyrazole to provide (S)-5-(2-(1-(2-(4-bromo-3-(trifluoromethyl)-1H-pyrazol-1-yl)acetamido)-2-(3,5-difluorophenyl)ethyl)pyridin-3-yl)-2-fluorobenzamide: MS (m/z): 626.6 [M+H]+; 1H NMR (400 MHz, cdcl3) δ 8.58 (d, J=4.7 Hz, 1H), 7.61 (d, J=10.6 Hz, 1H), 7.50 (d, J=7.6 Hz, 1H), 7.41 (s, 1H), 7.39-7.13 (m, 3H), 6.77 (s, 1H), 6.55 (t, J=8.7 Hz, 1H), 6.11 (d, J=6.3 Hz, 2H), 5.84 (s, 1H), 5.43 (dd, J=14.6, 7.9 Hz, 1H), 4.82 (s, 2H), 2.88 (dd, J=16.9, 9.0 Hz, 2H).

Example 464

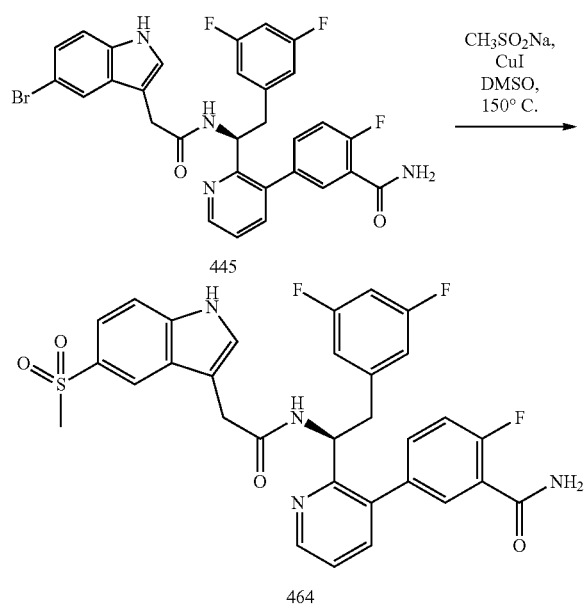

Synthesis of (S)-5-(2-(2-(3,5-difluorophenyl)-1-(2-(5-(methylsulfonyl)-1H-indol-3-yl)acetamido)ethyl)pyridin-3-yl)-2-fluorobenzamide (464)

A solution of (S)-5-(2-(1-(2-(5-bromo-1H-indol-3-yl)acetamido)-2-(3,5-difluorophenyl)ethyl)pyridin-3-yl)-2-fluorobenzamide (30 mg, 0.04 mmol), CuI (33 mg, 0.17 mmol) and sodium methanesulfinate (17 mg, 0.17 mmol) in DMSO (1.5 mL) was subjected to microwave heating at 150° C. for 30 min. The reaction mixture was purified by reverse phase HPLC eluting with acetonitrile/water to afford 2.7 mg of the title compound: MS (m/z): 607.3 [M+H]; $^1$H NMR (400 MHz, cdcl$_3$) δ 9.00 (s, 1H), 8.52 (s, 1H), 8.39 (d, J=5.3 Hz, 1H), 8.04-7.89 (m, 2H), 7.65 (dd, J=27.6, 8.5 Hz, 2H), 7.50 (d, J=8.6 Hz, 1H), 7.38-7.23 (m, 1H), 6.92 (m, 1H), 6.58 (m, 1H), 6.28 (d, J=5.9 Hz, 1H), 6.08 (s, 1H), 5.42 (d, J=7.9 Hz, 1H), 3.81 (d, J=15.7 Hz, 1H), 3.66 (d, J=15.7 Hz, 1H), 3.22-3.05 (m, 1H), 3.02 (s, 3H), 2.99-2.96 (m, 1H).

Example 465

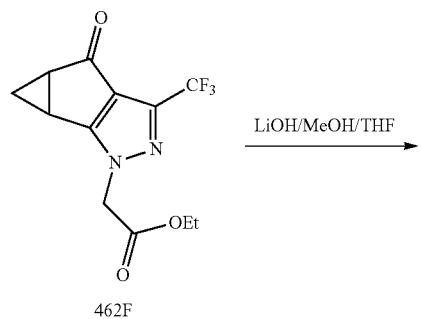

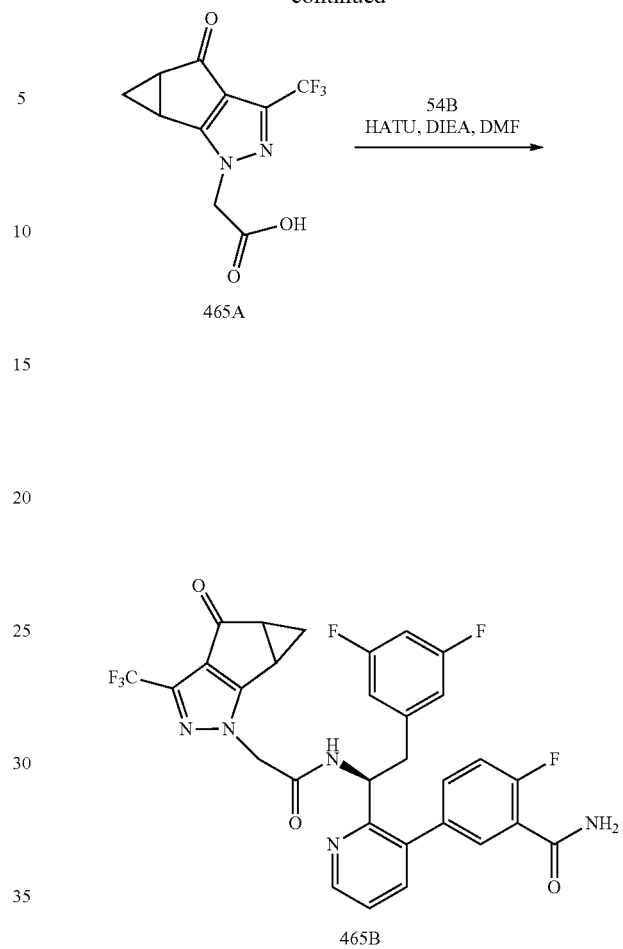

Synthesis of 2-(4-oxo-3-(trifluoromethyl)-4,4a,5,5a-tetrahydro-1H-cyclopropa[4,5]cyclopenta[1,2-c]pyrazol-1-yl)acetic acid (465A)

Example 465A was prepared according to the method presented for the synthesis of Example 60G utilizing 462F to provide the title compound: MS (m/z): 259.0 [M−H]$^-$.

Synthesis of 5-(2-((1S)-2-(3,5-difluorophenyl)-1-(2-(4-oxo-3-(trifluoromethyl)-4,4a,5,5a-tetrahydro-1H-cyclopropa[4,5]cyclopenta[1,2-c]pyrazol-1-yl)acetamido)ethyl)pyridin-3-yl)-2-fluorobenzamide (465B)

Example 465B was prepared (18.7 mg) according to the method presented for the synthesis of Example 13G utilizing 465A and 54B to provide the title compound: MS (m/z): 614.4 [M+H]$^+$. $^1$H NMR of the mixture of diastereomers (400 MHz, cdcl$_3$) δ 10.21 (d, J=7.2 Hz, 1H), 10.06 (d, J=7.0 Hz, 1H), 8.79 (d, J=5.4 Hz, 2H), 8.11-8.00 (m, 2H), 7.90-7.77 (m, 4H), 7.63 (m, 2H), 7.32 (t, J=9.9 Hz, 2H), 6.94-6.67 (m, 4H), 6.63 (t, J=9.0 Hz, 2H), 6.24 (m, 4H), 5.51 (dd, J=14.8, 7.2 Hz, 2H), 5.01-4.79 (m, 4H), 3.32-3.15 (m, 2H), 3.15-2.97 (m, 2H), 2.75-2.69 (m, 2H), 2.61 (d, J=4.4 Hz, 2H), 1.85-1.57 (m, 4H).

Example 466 and 467

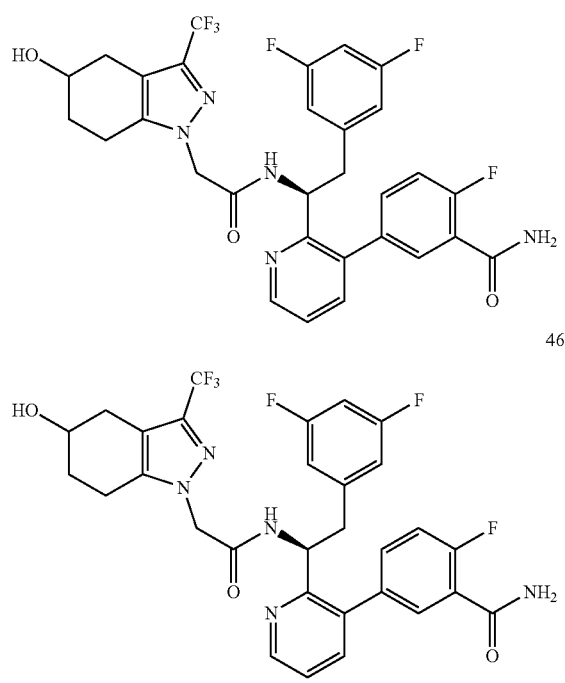

Synthesis of 5-(2-((1S)-2-(3,5-difluorophenyl)-1-(2-(5-hydroxy-3-(trifluoromethyl)-4,5,6,7-tetrahydro-1H-indazol-1-yl)acetamido)ethyl)pyridin-3-yl)-2-fluorobenzamide (466) and (467)

Compound 448 was synthesized as a mixture of two diastereomers. Separation of 448 by chiral HPLC (Chiralpak IA, Heptane:Ethanol 80:20) provided 466 (5 mg, fast eluting peak, MS (m/z): 636.4 [M+H]$^+$) and 467 (7 mg, slow eluting peak, MS (m/z): 636.4 [M+H]$^+$).

Example 468

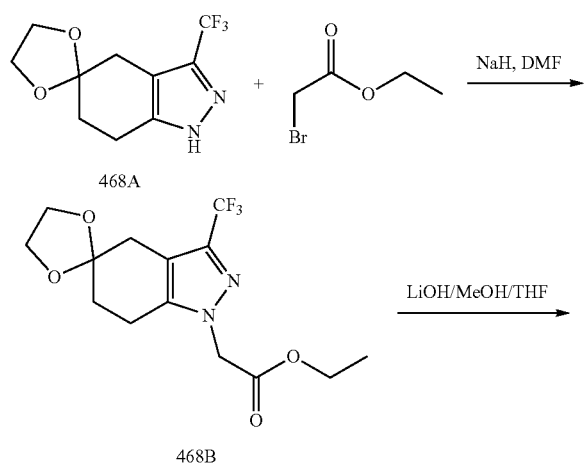

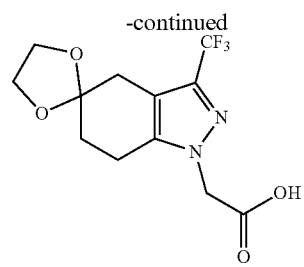

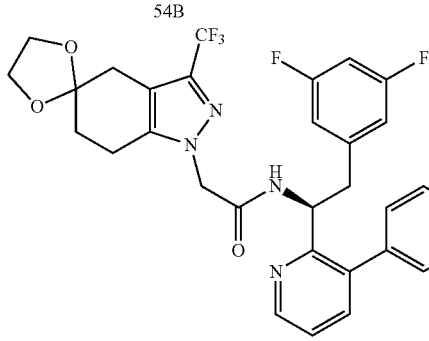

Synthesis of ethyl 2-(3'-(trifluoromethyl)-6',7'-dihydrospiro[[1,3]dioxolane-2,5'-indazole]-1'(4'H)-yl)acetate (468B)

To a solution of 3'-(trifluoromethyl)-1',4',6',7'-tetrahydrospiro[[1,3]dioxolane-2,5'-indazole] (5.0 g, 20 mmol) in DMF (100 mL) was added NaH (528 mg, 22 mmol) and ethyl 2-bromoacetate (4.0 g, 24 mmol). The reaction was stirred at 80° C. for 2 h and was then poured into ethyl acetate and washed with saturated NH$_4$Cl solution and brine. The organic layer was dried over sodium sulfate, filtered and concentrated. MS (m/z): 335.2 [M+H]$^+$; HPLC retention time 2.56 min (2-98% acetonitrile:water with 0.05% trifluoroacetic acid).

Synthesis of 2-(3'-(trifluoromethyl)-6',7'-dihydrospiro[[1,3]dioxolane-2,5'-indazole]-1'(4'H)-yl) acetic acid (468C)

The carboxylic acid 468C was prepared according to the method presented for the synthesis of Example 60G utilizing ethyl 2-(3'-(trifluoromethyl)-6',7'-dihydrospiro[[1,3]dioxolane-2,5'-indazole]-1'(4'H)-yl)acetate to provide 2-(3'-(trifluoromethyl)-6',7'-dihydrospiro[[1,3]dioxolane-2,5'-indazole]-1'(4'H)-yl)acetic acid: MS (m/z): 306.8 [M+H]$^+$; HPLC retention time 2.20 min (2-98% acetonitrile:water with 0.05% trifluoroacetic acid).

Synthesis of (S)-5-(2-(2-(3,5-difluorophenyl)-1-(2-(3'-(trifluoromethyl)-6',7'-dihydrospiro[[1,3]dioxolane-2,5'-indazole]-1'(4'H)-yl)acetamido)ethyl)pyridin-3-yl)-2-fluorobenzamide (468D)

Example 468D was prepared (5.7 mg) according to the method presented for the synthesis of Example 13G utilizing 54B and 2-(3'-(trifluoromethyl)-6',7'-dihydrospiro[[1,3]dioxolane-2,5'-indazole]-1'(4'H)-yl)acetic acid to provide the title compound: MS (m/z): 660.3 [M+H]+; HPLC retention time 1.06 min (2-98% acetonitrile:water with 0.05% trifluoroacetic acid). $^1$H NMR (400 MHz, cd$_3$od) δ 8.68 (d, J=3.0 Hz, 1H), 7.56 (dd, J=7.8, 1.6 Hz, 1H), 7.46-7.33 (m, 2H), 7.28 (s, 1H), 7.23 (dd, J=24.0, 13.5 Hz, 1H), 6.65 (d, J=9.1 Hz, 1H), 6.33 (d, J=6.3 Hz, 2H), 5.41-5.31 (m, 1H), 4.85-4.76 (m, 2H), 3.99 (s, 4H), 3.35-3.25 (m, 2H), 3.05 (dt, J=19.7, 13.0 Hz, 2H), 2.82-2.68 (m, 2H), 2.63 (d, J=6.8 Hz, 1H), 1.92 (dd, J=14.2, 7.5 Hz, 3H).

Example 469

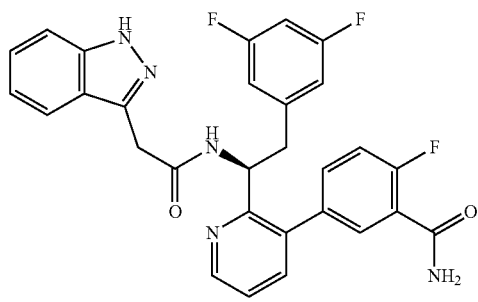

469

Synthesis of 5-(2-(1-(2-(1H-indazol-3-yl)acetamido)-2-(3,5-difluorophenyl)ethyl)pyridin-3-yl)-2-fluorobenzamide (469)

Example 469 was prepared (21.5 mg) according to the method presented for the synthesis of Example 13G utilizing 54B and 2-(1H-indazol-3-yl)acetic acid to provide the title compound: MS (m/z): 530.5 [M+H]+; $^1$H NMR (400 MHz, dmso) δ 8.91 (d, J=8.0 Hz, 1H), 8.70 (d, J=4.8 Hz, 1H), 7.62 (dd, J=18.7, 9.7 Hz, 3H), 7.48 (d, J=6.5 Hz, 1H), 7.45-7.35 (m, 4H), 7.25 (dd, J=15.4, 8.1 Hz, 2H), 6.93 (dd, J=14.6, 7.5 Hz, 2H), 6.57 (d, J=6.7 Hz, 2H), 5.15 (t, J=7.7 Hz, 1H), 3.78-3.64 (m, 2H), 3.02 (m, 2H).

Example 470

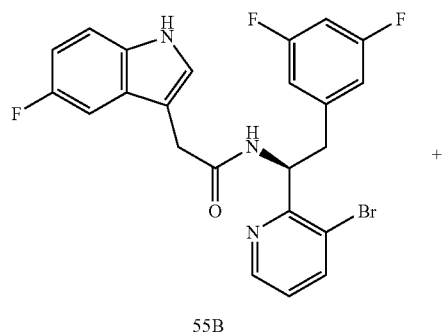

55B

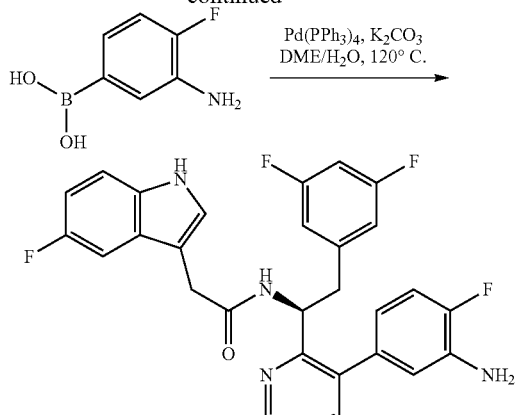

470

Synthesis of (S)—N-(1-(3-(3-amino-4-fluorophenyl)pyridin-2-yl)-2-(3,5-difluorophenyl)ethyl)-2-(5-fluoro-1H-indol-3-yl)acetamide (470)

To a solution of (S)—N-(1-(3-bromopyridin-2-yl)-2-(3,5-difluorophenyl)ethyl)-2-(5-fluoro-1H-indol-3-yl)acetamide (900 mg, 1.8 mmol) in a mixture of DME (6 mL) and H$_2$O (3 mL) was added 3-amino-4-fluorophenylboronic acid (370 mg, 2.4 mmol) and K$_2$CO$_3$ (552 mg, 4.0 mmol) and tetrakis triphenylphosphine palladium (115 mg, 0.1 mmol). The reaction tube was sealed and heated in a microwave reactor at 120° C. for 30 min. The reaction mixture was poured into ethyl acetate and washed with saturated NH$_4$Cl solution. The organic layer was dried over sodium sulfate, filtered and concentrated. The resulting residue was purified by silica gel chromatography eluting with EtOAc/hexanes to afford 630 mg of the title product. MS (m/z): 519.1 [M+H]+; HPLC retention time 3.85 min (2-98% acetonitrile:water with 0.05% trifluoroacetic acid). $^1$H NMR (400 MHz, cdcl$_3$) δ 8.40 (s, 1H), 8.15 (s, 1H), 7.52 (s, 1H), 7.33-7.07 (m, 4H), 7.05-6.86 (m, 2H), 6.48 (dd, J=36.6, 27.7 Hz, 3H), 6.37 (s, 1H), 6.12 (d, J=7.2 Hz, 2H), 5.62 (q, J=7.6 Hz, 1H), 3.81 (m, 1H), 3.67 (s, 2H), 2.86 (m, 1H).

Example 471

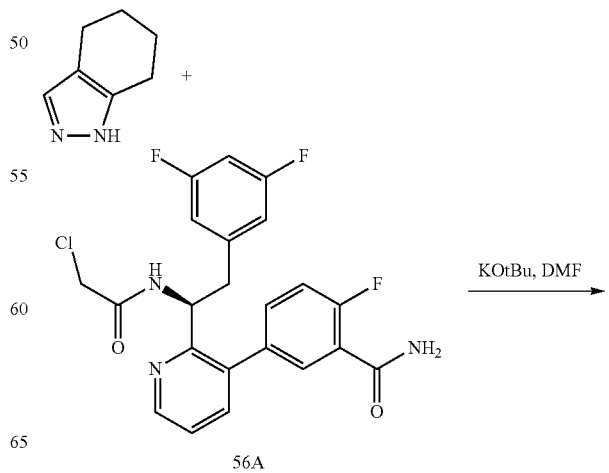

56A

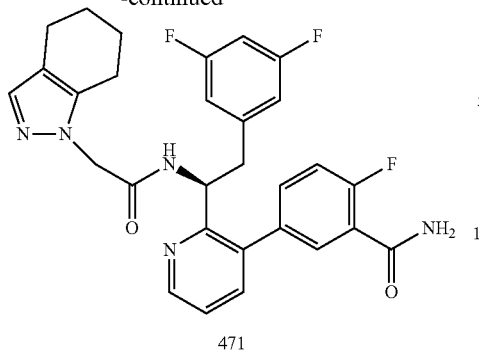

471

Synthesis of (S)-5-(2-(2-(3,5-difluorophenyl)-1-(2-(4,5,6,7-tetrahydro-1H-indazol-1-yl)acetamido)ethyl)pyridin-3-yl)-2-fluorobenzamide (471)

Example 471 was prepared (21 mg) according to the method presented for the synthesis of Example 58D utilizing 56A and 4,5,6,7-tetrahydro-1H-indazole to provide the title compound: MS (m/z): 534.0 [M+H]+; $^1$H NMR (400 MHz, cdcl$_3$) 9.51 (s, 1H), 8.79 (d, J=5.3 Hz, 1H), 7.94 (d, J=7.8 Hz, 1H), 7.68 (dd, J=28.6, 21.9 Hz, 1H), 7.59-7.53 (m, 1H), 7.53-7.19 (m, 2H), 6.97 (s, 1H), 6.61 (s, 1H), 6.22 (dd, J=13.2, 6.5 Hz, 2H), 5.46 (d, J=6.8 Hz, 1H), 4.98 (ddd, J=41.3, 20.7, 13.7 Hz, 2H), 3.18 (dd, J=12.9, 6.9 Hz, 1H), 3.11-2.95 (m, 1H), 2.71 (t, J=6.2 Hz, 1H), 2.52 (d, J=14.9 Hz, 3H), 1.83 (m, 2H), 1.77 (m, 2H).

Example 472

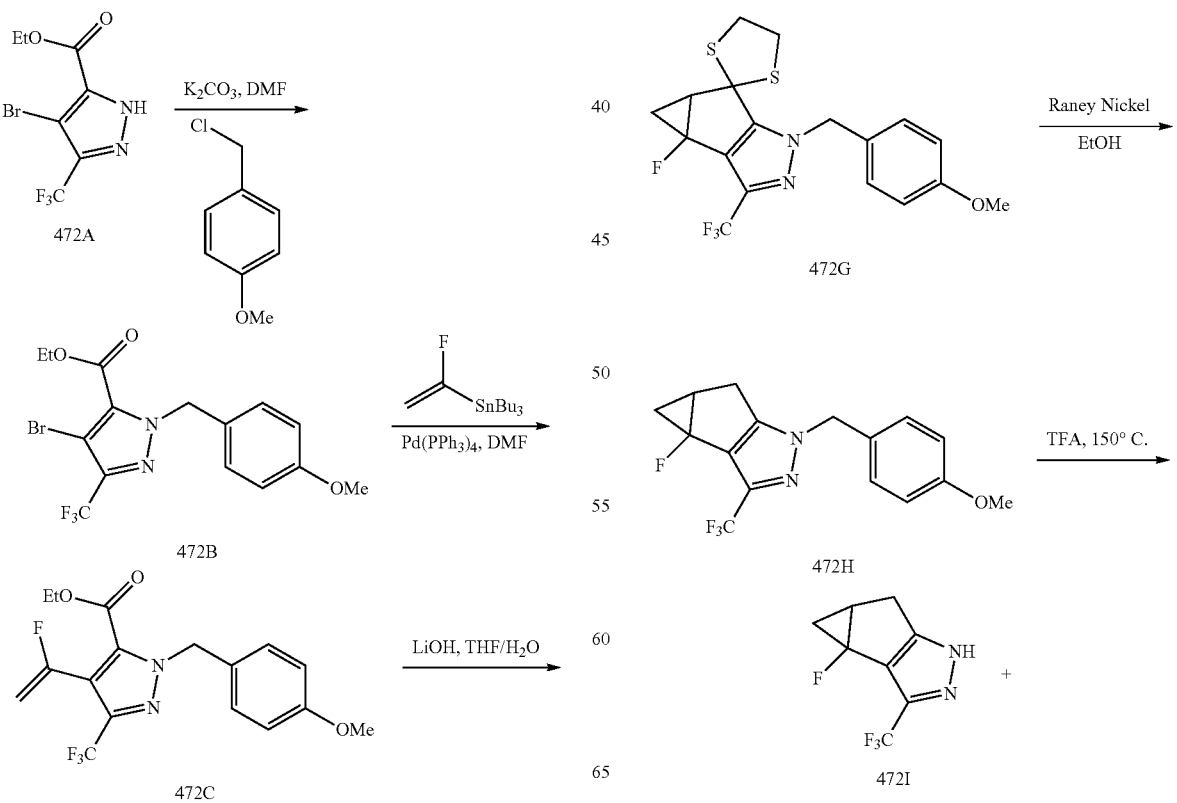

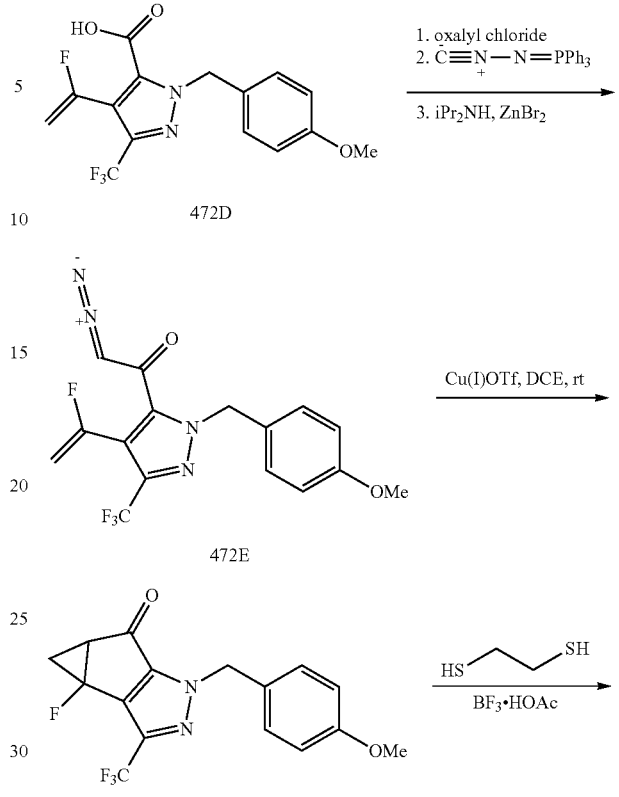

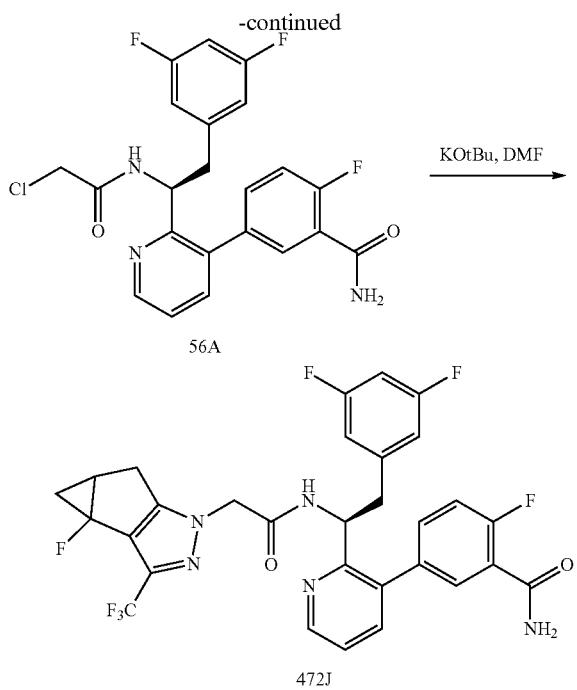

Synthesis of ethyl 4-bromo-1-(4-methoxybenzyl)-3-(trifluoromethyl)-1H-pyrazole-5-carboxylate (472B)

To a solution of ethyl 4-bromo-3-(trifluoromethyl)-1H-pyrazole-5-carboxylate (2.0 g, 7.0 mmol) in DMF (10 mL) was added $K_2CO_3$ (1.2 g, 8.4 mmol) and 1-(chloromethyl)-4-methoxybenzene (1.2 g, 7.7 mmol). The reaction was stirred at room temperature overnight and was then poured into ethyl acetate and washed with saturated $NH_4Cl$ solution and brine. The organic layer was dried over sodium sulfate, filtered and concentrated. The resulting residue was purified by silica gel chromatography eluting with EtOAc/hexanes to afford 2.5 g of the title product. MS (m/z): 406.6 $[M+H]^+$; HPLC retention time 1.60 min (2-98% acetonitrile:water with 0.05% trifluoroacetic acid).

Synthesis of ethyl 4-(1-fluorovinyl)-1-(4-methoxybenzyl)-3-(trifluoromethyl)-1H-pyrazole-5-carboxylate (472C)

To a solution of ethyl 4-bromo-1-(4-methoxybenzyl)-3-(trifluoromethyl)-1H-pyrazole-5-carboxylate (460 mg, 1.13 mmol) in DMF (6 mL) was added tributyl(1-fluorovinyl)stannane (492 mg, 1.4 mmol) and tetrakis triphenylphosphine palladium (130 mg, 0.12 mmol). The reaction was degassed with argon and heated at 100° C. overnight. The mixture was cooled to room temperature and then filtered through a pad of celite. The filtrate was diluted with ethyl acetate and washed with 5% LiCl solution and brine. The organic layer was dried over sodium sulfate, filtered and concentrated. The resulting residue was purified by silica gel chromatography eluting with EtOAc/hexanes to afford 400 mg of the title product. MS (m/z): 373.3 $[M+H]^+$; HPLC retention time 1.61 min (2-98% acetonitrile:water with 0.05% trifluoroacetic acid).

Synthesis of 4-(1-fluorovinyl)-1-(4-methoxybenzyl)-3-(trifluoromethyl)-1H-pyrazole-5-carboxylic acid (472D)

The carboxylic acid 472D was prepared according to the method presented for the synthesis of Example 60G utilizing ethyl 4-(1-fluorovinyl)-1-(4-methoxybenzyl)-3-(trifluoromethyl)-1H-pyrazole-5-carboxylate to provide 4-(1-fluorovinyl)-1-(4-methoxybenzyl)-3-(trifluoromethyl)-1H-pyrazole-5-carboxylic acid: MS (m/z): 342.8 $[M-H]^-$; HPLC retention time 1.30 min (2-98% acetonitrile:water with 0.05% trifluoroacetic acid).

Synthesis of 2-diazo-1-(4-(1-fluorovinyl)-1-(4-methoxybenzyl)-3-(trifluoromethyl)-1H-pyrazol-5-yl)ethanone (472E)

To a solution of 4-(1-fluorovinyl)-1-(4-methoxybenzyl)-3-(trifluoromethyl)-1H-pyrazole-5-carboxylic acid (34 mg, 0.1 mmol) in dichloroethane (1 mL) was added DMF (0.01 mL) and oxalyl chloride (25 mg, 0.2 mmol). The reaction was stirred at room temperature for 30 min. After removing the volatiles in vacuo, the residue was dissolved in 1 mL dichloroethane. This solution was added to a suspension of isocyanoiminotriphenylphosphorane (45 mg, 0.15 mmol) in 1 mL dichloroethane. The reaction was stirred at room temperature for 1 h and water (0.5 mL) was added. The mixture was stirred overnight. The reaction was diluted with dichloromethane and washed with brine. The organic layer was dried over sodium sulfate, filtered and concentrated. The resulting residue was purified by silica gel chromatography eluting with EtOAc/hexanes to afford 30 mg of (E)-2-(4-(1-fluorovinyl)-1-(4-methoxybenzyl)-3-(trifluoromethyl)-1H-pyrazol-5-yl)-2-oxoacetohydrazonoyl chloride: MS (m/z): 405.3 $[M+H]^+$; HPLC retention time 1.40 min (2-98% acetonitrile:water with 0.05% trifluoroacetic acid). The product from the previous step was dissolved in 1 mL dichloroethane. To this solution was added diisopropylamine (10 mg, 0.096 mmol) and $ZnBr_2$ (3.3 mg, 0.015 mmol). The resulting solution was stirred at room temperature for 3 days. After removing the volatile in vacuo, the resulting residue was purified by reverse phase HPLC eluting with acetonitrile/water to afford 10 mg of the title compound: MS (m/z): 369.0 $[M+H]^+$.

Synthesis of 3b-fluoro-1-(4-methoxybenzyl)-3-(trifluoromethyl)-4,4a-dihydro-1H-cyclopropa[3,4]cyclopenta[1,2-c]pyrazol-5(3bH)-one (472F)

To a solution of 2-diazo-1-(4-(1-fluorovinyl)-1-(4-methoxybenzyl)-3-(trifluoromethyl)-1H-pyrazol-5-yl)ethanone (10 mg, 0.028 mmol) in dichloroethane (1 mL) was added Cu(OTf) (10 mg, 0.034 mmol). The reaction was stirred at room temperature for 3 h. After removing the volatile in vacuo, the resulting residue was purified by reverse phase HPLC eluting with acetonitrile/water to afford 5 mg of the title compound: MS (m/z): 341.0 $[M+H]^+$.

Synthesis of 3b-fluoro-1-(4-methoxybenzyl)-3-(trifluoromethyl)-1,3b,4,4a-tetrahydrospiro[cyclopropa[3,4]cyclopenta[1,2-c]pyrazole-5,2'-[1,3]dithiolane] (472G)

Example 472G was prepared according to the method presented for the synthesis of Example 60E utilizing 472F to provide the title compound: MS (m/z): 417.1 $[M+H]^+$.

Synthesis of 3b-fluoro-1-(4-methoxybenzyl)-3-(trifluoromethyl)-3b,4,4a,5-tetrahydro-1H-cyclopropa[3,4]cyclopenta[1,2-c]pyrazole (472H)

To a solution of 472G (40 mg, 0.096 mmol) in ethanol (2 mL) was added Raney Nickel (1 mL slurry). The reaction was stirred at room temperature for 5 min. The insoluble solid were removed by filtration through a pad of celite. After removing the volatile in vacuo, the resulting residue was purified by reverse phase HPLC eluting with acetonitrile/water to afford the title compound: MS (m/z): 327.0 [M+H]$^+$.

Synthesis of 3b-fluoro-3-(trifluoromethyl)-3b,4,4a, 5-tetrahydro-1H-cyclopropa[3,4]cyclopenta[1,2-c] pyrazole (472I)

The solution of 472H (20 mg, 0.06 mmol) in TFA (1 mL) was subjected to microwave heating at 150° C. for 10 min. After removing the volatile in vacuo, the resulting crude was used in the next step without further purification: MS (m/z): 207.1 [M+H]$^+$.

Synthesis of 5-(2-((1S)-2-(3,5-difluorophenyl)-1-(2-(3b-fluoro-3-(trifluoromethyl)-3b,4,4a,5-tetrahydro-1H-cyclopropa[3,4]cyclopenta[1,2-c]pyrazol-1-yl) acetamido)ethyl)pyridin-3-yl)-2-fluorobenzamide (472J)

Example 472J was prepared (1.0 mg) according to the method presented for the synthesis of Example 13G utilizing 472I and 54B to provide the title compound: MS (m/z): 618.1 [M+H]$^+$. $^1$H NMR of the mixture of diastereomers (400 MHz, cdcl$_3$) δ 9.45 (m, 1H), 9.30 (m, 1H), 8.74 (d, J=4.1 Hz, 2H), 7.93 (s, 2H), 7.72 (s, 2H), 7.59 (s, 2H), 7.24 (m, 4H), 6.89 (s, 2H), 6.61 (s, 2H), 6.33 (s, 2H), 6.19 (s, 4H), 5.48 (s, 2H), 4.82-4.56 (m, 4H), 3.14 (m, 2H), 3.04 (m, 2H), 2.47 (m, 6H), 1.77 (m, 2H), 0.84 (m, 2H).

Example 473

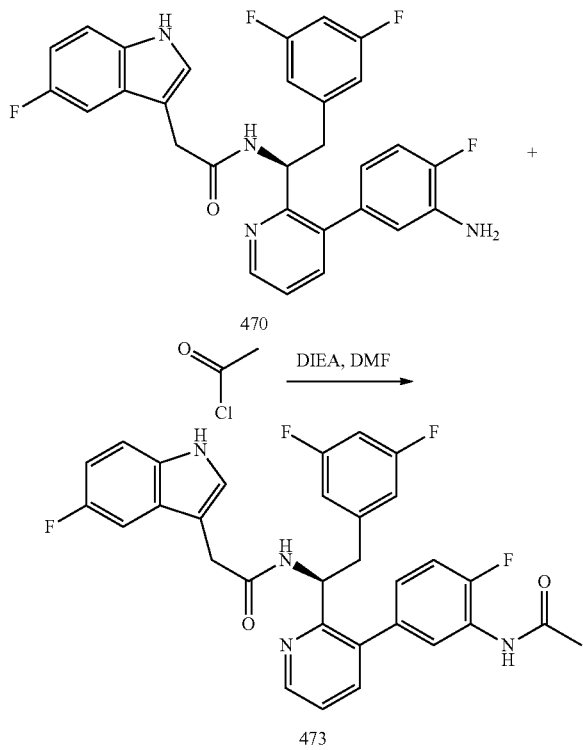

Synthesis of (S)—N-(1-(3-(3-acetamido-4-fluorophenyl)pyridin-2-yl)-2-(3,5-difluorophenyl)ethyl)-2-(5-fluoro-1H-indol-3-yl)acetamide (473)

To a solution of(S)—N-(1-(3-(3-amino-4-fluorophenyl) pyridin-2-yl)-2-(3,5-difluorophenyl)ethyl)-2-(5-fluoro-1H-indol-3-yl)acetamide (10 mg, 0.02 mmol) in DMF (1 mL) was added acetyl chloride (2.4 mg, 0.03 mmol) and DIEA (3.9 mg, 0.03 mmol). The reaction was stirred at room temperature for 30 min. The reaction mixture was then purified by reverse phase HPLC eluting with acetonitrile/water to afford 6.7 mg of the title compound. MS (m/z): 561.0 [M+H]$^+$; HPLC retention time 3.64 min (2-98% acetonitrile:water with 0.05% trifluoroacetic acid). $^1$H NMR (400 MHz, cdcl$_3$) δ 8.58 (d, J=5.3 Hz, 1H), 8.24 (d, J=31.7 Hz, 2H), 8.14 (d, J=7.7 Hz, 3H), 7.80-7.70 (m, 1H), 7.52 (s, 1H), 7.42-7.35 (m, 1H), 7.27 (d, J=12.7 Hz, 1H), 6.88 (dd, J=21.1, 9.4 Hz, 2H), 6.46 (s, 1H), 6.28 (d, J=5.9 Hz, 2H), 5.49-5.41 (m, 1H), 3.63 (d, J=2.7 Hz, 2H), 3.18 (d, J=9.7 Hz, 1H), 3.07 (d, J=6.8 Hz, 1H), 2.28 (s, 3H)

Example 474

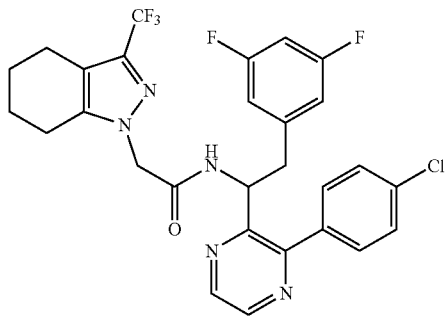

Synthesis of N-(1-(3-(4-chlorophenyl)pyrazin-2-yl)-2-(3,5-difluorophenyl)ethyl)-2-(3-(trifluoromethyl)-4,5,6,7-tetrahydro-1H-indazol-1-yl)acetamide (474)

Example 474 was prepared (10.7 mg) according to the method presented for the synthesis of Example 13G utilizing 443H and 2-(3-(trifluoromethyl)-4,5,6,7-tetrahydro-1H-indazol-1-yl)acetic acid to provide the title product: MS (m/z): 576.2 [M+H]$^+$; $^1$H NMR (400 MHz, dmso) δ 9.10 (d, J=8.1 Hz, 1H), 8.75 (s, 1H), 8.66 (s, 1H), 7.46 (dd, J=24.0, 8.4 Hz, 4H), 6.98 (t, J=9.4 Hz, 2H), 6.52 (d, J=6.9 Hz, 2H), 5.31 (d, J=7.2 Hz, 1H), 4.74 (s, 2H), 3.00 (dd, J=36.7, 29.6 Hz, 2H), 2.46 (m, 4H), 2.33 (m, 1H), 2.27 (m, 1H), 1.63 (s, 4H).

Example 475

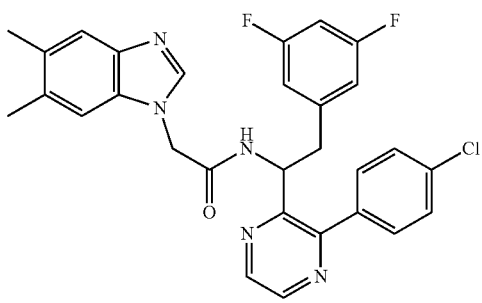

Synthesis of N-(1-(3-(4-chlorophenyl)pyrazin-2-yl)-2-(3,5-difluorophenyl)ethyl)-2-(5,6-dimethyl-1H-benzo[d]imidazol-1-yl)acetamide (475)

Example 475 was prepared (8.3 mg) according to the method presented for the synthesis of Example 13 G utilizing 443H and 2-(5,6-dimethyl-1H-benzo[d]imidazol-1-yl) acetic acid to provide the title product: MS (m/z): 532.1 [M+H]+; $^1$H NMR (400 MHz, dmso) δ 9.42 (d, J=8.0 Hz, 1H), 8.79 (s, 1H), 8.67 (s, 1H), 7.43 (dd, J=21.2, 8.3 Hz, 4H), 7.22 (d, J=6.5 Hz, 1H), 7.10 (s, 1H), 6.98 (s, 2H), 6.53 (d, J=7.1 Hz, 2H), 5.31 (d, J=7.6 Hz, 1H), 5.11 (s, 2H), 3.17-3.11 (m, 1H), 3.13-2.87 (m, 1H), 2.34 (s, 3H), 2.31 (s, 3H).

Example 476

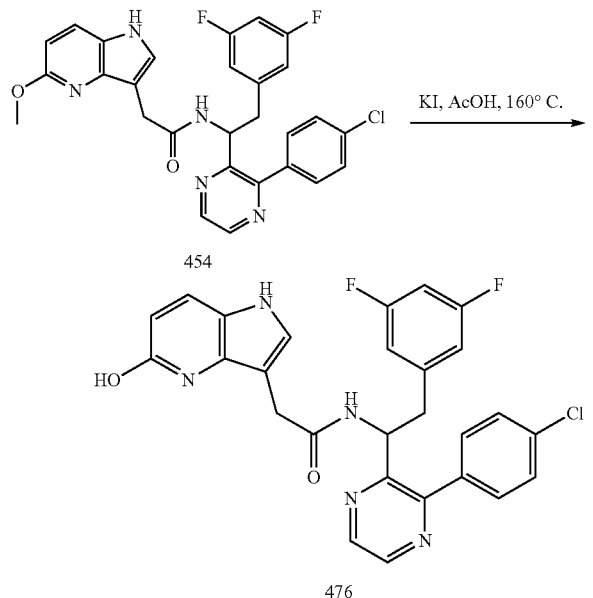

Synthesis of N-(1-(3-(4-chlorophenyl)pyrazin-2-yl)-2-(3,5-difluorophenyl)ethyl)-2-(5-hydroxy-1H-pyrrolo[3,2-b]pyridin-3-yl)acetamide (476)

A solution of N-(1-(3-(4-chlorophenyl)pyrazin-2-yl)-2-(3,5-difluorophenyl)ethyl)-2-(5-methoxy-1H-pyrrolo[3,2-b]pyridin-3-yl)acetamide (4.2 mg, 0.008 mmol) and KI (20 mg, 0.12 mmol) in 1 mL acetic acid in a sealed tube was subjected to microwave heating at 160° C. for 10 min. After removing the volatile in vacuo, the residue purified by reverse phase HPLC eluting with acetonitrile/water to afford 3.3 mg of the title compound. MS (m/z): 520.1 [M+H]+; $^1$H NMR (400 MHz, dmso) δ 11.38 (s, 1H), 8.82-8.70 (m, 2H), 8.63 (s, 1H), 7.79 (d, J=8.9 Hz, 1H), 7.44 (d, J=3.5 Hz, 4H), 7.13 (s, 1H), 6.90 (s, 1H), 6.42 (d, J=6.0 Hz, 2H), 6.29 (d, J=9.4 Hz, 1H), 5.29 (d, J=7.6 Hz, 1H), 3.45 (d, J=8.8 Hz, 2H), 3.21-2.91 (m, 2H).

Example 477

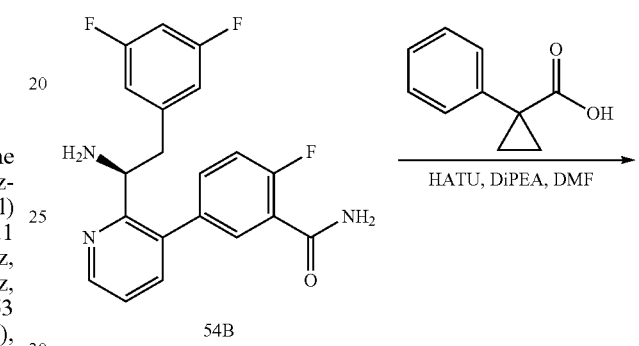

Synthesis of (S)-5-(2-(2-(3,5-difluorophenyl)-1-(1-phenylcyclopropanecarboxamido)ethyl)pyridin-3-yl)-2-fluorobenzamide (477)

The title compound was prepared according to the method presented in the synthesis of 34E substituting 1-phenylcyclopropanecarboxylic acid for 34D and 54B for (S)-2-(3,5-difluorophenyl)-1-(3-(4-methoxyphenyl)pyridin-2-yl)ethanamine to provide the desired compound (18.5 mg, 30%): $^1$H NMR (400 MHz, dmso) δ 8.45 (dd, 1H), 7.69 (d, 2H), 7.60 (dd, 1H), 7.54-7.48 (m, 1H), 7.42 (d, 1H), 7.34 (ddd, 5H), 7.23 (dd, 2H), 6.92 (t, 1H), 6.79 (d, 1H), 6.40 (d, 2H), 5.20 (dd, 1H), 2.80 (ddd, 2H), 1.17 (d, 2H), 0.91 (t, 2H); MS (m/z) 516.3 [M+H]+.

Examples 478 and 479

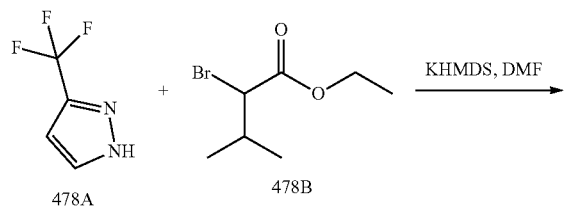

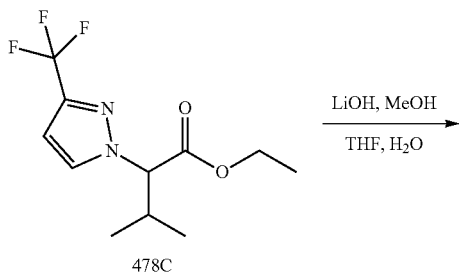

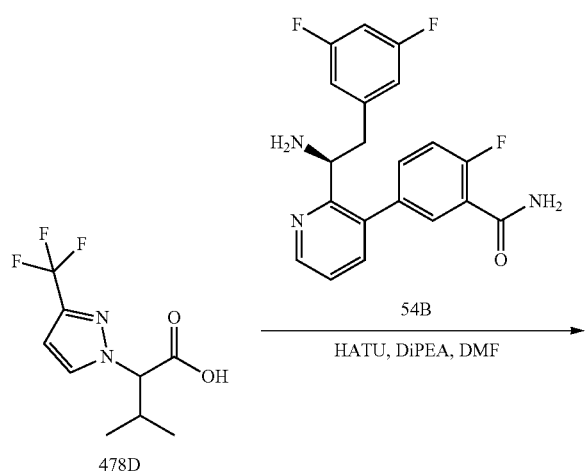

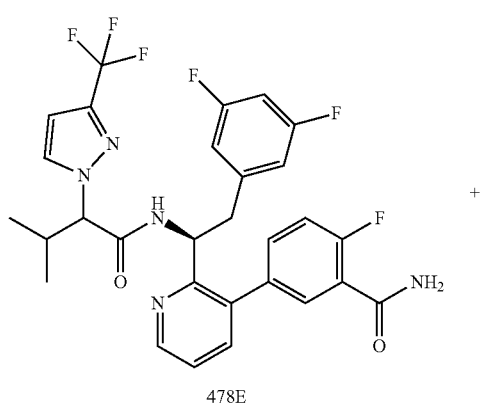

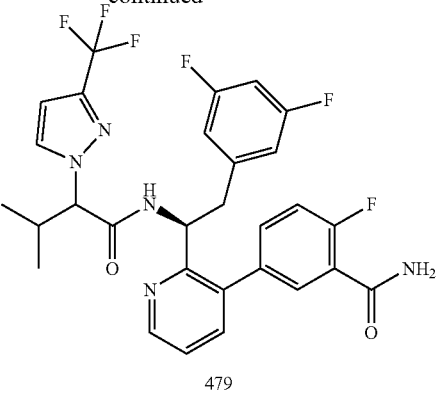

Synthesis of ethyl 3-methyl-2-(3-(trifluoromethyl)-1H-pyrazol-1-yl)butanoate (478C)

A 2 dram vial was charged with 3-(trifluoromethyl)-1H-pyrazole (500 mg, 3.8 mmol), DMF (5 ml), and KHMDS (1.1 g, 5.5 mmol). The resulting mixture was stirred for 10 minutes and then add ethyl 2-bromo-3-methylbutanoate (0.8 ml, 5.3 mmol). Stir at RT until done by LC/MS or TLC. Dilute the reaction with H$_2$O and extract 2× EtOAc. The combined organic layers were washed with brine then dried over sodium sulfate, concentrated, and purified by flash chromatography to give the desired compound (450 mg, 46%): MS (m/z) 265.2 [M+H]$^+$.

Synthesis of 3-methyl-2-(3-(trifluoromethyl)-1H-pyrazol-1-yl)butanoic acid (478D)

A 40 ml vial was charged with ethyl 3-methyl-2-(3-(trifluoromethyl)-1H-pyrazol-1-yl)butanoate (450 mg, 1.7 mmol), MeOH (2 ml), THF (5 ml), H$_2$O (2 ml), and LiOH (500 mg, 21 mmol). Stir at RT until done by LC/MS. Dilute the reaction with H$_2$O and extract with EtOAc. The water layer was acidified with 1 N HCl and extracted 2× EtOAc. The combined organic layers were dried over sodium sulfate, concentrated, and used crude in the next reaction: MS (m/z) 237.0 [M+H]$^+$.

Synthesis of 5-(2-((1S)-2-(3,5-difluorophenyl)-1-(3-methyl-2-(3-(trifluoromethyl)-1H-pyrazol-1-yl)butanamido)ethyl)pyridin-3-yl)-2-fluorobenzamide (478E and 479)

The title compounds were prepared according to the method presented in the synthesis of 54G substituting 3-methyl-2-(3-(trifluoromethyl)-1H-pyrazol-1-yl)butanoic acid for 2-(5-(trifluoromethyl)-1H-indol-3-yl)acetic acid to provide the desired compounds (478E, the first peak off HPLC 2.2 mg, 3%; 479, the second peak off HPLC, 2.6 mg, 3%): 478E $^1$H NMR (400 MHz, dmso) δ 8.63 (d, 1H), 8.43 (d, 1H), 7.88 (s, 1H), 7.66 (s, 2H), 7.57 (d, 1H), 7.45 (d, 1H), 7.37 (dd, 1H), 7.31 (d, 2H), 6.90 (s, 1H), 6.56 (s, 1H), 6.50 (d, 2H), 5.11 (d, 1H), 2.90 (d, 2H), 2.72-2.60 (m, 2H), 1.44 (d, 6H). MS (m/z) 590.6 [M+H]$^+$. 479 $^1$H NMR (400 MHz, dmso) δ 9.21 (d, 1H), 8.60 (d, 1H), 7.85 (s, 1H), 7.70 (d, 2H), 7.60 (d, 1H), 7.53 (d, 1H), 7.45-7.28 (m, 3H), 6.94 (s, 1H), 6.64 (s, 3H), 5.16 (s, 1H), 4.69 (d, 1H), 2.99 (d, 3H), 0.50 (t, 6H); MS (m/z) 591.1 [M+H]$^+$.

Example 480

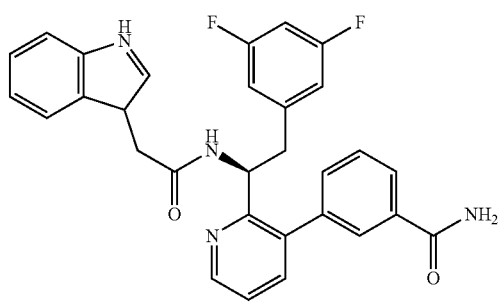

480

Synthesis of (S)-3-(2-(1-(2-(1H-indol-3-yl)acetamido)-2-(3,5-difluorophenyl)ethyl)pyridin-3-yl)benzamide (480)

The title compound was prepared according to the method presented in the synthesis of 50D utilizing 50C and 2-(1H-indol-3-yl)acetic acid to provide 5.1 mg the desired compound in a 12% yield: $^1$H NMR (400 MHz, dmso) δ 10.75 (s, 1H), 8.71-8.56 (m, 2H), 7.95 (s, 1H), 7.86 (d, 1H), 7.74 (s, 1H), 7.62 (dd, 1H), 7.50-7.35 (m, 4H), 7.26 (dd, 2H), 7.04-6.95 (m, 2H), 6.91 (t, 1H), 6.83 (t, 1H), 6.50 (d, 2H), 5.18 (dd, 1H), 3.45 (q, 2H), 2.95 (d, 2H); MS (m/z) 511.3 [M+H]$^+$.

Example 481

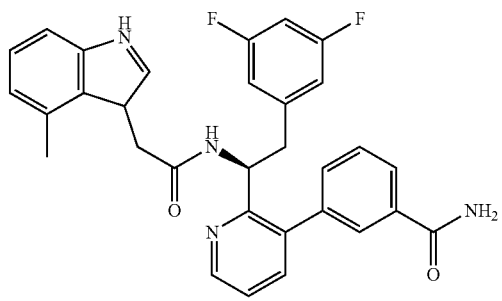

481

Synthesis of (S)-3-(2-(2-(3,5-difluorophenyl)-1-(2-(4-methyl-1H-indol-3-yl)acetamido)ethyl)pyridin-3-yl)benzamide (481)

The title compound was prepared according to the method presented in the synthesis of 50D utilizing 50C and 2-(4-methyl-1H-indol-3-yl)acetic acid to provide 17.6 mg of the desired compound in a 38% yield: $^1$H NMR (400 MHz, dmso) δ 10.73 (s, 1H), 8.60 (dd, 1H), 8.28 (d, 1H), 7.95 (s, 1H), 7.88 (d, 1H), 7.74 (s, 1H), 7.61 (dd, 1H), 7.42 (ddd, 4H), 7.08 (d, 1H), 6.89 (ddd, 3H), 6.56 (d, 1H), 6.46 (d, 2H), 5.21 (dd, 2H), 3.68-3.53 (m, 2H), 2.93 (d, 2H), 2.28 (s, 3H); MS (m/z) 525.3 [M+H]$^+$.

Examples 482 and 420

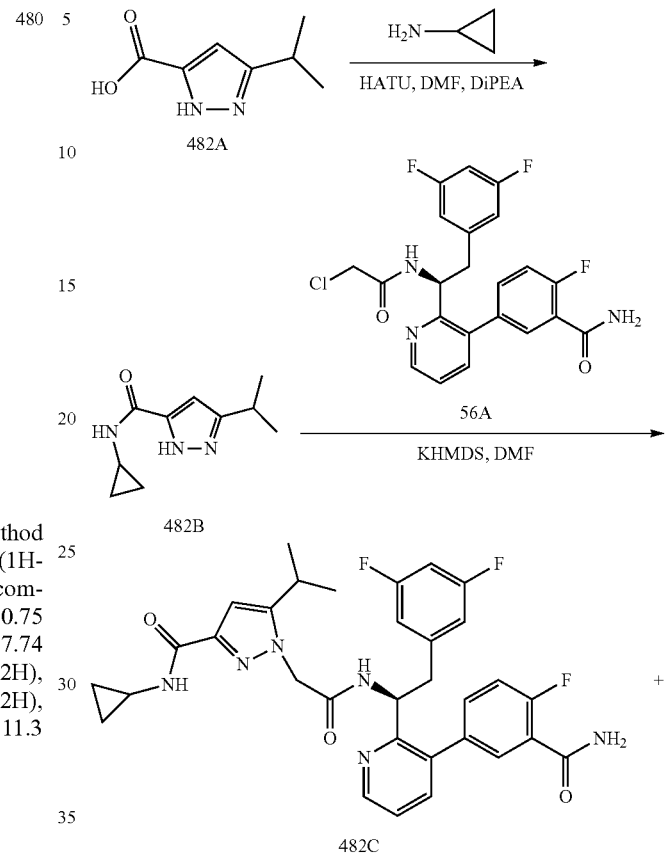

Synthesis of N-cyclopropyl-3-isopropyl-1H-pyrazole-5-carboxamide (482B)

A RB was charged with 3-isopropyl-1H-pyrazole-5-carboxylic acid (500 mg, 3.2 mmol), DMF (10 ml), HATU (1.2 g, 3.2 mmol), cyclopropanamine (0.45 ml, 6.4 mmol), and DiPEA (2.2 ml, 13 mmol). Stir at RT until done by LC/MS or TLC. Dilute the reaction with H$_2$O and extract 2× EtOAc. The combined organic layers were concentrated, and used as is in the next reaction. MS (m/z) 193.0 [M+H]$^+$.

Synthesis of (S)-1-(2-(1-(3-(3-carbamoyl-4-fluoro-phenyl)pyridin-2-yl)-2-(3,5-difluorophenyl)ethyl-amino)-2-oxoethyl)-N-cyclopropyl-5-isopropyl-1H-pyrazole-3-carboxamide (482C) and (S)-1-(2-(1-(3-(3-carbamoyl-4-fluorophenyl)pyridin-2-yl)-2-(3,5-difluorophenyl)ethylamino)-2-oxoethyl)-N-cyclopropyl-3-isopropyl-1H-pyrazole-5-carboxamide (520)

The title compounds were prepared according to the method presented in the synthesis of 56B substituting N-cyclopropyl-3-isopropyl-1H-pyrazole-5-carboxamide for 1H-benzo[g]indole to provide the desired compounds (482C (as a 1:1 mix of 482C and 520), 3 mg, 7%; 520, 8 mg, 20%): 482C MS (m/z) 605.5 [M+H]$^+$. 520 $^1$H NMR (400 MHz, dmso) δ 8.65 (d, 1H), 8.57 (d, 1H), 8.29 (d, 1H), 7.63 (s, 1H), 7.58 (d, 2H), 7.43-7.34 (m, 3H), 7.31-7.22 (m, 1H), 6.86 (s, 1H), 6.58 (s, 1H), 6.44 (d, 2H), 5.13 (d, 1H), 5.06 (s, 2H), 2.95 (d, 2H), 2.82-2.71 (m, 1H), 2.67 (s, 1H), 1.11 (d, 5H), 0.60 (d, 2H), 0.46 (s, 2H); MS (m/z) 605.4 [M+H]$^+$.

Examples 483 and 484

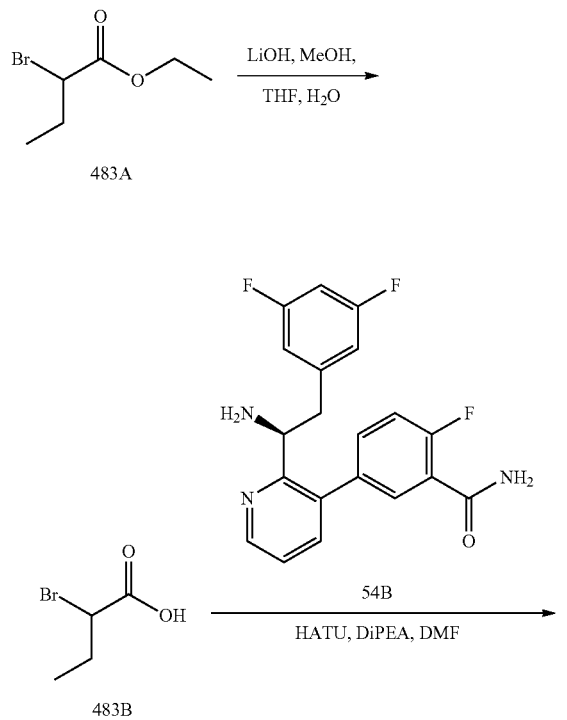

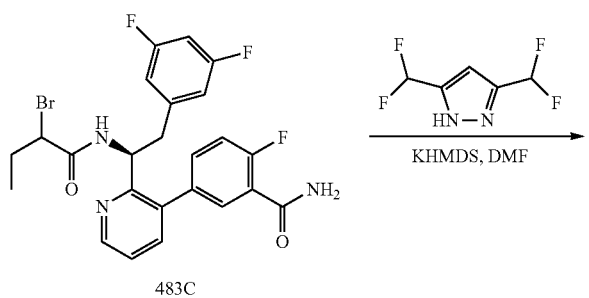

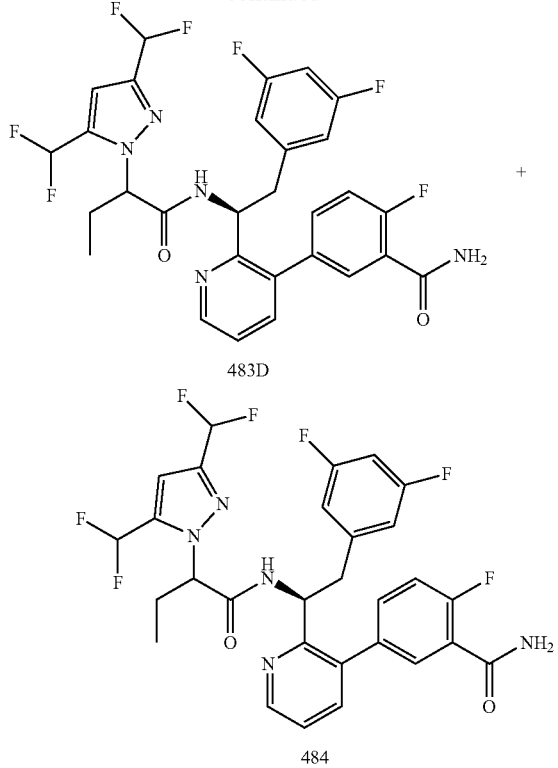

Synthesis of 2-bromobutanoic acid (483B)

A 40 ml vial was charged with ethyl 2-bromobutanoate (0.7 ml, 5.1 mmol), MeOH (2 ml), THF (5 ml), H$_2$O (2 ml), and LiOH (1 g, 42 mmol). Stir at RT for 1 hour. Dilute the reaction with H$_2$O and extract with EtOAc. The water layer was acidified with 1 N HCl and extracted 2× EtOAc. The combined organic layers were dried over sodium sulfate, concentrated, and used crude in the next reaction.

Synthesis of 5-(2-((1S)-1-(2-bromobutanamido)-2-(3,5-difluorophenyl)ethyl)pyridin-3-yl)-2-fluorobenzamide (483C)

The title compound was prepared according to the method presented in Example 54 substituting 2-bromobutanoic acid for 2-(5-(trifluoromethyl)-1H-indol-3-yl)acetic acid to provide the desired compound: MS (m/z) 522.0 [M+H]$^+$.

Synthesis of 5-(2-((1S)-1-(2-(3,5-bis(difluoromethyl)-1H-pyrazol-1-yl)butanamido)-2-(3,5-difluorophenyl)ethyl)pyridin-3-yl)-2-fluorobenzamide (483D and 484)

The title compounds were prepared according to the method presented in the synthesis of 56B substituting 3,5-bis(difluoromethyl)-1H-pyrazole for 1H-benzo[g]indole and 5-(2-((1S)-1-(2-bromobutanamido)-2-(3,5-difluorophenyl)ethyl)pyridin-3-yl)-2-fluorobenzamide for 56A to provide the desired compounds (483D, the first peak off HPLC, 3.7 mg, 6%; 484, the second peak off HPLC, 21 mg, 36%): 483D $^1$H NMR (400 MHz, dmso) δ 8.81 (d, 1H), 8.62 (d, 1H), 7.65 (d, 1H), 7.59 (d, 1H), 7.48 (d, 1H), 7.38 (dd, 2H), 7.35-7.26 (m, 1H), 7.15 (s, 1H), 7.10 (s, 1H), 7.02 (s, 1H), 6.95 (d, 1H), 6.83 (s, 11H), 6.54 (d, 2H), 5.10 (d, 1H), 5.03-4.94 (m, 1H), 2.96 (d, 2H), 1.96 (s, 2H), 0.64 (t, 3H); MS (m/z) 608.8 [M+H]⁺. 484 ¹H NMR (400 MHz, dmso) δ 8.83 (d, 1H), 8.65 (d, 1H), 7.66 (s, 2H), 7.61 (d, 1H), 7.47-7.38 (m, 3H), 7.31 (dd, 1H), 7.12 (d, 11H), 6.98 (d, 1H), 6.90-6.80 (m, 2H), 6.49 (d, 2H), 5.08 (d, 1H), 5.03-4.93 (m, 1H), 2.96 (t, 2H), 2.10-1.90 (m, 2H), 0.68 (t, 3H); MS (m/z) 608.8 [M+H]⁺.

Example 485

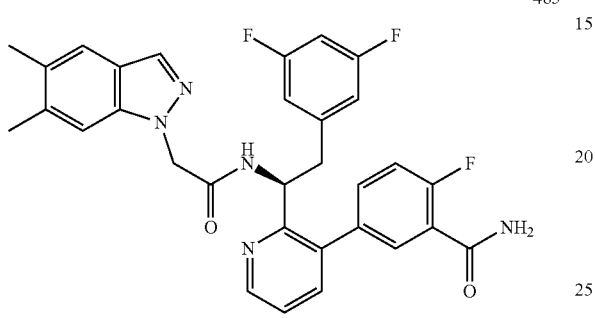

485

Synthesis of (S)-5-(2-(2-(3,5-difluorophenyl)-1-(2-(5,6-dimethyl-1H-indazol-1-yl)acetamido)ethyl)pyridin-3-yl)-2-fluorobenzamide (485)

The title compound was prepared according to the method presented in Example 56 substituting 5,6-dimethyl-1H-indazole for 1H-benzo[g]indole to provide the desired compound (13.6 mg, 38%): ¹H NMR (400 MHz, dmso) δ 8.82 (d, 1H), 8.71-8.65 (m, 1H), 7.80 (s, 1H), 7.66-7.55 (m, 3H), 7.41 (dd, 4H), 7.30-7.20 (m, 1H), 7.10 (s, 1H), 6.91 (t, 1H), 6.52 (d, 2H), 5.14 (dd, 1H), 4.95 (s, 2H), 2.99 (d, 2H), 2.25 (d, 6H); MS (m/z) 558.4 [M+H]⁺.

Example 486

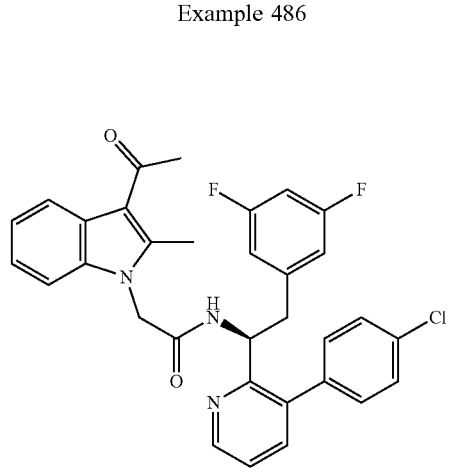

486

Synthesis of (S)-2-(3-acetyl-2-methyl-1H-indol-1-yl)-N-(1-(3-(4-chlorophenyl)pyridin-2-yl)-2-(3,5-difluorophenyl)ethyl)acetamide (486)

The title compound was prepared according to the method presented in the synthesis of 36F utilizing 36E and 2-(3-acetyl-2-methyl-1H-indol-1-yl)acetic acid to provide 19.5 mg of the desired compound in a 29% yield: ¹H NMR (400 MHz, dmso) δ 9.12 (d, 1H), 8.69 (dd, 1H), 7.91 (d, 1H), 7.58-7.54 (m, 1H), 7.40 (dd, 3H), 7.24 (t, 3H), 7.15-7.05 (m, 2H), 6.98 (t, 1H), 6.50 (d, 2H), 5.15 (dd, 1H), 4.89 (d, 2H), 3.04-2.90 (m, 2H), 2.49 (s, 3H), 2.47 (s, 3H); MS (m/z) 558.5 [M+H]⁺.

Examples 487 and 488

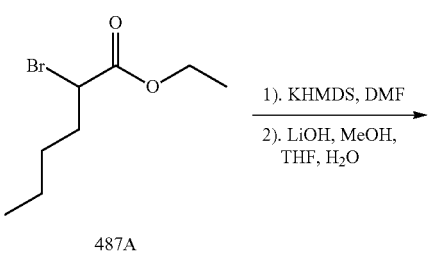

478A

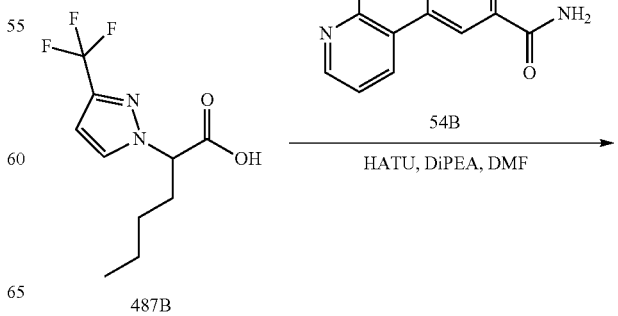

-continued

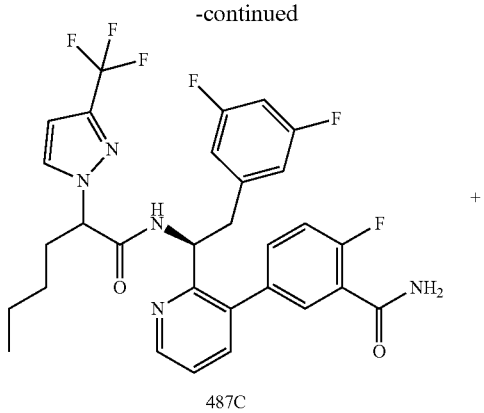

487C

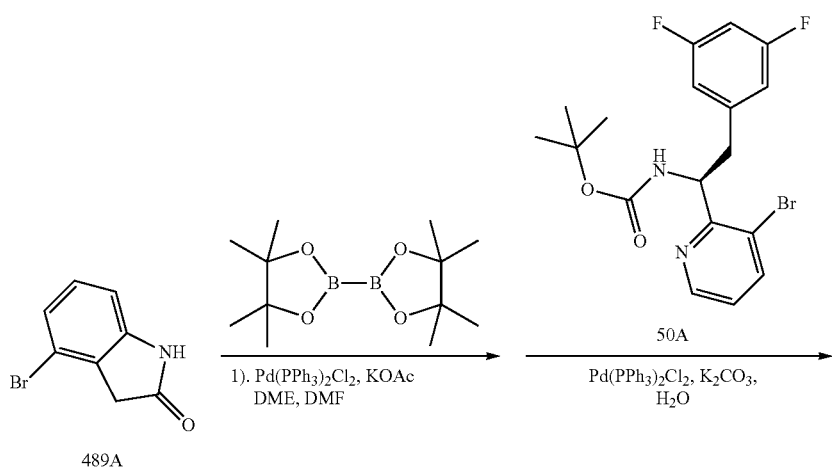

488

Synthesis of ethyl 2-(3-(trifluoromethyl)-1H-pyrazol-1-yl)hexanoate

The title compound was prepared according to the method presented in Example 478 substituting ethyl 2-bromo-hexanoate for ethyl 2-bromo-3-methylbutanoate to provide the desired compound: MS (m/z) 279.2 [M+H]$^+$.

Synthesis of 2-(3-(trifluoromethyl)-1H-pyrazol-1-yl)hexanoic acid (487B)

The title compound was prepared according to the method presented in Example 478 substituting ethyl 2-(3-(trifluoromethyl)-1H-pyrazol-1-yl)hexanoate for ethyl 2-bromo-3-methylbutanoate to provide the desired compound: MS (m/z) 251.0 [M+H]$^+$.

Synthesis of 5-(2-(((1S)-2-(3,5-difluorophenyl)-1-(2-(3-(trifluoromethyl)-1H-pyrazol-1-yl)hexanamido)ethyl)pyridin-3-yl)-2-fluorobenzamide (487C and 488)

The title compounds were prepared according to the method presented in the synthesis of 54G substituting 2-(3-(trifluoromethyl)-1H-pyrazol-1-yl)hexanoic acid for 2-(5-(trifluoromethyl)-1H-indol-3-yl)acetic acid to provide the desired compounds (487C, the first peak off HPLC, 6.5 mg, 8%; 488, the second peak off HPLC, 6.1 mg, 8%): 487C $^1$H NMR (400 MHz, dmso) δ 9.11 (d, 1H), 8.65-8.59 (m, 1H), 7.84 (s, 1H), 7.69 (d, 2H), 7.62 (dd, 1H), 7.56 (d, 1H), 7.44 (s, 1H), 7.39 (dd, 1H), 7.35-7.27 (m, 1H), 6.97 (t, 1H), 6.68 (d, 2H), 6.63 (d, 1H), 5.12 (d, 1H), 5.00 (t, 1H), 3.00 (d, 2H), 1.78-1.67 (m, 2H), 1.15 (dd, 2H), 0.84 (s, 2H), 0.73 (t, 3H); MS (m/z) 605.0 [M+H]$^+$. 488 $^1$H NMR (400 MHz, dmso) δ 9.02 (d, 1H), 8.65 (d, 1H), 7.87 (s, 1H), 7.67-7.57 (m, 3H), 7.47-7.36 (m, 3H), 7.35-7.27 (m, 1H), 6.83 (s, 1H), 6.63 (s, 1H), 6.45 (d, 2H), 5.14-4.97 (m, 2H), 2.98 (d, 2H), 1.85 (d, 2H), 1.17 (s, 2H), 0.98 (d, 2H), 0.73 (t, 3H); MS (m/z) 604.9 [M+H]$^+$.

Example 489

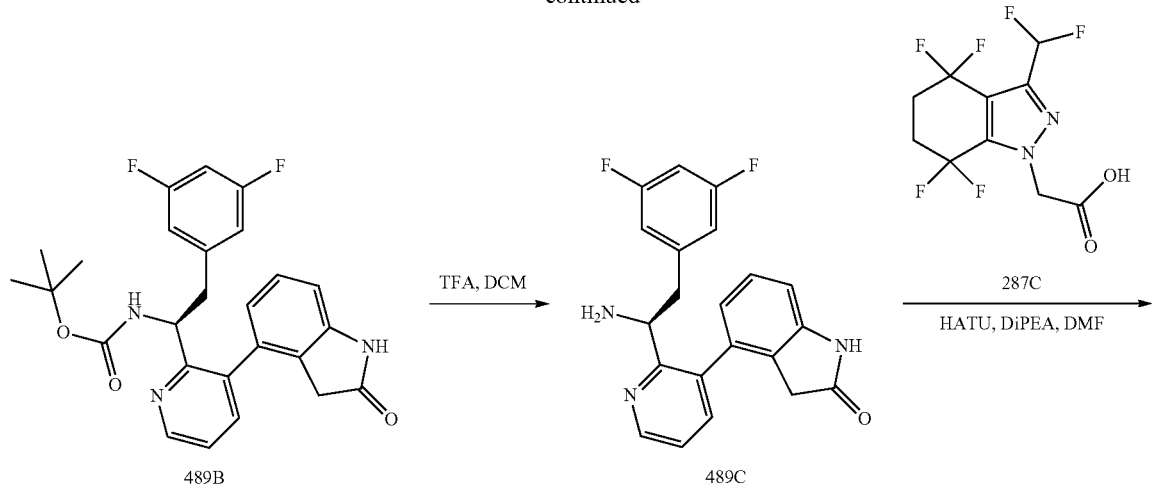

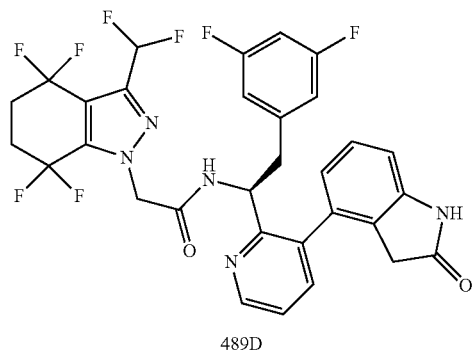

Synthesis of (S)-tert-butyl 2-(3,5-difluorophenyl)-1-(3-(2-oxoindolin-4-yl)pyridin-2-yl)ethylcarbamate (489B)

A microwave vial was charged with 4-bromoindolin-2-one (100 mg, 0.5 mmol), DME:DMF 4:1 (1.5 ml), 4,4,4',4',5,5,5',5'-octamethyl-2,2'-bi(1,3,2-dioxaborolane) (179 mg, 0.8 mmol), Pd(PPh$_3$)$_2$Cl$_2$ (16 mg, 0.02 mmol), and KOAc (92 mg, 1 mmol). Heat the mixture in a microwave at 150° C. for 15 minutes. Then add 50A (200 mg, 0.5 mmol), 2 M aq. K$_2$CO$_3$ (0.5 ml) and Pd(PPh$_3$)$_2$Cl$_2$ (16 mg, 0.02 mmol). Heat the mixture in a microwave at 150° C. for 20 minutes. Allow the reaction to cool then dilute with H$_2$O and extract 2× EtOAc. The combined organic layers were washed with brine then dried over sodium sulfate, concentrated, passed through a silica gel plug and concentrated to give the desired compound, which was used as is in the next reaction: MS (m/z) 466.3 [M+H]$^+$.

Synthesis of (S)-4-(2-(1-amino-2-(3,5-difluorophenyl)ethyl)pyridin-3-yl)indolin-2-one (489C)

The title compound was prepared according to the method presented in the synthesis of 50C substituting (S)-tert-butyl 2-(3,5-difluorophenyl)-1-(3-(2-oxoindolin-4-yl)pyridin-2-yl)ethylcarbamate for 50B to provide the desired compound: MS (m/z) 366.4 [M+H]$^+$.

Synthesis of (S)-2-(3-(difluoromethyl)-4,4,7,7-tetrafluoro-4,5,6,7-tetrahydro-1H-indazol-1-yl)-N-(2-(3,5-difluorophenyl)-1-(3-(2-oxoindolin-4-yl)pyridin-2-yl)ethyl)acetamide (489D)

The title compound was prepared according to the method presented in the synthesis of 61F substituting 287C for 61C and 489C for 61E to provide the desired compound (17 mg): $^1$H NMR (400 MHz, cd$_3$od) δ 8.70 (d, 1H), 7.66 (s, 1H), 7.57 (s, 1H), 7.40 (s, 1H), 7.26 (s, 1H), 7.18 (s, 1H), 6.97 (s, 1H), 6.90 (d, 1H), 6.78 (s, 1H), 6.71 (s, 2H), 6.37 (s, 1H), 6.29 (s, 1H), 6.23 (s, 1H), 5.05 (d, 3H), 3.17-3.04 (m, 2H), 2.98 (dd, 1H), 2.51 (s, 4H); MS (m/z) 650.2 [M+H]$^+$.

Example 490

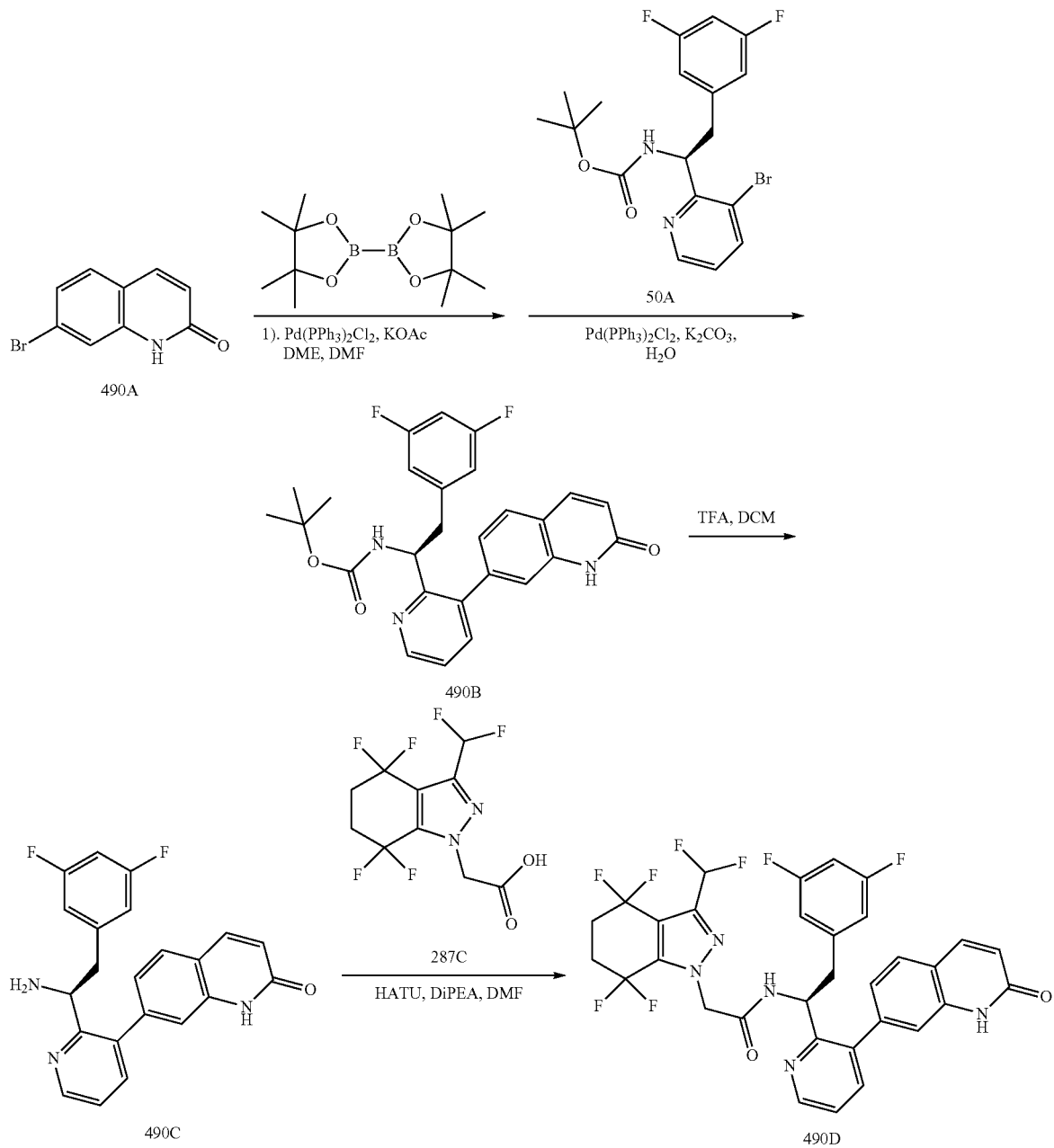

Synthesis of (S)-tert-butyl 2-(3,5-difluorophenyl)-1-(3-(2-oxo-1,2-dihydroquinolin-7-yl)pyridin-2-yl)ethylcarbamate (490B)

The title compound was prepared according to the method presented in the synthesis of 489B substituting 7-bromoquinolin-2(1H)-one for 489A to provide the desired compound: MS (m/z) 478.1 [M+H]+.

Synthesis of (S)-7-(2-(1-amino-2-(3,5-difluorophenyl)ethyl)pyridin-3-yl)quinolin-2(1H)-one (490C)

The title compound was prepared according to the method presented in the synthesis of 50C substituting (S)-tert-butyl 2-(3,5-difluorophenyl)-1-(3-(2-oxo-1,2-dihydroquinolin-7-yl)pyridin-2-yl)ethylcarbamate for 50B to provide the desired compound: MS (m/z) 378.1 [M+H]+.

Synthesis of (S)-2-(3-(difluoromethyl)-4,4,7,7-tetrafluoro-4,5,6,7-tetrahydro-1H-indazol-1-yl)-N-(2-(3,5-difluorophenyl)-1-(3-(2-oxo-1,2-dihydroquinolin-7-yl)pyridin-2-yl)ethyl)acetamide (490D)

The title compound was prepared according to the method presented in the synthesis of 61F substituting 287C for 61C and 490C for 61E to provide the desired compound (17 mg): $^1$H NMR (400 MHz, cd$_3$od) δ 8.74-8.66 (m, 1H), 7.97 (d, 1H), 7.67-7.56 (m, 2H), 7.41 (dd, 1H), 7.06 (s, 1H), 6.94 (s, 1H), 6.81 (s, 1H), 6.65 (dd, 2H), 6.20 (d, 2H), 5.49 (t, 1H), 5.10 (s, 2H), 3.00 (d, 2H), 2.62-2.42 (m, 4H); MS (m/z) 662.3 [M+H]⁺.

Examples 491 and 557

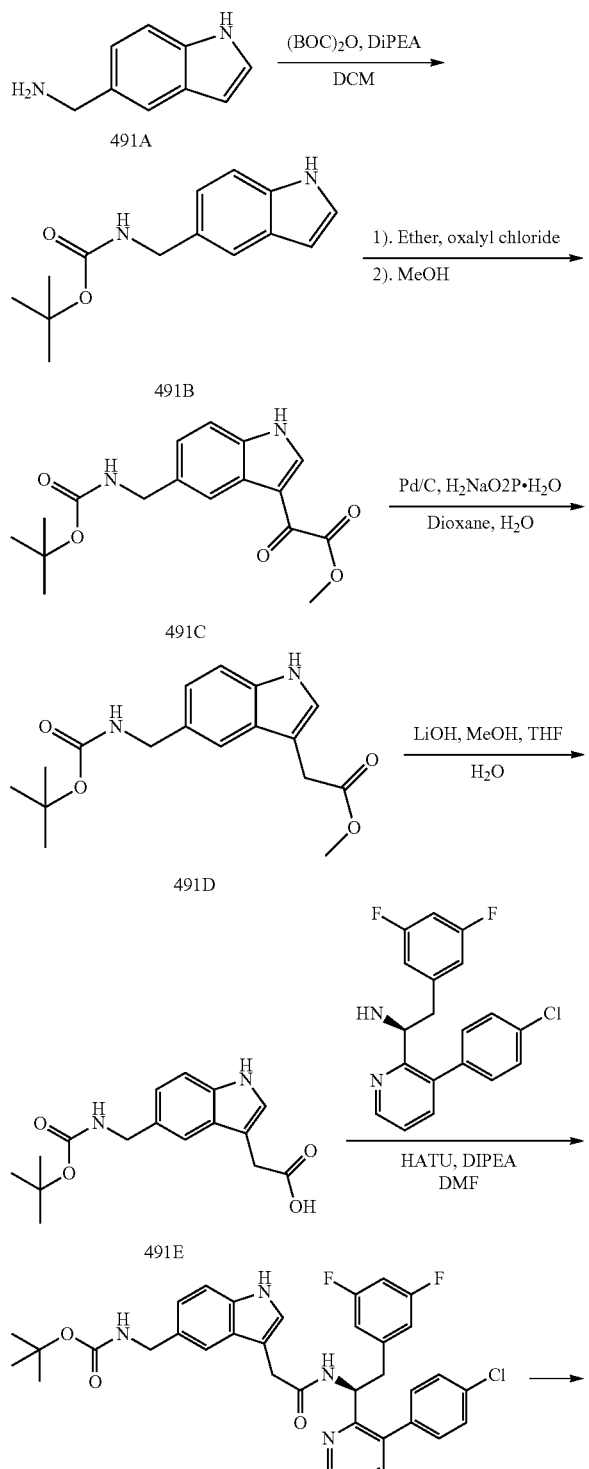

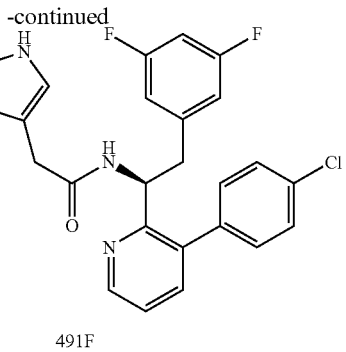

Synthesis of tert-butyl (1H-indol-5-yl)methylcarbamate (491B)

A round bottom flask was charged with (1H-indol-5-yl)methanamine (2 g, 14 mmol), (BOC)₂O (3 g, 14 mmol), DCM (100 ml), and DiPEA (2.4 ml, 14 mmol). The reaction was stirred until done by LC/MS. The reaction was diluted with H₂O and extracted 2×DCM and IX EtOAc. The combined organic layer was dried over sodium sulfate, filtered, concentrated and used crude in the next reaction. MS (m/z) 246.9 [M+H]⁺

Synthesis of methyl 2-(5-((tert-butoxycarbonylamino)methyl)-1H-indol-3-yl)-2-oxoacetate (491C)

A round bottom flask was charged with ether (20 mil) and tert-butyl (1H-indol-5-yl)methylcarbamate (3 g, 12 mmol) followed by slow addition of oxalyl chloride (1 ml, 11 mmol). The reaction was stirred until color changes and was then filtered. The solid was dissolved in MeOH (5 ml) and then precipitated out by adding ether. The mixture was filtered and dried under vacuum to obtain 1.4 g of the desired compound as the HCl salt which was used with no further purification. The yield was 36%.

Synthesis of methyl 2-(5-((tert-butoxycarbonylamino)methyl)-1H-indol-3-yl)acetate (491D)

A round bottom is charged with methyl 2-(5-((tert-butoxycarbonylamino)methyl)-1H-indol-3-yl)-2-oxoacetate (1.4 g, 4 mmol), dioxane (100 ml), Pd/C (0.5 g), H2NaO2P.H2O (1 g, 9 mmol), and H₂O (40 ml). The resulting mixture was stirred at 120° C. until done as indicated by LC/MS. The reaction mixture was cooled to RT and filtered over a plug of celite, rinsing with ethyl acetate. The layers were partitioned and the organic layer was dried over sodium sulfate, filtered, concentrated and purified by flash chromatography to give the desired compound as an oil (660 mg, 52%): MS (m/z) 318.8 [M+H]⁺

Synthesis of 2-(5-((tert-butoxycarbonylamino)methyl)-1H-indol-3-yl)acetic acid (491E)

The title compound was prepared according to the method presented in Example 478 substituting ethyl 2-(3-(trifluoromethyl)-1H-pyrazol-1-yl)hexanoate for methyl 2-(5-((tert-butoxycarbonylamino)methyl)-1H-indol-3-yl)acetate to provide the desired compound: MS (m/z) 305.1 [M+H]⁺.

Synthesis of (S)-tert-butyl (3-(2-(1-(3-(4-chlorophenyl)pyridin-2-yl)-2-(3,5-difluorophenyl)ethylamino)-2-oxoethyl)-1H-indol-5-yl)methylcarbamate (557)

The title compound was prepared according to the method presented in the synthesis of 36F utilizing 36E and 2-(5-((tert-butoxycarbonylamino)methyl)-1H-indol-3-yl)acetic acid to provide 20 mg of the desired compound in a 29% yield: $^1$H NMR (400 MHz, dmso) δ 10.72 (s, 1H), 8.63 (d, 1H), 8.50 (d, 1H), 7.51 (d, 1H), 7.36 (dd, 3H), 7.28-7.11 (m, 5H), 7.01 (s, 1H), 6.97-6.87 (m, 2H), 6.37 (d, 2H), 5.15 (d, 1H), 4.09 (s, 2H), 3.46 (s, 2H), 2.93 (s, 2H), 1.34 (s, 9H); MS (m/z) 631.5 [M+H]$^+$.

Synthesis of (S)-2-(5-(aminomethyl)-1H-indol-3-yl)-N-(1-(3-(4-chlorophenyl)pyridin-2-yl)-2-(3,5-difluorophenyl)ethyl)acetamide (491F)

A round bottom flask was charged (S)-tert-butyl (3-(2-(1-(3-(4-chlorophenyl)pyridin-2-yl)-2-(3,5-difluorophenyl)ethylamino)-2-oxoethyl)-1H-indol-5-yl)methylcarbamate (18 mg, 0.3 mmol) and TFA:DCM 1:1 (1 ml). The reaction was stirred at room temperature until done by LC/MS then concentrated 2× from DCM and then dissolved in ACN/H$_2$O and dried by lyopholization to obtain the desired compound (15 mg, 99%): $^1$H NMR (400 MHz, dmso) δ 10.94 (s, 1H), 8.64 (dd, 1H), 8.54 (d, 1H), 8.00 (s, 2H), 7.54 (dd, 1H), 7.47 (s, 1H), 7.42-7.30 (m, 4H), 7.19 (d, 2H), 7.11 (d, 2H), 6.91 (t, 1H), 6.40 (d, 2H), 5.14 (dd, 1H), 3.99 (d, 2H), 3.48 (dd, 2H), 2.99-2.87 (m, 2H); MS (m/z) 531.4 [M+H]$^+$.

Example 492

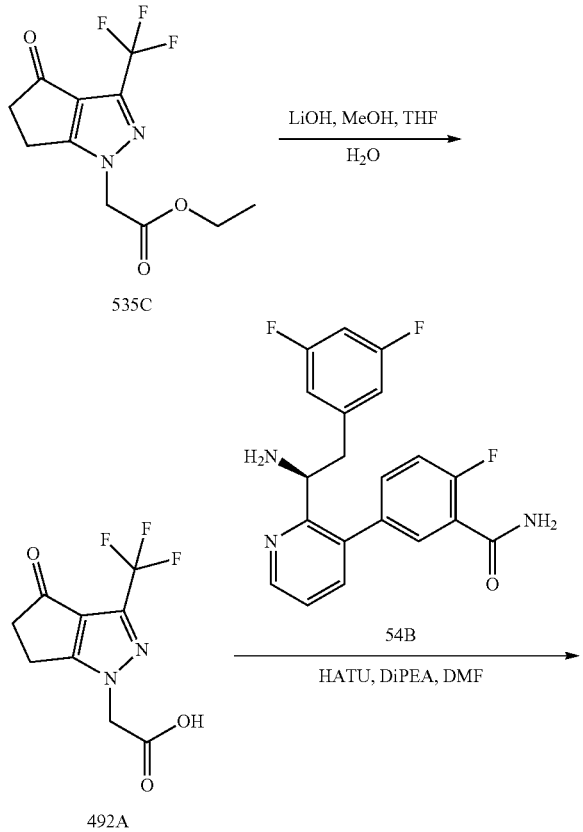

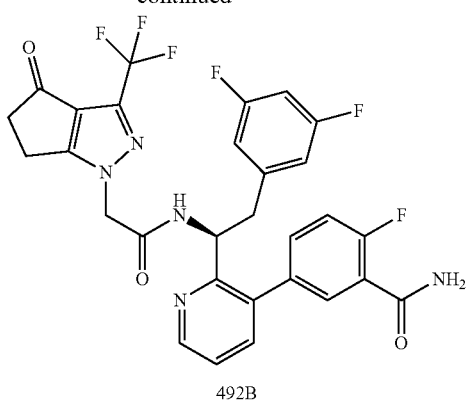

Synthesis of 2-(4-oxo-3-(trifluoromethyl)-5,6-dihydrocyclopenta[c]pyrazol-1(4H)-yl)acetic acid (492A)

The title compound was prepared according to the method presented in Example 491 substituting ethyl 2-(4-oxo-3-(trifluoromethyl)-5,6-dihydrocyclopenta[c]pyrazol-1(4H)-yl)acetate for 491D to provide the desired compound: MS (m/z) 249.0 [M+H]$^+$.

Synthesis of (S)-5-(2-(2-(3,5-difluorophenyl)-1-(2-(4-oxo-3-(trifluoromethyl)-5,6-dihydrocyclopenta[c]pyrazol-1 (4H)-yl)acetamido)ethyl)pyridin-3-yl)-2-fluorobenzamide (492B)

The title compound was prepared according to the method presented in the synthesis of 54G utilizing 54B and 2-(4-oxo-3-(trifluoromethyl)-5,6-dihydrocyclopenta[c]pyrazol-1 (4H)-yl)acetic acid to provide 15.3 mg of the desired compound in a 19% yield: $^1$H NMR (400 MHz, cd$_3$od) δ 8.70 (d, 1H), 7.63-7.57 (m, 1H), 7.48 (s, 1H), 7.41 (dd, 1H), 7.30 (s, 1H), 7.25-7.16 (m, 1H), 6.67 (d, 1H), 6.33 (d, 2H), 5.36 (t, 1H), 4.95 (s, 2H), 3.33 (s, 2H), 3.08 (dd, 4H), 2.96 (d, 2H); MS (m/z) 602.5 [M+H]$^+$.

Example 493

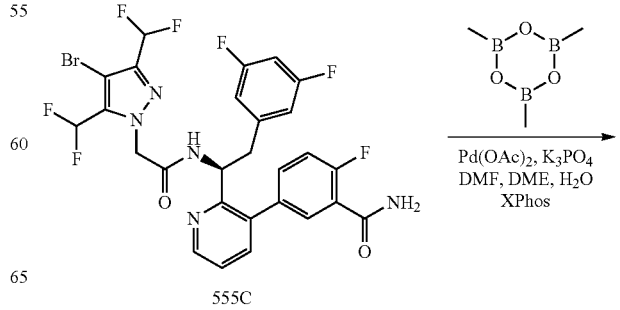

7.27 (d, 1H), 7.22 (s, 1H), 7.18 (d, 1H), 6.95 (d, 1H), 6.90 (s, 1H), 6.55 (d, 2H), 6.36 (d, 1H), 5.13 (d, 1H), 4.78 (s, 2H), 3.00 (d, 2H); MS (m/z) 563.8 [M+H]⁺.

Example 495

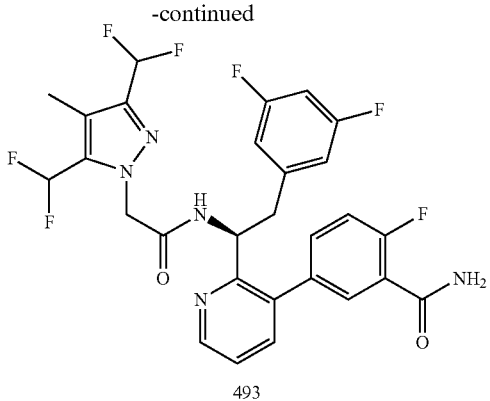

493

Synthesis of (S)-5-(2-(1-(2-(3,5-bis(difluoromethyl)-4-methyl-1H-pyrazol-1-yl)acetamido)-2-(3,5-difluorophenyl)ethyl)pyridin-3-yl)-2-fluorobenzamide (493)

A 40 ml vial was charged with 555C (100 mg, 0.15 mmol), DMF (1 ml), DME (4 ml), 2,4,6-trimethyl-1,3,5,2,4,6-trioxatriborinane (0.1 ml), Pd(OAc)₂ (10 mg, 0.01 mmol), XPhos (14 mg, 0.02 mmol) and 2N K₃PO₄ (0.6 ml). Heat the stirring mixture overnight at 86° C. Allow the reaction to cool then dilute with H₂O and extract 2× EtOAc. The combined organic layers were washed with brine then dried over sodium sulfate, concentrated, and purified by HPLC to give 8 mg of the desired compound. The yield was 9%: ¹H NMR (400 MHz, cd₃od) δ 8.73-8.67 (m, 1H), 7.65-7.56 (m, 1H), 7.49-7.37 (m, 2H), 7.29 (s, 1H), 7.26-7.16 (m, 1H), 7.09-6.68 (m, 2H), 6.65 (t, 1H), 6.30 (d, 2H), 5.36-5.28 (m, 1H), 4.97 (s, 2H), 3.12-2.96 (m, 2H), 2.21 (s, 3H); MS (m/z) 594.3 [M+H]⁺.

Example 494

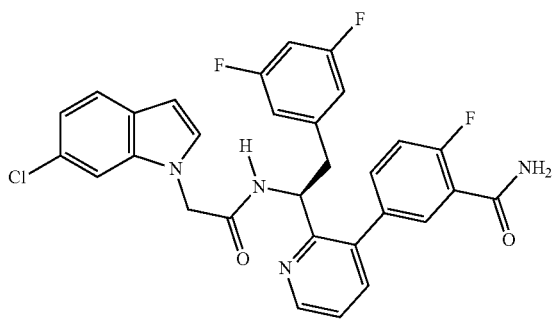

494

Synthesis of (S)-5-(2-(1-(2-(6-chloro-1H-indol-1-yl)acetamido)-2-(3,5-difluorophenyl)ethyl)pyridin-3-yl)-2-fluorobenzamide (494)

The title compound was prepared according to the method presented in Example 56 substituting 6-chloro-1H-indole for 1H-benzo[g]indole to provide the desired compound (3 mg, 8%): ¹H NMR (400 MHz, dmso) δ 8.98 (d, 1H), 8.71 (s, 1H), 7.64 (s, 2H), 7.58 (d, 1H), 7.46 (d, 2H), 7.40 (d, 2H),

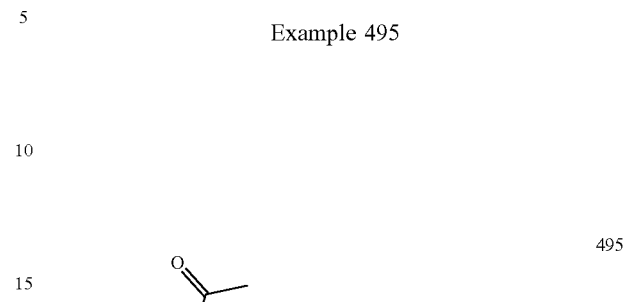

495

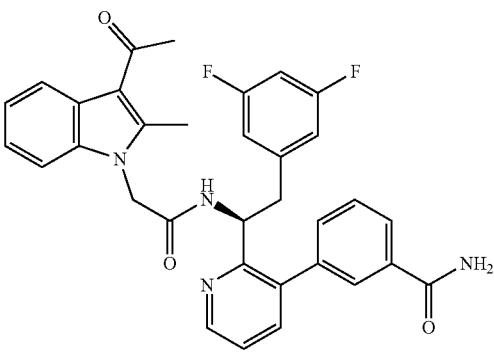

Synthesis of (S)-3-(2-(1-(2-(3-acetyl-2-methyl-1H-indol-1-yl)acetamido)-2-(3,5-difluorophenyl)ethyl)pyridin-3-yl)benzamide (495)

The title compound was prepared according to the method presented in the synthesis of 50D utilizing 50C and 2-(3-acetyl-2-methyl-1H-indol-1-yl)acetic acid to provide 20 mg of the desired compound in a 32% yield: ¹H NMR (400 MHz, dmso) δ 9.10 (d, 1H), 8.75-8.65 (m, 1H), 7.90 (dd, 3H), 7.75 (s, 1H), 7.65 (dd, 1H), 7.49-7.35 (m, 4H), 7.22 (d, 1H), 7.15-7.02 (m, 2H), 6.94 (t, 1H), 6.58 (d, 2H), 5.17 (d, 1H), 4.86 (d, 2H), 3.01 (d, 2H), 2.48 (s, 3H), 2.46 (s, 2H); MS (m/z) 567.4 [M+H]⁺.

Example 496

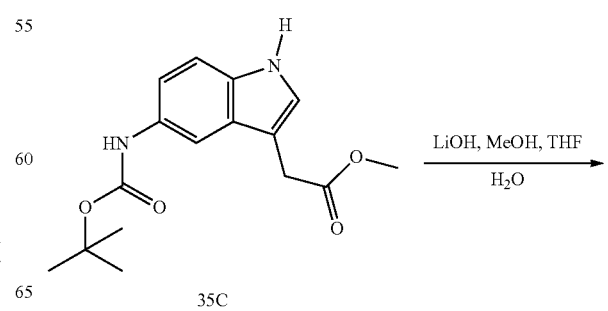

35C

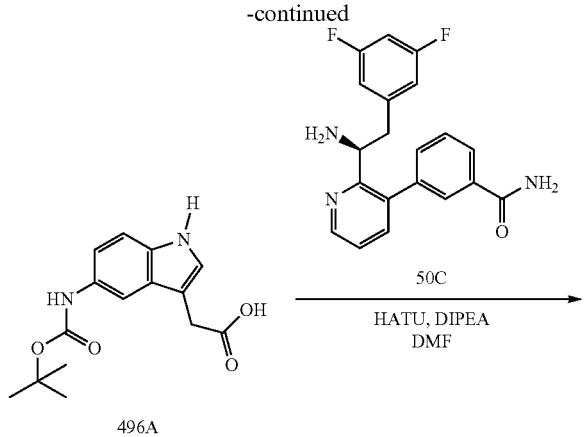

496A

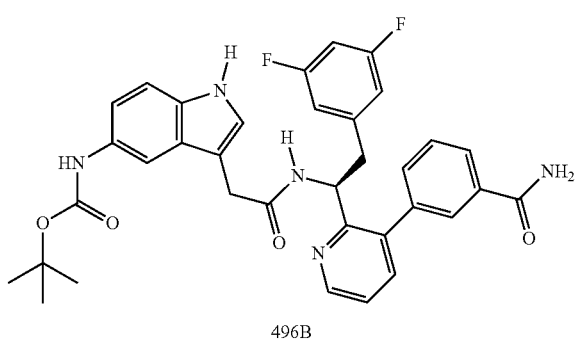

496B

Synthesis of 2-(5-(tert-butoxycarbonylamino)-1H-indol-3-yl)acetic acid (496A)

The title compound was prepared according to the method presented in Example 54 substituting 35C for 54E to provide the desired compound: MS (m/z) 291.1 [M+H]+.

Synthesis of (S)-tert-butyl 3-(2-(1-(3-(3-carbamoyl-phenyl)pyridin-2-yl)-2-(3,5-difluorophenyl)ethyl-amino)-2-oxoethyl)-1H-indol-5-ylcarbamate (496B)

The title compound was prepared according to the method presented in the synthesis of 50D utilizing 50C and 2-(5-(tert-butoxycarbonylamino)-1H-indol-3-yl)acetic acid to provide 11 mg of the desired compound in a 16% yield: $^1$H NMR (400 MHz, dmso) δ 10.65 (s, 1H), 8.93 (s, 1H), 8.62 (d, 1H), 8.51 (d, 1H), 7.96 (s, 1H), 7.85 (d, 1H), 7.68 (s, 1H), 7.58 (d, 2H), 7.43 (t, 1H), 7.37 (t, 3H), 7.14 (d, 1H), 6.97 (s, 2H), 6.84 (t, 1H), 6.37 (d, 2H), 5.22 (d, 1H), 3.43 (s, 2H), 2.94 (d, 2H), 1.42 (s, 9H); MS (m/z) 626.2 [M+H]+.

Example 497

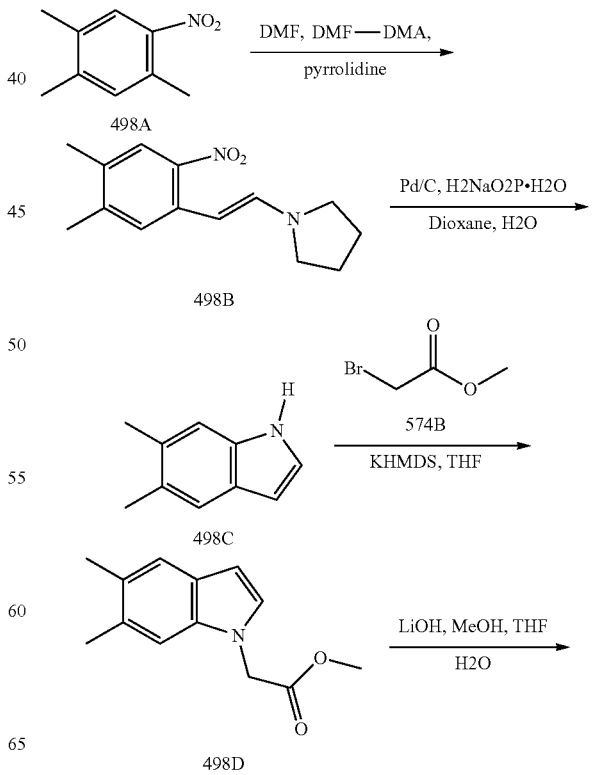

497

Synthesis of (S)-3-(2-(2-(3,5-difluorophenyl)-1-(2-(2-methyl-1H-indol-3-yl)acetamido)ethyl)pyridin-3-yl)benzamide (497)

The title compound was prepared according to the method presented in the synthesis of 50D utilizing 50C and 2-(2-methyl-1H-indol-3-yl)acetic acid to provide 22 mg of the desired compound in a 37% yield: $^1$H NMR (400 MHz, dmso) δ 10.63 (s, 1H), 8.64 (dd, 1H), 8.51 (d, 1H), 7.94 (s, 1H), 7.86 (d, 1H), 7.76 (s, 1H), 7.61 (dd, 1H), 7.44 (d, 2H), 7.39 (dd, 2H), 7.19 (d, 1H), 7.12 (d, 1H), 6.98-6.84 (m, 2H), 6.76 (t, 1H), 6.50 (d, 2H), 5.14 (dd, 1H), 3.39 (q, 2H), 2.93 (d, 2H), 2.18 (s, 3H); MS (m/z) 525.4 [M+H]+.

Example 498

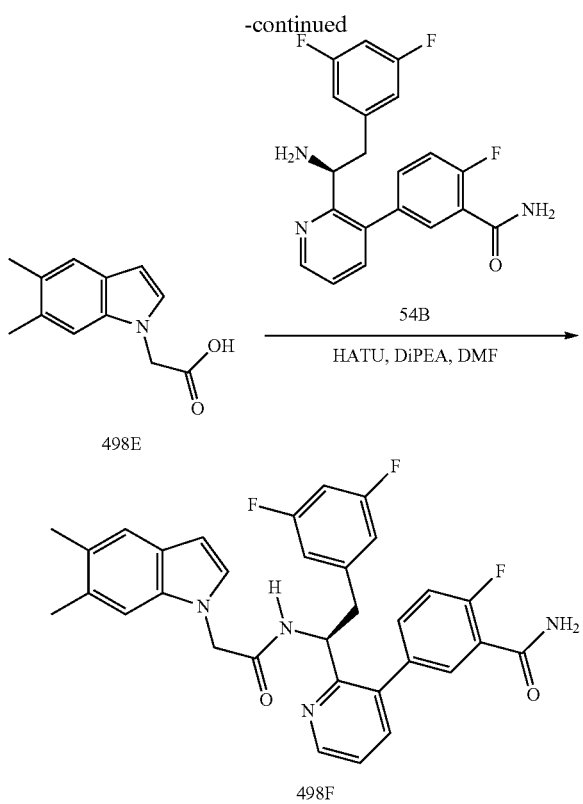

498E

54B
HATU, DiPEA, DMF

498F

Synthesis of 1-(4,5-dimethyl-2-nitrostyryl)pyrrolidine (498B)

The title compound was prepared according to the method presented in Example 536 substituting 1,2,4-trimethyl-5-nitrobenzene for 536C to provide the desired compound.

Synthesis of 5,6-dimethyl-1H-indole (498C)

The title compound was prepared according to the method presented in Example 536 substituting 1-(4,5-dimethyl-2-nitrostyryl)pyrrolidine for 536D to provide the desired compound: MS (m/z) 146.4 [M+H]$^+$.

Synthesis of methyl 2-(5,6-dimethyl-1H-indol-1-yl)acetate (498D)

The title compound was prepared according to the method presented in Example 478 substituting methyl 2-bromoacetate for 478B and 5,6-dimethyl-1H-indole for 478A to provide the desired compound: MS (m/z) 218.2 [M+H]$^+$.

Synthesis of 2-(5,6-dimethyl-1H-indol-1-yl)acetic acid (498E)

The title compound was prepared according to the method presented in Example 478 substituting methyl 2-(5,6-dimethyl-1H-indol-1-yl)acetate for 478C to provide the desired compound: MS (m/z) 204.2 [M+H]$^+$.

Synthesis of (S)-5-(2-(2-(3,5-difluorophenyl)-1-(2-(5,6-dimethyl-1H-indol-1-yl)acetamido)ethyl)pyridin-3-yl)-2-fluorobenzamide (498F)

The title compound was prepared according to the method presented in the synthesis of 54G substituting 2-(5,6-dimethyl-1H-indol-1-yl)acetic acid for 54F to provide the desired compound (5 mg, 9%): $^1$H NMR (400 MHz, dmso) δ 8.83 (d, 1H), 8.67 (d, 1H), 7.69-7.56 (m, 3H), 7.47 (d, 1H), 7.40 (dd, 2H), 7.30-7.22 (m, 1H), 7.20 (s, 1H), 7.00 (d, 1H), 6.92 (t, 1H), 6.84 (s, 1H), 6.58 (d, 2H), 6.17 (d, 1H), 5.12 (d, 1H), 4.68 (s, 2H), 3.00 (d, 2H), 2.19 (d, 6H); MS (m/z) 557.6 [M+H]$^+$.

Example 499

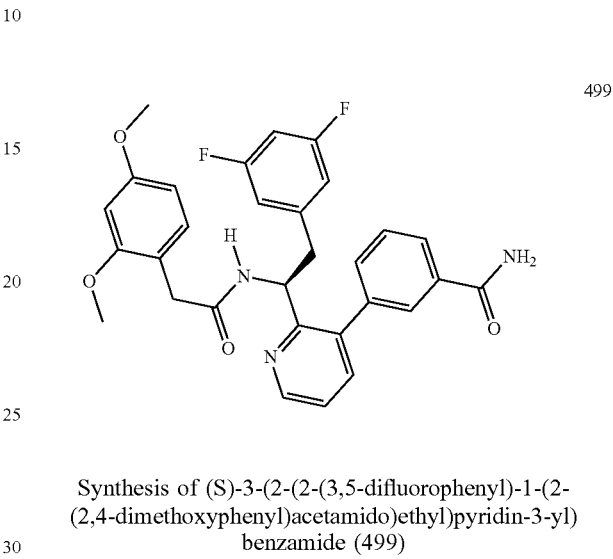

499

Synthesis of (S)-3-(2-(2-(3,5-difluorophenyl)-1-(2-(2,4-dimethoxyphenyl)acetamido)ethyl)pyridin-3-yl)benzamide (499)

The title compound was prepared according to the method presented in the synthesis of 50D utilizing 50C and 2-(2,4-dimethoxyphenyl)acetic acid to provide 21 mg of the desired compound in a 40% yield: $^1$H NMR (400 MHz, dmso) δ 8.65 (d, 1H), 8.30 (d, 1H), 7.94 (s, 1H), 7.88 (d, 1H), 7.74 (s, 1H), 7.66-7.59 (m, 1H), 7.48 (t, 1H), 7.45-7.35 (m, 3H), 6.91 (t, 1H), 6.81 (d, 1H), 6.46 (d, 2H), 6.42 (d, 1H), 6.33 (dd, 1H), 5.23-5.13 (m, 1H), 3.68 (s, 3H), 3.59 (s, 3H), 3.24 (s, 2H), 2.92 (d, 2H); MS (m/z) 532.2[M+H]$^+$.

Example 500

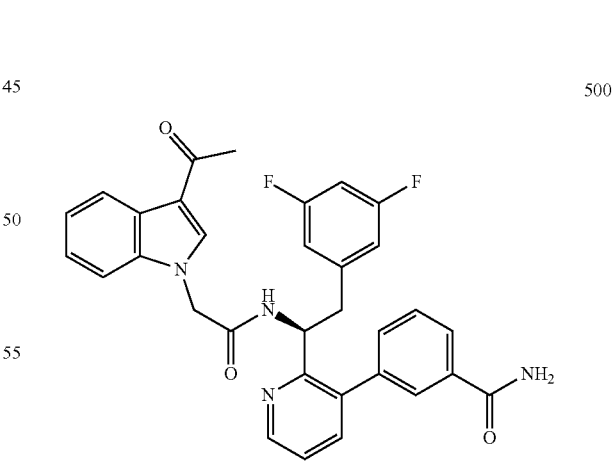

500

Synthesis of (S)-3-(2-(1-(2-(3-acetyl-1H-indol-1-yl)acetamido)-2-(3,5-difluorophenyl)ethyl)pyridin-3-yl)benzamide (500)

The title compound was prepared according to the method presented in the synthesis of 50D utilizing 50C and 2-(3- acetyl-1H-indol-1-yl)acetic acid to provide 22.6 mg of the desired compound in a 37% yield: $^1$H NMR (400 MHz, dmso) δ 9.11 (d, 1H), 8.72 (dd, 1H), 8.09 (d, 2H), 7.94 (s, 1H), 7.87 (d, 1H), 7.74 (s, 1H), 7.65 (dd, 1H), 7.49-7.34 (m, 4H), 7.11 (td, 2H), 7.03 (s, 1H), 6.96 (t, 1H), 6.60 (d, 2H), 5.18 (dd, 1H), 4.86 (s, 2H), 3.09-2.96 (m, 2H), 2.35 (s, 3H); MS (m/z) 553.34 [M+H]$^+$.

Example 501

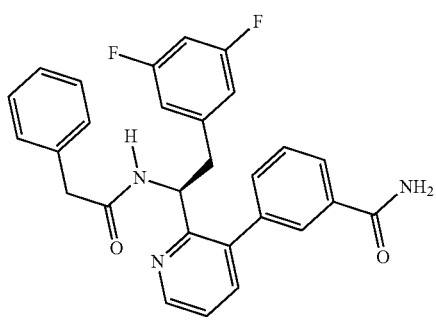

501

Example 502

Synthesis of (S)-3-(2-(2-(3,5-difluorophenyl)-1-(2-phenylacetamido)ethyl)pyridin-3-yl)benzamide (501)

The title compound was prepared according to the method presented in the synthesis of 50D utilizing 50C and 2-phenylacetic acid to provide 21 mg of the desired compound in a 40% yield: $^1$H NMR (400 MHz, dmso) δ 8.72 (d, 1H), 8.66 (d, 1H), 7.95 (s, 1H), 7.88 (d, 1H), 7.76 (s, 1H), 7.62 (d, 1H), 7.43 (ddd, 4H), 7.18-7.10 (m, 3H), 7.04 (d, 2H), 6.89 (t, 1H), 6.51 (d, 2H), 5.15 (d, 1H), 3.42 (d, 1H), 3.28 (d, 1H), 2.96 (d, 2H); MS (m/z) 472.3 [M+H]$^+$.

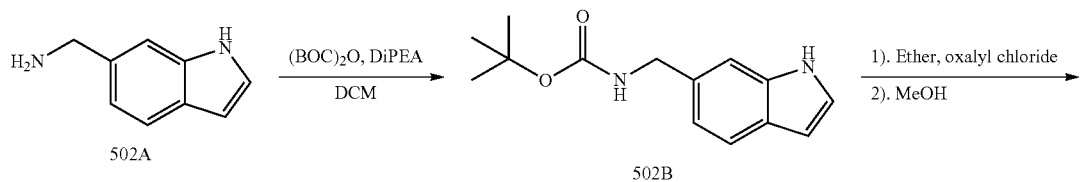

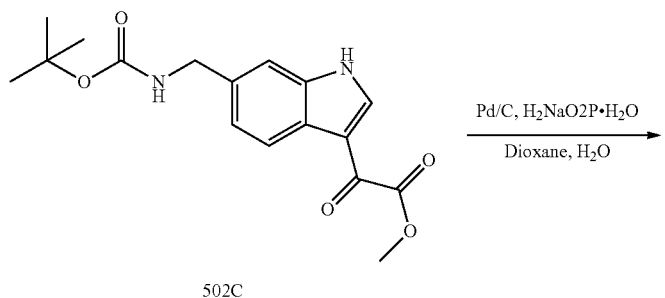

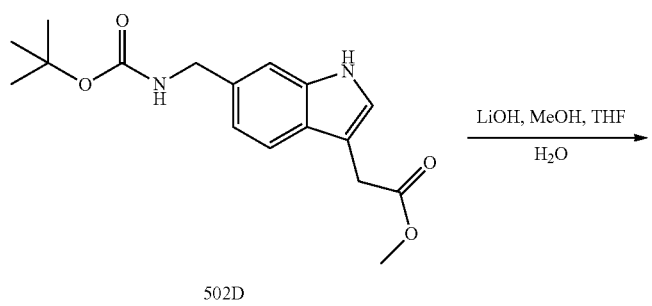

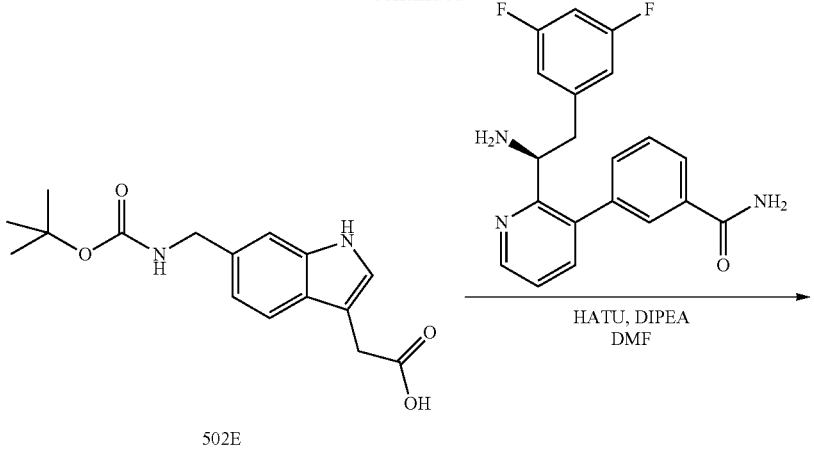

502E

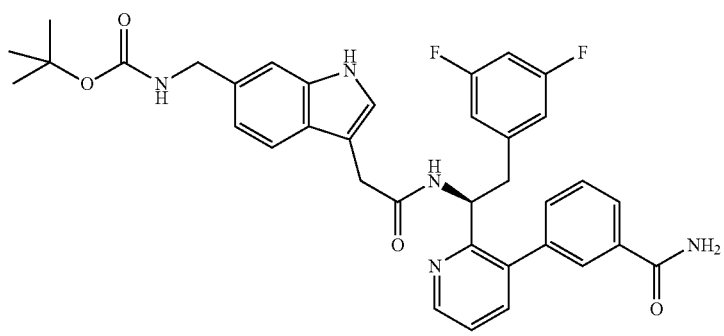

502F

Synthesis of ethyl tert-butyl (1H-indol-6-yl)methylcarbamate (502B)

The title compound was prepared according to the method presented in Example 491 substituting (1H-indol-6-yl)methanamine for ethyl 491A to provide the desired compound: MS (m/z) 246.7 [M+H]$^+$.

Synthesis of methyl 2-(6-((tert-butoxycarbonylamino)methyl)-1H-indol-3-yl)-2-oxoacetate (502C)

The title compound was prepared according to the method presented in Example 491 substituting tert-butyl (1H-indol-6-yl)methylcarbamate for 491B to provide the desired compound: MS (m/z) 333.9 [M+H]$^+$.

Synthesis of methyl 2-(6-((tert-butoxycarbonylamino)methyl)-1H-indol-3-yl)acetate (502D)

The title compound was prepared according to the method presented in Example 491 substituting methyl 2-(6-((tert-butoxycarbonylamino)methyl)-1H-indol-3-yl)-2-oxoacetate for 491C to provide the desired compound: MS (m/z) 319.0 [M+H]$^+$.

Synthesis of 2-(6-((tert-butoxycarbonylamino)methyl)-1H-indol-3-yl)acetic acid (502E)

The title compound was prepared according to the method presented in Example 491 substituting ethyl methyl 2-(6-((tert-butoxycarbonylamino)methyl)-1H-indol-3-yl)acetate for 491D to provide the desired compound: MS (m/z) 304.9 [M+H]$^+$.

Synthesis of (S)-tert-butyl (3-(2-(1-(3-(3-carbamoylphenyl)pyridin-2-yl)-2-(3,5-difluorophenyl)ethylamino)-2-oxoethyl)-1H-indol-6-yl)methylcarbamate (502F)

The title compound was prepared according to the method presented in the synthesis of 50D utilizing 50C and 2-(6-((tert-butoxycarbonylamino)methyl)-1H-indol-3-yl)acetic acid to provide 30 mg of the desired compound in a 44% yield: $^1$H NMR (400 MHz, dmso) δ 10.69 (s, 1H), 8.66-8.62 (m, 1H), 8.54 (d, 1H), 7.93 (s, 1H), 7.86 (d, 1H), 7.73 (s, 1H), 7.63-7.56 (m, 1H), 7.48-7.35 (m, 4H), 7.27 (s, 1H), 7.21 (d, 1H), 7.12 (s, 1H), 6.96 (s, 1H), 6.88 (t, 1H), 6.75 (d, 1H), 6.47 (d, 2H), 5.19 (d, 1H), 4.12 (d, 2H), 3.44 (d, 2H), 2.94 (d, 2H), 1.36 (s, 9H); MS (m/z) 640.2 [M+H]$^+$.

Example 503

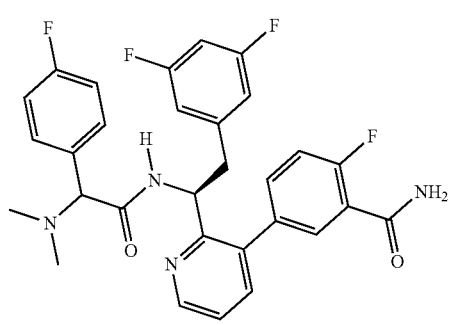

Synthesis of 5-(2-((1S)-2-(3,5-difluorophenyl)-1-(2-(dimethylamino)-2-(4-fluorophenyl)acetamido)ethyl)pyridin-3-yl)-2-fluorobenzamide (503)

The title compound was prepared according to the method presented in the synthesis of 54G substituting 2-(dimethylamino)-2-(4-fluorophenyl)acetic acid for 54F to provide the desired compound (the first peak off HPLC, 3 mg, 4%): $^1$H NMR (400 MHz, dmso) δ 10.07-9.97 (m, 1H), 9.51-9.44 (m, 1H), 8.45 (s, 1H), 7.72 (s, 2H), 7.58 (d, 1H), 7.49 (d, 1H), 7.38-7.21 (m, 6H), 6.98 (s, 1H), 6.68 (d, 2H), 5.26 (s, 1H), 4.80 (s, 1H), 3.07 (s, 2H), 2.49 (s, 3H), 2.30 (s, 3H); MS (m/z) 551.3 [M+H]$^+$.

Example 504

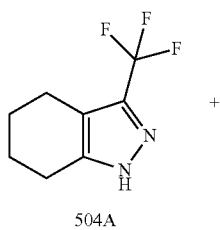

504A

+

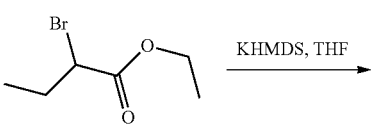

504B

KHMDS, THF →

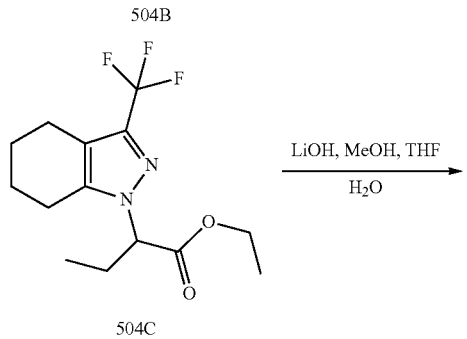

504C

LiOH, MeOH, THF / H$_2$O →

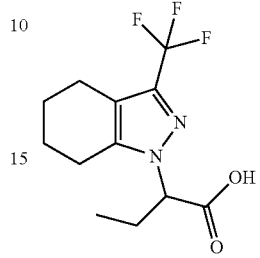

504D

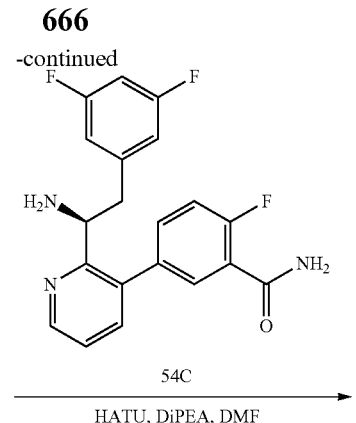

54C / HATU, DiPEA, DMF →

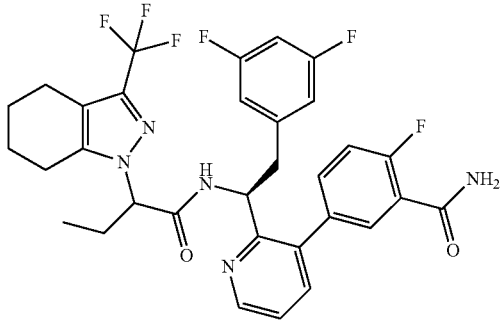

504E

Synthesis of ethyl 2-(3-(trifluoromethyl)-4,5,6,7-tetrahydro-1H-indazol-1-yl)butanoate (504C)

A RB was charged with 3-(trifluoromethyl)-4,5,6,7-tetrahydro-1H-indazole (1 g, 5 mmol), KHMDS (1.3 g, 7 mmol), and THF (5 ml). The resulting mixture was stirred for 10 minutes then ethyl 2-bromobutanoate (0.7 mg, 5 mmol) was added. The mixture was stirred until done by LC/MS then diluted with H$_2$O and extracted 2× EtOAc. The organic layers were dried over sodium sulfate, and concentrated to afford the desired compound which was used crude in the next reaction; MS (m/z) 305.3 [M+H]$^+$.

Synthesis of 2-(3-(trifluoromethyl)-4,5,6,7-tetrahydro-1H-indazol-1-yl)butanoic acid (504D)

The title compound was prepared according to the method presented in Example 54 substituting ethyl 2-(3-(trifluoromethyl)-4,5,6,7-tetrahydro-1H-indazol-1-yl)butanoate for 54E to provide the desired compound: MS (m/z) 277.3 [M+H]$^+$.

Synthesis of 5-(2-((1S)-2-(3,5-difluorophenyl)-1-(2-(3-(trifluoromethyl)-4,5,6,7-tetrahydro-1H-indazol-1-yl)butanamido)ethyl)pyridin-3-yl)-2-fluorobenzamide (504E)

The title compound was prepared according to the method presented in the synthesis of 54G substituting 2-(3-(trifluoromethyl)-4,5,6,7-tetrahydro-1H-indazol-1-yl)butanoic acid for 54F to provide the desired compound (24 mg, 28%): MS (m/z) 631.3 [M+H]⁺.

Example 505

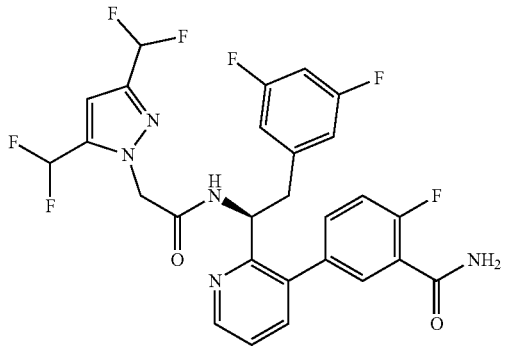

Synthesis of (S)-5-(2-(1-(2-(3,5-bis(difluoromethyl)-1H-pyrazol-1-yl)acetamido)-2-(3,5-difluorophenyl)ethyl)pyridin-3-yl)-2-fluorobenzamide (505)

The title compound was prepared according to the method presented in the synthesis of 56B substituting 3,5-bis(difluoromethyl)-1H-pyrazole for 1H-benzo[g]indole to provide the desired compound (25 mg, 62%): ¹H NMR (400 MHz, dmso) δ 9.01 (d, 1H), 8.68 (dd, 1H), 7.68-7.57 (m, 3H), 7.41 (dd, 2H), 7.38 (d, 1H), 7.33-7.24 (m, 1H), 7.11 (d, 1H), 6.97 (d, 1H), 6.89 (d, 1H), 6.80 (d, 1H), 6.51 (d, 2H), 5.21-5.10 (m, 1H), 4.94 (s, 2H), 2.98 (dd, 2H); MS (m/z) 579.3 [M+H]⁺.

Example 506

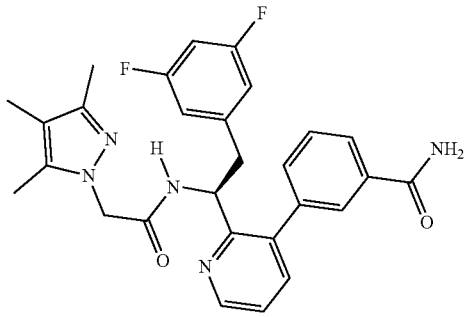

Synthesis of (S)-3-(2-(2-(3,5-difluorophenyl)-1-(2-(3,4,5-trimethyl-1H-pyrazol-1-yl)acetamido)ethyl)pyridin-3-yl)benzamide (506)

The title compound was prepared according to the method presented in the synthesis of 50D utilizing 50C and 2-(3,4,5-trimethyl-1H-pyrazol-1-yl)acetic acid to provide 21 mg of the desired compound in a 40% yield: ¹H NMR (400 MHz, dmso) δ 8.67 (dd, 2H), 7.94 (s, 1H), 7.89 (d, 1H), 7.72 (s, 1H), 7.65 (dd, 1H), 7.48 (t, 1H), 7.45-7.38 (m, 3H), 6.91 (t, 1H), 6.48 (d, 2H), 5.18 (dd, 1H), 4.60 (s, 2H), 3.04-2.88 (m, 2H), 1.99 (s, 3H), 1.87 (s, 3H), 1.78 (s, 3H); MS (m/z) 504.2 [M+H]⁺.

Example 507

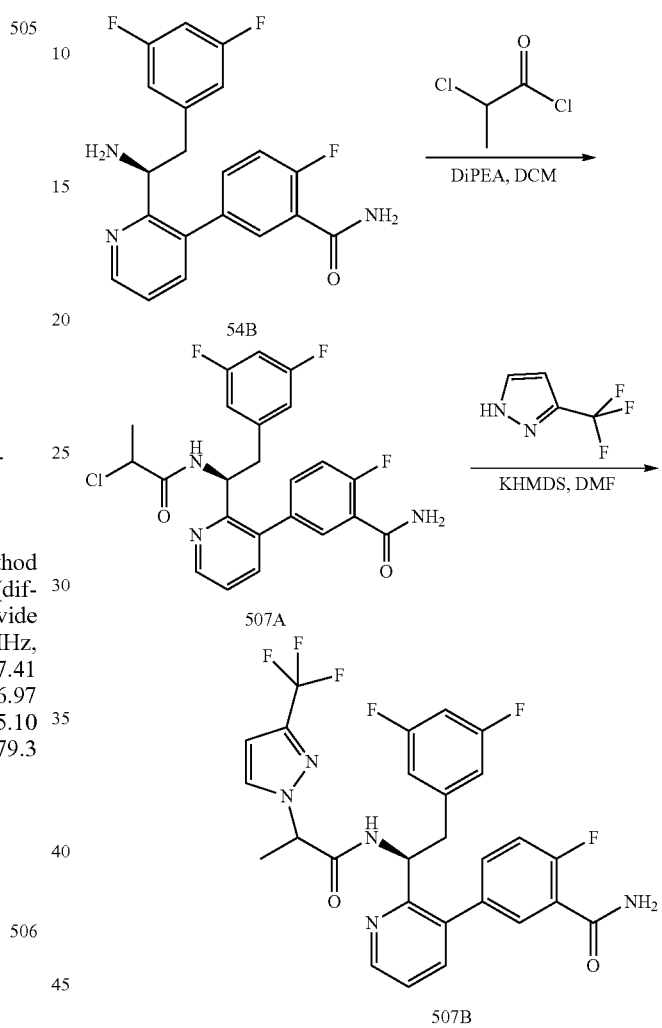

Synthesis of 5-(2-((1S)-1-(2-chloropropanamido)-2-(3,5-difluorophenyl)ethyl)pyridin-3-yl)-2-fluorobenzamide (507A)

The title compound was prepared according to the method presented in Example 56 substituting 2-chloropropanoyl chloride for 2-chloroacetyl chloride to provide the desired compound: MS (m/z) 462.9 [M+H]⁺.

Synthesis of 5-(2-((1S)-2-(3,5-difluorophenyl)-1-(2-(3-(trifluoromethyl)-1H-pyrazol-1-yl)propanamido)ethyl)pyridin-3-yl)-2-fluorobenzamide (507B)

The title compound was prepared according to the method presented in the synthesis of 56B substituting 3-(trifluoromethyl)-1H-pyrazole for 1H-benzo[g]indole and 507A for 56A to provide the desired compound (27 mg, 80%): MS (m/z) 562.3 [M+H]⁺.

Example 508

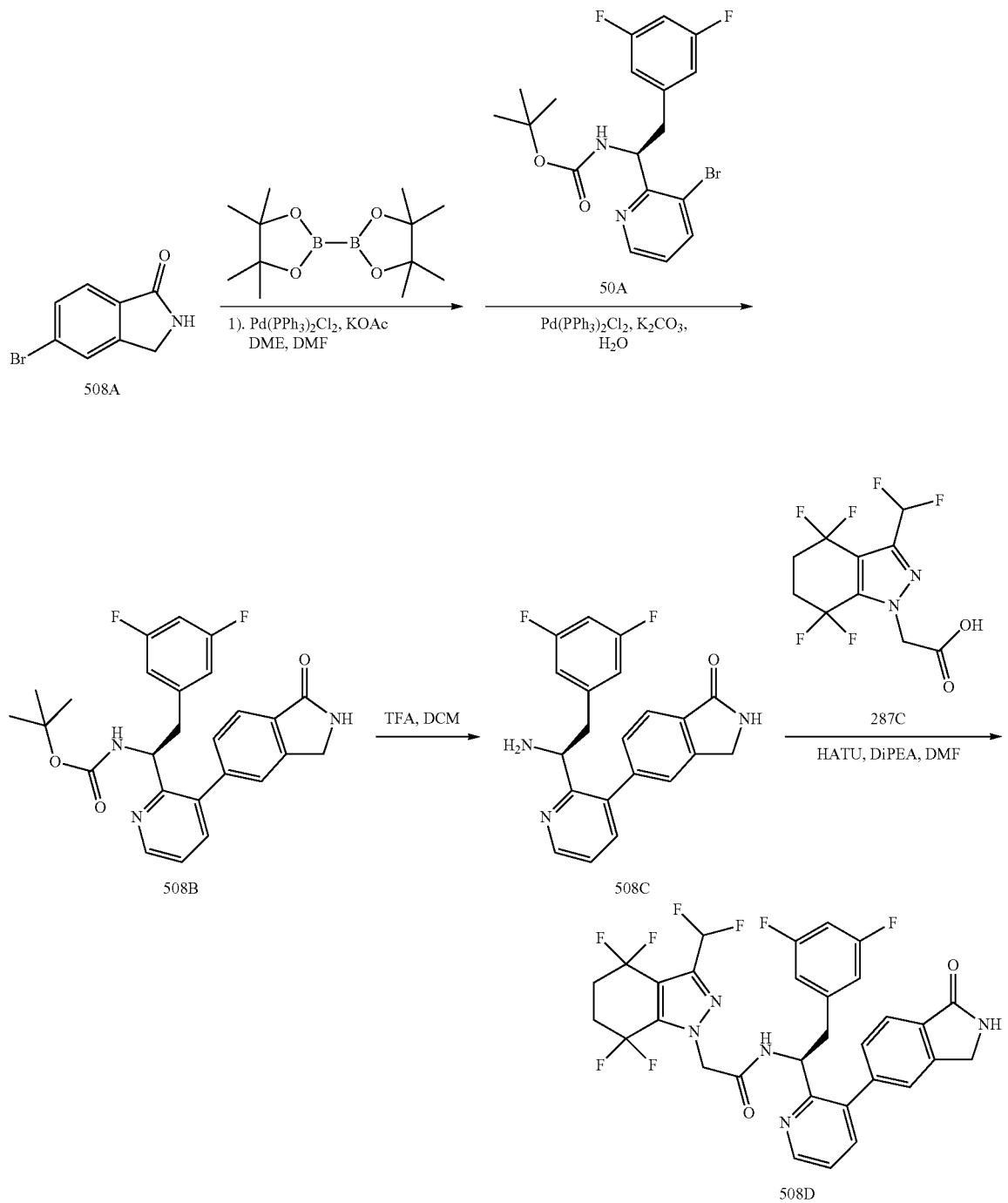

Synthesis of (S)-tert-butyl 2-(3,5-difluorophenyl)-1-(3-(1-oxoisoindolin-5-yl)pyridin-2-yl)ethylcarbamate (508B)

The title compound was prepared according to the method presented in the synthesis of 489B substituting 5-bromoisoindolin-1-one for 489A to provide the desired compound: MS (m/z) 466.2 [M+H]+.

Synthesis of (S)-5-(2-(1-amino-2-(3,5-difluorophenyl)ethyl)pyridin-3-yl)isoindolin-1-one (508C)

The title compound was prepared according to the method presented in the synthesis of 50C substituting of (S)-tert-butyl 2-(3,5-difluorophenyl)-1-(3-(1-oxoisoindolin-5-yl)pyridin-2-yl)ethylcarbamate for 50B to provide the desired compound: MS (m/z) 366.1 [M+H]+.

671

Synthesis of (S)-2-(3-(difluoromethyl)-4,4,7,7-tetrafluoro-4,5,6,7-tetrahydro-1H-indazol-1-yl)-N-(2-(3,5-difluorophenyl)-1-(3-(1-oxoisoindolin-5-yl)pyridin-2-yl)ethyl)acetamide (508D)

The title compound was prepared according to the method presented in the synthesis of 61F substituting 287C for 61C and 508C for 61E to provide the desired compound (34 mg): $^1$H NMR (400 MHz, cd$_3$od) δ 8.78-8.68 (m, 1H), 7.76 (d, 1H), 7.63 (dd, 1H), 7.43 (dd, 1H), 7.15 (s, 2H), 6.87 (d, 1H), 6.75-6.63 (m, 1H), 6.26 (d, 2H), 5.43-5.32 (m, 1H), 5.08 (s, 2H), 4.42 (q, 2H), 3.16-2.93 (m, 3H), 2.66-2.39 (m, 4H); MS (m/z) 650.4 [M+H]$^+$.

Example 509

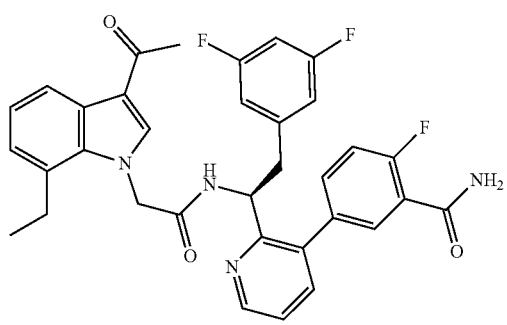

509

Synthesis of (S)-5-(2-(1-(2-(3-acetyl-7-ethyl-1H-indol-1-yl)acetamido)-2-(3,5-difluorophenyl)ethyl)pyridin-3-yl)-2-fluorobenzamide (509)

The title compound was prepared according to the method presented in the synthesis of 54G utilizing 54B and 2-(3-acetyl-7-ethyl-1H-indol-1-yl)acetic acid to provide 15 mg of the desired compound in a 18% yield: $^1$H NMR (400 MHz, dmso) δ 9.10 (d, 1H), 8.69 (dd, 1H), 8.12 (s, 1H), 8.01 (d, 1H), 7.64 (s, 2H), 7.60 (dd, 1H), 7.52-7.48 (m, 1H), 7.41 (dd, 2H), 7.32-7.24 (m, 1H), 7.07-6.92 (m, 2H), 6.86 (d, 1H), 6.63 (d, 2H), 5.14 (dd, 1H), 4.98 (s, 2H), 3.02 (d, 2H), 2.52 (dd, 3H), 2.33 (s, 3H); MS (m/z) 599.7 [M+H]$^+$.

Example 510

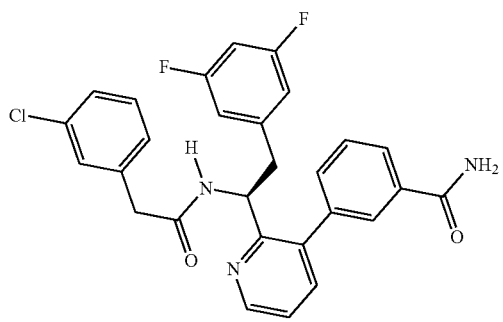

510

672

Synthesis of (S)-3-(2-(1-(2-(3-chlorophenyl)acetamido)-2-(3,5-difluorophenyl)ethyl)pyridin-3-yl)benzamide (510)

The title compound was prepared according to the method presented in the synthesis of 50D utilizing 50C and 2-(3-chlorophenyl)acetic acid to provide 18 mg of the desired compound in a 40% yield: $^1$H NMR (400 MHz, dmso) δ 8.79 (d, 1H), 8.67 (dd, 1H), 7.95 (s, 1H), 7.89 (d, 1H), 7.76 (s, 1H), 7.63 (dd, 1H), 7.44 (ddd, 4H), 7.19 (d, 2H), 7.11 (s, 1H), 7.01 (d, 1H), 6.88 (t, 1H), 6.50 (d, 2H), 5.15 (dd, 1H), 3.37 (dd, 21H), 2.96 (d, 2H); MS (m/z) 506.6 [M+H]$^+$.

Example 511

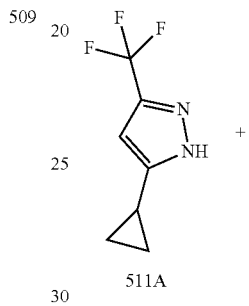

511A

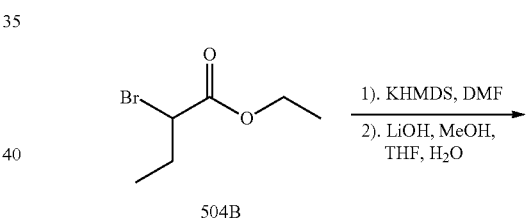

504B

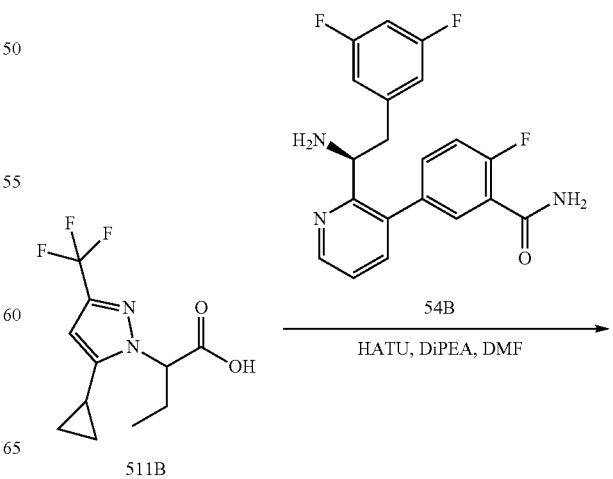

511B

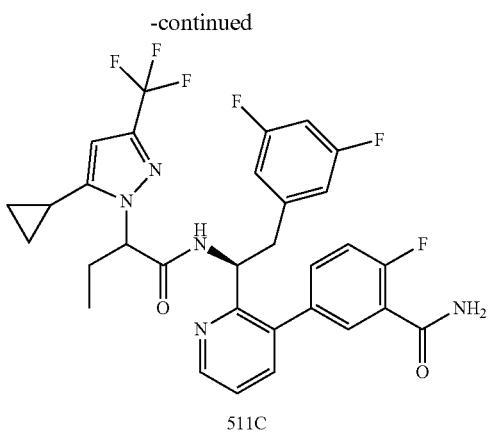

511C

Synthesis of ethyl 2-(5-cyclopropyl-3-(trifluoromethyl)-1H-pyrazol-1-yl)butanoate The title compound was prepared according to the method presented in Example 478 substituting 504B for 478B to provide the desired compound: MS (m/z) 291.1 [M+H]+.

Synthesis of 2-(5-cyclopropyl-3-(trifluoromethyl)-1H-pyrazol-1-yl)butanoic acid (511B)

The title compound was prepared according to the method presented in Example 478 substituting ethyl 2-(5-cyclopropyl-3-(trifluoromethyl)-1H-pyrazol-1-yl)butanoate for 478C to provide the desired compound: MS (m/z) 263.1 [M+H]+.

Synthesis of 5-(2-((1S)-1-(2-(5-cyclopropyl-3-(trifluoromethyl)-1H-pyrazol-1-yl)butanamido)-2-(3,5-difluorophenyl)ethyl)pyridin-3-yl)-2-fluorobenzamide (511C)

The title compound was prepared according to the method presented in the synthesis of 54G substituting 2-(5-cyclopropyl-3-(trifluoromethyl)-1H-pyrazol-1-yl)butanoic acid for 2-(5-(trifluoromethyl)-1H-indol-3-yl)acetic acid to provide the desired compound (32 mg, 39%): MS (m/z) 616.4 [M+H]+.

Examples 512 and 528

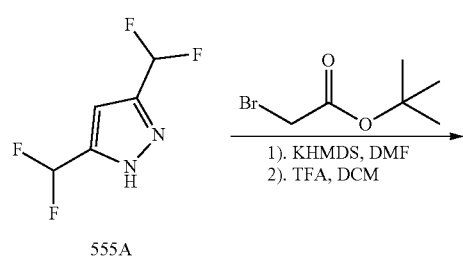

555A

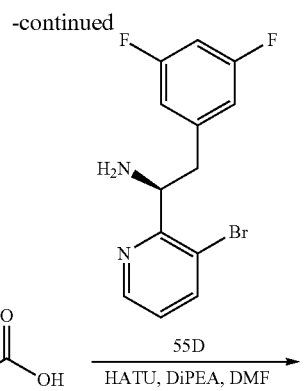

512A

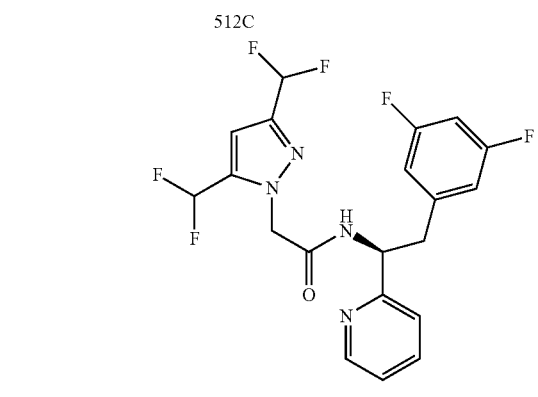

512B

512C

+

528

Synthesis of tert-butyl 2-(3,5-bis(difluoromethyl)-1H-pyrazol-1-yl)acetate

The title compound was prepared according to the method presented in Example 478 substituting tert-butyl 2-bromoacetate for ethyl 2-bromo-3-methylbutanoate to provide the desired compound: MS (m/z) 285.0 [M+H]⁺.

Synthesis of 2-(3,5-bis(difluoromethyl)-1H-pyrazol-1-yl)acetic acid (512A)

A round bottom flask was charged with tert-butyl 2-(3,5-bis(difluoromethyl)-1H-pyrazol-1-yl)acetate (1.3 g, 4.6 mmol) and TFA:DCM 1:1 (4 ml). The reaction was stirred at room temperature until done by LC/MS then concentrated 2× from DCM. The crude mixture was used as is in next reaction. MS (m/z) 227.0 [M+H]⁺.

Synthesis of (S)-2-(3,5-bis(difluoromethyl)-1H-pyrazol-1-yl)-N-(1-(3-bromopyridin-2-yl)-2-(3,5-difluorophenyl)ethyl)acetamide (512B)

The title compound was prepared according to the method presented in the synthesis of 54G substituting 2-(3,5-bis(difluoromethyl)-1H-pyrazol-1-yl)acetic acid for 2-(5-(trifluoromethyl)-1H-indol-3-yl)acetic acid and 55D for 54B to provide the desired compound: MS (m/z) 521.9 [M+H]⁺.

Synthesis of (S)—N-(1-(3-(1H-pyrrolo[2,3-b]pyridin-5-yl)pyridin-2-yl)-2-(3,5-difluorophenyl)ethyl)-2-(3,5-bis(difluoromethyl)-1H-pyrazol-1-yl)acetamide (512C) and (S)-2-(3,5-bis(difluoromethyl)-1H-pyrazol-1-yl)-N-(2-(3,5-difluorophenyl)-1-(pyridin-2-yl)ethyl)acetamide (528)

A microwave vial was charged with 512B (100 mg, 0.2 mmol), DMF (0.5 ml), DME (1.5 ml), 5-(4,4,5,5-tetramethyl-1,3,2-dioxaborolan-2-yl)-1H-pyrrolo[2,3-b]pyridine (51 mg, 0.2 mmol), Pd(PPh₃)₄ (11 mg, 0.01 mmol) and K₂CO₃ (39 mg, 0.3 mmol) dissolved in water (0.3 ml). Microwave the mixture at 150° C. for 30 minutes. Allow the reaction to cool then dilute with H₂O and extract 2× EtOAc. The combined organic layers were washed with brine then dried over sodium sulfate, concentrated, and purified by HPLC to give the desired compounds (512C, 5 mg, 5%) and (528, 5 mg, 6%): 512C ¹H NMR (400 MHz, dmso) δ 11.76 (s, 1H), 8.96 (s, 1H), 8.68 (d, 1H), 7.95 (s, 1H), 7.64 (d, 2H), 7.50 (s, 1H), 7.46-7.37 (m, 1H), 7.11 (d, 1H), 6.97 (d, 2H), 6.80 (d, 1H), 6.41 (d, 3H), 5.19 (d, 1H), 4.96 (s, 2H), 3.05 (d, 1H), 2.97 (d, 1H); MS (m/z) 559.1 [M+H]⁺; 528 ¹H NMR (400 MHz, dmso) δ 8.89 (d, 1H), 8.55 (d, 1H), 7.76 (t, 1H), 7.37-7.28 (m, 2H), 7.13 (d, 1H), 7.07-6.92 (m, 2H), 6.84 (dd, 4H), 5.13 (d, 1H), 4.97 (q, 2H), 3.17 (dd, 1H), 3.07-2.95 (m, 1H); MS (m/z) 443.0 [M+H]⁺.

Example 513

Synthesis of (S)—N-(1-(3-(4-chlorophenyl)pyridin-2-yl)-2-(3,5-difluorophenyl)ethyl)-2-(5-(trifluoromethyl)-1H-indol-3-yl)acetamide (513)

The title compound was prepared according to the method presented in the synthesis of 36F utilizing 36E and 54F to provide 17.8 mg of the desired compound in a 30% yield: ¹H NMR (400 MHz, dmso) δ 11.25 (s, 1H), 8.67 (d, 1H), 8.63 (dd, 1H), 7.82 (s, 1H), 7.53 (dd, 1H), 7.46 (d, 1H), 7.36 (dd, 3H), 7.29 (d, 1H), 7.23 (d, 1H), 7.15 (d, 2H), 6.87 (t, 1H), 6.38 (d, 2H), 5.14 (q, 1H), 3.55 (s, 2H), 2.91 (t, 2H); MS (m/z) 570.1 [M+H]⁺.

Example 514

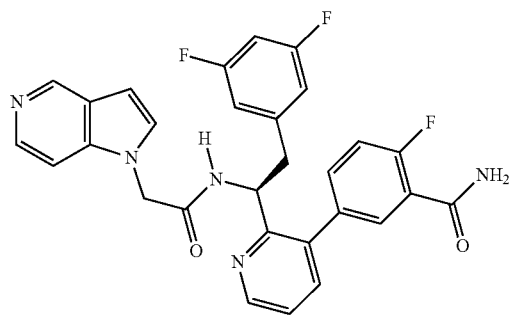

514

Synthesis of (S)-5-(2-(1-(2-(1H-pyrrolo[3,2-c]pyridin-1-yl)acetamido)-2-(3,5-difluorophenyl)ethyl)pyridin-3-yl)-2-fluorobenzamide (514)

The title compound was prepared according to the method presented in Example 56 substituting 1H-pyrrolo[3,2-c]pyridine for 1H-benzo[g]indole to provide the desired compound (23 mg, 62%): ¹H NMR (400 MHz, dmso) δ 9.21 (s, 1H), 9.12 (d, 1H), 8.72 (dd, 1H), 8.39 (d, 1H), 7.75 (d, 1H), 7.70 (d, 1H), 7.62 (dd, 3H), 7.52-7.46 (m, 1H), 7.43 (dd, 1H), 7.35 (s, 1H), 7.32-7.23 (m, 1H), 6.98 (d, 1H), 6.90 (t, 1H), 6.55 (d, 2H), 5.15 (dd, 1H), 5.07 (d, 2H), 3.10-2.96 (m, 2H); MS (m/z) 530.5 [M+H]⁺.

Example 515

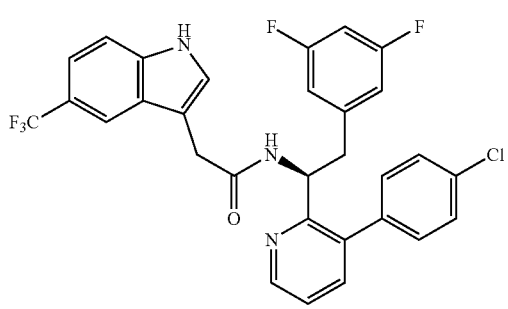

513

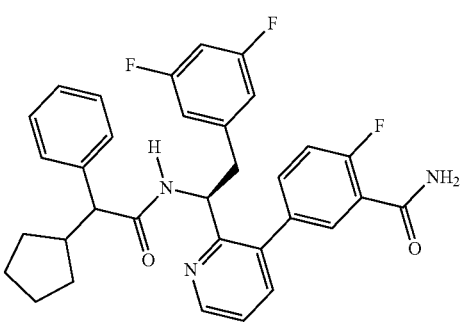

515

Synthesis of 5-(2-(((1S)-1-(2-cyclopentyl-2-phenylacetamido)-2-(3,5-difluorophenyl)ethyl)pyridin-3-yl)-2-fluorobenzamide (515)

The title compound was prepared according to the method presented in the synthesis of 54G substituting 2-cyclopentyl-2-phenylacetic acid for 54F to provide the desired compound (the second peak off HPLC, 12 mg, 16%): $^1$H NMR (400 MHz, dmso) δ 10.16-10.05 (m, 1H), 9.58 (s, 1H), 8.68 (d, 1H), 7.79-7.65 (m, 3H), 7.63 (s, 1H), 7.50 (s, 1H), 7.48-7.35 (m, 2H), 7.35-7.28 (m, 2H), 7.18 (t, 2H), 6.78 (s, 1H), 6.35 (d, 2H), 5.20 (s, 1H), 4.78 (s, 1H), 2.91 (d, 3H), 2.58 (s, 4H), 2.33 (s, 4H); MS (m/z) 558.6 [M+H]$^+$.

Example 516

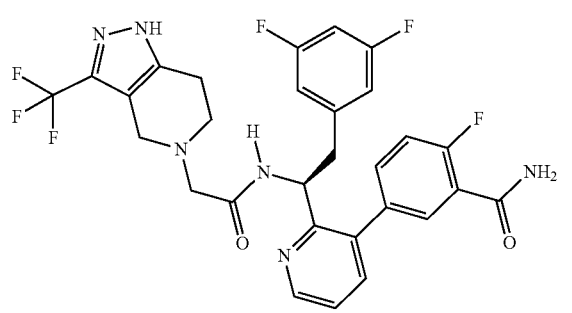

516

Synthesis of (S)-5-(2-(2-(3,5-difluorophenyl)-1-(2-(3-(trifluoromethyl)-6,7-dihydro-1H-pyrazolo[4,3-c]pyridin-5(4H)-yl)acetamido)ethyl)pyridin-3-yl)-2-fluorobenzamide (516)

The title compound was prepared according to the method presented in the synthesis of 56B substituting 3-(trifluoromethyl)-4,5,6,7-tetrahydro-1H-pyrazolo[4,3-c]pyridine for 1H-benzo[g]indole to provide the desired compound (1 mg, 2%): $^1$H NMR (400 MHz, cd$_3$od) δ 8.71 (s, 1H), 7.57 (d, 1H), 7.55-7.49 (m, 1H), 7.40 (d, 1H), 7.21 (d, 2H), 6.72-6.62 (m, 1H), 6.35 (s, 2H), 5.32 (s, 1H), 4.29 (s, 2H), 3.48 (d, 2H), 3.17-3.00 (m, 4H), 2.99-2.89 (m, 2H); MS (m/z) 603.3 [M+H]$^+$.

Example 517

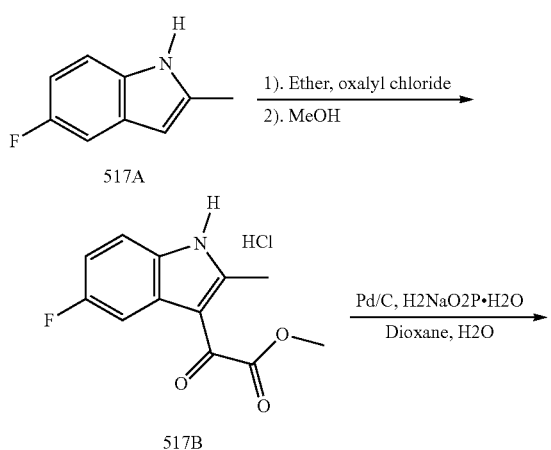

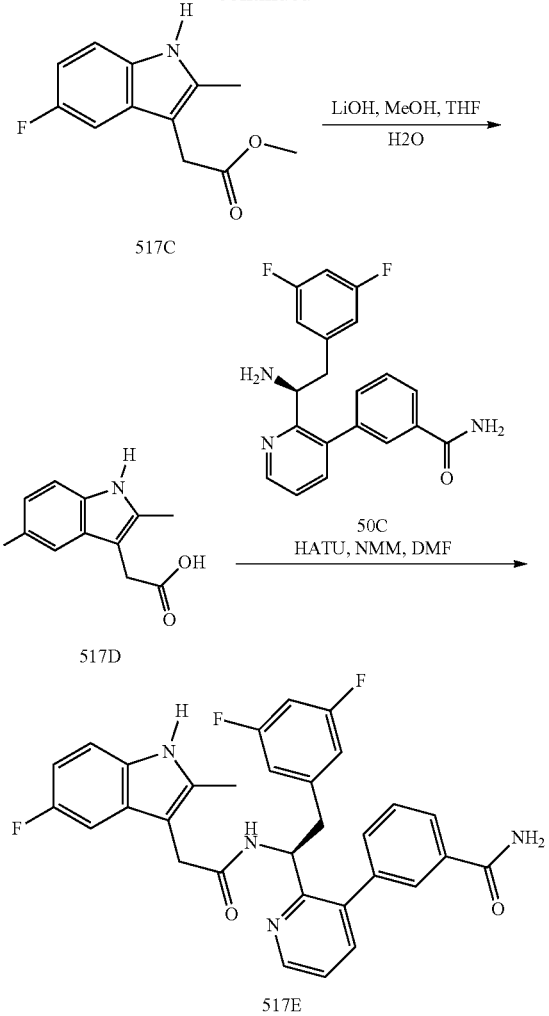

Synthesis of methyl 2-(5-fluoro-2-methyl-1H-indol-3-yl)-2-oxoacetate hydrochloride (517B)

The title compound was prepared according to the method presented in Example 54 substituting 5-fluoro-2-methyl-1H-indole for 54C to provide the desired compound: MS (m/z) 236.3 [M+H]$^+$.

Synthesis methyl 2-(5-fluoro-2-methyl-1H-indol-3-yl)acetate (517C)

The title compound was prepared according to the method presented in Example 54 substituting of methyl 2-(5-fluoro-2-methyl-1H-indol-3-yl)-2-oxoacetate hydrochloride for 54D to provide the desired compound: MS (m/z) 222.1 [M+H]$^+$.

Synthesis of 2-(5-fluoro-2-methyl-1H-indol-3-yl)acetic acid (517D)

The title compound was prepared according to the method presented in Example 54 substituting methyl 2-(5-fluoro-2-methyl-1H-indol-3-yl)acetate for 54E to provide the desired compound MS (m/z) 208.2 [M+H]$^+$.

Synthesis of (S)-3-(2-(2-(3,5-difluorophenyl)-1-(2-(5-fluoro-2-methyl-1H-indol-3-yl)acetamido)ethyl)pyridin-3-yl)benzamide (517E)

The title compound was prepared according to the method presented in the synthesis of 50D utilizing 50C and 2-(5-fluoro-2-methyl-1H-indol-3-yl)acetic acid to provide 17 mg of the desired compound in a 27% yield: $^1$H NMR (400 MHz, dmso) δ 10.75 (s, 1H), 8.64 (dd, 1H), 8.59 (d, 1H), 7.94 (s, 1H), 7.87 (d, 1H), 7.75 (s, 1H), 7.60 (dd, 1H), 7.45 (d, 2H), 7.39 (dd, 2H), 7.10 (dd, 1H), 7.04 (dd, 1H), 6.86 (t, 1H), 6.76-6.65 (m, 1H), 6.47 (d, 2H), 5.13 (t, 1H), 3.43-3.30 (m, 2H), 2.93 (d, 2H), 2.18 (s, 3H); MS (m/z) 543.8 [M+H]$^+$.

Example 518

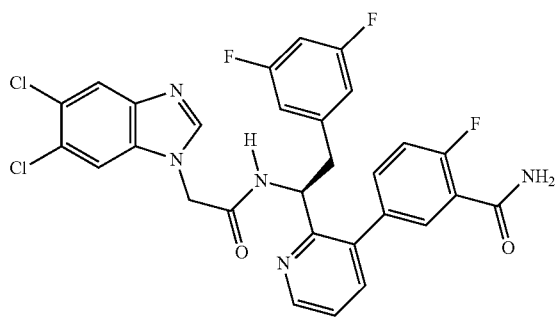

Synthesis of (S)-5-(2-(1-(2-(5,6-dichloro-1H-benzo[d]imidazol-1-yl)acetamido)-2-(3,5-difluorophenyl)ethyl)pyridin-3-yl)-2-fluorobenzamide (518)

The title compound was prepared according to the method presented in Example 56 substituting 5,6-dichloro-1H-benzo[d]imidazole for 1H-benzo[g]indole to provide the desired compound (19 mg, 45%): $^1$H NMR (400 MHz, dmso) δ 9.13 (d, 1H), 8.71 (d, 1H), 8.21 (s, 1H), 7.88 (s, 1H), 7.61 (dd, 3H), 7.53 (s, 1H), 7.47 (d, 1H), 7.44-7.35 (m, 2H), 7.31-7.23 (m, 1H), 6.89 (t, 1H), 6.55 (d, 2H), 5.20-5.10 (m, 1H), 4.92 (s, 2H), 3.02 (d, 2H); MS (m/z) 599.3 [M+H]$^+$.

Example 519

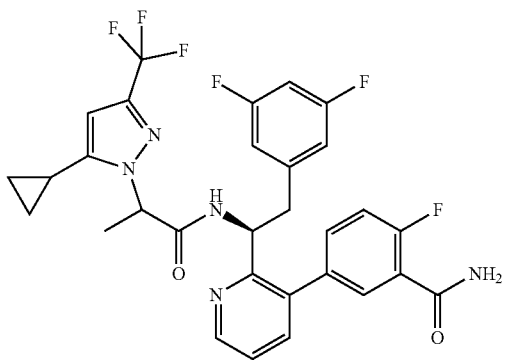

Synthesis of 5-(2-(((1S)-1-(2-(5-cyclopropyl-3-(trifluoromethyl)-1H-pyrazol-1-yl)propanamido)-2-(3,5-difluorophenyl)ethyl)pyridin-3-yl)-2-fluorobenzamide (519)

The title compound was prepared according to the method presented in the synthesis of 56B substituting 5-cyclopropyl-3-(trifluoromethyl)-1H-pyrazole for 1H-benzo[g]indole and 507A for 56A to provide the desired compound (23 mg, 64%): MS (m/z) 602.3 [M+H]$^+$.

Example 521

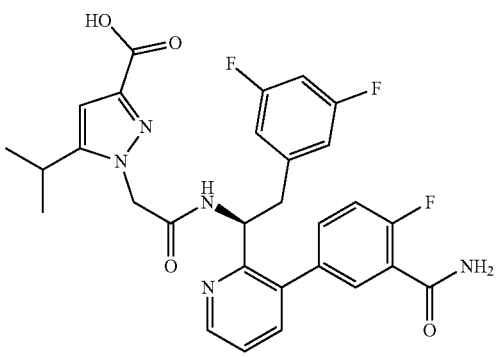

Synthesis of (S)-1-(2-(1-(3-(3-carbamoyl-4-fluorophenyl)pyridin-2-yl)-2-(3,5-difluorophenyl)ethylamino)-2-oxoethyl)-5-isopropyl-1H-pyrazole-3-carboxylic acid (521)

The title compound was prepared according to the method presented in the synthesis of 56B substituting 5-isopropyl-1H-pyrazole-3-carboxylic acid for 1H-benzo[g]indole to provide the desired compound (2 mg, 5%): $^1$H NMR (400 MHz, dmso) δ 8.71 (d, 1H), 8.65 (d, 1H), 7.69-7.56 (m, 3H), 7.48-7.36 (m, 3H), 7.34-7.26 (m, 1H), 6.89 (t, 1H), 6.50 (d, 3H), 5.16 (d, 1H), 4.59 (s, 2H), 3.03-2.88 (m, 4H), 1.18 (d, 6H); MS (m/z) 566.4 [M+H]$^+$.

Example 522

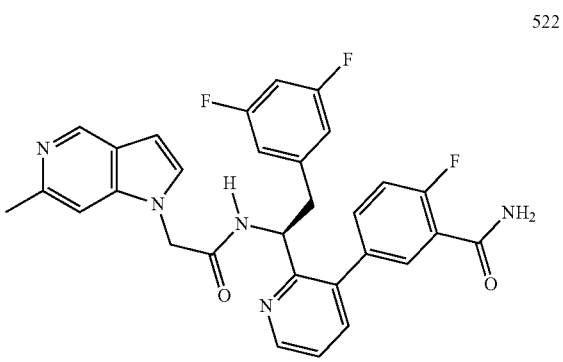 [SMILES: Cc1cc2c(ccn2CC(=O)N[C@@H](Cc2cc(F)cc(F)c2)c2ncccc2-c2ccc(F)c(C(N)=O)c2)cn1]

Synthesis of (S)-5-(2-(2-(3,5-difluorophenyl)-1-(2-(6-methyl-1H-pyrrolo[3,2-c]pyridin-1-yl)acetamido)ethyl)pyridin-3-yl)-2-fluorobenzamide (522)

The title compound was prepared according to the method presented in Example 56 substituting 6-methyl-1H-pyrrolo[3,2-c]pyridine for 1H-benzo[g]indole to provide the desired compound (9 mg, 24%): $^1$H NMR (400 MHz, dmso) δ 9.09 (d, 2H), 8.71 (d, 1H), 7.62 (dd, 4H), 7.54 (s, 1H), 7.49 (d, 1H), 7.43 (dd, 1H), 7.36 (s, 1H), 7.33-7.25 (m, 1H), 6.91 (s, 1H), 6.88 (d, 1H), 6.57 (d, 2H), 5.16 (s, 1H), 4.98 (d, 2H), 3.02 (d, 2H), 2.63 (s, 3H); MS (m/z) 544.5 [M+H]+.

Example 523

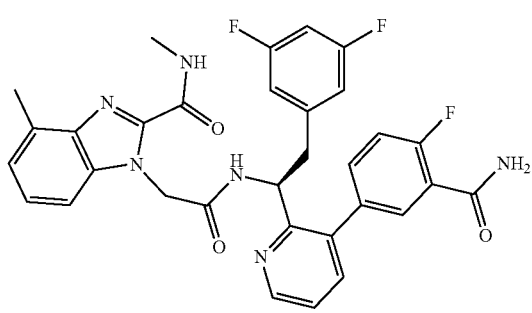

523

Synthesis of (S)-1-(2-(1-(3-(3-carbamoyl-4-fluorophenyl)pyridin-2-yl)-2-(3,5-difluorophenyl)ethylamino)-2-oxoethyl)-N,4-dimethyl-1H-benzo[d]imidazole-2-carboxamide (523)

The title compound was prepared according to the method presented in the synthesis of 54G substituting 2-(4-methyl-2-(methylcarbamoyl)-1H-benzo[d]imidazol-1-yl)acetic acid for 54F to provide the desired compound (24 mg, 37%): $^1$H NMR (400 MHz, dmso) δ 9.29 (d, 1H), 8.71 (dd, 1H), 8.25 (d, 1H), 7.72 (d, 1H), 7.69-7.60 (m, 3H), 7.54-7.48 (m, 1H), 7.48-7.35 (m, 4H), 7.33-7.24 (m, 1H), 6.93 (t, 1H), 6.60 (d, 2H), 5.21-5.07 (m, 4H), 4.01 (q, 2H), 3.02 (dd, 2H), 2.58 (d, 3H); MS (m/z) 601.4 [M+H]+.

Example 524

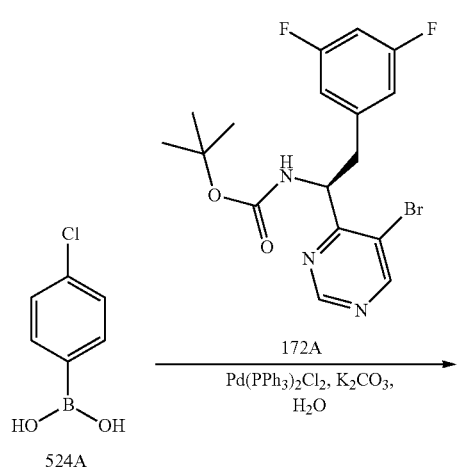

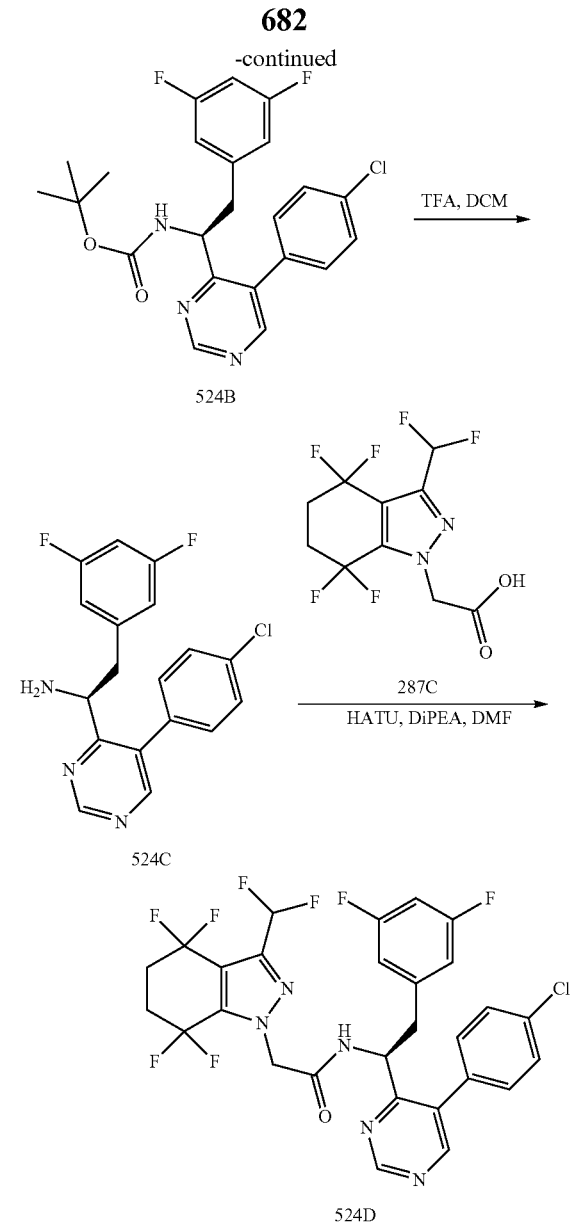

Synthesis of (S)-tert-butyl 1-(5-(4-chlorophenyl)pyrimidin-4-yl)-2-(3,5-difluorophenyl)ethylcarbamate (524B)

The title compound was prepared according to the method presented in the synthesis of 489B starting from step 2 and substituting 4-chlorophenylboronic acid for 489A and 172A for 50A to provide the desired compound: MS (m/z) 446.5 [M+H]+.

Synthesis of (S)-1-(5-(4-chlorophenyl)pyrimidin-4-yl)-2-(3,5-difluorophenyl)ethanamine (524C)

The title compound was prepared according to the method presented in the synthesis of 50C substituting (S)-tert-butyl 1-(5-(4-chlorophenyl)pyrimidin-4-yl)-2-(3,5-difluorophenyl)ethylcarbamate for 50B to provide the desired compound: MS (m/z) 346.3 [M+H]+.

683

Synthesis of (S)—N-(1-(5-(4-chlorophenyl)pyrimidin-4-yl)-2-(3,5-difluorophenyl)ethyl)-2-(3-(difluoromethyl)-4,4,7,7-tetrafluoro-4,5,6,7-tetrahydro-1H-indazol-1-yl)acetamide (524D)

The title compound was prepared according to the method presented in the synthesis of 61F substituting 287C for 61C and 524C for 61E to provide the desired compound (25 mg): $^1$H NMR (400 MHz, cd$_3$od) δ 9.21 (s, 1H), 9.06 (d, 1H), 8.52 (s, 1H), 7.41 (d, 2H), 7.14 (d, 2H), 6.94-6.61 (m, 2H), 6.34 (d, 2H), 5.41 (q, 1H), 5.06 (s, 2H), 3.03 (d, 2H), 2.62-2.40 (m, 4H); MS (m/z) 630.7 [M+H]$^+$.

Example 525

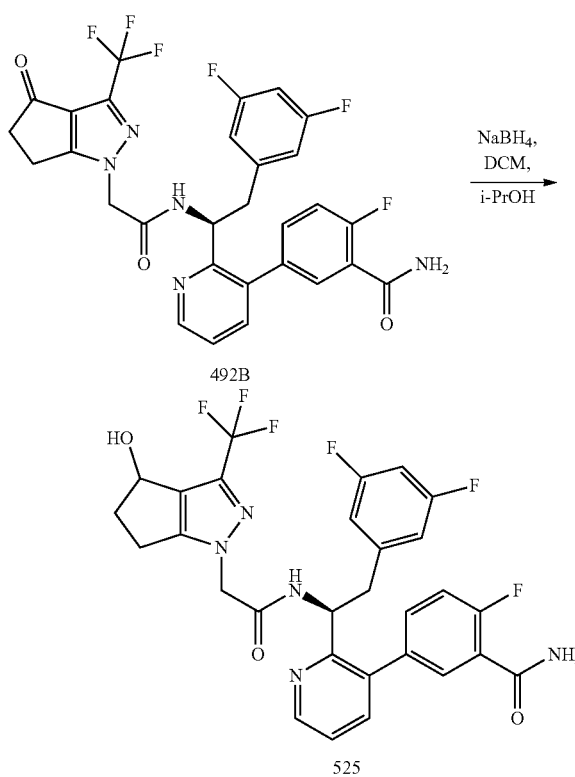

Synthesis of 5-(2-((1S)-2-(3,5-difluorophenyl)-1-(2-(4-hydroxy-3-(trifluoromethyl)-5,6-dihydrocyclopenta[c]pyrazol-1 (4H)-yl)acetamido)ethyl)pyridin-3-yl)-2-fluorobenzamide (525)

A round bottom flask was charged (S)-5-(2-(2-(3,5-difluorophenyl)-1-(2-(4-oxo-3-(trifluoromethyl)-5,6-dihydrocyclopenta[c]pyrazol-1(4H)-yl)acetamido)ethyl)pyridin-3-yl)-2-fluorobenzamide (10 mg, 0.2 mmol), DCM (3 ml), i-PrOH (0.25 ml), and NaBH$_4$ (8 mg, 0.2 mmol). The reaction was stirred at room temperature until done by LC/MS then quenched with 1 N HCl and concentrated. The mixture was dissolved in DMF, filtered, and purified by HPLC to obtain the desired compound (7.8 mg, 65%): $^1$H NMR (400 MHz, cd$_3$od) δ 8.69 (d, 1H), 7.60 (d, 1H), 7.47-7.38 (m, 2H), 7.28 (s, 1H), 7.22 (d, 1H), 6.66 (s, 1H), 6.33 (s, 2H), 5.35 (s, 1H), 5.07 (s, 1H), 4.80 (s, 2H), 3.06 (t, 2H), 2.83 (d, 2H), 2.56 (s, 2H), 2.41-2.30 (m, 1H); MS (m/z) 586.4 [M+H]$^+$.

684

Example 526

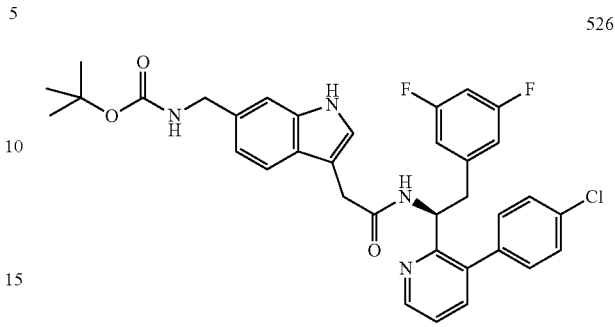

Synthesis of (S)-tert-butyl (3-(2-(1-(3-(4-chlorophenyl)pyridin-2-yl)-2-(3,5-difluorophenyl)ethylamino)-2-oxoethyl)-1H-indol-6-yl)methylcarbamate (526)

The title compound was prepared according to the method presented in the synthesis of 36F utilizing 36E and 2-(6-((tert-butoxycarbonylamino)methyl)-1H-indol-3-yl)acetic acid to provide 24 mg of the desired compound in a 33% yield: $^1$H NMR (400 MHz, dmso) δ 10.70 (s, 1H), 8.65-8.61 (m, 1H), 8.53 (d, 1H), 7.53 (dd, 1H), 7.41-7.32 (m, 3H), 7.27 (s, 1H), 7.21 (dd, 3H), 7.13 (s, 1H), 6.98 (s, 1H), 6.92 (t, 1H), 6.76 (d, 1H), 6.42 (d, 2H), 5.19-5.08 (m, 1H), 4.12 (d, 2H), 3.44 (d, 2H), 2.95-2.88 (m, 2H), 1.36 (s, 9H); MS (m/z) 631.7 [M+H]$^+$.

Example 527

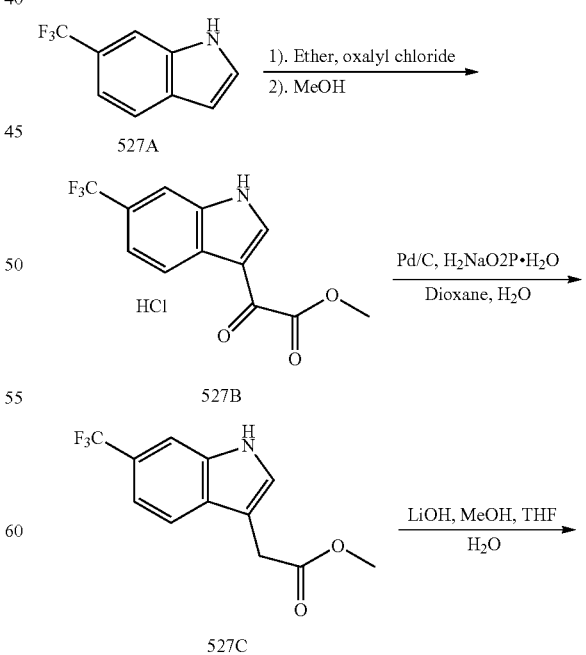

685

-continued

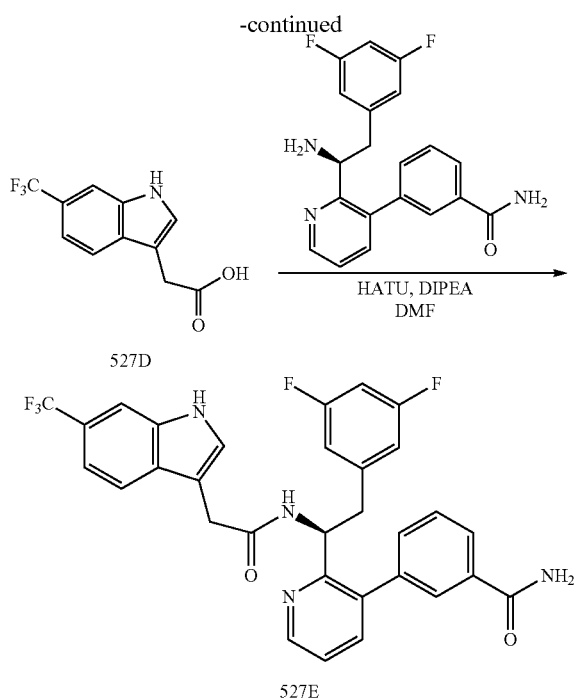

Synthesis of methyl 2-oxo-2-(6-(trifluoromethyl)-1H-indol-3-yl)acetate hydrochloride (527B)

The title compound was prepared according to the method presented in Example 54 substituting 6-(trifluoromethyl)-1H-indole for 54C to provide the desired compound: MS (m/z) 271.9 [M+H]$^+$.

Synthesis of methyl 2-(6-(trifluoromethyl)-1H-indol-3-yl)acetate (527C)

The title compound was prepared according to the method presented in Example 54 substituting methyl 2-oxo-2-(6-(trifluoromethyl)-1H-indol-3-yl)acetate hydrochloride for 54D to provide the desired compound: MS (m/z) 257.8 [M+H]$^+$.

Synthesis of methyl 2-(6-(trifluoromethyl)-1H-indol-3-yl)acetic acid (527D)

The title compound was prepared according to the method presented in Example 54 substituting methyl 2-(6-(trifluoromethyl)-1H-indol-3-yl)acetate for 54E to provide the desired compound MS (m/z) 243.9 [M+H]$^+$.

Synthesis of (S)-3-(2-(2-(3,5-difluorophenyl)-1-(2-(6-(trifluoromethyl)-1H-indol-3-yl)acetamido)ethyl)pyridin-3-yl)benzamide (527E)

The title compound was prepared according to the method presented in the synthesis of 50D utilizing 50C and 2-(6-(trifluoromethyl)-1H-indol-3-yl)acetic acid to provide 27.2 mg of the desired compound in a 55% yield: $^1$H NMR (400 MHz, dmso) δ 11.23 (s, 1H), 8.72 (d, 1H), 8.67 (dd, 1H), 7.96 (s, 1H), 7.87 (d, 1H), 7.75 (s, 1H), 7.64-7.57 (m, 2H), 7.53-7.37 (m, 4H), 7.26 (d, 1H), 7.11 (d, 1H), 6.87 (t, 1H), 6.49 (d, 2H), 5.17 (dd, 2H), 3.50 (dd, 2H), 2.96 (d, 2H); MS (m/z) 579.2 [M+H]$^+$.

686

Example 529

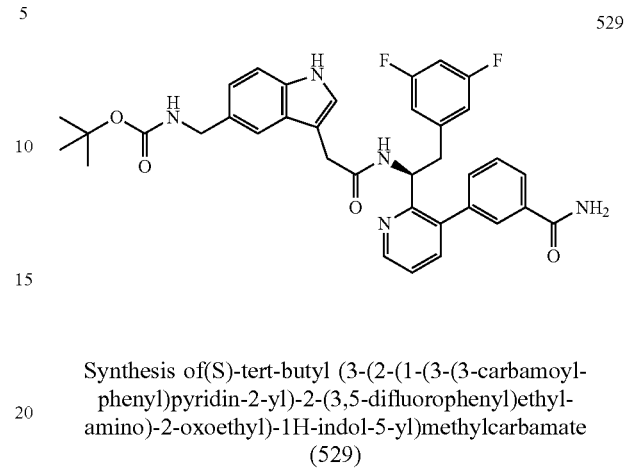

Synthesis of(S)-tert-butyl (3-(2-(1-(3-(3-carbamoylphenyl)pyridin-2-yl)-2-(3,5-difluorophenyl)ethylamino)-2-oxoethyl)-1H-indol-5-yl)methylcarbamate (529)

The title compound was prepared according to the method presented in the synthesis of 50D utilizing 50C and 491E to provide 20 mg of the desired compound in a 27% yield: $^1$H NMR (400 MHz, dmso) δ 10.71 (s, 1H), 8.64 (d, 1H), 8.52 (d, 1H), 7.93 (s, 1H), 7.86 (d, 1H), 7.71 (s, 1H), 7.59 (d, 1H), 7.47-7.33 (m, 4H), 7.27-7.14 (m, 3H), 7.00-6.91 (m, 2H), 6.86 (t, 1H), 6.41 (d, 2H), 5.22 (d, 1H), 4.10 (d, 2H), 3.45 (s, 2H), 2.94 (d, 2H), 1.34 (s, 9H); MS (m/z) 640.0 [M+H]$^+$.

Example 530

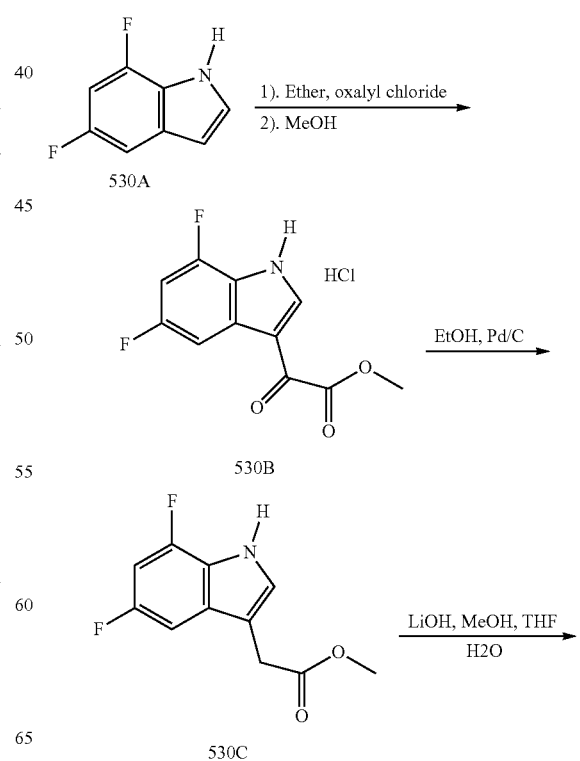

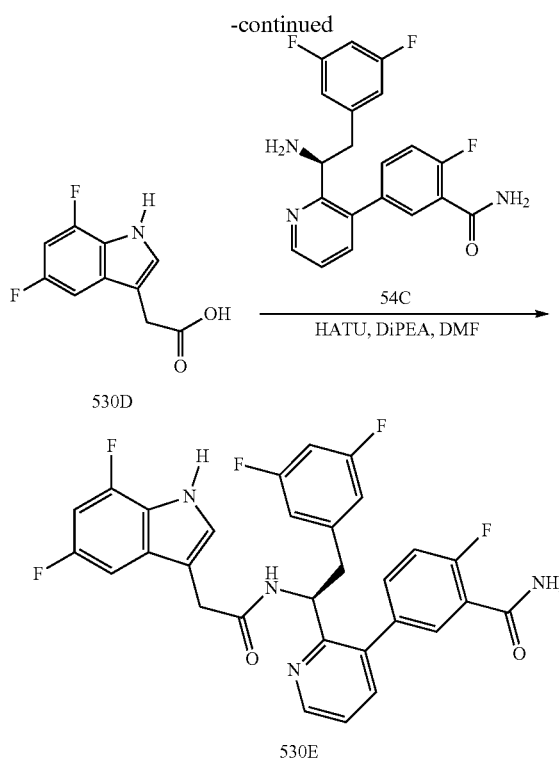

530D

530E

Synthesis of methyl 2-(5,7-difluoro-1H-indol-3-yl)-2-oxoacetate hydrochloride (530B)

The title compound was prepared according to the method presented in Example 54 substituting 5,7-difluoro-1H-indole for 54C to provide the desired compound: MS (m/z) 240.1 [M+H]$^+$.

Synthesis of methyl 2-(5,7-difluoro-1H-indol-3-yl)acetate (530C)

A flask is charged with methyl 2-(5,7-difluoro-1H-indol-3-yl)-2-oxoacetate hydrochloride (750 mg, 2.7 mmol), EtOH (150 ml), EtOAc (49 ml), and AcOH (1 ml). The mixture was passed through a flow hydrogenator fitted with a 10% Pd/C cartridge (0.8 ml/min, 40 bar, 100° C.). The mixture was collected into a flask charged with NaHCO$_3$. Once complete, the mixture is filtered and concentrated. The mixture was dissolved in DCM and remaining starting material is precipitated out by the addition of hexane. The organic layer is then concentrated to give the desired compound (150 mg, 25%): MS (m/z) 226.1 [M+H]$^+$.

Synthesis of 2-(5,7-difluoro-1H-indol-3-yl)acetic acid (530D)

The title compound was prepared according to the method presented in Example 54 substituting methyl 2-(5,7-difluoro-1H-indol-3-yl)acetate for 54E to provide the desired compound: MS (m/z) 212.1 [M+H]$^+$.

Synthesis of (S)-5-(2-(1-(2-(5,7-difluoro-1H-indol-3-yl)acetamido)-2-(3,5-difluorophenyl)ethyl)pyridin-3-yl)-2-fluorobenzamide (530E)

The title compound was prepared according to the method presented in the synthesis of 54G substituting 2-(5,7-difluoro-1H-indol-3-yl)acetic acid for 54F to provide the desired compound (33 mg, 41%): $^1$H NMR (400 MHz, dmso) δ 11.37 (s, 1H), 8.73-8.60 (m, 2H), 7.64 (d, 2H), 7.57 (dd, 1H), 7.48 (d, 1H), 7.38 (dd, 2H), 7.33-7.21 (m, 1H), 7.14 (d, 1H), 6.98 (dd, 1H), 6.84 (t, 2H), 6.50 (d, 2H), 5.13 (dd, 1H), 3.51-3.35 (m, 2H), 2.96 (d, 2H); MS (m/z) 565.6 [M+H]$^+$.

Example 531

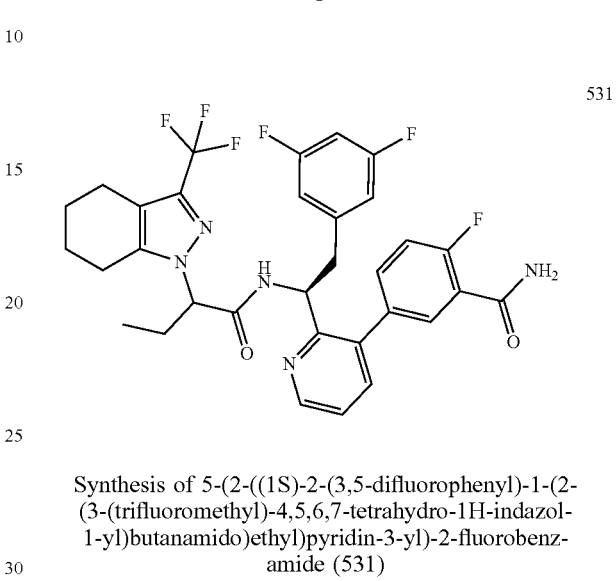

531

Synthesis of 5-(2-((1S)-2-(3,5-difluorophenyl)-1-(2-(3-(trifluoromethyl)-4,5,6,7-tetrahydro-1H-indazol-1-yl)butanamido)ethyl)pyridin-3-yl)-2-fluorobenzamide (531)

The title compound was separated from the diastereomeric mixture of 504E by semi-preparative chiral HPLC fitted with a Chiralcel AZ-H column running a 70:30 mixture of Hep:IPA to obtain the desired compound (RT 7.8 minutes, 4.9 mg): $^1$H NMR (400 MHz, dmso) δ 8.87 (d, 1H), 8.64 (d, 1H), 7.69 (s, 2H), 7.64 (d, 1H), 7.56 (d, 1H), 7.49 (s, 1H), 7.43-7.32 (m, 2H), 6.96 (s, 1H), 6.65 (d, 2H), 5.08 (d, 1H), 4.66 (s, 1H), 3.00 (d, 2H), 2.39 (s, 2H), 1.94 (s, 3H), 1.57 (s, 3H), 1.53-1.42 (m, 2H), 0.68 (t, 3H); MS (m/z) 630.9 [M+H]$^+$.

Example 532

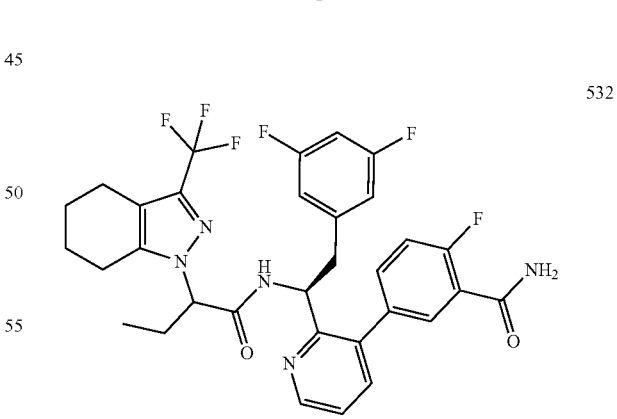

532

Synthesis of 5-(2-((1S)-2-(3,5-difluorophenyl)-1-(2-(3-(trifluoromethyl)-4,5,6,7-tetrahydro-1H-indazol-1-yl)butanamido)ethyl)pyridin-3-yl)-2-fluorobenzamide (532)

The title compound was separated from the diastereomeric mixture of 504E by semi-preparative chiral HPLC fitted with a Chiralcel AZ-H column running a 70:30 mixture of Hep:IPA to obtain the desired compound (RT 10.1 minutes, 4.9 mg): ¹H NMR (400 MHz, dmso) δ 8.77 (d, 1H), 8.61 (d, 1H), 7.66 (s, 2H), 7.61 (d, 1H), 7.54 (s, 1H), 7.50-7.43 (m, 1H), 7.41-7.37 (m, 1H), 7.37-7.29 (m, 1H), 6.94 (s, 1H), 6.56 (d, 2H), 5.12 (s, 1H), 4.71 (s, 1H), 2.96 (d, 2H), 2.62-2.44 (m, 2H), 2.41 (s, 2H), 2.29 (s, 2H), 1.91 (s, 2H), 1.60 (s, 3H), 0.63 (t, 3H); MS (m/z) 630.9 [M+H]⁺.

Example 533

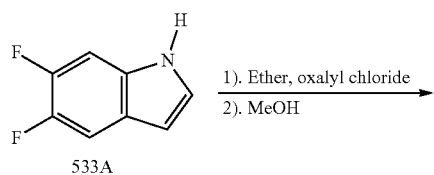

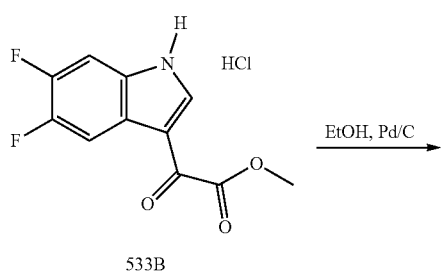

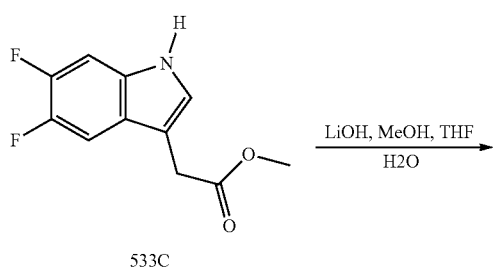

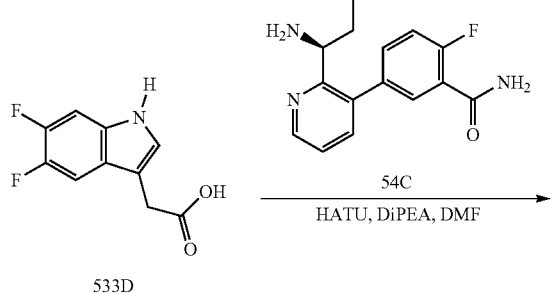

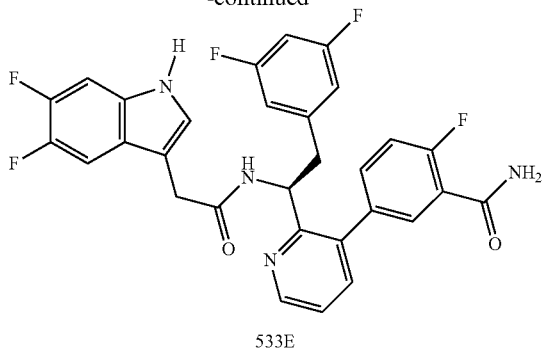

Synthesis of methyl 2-(5,6-difluoro-1H-indol-3-yl)-2-oxoacetate hydrochloride (533B)

The title compound was prepared according to the method presented in Example 54 substituting 5,6-difluoro-1H-indole for 54C to provide the desired compound: MS (m/z) 240.1 [M+H]⁺.

Synthesis of methyl 2-(5,6-difluoro-1H-indol-3-yl)acetate (533C)

The title compound was prepared according to the method presented in Example 530 substituting methyl 2-(5,6-difluoro-1H-indol-3-yl)-2-oxoacetate hydrochloride for 530B to provide the desired compound: MS (m/z) 226.0 [M+H]⁺.

Synthesis of 2-(5,6-difluoro-1H-indol-3-yl)acetic acid (533D)

The title compound was prepared according to the method presented in Example 54 substituting methyl 2-(5,6-difluoro-1H-indol-3-yl)acetate for 54E to provide the desired compound: MS (m/z) 212.1 [M+H]⁺.

Synthesis of (S)-5-(2-(1-(2-(5,6-difluoro-1H-indol-3-yl)acetamido)-2-(3,5-difluorophenyl)ethyl)pyridin-3-yl)-2-fluorobenzamide (533E)

The title compound was prepared according to the method presented in the synthesis of 54G substituting 2-(5,6-difluoro-1H-indol-3-yl)acetic acid for 54F to provide the desired compound (35 mg, 44%): ¹H NMR (400 MHz, dmso) δ 10.92 (s, 1H), 8.71-8.62 (m, 2H), 7.64 (d, 2H), 7.60-7.56 (m, 1H), 7.48 (dd, 1H), 7.38 (dd, 2H), 7.35-7.19 (m, 3H), 7.08 (d, 1H), 6.85 (t, 1H), 6.50 (d, 2H), 5.13 (dd, 1H), 3.49-3.34 (m, 2H), 3.02-2.91 (m, 2H); MS (m/z) 565.8 [M+H]⁺.

Example 534

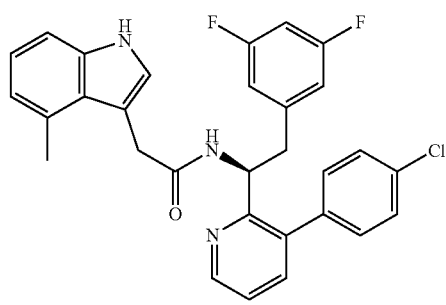

Synthesis of (S)—N-(1-(3-(4-chlorophenyl)pyridin-2-yl)-2-(3,5-difluorophenyl)ethyl)-2-(4-methyl-1H-indol-3-yl)acetamide (534)

The title compound was prepared according to the method presented in the synthesis of 36F utilizing 36E and 2-(4-methyl-1H-indol-3-yl)acetic acid to provide 17 mg of the desired compound in a 28% yield: $^1$H NMR (400 MHz, dmso) δ 10.74 (s, 1H), 8.59 (dd, 1H), 8.30 (d, 1H), 7.54 (dd, 1H), 7.41 (d, 2H), 7.36 (dd, 1H), 7.21 (d, 2H), 7.09 (d, 1H), 6.95 (dd, 2H), 6.88-6.81 (m, 1H), 6.57 (d, 1H), 6.41 (d, 2H), 5.17 (dd, 1H), 3.69-3.56 (m, 2H), 2.92 (dd, 2H), 2.30 (s, 3H); MS (m/z) 516.8 [M+H]$^+$.

Example 535

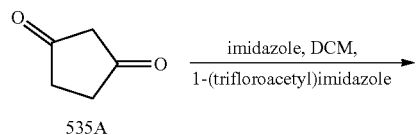

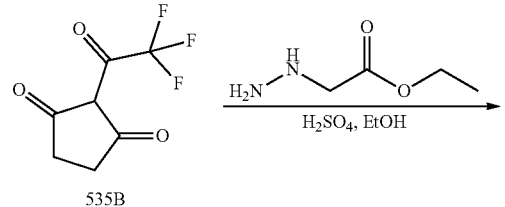

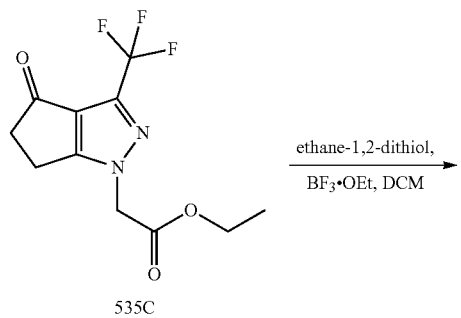

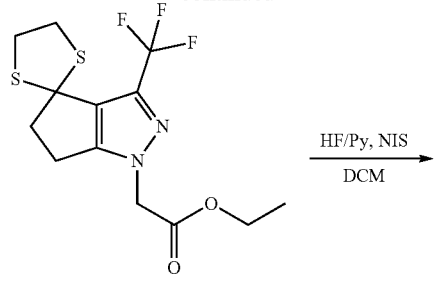

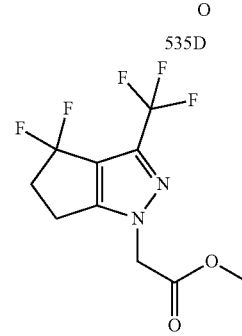

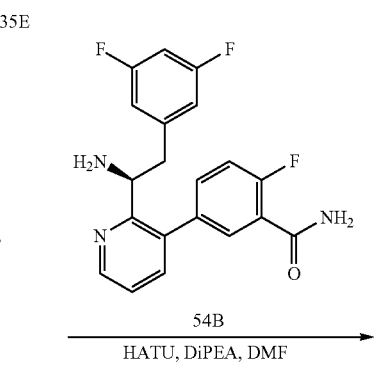

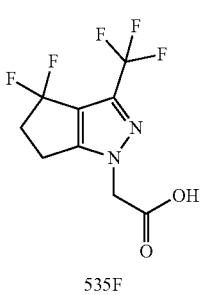

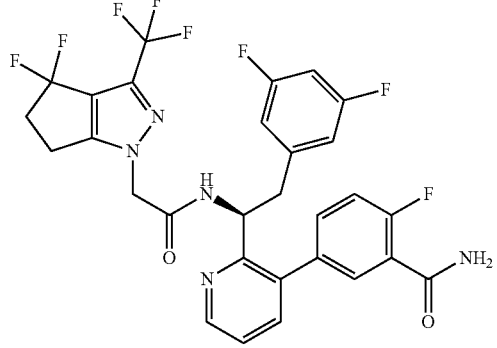

Synthesis of 2-(2,2,2-trifluoroacetyl)cyclopentane-1,3-dione (535B)

A round bottom is charged with cyclopentane-1,3-dione (2 g, 20 mmol), imidazole (1.4 g, 20 mmol), DCM (60 ml), and 1-(trifluoroacetyl)imidazole (3.35 g, 20 mmol). The resulting mixture was stirred for 3 hours and quenched with 1 M HCl. The resulting mixture was extracted 2× DCM. The organic layer was dried over sodium sulfate, filtered, concentrated and used with no further purification to give the desired compound (2.8 g, 70%): MS (m/z) 195.0 [M+H]$^+$.

Synthesis of ethyl 2-(4-oxo-3-(trifluoromethyl)-5,6-dihydrocyclopenta[c]pyrazol-1(4H)-yl)acetate (535C)

A round bottom is charged with 2-(2,2,2-trifluoroacetyl)cyclopentane-1,3-dione (2.8 g, 14 mmol), ethyl 2-hydrazinylacetate (1.9 g, 12 mmol), H$_2$SO$_4$ (0.3 ml), and EtOH (15 ml). The resulting mixture was stirred at reflux overnight. The mixture was concentrated and diluted with EtOAc and aq. NaHCO$_3$. The organic layer was dried over sodium sulfate, filtered, concentrated and purified by flash chromatography to give the desired compound (2.6 g, 67%): MS (m/z) 277.1 [M+H]$^+$.

Synthesis of ethyl 2-(3-(trifluoromethyl)-5,6-dihydro-1H-spiro[cyclopenta[c]pyrazole-4,2'-[1,3]dithiolane]-1-yl)acetate (535D)

A round bottom is charged with ethyl 2-(4-oxo-3-(trifluoromethyl)-5,6-dihydrocyclopenta[c]pyrazol-1(4H)-yl)acetate (300 mg, 1 mmol), DCM (2 ml), ethane-1,2-dithiol (0.1 ml, 1.2 mmol), Boron trifluoride etherate (0.13 ml, 1.1 mmol), and AcOH (1 ml). The resulting mixture was stirred overnight. The mixture was diluted with H$_2$O and extracted 2× DCM. The organic layers were dried over sodium sulfate, filtered, concentrated and was used without further purification to give the desired compound (320 mg, 91%): MS (m/z) 353.3 [M+H]$^+$.

Synthesis of ethyl 2-(4,4-difluoro-3-(trifluoromethyl)-5,6-dihydrocyclopenta[c]pyrazol-1 (4H)-yl) acetate (535E)

A round bottom is charged with ethyl 2-(3-(trifluoromethyl)-5,6-dihydro-1H-spiro[cyclopenta[c]pyrazole-4,2'-[1,3]dithiolane]-1-yl)acetate (100 mg, 0.3 mmol), DCM (1 ml), and HF/Py (1 ml). The resulting mixture was cooled to −45° C. and then a mixture of NIS (158 mg, 0.7 mmol) and DCM (1 ml) was added to the reaction. The mixture was stirred allowing to slowly warm to −30° C. over 3 hours. The reaction was quenched with aq. NaHCO$_3$ and extracted with DCM. The organic layer was washed with water, dried over sodium sulfate, filtered, concentrated and purified by flash chromatography to give the desired compound (35 mg, 42%): MS (m/z) 299.1 [M+H]$^+$.

Synthesis of 2-(4,4-difluoro-3-(trifluoromethyl)-5,6-dihydrocyclopenta[c]pyrazol-1(4H)-yl)acetic acid (535F)

The title compound was prepared according to the method presented in Example 491 substituting ethyl 2-(4,4-difluoro-3-(trifluoromethyl)-5,6-dihydrocyclopenta[c]pyrazol-1 (4H)-yl)acetate for 491D to provide the desired compound: MS (m/z) 271.0 [M+H]$^+$.

Synthesis of (S)-5-(2-(1-(2-(4,4-difluoro-3-(trifluoromethyl)-5,6-dihydrocyclopenta[c]pyrazol-1(4H)-yl)acetamido)-2-(3,5-difluorophenyl)ethyl)pyridin-3-yl)-2-fluorobenzamide (535G)

The title compound was prepared according to the method presented in the synthesis of 54G utilizing 54B and 2-(4,4-difluoro-3-(trifluoromethyl)-5,6-dihydrocyclopenta[c]pyrazol-1(4H)-yl)acetic acid to provide 20 mg of the desired compound in a 24% yield: $^1$H NMR (400 MHz, cd$_3$od) δ 8.69 (d, 1H), 7.58 (d, 1H), 7.43 (s, 1H), 7.39 (dd, 1H), 7.33-7.26 (m, 1H), 7.25-7.17 (m, 1H), 6.65 (s, 1H), 6.32 (d, 2H), 5.39-5.31 (m, 1H), 4.87 (s, 2H), 3.05 (ddd, 5H), 2.87 (s, 2H); MS (m/z) 624.2 [M+H]$^+$.

Example 536

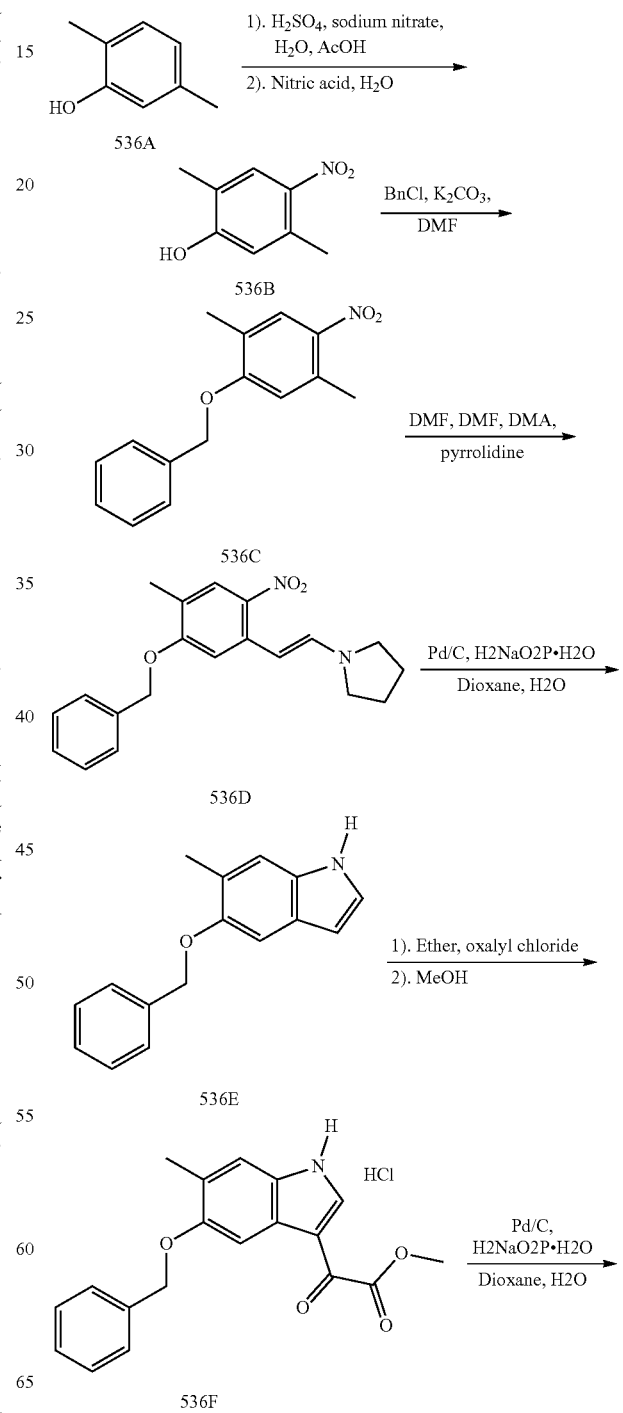

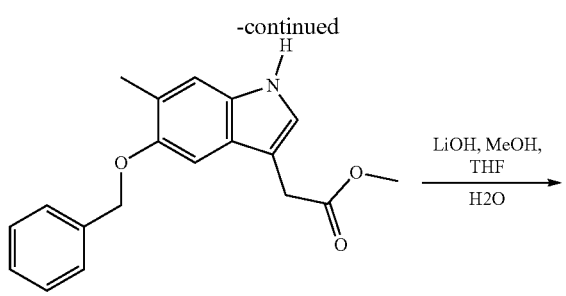

536G

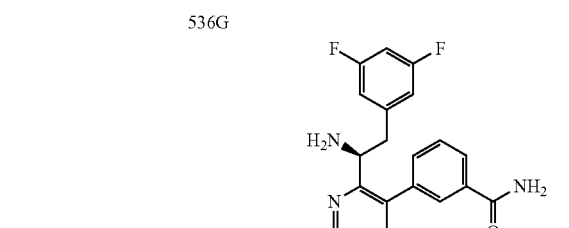

50C

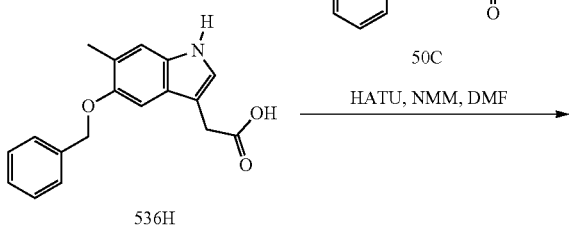

536H

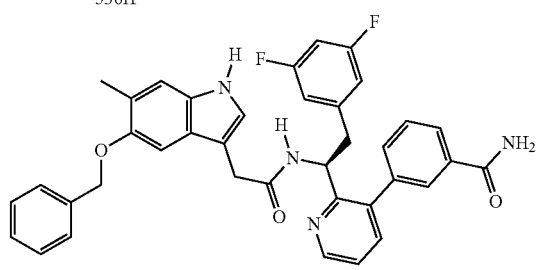

536I

Synthesis of 2,5-dimethyl-4-nitrophenol (536B)

A round bottom was charged with 2,5-dimethylphenol (2 g, 16.4 mmol), H$_2$SO$_4$ (0.7 ml), AcOH (5 ml), and cool the reaction to 0° C. To the cooled stirring reaction slowly add sodium nitrate (1.15 g, 14 mmol) dissolved in H$_2$O (3.3 ml) keeping the temperature between 8-10° C. After 10 minutes add ice and filter off solid. The solid was air dried for 30 minutes after which it was slowly added to a RB with a solution of 70% nitric acid (1.65 ml) and H$_2$O (5 ml) heated to 50° C. The reaction was allowed to stir overnight. Water was added and the solution was filtered. The cake was rinsed with water then dissolved in EtOAc, dried over sodium sulfate, filtered, concentrated. The mixture was dissolved in DCM followed by hexane to precipitate out solid, filtered, and dried under vacuum to give the desired compound (1.5 g, 56%): $^1$H NMR (400 MHz, cdcl$_3$) δ 7.92 (s, 1H), 7.24 (s, 1H), 6.65 (s, 1H), 5.26 (s, 1H), 2.55 (s, 3H), 2.25 (s, 3H).

Synthesis of 1-(benzyloxy)-2,5-dimethyl-4-nitrobenzene (536C)

A round bottom was charged with 2,5-dimethyl-4-nitrophenol (1.5 g, 9 mmol), DMF (11 ml), K$_2$CO$_3$ (1.3 g, 9.1 mmol), and BnCl (1.5 ml, 12 mmol). The mixture was stirred at RT for 2 hours. The reaction was diluted with H$_2$O and extracted 2× with EtOAc. The organic layer was dried over sodium sulfate, filtered, concentrated and purified by flash chromatography to give the desired compound (1.5 mg, 65%): MS (m/z) 258.0 [M+H]$^+$.

Synthesis of 1-(5-(benzyloxy)-4-methyl-2-nitrostyryl)pyrrolidine (536D)

A round bottom was charged with 1-(benzyloxy)-2,5-dimethyl-4-nitrobenzene (1.5 g, 5.8 mmol), DMF (5 ml), DMF DMA (1.2 ml, 9 mmol) and pyrrolidine (0.73 ml, 9 mmol). The resulting mixture was heated to 110° C. for 3 hours. The mixture was concentrated to ⅓ volume then diluted with DCM then the desired compound was precipitated by the addition of hexane. The solid was filtered and dried under vacuum to give the desired compound (1.4 g, 71%).

Synthesis of methyl 5-(benzyloxy)-6-methyl-1H-indole (536E)

A round bottom was charged with 1-(5-(benzyloxy)-4-methyl-2-nitrostyryl)pyrrolidine (1.1 g, 3.4 mmol), dioxane (38 ml), Pd/C (400 mg), H2NaO2P.H2O (800 mg, 7.5 mmol), and H$_2$O (3.8 ml). The resulting mixture was stirred at 65° C. until done as indicated by LC/MS. The reaction mixture was cooled to RT and filtered over a plug of celite, rinsing with ethyl acetate. The layers were partitioned and the organic layer was dried over sodium sulfate, filtered, concentrated and purified by flash chromatography to give the desired compound as a white solid (540 mg, 67%): MS (m/z) 238.0 [M+H]$^+$.

Synthesis of methyl 2-(5-(benzyloxy)-6-methyl-1H-indol-3-yl)-2-oxoacetate hydrochloride (536F)

The title compound was prepared according to the method presented in Example 54 substituting 5-(benzyloxy)-6-methyl-1H-indole for 54C to provide the desired compound: MS (m/z) 323.9 [M+H]$^+$.

Synthesis of methyl 2-(5-(benzyloxy)-6-methyl-1H-indol-3-yl)acetate (536G)

The title compound was prepared according to the method presented in Example 54 substituting methyl 2-(5-(benzyloxy)-6-methyl-1H-indol-3-yl)-2-oxoacetate hydrochloride for 54D to provide the desired compound: MS (m/z) 310.1 [M+H]$^+$.

Synthesis of 2-(5-(benzyloxy)-6-methyl-1H-indol-3-yl)acetic acid (536H)

The title compound was prepared according to the method presented in Example 54 substituting methyl 2-(5-(benzyloxy)-6-methyl-1H-indol-3-yl)acetate for 54E to provide the desired compound: MS (m/z) 296.0 [M+H]$^+$.

Synthesis of (S)-3-(2-(1-(2-(5-(benzyloxy)-6-methyl-1H-indol-3-yl)acetamido)-2-(3,5-difluorophenyl)ethyl)pyridin-3-yl)benzamide (536I)

The title compound was prepared according to the method presented in the synthesis of 50D utilizing 50C and 2-(5-(benzyloxy)-6-methyl-1H-indol-3-yl)acetic acid to provide 35 mg of the desired compound in a 40% yield: $^1$H NMR (400 MHz, dmso) δ 10.51 (s, 1H), 8.59 (d, 1H), 8.47 (d, 1H), 7.94 (s, 1H), 7.86 (d, 1H), 7.71 (s, 1H), 7.58 (d, 1H), 7.43 (t, 3H), 7.40-7.33 (m, 5H), 7.29 (d, 11H), 7.05 (d, 2H), 6.89 (s, 1H), 6.83 (t, 1H), 6.39 (d, 2H), 5.23 (d, 1H), 4.93 (s, 2H), 3.44 (s, 2H), 2.92 (d, 2H), 2.22 (s, 3H); MS (m/z) 631.4 [M+H]$^+$.

Example 537

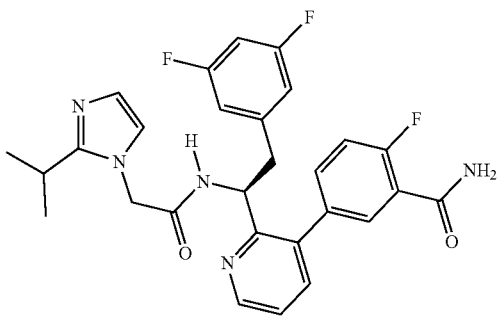

Synthesis of (S)-5-(2-(2-(3,5-difluorophenyl)-1-(2-(2-isopropyl-1H-imidazol-1-yl)acetamido)ethyl)pyridin-3-yl)-2-fluorobenzamide (537)

The title compound was prepared according to the method presented in Example 56 substituting 2-isopropyl-1H-imidazole for 1H-benzo[g]indole to provide the desired compound (14 mg, 38%): $^1$H NMR (400 MHz, dmso) δ 9.16 (d, 1H), 8.70 (d, 1H), 7.65 (dd, 3H), 7.53 (d, 2H), 7.43 (dd, 1H), 7.38 (d, 2H), 7.37-7.28 (m, 1H), 6.97 (t, 1H), 6.64 (d, 2H), 5.16 (d, 1H), 4.87 (q, 2H), 3.04 (dt, 2H), 2.86-2.74 (m, 1H), 1.07 (dd, 6H); MS (m/z) 522.7 [M+H]$^+$.

Example 538

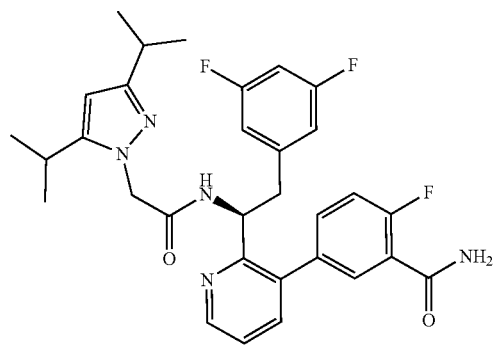

Synthesis of (S)-5-(2-(2-(3,5-difluorophenyl)-1-(2-(3,5-diisopropyl-1H-pyrazol-1-yl)acetamido)ethyl)pyridin-3-yl)-2-fluorobenzamide (538)

The title compound was prepared according to the method presented in the synthesis of 56B substituting 3,5-diisopropyl-1H-pyrazole for 1H-benzo[g]indole to provide the desired compound (8 mg, 20%): $^1$H NMR (400 MHz, dmso)

δ 8.63 (d, 1H), 8.47 (d, 1H), 7.63 (dd, 3H), 7.48 (d, 1H), 7.40 (dd, 2H), 7.36-7.26 (m, 1H), 6.92 (s, 1H), 6.53 (d, 2H), 5.82 (s, 1H), 5.17 (d, 1H), 4.57 (s, 2H), 2.96 (dd, 2H), 2.77-2.68 (m, 1H), 2.67-2.53 (m, 1H), 1.10 (d, 6H), 0.98 (d, 6H); MS (m/z) 564.4 [M+H]$^+$.

Example 539

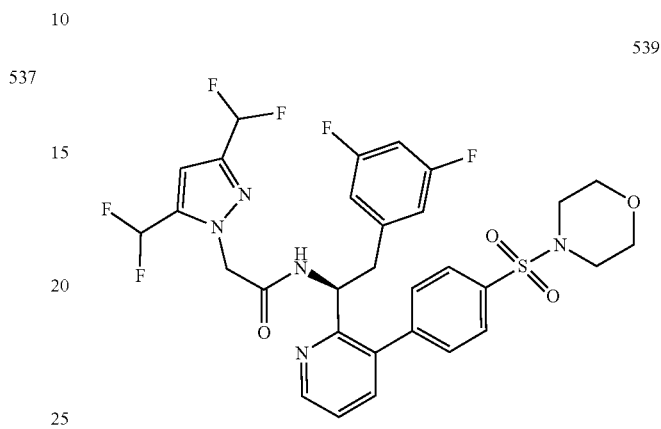

Synthesis of (S)-2-(3,5-bis(difluoromethyl)-1H-pyrazol-1-yl)-N-(2-(3,5-difluorophenyl)-1-(3-(4-(morpholinosulfonyl)phenyl)pyridin-2-yl)ethyl)acetamide (539)

The title compound was prepared according to the method presented in the synthesis of 512C substituting 4-(morpholinosulfonyl)phenylboronic acid for 5-(4,4,5,5-tetramethyl-1,3,2-dioxaborolan-2-yl)-1H-pyrrolo[2,3-b]pyridine to provide the desired compound (21 mg, 17%): $^1$H NMR (400 MHz, dmso) δ 9.09 (d, 1H), 8.72 (dd, 1H), 7.70 (d, 2H), 7.61 (dd, 1H), 7.49-7.35 (m, 3H), 7.15 (d, 1H), 7.08-6.80 (m, 4H), 6.34 (d, 2H), 5.14 (dd, 1H), 4.99 (s, 2H), 3.66-3.57 (m, 4H), 2.95 (d, 2H), 2.88 (d, 4H); MS (m/z) 668.2 [M+H]$^+$.

Examples 540 and 571

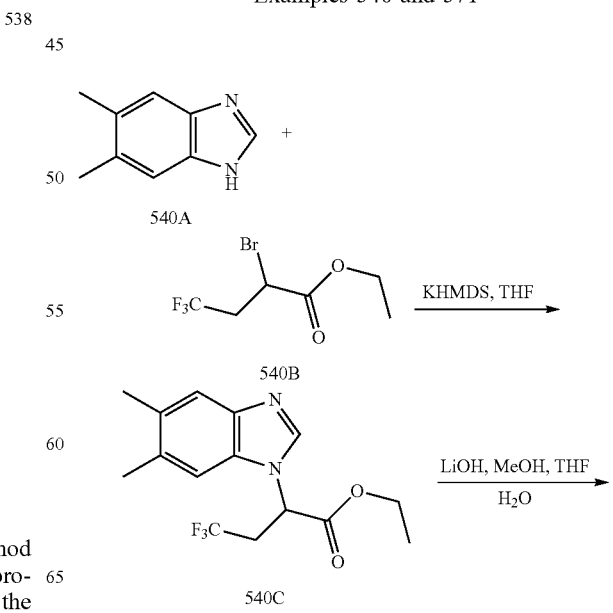

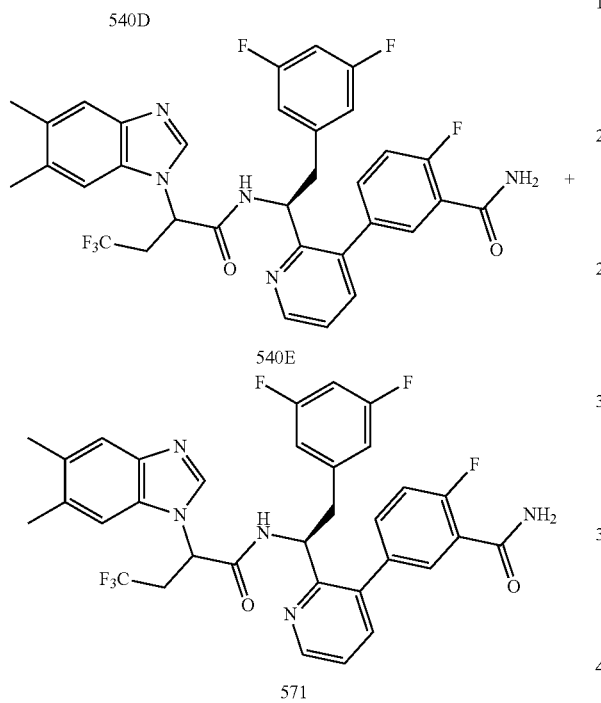

540D

54C
HATU, DiPEA, DMF

540E

571

Synthesis of ethyl 2-(5,6-dimethyl-1H-benzo[d]imidazol-1-yl)-4,4,4-trifluorobutanoate (540C)

The title compound was prepared according to the method presented in Example 478 substituting 540A for 478A and 540B for 478B to provide the desired compound: MS (m/z) 315.5 [M+H]$^+$.

Synthesis of 2-(5,6-dimethyl-1H-benzo[d]imidazol-1-yl)-4,4,4-trifluorobutanoic acid (540D)

The title compound was prepared according to the method presented in Example 478 ethyl 2-(5,6-dimethyl-1H-benzo[d]imidazol-1-yl)-4,4,4-trifluorobutanoate for 478C to provide the desired compound: MS (m/z) 287.3 [M+H]$^+$.

Synthesis of 5-(2-((1S)-2-(3,5-difluorophenyl)-1-(2-(5,6-dimethyl-1H-benzo[d]imidazol-1-yl)-4,4,4-trifluorobutanamido)ethyl)pyridin-3-yl)-2-fluorobenzamide (540E and 571)

The title compound was prepared according to the method presented in the synthesis of 54G substituting 2-(5,6-dimethyl-1H-benzo[d]imidazol-1-yl)-4,4,4-trifluorobutanoic acid for 2-(5-(trifluoromethyl)-1H-indol-3-yl)acetic acid to provide the desired compounds (540E, the first peak off HPLC, 7 mg, 8%; 571, the second peak off HPLC, 12 mg, 14%): 540E $^1$H NMR (400 MHz, dmso) δ 8.80 (d, 1H), 8.66 (d, 1H), 8.59-8.50 (m, 1H), 7.62 (s, 2H), 7.55 (d, 1H), 7.51 (s, 1H), 7.42 (s, 1H), 7.39 (d, 1H), 7.31 (s, 1H), 7.21 (d, 2H), 6.75 (s, 1H), 6.28 (d, 2H), 5.83-5.73 (m, 1H), 5.03 (d, 1H), 3.42-3.31 (m, 2H), 3.12 (s, 2H), 2.31 (s, 3H), 2.28 (s, 3H); MS (m/z) 640.4 [M+H]$^+$; 571 MS (m/z) 640.4 [M+H]$^+$.

Example 541

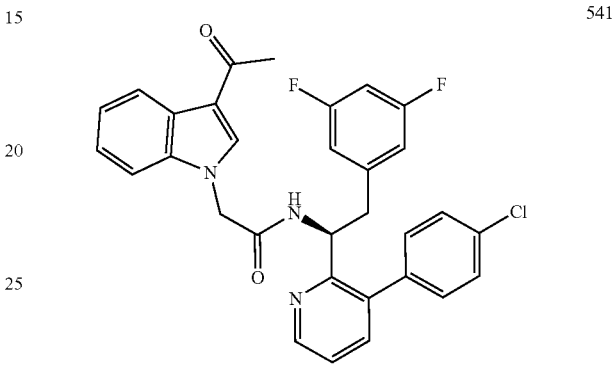

541

Synthesis of (S)-2-(3-acetyl-1H-indol-1-yl)-N-(1-(3-(4-chlorophenyl)pyridin-2-yl)-2-(3,5-difluorophenyl)ethyl)acetamide (541)

The title compound was prepared according to the method presented in the synthesis of 36F utilizing 36E and 2-(3-acetyl-1H-indol-1-yl)acetic acid to provide 16.2 mg of the desired compound in a 25% yield: $^1$H NMR (400 MHz, dmso) δ 9.13 (d, 1H), 8.71 (dd, 1H), 8.14 (s, 1H), 8.10 (d, 1H), 7.57 (dd, 1H), 7.40 (dd, 3H), 7.21 (d, 2H), 7.17-7.05 (m, 3H), 6.99 (t, 1H), 6.50 (d, 2H), 5.21-5.10 (m, 1H), 4.88 (s, 2H), 2.99 (d, 2H), 2.36 (s, 3H); MS (m/z) 544.7 [M+H]$^+$.

Example 542

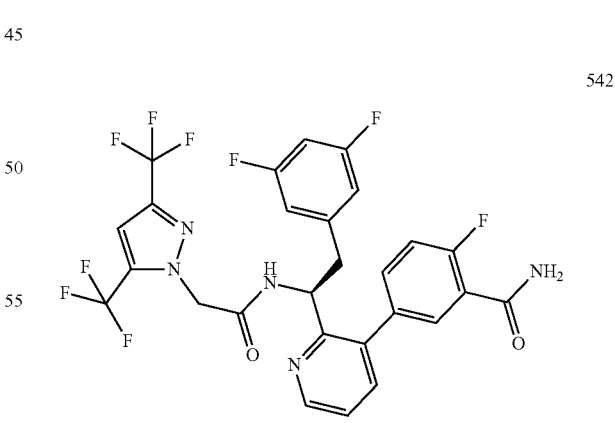

542

Synthesis of (S)-5-(2-(1-(2-(3,5-bis(trifluoromethyl)-1H-pyrazol-1-yl)acetamido)-2-(3,5-difluorophenyl)ethyl)pyridin-3-yl)-2-fluorobenzamide (542)

The title compound was prepared according to the method presented in Example 56 substituting 3,5-bis(trifluoromethyl)-1H-pyrazole for 1H-benzo[g]indole and heating to 95° C. to provide the desired compound (4 mg, 10%): ¹H NMR (400 MHz, dmso) δ 9.05 (d, 1H), 8.68 (d, 1H), 7.63 (dd, 3H), 7.47 (d, 2H), 7.45-7.41 (m, 1H), 7.40 (s, 1H), 7.35-7.27 (m, 1H), 6.91 (t, 1H), 6.57 (d, 2H), 5.14 (d, 1H), 5.09-4.95 (m, 2H), 3.08-2.90 (m, 2H); MS (m/z) 616.5 [M+H]⁺.

Example 543

543

Synthesis of 5-(2-((1S)-1-(2-(3-acetyl-1H-indol-1-yl)butanamido)-2-(3,5-difluorophenyl)ethyl)pyridin-3-yl)-2-fluorobenzamide (543)

The title compound was separated from the diastereomeric mixture of 554 by semi-preparative chiral HPLC fitted with a Chiralpak IA column running a 70:30 mixture of Hep:IPA to obtain the desired compound (RT 6.4 minutes, 11 mg): ¹H NMR (400 MHz, dmso) δ 9.21 (d, 1H), 8.61 (d, 1H), 8.23 (s, 11H), 8.10 (d, 1H), 7.66 (d, 2H), 7.51 (dd, 3H), 7.33 (dd, 2H), 7.16 (dt, 3H), 6.97 (s, 1H), 6.65 (d, 2H), 5.14 (d, 1H), 5.04 (t, 1H), 3.04 (d, 2H), 2.37 (s, 3H), 2.04-1.89 (m, 2H), 0.65 (t, 3H); MS (m/z) 599.6 [M+H]⁺.

Example 544

544

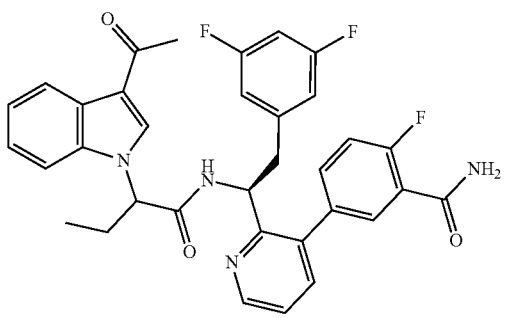

Synthesis of 5-(2-((1S)-1-(2-(3-acetyl-1H-indol-1-yl)butanamido)-2-(3,5-difluorophenyl)ethyl)pyridin-3-yl)-2-fluorobenzamide (544)

The title compound was separated from the diastereomeric mixture of 554 by semi-preparative chiral HPLC fitted with a Chiralpak IA column running a 70:30 mixture of Hep:IPA to obtain the desired compound (RT 9.5 minutes, 12 mg): ¹H NMR (400 MHz, dmso) δ 9.24 (d, 1H), 8.69 (s, 1H), 8.26 (s, 1H), 8.09 (s, 1H), 7.64 (d, 3H), 7.56-7.37 (m, 4H), 7.32 (d, 1H), 7.13 (d, 2H), 6.82 (s, 1H), 6.56 (d, 2H), 5.07 (s, 2H), 2.99 (d, 2H), 2.38 (s, 3H), 2.01 (s, 2H), 0.75 (t, 3H); MS (m/z) 599.6 [M+H]⁺.

Example 545

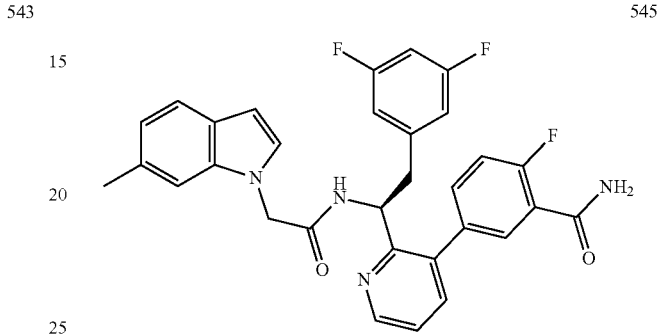

545

Synthesis of (S)-5-(2-(2-(3,5-difluorophenyl)-1-(2-(6-methyl-1H-indol-1-yl)acetamido)ethyl)pyridin-3-yl)-2-fluorobenzamide (545)

The title compound was prepared according to the method presented in the synthesis of 56B substituting 6-methyl-1H-indole for 1H-benzo[g]indole to provide the desired compound (7 mg, 18%): ¹H NMR (400 MHz, dmso) δ 8.89 (d, 1H), 8.68 (d, 1H), 7.67-7.56 (m, 3H), 7.48 (d, 1H), 7.40 (dd, 2H), 7.34 (dd, 1H), 7.30-7.22 (m, 1H), 7.05 (d, 1H), 6.93 (t, 1H), 6.85 (s, 1H), 6.77 (d, 1H), 6.60 (d, 2H), 6.25 (d, 1H), 5.13 (d, 1H), 4.71 (s, 2H), 3.01 (d, 2H), 2.29 (s, 3H); MS (m/z) 543.4 [M+H]⁺.

Example 546

530A

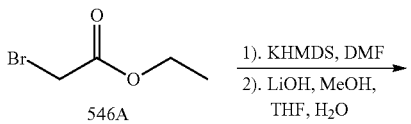

546A

1). KHMDS, DMF
2). LiOH, MeOH, THF, H₂O

703

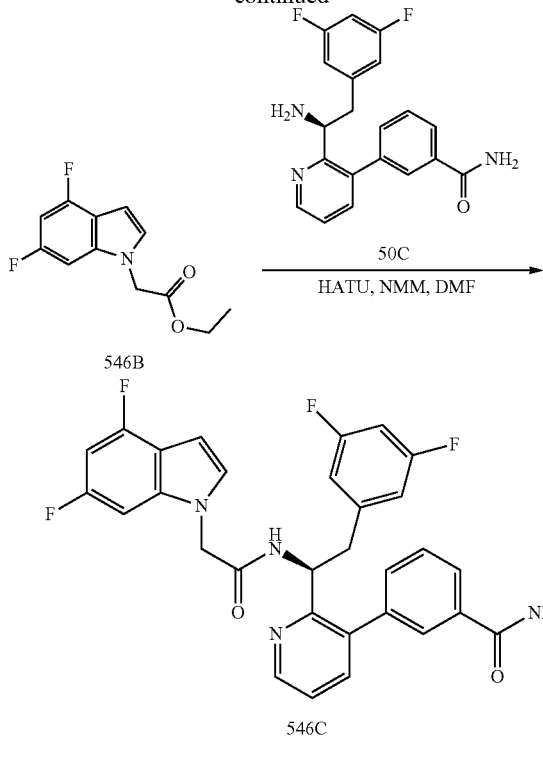

Synthesis of ethyl 2-(4,6-difluoro-1H-indol-1-yl)acetate

The title compound was prepared according to the method presented in Example 478 substituting ethyl 2-bromoacetate for 478B and 4,6-difluoro-1H-indole for 478A to provide the desired compound.

Synthesis of 2-(4,6-difluoro-1H-indol-1-yl)acetic acid (546B)

The title compound was prepared according to the method presented in Example 478 substituting ethyl 2-(4,6-difluoro-1H-indol-1-yl)acetate for 478C to provide the desired compound: MS (m/z) 212.2 [M+H]+.

704

Synthesis of (S)-3-(2-(1-(2-(4,6-difluoro-1H-indol-1-yl)acetamido)-2-(3,5-difluorophenyl)ethyl)pyridin-3-yl)benzamide (546C)

The title compound was prepared according to the method presented in the synthesis of 50C substituting 2-(4,6-difluoro-1H-indol-1-yl)acetic acid for 2-(5-fluoro-1H-indol-3-yl)acetic acid to provide the desired compound (23 mg, 36%): $^1$H NMR (400 MHz, dmso) δ 8.96 (d, 1H), 8.72-8.66 (m, 1H), 7.93 (s, 1H), 7.88 (d, 1H), 7.73 (s, 1H), 7.64 (dd, 1H), 7.49-7.36 (m, 4H), 7.17 (d, 1H), 6.88 (t, 1H), 6.82 (d, 1H), 6.76 (t, 1H), 6.53 (d, 2H), 6.39 (d, 1H), 5.17 (dd, 1H), 4.77 (s, 2H), 2.99 (d, 2H). MS (m/z) 547.6 [M+H]+.

Example 547

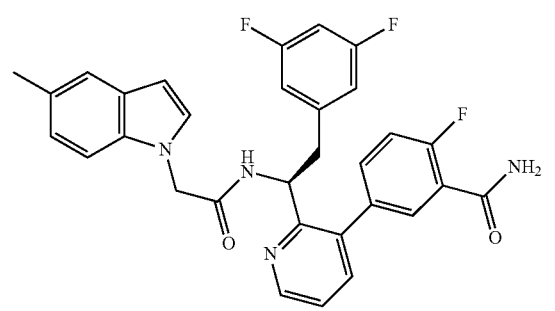

547

Synthesis of (S)-5-(2-(2-(3,5-difluorophenyl)-1-(2-(5-methyl-1H-indol-1-yl)acetamido)ethyl)pyridin-3-yl)-2-fluorobenzamide (547)

The title compound was prepared according to the method presented in the synthesis of 56B substituting 5-methyl-1H-indole for 1H-benzo[g]indole to provide the desired compound (7 mg, 18%): $^1$H NMR (400 MHz, dmso) δ 8.89 (d, 1H), 8.68 (d, 1H), 7.60 (dd, 3H), 7.48 (d, 1H), 7.40 (dd, 2H), 7.26 (t, 1H), 7.23 (s, 1H), 7.07 (d, 1H), 6.95 (d, 1H), 6.90 (d, 1H), 6.79 (d, 1H), 6.61 (d, 2H), 6.21 (d, 1H), 5.12 (d, 1H), 4.70 (s, 2H), 3.01 (d, 2H), 2.30 (s, 3H); MS (m/z) 543.4 [M+H]+.

Example 548

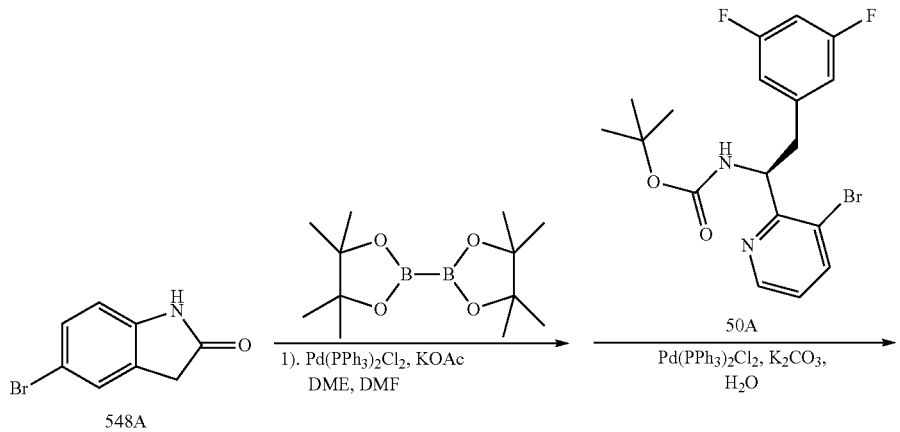

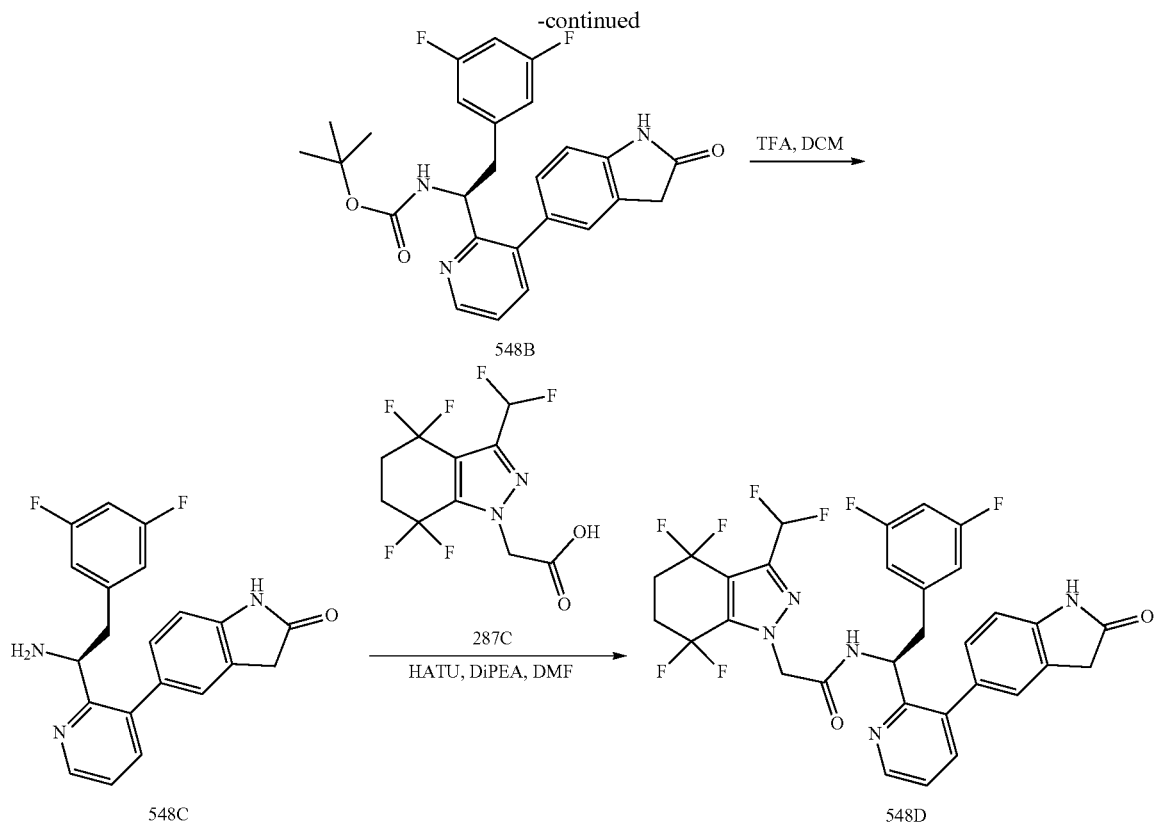

Synthesis of (S)-tert-butyl 2-(3,5-difluorophenyl)-1-(3-(2-oxoindolin-5-yl)pyridin-2-yl)ethylcarbamate (548B)

The title compound was prepared according to the method presented in the synthesis of 489B substituting 5-bromoindolin-2-one for 489A to provide the desired compound: MS (m/z) 466.3 [M+H]$^+$.

Synthesis of (S)-5-(2-(1-amino-2-(3,5-difluorophenyl)ethyl)pyridin-3-yl)indolin-2-one (548C)

The title compound was prepared according to the method presented in the synthesis of 50C substituting (S)-tert-butyl 2-(3,5-difluorophenyl)-1-(3-(2-oxoindolin-5-yl)pyridin-2-yl)ethylcarbamate for 50B to provide the desired compound: MS (m/z) 366.1 [M+H]$^+$.

Synthesis of (S)-2-(3-(difluoromethyl)-4,4,7,7-tetrafluoro-4,5,6,7-tetrahydro-1H-indazol-1-yl)-N-(2-(3,5-difluorophenyl)-1-(3-(2-oxoindolin-5-yl)pyridin-2-yl)ethyl)acetamide (548D)

The title compound was prepared according to the method presented in the synthesis of 61F substituting 287C for 61C and 548C for 61E to provide the desired compound (13 mg): $^1$H NMR (400 MHz, cd$_3$od) δ 8.64 (d, 1H), 7.63-7.55 (m, 1H), 7.40 (dd, 1H), 6.93 (d, 1H), 6.87 (d, 1H), 6.80 (s, 1H), 6.74-6.63 (m, 1H), 6.28 (d, 2H), 5.55-5.44 (m, 1H), 5.08 (s, 2H), 3.49 (q, 3H), 3.02 (dd, 2H), 2.64-2.42 (m, 4H); MS (m/z) 650.4 [M+H]$^+$.

Example 549

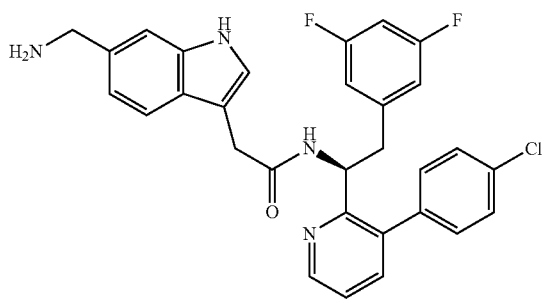

Synthesis of (S)-2-(6-(aminomethyl)-1H-indol-3-yl)-N-(1-(3-(4-chlorophenyl)pyridin-2-yl)-2-(3,5-difluorophenyl)ethyl)acetamide (549)

The title compound was prepared according to the method presented in the synthesis of 557 utilizing (S)-tert-butyl (3-(2-(1-(3-(4-chlorophenyl)pyridin-2-yl)-2-(3,5-difluorophenyl)ethylamino)-2-oxoethyl)-1H-indol-6-yl)methylcarbamate to provide 18 mg of the desired compound in a 99% yield: $^1$H NMR (400 MHz, dmso) δ 10.97 (s, 1H), 8.65 (dd, 1H), 8.60 (d, 1H), 8.00 (s, 2H), 7.53 (dd, 1H), 7.46-7.30 (m, 5H), 7.21 (d, 2H), 7.09 (s, 1H), 6.94 (t, 2H), 6.44 (d, 2H), 5.13 (dd, 2H), 4.04 (d, 3H), 3.56-3.40 (m, 3H), 3.00-2.86 (m, 2H); MS (m/z) 531.4 [M+H]$^+$.

Example 550

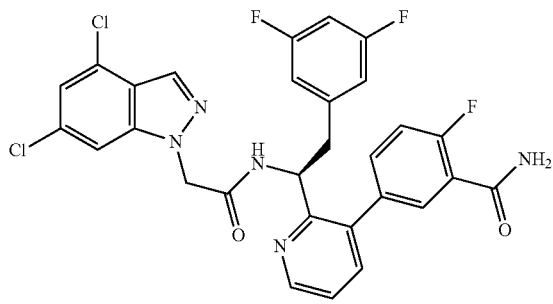

Synthesis of (S)-5-(2-(1-(2-(4,6-dichloro-1H-indazol-1-yl)acetamido)-2-(3,5-difluorophenyl)ethyl)pyridin-3-yl)-2-fluorobenzamide (550)

The title compound was prepared according to the method presented in the synthesis of 56B substituting 4,6-dichloro-1H-benzo[g]indole to provide the desired compound (4 mg, 10%): $^1$H NMR (400 MHz, dmso) δ 9.11 (d, 1H), 8.69 (d, 1H), 8.40 (s, 1H), 7.67-7.56 (m, 4H), 7.46-7.37 (m, 3H), 7.34-7.24 (m, 1H), 7.18 (d, 1H), 6.90 (s, 1H), 6.51 (d, 2H), 5.22-5.05 (m, 3H), 3.00 (d, 2H); MS (m/z) 598.6 [M+H]$^+$.

Example 551

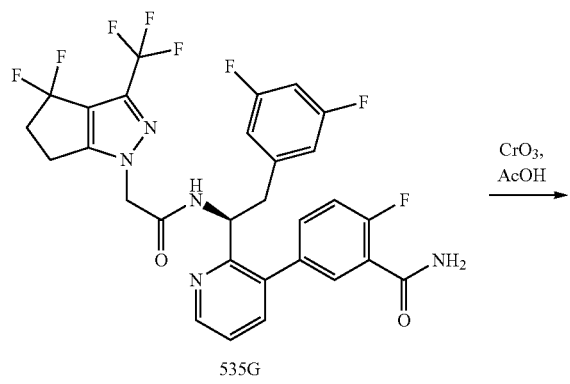

Synthesis of (S)-5-(2-(1-(2-(4,4-difluoro-6-oxo-3-(trifluoromethyl)-5,6-dihydrocyclopenta[c]pyrazol-1(4H)-yl)acetamido)-2-(3,5-difluorophenyl)ethyl)pyridin-3-yl)-2-fluorobenzamide (551)

A round bottom is charged with (S)-5-(2-(1-(2-(4,4-difluoro-3-(trifluoromethyl)-5,6 dihydrocyclopenta[c]pyrazol-1(4H)-yl)acetamido)-2-(3,5-difluorophenyl)ethyl)pyridin-3-yl)-2-fluorobenzamide (9 mg, 0.14 mmol), AcOH (2 ml), and CrO$_3$ (22 mg, 0.2 mmol). The mixture was stirred for 1.5 days. The reaction was concentrated then diluted with DMF, H$_2$O, and TFA, filtered and purified by HPLC to give the desired compound (2 mg, 24%): $^1$H NMR (400 MHz, cd$_3$od) δ 8.70 (s, 1H), 7.56 (d, 1H), 7.39 (dd, 2H), 7.29 (s, 1H), 7.23-7.15 (m, 1H), 6.64 (t, 1H), 6.29 (d, 2H), 5.38-5.31 (m, 1H), 5.10 (s, 2H), 3.61 (td, 1H), 3.46 (d, 1H), 3.14-3.03 (m, 3H); MS (m/z) 638.2 [M+H]$^+$.

Example 552

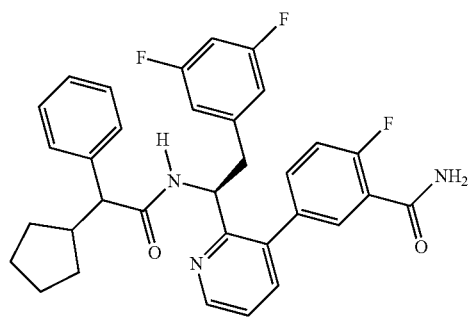

Synthesis of 5-(2-((1S)-1-(2-cyclopentyl-2-phenylacetamido)-2-(3,5-difluorophenyl)ethyl)pyridin-3-yl)-2-fluorobenzamide (552)

The title compound was prepared according to the method presented in the synthesis of 54G substituting 2-cyclopentyl-2-phenylacetic acid for 54F to provide the desired compound (the first peak off HPLC, 13 mg, 18%): $^1$H NMR (400 MHz, dmso) δ 8.72-8.62 (m, 2H), 7.67 (d, 2H), 7.57 (dd, 1H), 7.45 (d, 2H), 7.37 (dd, 1H), 7.35-7.25 (m, 1H), 7.15 (ddd, 5H), 6.77 (t, 1H), 6.43 (d, 2H), 4.97 (dd, 1H), 3.28 (d, 1H), 2.89 (dd, 2H), 2.37 (s, 1H), 1.56-1.19 (m, 6H), 1.01 (s, 1H), 0.83 (d, 1H); MS (m/z) 558.6 [M+H]$^+$.

Example 553

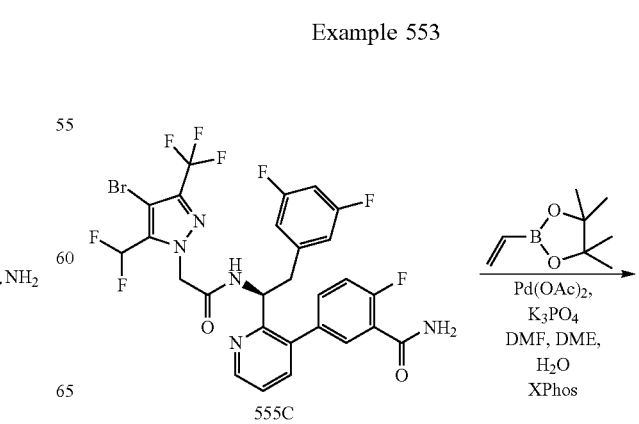

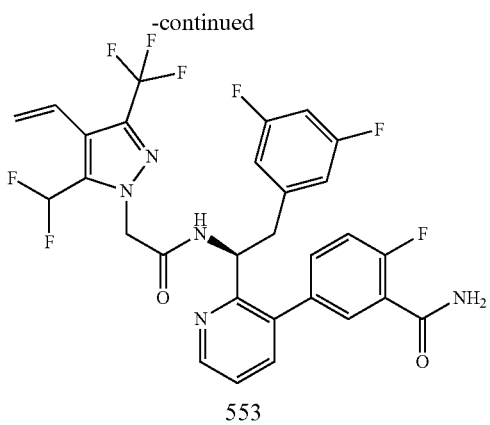

553

Synthesis of (S)-5-(2-(1-(2-(3,5-bis(difluoromethyl)-4-vinyl-1H-pyrazol-1-yl)acetamido)-2-(3,5-difluorophenyl)ethyl)pyridin-3-yl)-2-fluorobenzamide (533)

A 40 ml vial was charged with 555C (100 mg, 0.15 mmol), DMF (1 ml), DME (4 ml), 4,4,5,5-tetramethyl-2-vinyl-1,3,2-dioxaborolane (0.1 ml), Pd(OAc)$_2$ (10 mg, 0.01 mmol), XPhos (14 mg, 0.02 mmol) and 2 N K$_3$PO$_4$ (0.3 ml). Heat the stirring mixture overnight at 86° C. Allow the reaction to cool then dilute with H$_2$O and extract 2× EtOAc. The combined organic layers were washed with brine then dried over sodium sulfate, concentrated, and purified by HPLC to give 54 mg of the desired compound. The yield was 60%: $^1$H NMR (400 MHz, cd$_3$od) δ 8.69 (d, 1H), 7.57 (dd, 1H), 7.42-7.35 (m, 2H), 7.28 (s, 1H), 7.24-7.17 (m, 1H), 7.08-6.74 (m, 3H), 6.72 (s, 1H), 6.70-6.59 (m, 2H), 6.30 (d, 2H), 5.49 (dd, 2H), 5.38-5.29 (m, 1H), 5.04 (s, 2H), 3.12-2.98 (m, 2H), 1.21 (t, 2H); MS (m/z) 605.1 [M+H]$^+$.

Example 554

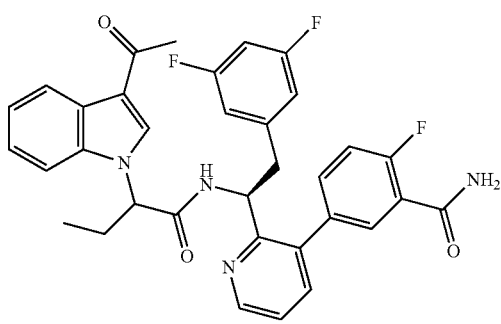

554

Synthesis of 5-(2-((1S)-1-(2-(3-acetyl-1H-indol-1-yl)butanamido)-2-(3,5-difluorophenyl)ethyl)pyridin-3-yl)-2-fluorobenzamide (554)

The title compound was prepared according to the method presented in the synthesis of 54G substituting 2-(3-acetyl-1H-indol-1-yl)butanoic acid for 54F to provide the desired compound (47 mg, 56%): MS (m/z) 599.6 [M+H]$^+$.

Example 155

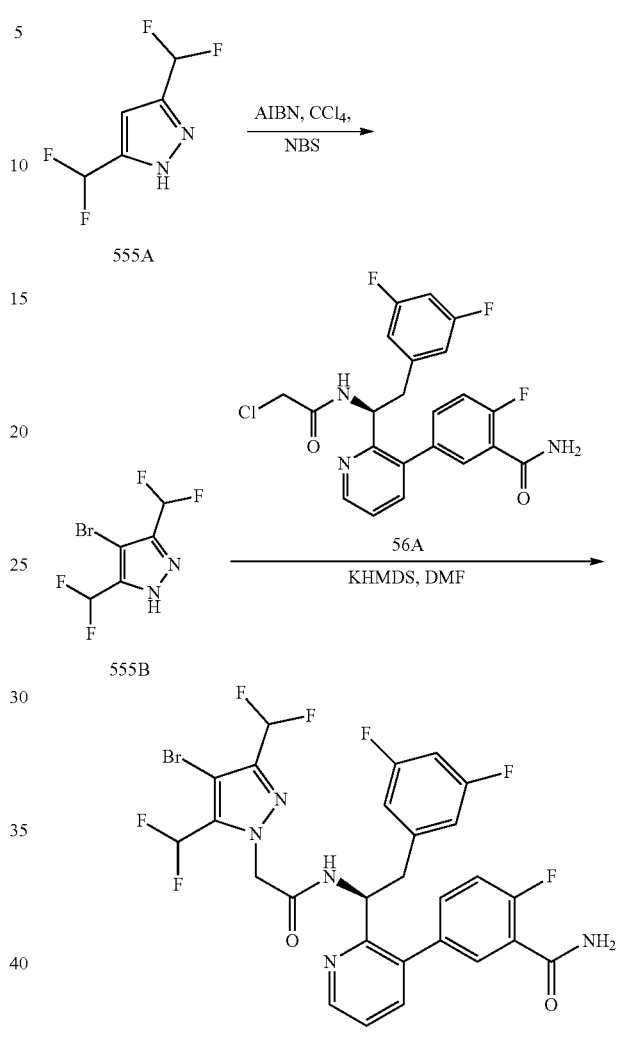

Synthesis of 4-bromo-3,5-bis(difluoromethyl)-1H-pyrazole (555B)

A round bottom flask was charged with 3,5-bis(difluoromethyl)-1H-pyrazole (5.3 g, 31 mmol) and CCl$_4$ (50 ml), NBS (8.1 g, 47 mmol), and lastly AIBN (5 mg). The mixture was stirred at 90° C. over night. After cooling the mixture was filtered and concentrated and purified by flash chromatography to yield 3.3 g of the desired compound in a yield of 43%. MS (m/z) 247.0 [M+H]$^+$.

Synthesis of (S)-5-(2-(1-(2-(4-bromo-3,5-bis(difluoromethyl)-1H-pyrazol-1-yl)acetamido)-2-(3,5-difluorophenyl)ethyl)pyridin-3-yl)-2-fluorobenzamide (555C)

The title compound was prepared according to the method presented in the synthesis of 56B substituting 4-bromo-3,5-bis(difluoromethyl)-1H-pyrazole for 1H-benzo[g]indole to provide the desired compound (780 mg, 68%): $^1$H NMR (400 MHz, dmso) δ 9.07 (d, 1H), 8.68 (d, 1H), 7.70-7.57 (m, 3H), 7.45-7.36 (m, 3H), 7.31 (d, 1H), 7.10 (s, 1H), 7.01 (d, 1H), 6.88 (d, 2H), 6.51 (d, 2H), 5.12 (s, 1H), 5.03 (s, 2H), 2.98 (d, 2H); MS (m/z) 658.4 [M+H]+.

Example 556

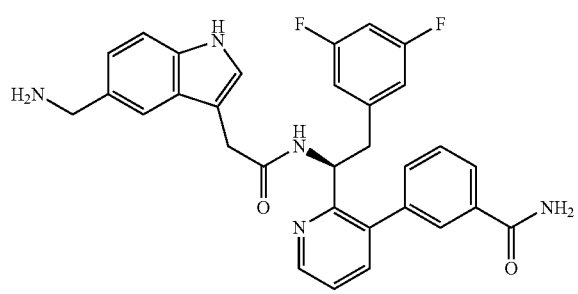

556

Synthesis of (S)-3-(2-(1-(2-(5-(aminomethyl)-1H-indol-3-yl)acetamido)-2-(3,5-difluorophenyl)ethyl)pyridin-3-yl)benzamide (556)

The title compound was prepared according to the method presented in the synthesis of 557 utilizing 529 to provide 14 mg of the desired compound in a 99% yield: 1H NMR (400 MHz, dmso) δ 10.92 (s, 1H), 8.64 (dd, 1H), 8.55 (d, 1H), 7.96 (s, 3H), 7.87 (d, 1H), 7.74 (s, 1H), 7.61 (dd, 1H), 7.48-7.35 (m, 5H), 7.32 (d, 1H), 7.13-7.04 (m, 2H), 6.87 (t, 1H), 6.46 (d, 2H), 5.25-5.13 (m, 1H), 3.98 (d, 2H), 3.47 (d, 2H), 2.95 (d, 2H); MS (m/z) 540.1 [M+H]+.

Examples 558 and 586

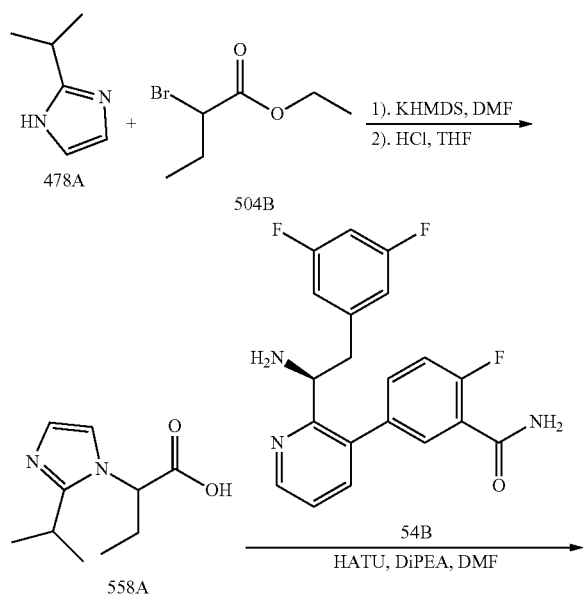

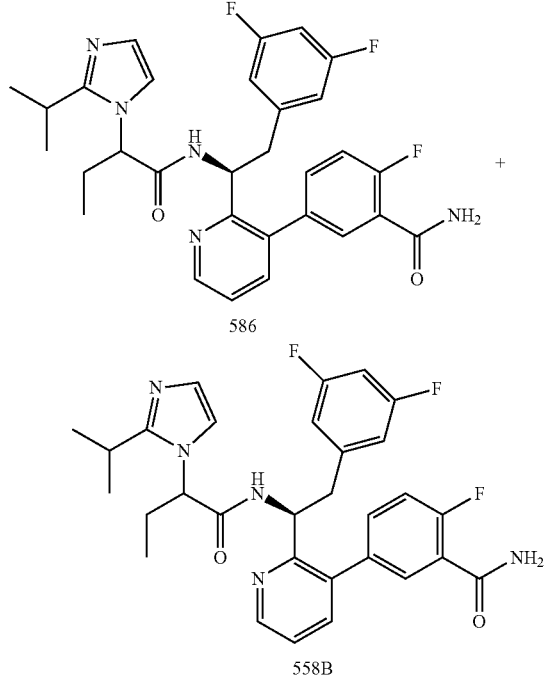

Synthesis of ethyl 2-(2-isopropyl-1H-imidazol-1-yl)butanoate

The title compound was prepared according to the method presented in Example 478 substituting 504B for 478B to provide the desired compound: MS (m/z) 225.2 [M+H]+.

Synthesis of 2-(2-isopropyl-1H-imidazol-1-yl)butanoic acid (558A)

A flask is charged ethyl 2-(2-isopropyl-1H-imidazol-1-yl)butanoate (1 g, 4.5 mmol), THF (5 ml) and HCl (2 ml). The reaction was stirred at reflux for 2 hours. The mixture was concentrated. The residue was diluted with EtOAc and concentrated to give the desired compound which was used crude in the next reaction: MS (m/z) 225.2 [M+H]+.

Synthesis of 5-(2-((1S)-2-(3,5-difluorophenyl)-1-(2-(2-isopropyl-1H-imidazol-1-yl)butanamido)ethyl)pyridin-3-yl)-2-fluorobenzamide (586 and 558B)

The title compounds were prepared according to the method presented in the synthesis of 54G substituting 2-(2-isopropyl-1H-imidazol-1-yl)butanoic acid for 2-(5-(trifluoromethyl)-1H-indol-3-yl)acetic acid to provide the desired compounds (586, first peak off of HPLC, 4 mg, 5%; 558B, second peak off of HPLC, 6 mg, 8%): 586 1H NMR (400 MHz, dmso) δ 9.27 (d, 1H), 8.68 (d, 1H), 7.66 (dd, 3H), 7.57-7.53 (m, 2H), 7.42 (ddd, 4H), 6.91 (t, 1H), 6.58 (d, 2H), 5.12 (d, 1H), 4.99 (s, 1H), 3.33-3.19 (m, 1H), 3.10-2.89 (m, 2H), 1.89 (dd, 2H), 1.25 (d, 3H), 1.07 (d, 3H), 0.70 (t, 3H); MS (m/z) 550.6 [M+H]+. 558C 1H NMR (400 MHz, dmso) δ 9.26 (d, 1H), 8.63 (d, 1H), 7.61 (ddd, 5H), 7.49 (d, 1H), 7.42-7.28 (m, 3H), 6.98 (t, 1H), 6.62 (d, 2H), 5.13 (d, 1H), 4.97 (d, 1H), 3.30-3.17 (m, 1H), 3.02 (d, 2H), 1.89 (dd, 2H), 1.27 (d, 3H), 0.94 (d, 3H), 0.63 (t, 3H); MS (m/z) 550.6 [M+H]+.

Example 559

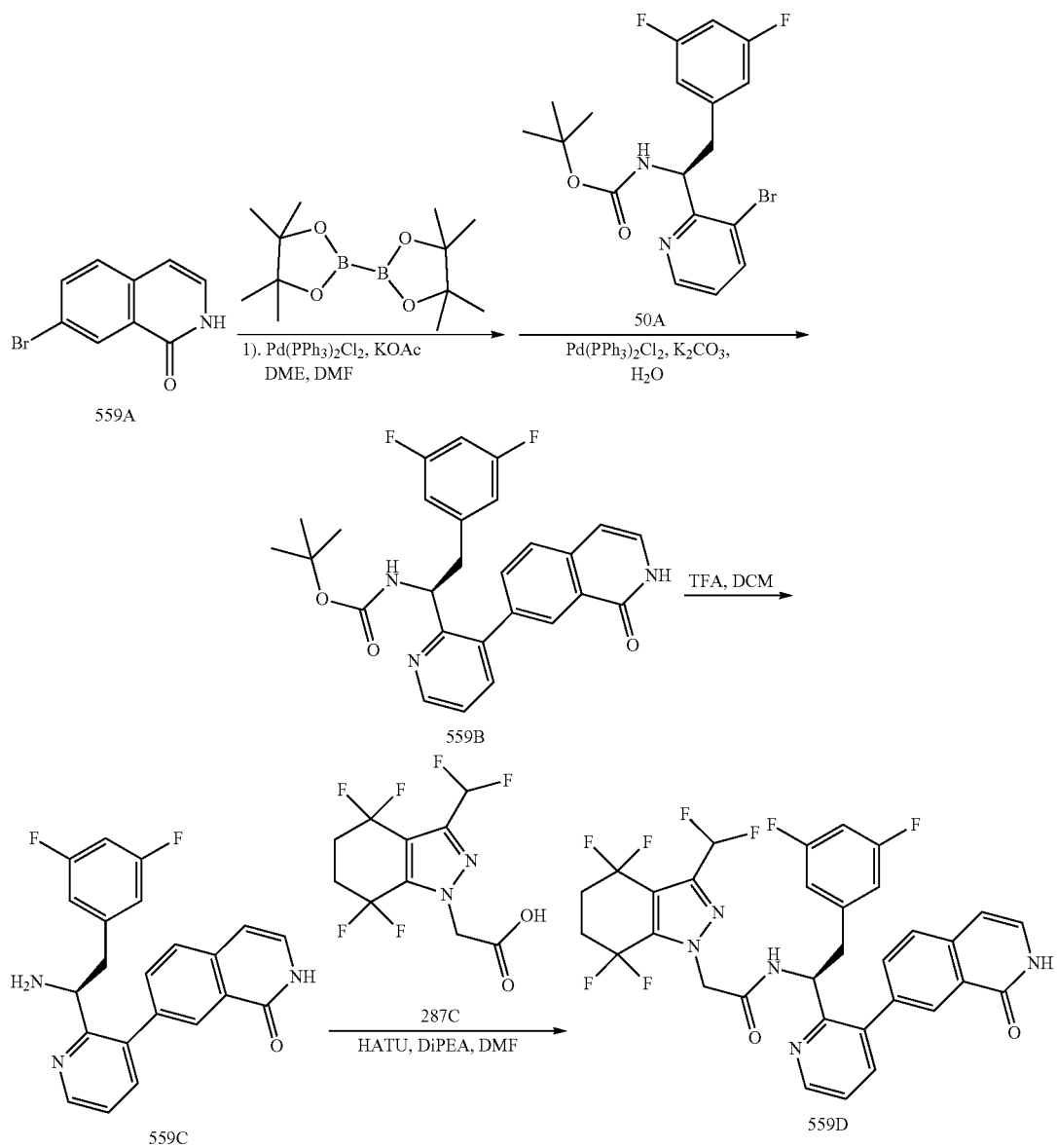

Synthesis of (S)-tert-butyl 2-(3,5-difluorophenyl)-1-(3-(1-oxo-1,2-dihydroisoquinolin-7-yl)pyridin-2-yl)ethylcarbamate (559B)

The title compound was prepared according to the method presented in the synthesis of 489B substituting 7-bromoisoquinolin-1(2H)-one for 489A to provide the desired compound: MS (m/z) 478.3 [M+H]+.

(S)-7-(2-(1-amino-2-(3,5-difluorophenyl)ethyl)pyridin-3-yl)isoquinolin-1(2H)-one (559C)

The title compound was prepared according to the method presented in the synthesis of 50C substituting (S)-tert-butyl 2-(3,5-difluorophenyl)-1-(3-(1-oxo-1,2-dihydroisoquinolin-7-yl)pyridin-2-yl)ethylcarbamate for 50B to provide the desired compound: MS (m/z) 378.5 [M+H]+.

Synthesis of (S)-2-(3-(difluoromethyl)-4,4,7,7-tetrafluoro-4,5,6,7-tetrahydro-1H-indazol-1-yl)-N-(2-(3,5-difluorophenyl)-1-(3-(1-oxo-1,2-dihydroisoquinolin-7-yl)pyridin-2-yl)ethyl)acetamide (559D)

The title compound was prepared according to the method presented in the synthesis of 61F substituting 287C for 61C and 559C for 61E to provide the desired compound (27 mg): $^1$H NMR (400 MHz, cd$_3$od) δ 8.72 (dd, 1H), 7.78 (s, 1H), 7.67 (ddd, 3H), 7.47 (dd, 1H), 7.20 (d, 1H), 6.86 (d, 1H), 6.73-6.55 (m, 2H), 6.23 (d, 2H), 5.41 (t, 1H), 5.08 (s, 2H), 3.04 (d, 2H), 2.64-2.36 (m, 4H); MS (m/z) 662.6 [M+H]+.

Example 560

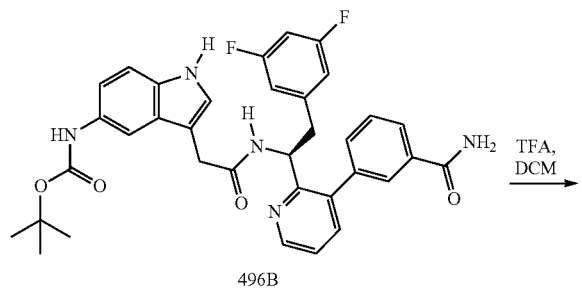

496B

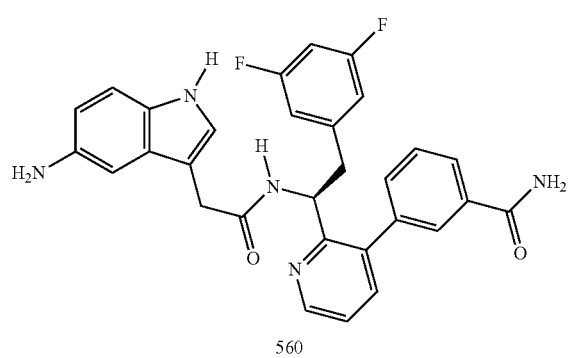

560

Synthesis of (S)-3-(2-(5-amino-1H-indol-3-yl)acet-
amido)-2-(3,5-difluorophenyl)ethyl)pyridin-3-yl)
benzamide (560)

The title compound was prepared according to the method presented in the synthesis of 491F utilizing 496B to provide 8 mg of the desired compound in a 80% yield: $^1$H NMR (400 MHz, dmso) δ 11.11 (s, 1H), 9.73 (s, 2H), 8.64 (dd, 2H), 7.99 (s, 1H), 7.86 (d, 1H), 7.72 (s, 1H), 7.60 (d, 1H), 7.40 (dt, 5H), 7.15 (s, 1H), 6.97 (d, 1H), 6.83 (t, 1H), 6.42 (d, 2H), 5.17 (d, 1H), 3.48 (dd, 3H), 2.95 (s, 2H); MS (m/z) 526.3 [M+H]$^+$.

Example 561

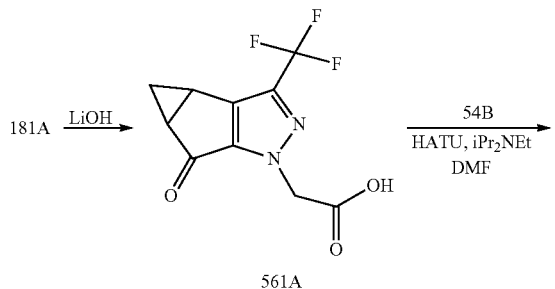

561A

-continued

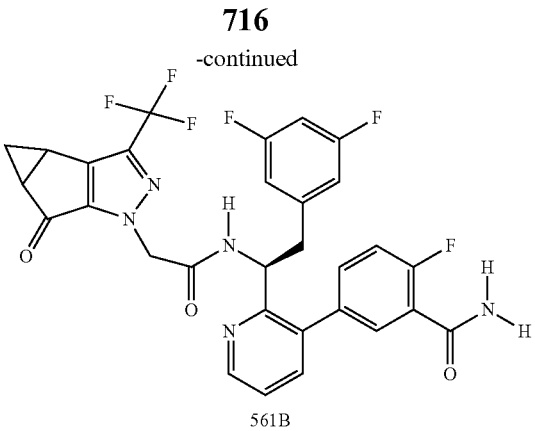

561B

Synthesis of 2-(5-oxo-3-(trifluoromethyl)-3b,4,4a,5-
tetrahydro-1H-cyclopropa[3,4]cyclopenta[1,2-c]
pyrazol-1-yl)acetic acid (561A)

The title compound was prepared according to the method presented in the synthesis of 122F in Example 122 utilizing 181A.

Synthesis of 5-(2-((1S)-2-(3,5-difluorophenyl)-1-(2-
(5-oxo-3-(trifluoromethyl)-3b,4,4a,5-tetrahydro-1H-
cyclopropa[3,4]cyclopenta[1,2-c]pyrazol-1-yl)acet-
amido)ethyl)pyridin-3-yl)-2-fluorobenzamide
(561B)

The title compound was prepared according to the method presented in the synthesis of Example 54 utilizing 54B and 561A. MS (m/z) 559.4 [M+H]$^+$. MS (m/z) 614.8 [M+H]$^+$.

Example 562

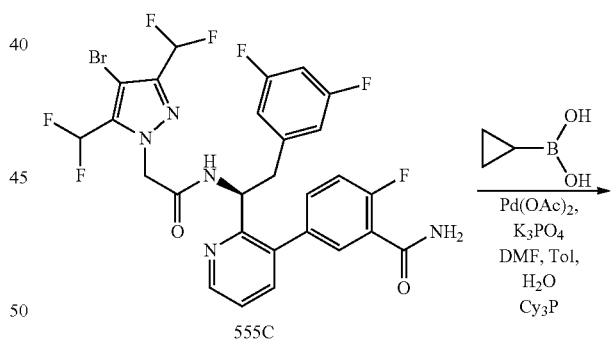

555C

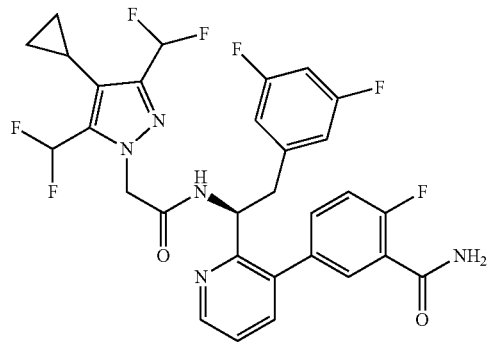

562

Synthesis of (S)-5-(2-(1-(2-(4-cyclopropyl-3,5-bis (difluoromethyl)-1H-pyrazol-1-yl)acetamido)-2-(3, 5-di fluorophenyl)ethyl)pyridin-3-yl)-2-fluorobenzamide (562)

A 40 ml vial was charged with 555C (100 mg, 0.15 mmol), DMF (0.5 ml), To (4 ml), cyclopropylboronic acid (60 mg, 0.7 mmol), Pd(OAc)$_2$ (10 mg, 0.01 mmol), Cy$_3$P (8 mg, 0.02 mmol), and K$_3$PO$_4$ (50 mg, 0.3 mmol) dissolved in water (0.2 ml). Heat the stirring mixture overnight at 110° C. Allow the reaction to cool then dilute with H$_2$O and extract 2× EtOAc. The combined organic layers were washed with brine then dried over sodium sulfate, concentrated, and purified by HPLC to give 7 mg of the desired compound. The yield was 8%: $^1$H NMR (400 MHz, cd$_3$od) δ 8.68 (d, 1H), 7.57 (d, 1H), 7.39 (dd, 2H), 7.29 (s, 1H), 7.25-7.15 (m, 1H), 7.04 (s, 1H), 6.90 (d, 1H), 6.75 (s, 1H), 6.63 (d, 2H), 6.29 (d, 2H), 5.39-5.27 (m, 1H), 4.98 (s, 2H), 3.05 (dd, 3H), 1.69 (s, 1H), 0.92 (d, 2H), 0.63 (d, 2H); MS (m/z) 620.2 [M+H]$^+$.

Example 563

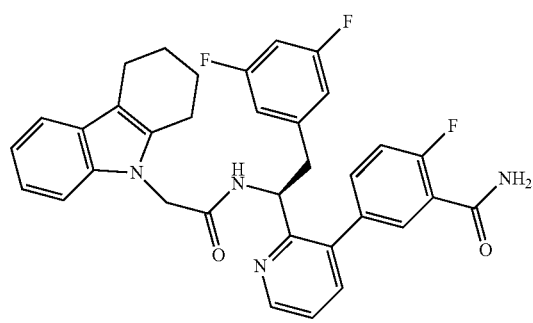

563

Synthesis of (S)-5-(2-(2-(3,5-difluorophenyl)-1-(2-(3,4-dihydro-1H-carbazol-9(2H)-yl)acetamido)ethyl) pyridin-3-yl)-2-fluorobenzamide (563)

The title compound was prepared according to the method presented in the synthesis of 54G substituting 2-(3,4-dihydro-1H-carbazol-9(2H)-yl)acetic acid for 54F to provide the desired compound (36 mg, 44%): $^1$H NMR (400 MHz, dmso) δ 10.86 (s, 1H), 8.69 (d, 2H), 7.65-7.51 (m, 5H), 7.39 (t, 2H), 7.24 (dd, 1H), 7.15-7.07 (m, 2H), 6.93-6.75 (m, 2H), 6.48 (d, 2H), 5.10 (d, 1H), 3.80-3.50 (m, 6H), 3.43 (s, 2H), 2.96 (t, 3H); MS (m/z) 583.7 [M+H]$^+$.

Example 564

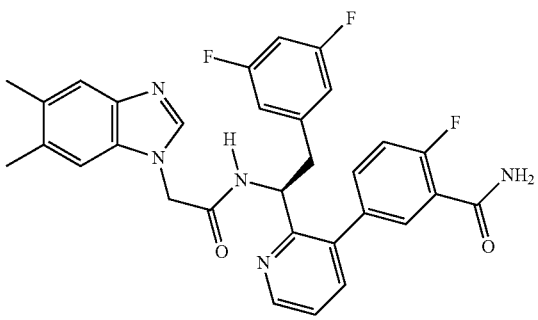

564

Synthesis of (S)-5-(2-(2-(3,5-difluorophenyl)-1-(2-(5,6-dimethyl-1H-benzo[d]imidazol-1-yl)acetamido) ethyl)pyridin-3-yl)-2-fluorobenzamide (564)

The title compound was prepared according to the method presented in the synthesis of 54G substituting 2-(5,6-dimethyl-1H-benzo[d]imidazol-1-yl)acetic acid for 54F to provide the desired compound (15 mg, 25%): $^1$H NMR (400 MHz, dmso) δ 9.28 (d, 1H), 9.17 (s, 1H), 8.72 (d, 1H), 7.63 (d, 3H), 7.54 (s, 1H), 7.49 (d, 1H), 7.43 (dd, 1H), 7.38 (s, 1H), 7.33-7.24 (m, 1H), 7.18 (s, 1H), 6.92 (s, 1H), 6.59 (d, 2H), 5.16 (d, 1H), 5.10 (s, 2H), 3.04 (d, 2H), 2.33 (s, 3H), 2.29 (s, 3H); MS (m/z) 558.7 [M+H]$^+$.

Example 565

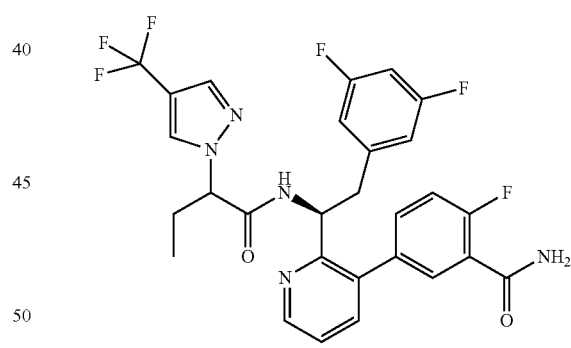

565

Synthesis of 5-(2-((1S)-2-(3,5-difluorophenyl)-1-(2-(4-(trifluoromethyl)-1H-pyrazol-1-yl)butanamido) ethyl)pyridin-3-yl)-2-fluorobenzamide (565)

The title compound was prepared according to the method presented in the synthesis of 483D utilizing 483C and 4-(trifluoromethyl)-1H-pyrazole to provide 16 mg (the first peak off HPLC) of the desired compound in a 29% yield: $^1$H NMR (400 MHz, dmso) δ 9.03 (d, 1H), 8.63 (d, 1H), 8.27 (s, 1H), 7.78 (s, 1H), 7.68 (d, 2H), 7.61 (dd, 1H), 7.53 (d, 1H), 7.43 (s, 1H), 7.41-7.37 (m, 1H), 7.34-7.27 (m, 1H), 6.95 (t, 1H), 6.62 (d, 2H), 5.13 (d, 1H), 4.92 (t, 1H), 2.98 (d, 2H), 1.86-1.74 (m, 2H), 0.57 (t, 3H); MS (m/z) 576.6 [M+H]$^+$.

Example 566

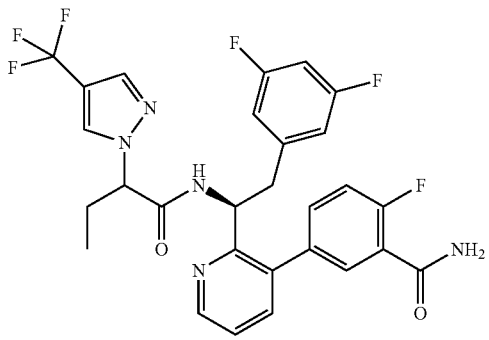

Synthesis of 5-(2-((1S)-2-(3,5-difluorophenyl)-1-(2-(4-(trifluoromethyl)-1H-pyrazol-1-yl)butanamido)ethyl)pyridin-3-yl)-2-fluorobenzamide (566)

The title compound was prepared according to the method presented in the synthesis of 483D utilizing 483C and 4-(trifluoromethyl)-1H-pyrazole to provide 22 mg (the second peak off HPLC) of the desired compound in a 40% yield: $^1$H NMR (400 MHz, dmso) δ 8.99 (d, 1H), 8.66 (d, 1H), 8.26 (s, 1H), 7.78 (s, 1H), 7.65 (s, 2H), 7.61-7.57 (m, 1H), 7.47-7.37 (m, 3H), 7.36-7.27 (m, 1H), 6.84 (t, 1H), 6.46 (d, 2H), 5.10 (d, 1H), 4.93 (t, 1H), 2.97 (d, 2H), 1.94-1.82 (m, 2H), 0.67 (t, 3H); MS (m/z) 576.6 [M+H]$^+$.

Example 567

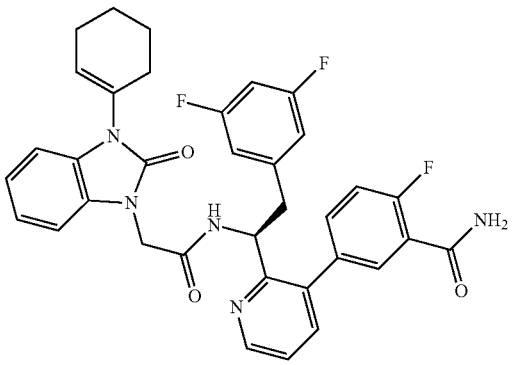

Synthesis of (S)-5-(2-(1-(2-(3-cyclohexenyl-2-oxo-2,3-dihydro-1H-benzo[d]imidazol-1-yl)acetamido)-2-(3,5-difluorophenyl)ethyl)pyridin-3-yl)-2-fluorobenzamide (567)

The title compound was prepared according to the method presented in the synthesis of 54G substituting 2-(3-cyclohexenyl-2-oxo-2,3-dihydro-1H-benzo[d]imidazol-1-yl)acetic acid for 54F to provide the desired compound (29 mg, 57%): $^1$H NMR (400 MHz, dmso) δ 9.01 (d, 1H), 8.70 (d, 1H), 7.69-7.57 (m, 3H), 7.49 (d, 1H), 7.42 (dd, 2H), 7.33-7.23 (m, 1H), 7.02-6.93 (m, 3H), 6.89 (dt, 1H), 6.60 (t, 3H), 5.80 (s, 1H), 5.16 (dd, 1H), 4.37 (dd, 2H), 3.02 (d, 2H), 2.20 (d, 4H), 1.70 (d, 2H), 1.61 (d, 2H); MS (m/z) 626.7 [M+H]$^+$.

Example 568

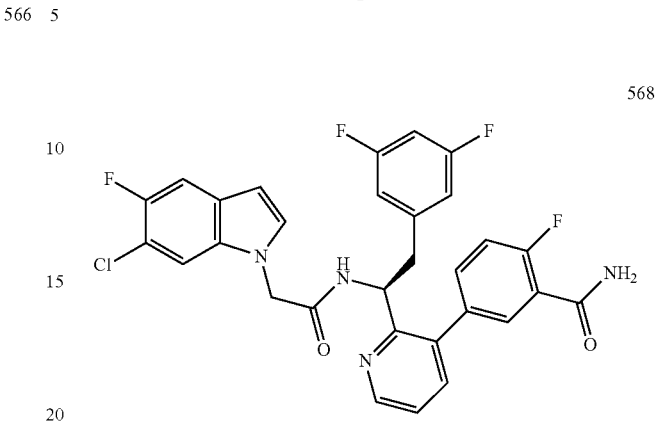

Synthesis of (S)-5-(2-(1-(2-(6-chloro-5-fluoro-1H-indol-1-yl)acetamido)-2-(3,5-difluorophenyl)ethyl)pyridin-3-yl)-2-fluorobenzamide (568)

The title compound was prepared according to the method presented in the synthesis of 56B substituting 6-chloro-5-fluoro-1H-indole for 1H-benzo[g]indole to provide the desired compound (7 mg, 17%): $^1$H NMR (400 MHz, dmso) δ 8.97 (d, 1H), 8.70 (d, 1H), 7.70-7.55 (m, 3H), 7.50-7.38 (m, 4H), 7.34 (d, 1H), 7.27 (dd, 2H), 6.90 (t, 1H), 6.55 (d, 2H), 6.36 (d, 1H), 5.13 (d, 1H), 4.78 (s, 2H), 3.00 (d, 2H); MS (m/z) 581.9 [M+H]$^+$.

Example 569

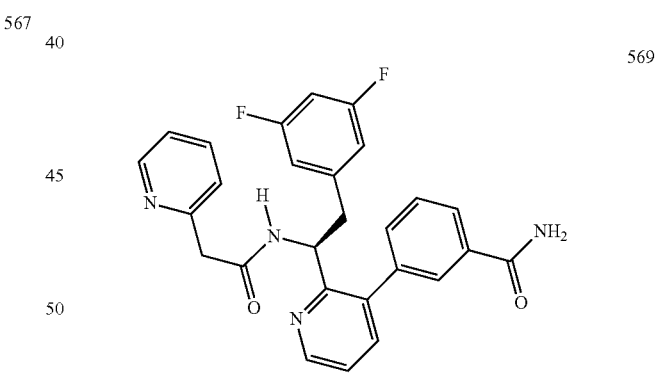

Synthesis of (S)-3-(2-(2-(3,5-difluorophenyl)-1-(2-(pyridin-2-yl)acetamido)ethyl)pyridin-3-yl)benzamide (569)

The title compound was prepared according to the method presented in the synthesis of 50D utilizing 50C and 2-(pyridin-2-yl)acetic acid to provide 21 mg of the desired compound in a 40% yield: $^1$H NMR (400 MHz, dmso) δ 9.02 (d, 1H), 8.72-8.64 (m, 2H), 8.22 (t, 1H), 7.94 (s, 1H), 7.88 (d, 1H), 7.70 (dd, 2H), 7.65 (dd, 1H), 7.59 (d, 1H), 7.53-7.38 (m, 4H), 6.89 (t, 1H), 6.48 (d, 2H), 5.19 (dd, 1H), 3.84 (q, 2H), 3.06-2.91 (m, 2H); MS (m/z) 473.2 [M+H]$^+$.

Example 570

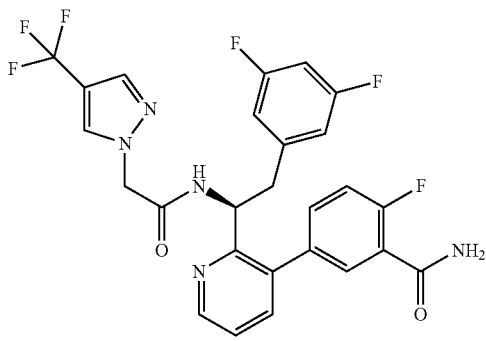

Synthesis of (S)-5-(2-(2-(3,5-difluorophenyl)-1-(2-(4-(trifluoromethyl)-1H-pyrazol-1-yl)acetamido)ethyl)pyridin-3-yl)-2-fluorobenzamide (570)

The title compound was prepared according to the method presented in the synthesis of 56B substituting 4-(trifluoromethyl)-1H-pyrazole for 1H-benzo[g]indole to provide the desired compound (30 mg, 78%): $^1$H NMR (400 MHz, dmso) δ 8.98 (d, 1H), 8.67 (dd, 1H), 8.17 (s, 1H), 7.78 (s, 1H), 7.65 (s, 2H), 7.60 (dd, 1H), 7.47-7.38 (m, 3H), 7.35-7.24 (m, 1H), 6.90 (t, 1H), 6.51 (d, 2H), 5.14 (dd, 1H), 4.83 (s, 2H), 2.99 (d, 2H); MS (m/z) 548.3 [M+H]$^+$.

Examples 572 and 573

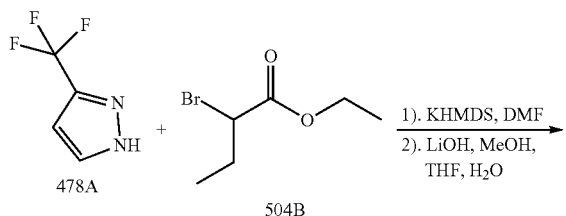

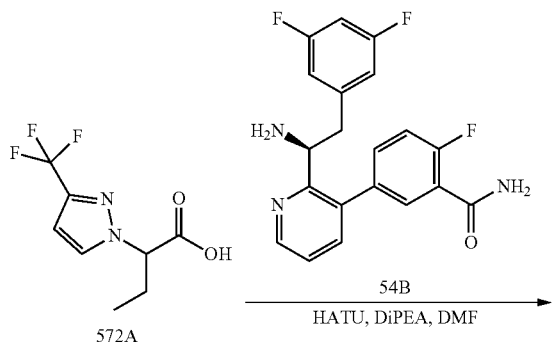

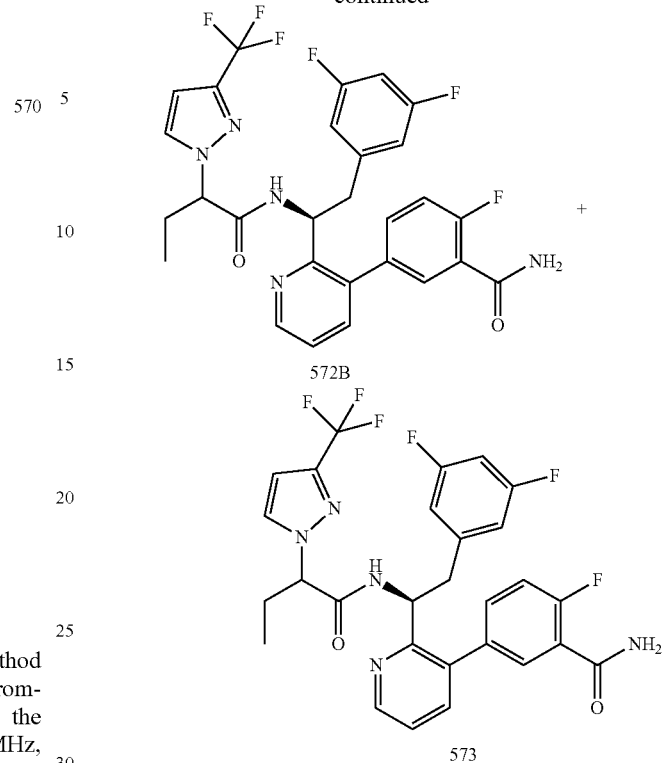

Synthesis of ethyl 2-(3-(trifluoromethyl)-1H-pyrazol-1-yl)butanoate

The title compound was prepared according to the method presented in Example 478 substituting 504B for 478B to provide the desired compound: MS (m/z) 251.2 [M+H]$^+$.

Synthesis of 2-(3-(trifluoromethyl)-1H-pyrazol-1-yl)butanoic acid (572A)

The title compound was prepared according to the method presented in Example 478 substituting ethyl 2-(3-(trifluoromethyl)-1H-pyrazol-1-yl)butanoate for 478C to provide the desired compound: MS (m/z) 223.0 [M+H]$^+$.

Synthesis of 5-(2-((1S)-2-(3,5-difluorophenyl)-1-(2-(3-(trifluoromethyl)-1H-pyrazol-1-yl)butanamido)ethyl)pyridin-3-yl)-2-fluorobenzamide (572B and 573)

The title compounds were prepared according to the method presented in the synthesis of 54G substituting 2-(3-(trifluoromethyl)-1H-pyrazol-1-yl)butanoic acid for 2-(5-(trifluoromethyl)-1H-indol-3-yl)acetic acid to provide the desired compounds (572B, peak 1 off HPLC, 8 mg, 10%; 573, peak 2 off HPLC, 10.4 mg, 13%): 572B $^1$H NMR (400 MHz, dmso) δ 9.08 (d, 1H), 8.63 (dd, 1H), 7.85 (s, 1H), 7.68 (d, 2H), 7.61 (dd, 1H), 7.52 (dd, 1H), 7.48-7.35 (m, 2H), 7.35-7.24 (m, 1H), 6.95 (t, 1H), 6.63 (d, 3H), 5.13 (dd, 1H), 4.94 (t, 1H), 2.99 (dd, 2H), 1.87-1.71 (m, 2H), 0.56 (t, 3H); MS (m/z) 577.1 [M+H]$^+$. $^1$H NMR (400 MHz, dmso) δ 9.03 (d, 1H), 8.66 (d, 1H), 7.87 (s, 1H), 7.65 (s, 2H), 7.59 (dd, 1H), 7.46-7.36 (m, 3H), 7.35-7.26 (m, 1H), 6.83 (t, 1H), 6.64

(s, 1H), 6.45 (d, 2H), 5.17-5.05 (m, 1H), 4.96 (t, 1H), 2.97 (d, 2H), 1.96-1.85 (m, 2H), 0.67 (t, 3H); MS (m/z) 577.1 [M+H]⁺.

Example 574

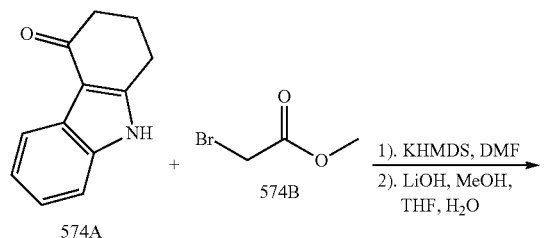

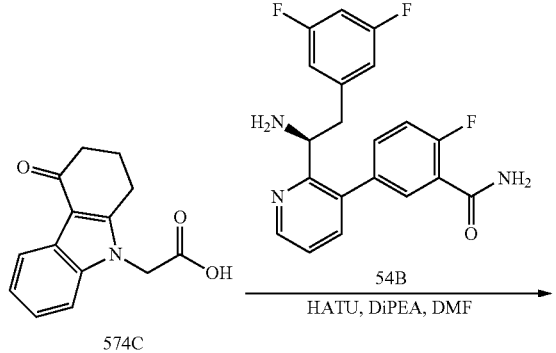

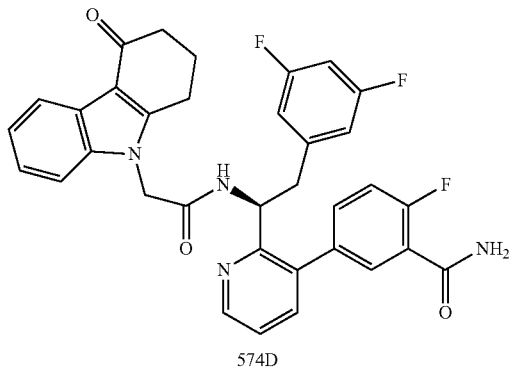

Synthesis of methyl 2-(4-oxo-3,4-dihydro-1H-carbazol-9(2H)-yl)acetate

The title compound was prepared according to the method presented in Example 478 substituting methyl 2-bromoacetate for 478B and 2,3-dihydro-1H-carbazol-4(9H)-one for 478A to provide the desired compound: MS (m/z) 258.4 [M+H]⁺.

Synthesis of 2-(4-oxo-3,4-dihydro-1H-carbazol-9(2H)-yl)acetic acid (574C)

The title compound was prepared according to the method presented in Example 478 substituting methyl 2-(4-oxo-3,4-dihydro-1H-carbazol-9(2H)-yl)acetate for 478C to provide the desired compound: MS (m/z) 244.3 [M+H]⁺.

Synthesis of (S)-5-(2-(2-(3,5-difluorophenyl)-1-(2-(4-oxo-3,4-dihydro-1H-carbazol-9(2H)-yl)acetamido)ethyl)pyridin-3-yl)-2-fluorobenzamide (574D)

The title compound was prepared according to the method presented in the synthesis of 54G substituting 2-(4-oxo-3,4-dihydro-1H-carbazol-9(2H)-yl)acetic acid for 54F to provide the desired compound (18 mg, 28): ¹H NMR (400 MHz, dmso) δ 9.12 (d, 1H), 8.70 (dd, 1H), 7.93-7.87 (m, 1H), 7.69-7.58 (m, 3H), 7.53 (dd, 1H), 7.42 (dd, 2H), 7.32-7.24 (m, 1H), 7.21 (d, 1H), 7.16-7.04 (m, 2H), 6.97 (t, 1H), 6.65 (d, 2H), 5.16 (dd, 1H), 4.81 (s, 2H), 3.03 (d, 2H), 2.74 (d, 1H), 2.68-2.57 (m, 1H), 2.34 (d, 2H), 2.00 (s, 2H); MS (m/z) 597.7 [M+H]⁺.

Example 575

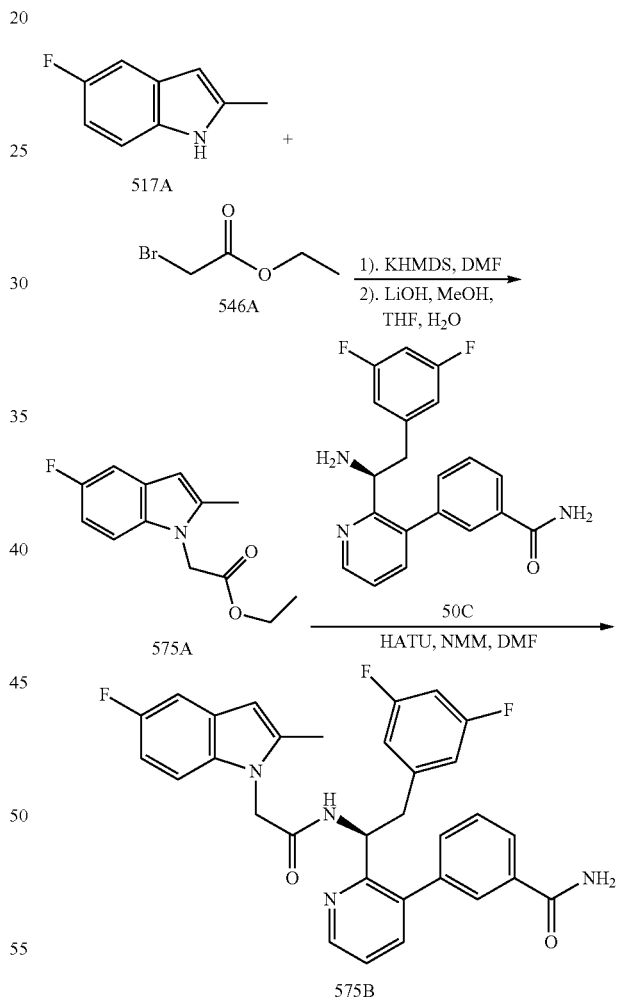

Synthesis of ethyl 2-(5-fluoro-2-methyl-1H-indol-1-yl)acetate

The title compound was prepared according to the method presented in Example 478 substituting ethyl 2-bromoacetate for 478B and 5-fluoro-2-methyl-1H-indole for 478A to provide the desired compound.

725

Synthesis of 2-(5-fluoro-2-methyl-1H-indol-1-yl) acetic acid (575A)

The title compound was prepared according to the method presented in Example 478 substituting ethyl 2-(5-fluoro-2-methyl-1H-indol-1-yl)acetate for 478C to provide the desired compound: MS (m/z) 208.3 [M+H]$^+$.

Synthesis of (S)-3-(2-(2-(3,5-difluorophenyl)-1-(2-(5-fluoro-2-methyl-1H-indol-1-yl)acetamido)ethyl) pyridin-3-yl)benzamide (575B)

The title compound was prepared according to the method presented in the synthesis of 50C substituting 2-(5-fluoro-2-methyl-1H-indol-1-yl)acetic acid for 2-(5-fluoro-1H-indol-3-yl)acetic acid to provide the desired compound (8 mg, 13%): $^1$H NMR (400 MHz, dmso) δ 8.91 (d, 1H), 8.68 (dd, 1H), 7.94 (s, 1H), 7.88 (d, 1H), 7.75 (s, 1H), 7.64 (dd, 1H), 7.49-7.36 (m, 4H), 7.11-7.03 (m, 2H), 6.95 (t, 1H), 6.73 (dd, 1H), 6.56 (d, 2H), 6.09 (s, 1H), 5.16 (dd, 1H), 4.70 (s, 2H), 2.98 (d, 2H), 2.13 (s, 3H); MS (m/z) 543.5 [M+H]$^+$.

Examples 576 and 598

726

Synthesis of (3-isopropyl-1H-pyrazol-5-yl)(3-methoxyazetidin-1-yl)methanone (576A)

The title compound was prepared according to the method presented in Example 482 substituting 3-methoxyazetidine for cyclopropanamine to provide the desired compound: MS (m/z) 224.2 [M+H]$^+$.

(S)-5-(2-(2-(3,5-difluorophenyl)-1-(2-(5-isopropyl-3-(3-methoxyazetidine-1-carbonyl)-1H-pyrazol-1-yl) acetamido)ethyl)pyridin-3-yl)-2-fluorobenzamide (576B) and (S)-5-(2-(2-(3,5-difluorophenyl)-1-(2-(3-isopropyl-5-(3-methoxyazetidine-1-carbonyl)-1H-pyrazol-1-yl)acetamido)ethyl)pyridin-3-yl)-2-fluorobenzamide (598)

The title compound was prepared according to the method presented in the synthesis of 56B substituting (3-isopropyl-1H-pyrazol-5-yl)(3-methoxyazetidin-1-yl)methanone for 1H-benzo[g]indole to provide the desired compounds (576B, 7 mg, 16%; 598, 9 mg, 20%): 576B $^1$H NMR (400 MHz, dmso) δ 8.65 (s, 1H), 8.62-8.52 (m, 1H), 7.68-7.55 (m, 3H), 7.39 (dd, 3H), 7.28 (d, 1H), 6.88 (s, 1H), 6.43 (d,

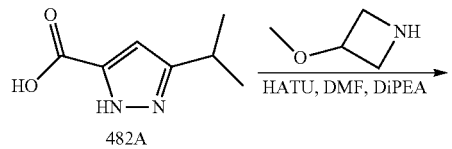

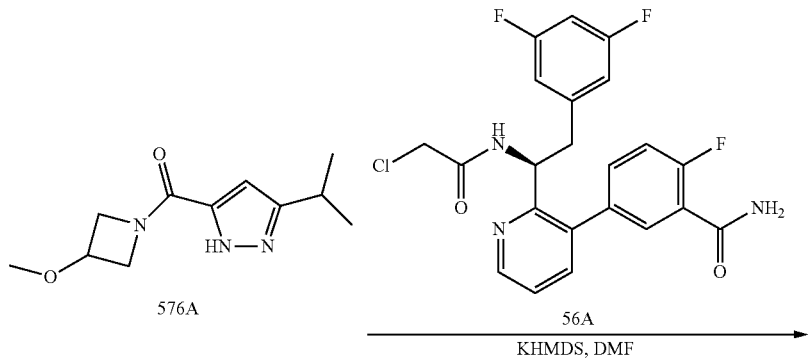

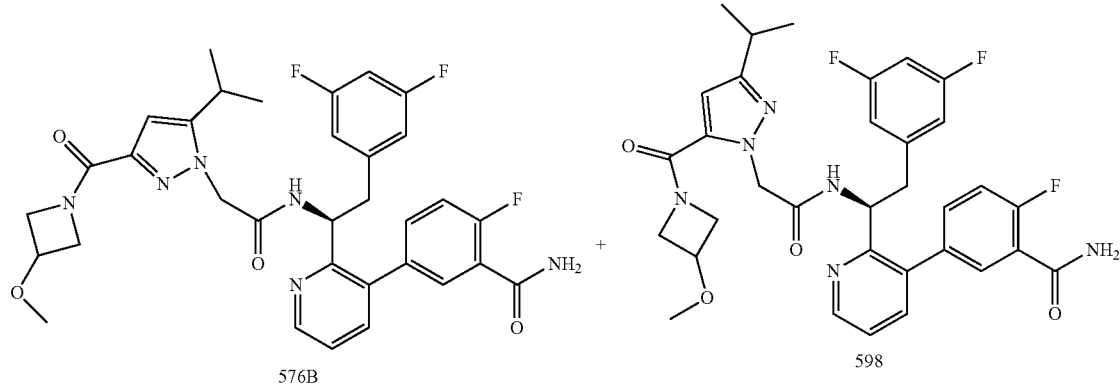

3H), 5.12 (d, 1H), 4.98 (s, 2H), 4.44-4.35 (m, 1H), 4.16 (s, 4H), 3.18 (s, 3H), 2.95 (s, 2H), 2.85-2.74 (m, 1H), 1.13 (d, 6H); MS (m/z) 635.5 [M+H]+. 598 1H NMR (400 MHz, dmso) δ 8.79 (s, 1H), 8.66 (d, 1H), 7.73-7.59 (m, 3H), 7.50 (s, 1H), 7.44-7.36 (m, 2H), 7.36-7.27 (m, 1H), 6.93 (s, 1H), 6.58 (d, 2H), 6.33 (s, 1H), 5.18 (s, 1H), 4.73 (s, 2H), 4.42 (s, 1H), 4.12 (d, 4H), 3.18 (s, 3H), 2.99 (d, 2H), 2.70-2.56 (m, 1H), 1.00 (t, 6H); MS (m/z) 635.5 [M+H]+.

Example 577

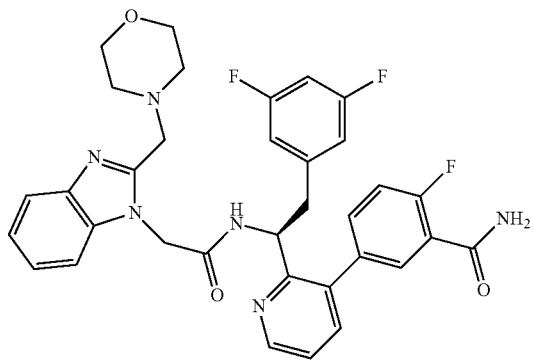

Synthesis of (S)-5-(2-(2-(3,5-difluorophenyl)-1-(2-(2-(morpholinomethyl)-1H-benzo[d]imidazol-1-yl)acetamido)ethyl)pyridin-3-yl)-2-fluorobenzamide (577)

The title compound was prepared according to the method presented in the synthesis of 54G substituting 2-(2-(morpholinomethyl)-1H-benzo[d]imidazol-1-yl)acetic acid for 54F to provide the desired compound (29 mg, 43%): 1H NMR (400 MHz, dmso) δ 9.34 (d, 1H), 8.72 (d, 1H), 7.64 (d, 4H), 7.55 (d, 1H), 7.52-7.36 (m, 3H), 7.31-7.21 (m, 3H), 6.94 (t, 1H), 6.64 (d, 2H), 5.15 (d, 1H), 5.02 (s, 2H), 4.45 (s, 2H), 3.69 (s, 4H), 3.05 (d, 6H); MS (m/z) 629.4 [M+H]+.

Example 578

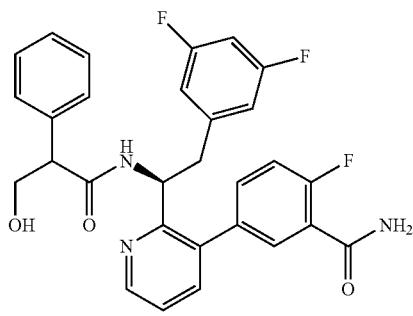

Synthesis of 5-(2-(((1S)-2-(3,5-difluorophenyl)-1-(3-hydroxy-2-phenylpropanamido)ethyl)pyridin-3-yl)-2-fluorobenzamide (578)

The title compound was prepared according to the method presented in the synthesis of 54G substituting 43-hydroxy-2-phenylpropanoic acid for 2-(5-(trifluoromethyl)-1H-indol-3-yl)acetic acid to provide the desired compound (12 mg, 17%): MS (m/z) 520.4 [M+H]+.

Example 579

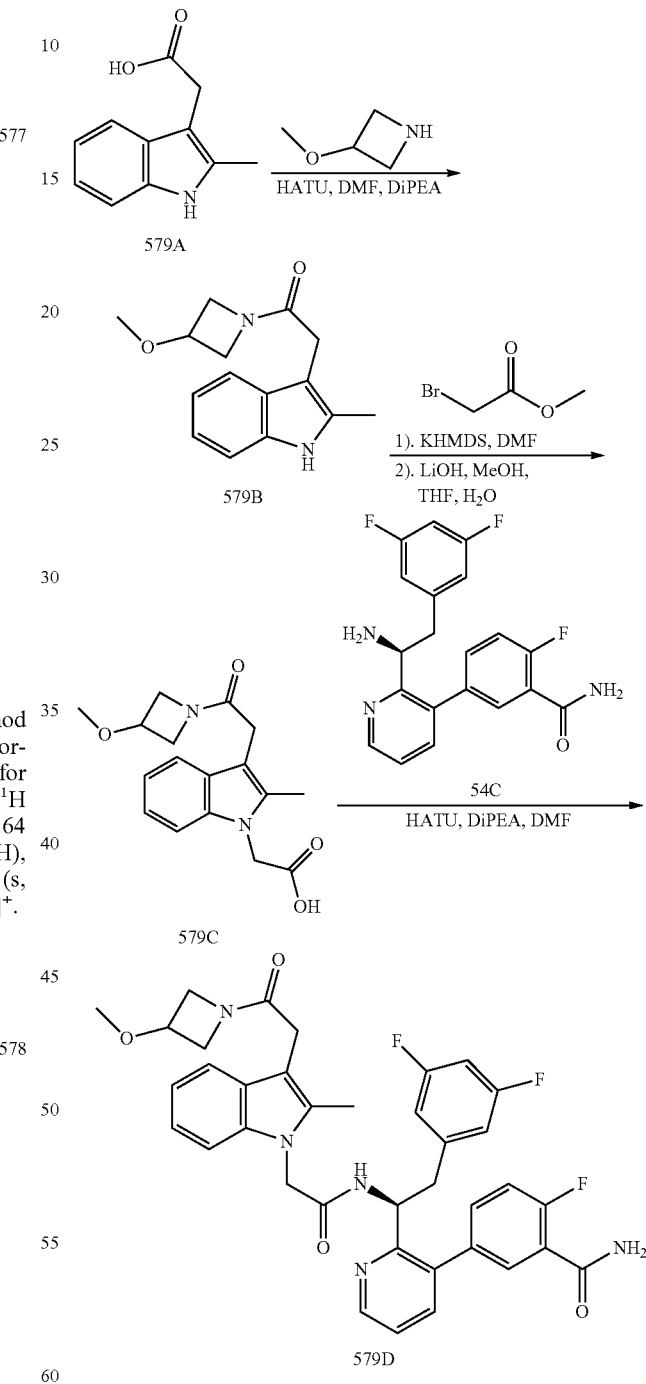

Synthesis of 1-(3-methoxyazetidin-1-yl)-2-(2-methyl-1H-indol-3-yl)ethanone (579B)

The title compound was prepared according to the method presented in Example 482 substituting 2-(2-methyl-1H-indol-3-yl)acetic acid for 482A and 3-methoxyazetidine for cyclopropanamine to provide the desired compound: MS (m/z) 259.4 [M+H]$^+$.

Synthesis methyl 2-(3-(2-(3-methoxyazetidin-1-yl)-2-oxoethyl)-2-methyl-1H-indol-1-yl)acetate The title compound was prepared according to the method presented in Example 478 substituting methyl 2-bromoacetate for 478B and 1-(3-methoxyazetidin-1-yl)-2-(2-methyl-1H-indol-3-yl)ethanone for 478A to provide the desired compound: MS (m/z) 330.3 [M+H]$^+$.

Synthesis of 2-(3-(2-(3-methoxyazetidin-1-yl)-2-oxoethyl)-2-methyl-1H-indol-1-yl)acetic acid (579C)

The title compound was prepared according to the method presented in Example 478 substituting methyl 2-(3-(2-(3-methoxyazetidin-1-yl)-2-oxoethyl)-2-methyl-1H-indol-1-yl)acetate for 478C to provide the desired compound: MS (m/z) 317.9 [M+H]$^+$.

Synthesis of (S)-5-(2-(2-(3,5-difluorophenyl)-1-(2-(3-(2-(3-methoxyazetidin-1-yl)-2-oxoethyl)-2-methyl-1H-indol-1-yl)acetamido)ethyl)pyridin-3-yl)-2-fluorobenzamide (579D)

The title compound was prepared according to the method presented in the synthesis of 54G substituting 2-(3-(2-(3-methoxyazetidin-1-yl)-2-oxoethyl)-2-methyl-1H-indol-1-yl)acetic acid for 54F to provide the desired compound (3 mg, 4%): $^1$H NMR (400 MHz, dmso) δ 8.92 (d, 1H), 8.68 (d, 1H), 7.60 (s, 3H), 7.47 (s, 1H), 7.45-7.36 (m, 2H), 7.35 (d, 1H), 7.30-7.24 (m, 1H), 7.06 (d, 1H), 7.00-6.84 (m, 3H), 6.60 (s, 2H), 5.14 (s, 1H), 4.69 (s, 2H), 4.16 (s, 1H), 4.07 (s, 1H), 3.92 (d, 2H), 3.87-3.79 (m, 1H), 3.40 (s, 2H), 3.11 (s, 3H), 3.00 (d, 2H), 2.10 (d, 3H); MS (m/z) 670.5 [M+H]$^+$.

Example 580

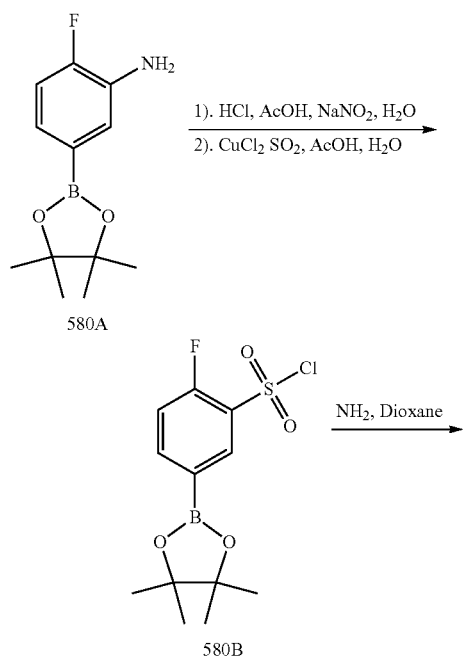

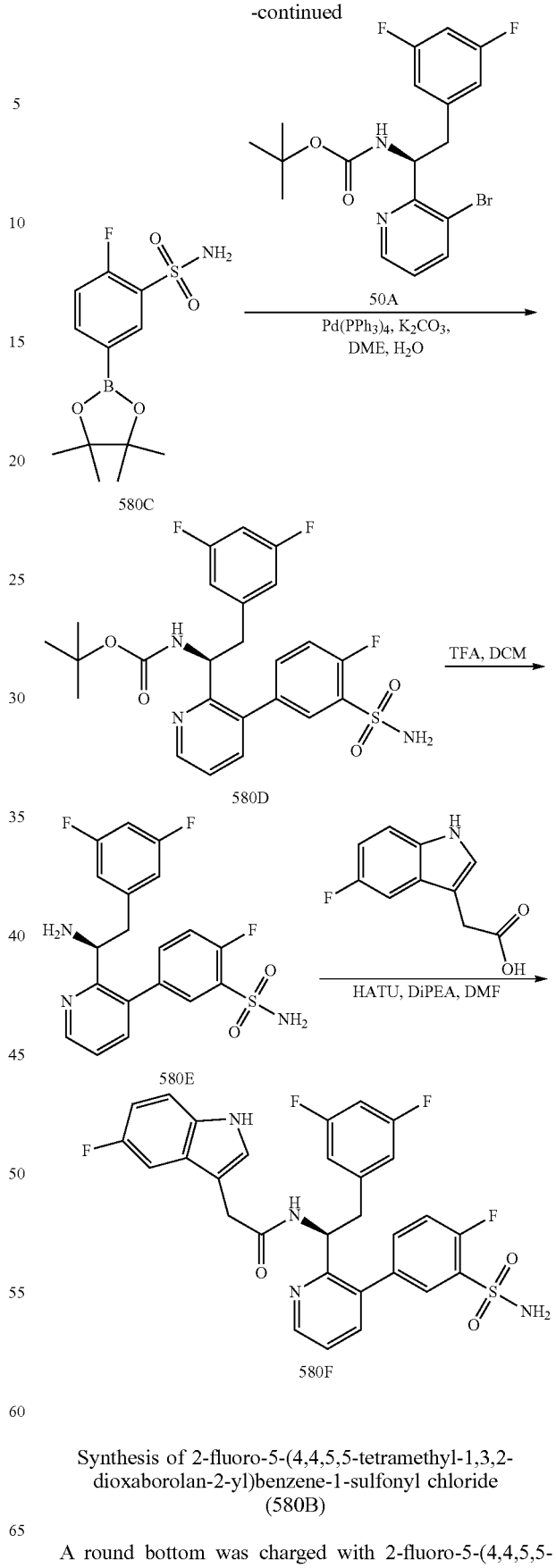

Synthesis of 2-fluoro-5-(4,4,5,5-tetramethyl-1,3,2-dioxaborolan-2-yl)benzene-1-sulfonyl chloride (580B)

A round bottom was charged with 2-fluoro-5-(4,4,5,5-tetramethyl-1,3,2-dioxaborolan-2-yl)aniline (1 g, 4.2 mmol), HCl (1.5 ml), AcOH (4.4 ml), and cool the reaction to 0° C. To the cooled stirring reaction slowly add sodium nitrate (318 mg, 4.6 mmol) dissolved in H₂O (0.7 ml). Remove the ice bath and stir at RT for 15 minutes and cool to 0° C. Make a mixture of CuCl₂ (373 mg, 2.2 mmol) and H₂O (0.44 ml) and add it to a cooled (0° C.) mixture of SO₂ saturated in AcOH (3.7 ml). Then add the Cu mixture into the aniline mixture and allow to warm to RT over 1 hour. Ice/water was added and the solution was filtered. The cake was dried under vacuum to give the desired compound (1 g, 74%).

Synthesis of 2-fluoro-5-(4,4,5,5-tetramethyl-1,3,2-dioxaborolan-2-yl)benzenesulfonamide (580C)

A round bottom was charged with 2-fluoro-5-(4,4,5,5-tetramethyl-1,3,2-dioxaborolan-2-yl)benzene-1-sulfonyl chloride (1 g, 3 mmol) and 4 N ammonia in dioxane (5 ml). The mixture was stirred at RT for 2 hours. The reaction was concentrated and used crude the next reaction.

Synthesis of (S)-tert-butyl 2-(3,5-difluorophenyl)-1-(3-(4-fluoro-3-sulfamoylphenyl)pyridin-2-yl)ethyl-carbamate (580D)

The title compound was prepared according to the method presented in Example 50 substituting 2-fluoro-5-(4,4,5,5-tetramethyl-1,3,2-dioxaborolan-2-yl)benzenesulfonamide for 3-carbamoylphenylboronic acid to provide the desired compound: MS (m/z) 508.1 [M+H]⁺.

Synthesis of (S)-5-(2-(1-amino-2-(3,5-difluorophenyl)ethyl)pyridin-3-yl)-2-fluorobenzenesulfonamide (580E)

The title compound was prepared according to the method presented in Example 50 substituting (S)-tert-butyl 2-(3,5-difluorophenyl)-1-(3-(4-fluoro-3-sulfamoylphenyl)pyridin-2-yl)ethylcarbamate for 50B to provide the desired compound: MS (m/z) 408.2 [M+H]⁺.

Synthesis of (S)—N-(2-(3,5-difluorophenyl)-1-(3-(4-fluoro-3-sulfamoylphenyl)pyridin-2-yl)ethyl)-2-(5-fluoro-1H-indol-3-yl)acetamide (580F)

The title compound was prepared according to the method presented in the synthesis of 50D substituting (S)-5-(2-(1-amino-2-(3,5-difluorophenyl)ethyl)pyridin-3-yl)-2-fluorobenzenesulfonamide for 50C to provide the desired compound (14 mg): ¹H NMR (400 MHz, dmso) δ 8.83 (d, 1H), 8.67 (d, 1H), 7.70-7.58 (m, 3H), 7.53 (d, 1H), 7.45 (s, 1H), 7.41 (dd, 1H), 7.28 (dd, 2H), 7.07 (d, 1H), 6.95 (t, 1H), 6.88 (dd, 2H), 6.63 (d, 2H), 5.15 (dd, 1H), 4.60 (s, 2H), 2.99 (d, 2H); MS (m/z) 583.6 [M+H]⁺.

Examples 581 and 582

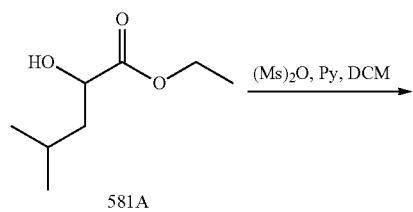

581A

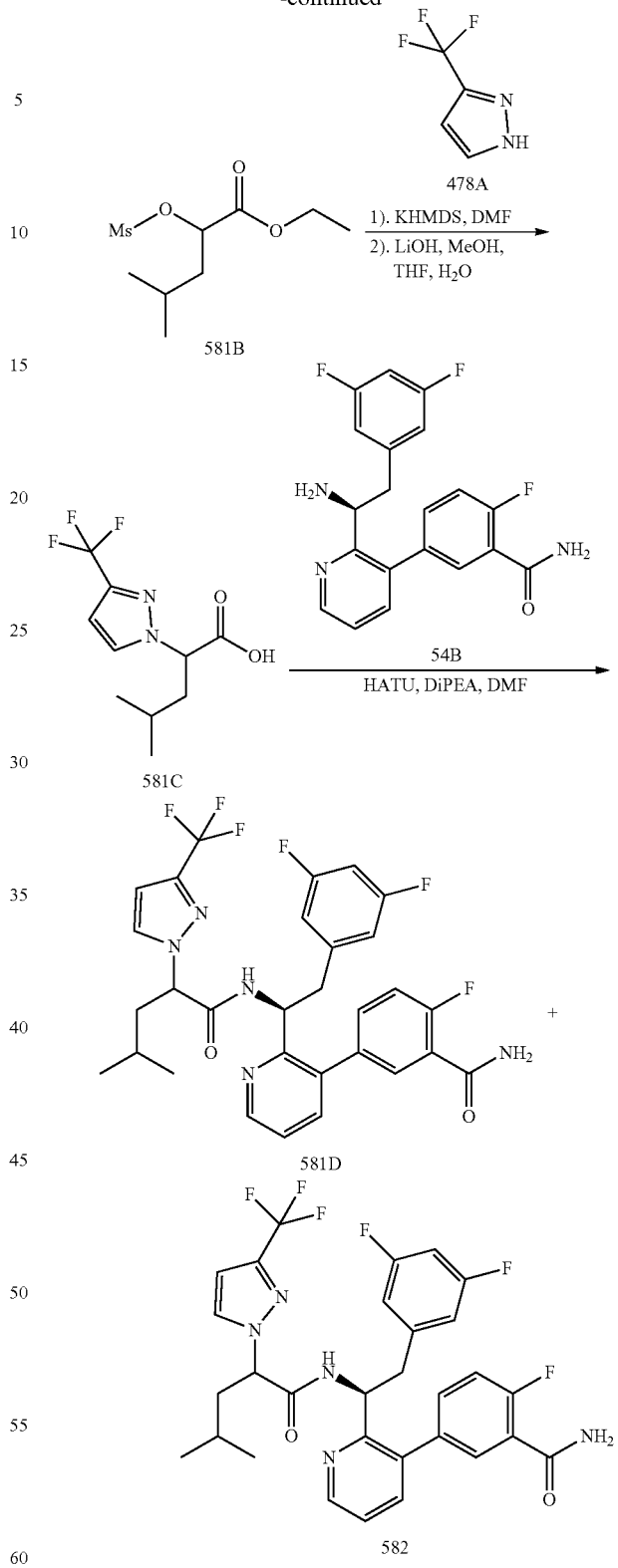

Synthesis of ethyl 4-methyl-2-(methylsulfonyloxy)pentanoate (581B)

A flask is charged ethyl 2-hydroxy-4-methylpentanoate (5 g, 31 mmol), DCM (100 ml), pyridine (3 ml, 37 mmol), and

Synthesis of ethyl 4-methyl-2-(3-(trifluoromethyl)-1H-pyrazol-1-yl)pentanoate The title compound was prepared according to the method presented in Example 478 substituting ethyl 4-methyl-2-(methylsulfonyloxy)pentanoate for 478B to provide the desired compound: MS (m/z) 279.2 [M+H]$^+$.

Synthesis of 4-methyl-2-(3-(trifluoromethyl)-1H-pyrazol-1-yl)pentanoic acid (581C)

The title compound was prepared according to the method presented in Example 478 substituting ethyl 4-methyl-2-(3-(trifluoromethyl)-1H-pyrazol-1-yl)pentanoate for 478C to provide the desired compound: MS (m/z) 251.0 [M+H]$^+$.

Synthesis of 5-(2-((1S)-2-(3,5-difluorophenyl)-1-(4-methyl-2-(3-(trifluoromethyl)-1H-pyrazol-1-yl)pentanamido)ethyl)pyridin-3-yl)-2-fluorobenzamide (581D and 582)

The title compounds were prepared according to the method presented in the synthesis of 54G substituting 4-methyl-2-(3-(trifluoromethyl)-1H-pyrazol-1-yl)pentanoic acid for 2-(5-(trifluoromethyl)-1H-indol-3-yl)acetic acid to provide the desired compounds (581D, peak 1 off HPLC, 8 mg, 10%; 582, peak 2 off HPLC, 12 mg, 15%): 581D $^1$H NMR (400 MHz, dmso) δ 9.19 (d, 1H), 8.63 (d, 1H), 7.84 (s, 1H), 7.70 (d, 2H), 7.60 (dd, 2H), 7.45 (s, 1H), 7.39 (dd, 1H), 7.37-7.28 (m, 1H), 6.99 (s, 1H), 6.69 (d, 2H), 6.62 (s, 1H), 5.19-5.02 (m, 2H), 3.00 (d, 2H), 1.62 (s, 1H), 1.55-1.42 (m, 1H), 0.92 (s, 1H), 0.73 (dd, 6H); MS (m/z) 605.0 [M+H]$^+$. 582 $^1$H NMR (400 MHz, dmso) δ 9.03 (d, 1H), 8.65 (d, 1H), 7.88 (s, 1H), 7.65 (s, 2H), 7.58 (d, 1H), 7.46-7.38 (m, 3H), 7.38-7.26 (m, 1H), 6.83 (d, 1H), 6.63 (s, 1H), 6.44 (d, 2H), 5.12 (dd, 2H), 2.97 (d, 2H), 1.82 (s, 1H), 1.65 (d, 1H), 1.11 (s, 1H), 0.77 (d, 6H); MS (m/z) 605.3 [M+H]$^+$.

Example 583

Synthesis of (S)-5-(2-(2-(3,5-difluorophenyl)-1-(2-(5,6-dimethyl-2H-indazol-2-yl)acetamido)ethyl)pyridin-3-yl)-2-fluorobenzamide (583)

The title compound was prepared according to the method presented in the synthesis of 56B substituting 5,6-dimethyl-1H-indazole for 1H-benzo[g]indole to provide the desired compound (5.4 mg, 15%): $^1$H NMR (400 MHz, dmso) δ 8.96 (d, 1H), 8.68 (d, 1H), 7.98 (s, 1H), 7.66-7.54 (m, 3H), 7.39 (dd, 4H), 7.25 (t, 2H), 6.90 (s, 1H), 6.49 (d, 2H), 5.14 (d, 1H), 5.00 (s, 2H), 2.99 (d, 2H), 2.24 (d, 6H); MS (m/z) 558.4 [M+H]$^+$.

Example 584

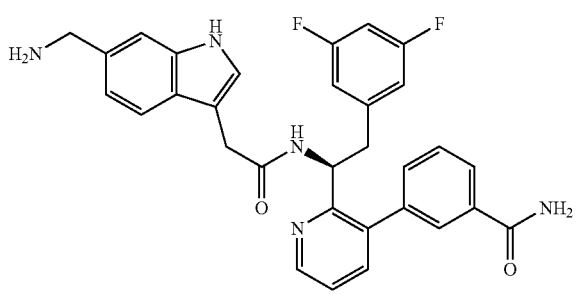

584

Synthesis of (S)-3-(2-(1-(2-(6-(aminomethyl)-1H-indol-3-yl)acetamido)-2-(3,5-difluorophenyl)ethyl)pyridin-3-yl)benzamide (584)

The title compound was prepared according to the method presented in the synthesis of 557 utilizing (S)-tert-butyl (3-(2-(1-(3-(3-carbamoylphenyl)pyridin-2-yl)-2-(3,5-difluorophenyl)ethylamino)-2-oxoethyl)-1H-indol-6-yl)methylcarbamate to provide 22 mg of the desired compound in a 99% yield $^1$H NMR (400 MHz, dmso) δ 10.96 (s, 1H), 8.70-8.65 (m, 1H), 8.62 (d, 1H), 8.00 (s, 2H), 7.95 (s, 1H), 7.86 (d, 1H), 7.75 (s, 1H), 7.61 (dd, 1H), 7.41 (ddd, 4H), 7.30 (d, 1H), 7.06 (s, 1H), 6.91 (d, 2H), 6.50 (d, 2H), 5.18 (dd, 2H), 4.03 (d, 2H), 3.47 (d, 2H), 2.95 (d, 2H); MS (m/z) 540.2 [M+H]$^+$.

Example 585

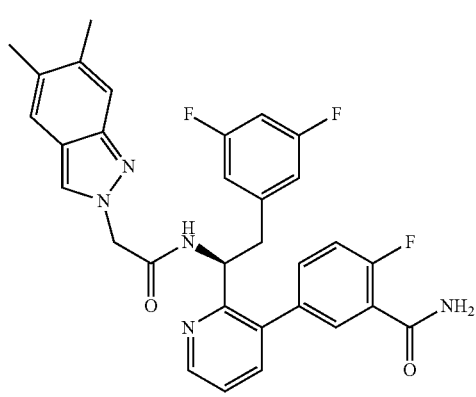

583

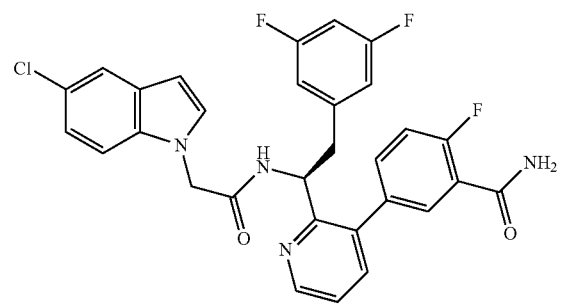

585

735

Synthesis of (S)-5-(2-(1-(2-(5-chloro-1H-indol-1-yl)acetamido)-2-(3,5-difluorophenyl)ethyl)pyridin-3-yl)-2-fluorobenzamide (585)

The title compound was prepared according to the method presented in the synthesis of 56B substituting 5-chloro-1H-indole for 1H-benzo[g]indole to provide the desired compound (24 mg, 61%): $^1$H NMR (400 MHz, dmso) δ 8.96 (d, 1H), 8.69 (d, 1H), 7.67-7.57 (m, 3H), 7.50 (s, 2H), 7.44-7.37 (m, 2H), 7.32-7.24 (m, 1H), 7.21 (d, 1H), 7.04 (d, 1H), 6.97 (d, 2H), 6.61 (d, 2H), 6.32 (d, 1H), 5.13 (s, 1H), 4.77 (s, 2H), 3.01 (d, 2H); MS (m/z) 563.9 [M+H]$^+$.

Example 587

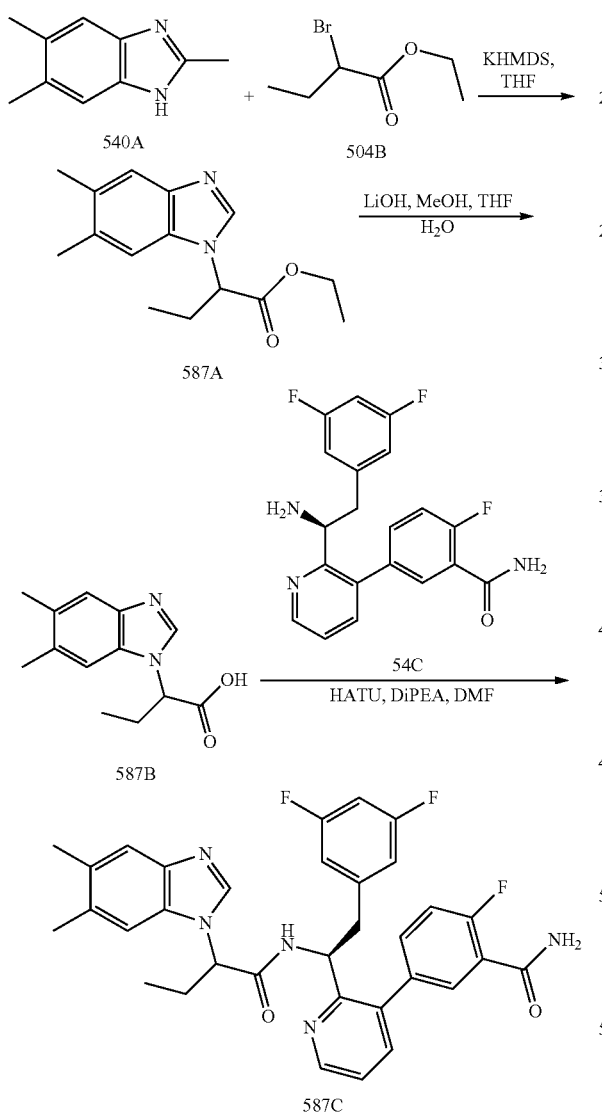

Synthesis of ethyl 2-(5,6-dimethyl-1H-benzo[d]imidazol-1-yl)butanoate (587A)

The title compound was prepared according to the method presented in Example 478 substituting 540A for 478A and 504B for 478B to provide the desired compound: MS (m/z) 261.3 [M+H]$^+$.

736

Synthesis of 2-(5,6-dimethyl-1H-benzo[d]imidazol-1-yl)butanoic acid (587B)

The title compound was prepared according to the method presented in Example 478 substituting ethyl 2-(5,6-dimethyl-1H-benzo[d]imidazol-1-yl)butanoate for 478C to provide the desired compound: MS (m/z) 233.3 [M+H]$^+$.

Synthesis of 5-(2-((1S)-2-(3,5-difluorophenyl)-1-(2-(5,6-dimethyl-1H-benzo[d]imidazol-1-yl)butanamido)ethyl)pyridin-3-yl)-2-fluorobenzamide (587C)

The title compound was prepared according to the method presented in the synthesis of 54G substituting 2-(5,6-dimethyl-1H-benzo[d]imidazol-1-yl)butanoic acid for 54F to provide the desired compound (11 mg, 14%): MS (m/z) 586.5 [M+H]$^+$.

Example 588

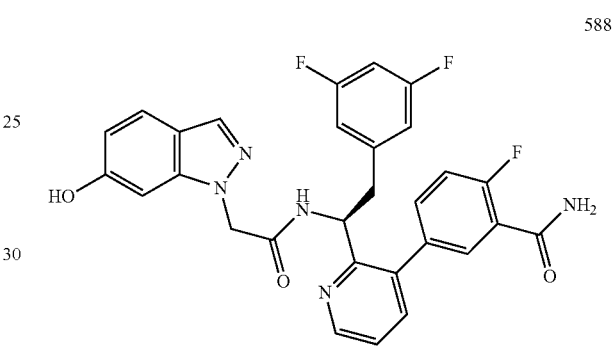

Synthesis of (S)-5-(2-(2-(3,5-difluorophenyl)-1-(2-(6-hydroxy-1H-indazol-1-yl)acetamido)ethyl)pyridin-3-yl)-2-fluorobenzamide (588)

The title compound was prepared according to the method presented in Example 56 substituting 1H-indazol-6-ol for 1H-benzo[g]indole to provide the desired compound (10 mg, 16%): $^1$H NMR (400 MHz, dmso) δ 8.70-8.63 (m, 1H), 8.56 (d, 1H), 7.90 (s, 1H), 7.67 (d, 2H), 7.63-7.54 (m, 2H), 7.49 (d, 1H), 7.43-7.37 (m, 2H), 7.32 (dd, 1H), 6.85 (dd, 2H), 6.75 (dd, 1H), 6.49 (d, 2H), 5.22 (dd, 1H), 4.46 (d, 2H), 3.09-2.91 (m, 3H); MS (m/z) 546.2 [M+H]$^+$.

Example 589

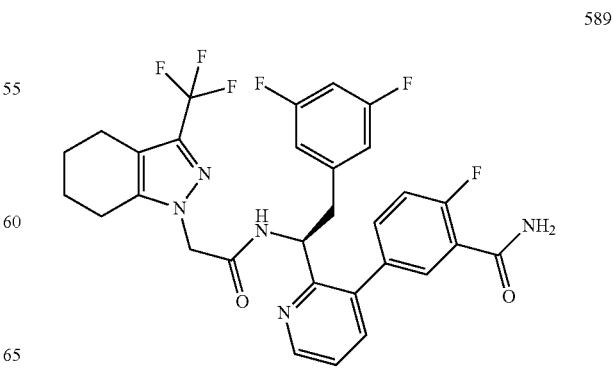

Synthesis of (S)-5-(2-(2-(3,5-difluorophenyl)-1-(2-(3-(trifluoromethyl)-4,5,6,7-tetrahydro-1H-indazol-1-yl)acetamido)ethyl)pyridin-3-yl)-2-fluorobenzamide (589)

The title compound was prepared according to the method presented in the synthesis of 54G utilizing 54B and 2-(3-(trifluoromethyl)-4,5,6,7-tetrahydro-1H-indazol-1-yl)acetic acid to provide 40 mg of the desired compound in a 50% yield: $^1$H NMR (400 MHz, dmso) δ 8.92 (d, 1H), 8.67 (dd, 1H), 7.66 (s, 1H), 7.62 (dd, 1H), 7.49 (dd, 1H), 7.41 (dd, 2H), 7.36-7.25 (m, 1H), 6.92 (t, 1H), 6.57 (d, 2H), 5.17 (dd, 1H), 4.70 (s, 3H), 3.07-2.94 (m, 2H), 2.41 (s, 2H), 2.32 (d, 1H), 2.17 (d, 1H), 1.59 (d, 4H); MS (m/z) 603.3 [M+H]$^+$.

Example 590

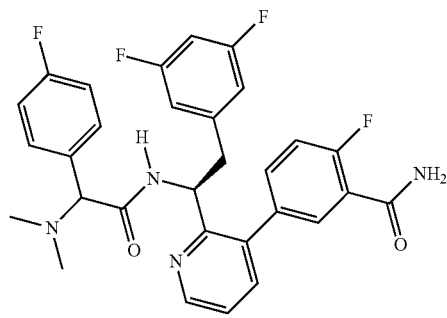

Synthesis of 5-(2-((1S)-2-(3,5-difluorophenyl)-1-(2-(dimethylamino)-2-(4-fluorophenyl)acetamido)ethyl)pyridin-3-yl)-2-fluorobenzamide (590)

The title compound was prepared according to the method presented in the synthesis of 54G substituting 2-(dimethylamino)-2-(4-fluorophenyl)acetic acid for 54F to provide the desired compound (the second peak off HPLC, 4 mg, 6%): $^1$H NMR (400 MHz, dmso) δ 10.15-10.06 (m, 1H), 9.58 (s, 1H), 8.68 (d, 1H), 7.77-7.66 (m, 2H), 7.63 (s, 1H), 7.50 (s, 1H), 7.48-7.36 (m, 2H), 7.36-7.28 (m, 2H), 7.18 (t, 2H), 6.78 (s, 1H), 6.35 (d, 2H), 5.20 (s, 1H), 4.78 (s, 1H), 2.91 (d, 2H), 2.58 (s, 3H), 2.33 (s, 3H); MS (m/z) 551.3 [M+H]$^+$.

Example 591

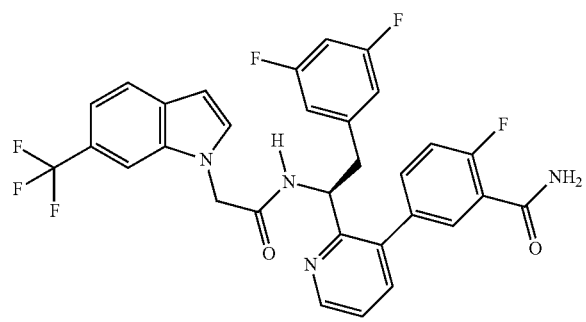

Synthesis of (S)-5-(2-(2-(3,5-difluorophenyl)-1-(2-(6-(trifluoromethyl)-1H-indol-1-yl)acetamido)ethyl)pyridin-3-yl)-2-fluorobenzamide (591)

The title compound was prepared according to the method presented in Example 56 substituting 6-(trifluoromethyl)-1H-indole for 1H-benzo[g]indole to provide the desired compound (15 mg, 36%): $^1$H NMR (400 MHz, dmso) δ 9.02 (d, 1H), 8.67 (d, 1H), 7.67 (d, 1H), 7.61 (d, 2H), 7.58 (s, 2H), 7.45 (d, 1H), 7.40 (t, 3H), 7.24 (t, 2H), 6.86 (s, 11H), 6.54 (d, 2H), 6.49 (d, 1H), 5.13 (d, 1H), 4.89 (s, 2H), 3.00 (d, 2H); MS (m/z) 598.1 [M+H]$^+$.

Example 592

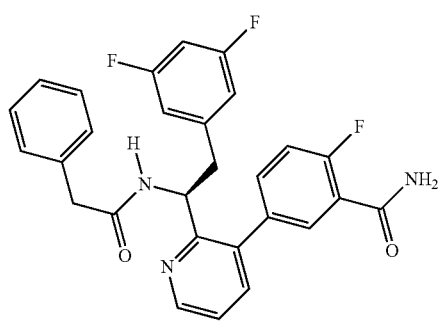

Synthesis of (S)-5-(2-(2-(3,5-difluorophenyl)-1-(2-(5,6-dimethyl-1H-indol-1-yl)acetamido)ethyl)pyridin-3-yl)-2-fluorobenzamide (592)

The title compound was prepared according to the method presented in the synthesis of 54G substituting 2-phenylacetic acid for 54F to provide the desired compound (23 mg, 44%): $^1$H NMR (400 MHz, dmso) δ 8.73 (d, 1H), 8.66 (dd, 1H), 7.65 (d, 2H), 7.59 (dd, 1H), 7.50 (dd, 1H), 7.39 (dd, 2H), 7.34-7.24 (m, 1H), 7.14 (dq, 3H), 7.04 (d, 2H), 6.90 (t, 1H), 6.56 (d, 2H), 5.10 (dd, 1H), 3.34 (dd, 2H), 2.98 (d, 2H); MS (m/z) 490.6 [M+H]$^+$.

Example 593

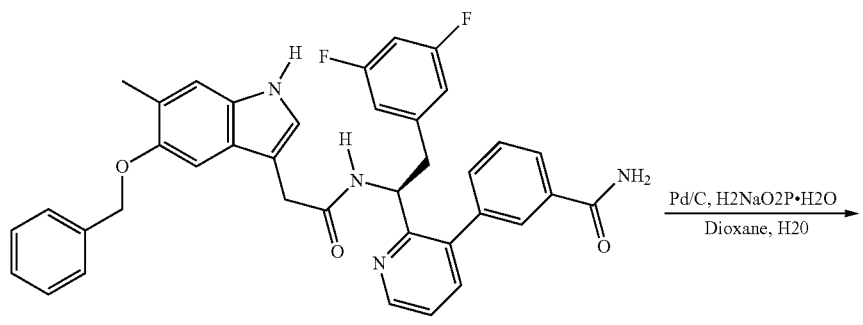

Synthesis of (S)-3-(2-(2-(3,5-difluorophenyl)-1-(2-(5-hydroxy-6-methyl-1H-indol-3-yl)acetamido)ethyl)pyridin-3-yl)benzamide (593)

A round bottom was charged with 536I (30 mg, 0.05 mmol), dioxane (5 ml), Pd/C (10 mg), H2NaO2P.H2O (60 mg, 0.6 mmol), and H$_2$O (1 ml). The resulting mixture was stirred at 95° C. until done as indicated by LC/MS. The reaction mixture was cooled to RT and filtered over a plug of celite, rinsing with ethyl acetate. The layers were partitioned and the organic layer was dried over sodium sulfate, filtered, concentrated and purified by HPLC to give the desired compound (16 mg, 66%): $^1$H NMR (400 MHz, dmso) δ 10.32 (s, 1H), 8.66-8.57 (m, 1H), 8.35 (d, 1H), 7.96 (s, 1H), 7.86 (d, 1H), 7.69 (s, 1H), 7.58 (dd, 1H), 7.44 (t, 1H), 7.36 (dt, 3H), 6.95 (s, 1H), 6.90-6.80 (m, 2H), 6.76 (s, 1H), 6.37 (d, 2H), 5.27-5.16 (m, 1H), 3.37 (s, 2H), 2.91 (d, 2H), 2.14 (s, 3H); MS (m/z) 541.2 [M+H]$^+$.

Example 594

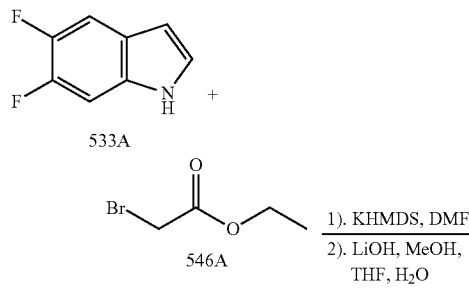

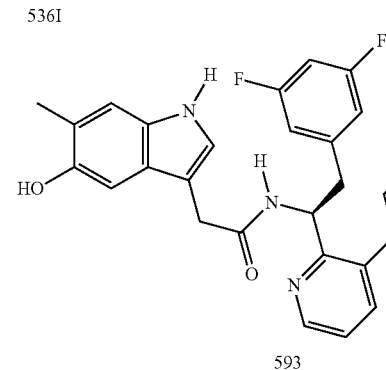

-continued

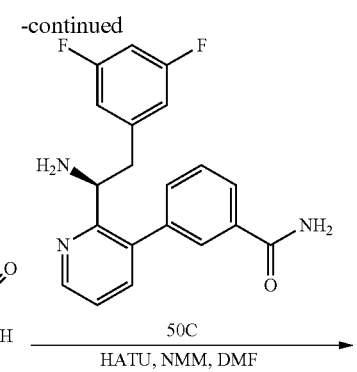

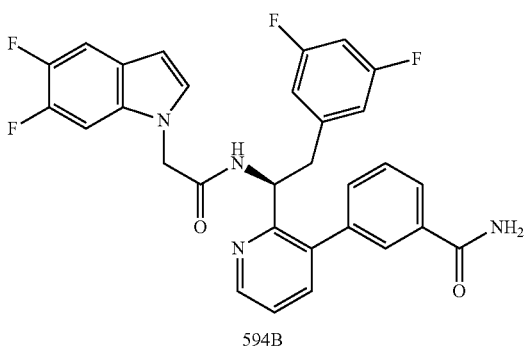

Synthesis of ethyl 2-(5,6-difluoro-1H-indol-1-yl)acetate

The title compound was prepared according to the method presented in Example 478 substituting ethyl 2-bromoacetate for 478B and 5,6-difluoro-1H-indole for 478A to provide the desired compound.

Synthesis of 2-(5,6-difluoro-1H-indol-1-yl)acetic acid (594A)

The title compound was prepared according to the method presented in Example 478 substituting ethyl 2-(5,6-difluoro-1H-indol-1-yl)acetate for 478C to provide the desired compound: MS (m/z) 212.2 [M+H]$^+$.

Synthesis of (S)-3-(2-(1-(2-(5,6-difluoro-1H-indol-1-yl)acetamido)-2-(3,5-difluorophenyl)ethyl)pyridin-3-yl)benzamide (594B)

The title compound was prepared according to the method presented in the synthesis of 50D substituting 2-(5,6-difluoro-1H-indol-1-yl)acetic acid for 2-(5-fluoro-1H-indol-3-yl)acetic acid to provide the desired compound (27 mg, 44%): $^1$H NMR (400 MHz, dmso) δ 8.92 (d, 1H), 8.68 (d, 1H), 7.94 (s, 1H), 7.88 (d, 1H), 7.73 (s, 1H), 7.64 (d, 1H), 7.52-7.35 (m, 5H), 7.19 (d, 1H), 7.15 (dd, 1H), 6.88 (t, 1H), 6.52 (d, 2H), 6.34 (d, 1H), 5.18 (dd, 1H), 4.75 (s, 2H), 3.05-2.94 (m, 2H); MS (m/z) 547.6 [M+H]$^+$.

Example 595

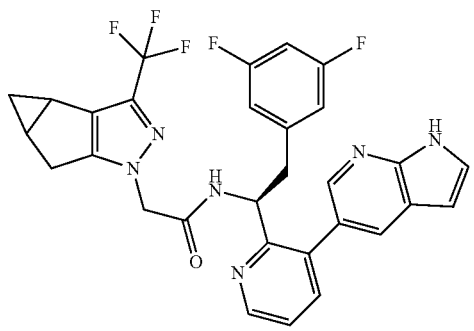

Synthesis of N—((S)-1-(3-(1H-pyrrolo[2,3-b]pyridin-5-yl)pyridin-2-yl)-2-(3,5-difluorophenyl)ethyl)-2-(3-(trifluoromethyl)-3b,4,4a,5-tetrahydro-1H-cyclopropa[3,4]cyclopenta[1,2-c]pyrazol-1-yl)acetamide (595)

The title compound was prepared according to the method presented in the synthesis of 61F substituting 122E for 61C to provide the desired compound (18 mg, 17%): $^1$H NMR (400 MHz, cd$_3$od) δ 8.47 (d, 1H), 7.77 (s, 1H), 7.58 (s, 1H), 7.41 (d, 1H), 7.32 (d, 1H), 7.19 (dd, 1H), 6.44 (d, 1H), 6.38 (d, 1H), 6.01 (d, 2H), 5.15-5.02 (m, 1H), 4.49-4.41 (m, 2H), 2.82 (d, 3H), 2.55 (d, 1H), 2.41 (dd, 1H), 1.82 (s, 2H), 0.83 (d, 2H); MS (m/z) 579.4 [M+H]$^+$.

Example 596

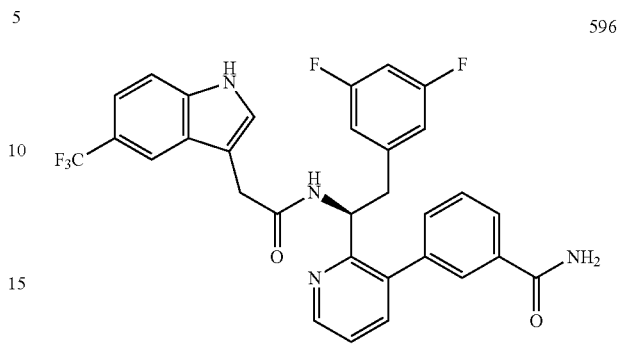

Synthesis of (S)-3-(2-(2-(3,5-difluorophenyl)-1-(2-(5-(trifluoromethyl)-1H-indol-3-yl)acetamido)ethyl)pyridin-3-yl)benzamide (596)

The title compound was prepared according to the method presented in the synthesis of 50D utilizing 50C and 54F to provide 23 mg of the desired compound in a 35% yield: $^1$H NMR (400 MHz, dmso) δ 11.24 (s, 1H), 8.69 (d, 1H), 8.63 (dd, 1H), 7.93 (s, 1H), 7.86 (d, 1H), 7.81 (s, 1H), 7.71 (s, 1H), 7.60 (dd, 1H), 7.48-7.34 (m, 4H), 7.28 (d, 1H), 7.20 (s, 1H), 6.82 (t, 1H), 6.43 (d, 2H), 5.19 (dd, 2H), 3.53 (s, 2H), 2.94 (d, 2H); MS (m/z) 579.2 [M+H]$^+$.

Example 597

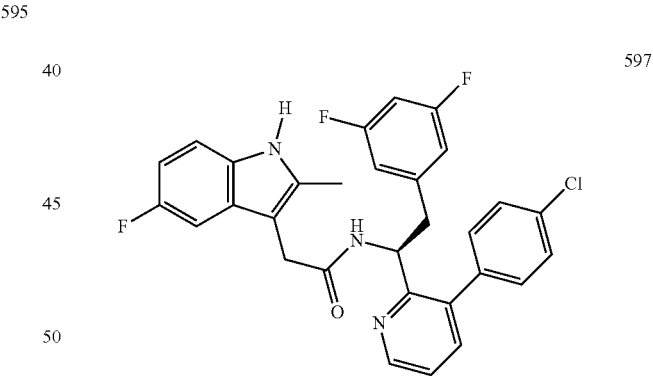

Synthesis of (S)—N-(1-(3-(4-chlorophenyl)pyridin-2-yl)-2-(3,5-difluorophenyl)ethyl)-2-(5-fluoro-2-methyl-1H-indol-3-yl)acetamide (597)

The title compound was prepared according to the method presented in the synthesis of 36F utilizing 36E and 517D to provide 13 mg of the desired compound in a 21% yield: $^1$H NMR (400 MHz, dmso) δ 10.76 (s, 1H), 8.63 (dd, 1H), 8.59 (d, 1H), 7.53 (dd, 1H), 7.44-7.32 (m, 3H), 7.23 (d, 2H), 7.11 (dd, 1H), 7.06 (dd, 1H), 6.91 (t, 1H), 6.71 (td, 1H), 6.42 (d, 2H), 5.11 (dd, 1H), 3.45-3.29 (m, 2H), 3.00-2.82 (m, 2H), 2.20 (s, 3H); MS (m/z) 534.6 [M+H]$^+$.

Example 599

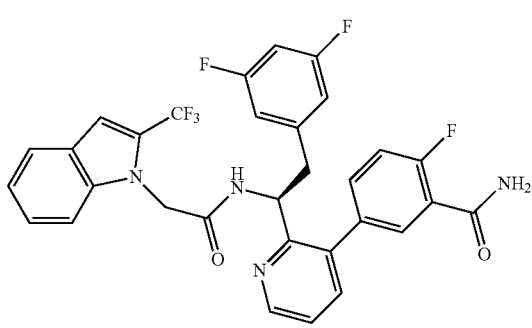

Synthesis of (S)-5-(2-(2-(3,5-difluorophenyl)-1-(2-(2-(trifluoromethyl)-1H-indol-1-yl)acetamido)ethyl)pyridin-3-yl)-2-fluorobenzamide (599)

The title compound was prepared according to the method presented in Example 56 substituting 2-(trifluoromethyl)-1H-indole for 1H-benzo[g]indole to provide the desired compound (14 mg, 34%): $^1$H NMR (400 MHz, dmso) δ 8.97 (d, 1H), 8.70 (d, 1H), 7.60 (dd, 4H), 7.49-7.36 (m, 3H), 7.30-7.18 (m, 3H), 7.10 (t, 1H), 7.01 (s, 1H), 6.94 (s, 1H), 6.58 (d, 2H), 5.13 (d, 1H), 4.88 (s, 2H), 3.00 (d, 2H); MS (m/z) 597.5 [M+H]$^+$.

Example 600

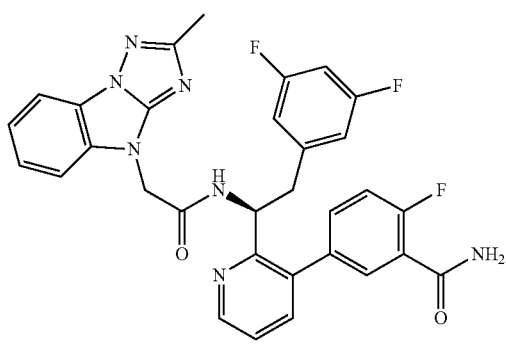

Synthesis of (S)-5-(2-(2-(3,5-difluorophenyl)-1-(2-(2-methyl-4H-benzo[4,5]imidazo[1,2-b][1,2,4]triazol-4-yl)acetamido)ethyl)pyridin-3-yl)-2-fluorobenzamide (600)

The title compound was prepared according to the method presented in the synthesis of 54G substituting 2-(2-methyl-4H-benzimidazo[1,2-b][1,2,4]triazol-4-yl)acetic acid. for 54F to provide the desired compound (12 mg, 25%): $^1$H NMR (400 MHz, dmso) δ 9.11 (d, 1H), 8.70 (d, 1H), 7.63 (dd, 4H), 7.49-7.35 (m, 3H), 7.29-7.18 (m, 4H), 6.94 (s, 1H), 6.58 (d, 2H), 5.15 (d, 1H), 4.82 (s, 2H), 3.03 (d, 2H), 2.32 (s, 3H); MS (m/z) 584.6 [M+H]$^+$.

Example 601

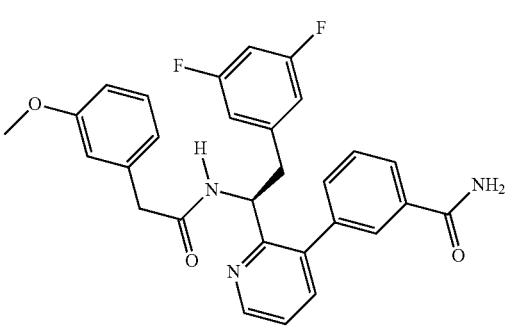

Synthesis of (S)-3-(2-(2-(3,5-difluorophenyl)-1-(2-(3-methoxyphenyl)acetamido)ethyl)pyridin-3-yl)benzamide (601)

The title compound was prepared according to the method presented in the synthesis of SOD utilizing 50C and 2-(3-methoxyphenyl)acetic acid to provide 18 mg of the desired compound in a 40% yield: $^1$H NMR (400 MHz, dmso) δ 8.71 (d, 1H), 8.66 (d, 1H), 7.94 (s, 1H), 7.88 (d, 1H), 7.75 (s, 1H), 7.62 (dd, 1H), 7.47 (t, 1H), 7.44-7.37 (m, 3H), 7.06 (t, 1H), 6.88 (t, 1H), 6.68 (d, 1H), 6.65 (s, 1H), 6.61 (d, 1H), 6.48 (d, 2H), 5.16 (d, 1H), 3.64 (s, 3H), 3.32 (dd, 2H), 2.95 (d, 2H); MS (m/z) 502.2 [M+H]$^+$.

Example 602

The following illustrate representative pharmaceutical dosage forms, containing a compound of formula I ('Compound X'), for therapeutic or prophylactic use in humans

| (i) Tablet 1 | mg/tablet |
|---|---|
| Compound X= | 100.0 |
| Lactose | 77.5 |
| Povidone | 15.0 |
| Croscarmellose sodium | 12.0 |
| Microcrystalline cellulose | 92.5 |
| Magnesium stearate | 3.0 |
| | 300.0 |

| (ii) Tablet 2 | mg/tablet |
|---|---|
| Compound X= | 20.0 |
| Microcrystalline cellulose | 410.0 |
| Starch | 50.0 |
| Sodium starch glycolate | 15.0 |
| Magnesium stearate | 5.0 |
| | 500.0 |

| (iii) Capsule | mg/capsule |
|---|---|
| Compound X= | 10.0 |
| Colloidal silicon dioxide | 1.5 |

-continued

| (iii) Capsule | mg/capsule |
|---|---|
| Lactose | 465.5 |
| Pregelatinized starch | 120.0 |
| Magnesium stearate | 3.0 |
| | 600.0 |

| (iv) Injection 1 (1 mg/ml) | mg/ml |
|---|---|
| Compound X = (free acid form) | 1.0 |
| Dibasic sodium phosphate | 12.0 |
| Monobasic sodium phosphate | 0.7 |
| Sodium chloride | 4.5 |
| 1.0N Sodium hydroxide solution (pH adjustment to 7.0-7.5) | q.s. |
| Water for injection | q.s. ad 1 mL |

| (v) Injection 2 (10 mg/ml) | mg/ml |
|---|---|
| Compound X = (free acid form) | 10.0 |
| Monobasic sodium phosphate | 0.3 |
| Dibasic sodium phosphate | 1.1 |
| Polyethylene glycol 400 | 200.0 |
| 1.0N Sodium hydroxide solution (pH adjustment to 7.0-7.5) | q.s. |
| Water for injection | q.s. ad 1 ml. |

| (vi) Aerosol | mg/can |
|---|---|
| Compound X= | 20.0 |
| Oleic acid | 10.0 |
| Trichloromonofluoromethane | 5,000.0 |
| Dichlorodifluoromethane | 10,000.0 |
| Dichlorotetrafluoroethane | 5,000.0 |

The above formulations may be obtained by conventional procedures well known in the pharmaceutical art.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A method for treating an HIV infection in a human, comprising administering a compound of formula I:

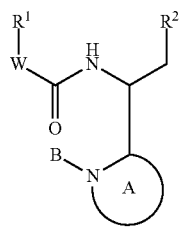

or a pharmaceutically acceptable salt thereof, to the human, wherein:

A is pyridinyl, pyrimidinyl, pyrazinyl or pyridazinyl, wherein any pyridinyl, pyrimidinyl, pyrazinyl, or pyridazinyl of A is substituted with one $Z^1$ group and optionally substituted with 1, 2, or 3 $Z^2$ groups;

B is absent; or B is —$O^-$ and the nitrogen to which the —$O^-$ group is attached is $N^+$;

W is —$CR^{3a}R^{3b}$—;

$R^1$ is a bicyclic-heteroaryl, tricyclic-heteroaryl, bicyclic-heterocycle or tricyclic-heterocycle, wherein any bicyclic-heteroaryl, tricyclic-heteroaryl, bicyclic-heterocycle or tricyclic-heterocycle of $R^1$ is optionally substituted with 1, 2, 3, 4, or 5 $Z^3$ groups;

$R^2$ is a 6-membered aryl, 5-membered heteroaryl or 6-membered heteroaryl, wherein any 6-membered aryl, 5-membered heteroaryl or 6-membered heteroaryl of $R^2$ is optionally substituted with 1, 2, or 3 $Z^4$ groups;

each $R^{3a}$ and $R^{3b}$ is independently selected from H, $(C_1$-$C_6)$alkyl, $(C_1$-$C_3)$haloalkyl, $(C_1$-$C_6)$heteroalkyl, heterocyclyl$(C_1$-$C_6)$alkyl-;

each $Z^1$ is independently selected from $(C_2$-$C_8)$alkyl, $(C_2$-$C_8)$alkenyl, $(C_2$-$C_8)$alkynyl, $(C_3$-$C_7)$carbocycle, $(C_6$-$C_{20})$aryl, heteroaryl, heterocycle and —$OR_{n1}$, wherein any $(C_3$-$C_7)$carbocycle, $(C_6$-$C_{20})$aryl, heteroaryl and heterocycle of $Z^1$ is optionally substituted with 1, 2, 3, 4, or 5 $Z^{1a}$ or $Z^{1b}$ groups and wherein any $(C_2$-$C_8)$alkyl, $(C_2$-$C_8)$alkenyl and $(C_2$-$C_8)$alkynyl of $Z^1$ is optionally substituted with 1, 2, 3, 4, or 5 $Z^{1a}$ groups;

each $Z^{1a}$ is independently selected from $(C_3$-$C_7)$carbocycle, $(C_6$-$C_{20})$aryl, heteroaryl, heterocycle, halogen, —CN, —$OR_{n2}$, —$OC(O)R_{p2}$, —$OC(O)NR_{q2}R_{r2}$, —$SR_{n2}$, —$S(O)R_{p2}$, —$S(O)_2OH$, —$S(O)_2R_{p2}$, —$S(O)_2 NR_{q2}R_{r2}$, —$NR_{q2}R_{r2}$, —$NR_{n2}COR_{p2}$, —$NR_{n2}CO_2R_{p2}$, —$NR_{n2}CONR_{q2}R_{r2}$, —$NR_{n2}S(O)_2R_{p2}$, —$NR_{n2}S(O)_2OR_{p2}$, —$NR_{p2}S(O)_2NR_{q2}R_{r2}$, $NO_2$, —$C(O)R_{n2}$, —$C(O)OR_{n2}$, —$C(O)NR_{q2}R_{r2}$ and —$S(O)_2 NR_{n2}COR_{p2}$, wherein any $(C_3$-$C_7)$carbocycle, $(C_6$-$C_{20})$aryl, heteroaryl and heterocycle of $Z^{1a}$ is optionally substituted with 1, 2, 3, 4, or 5 $Z^{1c}$ or $Z^{1d}$ groups;

each $Z^{1b}$ is independently selected from $(C_1$-$C_8)$alkyl, $(C_2$-$C_8)$alkenyl and $(C_2$-$C_8)$alkynyl, wherein any $(C_1$-$C_8)$alkyl, $(C_2$-$C_8)$alkenyl and $(C_2$-$C_8)$alkynyl of $Z^{1b}$ is optionally substituted with 1, 2, 3, 4, or 5 $Z^{1c}$ groups;

each $Z^{1c}$ is independently selected from $(C_3$-$C_7)$carbocycle, $(C_6$-$C_{20})$aryl, heteroaryl, heterocycle, halogen, —CN, —$OR_{n3}$, —$OC(O)R_{p3}$, $C(O)NR_{q3}R_{r3}$, —$SR_{n3}$, —$S(O)R_{p3}$, —$S(O)_2$ OH, —$S(O)_2R_{p3}$, —$S(O)_2 NR_{q3}R_{r3}$, —$NR_{q3}R_{r3}$, —$NR_{n3}COR_{p3}$, —$NR_{n3} CO_2R_{p3}$, —$NR_{n3} ONR_{q3}R_{r3}$, —$NR_{n3} S(O)_2R_{p3}$, —$NR_{n3} S(O)_2 OR_{p3}$, —$NR_{n3}S(O_2NR_{q3}R_{r3}$, $NO_2$, —$C(O)R_{n3}$, —$C(O)OR_{n3}$, —$C(O)NR_{q3}R_{r3}$, $(C_6$-$C_{20})$haloaryl, haloheteroaryl, haloheterocycle and $(C_1$-$C_8)$heteroalkyl;

each $Z^{1d}$ is independently selected from $(C_1$-$C_8)$alkyl, $(C_2$-$C_8)$alkenyl, $(C_2$-$C_8)$alkynyl and $(C_1$-$C_8)$haloalkyl;

each $R_{n1}$ is independently selected from $(C_1$-$C_8)$alkyl, $(C_2$-$C_8)$alkenyl, $(C_2$-$C_8)$alkynyl, $(C_3$-$C_7)$carbocycle, heterocycle, heteroaryl and $(C_6$-$C_{20})$aryl, wherein any $(C_3$-$C_7)$carbocycle, $(C_6$-$C_{20})$aryl, heteroaryl and heterocycle of $R_{n1}$ is optionally substituted with 1, 2, 3, 4, or 5 $Z^{1a}$ or $Z^{1b}$ groups, and wherein any $(C_1$-$C_8)$alkyl, $(C_2$-$C_8)$alkenyl and $(C_2$-$C_8)$alkynyl of $R_{n1}$ is optionally substituted with 1, 2, 3, 4, or 5 $Z^{1a}$ groups;

each $R_{n2}$ is independently selected from H, $(C_1$-$C_8)$alkyl, $(C_2$-$C_8)$alkenyl, $(C_2$-$C_8)$alkynyl, $(C_3$-$C_7)$carbocycle, heterocycle, heteroaryl and $(C_6$-$C_{20})$aryl, wherein any $(C_3$-$C_7)$carbocycle, $(C_6$-$C_{20})$aryl, heteroaryl and heterocycle of $R_{n2}$ is optionally substituted with 1, 2, 3, 4, or 5 $Z^{1c}$ or $Z^{1a}$ groups, and wherein any $(C_1-C_8)$alkyl, $(C_2-C_8)$alkenyl and $(C_2-C_8)$alkynyl of $R_{n2}$ is optionally substituted with 1, 2, 3, 4, or 5 $Z^{1c}$ groups;

each $R_{p2}$ is independently selected from $(C_1-C_8)$alkyl, $(C_2-C_8)$alkenyl, $(C_2-C_8)$alkynyl, $(C_3-C_7)$carbocycle, heterocycle, heteroaryl and $(C_6-C_{20})$aryl, wherein any $(C_3-C_7)$carbocycle, $(C_6-C_{20})$aryl, heteroaryl and heterocycle of $R_{p2}$ is optionally substituted with 1, 2, 3, 4, or 5 $Z^{1c}$ or $Z^{1a}$ groups, and wherein any $(C_1-C_8)$alkyl, $(C_2-C_8)$alkenyl and $(C_2-C_8)$alkynyl of $R_{p2}$ is optionally substituted with 1, 2, 3, 4, or 5 $Z^{1c}$ groups;

$R_{q2}$ and $R_{r2}$ are each independently selected from H, $(C_1-C_8)$alkyl, $(C_2-C_8)$alkenyl, $(C_2-C_8)$alkynyl, $(C_3-C_7)$ carbocycle, heterocycle, heteroaryl and $(C_6-C_{20})$aryl, wherein any $(C_3-C_7)$carbocycle, $(C_6-C_{20})$aryl, heteroaryl and heterocycle of $R_{q2}$ or $R_{r2}$ is optionally substituted with 1, 2, 3, 4, or 5 $Z^{1c}$ or $Z^{1d}$ groups, and wherein any $(C_1-C_8)$alkyl, $(C_2-C_8)$alkenyl and $(C_2-C_8)$alkynyl of $R_{q2}$ or $R_{r2}$ is optionally substituted with 1, 2, 3, 4, or 5 $Z^{1c}$ groups, or $R_{q2}$ and $R_{r2}$ together with the nitrogen to which they are attached form a 5, 6 or 7-membered heterocycle, wherein the 5, 6 or 7-membered heterocycle is optionally substituted with 1, 2, 3, 4 or 5 $Z^{1c}$ or $Z^{1d}$ groups;

each $R_{n3}$ is independently selected from H, $(C_1-C_8)$alkyl, $(C_2-C_8)$alkenyl, $(C_2-C_8)$alkynyl, $(C_3-C_7)$carbocycle, heterocycle, heteroaryl, $(C_6-C_{20})$aryl, $(C_6-C_{20})$haloaryl, haloheteroaryl, haloheterocycle, $(C_1-C_8)$haloalkyl and $(C_1-C_8)$heteroalkyl;

each $R_{p3}$ is independently selected from $(C_1-C_8)$alkyl, $(C_2-C_8)$alkenyl, $(C_2-C_8)$alkynyl, $(C_3-C_7)$carbocycle, heterocycle, heteroaryl, $(C_6-C_{20})$aryl, $(C_6-C_{20})$haloaryl, haloheteroaryl, haloheterocycle, $(C_1-C_8)$haloalkyl and $(C_1-C_8)$heteroalkyl;

$R_{q3}$ and $R_{r3}$ are each independently selected from H, $(C_1-C_8)$alkyl, $(C_2-C_8)$alkenyl, $(C_2-C_8)$alkynyl, $(C_3-C_7)$ carbocycle, heterocycle, heteroaryl, $(C_6-C_{20})$aryl, haloaryl, haloheteroaryl, haloheterocycle, $(C_1-C_8)$haloalkyl and $(C_1-C_8)$heteroalkyl, or $R_{q3}$ and $R_{r3}$ together with the nitrogen to which they are attached form a 5, 6 or 7-membered heterocycle;

each $Z^2$ is independently selected from $(C_1-C_6)$alkyl, $(C_1-C_6)$haloalkyl, $(C_3-C_7)$carbocycle, halogen, CN, OH and —O$(C_1-C_6)$alkyl;

each $Z^3$ is independently selected from $(C_1-C_8)$alkyl, $(C_2-C_8)$alkenyl, $(C_2-C_8)$alkynyl, $(C_3-C_7)$carbocycle, $(C_6-C_{20})$aryl, halogen, —CN, —OR$_{n4}$, —S(O)R$_{p4}$, —NR$_{n4}$CO$_2$R$_{p4}$, —NR$_{n4}$S(O)$_2$R$_{p4}$, —C(O)R$_{n4}$, —C(O)OR$_{n4}$, —C(O)NR$_{q4}$R$_{r4}$ and —B(OR$_{q4}$)(OR$_{r4}$) wherein any $(C_3-C_7)$carbocycle and $(C_6-C_{20})$aryl of $Z^3$ is optionally substituted with 1, 2, 3, 4, or 5 $Z^{3a}$ or $Z^{3b}$ groups, and wherein any $(C_1-C_8)$alkyl, $(C_2-C_8)$alkenyl and $(C_2-C_8)$alkynyl of $Z^3$ is optionally substituted with 1, 2, 3, 4, or 5 $Z^{3a}$ groups;

each $Z^{3a}$ is independently selected from $(C_3-C_7)$carbocycle, $(C_6-C_{20})$aryl, heteroaryl, heterocycle, halogen, —CN, —OR$_{n5}$, —OC(O)R$_{p5}$, —OC(O)NR$_{q5}$R$_{r5}$, —SR$_{n5}$, —S(O)R$_{p5}$, —S(O)$_2$OH, —S(O)$_2$R$_{p5}$, —S(O)$_2$ NR$_{q5}$R$_{r5}$, —NR$_{q5}$R$_{r5}$, —NR$_{n5}$COR$_{p5}$, —NR$_{n5}$CO$_2$R$_{p5}$, —NR$_{n5}$CONR$_{q5}$R$_{r5}$, —NR$_{n5}$S(O)$_2$ R$_{p5}$, —NR$_{n5}$S(O)$_2$OR$_{p5}$, —NR$_{n5}$S(O)$_2$NR$_{q5}$R$_{r5}$, NO$_2$, —C(O)R$_{n5}$, —C(O)OR$_{n5}$, and —C(O)NR$_{q5}$R$_{r5}$, wherein any $(C_3-C_7)$carbocycle, $(C_6-C_{20})$aryl, heteroaryl and heterocycle of $Z^{1a}$ is optionally substituted with 1, 2, 3, 4, or 5 $Z^{3c}$ or $Z^{3d}$ groups;

each $Z^{3b}$ is independently selected from $(C_1-C_8)$alkyl, $(C_2-C_8)$alkenyl and $(C_2-C_8)$alkynyl, wherein any $(C_1-C_8)$alkyl, $(C_2-C_8)$alkenyl and $(C_2-C_8)$alkynyl of $Z^{3b}$ is optionally substituted with 1, 2, 3, 4, or 5 $Z^{3c}$ groups;

each $Z^{3c}$ is independently selected from $(C_3-C_7)$carbocycle, $(C_6-C_{20})$aryl, heteroaryl, heterocycle, halogen, —CN, —OR$_{n6}$, —OC(O)R$_{p6}$, —OC(O)NR$_{q6}$R$_{r6}$, —SR$_{n6}$, —S(O)R$_{p6}$, —S(O)$_2$OH, —S(O)$_2$R$_{p6}$, —S(O)$_2$ NR$_{q6}$R$_{n5}$, —NR$_{q6}$R$_{r6}$, —NR$_{n6}$COR$_{p6}$, —NR$_{n6}$CO$_2$R$_{p6}$, —NR$_{n6}$CONR$_{q6}$R$_{r6}$, —NR$_{n6}$S(O)$_2$ R$_{p6}$, —NR$_{n6}$S(O)$_2$OR$_{p6}$, —NR$_{n6}$S(O)$_2$ NR$_{q6}$R$_{r6}$, NO$_2$, —C(O)R$_{n6}$, —C(O)OR$_{n6}$, —C(O)NR$_{q6}$R$_{r6}$, $(C_6-C_{20})$ haloaryl, haloheteroaryl, haloheterocycle and $(C_1-C_8)$ heteroalkyl;

each $Z^{3d}$ is independently selected from $(C_1-C_8)$alkyl, $(C_2-C_8)$alkenyl, $(C_2-C_8)$alkynyl, and $(C_1-C_8)$haloalkyl;

each $R_{n4}$ is independently selected from H, $(C_1-C_8)$alkyl, $(C_2-C_8)$alkenyl, $(C_2-C_8)$alkynyl, $(C_3-C_7)$carbocycle, heterocycle, heteroaryl and $(C_6-C_{20})$aryl, wherein any $(C_3-C_7)$carbocycle, $(C_6-C_{20})$aryl, heteroaryl and heterocycle of $R_{n4}$ is optionally substituted with 1, 2, 3, 4, or 5 $Z^{3a}$ or $Z^{3b}$ groups, and wherein any $(C_1-C_8)$alkyl, $(C_2-C_8)$alkenyl and $(C_2-C_8)$alkynyl of $R_{n4}$ is optionally substituted with 1, 2, 3, 4, or 5 $Z^{3a}$ groups;

each $R_{p4}$ is independently selected from $(C_1-C_8)$alkyl, $(C_2-C_8)$alkenyl, $(C_2-C_8)$alkynyl, $(C_3-C_7)$carbocycle, heterocycle, heteroaryl and $(C_6-C_{20})$aryl, wherein any $(C_3-C_7)$carbocycle, $(C_6-C_{20})$aryl, heteroaryl, or heterocycle of $R_{p4}$ is optionally substituted with 1, 2, 3, 4, or 5 $Z^{3a}$ or $Z^{3b}$ groups, and wherein any $(C_1-C_8)$alkyl, $(C_2-C_8)$alkenyl or $(C_2-C_8)$alkynyl of $R_{p4}$ is optionally substituted with 1, 2, 3, 4, or 5 $Z^{3a}$ groups;

$R_{q4}$ and $R_{r4}$ are each independently selected from H, $(C_1-C_8)$alkyl, $(C_2-C_8)$alkenyl, $(C_2-C_8)$alkynyl, $(C_3-C_7)$ carbocycle, heterocycle, heteroaryl and $(C_6-C_{20})$aryl, wherein any $(C_3-C_7)$carbocycle, $(C_6-C_{20})$aryl, heteroaryl and heterocycle of $R_{q4}$ or $R_{r4}$ is optionally substituted with one or more $Z^{3a}$ or $Z^{3b}$ groups, and wherein any $(C_1-C_8)$alkyl, $(C_2-C_8)$alkenyl and $(C_2-C_8)$ alkynyl of $R_{q4}$ or $R_{r4}$ is optionally substituted with 1, 2, 3, 4, or 5 $Z^{1a}$ groups, or $R_{q4}$ and $R_{r4}$ together with the nitrogen to which they are attached form a 5, 6 or 7-membered heterocycle, wherein the 5, 6 or 7-membered heterocycle is optionally substituted with 1, 2, 3, 4, or 5 $Z^{3a}$ or $Z^{3b}$ groups;

each $R_{n5}$ is independently selected from H, $(C_1-C_8)$alkyl, $(C_2-C_8)$alkenyl, $(C_2-C_8)$alkynyl, $(C_3-C_7)$carbocycle, heterocycle, heteroaryl and $(C_6-C_{20})$aryl, wherein any $(C_3-C_7)$carbocycle, $(C_6-C_{20})$aryl, heteroaryl and heterocycle of $R_{n5}$ is optionally substituted with 1, 2, 3, 4, or 5 $Z^{3c}$ or $Z^{3d}$ groups, and wherein any $(C_1-C_8)$alkyl, $(C_2-C_8)$alkenyl and $(C_2-C_8)$alkynyl of $R_{n5}$ is optionally substituted with 1, 2, 3, 4, or 5 $Z^{3a}$ groups;

each $R_{p5}$ is independently selected from $(C_1-C_8)$alkyl, $(C_2-C_8)$alkenyl, $(C_2-C_8)$alkynyl, $(C_3-C_7)$carbocycle, heterocycle, heteroaryl and $(C_6-C_{20})$aryl, wherein any $(C_3-C_7)$carbocycle, $(C_6-C_{20})$aryl, heteroaryl and heterocycle of $R_{p5}$ is optionally substituted with 1, 2, 3, 4, or 5 $Z^{3c}$ or $Z^{3d}$ groups, and wherein any $(C_1-C_8)$alkyl, $(C_2-C_8)$alkenyl and $(C_2-C_8)$alkynyl of $R_{p5}$ is optionally substituted with 1, 2, 3, 4, or 5 $Z^{3c}$ groups;

$R_{q5}$ and $R_{r5}$ are each independently selected from H, $(C_1-C_8)$alkyl, $(C_2-C_8)$alkenyl, $(C_2-C_8)$alkynyl, $(C_3-C_7)$ carbocycle, heterocycle, heteroaryl and $(C_6-C_{20})$aryl, wherein any $(C_3-C_7)$carbocycle, $(C_6-C_{20})$aryl, heteroaryl and heterocycle of $R_{q5}$ or $R_{r5}$ is optionally substituted with 1, 2, 3, 4, or 5 $Z^{3c}$ or $Z^{3d}$ groups, and wherein any $(C_1-C_8)$alkyl, $(C_2-C_8)$alkenyl and $(C_2-C_8)$ alkynyl of $R_{q5}$ or $R_{r5}$ is optionally substituted with 1, 2, 3, 4, or 5 $Z^{3c}$ groups, or $R_{q5}$ and $R_{r5}$ together with the nitrogen to which they are attached form a 5, 6 or 7-membered heterocycle, wherein the 5, 6 or 7-membered heterocycle is optionally substituted with 1, 2, 3, 4, or 5 $Z^{3c}$ or $Z^{3d}$ groups;

each $R_{n6}$ is independently selected from H, $(C_1-C_8)$alkyl, $(C_2-C_8)$alkenyl, $(C_2-C_8)$alkynyl, $(C_3-C_7)$carbocycle, heterocycle, heteroaryl, $(C_6-C_{20})$aryl, $(C_6-C_{20})$haloaryl, haloheteroaryl, haloheterocycle, $(C_1-C_8)$haloalkyl and $(C_1-C_8)$heteroalkyl;

each $R_{p6}$ is independently selected from $(C_1-C_8)$alkyl, $(C_2-C_8)$alkenyl, $(C_2-C_8)$alkynyl, $(C_3-C_7)$carbocycle, heterocycle, heteroaryl, $(C_6-C_{20})$aryl, $(C_6-C_{20})$haloaryl, haloheteroaryl, haloheterocycle, $(C_1-C_8)$haloalkyl and $(C_1-C_8)$heteroalkyl;

$R_{q6}$ and $R_{r6}$ are each independently selected from H, $(C_1-C_8)$alkyl, $(C_2-C_8)$alkenyl, $(C_2-C_8)$alkynyl, $(C_3-C_7)$carbocycle, heterocycle, heteroaryl, $(C_6-C_{20})$aryl, $(C_6-C_{20})$haloaryl, haloheteroaryl, haloheterocycle, $(C_1-C_8)$haloalkyl and $(C_1-C_8)$heteroalkyl, or $R_{q6}$ and $R_{r6}$ together with the nitrogen to which they are attached form a 5, 6 or 7-membered heterocycle;

each $Z^4$ is independently selected from $(C_3-C_7)$carbocycle, halogen, methyl and —CN;

each $Z^{4c}$ is independently selected from of $(C_3-C_7)$carbocycle, $(C_6-C_{20})$aryl, heteroaryl, heterocycle, halogen, —CN, —$OR_{n9}$, —$OC(O)R_{p9}$, —$OC(O)NR_{q9}R_{r9}$, —$SR_{n9}$, —$S(O)R_{p9}$, —$S(O)_2OH$, —$S(O)_2R_{p9}$, —$S(O)_2NR_{q9}R_{r9}$, —$NR_{q9}R_{r9}$, —$NR_{n9}COR_{p9}$, —$NR_{n9}CO_2R_{p9}$, —$NR_{n9}CONR_{q9}R_{r9}$, —$NR_{n9}S(O)_2R_{p9}$, —$NR_{n9}S(O)_2OR_{p9}$, —$NR_{n9}S(O)_2NR_{q9}R_{r9}$, $NO_2$, —$C(O)R_{n9}$, —$C(O)OR_{n9}$, —$C(O)NR_{q9}R_{r9}$, $(C_6-C_{20})$haloaryl, haloheteroaryl, haloheterocycle and $(C_1-C_8)$heteroalkyl;

each $Z^{4d}$ is independently selected from of $(C_1-C_8)$alkyl, $(C_2-C_8)$alkenyl, $(C_2-C_8)$alkynyl and $(C_1-C_8)$haloalkyl;

each $R_{n9}$ is independently selected from H, $(C_1-C_8)$alkyl, $(C_2-C_8)$alkenyl, $(C_2-C_8)$alkynyl, $(C_3-C_7)$carbocycle, heterocycle, heteroaryl, $(C_6-C_{20})$aryl, $(C_6-C_{20})$haloaryl, haloheteroaryl, haloheterocycle, $(C_1-C_8)$haloalkyl and $(C_1-C_8)$heteroalkyl;

each $R_{p9}$ is independently selected from $(C_1-C_8)$alkyl, $(C_2-C_8)$alkenyl, $(C_2-C_8)$alkynyl, $(C_3-C_7)$carbocycle, heterocycle, heteroaryl, $(C_6-C_{20})$aryl, $(C_6-C_{20})$haloaryl, haloheteroaryl, haloheterocycle, $(C_1-C_8)$haloalkyl and $(C_1-C_8)$heteroalkyl; and $R_{q9}$ and $R_{r9}$ are each independently selected from H, $(C_1-C_8)$alkyl, $(C_2-C_8)$alkenyl, $(C_2-C_8)$alkynyl, $(C_3-C_7)$carbocycle, heterocycle, heteroaryl, $(C_6-C_{20})$aryl, $(C_6-C_{20})$haloaryl, haloheteroaryl, haloheterocycle, $(C_1-C_8)$haloalkyl and $(C_1-C_8)$heteroalkyl; or $R_{q9}$ and $R_{r9}$ together with the nitrogen to which they are attached form a 5, 6 or 7-membered heterocycle.

2. The method of claim 1, wherein the compound of formula I is a compound of formula Icc:

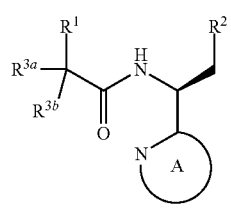

Icc or a pharmaceutically acceptable salt thereof.

3. The method of claim 1, wherein each $R^{3a}$ and $R^{3b}$ is H.

4. The method of claim 1, wherein A is selected from:

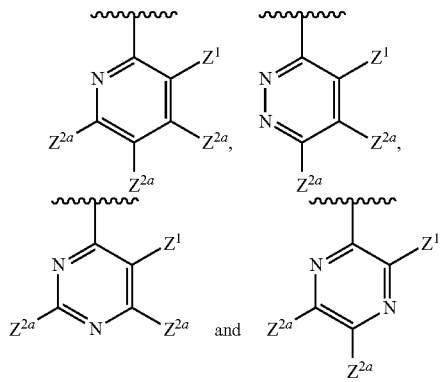

wherein each $Z^{2a}$ is independently selected from H and $Z^2$.

5. The method of claim 1, wherein $Z^1$ is selected from $(C_6-C_{20})$aryl, heteroaryl and heterocycle, wherein any $(C_6-C_{20})$aryl, heteroaryl, or heterocycle of $Z^1$ is optionally substituted with 1, 2, 3, 4, or 5 $Z^{1a}$ or $Z^{1b}$ groups.

6. The method of claim 1, wherein each $Z^{1a}$ is independently selected from $(C_6-C_{20})$aryl, heteroaryl, heterocycle, $(C_3-C_7)$carbocycle, halogen, —CN, —$OR_{n2}$, —$S(O)_2R_{p2}$, —$S(O)_2NR_{q2}R_{r2}$, —$NR_{q2}R_{r2}$, —$NR_{n2}COR_{p2}$, —$NR_{n2}CO_2R_{p2}$, —$NR_{n2}CONR_{q2}R_{r2}$, —$NR_{n2}S(O)_2R_{p2}$, —$C(O)R_{n2}$ and —$C(O)NR_{q2}R_{r2}$, wherein any $(C_6-C_{20})$aryl, heteroaryl, heterocycle and $(C_3-C_7)$carbocycle of $Z^{1a}$ is optionally substituted with 1, 2, 3, 4, or 5 $Z^{1c}$ or $Z^{1d}$ groups; and each $Z^{1b}$ is independently selected from $(C_1-C_8)$alkyl and $(C_2-C_8)$alkynyl, wherein any $(C_1-C_8)$alkyl and $(C_2-C_8)$alkynyl of $Z^{1b}$ is optionally substituted with 1, 2, 3, 4, or 5 $Z^{1c}$ groups.

7. The method of claim 1, wherein $R^2$ is a 6-membered aryl wherein the 6-membered aryl is optionally substituted with 1, 2, or 3 $Z^4$ groups.

8. The method of claim 1, wherein $R^2$ is selected from:

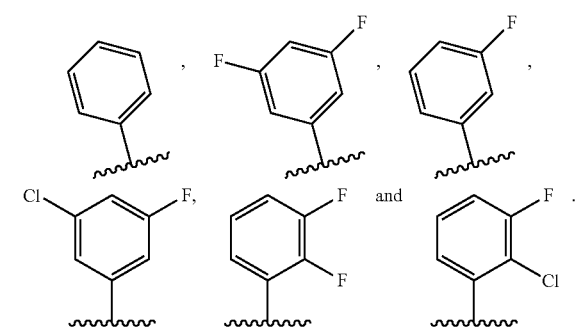

9. The method of claim 1, wherein $R^1$ is bicyclic-heteroaryl, tricyclic-heteroaryl, bicyclic-heterocycle or tricyclic-heterocycle, wherein any bicyclic-heteroaryl, tricyclic-heteroaryl, bicyclic-heterocycle or tricyclic-heterocycle of $R^1$ contains at least one partially unsaturated ring, and wherein any bicyclic-heteroaryl, tricyclic-heteroaryl, bicyclic-heterocycle or tricyclic-heterocycle of $R^1$ is optionally substituted with 1, 2, 3, 4, or 5 $Z^3$ groups.

10. The method of claim 1, wherein each $Z^3$ is independently selected from methyl, trifluoromethyl, hydroxy, methoxy, benzyloxy, fluoro, —NHSO₂CH₃, 2-hydroxyprop-2yl, difluoromethyl and amino.
11. The method of claim 1, wherein the compound of formula I is selected from:
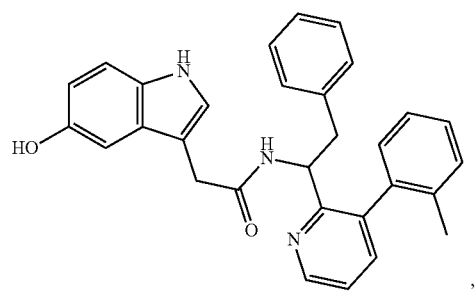
,
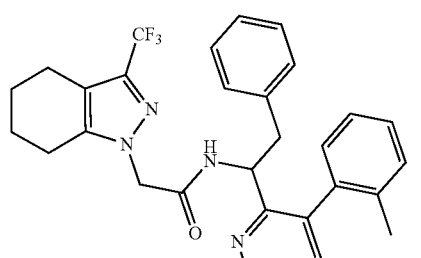
,
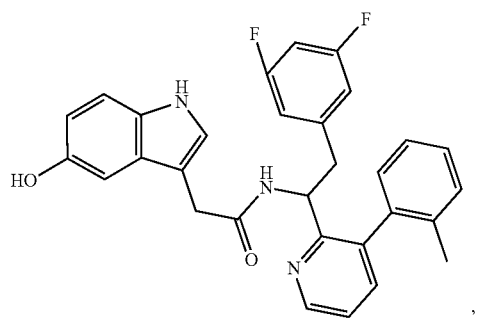
,
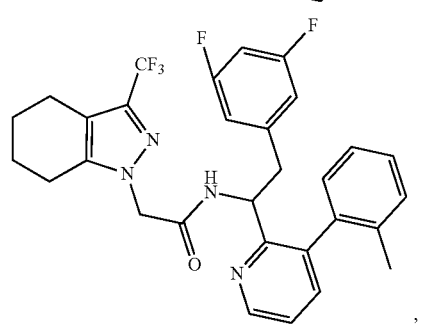
,
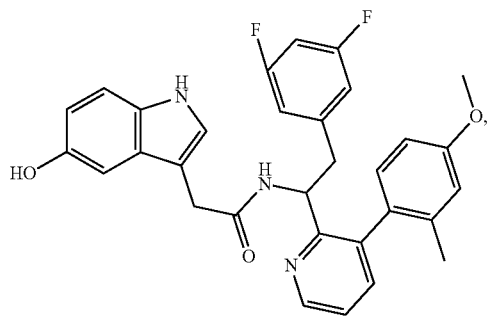
,
-continued
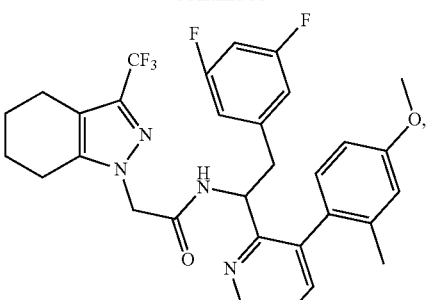
,
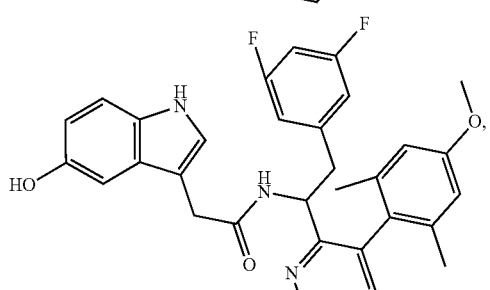
,
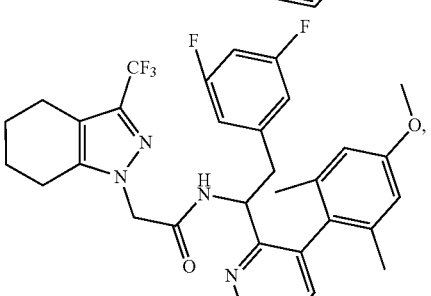
,
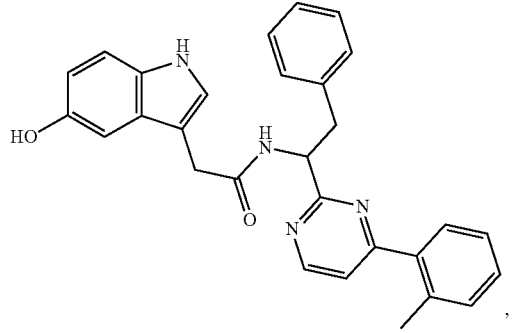
,
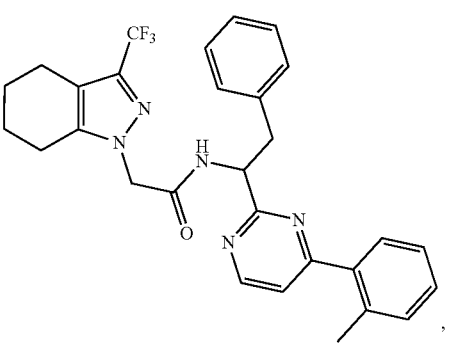
, 753
-continued
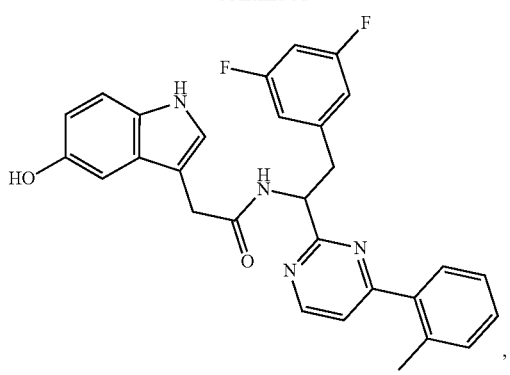
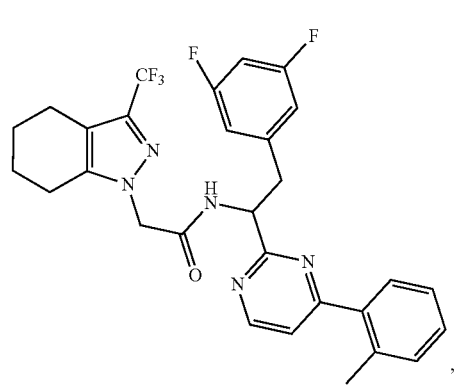
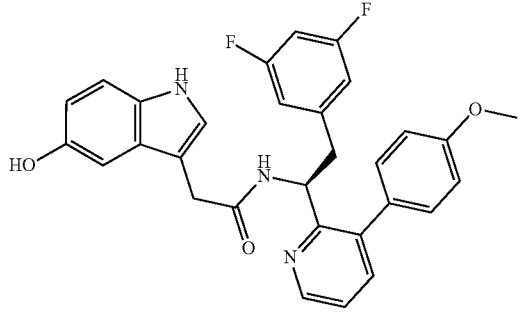
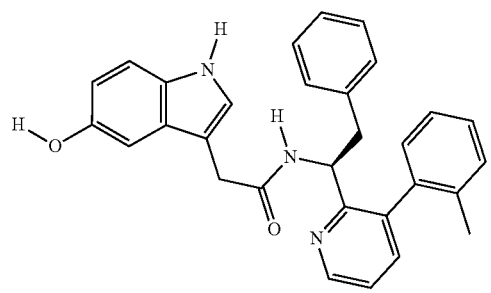
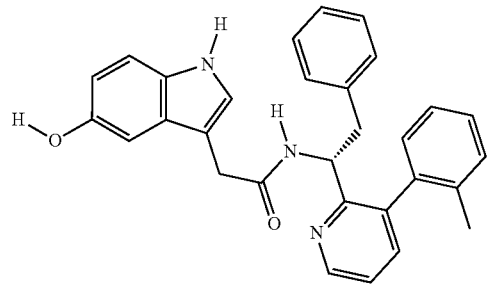
754
-continued
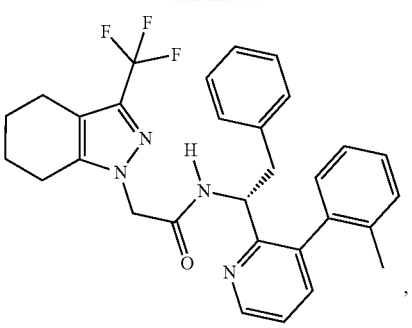
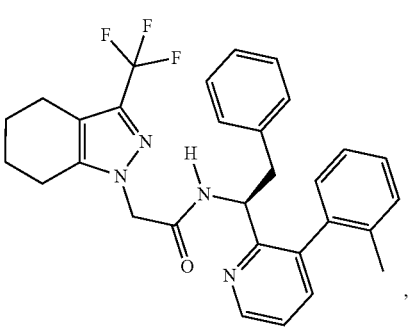
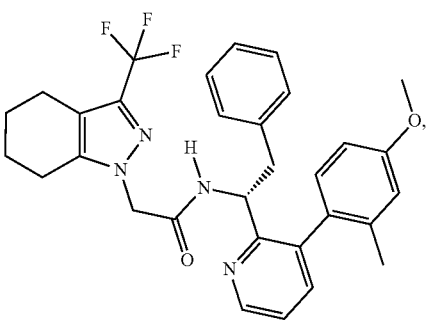
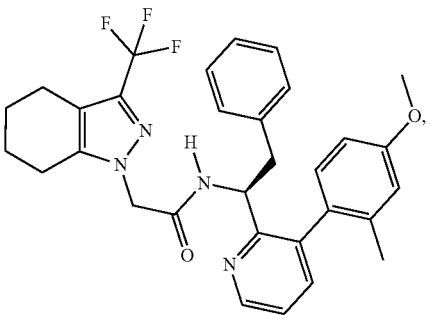
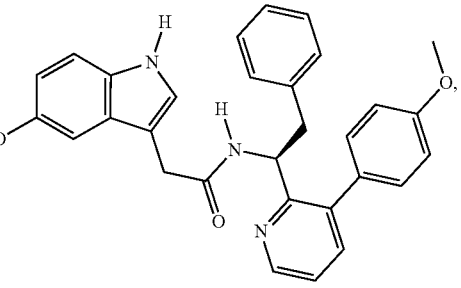

755
-continued
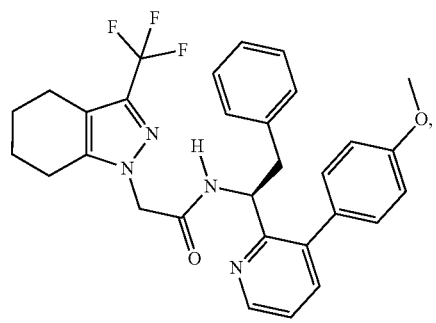
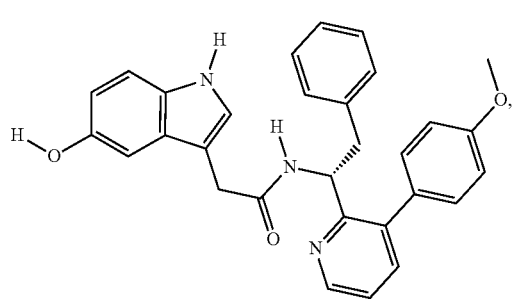
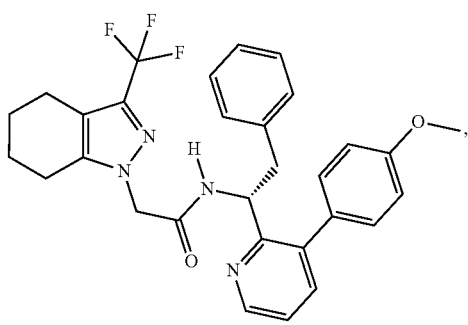
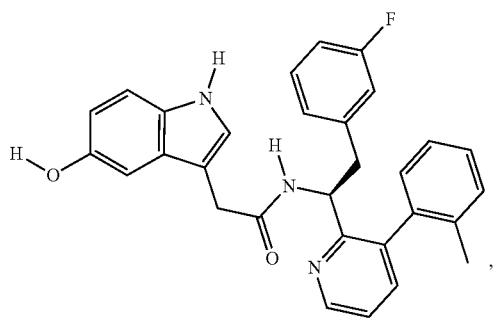
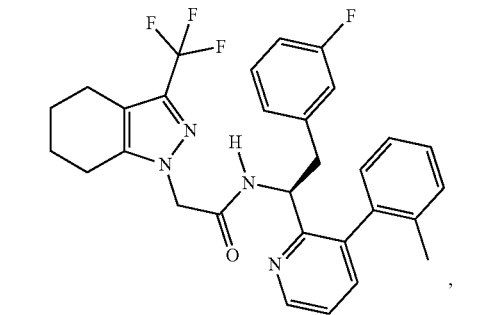
756
-continued
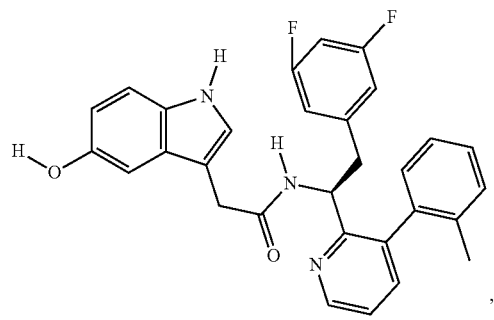
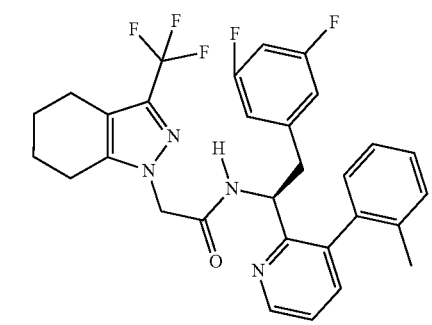
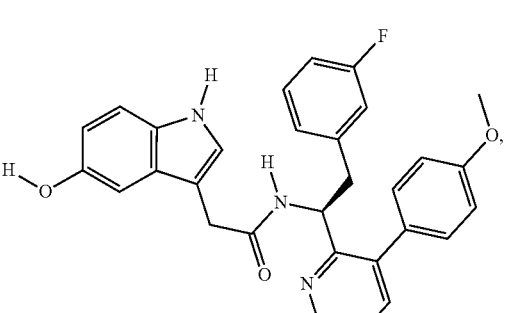
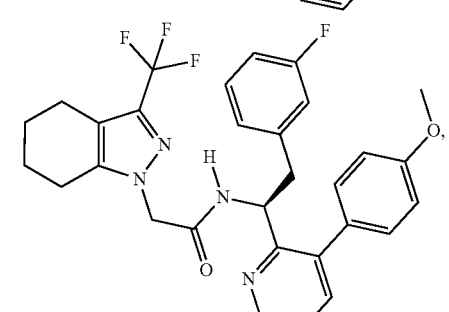
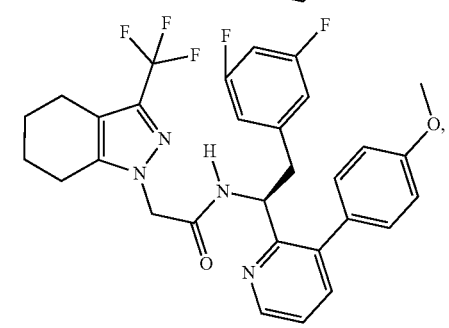

757
-continued
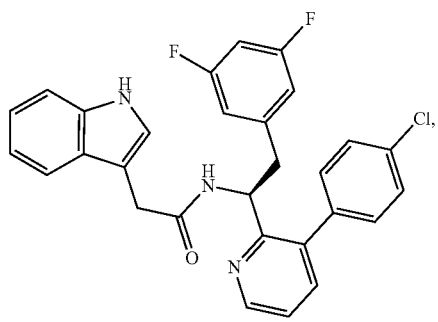
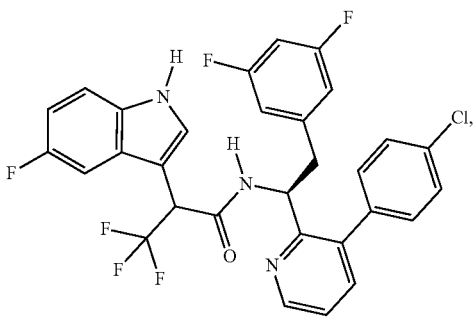
758
-continued
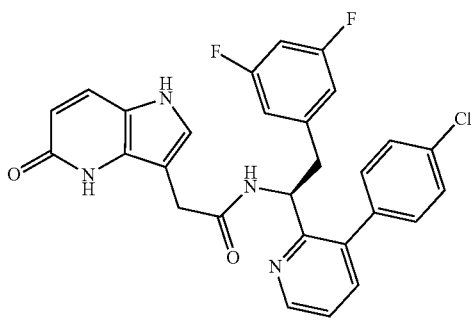
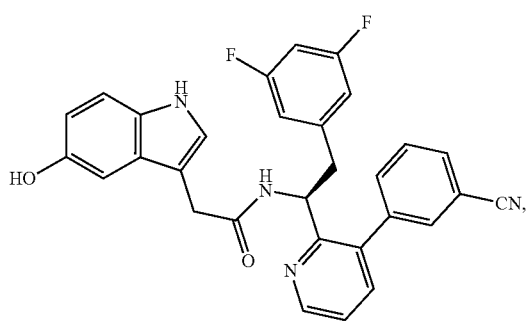
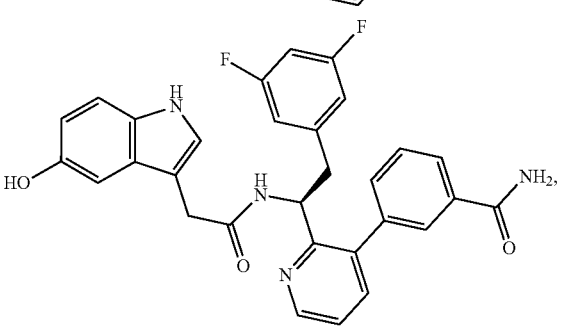
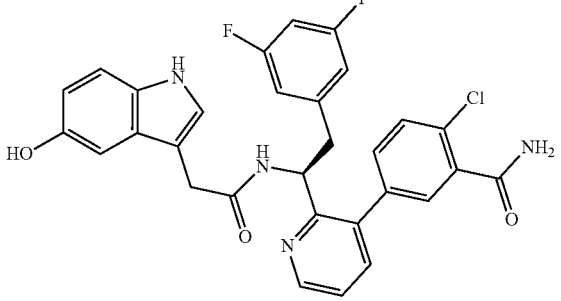

759
-continued
760
-continued
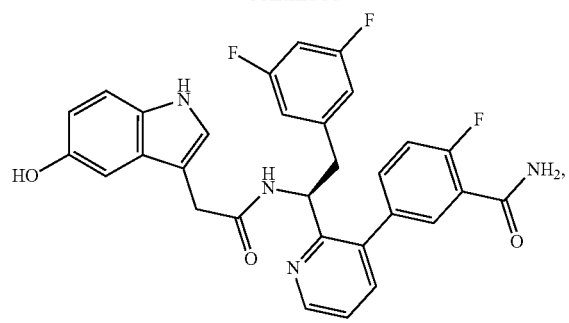
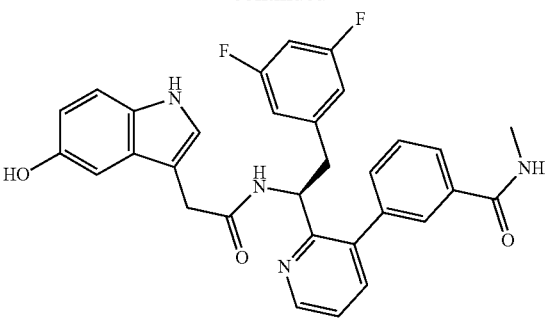
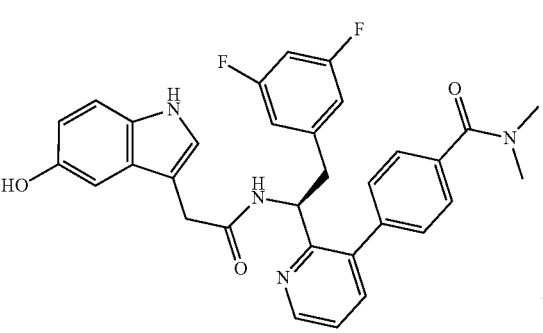
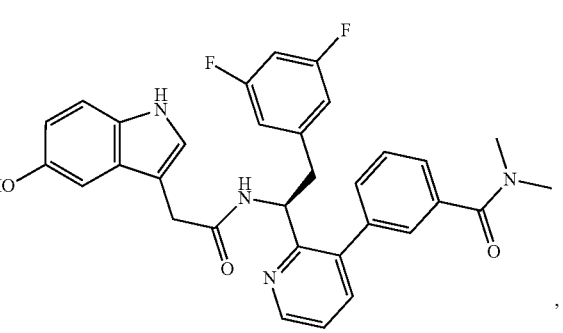
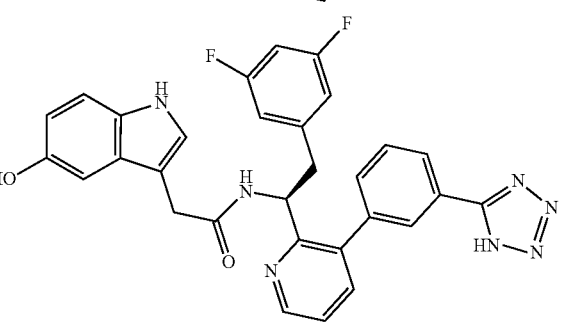
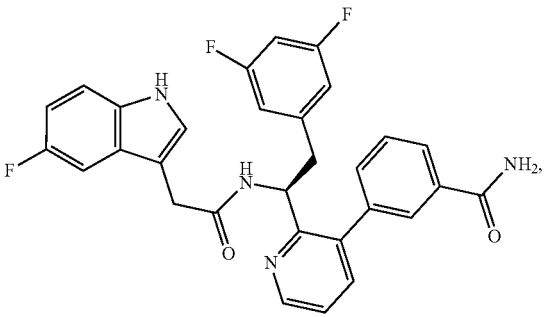

761
-continued
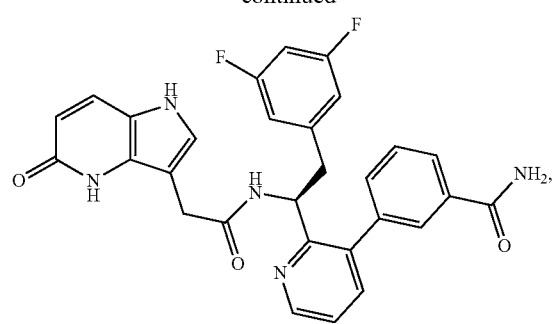
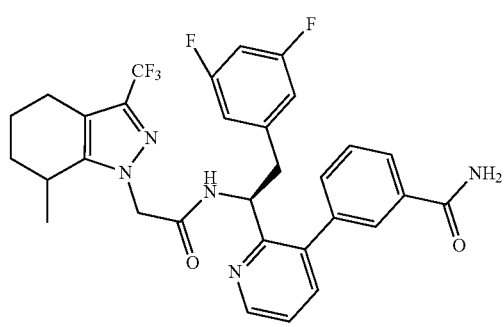
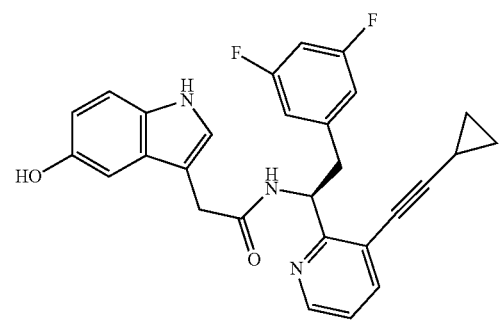
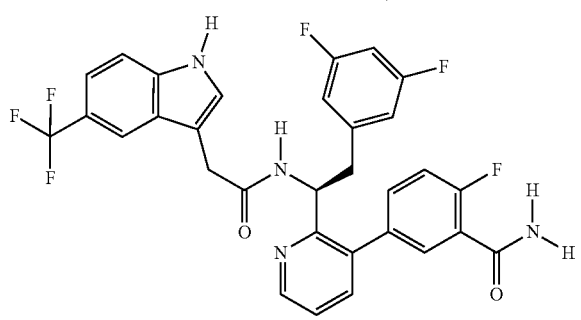
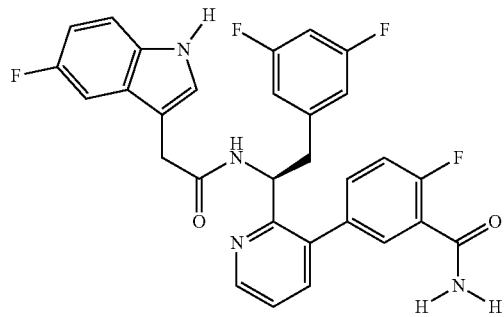
762
-continued
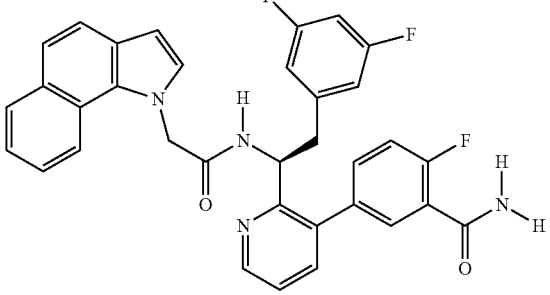
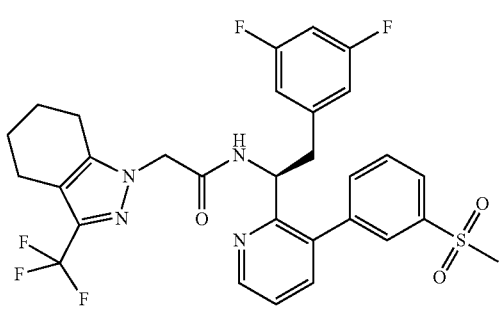
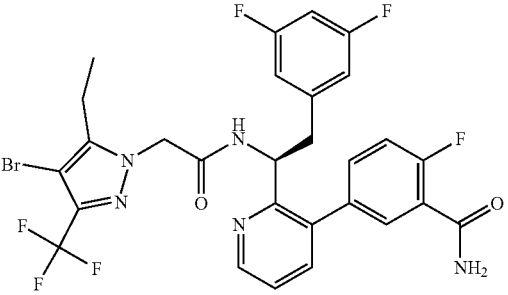
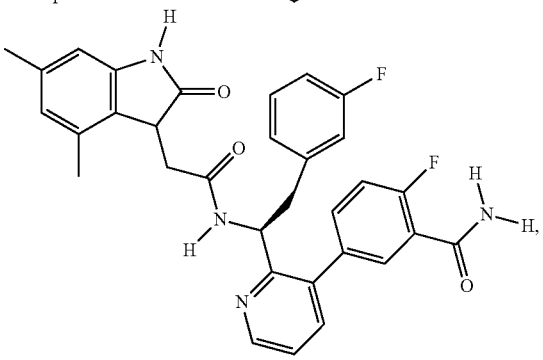
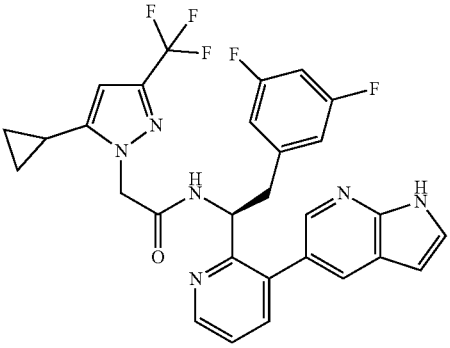

763
-continued
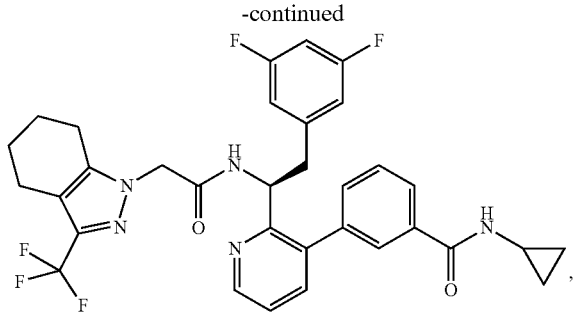
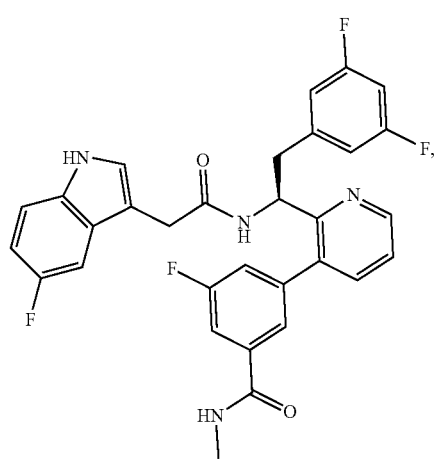
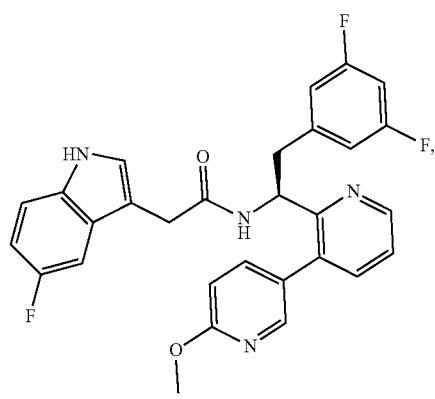
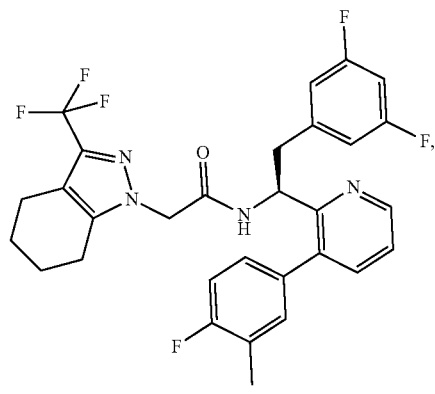
764
-continued
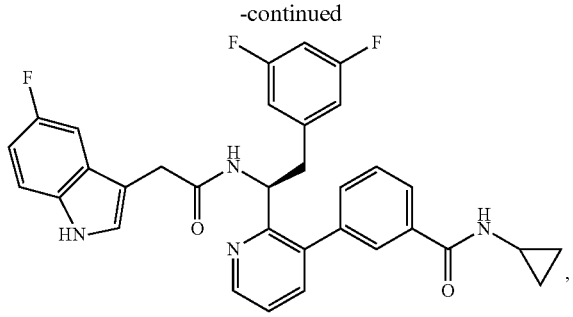
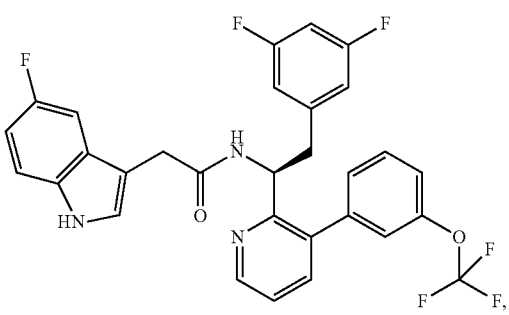
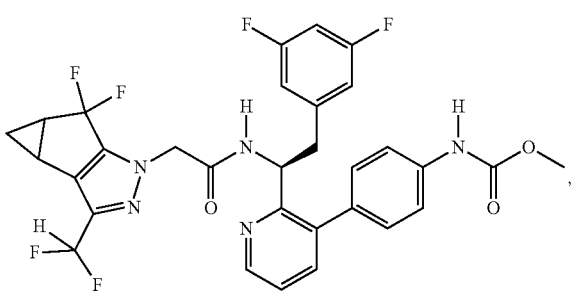
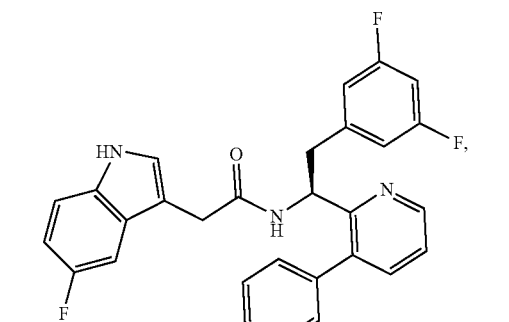
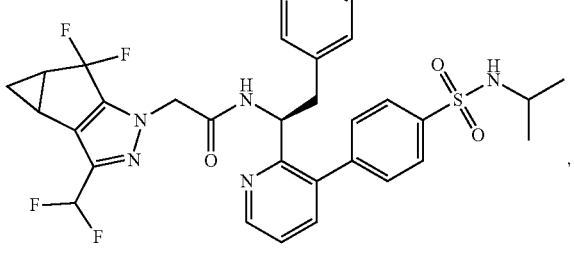

765
-continued
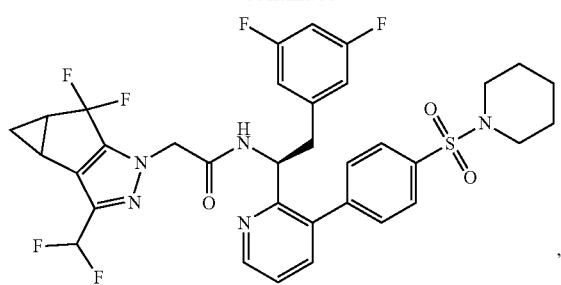
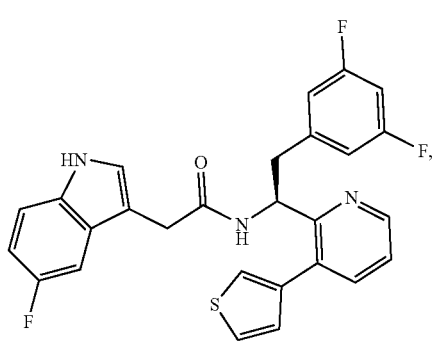
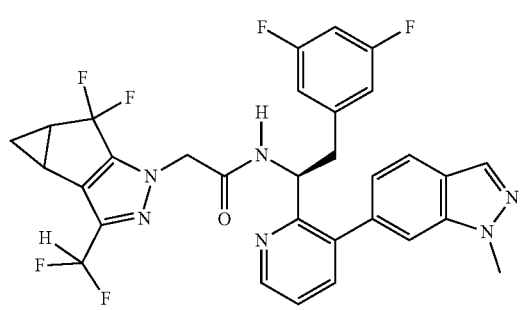
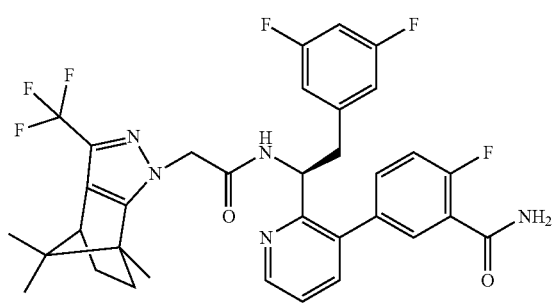
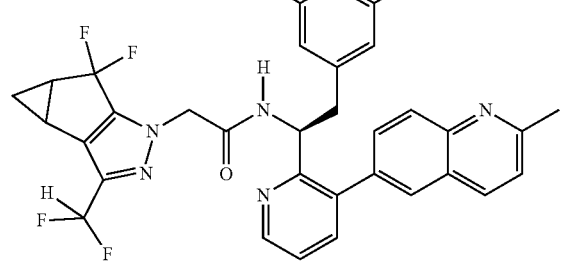
766
-continued
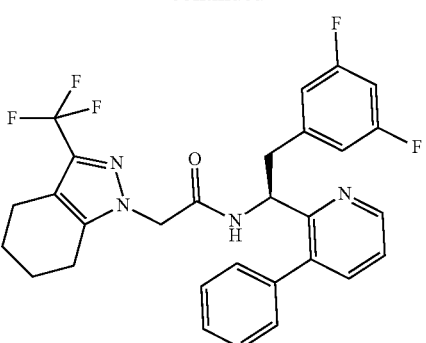
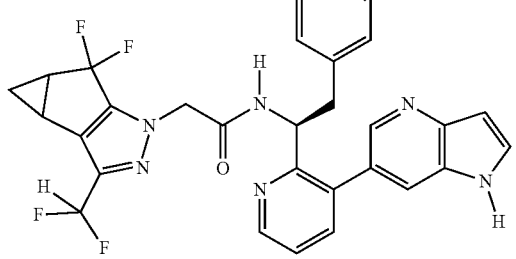
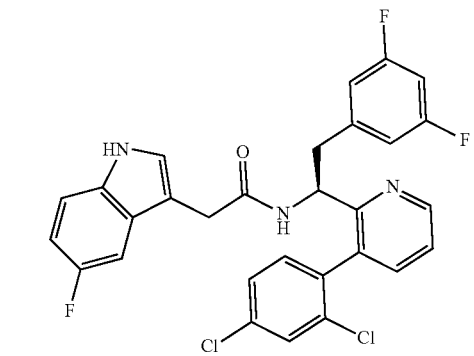
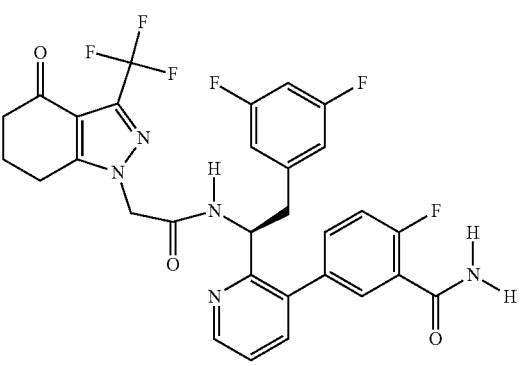
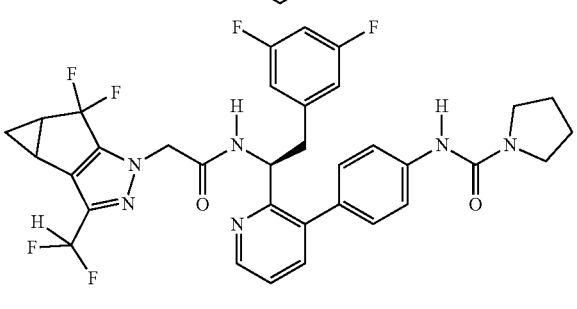

767
-continued
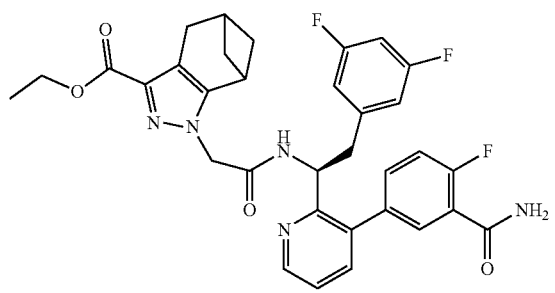
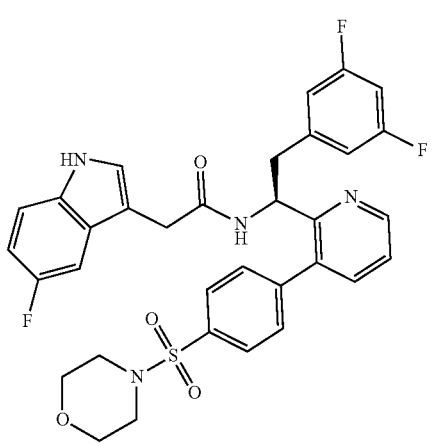
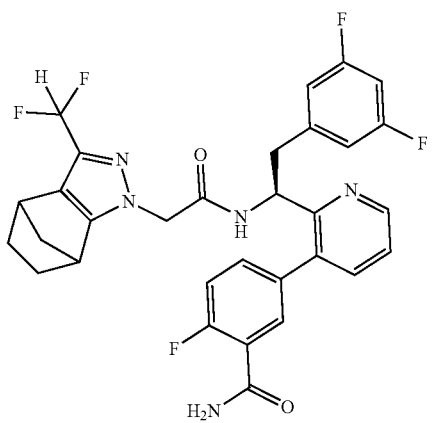
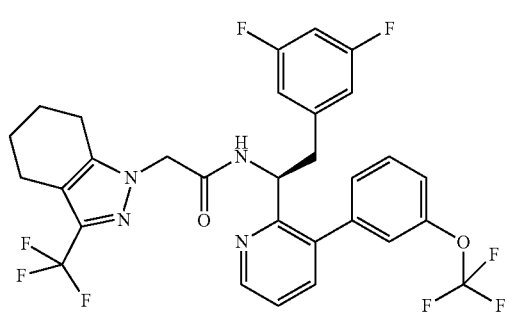
768
-continued
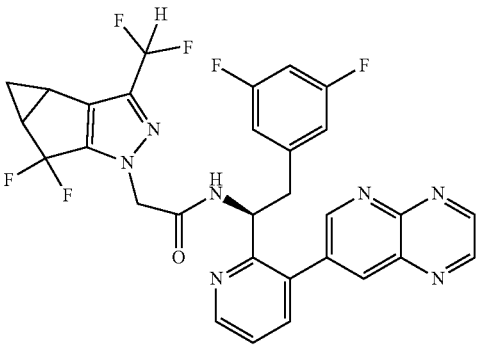
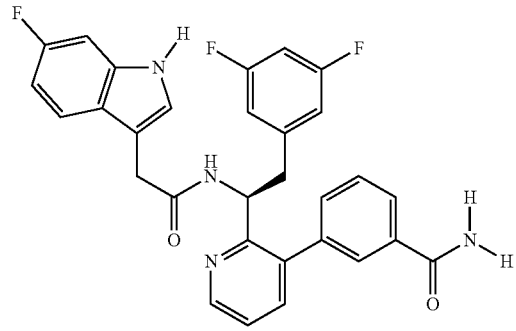
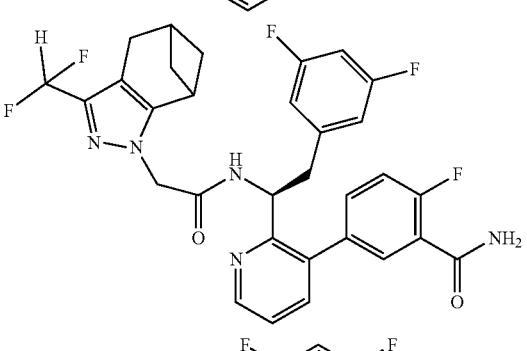
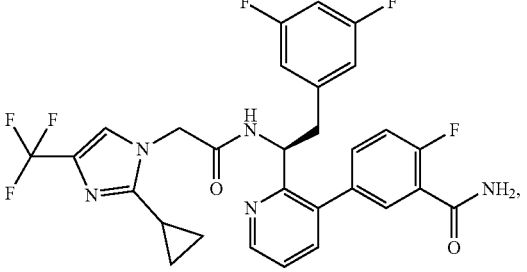
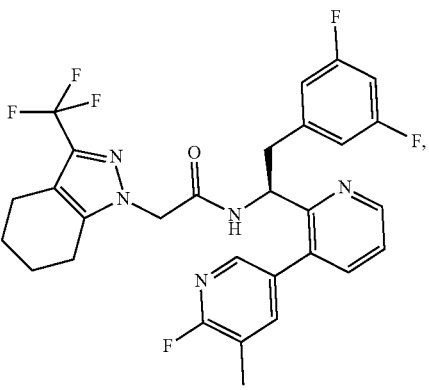

769
-continued
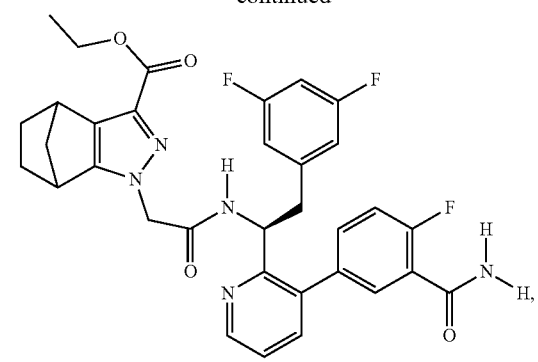
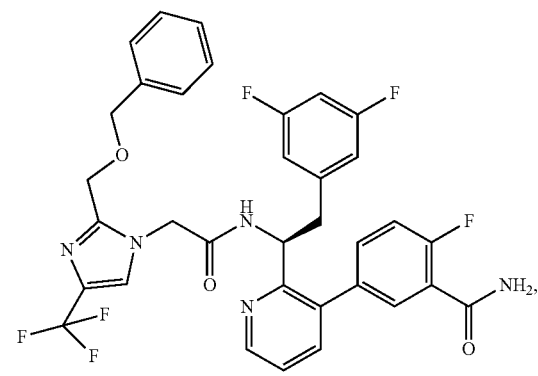
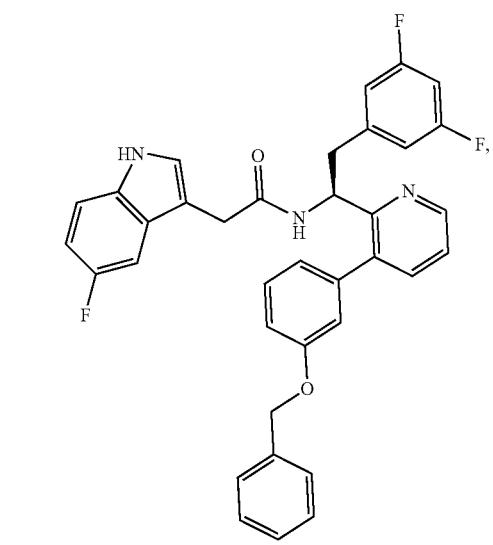
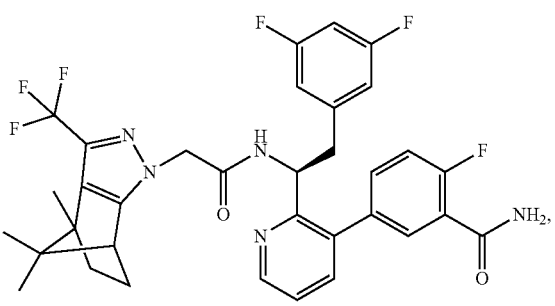
770
-continued
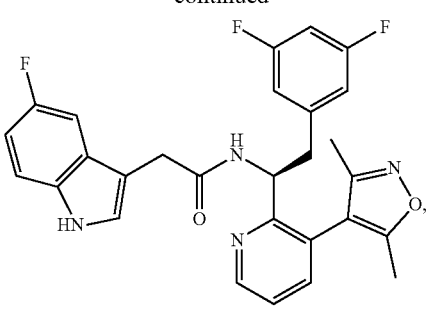
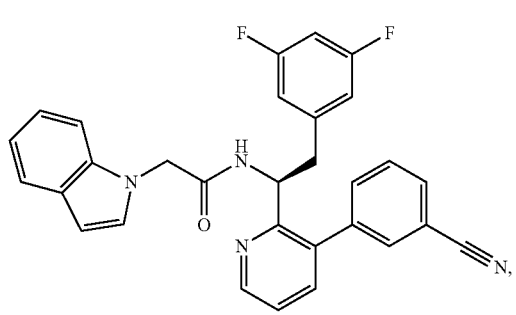
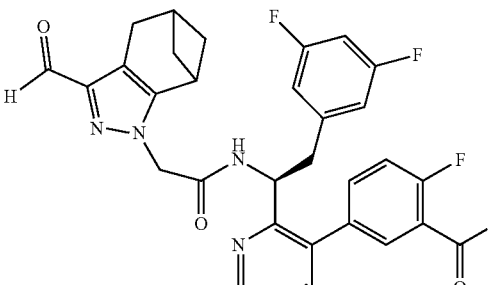
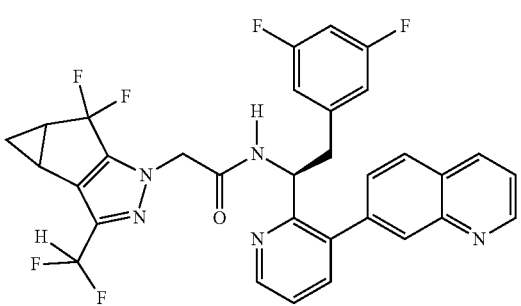
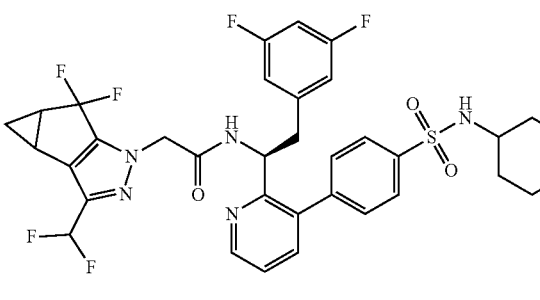

771
-continued
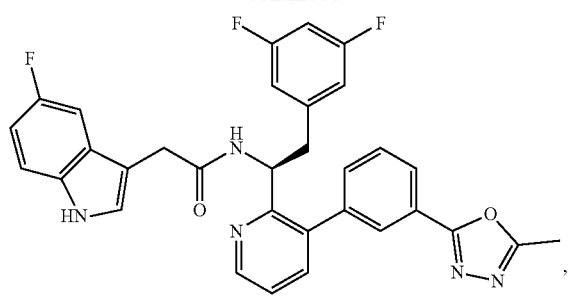
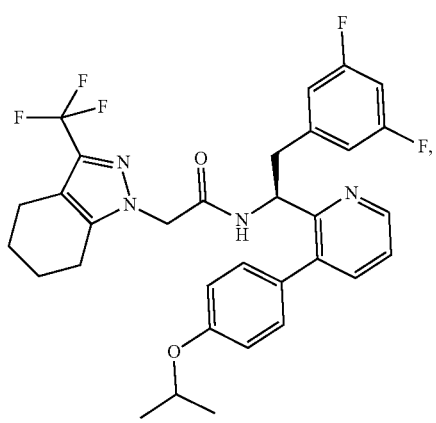
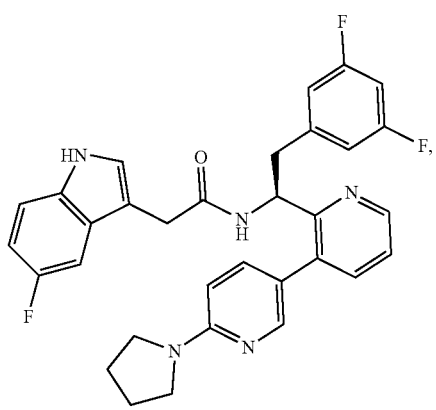
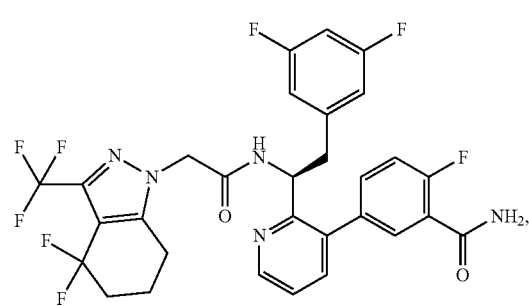
772
-continued
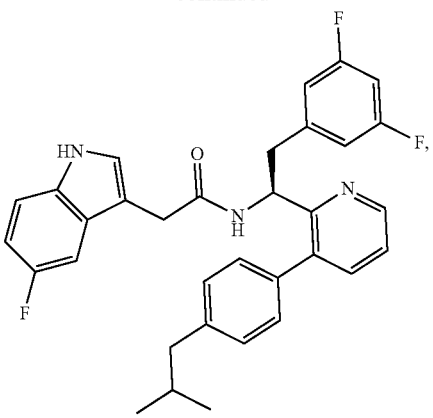
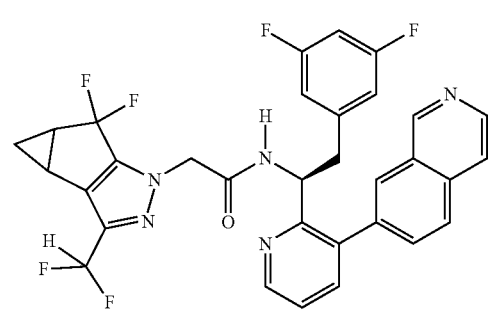
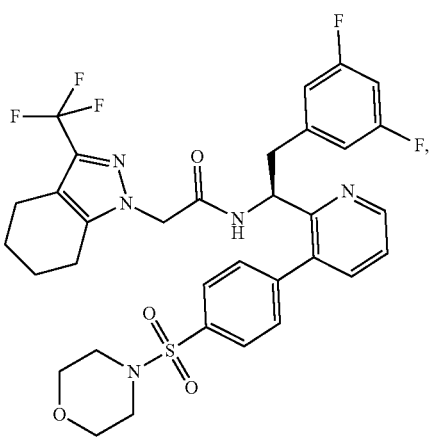
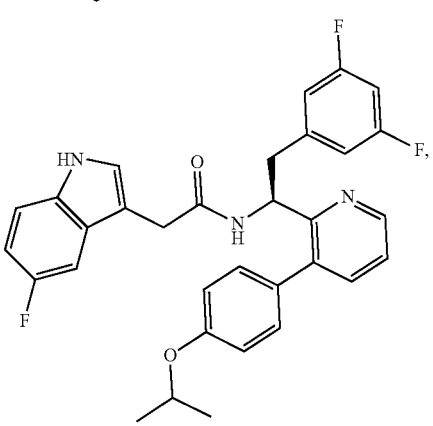

773
-continued
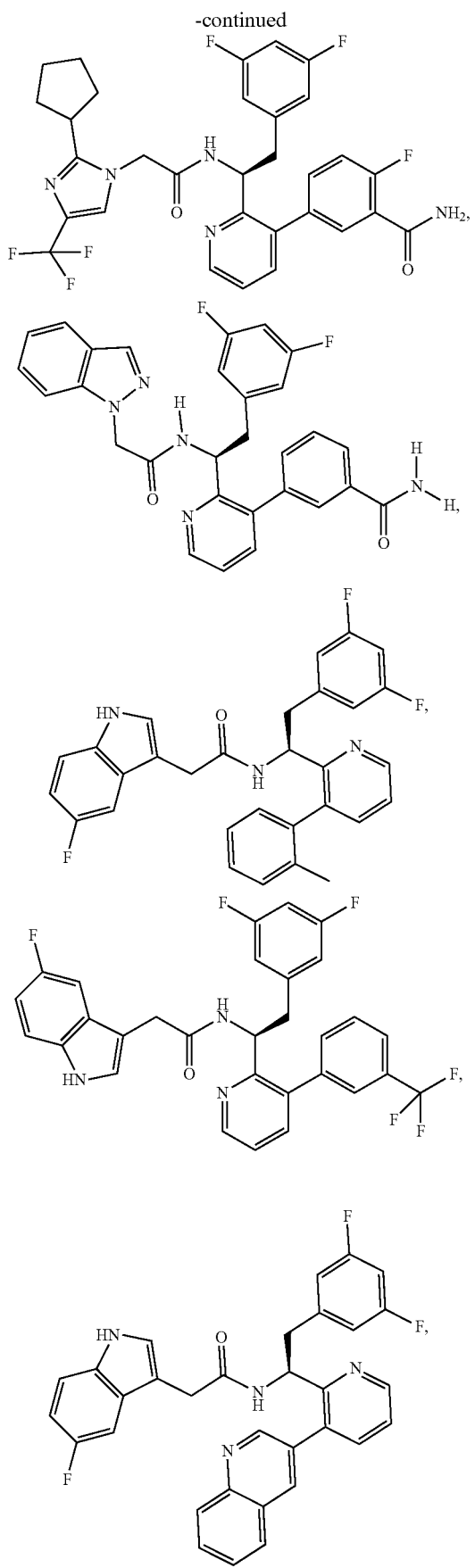
774
-continued
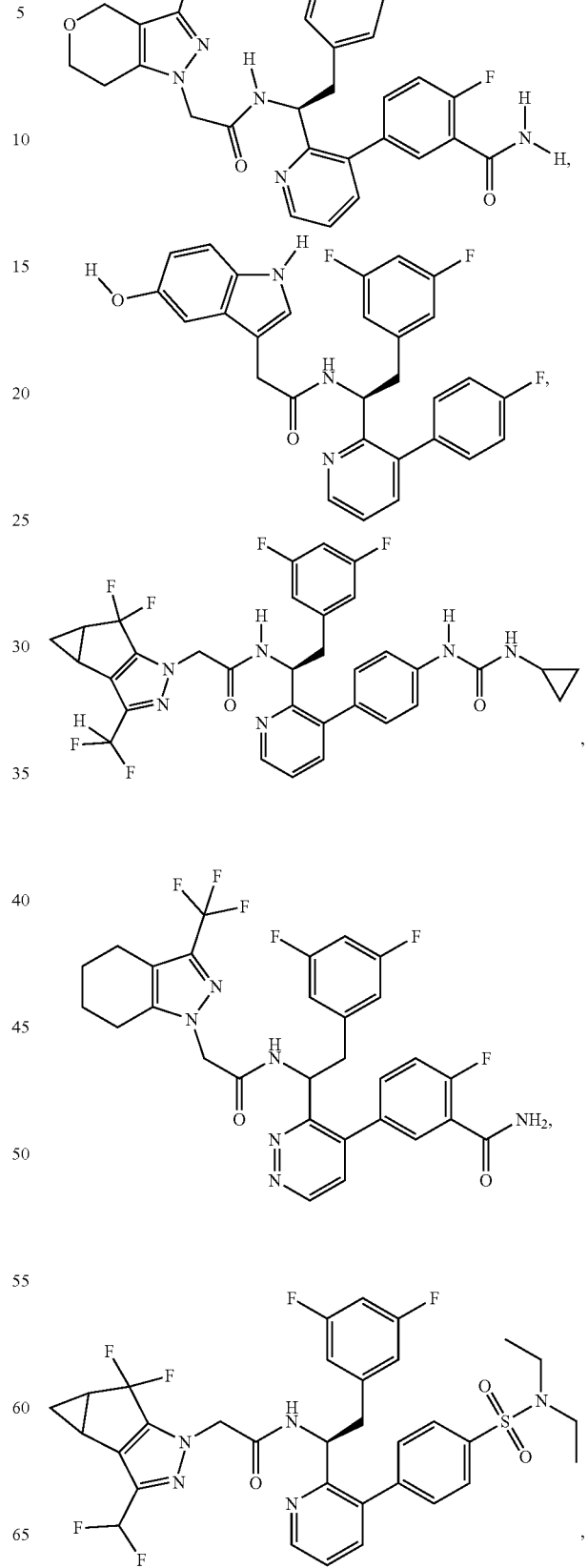

775
-continued
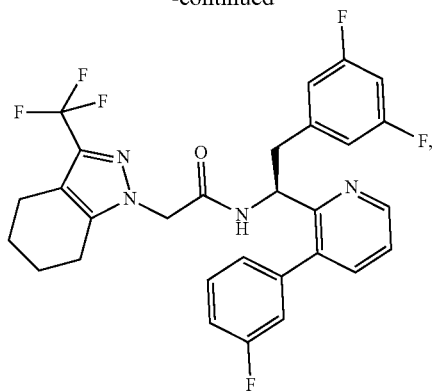
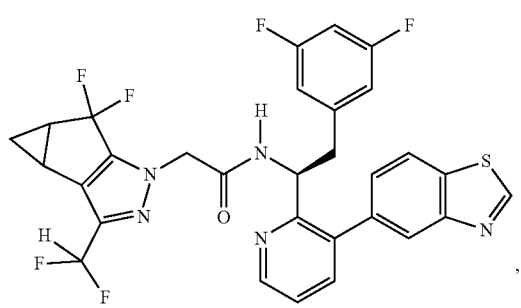
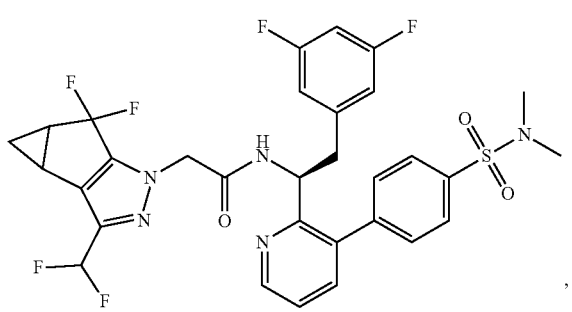
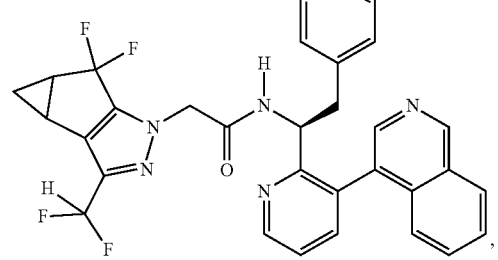
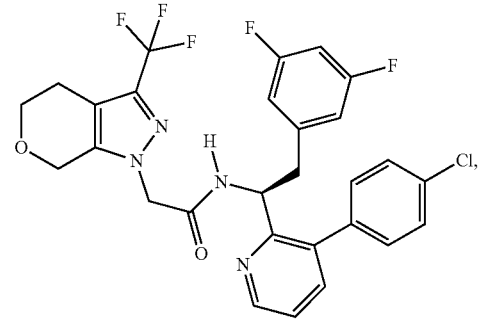
776
-continued
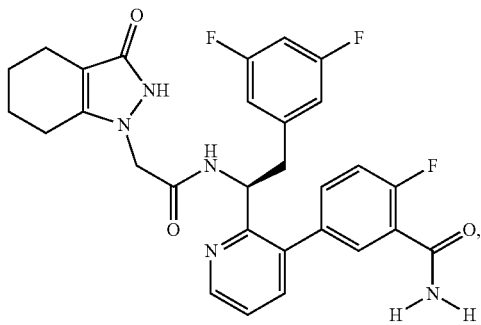
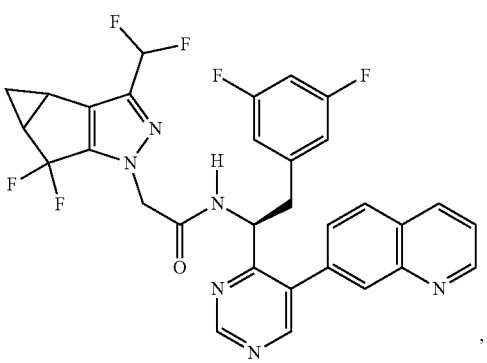
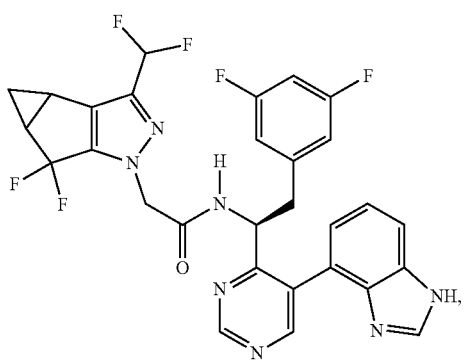
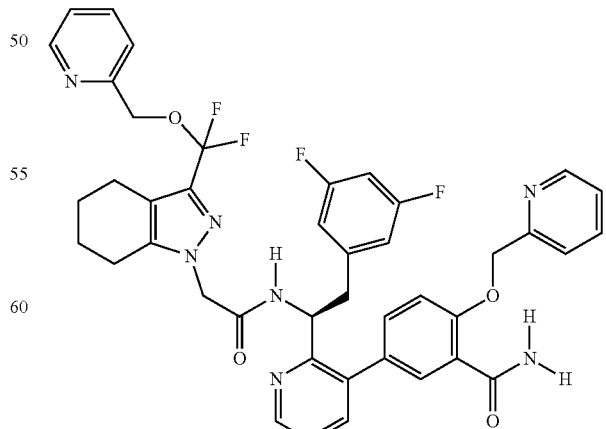

777 -continued
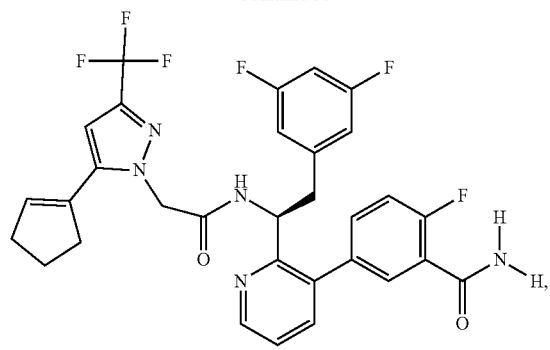
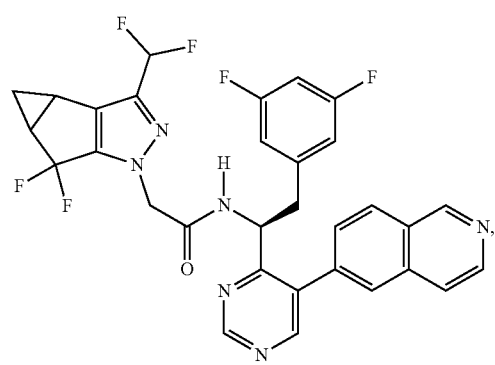
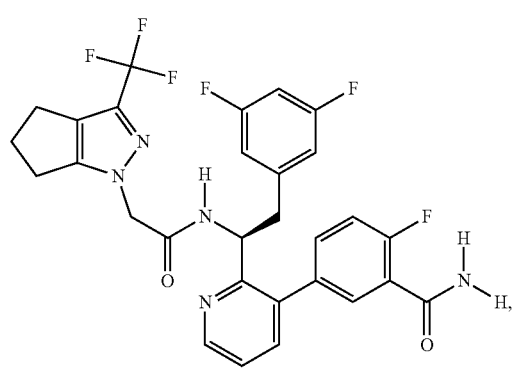
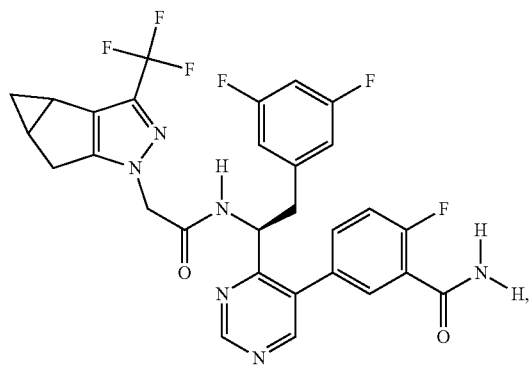
778 -continued
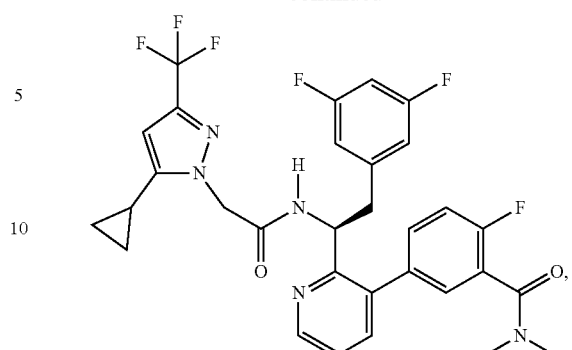
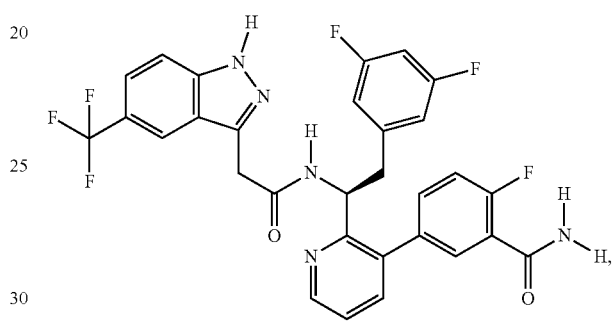
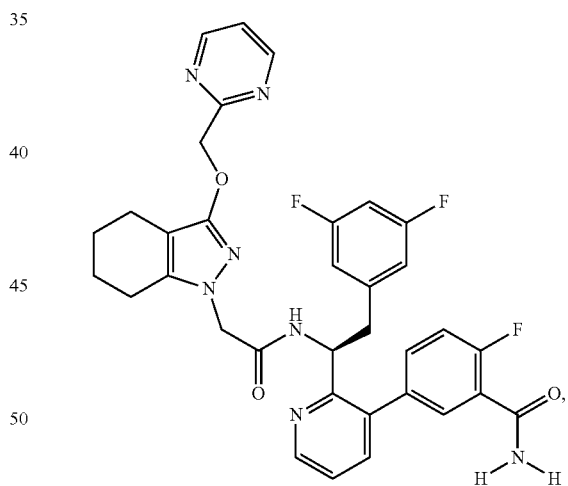
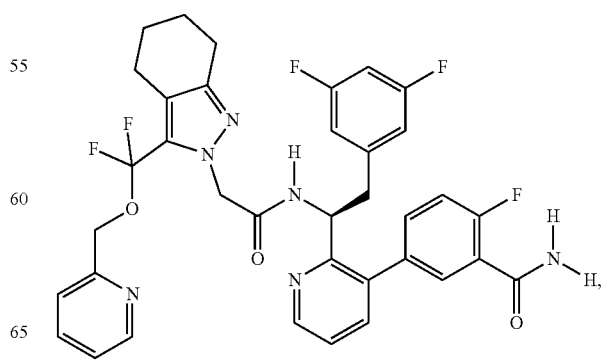

-continued
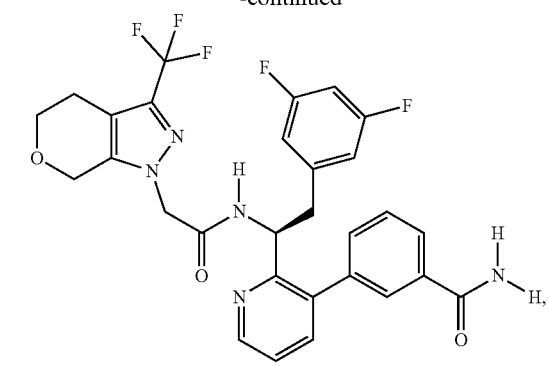
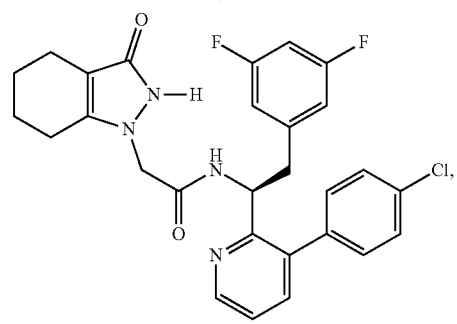
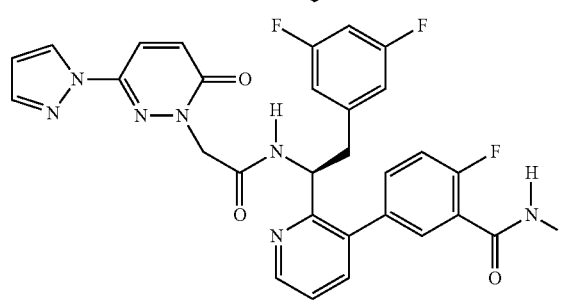
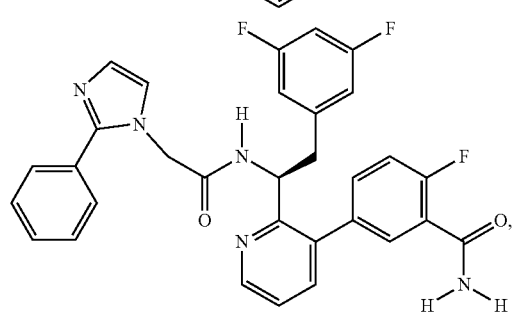
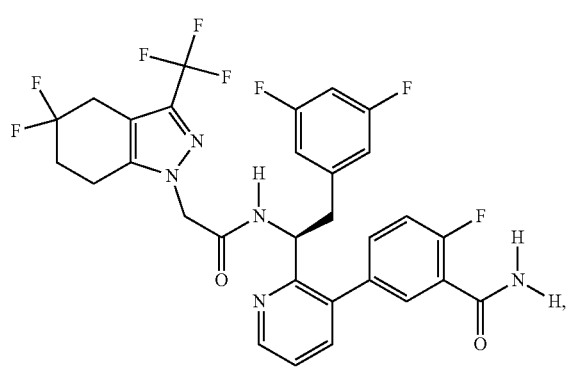
-continued
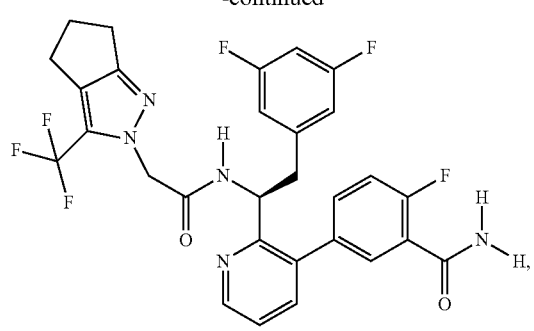
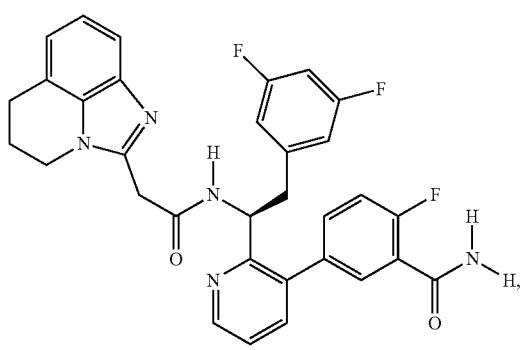
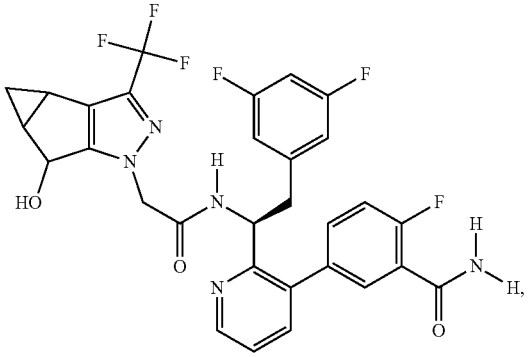
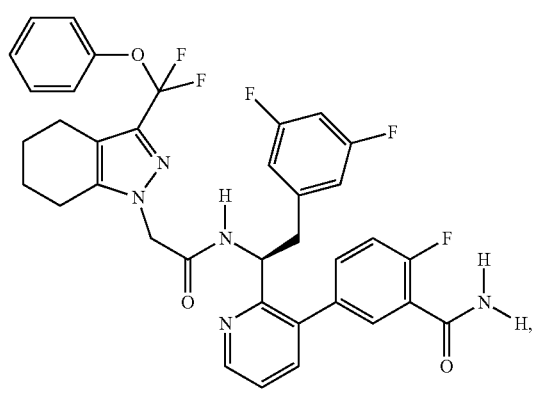

781
-continued
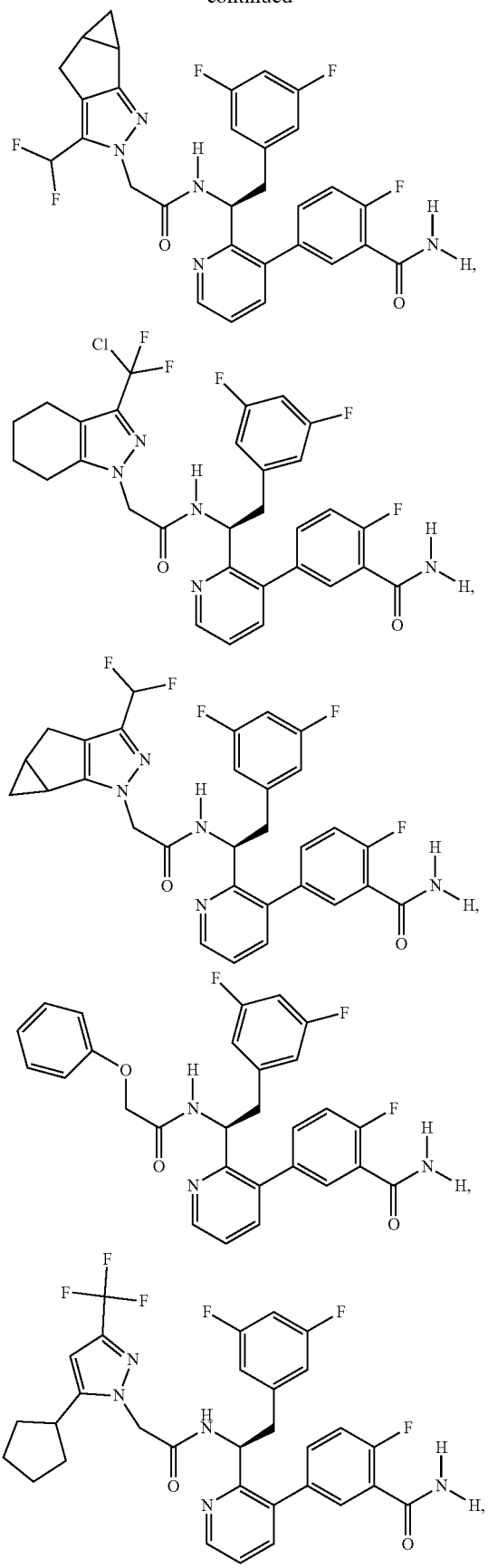
782
-continued
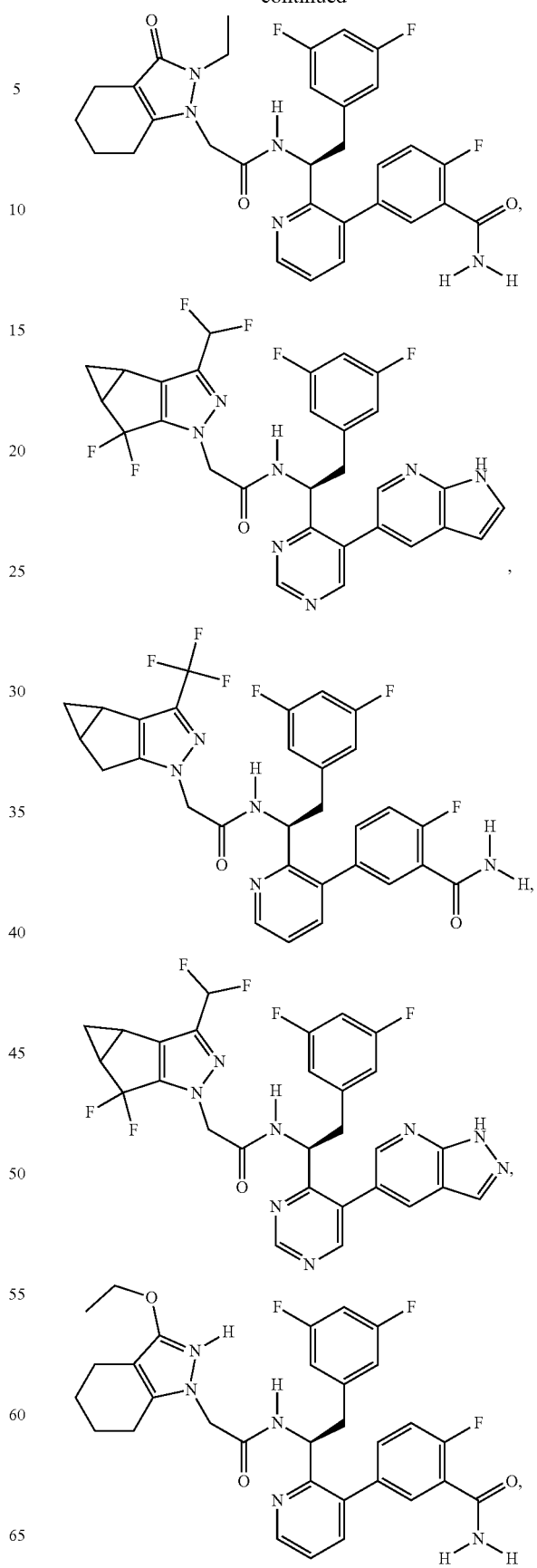

-continued
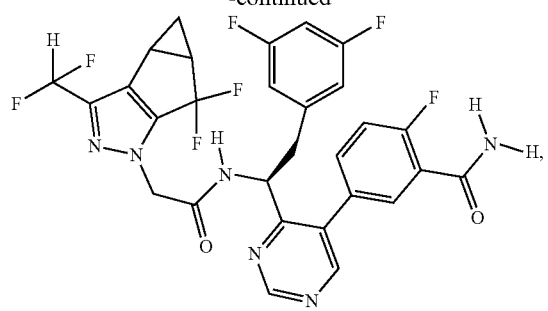 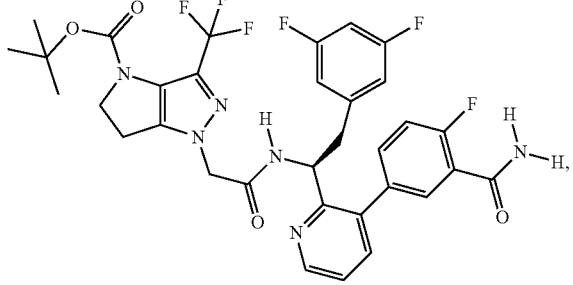
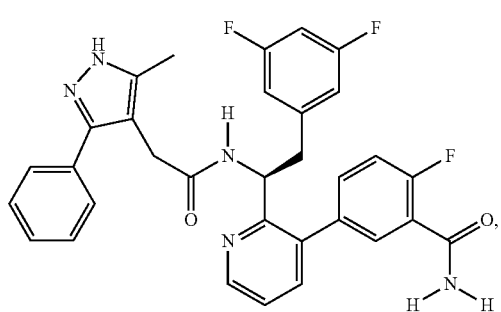 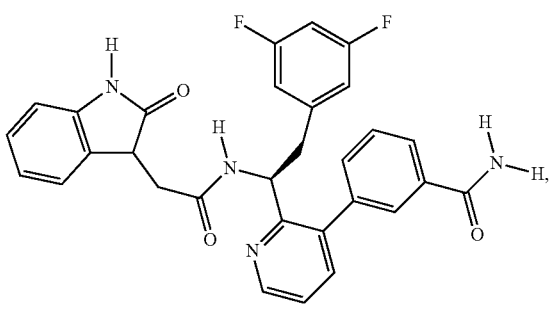
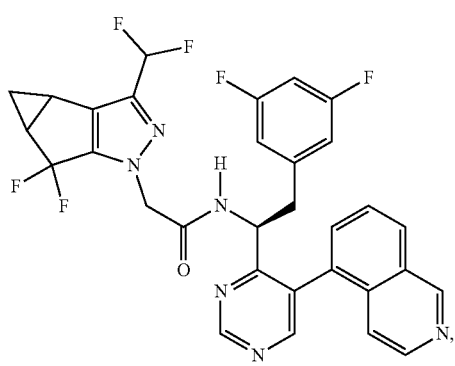 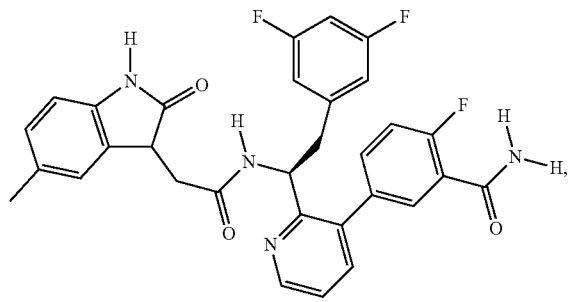
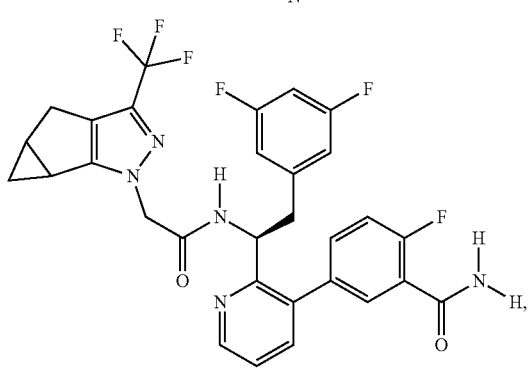 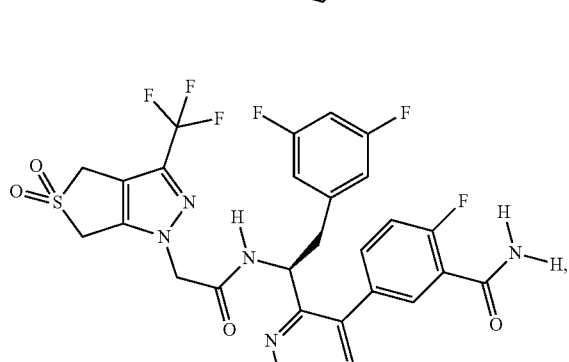
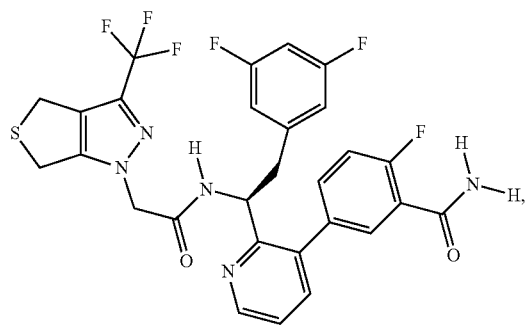 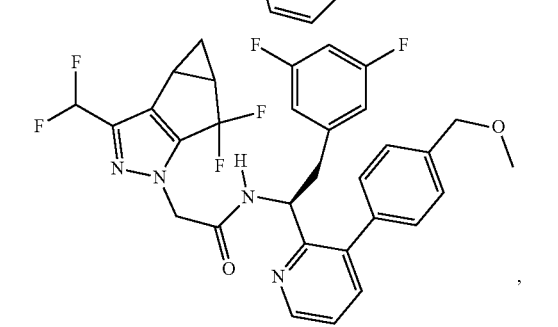

785
-continued
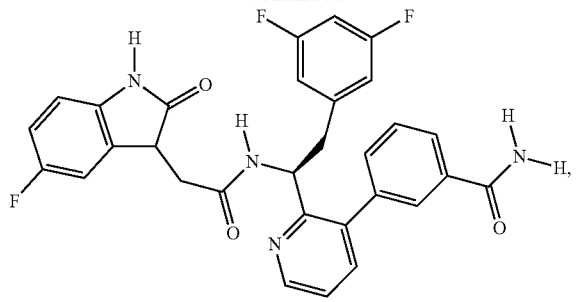
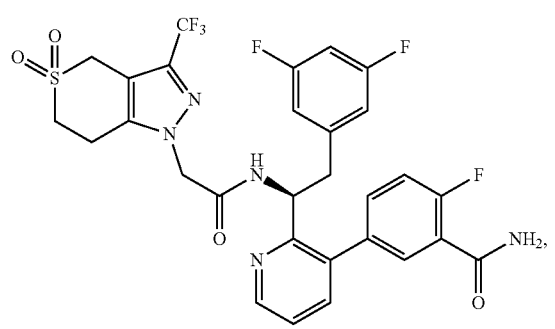
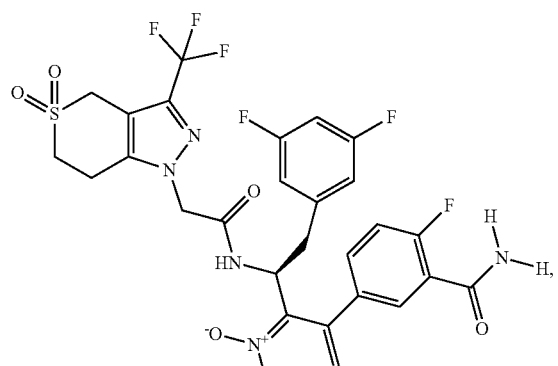
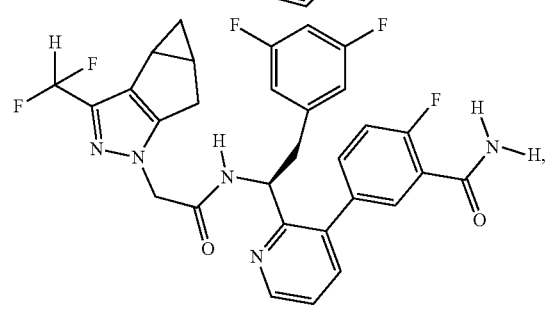
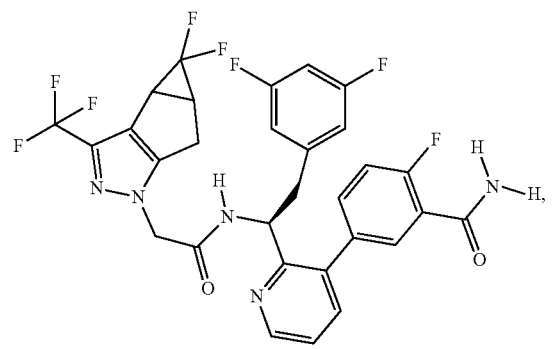
786
-continued
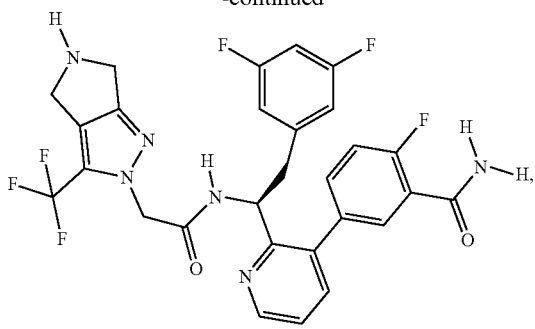
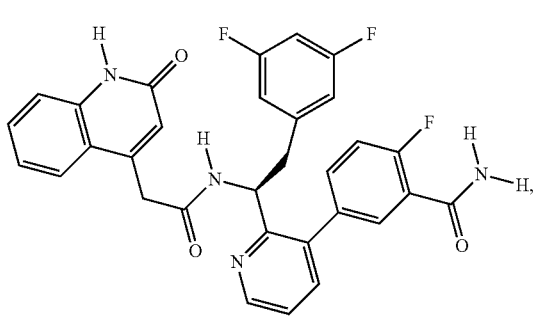
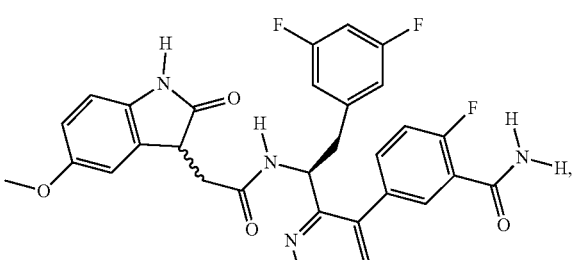
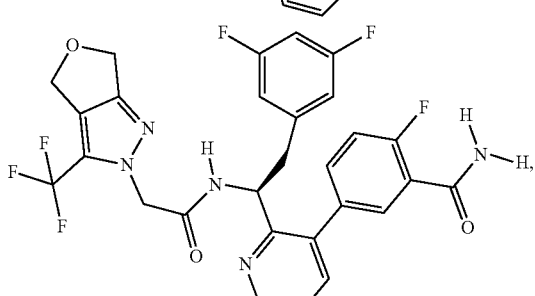
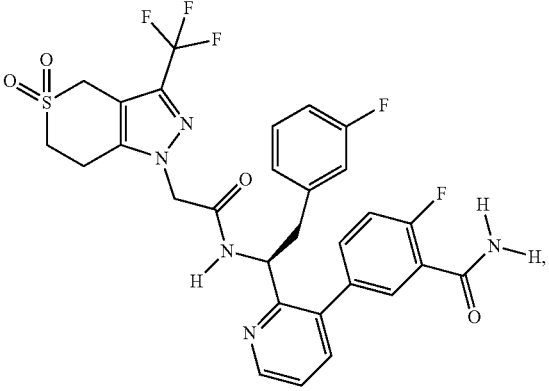

787 -continued
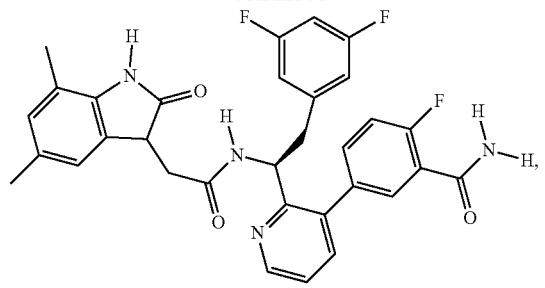
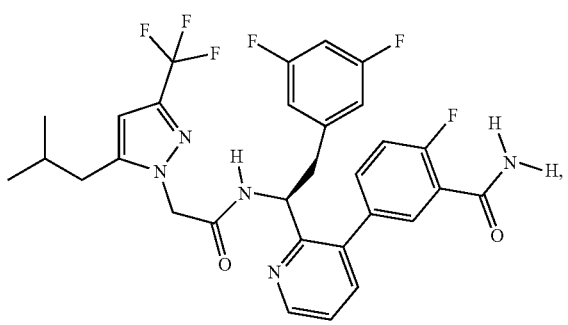
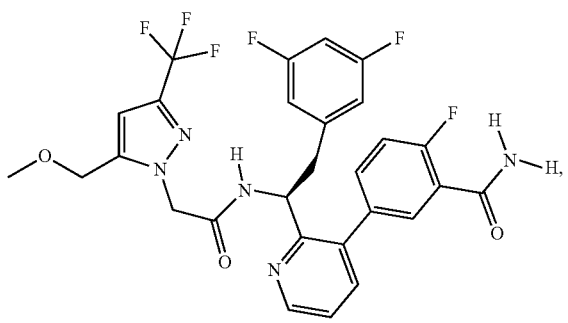
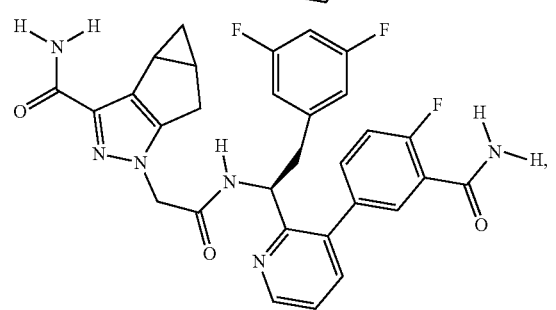
788 -continued
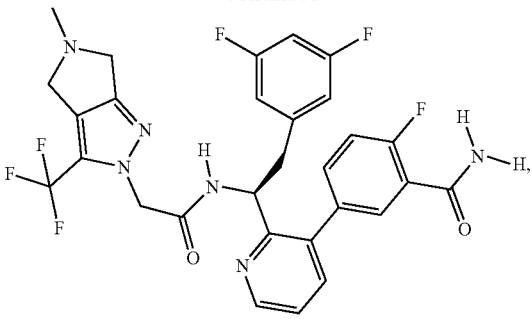
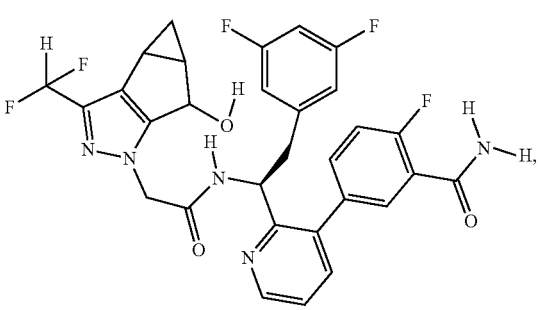
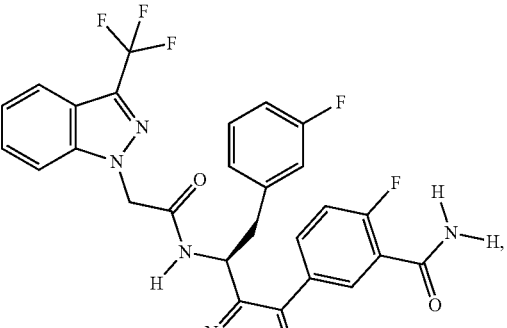
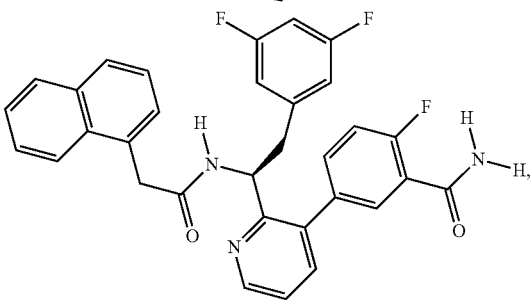

789
-continued
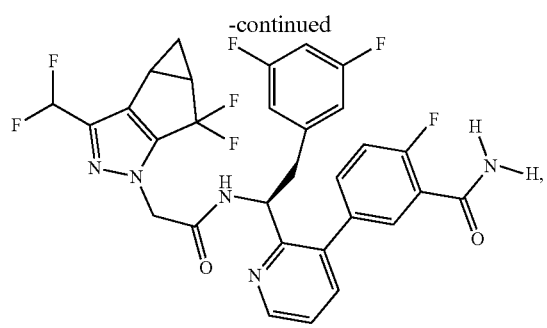
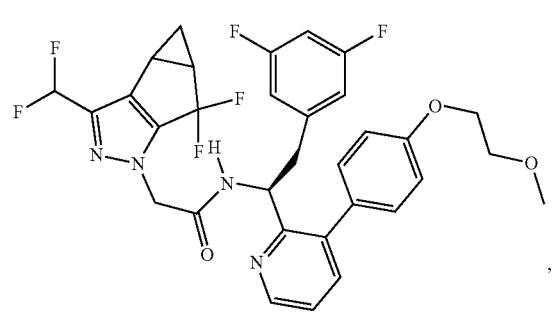
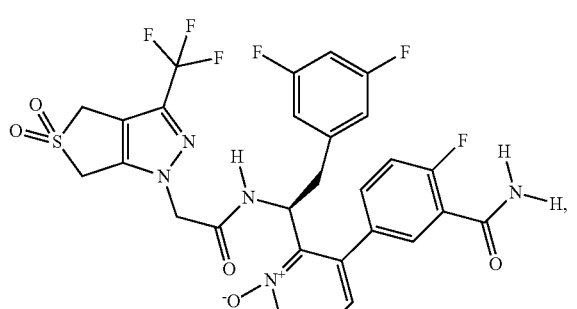
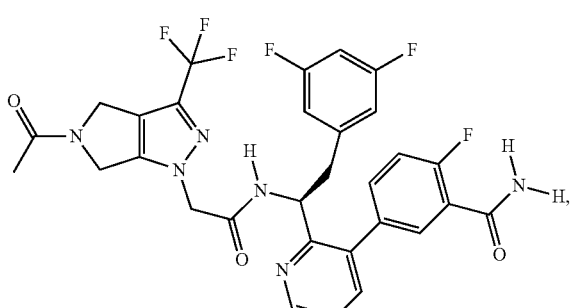
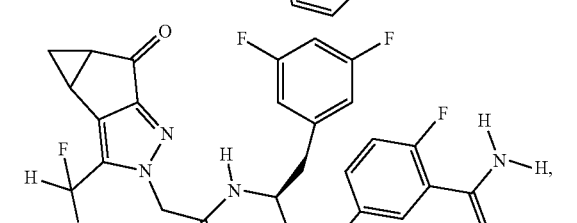
790
-continued
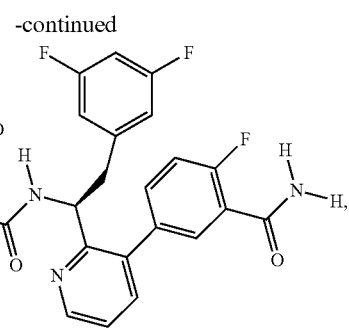
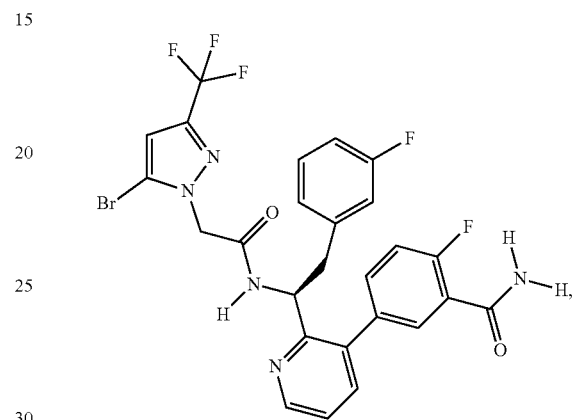
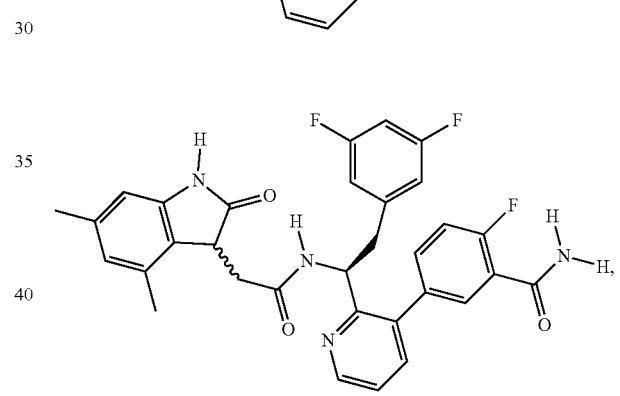
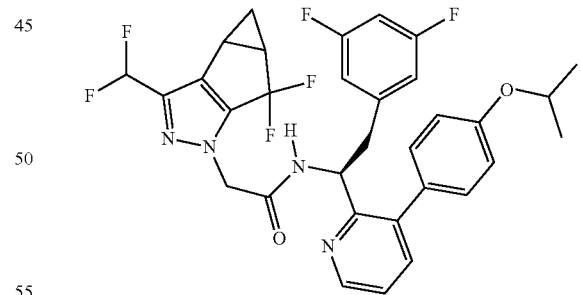
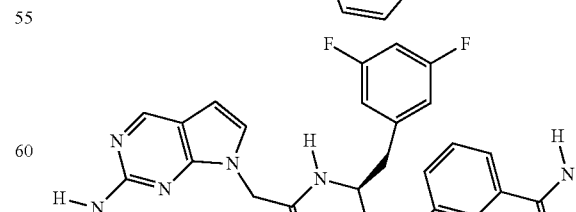

791
-continued
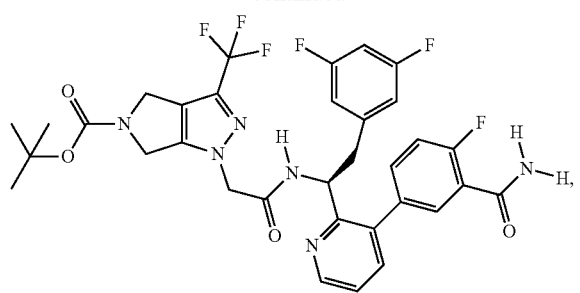
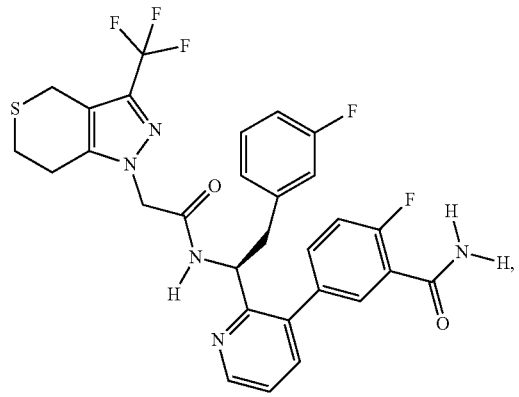
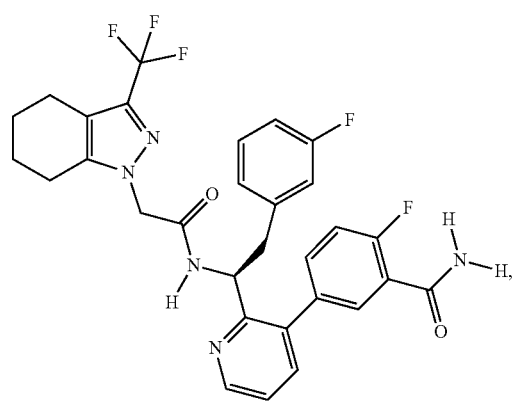
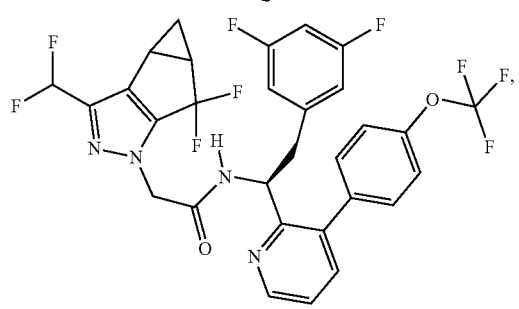
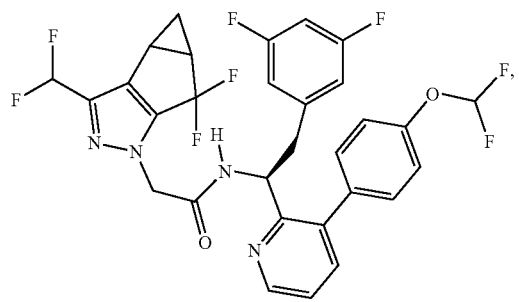
792
-continued
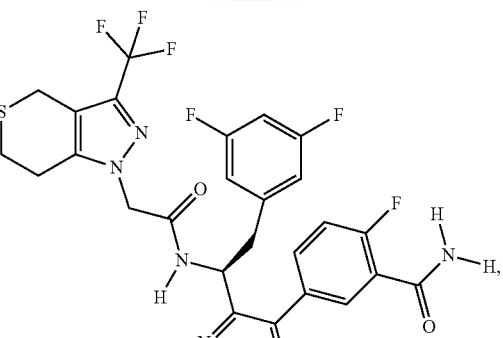
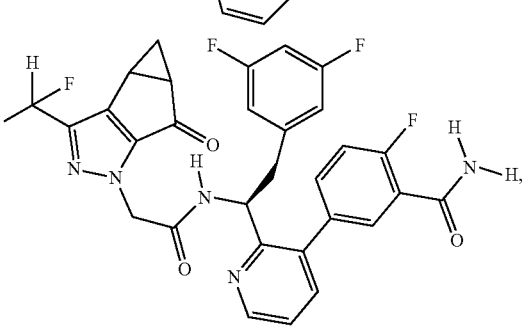
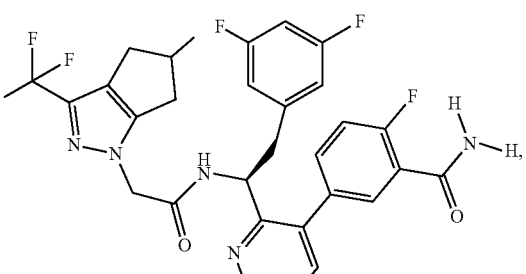
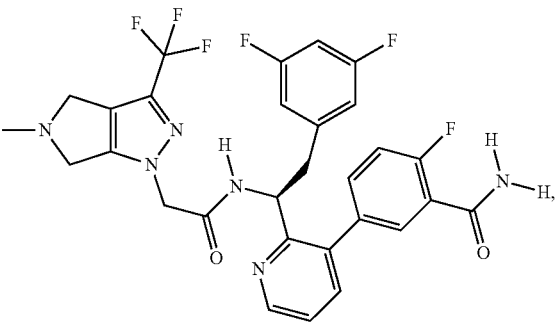
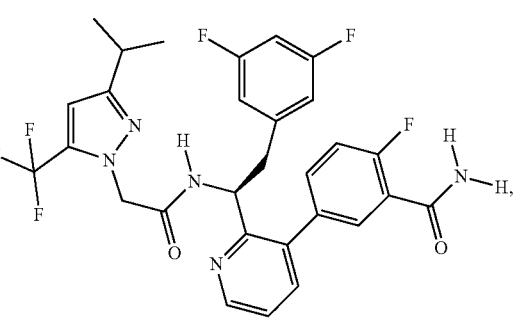

793
-continued
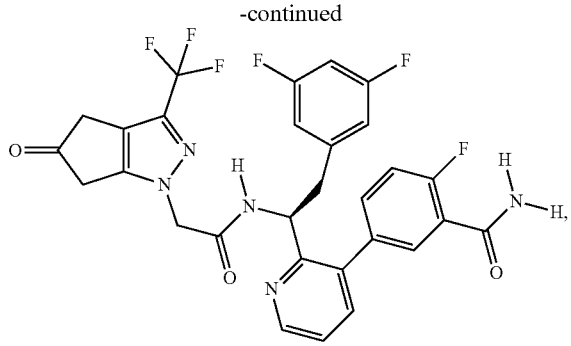
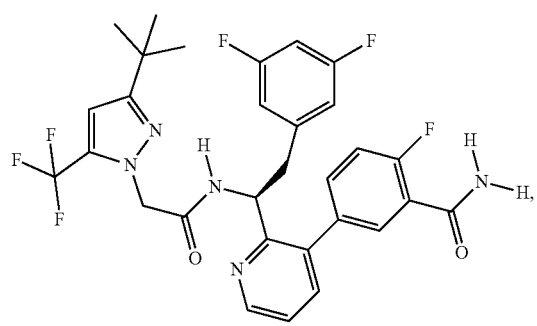
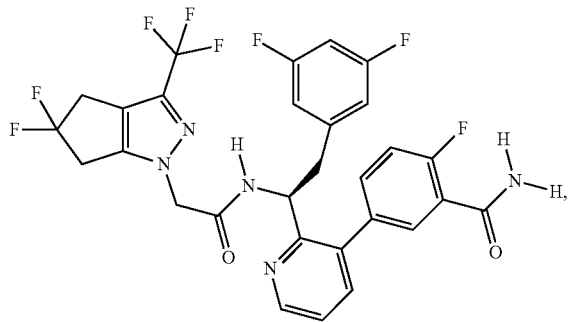
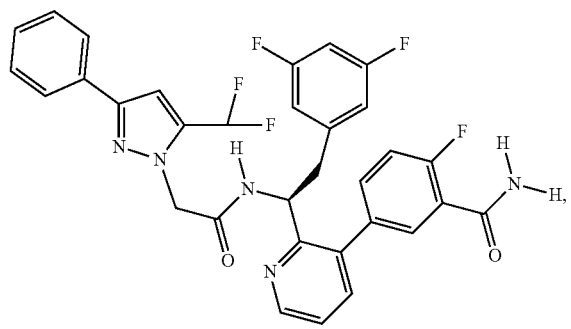
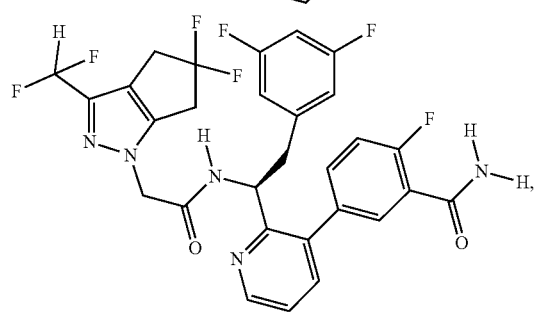
794
-continued
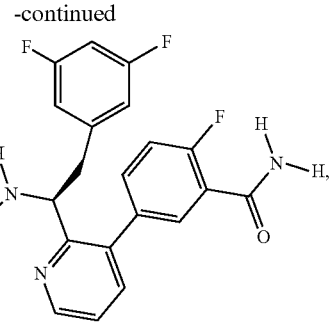
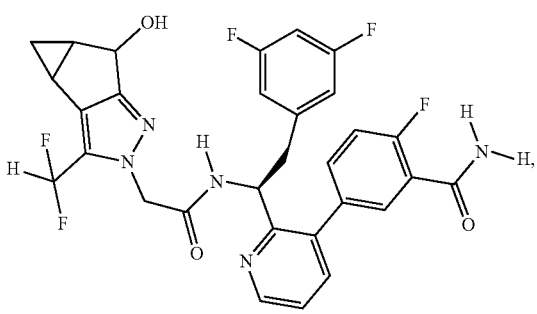
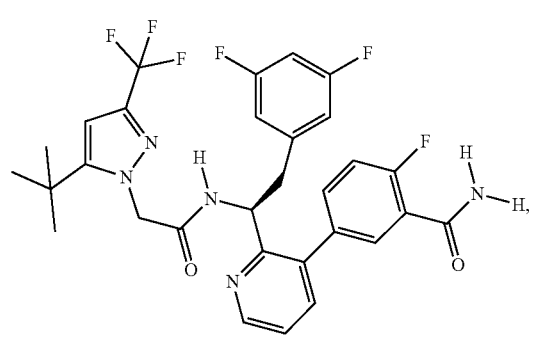
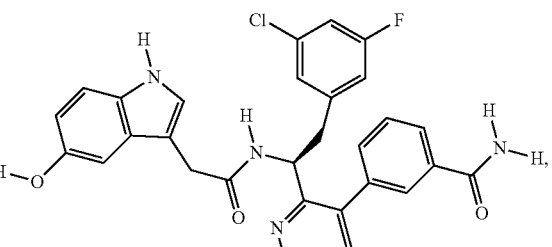
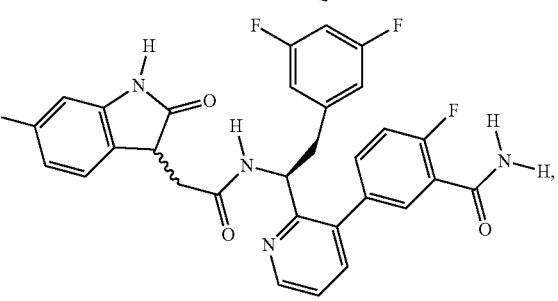

795
-continued
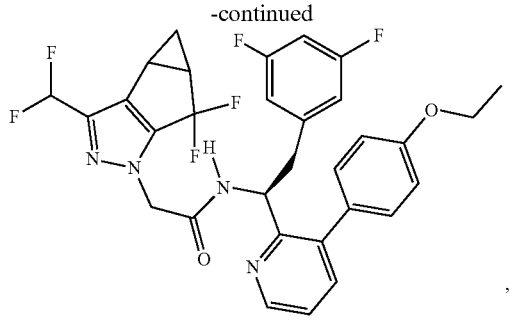
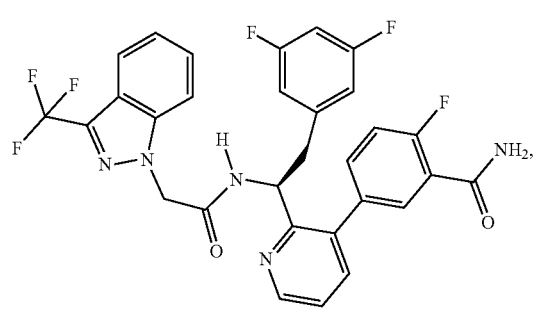
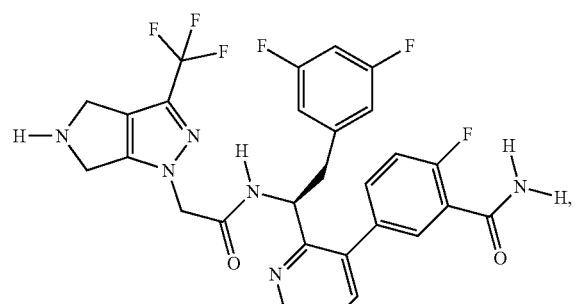
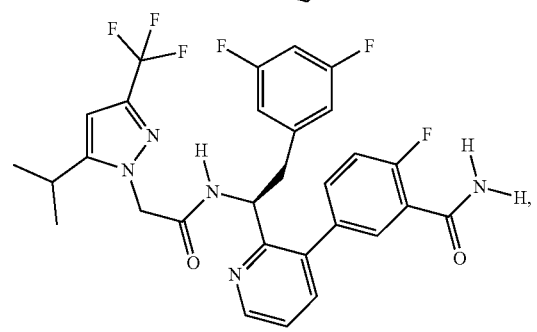
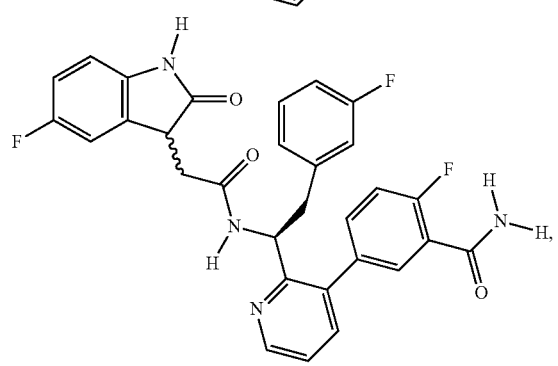
796
-continued
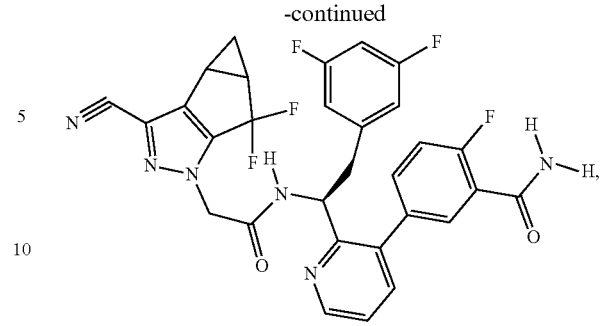
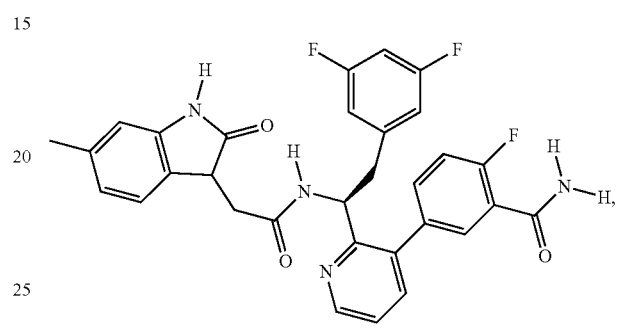
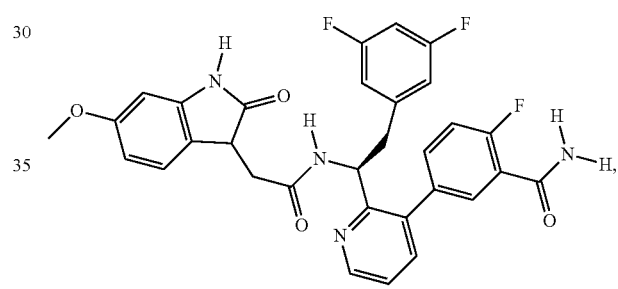
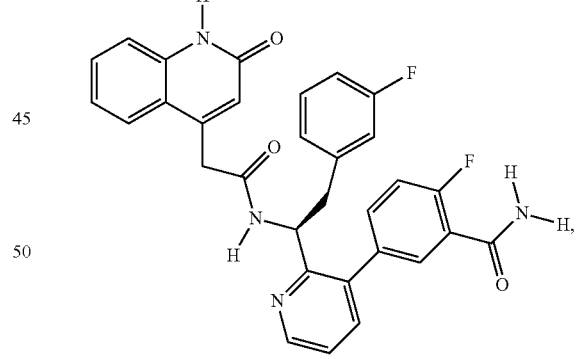
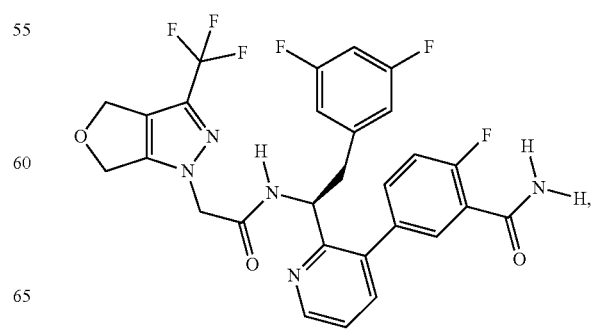

797
-continued
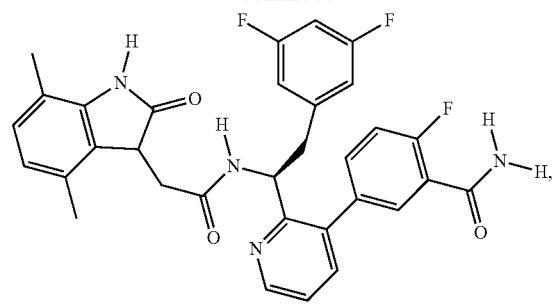
798
-continued
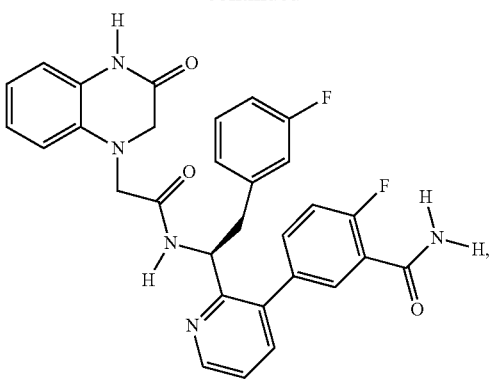
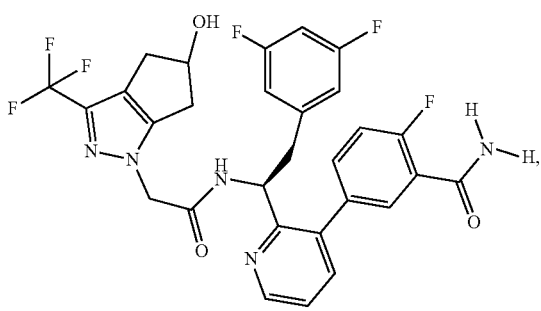
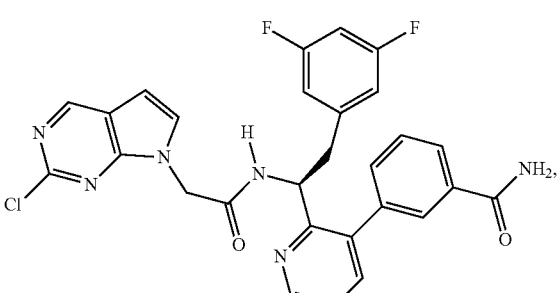
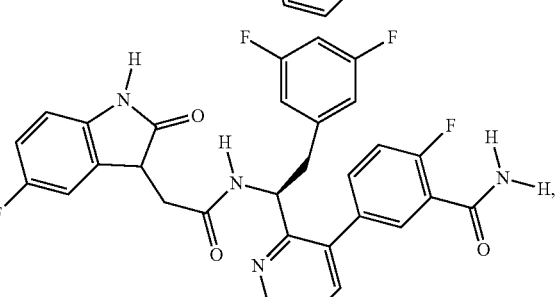
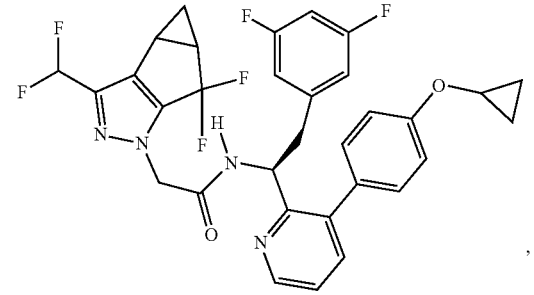

799
-continued
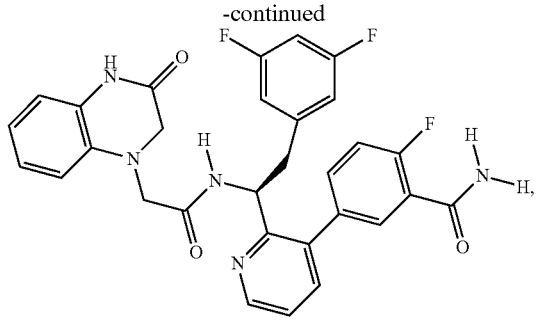
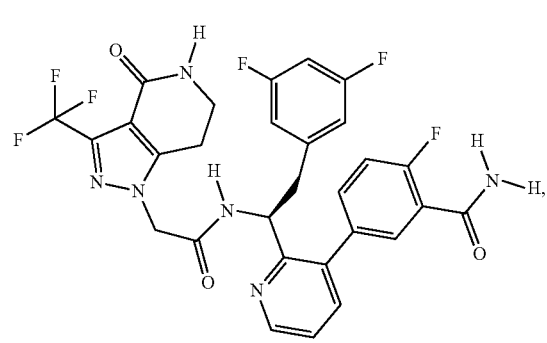
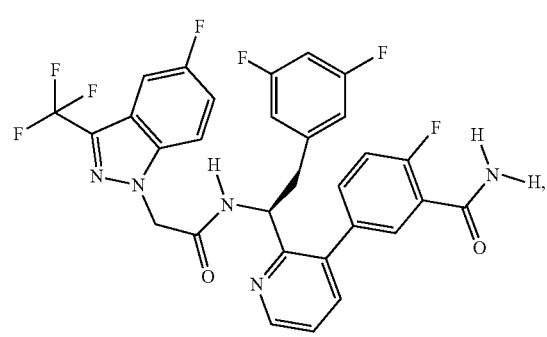
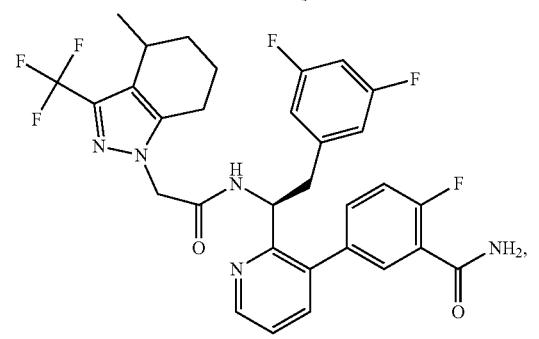
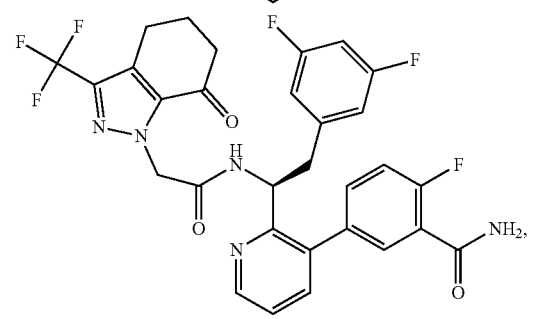
800
-continued
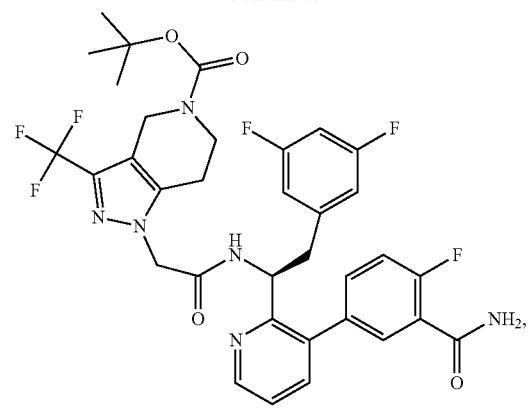
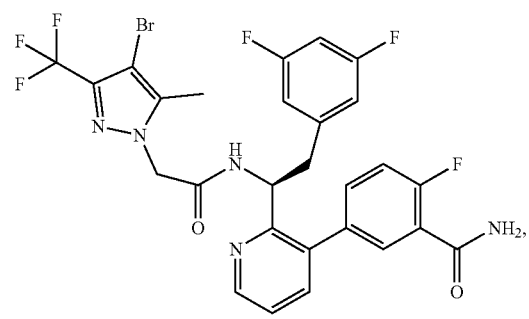
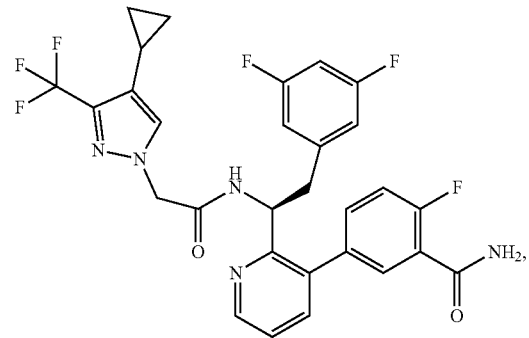
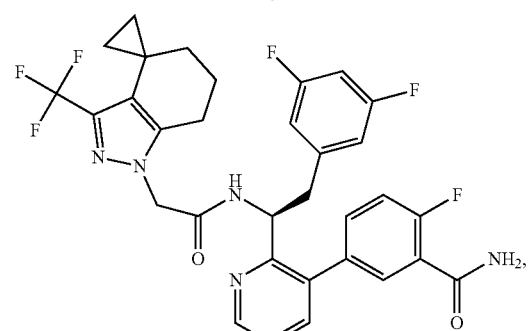
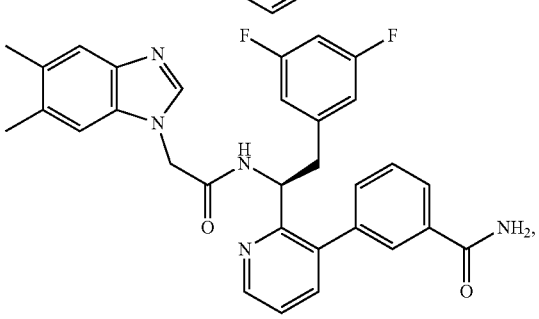

801
-continued
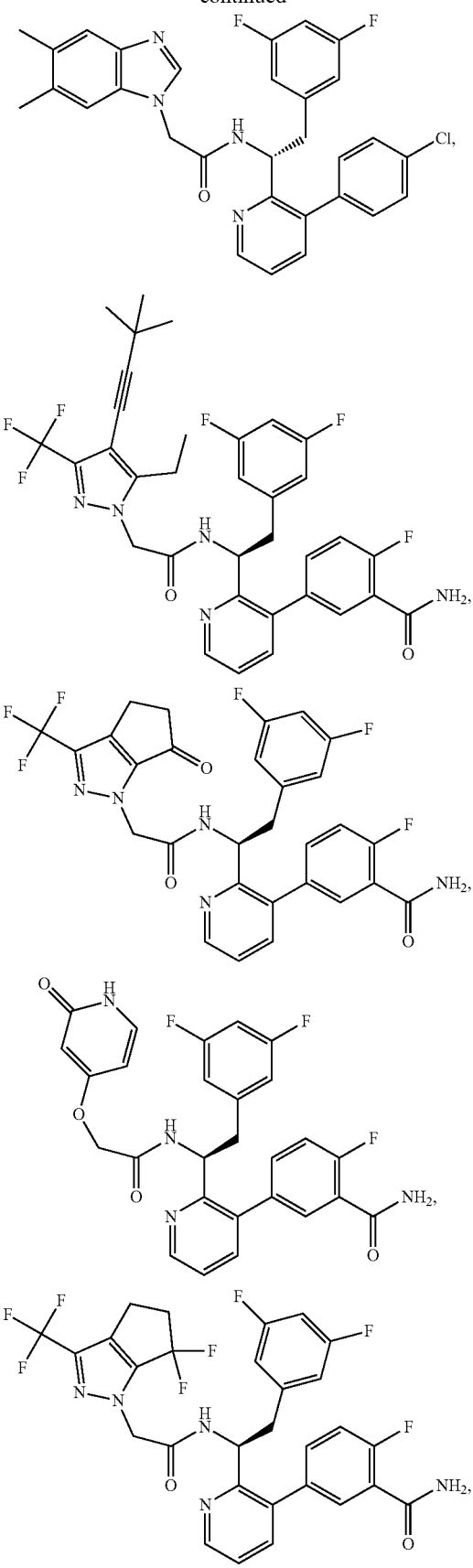
802
-continued
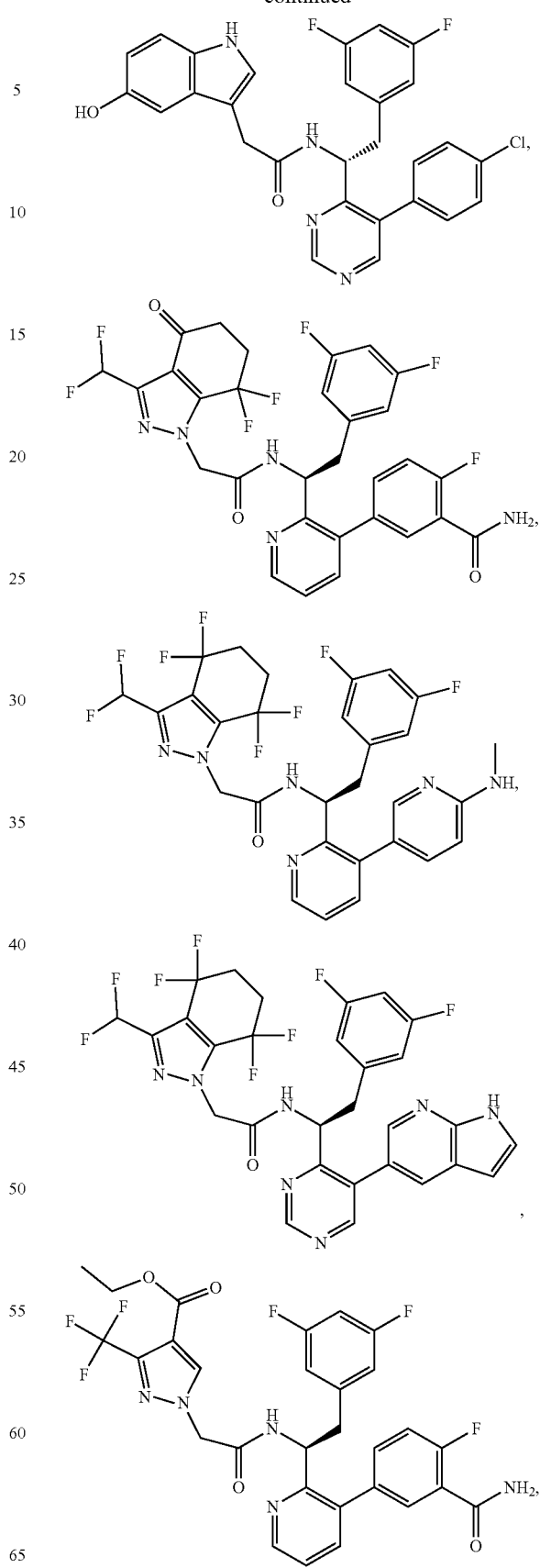

803
-continued
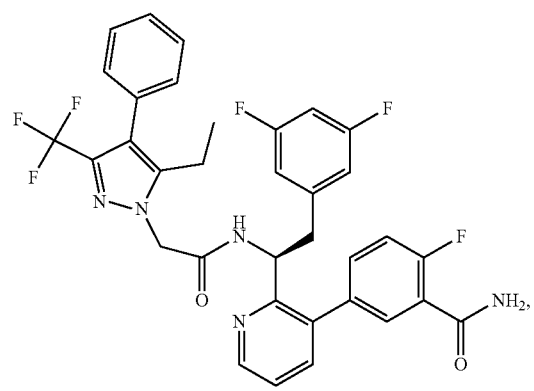
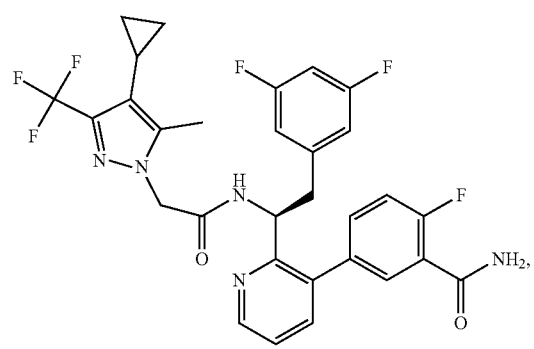
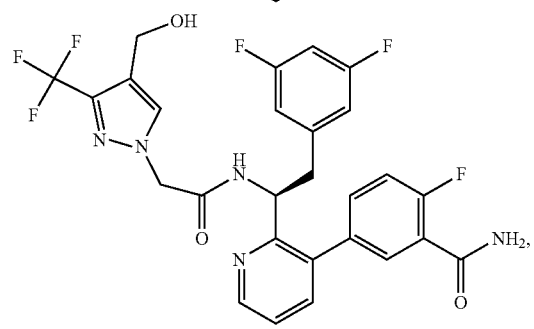
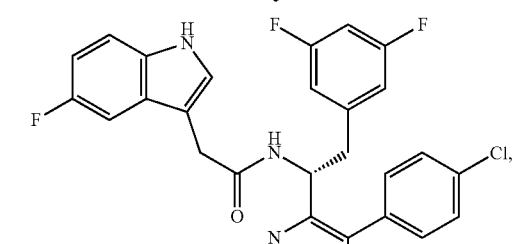
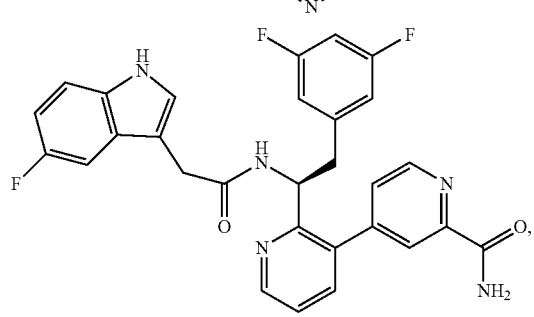
804
-continued
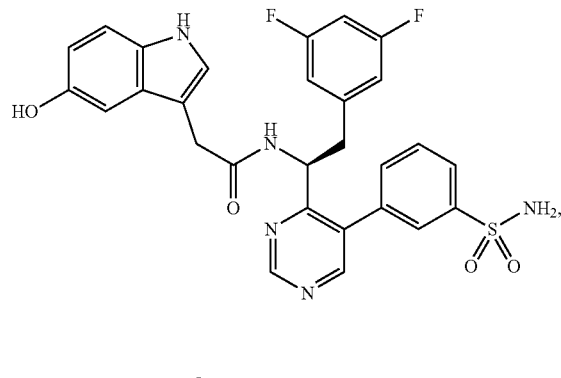
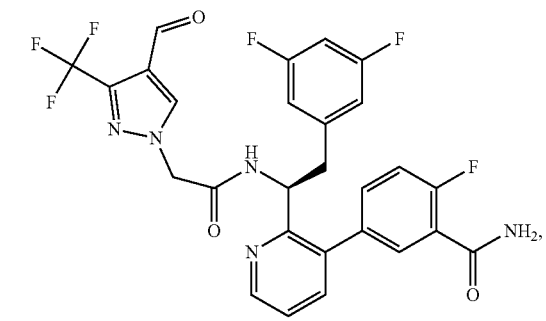
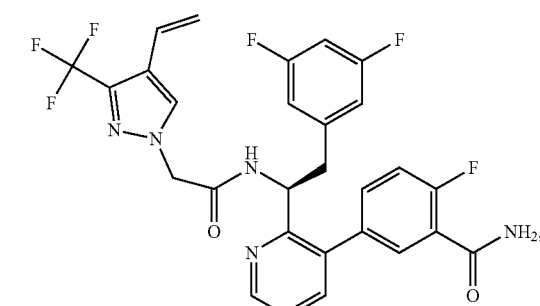
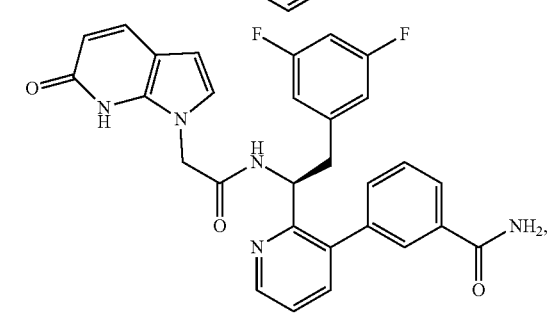
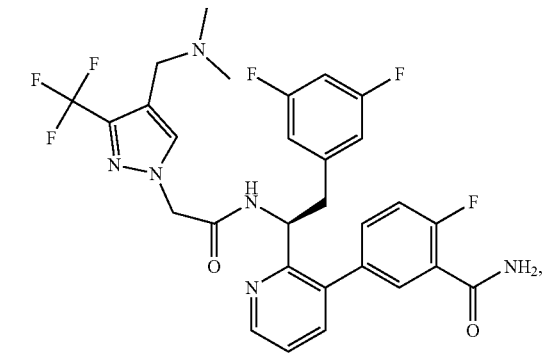

805
-continued
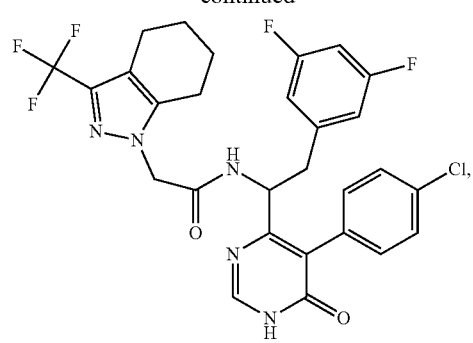
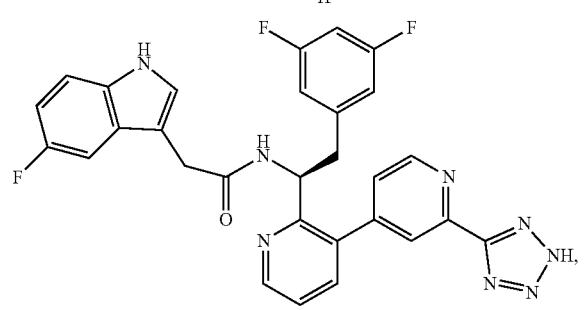
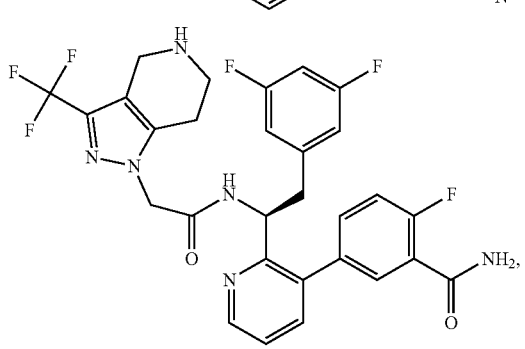
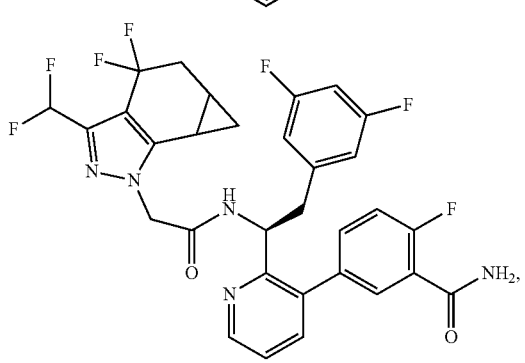
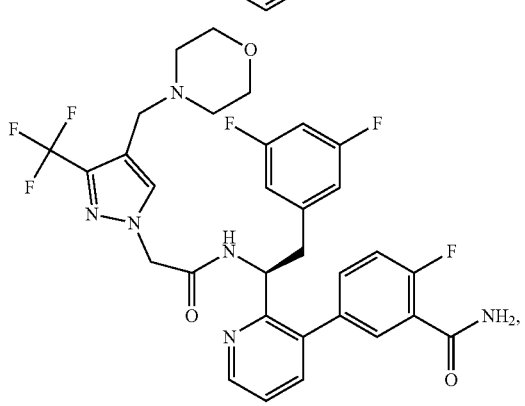
806
-continued
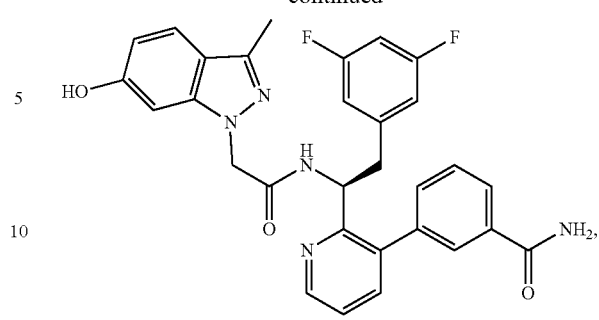
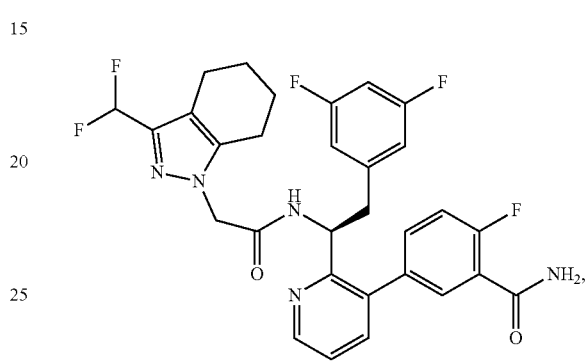
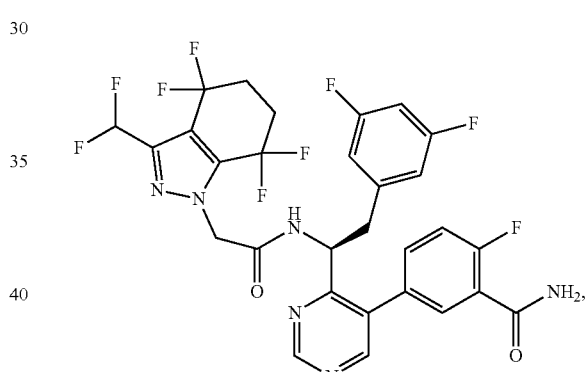
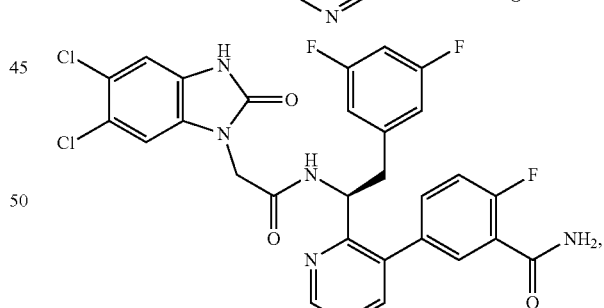
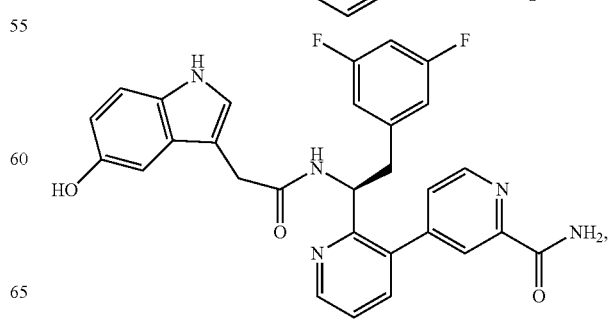

807
-continued
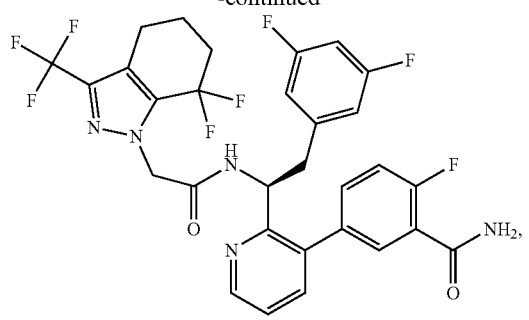
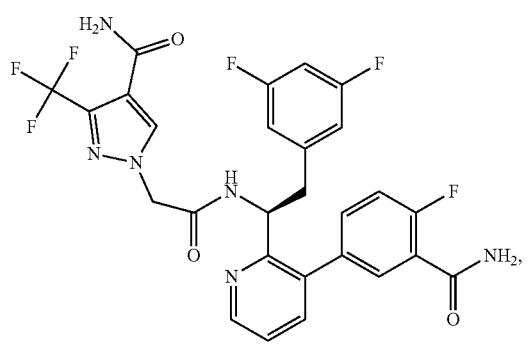
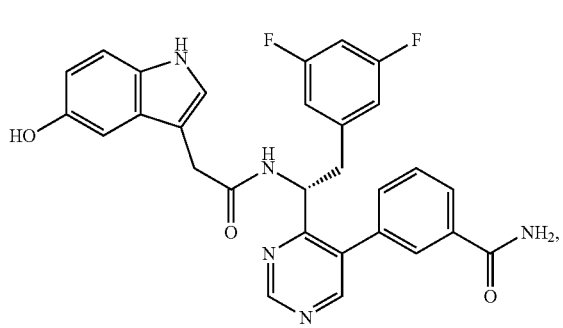
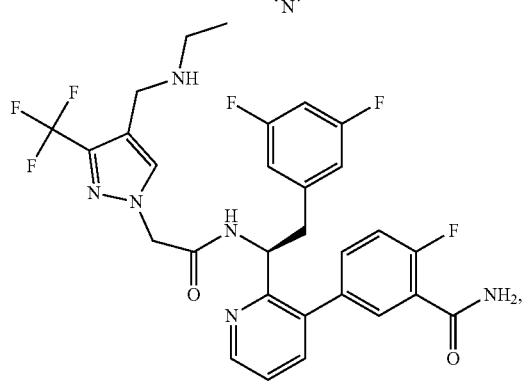
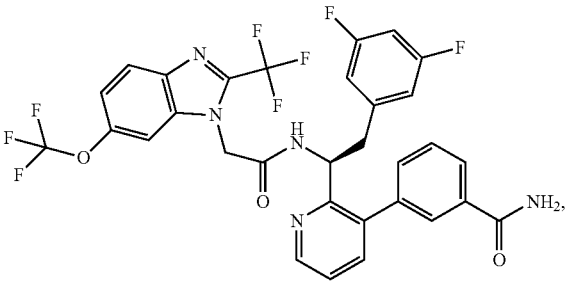
808
-continued
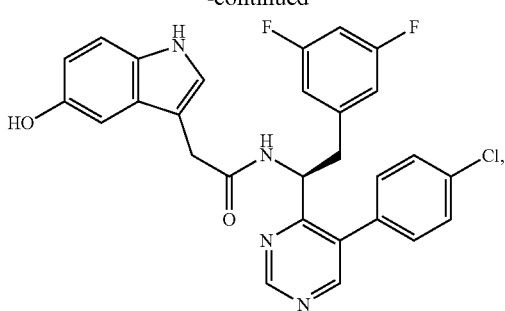
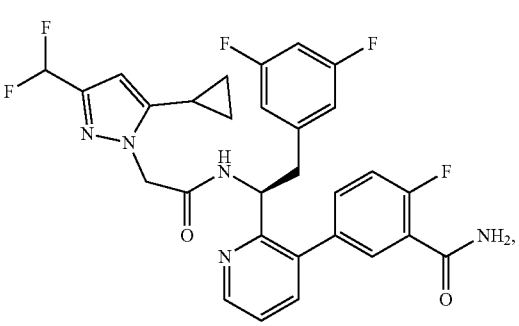
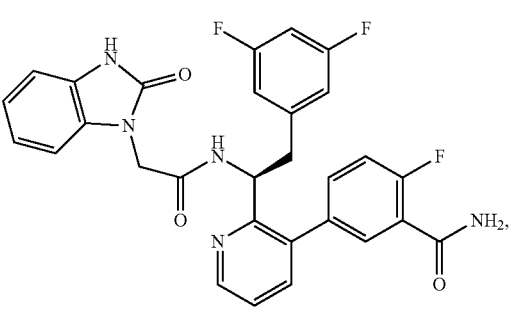
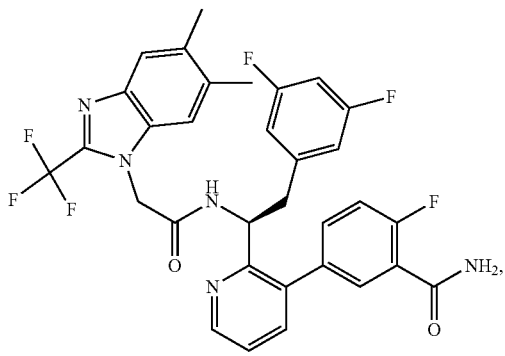
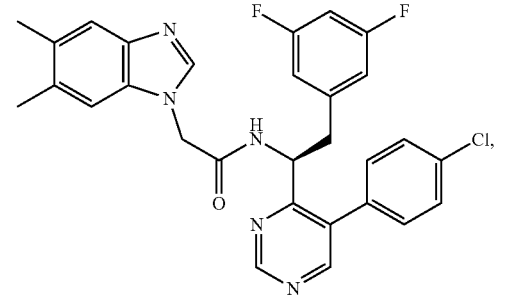

809
-continued
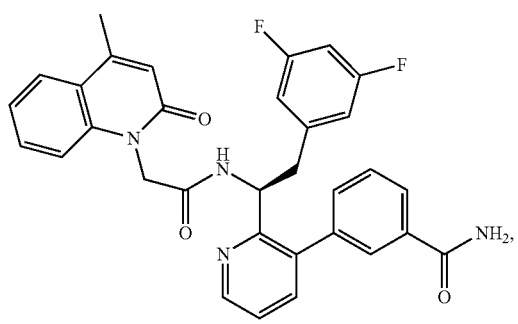
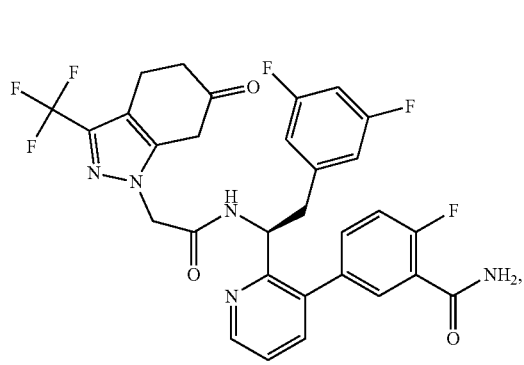
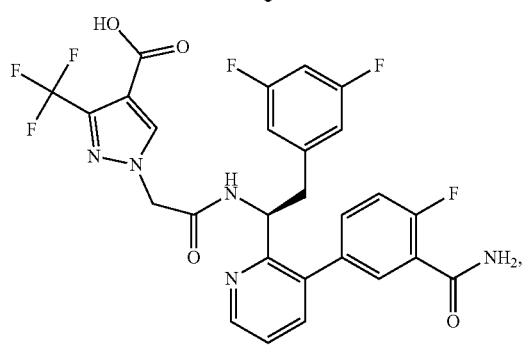
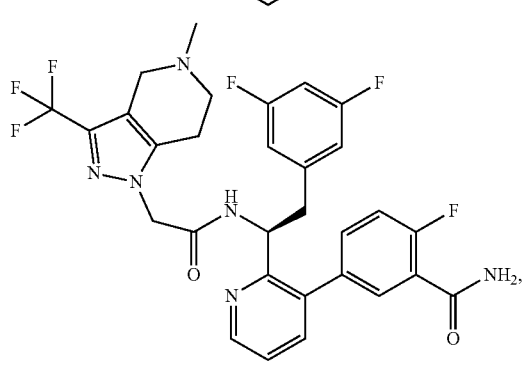
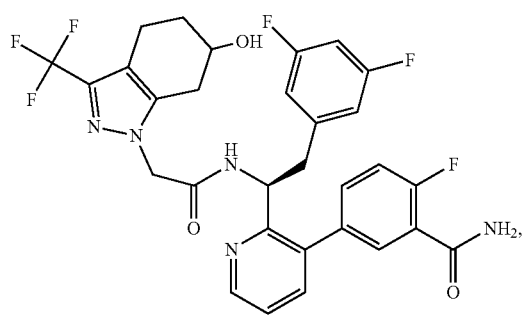
810
-continued
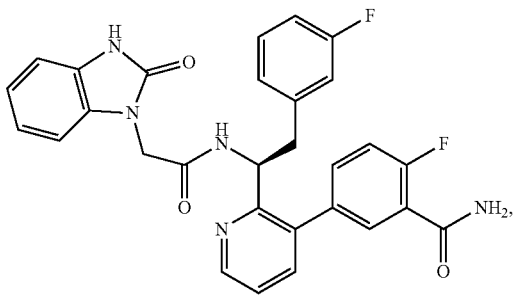
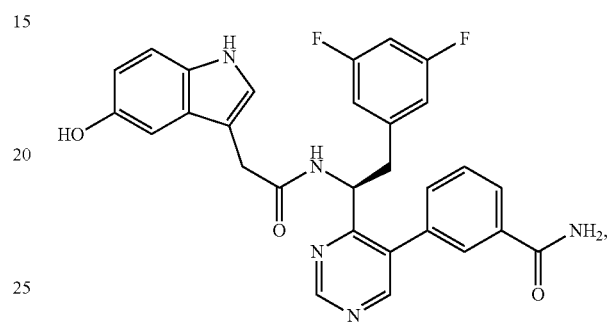
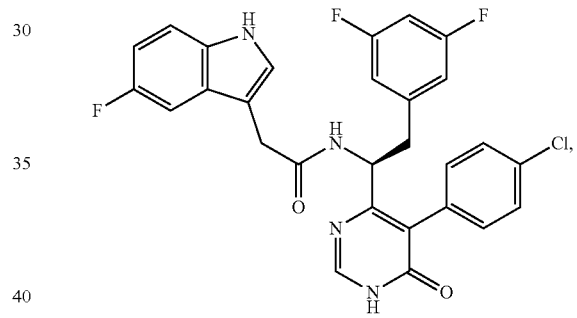
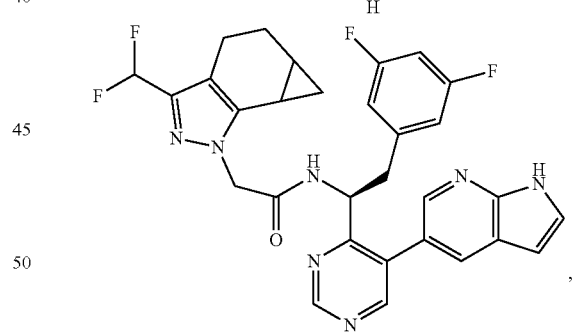
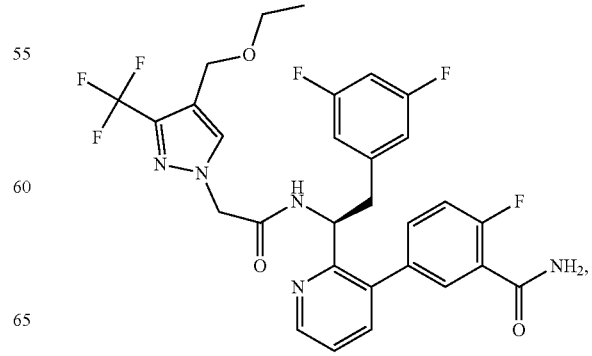

811
-continued
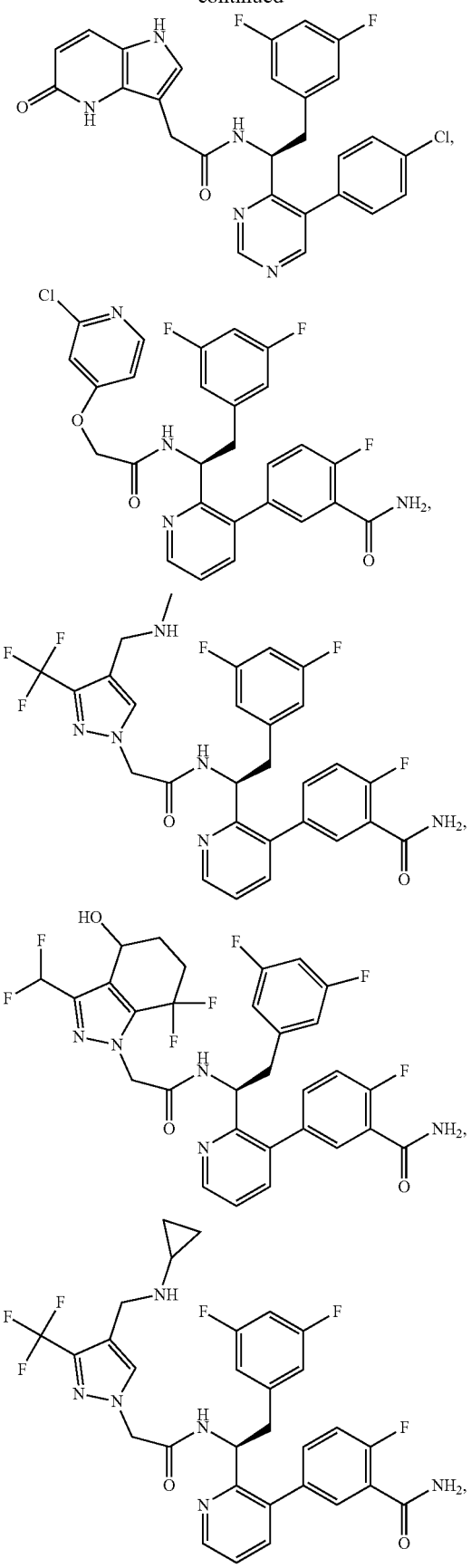
812
-continued
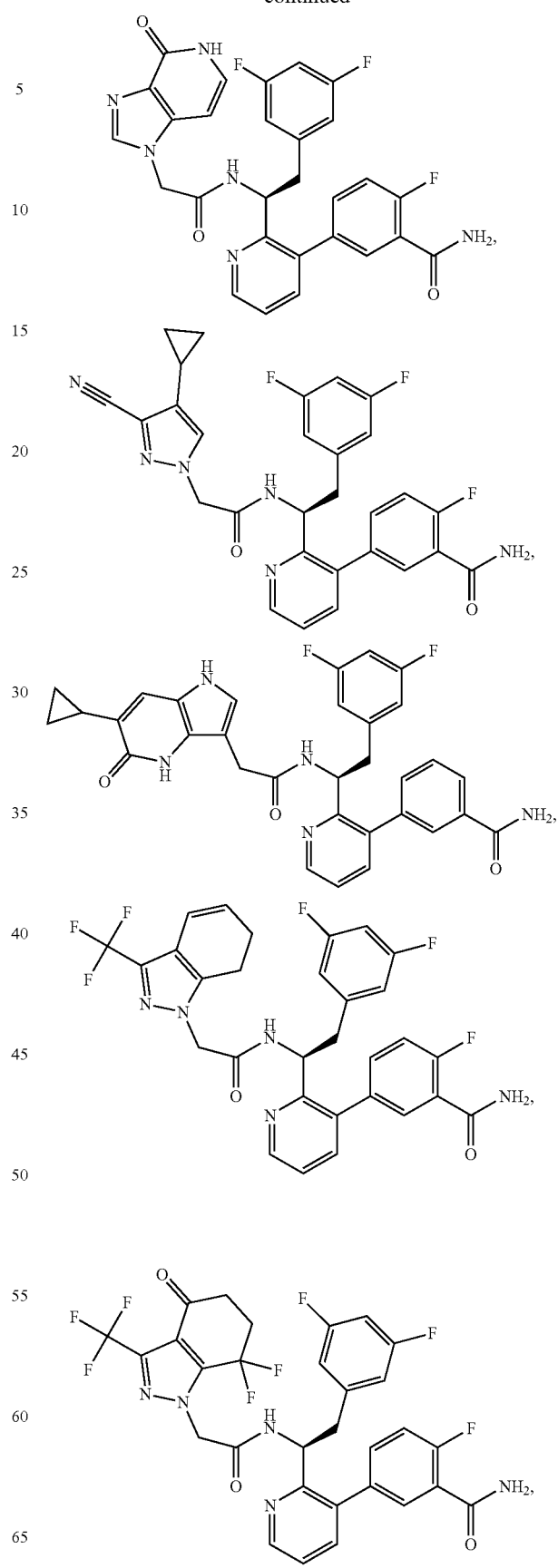

813
-continued
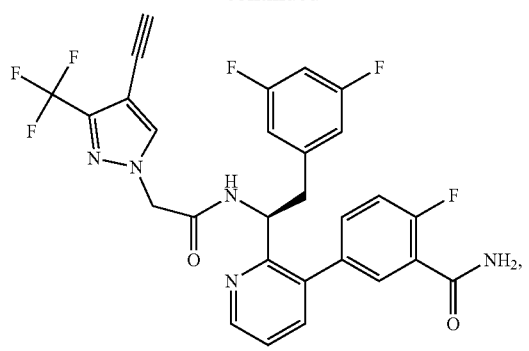
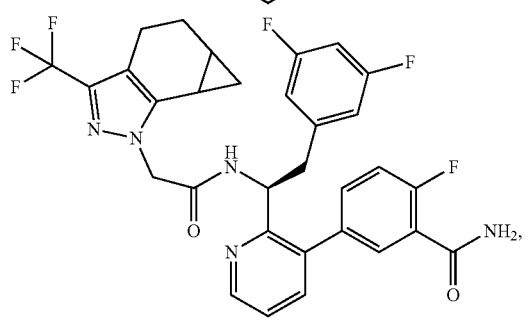
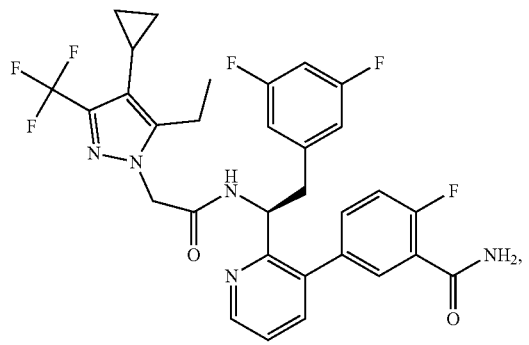
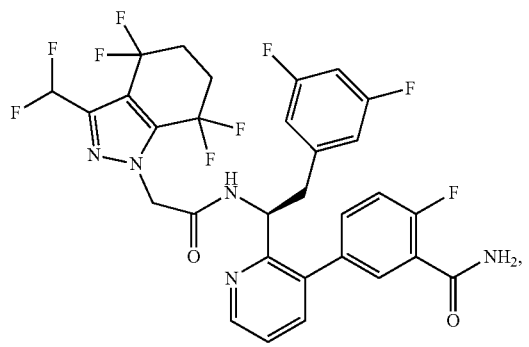
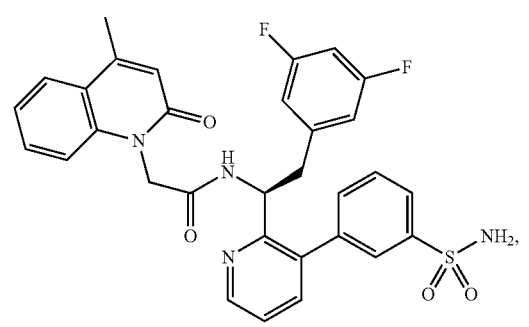
814
-continued
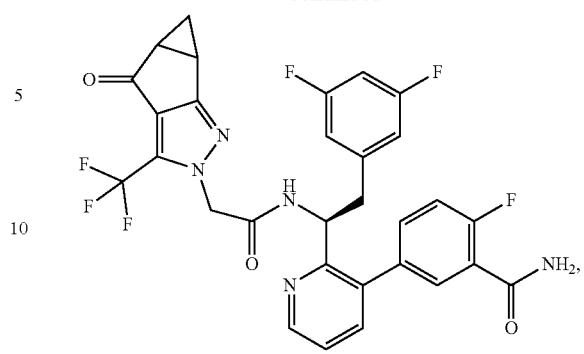
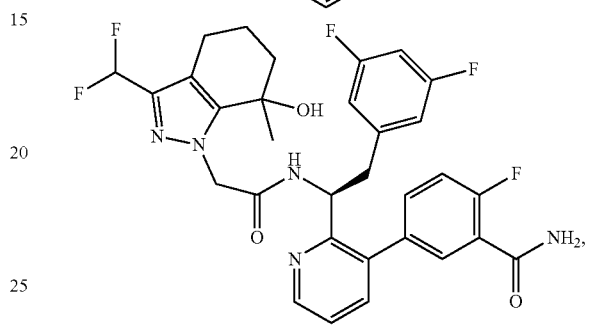
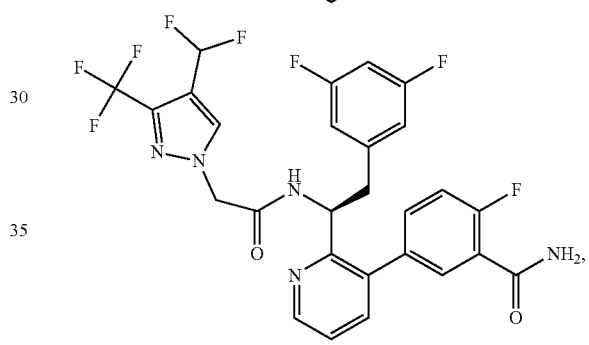
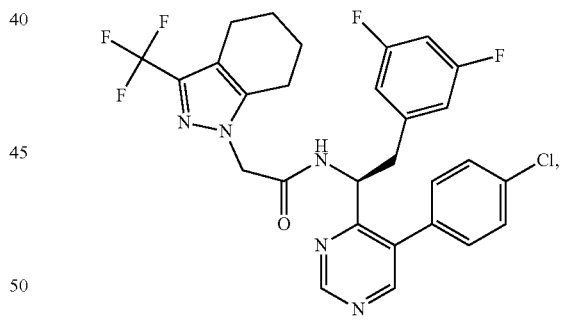
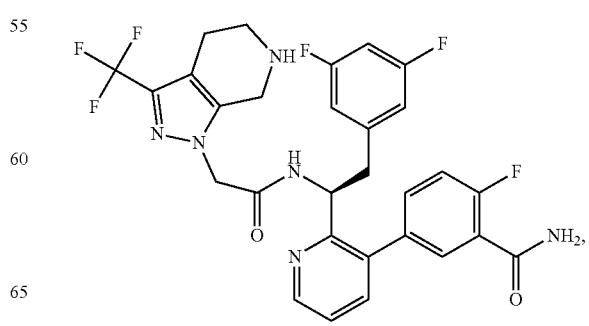

815
-continued
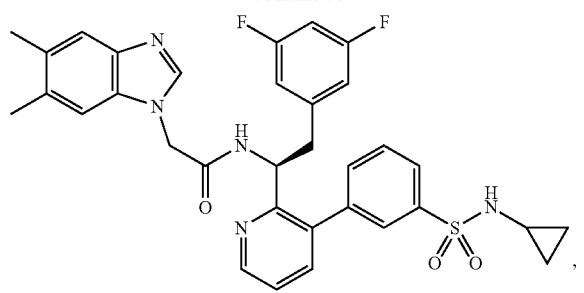
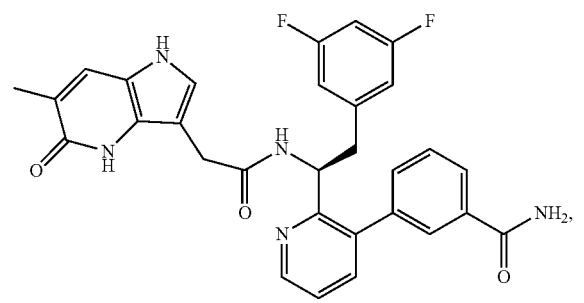
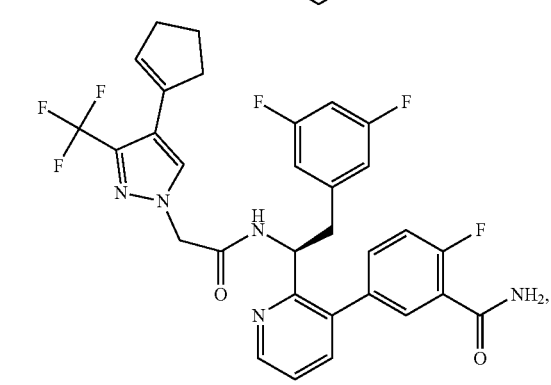
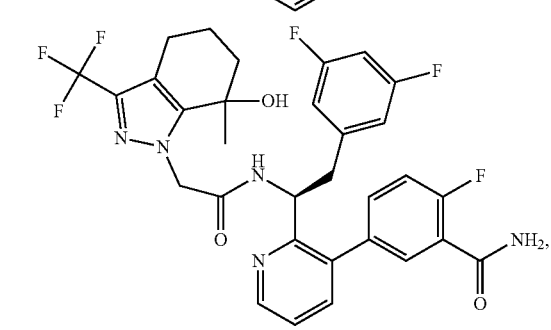
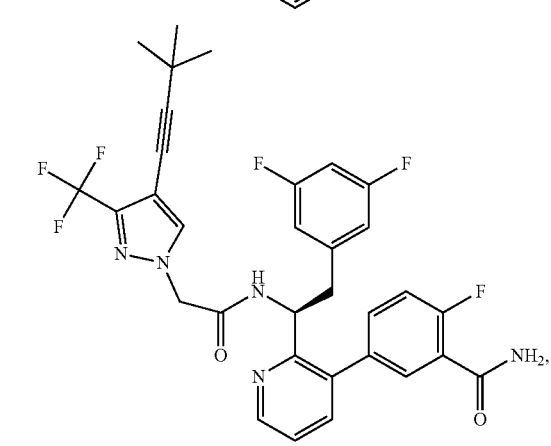
816
-continued
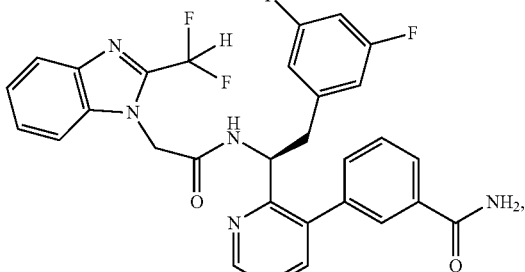
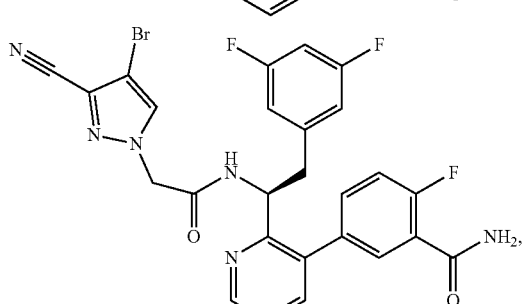
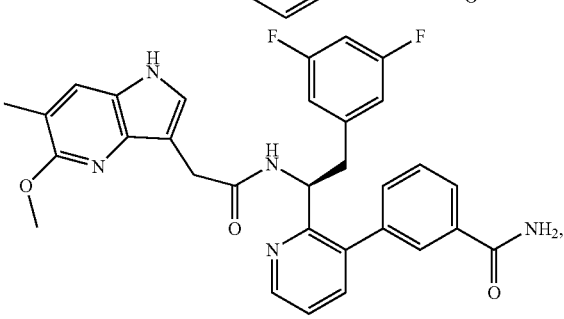
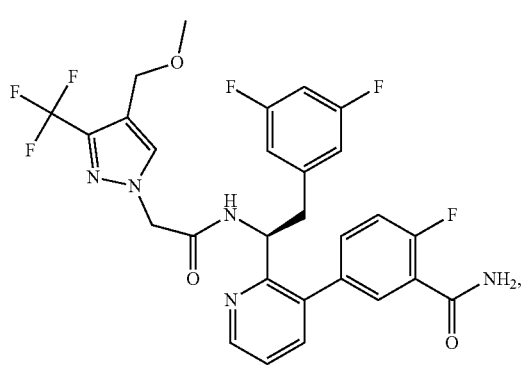
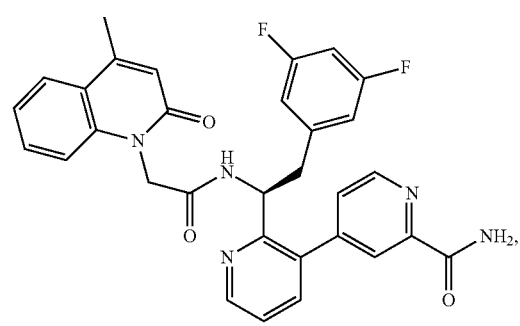

817
-continued
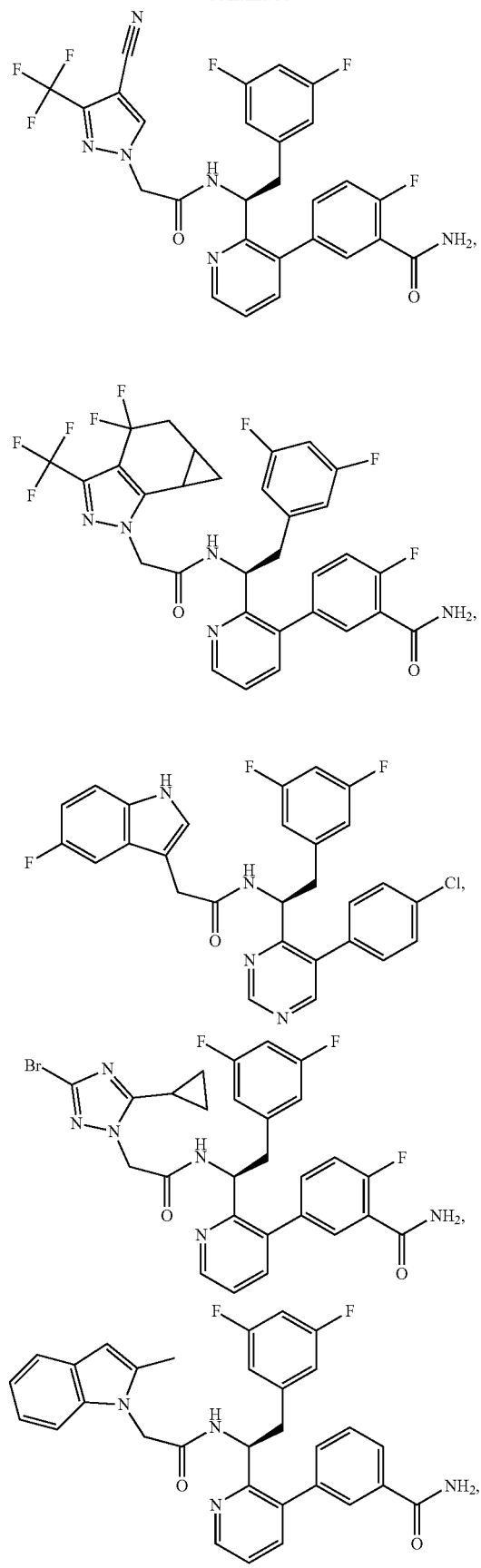
818
-continued
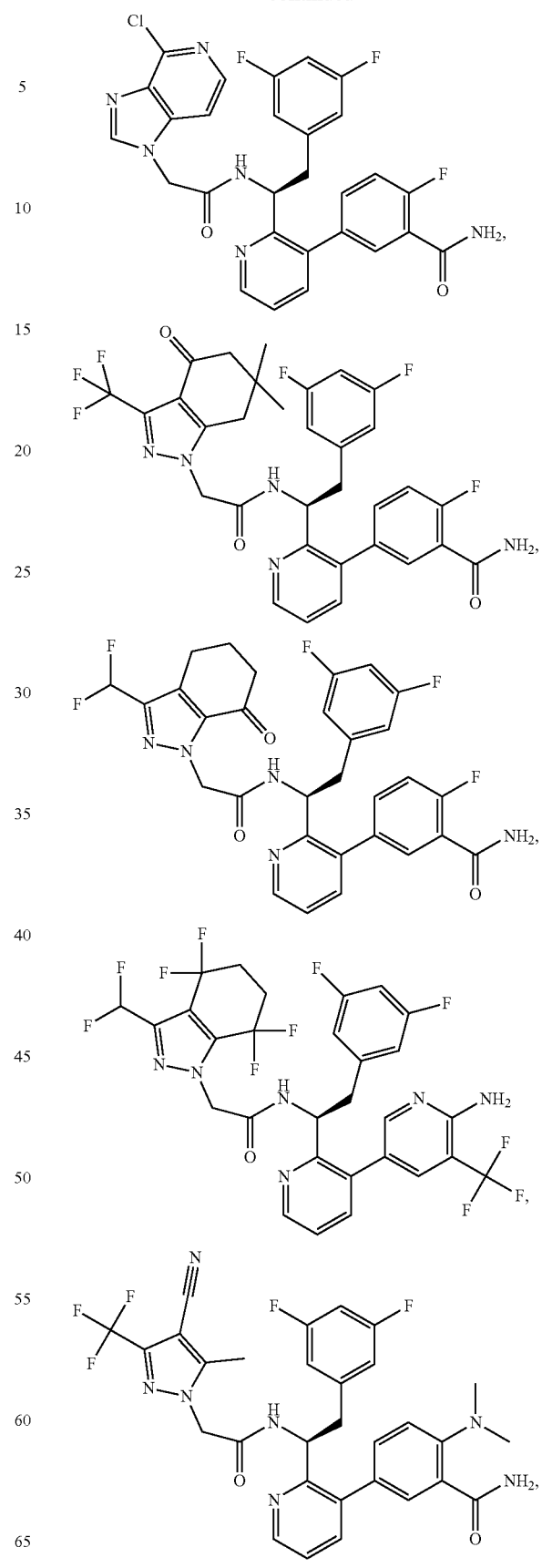

819
-continued
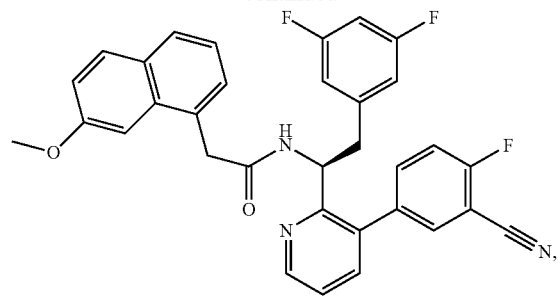
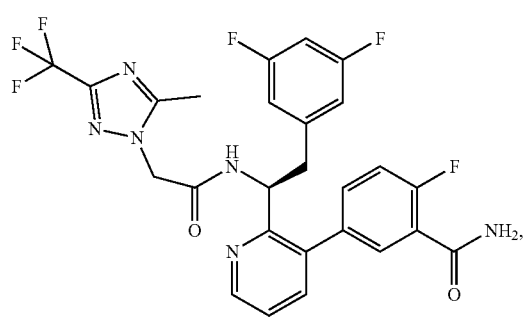
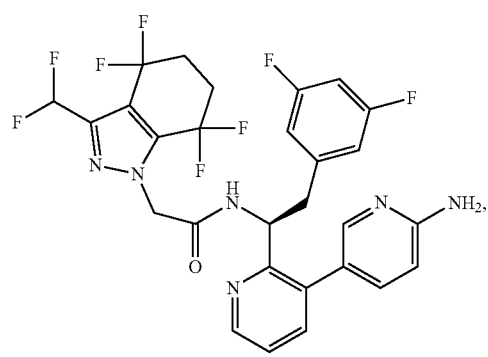
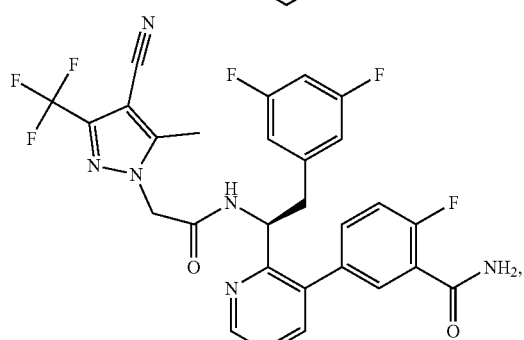
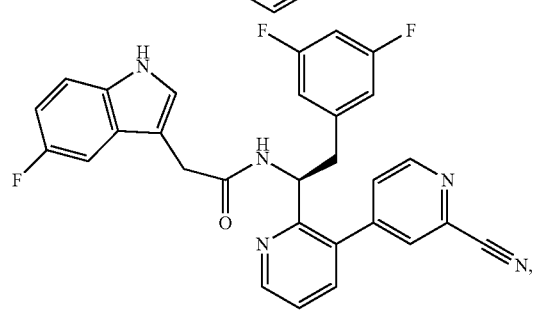
820
-continued
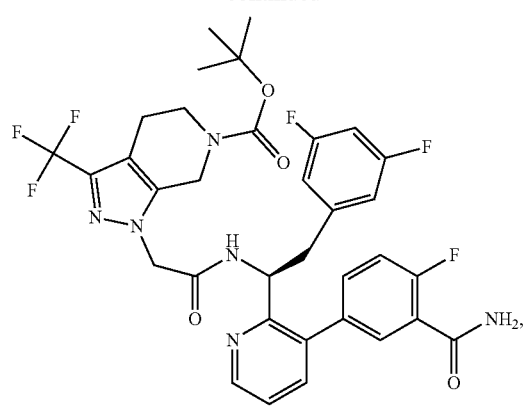
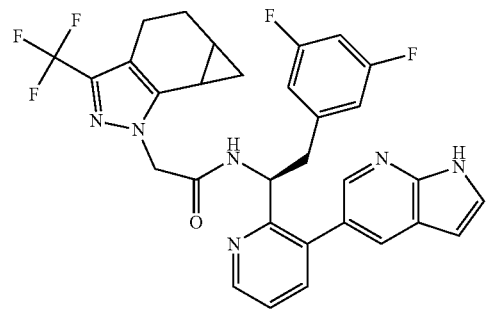
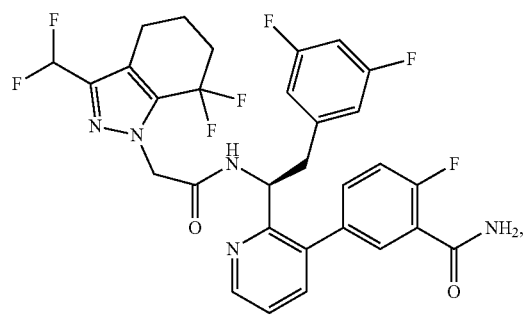
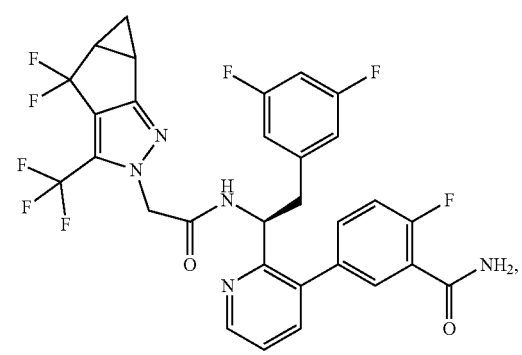
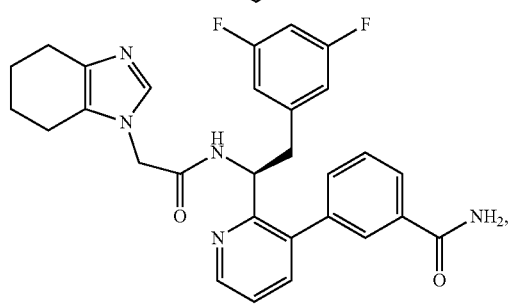

821
-continued
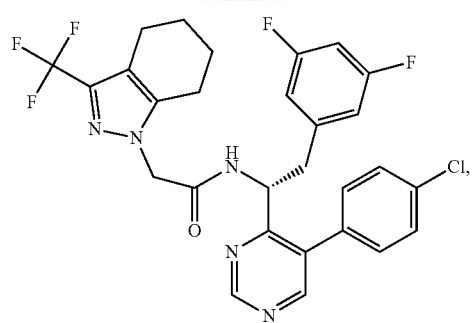
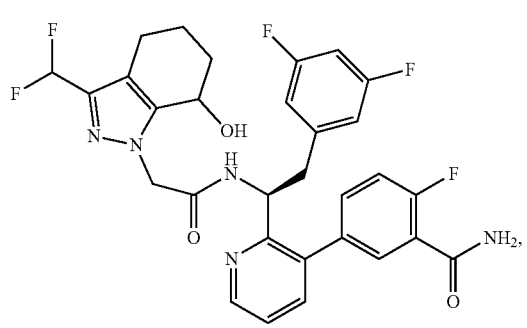
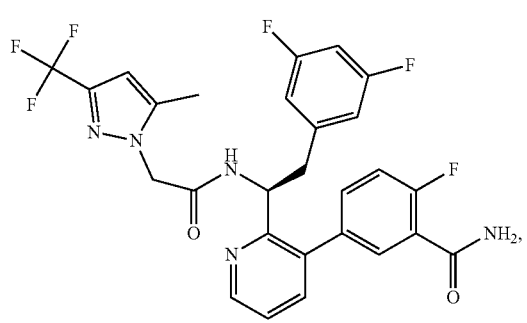
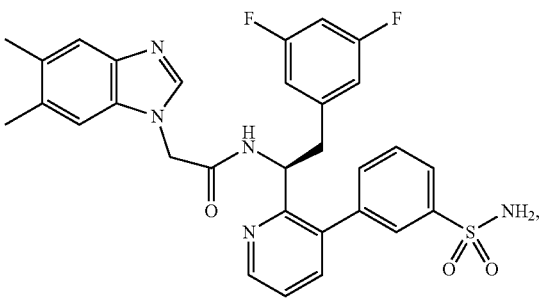
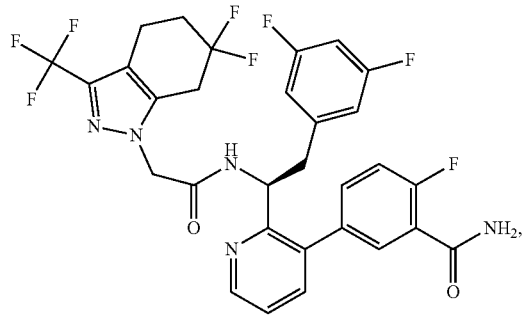
822
-continued
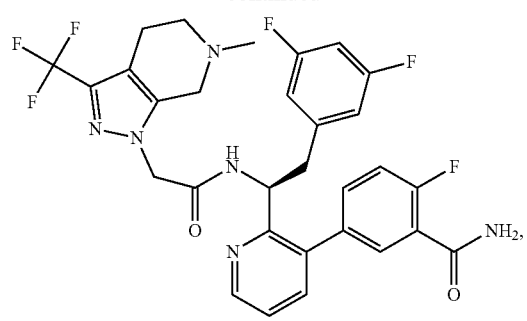
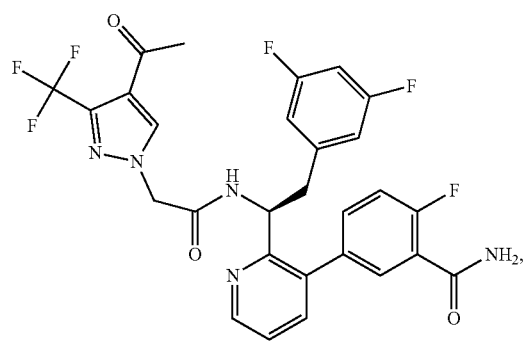
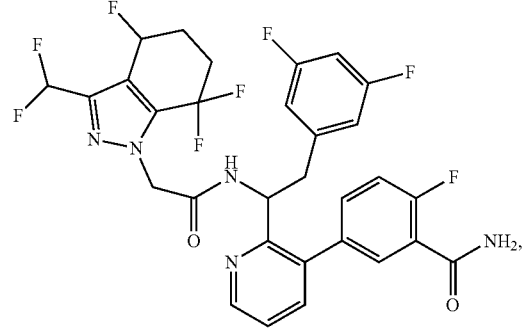
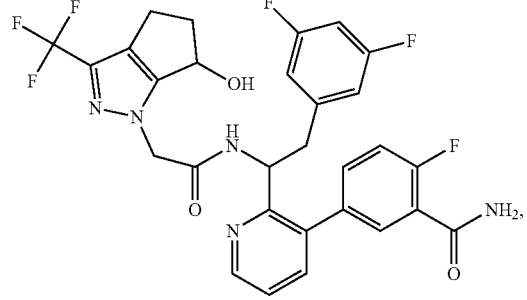
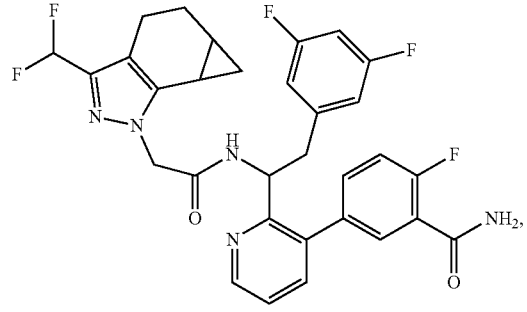

823
-continued
824
-continued
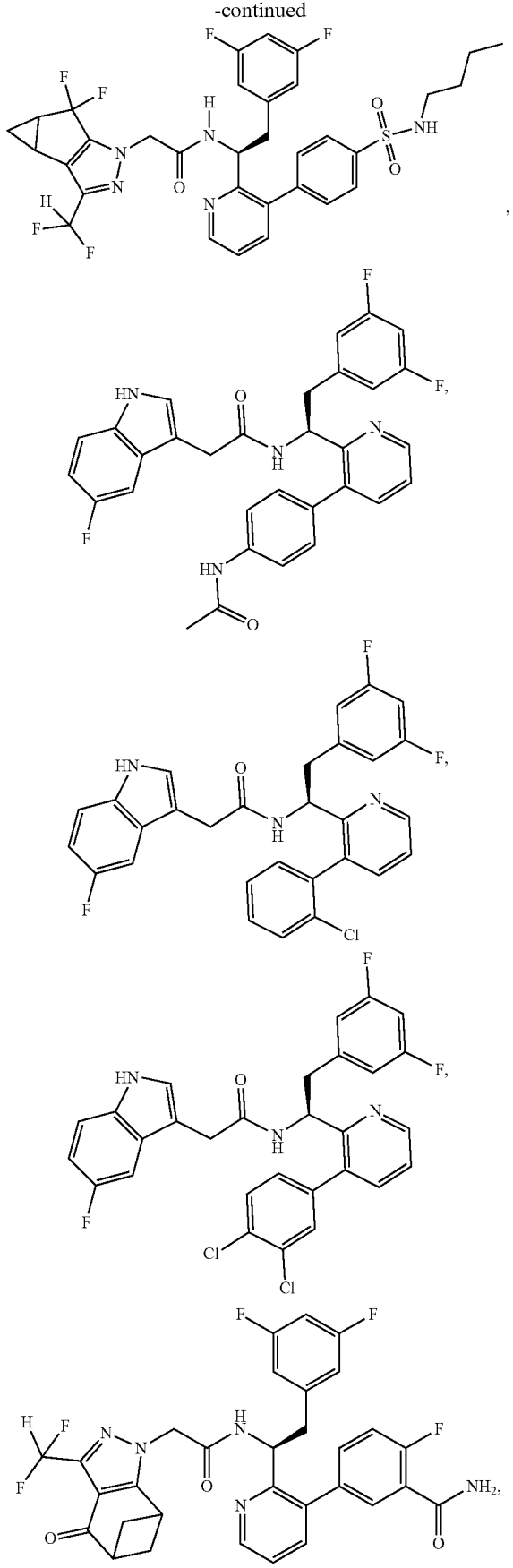
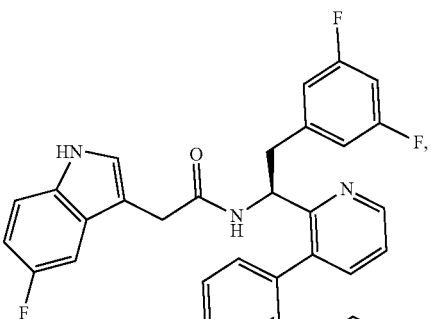
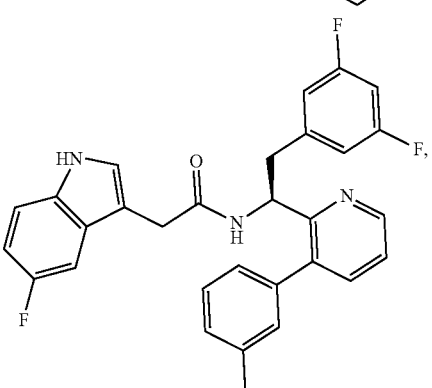
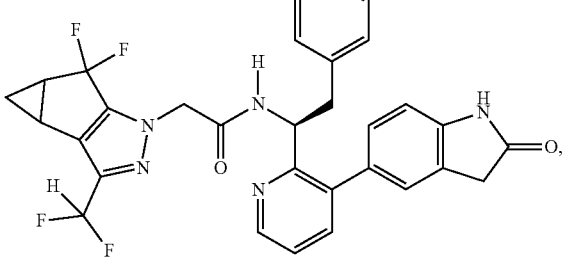
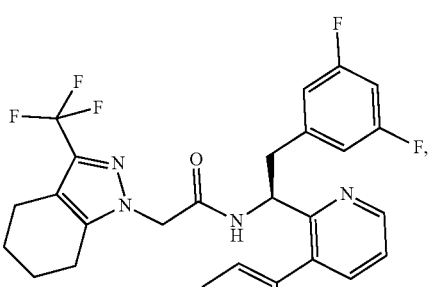
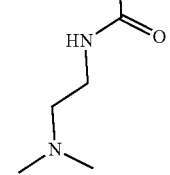

825
-continued
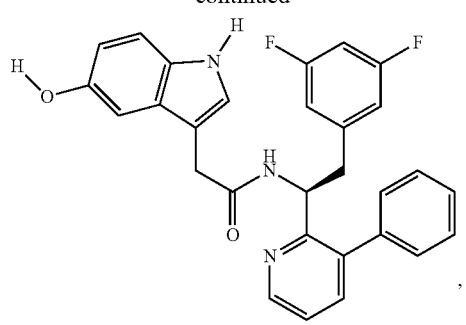
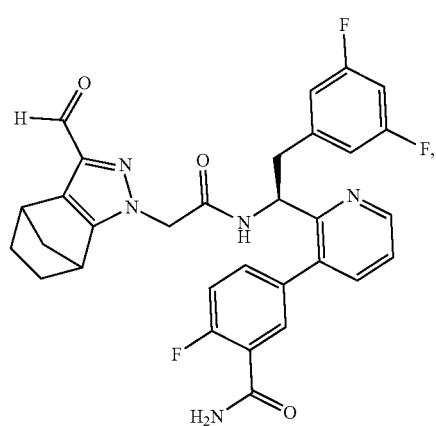
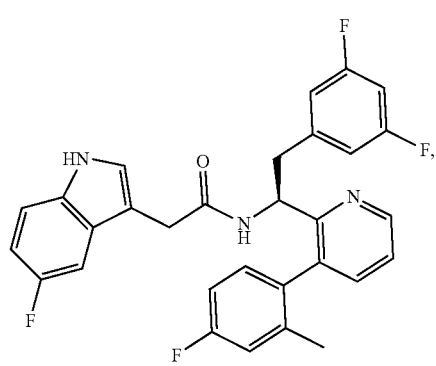
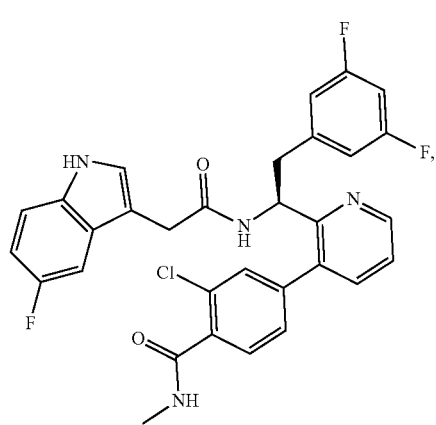
826
-continued
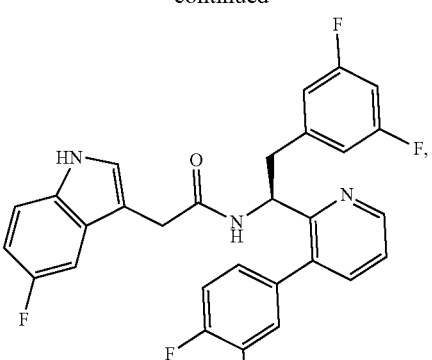
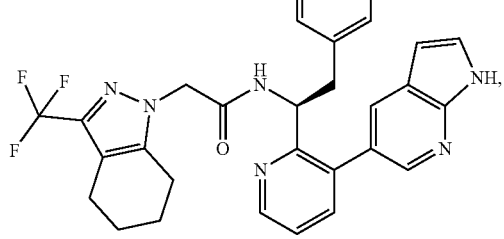
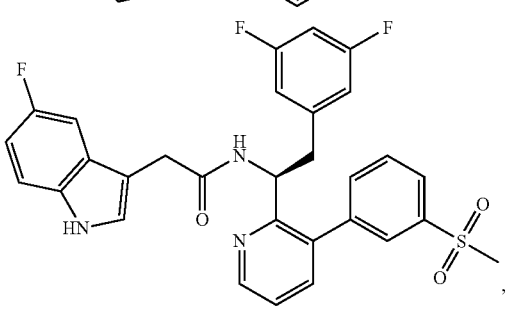
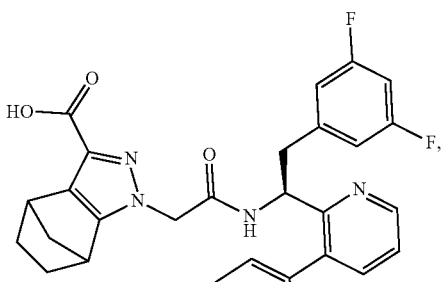
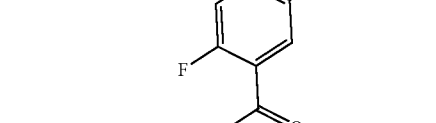
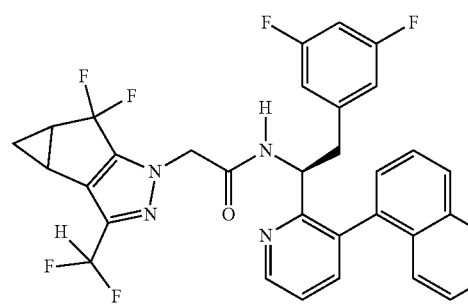

827
-continued
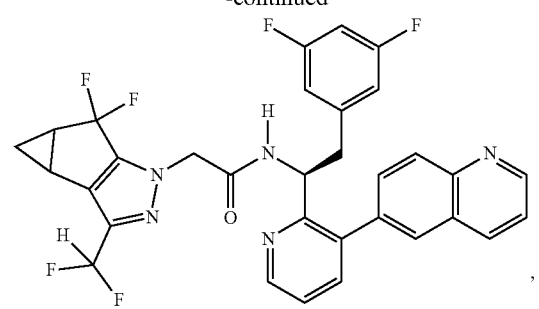
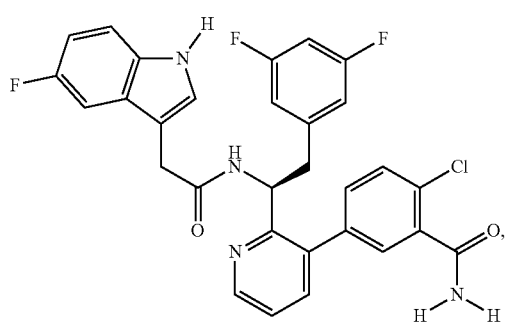
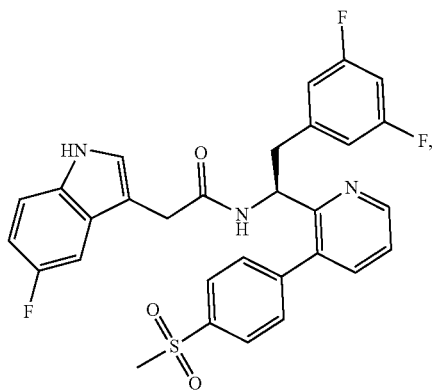
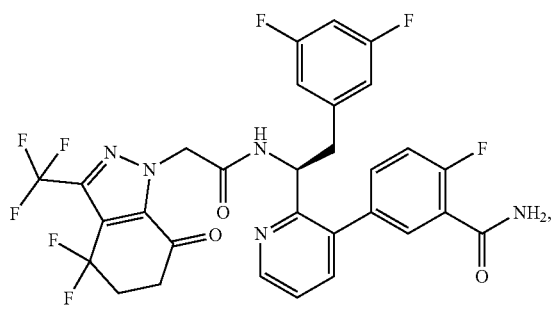
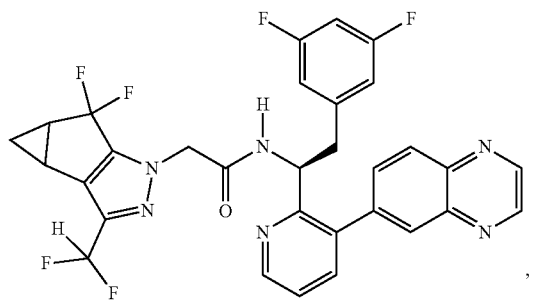
828
-continued
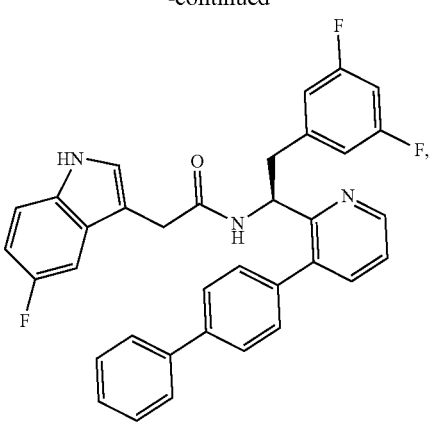
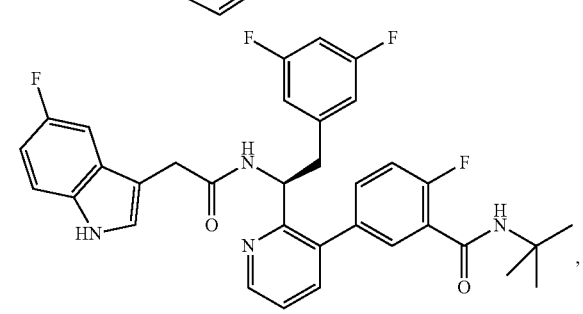
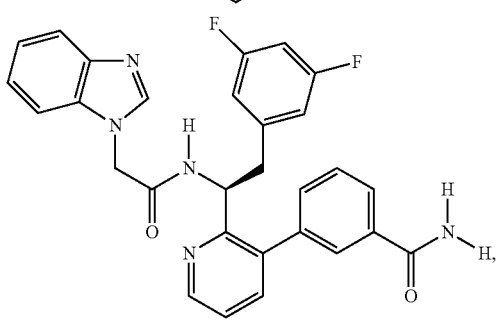
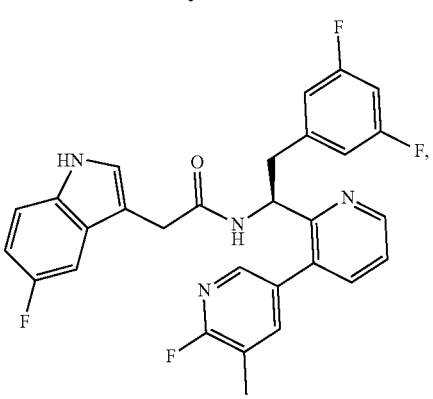
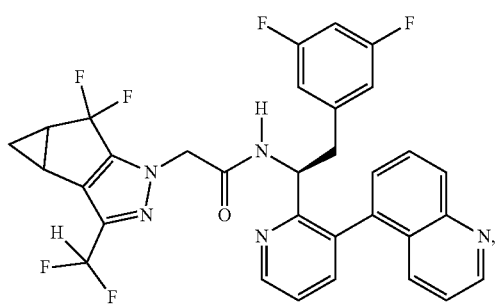

829
-continued
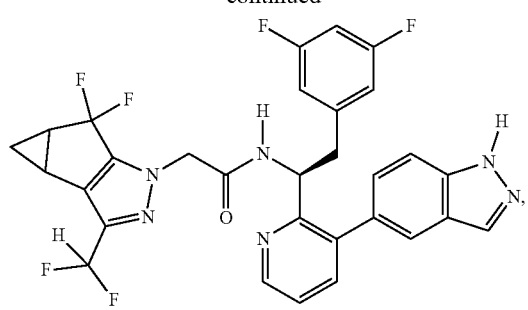
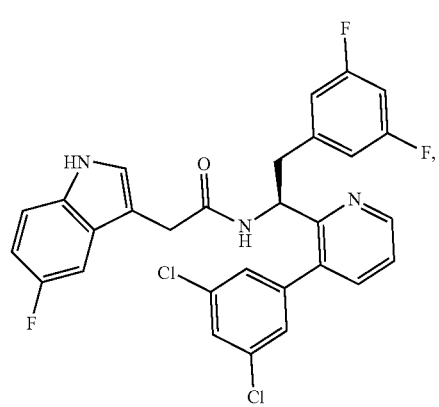
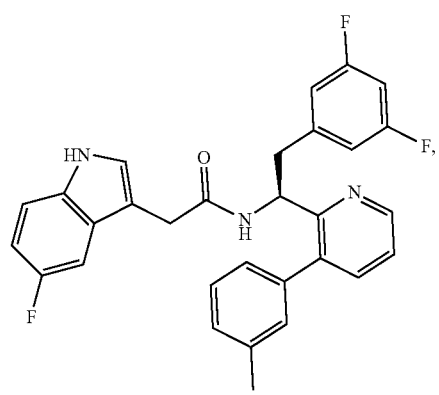
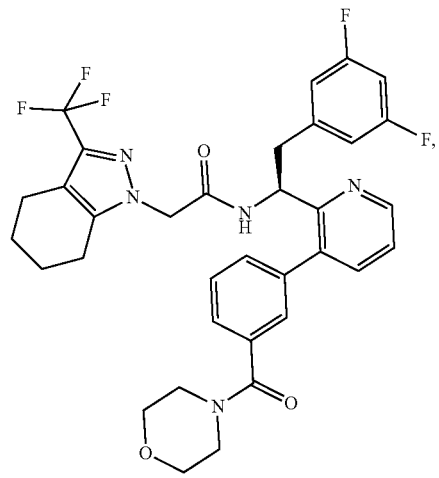
830
-continued
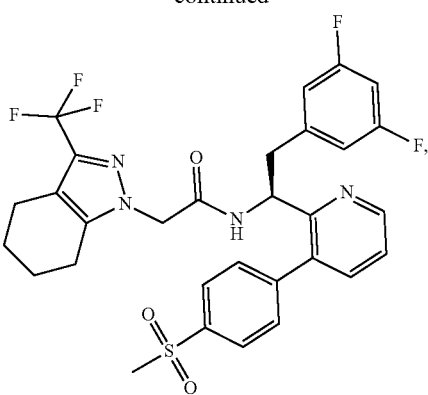
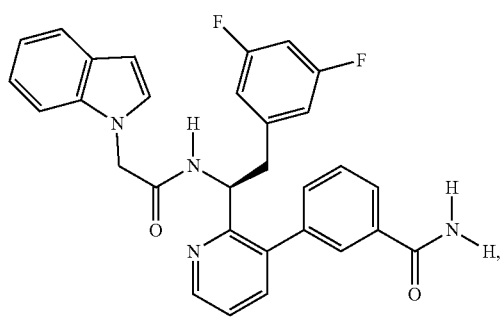
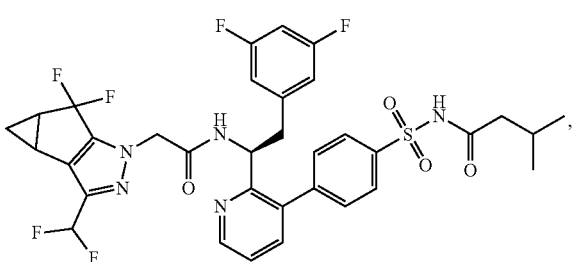
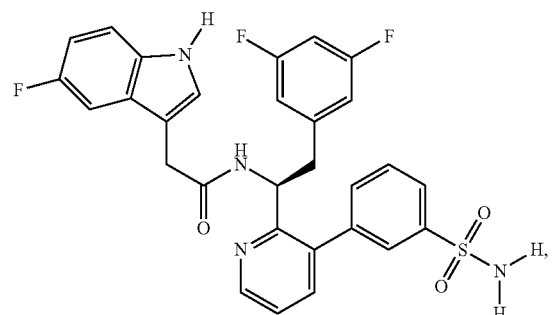
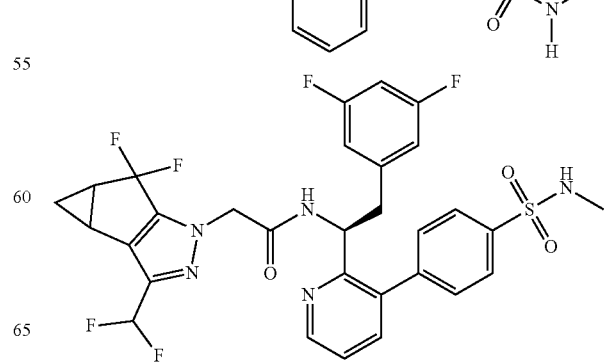

831
-continued
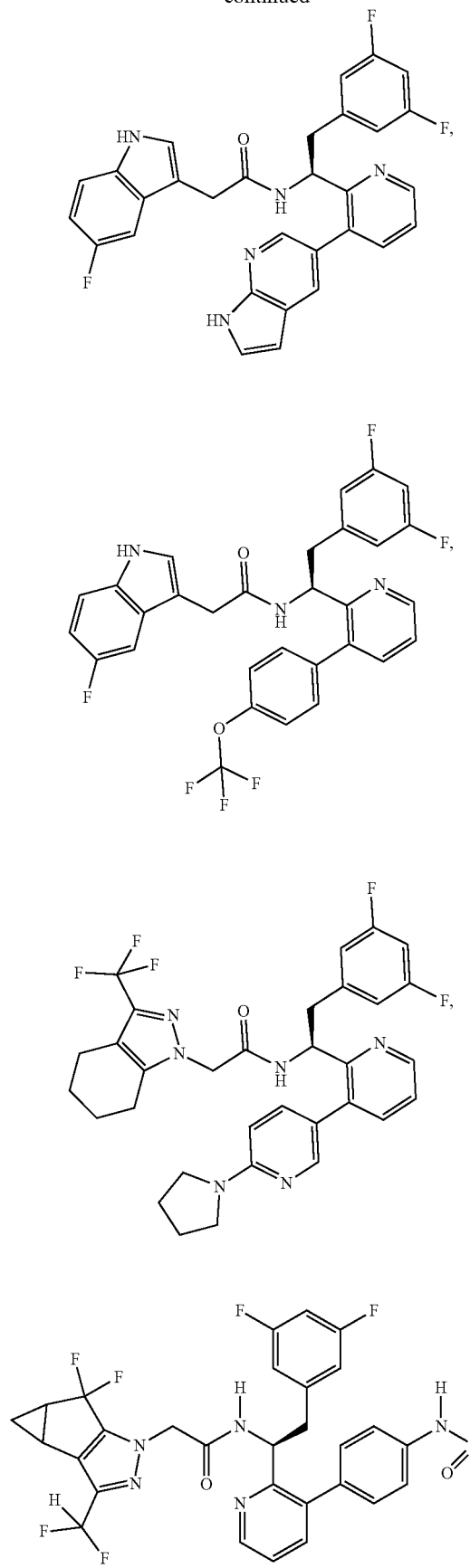
832
-continued
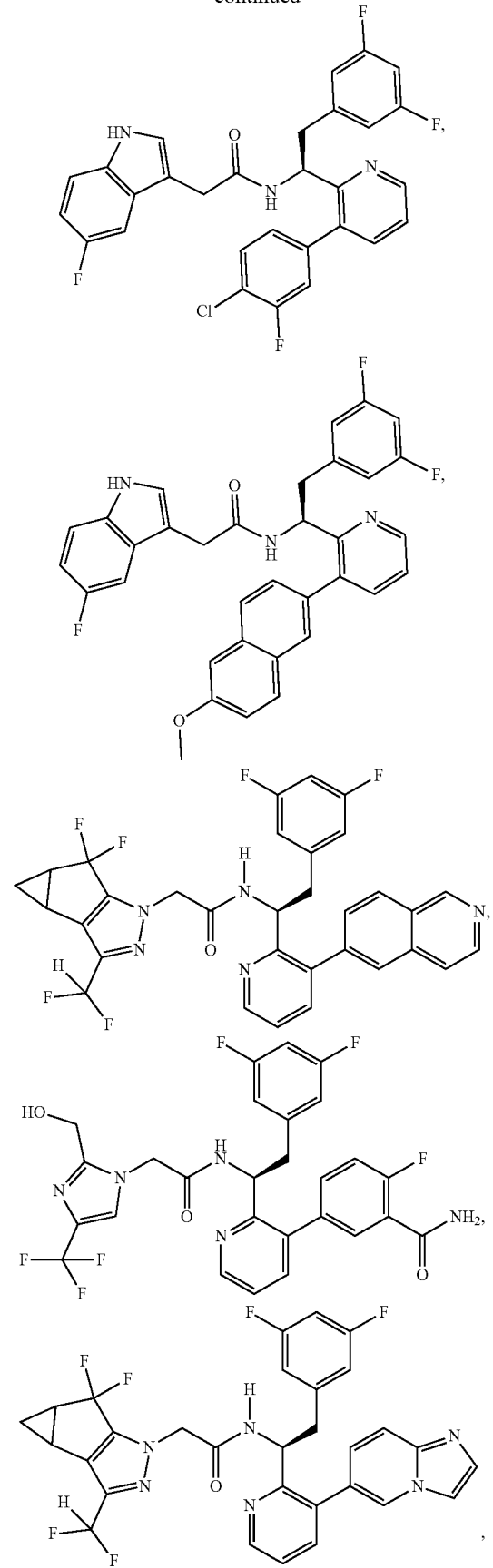

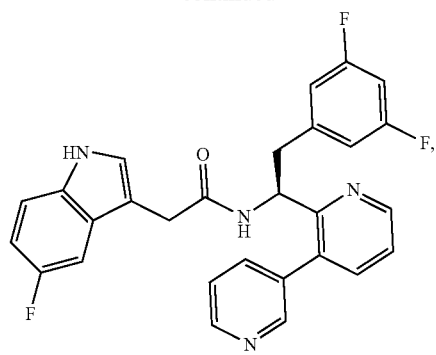
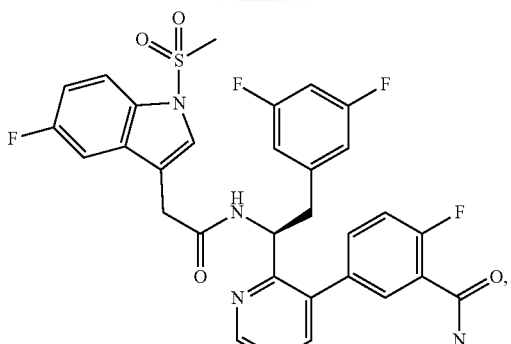
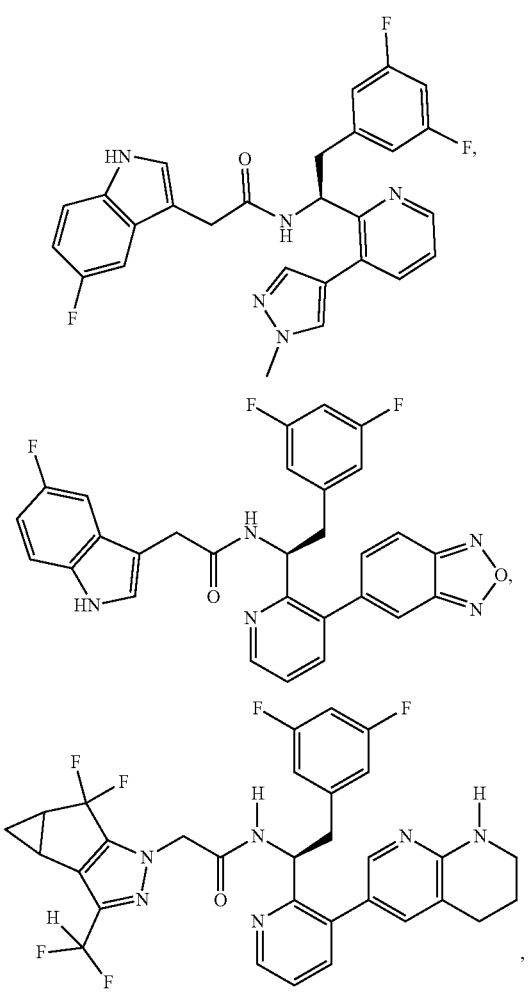
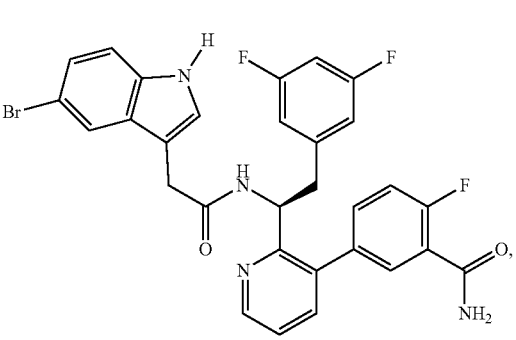
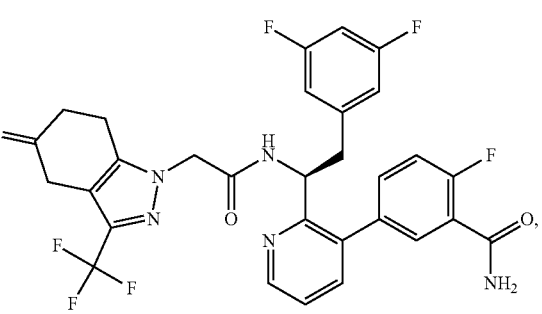
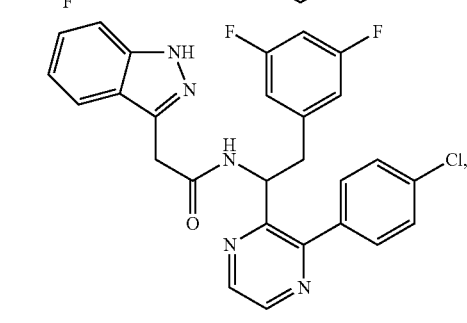
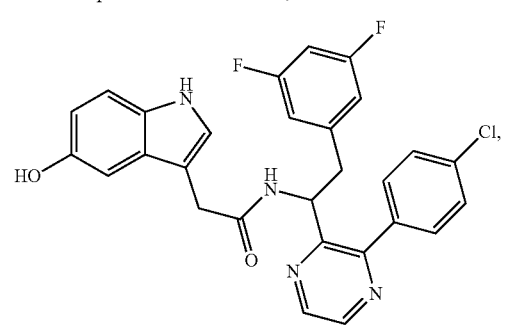
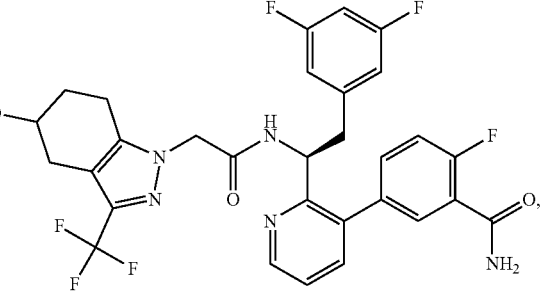

835
-continued
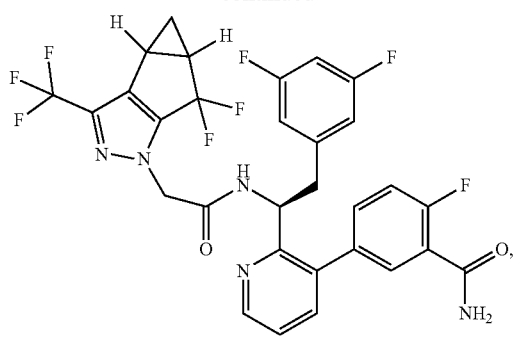
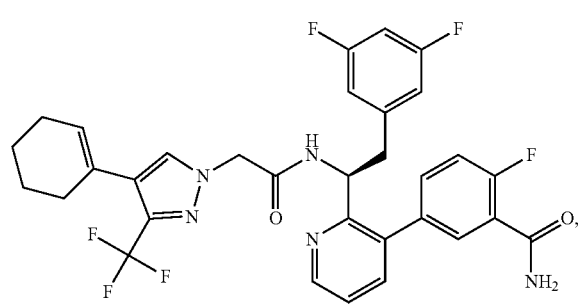
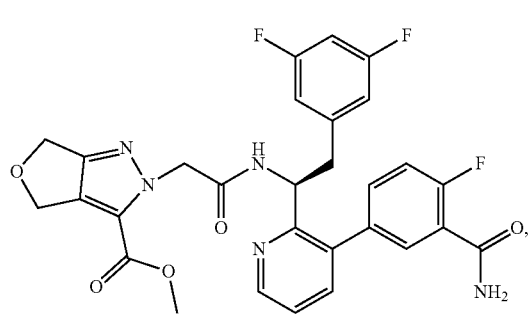
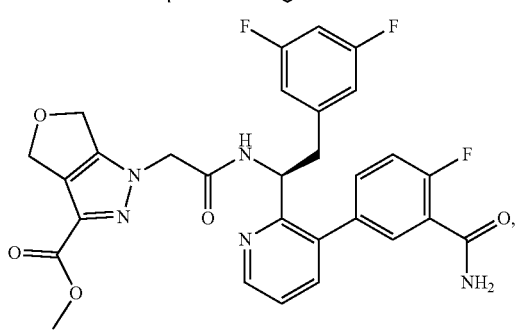
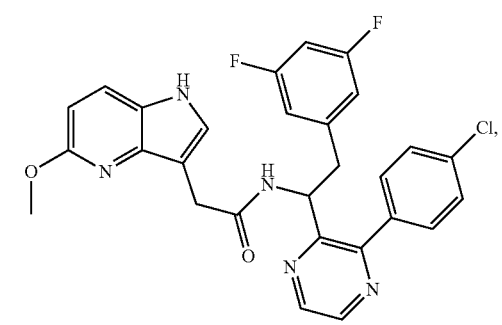
836
-continued
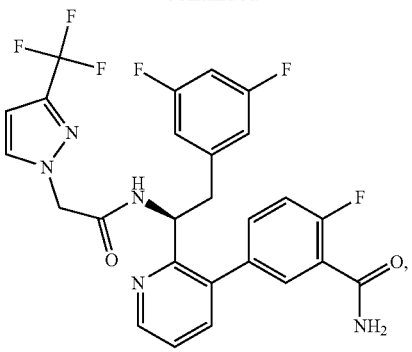
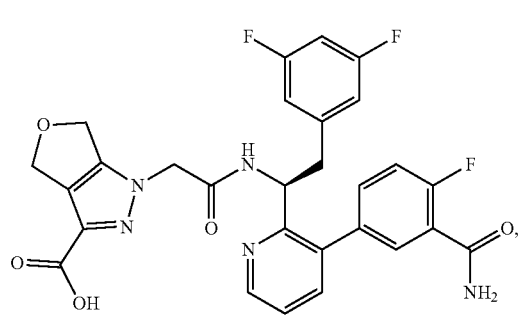
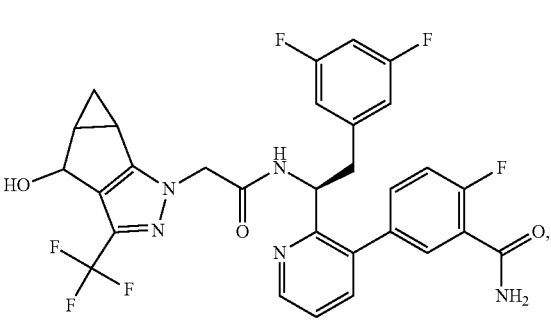
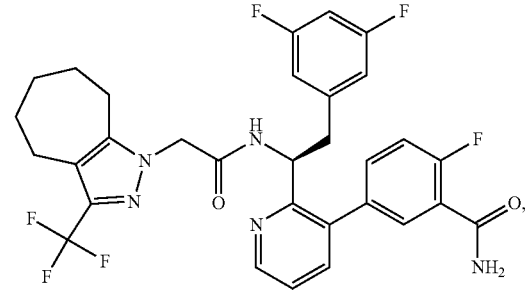
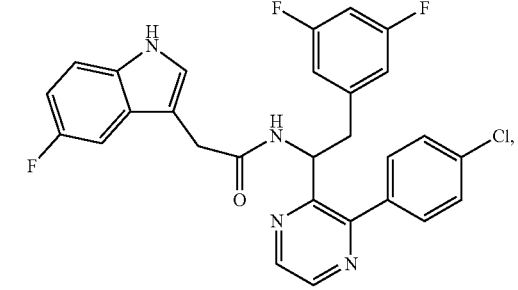

837
-continued
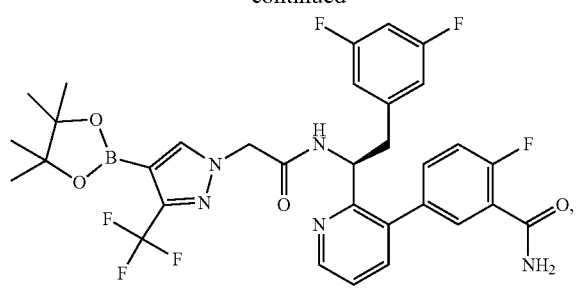
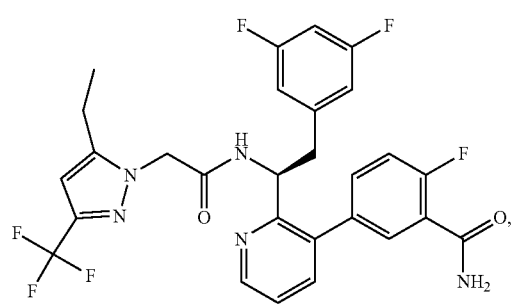
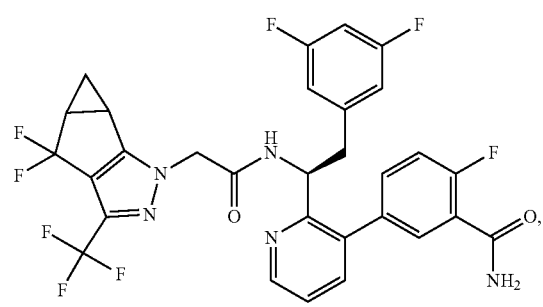
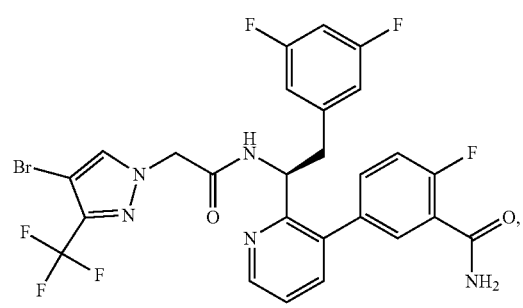
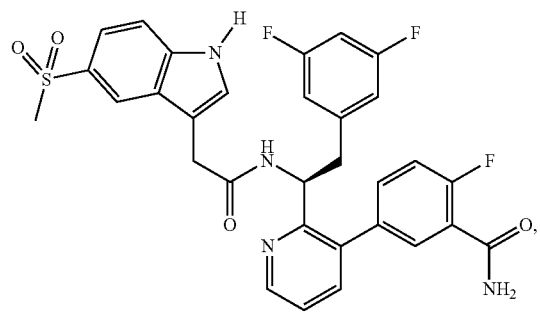
838
-continued
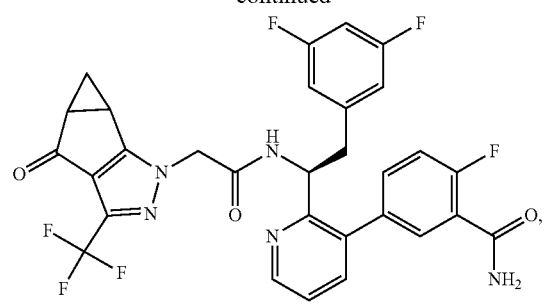
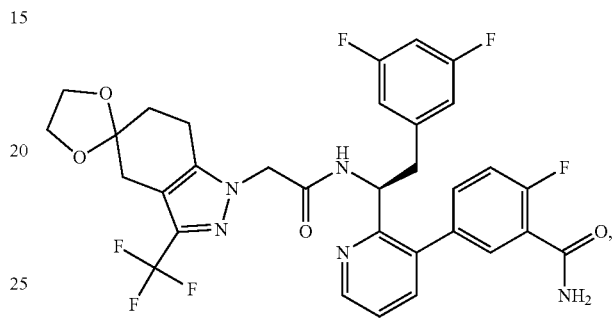
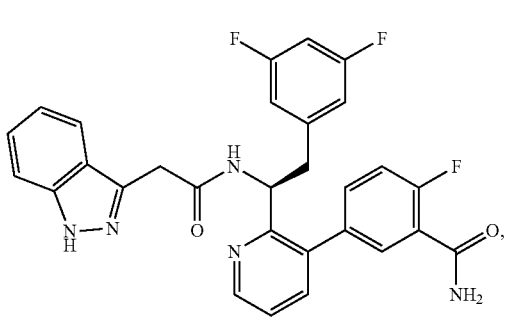
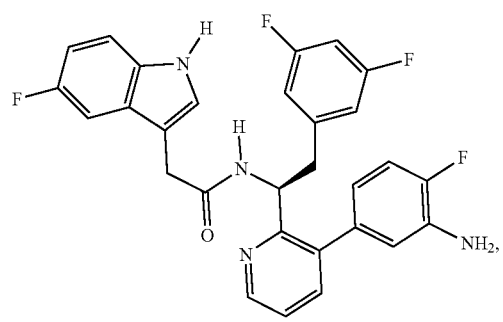
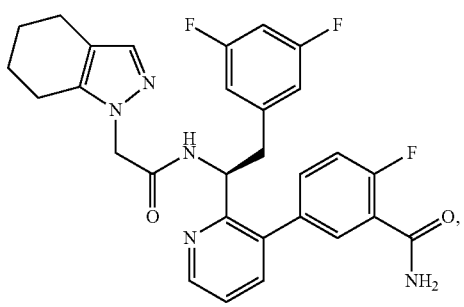

839
-continued
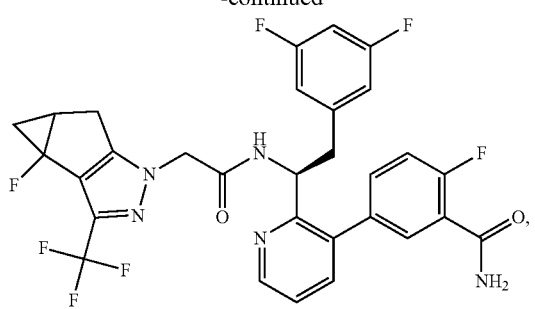
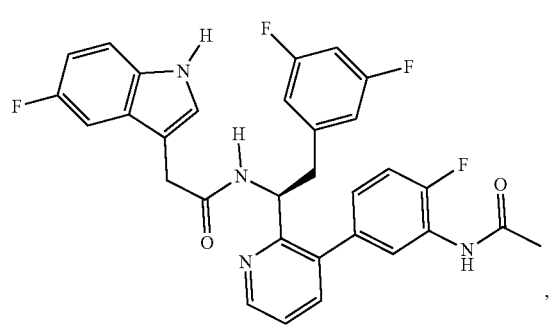
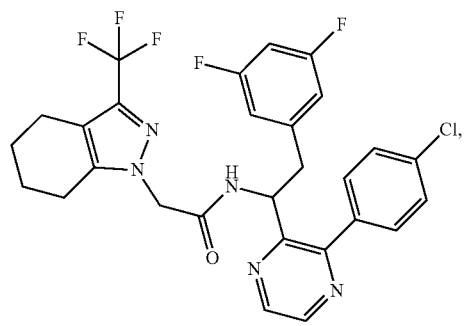
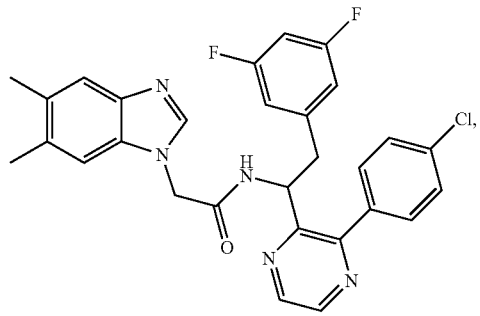
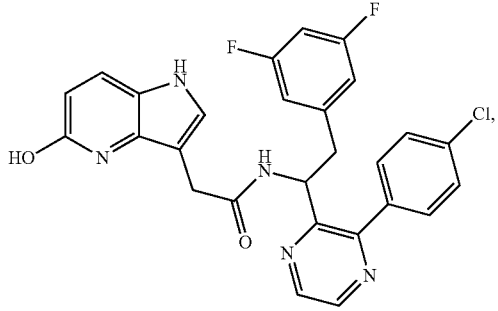
840
-continued
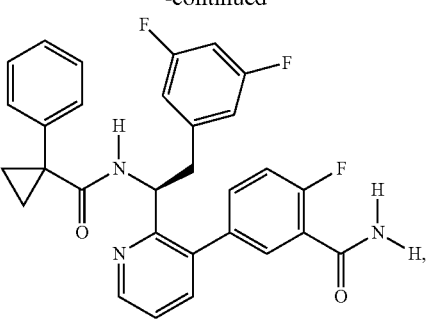
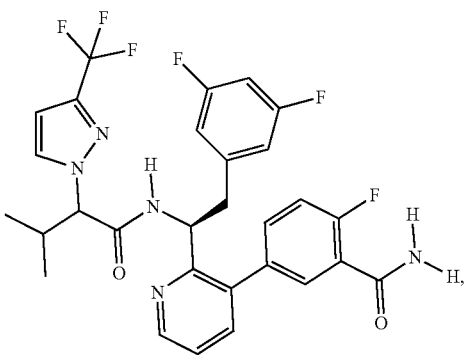
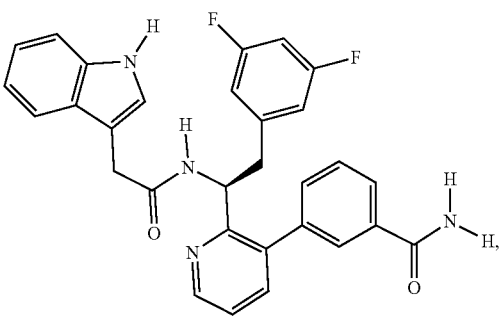
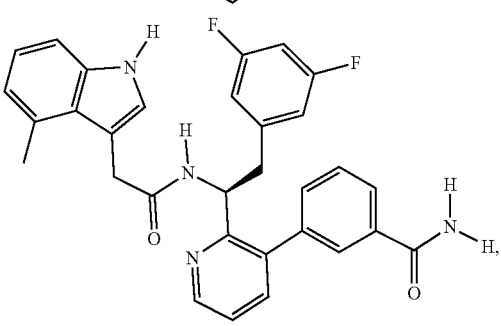
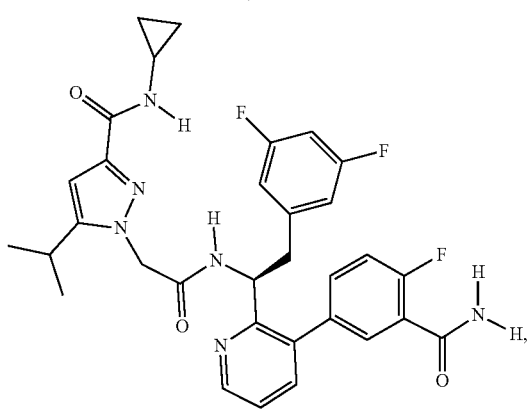

841
-continued
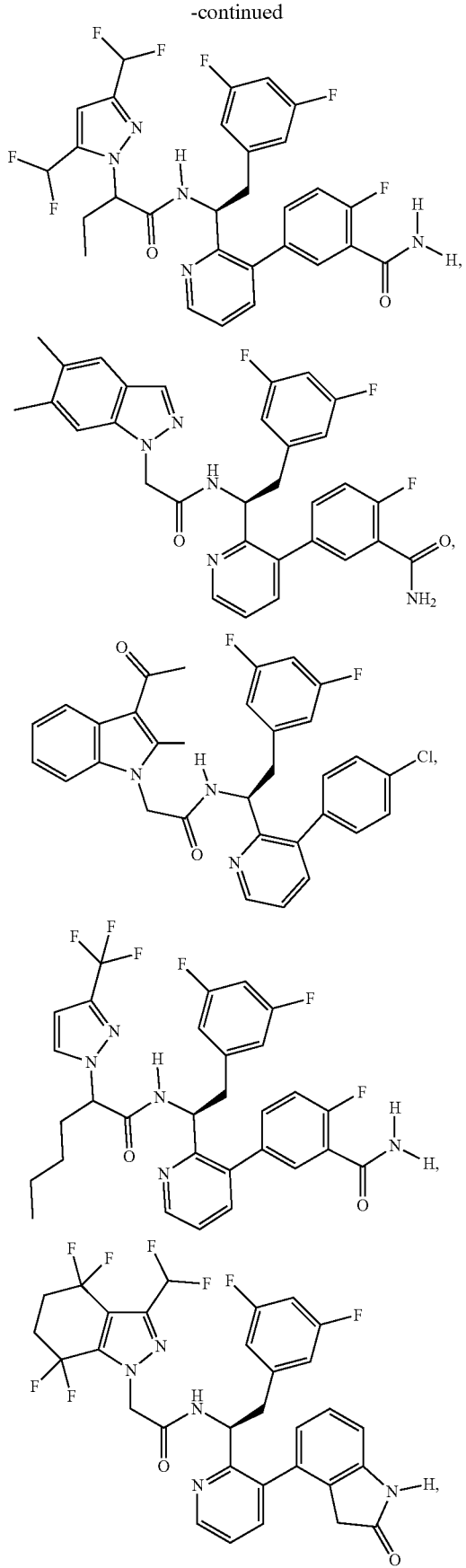
842
-continued
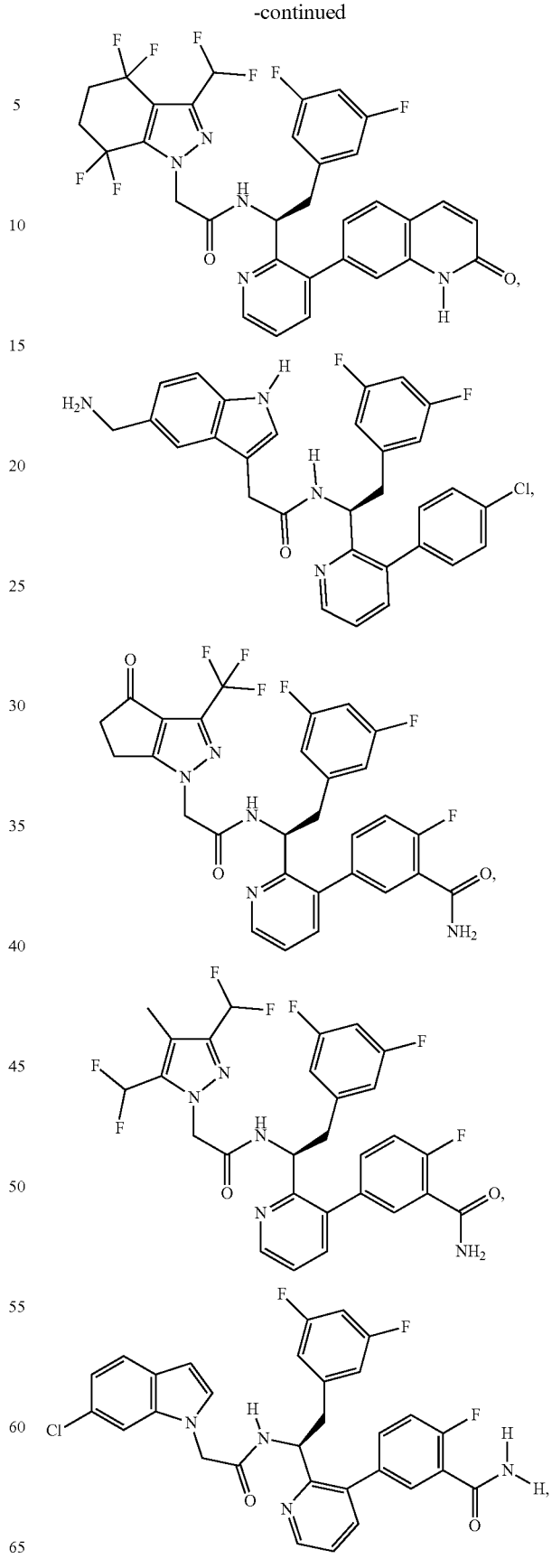

843
-continued
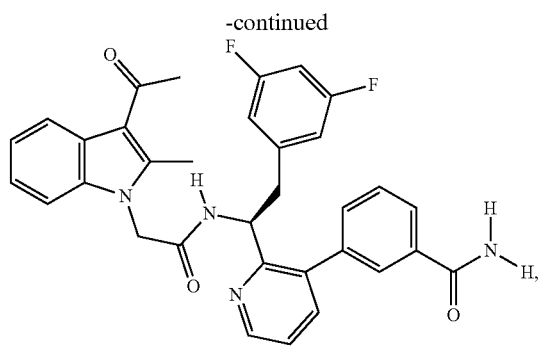
844
-continued
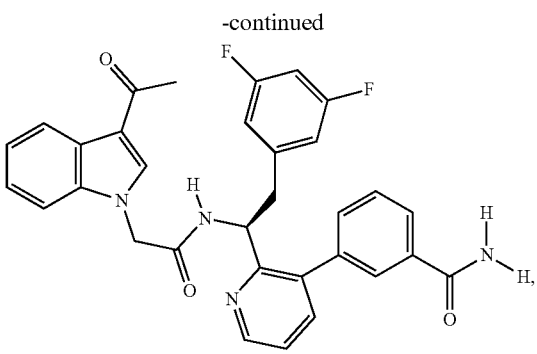

845
-continued
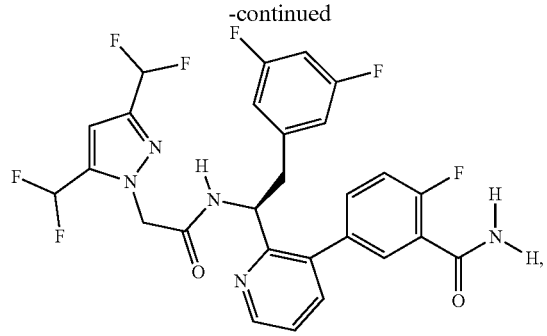
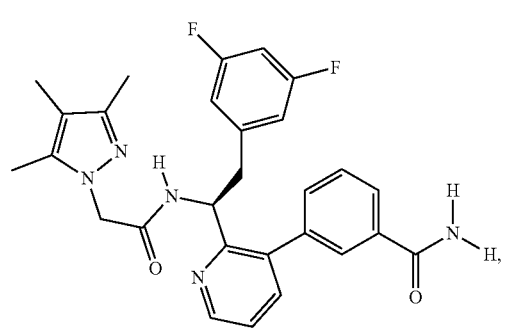
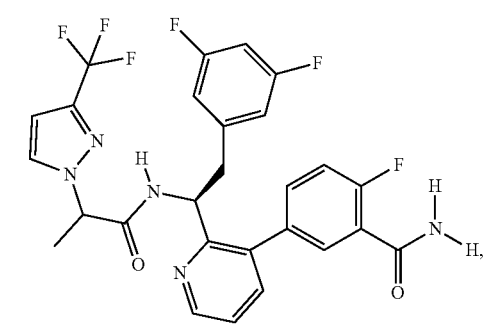
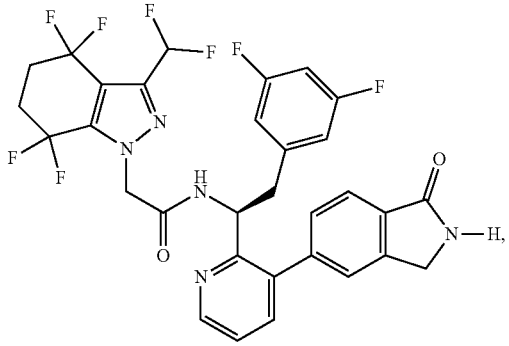
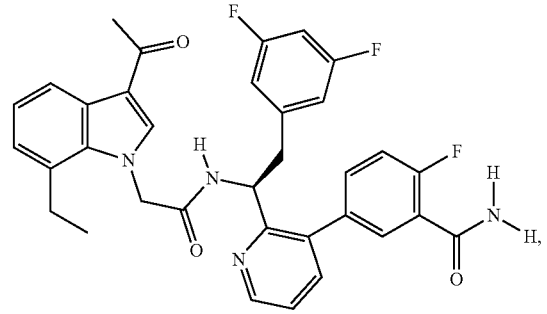
846
-continued
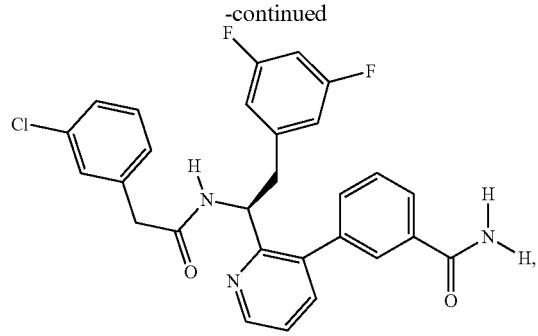
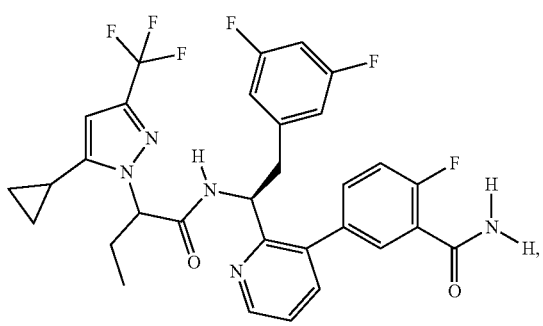
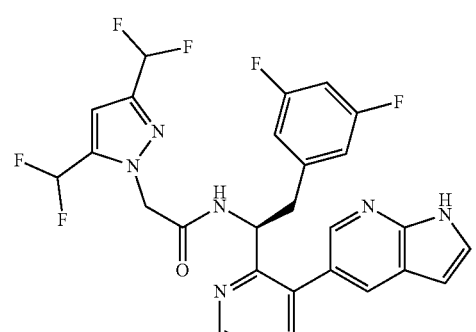
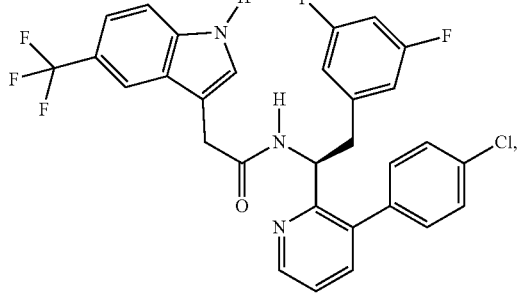
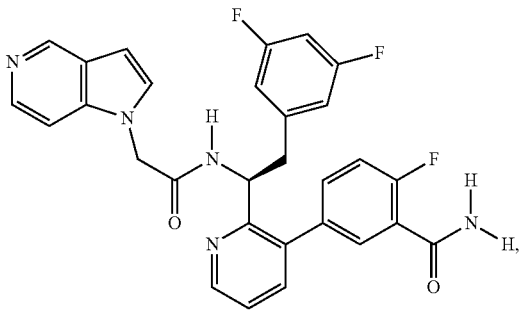

847
-continued
848
-continued
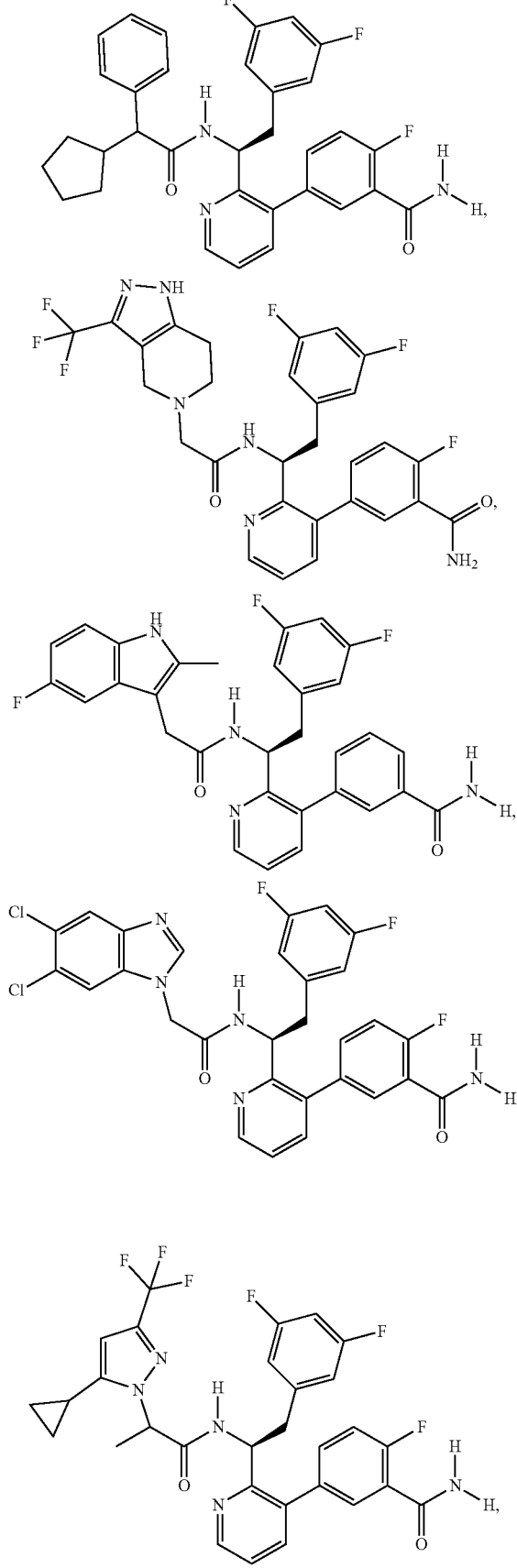
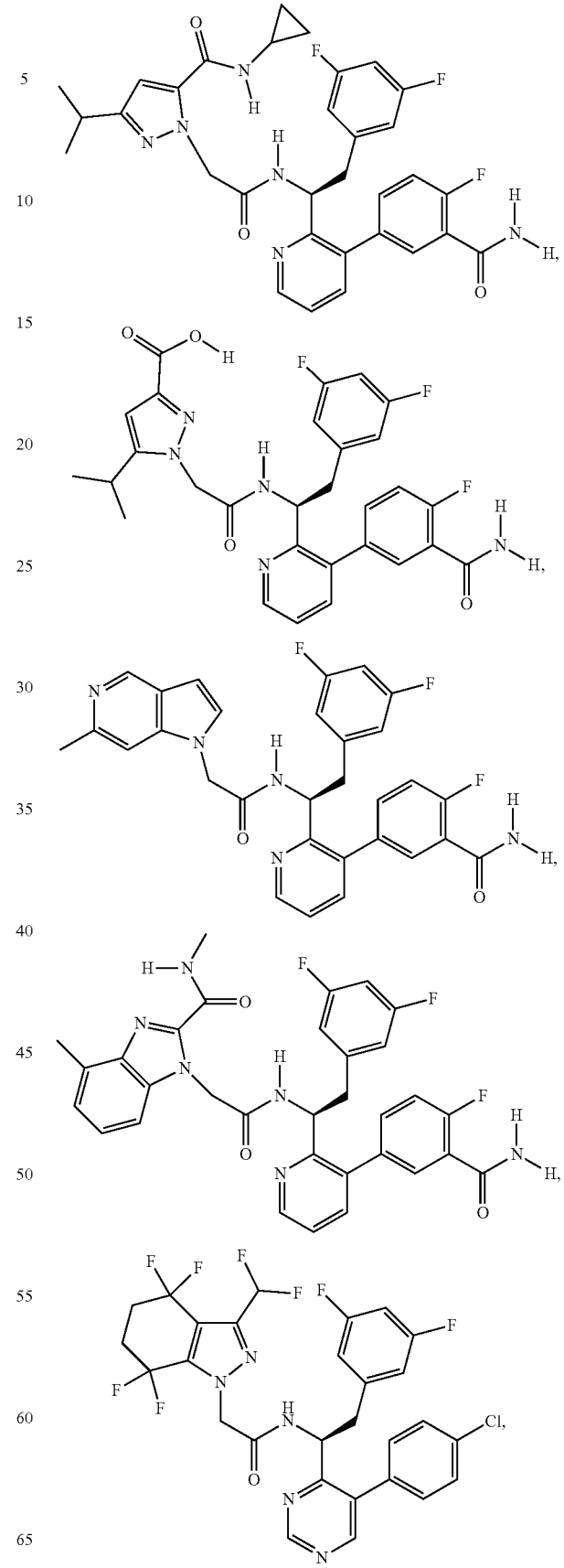

849 850

851
-continued
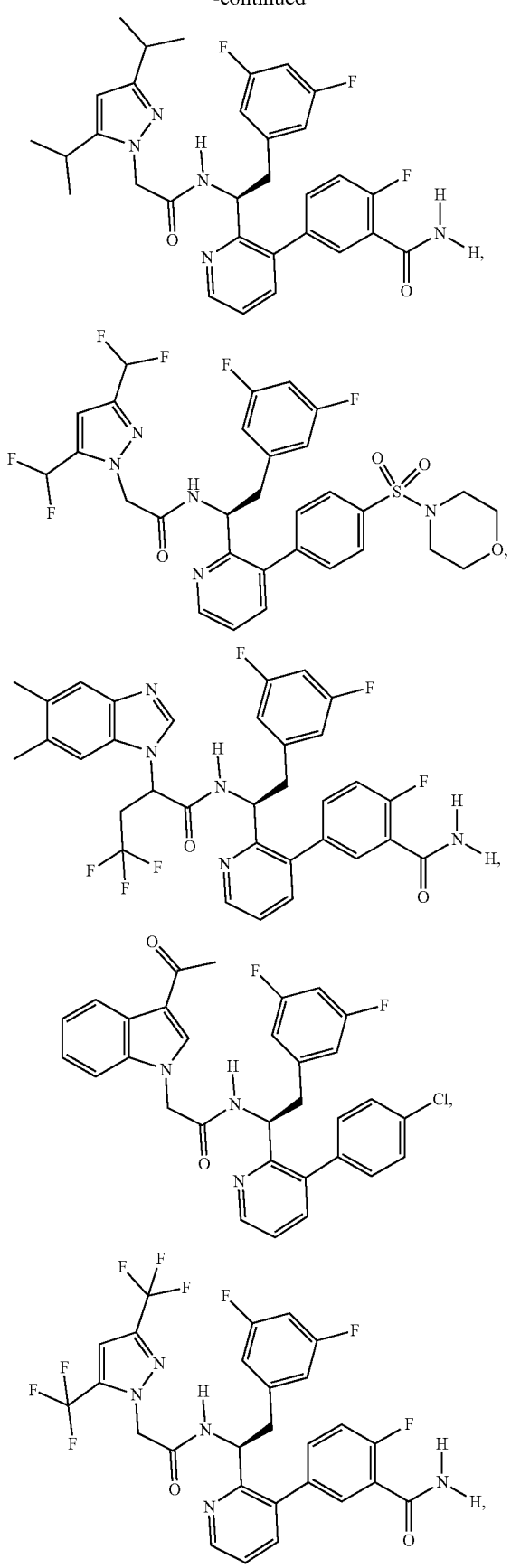
852
-continued
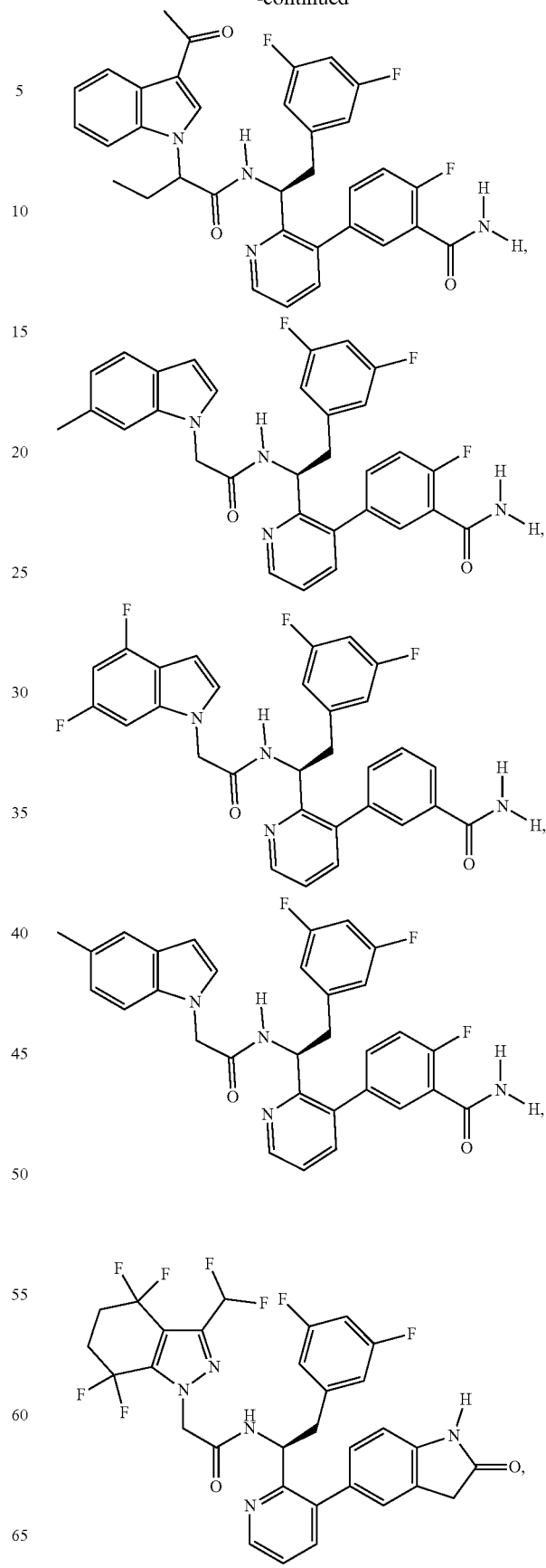

853
-continued
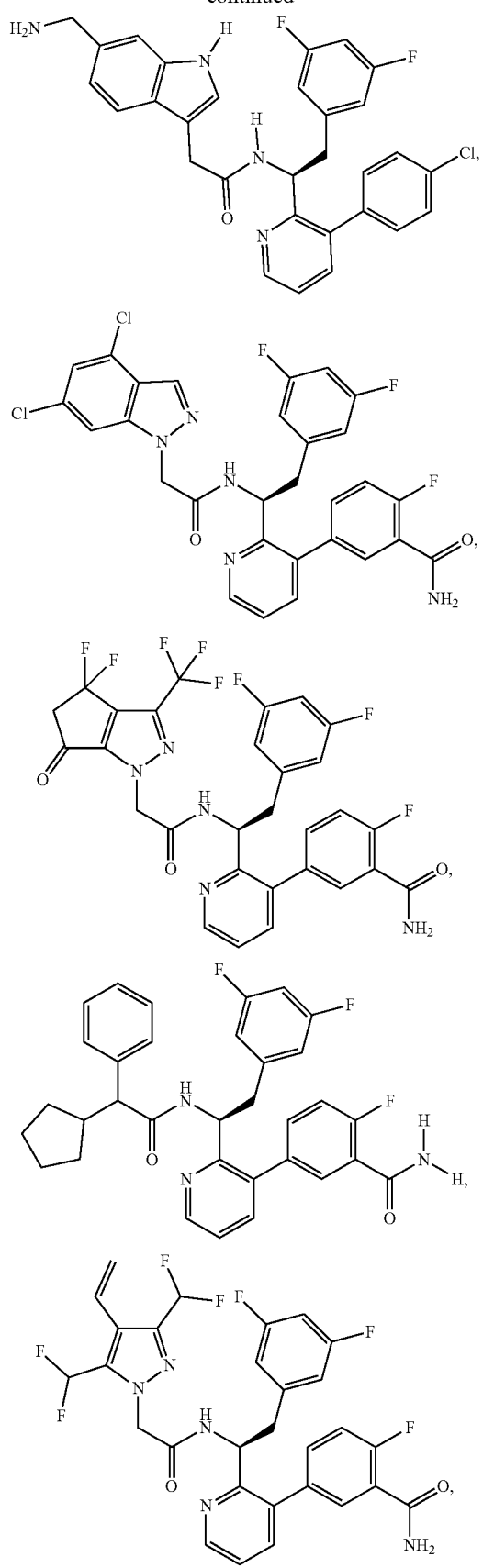
854
-continued
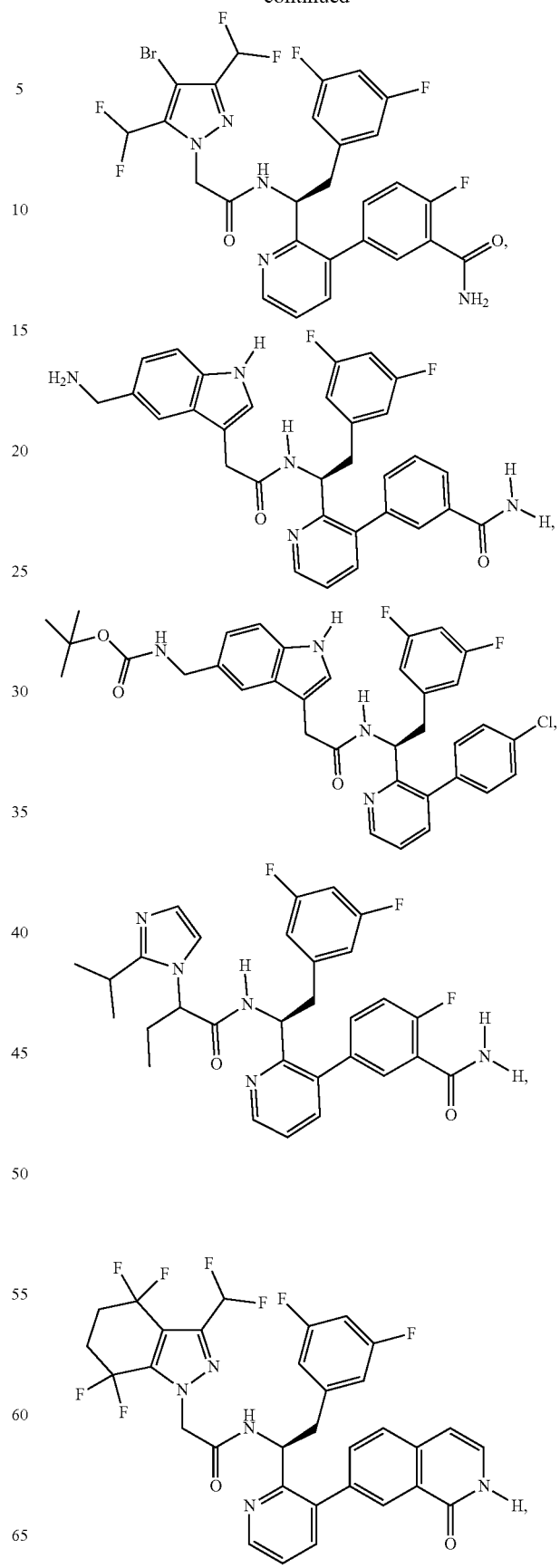

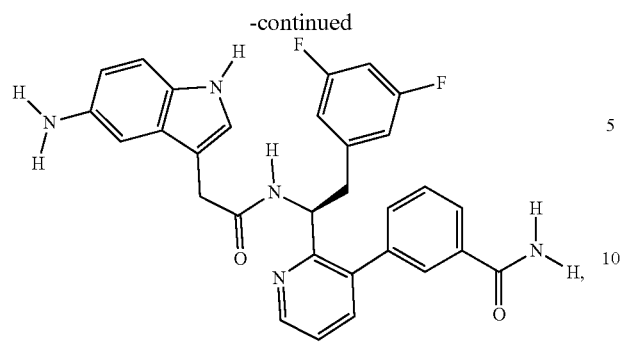
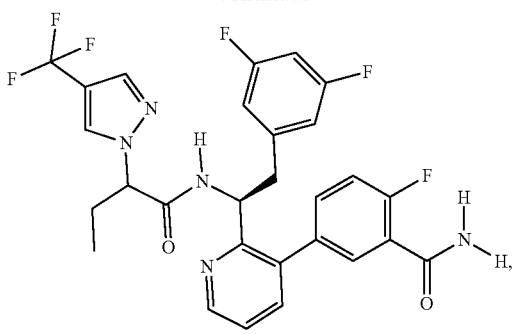
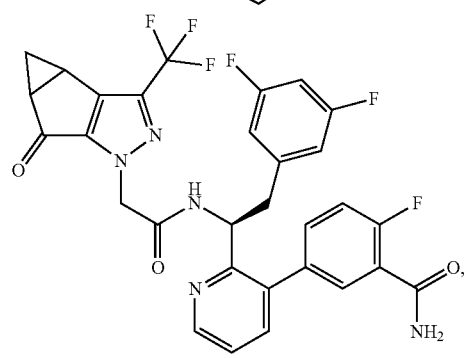
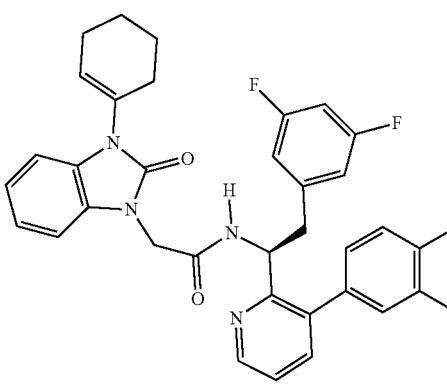
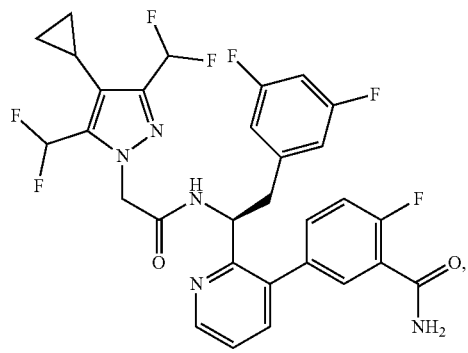
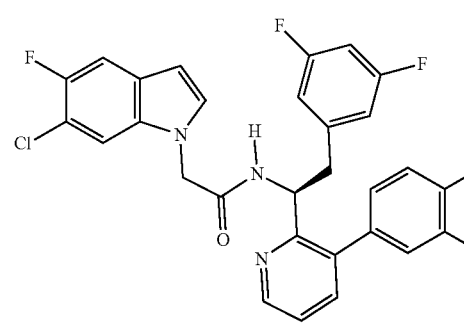
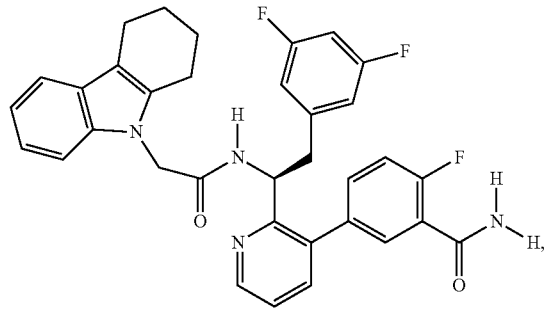
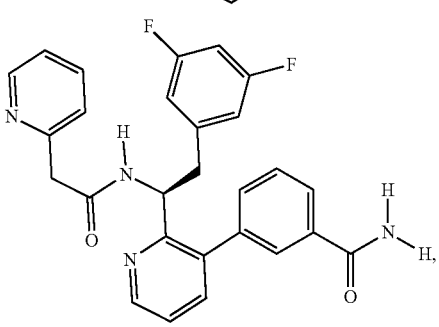
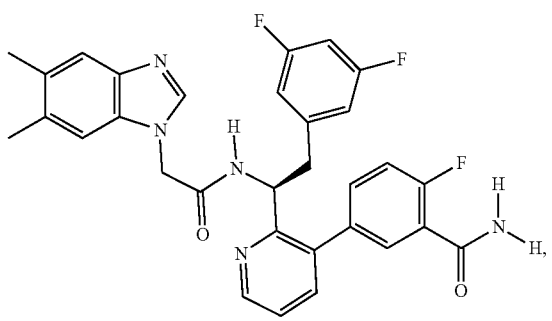
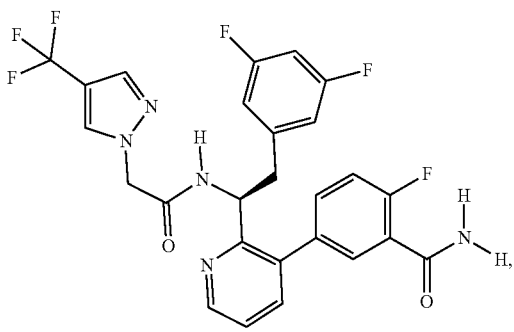

857
-continued
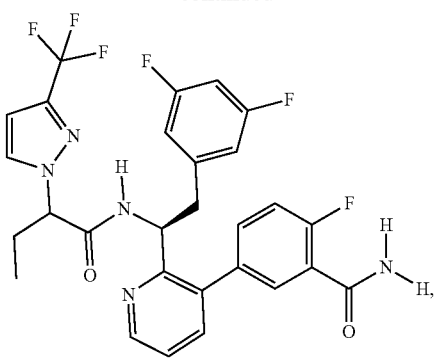
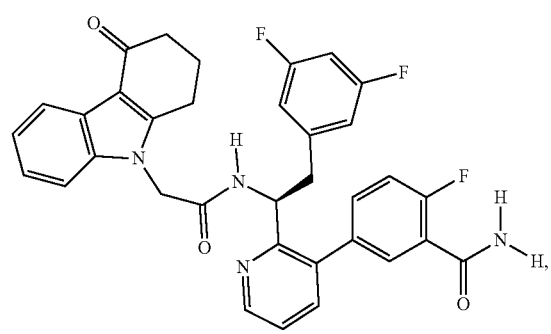
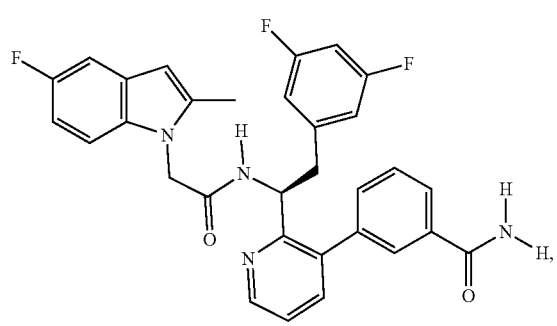
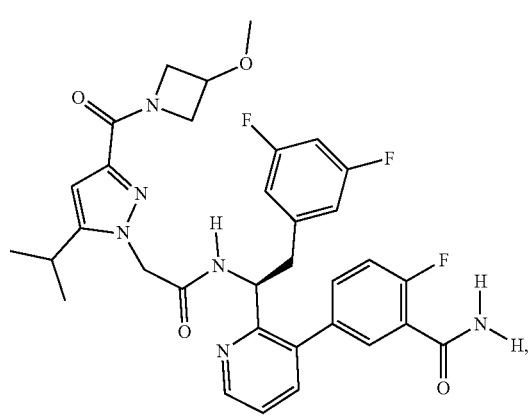
858
-continued
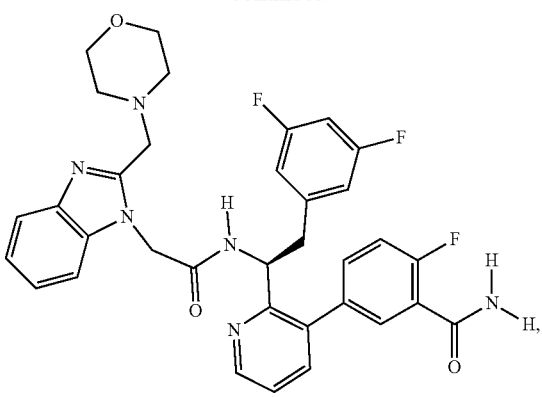
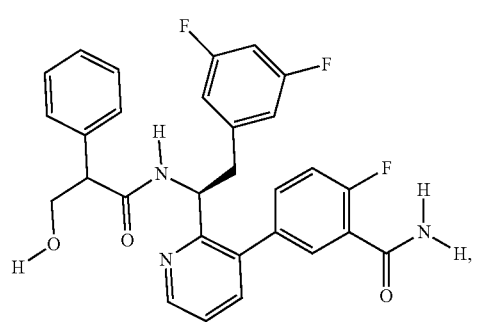
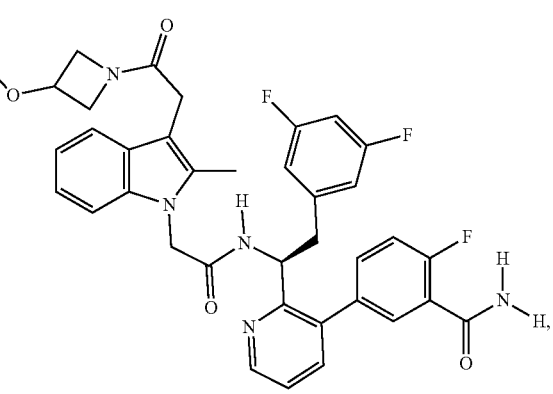
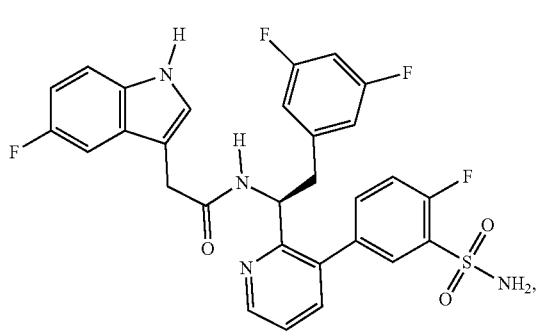

859
-continued
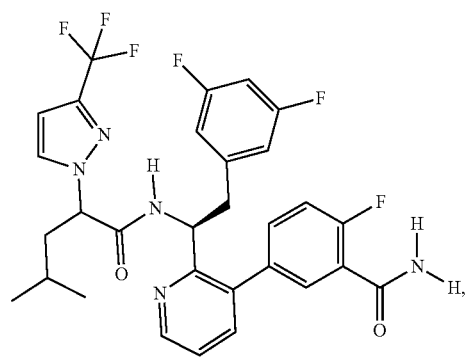
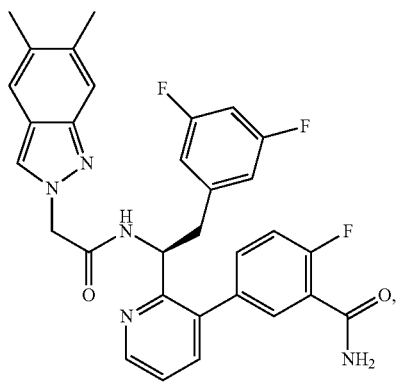
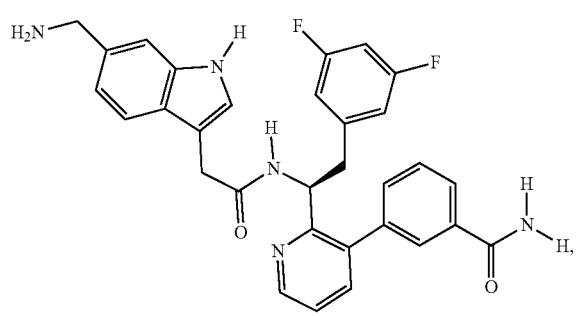
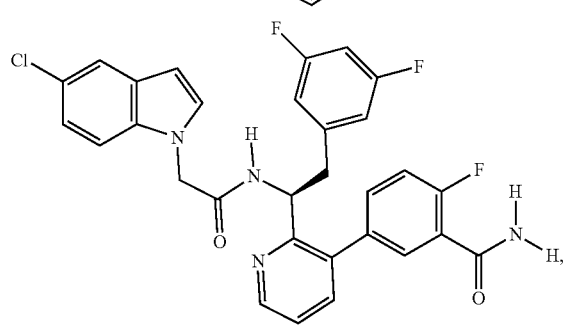
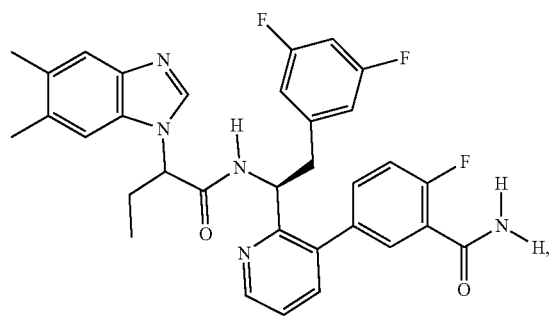
860
-continued
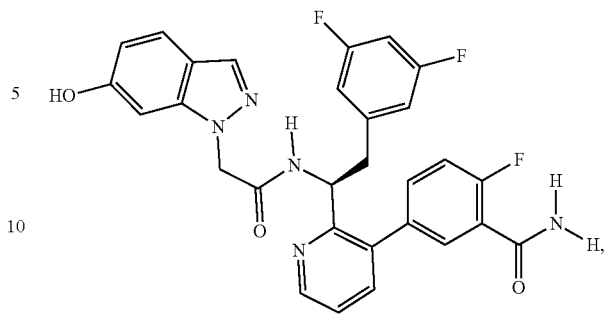
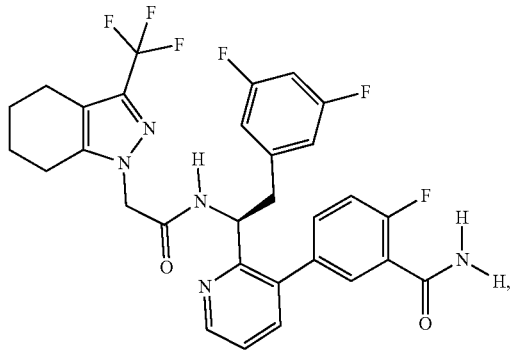
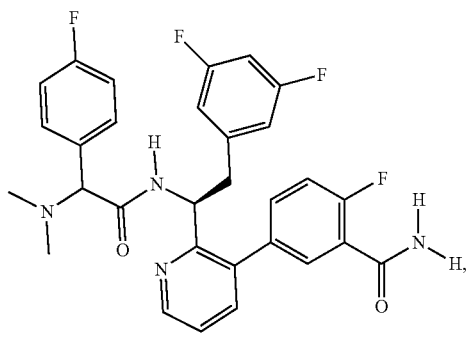
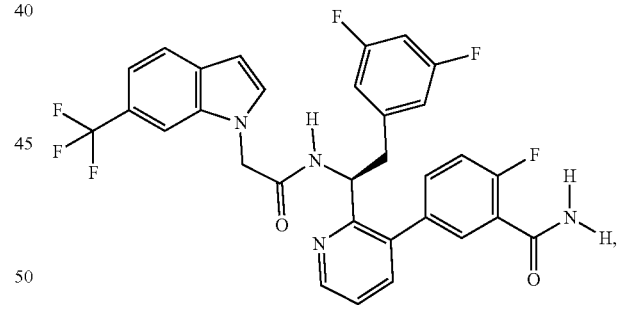
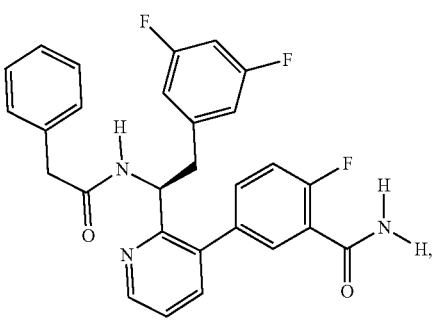

861
-continued
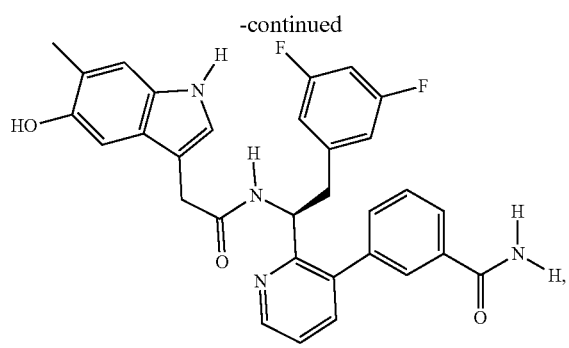
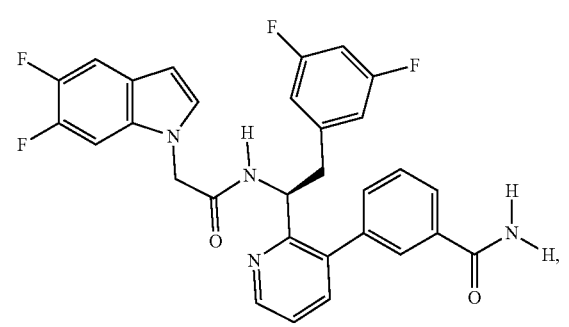
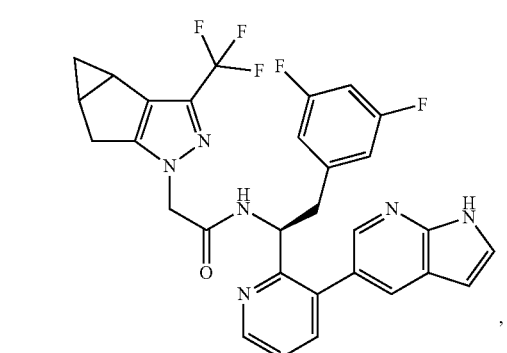
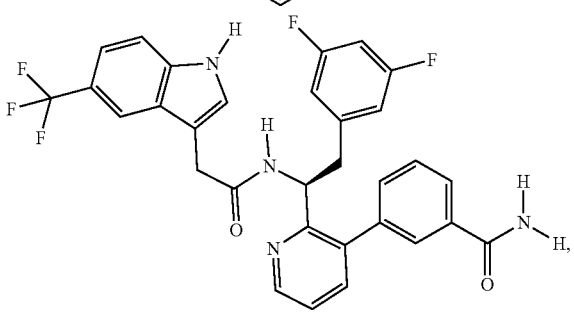
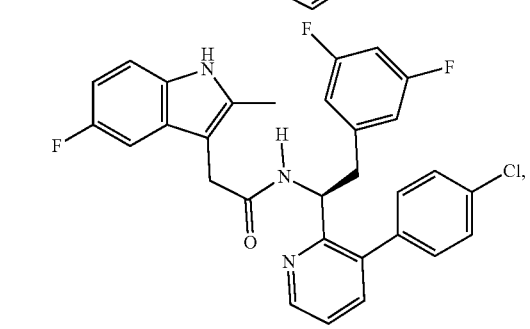
862
-continued
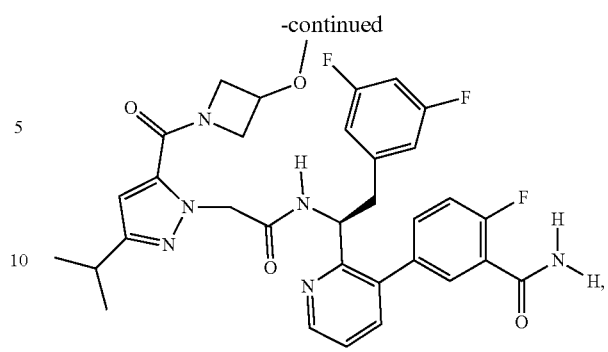
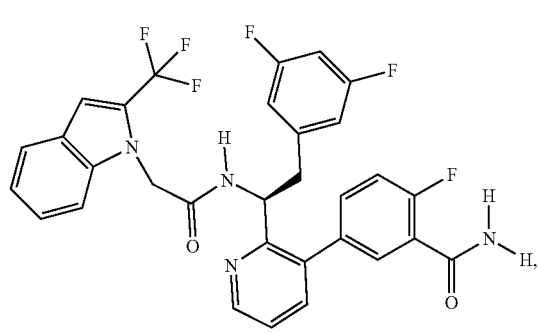
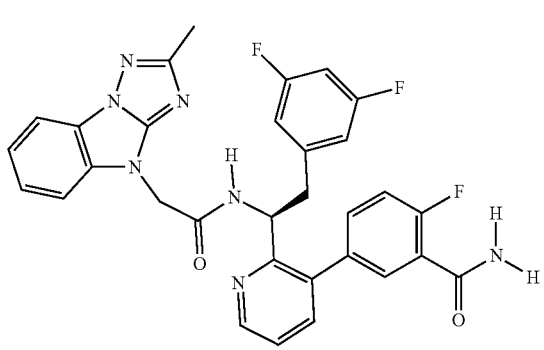
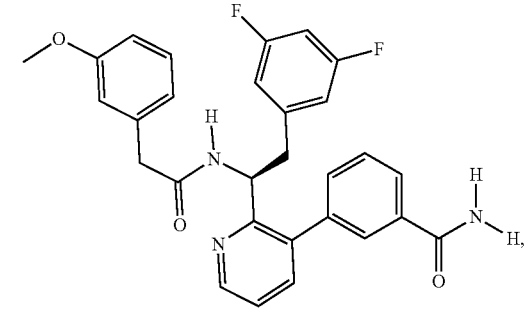
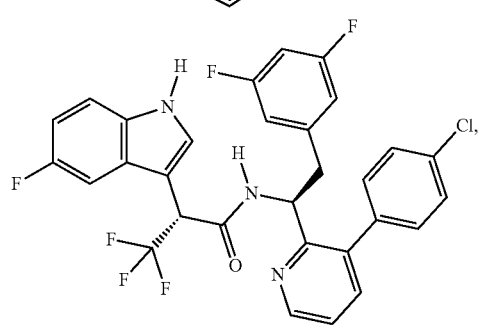

863 -continued

864 -continued

865
-continued
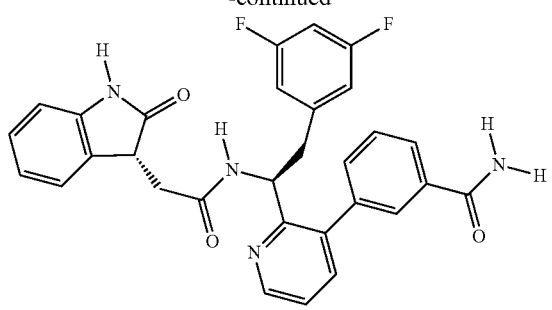
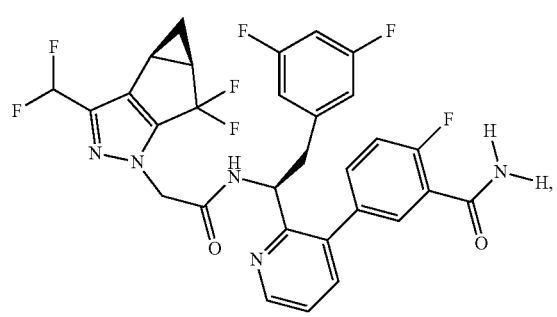
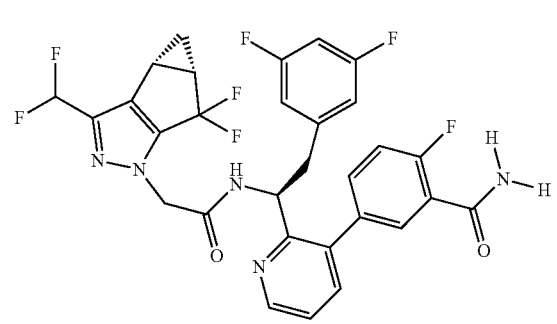
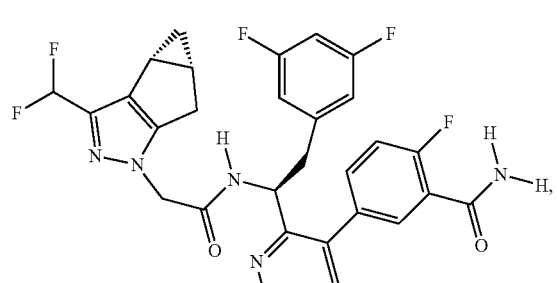
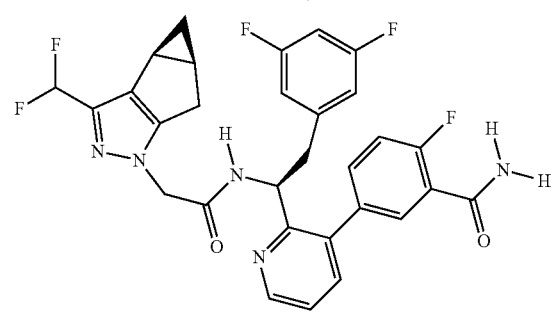
866
-continued
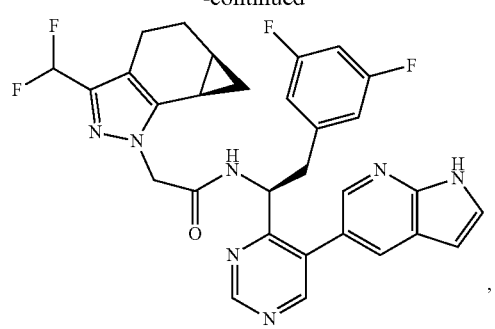
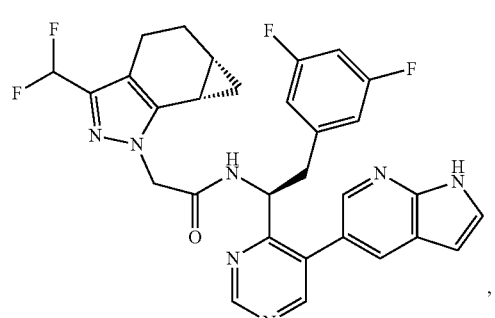
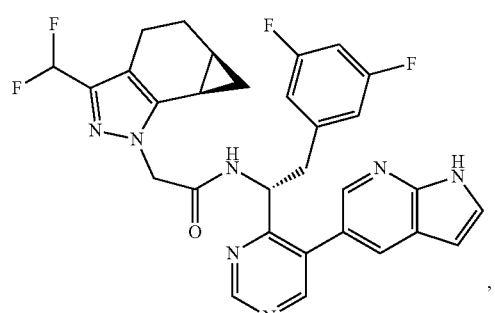
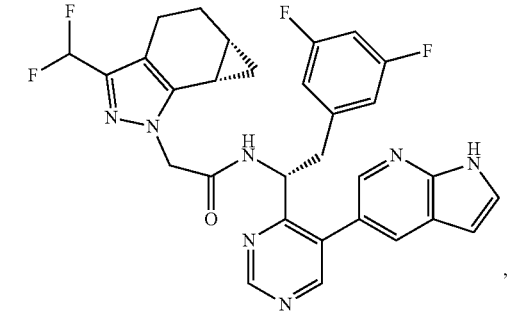
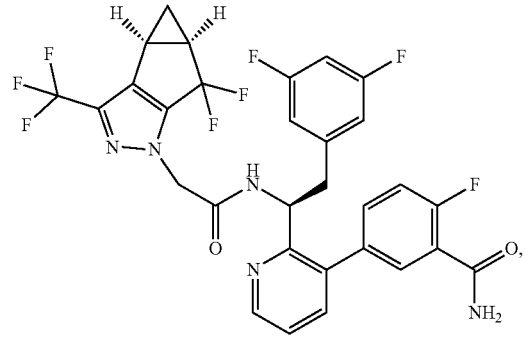

867
-continued
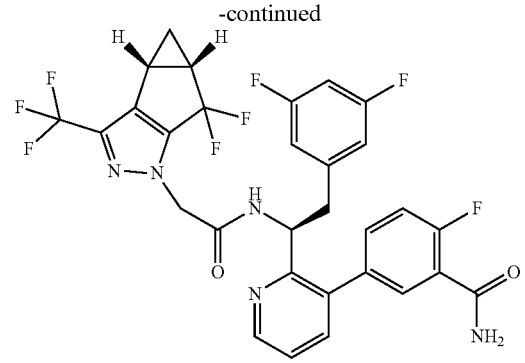
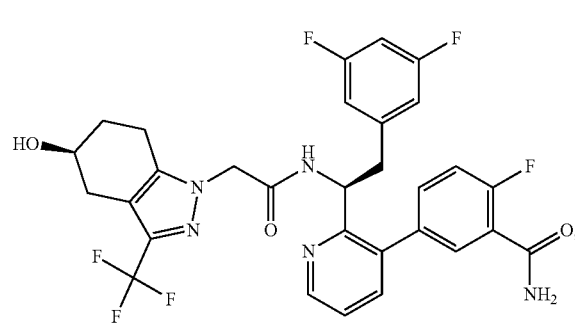
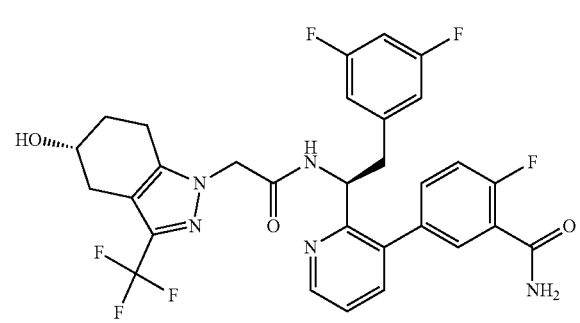
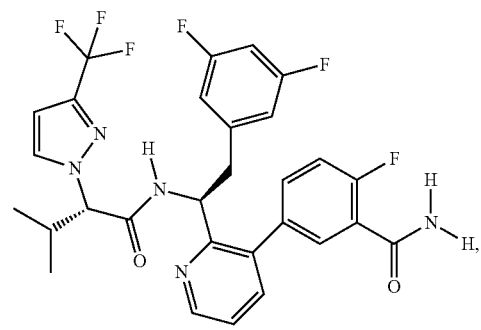
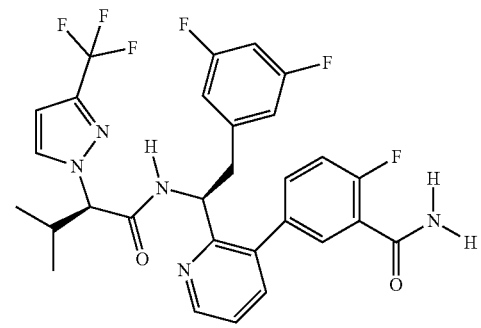
868
-continued
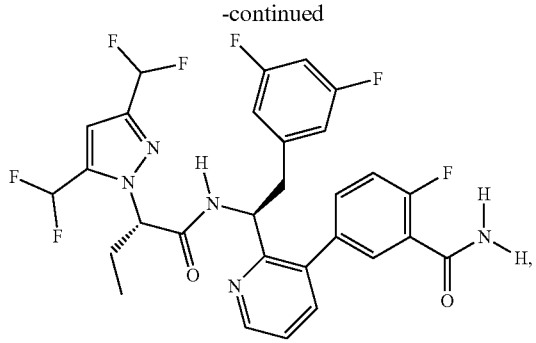
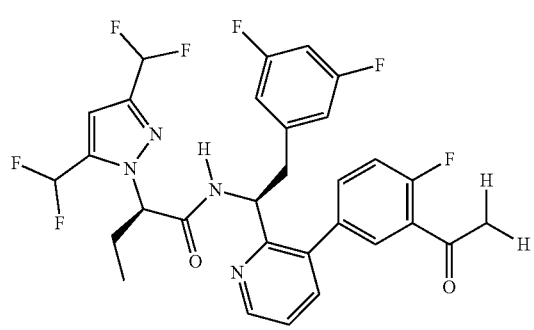
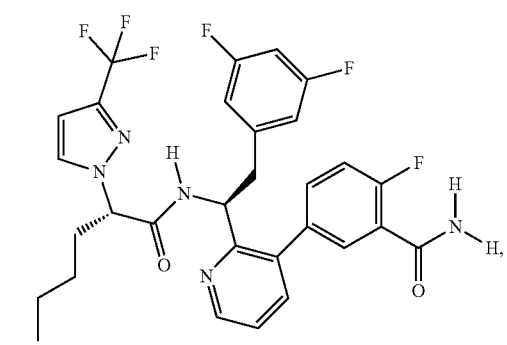
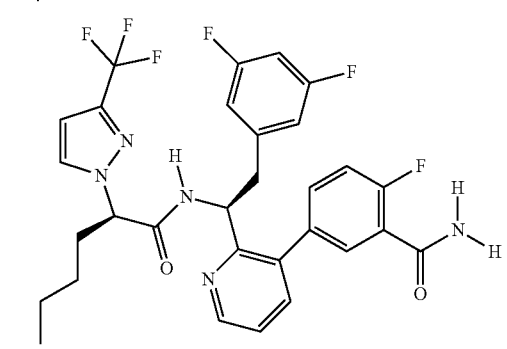
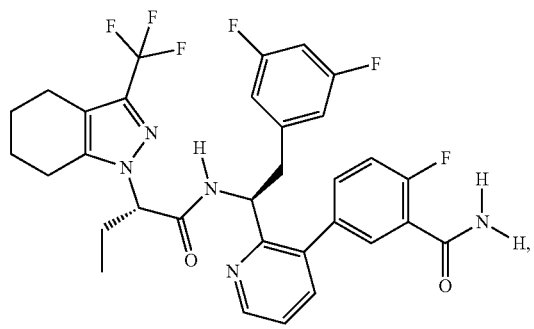

869
-continued

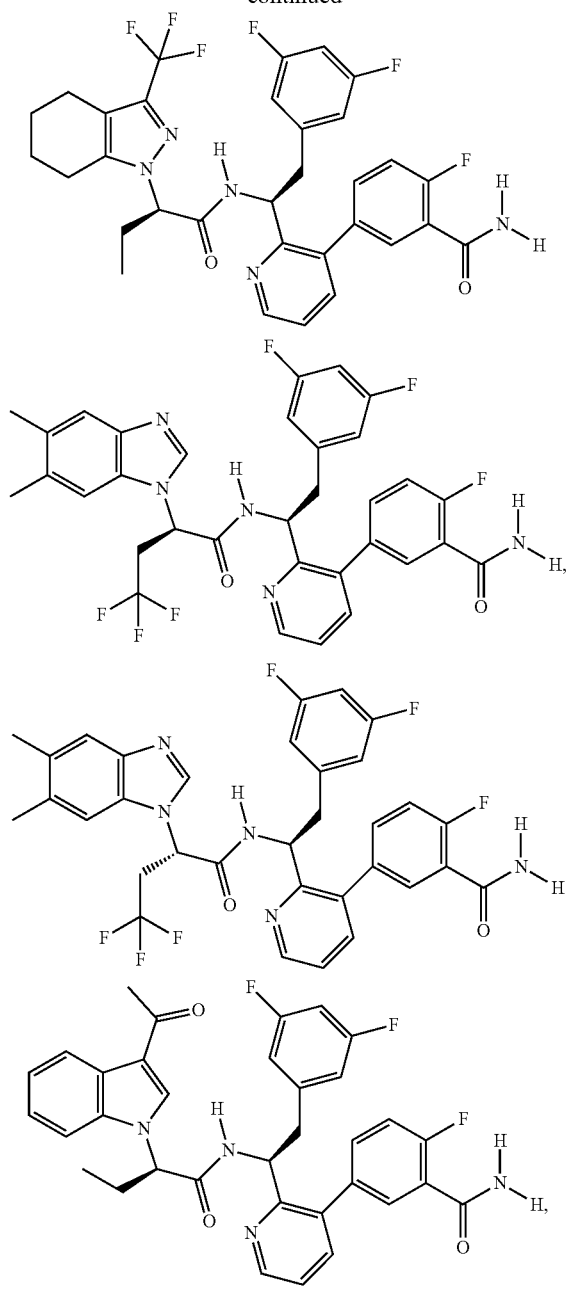

870
-continued

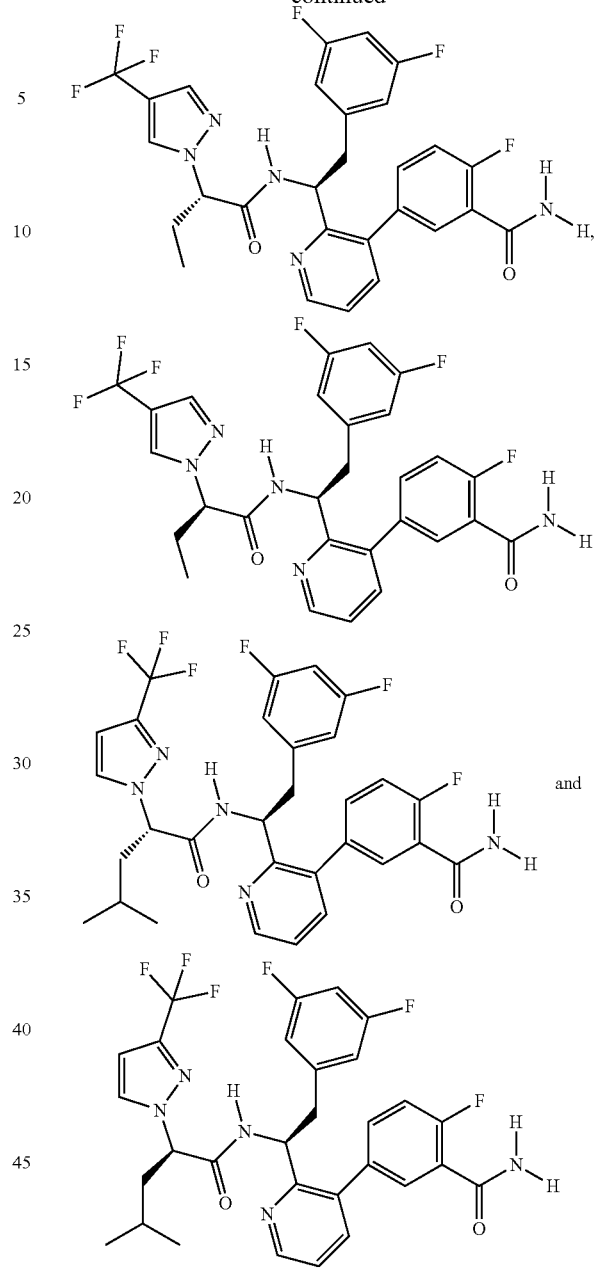

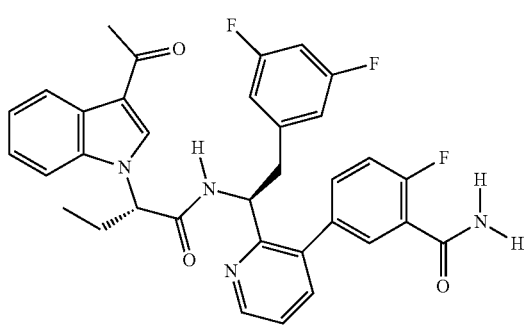

or a pharmaceutically acceptable salt thereof.

12. The method of claim 1, comprising administering to the human in need thereof a therapeutically effective amount of a compound of formula I, or a pharmaceutically acceptable salt thereof, in combination with a therapeutically effective amount of one or more additional therapeutic agents selected from the group consisting HIV protease inhibiting compounds, HIV non-nucleoside inhibitors of reverse transcriptase, HIV nucleoside inhibitors of reverse transcriptase, HIV nucleotide inhibitors of reverse transcriptase, HIV integrase inhibitors, gp41 inhibitors, CXCR4 inhibitors, gp120 inhibitors, CCR5 inhibitors, capsid polymerization inhibitors, and other drugs for treating HIV, and combinations thereof.

* * * * *

UNITED STATES PATENT AND TRADEMARK OFFICE
CERTIFICATE OF CORRECTION

PATENT NO. : 10,370,358 B2  
APPLICATION NO. : 15/902883  
DATED : August 6, 2019  
INVENTOR(S) : Steven S. Bondy et al.

Page 1 of 2

It is certified that error appears in the above-identified patent and that said Letters Patent is hereby corrected as shown below:

In the Claims

Column 746, Line 34, Claim 1, delete "—$NR_{p2} S(O)_2NR_{q2}R_{r2}$," and insert -- —$NR_{n2}S(O)_2NR_{q2}R_{r2}$, --, therefor.

Column 746, Line 46, Claim 1, delete "$C(O)NR_{q3}R_{r3}$," and insert -- —$OC(O)NR_{q3}R_{r3}$, --, therefor.

Column 746, Line 47, Claim 1, delete "—$S(O)_2 OH$," and insert -- —$S(O)_2OH$, --, therefor.

Column 746, Line 48, Claim 1, delete "—$NR_{n3} CO_2R_{p3}$," and insert -- —$NR_{n3}CO_2R_{p3}$, --, therefor.

Column 746, Line 49, Claim 1, delete "—$NR_{n3} ONR_{q3}R_{r3}$," and insert -- —$NR_{n3}CONR_{q3}R_{r3}$, --, therefor.

Column 746, Line 49, Claim 1, delete "—$NR_{n3} S(O)_2R_{p3}$, —$NR_{n3} S(O)_2 OR_{p3}$," and insert -- —$NR_{n3}S(O)_2R_{p3}$, —$NR_{n3}S(O)_2OR_{p3}$, --, therefor.

Column 746, Line 50, Claim 1, delete "—$NR_{n3}S(O2NR_{q3}R_{r3}$," and insert -- —$NR_{n3}S(O)_2NR_{q3}R_{r3}$, --, therefor.

Column 747, Line 1, Claim 1, delete "$Z^{1a}$" and insert -- $Z^{1d}$ --, therefor.

Column 747, Line 9, Claim 1, delete "$Z^{1a}$" and insert -- $Z^{1d}$ --, therefor.

Column 747, Line 64, Claim 1, delete "$Z^{1a}$" and insert -- $Z^{3a}$ --, therefor.

Column 748, Line 7, Claim 1, delete "—$S(O)_2 NR_{q6}R_{n5}$," and insert -- —$S(O)_2NR_{q6}R_{r6}$, --, therefor.

Column 748, Line 39, Claim 1, delete "$Z^{1a}$" and insert -- $Z^{3a}$ --, therefor.

Signed and Sealed this  
Thirty-first Day of December, 2019

Andrei Iancu  
*Director of the United States Patent and Trademark Office*

Column 748, Line 51, Claim 1, delete "$Z^{3a}$" and insert -- $Z^{3c}$ --, therefor.

Column 751, Lines 1-2, Claim 10, delete "2-hydroxyprop-2yl," and insert -- 2-hydroxyprop-2-yl, --, therefor.